(12) United States Patent
Lang

(10) Patent No.: US 11,348,257 B2
(45) Date of Patent: May 31, 2022

(54) AUGMENTED REALITY GUIDANCE FOR ORTHOPEDIC AND OTHER SURGICAL PROCEDURES

(71) Applicant: Philipp K. Lang, Lexington, MA (US)

(72) Inventor: Philipp K. Lang, Lexington, MA (US)

(*) Notice: Subject to any disclaimer, the term of this patent is extended or adjusted under 35 U.S.C. 154(b) by 109 days.

(21) Appl. No.: 16/965,274

(22) PCT Filed: Jan. 29, 2019

(86) PCT No.: PCT/US2019/015522
§ 371 (c)(1),
(2) Date: Jul. 27, 2020

(87) PCT Pub. No.: WO2019/148154
PCT Pub. Date: Aug. 1, 2019

(65) Prior Publication Data
US 2021/0192759 A1    Jun. 24, 2021

Related U.S. Application Data

(60) Provisional application No. 62/731,175, filed on Sep. 14, 2018, provisional application No. 62/714,790, (Continued)

(51) Int. Cl.
*G09G 5/00* (2006.01)
*G06T 7/33* (2017.01)
(Continued)

(52) U.S. Cl.
CPC ............ *G06T 7/33* (2017.01); *A61B 6/14* (2013.01); *A61B 34/10* (2016.02); *A61B 34/25* (2016.02);
(Continued)

(58) Field of Classification Search
CPC ... A61B 17/15; A61B 17/154; A61B 17/1714; A61B 17/1746; A61B 17/1757;
(Continued)

(56) References Cited

U.S. PATENT DOCUMENTS 5,526,812 A    6/1996  Dumoulin et al.
5,676,673 A   10/1997  Ferre et al.
(Continued)

FOREIGN PATENT DOCUMENTS

EP    1028659    2/2004
GB    2498833   12/2016
(Continued)

OTHER PUBLICATIONS

International Search Report in International Application No. PCT/US2019/015522 dated May 6, 2019.
(Continued)

*Primary Examiner* — Insa Sadio
(74) *Attorney, Agent, or Firm* — Greenberg Traurig, LLP; Natalie Salem; Barry Schindler

(57) ABSTRACT

Aspects of the present disclosure relate to systems, devices and methods for performing a surgical step or surgical procedure with visual guidance using an optical head mounted display. Aspects of the present disclosure relate to systems, devices and methods for displaying, placing, fitting, sizing, selecting, aligning, moving a virtual implant on a physical anatomic structure of a patient and, optionally, modifying or changing the displaying, placing, fitting, sizing, selecting, aligning, moving, for example based on kinematic information.

19 Claims, 96 Drawing Sheets

Related U.S. Application Data filed on Aug. 6, 2018, provisional application No. 62/700,096, filed on Jul. 18, 2018, provisional application No. 62/623,014, filed on Jan. 29, 2018.

(51) Int. Cl.

| | |
|---|---|
| *A61B 34/10* | (2016.01) |
| *A61B 34/00* | (2016.01) |
| *A61B 34/32* | (2016.01) |
| *A61B 90/00* | (2016.01) |
| *A61B 90/53* | (2016.01) |
| *A61B 90/92* | (2016.01) |
| *A61B 90/98* | (2016.01) |
| *A61C 5/40* | (2017.01) |
| *A61B 6/14* | (2006.01) |
| *A61C 1/08* | (2006.01) |
| *A61C 19/00* | (2006.01) |
| *A61F 2/46* | (2006.01) |
| *G02B 27/01* | (2006.01) |
| *G06T 3/40* | (2006.01) |
| *A61B 90/50* | (2016.01) |
| *A61B 6/00* | (2006.01) |
| *A61F 2/38* | (2006.01) |

(52) U.S. Cl.
CPC .............. *A61B 34/32* (2016.02); *A61B 90/37* (2016.02); *A61B 90/39* (2016.02); *A61B 90/53* (2016.02); *A61B 90/92* (2016.02); *A61B 90/98* (2016.02); *A61C 1/084* (2013.01); *A61C 5/40* (2017.02); *A61C 19/00* (2013.01); *A61F 2/4684* (2013.01); *G02B 27/0172* (2013.01); *G06T 3/40* (2013.01); *A61B 6/584* (2013.01); *A61B 2034/104* (2016.02); *A61B 2034/105* (2016.02); *A61B 2034/107* (2016.02); *A61B 2034/108* (2016.02); *A61B 2034/252* (2016.02); *A61B 2034/254* (2016.02); *A61B 2034/256* (2016.02); *A61B 2090/363* (2016.02); *A61B 2090/365* (2016.02); *A61B 2090/367* (2016.02); *A61B 2090/368* (2016.02); *A61B 2090/372* (2016.02); *A61B 2090/373* (2016.02); *A61B 2090/374* (2016.02); *A61B 2090/376* (2016.02); *A61B 2090/3735* (2016.02); *A61B 2090/3762* (2016.02); *A61B 2090/397* (2016.02); *A61B 2090/3945* (2016.02); *A61B 2090/3966* (2016.02); *A61B 2090/3983* (2016.02); *A61B 2090/502* (2016.02); *A61F 2/3877* (2013.01); *A61F 2002/4633* (2013.01); *G02B 2027/0138* (2013.01); *G02B 2027/0141* (2013.01); *G06T 2200/24* (2013.01); *G06T 2207/10116* (2013.01); *G06T 2207/30036* (2013.01); *G06T 2207/30204* (2013.01)

(58) Field of Classification Search
CPC ...... A61B 17/1764; A61B 2017/00203; A61B 2017/00207; A61B 2017/00216; A61B 2017/00221; A61B 2017/00707; A61B 2017/00725; A61B 2017/00734; A61B 2034/102; A61B 2034/104; A61B 2034/105; A61B 2034/107; A61B 2034/108; A61B 2034/2048; A61B 2034/2051; A61B 2034/2057; A61B 2034/2065; A61B 2034/252; A61B 2034/254; A61B 2034/256; A61B 2090/306; A61B 2090/309; A61B 2090/3614; A61B 2090/363; A61B 2090/365; A61B 2090/366; A61B 2090/367; A61B 2090/368; A61B 2090/371; A61B 2090/372; A61B 2090/373; A61B 2090/3735; A61B 2090/374; A61B 2090/376; A61B 2090/3762; A61B 2090/378; A61B 2090/3908; A61B 2090/3937; A61B 2090/3945; A61B 2090/3966; A61B 2090/397; A61B 2090/3983; A61B 2090/3991; A61B 2090/502; A61B 34/10; A61B 34/20; A61B 34/25; A61B 34/30; A61B 34/32; A61B 6/14; A61B 6/584; A61B 90/03; A61B 90/13; A61B 90/361; A61B 90/37; A61B 90/39; A61B 90/53; A61B 90/92; A61B 90/94; A61B 90/96; A61B 90/98; A61C 19/00; A61C 1/084; A61C 5/40; A61C 9/004; A61F 2002/4633; A61F 2/3877; A61F 2/4684; G02B 2027/0138; G02B 2027/0141; G02B 27/0172; G06T 2200/24; G06T 2207/10116; G06T 2207/30036; G06T 2207/30204; G06T 3/40; G06T 7/33
See application file for complete search history.

(56) References Cited

U.S. PATENT DOCUMENTS

| | | |
|---|---|---|
| 5,800,352 A | 9/1998 | Ferre et al. |
| 5,803,089 A | 9/1998 | Ferre et al. |
| 5,829,444 A | 11/1998 | Ferre et al. |
| 5,873,822 A | 2/1999 | Ferre et al. |
| D415,146 S | 10/1999 | Hori |
| 5,967,980 A | 10/1999 | Ferre et al. |
| 6,175,756 B1 | 1/2001 | Ferre et al. |
| 6,341,231 B1 | 1/2002 | Ferre et al. |
| 6,396,497 B1 | 5/2002 | Reichlen |
| 6,445,943 B1 | 9/2002 | Ferre et al. |
| 6,599,247 B1 | 7/2003 | Stetten |
| 6,714,810 B2 | 3/2004 | Grzeszczuk et al. |
| 7,130,676 B2 | 10/2006 | Barrick |
| 7,774,044 B2 | 8/2010 | Sauer et al. |
| 7,812,815 B2 | 10/2010 | Banerjee et al. |
| 8,320,612 B2 | 11/2012 | Knobel et al. |
| 8,730,266 B2 | 5/2014 | Brown et al. |
| 8,989,843 B2 | 3/2015 | Chien |
| 9,068,820 B2 | 6/2015 | Kosmecki et al. |
| 9,068,824 B2 | 6/2015 | Findeisen et al. |
| 9,123,155 B2 | 9/2015 | Cunningham et al. |
| 9,183,560 B2 | 11/2015 | Abelow |
| 9,215,293 B2 | 12/2015 | Miller |
| 9,299,138 B2 | 3/2016 | Zellner et al. |
| 9,310,559 B2 | 4/2016 | Macnamara |
| 9,311,284 B2 | 4/2016 | Warila et al. |
| 9,389,424 B1 | 7/2016 | Schowengerdt |
| 9,417,452 B2 | 8/2016 | Schowengerdt et al. |
| 9,429,752 B2 | 8/2016 | Schowengerdt et al. |
| 9,503,681 B1 | 11/2016 | Popescu et al. |
| 9,547,940 B1 | 1/2017 | Sun et al. |
| 9,582,717 B2 | 2/2017 | Lee et al. |
| 9,792,721 B2 | 10/2017 | Kosmecki et al. |
| 9,861,446 B2 | 1/2018 | Lang |
| 9,980,780 B2 | 5/2018 | Lang |
| 10,078,221 B2 | 9/2018 | Pilkinton et al. |
| 10,136,952 B2 | 11/2018 | Couture et al. |
| 10,154,239 B2 | 12/2018 | Casas |
| 10,159,530 B2 | 12/2018 | Lang |
| 10,278,777 B1 | 5/2019 | Lang |
| 10,292,768 B2 | 5/2019 | Lang |
| 10,368,947 B2 | 8/2019 | Lang |
| 10,405,927 B1 | 9/2019 | Lang |
| 10,603,113 B2 | 3/2020 | Lang |
| 10,743,939 B1 | 8/2020 | Lang |
| 10,799,296 B2 | 10/2020 | Lang |
| 10,849,693 B2 | 12/2020 | Lang |

(56) References Cited

U.S. PATENT DOCUMENTS

| | | |
|---|---|---|
| 11,013,560 B2 | 5/2021 | Lang |
| 11,172,990 B2 | 11/2021 | Lang |
| 2001/0041838 A1 | 11/2001 | Holupka et al. |
| 2002/0016349 A1 | 2/2002 | Heywang et al. |
| 2002/0082498 A1 | 6/2002 | Wendt et al. |
| 2005/0113846 A1 | 5/2005 | Carson |
| 2005/0215879 A1 | 9/2005 | Chuanggui |
| 2005/0028146 A1 | 12/2005 | Marquart et al. |
| 2005/0267353 A1 | 12/2005 | Marquart et al. |
| 2005/0281465 A1 | 12/2005 | Marquart et al. |
| 2006/0142739 A1 | 6/2006 | Disilestro et al. |
| 2007/0015999 A1 | 1/2007 | Heldreth et al. |
| 2007/0035511 A1 | 2/2007 | Banerjee et al. |
| 2007/0038944 A1 | 2/2007 | Carignano et al. |
| 2007/0236514 A1 | 10/2007 | Agusanto et al. |
| 2007/0276234 A1 | 11/2007 | Shahidi |
| 2008/0269596 A1 | 10/2008 | Revie et al. |
| 2009/0068620 A1 | 3/2009 | Knobel et al. |
| 2009/0089081 A1 | 4/2009 | Haddad |
| 2009/0138019 A1 | 5/2009 | Wasielewski |
| 2009/0267805 A1 | 10/2009 | Jin et al. |
| 2011/0190637 A1 | 8/2011 | Knobel et al. |
| 2013/0093829 A1 | 4/2013 | Rosenblatt et al. |
| 2013/0096373 A1 | 4/2013 | Chabanas et al. |
| 2013/0116574 A1 | 5/2013 | Knobel et al. |
| 2013/0169683 A1 | 7/2013 | Perez et al. |
| 2013/0261503 A1 | 10/2013 | Sherman et al. |
| 2013/0261504 A1 | 10/2013 | Claypool et al. |
| 2013/0261633 A1 | 10/2013 | Thornberry |
| 2013/0296682 A1 | 11/2013 | Clavin et al. |
| 2013/0326364 A1 | 12/2013 | Latta et al. |
| 2014/0081659 A1 | 3/2014 | Nawana et al. |
| 2014/0085203 A1 | 3/2014 | Kobayashi |
| 2014/0088941 A1 | 3/2014 | Banerjee et al. |
| 2014/0118335 A1 | 5/2014 | Gurman |
| 2014/0135746 A1 | 5/2014 | Schoepp |
| 2014/0198190 A1 | 7/2014 | Okumu |
| 2014/0218366 A1 | 8/2014 | Kosmecki et al. |
| 2014/0275760 A1 | 9/2014 | Lee et al. |
| 2014/0303491 A1 | 10/2014 | Shekhar et al. |
| 2014/0334670 A1 | 11/2014 | Guigues et al. |
| 2015/0100067 A1 | 4/2015 | Cavanagh et al. |
| 2015/0206218 A1 | 7/2015 | Banerjee et al. |
| 2015/0310668 A1 | 10/2015 | Ellerbrock |
| 2015/0366628 A1 | 12/2015 | Ingmanson |
| 2016/0163105 A1 | 6/2016 | Hong et al. |
| 2016/0182877 A1 | 6/2016 | DeLuca |
| 2016/0191887 A1* | 6/2016 | Casas .................. G06T 19/006 348/47 |
| 2016/0206379 A1 | 7/2016 | Flett et al. |
| 2016/0220105 A1 | 8/2016 | Duret |
| 2016/0225192 A1 | 8/2016 | Jones et al. |
| 2016/0228193 A1 | 8/2016 | Moctezuma de la Barrera et al. |
| 2016/0287337 A1 | 10/2016 | Aram et al. |
| 2016/0324580 A1 | 11/2016 | Esterberg |
| 2016/0381256 A1 | 12/2016 | Aguirre-Valencia |
| 2017/0027651 A1 | 2/2017 | Esterberg |
| 2017/0035517 A1 | 2/2017 | Geri et al. |
| 2017/0071673 A1 | 3/2017 | Ferro et al. |
| 2017/0108930 A1 | 4/2017 | Banerjee et al. |
| 2017/0160549 A1 | 6/2017 | Badiali et al. |
| 2017/0178375 A1 | 6/2017 | Benishti et al. |
| 2017/0202633 A1 | 7/2017 | Liu |
| 2017/0231714 A1 | 8/2017 | Kosmecki et al. |
| 2017/0258526 A1* | 9/2017 | Lang .................. H05K 999/99 |
| 2017/0312032 A1 | 11/2017 | Amanatullah et al. |
| 2018/0049622 A1 | 2/2018 | Ryan et al. |
| 2018/0116728 A1 | 5/2018 | Lang |
| 2018/0125584 A1 | 5/2018 | Lang |
| 2018/0256256 A1 | 9/2018 | May et al. |
| 2018/0263704 A1 | 9/2018 | Lang |
| 2019/0000564 A1 | 1/2019 | Navab et al. |
| 2019/0110842 A1 | 4/2019 | Lang |
| 2019/0192226 A1 | 6/2019 | Lang |
| 2019/0216452 A1 | 7/2019 | Nawana et al. |
| 2019/0262078 A1 | 8/2019 | Lang |
| 2019/0380784 A1 | 12/2019 | Lang |
| 2020/0060767 A1 | 2/2020 | Lang |
| 2020/0246074 A1 | 8/2020 | Lang |
| 2020/0305980 A1 | 10/2020 | Lang |
| 2021/0022808 A1 | 1/2021 | Lang |
| 2021/0106386 A1 | 4/2021 | Lang |
| 2021/0267691 A1 | 9/2021 | Lang |

FOREIGN PATENT DOCUMENTS

| | | |
|---|---|---|
| WO | WO1993025157 | 12/1993 |
| WO | WO 2005088539 | 9/2005 |
| WO | WO 2010034117 | 4/2010 |
| WO | WO 2014057352 | 4/2014 |
| WO | WO 2015110859 | 7/2015 |
| WO | WO 2015145395 | 10/2015 |
| WO | WO 2016028828 | 2/2016 |
| WO | WO 2016162789 | 10/2016 |
| WO | WO 2016195401 | 12/2016 |
| WO | WO 2016207628 | 12/2016 |
| WO | WO 2017160651 | 9/2017 |
| WO | WO 2018085417 | 5/2018 |
| WO | WO 2018085691 | 5/2018 |
| WO | WO 2018132804 | 7/2018 |
| WO | WO 2018052966 | 10/2018 |

OTHER PUBLICATIONS

3D Optical Microscopy for Orthopedic Implants; Bruker Nano Surfaces, Jun. 17, 2016.

A Look into the Body—Augmented Reality in Computer Aided Surgery, Department of Informatics, Research-Highlights; Technische Universitat Munchen.

Abe et al., "A Novel 3D Guidance System Using Augmented Reality for Percutaneous Vertebroplasty", Journal of Neurological Spine, vol. 19, pp. 492-501, Oct. 2013.

Aguerreche L. et al., "Reconfigurable Tangible Devices for 3D Virtual Object Manipulation by Single or Multiple Users." VRST 2010, Nov. 2010, Hong Kong, Hong Kong SAR China inria-00534095.

Aichert et al., "Image-Based Tracking of the Teeth for Orthodontic Augmented Reality", Medical Image Computing and Computer-Assisted Intervention, Lecture Notes in Computer Science, vol. 7511, Springer, pp. 601-608, 2012.

Anderson et al., "Virtual annotations of the surgical field through an augmented reality transparent display", The Visual Computer, vol. 32, Issue 11, pp. 1481-1498, Nov. 2016.

Armstrong et al., "A Heads-Up Display for Diabetic Limb Salvage Surgery: A View Through the Google Looking Glass"; Journal of Diabetes Science and Technology 2014, vol. 8(5) 951-956.

Azura, R., "A survey of augmented reality." Teleoperators and Virtual Environments, vol. 6, Issue 4, Aug. 1997, pp. 355-385.

Bajura, M., et al., "Merging Virtual Objects with the Real World: Seeing Ultrasound Imagery Within the Patient.", In Proceedings of SIGGRAPH '92, 1992, New York: ACM Press, pp. 203-210.

Baker et al., "The Emergence of Augmented Reality in Orthopaedic Surgery and Education", The Orthopaedic Journal at Harvard Medical School, vol. 16, pp. 8-16, Jun. 2015.

Bauer et al., "Joint ToF Image Denoising and Registration with a CT Surface in Radiation Therapy", Scale Space and Variational Methods in Computer Vision, Lecture Notes in Computer Science, Springer, vol. 6667, pp. 98-109.

Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.

Bauer et al., "Real-Time Range Imaging in Health Care: A Survey", Time-of-Flight and Depth Imaging, Sensors, Algorithms, and Applications. Lecture Notes in Computer Science, vol. 8200, pp. 228-254, 2017.

(56) References Cited

OTHER PUBLICATIONS

Bauer, Sebastian, Doctoral Thesis, "Rigid and Non-Rigid Surface Registration for Range Imaging Applications in Medicine", urn:nbn:de:bvb:29-opus4-54665, Nov. 27, 2014.

Benford, S. et al., "User embodiment in collaborative virtual environments", Proceedings of the SIGCHI conference on Human factors in computing systems, CHI '95, pp. 242-249, 1995.

Besl PJ, McKay ND. 2, 1992. A method for registration of 3-D shapes. IEEE Trans PAMI, vol. 14, pp. 239-256.

Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.

Bichlmeier et al., "Virtually Extended Surgical Drilling Device: Virtual Mirror for Navigated Spine Surgery"; MICCAI 2007, Part I, LNCS 4791, pp. 434-441.

Billinghurst, et al., "The MagicBook: A Transitional AR Interface.", Computers and Graphics, Nov. 2001, pp. 745-753.

Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.

Billinghurst, M., et al., "Collaborative Augmented Reality.", Communications of the ACM 2002, vol. 45. Issue 7, pp. 64-70 (2002).

Billinghurst, M., et al., "Experiments with Face to Face Collaborative AR Interfaces.", Virtual Reality Journal, vol. 4, No. 2, (2002).

Birkfellner et al., "A Head-Mounted Operating Binocular for Augmented Reality Visualization in Medicine—Design and Initial Evaluation", IEEE Transactions on Medical Imaging, vol. 21, No. 8, pp. 991-997, Aug. 2002.

Birkfellner et al., "Computer-enhanced stereoscopic vision in a head-mounted operating binocular", Physics in Medicine & Biology, vol. 48, No. 3, pp. 49-57, Feb. 7, 2003.

Birkfellner et al., "In-Vitro Aassessment of a Registration Protocol for Image Guided Implant Dentistry", Clinical Oral Implants Research, vol. 12, Issue 1, pp. 69-78, Feb. 2001.

Blackwell et al., "An Image Overlay System for Medical Data Visualization", In: Wells W.M., Colchester A., Delp S. (eds) Medical Image Computing and Computer-Assisted Intervention—MICCAI'98. MICCAI 1998. Lecture Notes in Computer Science, vol. 1496. Springer, Berlin, Heidelberg; pp. 232-240.

Blackwell et al., "An Image Overlay System for Medical Data Visualization", Medical Image Analysis vol. 4, pp. 67-72, 2000.

Blackwell et al., "Augmented Reality and Its Future in Orthopaedics", Clinical Orthopaedics & Related Research, vol. 354, pp. 111-122, Sep. 1998.

Castillo et al., "Augmented Reality for Assistance of Total Knee Replacement", Journal of Electrical and Computer Engineering, vol. 2016, Article 9358369, pp. 1-6, 2016.

Catani et al., "Knee Surgery Using Computer Assisted Surgery and Robotics", Springer Heidelberg Publishing, Book, pp. 1-221, 2013.

Chandak, "MEMS Based Wireless Controlled Robot with Voice and Video Camera"; International Journal of Scientific & Engineering Research, vol. 5, Issue 4, Apr. 2014.

Charbonnier et al., "Real Virtuality: Perspectives offered by the combination of Virtual Reality headsets and Motion Capture", Artanim, Real Virtuality White Paper, Aug. 23, 2015.

Chen et al., "Development of a surgical navigation system based on augmented reality using an optical see-through head-mounted display"; Journal of Biomedical Informatics 55 (2015) 124-131.

Cruz-Neira C. et al., "The cave: audio visual experience automatic virtual environment.", Commun. ACM, vol. 35, No. 6, pp. 64-72, Jun. 1992.

Cui et al., "KinectAvatar: Fully Automatic Body Capture Using a Single Kinect", ACCV'12 Proceedings of the 11th International Conference on Computer Vision—vol. 2, pp. 133-147, Nov. 2012.

Daniel and Ramos, "Augmented Reality for Assistance of Total Knee Replacement", Journal of Electrical and Computer Engineering, vol. 2016, Article ID 9358369, Hindawi Publishing Corporation.

Davies et al., "Computer Assisted Orthopaedic Surgery", 8th Annual Meeting of CAOS—International Proceedings, Apr. 2008.

deLambert et al., "Electromagnetic Tracking for Registration and Navigation in Endovascular Aneurysm Repair: A Phantom Study" European Journal of Vascular and Endovascular Surgery, vol. 43, pp. 684-689, 2012.

Draelos, Mark, "The Kinect Up Close: Modifications for Short-Range Depth Imaging", NC State Theses and Dissertations, pp. 1-88, Mar. 26, 2012.

Elmi-Terander et al., "Surgical Navigation Technology Based on Augmented Reality and Integrated 3D lntraoperative Imaging"; Spine Surgery, vol. 41, No. 21, pp. E1303-E1311, 2016.

Ferrari et al., "Video See-Through in the Clinical Practice", 1st International Workshop on Engineering Interactive Computing Systems for Medicine and Health Care, EICS4Med. vol. 727, pp. 19-24, 2011.

Fischer et al., "Medical Augmented Reality Based on Commercial Image Guided Surgery", European Association for Computer Graphics, Proceedings of the 10th Eurographics Symposium on Virtual Environments, pp. 83-86, Jun. 2004.

Fitzmaurice, G., et al., "Bricks: Laying the Foundations for Graspable User Interfaces.", Proceedings of Conference on Human Factors in Computing Systems (CHI '95), Denver, Colorado, ACM Press, 442-449.

Flusser et al., "Image Fusion: Principles, Methods and Applications", Tutorial EISIPCO 2007 Lecture Notes.

Fritz et al., "Augmented Reality Visualization with Image Overlay for MRI-Guided Intervention: Accuracy for Lumbar Spinal Procedures with a 1.5-T MRI System", Vascular and Interventional Radiology, AJR: 198, Mar. 2012.

Fritz et al., "Augmented Reality Visualization with Use of Image Overlay Technology for MR Imaging—guided Interventions: Assessment of Performance in Cadaceric Shoulder and Hip Arthrography at 1.5T"; Radiology: vol. 265, No. 1, Oct. 2012, pp. 254-259.

Garon, Mathieu; Boulet, Pierre-Olivier; Doiron, Jean-Philippe; Beaulieu, Luc; Lalonde, Jean-François (2016): Real-time High Resolution 3D Data on the HoloLens. In: International Symposium on Mixed and Augmented Reality (ISMAR).

Garrido-Jurado, S.; Muñoz-Salinas, R.; Madrid-Cuevas, F. J.; Marin-Jiménez, M. J. (2014): Automatic. generation and detection of highly reliable fiducial markers under occlusion. In: Pattern Recognition 47 (6), S. 2280-2292. DOI: 10.1016/j.patcog.2014.01.005.

Gavaghan et al., "Augmented Reality Image Overlay Projection for Image Guided Open Liver Ablation of Metastatic Liver Cancer"; C.A. Linte et al. (Eds.): AE-CAI 2011, LNCS, pp. 36-46, 2012.

Gee A, et al., "Processing and visualizing three-dimensional ultrasound data.", The British Journal of Radiology, vol. 77, S186-S193, (2004).

George et al., "Low Cost Augmented Reality for Training of MRI-Guided Needle Biopsy of the Spine", Medicine Meets Virtual Reality 16, pp. 138-140, IOS Press, 2008.

Germano et al., Advanced Techniques in Image-Guided Brain and Spine Surgery, Thieme Medical Publishers, Incorporated, 2002.

Gonzalez, Smart Multi-Level Tool for Remote Patient Monitoring Based on a Wireless Sensor Network and Mobile Augmented Reality, Sensors, Sep. 2014; 14(9): 17212-17234.

Gorbert, M. et al., "Triangles: Tangible Interface for Manipulation and Exploration of Digital Information Topography.", Proceedings of CHI '98, Apr. 18-23, 1998, © 1998 ACM.

Gromov et al., "What is the optimal alignment of the tibial and femoral components in knee arthroplasty?: An overview of the literature"; Acta Orthopaedica 2014; 85(5): 480-487.

Hayashibe et al., "Surgical Navigation Display System Using Volume Rendering of Intraoperatively Scanned CT Images", Computer Aided Surgery, vol. 11, No. 5, pp. 240-246, Sep. 2006.

Hinterstoisser, S. Holzer S.; Cagniart, C.; Ilic, S.; Konolige, K.; Navab, N.; Lepetit, V. (2011b): Multimodal Templates for Real-Time Detection of Texture-less Objects in Heavily Cluttered Scenes.

(56) References Cited

OTHER PUBLICATIONS

Hinterstoisser, S.; Cagniart, C.; Ilic, S.; Sturm, P.; Navab, N.; Fua, P.; Lepetit, V. (2012a): Gradient Response Maps for Real-Time Detection of Texture-Less Objects. In: IEEE Transactions on Pattern Analysis and Machine Intelligence.

Hinterstoisser, S.; Lepetit, V.; Benhimane, S.; Fua, P.; Navab, N. (2011a): Learning Real-Time Perspective Patch Rectification. In: International Journal of Computer Vision (IJCV), Springer. DOI: 10.1007/s11263-010-0379-x.

Hinterstoisser, S.; Lepetit, V.; Ilic, S.; Holzer, S.; Bradski, G.; Konolige, K.; Navab, N. (2012b): Model Based Training, Detection and Pose Estimation of Texture-Less 3D Objects in Heavily Cluttered Scenes.

Hoff, "Fusion of Data from Head-Mounted and Fixed Sensors"; First International Workshop on Augmented Reality, 1, 1998, pp. 1-15.

Holographic weapon sight—Wikipedia https://en.wikipedia.org/wiki/Holographic_weapon_sight retrieved on Nov. 22, 2016.

Hu et al., "A Convenient Method of Video See-through Augmented Reality Based on Image-Guided Surgery System", Internet Computing for Engineering and Science, 2013 Seventh International Conference on Internet Computing for Engineering and Science, Shanghai, pp. 100-103, Date of Conference: Sep. 20-22, 2013, IEEE Xplore Dec. 12, 2013.

Hua et al., "A 3D Integral Imaging Optical See-Through Head-Mounted Display", Optical Society of America, vol. 22, No. 11, pp. 1-8, Jun. 2, 2014.

Ishii, H., et al., "Iterative Design of Seamless Collaboration Media.", Communications of the ACM, vol. 37, No. 8, Aug. 1994, pp. 83-97.

Ji et al., "Real-Time Eye, Gaze, and Face Pose Tracking for Monitoring Driver Vigilance"; Real-Time Imaging 8, pp. 357-377, 2002.

Jiang et al., "A Robust Automated Markerless Registration Framework for Neurosurgery Navigation", The International Journal of Medical Robotics and Computer Assisted Surgery, vol. 11, pp. 436-447, Oct. 19, 2014.

Jolesz, Ferenc A., "Intraoperative Imaging and Image-Guided Therapy", Springer Science & Business Media, 893 pages, Jan. 14, 2014.

Kanade et al., "Simulation, Planning, and Execution of Computer-Assisted Surgery", Proceedings of the NSF Grand Challenges Workshop, 1996.

Kato, H.; Billinghurst, M. (1999): Marker tracking and HMD calibration for a video-based augmented reality conferencing system. In: Augmented Reality, 1999. (IWAR '99) Proceedings. 2nd IEEE and ACM International Workshop on, S. 85-94.

Kersten-Oertel et al., "The State of the Art of Visualization in Mixed Reality Image Guided Surgery", Computerized Medical Imaging and Graphics, vol. 37, pp. 98-112, Jan. 2013.

Kim et al., "Registration Accuracy Enhancement of a Surgical Navigation System for Anterior Cruciate Ligament Reconstruction: A Phantom and Cadaveric Study", The Knee, vol. 24, pp. 329-339, 2017.

Kolodzey et al., "Wearable technology in the operating room: a systematic review"; GMJ Innov 2017; 3:55-63.

Kumar et al., "A Portable Wireless Head Movement Controlled Human-Computer Interface for People with Disabilities", International Journal of Advanced Research in Electrical, Electronics and Instrumentation Engineering, vol. 3, Issue 7, Jul. 2014.

Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.

Lamata et al., "Augmented Reality for Minimally Invasive Surgery: Overview and Some Recent Advances"; Augmented Reality, Jan. 2010.

Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, Jun. 2010.

Liao et al., "Surgical Navigation by Autostereoscopic Image Overlay of Integral Videography", IEEE Transactions on Information Technology in Biomedicine, vol. 8, No. 2, pp. 114-121, Jun. 2004.

Lievin et al., "Stereoscopic Augmented Reality System for Computer-Assisted Surgery", International Congress Series, vol. 1230, pp. 107-111, Jun. 2001.

Lindert et al., "The use of a head-mounted display for visualization in neuroendoscopy", Computer Aided Surgery, 2004; 9(6): 251-256.

Linte et al., "On Mixed Reality Environments for Minimally Invasive Therapy Guidance: Systems Architecture, Successes and Challenges in their Implementation from Laboratory to Clinic", Comput Med Imaging Graph, Mar. 2013; 37(2): 83-97, DOI: 10.1016/j.compmedimag.2012.12.002.

Liu et al., "An Optical See-Through Head Mounted Display with Addressable Focal Planes" IEEE International Symposium on Mixed and Augmented Reality, Cambridge, UK, pp. 33-42, Oct. 3, 2008.

Lorensen WE, Cline HE. [ed.], in M.C. Stone. 1987. Marching cubes: A high resolution 3d surface construction algorithm. Proceedings of SIGGRAPH 87. pp. 163-169.

Maier-Hein et al., "Optical Techniques for 3D Surface Reconstruction in Computer-Assisted Laparoscopic Surgery", Medical Image Analysis, vol. 17, pp. 974-996, May 3, 2013.

Maier-Hein, L. et al., "Towards Mobile Augmented Reality for On-Patient Visualization of Medical Images.", Bildverarbeitung für die Medizin 2011: Algorithmen—Systeme—Anwendungen Proceedings des Workshops vom 20.-Mar. 22, 2011 in Lübeck (pp. 389-393).

Masamune et al., "An Image Overlay System with Enhanced Reality for Percutaneous Therapy Performed Inside CT Scanner", Medical Image Computing and Computer-Assisted Intervention, Lecture Notes in Computer Science, vol. 2489, pp. 77-84, Oct. 2002.

Maurer et al., "Augmented-Reality Visualization of Brain Structures with Stereo and Kinetic Depth Cues: System Description and Initial Evaluation with Head Phantom", Proceedings, vol. 4319, Medical Imaging 2001: Visualization, Display, and Image-Guided Procedures, pp. 445-456, May 28, 2001.

Medeiros D. et al., "Proposal and evaluation of a tablet-based tool for 3D virtual environments.", SBC Journal on 3D Interactive Systems, vol. 4, No. 2, pp. 30-40, (2013).

Melzer, "Head-Mounted Displays", The Avionics Handbook, 2001.

Menozzi et al., "Development of Vision-Aided Navigation for a Wearable Outdoor Augmented Reality System", IEEE Plans, Position Location and Navigation Symposium, Article No. 6851442, pp. 760-772, 2014.

MicroVision 2015 Annual Report and Proxy Statement for 2016 Annual Meeting of Shareholders.

Moore et al., "Image Guidance for Spinal Facet Injections Using Tracked Ultrasound", MICCAI 2009, Part I, LNCS 5761, pp. 516-523 2009.

Muller et al., "Automatic Multi-Modal ToF/CT Organ Surface Registration", Bildverarbeitung für die Medizin, pp. 154-158, Mar. 2011.

Newcombe, R. A.; Izadi, S.; Hilliges, O.; Molyneaux, D.; Kim, D.; Davison, A. J. et al. (2011): KinectFusion. Real-time dense surface mapping and tracking. In: 2011 10th IEEE International Symposium on Mixed and Augmented Reality, S. 127-136.

Nicolau, "Augmented Reality in Laparoscopic Surgical Oncology.", Surgical Oncology, vol. 20, pp. 89-201 (2011).

Nikou et al., "Augmented Reality Imaging Technology for Orthopaedic Surgery", Operative Techniques in Orthopaedics, vol. 10, No. 1 (Jan.), 2000: pp. 82-86.

Noonan et al., "The Design and Initial Calibration of an Optical Tracking System Using the Microsoft Kinect", IEEE Nuclear Science Symposium Conference Record, pp. 3614-3617, Oct. 2011.

Okamura, Allison, "Tracking and Surgical Navigation, Registration", Stanford Lecture 8: ME 328: Medical Robotics, pp. 1-19, Spring 2013.

(56) References Cited

OTHER PUBLICATIONS

Ortega et al., "Usefulness of a head mounted monitor device for viewing intraoperative fluoroscopy during orthopaedic procedures", Arch Orthop Trauma Surg (2008) 128:1123-1126.

Paprosky et al., "Intellijoint HIP: a 3D mini-optical navigation tool for improving intraoperative accuracy during total hip arthroplasty"; Med Devices (Auckl). 2016; 9: 401-408.

Pauly et al., "Machine Learning-Based Augmented Reality for Improved Surgical Scene Understanding", Computerized Medical Imaging and Graphics, vol. 1280, pp. 1-6, Jun. 2014.

Peters et al., "Image-Guided Interventions, Technology and Applications", Springer Science and Business Media, 576 pages 2018.

Ponce et al., "Emerging Technology in Surgical Education: Combining Real-Time Augmented Reality and Wearable Computing Devices", The Cutting Edge, Nov. 2014, vol. 37, No. 11.

Qian, Long; Azimi, Ehsan; Kazanzides, Peter; Navab, Nassir (2017): Comprehensive Tracker Based Display Calibration for Holographic Optical See-Through Head-Mounted Display.

Ren et al., "Marker-Based Surgical Instrument Tracking Using Dual Kinect Sensors", IEEE Transactions on Automation Science and Engineering, vol. 11, No. 3, pp. 921-924, Jul. 2014.

Rhodes, "A brief history of wearable computing", MIT Wearable Computing Project.

Rinaldi et al., "Computer-Guided Applications for Dental Implants, Bone Grafting, and Reconstructive Surgery", Elsevier Inc., 556 pages, 2016.

Robinett et al., "A Computational Model for the Stereoscopic Optics of a Head-Mounted Display", Proceedings vol. 1457, Stereoscopic Displays and Applications II, pp. 140-160, 1991.

Rolland et al., "A Comparison of Optical and Video See-through Head-mounted Displays", Proceedings vol. 2351, Telemanipulator and Telepresence Technologies, pp. 293-307, Dec. 21, 1995.

Rolland et al., "Optical Versus Video See-Through Head-Mounted Displays in Medical Visualization", Presence: Teleoperators and Virtual Environments, vol. 9, Issue 3, pp. 287-309, Jun. 2000.

Rosenthal et al., "Augmented Reality Guidance for Needle Biopsies: A Randomized, Controlled Trial in Phantoms"; MICCAI 2001, LNCS 2208: 240-248.

Rosman et al., "Articulated Motion Segmentation of Point Clouds by Group-Valued Regularization", Eurographics Workshop on 3D Object Retrieval, EG 3DOR, pp. 77-84, May 2012.

Salmi Jamali, S. et al., "Utilising Mobile-Augmented Reality for Learning Human Anatomy.", 7th World. Conference on Educational Sciences, (WCES-2015), Feb. 5-7, 2015, Novotel Athens Convention Center, Athens, Greece.

Sanko, "Microvision's Nomad Augmented Vision System: The How and the Why"; SID Pacific Northwest Chapter Meeting, Jun. 11, 2003.

Sauer et al., "An Augmented Reality Navigation System with a Single-Camera Tracker: System Design and Needle Biopsy Phantom Trial", Proceedings of the 5th International Conference on Medical Image Computing and Computer-Assisted Intervention—Part II, pp. 116-124, Sep. 2002.

Sauer et al., "Augmented Workspace: Designing an AR Testbed", Proceedings IEEE and ACM International Symposium on Augmented Reality, pp. 47-53, Munich 2000.

Schramm, Kinect: The Company Behind the Tech Explains How it Works, Jun. 19, 2010, https://www.engadget.com/2010/06/19/kinect-how-it-works-from-the-company-behind-the-tech/?guccounter=1&guce_referrer=aHR0cHM6Ly93d3cuZ29vZ2x1LmNvbS8&guce_referrer_sig=AQAAAKHcnRaFMexHHXiiRrcGjKYjWQ2VJGsMA556eCVncvte7f0VM4aN3GpWj1WqU3RfCnTwHcTbxmibv1Iz_TUFgILvsRhShqXDrSM63OcvvjlSzpUoBvsC2LsOmHqf-zifqdYelctf0D0MDM78YhH-u7w9JUfxuLDGVUxUi9hDQLZo.

Scuderi et al., "Total Knee Arthroplasty with a Novel Navigation System Within the Surgical Field", Orthopedic Clinics, vol. 45, Issue 2, pp. 167-173, Apr. 2014.

Shen et al., "3D Augmented Reality with Integral Imaging Display", Proceedings of SPIE—The International Society for Optical Engineering, vol. 9867, Article No. 98670Y, Apr. 2016.

Sherstyuk et al., "Dynamic Eye Convergence for Head-Mounted Displays Improves User Performance in Virtual Environments", Proceedings of the ACM SIGGRAPH Symposium on Interactive 3D Graphics and Games, pp. 23-30, Mar. 2012.

State et al., "Stereo Imagery from the UNC Augmented Reality System for Breast Biopsy Guidance", MMVR 2003.

Tan, D. J.; Tombari, F.; Ilic, S.; Navab, N. (2015): A Versatile Learning-Based 3D Temporal Tracker. Scalable, Robust, Online. In: 2015 IEEE International Conference on Computer Vision (ICCV), S. 693-701.

Tong et al., "Scanning 3D Full Human Bodies Using Kinects", IEEE Transactions on Visualization and Computer Graphics, vol. 18, Issue 4, pp. 643-650, Apr. 1, 2012.

Traub, J., Stefan, P., Heining, S.M., Sielhorst, T., Riquarts, C., Eulerz, E., Navab, N. (2006): Hybrid Navigation Interface for Orthopedic and Trauma. Surgery. R. Larsen, M. Nielsen, and J. Sporring (Eds.): MICCAI 2006, LNCS 4190, pp. 373-380.

Trevisan et al., "Towards Markerless Augmented Medical Visualization", AMI-ARCS, pp. 57-66, 2004.

Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.

Vercauteren et al., "Real Time Autonomous Video Image Registration for Endomicroscopy: Fighting the Compromises", Three-Dimensional and Multidimensional Microscopy: Image Acquisition and Processing XV., vol. 6861, pp. 68610C. International Society for Optics and Photonics, Feb. 12, 2008.

Vogt et al., "Reality Augmentation for Medical Procedures: System Architecture, Single Camera Marker Tracking, and System Evaluation", International Journal of Computer Vision, vol. 70, No. 2, pp. 179-190, 2006.

Vogt, Sebastian, "Real-Time Augmented Reality for Image-Guided Interventions", PhD Thesis, Nürnberg: Der Technischen Fakultät der Universität Erlangen, 2009.

Wang et al., "3D Modeling from Wide Baseline Range Scans Using Contour Coherence", Proceedings of the IEEE Conference on Computer Vision and Pattern Recognition, pp. 4018-4025, 2014.

Wang et al., "Augmented Reality 3D Displays with Micro Integral Imaging"; Journal of Display Technology, Oct. 2014.

Wang et al., "Augmented Reality Navigation with Automatic Marker-Free Image Registration Using 3-D Image Overlay for Dental Surgery", IEEE Transactions on Biomedical Engineering, vol. 61, No. 4, pp. 1295-1304, Apr. 2014.

Wang H. et al., "Precision insertion of percutaneous sacroiliac screws using a novel augmented reality-based navigation system: a pilot study"., Intl. Orthop. (SICOT) 2016, 40: 1941-1947.

Watsen, K., et al., "A Handheld Computer as an Interaction Device to a Virtual Environment.", Proceedings of the International Projection Technologies Workshop, Stuttgart, Germany, May 10-11, 1999.

Weiss et al., "Augmented Reality Visualization Using Image-Overlay for MR-Guided Interventions: System Description, Feasibility, and Initial Evaluation in a Spine Phantom", Musculoskeletal Imaging, AJR:196, Mar. 2011, DOI:10.2214/AJR.10.5038.

Wellner, P., "Interacting with Paper on the DigitalDesk.", Communications of the ACM. 36, 7, 87-96, (1993).

Wilson et al., "Validation of Three-Dimensional Models of the Distal Femur Created from Surgical Navigation Point Cloud Data"; CAOS 2015.

Yamazaki, K. et al., "Gesture Laser and Gesture Laser Car—Development of an Embodied Space to Support Remote Instruction.", In Bodker, S., Kyng, M. and Schmidt, K. (eds.), Proceedings of the Sixth European Conference on Computer Supported Cooperative Work—ECSC W'99, Sep. 12-16, Copenhagen, Denmark. Kluwer Academic Publishers, Dordrecht.

Yang H. et al., "Exploring collaborative navigation.", Proceedings of the 4th international conference on Collaborative virtual environments, CVE, pp. 135-142, (2002).

Ye et al., "Accurate 3D Pose Estimation from a Single Depth Image", IEEE International Conference on Computer Vision (ICCV), pp. 731-738, Nov. 2011.

(56) References Cited

OTHER PUBLICATIONS

Yoon et al., "Technical Feasibility and Safety of an Intraoperative Head-Up Display Device During Spine Instrumentation", The International Journal of Medical Robotics and Computer Assisted Surgery, vol. 13, No. 3, pp. 1-9, Sep. 2017.

* cited by examiner

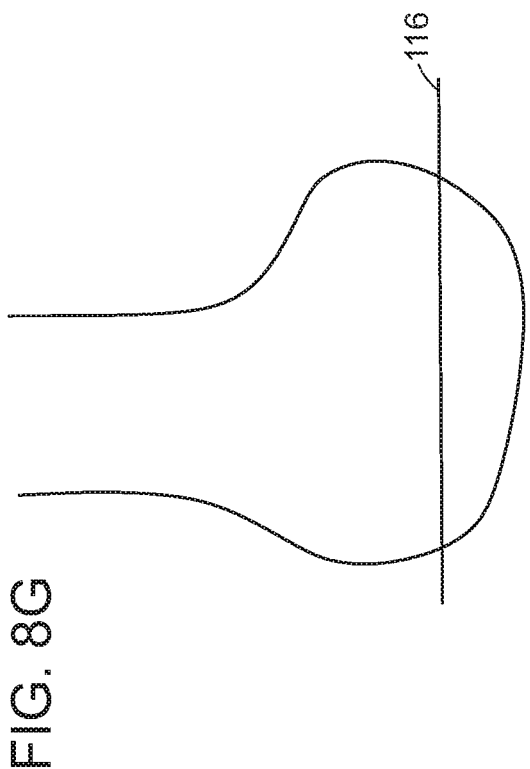
FIG. 8E
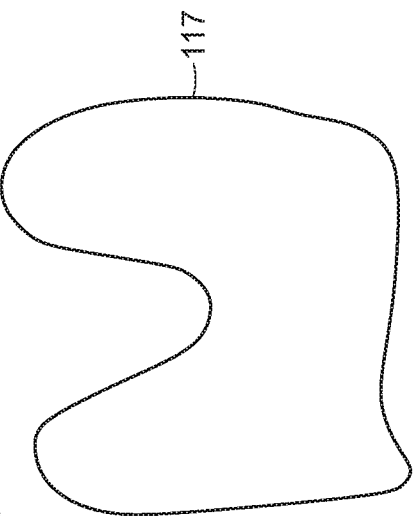
FIG. 8G
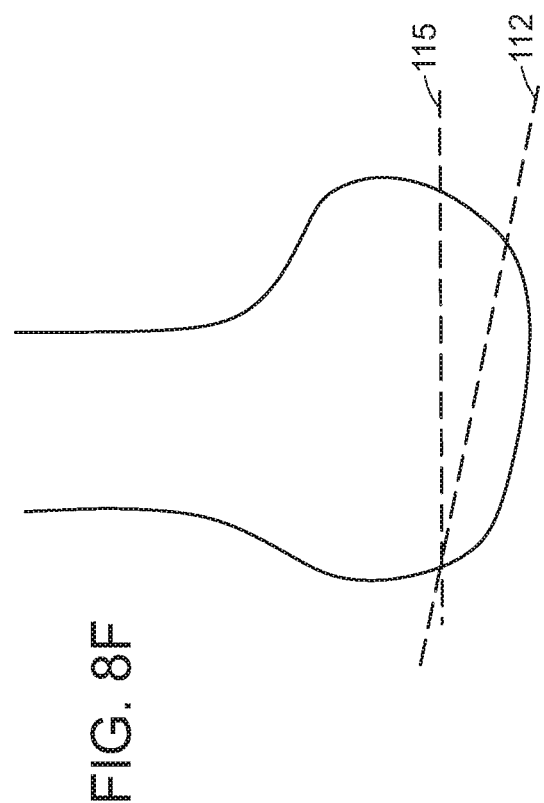
FIG. 8F
FIG. 8H

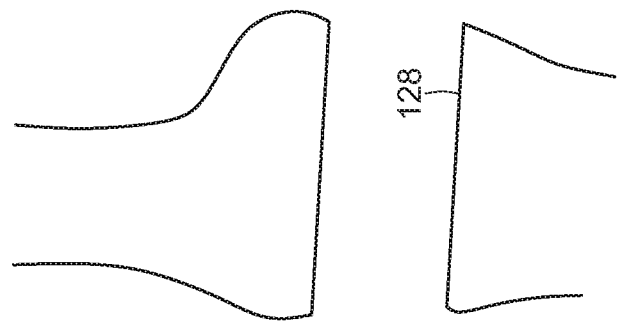
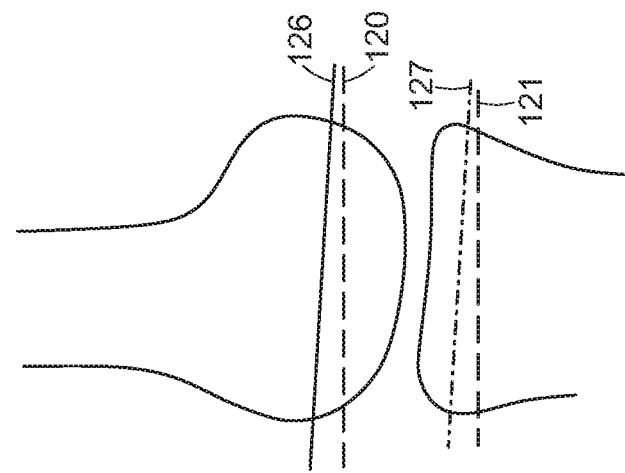

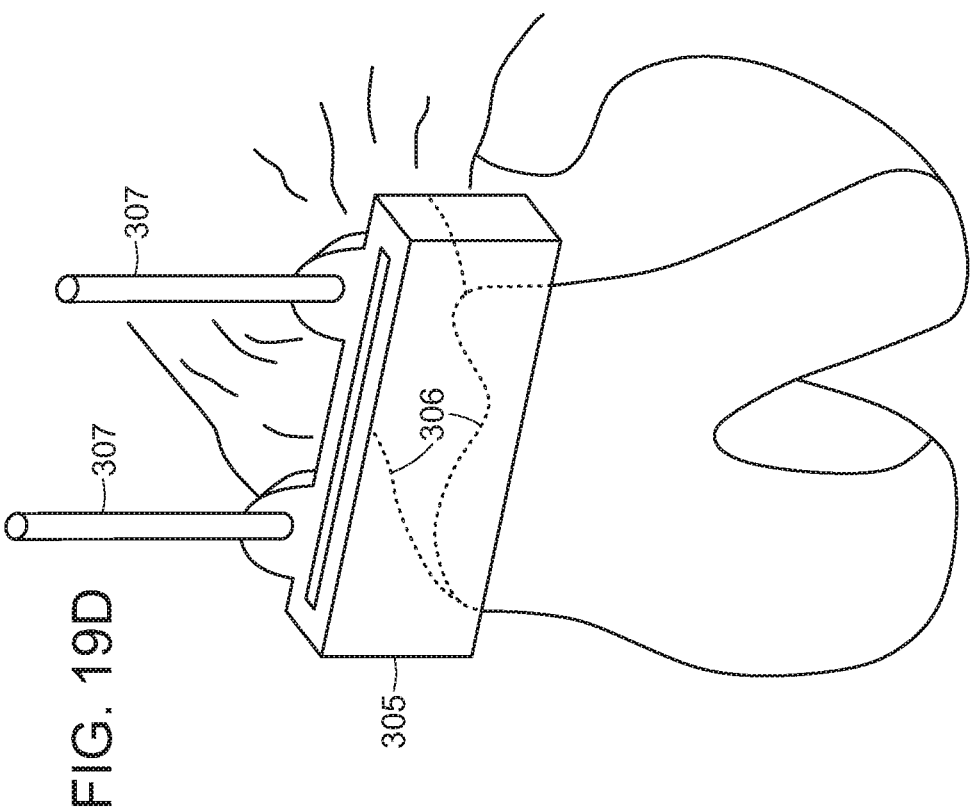
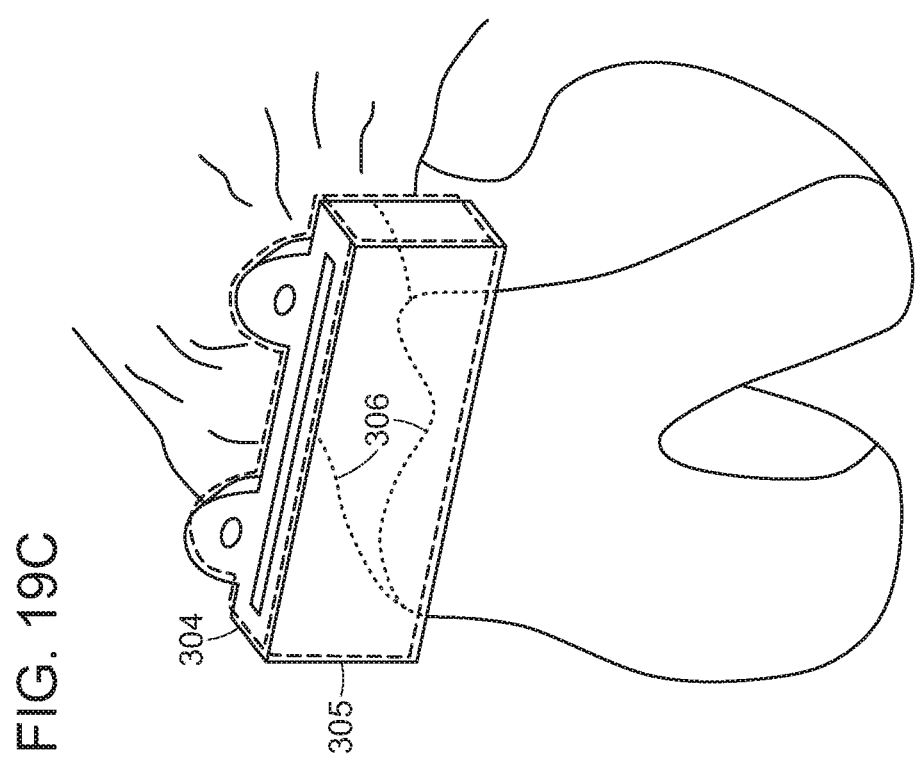

Display pelvic x-ray
- Optional supine
- Optional also upright pelvic x-ray
- Use templating software
- Size femoral component (stem incl. neck, optionally head), align femoral component
  o Shows intended neck cut
- Size acetabular component, align acetabular component in 2D (acetabular angle)
- Sizing & aligning = 2D virtual surgical plan
- Optionally measure distance from greater to lesser trochanter for left leg and right leg, for example as an estimate of pre-existing leg length discrepancy

702

Position patient on OR table, e.g. in neutral position
- For example, leg positioned identical to position on 2D x-rays
  o (e.g. for neck cut planning and execution)

704

Import femoral and acetabular sizing & alignment data (from x-rays and templating) into OHMD system & software

706

Incision, exposure, capsulotomy, expose femoral neck, proximal femur

708

Identify sulcus point
- Lowest point between greater trochanter and femoral neck
- Mark, e.g. with
  o RF marker, optical marker, navigation marker / pointer tip
  o Screw (and then optionally point RF marker, optical marker, navigation marker)
  o LED
  o India ink

710

Optionally identify additional points on proximal femur
- Highest point of greater trochanter
- Highest point of lesser trochanter, e.g. at transition to femoral neck

FIG. 39B

712

Using sulcus point (or other or additional points) and, optionally, using same/comparable position between 2D x-ray and OR table position
- Compute neck cut
o Optionally consider pre-existing left / right leg length discrepancy (e.g. as determined pre-operatively, e.g. from x-ray)
- Project neck cut with OHMD onto surgical site / proximal femur
o 2D line or 3D cut plane
- Optionally cut with some AP angulation, surgeon selected, e.g. 0 degrees or 8 degrees or any other number (e.g. depending on anterior or posterior approach and/or patient anatomy and/or surgeon preference)
- Optionally project 2 neck cuts if napkin ring cut for anterior approach hip replacement, both cuts will have slight angle (optionally creating wedge for easier extraction, wedge is posteriorly less high than anteriorly thereby facilitating extraction)
- Optionally project outline of neck cut tool, e.g. for single neck cut or for napkin ring dual cut

714

Perform neck cut, optionally dual (napkin ring) neck cut for anterior approach, extract femoral head, expose acetabulum (including, for example, resection of residual labrum, pulvinar, fat etc.; optionally removal of rim osteophytes)

FIG. 39C

716

Define center or acetabulum
- Various options available to find center of acetabulum
  - E.g. partial or full radius acetabular placement tool (e.g. head portion selected based on radiograph, templating) (e.g. with radius 1/2 or 2/3 or 1/1 of acetabular radius, e.g. on x-ray), central stem / extender indicating center of acetabulum, anteversion
    - Visually place in center of acetabulum after femoral neck cut and head removal (covering then 1/2 or 2/3 or 1/1 of acetabulum), optional cut outs, see through windows, optionally transparent
      - Since known from x-ray templating what size acetabular component, and since know radius of partial radius acetabular placement tool, can estimate rim of acetabular cup component
    - Optional image capture of central stem, extender location, position, orientation including acetabular anteversion (optional RF markers, optical markers, navigation markers, LED's attached)
  - Optional image capture of acetabulum using image capture system integrated into, or attached to or separate from OHMD
  - Optional laser scan or 3D scan of acetabulum, optionally on a tripod
  - Optional mechanical probe with attached RF markers, optical markers, navigation markers, LED's, detect optionally acetabular rim also, in addition to center
  - Optional patient specific marker, e.g. at edge of acetabulum or center of acetabulum
- Option to medialize, option to lateralize
  - By moving partial radius tool followed by image capture of central stem, extender location, position, orientation including acetabular anteversion
  - Via software and adjusted cup position then displayed by OHMD

718

Select acetabular component
- Compare to 2D x-ray
- Optional acetabular trial components

FIG. 39D

720

Define center of rotation
- Use the patient's center of acetabulum
    - Measured, for example, using partial radius acetabular placement tool
    - Rim estimated, for example, using partial radius acetabular placement tool
- Derived either based on selected acetabular component
- OR derived from femoral head radius / center of femoral head measured on AP and/or frogleg radiograph
- OR measure excised femoral head of the patient

722

Optional: Place resected femoral head and neck into caliber/physical measurement apparatus or use standard calipers
- Measure femoral head radius, e.g. at equator (e.g. parallel to neck cut)
- Measure height from neck cut
- Using known neck cut angle from virtual surgical plan, calculate
    - Femoral anteversion of the patient using resected femoral head and neck
    - Femoral offset of the patient using resected femoral head and neck
    - If napkin ring / dual femoral neck cut was performed, measure napkin ring / dual cut bone piece separately or add to resected bone construct and measure together
    - If composite height of resected bone is greater than height in virtual surgical plan, femoral neck has been over-resected (which can result in leg length discrepancy)
        - Optionally adjust via broaching, e.g. broach less
        - Optionally select different femoral component, e.g. stem with 130 degrees instead of 127 degrees or high/different offset vs. standard offset component (depending on implant system configuration)
        - Optionally select different head, e.g. +2, +4, +6 mm etc. (depending on availability in system)
    - If composite height of resected bone is less than height in virtual surgical plan, femoral neck has been under-resected (which can result in leg length discrepancy)
        - Optionally adjust broaching, e.g. broach more
        - Optionally select different femoral component, e.g. stem with 127 degrees instead of 130 degrees or standard vs. high/different offset component (depending on implant system configuration)
        - Optionally select different head, e.g. -2, -4, -6 mm etc. (depending on availability in system)
        - Optionally recut and remove more bone
    - Optionally include saw blade thickness in calculation of composite height of resected bone to account for bone lost from sawing
        - If napkin / dual neck cut performed, need to apply twice
    - Optionally consider pre-existing leg length discrepancy and need to correct

Check if center of rotation is maintained for selected combination of acetabular component and liner in virtual surgical plan
- Optionally select different liner
- Optionally include in virtual surgical plan

↓ 726

Check if center of rotation is maintained for selected medialization or lateralization of cup during reaming in virtual surgical plan
- Optionally select different liner, e.g. rimmed liner, lipped liner etc. (depending on availability of different configurations for given hip implant system)
- Optionally include in virtual surgical plan

↓ 728

Optionally determine desired reaming depth in virtual surgical plan
- E.g. based on pre-operative x-ray
- E.g. based on intra-operative acetabular site / condition (e.g. bone conditions, e.g. soft bone / hard bone upon optional mechanical probing)

↓ 730

Project acetabular component central axis / reaming axis with OHMD onto surgical site / acetabulum
- Accounting for predetermined / intended anteversion
  o Optional: As measured, e.g. using partial radius acetabular placement tool with central extender (e.g. measured with image capture) or as measured with other techniques, e.g. image capture, laser scan, 3D scan, mechanical probe
  o Optional: Use standard anteversion, e.g. as measured relative to OR table, or surgeon selects desired anteversion for the patient, e.g. based on pre-operative CT or MRI scan
- Accounting for any desired medialization or lateralization
  o E.g. set using partial radius acetabular placement tool with central extender or
  o Set using software, virtual surgical plan

Obtain standing lower extremity x-rays
- Full leg lower extremity standing or
- Hip, knee, ankle x-rays standing
- Derive mechanical axis
- Determine desired varus, valgus correction
- (If no weight-bearing views available, can be substituted with non-image guided navigation, find center of hip via lower extremity movement, identify medial & lateral malleolus with navigation marker)

762

Obtain AP & lateral knee x-rays
- Optional patellofemoral views, e.g. Merchant view
- Determine ML dimensions of knee
    - Overall ML width
    - Optional medial, lateral condyle width
- Determine AP dimensions of knee
    - Overall AP length
    - Optional medial condyle length
    - Optional lateral condyle length
- Optional: Patellofemoral
    - Determine trochlear angle
    - PF joint width
    - Patellar dimensions
- Optional: Determine trochlear flange height
- Optional: Determine femoral offsets
- Optional: Determine tibial slope
- Optional: Determine femoral curvatures
- Optional: Determine tibial curvatures
- Optional: Determine epicondylar axis, posterior condylar axis, Q-angle, other axes
- Optional: Determine multiple landmarks, e.g. notch (medial wall, lateral wall, highest point, highest point medial, lateral condyle etc.)

FIG. 40B

764 Optional: 2D to 3D bone morphing
- Using landmarks
- Using AP, ML, SI dimensions
- Using axes
- Using curvatures
- Using offets
- Optionally use intra-operative scan, e.g. using laser scanner, optical scanner, image capture, mechanical probe with one or more RF markers, optical markers, navigation markers, LED's, IMU's attached, e.g. as an alternative to deriving shape

766 Femoral, tibial, patellar implant sizing, selection
- Based on 2D information
  - AP, lateral knee radiographs
  - For example, using standard 2D templating software
- Or using 3D model (e.g. from bone morphing or laser scan or optical scan or image capture or mechanical scan of knee post incision)
- Or both 2D radiographs and 3D model

768 Virtual surgical plan
- Using 2D sizing or
- Using 3D sizing
- Accounting for desired mechanical axis correction
- Accounting for desired flexion / extension deficit, correction
- Accounting for desired slope
- Accounting for planned bone resections for a given implant design, e.g.
  - Femoral
  - Tibial
  - Patellar
- Accounting for femoral component rotation
- Accounting for tibial component rotation
- Accounting for other features, e.g. offsets

770 Position patient on OR table in neutral position
- For example, leg positioned similar to position on 2D x-rays

FIG. 40D

778

Project femoral and/or tibial and/or patellar virtual surgical guide(s) with OHMD
- Virtual 3D representation of physical guide, cut guide, tool, instrument, or virtual placement indicator thereof or combination thereof, or
- 2D or 3D axis, e.g. for guiding drill, burr, reamer, broach, impactor, mill, etc., or
- 2D or 3D line projected onto bone, or
- 3D cut plane, e.g. projected onto surface of the bone, optionally extending into bone, through bone
- Femur first or tibia first technique
- For example, insert actual saw blade or dummy saw blade into physical saw guides of different femoral, tibial or patellar cut blocks
  - Align saw blade or dummy saw blade with projected/intended virtual cut/cut plane by OHMD
  - Pin cut block
  - Perform actual cut with actual saw
- Femur:
  - Project distal cut with desired mechanical axis correction, flexion contracture correction
  - Project AP cut, with desired femoral component rotation
  - Project posterior cut, with desired femoral component rotation
  - Project chamfer cuts, with desired femoral component rotation
- Tibia:
  - Project proximal tibial cut with desired mechanical axis correction, slope
  - Project intended area for tibial keel / keel punch
    - E.g. project outline of keel or keel punch, project center point onto tibial plateau
    - E.g. project cross indicating center point and intended location of tibial keel flanges
    - With desired tibial component rotation
  - Optional: OHMD projects long axis of tibial punch
  - Optional: OHMD projects flanges of tibial punch, with desired tibial component rotation
- Patella:
  - Project intended patellar cut

780

Optional: Ligament balancing
- Soft-tissue
- Recuts
  - Project intended recut, e.g. +2mm, +4mm, e.g. in amended or revised surgical plan

AUGMENTED REALITY GUIDANCE FOR ORTHOPEDIC AND OTHER SURGICAL PROCEDURES

RELATED APPLICATIONS

This application is a U.S. national phase application under 35 U.S.C. 371 of PCT International Application No. PCT/US2019/015522, filed Jan. 29, 2019, which claims the benefit of and priority to U.S. Provisional Application Ser. No. 62/623,014, filed Jan. 29, 2018, U.S. Provisional Application Ser. No. 62/700,096, filed Jul. 18, 2018, U.S. Provisional Application Ser. No. 62/714,790, filed Aug. 6, 2018, U.S. Provisional Application Ser. No. 62/731,175, filed Sep. 14, 2018, the entire contents of each of which are hereby incorporated by reference in their entireties.

TECHNICAL FIELD

Aspects of the present disclosure generally relate to systems, devices and methods for performing a surgical step or surgical procedure with visual guidance using an optical head mounted display.

BACKGROUND

With computer assisted surgery, e.g. surgical navigation or robotics, pre-operative imaging studies of the patient can be used. The imaging studies can be displayed in the OR on an external computer monitor and the patient's anatomy, e.g. landmarks, can be registered in relationship to the information displayed on the monitor. Since the surgical field is in a different location and has a different view coordinate system for the surgeon's eyes than the external computer monitor, hand-eye coordination can be challenging for the surgeon.

SUMMARY

Various embodiments of the present disclosure relate to systems and methods for performing a surgical step or surgical procedure with visual guidance using an optical head mounted display. The optical head mounted display can be, for example, of see through, e.g. augmented reality, and non see through, e.g. virtual reality, type. The optical head mounted display can provide surgical guidance in a mixed reality environment.

In some embodiments, a method of preparing a physical joint in a patient is provided. In some embodiments, the method comprises (a) generating, by at least one computer, a first virtual implant component, a second implant component and combinations thereof, the first virtual implant component being a three-dimensional digital representation corresponding to at least one portion of a first physical implant component, a placement indicator of a first physical implant component, or a combination thereof, and the second virtual implant component being a three-dimensional digital representation corresponding to at least one portion of a second physical implant component, a placement indicator of a second physical implant component, or a combination thereof; (b) displaying at least a portion of the first virtual implant component, a portion of the second virtual implant component or a combination thereof, using a see through optical head mounted display, so as to superimpose at least a portion of the first virtual implant component onto a first articular surface of the physical joint of the patient visible directly through the see through optical head mounted display, and so as to superimpose at least a portion of the second virtual implant component onto a second articular surface of the physical joint of the patient visible directly through the see through optical head mounted display, wherein the display of the at least a portion of the first virtual implant component is maintained in relationship to the first articular surface when the physical joint of the patient moves, and wherein the display of the at least a portion of the second virtual implant component is maintained in relationship to the second articular surface when the physical joint of the patient moves; and (c) displaying using the see through optical head mounted display at least a normal motion, an abnormal motion, a pathologic motion, or an instability of the first virtual implant component, of the second virtual implant component or a combination thereof or a motion conflict between the first virtual implant component and the second virtual implant component when the physical joint of the patient moves.

In some embodiments, a system for preparing a physical joint in a patient is provided. In some embodiments, the system comprises (a) at least one computer configured to generate a first virtual implant component, a second virtual implant component or a combination thereof, and (b) a see through optical head mounted display configured to display the first virtual implant component, the second virtual implant component or a combination thereof, the first virtual implant component being a three-dimensional digital representation corresponding to at least one portion of a first physical implant component, a placement indicator of a first physical implant component, or a combination thereof and the second virtual implant component being a three-dimensional digital representation corresponding to at least one portion of a second physical implant component, a placement indicator of a second physical implant component, or a combination thereof. In some embodiments, the at least one computer is configured to allow superimposition and alignment of at least a portion of the first virtual implant component onto at least a portion of a first articular surface of the physical joint of the patient visible directly through the see through optical head mounted display; to allow superimposition and alignment of at least a portion of the second virtual implant component onto at least a portion of a second articular surface of the physical joint of the patient visible directly through the see through optical head mounted display; to maintain the display of the at least a portion of the first virtual implant component onto the at least a portion of the first articular surface when the physical joint of the patient moves and to maintain the display of the at least a portion of the second virtual implant component onto the at least a portion of the second articular surface when the physical joint of the patient moves; and to display at least a normal motion, an abnormal motion, a pathologic motion, or an instability of the first virtual implant component, the second virtual implant component or a combination thereof or a motion conflict between the first virtual implant component and the second virtual implant component when the physical joint of the patient moves.

In some embodiments, the at least one computer is configured to modify the position and/or orientation of the display of the first virtual implant component relative to the first articular surface, the position and/or orientation of the display of the second virtual implant component relative to the second articular surface, or a combination thereof to correct the abnormal motion, pathologic motion, or instability or the motion conflict.

In some embodiments, the at least one computer is configured to change the alignment of the display of the first virtual implant component relative to the first articular surface, alignment of the display of the second virtual implant component relative to the second articular surface, or a combination thereof to correct the abnormal motion, pathologic motion, or instability or the motion conflict.

In some embodiments, the system is for preparing a joint for a prosthesis. The prosthesis can be for a knee replacement, hip replacement, shoulder joint replacement, or ankle joint replacement.

In some embodiments, the see through optical head mounted display is registered in the coordinate system. In some embodiments, the first virtual implant component, the second virtual implant component or a combination thereof is registered in the coordinate system.

In some embodiments, the first articular surface, the second articular surface, or a combination thereof is registered in the coordinate system.

In some embodiments, the at least one computer is configured to display, by the optical head mounted display, the first virtual implant component onto the first articular surface, the second virtual implant component onto the second articular surface, or a combination thereof, at a predetermined position, predetermined orientation, predetermined rotation, predetermined alignment, predetermined resection level or combination thereof. In some embodiments, the at least one computer is configured to facilitate modification of the predetermined position, predetermined orientation, predetermined rotation, predetermined alignment, predetermined resection level or combination thereof of the first virtual implant component, the second virtual implant component or a combination thereof to account for ligamentous laxity or instability. In some embodiments, the predetermined position, predetermined orientation, predetermined rotation, predetermined alignment, predetermined resection level or combination thereof of the first virtual implant component, the second virtual implant component, or a combination thereof, comprises a predetermined varus correction, a predetermined valgus correction, a predetermined femoral component flexion, a predetermined femoral component extension, a predetermined femoral component rotation, a predetermined femoral component position relative to an anterior cortex, a predetermined tibial component slope, a predetermined tibial component rotation, a predetermined tibial component position relative to a tibial cortical rim in a knee replacement. In some embodiments, the predetermined position, predetermined orientation, predetermined rotation, predetermined alignment, predetermined resection level or combination thereof of the first virtual implant component, the second virtual implant component, or a combination thereof, comprises a predetermined femoral neck resection for a femoral component, a predetermined leg length, a predetermined femoral component anteversion, a predetermined acetabular component anteversion, a predetermined acetabular component inclination, a predetermined acetabular component offset in a hip replacement.

In some embodiments, the first virtual implant component, the second virtual implant component, or a combination thereof comprises at least one of a predetermined rotation axis, a predetermined flexion axis, a predetermined extension axis.

In some embodiments, the at least one computer is configured to select the first virtual implant component, the second virtual implant component, or a combination thereof, from a library of virtual implants. In some embodiments, the library of virtual implant components is composed of virtual implant components of different sizes and/or shapes, each virtual implant component of the library being a three-dimensional digital representation corresponding to at least one portion of a corresponding physical implant component, a placement indicator of a corresponding physical implant component, a physical trial implant component, a placement indicator of a corresponding physical trial implant component, or a combination thereof. The different sizes and/or shapes of the virtual implant components can be color coded.

In some embodiments, the at least one computer system is configured to adjust the transparency of the first virtual implant component, second virtual implant component, or combination thereof, and wherein at least one portion of the physical joint is visible through the first virtual implant component, second virtual implant component, or combination thereof. In some embodiments, the at least one computer is configured to display the first and the second virtual implant components with a different color. In some embodiments, the at least one computer is configured to display the first and the second virtual implant components with a different degree of transparency.

In some embodiments, the at least one computer is configured to display the first virtual implant component, second virtual implant component, or combination thereof, in a predetermined position, a predetermined orientation, a predetermined alignment or a combination thereof relative to at least one of an anatomic axis, a biomechanical axis, or a deformity.

In some embodiments, the at least one computer is configured to display the first virtual implant component, second virtual implant component, or combination thereof, with at least one of a predetermined resection level, a predetermined varus angle, a predetermined valgus angle, a predetermined rotation, a predetermined flexion, a predetermined slope, a predetermined alignment or a combination thereof. In some embodiments, the at least one computer is configured to facilitate changing the position or orientation of the display of the first virtual implant component, second virtual implant component, or combination thereof, relative to the predetermined resection level, predetermined varus angle, predetermined valgus angle, predetermined rotation, predetermined flexion, predetermined slope, predetermined alignment or combination thereof.

In some embodiments, the system further comprises a user interface and wherein the at least one computer is configured to facilitate moving the first virtual implant component in relationship to the first articular surface, the second virtual implant component in relationship to the second articular surface or a combination thereof by the user interface. The user interface can comprise at least one of a graphical user interface, a voice recognition, a gesture recognition, a virtual interface displayed by the optical head mounted display, a virtual keyboard displayed by the optical head mounted display, a physical keyboard, a physical computer mouse, or a physical track pad.

In some embodiments, the first virtual implant component, second virtual implant component, or combination thereof is a virtual trial implant. In some embodiments, the first virtual trial implant component, second virtual trial implant component, or combination thereof, comprises at least one of a virtual trial femoral component, a virtual trial tibial component, a virtual trial tibial insert, a virtual trial patellar component.

In some embodiments, the at least one computer is configured to display, by the optical head mounted display, the position, orientation, alignment, flexion gap, extension gap, or combinations thereof, of the first virtual component, the second virtual component, or a combination thereof, in flexion, extension or through a range of motion.

In some embodiments, the at least one computer system is configured to superimpose, by the optical head mounted display, the first virtual implant component onto the corresponding first physical implant component after implantation and/or the second virtual implant component onto the corresponding second physical implant component after implantation, wherein the display of the first virtual implant component is configured to compare the position and/or orientation of the corresponding first physical implant component with the position and/or orientation of the display of the first virtual implant component and wherein the display of the second virtual implant component is configured to compare the position and/or orientation of the corresponding second physical implant component with the position and/or orientation of the display of the second virtual implant component.

In some embodiments, the at least one computer is configured to adjust the position, location, orientation, alignment and/or coordinates of the display of the first virtual implant component, the second virtual implant component, or combination thereof, by the optical head mounted display, to correct the one or more of the abnormal motion, pathologic motion, instability of the first and/or second virtual implant component or motion conflict between the first virtual implant component and the second virtual implant component.

In some embodiments, the at least one computer is configured to display during stress testing of the joint the one or more of the normal motion, abnormal motion, pathologic motion, instability of the first and/or second virtual implant component or motion conflict between the first virtual implant component and the second virtual implant component. The stress testing can comprise a varus stress, a valgus stress, a Lachman test, an instability test, an abduction stress, an adduction stress, a hyperflexion stress test, a hyperextension stress test or combinations thereof.

In some embodiments, the at least one computer uses a kinematic simulation. The kinematic simulation can comprise kinematic data obtained from the physical joint.

In some embodiments, the at least one computer is configured to obtain one or more intra-operative measurements from the physical joint of the patient to determine one or more coordinates of the physical joint.

In some embodiments, a system for preparing a physical joint in a patient comprising (a) at least one computer configured to generate a first virtual implant component, a second virtual implant component or a combination thereof; and (b) a see through optical head mounted display configured to display the first virtual implant component, the second virtual implant component or a combination thereof, wherein the first virtual implant component is a three-dimensional digital representation corresponding to at least one portion of a first physical implant component, a placement indicator of a first physical implant component, or a combination thereof, wherein the second virtual implant component is a three-dimensional digital representation corresponding to at least one portion of a second physical implant component, a placement indicator of a second physical implant component, or a combination thereof. In some embodiments, the at least one computer is configured to allow superimposition and alignment of the at least a portion of the first virtual implant component with a first anatomic structure of the physical joint of the patient visible directly through the see through optical head mounted display; the at least one computer is configured to allow superimposition and alignment of the at least a portion of the second virtual implant component with a second anatomic structure of the physical joint of the patient visible directly through the see through optical head mounted display; the at least one computer is configured to maintain the display of the at least a portion of the first virtual implant component in relationship to the first anatomic structure when the physical joint of the patient moves; the at least one computer is configured to maintain the display of the at least a portion of the second virtual implant component in relationship to the second anatomic structure when the physical joint of the patient moves, and the at least one computer is configured to display at least a normal motion, an abnormal motion, a pathologic motion, or an instability of the first virtual implant component, the second virtual implant component or a combination thereof or a motion conflict between the first virtual implant component and the second virtual implant component when the physical joint of the patient moves.

In some embodiments, the first anatomic structure and/or the second anatomic structure comprises at least one of an anatomic landmark, an anatomic plane, an articular surface, a cartilage surface, a subchondral bone surface, a cortical bone surface, a cut bone surface, a reamed bone surface, a milled bone surface, an impacted bone surface, a tissue resection, a surface, one or more surface points, an anterior-posterior dimension of at least a portion of the physical joint, a medio-lateral dimension of at least a portion of the physical joint, a superior-inferior dimension of at least a portion of the physical joint, a joint space in extension, a joint space in flexion, a flexion gap, an extension gap, an anatomic axis, a biomechanical axis, a mechanical axis or a combination thereof.

In some embodiments, the first anatomic structure and the second anatomic structure are the same or different.

In some embodiments, the at least one computer is configured to modify the position and/or orientation of the display of the first virtual implant component relative to the first anatomic structure of the physical joint, the second virtual implant component relative to the second anatomic structure of the physical joint, or a combination thereof to correct the abnormal motion, pathologic motion, or instability or the motion conflict.

In some embodiments, the at least one computer is configured to change the alignment of the display of the first virtual implant component relative to the first anatomic structure of the physical joint, the second virtual implant component relative to the second anatomic structure of the physical joint, or a combination thereof to correct the abnormal motion, pathologic motion, or instability or the motion conflict.

In some embodiments, the system is for preparing a joint for a prosthesis. The prosthesis can be for a knee replacement, hip replacement, shoulder joint replacement, or ankle joint replacement.

In some embodiments, the see through optical head mounted display is registered in the coordinate system. In some embodiments, the first anatomic structure, the second anatomic structure or a combination thereof is registered in a coordinate system. In some embodiments, the first virtual implant component, the second virtual implant component or a combination thereof is registered in the coordinate system.

In some embodiments, the at least one computer is configured to display, by the optical head mounted display, the first virtual implant component in relationship to the first anatomic structure, the second virtual implant component in relationship to the second anatomic structure, or a combination thereof at a predetermined position, predetermined orientation, predetermined rotation, predetermined alignment, predetermined resection level or combination thereof.

In some embodiments, the first virtual implant component, the second virtual implant component, or a combination thereof comprises at least one of a predetermined rotation axis, a predetermined flexion axis, a predetermined extension axis.

In some embodiments, the at least one computer is configured to modify the predetermined position, predetermined orientation, predetermined rotation, predetermined alignment, predetermined resection level or combination thereof of the first virtual implant component, the second virtual implant component or a combination thereof to account for ligamentous laxity or instability. In some embodiments, the predetermined position, predetermined orientation, predetermined rotation, predetermined alignment, predetermined resection level or combination thereof of the first virtual implant component, the second virtual implant component, or a combination thereof includes a predetermined varus correction, a predetermined valgus correction, a predetermined femoral component flexion, a predetermined femoral component extension, a predetermined femoral component rotation, a predetermined femoral component position relative to an anterior cortex, a predetermined tibial component slope, a predetermined tibial component rotation, a predetermined tibial component position relative to a tibial cortical rim in a knee replacement. In some embodiments, the predetermined position, predetermined orientation, predetermined rotation, predetermined alignment, predetermined resection level or combination thereof of the first virtual implant component, the second virtual implant component, or a combination thereof comprises a predetermined femoral neck resection for a femoral component, a predetermined leg length, a predetermined femoral component anteversion, a predetermined acetabular component anteversion, a predetermined acetabular component inclination, a predetermined acetabular component offset in a hip replacement.

In some embodiments, the at least one computer is configured to select the first virtual implant component, the second virtual implant component, or a combination thereof from a library of virtual implants. The library of virtual implant components can be composed of virtual implant components of different sizes and/or shapes, wherein each virtual implant component of the library is a three-dimensional digital representation corresponding to at least one portion of a corresponding physical implant component, a placement indicator of a corresponding physical implant component, a physical trial implant component, a placement indicator of a corresponding physical trial implant component, or a combination thereof. In some embodiments, the different sizes and/or shapes of the virtual implant components are color coded.

In some embodiments, the at least one computer system is configured to adjust the transparency of the first and/or second virtual implant component and at least one portion of the physical joint is visible through the first and/or second virtual implant component. In some embodiments, the at least one computer is configured to display the first and the second virtual implant components with a different color. In some embodiments, the at least one computer is configured to display the first and the second virtual implant components with a different degree of transparency.

In some embodiments, the at least one computer is configured to display the first and the second virtual implant components in a predetermined position, a predetermined orientation, a predetermined alignment or a combination thereof relative to at least one of an anatomic axis, a biomechanical axis, or a deformity.

In some embodiments, the at least one computer is configured to display the first and the second virtual implant components with at least one of a predetermined resection level, a predetermined varus angle, a predetermined valgus angle, a predetermined rotation, a predetermined flexion, a predetermined slope, a predetermined alignment or a combination thereof.

In some embodiments, the at least one computer is configured to change the position or orientation of the display of the first and/or the second virtual implant components relative to the predetermined resection level, predetermined varus angle, predetermined valgus angle, predetermined rotation, predetermined flexion, predetermined slope, predetermined alignment or combination thereof.

In some embodiments, the system further comprises a user interface and the at least one computer is configured to move the first virtual implant component in relationship to the first anatomic structure, the second virtual implant component in relationship to the second anatomic structure or a combination thereof by the user interface. The user interface can comprise at least one of a graphical user interface, a voice recognition, a gesture recognition, a virtual interface displayed by the optical head mounted display, a virtual keyboard displayed by the optical head mounted display, a physical keyboard, a physical computer mouse, or a physical track pad.

In some embodiments, the first and/or the second virtual implant component is a virtual trial implant. In some embodiments, the first virtual trial implant component, the second virtual trial implant component or combinations thereof comprises at least one of a virtual trial femoral component, a virtual trial tibial component, a virtual trial tibial insert, a virtual trial patellar component.

In some embodiments, the at least one computer is configured to display, by the optical head mounted display, the position, orientation, alignment, flexion gap, extension gap, or combinations thereof of the virtual trial femoral component, virtual trial tibial component, virtual trial tibial insert, virtual trial patellar component or a combination thereof in flexion, extension or through a range of motion.

In some embodiments, the at least one computer is configured to display, by the optical head mounted display, the position, orientation, alignment, flexion gap, extension gap, or combinations thereof of the first virtual component, the second virtual component, or a combination thereof in flexion, extension or through a range of motion.

In some embodiments, the at least one computer system is configured to superimpose, by the optical head mounted display, the first virtual implant component onto the corresponding first physical implant component after implantation and/or the second virtual implant component onto the corresponding second physical implant component after implantation, wherein the display of the first virtual implant component is configured to compare the position and/or orientation of the corresponding first physical implant component with the position and/or orientation of the display of the first virtual implant component and wherein the display of the second virtual implant component is configured to compare the position and/or orientation of the corresponding second physical implant component with the position and/or orientation of the display of the second virtual implant component.

In some embodiments, the at least one computer is configured to adjust the position, location, orientation, alignment and/or coordinates of the display of the first virtual implant component, the second virtual implant component, or combination thereof, by the optical head mounted display, to correct the one or more of the abnormal motion, pathologic motion, instability of the first and/or second virtual implant component or motion conflict between the first virtual implant component and the second virtual implant component.

In some embodiments, the at least one computer is configured to display during stress testing of the joint the one or more of the normal motion, abnormal motion, pathologic motion, instability of the first and/or second virtual implant component or motion conflict between the first virtual implant component and the second virtual implant component. The stress testing can comprise a varus stress, a valgus stress, a Lachman test, an instability test, an abduction stress, an adduction stress, a hyperflexion stress test, a hyperextension stress test or combinations thereof.

In some embodiments, the at least one computer uses a kinematic simulation. The kinematic simulation comprises kinematic data obtained from the physical joint of the patient.

In some embodiments, the at least one computer is configured to obtain one or more intra-operative measurements from the physical joint of the patient to determine one or more coordinates of the physical joint.

BRIEF DESCRIPTION OF THE DRAWINGS

Illustrative, non-limiting example embodiments will be more clearly understood from the following detailed description taken in conjunction with the accompanying drawings.

FIGS. 8A-H depict illustrative examples of a distal femoral cut and techniques to correct a distal femoral cut according to some embodiments of the present disclosure.

FIGS. 9A-G depict illustrative examples of a distal femoral cut and techniques to correct a distal femoral cut according to some embodiments of the present disclosure.

FIGS. 19A-D provide an illustrative, non-limiting example of the use of virtual surgical guides such as a distal femoral cut block displayed by an OHMD and physical surgical guides such as physical distal femoral cut blocks for knee replacement according to some embodiments of the present disclosure.

FIGS. 39A-G is an illustrative, non-limiting example of a process flow for OHMD guided surgery for hip replacement.

FIGS. 40A-D is an illustrative, non-limiting example of a process flow for OHMD guided surgery for knee replacement, for example with femur first or tibia first technique, measured resection or ligament balancing.

DETAILED DESCRIPTION

Figure 1:
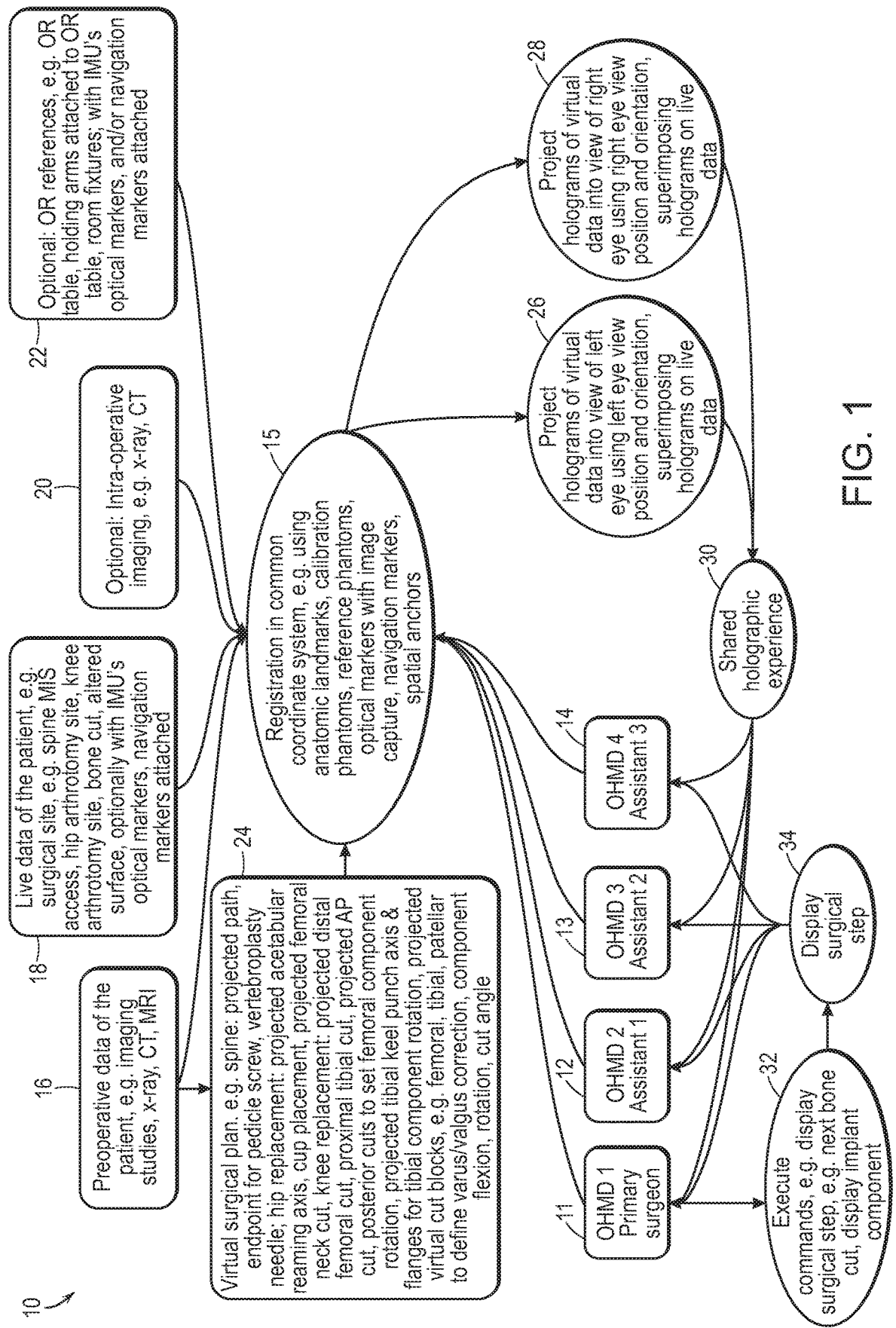
FIG. 1 shows the use of multiple OHMDs for multiple viewer's, e.g. a primary surgeon, second surgeon, surgical assistant(s) and/or nurses(s) according to some embodiments of the present disclosure.

Aspects of the present disclosure provide among other things, for a simultaneous visualization of live data of the patient and digital representations of virtual data such as virtual cuts and/or virtual surgical guides including cut blocks or drilling guides through an optical head mounted display (OHMD). In some embodiments, the surgical site including live data of the patient, the OHMD, and the virtual data are registered in a common coordinate system. In some embodiments, the virtual data are superimposed onto and aligned with the live data of the patient. Unlike virtual reality head systems that blend out live data, the OHMD allows the surgeon to see the live data of the patient, e.g. the surgical field, while at the same time observing virtual data of the patient and/or virtual surgical instruments or implants with a predetermined position and/or orientation using the display of the OHMD unit.

Aspects of the present disclosure describe novel devices for performing a surgical step or surgical procedure with visual guidance using an optical head mounted display, e.g. by displaying virtual representations of one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

Aspects of the present disclosure relate to a device comprising at least one optical head mounted display, the device being configured to generate a virtual surgical guide. In some embodiments, the virtual surgical guide is a three-dimensional representation in digital format which corresponds to at least one of a portion of a physical surgical guide, a placement indicator of a physical surgical guide, or a combination thereof. In some embodiments, the at least one optical head mounted display is configured to display the virtual surgical guide superimposed onto a physical joint based at least in part on coordinates of a predetermined position of the virtual surgical guide, and the virtual surgical guide is configured to align the physical surgical guide or a physical saw blade with the virtual surgical guide to guide a bone cut of the joint. In some embodiments, the device comprises one, two, three or more optical head mounted displays.

In some embodiments, the virtual surgical guide is configured to guide a bone cut in a knee replacement, hip replacement, shoulder joint replacement or ankle joint replacement.

In some embodiments, the virtual surgical guide includes a virtual slot for a virtual or a physical saw blade. In some embodiments, the virtual surgical guide includes a planar area for aligning a virtual or a physical saw blade. In some embodiments, the virtual surgical guide includes two or more virtual guide holes or paths for aligning two or more physical drills or pins.

In some embodiments, the predetermined position of the virtual surgical guide includes anatomical information, and/or alignment information of the joint. For example, the anatomic and/or alignment information of the joint can be based on at least one of coordinates of the joint, an anatomical axis of the joint, a biomechanical axis of the joint, a mechanical axis, or combinations thereof.

In some embodiments, the at least one optical head mounted display is configured to align the virtual surgical guide based on a predetermined limb alignment. For example, the predetermined limb alignment can be a normal mechanical axis alignment of a leg.

In some embodiments, the at least one optical head mounted display is configured to align the virtual surgical guide based on a predetermined femoral or tibial component rotation. In some embodiments, the at least one optical head mounted display is configured to align the virtual surgical guide based on a predetermined flexion of a femoral component or a predetermined slope of a tibial component.

In some embodiments, the virtual surgical guide is configured to guide a proximal femoral bone cut based on a predetermined leg length.

In some embodiments, the virtual surgical guide is configured to guide a bone cut of a distal tibia or a talus in an ankle joint replacement and the at least one optical head mounted display is configured to align the virtual surgical guide based on a predetermined ankle alignment, wherein the predetermined ankle alignment includes a coronal plane implant component alignment, a sagittal plane implant component alignment, an axial plane component alignment, an implant component rotation or combinations thereof.

In some embodiments, the virtual surgical guide is configured to guide a bone cut of a proximal humerus in a shoulder joint replacement and the at least one optical head mounted display is configured to align the virtual surgical guide based on a predetermined humeral implant component alignment, wherein the humeral implant component alignment includes a coronal plane implant component alignment, a sagittal plane implant component alignment, an axial plane component alignment, an implant component, or combinations thereof.

In some embodiments, the predetermined position of the surgical guide is based on a pre-operative or intra-operative imaging study, one or more intra-operative measurements, intra-operative data or combinations thereof.

Aspects of the invention relate to a device comprising two or more optical head mounted displays for two or more users, wherein the device is configured to generate a virtual surgical guide, wherein the virtual surgical guide is a three-dimensional representation in digital format which corresponds to at least one of a portion of a physical surgical guide, a placement indicator of a physical surgical guide, or a combination thereof, wherein the optical head mounted display is configured to display the virtual surgical guide superimposed onto a physical joint based at least in part on coordinates of a predetermined position of the virtual surgical guide, and wherein the virtual surgical guide is configured for aligning the physical surgical guide or a saw blade to guide a bone cut of the joint.

Aspects of the invention relate to a device comprising at least one optical head mounted display and a virtual bone cut plane, wherein the virtual bone cut plane is configured to guide a bone cut of a joint, wherein the virtual bone cut plane corresponds to at least one portion of a bone cut plane, and wherein the optical head mounted display is configured to display the virtual bone cut plane superimposed onto a physical joint based at least in part on coordinates of a predetermined position of the virtual bone cut plane. In some embodiments, the virtual bone cut plane is configured to guide a bone cut in a predetermined varus or valgus orientation or in a predetermined tibial slope or in a predetermined femoral flexion of an implant component or in a predetermined leg length.

Aspects of the invention relate to a method of preparing a joint for a prosthesis in a patient.

In some embodiments, the method comprises registering one or more optical head mounted displays worn by a surgeon or surgical assistant in a coordinate system, obtaining one or more intra-operative measurements from the patient's physical joint to determine one or more intra-operative coordinates, registering the one or more intra-operative coordinates from the patient's physical joint in the coordinate system, generating a virtual surgical guide, determining a predetermined position and/or orientation of the virtual surgical guide based on the one or more intra-operative measurements, displaying and superimposing the virtual surgical guide, using the one or more optical head mounted displays, onto the physical joint based at least in part on coordinates of the predetermined position of the virtual surgical guide, and aligning the physical surgical guide or a physical saw blade with the virtual surgical guide to guide a bone cut of the joint.

In some embodiments, the one or more OHMDs are registered in a common coordinate system. In some embodiments, the common coordinate system is a shared coordinate system.

In some embodiments, the virtual surgical guide is used to guide a bone cut in a knee replacement, hip replacement, shoulder joint replacement or ankle joint replacement.

In some embodiments, the predetermined position of the virtual surgical guide determines a tibial slope for implantation of one or more tibial implant components in a knee replacement.

In some embodiments, the predetermined position of the virtual surgical guide determines an angle of varus or valgus correction for a femoral and/or a tibial component in a knee replacement.

In some embodiments, the virtual surgical guide corresponds to a physical distal femoral guide or cut block and the predetermined position of the virtual surgical guide determines a femoral component flexion. In some embodiments, the virtual surgical guide corresponds to a physical anterior or posterior femoral surgical guide or cut block and the predetermined position of the virtual surgical guide determines a femoral component rotation. In some embodiments, the virtual surgical guide corresponds to a physical chamfer femoral guide or cut block. In some embodiments, the virtual surgical guide corresponds to a physical multi-cut femoral guide or cut block and the predetermined position of the virtual surgical guide determines one or more of an anterior cut, posterior cut, chamfer cuts and a femoral component rotation.

In some embodiments, the virtual surgical guide is used in a hip replacement and the predetermined position of the virtual surgical guide determines a leg length after implantation.

In some embodiments, the virtual surgical guide is a virtual plane for aligning the physical saw blade to guide the bone cut of the joint.

In some embodiments, the one or more intraoperative measurements include detecting one or more optical markers attached to the patient's joint, the operating room table, fixed structures in the operating room or combinations thereof. In some embodiments, one or more cameras or image capture or video capture systems and/or a 3D scanner included in the optical head mounted display detect one or more optical markers including their coordinates (x, y, z) and at least one or more of a position, orientation, alignment, direction of movement or speed of movement of the one or more optical markers.

In some embodiments, registration of one or more of OHMDs, surgical site, joint, spine, surgical instruments or implant components can be performed with use of spatial mapping techniques. In some embodiments, registration of one or more of OHMDs, surgical site, joint, spine, surgical instruments or implant components can be performed with use of depth sensors.

In some embodiments, the virtual surgical guide is used to guide a bone cut of a distal tibia or a talus in an ankle joint replacement and the one or more optical head mounted display is used to align the virtual surgical guide based on a predetermined tibial or talar implant component alignment, wherein the predetermined tibial or talar implant component alignment includes a coronal plane implant component alignment, a sagittal plane implant component alignment, an axial plane component alignment, an implant component rotation of an implant component or combinations thereof.

In some embodiments, the virtual surgical guide is used to guide a bone cut of a proximal humerus in a shoulder joint replacement and wherein the one or more optical head mounted display is used to align the virtual surgical guide based on a predetermined humeral implant component alignment, wherein the humeral implant component alignment includes a coronal plane implant component alignment, a sagittal plane implant component alignment, an axial plane component alignment, a humeral implant component rotation, or combinations thereof.

Aspects of the invention relate to a system comprising at least one optical head mounted display and a virtual library of implants, wherein the virtual library of implants comprises at least one virtual implant component, wherein the virtual implant component has at least one dimension that corresponds to a dimension of the implant component or has a dimension that is substantially identical to the dimension of the implant component, wherein the at least one optical head mounted display is configured to display the virtual implant component in substantial alignment with a tissue intended for placement of the implant component, wherein the placement of the virtual implant component is intended to achieve a predetermined implant component position and/or orientation.

Aspects of the invention relate to methods of selecting a prosthesis in three dimensions in a surgical site of a physical joint of a patient. In some embodiments, the method comprises registering, in a coordinate system, one or more optical head mounted displays worn by a user. In some embodiments, the optical head mounted display is a see-through optical head mounted display. In some embodiments, the method comprises obtaining one or more intra-operative measurements from the physical joint of the patient to determine one or more intra-operative coordinates. In some embodiments, the method comprises registering the one or more intra-operative coordinates from the physical joint of the patient in the coordinate system. In some embodiments, the method comprises displaying a three-dimensional graphical representation of a first prosthesis projected over the physical joint using the one or more optical head mounted displays. In some embodiments, the three-dimensional graphical representation of the first prosthesis is from a library of three-dimensional graphical representations of physical prostheses. In some embodiments, the three-dimensional graphical representation corresponds to at least one portion of the physical prosthesis. In some embodiments, the method comprises moving the three-dimensional graphical representation of the first prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint. In some embodiments, the method comprises visually evaluating the fit or alignment between the three-dimensional graphical representation of the first prosthesis and the one or more of an internal or external margin, periphery, edge, perimeter, anteroposterior, mediolateral, oblique dimension, diameter, radius, curvature, geometry, shape or surface, of the one or more structures of the physical joint. In some embodiments, the method comprises repeating the steps of displaying, optionally moving and visually evaluating the fit or alignment with one or more three-dimensional graphical representations of one or more additional physical prostheses, wherein the one or more additional physical prostheses have one or more of a different dimension, size, diameter, radius, curvature, geometry shape or surface than the first and subsequently evaluated prosthesis. In some embodiments, the method comprises selecting a three-dimensional graphical representation of a prosthesis with a satisfactory fit relative to the one or more structures of the physical joint from the library of three-dimensional graphical representations of physical prostheses.

In some embodiments, the method comprises obtaining one or more intra-operative measurements from the physical joint of the patient to determine one or more intra-operative coordinates and registering the one or more intra-operative coordinates from the physical joint of the patient in the coordinate system.

In some embodiments, the visually evaluating the fit includes comparing one or more of a radius, curvature, geometry, shape or surface of the graphical representation of the first or subsequent prosthesis with one or more of an articular radius, curvature, shape or geometry of the joint. In some embodiments, the graphical representation of the first or subsequent prosthesis is moved to improve the fit between the one or more of a radius, curvature, geometry, shape or surface of the graphical representation of the first or subsequent prosthesis and the one or more of an articular radius, curvature, shape or geometry of the joint. In some embodiments, the one or more of the size, location, position, and orientation of the selected graphical representation of the prosthesis with its final coordinates is used to develop or modify a surgical plan for implantation of the prosthesis. In some embodiments, the one or more of the location, position or orientation of the selected graphical representation is used to determine one or more bone resections for implantation of the prosthesis. In some embodiments, the one or more of an internal or external margin, periphery, edge, perimeter, anteroposterior, mediolateral, oblique dimension, diameter, radius, curvature, geometry, shape or surface of one or more structures of the physical joint have not been surgically altered. In other embodiments, the one or more of an internal or external margin, periphery, edge, perimeter, anteroposterior, mediolateral, oblique dimension, diameter, radius, curvature, geometry, shape or surface of one or more structures of the physical joint have been surgically altered. For example, the surgically altering can include removal of bone or cartilage. In some embodiments, the bone removal can be a bone cut.

In some embodiments, the optical head mounted display is a virtual reality type optical head mounted display and the joint of the patient is imaged using one or more cameras and the images are displayed by the optical head mounted display.

In some embodiments, the satisfactory fit includes a fit within 1, 2, 3, 4 or 5 mm distance between the selected graphical representation of the prosthesis and at least portions of the one or more of an internal or external margin, periphery, edge, perimeter anteroposterior, mediolateral, oblique dimension, radius, curvature, geometry, shape or surface, of the one or more structures of the physical joint.

In some embodiments, the one or more structures of the physical joint include one or more anatomic landmarks. In some embodiments, the one or more anatomic landmarks define one or more anatomical or biomechanical axes.

In some embodiments, the steps of moving and visually evaluating the fit of the graphical representation of the prosthesis include evaluating the alignment of the graphical representation of the prosthesis relative to the one or more anatomic or biomechanical axis.

In some embodiments, the step of moving the three-dimensional graphical representation of the prosthesis is performed with one, two, three, four, five or six degrees of freedom. In some embodiments, the step of moving the three-dimensional graphical representation of the prosthesis includes one or more of translation or rotation of the three-dimensional graphical representation of the prosthesis.

In some embodiments, the step of visually evaluating the fit or alignment between the three-dimensional graphical representation of the first or subsequent prosthesis includes comparing one or more of an anteroposterior or mediolateral dimension of one or more of the prosthesis components with one or more with one or more of an anteroposterior or mediolateral dimension of the distal femur or the proximal tibia of the joint. In some embodiments, the step of visually evaluating the fit or alignment between the three-dimensional graphical representation of the first or subsequent prosthesis includes comparing one or more of a dimension, size, radius, curvature, geometry shape or surface of at least portions of the prosthesis with one or more of a dimension, size, radius, curvature, geometry shape or surface of at least portions of a medial condyle or a lateral condyle of the joint.

In some embodiments, the joint is a knee joint and the prosthesis includes one or more components of a knee replacement device. In some embodiments, the joint is a hip joint and the prosthesis includes one or more components of a hip replacement device. In some embodiments, the joint is a shoulder joint and the prosthesis includes one or more components of a shoulder replacement device. In some embodiments, the joint is an ankle and the prosthesis includes one or more components of an ankle replacement device.

In some embodiments, the library of three-dimensional graphical representations of physical prostheses includes symmetrical and asymmetrical prosthesis components. In some embodiments, the symmetrical or asymmetrical prosthesis components include at least one of symmetrical and asymmetrical femoral components and symmetrical and asymmetrical tibial components.

Aspects of the invention relate to methods of selecting a medical device in three dimensions in a physical site of a patient selected for implantation. In some embodiments, the method comprises registering, in a coordinate system, one or more optical head mounted displays worn by a user. In some embodiments, the method comprises obtaining one or more measurements from the physical site of the patient to determine one or more coordinates.

In some embodiments, the method comprises registering the one or more coordinates from the physical site of the patient in the coordinate system. In some embodiments, the method comprises displaying a three-dimensional graphical representation of a first medical device projected over the physical site using the one or more optical head mounted displays. In some embodiments, the three-dimensional graphical representation of the first medical device is from a library of three-dimensional graphical representations of physical medical devices and the three-dimensional graphical representation corresponds to at least one portion of the physical first medical device.

In some embodiments, the method comprises moving the three-dimensional graphical representation of the first medical device to align with or to be near with or to intersect one or more of an internal or external margin, periphery, edge, perimeter, anteroposterior, mediolateral, oblique dimension, diameter, radius, curvature, geometry, shape or surface of one or more structures at the physical site. In some embodiments, the method comprises visually evaluating the fit or alignment between the three-dimensional graphical representation of the first medical device and the one or more of an internal or external margin, periphery, edge, perimeter, anteroposterior, mediolateral, oblique dimension, diameter, radius, curvature, geometry, shape or surface, of the one or more structures at the physical site. In some embodiments, the method comprises repeating the steps of displaying, optionally moving and visually evaluating the fit or alignment with one or more three-dimensional graphical representations of one or more additional physical medical devices, wherein the one or more additional physical medical devices have one or more of a different dimension, size, diameter, radius, curvature, geometry shape or surface than the first and subsequently evaluated medical device. In some embodiments, the method comprises selecting a three-dimensional graphical representation of a medical device with a satisfactory fit relative to the one or more structures at the physical site from the library of three-dimensional graphical representations of physical medical devices.

In some embodiments, the one or more structures at the physical site include an anatomic or pathologic tissue intended for implantation. In some embodiments, the one or more structures at the physical site include an anatomic or pathologic tissue surrounding or adjacent or subjacent to the intended implantation site. In some embodiments, the one or more structures at the physical site include a pre-existing medical device near the implantation site or adjacent or subjacent or opposing or articulating with or to be connected with the medical device planned for implantation. In some embodiments, the one or more structures at the physical site include a one or more of a tissue, organ or vascular surface, diameter, dimension, radius, curvature, geometry, shape or volume.

In some embodiments, the one or more optical head mounted displays display registered with and superimposed onto the physical site one or more of a pre- or intra-operative imaging study, 2D or 3D images of the patient, graphical representations of one or more medical devices, CAD files of one or more medical devices.

In some embodiments, the information from the one or more structures at the physical site and from the one or more of a pre- or intra-operative imaging study, 2D or 3D images of the patient, graphical representations of one or more medical devices, CAD files of one or more medical devices are used to select one or more of an anchor or attachment mechanism or fixation member.

In some embodiments, the information from the one or more structures at the physical site and from the one or more of a pre- or intra-operative imaging study, 2D or 3D images of the patient, graphical representations of one or more medical devices, CAD files of one or more medical devices are used to direct one or more of an anchor or attachment mechanism or fixation member.

In some embodiments, the medical device is one or more of an implant, an implant component, an instrument, a joint replacement implant, a stent, a wire, a catheter, a screw, an otoplasty prosthesis, a dental implant, a dental implant component, a prosthetic disk, a catheter, a guide wire, a coil, an aneurysm clip.

Aspects of the invention relates to methods of aligning a prosthesis in a joint of a patient. In some embodiments, the method comprises registering, in a coordinate system, one or more optical head mounted displays worn by a user. In some embodiments, the method comprises obtaining one or more intra-operative measurements from the physical joint of the patient to determine one or more coordinates of the physical joint. In some embodiments, the method comprises registering the one or more coordinates of the physical joint of the patient in the coordinate system. In some embodiments, the method comprises displaying a three-dimensional graphical representation of a prosthesis or prosthesis component projected over the physical joint using the one or more optical head mounted displays, wherein the three-dimensional graphical representation corresponds to at least one portion of the physical prosthesis. In some embodiments, the method comprises moving the three-dimensional graphical representation of the prosthesis to align with or to be near with or to intersect one or more of an internal or external margin, periphery, edge, perimeter, anteroposterior, mediolateral, oblique dimension, diameter, radius, curvature, geometry, shape or surface of one or more structures of the physical joint. In some embodiments, the method comprises registering one or more coordinates from the graphical representation of the prosthesis in the coordinate system after the moving and aligning.

In some embodiments, the moving of the three-dimensional graphical representation of the prosthesis is performed using one or more of a computer interface, an acoustic interface, optionally including voice recognition, a virtual interface, optionally including gesture recognition. In some embodiments, the one or more coordinates from the graphical representation of the prosthesis in the coordinate system after the moving and aligning are used to derive or modify a surgical plan. In some embodiments, the one or more coordinates from the graphical representation of the prosthesis in the coordinate system after the moving and aligning are used to determine one or more of a location, orientation, or alignment or coordinates of a bone removal for placing the prosthesis. In some embodiments, the bone removal is one or more of a bone cut, a burring, a drilling, a pinning, a reaming, or an impacting. In some embodiments, the surgical plan is used to derive one or more of a location, position, orientation, alignment, trajectory, plane, start point, or end point for one or more surgical instruments. In some embodiments, the one or more of a location, orientation, or alignment or coordinates of bone removal are used to derive one or more of a location, position, orientation, alignment, trajectory, plane, start point, or end point for one or more surgical instruments. In some embodiments, the one or more optical head mounted displays visualize the one or more of a location, position, orientation, alignment, trajectory, plane, start point, or end point for one or more surgical instruments projected onto and registered with the physical joint. In some embodiments, the prosthesis is an acetabular cup of a hip replacement and wherein a graphical representation of the acetabular up is aligned with at least a portion of the physical acetabular rim of the patient. In some embodiments, the prosthesis is a femoral component of a hip replacement and wherein a graphical representation of the femoral component is aligned with at least a portion of the physical endosteal bone or cortical bone of the patient. In some embodiments, the aligning means positioning the femoral component in substantially equidistant location between at least a portion of one or more of an anterior and a posterior endosteal or cortical bone or a medial and a lateral endosteal bone or cortical bone. In some embodiments, the femoral component includes a femoral neck. In some embodiments, the one or more coordinates from the femoral component in the coordinate system after the moving and aligning is used to determine at least one of a femoral component stem position, a femoral component stem orientation, a femoral component neck angle, a femoral component offset, and a femoral component neck anteversion. In some embodiments, the prosthesis is a glenoid component of a shoulder replacement and wherein a graphical representation of the glenoid component is aligned with at least a portion of the physical glenoid rim of the patient. In some embodiments, the prosthesis is a humeral component of a shoulder replacement and wherein a graphical representation of the humeral component is aligned with at least a portion of the physical endosteal bone or cortical bone of the patient. In some embodiments, the aligning means positioning the humeral component in substantially equidistant location between at least a portion of one or more of an anterior and a posterior endosteal or cortical bone or a medial and a lateral endosteal bone or cortical bone. In some embodiments, the humeral component includes a humeral neck. In some embodiments, the one or more coordinates from the humeral component in the coordinate system after the moving and aligning is used to determine at least one of a humeral component stem position, a humeral component stem orientation, a humeral component neck angle, a humeral component offset, and a humeral component neck anteversion. In some embodiments, the one or more of a margin, periphery, edge, perimeter, anteroposterior, mediolateral, oblique dimension, diameter, radius, curvature, geometry, shape or surface of one or more structures of the physical joint includes one or more of a cartilage, normal cartilage, damaged or diseased cartilage, subchondral bone or osteophyte. In some embodiments, the one or more of a margin, periphery, edge, perimeter, anteroposterior, mediolateral, oblique dimension, diameter, radius, curvature, geometry, shape or surface of one or more structures of the physical joint excludes one or more of a cartilage, normal cartilage, damaged or diseased cartilage, subchondral bone or osteophyte. In some embodiments, the one or more optical head mounted displays display registered with and superimposed onto the physical joint one or more of a pre- or intra-operative imaging study, 2D or 3D images of the patient, graphical representations of one or more medical devices, CAD files of one or more medical devices, wherein the display assists with the moving and aligning of the three-dimensional graphical representation of the graphical representation of the prosthesis. In some embodiments, the prosthesis is a femoral component or a tibial component of a knee replacement system, wherein the one or more coordinates from the graphical representation of the prosthesis in the coordinate system after the moving and aligning include a center of the graphical representation of the femoral component or a center of the graphical representation of the tibial component. In some embodiments, the moving or aligning includes aligning the femoral component on the distal femur. In some embodiments, the aligning includes aligning the femoral component substantially equidistant to a medial edge of the medial femoral condyle and the lateral edge of a lateral femoral condyle. In some embodiments, the aligning includes aligning the femoral component tangent with the articular surface of at least one of the medial condyle and the lateral condyle in at least one of a distal weight-bearing zone or a weight-bearing zone at 5, 10, 15, 20, 25, 30, 40 or 45 degrees of knee flexion. In some embodiments, the moving or aligning includes aligning the tibial component on the proximal tibia. In some embodiments, the aligning includes aligning the tibial component substantially equidistant to a medial edge of the medial tibial plateau and the lateral edge of a lateral tibial plateau and/or the anterior edge of the anterior tibial plateau and the posterior edge of the posterior tibial plateau or centered over the tibial spines. In some embodiments, the aligning includes aligning the tibial component tangent with at least portions of the articular surface of at least one of the medial tibial plateau and the lateral tibial plateau.

In some embodiments, the center of the graphical representation of the femoral component after the aligning and the center of the hip joint are used to determine a femoral mechanical axis. In some embodiments, the center of the graphical representation of the tibial component after aligning and the center of the ankle joint are used to determine a tibial mechanical axis. In some embodiments, the femoral and tibial mechanical axes are used to determine a desired leg axis correction relative to the mechanical axis of the leg. In some embodiments, the leg axis correction is one of a full correction to normal mechanical axis, partial correction to normal mechanical axis or no correction to normal mechanical axis. In some embodiments, the leg axis correction is used to determine the coordinates and/or alignment for the bone removal or bone cuts. In some embodiments, the bone removal or bone cuts for a full correction to normal mechanical axis or a partial correction to normal mechanical axis or no correction to normal mechanical axis are used to adjust the femoral and/or tibial prosthesis coordinates. In some embodiments, the bone removal or bone cuts are executed using at least one of a robot guidance, a surgical navigation system and visual guidance using the one or more of an optical head mounted displays. In some embodiments, the one or more optical head mounted display project a graphical representation of one or more of a cut block, a cut plane or a drill path registered with and superimposed onto the physical joint for aligning one or more of a physical cut guide, a saw blade or a drill.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

The term live data of the patient, as used herein, includes the surgical site, anatomy, anatomic structures or tissues and/or pathology, pathologic structures or tissues of the patient as seen by the surgeon's or viewer's eyes without information from virtual data, stereoscopic views of virtual data, or imaging studies. The term live data of the patient does not include internal or subsurface tissues or structures or hidden tissues or structures that can only be seen with assistance of a computer monitor or OHMD.

The terms "real surgical instrument", "actual surgical instrument", "physical surgical instrument" and "surgical instrument" are used interchangeably throughout the application; the terms real surgical instrument, actual surgical instrument, physical surgical instrument and surgical instrument do not include virtual surgical instruments. For example, the physical surgical instruments can be surgical instruments provided by manufacturers or vendors for spinal surgery, pedicle screw instrumentation, anterior spinal fusion, knee replacement, hip replacement, ankle replacement and/or shoulder replacement; physical surgical instruments can be, for example, cut blocks, pin guides, awls, reamers, impactors, broaches. Physical surgical instruments can be re-useable or disposable or combinations thereof. Physical surgical instruments can be patient specific. The term virtual surgical instrument does not include real surgical instrument, actual surgical instrument, physical surgical instrument and surgical instrument.

The terms "real surgical tool", "actual surgical tool", "physical surgical tool" and "surgical tool" are used interchangeably throughout the application; the terms real surgical tool, actual surgical tool, physical surgical tool and surgical tool do not include virtual surgical tools. The physical surgical tools can be surgical tools provided by manufacturers or vendors. For example, the physical surgical tools can be pins, drills, saw blades, retractors, frames for tissue distraction and other tools used for orthopedic, neurologic, urologic or cardiovascular surgery. The term virtual surgical tool does not include real surgical tool, actual surgical tool, physical surgical tool and surgical tool.

The terms real implant or implant component, actual implant or implant component, physical implant or implant component and implant or implant component are used interchangeably throughout the application; the terms real implant or implant component, actual implant or implant component, physical implant or implant component and implant or implant component do not include virtual implant or implant components. The physical implants or implant components can be implants or implant components provided by manufacturers or vendors. For example, the physical surgical implants can be a pedicle screw, a spinal rod, a spinal cage, a femoral or tibial component in a knee replacement, an acetabular cup or a femoral stem and head in hip replacement. The term virtual implant or implant component does not include real implant or implant component, actual implant or implant component, physical implant or implant component and implant or implant component.

The terms "image capture system", "video capture system", "image or video capture system", "image and/or video capture system, and/or optical imaging system" can be used interchangeably. In some embodiments, a single or more than one, e.g. two or three or more, image capture system, video capture system, image or video capture system, image and/or video capture system, and/or optical imaging system can be used in one or more locations (e.g. in one, two, three, or more locations), for example integrated into, attached to or separate from an OHMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, or an internal to a vascular lumen), internal to a vascular bifurcation, internal to a bowel, internal to a small intestine, internal to a stomach, internal to a biliary structure, internal to a urethra and or ureter, internal to a renal pelvis, external to the patient's skin, external to a surgical site, external to a target tissue, external to an organ, external to a cavity (e.g. an abdominal cavity or a bladder cavity or a cistern or a CSF space, or an external to a vascular lumen), external to a vascular bifurcation, external to a bowel, external to a small intestine, external to a stomach, external to a biliary structure, external to a urethra and or ureter, and/or external to a renal pelvis. In some embodiments, the position and/or orientation and/or coordinates of the one or more image capture system, video capture system, image or video capture system, image and/or video capture system, and/or optical imaging system can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ described in the specification or known in the art. Tracking of the one or more image capture system, video capture system, image or video capture system, image and/or video capture system, and/or optical imaging system can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, a single or more than one, e.g. two or three or more, 3D scanners can be present in one or more locations (e.g. in one, two, three, or more locations), for example integrated into, attached to or separate from an OHMD, attached to an OR table, attached to a fixed structure in the OR, integrated or attached to or separate from an instrument, integrated or attached to or separate from an arthroscope, integrated or attached to or separate from an endoscope, internal to the patient's skin, internal to a surgical site, internal to a target tissue, internal to an organ, internal to a cavity (e.g. an abdominal cavity or a bladder cavity or a cistern or a CSF space, and/or internal to a vascular lumen), internal to a vascular bifurcation, internal to a bowel, internal to a small intestine, internal to a stomach, internal to a biliary structure, internal to a urethra and or ureter, internal to a renal pelvis, external to the patient's skin, external to a surgical site, external to a target tissue, external to an organ, external to a cavity (e.g. an abdominal cavity or a bladder cavity or a cistern or a CSF space, and/or external to a vascular lumen), external to a vascular bifurcation, external to a bowel, external to a small intestine, external to a stomach, external to a biliary structure, external to a urethra and or ureter, and/or external to a renal pelvis. In some embodiments, the position and/or orientation and/or coordinates of the one or more 3D scanners can be tracked using any of the registration and/or tracking methods described in the specification, e.g. direct tracking using optical imaging systems and/or a 3D scanner(s), in any of the foregoing locations and/or tissues and/or organs and any other location and/or tissue and/or organ mentioned in the specification or known in the art. Tracking of the one or more 3D scanners can, for example, be advantageous when the one or more 3D scanners are integrated into or attached to an instrument, an arthroscope, an endoscope, and/or when they are located internal to any structures, e.g. inside a joint or a cavity or a lumen.

In some embodiments, one or more image capture system, video capture system, image or video capture system, image and/or video capture system, and/or optical imaging system can be used in conjunction with one or more 3D scanners, e.g. in any of the foregoing locations and/or tissues and/or organs and any other location and/or tissue and/or organ described in the specification or known in the art.

With surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations of the first and the second virtual instruments are compared.

Aspects of the invention relates to devices, systems and methods for positioning a virtual path, virtual plane, virtual tool, virtual surgical instrument or virtual implant component in a mixed reality environment using a head mounted display device, optionally coupled to one or more processing units.

With guidance in mixed reality environment, a virtual surgical guide, tool, instrument or implant can be superimposed onto the physical joint, spine or surgical site. Further, the physical guide, tool, instrument or implant can be aligned with the virtual surgical guide, tool, instrument or implant displayed or projected by the OHMD. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In various embodiments, the OHMD can display one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration.

Any of a position, location, orientation, alignment, direction, speed of movement, force applied of a surgical instrument or tool, virtual and/or physical, can be predetermined using, for example, pre-operative imaging studies, pre-operative data, pre-operative measurements, intra-operative imaging studies, intra-operative data, and/or intra-operative measurements.

Any of a position, location, orientation, alignment, sagittal plane alignment, coronal plane alignment, axial plane alignment, rotation, slope of implantation, angle of implantation, flexion of implant component, offset, anteversion, retroversion, and position, location, orientation, alignment relative to one or more anatomic landmarks, position, location, orientation, alignment relative to one or more anatomic planes, position, location, orientation, alignment relative to one or more anatomic axes, position, location, orientation, alignment relative to one or more biomechanical axes, position, location, orientation, alignment relative to a mechanical axis of a trial implant, an implant component or implant, virtual and/or physical, can be predetermined using, for example, pre-operative imaging studies, pre-operative data, pre-operative measurements, intra-operative imaging studies, intra-operative data, and/or intra-operative measurements. Intra-operative measurements can include measurements for purposes of registration, e.g. of a joint, a spine, a surgical site, a bone, a cartilage, an OHMD, a surgical tool or instrument, a trial implant, an implant component or an implant.

In some embodiments, multiple coordinate systems can be used instead of a common or shared coordinate system. In this case, coordinate transfers can be applied from one coordinate system to another coordinate system, for example for registering the OHMD, live data of the patient including the surgical site, virtual instruments and/or virtual implants and physical instruments and physical implants.

Optical Head Mounted Displays

In some embodiments, a pair of glasses is utilized. The glasses can include an optical head-mounted display. An optical head-mounted display (OHMD) can be a wearable display that has the capability of reflecting projected images as well as allowing the user to see through it. Various types of OHMDs can be used to practice the present disclosure. These include curved mirror or curved combiner OHMDs as well as wave-guide or light-guide OHMDs. The OHMDs can optionally utilize diffraction optics, holographic optics, polarized optics, and reflective optics.

Traditional input devices that can be used with the OHMDs include, but are not limited to touchpad or buttons, smartphone controllers, speech recognition, and gesture recognition. Advanced interfaces are possible, e.g. a brain-computer interface.

Optionally, a computer or server or a workstation can transmit data to the OHMD. The data transmission can occur via cable, Bluetooth, WIFI, optical signals and any other method or mode of data transmission known in the art. The OHMD can display virtual data, e.g. virtual data of the patient, in uncompressed form or in compressed form. Virtual data of a patient can optionally be reduced in resolution when transmitted to the OHMD or when displayed by the OHMD.

When virtual data are transmitted to the OHMD, they can be in compressed form during the transmission. The OHMD can then optionally decompress them so that uncompressed virtual data are being displayed by the OHMD.

Alternatively, when virtual data are transmitted to the OHMD, they can be of reduced resolution during the transmission, for example by increasing the slice thickness of image data prior to the transmission. The OHMD can then optionally increase the resolution, for example by re-interpolating to the original slice thickness of the image data or even thinner slices so that virtual data with resolution equal to or greater than the original virtual data or at least greater in resolution than the transmitted data are being displayed by the OHMD.

In some embodiments, the OHMD can transmit data back to a computer, a server or a workstation. Such data can include, but are not limited to:

- Positional, orientational or directional information about the OHMD or the operator or surgeon wearing the OHMD
- Changes in position, orientation or direction of the OHMD
- Data generated by one or more IMUs
- Data generated by markers (radiofrequency, optical, light, other) attached to, integrated with or coupled to the OHMD
- Data generated by a surgical navigation system attached to, integrated with or coupled to the OHMD
- Data generated by an image and/or video capture system attached to, integrated with or coupled to the OHMD
- Parallax data, e.g. using two or more image and/or video capture systems attached to, integrated with or coupled to the OHMD, for example one positioned over or under or near the left eye and a second positioned over or under or near the right eye
- Distance data, e.g. parallax data generated by two or more image and/or video capture systems evaluating changes in distance between the OHMD and a surgical field or an object
- Motion parallax data
- Data related to calibration or registration phantoms (see other sections of this specification)
- Any type of live data of the patient captured by the OHMD including image and/or video capture systems attached to, integrated with or coupled to the OHMD For example, alterations to a live surgical site For example, use of certain surgical instruments detected by the image and/or video capture system For example, use of certain medical devices or trial implants detected by the image and/or video capture system Any type of modification to a surgical plan Portions or aspects of a live surgical plan Portions or aspects of a virtual surgical plan Radiofrequency tags used throughout the embodiments can be of active or passive kind with or without a battery.

Exemplary optical head mounted displays include the ODG R-7, R-8 and R-8 smart glasses from ODG (Osterhout Group, San Francisco, Calif.), the NVIDIA 942 3-D vision wireless glasses (NVIDIA, Santa Clara, Calif.) the Microsoft HoloLens (Microsoft, Redmond, Wis.), the Daqri Smart Glass (Daqri, Los Angeles, Calif.) the Metal (Meta Vision, San Mateo, Calif.), the Moverio BT-300 (Epson, Suwa, Japan), the Blade 3000 and the Blade M300 (Vuzix, West Henrietta, N.Y.). The Microsoft HoloLens is manufactured by Microsoft. It is a pair of augmented reality smart glasses. Hololens is a see through optical head mounted display. Hololens can use the Windows 10 operating system. The front portion of the Hololens includes, among others, sensors, related hardware, several cameras and processors. The visor includes a pair of transparent combiner lenses, in which the projected images are displayed. The HoloLens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present. The HoloLens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor. Hololens has an Intel Cherry Trail SoC containing the CPU and GPU. HoloLens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. HoloLens includes a IEEE 802.11ac Wi-Fi and Bluetooth 4.1 Low Energy (LE) wireless connectivity. The headset uses Bluetooth LE and can connect to a clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application, FreeForm, integrating HoloLens with the Autodesk Fusion 360 cloud-based 3D development application, and others. HoloLens utilizing the HPU can employ sensual and natural interface commands—voice, gesture, and gesture. Gaze commands, e.g. head-tracking, allows the user to bring application focus to whatever the user is perceiving. Any virtual application or button can be selected using an air tap method, similar to clicking a virtual computer mouse. The tap can be held for a drag simulation to move a display. Voice commands can also be utilized. The HoloLens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around. The Microsoft HoloLens App for Windows 10 PC's and Windows 10 Mobile devices can be used by developers to run apps and to view live stream from the HoloLens user's point of view, and to capture augmented reality photos and videos. Almost all Universal Windows Platform apps can run on Hololens. These apps can be projected in 2D. Select Windows 10 APIs are currently supported by HoloLens. Hololens apps can also be developed on Windows 10 PC's. Holographic applications can use Windows Holographic APIs. Unity (Unity Technologies, San Francisco, Calif.) and Vuforia (PTC, Inc., Needham, Mass.) are some apps that can be utilized. Applications can also be developed using DirectX and Windows API's.

Many of the embodiments throughout the specification can be implemented also using non see through optical head mounted displays, e.g. virtual reality optical head mounted displays. Non see through optical head mounted displays can be used, for example, with one or more image or video capture systems (e.g. cameras) or 3D scanners to image the live data of the patient, e.g. a skin, a subcutaneous tissue, a surgical site, an anatomic landmark, an organ, or an altered tissue, e.g. a surgically altered tissue, as well as any physical surgical tools, instruments, devices and/or implants, or portions of the surgeon's body, e.g. his or her fingers, hands or arms. Non see through OHMDs can be used, for example, for displaying virtual data, e.g. pre- or intra-operative imaging data of the patient, virtual surgical guides, virtual tools, virtual instruments, virtual implants and/or virtual implants, for example together with live data of the patient, e.g. from the surgical site, imaged through the one or more cameras or video or image capture systems or 3D scanners, for knee replacement surgery, hip replacement surgery, shoulder replacement surgery, ankle replacement surgery, spinal surgery, e.g. spinal fusion, brain surgery, heart surgery, lung surgery, liver surgery, spleen surgery, kidney surgery vascular surgery or procedures, prostate, genitourinary, uterine or other abdominal or pelvic surgery, and trauma surgery. Exemplary non see through optical head mounted displays, e.g. virtual reality optical head mounted displays, are, for example, the Oculus Rift (Google, Mountain View, Calif.), the HTC Vive (HTC, Taipei, Taiwan) and the Totem (Vrvana, Apple, Cupertino, Calif.).

Computer Graphics Viewing Pipeline

Figure 16A:
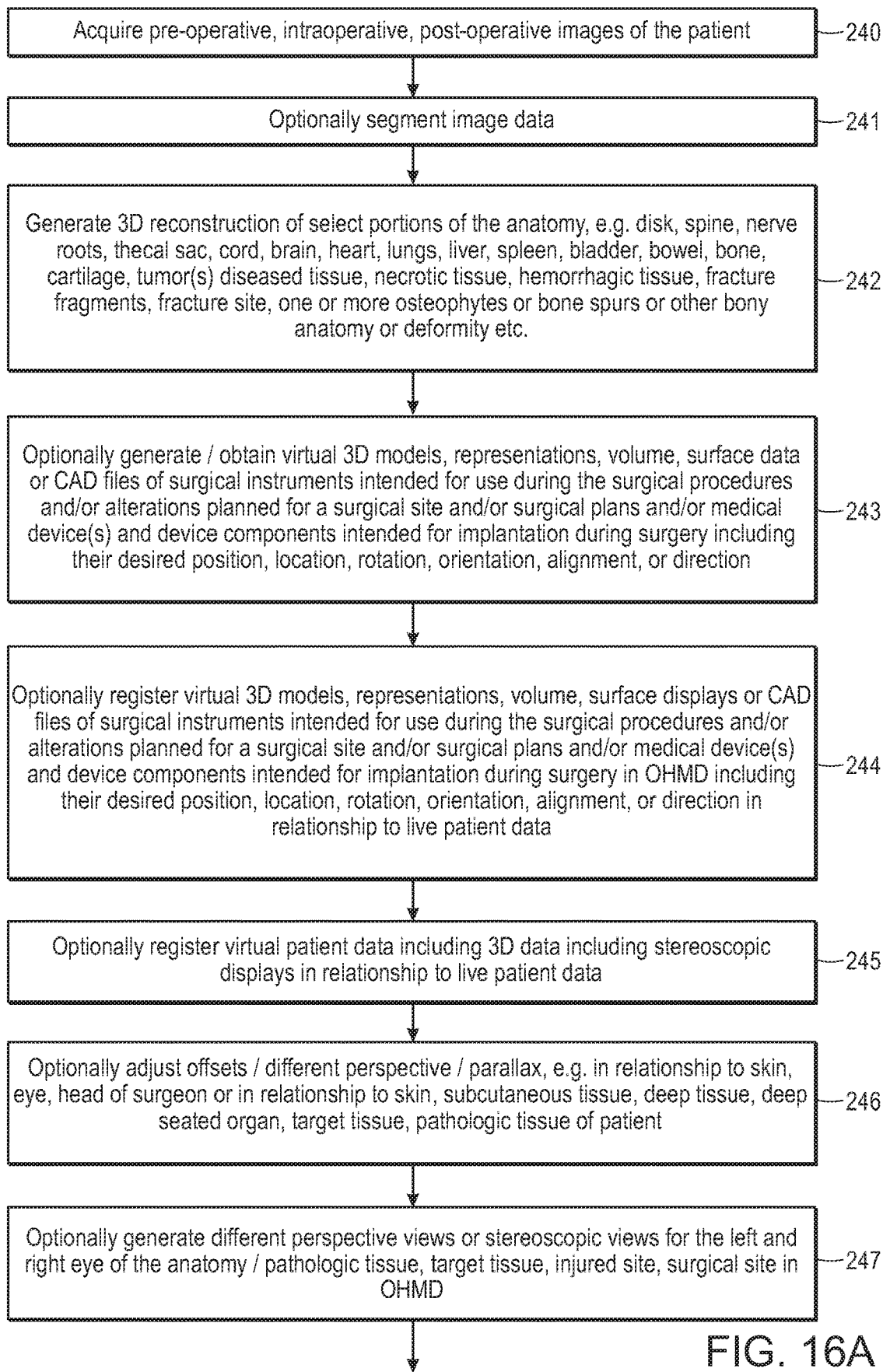
FIGS. 16A-C are flow charts summarizing model generation, registration and view projection for one or more OHMDs, e.g. by a primary surgeon, second surgeon, surgical assistant nurse, or others according to some embodiments of the present disclosure.
Figure 16B:
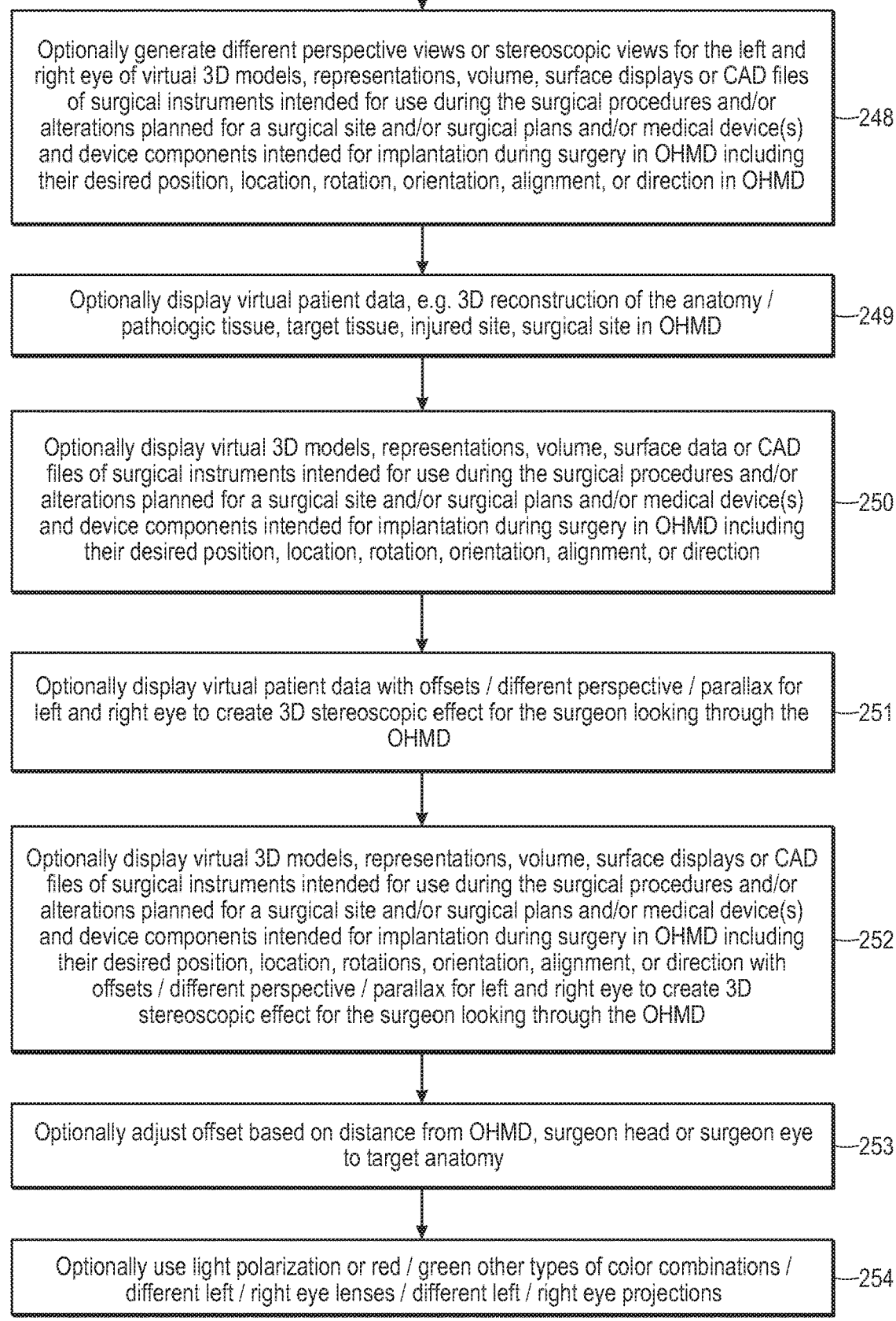
Figure 16C:
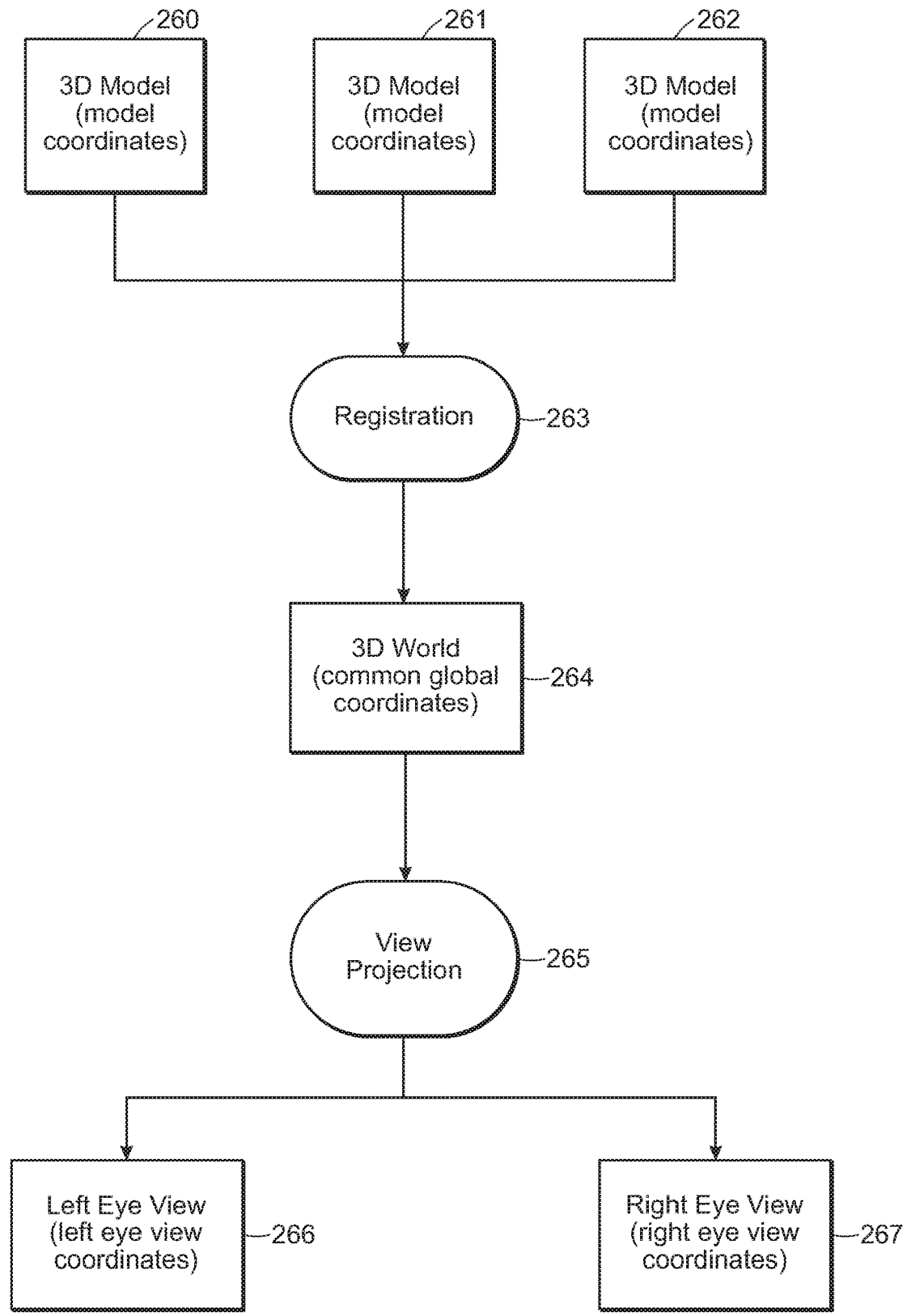

In some embodiments, the optical head mount display uses a computer graphics viewing pipeline that consists of the following steps to display 3D objects or 2D objects positioned in 3D space or other computer-generated objects and models FIG. 16B:

1. Registration
2. View Projection

Registration:

The different objects to be displayed by the OHMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process.

For augmented reality OHMDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection:

Once all objects to be displayed have been registered and transformed into the common global coordinate system, they are prepared for viewing on a display by transforming their coordinates from the global coordinate system into the view coordinate system and subsequently projecting them onto the display plane. This view projection step uses the viewpoint and view direction to define the transformations applied in this step. For stereoscopic displays, such as an OHMD, two different view projections can be used, one for the left eye and the other one for the right eye. For augmented reality OHMD the position of the viewpoint and view direction relative to the physical environment can be known to correctly superimpose the computer-generated objects with the physical environment. As the viewpoint and view direction change, for example due to head movement, the view projections are updated so that the computer-generated display follows the new view.

Positional Tracking Systems

In certain embodiments, the position and/or orientation of the OHMD can be tracked. For example, in order to calculate and update the view projection of the computer graphics view pipeline as described in the previous section and to display the computer-generated overlay images in the OHMD, the view position and direction needs to be known.

Different methods to track the OHMD can be used. For example, the OHMD can be tracked using outside-in tracking. For outside-in tracking, one or more external sensors or cameras can be installed in a stationary location, e.g. on the ceiling, the wall or on a stand. The sensors or camera capture the movement of the OHMD, for example through shape detection or markers attached to the OHMD or the user's head. The sensor data or camera image is typically processed on a central computer to which the one or more sensors or cameras are connected. The tracking information obtained on the central computer is then used to compute the view projection. The view projection can be computed on the central computer or on the OHMD.

In another embodiment, the inside-out tracking method is employed. One or more sensors or cameras are attached to the OHMD or the user's head or integrated with the OHMD. The sensors or cameras can be dedicated to the tracking functionality. In other embodiments, the data collected by the sensors or cameras is used for positional tracking as well as for other purposes, e.g. image recording or spatial mapping. Information gathered by the sensors and/or cameras is used to determine the OHMD's position and orientation in 3D space. This can be done, for example, by detecting optical, infrared or electromagnetic markers attached to the external environment. Changes in the position of the markers relative to the sensors or cameras are used to continuously determine the position and orientation of the OHMD. Data processing of the sensor and camera information is typically performed by a mobile processing unit attached to or integrated with the OHMD, which allows for increased mobility of the OHMD user as compared to outside-in tracking. Alternatively, the data can be transmitted to and processed on the central computer.

Inside-out tracking can also utilize markerless techniques. For example, spatial mapping data acquired by the OHMD sensors can be aligned with a virtual model of the environment, thus determining the position and orientation of the OHMD in the 3D environment. Alternatively, or additionally, information from inertial measurement units can be used. Potential advantages of inside-out tracking include greater mobility for the OHMD user, a greater field of view not limited by the viewing angle of stationary cameras and reduced or eliminated problems with marker occlusion.

Eye Tracking Systems

The present disclosure provides for methods of using the human eye including eye movements and lid movements as well as movements induced by the peri-orbital muscles for executing computer commands. Methods of executing computer commands by way of facial movements and movements of the head are provided.

Command execution induced by eye movements and lid movements as well as movements induced by the peri-orbital muscles, facial movements and head movements can be advantageous in environments where an operator does not have his hands available to type on a keyboard or to execute commands on a touchpad or other hand-computer interface. Such situations include, but are not limited, to industrial applications including automotive and airplane manufacturing, chip manufacturing, medical or surgical procedures and many other potential applications.

In some embodiments, the optical head mount display can include an eye tracking system. Different types of eye tracking systems can be utilized. The examples provided below are in no way thought to be limiting. Any eye tracking system known in the art now can be utilized. Eye movement can be divided into fixations and saccades—when the eye gaze pauses in a certain position, and when it moves to another position, respectively. The resulting series of fixations and saccades can be defined as a scan path. The central one or two degrees of the visual angle provide most of the visual information; the input from the periphery is less informative. Thus, the locations of fixations along a scan path show what information locations were processed during an eye tracking session, for example during a surgical procedure.

Eye trackers can measure rotation or movement of the eye in several ways, for example via measurement of the movement of an object (for example, a form of contact lens) attached to the eye, optical tracking without direct contact to the eye, and measurement of electric potentials using electrodes placed around the eyes.

If an attachment to the eye is used, it can, for example, be a special contact lens with an embedded mirror or magnetic field sensor. The movement of the attachment can be measured with the assumption that it does not slip significantly as the eye rotates. Measurements with tight fitting contact lenses can provide very accurate measurements of eye movement. Additionally, magnetic search coils can be utilized which allow measurement of eye movement in horizontal, vertical and torsion direction.

Alternatively, non-contact, optical methods for measuring eye motion can be used. With this technology, light, optionally infrared, can be reflected from the eye and can be sensed by an optical sensor or a video camera. The information can then be measured to extract eye rotation and/or movement from changes in reflections. Optical sensor or video-based eye trackers can use the corneal reflection (the so-called first Purkinje image) and the center of the pupil as features to track, optionally over time. A more sensitive type of eye tracker, the dual-Purkinje eye tracker, uses reflections from the front of the cornea (first Purkinje image) and the back of the lens (fourth Purkinje image) as features to track. An even more sensitive method of tracking is to image features from inside the eye, such as the retinal blood vessels, and follow these features as the eye rotates and or moves. Optical methods, particularly those based on optical sensors or video recording, can be used for gaze tracking.

In some embodiments, optical or video-based eye trackers can be used. A camera focuses on one or both eyes and tracks their movement as the viewer performs a function such as a surgical procedure. The eye-tracker can use the center of the pupil for tracking. Infrared or near-infrared non-collimated light can be utilized to create corneal reflections. The vector between the pupil center and the corneal reflections can be used to compute the point of regard on a surface or the gaze direction. Optionally, a calibration procedure can be performed at the beginning of the eye tracking.

Bright-pupil and dark-pupil eye tracking can be employed. Their difference is based on the location of the illumination source with respect to the optics. If the illumination is co-axial relative to the optical path, then the eye acts is retroreflective as the light reflects off the retina creating a bright pupil effect similar to a red eye. If the illumination source is offset from the optical path, then the pupil appears dark because the retroreflection from the retina is directed away from the optical sensor or camera.

Bright-pupil tracking can have the benefit of greater iris/pupil contrast, allowing more robust eye tracking with all iris pigmentation. It can also reduce interference caused by eyelashes. It can allow for tracking in lighting conditions that include darkness and very bright lighting situations.

The optical tracking method can include tracking movement of the eye including the pupil as described above. The optical tracking method can also include tracking of the movement of the eye lids and also periorbital and facial muscles.

In some embodiments, the eye-tracking apparatus is integrated in an optical head mounted display. In some embodiments, head motion can be simultaneously tracked, for example using a combination of accelerometers and gyroscopes forming an inertial measurement unit (see below).

In some embodiments, electric potentials can be measured with electrodes placed around the eyes. The eyes generate an electric potential field, which can also be detected if the eyes are closed. The electric potential field can be modelled to be generated by a dipole with the positive pole at the cornea and the negative pole at the retina. It can be measured by placing two electrodes on the skin around the eye. The electric potentials measured in this manner are called an electro-oculogram.

If the eyes move from the center position towards the periphery, the retina approaches one electrode while the cornea approaches the opposing one. This change in the orientation of the dipole and consequently the electric potential field results in a change in the measured electro-oculogram signal. By analyzing such changes eye movement can be assessed. Two separate movement directions, a horizontal and a vertical, can be identified. If a posterior skull electrode is used, a EOG component in radial direction can be measured. This is typically the average of the EOG channels referenced to the posterior skull electrode. The radial EOG channel can measure saccadic spike potentials originating from extra-ocular muscles at the onset of saccades.

EOG can be limited for measuring slow eye movement and detecting gaze direction. EOG is, however, well suited for measuring rapid or saccadic eye movement associated with gaze shifts and for detecting blinks. Unlike optical or video-based eye-trackers, EOG allows recording of eye movements even with eyes closed. The major disadvantage of EOG is its relatively poor gaze direction accuracy compared to an optical or video tracker. Optionally, both methods, optical or video tracking and EOG, can be combined in select embodiments.

A sampling rate of 15, 20, 25, 30, 50, 60, 100, 120, 240, 250, 500, 1000 Hz or greater can be used. Any sampling frequency is possibly. In many embodiments, sampling rates greater than 30 Hz will be preferred.

Measuring Location, Orientation, Acceleration

The location, orientation, and acceleration of the human head, portions of the human body, e.g. hands, arms, legs or feet, as well as portions of the patient's body, e.g. the patient's head or extremities, including the hip, knee, ankle, foot, shoulder, elbow, hand or wrist and any other body part, can, for example, be measured with a combination of gyroscopes and accelerometers. In select applications, magnetometers may also be used. Such measurement systems using any of these components can be defined as inertial measurement units (IMU). As used herein, the term IMU relates to an electronic device that can measure and transmit information on a body's specific force, angular rate, and, optionally, the magnetic field surrounding the body, using a combination of accelerometers and gyroscopes, and, optionally, magnetometers. An IMU or components thereof can be coupled with or registered with a navigation system or a robot, for example by registering a body or portions of a body within a shared coordinate system. Optionally, an IMU can be wireless, for example using WIFI networks or Bluetooth networks.

Pairs of accelerometers extended over a region of space can be used to detect differences (gradients) in the proper accelerations of frames of references associated with those points.

Single- and multi-axis models of accelerometer are available to detect magnitude and direction of the acceleration, as a vector quantity, and can be used to sense orientation (because direction of weight changes), coordinate acceleration (so long as it produces g-force or a change in g-force), vibration, shock. Micromachined accelerometers can be utilized in some embodiments to detect the position of the device or the operator's head.

Piezoelectric, piezoresistive and capacitive devices can be used to convert the mechanical motion into an electrical signal. Piezoelectric accelerometers rely on piezoceramics or single crystals Piezoresistive accelerometers can also be utilized. Capacitive accelerometers typically use a silicon micro-machined sensing element.

Accelerometers used in some of the embodiments can include small micro electro-mechanical systems (MEMS), consisting, for example, of little more than a cantilever beam with a proof mass.

Optionally, the accelerometer can be integrated in the optical head mounted devices and both the outputs from the eye tracking system and the accelerometer(s) can be utilized for command execution.

With an IMU, the following exemplary information can be captured about the operator and the patient and respective body parts including a moving joint: Speed, velocity, acceleration, position in space, positional change, angular orientation, change in angular orientation, alignment, orientation, and/or direction of movement and or speed of movement (e.g. through sequential measurements). Operator and/or patient body parts about which such information can be transmitted by the IMU include, but are not limited to: head, chest, trunk, shoulder, elbow, wrist, hand, fingers, arm, hip, knee, ankle, foot, toes, leg, inner organs, e.g. brain, heart, lungs, liver, spleen, bowel, bladder, etc.

Any number of IMUs can be placed on the OHMD, the operator and/or the patient and, optionally, these IMUs can be cross-referenced to each other within a single or multiple coordinate systems or, optionally, they can be cross-referenced in relationship to an OHMD, a second and third or more OHMDs, a navigation system or a robot and one or more coordinate systems used by such navigation system and/or robot. A navigation system can be used in conjunction with an OHMD without the use of an IMU. For example, navigation markers including infrared markers, retroreflective markers, RF markers can be attached to an OHMD and, optionally, portions or segments of the patient or the patient's anatomy. The OHMD and the patient or the patient's anatomy can be cross-referenced in this manner or registered in one or more coordinate systems used by the navigation system and movements of the OHMD or the operator wearing the OHMD can be registered in relationship to the patient within these one or more coordinate systems. Once the virtual data and the live data of the patient and the OHMD are registered in the same coordinate system, e.g. using IMUs, optical markers, navigation markers including infrared markers, retroreflective markers, RF markers, and any other registration method described in the specification or known in the art, any change in position of any of the OHMD in relationship to the patient measured in this fashion can be used to move virtual data of the patient in relationship to live data of the patient, so that the visual image of the virtual data of the patient and the live data of the patient seen through the OHMD are always aligned, irrespective of movement of the OHMD and/or the operator's head and/or the operator wearing the OHMD. Similarly, when multiple OHMDs are used, e.g. one for the primary surgeon and additional ones, e.g. two, three, four or more, for other surgeons, assistants, residents, fellows, nurses and/or visitors, the OHMDs worn by the other staff, not the primary surgeon, will also display the virtual representation(s) of the virtual data of the patient aligned with the corresponding live data of the patient seen through the OHMD, wherein the perspective of the virtual data that is with the patient and/or the surgical site for the location, position, and/or orientation of the viewer's eyes for each of the OHMDs used and each viewer. The foregoing embodiments can be achieved since the IMUS, optical markers, RF markers, infrared markers and/or navigation markers placed on the operator and/or the patient as well as any spatial anchors can be registered in the same coordinate system as the primary OHMD and any additional OHMDs. The position, orientation, alignment, and change in position, orientation and alignment in relationship to the patient and/or the surgical site of each additional OHMD can be individually monitored thereby maintaining alignment and/or superimposition of corresponding structures in the live data of the patient and the virtual data of the patient for each additional OHMD irrespective of their position, orientation, and/or alignment in relationship to the patient and/or the surgical site.

Referring to FIG. 1, a system 10 for using multiple OHMDs 11, 12, 13, 14 for multiple viewer's, e.g. a primary surgeon, second surgeon, surgical assistant(s) and/or nurses(s) is shown. The multiple OHMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMU's, optical markers, navigation markers, image or video capture systems and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUS, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The OHMDs 11, 12, 13, 14 can project digital holograms of the virtual data or virtual data into the view of the left eye using the view position and orientation of the left eye 26 and can project digital holograms of the virtual data or virtual data into the view of the right eye using the view position and orientation of the right eye 28 of each user, resulting in a shared digital holographic experience 30. Using a virtual or other interface, the surgeon wearing OHMD 1 11 can execute commands 32, e.g. to display the next predetermined bone cut, e.g. from a virtual surgical plan or an imaging study or intra-operative measurements, which can trigger the OHMDs 11, 12, 13, 14 to project digital holograms of the next surgical step 34 superimposed onto and aligned with the surgical site in a predetermined position and/or orientation.

Virtual data of the patient can be projected superimposed onto live data of the patient for each individual viewer by each individual OHMD for their respective view angle or perspective by registering live data of the patient, e.g. the surgical field, and virtual data of the patient as well as each OHMD in a common, shared coordinate system. Thus, virtual data of the patient including aspects of a virtual surgical plan can remain superimposed and/or aligned with live data of the patient irrespective of the view angle or perspective of the viewer and alignment and/or superimposition can be maintained as the viewer moves his or her head or body.

Novel User Interfaces

The present disclosure provides a novel user interface where the human eye including eye movements and lid movements including movements induced by the orbital and peri-orbital and select skull muscles are detected by the eye tracking system and are processed to execute predefined, actionable computer commands.

An exemplary list of eye movements and lid movements that can be detected by the system is provided in Table 1.

TABLE 1

Exemplary list of eye movements and lid movements detected by the eye tracking software 1 blink; 2 blinks; 3 blinks; Fast blink, for example less than 0.5 seconds; Slow blink, for example more than 1.0 seconds; 2 or more blinks with fast time interval, e.g. less than 1 second; 2 or more blinks with long time interval, e.g. more than 2 seconds (typically chosen to be less than the natural time interval between eye blinks); Blink left eye only; Blink right eye only; Blink left eye and right eye simultaneously; Blink left eye first, then within short time interval (e.g. less than 1 second), blink right eye; Blink right eye first, then within short time interval (e.g. less than 1 second), blink left eye; Blink left eye first, then within long time interval (e.g. more than 2 seconds), blink right eye; Blink right eye first, then within long time interval (e.g. more than 2 seconds), blink left eye; Rapid eye movement to left; Rapid eye movement to right; Rapid eye movement up; Rapid eye movement down; Widen eyes, hold for short time interval, e.g. less than 1 second; Widen eyes, hold for long time interval, e.g. more than 2 seconds; Close both eyes for 1 second etc.; Close both eyes for 2 seconds or more etc.; Close both eyes, hold, then open and follow by fast blink; Close left eye only 1 second, 2 seconds etc.; Close right eye only 1 second, 2 seconds etc.; Close left eye, then right eye; Close right eye, then left eye; Blink left eye, then right eye; Blink right eye, then left eye; Stare at field, virtual button for 1, 2, 3 or more seconds; activate function, e.g. Zoom in or Zoom out.

Any combination of blinks, eye movements, sequences, and time intervals is possible for encoding various types of commands. These commands can be computer commands that can direct or steer, for example, a surgical instrument or a robot. Methods of executing commands by way of facial movements and movements of the head are also provided.

An exemplary list of facial movements and head movements that can be detected by the system is provided in Table 2. (This list is only an example and by no way meant to be exhaustive; any number or combination of movements is possible).

TABLE 2

Exemplary list of facial movements and head movements detected:
Move head fast to right and hold; Move head fast to left and hold; Move head fast down and hold; Move head fast down and hold; Move head fast to right and back; Move head fast to left and back; Move head fast down and back; Move head fast down and back; Tilt head to left and hold; Tilt head to right and hold; Tilt head to left and back; Tilt head to right and back; Open mouth and hold; Open mouth and close; Twitch nose once; Twitch nose twice etc.

Exemplary commands executed using eye movements, lid movements, facial movements and head movements are listed in Table 3.

TABLE 3

Exemplary list of commands that can be executed by tracking eye movement, lid movement, facial movement and head movement (this list is only an example and by no way meant to be exhaustive; any number or combination of commands is possible; application specific commands can be executed in this manner as well).
Click; Point; Move pointer (Slow, Fast); Scroll, e.g. through images (Fast scroll, Slow scroll); Scroll up; Scroll down; Scroll left; Scroll right; Drag; Swoosh; Register; Toggle 2D vs. 3D; Switch imaging study; Overlay images; Fuse images; Register images; Cut; Paste; Copy; Undo; Redo; Delete; Purchase; Provide credit card information; Authorize; Go to shopping card; OHMD on; OHMD off; Eye tracking on; Eye tracking off; Eye command execution on; Eye command execution off; Facial command execution on; Facial command execution off; Turn surgical instrument on (e.g. oscillating saw, laser etc.); Turn surgical instrument off; Increase intensity, speed, energy deposed of surgical instrument; Reduce intensity, speed, energy deposed of surgical instrument; Change direction of surgical instrument; Change orientation of surgical instrument; Change any type of setting surgical instrument.

In some embodiments, eye movements, lid movements, facial movement, head movements alone or in combination can be used to signal numerical codes or sequences of numbers or sequences of machine operations. Such sequences of numbers can, for example, be used to execute certain machine operating sequences.

Head Movement to Control Movement of a Surgical Instrument

In some embodiments, head movement can be used to control a surgical instrument. For example, in a robot assisted procedure with haptic feedback from the robot, the surgeon can use his or her hands in controlling the direction of a surgical instrument. The surgeon can move the head forward. This forward motion is captured by an IMU and translated into a forward movement of a robotic arm holding a surgical instrument along the direction of the surgical instrument. A backward movement of the head can be captured by the IMU and can be translated into a backward movement of the robotic arm holding a surgical instrument along the direction of the surgical instrument.

In some embodiments, eye movements, lid movements, facial movement, head movements alone or in combination can be used to signal Morse codes. The International Morse Code encodes the Latin alphabet using a small set of punctuation and procedural signals as standardized sequences of short and long signals called dots and dashes. Each character (letter or numeral) is represented by a unique sequence of dots and dashes. The duration of a dash is three times the duration of a dot. Each dot or dash is followed by a short silence, equal to the dot duration. The letters of a word are separated by a space equal to three dots (one dash), and the words are separated by a space equal to seven dots.

An example how Morse code can be executed using eye commands is provided as follows; this is in no way meant to be limiting. Many different implementations are possible. A dot can be executed, for example, using a fast blink of both eyes (typically less than 1 sec), while a dash can be executed by closing the right eye only, for example for one second. The letter A in Morse code is a dot followed by a dash. With this encoding of Morse code, the letter A can be executed with a fast blink of both eyes (dot), followed by closing the right eye only for one second (dash). The letter B (dash, three dots), can be executed by closing the right eye only for one second (dash) followed by three fast blinks of both eyes (three dots) and so forth. Letters can be separated, for example, by maintaining a two second or longer break between eye commands. Alternatively, in another example, letters can be separate by closing only the left eye for about one second.

Binary codes can optionally also be executed using eye commands. For example, a fast blink of both eyes can represent the number 0, while closing the right eye only for about one second can represent the number 1. Alternatively, closing the right eye only for about one second can represent the number 0, while closing the left eye only for about one second can represent the number 1. Many different types of encoding are possible. Other numericals can also be executed using, for example, some of the eye, lid, facial and/or head movements shown in Tables 1 and 2.

Many different languages can be executed in this fashion. These include, optionally, also computer languages, e.g. Fortran, Pascal, C, C++, C--, Basic and many others known in the art. In some embodiments, eye, lid, facial and head movement commands can be paired or used in conjunction with voice commands, hand commands, gesture commands, keyboard commands, track pad commands, mouse commands, graphical user interface commands and any other command input device known in the art. The OHMD can optionally also include one or more touch sensitive sensors.

In select environments, eye commands add benefit of being able to navigate a screen or execute commands while maintaining privacy or confidentiality related to the commands. For example, in a hospital environment, with other patients or visitors nearby, eye commands can be utilized to access a patient's medical records or to order lab tests or other diagnostic tests without bystanders being aware that these records are being reviewed or that these tests are being ordered.

At a conference, the wearer of an optical head mounted display can utilize eye commands to turn on a video or audio recording function or transmission to a remote site or remote conference room without disclosing that the recording function has been activated. This is quite different from manual activation of a recording function, where the user would, for example, push a button or a touch sensitive sensor on the optical head mounted display in order to activate the recording function.

In some embodiments, a user can utilize eye movements, facial movements or head movements to direct digital camera for taking photographs or videos. Commands can include but are not limited to zoom in, zoom out, move region of interest left, right up, down, take photo, take sequence of photos, turn on/off flash start video recording, stop video recording, change resolution, increase resolution, decrease resolution.

Any other camera command known in the art can be executed in this manner using eye movement, facial movement or head movement based commands. By utilizing one or more commands of this type, the user can maintain privacy while obtaining image information about the surrounding environment.

Eye commands can be useful to surgeons or operating room personnel to execute commands without use of the hands and thereby maintaining sterility.

Fusing Physical World with Imaging and Other Data of a Patient

In some embodiments, an operator such as a surgeon may look through an OHMD observing physical data or information on a patient, e.g. a surgical site or changes induced on a surgical site, while pre-existing data of the patient are superimposed onto the physical visual representation of the live patient. Systems, methods and techniques to improve the accuracy of the display of the virtual data superimposed onto the live data of the patient are described in International Patent Application No. PCT/US2018/012459, which is incorporated herein by reference in its entirety.

The pre-existing data of the patient can be an imaging test or imaging data or other types of data including metabolic information or functional information.

The pre-existing data of the patient including one or more imaging tests or other types of data including metabolic or functional information can be obtained at a time different from the time of the surgical procedure. For example, the pre-existing data of the patient can be obtained one, two, three or more days or weeks prior to the surgical procedure.

The pre-existing data of the patient including one or more imaging tests or other types of data including metabolic or functional information are typically obtained with the patient or the surgical site being located in a different location or a different object coordinate system in the pre-existing data when compared to the location or the object coordinate system of the live patient or the surgical site in the live patient. Thus, pre-existing data of the patient or the surgical site are typically located in a first object coordinate system and live data of the patient or the surgical site are typically located in a second object coordinate systems; the first and the second object coordinate system are typically different from each other. The first object coordinate system with the pre-existing data needs to be registered with the second object coordinate system with the live data of the patient including, for example, the live surgical site.

Scan Technology

The following is an exemplary list of scanning and imaging techniques that can be used or applied for various aspects of the present disclosure; this list is not exhaustive, but only exemplary. Anyone skilled in the art can identify other scanning or imaging techniques that can be used in practicing the present disclosure: X-ray imaging, 2D, 3D, supine, upright or in other body positions and poses, including analog and digital x-ray imaging; Digital tomosynthesis; Cone beam CT; Ultrasound; Doppler ultrasound; Elastography, e.g. using ultrasound or MRI; CT; MRI, including, for example, fMRI, diffusion imaging, stroke imaging, MRI with contrast media; Functional MRI (fMRI), e.g. for brain imaging and functional brain mapping; Magnetic resonance spectroscopy; PET; SPECT-CT; PET-CT; PET-MRI; Upright scanning, optionally in multiple planes or in 3D using any of the foregoing modalities, including x-ray imaging, ultrasound etc.; Contrast media (e.g. iodinated contrast agents for x-ray and CT scanning, or MRI contrast agents; contrast agents can include antigens or antibodies for cell or tissue specific targeting; other targeting techniques, e.g. using liposomes, can also be applied; molecular imaging, e.g. to highlight metabolic abnormalities in the brain and target surgical instruments towards area of metabolic abnormality; any contrast agent known in the art can be used in conjunction with the present disclosure); 3D optical imaging, including Laser scanning, Confocal imaging, e.g. including with use of fiberoptics, single bundle, multiple bundle, Confocal microscopy, e.g. including with use of fiberoptics, single bundle, multiple bundles, Optical coherence tomography, Photogrammetry, Stereovision (active or passive), Triangulation (active or passive), Interferometry, Phase shift imaging, Active wavefront sampling, Structured light imaging, Other optical techniques to acquire 3D surface information, Combination of imaging data, e.g. optical imaging, wavefront imaging, interferometry, optical coherence tomography and/or confocal laser imaging or scanning, Image fusion or co-display of different imaging modalities, e.g. in 2D or 3D, optionally registered, optionally more than two modalities combined, fused or co-displayed, e.g. optical imaging, e.g. direct visualization or through an arthroscope, and/or laser scan data, e.g. direct visualization or through an arthroscope, and/or virtual data, e.g. intra-articular, extra-articular, intra-osseous, hidden, not directly visible, and/or external to skin, and/or confocal imaging or microscopy images/data, e.g. direct visualization or through an arthroscope. For a detailed description of illustrative scanning and imaging techniques, see for example, Bushberg et al. The Essential Physics of Medical Imaging, $3^{rd}$ edition, Wolters, Kluwer, Lippincott, 2012.

In embodiments, 3D scanning can be used for imaging of the patient and/or the surgical site and/or anatomic landmarks and/or pathologic structures and/or tissues (e.g. damaged or diseased cartilage or exposed subchondral bone) and/or the surgeon's hands and/or fingers and/or the OR table and/or reference areas or points and/or marker, e.g. optical markers, in the operating room and/or on the patient and/or on the surgical field. 3D scanning can be accomplished with multiple different modalities including combinations thereof, for example, optical imaging, e.g. using a video or image capture system integrated into, attached to, or separate from one or more OHMDs, laser scanning, confocal imaging, optical coherence tomography, photogrammetry, active and passive stereovision and triangulation, interferometry and phase shift principles and/or imaging, wavefront sampling and/or imaging. One or more optical imaging systems or 3D scanners can, for example, be used to image and/or monitor, e.g. the coordinates, position, orientation, alignment, direction of movement, speed of movement of, Anatomic landmarks, patient surface(s), organ surface(s), tissue surface(s), pathologic tissues and/or surface(s), e.g. for purposes of registration, e.g. of the patient and/or the surgical site, e.g. one or more bones or cartilage, and/or one or more OHMDs, e.g. in a common coordinate system The surgeon's hands and/or fingers, e.g. for Monitoring steps in a surgical procedure. Select hand and/or finger movements can be associated with corresponding surgical steps. When the 3D scanner system detects a particular hand and/or finger movement, it can trigger the display of the corresponding surgical step or the next surgical step, e.g. by displaying a predetermined virtual axis, e.g. a reaming, broaching or drilling axis, a virtual cut plane, a virtual instrument, a virtual implant component etc.

Executing virtual commands, e.g. using gesture recognition or a virtual interface, e.g. a virtual touch pad One or more OHMDs, e.g. registered in a common coordinate system, e.g. with the surgical site and/or the surgeon's hands and/or fingers The use of optical imaging systems and/or 3D scanners for registration, e.g. of the surgical site and/or one or more OHMDs can be helpful when markerless registration is desired, e.g. without use of optical markers, e.g. with geometric patterns, and/or IMU's, and/or LED's, and/or navigation markers. The use of optical imaging systems and/or 3D scanners for registration can also be combined with the use of one or more of optical markers, e.g. with geometric patterns, and/or IMU's, and/or LED's, and/or navigation markers.

In embodiments, one or more 3D models and/or 3D surfaces generated by an optical imaging system and/or a 3D scanner can be registered with, superimposed with and/or aligned with one or more 3D models and/or 3D surfaces generated by another imaging test, e.g. a CT scan, MRI scan, PET scan, other scan, or combinations thereof, and/or a 3D model and/or 3D surfaces generated from or derived from an x-ray or multiple x-rays, e.g. using bone morphing technologies, as described in the specification or known in the art.

With optical imaging systems or 3D scanners, a virtual 3D model can be reconstructed by postprocessing single images, e.g. acquired from a single perspective. In this case, the reconstruction cannot be performed in real time with continuous data capture. Optical imaging systems or 3D scanners can also operate in real time generating true 3D data.

For example, with confocal microscopy using, for example, an active triangulation technique, a projector can project a changing pattern of light, e.g. blue light, onto the surgical field, e.g. an articular surface exposed by arthroscopy or a bone or a soft-tissue, e.g. using projection grids that can have a transmittance random distribution and which can be formed by sub regions containing transparent and opaque structures. By using elements for varying the length of the optical path, it can possible, for each acquired profile, to state a specific relationship between the characteristic of the light and the optical distance of the image plane from the imaging optics. A light source can produce an illumination beam that can be focused onto the surface of the surgical field, e.g. the articular surface. An image sensor can receive the observation beam reflected by the surface of the target object. A focusing system can focus the observation beam onto the image sensor. The light source can split into a plurality of regions that can be independently regulated in terms of light intensity. Thus, the intensity of light detected by each sensor element can be a direct measure of the distance between the scan head and a corresponding point on the target object.

Parallel confocal imaging can be performed, e.g. by shining an array of incident laser light beams, e.g. passing through focusing optics and a probing face, on the surgical field, e.g. an articular surface, a bone or a soft-tissue. The focusing optics can define one or more focal planes forward to the probe face in one or more positions which can be changed, e.g. by a motor or other mechanism. The laser light beams can generate illuminated spots or patterns on the surgical field and the intensity of returning light rays can be measured at various positions of the focal plane determining spot-specific positions yielding a maximum intensity of the reflected light beams. Data can be generated which can represent the topology of the three-dimensional structure of the surgical field, e.g. an articular surface, e.g. exposed and/or visible and/or accessible during arthroscopy, a bone or a soft-tissue. By determining surface topologies of adjacent portions or tissues, e.g. an adjacent articular surface or bone or soft-tissue, from two or more different angular locations and then combining such surface topologies, a complete three-dimensional representation of the entire surgical field can be obtained. Optionally, a color wheel can be included in the acquisition unit itself. In this example, a two-dimensional (2D) color image of the 3D structure of the surgical field, e.g. an articular surface, a bone or a soft-tissue, can also be taken at the same angle and orientation with respect to the structure. Thus, each point with its unique coordinates on the 2D image can correspond to a similar point on the 3D scan having the same x and y coordinates. The imaging process can be based on illuminating the target surface with three differently-colored illumination beams (e.g. red, green or blue light) combinable to provide white light, thus, for example, capturing a monochromatic image of the target portion of the surgical field, e.g. an articular surface, a bone, a cartilage or a soft-tissue, corresponding to each illuminating radiation. The monochromatic images can optionally be combined to create a full color image.

Three differently-colored illumination beams can be provided by means of one white light source optically coupled with color filters.

With optical coherence tomography (OCT), using, for example, a confocal sensor, a laser digitizer can include a laser source, e.g. coupled to a fiber optic cable, a coupler and a detector. The coupler can split the light from the light source into two paths. The first path can lead to the imaging optics, which can focus the beam onto a scanner mirror, which can steer the light to the surface of the surgical field, e.g. an articular surface, e.g. as seen or accessible during arthroscopy, a cartilage, a bone and/or a soft-tissue. A second path of light from the light source can be coupled via the coupler to the optical delay line and to the reflector. The second path of light, e.g. the reference path, can be of a controlled and known path length, as configured by the parameters of the optical delay line. Light can be reflected from the surface of the surgical field, e.g. an articular surface, a cartilage, a bone and/or a soft-tissue, returned via the scanner mirror and combined by the coupler with the reference path light from the optical delay line. The combined light can be coupled to an imaging system and imaging optics via a fiber optic cable. By utilizing a low coherence light source and varying the reference path by a known variation, the laser digitizer can provide an optical coherence tomography (OCT) sensor or a low coherence reflectometry sensor. The focusing optics can be placed on a positioning device in order to alter the focusing position of the laser beam and to operate as a confocal sensor. A series of imaged laser segments on the object from a single sample/tissue position can be interlaced between two or multiple 3D maps of the sample/tissue from essentially the same sample/tissue position. The motion of the operator between each subframe can be tracked mathematically through reference points. Operator motion can optionally be removed.

Active wavefront sampling and/or imaging can be performed using structured light projection. The scanning system can include an active three-dimensional imaging system that can include an off-axis rotating aperture element, e.g. placed in the illumination path or in the imaging path. Out-of-plane coordinates of object points can be measured by sampling the optical wavefront, e.g. with an off-axis rotating aperture element, and measuring the defocus blur diameter. The system can include a lens, a rotating aperture element and an image plane. The single aperture can help avoid overlapping of images from different object regions and can help increase spatial resolution. The rotating aperture can allow taking images at several aperture positions. The aperture movement can make it possible to record on a CCD element a single exposed image at different aperture locations. To process the image, localized cross correlation can be applied to reveal image disparity between image frames.

In another embodiment, a scanner can use a polarizing multiplexer. The scanner can project laser sheet onto the surgical cite, e.g. an articular surface, e.g. as exposed or accessible during arthroscopy, a cartilage, damaged, diseased or normal, a subchondral bone, a cortical bone etc., and can then utilize the polarizing multiplexer to optically combine multiple views of the profile illuminated by the sheet of laser light. The scanner head can use a laser diode to create a laser beam that can pass through a collimating lens which can be followed by a sheet generator lens that can convert the beam of laser light into a sheet of laser light. The sheet of laser light can be reflected by a folding mirror and can illuminate the surface of the surgical field. A system like this can optionally combine the light from two perspectives onto a single camera using passive or active triangulation. A system like this system can be configured to achieve the independence of lateral resolution and depth of field. In order to achieve this independence, the imaging system, can be physically oriented so as to satisfy the Scheimpflug principle. The Scheimpflug principle is a geometric rule that describes the orientation of the plane of focus of an optical system wherein the lens plane is not parallel to the image plane. This enables sheet of light based triangulation systems to maintain the high lateral resolution required for applications requiring high accuracy, e.g. accuracy of registration, while providing a large depth of focus.

A 3D scanner probe can sweep a sheet of light across one or more tissue surfaces, where the sheet of light projector and imaging aperture within the scanner probe can rapidly move back and forth along all or part of the full scan path, and can display, for example near real-time, a live 3D preview of the digital 3D model of the scanned tissue surface(s). A 3D preview display can provide feedback on how the probe is positioned and oriented with respect to the target tissue surface.

In other embodiments, the principle of active stereophotogrammetry with structured light projection can be employed. The surgical field can be illuminated by a 2D array of structured illumination points. 3D models can be obtained from the single image by triangulation with a stored image of the structured illumination onto a reference surface such as a plane. A single or multiple camera can be used. To obtain information in z-direction, the surgical site can be illuminated by a 2D image of structured illumination projected from a first angle with respect to the surgical site. Then the camera can be positioned at a second angle with respect to the surgical site, to produce a normal image containing two-dimensional information in x and y direction as seen at that second angle. The structured illumination projected from a photographic slide can superimpose a 2D array of patterns over the surgical site and can appear in the captured image. The information in z-direction is then recovered from the camera image of the surgical site under the structured illumination by performing a triangulation of each of the patterns in the array on the image with reference to an image of the structured illumination projected on a reference plane, which can also be illuminated from the first angle. In order to unambiguously match corresponding points in the image of the surgical site and in the stored image, the points of the structured illumination can be spatially-modulated with two-dimensional random patterns which can be generated and saved in a projectable medium. Random patterns are reproducible, so that the patterns projected onto the surgical site to be imaged are the same as the corresponding patterns in the saved image.

Accordion fringe interferometry (AFI) can employ light from two-point sources to illuminate an object with an interference fringe pattern. A high precision digital camera can be used to record the curvature of the fringes. The degree of apparent fringe curvature coupled with the known geometry between the camera and laser source enable the AFI algorithms to digitize the surface of the object being scanned. AFI can offer advantages over other scanners as lower sensitivity to ambient light variations and noise, high accuracy, large projector depth of field, enhanced ability to scan shiny and translucent surfaces, e.g. cartilage, and the ability to scan without targets and photogrammetric systems. A grating and lens can be used. Alternatively, coherent point source of electromagnetic radiation can also be generated without a grating and lens. For example, electromagnetic radiation can be emitted from a pair or pairs of optical fibers which can be used to illuminate target objects with interferometric fringes. Consequently, movement of a macroscopic grating which requires several milliseconds or more to effect a phase shift can be avoided. A fiber-based phase shifter can be used to change the relative phase of the electromagnetic radiation emitted from the exit ends of two optical fibers in a few microseconds or less. Optical radiation scattered from surfaces and subsurface regions of illuminated objects can be received by a detector array. Electrical signals can be generated by a detector array in response to the received electromagnetic radiation. A processor receives the electrical signals and calculates three-dimensional position information of tissue surfaces based on changes in the relative phase of the emitted optical radiation and the received optical radiation scattered by the surfaces. Sources of optical radiation with a wavelength between about 350 nm and 500 nm can be used; other wavelengths are possible.

Other optical imaging systems and/or 3D scanners can use the principle of human stereoscopic vision and the principle of linear projection: if straight lines are projected onto an object the lines will be curved around the object. This distortion of the lines allows conclusions to be drawn about the surface contour.

When optical imaging and/or 3D scanning is performed in the context of an arthroscopy procedure, the optical imaging and/or 3D scanning apparatus can be integrated into the endoscope, including by sharing the same fiberoptic(s) or with use of separate fiberoptic(s), e.g. in the same housing or a separate housing. An arthroscopic optical imaging and/or 3D scanning probe can be inserted through the same portal as the one used for the arthroscope, including when integrated into the arthroscope or in a common housing with the arthroscope, or it can be inserted through a second, separate portal. An optical imaging and/or 3D scanning probe used with an arthroscopic procedure can optionally be tracked by tracking the position, location, orientation, alignment and/or direction of movement using optical markers, e.g. with one or more geometric patterns, e.g. in 2D or 3D, or LED's using one or more camera or video systems integrated into, attached to, or separate from one or more OHMDs. The camera or video systems can be arranged at discrete, defined angles thereby utilizing angular information including parallax information for tracking distances, angles, orientation or alignment of optical markers attached to the probe, e.g. the arthroscope and/or optical imaging and/or 3D scanning probe. An optical imaging and/or 3D scanning probe and/or an arthroscope used with an arthroscopic procedure can optionally be tracked by tracking the position, location, orientation, alignment and/or direction of movement using navigation markers, e.g. infrared or RF markers, and a surgical navigation system. An optical imaging and/or 3D scanning probe and/or an arthroscope used with an arthroscopic procedure can optionally be tracked by tracking the position, location, orientation, alignment and/or direction of movement directly with one or more camera or video systems integrated into, attached to or separate from one or more OHMDs, wherein a computer system and software processing the information can use image processing and pattern recognition to recognize the known geometry of the one or more probes and their location within a coordinate system, e.g. in relationship to the patient, the surgical site and/or the OR table.

With any of the optical imaging and/or 3D scanner techniques, if there are holes in the acquisition and/or scan and/or 3D surface, repeat scanning can be performed to fill the holes. The scanned surface can also be compared against a 3D surface or 3D model of the surgical site, e.g. an articular surface, a cartilage, damaged or diseased or normal, a subchondral bone, a bone and/or a soft-tissue, obtained from an imaging study, e.g. an ultrasound, a CT or MRI scan, or obtained via bone morphing from x-rays as described in other parts of the specification. Discrepancies in surface geometry between the 3D model or 3D surface generated with the optical imaging system and/or the 3D scanner and the 3D surface or 3D model obtained from an imaging study or bone morphing from x-rays, can be determined; similarly, it can be determined if the surfaces or 3D models display sufficient commonality to allow for registration of the intra-operative 3D surface or 3D model obtained with the optical imaging system and/or 3D scanner and the 3D surface or 3D model obtained from the pre-operative imaging study or bone morphing from x-rays. If there is not sufficient commonality, additional scanning can be performed using the optical imaging and/or 3D scanner technique, for example to increase the spatial resolution of the scanned data, the accuracy of the scanned data and/or to fill any holes in the model or surface. Any surface matching algorithm known in the art can be utilized to register overlapping surface areas and thereby transform all surface portions into the same coordinate space, for example the Iterative Closest Point method described in Besl et al., *A Method for Registration of 3-D Shapes;* 1992; *IEEE Trans PAMI* 14(2): 239-255.

Optionally, with any of the foregoing embodiments, the optical imaging system or 3D scanner can have a form of boot or stabilization advice attached to it, which can, for example, be rested against and moved over the target tissue, e.g. an articular surface, a bone or a soft-tissue. The boot or stabilization device can help maintain a constant distance between the scanner and the target tissue. The boot or stabilization device can also help maintain a constant angle between the scanner and the target tissue. For example, a boot or stabilization device can be used with an optical imaging system or scanner used during arthroscopy, maintaining, for example, a constant distance to the articular surface or intra-articular ligament, cartilage, bone or other structures, e.g. a femoral notch or a tibial spine or a tri-radiate cartilage region or fovea capitis in a hip.

Multi-Dimensional Imaging, Reconstruction and Visualization

Various embodiments can be practiced in one, two, three or more dimensions. The following is an exemplary list of potential dimensions, views, projections, angles, or reconstructions that can be applied; this list is not exhaustive, but only exemplary. Anyone skilled in the art can identify additional dimensions, views, projections, angles or reconstructions that can be used in practicing the present disclosure. Exemplary dimensions are listed in Table 4.

TABLE 4

Exemplary list of potential dimensions, views, projections, angles, or reconstructions that can be displayed using virtual representations with optical head mounted display(s), optionally stereoscopic $1^{st}$ dimension: superoinferior, e.g. patient physical data
$2^{nd}$ dimension: mediolateral, e.g. patient physical data
$3^{rd}$ dimension: anteroposterior, e.g. patient physical data
$4^{th}$-$6^{th}$ dimension: head motion (and with it motion of glasses/OHMD) in 1, 2 or 3 dimensions
$7^{th}$-$9^{th}$ dimension: instrument motion in 1, 2 or 3 dimensions, e.g. in relationship to surgical field, organ or head including head motion
$10^{th}$-$13^{th}$ dimension: arm or hand motion in 1, 2 or 3 dimensions, e.g. in relationship to surgical field, organ or head including head motion
$14^{th}$-$16^{th}$ dimension: virtual 3D data of patient, obtained, for example from a scan or intraoperative measurements
$17^{th}$-$19^{th}$ dimension: vascular flow; in 1, 2 or 3 dimensions, e.g. in relationship to surgical field, organ or head including head motion
$20^{th}$-$22^{nd}$ dimension: temperature map (including changes induced by cryo- or hyperthermia), thermal imaging, in 1, 2 or 3 dimensions, e.g. in relationship to surgical field
$25^{th}$-$28^{th}$ dimension: metabolic map (e.g. using MRS, PET-CT, SPECT-CT), in 1, 2 or 3 dimensions, e.g. in relationship to surgical field
$29^{th}$-$32^{nd}$ dimension: functional map (e.g. using fMRI, PET-CT, SPECT-CT, PET, kinematic imaging), in 1, 2 or 3 dimensions, e.g. in relationship to surgical field or patient
$33^{rd}$-$35^{th}$ dimension: confocal imaging data and/or microscopy data in 1, 2, or 3 dimensions, e.g. in relationship to surgical field or patient, e.g. obtained through an endoscope or arthroscope or dental scanner or direct visualization/imaging of an exposed surface
$36^{th}$-$38^{th}$ dimension: optical imaging data in 1, 2 or 3 dimensions, e.g. in relationship to surgical field or patient, e.g. obtained through an endoscope or arthroscope or dental scanner or direct visualization/imaging of an exposed surface
$39^{th}$-$40^{th}$ dimension: laser scan data in 1, 2 or 3 dimensions, e.g. in relationship to surgical field or patient, e.g. obtained through an endoscope or arthroscope or dental scanner or direct visualization/imaging of an exposed surface Any oblique planes are possible. Any perspective projections are possible. Any oblique angles are possible. Any curved planes are possible. Any curved perspective projections are possible.

Any combination of 1D, 2D, and 3D data between the different types of data is possible.

Registering Virtual Data with Live Data Seen Through Optical Head Mounted Display In some embodiments, virtual data of a patient can be superimposed onto live data seen through the optical head mounted display. The virtual data can be raw data in unprocessed form, e.g. preoperative images of a patient, or they can be processed data, e.g. filtered data or segmented data.

Data Segmentation

Figure 2:
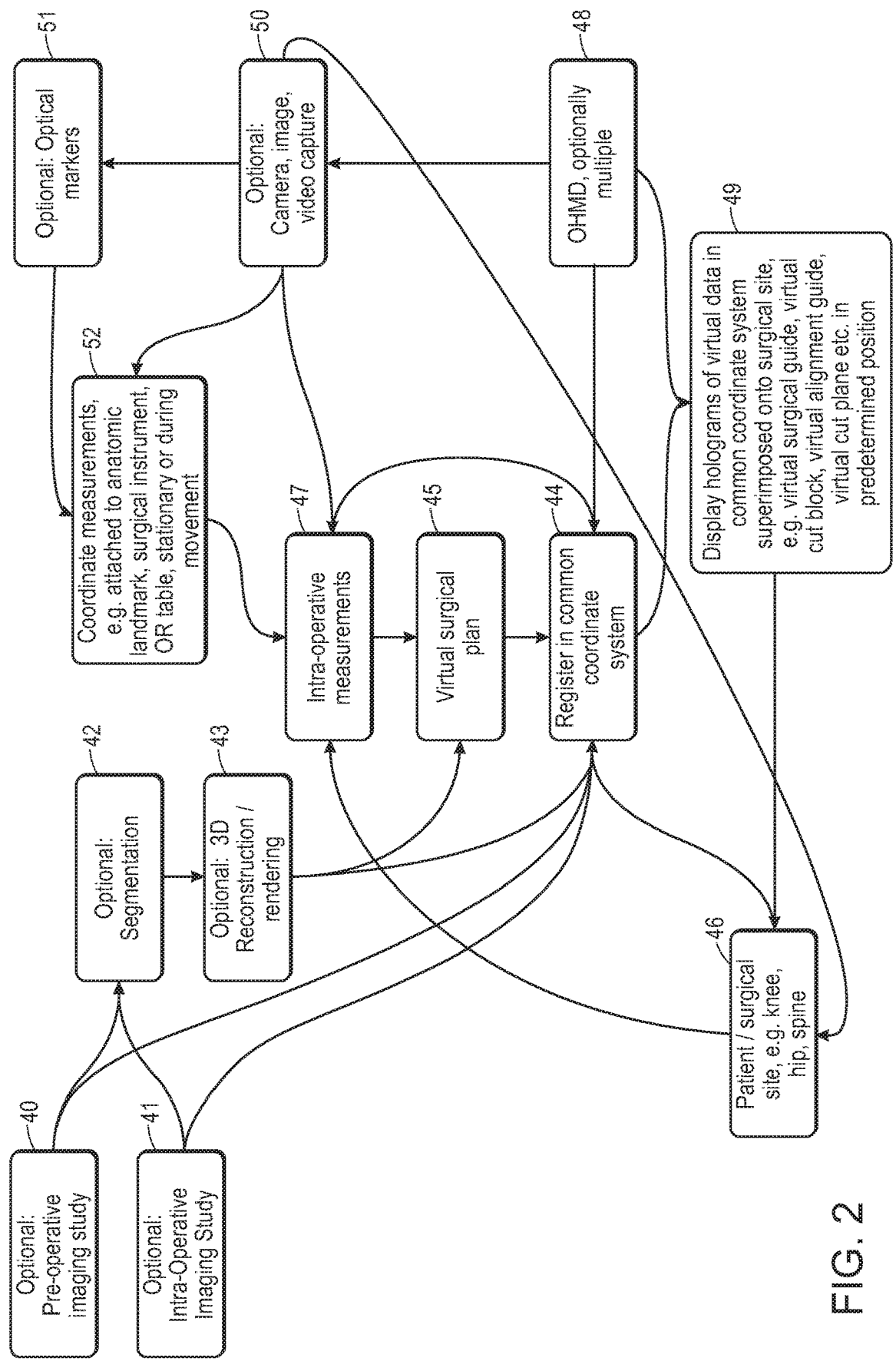
FIG. 2 shows a workflow for segmentation and select subsequent steps according to some embodiments of the present disclosure.

When images of the patient are superimposed onto live data seen through the optical head mounted display, in many embodiments image segmentation can be desirable. Any known algorithm in the art can be used for this purpose, for example thresholding, seed point techniques, live wire, deformable models, statistical models, active shape models, level set methods, marching cubes algorithms, artificial neural networks, deep learning techniques, or combinations thereof and the like. Many of these algorithms are available is part of open-source or commercial libraries, for instance the Insight Segmentation and Registration Toolkit (ITK), the Open Source Computer Vision Library OpenCV, G'MIC (GREYC's Magic for Image Computing), Caffe, or MATLAB (MathWorks, Natick, Mass.). A representative workflow for segmentation and subsequent is provided in FIG. 2. An optional pre-operative imaging study 40 can be obtained. An optional intra-operative imaging study 41 can be obtained. The pre-operative 40 or intra-operative 41 imaging study can be segmented 42, extracting, for example, surfaces, volumes or key features. An optional 3D reconstruction or 3D rendering 43 can be generated. The pre-operative 40 or intra-operative 41 imaging study and any 3D reconstruction or 3D rendering 43 can be registered in a common coordinate system 44. The pre-operative 40 or intra-operative 41 imaging study and any 3D reconstruction or 3D rendering 43 can be used for generating a virtual surgical plan 45. The virtual surgical plan 45 can be registered in the common coordinate system 44. The surgical site 46 can be registered in the common coordinate system 44. Intra-operative measurements 47 can be obtained and can be used for generating a virtual surgical plan 45. An optical head mounted display 48 can project or display digital holograms of virtual data or virtual data 49 superimposed onto and aligned with the surgical site. The OHMD 48 is configured to use a built-in camera or image capture or video capture system 50 to optionally detect and/or measure the position and/or orientation and/or alignment of one or more optical markers 51, which can be used for the coordinate measurements 52, which can be part of the intra-operative measurements 47.

Software and Algorithms for Registration

Registration of virtual data with live data can be performed using a variety of techniques know in the art. These include, but are not limited to, surface registration algorithms such as the Iterative Closest Point algorithm, statistical models, Active Shape Models, mutual information-based or other volume registration algorithms, object recognition, pattern recognition or computer vision techniques, deep learning or other artificial intelligence methods. The processed data can, for example, consist of mesh data, parametric surface data, point cloud data, volume data or a combination thereof. These methods are known in the art and have been implemented in publicly and/or commercially available code libraries and application programming interfaces (API's), such as the Insight Segmentation and Registration Toolkit (ITK), the open-source computer vision library OpenCV, Elastix, Plastimatch, or the Medical Image Registration Toolkit (MIRTK).

Superimposition of Virtual Data and Live Data by the OHMD

In some embodiments, segmented data or raw data can be superimposed on the patient's live data seen through the optical head mounted display. This superimposition can occur in unregistered form, i.e. the patient's virtual data may not be aligned with the live data seen through the optical head mounted display. In this case, the operator who is wearing the OHMD may move his/her head in a direction of orientation that will superimpose corresponding features of virtual data and live patient data. The surgeon or operator can also move and re-orient the virtual data using other means, e.g. a trackball or a virtual display interface displayed in the OHMD, unrelated to the surgeon/operator head movement. The operator can adjust the magnification of the live data so that the size, shape, length, thickness of certain features of the virtual data matches that of the live data for a given distance to the object/patient.

For example, during brain surgery, the surgeon may visually in live data look at the exposed gyri and sulci of the patient's brain. The OHMD can display a virtual 3D model of the gyri and sulci of the patient. The surgeon can optionally adjust the magnification of the 3D model so that the model will match the size or width or the length of the corresponding gyri and sulci in the live data. The surgeon can optionally adjust the transparency or opacity of the virtual data displayed in the OHMD. The ratio of virtual vs. live data transmitted through the OHMD can be 1:10, 1:9, 1:8, 1:5, 1:2, 1:1, 2:1, 3:1, 5:1, 8:1, 10:1, as well as fractions or multiples thereof. Any combination of transparency or opacity of virtual data and live data is possible. The surgeon can move his/her head in a direction or orientation that will superimpose virtual features, e.g. the patient's gyri and sulci, with the live patient data.

Once the data have been superimposed, the surgeon can optionally register the virtual data with the live data. This registration can be as simple as described here, e.g. a visual confirmation from the surgeon that virtual and live data are substantially matching or substantially superimposed. At this time, the surgeon can optionally reference the virtual data and/or the coordinate system of the virtual data in 2, 3 or more dimensions with the live data and/or the coordinate system of the live data. Once the data are registered, the surgeon can move his/her head into any desired position or orientation, for example for viewing the patient's brain or a lesion and adjacent, e.g. sensitive, anatomy from different view angles. The IMU of the OHMD will register the head movement, the direction of the head movement, the new head position and head orientation. The change in location and orientation of the surgeon's head can be simultaneously or, if desired, non-simultaneously applied to the virtual data which can now be superimposed with the resultant new position and orientation in relationship to the live data. In addition, when the surgeon moves his/her head or body further away from the target anatomy, the change in position and the increase in distance from the target anatomy can be measured by the IMU. Depending on the distance from the IMU, a magnification or minification factor can be applied to the virtual data so that the size, shape and dimensions of the virtual data will, in some embodiments, be close to or match the size, shape and dimensions of the live data, irrespective of the distance, location and orientation of the surgeon's head.

For purposes of registration of virtual data and live data, the OHMD can be optionally placed in a fixed position, e.g. mounted on a stand or on a tripod. While the OHMD is placed in the fixed position, live data can be viewed by the surgeon and they can be, optionally recorded with a camera and/or displayed on a monitor. Virtual data can then be superimposed and the matching and registration of virtual data and live data can be performed. At this point, the surgeon or an operator can remove OHMD from the fixed position and the surgeon can wear the OHMD during the surgical procedure.

The virtual data can optionally be displayed using a different color, e.g. red, green, yellow etc. Optionally, only the outline of select features of the virtual data may be displayed. For example, these features can be the sulci of the patient's brain (e.g. with a black line or black or lines with other colors), with no visualization of the gyri that these sulci border. Or, for example, only a lesion, e.g. a tumor such as, in the example of the brain, glioblastoma, can be displayed. Or combinations of virtual data of normal tissue and pathologic tissue can be displayed.

The virtual data can be registered with the live data seen through the optical head mounted display. The registration can occur using any method known in the art for registering or cross-referencing virtual and live data, in 2, 3, or more dimensions.

In some embodiments, the registration of the virtual data and the live data will be maintained through the surgical procedure. In some embodiments, the registration of the virtual data and the live data will be maintained during select portions of the surgical procedure or the surgical plan, which can be or can include a virtual, e.g. a preoperatively generated, surgical plan.

In some embodiments, the superimposition of the virtual data and the live data by the OHMD occurs simultaneously. In some embodiments, the superimposition of the virtual data and the live data by the OHMD is not simultaneous. For example, the virtual data can be superimposed intermittently.

Virtual data can be transparent, translucent or opaque. If virtual data are opaque, they may be displayed intermittently so that the operator or surgeon can see how they project in relationship to the live data of the patient.

If combinations of virtual data are displayed simultaneously with the live data, the different types of virtual data can be displayed with different colors. Representative combinations of virtual and live data are provided below. The following is only illustrative in nature and by no means meant to be limiting:

Live data: the patient's brain; surgically exposed gyri and sulci.

Live data: surgical instrument, e.g. biopsy needle or cutting tool

Virtual data: the patient's brain with gyri and sulci derived and optionally segmented from an imaging modality, e.g. a CT scan or an MRI scan Virtual data: a brain tumor, deep seated inside the brain Virtual data: the same surgical instrument currently used by the surgeon, in a virtual representation of the instrument, the virtual data indicating the desired orientation, location or direction of the surgical instrument.

Any of the foregoing virtual data can be displayed in two dimensions or three dimensions.

Multi-dimensional displays as outlined in other sections of the specification are possible.

For example, the patient's normal tissue, e.g. normal brain tissue, can optionally be displayed in two dimensions, e.g. using grey level images, while the patient's abnormal tissue, e.g. a stroke, a hemorrhage or a tumor, can be displayed in three dimensions. Any combination of 2D, 3D, and multi-dimensional images is possible for display by the OHMD; any combination of 2D, 3D, and multi-dimensional images can be superimposed on live patient data by the OHMD.

The virtual 2D, 3D, and multi-dimensional data can be generated or acquired by different data acquisition technologies, e.g. different imaging tests etc.

Locking or Moving of Virtual Data

In some embodiments, virtual data can be locked in relationship to the surgeon or operator or in relationship to the patient or a certain target anatomy within a patient. This means even if the surgeon moves his or her head or the body or parts of the patient's anatomy are being moved, the virtual data will not move in the OHMD display. For example, once registration has occurred, the OHMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, the virtual data will not move, but are being displayed within the same location.

In some embodiments, virtual data can move in relationship to the surgeon or operator or in relationship to the patient or a certain target anatomy within a patient. This means if the surgeon moves his or her head or the body or parts of the patient's anatomy are being moved, the virtual data will move in the OHMD display. For example, once registration has occurred, the OHMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, the virtual data will move and change location and orientation the same way how the surgeon moves his/her head or body, typically reflecting the change in perspective or view angle that the surgeon obtained by moving his or her head or body.

Optionally the moving of the virtual data can be at greater virtual distance or greater angle or lesser virtual distance or lesser angle than the movement of the surgeon's head or body.

Improving the Accuracy of Moving or Re-Orienting Virtual Data

Once registration between virtual data and physical data has occurred, the moving or re-orienting of virtual data to follow, for example, the surgeon's head movements or body movements or operating arm or hand movements, or the movements of the patient or certain body parts of the patient can be accomplished, for example, by monitoring the movement and change in location and/or orientation of the surgeon's head using the IMU of the OHMD. In some embodiments, optical or RF tracker's or other tracking devices known in the art can be applied to the OHMD and/or the patient including select body parts or target tissues of the patient, e.g. the patient's knee. Using standard surgical navigation techniques known in the art, the spatial location of the optical or RF trackers can be recorded, for example for a starting pose or position or location. Movement of the trackers, e.g. induced by movement of the surgeon's head or body or by movement of at least a part of the patient, can then be tracked using the navigation system. The information on positional change, orientational change or movement direction of the surgeon's head or the patient or both can then be used to update the virtual data, or the display of the virtual data in the OHMD, or both correspondingly. In this manner, the virtual data and the live data can be superimposed by the OHMD, typically in an accurate manner.

Optionally, positional, orientational, directional data and the like generated by the IMU can be used in conjunction with such data generated by a surgical navigation system. A combination of data can be beneficial for more accurate measurement of changes in position or orientation of the surgeon's head, body, operating arm, hand, or the patient.

Use of Virtual Data in 2 or More Dimensions

In some embodiments, the OHMD can display a 2D virtual image of the patient. The image can be a transmission type image, e.g. an x-ray or CT scout scan. The image can be a cross-sectional image of select anatomy of the patient. The image can be an original image or a reformatted, reconstructed or segmented or partially segmented image of the patient.

In some embodiments, a surgeon will look through the OHMD at the patient's live data, e.g. the exposed brain surface with the patient's gyri and sulci. The surgeon can register virtual data of the patient, e.g. an MRI scan of the patient's brain, relative to the patient's live data. Registration can occur in 2, 3 or more dimensions. Registration of virtual data in relationship to live data can include registration of different types of virtual data, e.g. different types of normal or diseased tissue, different imaging modalities used, different dimensions used for different types of normal or diseased tissue etc. More than one 2D scan plane can be displayed simultaneously. These 2D scan planes can be parallel or non-parallel, orthogonal or non-orthogonal at variable angles.

Scrolling Through, Moving of Virtual Data Superimposed onto Live Data

In some embodiments, a surgeon or operator may optionally scroll through a set of consecutive or non-consecutive virtual 2D image data or 3D image data (optionally sectioned into 2D slices) which are being superimposed onto the patient's live data, typically live data from the same anatomic region, e.g. a brain, a spine, a hip, a knee etc. The scrolling can be directed through any type of user interface, known in the art. For example, a surgeon can use a virtual interface projected by the OHMD where he or she can move a virtual arrow up or down or left or right to scroll the images backward or forward or, for example, to rotate the images or to display them in different multiplanar angles or to change the view angle or projection angle.

Optionally, the surgeon can scroll through the virtual image data or move virtual image data by moving his head back and forth, e.g. for scrolling backward or forward in a virtual image volume. The surgeon can move his or her head left or right for example, to rotate the images or to display them in different multiplanar angles or to change the view angle or projection angle of a 3D image.

Optionally, the surgeon can scroll through the virtual image data by moving his or her hand or finger or any other body part back and forth, e.g. for scrolling backward or forward in a virtual image volume. The surgeon can move his or her hand or finger or any other body part back and forth left or right for example, to rotate the images or to display them in different multiplanar angles or to change the view angle or projection angle. The surgeon can move his or her hand or finger in a spinning or rotating movement to spin or rotate the virtual data. Any combination of head or hand or eye and other body signals can be used for changing the display of the virtual data.

Optionally, these display changes of the virtual data can be executed in the OHMD using the same location, position, orientation, angular, direction and movement related changes that are made by the surgeon's body part used to trigger the change in display. Alternatively, any one of location, position, orientation, angular, direction and movement related changes of the virtual data can be executed using a magnification factor or a minification factor in relationship to the changes in location, position, orientation, angular, direction and movement of the surgeon's body part. The magnification or minification factors can be linear or non-linear, e.g. exponential or logarithmic. In some embodiments, the further the surgeon's body part controlling the movement of the virtual data in the OHMD display moves away from its original position, the greater the induced change on the movement of the virtual data in the OHMD. In some embodiments, the further the surgeon's body part controlling the movement of the virtual data in the OHMD display moves away from its original position, the smaller the induced change on the movement of the virtual data in the OHMD.

When the computer processor scrolls through 2D images, the registration can be maintained for each 2D image or 2D image slice, e.g. from a 3D dataset [e.g. an ultrasound, CT, MRI, SPECT, SPECT-CT, PET, PET-CT], in relationship to the corresponding cross-section of the physical body of the patient. For example, after an initial or subsequent registration, an imaging study, e.g. a 3D dataset [e.g. an ultrasound, CT, MRI, SPECT, SPECT-CT, PET, PET-CT], the physical body of the patient or the physical surgical site, optionally one or more physical tools, physical instruments, and/or physical implants, optionally one or more virtual tools, virtual instruments, virtual implants and/or at least portions of a virtual surgical plan, and one or more OHMDs can be registered in the same coordinate system, e.g. a common coordinate system. The imaging study can be displayed by the OHMD in three dimensions with virtual anatomic structures, surfaces, organs, volumes or body portions aligned with and superimposed onto corresponding physical anatomic structures, surfaces, organs, volumes or body portions. The imaging study can be displayed by the OHMD in two dimensions, e.g. a 2D slice mode, with virtual anatomic structures, surfaces, organs, volumes or body portions aligned with and superimposed onto corresponding physical anatomic structures, surfaces, organs, volumes or body portions. For example, the computer processor can match a virtual 2D image, e.g. an imaging data slice, with a corresponding 2D slice of physical tissue in the live patient. Thus, virtual 2D imaging data can be superimposed onto and/or aligned with a corresponding 2D cross-section of the physical tissue of the patient or can be displayed superimposed onto and/or aligned with the corresponding coordinates and the associated tissue in the physical tissue and live, physical data of the patient. As the surgeon scrolls through the 2D imaging data or slices, their position and/or orientation can move in the OHMD display to the next, corresponding portion of the physical tissue or physical body portion of the patient. If the imaging slice has a thickness of 5 mm, the corresponding cross-section of physical tissue inside the patient can also be 5 mm. Optionally, the imaging slice can be thicker or thinner than the corresponding cross-section of physical tissue inside the patient; in this case, for example, the imaging slice can be centered over the corresponding cross-section of physical tissue of the patient. For example, a 10 mm thick imaging slice or slice of imaging data can be superimposed onto and/or aligned with a 5 mm thick corresponding cross-section of physical tissue inside the patient, in which case, for example, the imaging slice or slice of imaging data can extend 2.5 mm in either direction relative to the physical tissue inside the patient. A 3 mm thick imaging slice or slice of imaging data can be superimposed onto and/or aligned with a 5 mm thick corresponding cross-section of physical tissue inside the patient, in which case, for example, the physical tissue inside the patient can extend 1.0 mm in either direction relative to the imaging slice or slice of imaging data. The imaging slice or imaging data can also be superimposed onto and/or aligned with the physical tissue inside the patient at a defined offset and/or overlap. For example, a 5 mm imaging slice or slice of imaging data can be superimposed onto and/or aligned with a 2 mm slice or cross-section of physical tissue inside the patient, wherein 2 mm of the imaging slice and or slice of imaging data can overlap the cross-section of physical tissue and 3 mm cannot be overlapping in at least one direction.

The surgeon can change the orientation of the imaging data displayed by the OHMD in 2D slice or cross-section format, e.g. to view the imaging data in a sagittal, coronal, axial, oblique sagittal, oblique coronal, oblique axial, curved sagittal, curved coronal, curved axial or any desired orientation. The imaging data, e.g. 3D imaging dataset [e.g. an ultrasound, CT, MRI, SPECT, SPECT-CT, PET, PET-CT], can be maintained in their registration in the coordinate system and the 2D imaging data can be superimposed onto and/or aligned with a corresponding 2D cross-section or slice of the physical tissue of the patient or can be displayed superimposed onto and/or aligned with the corresponding coordinates and the associated tissue in the physical tissue and live, physical data of the patient. As the surgeon scrolls through the (virtual) imaging data, e.g. from anterior to posterior, medial to lateral, superior to inferior, the next slice or cross-section of imaging data can move to the corresponding next slice or cross-section of the physical tissue of the live patient.

The term imaging slice, slice, and cross-section can be used interchangeably in this context for imaging data and physical tissue of the live patient.

In some embodiments, the scrolling can be automatic. For example, a physical tool, a physical instrument, a physical implant or any other physical device can be tracked using any of the registration and tracking methods described in the specification. As the physical tool, physical instrument, physical implant or any other physical device is moved, rotated, tilted or advanced inside or in the physical tissue of the patient, the computer processor can use the tracking information and the location, orientation, alignment, and/or direction of movement information of the physical tool, physical instrument, physical implant or any other physical device inside the coordinate system and inside the physical tissue of the live patient and can move a 2D imaging slice or cross-section to coincide with, intersect with, be tangent with, be at a predetermined offset with, be at a predetermined angle with, be orthogonal with a portion of the physical tool, physical instrument, physical implant or any other physical device, e.g. tip or distal end of the physical tool, physical instrument, physical implant or any other physical device. Thus, as the physical tool, physical instrument, physical implant or any other physical device is moved, rotated, tilted or advanced inside or in the physical tissue of the patient, the computer processor can display a slice that corresponds and coincides with, intersects with, is tangent with, is at a predetermined offset with, is at a predetermined angle with, is orthogonal with the new location of the physical tool, physical instrument, physical implant or any other physical device. As the physical tool, physical instrument, physical implant or any other physical device is moved, rotated, tilted or advanced inside or in the physical tissue of the patient from a first position or a first set of coordinates to a second position or a second set of coordinates in the coordinate system, the computer processor can initially display a first 2D imaging slice or cross-section that corresponds and coincides with, intersects with, is tangent with, is at a predetermined offset with, is at a predetermined angle with, is orthogonal with the first position or the first set of coordinates of the physical tool, physical instrument, physical implant or any other physical device and the computer processor can display a second 2D imaging slice or cross-section that corresponds and coincides with, intersects with, is tangent with, is at a predetermined offset with, is at a predetermined angle with, is orthogonal with the second position or the second set of coordinates of the physical tool, physical instrument, physical implant or any other physical device. The process can be repeated for a third, fourth, fifth, and any number of positions or coordinates of the physical tool, physical instrument, physical implant or any other physical device as it is moved and/or advanced inside the physical tissue of the patient.

In some embodiments, the computer processor can maintain the 2D imaging slice or imaging cross-section projected by the OHMD superimposed and/or aligned with the physical tissue of the patient always in a constant or the same position and/or orientation relative to the physical tool, physical instrument, physical implant, e.g. intersecting with the tip or located at the tip and/or orthogonal or at a predetermined offset or at a predetermined angle with the tip of the physical tool, physical instrument, physical implant. This can be advantageous, for example, when a biopsy needle or a tissue harvester is moved or advanced through soft-tissue or hard tissue, e.g. during a brain, heart, lung, thyroid, parathyroid, liver, spleen, kidney, adrenal, prostate, ovary, bone, cartilage or any other biopsy. This can also be advantageous, for example, for any surgical procedure where a physical surgical tool, physical surgical instrument, physical implant or any other physical surgical device is moved or advanced through soft-tissue or hard tissue, e.g. through a brain, heart, lung, thyroid, parathyroid, liver, spleen, kidney, adrenal, prostate, ovary, bone, cartilage or any other tissue. For example, as a surgeon moves and advances a physical needle, physical awl, physical screw through a vertebra or a portion of a vertebra, e.g. a pedicle [for example for a spinal fusion], the computer processor can move and/or advance 2D imaging slices through the vertebra, portion of the vertebra, e.g. the pedicle and the imaging slices can always be located at the tip of the tracked physical needle, physical awl or physical screw and can always be orthogonal to the long axis of the physical needle, physical awl or physical screw irrespective where the surgeon moves the physical needle, physical awl or physical screw. Thus, as the surgeon moves the physical needle, physical awl or physical screw from a first position with a first set of coordinates to a second position with a second set of coordinates, the OHMD can display a first 2D imaging slice through the pedicle at the first position, with the 2D imaging slices intersecting with or located at the tip of the physical needle, physical awl or physical screw and orthogonal with the long axis of the physical needle, physical awl or physical screw and the OHMD can then display a second 2D imaging slice through the pedicle at the second position, with the 2D imaging slices intersecting with or located at the tip of the physical needle, physical awl or physical screw and orthogonal with the long axis of the physical needle, physical awl or physical screw. In this manner, the surgeon can always monitor the location of the physical needle, physical awl or physical screw inside the physical tissue of the patient and relative to the 2D images obtained pre- or intra-operatively from the patient. This can be beneficial, for example, when complex 3D structures, e.g. a spine reconstructed in 3D from a CT scan or MRI scan, can potentially obscure fine anatomic detail inside the patient due to superimposition of multiple structures. This can also be beneficial during spinal fusion surgery with pedicle screws since the cortex of the pedicle and the inner pedicle wall or endosteum can be difficult to see on a superimposed and/or aligned 3D display of the spine, e.g. reconstructed from a CT scan, while it can be readily visible on the superimposed and/or aligned 2D imaging, e.g. a CT slice superimposed and/or aligned with the corresponding physical tissue/pedicle slice of the patient.

In some embodiments, the computer processor can maintain the 2D imaging slice or imaging cross-section projected by the OHMD superimposed and/or aligned with the physical tissue of the patient always in a constant or the same position relative to the physical tool, physical instrument, physical implant, e.g. intersecting with the tip or located at the tip, while maintaining a fixed anatomic orientation, e.g. sagittal, coronal, axial, oblique sagittal, oblique coronal, oblique axial, curved sagittal, curved coronal, curved axial. This can be advantageous, for example, when a biopsy needle or a tissue harvester is moved or advanced through soft-tissue or hard tissue, e.g. during a brain, heart, lung, thyroid, parathyroid, liver, spleen, kidney, adrenal, prostate, ovary, bone, cartilage or any other biopsy. This can also be advantageous, for example, for any surgical procedure where a physical surgical tool, physical surgical instrument, physical implant or any other physical surgical device is moved or advanced through soft-tissue or hard tissue, e.g. through a brain, heart, lung, thyroid, parathyroid, liver, spleen, kidney, adrenal, prostate, ovary, bone, cartilage or any other tissue. For example, as a surgeon moves and advances a physical needle, physical awl, physical screw through a vertebra or a portion of a vertebra, e.g. a pedicle [for example for a spinal fusion], the computer processor can move and/or advance 2D imaging slices through the vertebra, portion of the vertebra, e.g. the pedicle, and the imaging slices can always be located at the tip of the tracked physical needle, physical awl or physical screw and can always be in a fixed anatomic orientation, e.g. in a sagittal, coronal, axial, oblique sagittal, oblique coronal, oblique axial, curved sagittal, curved coronal, or curved axial plane. Thus, as the surgeon moves the physical needle, physical awl or physical screw from a first position with a first set of coordinates to a second position with a second set of coordinates, the OHMD can display a first 2D imaging slice through the pedicle at the first position, with the 2D imaging slices intersecting with or located at the tip of the physical needle, physical awl or physical screw and, for example, oriented in a coronal plane or a sagittal plane or an axial plane at the first position or first coordinates and the OHMD can then display a second 2D imaging slice through the pedicle at the second position, with the 2D imaging slices intersecting with or located at the tip of the physical needle, physical awl or physical screw and, for example, oriented in a coronal plane or a sagittal plane or an axial plane at the second position or second coordinates. In this manner, the surgeon can always monitor the location of the physical needle, physical awl or physical screw inside the physical tissue of the patient and relative to the 2D images obtained pre- or intra-operatively from the patient. This can be beneficial, for example, when complex 3D structures, e.g. a spine reconstructed in 3D from a CT scan or MRI scan, can potentially obscure fine anatomic detail inside the patient due to superimposition of multiple structures. This can also be beneficial during spinal fusion surgery with pedicle screws since the cortex of the pedicle and the inner pedicle wall or endosteum can be difficult to see on a superimposed and/or aligned 3D display of the spine, e.g. reconstructed from a CT scan, while it can be readily visible on the superimposed and/or aligned 2D imaging, e.g. a CT slice superimposed and/or aligned with the corresponding physical tissue/pedicle slice of the patient. In some embodiments, the 2D image(s) displayed by the OHMD can be maintained by the computer processor in a fixed location, e.g. the center of a pedicle, while the physical tool, physical instrument, physical implant or physical device is moved, e.g. inside the pedicle.

In some embodiments, more than one 2D slice can be displayed by the OHMD, for example at least two or more of a sagittal, coronal, axial, oblique sagittal, oblique coronal, oblique axial, curved sagittal, curved coronal, or curved axial slices or images. The two or more 2D slices can be moved through the tissue, e.g. anterior, posterior, medial, lateral, superior, inferior, by the computer processor of the OHMD display following the movement of a tracked physical tool, physical instrument, physical implant or physical device so that the two or more 2D slices displayed by the computer processor of the OHMD display are always superimposed onto and/or aligned with a corresponding slice of the patient's physical tissue in the coordinate system while the physical tool, physical instrument, physical implant or physical device is moved in the patient's tissue and in the coordinate system and their position and/or orientation relative to the physical tool, physical instrument, physical implant or physical device can be maintained during the movement. The two or more 2D slices or cross-sections can intersect in the display of the OHMD. The intersection can be, for example, centered around an anatomic structure or maintained [e.g. during movement of the patient, the surgical site, the OHMD, the physical tool, physical instrument, physical implant or physical device] at or over an anatomic structure or site, e.g. the center of a pedicle or a line through the pedicle. The intersection can be centered around or maintained at or around a physical surgical tool, physical surgical instrument, physical implant or any other physical surgical device, e.g. around a long axis or other portion of the physical surgical tool, physical surgical instrument, physical implant or any other physical surgical device. The maintaining of the intersection of the two or more imaging planes over a portion of the physical surgical tool, physical surgical instrument, physical implant or any other physical surgical device can be performed by the computer processor while the tracked physical surgical tool, physical surgical instrument, physical implant or any other physical surgical device are moved inside the physical tissue of the patient, e.g. while an awl is advanced inside a pedicle.

2D imaging data or imaging slices or cross-sections as well as 3D displays, e.g. a 3D reconstruction from a CT or MRI scan [e.g. of a spine, or a hip, or a knee] and any virtual data, e.g. a predetermined path, predetermined start or end point, predetermined virtual axis, virtual tool, virtual instrument, virtual implant, virtual device, displayed by the OHMD can be magnified by the OHMD display in any of the embodiments throughout the specification. The magnification can be centered around an anatomic structure, e.g. the center of a pedicle or a line through the pedicle, e.g. a center line of a pedicle. The magnification can be centered around the center of a left pedicle, the center of a right pedicle, the center of both pedicles, a left facet joint, a right facet joint, a lamina, a spinous process, a posterior vertebral wall or an anterior vertebral wall. Other locations are possible, e.g. an anterior third of a pedicle, a posterior third of a pedicle. The magnification can be centered around a physical surgical tool, physical surgical instrument, physical implant or any other physical surgical device, e.g. around a long axis of the physical surgical tool, physical surgical instrument, physical implant or any other physical surgical device. The magnification can be centered around a virtual surgical guide [e.g. a virtual axis], a virtual surgical tool, virtual surgical instrument, virtual implant or any other virtual surgical device, e.g. around a long axis of the virtual surgical tool, virtual surgical instrument, virtual implant or any other virtual surgical device.

In surgery employing a surgical microscope, 2D or 3D images [e.g. pre- or intra-operatively obtained images] and any virtual data, e.g. a predetermined path, predetermined start or end point, predetermined virtual axis, virtual tool, virtual instrument, virtual implant, virtual device, can be magnified in the OHMD display by a computer processor, optionally matching the magnification of the microscope. Optionally, the magnification of the 2D or 3D imaging studies and any virtual data, e.g. a predetermined path, predetermined start or end point, predetermined virtual axis, virtual tool, virtual instrument, virtual implant, virtual device, displayed by the OHMD can be greater than that of the microscope and the microscopic view of the physical tissue of the patient or it can be less than that of the microscope and the microscopic view of the physical tissue of the patient. The magnification of the 2D or 3D imaging studies and any virtual data, e.g. a predetermined path, predetermined start or end point, predetermined virtual axis, virtual tool, virtual instrument, virtual implant, virtual device, displayed by the OHMD can be centered around the center of the microscopic view or the central axis of the lens system of the microscopy system. The magnification of the 2D or 3D imaging studies and any virtual data, e.g. a predetermined path, predetermined start or end point, predetermined virtual axis, virtual tool, virtual instrument, virtual implant, virtual device, displayed by the OHMD can be centered around an anatomic structure, e.g. the center of a pedicle or a line through the pedicle, e.g. a center line of a pedicle. The magnification can be centered around the center of a left pedicle, the center of a right pedicle, the center of both pedicles, a left facet joint, a right facet joint, a lamina, a spinous process, a posterior vertebral wall or an anterior vertebral wall. Other locations are possible, e.g. an anterior third of a pedicle, a posterior third of a pedicle. The magnification can be centered around a physical surgical tool, physical surgical instrument, physical implant or any other physical surgical device, e.g. around a long axis of the physical surgical tool, physical surgical instrument, physical implant or any other physical surgical device. The magnification can be centered around a virtual surgical guide [e.g. a virtual axis], a virtual surgical tool, virtual surgical instrument, virtual implant or any other virtual surgical device, e.g. around a long axis of the virtual surgical tool, virtual surgical instrument, virtual implant or any other virtual surgical device.

Use of Virtual Data in 3 or More Dimensions

In some embodiments, the OHMD can display a 3D virtual image of the patient. A 3D representation of the patient can include a 3D display of different types of anatomy, for example in an area of intended surgery or a surgical site.

A 3D reconstruction of image data or other data of the patient can be generated preoperatively, intraoperatively and/or postoperatively. A virtual 3D representation can include an entire anatomic area or select tissues or select tissues of an anatomic area. Different tissues can be virtually displayed by the OHMD in 3D using, for example, different colors. Normal tissue(s) and pathologic tissue(s) can be displayed in this manner.

Normal tissue can, for example, include brain tissue, heart tissue, lung tissue, liver tissue, vascular structures, bone, cartilage, spinal tissue, intervertebral disks, nerve roots. Any tissue can be visualized virtually by the OHMD.

Registration of Virtual Data and Live Data of a Patient, for Example Over a Surgical Site In some embodiments, virtual data of a patient displayed by an OHMD and live data of a patient seen through an OHMD are spatially registered in relationship to each other, for example in a common coordinate system, for example with one or more optical OHMDs in the same common coordinate system. Virtual and physical surgical instruments and implant components can also be registered in the common coordinate system. Spatial co-registration can have the benefit that the simultaneous display of virtual and live data of the patient is not affected or less affected when the surgeon moves his or her head or body, when the OHMD moves or when the patient moves. Thus, the view perspective of the live data of the patient seen by the surgeon's eyes through the OHMD, e.g. the live surgical field, can stay the same as the view perspective of the virtual data of the patient seen by the surgeon's eyes through the display of the OHMD unit, e.g. the virtual surgical field, virtual surgical plane, virtual paths, virtual cut paths or planes, projected into the surgeon's eyes, even as the surgeon moves his or her head or body. In this manner, the surgeon does not need to re-think or adjust his hand eye coordination since live data of the patient seen through the surgeon's eye and virtual data of the patient seen through the OHMD display are superimposed, which is fundamentally different from other approaches such as surgical navigation which employ a separate computer monitor in the OR with a view angle for the surgeon that is different than his or her view angle for the live data of the patient and the surgical field. Also, with surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations the first and the second virtual instruments are compared.

With guidance in mixed reality environment, e.g. with stereoscopic display like an electronic holographic environment, a virtual surgical guide, tool, instrument or implant can be superimposed onto the joint, spine or surgical site. Further, the physical guide, tool, instrument or implant can be aligned with the 2D or 3D representation of the virtual surgical guide, tool, instrument or implant. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, virtual data can move in relationship to the surgeon or operator or in relationship to the patient or a certain target anatomy within a patient. This means if the surgeon moves his or her head or the body or parts of the patient's anatomy are being moved, the virtual data will move in the OHMD display. For example, once registration of the OHMD, the virtual data of the patient and the live data of the patient in a common coordinate system has occurred, the OHMD can display a virtual image of a target tissue or adjacent tissue. The virtual image of the target tissue or adjacent tissue can be, for example, an image of or through a tumor or other type of pathologic tissue or a spine or a spinal pedicle. As the surgeon or operator moves his or her head or body during the surgical procedure, the virtual data will move and change location and orientation the same way how the surgeon moves his/her head or body, typically reflecting the change in perspective or view angle that the surgeon obtained by moving his or her head or body. The virtual data can include a 3D representation of a surgical tool or instrument such as a needle for kyphoplasty or vertebroplasty, where the virtual representation of the needle shows its intended location, orientation or path in relationship to the spine and/or a pedicle. The virtual data can also include a medical device, such as a pedicle screw, wherein the virtual data of the pedicle screw shows its intended location, orientation or path in relationship to the spine, and/or a pedicle, and/or a vertebral body.

In some embodiments, registration is performed with at least three or more points that can be superimposed or fused into a common object coordinate system for virtual data and live data. Registration can also be performed using a surface or a 3D shape of an anatomic structure present in both virtual data and live data of the patient. In this case the virtual surface can be moved until it substantially matches the live surface of the patient or the virtual shape can be moved until it substantially matches the live shape of the patient.

Registration of virtual data of a patient and live data of a patient can be achieved using different means. The following is by no means meant to by limiting, but is only exemplary in nature.

Registration of Virtual Patient Data and Live Patient Data Using Directly or Indirectly Connected Object Coordinate Systems Registration of virtual and live data of the patient can be performed if the virtual data, e.g. imaging data of the patient, are acquired with the patient located in a first object coordinate system and the live data, e.g. during surgery, are observed or acquired with the patient located in a second object coordinate system, wherein the first and the second object coordinate system can be connected by direct, e.g. physical, or indirect, e.g. non-physical, means. A direct connection of the first and second object coordinate system can be, for example, a physical connection between the first and second object coordinate system. For example, the patient can be moved from the first to the second object coordinate system along the length of a tape measure. Or the patient can be scanned inside a scanner, e.g. a CT scanner or MRI scanner, and the scanner table can be subsequently moved out of the scanner for performing a surgical procedure with the patient still located on the scanner table. In this case, the scanner table can be a form of physical connection between the first and the second object coordinate system and the length of the table movement between the scan position and the outside the scanner position (for the live data, e.g. the surgical procedure) can define the coordinate transformation from the first to the second object coordinate system.

An indirect connection between the first (virtual data) and second (live data) object can be established if the patient is moved between the acquiring the virtual data, e.g. using an imaging test, and the live data, e.g. while performing a surgical procedure, along a defined path, wherein the direction(s) and angle(s) of the path are known so that the first and the second object coordinate system can be cross-referenced and an object coordinate transfer can be applied using the known information of the defined path and virtual data of the patient, live data of the patient and the OHMD can be registered in a common coordinate system. Virtual and physical surgical instruments and implant components can also be registered in the common coordinate system.

Registration of virtual patient data and live patient data is also possible without directly or indirectly connected object coordinate systems using other means and methods as will be explained in the following paragraphs and columns, for example when the patient performed one or more movements of unknown direction, length or magnitude. Combinations of all different registration methods described in the specification are possible, e.g. for switching registration methods during a procedure or for simultaneously using multiple registration methods, e.g. for enhancing the accuracy of the registration.

Registration Using Spatial Mapping

Live data, e.g. live data of the patient, the position and/or orientation of a physical instrument, the position and/or orientation of an implant component, the position and/or orientation of one or more OHMDs, can be acquired or registered, for example, using a spatial mapping process. This process creates a three-dimensional mesh describing the surfaces of one or more objects or environmental structures using, for example and without limitation, a depth sensor, laser scanner, structured light sensor, time of flight sensor, infrared sensor, or tracked probe. These devices can generate 3D surface data by collecting, for example, 3D coordinate information or information on the distance from the sensor of one or more surface points on the one or more objects or environmental structures. The 3D surface points can then be connected to 3D surface meshes, resulting in a three-dimensional surface representation of the live data. The surface mesh can then be merged with the virtual data using any of the registration techniques described in the specification.

The live data can be static, or preferably, it can be continuously updated with additional information to incorporate changes in the position or surface of the one or more objects or environmental structures. The additional information can, for example be acquired by a depth sensor, laser scanner, structured light sensor, time of flight sensor, infrared sensor, or tracked probe.

For initial spatial mapping and updating of mapping data, commonly available software code libraries can be used. For example, this functionality can be provided by the Microsoft HoloToolkit or the Google Project Tango platform. Various techniques have been described for spatial mapping and tracking including those described in U.S. Pat. No. 9,582,717, which is expressly incorporated by reference herein.

Registration of Virtual Patient Data and Live Patient Data Using Visual Anatomic Features
a) Visual registration of virtual patient data in relationship to live patient data by the surgeon or operator In some embodiments, a surgeon or operator can visually align or match virtual patient data with live patient data. Such visually aligning or matching of virtual patient data and live patient data can, for example, be performed by moving the OHMD, for example via movement of the head of the operator who is wearing the OHMD. In this example, the virtual patient data can be displayed in a fixed manner, not changing perspective as the operator moves the OHMD. The operator will move the OHMD until the live patient data are aligned or superimposed onto the fixed projection of the virtual patient data. Once satisfactory alignment, matching or superimposition of the live patient data with the virtual patient data has been achieved, the surgeon can execute a registration command, for example via a voice command or a keyboard command. The virtual patient data and the live patient data are now registered. At this point, upon completion of the registration, the virtual patient data will move corresponding to the movement of the OHMD, for example as measured via the movement of an integrated IMU, image and field of view tracking, e.g. using anchor points in an image or field of view using an image and/or video capture system, and/or an attached navigation system with optical or RF or other trackers, which can be attached to the patient, the surgical site, a bone or any other tissue of the patient, the surgeon, the surgeon's arm, the surgeon's head or an OHMD worn by the surgeon.

Thus, once a satisfactory alignment or match has been achieved the surgeon can execute a command indicating successful registration. The registration can include changes in at least one of position, orientation, and magnification of the virtual data and the live data in order to achieve the alignment or match. Magnification applied to the virtual data can be an indication of the distance from the OHMD or the surgeon's head to the matched tissue. As a means of maximizing the accuracy of the registration, the estimated distance between the OHMD and the target tissue or the skin surface or other reference tissue can be confirmed with an optional physical measurement of the distance, in particular if the OHMD is, for example, in a fixed position, e.g. on a stand or tripod, which may be used optionally during the initial registration. Upon successful alignment or matching, the surgeon command can register, for example, the virtual patient data and the live patient data or images and the OHMD in the same common coordinate system. Virtual and physical surgical instruments and implant components can also be registered in the common coordinate system.

In some embodiments, the visual anatomic data can be, for example, gyri of the brain or osteophytes or bone spurs or pathologic bone deformations or tumor nodes or nodules, e.g. on the surface of a liver or a brain.

Figure 3:
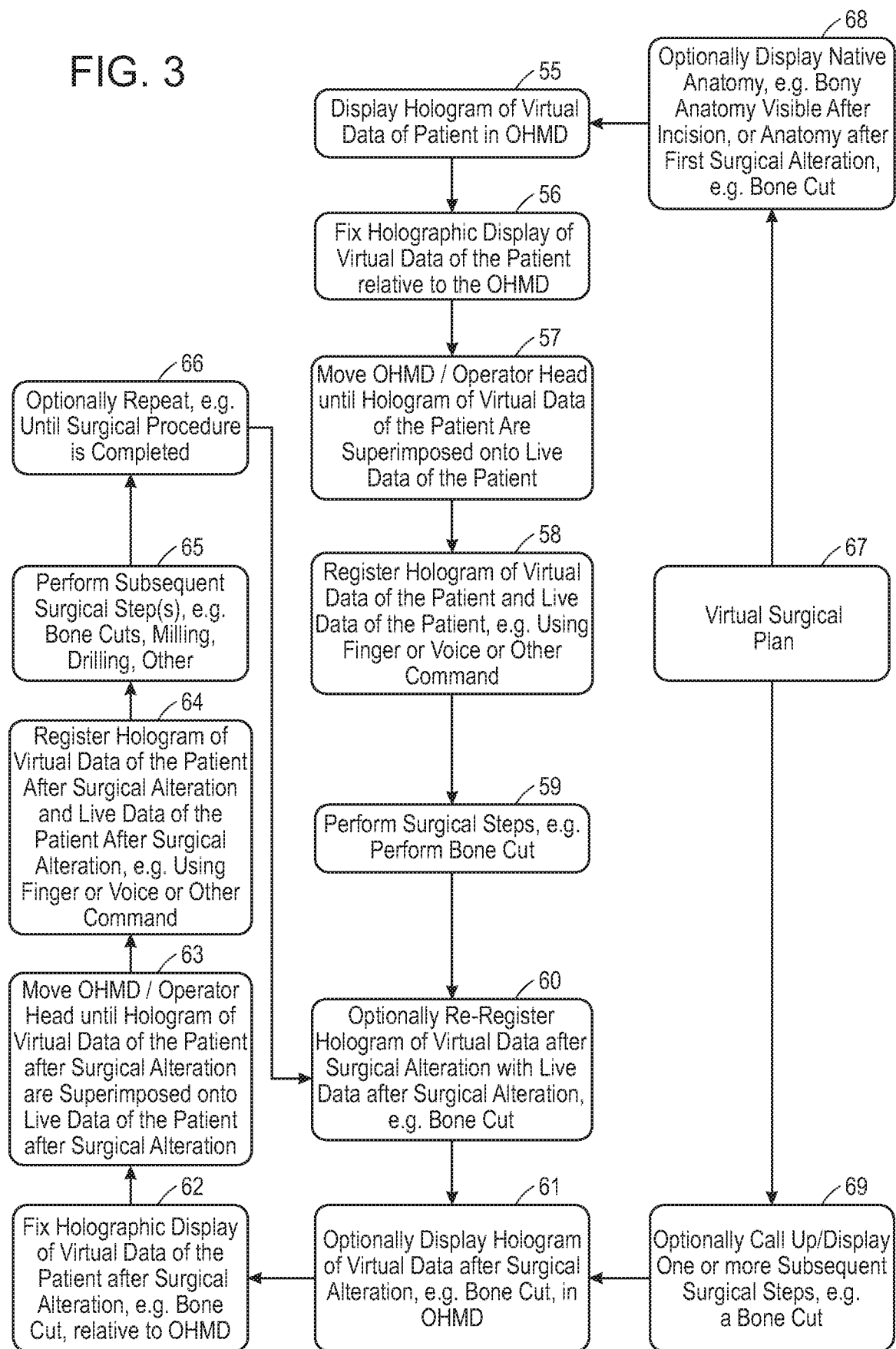
FIG. 3 illustrates an example of registering a digital hologram for an initial surgical step, performing the surgical step and re-registering one or more digital holograms for subsequent surgical steps according to some embodiments of the present disclosure.

In some embodiments, the registration of virtual patient data and live patient data using the methods described herein can be repeated after one or more surgical steps have been performed. In this case, the surgically altered tissue or tissue surface or tissue contour or shape, e.g. shape of a bone after milling or reaming, or tissue perimeter, e.g. perimeter of a bone cut, or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, with substantially identical view angle of the virtual data of the patient seen by the surgeon's eyes through the display of the OHMD unit and the live data of the patient seen by the surgeon's eyes through the OHMD unit. The matching, superimposing and/or registering of the live data of the patient and the virtual data of the patient after the surgical tissue alteration can be performed using the same methods described in the foregoing or any of the other registration methods described in the specification or any other registration method known in the art. Referring to FIG. 3, FIG. 3 illustrates an example of registering a digital hologram or virtual data for an initial surgical step, performing the surgical step and re-registering one or more holograms for subsequent surgical steps. An optical head mounted display can project or display a digital hologram of virtual data or virtual data of the patient 55. The digital hologram can optionally be fixed to the OHMD so that it will move with the movement of the OHMD 56. The operator can move the OHMD until digital hologram of the virtual data or virtual data of the patient is superimposed and aligned with the live data of the patient, e.g. the surgical site 57. The digital hologram of the virtual data or virtual data can then be registered using the same or similar coordinates as those of the live data with which the digital hologram is superimposed 58. The surgeon can then perform one or more predetermined surgical steps, e.g. bone cuts 59. A digital hologram of the virtual data or virtual data can optionally be registered or re-registered after the surgical alteration with the live data 60. The digital hologram of the virtual data or virtual data after the surgical alteration can optionally be displayed by the OHMD 61. The digital hologram of the virtual data or virtual data after the surgical alteration can optionally be fixed relative to the OHMD so that it will move with the movement of the OHMD 62. The operator can move the OHMD until digital hologram of the virtual data or virtual data of the patient after the surgical alteration is superimposed and aligned with the live data of the patient after the surgical alteration 63. The digital hologram of the virtual data or virtual data can then be registered using the same or similar coordinates as those of the live data after the surgical alteration with which the digital hologram is superimposed 64. The surgeon can then perform one or more predetermined subsequent surgical steps, e.g. bone cuts, milling or drilling 65. The preceding steps can optionally be repeated until the surgical procedures are completed 66. A virtual surgical plan 67 can be utilized. Optionally, the native anatomy of the patient including after a first surgical alteration can be displayed by the OHMD 68. The OHMD can optionally display digital holograms of subsequent surgical steps 69.

b) Automatic or semi-automatic registration of virtual patient data in relationship to live patient data using image processing and/or pattern recognition and matching techniques c) In some embodiments, image processing techniques, pattern recognition techniques or deep learning/artificial neural-network based techniques can be used to match virtual patient data and live patient data. Optionally, image processing and/or pattern recognition algorithms can be used to identify certain features, e.g. gyri or sulci on the brain surface of virtual data of a patient. An ear including its unique shape can also be used for the purpose of matching virtual patient data and live patient data.

For example, with brain surgery, the patient can be placed on the operating table. Optionally, cleaning or sterilization fluid can be applied to the shaved skull, for example using betadine. The OHMD can be placed over the patient, either on a tripod or worn by the operator, for example with the head of the patient turned sideways over the live patient's ear and lateral skull. The OHMD will be placed over an area of the live patient that includes the virtual data of the patient to be displayed.

Virtual data of the patient can be displayed in the OHMD. The virtual data of the patient can include, for example, a visualization of the patient's skin or other data, e.g. the patient's ear or nose, for example derived from preoperative MRI data. The virtual data of the patient's skin or other structures, e.g. the patient's ear or nose, can be displayed simultaneous with the live patient data. The virtual data of the patient can then be moved, re-oriented, re-aligned and, optionally, magnified or minified until a satisfactory alignment, match or superimposition has been achieved. Optionally, the OHMD can be moved also during this process, e.g. to achieve a satisfactory size match between virtual data and live data of the patient, optionally without magnification or minification of the virtual data of the patient.

Once a satisfactory alignment, match or superimposition has been achieved between virtual data and live data of the patient, the operator can execute a command indicating successful registration. Changes in position, orientation, or direction of the OHMD, for example as measured via an integrated IMU, image and field of view tracking, e.g. using anchor points in an image or field of view using an image and/or video capture system, and/or a navigation system attached to the OHMD, can be used to move the virtual patient data with the view of the live patient data through the OHMD, with substantially identical object coordinates of the virtual data of the patient and the live data of the patient, thereby maintaining registration during the course of the surgery irrespective of any movements of the OHMD, e.g. head movement by the operator wearing the OHMD, and ensuring that the virtual data of the patient is correctly superimposed with the live data of the patient when projected into the surgeon's view.

After successful registration of the virtual patient data to the patient's skin or other structures, e.g. an ear or a nose, the operator or an assistant can apply a marker or calibration or registration phantom or device on the patient, for example close to the intended site of a craniotomy. The marker or calibration or registration phantom or device will not be covered by any drapes or surgical covers that will be placed subsequently. A secondary registration of the virtual patient data to the live patient data can then occur, by registering the virtual patient data to the live patient data, using the live marker or calibration or registration phantom or device placed on the patient and by cross-referencing these to the live data of the patient's skin or other structures, e.g. an ear or a nose. This can be achieved, for example, by registering the patient's skin or other structures, e.g. an ear or a nose, in the same coordinate system as the marker or calibration or registration phantom or device placed on the patient, e.g. by co-registering the virtual patient data of the patient's skin or other structures, e.g. an ear or a nose or an osteophyte or bone spur or other bony anatomy or deformity, with the live data of the marker or calibration or registration phantom or device. The distance, offset, angular offset or overall difference in coordinates between the patient's skin or other structures, e.g. an ear or nose or an osteophyte or bone spur or other bony anatomy or deformity, to the marker or calibration or registration phantom or device attached to the patient can be measured and can be used to switch the registration of the virtual patient data to the live patient data from the live data of the patient's skin or other structures, e.g. an ear or a nose, to the live data of the marker or calibration or registration phantom or device. Optionally, registration can be maintained to both the live data of the patient's skin or other structures, e.g. an ear or a nose, and the live data of the marker or calibration or registration phantom or device. Optionally, the system can evaluate if registration to the live data of the patient's skin or other structures, e.g. an ear or a nose, or to the live data of the marker or calibration or registration phantom or device is more accurate and the system can switch back and forth between either. For example, if the distance increases or decreases from the OHMD to the patient's skin or other structure, e.g. an ear or a nose, beyond a certain level, e.g. a threshold, which can be optionally predefined, or if some of them is partially covered by a drape, the system can switch the registration to the live data of the marker or calibration or registration phantom or device. The reverse is possible. Or, if the angle from the OHMD increases or decreases beyond a certain level, e.g. a threshold, which can be optionally predefined, to the patient's skin or other structure, e.g. an ear or a nose or an osteophyte or bone spur or other bony anatomy or deformity, the system can switch the registration to the live data of the marker or calibration or registration phantom or device. The reverse is possible.

The operator or the assistants can then place sterile drapes or surgical covers over the site, however preferably not covering the marker or calibration or registration phantom or device. Registration can be maintained via the live data of the marker or calibration or registration phantom or device attached to the patient, e.g. adjacent to or inside a craniotomy site.

Image processing and/or pattern recognition of the live data of the patient can then be performed through the OHMD, e.g. using a built-in image capture apparatus and/or a 3D scanner for capturing the live data of the patient or image and/or video capture systems and/or a 3D scanner attached to, integrated with or coupled to the OHMD.

Virtual and live data features or patterns can then be matched. The matching can include a moving and/or reorienting and/or magnification and/or minification of virtual data for successful registration with the live data of the patient and superimposition of both. Virtual and live data can include an osteophyte or bone spur or other bony anatomy or deformity.

Combination of (a) and (b), e.g. automatic registration with manual adjustment option, e.g. by moving the virtual image data in relation to the live image data after image processing software and/or pattern recognition software and/or matching software have identified a potential match or performed an initial matching, which can then be followed by manual/operator based adjustments. Alternatively, manual/operator based matching and registration can be performed first, followed then by fine-tuning via software or algorithm (image processing, pattern recognition, etc.) based matching and registration. Virtual and live data can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Anatomic Landmarks In some embodiments, a surgeon can identify select anatomic landmarks on virtual data of the patient, e.g. on an electronic preoperative plan of the patient, and on live data of the patient. For example, the surgeon can identify a landmark by placing a cursor or a marker on it on an electronic image of the virtual data of the patient and by clicking on the landmark once the cursor or marker is in the desired location. In a spine, such a landmark can be, for example, the posterior tip of a spinous process, a spinal lamina, an inferior facet on the patient's left side, a superior facet on the patient's left side, an inferior facet on the patient's right side, a superior facet on the patient's right side, a tip of a facet joint, a bone spur, an osteophyte etc. In a hip, such landmarks can be the most anterior point of the acetabulum, an osteophyte, e.g. on the acetabular rim, in the acetabulum, adjacent to the acetabulum, on the femoral head, on the femoral neck or the neck shaft junction, the center of the femoral head in a 2D or 3D image, the most anterior point of the femoral head, an anterosuperior iliac spine, an anteroinferior iliac spine, a symphysis pubis, a greater trochanter, a lesser trochanter etc. In a knee, such landmarks can be a femoral condyle, a femoral notch, an intercondylar space, a medial or lateral epicondyle, a femoral axis, an epicondylar axis, a trochlear axis, a mechanical axis, a trochlear groove, a femoral osteophyte, a marginal femoral osteophyte, a central femoral osteophyte, a dome of the patella, a superior, medial, lateral, inferior edge of the patella or the femur or femoral articular surface, a patellar osteophyte, an anterior tibia, a tibial spine, a medial, lateral, anterior, posterior edge of the tibia, a tibial osteophyte, a marginal tibial osteophyte, a central tibial osteophyte. The surgeon can then identify the same landmarks live in the patient. For example, as the surgeon looks through the OHMD, the surgeon can point with the finger or with a pointing device at the corresponding anatomic landmark in the live data. The tip of the pointer or the tip of the finger can, optionally, include a tracker which locates the tip of the pointer or the finger in space. Such locating can also be done visually using image and/or video capture and/or a 3D scanner, e.g. in a stereoscopic manner through the OHMD for more accurate determination of the distance and location of the pointer or finger in relationship to the OHMD. An image and/or video capture system and/or a 3D scanner can also be attached to, integrated with or coupled to the OHMD. Virtual and live data can include an osteophyte or bone spur or other bony anatomy or deformity.

Representative anatomic landmarks that can be used for registration of virtual and live data of the patient can include (but are not limited to):

In Spine: A portion or an entire spinous process; A portion or an entire spinal lamina; A portion or an entire spinal articular process; A portion of or an entire facet joint; A portion of or an entire transverse process; A portion of or an entire pedicle; A portion of or an entire vertebral body; A portion of or an entire intervertebral disk; A portion of or an entire spinal osteophyte; A portion of or an entire spinal bone spur; A portion of or an entire spinal fracture; A portion of or an entire vertebral body fracture or Combinations of any of the foregoing Hip: A portion of or an entire acetabulum; A portion of or an entire edge of an acetabulum; Multiple portions of an edge of an acetabulum; A portion of an iliac wall; A portion of a pubic bone; A portion of an ischial bone; An anterior superior iliac spine; An anterior inferior iliac spine; A symphysis pubis; A portion of or an entire greater trochanter; A portion of or an entire lesser trochanter; A portion of or an entire femoral shaft; A portion of or an entire femoral neck; A portion of or an entire femoral head; A fovea capitis; A transverse acetabular ligament; A pulvinar; A ligamentum teres; A labrum; One or more osteophytes, femoral and/or acetabular or Combinations of any of the foregoing Knee: A portion or an entire medial femoral condyle; A portion or an entire lateral femoral condyle; A portion or an entire femoral notch; A portion or an entire trochlea; A portion of an anterior cortex of the femur; A portion of an anterior cortex of the femur with adjacent portions of the trochlea; A portion of an anterior cortex of the femur with adjacent portions of the trochlea and osteophytes when present; One or more osteophytes femoral and/or tibial; One or more bone spurs femoral and/or tibial; An epicondylar eminence; A portion or an entire medial tibial plateau; A portion or an entire lateral tibial plateau; A portion or an entire medial tibial spine; A portion or an entire lateral tibial spine; A portion of an anterior cortex of the tibia; A portion of an anterior cortex of the tibia and a portion of a tibial plateau, medially or laterally or both; A portion of an anterior cortex of the tibia and a portion of a tibial plateau, medially or laterally or both and osteophytes when present; A portion or an entire patella; A medial edge of a patella; A lateral edge of a patella; A superior pole of a patella; An inferior pole of a patella; A patellar osteophyte; An anterior cruciate ligament; A posterior cruciate ligament; A medial collateral ligament; A lateral collateral ligament; A portion or an entire medial meniscus; A portion or an entire lateral meniscus or Combinations of any of the foregoing Shoulder: A portion or an entire glenoid; A portion or an entire coracoid process; A portion or an entire acromion; A portion of a clavicle; A portion or an entire humeral head; A portion or an entire humeral neck; A portion of a humeral shaft; One or more humeral osteophytes; One or more glenoid osteophytes; A portion or an entire glenoid labrum; A portion or an entire shoulder ligament, e.g. a coracoacromial ligament, a superior, middle, or inferior glenohumeral ligament; A portion of a shoulder capsule or Combinations of any of the foregoing Skull and brain: A portion of a calvarium; A portion of an occiput; A portion of a temporal bone; A portion of a occipital bone; A portion of a parietal bone; A portion of a frontal bone; A portion of a facial bone; A portion of a facial structure; A portion or an entire bony structure inside the skull; Portions or all of select gyri; Portions or all of select sulci; A portion of a sinus; A portion of a venous sinus; A portion of a vessel; A portion of an ear; A portion of an outer auditory canal or combinations of any of the foregoing.

Organs: A portion of an organ, e.g. a superior pole or inferior pole of a kidney; An edge or a margin of a liver, a spleen, a lung; A portion of a hepatic lobe; A portion of a vessel; A portion of a hiatus, e.g. in the liver or spleen; A portion of a uterus.

Someone skilled in the art can identify other anatomic landmarks of hard tissues, soft-tissues and or organs including brain that can be used for registration of virtual data (including optionally including virtual surgical plans) and live data of the patient and the OHMD in a common coordinate system. Virtual and physical surgical instruments and implant components can also be registered in the common coordinate system.

In some embodiments, the OHMD can display an arbitrary virtual plane over the surgical field. The arbitrary virtual plane can be moveable using a virtual or other interface. For example, the arbitrary virtual plane can include a "touch area", wherein gesture recognition software, for example the one provided by Microsoft with the Microsoft Hololens including, for example, the integrated virtual "drag function" for holograms can be used to move the arbitrary virtual plane. For example, one or more cameras integrated or attached to the OHMD can capture the movement of the surgeon's finger(s) in relationship to the touch area; using gesture tracking software, the virtual plane can then be moved by advancing the finger towards the touch area in a desired direction.

The OHMD can display the arbitrary virtual plane in any location initially, e.g. projected onto or outside the surgical field, e.g. a hip joint, knee joint, shoulder joint, ankle joint, or a spine. The OHMD can optionally display the arbitrary virtual plane at a defined angle, e.g. orthogonal or parallel, relative to a fixed structure in the operating room, which can, for example, be recognized using one or more cameras, image capture or video capture systems and/or a 3D scanner integrated into the OHMD and spatial recognition software such as the one provided by Microsoft with the Microsoft Hololens or which can be recognized using one or more attached optical markers or navigation markers including infrared or RF markers. For example, one or more optical markers can be attached to an extension of the operating table. The OHMD can detect these one or more optical markers and determine their coordinates and, with that, the horizontal plane of the operating room table. The arbitrary virtual plane can then be displayed perpendicular or at another angle relative to the operating room table.

For example, in a hip replacement, the OHMD can display a virtual arbitrary plane over the surgical site. The virtual arbitrary plane can be perpendicular to the operating table or at another predefined or predetermined angle relative to the OR table. Using a virtual interface, e.g. a touch area on the virtual surgical plane and gesture tracking, the OHMD can detect how the surgeon is moving the virtual arbitrary plane. Optionally, the virtual arbitrary plane can maintain its perpendicular (or of desired other angle) orientation relative to the OR table while the surgeon is moving and/or re-orienting the plane; a perpendicular orientation can be desirable when the surgeon intends to make a perpendicular femoral neck cut. A different angle can be desirable, when the surgeon intends to make the femoral neck cut with another orientation.

Using the touch area or other virtual interface, the surgeon can then move the arbitrary virtual plane into a desired position, orientation and/or alignment. The moving of the arbitrary virtual plane can include translation and rotation or combinations thereof in any desired direction using any desired angle or vector. The surgeon can move the arbitrary virtual plane to intersect with select anatomic landmarks or to intersect with select anatomic or biomechanical axes. The surgeon can move the arbitrary virtual plane to be tangent with select anatomic landmarks or select anatomic or biomechanical axes.

Figure 4A:
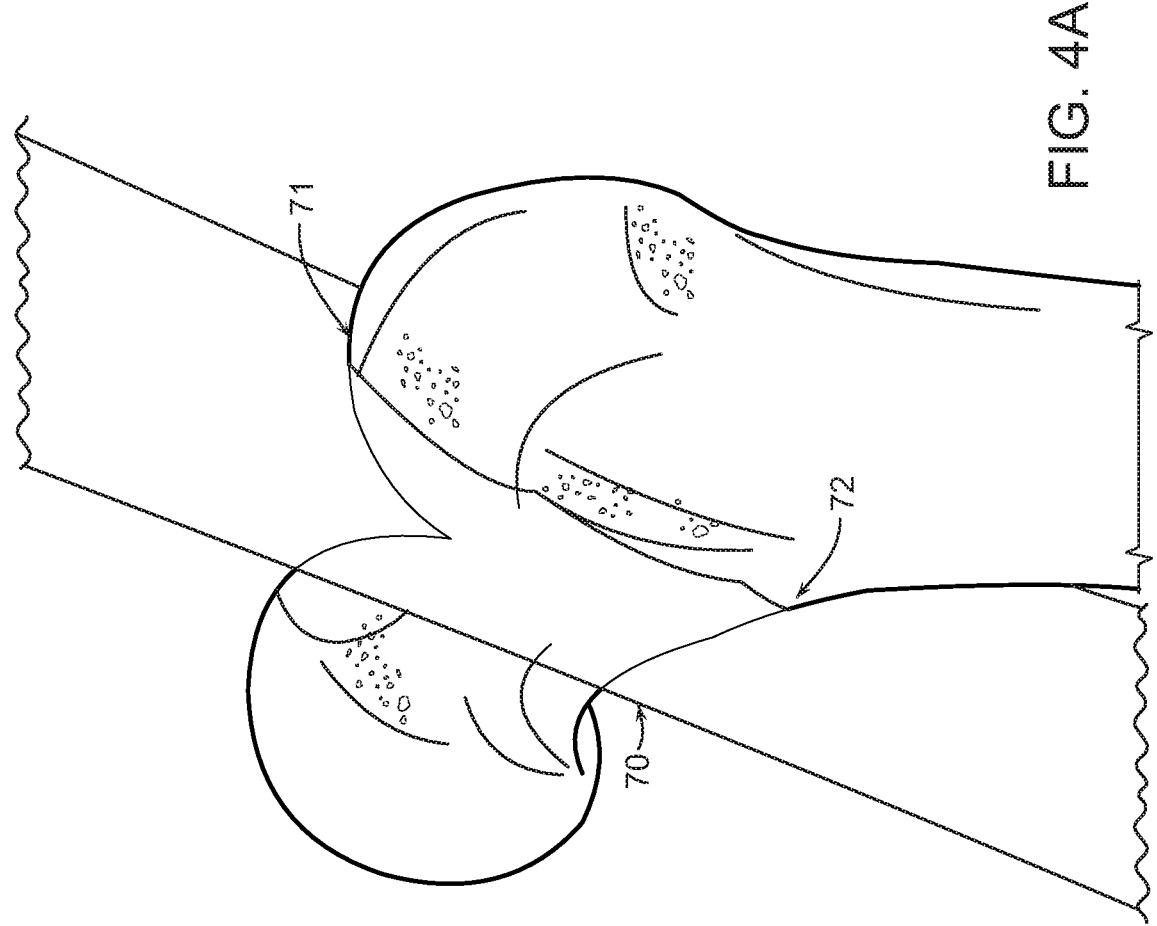
FIGS. 4A-C are illustrative examples of arbitrary virtual planes in the hip and a femoral neck cut plane according to some embodiments of the present disclosure.
Figure 4B:
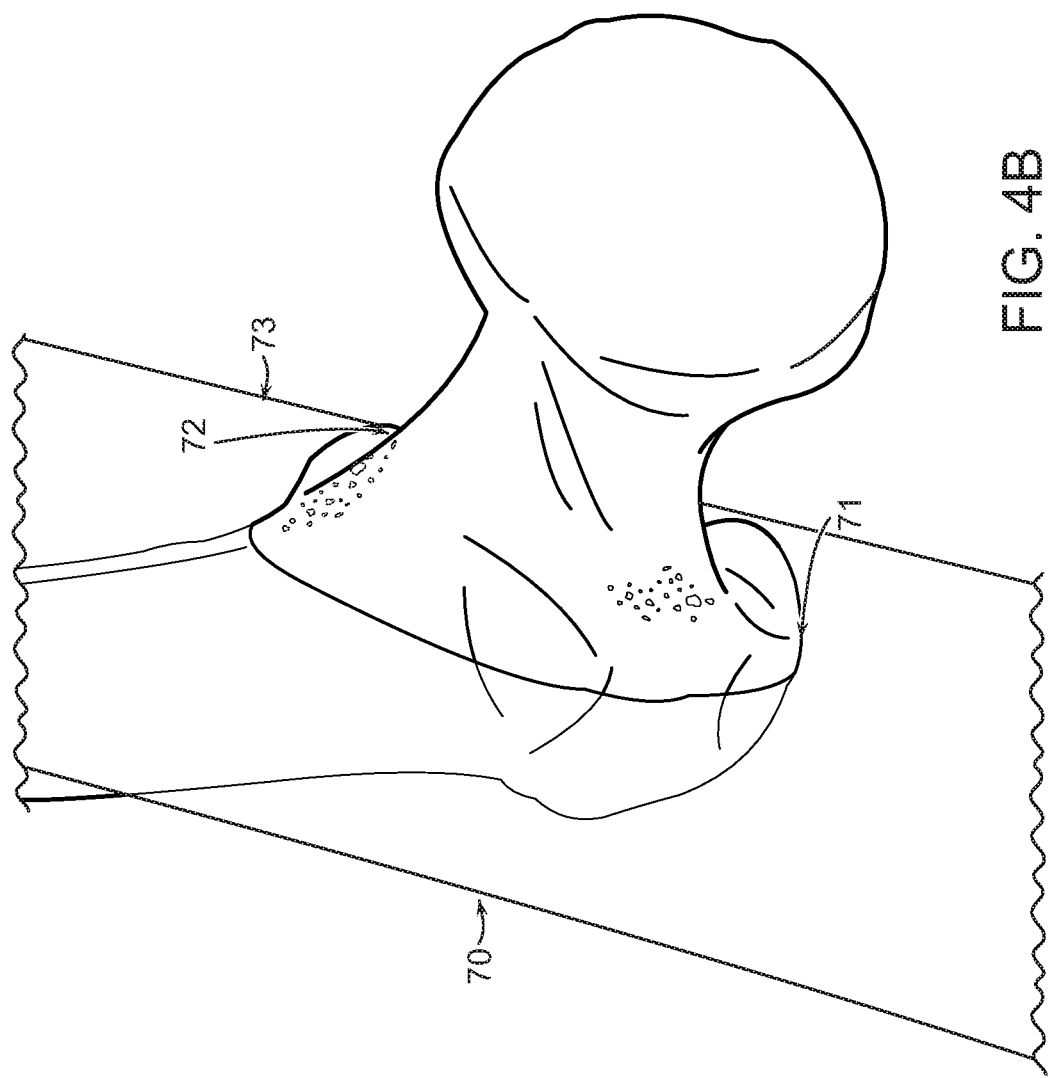

For example, in a hip replacement, the surgeon can move the arbitrary virtual plane to be tangent with the most superior aspect of the greater trochanter and the most superior aspect of the lesser trochanter. FIG. 4A shows an illustrative example of a virtual plane 70 that a primary surgeon has moved and aligned to be tangent with the most superior aspect of the greater trochanter 71 and the most superior aspect of the lesser trochanter 72. FIG. 4B shows an illustrative example of the same virtual plane 70 that the primary surgeon has moved and aligned to be tangent with the most superior aspect of the greater trochanter 71 and the most superior aspect of the lesser trochanter 72, now with the view from the optical head mounted display of a second surgeon or surgical assistant, e.g. on the other side of the OR table.

Figure 4C:
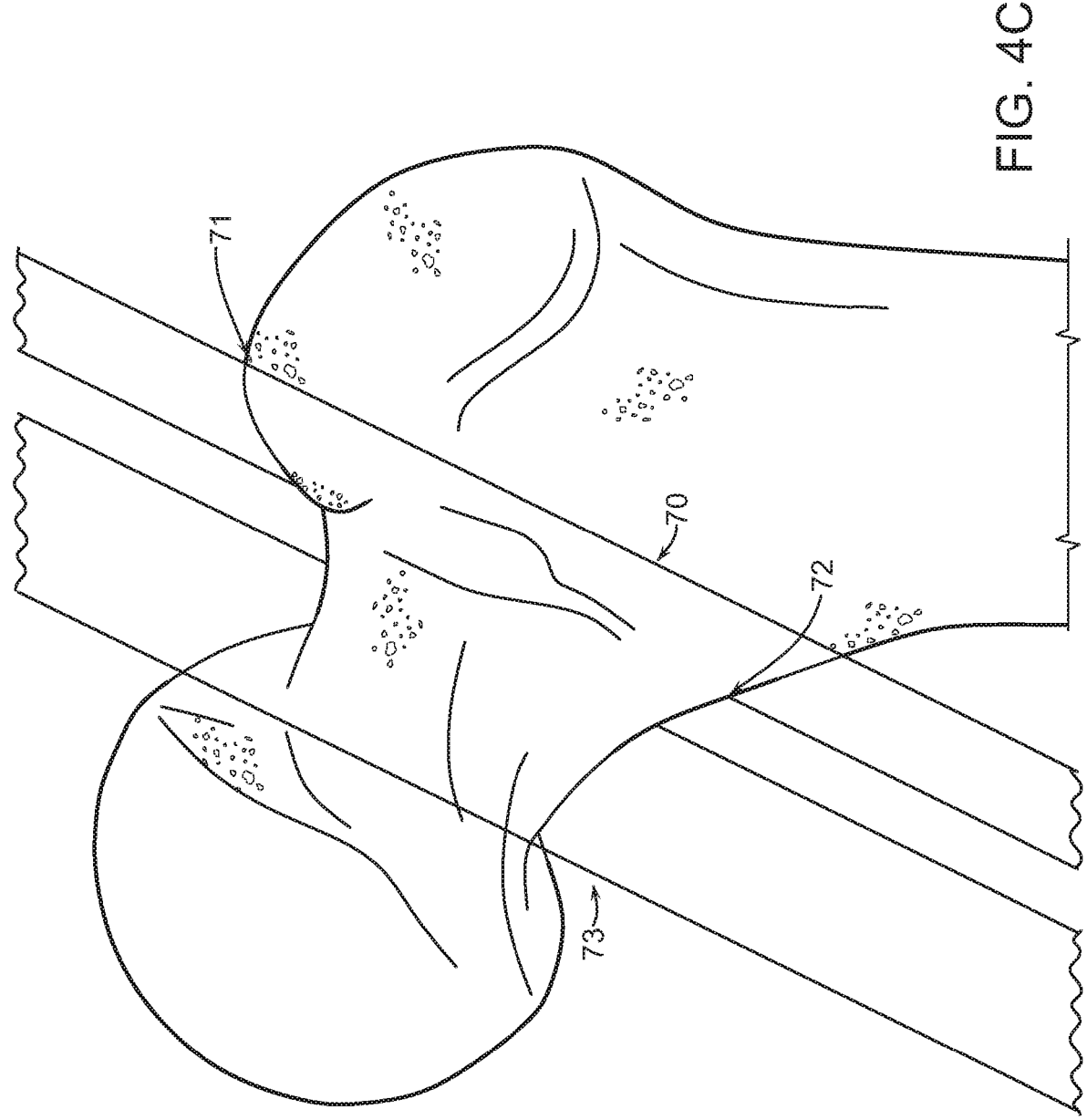

Optionally, for example with a pointer with an attached optical marker or an attached navigation marker, or with his finger detected using an image or video capture system integrated into the OHMD and gesture recognition software such as the one provided by Microsoft with the Hololens, or with his finger with an attached optical marker or navigation marker, the surgeon can point at and identify the sulcus point, e.g. the lowest point between the greater trochanter and the femoral neck, which can be an additional reference. The line connecting the most superior aspect of the greater trochanter and the most superior aspect of the lesser trochanter can then be determined on a pre-operative or intra-operative AP radiograph of the hip; optionally, the sulcus point can also be detected on the AP radiograph. The AP radiograph can include a template used by the surgeon for selecting and sizing, for example, the femoral and acetabular component, as well as the liner and/or femoral heads. The radiographic template can include an indication for the femoral neck cut. The angle between the line connecting the most superior aspect of the greater trochanter and the most superior aspect of the lesser trochanter and the indication for the femoral neck cut can be determined. FIG. 4C is an illustrative example that shows that a second virtual plane 73, the virtual femoral neck cut plane 73, can then be projected or displayed by the OHMD, also perpendicular to the OR table like the arbitrary virtual plane 70, the latter tangent with the most superior aspect of the greater trochanter 71 and the most superior aspect of the lesser trochanter 72, and the femoral neck cut plane 73 at the same angle and/or distance to the arbitrary virtual plane as the angle and distance between the line connecting the most superior aspect of the greater trochanter and the most superior aspect of the lesser trochanter and the indication for the femoral neck cut on the radiograph. In this manner, the femoral neck cut plane can be defined using a second virtual plane prescribed or predetermined based on the intra-operatively placed arbitrary virtual plane, moved by the operator to be tangent with the most superior aspect of the greater trochanter and the most superior aspect of the lesser trochanter. The virtual femoral neck cut plane prescribed and projected or displayed in this manner can also be a virtual guide, e.g. a virtual cut block that projects, for example, a virtual slot for guiding a physical saw. The virtual guide or virtual cut block can have one or more dimensions identical to a physical guide or cut block, so that the physical guide or cut block can be aligned with the virtual guide or cut block. The virtual guide or cut block can be an outline, 2D or 3D, partial or complete, of the physical guide or cut block, with one or more identical dimensions, so that the surgeon can align the physical guide or cut block with the virtual guide or cut block. The virtual guide or cut block can include placement indicia for the physical guide or cut block.

If radiographic magnification is a concern for prescribing a second virtual plane, e.g. a virtual cut plane, based on a first virtual plane, e.g. a plane tangent with or intersecting one or more anatomic landmarks or one or more anatomic or biomechanical axes, at an angle incorporated from or derived from a pre-operative radiograph, optionally, distance measurements can be incorporated and magnification correction can be applied. For example, the distance between one or more landmarks, e.g. the ones with which the virtual plane is tangent with or that the virtual plane intersects, can be measured in the live data of the patient and can be measured on the radiograph. If the radiographic distance is larger or smaller than the distance in the live patient, a magnification correction can be applied and, for example, the distance between the first virtual plane, e.g. a plane tangent with or intersecting one or more anatomic landmarks or one or more anatomic or biomechanical axes, and the second virtual plane, e.g. a virtual cut plane, can be corrected based on the radiographic magnification factor.

In addition to virtual planes, the surgeon can place one or more virtual points, e.g. with a pointer with an attached optical marker or an attached navigation marker, or with his or her finger detected using an image or video capture system integrated into the OHMD and gesture recognition software such as the one provided by Microsoft with the Hololens, or with his or her finger with an attached optical marker or navigation marker. The surgeon can point at and identify an anatomic landmark, e.g. a medial epicondyle of a knee or a sulcus point in a proximal femur or a medial malleolus, using any of the foregoing methods and/or devices. Optionally, the surgeon can then fixate optical markers to the virtual point and the underlying or corresponding anatomic landmark, for example using a screw or pin. By identifying two or more virtual points the surgeon can define a virtual axis or vector. For example, by identifying, e.g. with use of one or more optical markers applied to the anatomic landmark, a medial epicondyle of the knee and a lateral epicondyle of the knee, the transepicondylar axis can be determined in a patient. By identifying three or more virtual points, the surgeon can define a virtual plane. For example, by identifying, e.g. with use of one or more optical markers applied to the anatomic landmark, a left anterior superior iliac spine, a right anterior superior iliac spine and a symphysis pubis, the system can determine an anterior pelvic plane in a patient.

Figure 5:
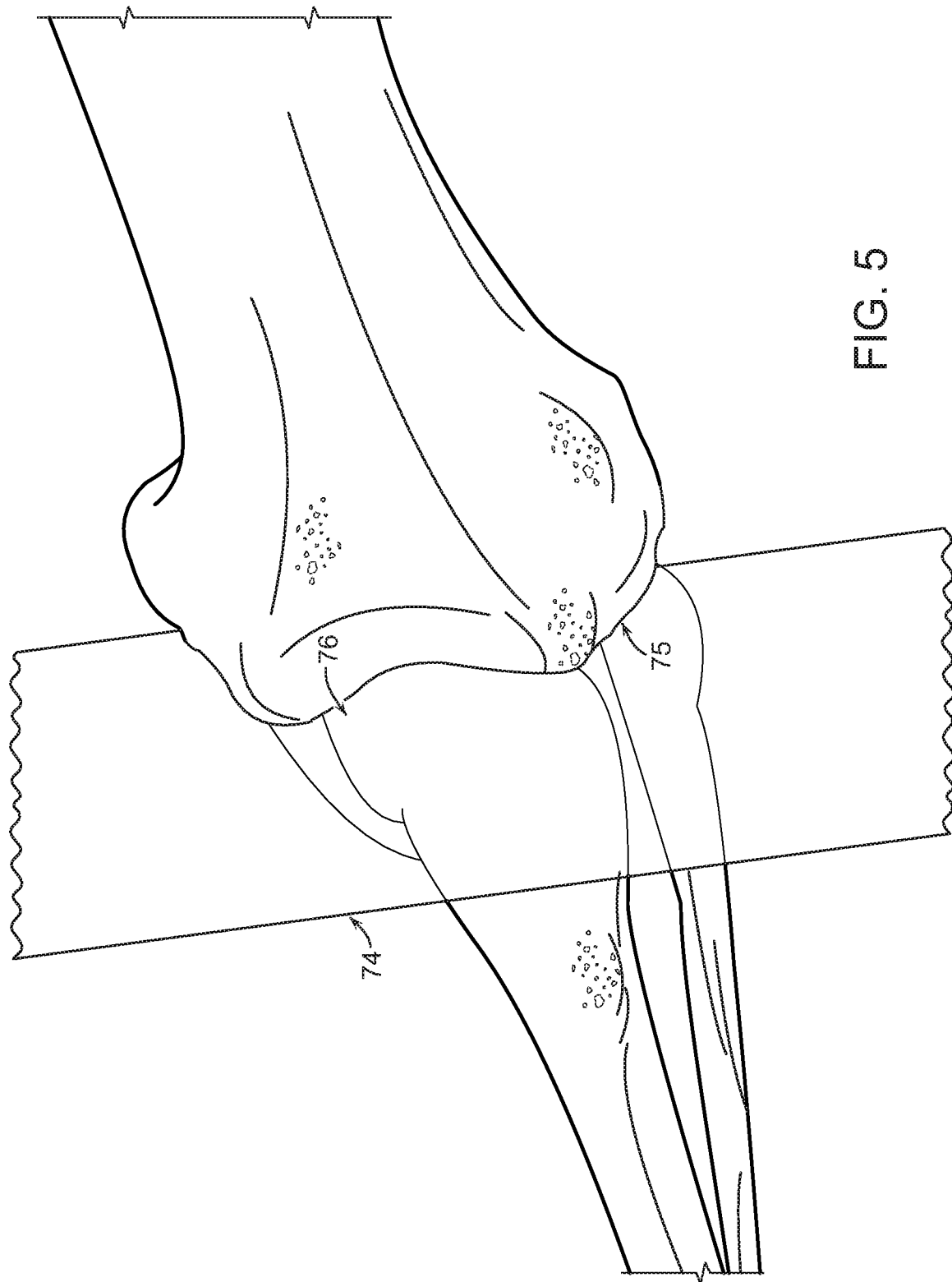
FIG. 5 is an illustrative example of an arbitrary virtual plane in the knee extending through the medial and lateral joint space according to some embodiments of the present disclosure.

In another example, an arbitrary virtual plane can be projected or displayed outside of or over the surgical field in a knee replacement. Optionally, the arbitrary virtual plane can be, at least initially, perpendicular to the OR table or at a defined angle to the OR table. If the mechanical axis of the leg has been determined in a preceding step, e.g. using an intra-operative measurement, for example with optical markers applied to the thigh and one or more optical markers applied to the ankle joint, for determining the center of rotation of the hip joint and the center of the ankle joint using an image capture or video capture system and/or a 3D scanner integrated into, attached to or separate from the OHMD, the arbitrary virtual plane can be configured to be perpendicular to the mechanical axis of the leg. Using a virtual interface, e.g. a touch area, and an image or video capture system integrated or attached to the OHMD and optional gesture tracking software, the surgeon can move and/or re-align the arbitrary virtual plane, for example to intersect with the medial and lateral joint space of the exposed knee joint, for example in extension or at 5, 10, 15, 20, 30, 45, or more degrees of flexion. FIG. 5 is an illustrative example of an arbitrary virtual plane 74 in the knee that intersects with the medial 76 and lateral 75 joint space in extension.

One or more additional arbitrary virtual planes can then optionally be projected, for example perpendicular or at another angle relative to the operating table or using a desired femoral component flexion angle or a desired tibial slope. The surgeon can optionally move these one or more arbitrary virtual planes to coincide with one or more anatomic axes, for example the anatomic femoral shaft axis or the anatomic tibial shaft axis in the live patient. The surgeon can also move a virtual arbitrary plane to be placed and oriented in the center of the femoral notch, parallel to the notch walls and extending centered between the medial and the lateral femoral shaft cortex as a means of estimating the anatomic femoral shaft axis.

Once the anatomic femoral and/or tibial axes have been determined or estimated, a virtual surgical plan with femoral and tibial resections designed to achieve a desired femoral mechanical axis correction, e.g. from the patient's mechanical axis alignment, e.g. 5, 10, 15 degrees of varus or valgus, to normal mechanical axis alignment or any desired residual, e.g. congenital varus or valgus, can be developed or generated. Implant size and desired polyethylene thickness can be factored into the virtual surgical plan. The OHMD can then, for example, project virtual surgical cut planes based on the virtual surgical plan and/or the intra-operative measurements, the desired varus and/or valgus correction, desired slope, and/or desired implant rotation. The surgeon can then align the physical saw blade with the projected or displayed virtual saw blade or cut plane. Alternatively, the OHMD can display a virtual guide or virtual cut block with at least one or more dimensions identical to the physical guide or physical cut block and the surgeon can align the physical cut guide or cut block with the virtual guide or cut block, in the physical guide or cut block, insert the saw blade into the physical guide or cut block and execute the one or more blocks.

The foregoing concepts of projecting arbitrary virtual planes and aligning them with one or more anatomic landmarks, anatomic axes or biomechanical or mechanical axes can be applied to any joint and also the spine. Similarly, these concepts can be applied to brain surgery, where one or more virtual planes can be projected or displayed and moved to be tangent with or intercept one or more landmarks, e.g. gyri, pons, cerebellum etc. Similarly, these concepts can be applied to organ surgery, where one or more virtual planes can be projected or displayed and moved to be tangent with or intercept one or more landmarks, e.g. liver portal, anterior liver edge, one or more cardiac valves etc.

Other arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with internal, subsurface, or hidden patient anatomy, internal, subsurface, or hidden pathology, internal, subsurface, or hidden anatomic axes, internal, subsurface, or hidden biomechanical including mechanical axes, internal, subsurface, or hidden anatomic planes, internal, subsurface, or hidden 3D shapes, internal, subsurface, or hidden 2D and/or 3D geometries, internal, subsurface, or hidden 3D surfaces, and/or internal, subsurface, or hidden 3D volumes of any organs, soft-tissues or hard tissues of the patient. Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with external patient anatomy, external pathology, external anatomic axes, external biomechanical including mechanical axes, external anatomic planes, external 3D shapes, external 2D and/or 3D geometries, external 3D surfaces, and/or external 3D volumes of any organs, soft-tissues or hard tissues of the patient. Arbitrary 2D and/or 3D virtual shapes or outlines or surfaces, e.g. cubes, cuboids, prisms, cones, cylinders, spheres, ellipsoid derived 3D shapes, irregular shapes, 2D and/or 3D virtual shapes or outlines or surfaces of virtual instruments and/or virtual implant components can be virtually projected or displayed and automatically or using a virtual or other user interface moved, oriented or aligned to coincide, to be tangent with, to intersect, to be offset with, to be partially or completely superimposed with patient anatomy directly visible to the operator's eye, e.g. without using a display of an OHMD, pathology directly visible to the operator's eye, e.g. without using a display of an OHMD, anatomic axes directly visible to the operator's eye, e.g. without using a display of an OHMD, biomechanical including mechanical axes directly visible to the operator's eye, e.g. without using a display of an OHMD, anatomic planes directly visible to the operator's eye, e.g. without using a display of an OHMD, 3D shapes directly visible to the operator's eye, e.g. without using a display of an OHMD, 2D and/or 3D geometries directly visible to the operator's eye, e.g. without using a display of an OHMD, 3D surfaces directly visible to the operator's eye, e.g. without using a display of an OHMD, and/or 3D volumes directly visible to the operator's eye, e.g. without using a display of an OHMD, of any organs, soft-tissues or hard tissues of the patient. Patient anatomy can include an implantation site, a bone for implanting a medical device, a soft-tissue for implanting a medical device, an anatomic structure adjacent to an implantation site, e.g. an adjacent tooth with which a dentist can virtually align a virtual implant component.

After the moving, orienting or aligning, the coordinate information of the 2D and/or 3D virtual shapes or outlines or surfaces can then be measured. Optionally, based on the coordinate information, additional intraoperative measurements can be performed and/or, optionally, a virtual surgical plan can be developed or modified using the information.

Systems, methods and techniques for superimposing and/or aligning one or more of virtual surgical guides, e.g. a virtual axis or a virtual plane (e.g. for aligning a saw), virtual tools, virtual instruments, and/or virtual trial implants are described in International Patent Application No. PCT/US17/21859 and U.S. Pat. No. 9,861,446 which are incorporated herein by reference in their entireties.

In any of the embodiments, the OHMD display of virtual data, e.g. of one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be performed in relationship to and/or with a predetermined location, orientation, and/or alignment to a normal, damaged and/or diseased cartilage, cartilage surface, and/or cartilage shape, and/or a subchondral bone, subchondral bone surface and/or subchondral bone shape and/or cortical bone, cortical bone surface and/or cortical bone shape. The predetermined location, orientation, and/or alignment can be external and/or internal to a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. The predetermined location, orientation, and/or alignment can be tangent with and/or intersecting with a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. The intersecting can be at one or more predetermined angles. The predetermined location, orientation, and/or alignment can be at an offset to a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape, e.g. an offset of 0.5, 1.0, 1.5, 2.0, 3.0, 4.0, 5.0, 7.0, 10.0, 15.0, 20.0 mm, or a range from 0.1 to 50 mm in x, y and/or z-direction relative to the normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. For example, a virtual surgical guide and/or any virtual placement indicators for a physical surgical guide can be projected by one or more OHMDs so that at least portions of the virtual surgical guide and/or virtual placement indicators are tangent with, intersecting with and/or offset with a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape of the patient.

In embodiments, the OHMD display of virtual data, e.g. of one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, can be superimposed onto and/or aligned with the corresponding anatomic structure, e.g. a target tissue or an exposed joint surface, e.g. an exposed articular surface, seen directly through the see-through optical head mounted display (as they would be seen by the surgeon without wearing an OHMD). The surgeon can then, for example, move a physical instrument, surgical guide, surgical tool, implant, implant component, device to align with the virtual projection.

Orienting, Aligning, Projecting and/or Superimposing Virtual Data Relative to Anatomic Structures and/or Surfaces In embodiments, the OHMD display of virtual data, e.g. of one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration, can be projected onto and/or superimposed onto and/or aligned with and/or oriented with the surface of an anatomic structure seen directly through the see-through optical head mounted display (as they would be seen by the surgeon without wearing an OHMD). The one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected onto and/or superimposed onto and/or aligned with and/or oriented with so that at least portions of them are tangent with, intersecting with, orthogonal to, at a defined angle to, and/or offset with, e.g. at a predetermined distance or angle, with the surface of the anatomic structure.

The surface of the anatomic structure can be at least a portion of one or more of a cartilage, a damaged or diseased cartilage, a subchondral bone, a cortical bone, any combination of a cartilage, a damaged or diseased cartilage, a subchondral bone, or a cortical bone, an articular surface, a weight-bearing zone of an articular surface, a non-weight bearing zone of an articular surface, a periosteum, a soft-tissue, a fascia, a muscle, a tendon, a ligament, a meniscus, a labrum, an intervertebral disk, a skin, a subcutaneous tissue (e.g. in an incision), a subcutaneous fat (e.g. in an incision), a mucosa or mucosal surface (e.g. of an oral cavity, a sinus, a nose, a nasopharyngeal area, a pharynx, a larynx, a gut, a small or large bowel, a colon, a rectum an intestine, a stomach, an esophagus, a bile duct, a pancreatic duct, a gallbladder, a gallbladder duct, or a bladder), a mucosal fold, a gingiva, a gingival fold, a marginal gum, an attached gum, an interdental gum, an enamel, a tooth, an epithelium or epithelial surface (e.g. in a lumen), a synovial membrane (e.g. in an exposed joint), a peritoneum or peritoneal surface (e.g. in an abdominal cavity or a pelvis, e.g. lining a mesentery or internal organs or a liver surface or a spleen), a capsule (e.g. a Glisson capsule of a liver or a renal capsule, an adrenal capsule, a thyroid capsule or a parathyroid capsule), a diaphragm, a pleura, a pericardium, a meninx (e.g. a dura mater, arachnoid mater, pia mater), a sinus (e.g. a cavernous sinus or a sigmoid or other sinus), a calvarium, a facial structure (e.g. a nose, an ear, an earlobe), a surface of an eye (e.g. a cornea, a lens, a sclera), an eyelid.

The surface(s) of these one or more anatomic structures can be exposed during surgery, e.g. using an incision or tissue removal, and the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, and/or one or more of a virtual predetermined tissue change or alteration can be projected, aligned and/or superimposed by one or more OHMDs onto the surface(s) of the one or more anatomic structures so that at least portions of the virtual data and/or virtual display(s) are tangent with, intersecting with, orthogonal to, at a defined angle to, and/or offset with, e.g. at a predetermined distance or angle, with the surface(s) of the one or more anatomic structures. Once the anatomic surface(s) is (are) exposed, the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected, aligned and/or superimposed by one or more OHMDs onto the surface(s) of the one or more anatomic structures and the surgeon or a robot can then, for example, move and/or align and/or superimpose a physical tool, a physical instrument, a physical surgical guide, physical implant component, a physical implant and/or a physical device to align and/or superimpose it with the virtual projection(s).

Orienting, Aligning, Projecting and/or Superimposing Virtual Data Relative to Voids and Tissue Voids In embodiments, the OHMD display of virtual data, e.g. of one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration, can be projected onto or into and/or superimposed onto or into and/or aligned with and/or oriented relative to a void or tissue void seen directly through the see-through optical head mounted display (as it would be seen by the surgeon without wearing an OHMD). The one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected onto or into and/or superimposed onto or into and/or aligned with and/or oriented with so that at least portions of them are tangent with, intersecting with, orthogonal to, at a defined angle to, and/or offset with, e.g. at a predetermined distance or angle, with the void or tissue void, for example relative to the center of the void or tissue void or the periphery or border or margin of the void or tissue void. The term void or tissue void can be used interchangeably throughout the specification.

The void or tissue void can be at least a portion of an area or volume of a previously lost or missing or surgically removed tissue, brain, brain tissue, organ, organ tissue and or anatomic structure. The void or tissue void can be a defect, e.g. a defect in a tissue or an organ, for example a defect in an articular surface, or a defect in a bone, or a defect in a tissue, or a defect in an organ, or a defect in a brain matter. A defect can be a loss of tissue or cells. The defect can be caused by a disease. The defect can be caused by tissue necrosis. The defect can be the result of surgical removal. The void or tissue void can be an area or a volume of lost or removed tissue, e.g. by a tissue resection or removal, e.g. in a brain, an organ or a joint or a spine. The void or tissue void can be the result of a tissue, partial organ, bone or cartilage removal or resection, e.g. a brain resection, a tumor removal or resection, a wedge resection. The void or tissue void can be the result of an organ resection, e.g. a splenectomy or a pulmonary lobectomy. The void or tissue void can be a space within a surgical site or implantation site not filled by an anatomic structure, e.g. a dental or oral or an abdominal or a brain structure. The void or tissue void can also be a space within a surgical site or implantation site, e.g. created by a tissue resection, e.g. a bone removal. The void or tissue void can be a space between two implants or implant components. The void or tissue void can be a cerebrospinal fluid (CSF) space, e.g. a CSF space in a brain, for example inside a ventricle, or a CSF space in a spine, for example inside a thecal sac. The void or tissue void can be a lumen, e.g. in a vessel, a vascular structure, a gut, a small or large bowel, a colon, a rectum, an intestine, a stomach, an esophagus, a bile duct, a pancreatic duct, a gallbladder, a gallbladder duct, a bladder or a ureter or urethra. The void or tissue void can be a space inside a renal pelvis. The void or tissue void can be an oral cavity. The void or tissue void can be a pharyngeal cavity. The void or tissue void can be a nasopharyngeal space. The void or tissue void can be a sinus cavity. The void or tissue void can be an area or volume of a previously lost or missing or extracted tooth. The void or tissue void can be a body cavity. The void or tissue void can be a recess, e.g. between two tissue folds or two tissue layers. The void or tissue void can have a margin, border, edge, perimeter, dimension, geometry and/or shape. The margin, border, edge, perimeter, dimension, geometry and/or shape of the void or tissue void can be determined or defined, for example, with use of adjacent normal or pathologic tissue, e.g. tissue that has not been lost, or with use of an adjacent organ or an adjacent anatomic structure. The margin, border, edge, perimeter, dimension, geometry and/or shape of the void or tissue void can be determined or defined, for example, using information about the margin, border, edge, perimeter, dimension, geometry and/or shape of resected, removed or lost tissue.

The void or tissue void can be exposed during surgery, e.g. using an incision or tissue removal, and the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, and/or one or more of a virtual predetermined tissue change or alteration can be projected, aligned and/or superimposed by one or more OHMDs onto or into the one or more voids or tissue voids so that at least portions of the virtual data and/or virtual display(s) are tangent with, intersecting with, orthogonal to, at a defined angle to, and/or offset with, e.g. at a predetermined distance or angle, with the surface(s) of the one or more voids or tissue voids. Once the void(s) or tissue void(s) is (are) exposed, the one or more of virtual surgical tool, a virtual surgical instrument, a virtual surgical guide, which can be one or more of a virtual plane, a virtual axis, or a virtual cut block, a virtual trial implant, a virtual implant component, a virtual implant or a virtual device, all optionally selected from a virtual library, a virtual predetermined start point, a virtual predetermined start position, a virtual predetermined start orientation or alignment, a virtual predetermined intermediate point(s), a virtual predetermined intermediate position(s), a virtual predetermined intermediate orientation or alignment, a virtual predetermined end point, a virtual predetermined end position, predetermined end orientation or alignment, a virtual predetermined path, a virtual predetermined plane, a virtual predetermined cut plane, a virtual predetermined contour or outline or cross-section or surface features or shape or projection, a virtual predetermined depth marker or depth gauge, a virtual predetermined stop, a virtual predetermined angle or orientation or rotation marker, a virtual predetermined axis, e.g. rotation axis, flexion axis, extension axis, a virtual predetermined axis of the virtual surgical tool, non-visualized portions for one or more devices or implants or implant components or surgical instruments or surgical tools, and/or one or more of a virtual predetermined tissue change or alteration can be projected, aligned and/or superimposed by one or more OHMDs onto or into the one or more voids or tissue voids and the surgeon or a robot can then, for example, move and/or align and/or superimpose a physical tool, a physical instrument, a physical surgical guide, physical implant component, a physical implant and/or a physical device to align and/or superimpose it with the virtual projection(s).

In some embodiments, the registration of virtual patient data and live patient data using the methods described herein including anatomic landmarks can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art. Optionally, different anatomic landmarks can also be used for the first registration and any of the subsequent registrations. Or the same anatomic landmarks can be used for the first registration and any of the subsequent registrations.

Using Light Sources for Referencing Live Anatomic Landmarks

The tracker or pointing device can also be a light source, which can, for example, create a red point or green point created by a laser on the patient's tissue highlighting the anatomic landmark intended to be used for registration. A light source can be chosen that has an intensity and/or a color that will readily distinguish it from the live tissue of the patient.

The laser or other light source can optionally be integrated into or attached to the OHMD. For example, the laser or the light source can be integrated into or attached to a bridge connecting the frame pieces between the left and the right eye portion of the OHMD, for example over the nasal region.

Image and/or video capture and/or a 3D scanner, for example integrated into or attached to or coupled to the OHMD, can be used to identify the location of the light on the patient's tissue or the patient's anatomic landmark. Once the light has been directed to the desired location on the live data of the patient, specifically, the live landmark of the patient, registration can be performed by executing a registration command, registering the live data of the patient with the virtual data of the patient, e.g. the live landmark with the laser or other light being reflected of it and the corresponding virtual landmark of the patient. This process can be repeated for different anatomic landmarks, e.g. by pointing the light source at the next live anatomic landmark of the patient, confirming accurate placement or pointing, the light, e.g. a red or green laser point being reflected from the live patient landmark can be captured via the image and/or video capture device and/or 3D scanner, and the next anatomic live landmark can be registered with the corresponding virtual anatomic landmark of the patient. Virtual and live data can include an osteophyte or bone spur or other bony anatomy or deformity. In this manner, the OHMD, live data of the patient and virtual data of the patient can be registered in a common coordinate system. Virtual and physical surgical instruments and implant components can also be registered in the common coordinate system.

In some embodiments, more than one live and virtual anatomic landmark of the patient will be used, e.g. two, three or more.

In some embodiments, ultrasound or a radiofrequency transmitter can be used to pinpoint certain live anatomic landmarks. For example, an ultrasonic transmitter or a radiofrequency transmitter can be integrated into a point device, for example the tip of a pointing device. When the tip touches the desired live anatomic landmark, the transmitter can transmit and ultrasonic or RF signal which can be captured at a receiving site, optionally integrated into the OHMD. Optionally, for example as a means of increasing the accuracy of live data registration, multiple receiving sites can be used in spatially different locations. Virtual and live data can include an osteophyte or bone spur or other bony anatomy or deformity.

In some embodiments, the dimensions of the pointer have been previously scanned and registered with the OHMD. The image and/or video capture system attached to, integrated with or coupled to the OHMD can recognize the pointer in the live data and can identify the tip of the pointer. When the tip of the pointer touches the live landmark on the patient that corresponds to the landmark in the virtual data, the surgeon can, for example, click to indicate successful cross-referencing. The two data points can then optionally be fused or superimposed in a common coordinate system. Virtual and live data and data points can include or can be generated from an osteophyte or bone spur or other bony anatomy or deformity. Virtual and physical surgical instruments and implant components can also be registered in the common coordinate system.

Anatomic landmarks can include an unaltered surface shape, e.g. skin, facial features, e.g. the tip of the nose, a distance between both eyes, the location of an ear, the shape of the ear.

Anatomic landmarks can also be bony landmarks, e.g. a medial or lateral malleolus, a tibial tuberosity, a medial or lateral epicondyle, a trochlear notch, a spinous process etc. Virtual and live data and virtual and live anatomic landmarks can include an osteophyte or bone spur or other bony anatomy or deformity.

Optionally, a live anatomic surface can be used for registration purposes. In this embodiment, the live anatomic surface can be derived, for example, using a light scanning, infrared scanning or ultrasound technique, or ultrasonic scanning technique during the surgery. The live surfaces of the patient that are detected and generated in this manner can be matched or aligned with virtual surfaces of the patient, for example obtained preoperatively using an imaging test such as x-ray imaging, ultrasound, CT or MRI or any other technique known in the art. Virtual and live data and anatomic surfaces can include an osteophyte or bone spur or other bony anatomy or deformity.

In some embodiments, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Implantable or Attachable Markers or Calibration or Registration Phantoms or Devices Including Optical Markers In some embodiments, a surgeon is optionally using implantable or attachable markers to register virtual data of the patient with live data of the patient. This embodiment can, for example, be useful if the surgery is very extensive and results in the removal of tissue in the surgical site, as can be the case during brain surgery, e.g. removal of a brain tumor, liver surgery, e.g. removal of a liver tumor, joint replacement surgery and many other types of surgery. Virtual and live data can include an osteophyte or bone spur or other bony anatomy or deformity.

The terms implantable markers, attachable markers, skin markers, soft-tissue markers, calibration or registration phantoms or devices, and image capture markers as used throughout the application can include optical markers, e.g. optical markers with different geometric shapes or patterns, with QR codes, with bar codes, with alphanumeric codes. Implantable or attachable markers or calibration or registration phantoms or devices can be implanted prior to the actual surgery and can be included in pre-, intra- and/or postoperative imaging. Implantable or attachable markers or calibration or registration phantoms or devices can be implanted on or attached to osteophytes or bone spurs or other bony anatomy or deformity.

If the implantable or attachable markers or calibration or registration phantoms or devices are present in the virtual image data, the surgeon can optionally identify the implantable or attachable markers or calibration or registration phantoms or devices after an incision as he or she gains access to the target tissue and the implantable markers placed next to the target tissue or inside the target tissue. Such implantable or attachable markers or calibration or registration phantoms or devices can, for example, include radiation beets or metallic beets, for example also used for stereographic imaging or registration.

Alternatively, implantable or attachable markers or calibration or registration phantoms or devices can be placed during the surgery and, for example using an image and/or video capture system and/or 3D scanner attached to, integrated with or coupled to the OHMD, the location of the implantable or attachable markers or calibration or registration phantoms or devices can be determined. The location of the implantable or attachable markers or calibration or registration phantoms or devices on the patient in the live data of the patient can then be matched with the location of the anatomic structure to which the implantable or attachable markers or calibration or registration phantoms or devices is attached in the virtual data of the patient. For example, the anatomic structure in the virtual and live data can include an osteophyte or bone spur or other bony anatomy or deformity. In some embodiments, a pointer or pointing device can optionally include implantable or attachable markers or calibration or registration phantoms or device or optical markers followed by image capture through the OHMD or other image and/or video capture device and/or 3D scanner attached to, integrated with or coupled to the OHMD and registration of the tip of the pointer. In this manner, the OHMD, the implantable or attachable markers or calibration or registration phantoms or devices including optical markers and, through the use of the implantable or attachable markers or calibration or registration phantoms or devices including optical markers, the anatomic structures, pathologic structures, instruments, implant components and any other objects to which one or more implantable or attachable markers or calibration or registration phantoms or devices including optical markers can be attached, as well as the virtual data of the patient can be registered in a common coordinate system. Virtual and physical surgical instruments and implant components can also be registered in the common coordinate system.

Implantable or attachable markers or calibration or registration phantoms or devices can include rigid or fixed registration markers. Such rigid or fixed registration markers can be used to maintain registration as surgical field is being altered. A rigid or fixed registration marker can, for example, be a screw or a pin. Virtual and live data can include an osteophyte or bone spur or other bony anatomy or deformity. The rigid or fixed registration marker can be attached to the osteophyte or bone spur or other bony anatomy or deformity. In some embodiments, the medical device that is being implanted or a component thereof that has been, for example, already temporarily or permanently attached to the patient's tissue, e.g. an osteophyte or bone spur or bony anatomy or deformity, or the anatomic site or the surgical site can be used as an implantable or attachable marker or calibration or registration phantom or device during the surgery, for example while subsequent steps of the surgery are being completed. Such subsequent steps can, for example, include the implantation of additional components of the medical device. For example, in spinal fusion surgery, a first pedicle screw can be implanted. Live data and virtual data of the first pedicle screw can be registered. Subsequent pedicle screws or other components can be virtually displayed in the OHMD including their intended path, position, location or orientation, by maintaining registration between live and virtual data using the registered first pedicle screw. Any other rigid or fixed registration marker or implantable device can be used in this manner for different types of surgeries of the human body.

The one or more implantable or attachable markers or calibration or registration phantoms or devices can be attached to bone, cartilage, soft-tissues, organs or pathologic tissues such as osteophytes or bone spur or other bony anatomy or deformity, etc.

The one or more implantable or attachable markers or calibration or registration phantoms or devices can optionally include optical markers, retroreflective markers, infrared markers, or RF markers or any other marker device described in the art.

Optical markers are markers that can reflect light within the visible spectrum, i.e. the portion of the electromagnetic spectrum that is visible to the human eye, with wavelengths from about 390 to 700 nm or a frequency band from about 430-770 THz. Optical markers can also reflect light that includes a mix of different wavelengths within the visible spectrum. The light reflected by the optical markers can be detected by an image and/or video capture system integrated into, attached to or separate from the OHMD. Optical markers can be detected with regard to their location, position, orientation, alignment and/or direction of movement and/or speed of movement with use of an image and/or video capture system integrated into, attached to or separate from the OHMD with associated image processing and, optionally, pattern recognition software and systems. Optical markers can include markers with select geometric patterns and/or geometric shapes that an image and/or video capture system, for example integrated into, attached to or separate from the OHMD, can recognize, for example using image processing and/or pattern recognition techniques. Optical markers can include markers with select alphabetic codes or patterns and/or numeric codes or patterns and/or alphanumeric codes or patterns or other codes or patterns, e.g. bar codes or QR codes, that an image and/or video capture system, for example integrated into, attached to or separate from the OHMD, can recognize, for example using image processing and/or pattern recognition techniques. QR codes or quick response codes include any current or future generation matrix code including barcode. Barcodes and QR codes are machine readable optical labels that can include information, for example, about the patient including patient identifiers, patient condition, type of surgery, about the surgical site, the spinal level operated if spine surgery is contemplated, the patient's side operated, one or more surgical instruments, one or more trial implants, one or more implant components, including type of implant used and/or implant size, type of polyethylene, type of acetabular liner (e.g. standard, lipped, offset, other) if hip replacement is contemplated. A QR code can use different standardized encoding modes, e.g. numeric, alphanumeric, byte/binary, and/or kanji to store data. Other encoding modes can be used. Any current and/or future version of QR codes can be used. QR codes using single or multi-color encoding can be used. Other graphical markers, such as the ones supported by the Vuforia (PTC, Needham, Mass.) augmented reality platform, can be used as well.

A bar code, QR code or other graphical marker can be the optical marker. A bar code, QR code or other graphical marker can be part of an optical marker or can be integrated into an optical marker. The same OR code or bar code or other graphical marker can contain information related to the patient and/or the surgical site, e.g. patient identifiers, age, sex, BMI, medical history, risk factors, allergies, site and side (left, right), spinal level to be operated information related to inventory management, e.g. of surgical instruments and/or implants or implant components, e.g. left vs. right component, selected component size (match against virtual surgical plan and/or templating and/or sizing)

and can be used to obtain information about the location, position, orientation, alignment and/or direction of movement, and/or speed of movement, if applicable, of the surgical site, surgically altered tissue, one or more surgical instruments and one or more trial implants and/or implant components.

Geometric patterns, geometric shapes, alphabetic, numeric, alphanumeric, and other codes or patterns including bar codes and QR codes included in or part of one or more optical markers can be predefined and, optionally, stored in database accessible by an image and/or video capture system and associated image processing software and pattern recognition software. Geometric patterns, geometric shapes, alphabetic, numeric, alphanumeric, and other codes or patterns including bar codes and QR codes included in or part of one or more optical markers can be in 2D and some of it in 3D. For example, one or more planar or 2D patterns can be used in select embodiments. Alternatively, select 3D geometric shapes can be used, e.g. cubes, cuboids, prisms, cones, cylinders, spheres. Any 3D shape can be used including irregular shapes and/or asymmetric shapes. The 3D geometric shape can include 2D geometric patterns and/or alphabetic, numeric, alphanumeric, and other codes or patterns including bar codes and QR codes on one or more surfaces. For example, if a cuboid or other 3D shape is used for an optical marker, the same or different geometric patterns and/or alphabetic, numeric, alphanumeric, and other codes or patterns including bar codes and QR codes can be included in, affixed to or integrated into one or more of its surfaces or faces, e.g. two opposing surfaces or two adjacent surfaces oriented, for example, perpendicularly. 2D geometric patterns and/or alphabetic, numeric, alphanumeric, and other codes or patterns including bar codes and QR codes included in, affixed to or integrated into one or more surfaces or faces of a 3D geometric shape can be used to determine the orientation of select surfaces or faces of the geometric shape including the optical marker and, with that, the orientation and/or alignment of the surface or face and with that the geometric shape, for example in relationship to a surgical site, a surgical alteration, e.g. a cut bone surface or a reamed bone surface, a surgical instrument and/or one or more implant components including trial implants. In this manner, movement of a limb or surgical site can be tracked in embodiments. For example, an optical marker with a 3D shape can be attached to a trochlea or an anterior tibia. The optical marker can have a first surface with a first geometric pattern. The optical marker can have a second surface with a second geometric pattern. The first surface with the first geometric pattern can, for example, be anteriorly facing. The second surface with the second geometric pattern can, for example, be medially or laterally facing. When the operator looks through the OHMD, optionally with one or more video systems integrated into, attached to or separate from the OHMD, at the optical marker and the video system, in this example, detects predominantly the first surface, the information can be used to indicate that the knee is in a frontal, e.g. non-rotated position; if the video system detects a different ratio of first vs. second surface visible or detectable, e.g. with a larger portion of the second surface visible or detectable, the information can be used to indicate that the knee is in a somewhat or more rotated position. Similarly, a third surface with a third geometric pattern can be superior or inferior facing. If the video detects that a greater portion of the third surface is visible or detectable, the information can indicate that the knee is in a more flexed position. Any combination is possible.

A 3D optical marker can, optionally, not have distinct surfaces with distinct geometric patterns, but can include a continuum of the same or, optionally changing, geometric patterns along its 3D surface or 3D surfaces. The location and/or or position and/or orientation and/or coordinates of the changing, different portions of the geometric pattern along the 3D surface(s) can be known, e.g. prior to tracking a surgical site, a surgical instrument, an implant, a medical device or a limb or bone, e.g. during movement. A video system integrated into, attached to or separate from the OHMD can detect the location and/or position and/or orientation and/or coordinates of one or more of the different portions of the geometric patterns and can use the information to track a surgical site, a surgical instrument, an implant, a medical device or a limb or bone, e.g. during movement.

The detection of one or more surfaces with geometric patterns or one or more portions of geometric patterns, e.g. on a 2D optical marker or a 3D optical marker, can be used to trigger one or more computer demands. Similarly, the disappearance of one or more surfaces with geometric patterns or one or more portions of geometric patterns or an entire geometric pattern can be used to trigger one or more computer demands. Such computer commands can, for example, include activating a motion tracking mode, de-activating a motion tracking mode, activating an OHMD display, de-activating an OHMD display, displaying a surgical step, e.g. a next surgical step or a prior surgical step, displaying a proposed correction for a surgical step, initiating an alarm, terminating an alarm, displaying a surgical instrument, tracking a surgical instrument, displaying a next surgical instrument, displaying an implant component, displaying a medical device, tracking any of the foregoing, terminating any of the foregoing commands. Someone skilled in the art can recognize other commands that can be initiated or executed in this manner. Such commands can also be used, for example, to initiate action by a robot, e.g. activating a bone saw, guiding a robot or executing a bone cut or bone removal with a robot.

In another embodiment, one or more video systems or cameras integrated into, attached to or separate from an OHMD can detect a change in angular orientation of a 2D or 3D optical marker and/or geometric pattern and/or portions of one or more of the foregoing; the change in angular orientation detected in this manner can also be used to trigger or execute one or more commands.

Geometric patterns and/or geometric shapes, alphabetic, numeric, alphanumeric, and other codes or patterns including bar codes and QR codes can be in color or black and white. Geometric patterns and/or geometric shapes and/or alphabetic, numeric, alphanumeric, and other codes or patterns including bar codes and QR codes can include portions that include color and black and white sections, portions that include only color and portions that are only black and white. Geometric shapes can include faces or surfaces that include color and black and white, faces or surfaces that include only black and white, and faces or surfaces that include only color. Different colors and different color codes can be used for different faces or surfaces of a geometric shape part of an optical marker. Different colors and different color codes can be used for different geometric patterns and/or geometric shapes and/or alphabetic, numeric, alphanumeric, and other codes or patterns including bar codes and QR codes. Different colors and different color codes can be used for different optical markers. Different colors, e.g. red, blue, green, orange, cyan etc., can be used for different geometric patterns and/or geometric shapes and/or alphabetic, numeric, alphanumeric, and other codes or patterns including bar codes and QR codes. Different colors, e.g. red, blue, green, orange, yellow, pink, cyan can be used for different optical markers. Different optical markers can optionally be associated with different surgical steps and/or different surgical instruments and/or different implant components; the use of a particular marker can be recognized by an image and/or video capture system integrated into, attached to or separate from the OHMD using standard image processing and/or pattern recognition software, including, optionally a database of patterns, e.g. with their associations with a particular surgical step and/or surgical instruments. As the image and/or video capture system recognizes a particular optical marker in the field of view, for example based on a particular geometric patterns and/or geometric shape and/or alphabetic, numeric, alphanumeric, and other codes or patterns including bar codes and QR codes used, it can then optionally display the corresponding surgical step and/or surgical instrument and/or implant component associated with that optical marker.

2D geometric patterns, alphabetic, numeric, alphanumeric, and other codes or patterns including bar codes and QR codes or combinations thereof, optionally with color and/or black and white coding, included in, affixed to or integrated into one or more surfaces or faces of a 3D geometric shape can be used to determine the orientation and/or alignment of select surfaces or faces of the geometric shape and, with that, the orientation and/or alignment of the geometric shape and/or the optical marker, for example in relationship to an anatomic landmark, a surgical site, a surgical alternation, e.g. a cut bone surface or a reamed bone surface, a surgical instrument and/or one or more implant components including trial implants. One or more 2D geometric patterns, alphabetic, numeric, alphanumeric, and other codes or patterns including bar codes and QR codes, optionally with color and/or black and white coding, included in, affixed to or integrated into an optical marker can be used to determine the orientation and/or alignment of the optical marker, which can, for example, be affixed to or integrated into an anatomic landmark, a surgical site, a surgical alternation, e.g. a cut bone surface or a reamed bone surface, a surgical instrument and/or one or more implant components including trial implants. Optical markers can be affixed to an anatomic landmark, a surgical site, a surgical alteration, e.g. a cut bone surface or a reamed bone surface, or a drill hole of the patient and the corresponding anatomic landmark, surgical site, or surgical alternation can be identified in the virtual data of patient thereby enabling registration of the virtual data and the live data of the patient in the same coordinate system.

Executing Commands Using Optical Markers: Optical markers can be hidden or removed. The hiding or removal of an optical marker can be used to trigger a computer command. For example, a camera integrated into, attached to or separate from an OHMD can monitor the presence of an optical marker. If the optical marker is hidden, for example by placing a drape over it or by covering it with the surgeon's or the surgical assistant's hand, or removed, the hiding or removal can trigger a command. The command can, for example, be to initiate a different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. Un-hiding the optical marker can be used to reverse the command, e.g. to return to a prior display state or display type of the optical head mounted display(s). Un-hiding the optical marker can also be used to advance to yet different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. The hiding or removal can include hiding or removing only a portion of the optical marker. For example, when an optical marker has a 3D shape, for example with select 2D portions and 2D geometric patterns or continuous, optionally changing 3D geometric pattern(s), one or more of the 2D portions or 2D geometric patterns can optionally be hidden or removed, for example by manually or through other means removing the 2D portion or 2D geometric pattern or continuous, optionally changing 3D geometric pattern(s) from the 3D shape of the optical marker; this is feasible, for example, when the 2D portion or 2D geometric pattern is attached to or inserted into the optical marker with the attachment or insertion mechanism providing the capability for removal of the 2D portion or 2D geometric pattern. Alternatively, a 3D portion of the 3D shape of the optical marker can be removed or hidden. Such removal or hiding can also trigger one or more commands as described in the foregoing embodiments, e.g. to initiate a different display, to turn on or turn off a display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Optical markers can be added or re-displayed. The addition or re-displaying of an optical marker can be used to trigger a computer command. For example, a camera integrated into, attached to or separate from an OHMD can monitor the presence of an optical marker. If the optical marker is re-displayed, for example by removing a drape from it or by uncovering it by removing the surgeon's or the surgical assistant's hand, or added, the adding or re-displaying can trigger a command. The command can, for example, be to initiate a different display, to turn on or to turn off a display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. Hiding or removing the optical marker can be used to reverse the command, e.g. to return to a prior display state or display type of the optical head mounted display(s). Re-displaying or adding then the optical marker again can also be used to advance to yet different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees. The adding or re-displaying can include adding or re-displaying only a portion of the optical marker. For example, when an optical marker has a 3D shape, for example with select 2D portions and 2D geometric patterns or a 3D geometric pattern, one or more of the 2D portions or 2D geometric patterns or 3D geometric patterns can optionally be added or re-displayed, for example by manually or through other means adding the 2D portion or 2D geometric pattern or 3D geometric pattern to the 3D shape of the optical marker; this is feasible, for example, when the 2D portion or 2D geometric pattern or 3D geometric pattern can be attached to or inserted into the optical marker with the attachment or insertion mechanism providing the capability for adding or re-displaying the 2D portion or 2D geometric pattern or 3D geometric pattern. Alternatively, a 3D portion of the 3D shape of the optical marker can be added or re-displayed. Such adding or re-displaying can also trigger one or more commands as described in the foregoing embodiments, e.g. to initiate a different display, to turn on or turn off a display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Similarly, the activation, e.g. turning on, of one or more LED's or the de-activation, e.g. turning off, of one or more LED's can be detected by one or more camera systems integrated into, attached to or separate from the OHMD and can be used to trigger or reverse one or more commands, e.g. to initiate a different display, to magnify or minify a display, to highlight certain structures or virtual features, to display a different surgical step, to display a different virtual surgical instrument or implant component, to upsize or downsize and implant component, to modify a surgical step, to change an alignment and/or a rotation, e.g. by 1, 2, 3, 4, 5 or other degrees.

Optical markers on OHMDs: Optical markers can also be attached to an OHMD including multiple OHMDs if multiple OHMDs are used during a surgery. Optionally, optical markers, e.g. with QR codes, can be used to differentiate a first from a second, third, fourth and/or more OHMDs. One or more optical markers can optionally be attached to the operating room table and they can be registered in a coordinate system, for example the same coordinate system in which the one or more OHMDs, the patient, and portions of the surgical site can be registered. One or more optical markers can optionally be attached to other structures in the operating room including fixed structures, e.g. walls, and movable structures, e.g. OR lights, and they can be registered in a coordinate system, for example the same coordinate system in which the one or more OHMDs, the patient, and portions of the surgical site can be registered. In this example, optical markers can also be mounted to fixed structures on holding arms or extenders, optionally moveable and, for example, of known dimensions, orientations, lengths and angles.

Optical markers attached to fixed structures such as OR walls can be used to enhance the accuracy of room recognition and spatial mapping, in particular when the coordinates and/or the angles and/or distances between different optical markers are known. Optical markers attached to fixed structures such as OR walls can also be used to enhance the determination of the location and pose and change in location or pose or the coordinates and change in coordinates of one or more optical head mounted displays, which can assist with increasing the accuracy of the display of virtual data and their superimposition on corresponding live data.

Optical markers attached to movable structures can be used to track their location in the operating room. Optical markers attached to OR lights can be used to estimate the direction of light and the orientation and/or trajectory of shadows in the OR or a room. If the orientation and/or trajectory of shadows in the OR or the room is known, virtual shadowing or shading with the same or similar orientation or trajectory can be applied to virtual data display by the OHMD.

Different coordinate systems can be used. For example, a global coordinate system, can include one or more of a femoral coordinate system, tibial coordinate system, ankle coordinate system, hip coordinate system, acetabular coordinate system, humeral coordinate system, glenoid coordinate system, vertebral coordinate system etc. Someone skilled in the art can readily recognize other sub-coordinate systems in the global coordinate system.

In one example, one or more optical markers including one or more geometric shapes, geometric patterns, alphabetic, numeric, alphanumeric, and other codes or patterns including bar codes and QR codes or combinations thereof can be attached to a medial femoral epicondyle, for example using a pin or a screw or an adhesive. An image and/or video capture system integrated into, attached to or separate from the OHMD can be used to monitor the position, and/or orientation and/or alignment and/or direction of movement and/or speed of movement of the optical marker in relationship to the image and/or video capture system and/or the coordinate system, e.g. a femoral coordinate system, a tibial coordinate system or a global coordinate system or combinations thereof; as the distal femur moves, the image and/or video capture system can detect the marker, for example based on its pre-programmed geometric shape, geometric pattern, alphabetic, numeric, alphanumeric, and other codes or patterns including bar codes and QR codes, and can monitor and, optionally, record the movement. If a second optical marker, including one or more geometric shapes, geometric patterns, alphabetic, numeric, alphanumeric, and other codes or patterns including bar codes and QR codes or combinations thereof is attached to the lateral femoral condyle in the same example, the image and/or video capture system can also monitor and, optionally record the position, and/or orientation and/or alignment and/or direction of movement and/or speed of movement of the second optical marker in relationship to the image and/or video capture system and/or the coordinate system, e.g. a femoral coordinate system, a tibial coordinate system or a global coordinate system or combinations thereof; by monitoring the position, and/or orientation and/or alignment and/or direction of movement and/or speed of movement of the first optical marker on the medial femoral epicondyle and the position, and/or orientation and/or alignment and/or direction of movement and/or speed of movement of the second optical marker on the lateral femoral epicondyle, the image and/or video capture system and related image processing and pattern recognition software can also monitor and, optionally, record the movement, e.g. direction of movement or speed of movement, of the femoral epicondylar axis, for example during flexion and extension of the knee. One or more optical markers including one or more geometric shapes, geometric patterns, alphabetic, numeric, alphanumeric, and other codes or patterns including bar codes and QR codes or combinations thereof can be attached to a proximal tibia, e.g. an anterior tibial rim, a medial and/or lateral tibial spine, a lowest point of a medial plateau and/or a highest point of a lateral tibial plateau, for example in the same example. The image and/or video capture system integrated into, attached to or separate from the OHMD can be used to monitor the position, and/or orientation and/or alignment and/or direction of movement and/or speed of movement of the optical marker(s) attached to the tibia in relationship to the image and/or video capture system and in relationship to one or more femoral optical markers and/or the coordinate system, e.g. a femoral coordinate system, a tibial coordinate system or a global coordinate system or combinations thereof, thereby monitoring and, optionally recording, tibiofemoral motion, e.g. during a surgery. One or more optical markers including one or more geometric shapes, geometric patterns, alphabetic, numeric, alphanumeric, and other codes or patterns including bar codes and QR codes or combinations thereof can be attached to a patella, e.g. a most superior aspect, a most inferior aspect, a most lateral aspect and/or a most medial aspect, for example in the same example. The image and/or video capture system integrated into, attached to or separate from the OHMD can be used to monitor the position, and/or orientation and/or alignment and/or direction of movement and/or speed of movement of the optical marker(s) attached to the patella in relationship to the image and/or video capture system and in relationship to one or more femoral optical markers and/or the coordinate system, e.g. a femoral coordinate system, a tibial coordinate system, a patellar coordinate system or a global coordinate system or combinations thereof, thereby monitoring and, optionally recording, patellofemoral motion, e.g. during a surgery. The image and/or video capture system integrated into, attached to or separate from the OHMD can be used to monitor the position, and/or orientation and/or alignment and/or direction of movement and/or speed of movement of the optical marker(s) attached to the patella in relationship to the one or more tibial optical markers, thereby monitoring and, optionally recording, patellar motion in relationship to the tibia, e.g. during tibial adduction or abduction.

In some embodiments, an optical marker, for example with one or more specific geometric shapes, geometric patterns, alphabetic, numeric, alphanumeric, and other codes or patterns including bar codes and QR codes or combinations thereof, can be assigned to a virtual surgical step. The marker can, for example, include written text defining the surgical step or corresponding to the surgical step, which can be the immediately preceding surgical step or the next surgical step, for example in a virtual surgical plan. In some embodiments, the text can be a number, for example a number corresponding to a particular surgical step, e.g. 1—for distal femoral cut, 2—for anterior femoral cut, 3—for posterior femoral cut, 4—for first chamfer cut, 5—for second chamfer cut. The number can be recognized by the image and/or video capture system, which can then display the virtual view for the corresponding surgical step, e.g. for 1—a cut plane for the distal femoral cut or a virtual outline of the corresponding physical distal femoral cut block. A combination of numbers and text can be used and the image and/or video capture system and associated software and optional pattern recognition software and systems can recognize the numbers and text and trigger a command to display the corresponding virtual view of the corresponding virtual surgical step, e.g. 1F—distal femoral cut, 2F—anterior femoral cut, 1T—proximal tibial cut, 2T—tibial keel punch etc.

In another example, an optical marker with one or more specific geometric shapes, geometric patterns, alphabetic, numeric, alphanumeric, and other codes or patterns including bar codes and QR codes or combinations thereof can be assigned to the step "distal femoral cut" in a virtual surgical plan for a total knee replacement in a patient; the optical marker can include the text "distal femoral cut". The surgeon can, for example, affix the marker to the cut bone surface of the distal femur or somewhere adjacent to it. An image and/or video capture system and/or 3D scanner integrated into, attached to or separate from an OHMD can detect the optical marker with the one or more specific geometric patterns and/or specific geometric shapes assigned to "distal femoral cut", indicating that the distal femoral cut has been completed; the image capture signal and/or 3D scanner signal can then initiate a command to the OHMD to display the next surgical step, e.g. an anterior cut plane or an outline of an anterior cut block or cut guide, as the surgeon prepares to perform the next cut, e.g. the anterior femoral cut in this example.

In some embodiments, an optical marker, for example with one or more specific geometric shapes, geometric patterns, alphabetic, numeric, alphanumeric, and other codes or patterns including bar codes and QR codes or combinations thereof, can be integrated into, included in, or attached to a surgical instrument used for a surgical step in a virtual surgical plan. For example, the optical marker can be included in, integrated into or attached to a surgical cut block or cutting tool, e.g. for a proximal tibial cut. Optionally, the marker can include written text defining the surgical step or corresponding to the surgical step, e.g. in a virtual surgical plan. In the immediately foregoing example, an optical marker with one or more specific geometric shapes, geometric patterns, alphabetic, numeric, alphanumeric, and other codes or patterns including bar codes and QR codes or combinations thereof can be assigned to the step "proximal tibial cut" in a virtual surgical plan for a total knee replacement in a patient; the optical marker can include the text "proximal tibial cut" which the surgeon can read and ensure that the correct marker is used for the next surgical step that he or she is contemplating, in this example a proximal tibial cut.

As the optical marker enters the surgeon's field of view, an image and/or video capture system integrated into or attached to the OHMD on the surgeon's head can detect the optical marker and display the next virtual surgical step, e.g. an outline of a virtual proximal tibial cut block corresponding to the physical proximal tibial cut block, so that the surgeon can align or superimpose the physical surgical cut block or instrument onto the outline of the virtual surgical cut block or instrument. Alternatively, as the optical marker enters the surgeon's field of view, an image and/or video capture system integrated into or attached to the OHMD on the surgeon's head can detect the optical marker and display the next virtual surgical step, e.g. a virtual cut plane with a predetermined resection level, varus or valgus angle and/or slope, so that the surgeon can align or superimpose the physical surgical cut block and/or the physical surgical saw with the virtual cut plane. Once the surgical step is completed, e.g. a proximal tibial cut, and the surgeon removes the physical surgical instrument with the integrated, included or attached optical markers from the surgical field and/or the field of view of the image and/or video capture system, the image and/or video capture system can detect that the optical marker is not present in the field of view anymore and software can generate a command to turn off the display of OHMD, e.g. as a means of preserving battery power in the OHMD, or the display of the completed virtual surgical step. Optionally, a command can be generated at this time, optionally automatically, to display the next surgical step, e.g. a tibial keel punch including, for example, setting tibial rotation. Alternatively, the display of the OHMD unit can display the next surgical step as the next surgical instrument with the corresponding optical marker for the next surgical step enters the field of view, e.g. in the surgeon's hand.

In a similar example, an optical marker can be attached to an acetabular reamer used for hip replacement. An image and/or video capture system integrated into or attached to an OHMD can detect the optical marker as it enters the surgeon's field of view triggering a command to display the reaming axis or a virtual display of the reamer with the intended alignment and/or direction for the reaming step; as the optical marker with the surgical instruments exits the surgeon's field of view, the image and/or video capture system can detect it triggering a command to stop the display of the reaming axis or virtual display of the reamer, optionally switching to the next surgical step.

In some embodiments, one or more optical markers can be included in, integrated into or attached to an insert for a cutting block or guide. The insert can be configured to fit into one or more slots or guides within the cutting block or guide for guiding a saw blade. Representative cutting blocks or guides are, for example, cutting blocks or guides used in knee replacement, shoulder replacement, hip replacement, and ankle replacement. These cutting blocks or guides are, for example, used to remove bone at the articular surface to fit the patient's bone to the bone facing side of an implant or implant component. The insert can be designed to partially or substantially fill the entire slot or guide, e.g. in x and y direction or x and z direction or y and z direction depending on the shape and/or design of the cutting block or guide. If the insert partially fills or substantially fills the slot or guide in x and y direction, the insert can be configured to extend beyond the slot or guide in z direction. If the insert partially fills or substantially fills the slot or guide in x and z direction, the insert can be configured to extend beyond the slot or guide in y direction. If the insert partially fills or substantially fills the slot or guide in y and z direction, the insert can be configured to extend beyond the slot or guide in x direction. Any direction is possible including oblique directions, orthogonal directions and non-orthogonal directions depending on the configuration of the cutting block or guide and the associated slots or guides. Oblique slots can, for example, be used for chamfer cuts in total knee replacement or oblique talar cuts in total ankle replacement.

The portion(s) of the insert that extend beyond the slot or guide can, for example, include one or more integrated or attached optical markers. If more than one optical marker is used, the optical markers can be arranged at predefined angles and locations, e.g. 90 degrees or less than 90 degrees or more than 90 degrees. The insert can have similar dimensions to a representative saw blade used with the cutting block or guide. The insert can indicate the position, location, orientation, alignment and direction of travel for a saw blade that will subsequently be inserted. The surgeon can place the insert inside the slot or guide of the physical cutting block or guide and align the insert, for example, with a virtual cut plane or a virtual outline of the insert or cutting block or guide projected by the OHMD onto the surgical site, e.g. a distal femur in total knee replacement or a proximal femur in total hip replacement. Once the insert is substantially aligned and/or superimposed with the virtual cut plane, the virtual outline of the insert or cutting block or guide, the surgeon can pin the physical cutting block or guide onto the bone, thereby affixing the cutting block or guide to the bone in a position where the virtual surgical plan, e.g. the virtual cut plane or virtual outline of the insert or cutting block or guide is substantially aligned with the physical cut plane and or the physical insert or cutting block or guide. The surgeon can then insert the physical saw blade and perform the physical cut. The insert can be configured to have a shape substantially similar to the physical saw blade, serving as a dummy saw blade.

Alternatively, the surgeon can place the physical saw blade inside the slot or guide of the physical cutting block or guide and the surgeon can align the physical saw blade, for example, with a virtual cut plane or a virtual outline of the saw blade or cutting block or guide projected by the OHMD onto the surgical site, e.g. a distal femur in total knee replacement or a proximal femur in total hip replacement. Once the physical saw blade is substantially aligned and/or superimposed with the virtual cut plane, the virtual outline of the saw blade or cutting block or guide, the surgeon can pin the physical cutting block or guide onto the bone, thereby affixing the cutting block or guide to the bone in a position where the virtual surgical plan, e.g. the virtual cut plane or virtual outline of the saw blade or cutting block or guide is substantially aligned with the physical cut plane and or the physical saw blade or cutting block or guide. The surgeon can then advance the physical saw blade and perform the physical cut. Optical markers can be included in, integrated into or attached to the cutting block or guide or the insert, e.g. a dummy saw blade. Optical markers can also be attached or affixed the saw blade. The optical markers can include a text or alphanumeric code for the surgeon that designates, for example, a specific surgical step, e.g. 1F—distal femoral cut, 2F—anterior femoral cut, 1T—proximal tibial cut, 2T—tibial keel punch etc. The optical markers can also include one or more specific geometric shapes, geometric patterns, alphabetic, numeric, alphanumeric, and other codes or patterns including bar codes and QR codes or combinations thereof. The one or more specific geometric shapes, geometric patterns, alphabetic, numeric, alphanumeric, and other codes or patterns including bar codes and QR codes or combinations thereof can be specific for the surgical step, corresponding, for example, to the lettering or alphanumeric code that indicates the surgical step to the surgeon. An image and/or video capture system integrated into, attached to or separate from the OHMD can detect the one or more specific geometric shapes, geometric patterns, alphabetic, numeric, alphanumeric, and other codes or patterns including bar codes and QR codes or combinations thereof as the optical marker(s) enters the field of view; the specific geometric shapes, geometric patterns, alphabetic, numeric, alphanumeric, and other codes or patterns can be recognized using image processing and/or pattern recognition software triggering, for example, a command to display corresponding virtual surgical step in the OHMD superimposed onto the surgical field with the view angle for the surgeon aligned with the surgical field or target anatomy or bone cut. When the cutting block or guide, the insert, e.g. a dummy saw blade, or the physical saw blade with the optical marker is removed, the image and/or video capture system can detect that the optical marker is not present in the field of view any longer, triggering, for example a command to turn off the OHMD display, e.g. as a means of preserving battery power, or the display of the completed surgical step or to switch to the display of the next surgical step and corresponding virtual display.

In some embodiments, one or more optical markers, e.g. at select angles, e.g. 90 degrees or less or more or parallel or on one axis, can be included in, integrated into or attached to a cutting block or guide.

In some embodiments, one or more optical markers can be used in conjunction with a spinal surgery, e.g. a vertebroplasty, a kyphoplasty, a posterior spinal fusion, an anterior spinal fusion, a lateral spinal fusion and/or a disk replacement. For example one or more optical markers can be included in, integrated into, or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps and the like. The foregoing list is only exemplary and not to be construed limiting. The one or more optical markers can be used to designate the patient's left side and the patient's right side and/or they can be used to designate the patient's spinal level, using, for example, one or more geometric shapes, geometric patterns, alphabetic, numeric, alphanumeric, and other codes or patterns that can be detected with an image and/or video capture system integrated into, attached to or separate from the OHMD and that can be recognized using image processing and/or pattern recognition.

One or more optical markers can be used to determine the position, location, orientation, alignment and/or direction of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component with use of an image and/or video capture system integrated into, attached to or separate from the OHMD. For example, after the initial registration or any subsequent registration of the patient, the surgical site, the OHMD, optionally an image and/or video capture system integrated into, attached to or separate from the OHMD, the virtual data and/or the live data of the patient have been performed, the image and/or video capture system can detect an optical marker included in, integrated into, and/or attached to the surgical instrument. Since the location, position, alignment and/or orientation of the optical marker on the surgical instrument are known and the dimensions, e.g. at least one of them, or geometry of the surgical instrument are known, the image and/or video capture system can track the optical marker and the surgical instrument with regard to its location, position, orientation, alignment and/or direction of movement.

In another example, two or more optical markers can be integrated into or attached to different, optionally defined locations along the long axis of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component, for example instruments or trial implants or implant components in knee replacement or hip replacement. An image and/or video capture system can detect the two or more optical markers and their respective location can be determined. With the location of the two or more optical markers captured and defined by the image and/or video capture system, the long axis of the needle, pin, awl, probe, tap, mill, saw, reamer, broach, impactor, and/or other surgical instrument and/or trial implant and/or implant component can be determined; other axes can be determined in addition to the long axis or instead of the long axis. With the location of the optical markers on the needle, pin, awl, probe, tap, mill, saw, reamer, broach, impactor, and/or other surgical instrument and/or trial implant and/or implant component known, the long axis or other axis of the needle, pin, awl, probe, tap, mill, saw, reamer, broach, impactor, and/or other surgical instrument and/or trial implant and/or implant component known and the dimensions of the needle, pin, awl, probe, tap, mill, saw, reamer, broach, impactor, and/or other surgical instrument and/or trial implant and/or implant component known, any portions of the needle, pin, awl, probe, tap, mill, saw, reamer, broach, impactor, and/or other surgical instrument and/or trial implant and/or implant component hidden by the tissue, e.g. below the skin and/or inside or within muscle or the cartilage or the bone, can be estimated and can optionally be displayed by the OHMD in addition to the virtual or intended path or projected path or any other aspects of a virtual surgical plan. Rather than using two or more optical markers in the foregoing embodiment, an optical marker long enough or wide enough or deep enough to define one or more axes of a needle, pin, awl, probe, tap, mill, saw, reamer, broach, impactor, and/or other surgical instrument and/or trial implant and/or implant component can also be used.

Optionally, when two or more optical markers are used included in, integrated into or attached to a surgical instrument, the optical markers, can be arranged at the same angles, e.g. parallel or on the same axis, or at different angles, e.g. orthogonal angles or non-orthogonal angles.

Similarly, in determining an axis of a joint, e.g. an epicondylar axis, optical markers, e.g. optical markers attached to a medial or a lateral femoral epicondyle, can be arranged at the same angles, e.g. parallel or on the same axis, or at different angles, e.g. orthogonal angles or non-orthogonal angles. This can be particularly useful, when the optical markers include one or more of a geometric shape, geometric pattern, alphabetic, numeric, alphanumeric, and other codes or patterns including bar codes and QR codes or combinations thereof. By arranging the optical markers and any associated geometric shapes, geometric patterns, alphabetic, numeric, alphanumeric, and other codes or patterns including bar codes and QR codes or combinations thereof in this manner, the angular orientation of the surgical instrument or an axis can be determined in a more accurate manner. For example, at certain view angles from an image and/or video capture system integrated into or attached to an OHMD select geometric shapes, geometric patterns, alphabetic, numeric, alphanumeric, and other codes or patterns including bar codes and QR codes or combinations thereof of a first optical marker on a surgical instrument or an anatomic landmark may be only partially visualized or not visualized at all due to the angular orientation; when a second optical marker is oriented at a different angle, location and/or orientation on the same surgical instrument or an anatomic landmark, the view angle from the image and/or video capture system integrated into or attached to the OHMD to the second optical marker can allow for a complete or a more complete visualization of the one or more geometric shapes, geometric patterns, alphabetic, numeric, alphanumeric, and other codes or patterns including bar codes and QR codes or combinations thereof, thereby allowing a more accurate determination of the angular orientation of the second optical marker and, with that, the surgical instrument. In addition, the respective projections of the first optical marker and/or the second optical marker measured by the image and/or video capture system, optionally paired with any parallax information when two or more cameras are used, e.g. one positioned near the left eye and another positioned near the right eye, can be used to more accurately determine their relative position and the position of the surgical instrument.

An image and/or video capture system integrated into or attached to or separate from an OHMD can detect an optical marker included in, integrated into or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach an impactor, a cutting or drilling block, and/or other surgical instrument and/or trial implant and/or implant component as it enters the surgeon's field of view triggering a command to display the predetermined path or plane or a virtual display of the a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component or other display mode or type of the virtual surgical plan, for example with the intended position, location and/or alignment and/or direction for the intended surgical step; as the optical marker with the surgical instrument exits the surgeon's field of view, the image and/or video capture system can detect it triggering a command to stop the display of the predetermined path or the virtual display of the surgical instrument or other aspects of the virtual surgical plan, optionally switching to the next surgical step and corresponding virtual display. In a spinal procedure as well as select other procedures, the next surgical step can involve the same side of the patient or the opposite side of the patient at the same spinal level, where the corresponding virtual display for the next surgical step for a given level and side can be initiated by the OHMD display. The next surgical step can involve the same side of the patient or the opposite side of the patient at an adjoining or different spinal level, where the corresponding virtual display for the next surgical step for a given level and side can be initiated by the OHMD display.

Optical markers can include one or more QR codes. QR codes can be part of or can be embedded in a geometric pattern or geometric shape included in an optical marker. Optical markers can be a QR code.

If an optical marker is attached to a surgical instrument, the attachment can occur in a defined location and/or position and/or alignment, for example at an end of the surgical instrument. The attachment can include, for example, an opening with a stop thereby defining the location and/or position and/or alignment of the optical marker on the surgical instrument. For example, the optical marker can have an opening with a stop that is large enough to accommodate the surgeon facing end of a pin or drill, for example inserted into a spinous process or a facet joint or a portion of a pedicle. With this type of attachment and other attachments that secure the marker in a defined location, position and/or orientation on the surgical instrument, an image and/or video capture system can detect the optical marker and its location, position and/or orientation can be used to determine the location, position, and/or orientation of the surgical instrument, e.g. a pin, including its tip or frontal portion inside the patient due to their defined spatial relationship and due to the known geometry of the surgical instrument.

In some embodiments, an optical marker can be used to determine or identify the position, location, orientation, alignment, dimensions, axis or axes, plane or planes of a surgical alteration. For example, if a bone cut has been performed in a surgical step, one or more optical markers can be attached to the cut bone to determine one or more of its position, location, orientation, alignment, dimensions, shape, geometry, axis or axes, plane or planes. For example, one, two or more optical markers can be placed near or attached to the periphery or the edge of the cut bone or surgical alteration; an image and/or video capture system integrated into, attached to or separate from the OHMD can detect the location, position, and/or orientation of the optical markers and software can be used, for example, to analyze the location, position, and/or orientation information of the optical markers to derive information on the periphery and/or edge and/or shape of the cut bone or surgical alteration. One, two or more optical markers can be placed near or attached to the cut bone or surgical alteration; an image and/or video capture system integrated into, attached to or separate from the OHMD can detect the location, position, and/or orientation of the optical markers and software can be used, for example, to analyze the location, position, and/or orientation information of the optical markers to derive information on the shape or geometry of the cut bone or surgical alteration. If the bone cut is planar, one or more optical markers with a planar bone facing surface or one or more optical markers attached to a carrier or instrument, e.g. a plastic piece, with a planar bone facing surface can be held against, affixed to or attached to the cut bone surface; an image and/or video capture system integrated into, attached to or separate from an OHMD can then be used to detect the one or more optical markers and software can be used, for example, to analyze the location, position and/or orientation information of the one or more optical markers to derive information on the location and/or position and/or orientation and/or alignment of the plane of the bone cut, including for example in relationship to other anatomic landmarks and/or other optical markers. The carrier or instrument for the optical marker can be transparent or semi-transparent so that the surgeon can check or confirm that the carrier or instrument and the attached optical marker(s) are flush against the bone cut prior to determining or confirming, for example, the plane of the bone cut. Once the plane of the bone cut has been determined or confirmed in this manner, the optical marker(s) attached to the cut bone and/or the determined plane of the bone cut can be used to plan the next surgical alteration, e.g. the next bone cut or surgical alteration, e.g. an anterior or posterior femoral cut after the distal femoral cut in knee replacement, or a chamfer cut after the anterior and posterior femoral cuts in knee replacement, or a cut on an opposing articular surface. By determining, confirming and/or referencing a preceding surgical alteration, e.g. a bone cut, in this manner, the accuracy of subsequent surgical steps can be improved thereby ultimately improving the overall accuracy of the surgical procedure.

Mechanical axis assessment: In some embodiments, the mechanical axis of the lower extremity can be determined. The mechanical axis can be determined, for example, by estimating the location of the center of the hip joint, e.g. the center of the femoral head, and by estimating the center or, optionally, lateral one third or medial one third of the ankle joint or other anatomic landmarks of the ankle joint.

In some embodiments, the hip, the ankle, and optionally, the knee can be imaged with an ultrasound device. Similarly, one or more radiographs can be obtained to image the hip, the knee and/or the ankle joint, e.g. in supine or standing position. Standing full leg length x-rays can be obtained, e.g. in AP projection or lateral projection and/or optionally one or more oblique positions. Alternatively, a CT scout scan can be used to image the hip, knee and ankle. Alternatively, 2D or 3D images or data can be obtained through the hip, the knee, and/or the ankle using CT or MRI, using, for example, standard or spiral CT acquisition, or using 2DFT or 3DFT MRI acquisitions and images or upright x-ray imaging, for example with a system made by EOS Imaging, 75011 Paris, France. The desired anatomic center of the hip and the ankle joint can be identified or derived from the 2D or 3D supine or upright image or scan data. In some embodiments, upright scans can be preferred. In another embodiment, the difference in knee alignment between supine and upright scans can be used to modify the virtual surgical plan, for example by introducing more or less deformity correction, e.g. correction in mechanical axis or rotational deformity.

For example, if a 2D or volumetric image or scan of the femoral head has been obtained, the centroid of the femoral head can be derived using standard geometric methods known in the art, e.g. in 2D or in 3D. Similarly, the center or other location of the ankle joint, e.g. outer or inner one third, can be determined using standard geometric methods known in the art, e.g. in 2D or in 3D. If the line connecting the chosen landmarks in the hip and in the ankle passes medially to the knee center, a varus deformity is present; if the line passes laterally to the knee center or center of the distal femur, a valgus deformity exists.

Optionally, the patient's mechanical axis information can be used in the virtual surgical plan and, optionally, displayed for example by the OHMD during surgery. For example, a virtual surgical plan for partial or total knee replacement or other surgical procedures around the knee can include partial or complete correction of varus or valgus deformity, e.g. virtually correcting a varus or valgus deformity to neutral mechanical axis alignment. In another embodiment, if the patient, for example, has only mild varus or valgus deformity or is thought to have inherent or congenital valgus or valgus deformity, the surgeon can elect not to perform a mechanical axis deformity correction in the virtual surgical plan or the surgeon can elect to perform only a partial mechanical axis deformity correction in the virtual surgical plan, e.g. from 10 degrees varus or valgus pre-operatively to 5, 4, or 3 degrees or any other desired value in the virtual surgical plan, for example, as displayed by the OHMD during surgery, and, ultimately, the actual surgery in the live patient (see also FIG. 35).

In some embodiments, one or more optical markers and/or LED's can be attached to or affixed to a patient's thigh or distal femur. The one or more optical markers and/or LED's can, for example, be attached to the skin of the distal thigh, e.g. above the knee joint space. The attachment can be performed using, for example, an adhesive that attaches the one or more optical marker and/or LED's to the patient's skin. The one or more optical marker and/or LED's can optionally be sterile. The one or more optical marker and/or LED's can optionally be magnetic. In this example, a magnetic base can optionally be attached to the patient's skin, for example using an adhesive. A surgical drape which can be transparent, semi-transparent or not transparent can then be placed over the magnetic base and the magnetic optical marker can then be attached to the magnetic base attached to the patient's skin. Optionally, the magnetic base can be radiopaque thereby allowing identification of the location and/or position and/or orientation and/or coordinates of the optical marker in radiographic images or other images using ionizing radiation. Alternatively, once a skin incision is made, one or more optical marker and/or LED's can be rigidly attached to one or more bones, e.g. the distal femur and/or the proximal tibia. The rigid attachment can be done using pins or screws or other attachment mechanisms.

An image and/or video capture system integrated into, attached to or separate from the OHMD can register the location and/or position and/or orientation and/or alignment of the one or more optical marker and/or LED's, for example while the leg is in neutral position and/or extension and/or any other position, including arbitrary positions or positions chosen by the surgeon and/or operator. The surgeon and/or operator can then move the leg and thigh into multiple different positions and/or orientations and/or alignments and/or the surgeon and/or operator can move the leg and thigh in circular fashion or semicircular fashion. An image and/or video capture system integrated into, attached to or separate from the OHMD can register the location and/or position and/or orientation and/or alignment of the one or more optical marker and/or LED's for these multiple different positions and/or orientations and/or alignments of the leg or thigh and/or during the different circular or semicircular movements. The resultant information can be used to determine the center of rotation, which, in this example, can be the center of the hip joint. Using this or similar approaches, e.g. with different motion patterns, e.g. elliptical, sinusoidal etc., the center of rotation can be determined for any joint. Similarly, the center of flexion or rotation can be determined for spinal levels, e.g. in a lumbar spine.

In some embodiments, an ankle clamp can be applied to the ankle of the patient's leg. The ankle clamp can include one or more optical marker and/or LED's including, for example, one or more QR codes. The ankle clamp and/or the optical marker and/or LED's can be disposable. The ankle clamp and the integrated or attached optical marker and/or LED's can be used to determine the position of the medial and lateral malleolus and with that, for example, the center or ⅓ or ⅔ distance points or the halfway point between the malleoli of the ankle joint using an image and/or video capture system integrated into, attached to or separate from the OHMD. Alternatively, one or more optical marker and/or LED's can be applied to medial and/or lateral malleolus. In some embodiments, a magnetic base can be affixed to the medial and lateral malleolus. The ankle can then be prepped and draped in sterile technique and one or more sterile, magnetic optical marker and/or LED's can be applied over the drape or surgical cover affixing the one or more optical marker and/or LED's to the magnetic base with the interposed drape or surgical cover. An image and/or video capture system integrated into, attached to or separate from the OHMD can then be used to identify the optical marker and/or LED's over the medial and lateral malleolus and the center, ⅓ or ⅔ distance points of the ankle joint.

With the center of the hip joint determined using the one or more optical marker and/or LED's on the thigh or distal femur and the center or ⅓ or ⅔ distance points of the ankle joint determined using the ankle clamp and/or one or more optical marker and/or LED's, the system can derive the patient's mechanical axis and any surgical interventions, e.g. correction of varus or valgus deformity with corresponding femoral and/or tibial and/or talar bone cuts can be planned and subsequently projected using the OHMD.

In some embodiments, the OHMD can display the patient's native mechanical axis, for example through a colored or dotted line or plane. The OHMD can also display the intended mechanical axis correction, for example as defined in a virtual surgical plan. The intended mechanical axis correction can be displayed with a colored or dotted line or plane, optionally different from the patient's native mechanical axis if it is also being displayed. The surgeon can then direct a bone saw or burr or other surgical instrument so that the bone saw, burr or other surgical instrument will substantially execute a removal of portions of the distal femur or proximal tibial plateau to achieve placement of the implant with the intended mechanical axis correction.

In another embodiment, the OHMD can display the intended mechanical axis correction, optionally with lines or planes, e.g. perpendicular to the intended mechanical axis, through the distal femur and/or proximal tibia to indicate the location of one or more intended distal femoral and or proximal tibial bone cuts. Alternatively, the intended mechanical axis correction is not displayed by the OHMD, but only the intended distal femoral and/or proximal tibial bone cuts that will yield the intended mechanical axis correction are displayed, for example as defined in the virtual surgical plan. The surgeon can then optionally align an actual distal femoral cut block or an actual proximal tibial cut block with the intended distal femoral and/or proximal tibial bone cuts so that the actual cut block surface or the actual slot for the saw is substantially aligned with the intended, virtual proximal femoral cut and/or proximal tibial cut. The surgeon can the direct the saw blade, burr or other surgical instrument along the actual cut block surface or the actual slot to execute the intended, virtual surgical plan in the live patient. Optionally, the surgeon can check the alignment and/or direction of the saw blade or burr or other surgical instrument against the intended, virtual cut and the surgeon can make adjustments in alignment and/or direction of the saw blade or burr or other surgical instrument during the live surgery using the virtual data and/or virtual surgical plan. In some embodiments, one or more optical marker and/or LED's can be attached to or affixed to a patient's arm. The one or more optical marker and/or LED's can, for example, be attached to the skin of the upper arm, e.g. above the elbow. The attachment can be performed using, for example, an adhesive that attaches the one or more optical marker and/or LED's to the patient's skin. The one or more optical marker and/or LED's can optionally be sterile. The one or more optical marker and/or LED's can optionally be magnetic. In this example, a magnetic base can optionally be attached to the patient's skin, for example using an adhesive. A surgical drape which can be transparent, semi-transparent or not transparent can then be placed over the magnetic base and the magnetic optical marker can then be attached to the magnetic base attached to the patient's skin. Alternatively, once a skin incision is made, one or more optical marker and/or LED's can be rigidly attached to one or more bones, e.g. the proximal humerus. The rigid attachment can be done using pins or screws or other attachment mechanisms.

An image and/or video capture system integrated into, attached to or separate from the OHMD can register the location and/or position and/or orientation and/or alignment of the one or more optical marker and/or LED's, for example while the arm is in neutral position and/or extension and/or abduction and/or any other position, including arbitrary positions or positions chosen by the surgeon and/or operator. The surgeon and/or operator can then move the arm into multiple different positions and/or orientations and/or alignments and/or the surgeon and/or operator can move the arm in circular fashion or semicircular or other fashion. An image and/or video capture system integrated into, attached to or separate from the OHMD can register the location and/or position and/or orientation and/or alignment of the one or more optical marker and/or LED's for these multiple different positions and/or orientations and/or alignments of the arm and/or during the different circular or semicircular movements. The resultant information can be used to determine the center of rotation, which, in this example, can be the center of rotation of the shoulder joint.

Measuring kinematics using optical markers with geometric patterns: In some embodiments, an operator, e.g. a nurse, a surgeon assistant, a physical therapist, or surgeon optionally palpates the joint space of the knee joint, e.g. medially or laterally. The identification of the joint space can be aided by the nurse, surgeon assistant, physical therapist, or surgeon moving the patient's joint through a range of motion. The nurse, surgeon assistant, physical therapist, or surgeon can also optionally identify the patella by palpation. Optionally, the joint space can be identified with an imaging study used by the operator, e.g. an office based ultrasound.

IMU's: One, two, three or more IMU's, including, for example, a gyrometer, an accelerometer, a magnetometer, are placed by an operator, e.g. a physical therapist, on the distal femur of the patient, proximal to the medial joint space. If more than one IMU is used, the IMU's are placed in anteroposterior direction, preferably along the contour of the distal medial femur/femoral condyle as identified by palpation or imaging.

Optionally, one, two, three or more IMU's, including, for example, a gyrometer, an accelerometer, a magnetometer, are placed by an operator, e.g. a physical therapist, on the distal femur of the patient, proximal to the lateral joint space. If more than one IMU is used, the IMU's are placed in anteroposterior direction, preferably along the contour of the distal lateral femur/femoral condyle as identified by palpation or imaging.

One, two, three or more IMU's, including, for example, a gyrometer, an accelerometer, a magnetometer, are placed by an operator, e.g. a physical therapist, on the proximal tibia of the patient, distal to the medial joint space. If more than one IMU is used, the IMU's are placed in anteroposterior direction, preferably along the contour of the proximal medial tibia/tibial plateau as identified by palpation or imaging.

Optionally, one, two, three or more IMU's, including, for example, a gyrometer, an accelerometer, a magnetometer, are placed by an operator, e.g. a physical therapist, on the proximal tibia of the patient, distal to the lateral joint space. If more than one IMU is used, the IMU's are placed in anteroposterior direction, preferably along the contour of the proximal lateral tibia/tibial plateau as identified by palpation or imaging.

Navigation: In another embodiment, markers, e.g. RF or retroreflective markers, used in conjunction with a surgical navigation system are applied to the joint in a similar manner: One, two, three or more navigation markers are placed by an operator, e.g. a physical therapist, on the distal femur of the patient, proximal to the medial joint space. If more than one navigation marker is used, the navigation markers are placed in anteroposterior direction, preferably along the contour of the distal medial femur/femoral condyle as identified by palpation or imaging.

Optionally, one, two, three or more navigation markers are placed by an operator, e.g. a physical therapist, on the distal femur of the patient, proximal to the lateral joint space. If more than one navigation marker is used, the navigation markers are placed in anteroposterior direction, preferably along the contour of the distal lateral femur/femoral condyle as identified by palpation or imaging.

One, two, three or more navigation markers are placed by an operator, e.g. a physical therapist, on the proximal tibia of the patient, distal to the medial joint space. If more than one navigation markers are used, the navigation markers are placed in anteroposterior direction, preferably along the contour of the proximal medial tibia/tibial plateau as identified by palpation or imaging.

Optionally, one, two, three or more navigation markers are placed by an operator, e.g. a physical therapist, on the proximal tibia of the patient, distal to the lateral joint space. If more than one navigation marker is used, the navigation markers are placed in anteroposterior direction, preferably along the contour of the proximal lateral tibia/tibial plateau as identified by palpation or imaging.

Image Capture: In another embodiment, markers that can be used with an image and/or video capture system, optionally integrated or attached to an OHMD or separate from an OHMD, e.g. LED markers, reflective markers and any other marker amenable to image and/or video capture based tracking, are applied to the joint or related bones, soft-tissue or skin in a similar manner. Such markers can include optical markers with geometric patterns. The image and/or video capture system can include one, two, three or more cameras integrated, attached to or separate from an OHMD. The cameras can be arranged at defined locations, positions, orientations and/or angles, e.g. over the left eye and the right eye of the user wearing the OHMD, e.g. to approximate or mimic the left and right eye parallax of the user. Thus, image and/or video capture systems can obtain, for example, the following data:

Data generated by an image and/or video capture system attached to, integrated with or coupled to the OHMD Parallax data, e.g. data generated using two or more image and/or video capture systems integrated into, attached to or separate from one or more OHMDs, for example one positioned over or under or near the left eye and a second positioned over or under or near the right eye Distance data, e.g. parallax data generated by two or more image and/or video capture systems evaluating changes in distance between an OHMD and a surgical field or an object, e.g. the patient's joint. Distance data can use the known geometry of one or more optical markers to determine distances, e.g. between the surgical field and the optical head mounted display, for example by placing or attaching an optical marker with a geometric pattern to a portion of the surgical field, e.g. an exposed or cut bone, wherein the dimensions and distances, e.g. the distances between and the edge coordinates or other coordinates of the geometric patterns, e.g. lines, can be known and can be used, for example, to calculate or determine the distance of the surgeon and/or OHMD to the optical marker and/or surgical field or the change in distances related to joint movement.

Geometric data, e.g. data generated by one, two or more image and/or video capture systems evaluating changes in geometry between an OHMD and a surgical field or an object, e.g. the patient's joint; geometric data can also be generated using parallax data. Geometric data can use the known geometry of one or more optical markers to determine distances and/or angles, e.g. between the surgical field and the optical head mounted display, for example by placing or attaching an optical marker with a geometric pattern to a portion of the surgical field, e.g. an exposed or cut bone, wherein the dimensions, angles and distances, e.g. the distances and/or angles between and the edge coordinates or other coordinates of the geometric patterns, e.g. lines, can be known and can be used, for example, to calculate or determine the distance and/or angle of the surgeon and/or OHMD to the optical marker and/or surgical field or the change in distance and/or angle related to joint movement.

Angular data, e.g. data generated by one, two or more image and/or video capture systems evaluating changes in angle between an OHMD and a surgical field or an object, e.g. the patient's joint. Angular data can use the known geometry of one or more optical markers to determine angles, e.g. between the surgical field and the optical head mounted display, for example by placing or attaching an optical marker with a geometric pattern to a portion of the surgical field, e.g. an exposed or cut bone, wherein the dimensions and angles, e.g. the angles between and the edge coordinates or other coordinates of the geometric patterns, e.g. lines, can be known and can be used, for example, to calculate or determine the angle of the surgeon and/or OHMD to the optical marker and/or surgical field or the change in angle related to joint movement.

Motion data, e.g. data obtained from a joint and/or its surrounding tissues including soft-tissue, muscle, skin or bone, and/or neighboring tissues or joints during joint motion and/or load bearing and/or weight-bearing or non-weight-bearing conditions. Motion data can use the known geometry of one or more optical markers to determine distances and/or angles, e.g. between the surgical field and the optical head mounted display, for example by placing or attaching an optical marker with a geometric pattern to a portion of the surgical field, e.g. an exposed or cut bone, wherein the dimensions, angles and distances, e.g. the distances and/or angles between and the edge coordinates or other coordinates of the geometric patterns, e.g. lines, can be known and can be used, for example, to calculate or determine the distance and/or angle of the surgeon and/or OHMD to the optical marker and/or surgical field or the change in distance and/or angle related to joint movement. The change in distance per unit time can be used to calculate the speed of movement. The change in coordinates of the one or more optical markers can be used to calculate the direction of movement.

Similar data can be generated using LED's and one or more image and/or video capture systems. Two or more LED's can optionally be arranged with a known geometry, e.g. distance and/or angles, e.g. in 2D or 3D, thereby allowing to capture parallax data, distance data, geometric data, angular data, and/or motion data.

The accuracy of alignment and/or kinematic measurements using markers for image and/or video capture systems, e.g. LED markers or optical markers with geometric patterns, can be improved by using multiple cameras with different view angles. For example, the accuracy can improve in case the line of sight of one of the cameras is obstructed; in that example, another camera with a clear line of sight can still capture the position, location, orientation, alignment and/or movement, direction of movement, and/or speed of movement of the one or more markers.

In addition, the accuracy of alignment and/or kinematic measurements using markers for image and/or video capture systems can be improved by using parallax information obtained from multiple cameras, e.g. integrated into or attached to or separate from the same OHMD or integrated or attached to or separate from multiple OHMDs. For example, by measuring distances, geometric data, angular data, motion data including, for example, direction of movement and/or speed of movement, acceleration or deceleration, e.g. with joint flexion or extension, using multiple cameras integrated into, attached to or separate from one or more OHMDs, the accuracy and/or reproducibility of the measurements can be improved during joint motion. Data averaging strategies can be employed for improving the accuracy and/or reproducibility of measurements. Any statistical method known in the art for improving the accuracy and/or reproducibility of measured data using multiple data input sources can be employed.

The accuracy of such image acquisitions and reconstruction of 3D volumes, 3D surfaces and/or 3D shapes can optionally be enhanced with image and/or video capture systems that use two or more cameras, which can be used to generated parallax information and/or stereoscopic information of the same structures, wherein, for example, the parallax and/or stereoscopic information can be used to enhance the accuracy of the reconstructions. Alternatively, the information from two or more cameras can be merged by averaging the 3D coordinates or detected surface points or other geometric structures such as planes or curved surfaces.

Optionally, parallax measurements can be performed using multiple OHMDs from different view angles with multiple cameras, image capture or video systems. Each OHMD can have one, two or more cameras. Information collected from the one or more cameras from a first OHMD can be combined with information from the one or more cameras from a second, third, fourth and so forth OHMD. Some OHMDs can only include one camera, while other OHMDs can include multiple cameras.

One, two, three or more image capture markers, e.g. optical markers, can be placed by an operator, e.g. a physical therapist, on the distal femur of the patient, proximal to the medial joint space. If more than one image capture marker is used, the image capture markers can be placed in anteroposterior direction, e.g. along the contour of the distal medial femur/femoral condyle as identified by palpation or imaging.

Optionally, one, two, three or more image capture markers can be placed by an operator, e.g. a physical therapist, on the distal femur of the patient, proximal to the lateral joint space. If more than one image capture marker is used, the image capture markers can be placed in anteroposterior direction, e.g. along the contour of the distal lateral femur/femoral condyle as identified by palpation or imaging.

One, two, three or more image capture markers can be placed by an operator, e.g. a physical therapist, on the proximal tibia of the patient, distal to the medial joint space. If more than one image capture markers are used, the image capture markers can be placed in anteroposterior direction, e.g. along the contour of the proximal medial tibia/tibial plateau as identified by palpation or imaging.

Optionally, one, two, three or more image capture markers can be placed by an operator, e.g. a physical therapist, on the proximal tibia of the patient, distal to the lateral joint space. If more than one image capture marker is used, the image capture markers can be placed in anteroposterior direction, e.g. along the contour of the proximal lateral tibia/tibial plateau as identified by palpation or imaging.

Patella, Other Areas: In some embodiments, one, two, three or more IMU's, including, for example, a gyrometer, an accelerometer, a magnetometer, can be placed by an operator, e.g. a physical therapist, on the patella of the patient, e.g. in the center of the patella, on the superior pole of the patella, the inferior pole of the patella and/or the medial and/or lateral edge of the patella.

Optionally, one, two, three or more IMU's, including, for example, a gyrometer, an accelerometer, a magnetometer, can be placed by an operator, e.g. a physical therapist, on the tibial tuberosity, the patella tendon, the quadriceps tendon, or over select muscles and muscle bellies, e.g. the vastus medialis, vastus lateralis, rectus femoris, etc. One, two, three or more IMU's can be applied over any of the muscles surrounding the knee joint or influencing the motion of the knee joint. Optionally, one, two or three IMU's can also be applied to the skin around the hip joint, and/or the ankle joint.

In another embodiment, one, two, three or more navigation markers can be placed by an operator, e.g. a physical therapist, on the patella of the patient, e.g. in the center of the patella, on the superior pole of the patella, the inferior pole of the patella and/or the medial and/or lateral edge of the patella.

Optionally, one, two, three or more navigation markers can be placed by an operator, e.g. a physical therapist, on the tibial tuberosity, the patella tendon, the quadriceps tendon, or over select muscles and muscle bellies, e.g. the vastus medialis, vastus lateralis, rectus femoris, etc. One, two, three or more navigation markers can be applied over any of the muscles surrounding the knee joint or influencing the motion of the knee joint. Optionally, one, two or three navigation markers can also be applied to the skin around the hip joint, and/or the ankle joint.

In another embodiment, one, two, three or more image capture markers can be placed by an operator, e.g. a physical therapist, on the patella of the patient, e.g. in the center of the patella, on the superior pole of the patella, the inferior pole of the patella and/or the medial and/or lateral edge of the patella. Optionally, one, two, three or more image capture markers can be placed by an operator, e.g. a physical therapist, on the tibial tuberosity, the patella tendon, the quadriceps tendon, or over select muscles and muscle bellies, e.g. the vastus medialis, vastus lateralis, rectus femoris, etc. One, two, three or more image capture markers can be applied over any of the muscles surrounding the knee joint or influencing the motion of the knee joint. Optionally, one, two or three image capture markers can also be applied to the skin around the hip joint, and/or the ankle joint.

In another embodiment, IMU's and navigation markers, IMU's and image capture markers, navigation and image capture markers, or IMU's, navigation and image capture markers, image capture markers including, for example, LED's and/or optical markers, e.g. with geometric patterns, e.g. in 2D or 3D, e.g. on cubes, spheres, can be used in conjunction with each other and can be placed in any combination possible proximal and/or distal to the medial and/or lateral joint space of the knee and/or around the patellofemoral joints and/or any other location around the knee joint, hip joint and/or ankle joint. Optionally, two or more IMU's and/or navigation markers and/or image capture markers can be placed in the same housing which can then be applied to the skin around the knee joint in one or more locations proximal and/or distal to the medial and/or lateral joint space of the knee. Optionally, RF navigation markers can be combined or used in conjunction with infrared or retro-reflective navigation markers in case the line of sight is obscured, e.g. attached to each other or separate from each other. Optionally, RF navigation markers can be combined or used in conjunction with image capture markers, e.g. optical markers with geometric patterns and/or LED's, in case the line of sight is obscured, e.g. attached to each other or separate from each other. Optionally, IMU's can be combined or used in conjunction with infrared or retro-reflective navigation markers in case the line of sight is obscured, e.g. attached to each other or separate from each other. Optionally, IMU's can be combined or used in conjunction with image capture markers, e.g. optical markers with geometric patterns and/or LED's, in case the line of sight is obscured, e.g. attached to each other or separate from each other.

In another embodiment, when two or more IMU's and/or navigation markers and/or image capture markers, e.g. optical markers with geometric patterns and/or LED's, are used, e.g. applied to the distal femur and/or the proximal tibia, optionally medially or laterally, or around the patellofemoral joint or any other location around the knee joint, hip joint and/or ankle joint, the IMU's and/or navigation markers and/or image capture markers or combinations thereof can be optionally attached to a holding device or a form of mount so that the application to the distal femur and/or the proximal tibia or other locations can occur in a single step or one or two or three steps only. The holding device or mount can, for example, have a curvilinear arrangement or shape for use on the femur that is designed to follow the sagittal profile of the distal femoral condyles. The holding device or mount can, for example, have a more linear or straight arrangement or shape for use on the tibia that is designed to follow the sagittal profile of the proximal tibia and/or tibial plateau. The holding device or mount can be flexible or semi-flexible, e.g. with use of a soft plastic, so that it can be applied to the skin of the distal femur and/or proximal tibia. The holding device or mount can include straps or adhesive for application to the skin. The holding device can hold a single row of IMU's and/or navigation markers and/or image capture markers, e.g. on the distal femur or proximal tibia or patella. The holding device can hold multiple rows of IMU's and/or navigation markers and/or image capture markers, e.g. on the distal femur or proximal tibia or patella. The holding device can hold an array of IMU's and/or navigation markers and/or image capture markers, e.g. on the distal femur or proximal tibia or patella. The holding device can be an elastic or soft brace that can encircle or wrap around the knee, optionally with use of Velcro straps. In some embodiments, the elastic or soft brace can be pulled over the foot and calf onto the patient's knee. The elastic or soft brace can optionally include a medial and a lateral hinge mechanism, to allow for knee flexion or extension. In another embodiment, the elastic or soft brace is sufficiently elastic not to interfere with the natural movement(s) of the patient's knee. The elastic or soft brace can include multiple rows of IMU's and/or navigation markers and/or image capture markers, e.g. optical markers with geometric patterns and/or LED's, e.g. positioned over the distal femur or proximal tibia or patella. In an embodiment, the elastic or soft brace can hold an array of IMU's and/or navigation markers and/or image capture markers, e.g. on the distal femur or proximal tibia or patella. Optionally, a holding device, e.g. an elastic or soft brace, including one or more IMU's and/or navigation markers and/or image capture markers can be attached to or positioned over the area of the hip joint and the ankle joint and/or foot.

Optical markers on fixed structures in the OR: In some embodiments, one or more optical marker and/or LED's can be attached to an operating room (OR) table. If the optical marker is parallel to the OR table, a single marker can be sufficient to determine the principal plane of the OR table, e.g. the horizontal plane, which can be the plane on which the patient is resting, for example in supine, prone, lateral or oblique or other positions known in the art. This can be aided by using optical marker and/or LED's that include a surface or plane that is parallel or perpendicular or at a defined angle to the OR table and that is large enough to be detected by the camera, image or video capture system integrated into, attached to or separate from the OHMD. For example, such a plane of the optical marker can measure 1×1 cm, 2×2 cm, 2×3 cm, 4×4 cm, 4×6 cm and so forth. Alternatively, multiple, e.g. two, three or more, optical marker and/or LED's can be used to determine a plane through the markers corresponding to the principal plane of the OR table or a plane parallel to the principal plane of the OR table or, for example, a plane vertical to the OR table or, for example, a plane at a defined angle to the OR table. If the OR table is hidden by surgical drapes, one or more magnetic or otherwise attachable bases can be attached to the OR table prior to placing the drapes. After the drapes have been placed, one or more magnetic or otherwise attachable optical marker and/or LED's can be affixed to the magnetic bases or attachment mechanisms with the interposed surgical drapes. The magnetic base can be radiopaque which can help identify the location, orientation and/or coordinates of the optical marker(s) in radiographic images or other images using ionizing radiation. Alternatively, one or more holding arms or extenders of known geometry can be attached to the OR table and one or more optical marker and/or LED's can be attached to or can be integrated into the holding arms or extenders. An image and/or video capture system integrated into, attached to or separate from the OHMD can then identify the location, position, orientation and/or alignment of the one or more optical marker and/or LED's. The resultant information can be used to determine the principal plane of the OR table on which the patient is lying. One or more OHMDs can be referenced using, for example, an image and/or video capture system integrated into or attached to the OHMD relative to the OR table and/or the attached optical marker and/or LED's. Once the principal plane of the OR table is determined in the system, virtual surgical steps can be planned in the virtual surgical plan of the patient in relationship to the principal plane of the OR table. For example, one or more bone cuts can be planned and/or performed perpendicular to the principal plane of the OR table, for example with the patient in supine or prone position or any other desired position. One or more bone cuts can be planned and/or performed at defined angles other than 90 degrees relative to the horizontal plane of the OR table, for example with the patient in supine or prone position or any other desired position. One or more bone cuts can be planned and/or performed at a non-orthogonal plane or orientation relative to the principal plane or horizontal plane of the OR table, for example with the patient in supine or prone position or any other desired position, optionally referencing a plane vertical to the OR table, displayed by the OHMD. The principal plane of the OR table can be used as a reference in this manner including for comparing or referencing virtual data of the patient and live data of the patient and including for comparing or referencing a virtual surgical plan. Such bone cuts at orthogonal angles or non-orthogonal angles, e.g. relative to the OR table or relative to anatomy, anatomic landmarks, anatomic or biomechanical axes of the patient, can be executed using one or more virtual surgical guides or cut blocks and/or one or more physical surgical guides or cut blocks. Virtual surgical guides or cut blocks can include one or more dimensions corresponding to physical surgical guides or cut blocks. One or more anatomic axes or biomechanical axes or combinations thereof can also be referenced to the OR table in this manner, e.g. the principal plane of the OR table, a plane parallel to the OR table, a plane perpendicular to the OR table, a plane oblique to the OR table or combinations thereof.

One or more optical marker and/or LED's attached to or referencing the OR table can also serve as a fixed reference for the one or more OHMDs during a surgical procedure. This can be useful, for example, when the patient and/or the extremity and/or the surgical site moves during the procedure. A fixed reference to the OR table can aid in maintaining registration of the one or more OHMDs and the virtual surgical plan and the live data of the patient and/or OR.

In some embodiments, one or more optical marker and/or LED's can be placed on or attached to the patient in the area of the surgical field and/or in an area away from the surgical field. An image and/or video capture system integrated into, attached to or separate from the OHMD can be used to identify the one or more optical marker and/or LED's and to determine their location, position, orientation and/or alignment. The image and/or video capture system can also, optionally, determine the location, position, orientation and/or alignment of one or more optical marker and/or LED's attached to or referencing the OR table. The system can reference the coordinates and/or the spatial relationship of the one or more optical marker and/or LED's attached to the patient in the area of the surgical field and/or in an area away from the surgical field and the one or more optical marker and/or LED's attached to or referencing the OR table. In this manner, if the patient's body moves during the procedure, e.g. during a broaching of a proximal femur or an acetabular reaming during hip replacement, or a femoral or tibial component impacting during knee replacement, or during a pinning or cutting of a bone, or during a placement of a spinal device, e.g. a cage or a pedicle screw, the movement between the one or more optical marker and/or LED's attached to the patient in the area of the surgical field and/or in an area away from the surgical field and the one or more optical marker and/or LED's attached to or referencing the OR table and the change in coordinates of the one or more optical marker and/or LED's attached to the patient in the area of the surgical field and/or in an area away from the surgical field can be detected and the amount of movement, direction of movement and magnitude of movement can be determined; the resultant information can, for example, be used to update or adjust or modify a virtual surgical plan or to update or adjust or modify the display of the virtual surgical plan or virtual surgical steps or virtual displays for the movement of the patient, including for example by updating, moving or adjusting one or more aspects or components of the virtual surgical plan including one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the new patient coordinates or the new coordinates of the surgical field.

Radiopaque optical markers: In some embodiments, portions of the optical marker or the entire optical marker can be radiopaque, so that the optical marker can also be visible on a radiograph or other imaging studies that utilize ionizing radiation including, for example, fluoroscopy, digital tomosynthesis, cone beam CT, and/or computed tomography. Different levels or degrees of radiopacity can be present in different portions or areas of the optical marker. Different levels or degrees of radiopacity can be utilized to encode information. For example, different levels of radiopacity can be used to encode information also contained, for example, in an optically readable alphanumeric code, bar code or QR or other code. The different levels of radiopacity can optionally be arranged in a bar like thickness distribution, which can optionally mirror portions or all of the information contained in a bar code. The different levels of radiopacity can optionally be arranged in a point or square like thickness distribution, which can optionally mirror portions of the information contained in a QR code. Different radiopacity can be obtained by varying the thickness of the metal, e.g. lead. Radiopaque optical marker and/or LED's with information encoded in such manner can, for example, be manufactured using 3D metal printers. They can also be CNC machined, e.g. from bar stock or cast blanks. Optical markers can include portions that are radiopaque and portions that are not radiopaque. Radiopaque portions can include radiopaque elements, e.g. radiopaque struts, disks, sphere and/or other shapes. Any shape known in the art can be used. The optical marker can be attached to the radiopaque elements and/or radiopaque portions. The optical marker can be integrated into the radiopaque elements and/or radiopaque portions. The optical marker can be separate from the radiopaque elements and/or radiopaque portions, e.g. at a defined or known distance, defined or known angle and/or defined or known geometric and/or spatial arrangement.

The radiopaque portions of the optical marker can include information on laterality, e.g. L for left and R for right, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the OHMD. The radiopaque portions of the optical marker can include information on anatomical site, e.g. L5 or L4, T1 or T2, C3 or C7, knee, hip, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the OHMD. Image processing techniques and/or software can be applied to the radiographic information including the optical marker and radiographically encoded information such as laterality and/or site and the information included in the radiograph can be compared against the information included on the optical scan. If any discrepancies are detected, an alert can be triggered, which can, for example, be displayed in the OHMD.

Multiple partially or completely radiopaque optical markers can be used. The radiopaque optical markers can be applied at different locations and in different planes around the surgical site. In spinal surgery, for example, one, two, three or more radiopaque optical markers can be applied to the skin around the spinal levels for the intended surgery; one, two, three or more radiopaque optical markers can be attached to a pin, drill or screw inserted into a spinous process and/or a pedicle or other spinal element; one, two, three or more radiopaque optical markers can be applied to the patient's flank or abdomen. In hip replacement surgery, one, two, three or more radiopaque optical markers can be applied to the anterior superior iliac spine on the patient's intended surgical side, e.g. with an adhesive to the skin or attached to a pin or drill to the bone; one, two, three or more radiopaque optical markers can be applied to the anterior superior iliac spine on the patient's contralateral side, e.g. with an adhesive to the skin or attached to a pin or drill to the bone; one, two, three or more radiopaque optical markers can be applied to the symphysis pubis, e.g. with an adhesive to the skin or attached to a pin or drill to the bone; one, two, three or more radiopaque optical markers can be applied to the acetabulum on the patient's intended surgical side, e.g. attached to a pin or drill to the bone; one, two, three or more radiopaque optical markers can be applied to the greater trochanter on the patient's intended surgical side, e.g. attached to a pin or drill to the bone. By using multiple radiopaque optical markers in multiple different locations and in different planes around the surgical site, the accuracy of any three-dimensional spatial registration and cross-reference of the optical markers in different modalities, e.g. radiographs, image capture, can be increased, for example by obtaining multiple x-rays at different angles, e.g. AP, lateral and/or oblique, and/or by imaging the radiopaque optical markers from multiple view angles using an image and/or video capture system integrated into, attached to or separate from the OHMD or by imaging the radiopaque optical markers from multiple view angles using multiple image and/or video capture system integrated into, attached to or separate from the OHMD leveraging information from multiple view angles or leveraging parallax information. By using multiple optical markers in multiple different locations and in different planes around the surgical site, the accuracy of any three-dimensional spatial registration of the optical markers can be increased, for example by imaging the optical markers from multiple view angles using an image and/or video capture system integrated into, attached to or separate from the OHMD. In addition, the accuracy of the registration can be better maintained as the view angle or radiographic angle changes, for example during the course of the surgical procedure or due to patient movement.

In some embodiments, the system performance can be tested. System performance tests can, for example, measure a phantom including two or more optical markers at known locations, positions, orientations and/or alignment. With the coordinates of the two or more optical markers known along with the distance(s) and angle(s) between the markers, the accuracy of performing distance measurements and/or angle measurements and/or area measurements and/or volume measurements using an image and/or video capture system integrated into, attached to or separate from the OHMD can be determined. In addition, by repeating the measurements, the reproducibility and/or precision of performing distance measurements and/or angle measurements and/or area measurements and/or volume measurements using an image and/or video capture system integrated into, attached to or separate from the OHMD can be determined. The accuracy and/or the reproducibility and/or the precision of performing distance measurements and/or angle measurements and/or area measurements and/or volume measurements using an image and/or video capture system integrated into, attached to or separate from the OHMD can be determined for static and dynamic conditions. Static conditions can be conditions where a patient, a spine, an extremity, a joint and/or a bone do not move. Dynamic conditions can be conditions where a patient, a spine, an extremity, a joint and/or a bone move during the image capture. Dynamic conditions can, for example, be useful in determining the center of rotation of a joint. Measurements for static conditions and for dynamic conditions can be performed for different view angles and distances of the image and/or video capture system integrated into, attached to or separate from the OHMD. More than one image and/or video capture system integrated into, attached to or separate from the OHMD can be used leveraging information from multiple view angles or leveraging parallax information. Measurements for static conditions and for dynamic conditions can be performed with the OHMD at rest, not moving. Measurements for static conditions and for dynamic conditions can be performed with the OHMD not at rest, but moving, for example moving with the operator's head.

Table 5 shows exemplary tests with various combinations of test conditions and test parameters for which the accuracy and the reproducibility and/or the precision of the measurements can be determined. Any combination is possible. Other parameters, e.g. reproducibility of color temperature (e.g. in Kelvin), can be measured. Other statistical tests can be applied. All measurements and all statistical determinations and parameters can be assessed for static, dynamic, OHMD at rest and OHMD moving conditions including at different angles and distances of the image and/or video capture system to the target anatomy and/or test apparatus and/or phantom.

reproducibility tests can be performed intermittently, e.g. every 3 seconds, 5 seconds, 10 seconds, 20 seconds, 30 seconds, 1 minutes, 2 minutes and so forth. System tests can be performed continuously. System tests can be performed intermittently or continuously but limited to times when virtual data are displayed by the OHMD. System tests can be performed intermittently or continuously but limited to

|  | Coordinates of optical markers | Distance between optical markers | Angle between optical markers | Area enclosed by optical markers | Volume of optical marker(s) | Volume enclosed by multiple optical markers | Axis defined by two or more optical markers | Speed of Movement of optical marker | Direction of movement of optical marker |
|---|---|---|---|---|---|---|---|---|---|
| Accuracy | X | X | X | X | X | X | X | X | X |
| Reproducibility/ | X | X | X | X | X | X | X | X | X |
| Static | X | X | X | X | X | X | X | — | — |
| Dynamic | X | X | X | X | X | X | X | X | X |
| OHMD at rest | X | X | X | X | X | X | X | X | X |
| OHMD moving | X | X | X | X | X | X | X | X | X |

Once the accuracy and/or the reproducibility and/or the precision of performing distance measurements and/or angle measurements and/or area measurements and/or volume measurements and/or coordinate measurements using one or more image and/or video capture system integrated into, attached to or separate from the OHMD has been determined, threshold values can, for example, be defined that can indicate when the system is operating outside a clinically acceptable performance range. The threshold values can be determined using standard statistical methods known in the art. For example, when a view angle and/or a distance or a movement speed of an image and/or video capture system integrated into an OHMD indicate that a measurement value can fall outside two standard deviations of the system performance including overall system performance, it can trigger an alert to the surgeon that the display of virtual data, e.g. portions of a virtual surgical plan, virtual projected paths or virtual planes, e.g. virtual cut planes, may not be accurate. A binary, e.g. yes, no, system can be used for triggering an alert that the image and/or video capture system and/or the OHMD display are operating outside a clinically acceptable performance range, e.g. exceeding certain view angles, exceeding or being below certain distances to the target anatomy, or exceeding an acceptable movement speed. Alternatively, a sliding scale can be used as the system enters progressively into a range outside the clinically acceptable performance range. The sliding scale can, for example, be a color scale from green to red with mixed colors in between. The sliding scale can be an acoustic signal that increases in intensity or frequency the further the system operates outside the clinically acceptable range. The sliding scale can be a vibration signal that increases in intensity or frequency the further the system operates outside the clinically acceptable range. In some embodiments, the OHMD can optionally turn off the display of any virtual data of the patient, e.g. virtual plan information, virtual surgical guides or cut blocks or virtual planes or intended paths, or one or more desired or predetermined alignment axes, anatomical axes, biomechanical axes and/or rotation axes when one or more test data indicate that the system is operating outside its clinically acceptable performance range. When test data indicate that the system is operating again inside the clinically acceptable performance range, the OHMD display can turn back on. System tests including accuracy tests and reproducibility tests can be performed intermittently, e.g.

times when surgical steps that require high accuracy or reproducibility are being performed. Such steps requiring high accuracy or high reproducibility can be identified for example by the surgeon through voice commands or other commands or they can be identified in the virtual surgical plan, e.g. automatically or by surgeon choice.

In some embodiments, radiopaque and non-radiopaque optical markers can optionally be attached to or applied to extenders that increase the distance of the optical marker from the patient's skin. Such extenders can, for example, be anchored in a spinous process, a pedicle or other spinal element or a femoral condyle or tibial tubercle via a pin, drill or screw. The use of extenders with attached radiographic optical markers can increase the accuracy of registration between radiographic data and image capture data, for example when AP and lateral radiographs are used. The use of extenders with attached optical markers can help define anatomic or instrument axes and other information when image capture is used. When two or more markers are used with extenders and the markers are separated by a distance greater than the spatial resolution of the image and/or video capture system, the accuracy in determining, for example, an axis between the two markers can increase, for example as the length of the extender and the distance between the markers increases.

Optical markers can be visible with other imaging modalities, e.g. MRI, nuclear scintigraphy, SPECT or PET. Optical markers can, for example, be doped with an MRI contrast agent such as Gadolinium-DTPA so that they are MRI visible. Optical markers can, for example, be doped with an isotope or positron emitter so that they are SPECT or PET visible.

When an optical marker includes a QR code or when a QR code is used as an optical marker, it can also address inventory management issues and quality concerns before, during and after surgery. Operating the wrong side of a patient is a common quality problem related to surgery, which can have devastating consequences for the patient. Similarly, in spinal surgery, operating the wrong spinal level can result in serious injury of the patient. Optical markers used for determining the location, position, orientation, alignment and/or direction of travel, if applicable, of a patient, a limb, a joint, a surgical site, a surgical instrument, a trial implant and/or an implant component can also include information any of the following using, for example, bar codes or QR codes included in, integrated into or attached to the optical marker:

- Patient identifiers
- Patient demographics, e.g. age, sex, height, BMI
- Patient medical history
- Patient risk factors
- Patient allergies
- Side to be operated, e.g. left vs. right
- Site to be operated, e.g. knee vs. hip, spinal level L1 vs. L2, etc.
- Spinal level(s) to be operated
- Portions of virtual surgical plan, e.g. resection amounts, resection levels for a given surgical step, position and/or orientation of bone cuts, slope of a tibial cut, implant rotation, e.g. femoral component rotation, tibial component rotation, implant flexion, e.g. femoral component flexion, intended depth, location, position, orientation, direction, coordinates of burring; intended depth, location, position, orientation, direction, coordinates of reaming; intended depth, location, position, orientation, direction, coordinates of milling; angle of a femoral neck cut; acetabular angle; acetabular anteversion; femoral anteversion; offset; femoral shaft axis; femoral neck axis; femoral neck angle; femoral neck anteversion/retroversion; glenoid anteversion/retroversion; humeral anteversion/retroversion; offset; humeral shaft axis; humeral neck axis; humeral neck angle; intended implant component axes/alignment; intended polyethylene components, thickness (e.g. hip acetabular liner, knee tibial inserts, shoulder glenoid inserts)
- Templating or sizing related information
  - Size of selected implant component, e.g. knee femoral, tibial or patellar component, hip acetabular shell, acetabular liner, femoral stem, femoral head, with mobile bearing components femoral neck portion
  - Side of implant component, left vs. right
- Inventory management information, e.g. Version, type, model of instrument used; Lot number of instrument used; Place of manufacture of instrument used; Date of manufacture of instrument used; Date of first sterilization of instrument used; Number of sterilization cycles applied to instrument used; Date of last sterilization of instrument used; Sterilization center used; Sterilization method used; Recommended sterilization method; Discrepancy between recommended sterilization method and sterilization method use, optionally with alert, e.g. transmitted optically using OHMD; Date instrument delivered to hospital or surgery center; Version, type, model of implant component used; Lot number of implant component used; Place of manufacture of implant component used; Date of manufacture of implant component used; Date of sterilization of implant component used; Type of sterilization of implant component used; Allowed shelf life of implant component, e.g. for given packaging and/or sterilization method; Date implant component delivered to hospital or surgery center; Any other information relevant to inventory management.

Optionally, QR codes that include some of this information can also be separate from the optical marker. In some embodiments, separate bar code and/or QR code readers can be used prior to, during and/or after the surgery to read the information included on the bar codes and/or QR codes. In some embodiments, an image and/or video capture system integrated into or attached to or separate from the OHMD can be used to read the information included on the bar codes and/or QR codes. The information read from the bar code and/or QR code can then, for example, be compared against portions of the virtual surgical plan and/or, for example, the physical patient's side prepared for surgery, e.g. left vs. right, the physical patient site prepared for surgery, e.g. spinal level L4 vs. L5 (as seen, for example, on radiographs), the physical surgery executed, the physical instrument selected, the physical implant trial selected, the physical implant component selected.

When a pin or a screw is placed in a surgical site including a joint and/or a bone, for example also in a spinal level, e.g. a spinous process or pedicle, with an integrated or attached optical marker with a QR code or when an instrument, a trial implant, and/or an implant component with an integrated or attached optical marker with a QR code enters the field of view of a bar code and/or QR code reader and/or an image and/or video capture system integrated or attached to the OHMD, or enters the proximity of the surgical field or surgically altered tissue, the information on the bar code or QR code on the physical pin or screw, the physical instrument, the physical trial implant, and/or the physical implant component can be read and compared against the intended surgical site information and/or the intended laterality information and/or the virtual surgical plan and/or the intended sizing information and/or the intended templating information. In the example of a spinal level, the bar code and/or QR code reader and/or the image and/or video capture system integrated or attached to the OHMD, can read the QR code identifying the intended spinal level and side (left vs. right) for a pin or a pedicle screw or other device(s). The information can be compared to the virtual surgical plan of the patient and/or x-ray information. For example, intra-operative x-rays can be used by the system to automatically or semi-automatically or user-operated identify spinal levels, e.g. counting up from the sacrum, e.g. by detecting the sacral endplate and opposing endplates and/or pedicles. If the system detects a discrepancy in spinal level or laterality between the information read from the pin, screw or device and the integrated or attached optical marker and bar code or QR code, the virtual surgical plan and/or the radiographic information, it can trigger an alert to check the device, check the surgical plan, and/or to re-confirm the spinal level and/or side. The foregoing example is not limited to radiographic information; other imaging tests known in the art, e.g. CT, MRI, etc., can be used for determining or identifying the anatomic site and side, including for spinal levels.

If the reading of the QR code indicates a discrepancy in any of the information embedded in the QR code, e.g. site, laterality, level, portions or aspects of virtual surgical plan, sizing or templating information, vs. the physical live data during the surgery, e.g. the physical position or spinal level or laterality of the inserted pin or screw, the physical instrument used, the physical trial implant used, and/or the physical implant component used, an alert can be triggered, for example in the OHMD or on a computer monitor used for planning, display, or modifying the virtual surgical plan. The alert can be visual, e.g. red warning signs or stop signs or alert signs displayed, or acoustic, or a vibration, or combinations thereof. Any other alert known in the art can be used.

For example, when a surgeon is operating on a patient to replace the patient's left knee, one or more implant components or an attached holder or packaging label or sterile package can include an optical marker including a QR marker. The QR marker can indicate the laterality, e.g. left femoral component vs. right femoral component. If the scrub technician accidentally hands the surgeon a right femoral component for implantation into the patient's left knee, an image and/or video capture system integrated or attached to the OHMD that the surgeon is wearing can read the QR code as the surgeon takes the femoral component and as the femoral component with the attached optical marker and QR code enters the surgeon's field of view or enters the proximity of the surgical field. The image and/or video capture system and related system software can read the QR code identifying that the implant component is for a right knee; the system software can then compare the information to the virtual surgical plan of the patient or the templating and/or sizing information which can indicate that a left knee was planned, then triggering an alert that an incorrect femoral component has entered the field of view of the surgeon or has entered into the proximity of the surgical field, as for example demarcated by another optical marker. The alert can assist the surgeon in correcting the error by switching to the correct side component.

Arrangement of optical markers inside sterile barriers indicating use of a medical device: In another example, when a surgeon is operating on a patient to replace the patient's left knee, one or more implant components or an attached holder or packaging label or sterile package can include an optical marker including a QR marker. Optionally, the optical marker, e.g. including a QR code, barcode or other inventory management code can be included inside the sterile package. In some embodiments, the sterile package can include a first and a second sterile barrier. A QR code, barcode or other inventory management code can be included inside the first sterile barrier. A QR code, barcode or other inventory management code can be included inside the second sterile barrier. A QR code, barcode or other inventory management code can be included inside the first and the second sterile barrier. Optionally a QR code, barcode or other inventory management code reader can be used to read the code when the first and/or second sterile barrier is opened. The QR code, barcode or other inventory management code are intentionally placed and/or arranged inside the sterile barrier so that they can only be read or detected once the first and/or second sterile barrier is opened, e.g. by removing a cover or seal from the package, indicating and/or confirming the use of the medical device, which can trigger the billing charge or invoice, for example. The QR code, barcode or other inventory management code can be not visible, can be hidden and/or can be obscured inside the sterile barrier so that they are only exposed with the opening of the sterile package and so that they can only be read or detected once the first and/or second sterile barrier is opened, e.g. by removing a cover or seal from the package, indicating and/or confirming the use of the medical device, which can trigger the billing charge or invoice, for example. The QR code, barcode or other inventory management code can be intentionally not visible, can be intentionally hidden and/or can be intentionally obscured inside the sterile barrier so that they are only exposed with the opening of the sterile package and so that they can only be read or detected once the first and/or second sterile barrier is opened, e.g. by removing a cover or seal from the package, indicating and/or confirming the use of the medical device, which can trigger the billing charge or invoice, for example. A camera or image capture system and/or 3D scanner integrated into, attached to or separate from the OHMD can detect and/or read the QR code, bar code or other inventory management codes. Thus, for example, when a nurse, surgical assistant or surgeon, opens the first sterile barrier, a QR code, bar code or other inventory management code readers including, for example, a camera or image and/or video capture system and/or 3D scanner integrated into, attached to or separate from the OHMD, e.g. the OHMD worn by the nurse, surgical assistant or surgeon, can read the QR code, bar code or other inventory management code sending a signal that the first sterile barrier of the implant component has been opened. When a nurse, surgical assistant or surgeon opens the second sterile barrier, a QR code, bar code or other inventory management code readers including, for example, a camera or image and/or video capture system and/or 3D scanner integrated into, attached to or separate from the OHMD, e.g. the OHMD worn by the nurse, surgical assistant or surgeon, can read the QR code, bar code or other inventory management code sending a signal that the second sterile barrier of the implant component has been opened. The opening of the first and/or the second sterile barrier can trigger a signal or command indicating that the implant component has been used during the surgery; the signal or command can be transmitted to the hospital management system or the manufacturer, e.g. to their respective inventory management system, triggering one or more additional commands, e.g. to replenish the inventory for the used implant component and/or the pay the manufacturer for the used implant component and/or to generate a purchase order and/or an invoice to the hospital. The opening of the first and/or the second sterile barrier can trigger a signal or command to print a bill of materials, to release a replacement component for replenishing the stock of used components, print a shipping label, issue shipping instructions and to ship a replacement component to replenish any inventory in the hospital or surgery center.

The QR marker can indicate the size of the implant component, e.g. size 5 or 6 or other femoral component or size 5 or 6 or other tibial component or size 2 or 3 or other patellar component. If the scrub technician accidentally hands the surgeon a size 4 femoral component for implantation into the patient's which has been templated for a size 6 femoral component, an image and/or video capture system integrated or attached to the OHMD that the surgeon is wearing can read the QR code as the surgeon takes the femoral component and as the femoral component with the attached optical marker and QR code enters the surgeon's field of view or enters the proximity of the surgical field. The image and/or video capture system and related system software can read the QR code identifying that the implant component is of a size 4; the system software can then compare the information to the virtual surgical plan of the patient or the templating and/or sizing information which can indicate that a size 6 femoral component was planned, then triggering an alert that an incorrect femoral component has entered the field of view of the surgeon or has entered into the proximity of the surgical field, as for example demarcated by another optical marker. The alert can assist the surgeon in correcting the error by switching to the correct size component.

An image and/or video capture system and/or a bar code and/or QR code reader integrated into, attached to or separate from the OHMD can also be used to read embedded information on the virtual surgical instruments and/or implant components for inventory management and billing and invoicing purposes. For example, the image and/or video capture system and/or a bar code and/or QR code reader can detect which instruments were used, monitor their frequency of use, and when a certain recommended frequency of used has been reached, the system can trigger an alert to send the instrument for servicing. In some embodiments, the image and/or video capture system and/or a bar code and/or QR code reader can detect which instruments were used and trigger an alert to send the instruments used for sterilization. In some embodiments, the image and/or video capture system and/or a bar code and/or QR code reader can detect which disposable instruments were used and trigger an alert in the system to replenish the supply and send new, additional disposable instruments to replace the ones used. In some embodiments, the image and/or video capture system and/or a bar code and/or QR code reader can detect which implant components and other chargeable components were used and trigger an alert in the system to replenish the supply and send new, additional implant to replace the ones used; the alert can also trigger a command to generate an invoice to the hospital and/or surgery center and to monitor payment.

Any of the foregoing embodiments can be applied to any surgical step and any surgical instrument or implant component during any type of surgery, e.g. knee replacement, hip replacement, shoulder replacement, ligament repair including ACL repair, spinal surgery, spinal fusion, e.g. anterior and posterior, vertebroplasty and/or kyphoplasty.

In some embodiments, pins or other implantable or attachable markers or calibration or registration phantoms or devices including optical markers can be placed initially, for example in a bone or an osteophyte or bone spur or other bony anatomy or deformity. Registration of virtual image data, for example using anatomic landmarks or locations or an osteophyte or bone spur or other bony anatomy or deformity, where the pins have been physically placed and optionally marking those on an electronic image, and live patient data can be performed. The pins can be optionally removed then, for example if they would interfere with a step of the surgical procedure. After the step of the surgical procedure has been performed, e.g. a bone cut, the pins can optionally be re-inserted into the pin holes remaining in the residual bone underneath the bone cut and the pins can be used for registered the virtual data of the patient with the live data of the patient even though the surgical site and anatomy has been altered by the surgical procedure.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Patient Specific Markers or Templates Various techniques have been described for registering virtual patient data with live patient data using patient specific markers or templates including those described in WO9325157A1, which is expressly incorporated by reference herein.

In some embodiments, pre-operative imaging is performed to acquire 3D data of the patient. The pre-operative imaging can, for example, entail ultrasound, CT or MRI, any of the foregoing, optionally with administration of a contrast agent.

The pre-operative imaging can include a single area or region, such as a lumbar spine or portions of a lumbar spine or one or more spinal segments, or a single joint, such as a knee joint, hip joint, ankle joint, shoulder joint, elbow joint or wrist joint. Alternatively, the pre-operative imaging can include scanning through portions or all of one or more adjacent joints. This approach can be beneficial when information about a length of an extremity or axis alignment or rotational alignment is desirable. For example, in planning a hip replacement surgery, it can be beneficial to have image information through the distal femur and, optionally, the knee joint and/or the ankle joint available to determine, for example, leg length. In planning a knee replacement surgery, it can be beneficial to have image information through the hip joint and the ankle joint available. In this manner, the center of the hip and the ankle joint can be, for example, determined. This information can be used to determine the mechanical axis alignment of the patient and, optionally, to plan for any mechanical axis correction.

The pre-operative imaging can also entail imaging in one or more positions, e.g. prone, supine, upright, flexion, extension, lateral bending. Data obtained from scans with the patient in different positions can optionally be combined or fused. For example, an upright standing weight-bearing partial or full leg x-ray can be used to determine the mechanical axis alignment of the leg. 3D data of the knee, e.g. from CT or MRI can be used to obtain detailed anatomic information about the joint, for example to derive a surface shape and to design a patient specific marker or template. The information from the upright scan can be used to align the patient specific marker or template or aspects of it in relationship to the mechanical axis. The information from the 3D knee scan can be used to derive one or more patient specific surfaces that fit to the unique shape of the patient.

In a patient with spinal symptoms, 3D data of the spine can be obtained, for example, with a CT or MRI scan or a rotational fluoroscopy or C-arm scan. Upright imaging, for example in flexion and extension, can be used to determine the presence and degree of spinal instability, for example prior to an intended spinal fusion surgery with pedicle screws and/or cages. The degree of instability or slippage can be determined and used to decide on the degree of intended correction, if any, or the degree of a required foraminotomy, both of which can be optionally planned on the 3D data. Lateral bending views can optionally be used to determine the degree and angle of a partial vertebral corpectomy and the desired placement and/or height of intervertebral cages. Thus, data from upright imaging studies can be combined or optionally fused with data from supine or prone imaging studies. Data from 2D imaging studies can be combined or fused with data from 3D imaging studies. The 3D data can be used to derive one or more patient specific surfaces that fit to the unique shape of the patient, e.g. to the unique shape of one or more of the patient's spinous processes, one or more of the patient's transverse processes, one or more of the patient's laminae, one or more of the patient's articular processes, one or more of the patient's vertebral body.

The patient specific marker or template can include one or more surfaces that are designed and manufactured to fit the corresponding surface of the patient, typically like a negative or substantially a negative. Optional smoothing of the surface can be performed. Alternatively, the surface can be intentionally "roughened" to include more surface features than the segment 3D surface of the patient's target anatomy. Such surface features can, for example, include spike or pin-like structures to allow for enhanced fixation of the patient specific marker or template on the patient's tissue surface.

The patient specific marker or template can be developed from CT, MRI or ultrasound scans as well as x-ray imaging. Principally, any multi-planar 2D or 3D imaging modality is applicable, in particular when it provides information on surface shape or provides information to derive estimates of surface shape of an anatomic region. The patient specific marker or template can include one or more surfaces that are designed or manufactured to fit in any joint or in a spine or other anatomic locations a corresponding Cartilage surface of a patient; Subchondral bone surface of a patient; Cortical bone surface of a patient; Osteophyte or bone spur of a patient; Bone defect of a patient; Exuberant bone formation of a patient; Subchondral cyst of a patient;

Soft-tissue shape, e.g. the shape of a thigh or calf or lower back, or thoracic region, or neck region, or foot or ankle region, or shoulder region; Soft-tissue shape in different body poses or positions, e.g. in prone position or in supine position or in lateral position; Ligament of a patient; Labrum of a patient; Meniscus of a patient; Organ shape of a patient; Organ rim or edge of a patient, e.g. a liver edge or spleen edge.

Different imaging tests can be particularly amenable for a given tissue. For example, if the patient specific marker or template is designed to fit the cartilage shape of the patient, MRI and ultrasound or CT arthrography are ideally suited to provide the surface information. If the patient specific marker or template is intended to fit the subchondral bone shape or cortical bone shape, CT can be used, although MRI and ultrasound can also provide information on bone shape.

Patient specific markers or templates can be manufactured using different materials, e.g. ABS or nylon or different types of plastics or metals. They can be machined, e.g. from a blank, wherein a CAD/CAM process transfers the patient specific shape information into the milling machines. They can also be produced using stereolithography or 3D printing techniques known in the art. If 3D printing is used, any residual powder can be removed using an air cleaning operation and/or a water bath. 3D printing can be performed using powder based or liquid resin based approaches, including, but not limited to continuous liquid interface production.

Patient specific markers or templates can include or incorporate optical markers, e.g. optical markers with different geometric shapes or patterns, with QR codes, with bar codes, with alphanumeric codes. Optionally, geometric shapes or patterns, QR codes, bar codes, alphanumeric codes can be printed, for example when 3D printing is used for manufacturing patient specific markers or templates. 3D printing can be performed with software, e.g. Materialise Magics (Materialise, Leuven, Belgium), and hardware known in the art, e.g. 3D printers from 3D Systems, Rock Hill, S.C., or Concept Laser, Lichtenfels, Germany.

Patient specific markers or templates can be made with different material properties. For example, they can be non-elastic, semi-elastic or elastic. They can be hard. They can be solid or include hollow spaces or openings. They can be opaque. Patient specific markers or templates can be semi-opaque. Patient specific markers can be transparent. In some embodiments, a patient specific marker or template can be semi-opaque or semi-transparent. However, when the patient specific marker or templates comes in contact with the patient and the patient specific surface(s) of the marker or template achieves a good fit with the corresponding surface of the patient, the patient specific marker or template becomes transparent due to the tissue moisture on the corresponding surface of the patient.

One or more patient specific markers or templates can be used on a first surface of a joint. One or more patient specific markers can be used on a second surface of a joint. The first and second surface can be on the same weight-bearing side of the joint. The first and second surface can be on opposite sides of the joint. The one or more patient specific markers or templates on the first surface of the joint cannot be connected to the one or more patient specific markers or templates on the second surface of the joint. In some embodiments, the one or more patient specific markers or templates on the first surface of the joint can, optionally, be connected or linked to the second surface of the joint. Thus, one or more patient specific markers or templates can optionally be cross-referenced.

Patient specific markers or templates can be designed for any joint, any portion of a spine, and any tissue of the human body. Patient specific markers or templates typically include one or more surfaces or shapes designed to fit a corresponding surface or shape of a patient. Representative, non-limiting examples of patient surfaces to which patient specific markers or templates can be designed and/or fitted include:

Spine:
A portion or an entire spinous process
A portion or an entire spinal lamina
A portion or an entire spinal articular process
A portion of or an entire facet joint
A portion of or an entire transverse process
A portion of or an entire pedicle
A portion of or an entire vertebral body
A portion of or an entire intervertebral disk
A portion of or an entire spinal osteophyte
A portion of or an entire spinal bone spur
A portion of or an entire spinal fracture
A portion of or an entire vertebral body fracture
Combinations of any of the foregoing
Hip:
A portion of or an entire acetabulum
A portion of or an entire edge of an acetabulum
Multiple portions of an edge of an acetabulum
A portion of an iliac wall
A portion of a pubic bone
A portion of an ischial bone
A portion of or an entire greater trochanter
A portion of or an entire lesser trochanter
A portion of or an entire femoral shaft
A portion of or an entire femoral neck
A portion of or an entire femoral head
A fovea capitis
A transverse acetabular ligament
A pulvinar
A ligamentum teres
A labrum
One or more osteophytes, femoral and/or acetabular
Combinations of any of the foregoing
Knee:
A portion or an entire medial femoral condyle
A portion or an entire lateral femoral condyle
A portion or an entire femoral notch
A portion or an entire trochlea
A portion of an anterior cortex of the femur
A portion of an anterior cortex of the femur with adjacent portions of the trochlea
A portion of an anterior cortex of the femur with adjacent portions of the trochlea and osteophytes when present One or more osteophytes femoral and/or tibial
One or more bone spurs femoral and/or tibial
An epicondylar eminence
A portion or an entire medial tibial plateau
A portion or an entire lateral tibial plateau
A portion or an entire medial tibial spine
A portion or an entire lateral tibial spine
A portion of an anterior cortex of the tibia
A portion of an anterior cortex of the tibia and a portion of a tibial plateau, medially or laterally or both
A portion of an anterior cortex of the tibia and a portion of a tibial plateau, medially or laterally or both and osteophytes when present
A portion or an entire patella
A medial edge of a patella
A lateral edge of a patella
A superior pole of a patella
An inferior pole of a patella
A patellar osteophyte
An anterior cruciate ligament
A posterior cruciate ligament
A medial collateral ligament
A lateral collateral ligament
A portion or an entire medial meniscus
A portion or an entire lateral meniscus
Combinations of any of the foregoing
Shoulder:
A portion or an entire glenoid
A portion or an entire coracoid process
A portion or an entire acromion
A portion of a clavicle
A portion or an entire humeral head
A portion or an entire humeral neck
A portion of a humeral shaft
One or more humeral osteophytes
One or more glenoid osteophytes
A portion or an entire glenoid labrum
A portion or an entire shoulder ligament, e.g. a coracoacromial ligament, a superior, middle, or inferior glenohumeral ligament
A portion of a shoulder capsule
Combinations of any of the foregoing
Skull and Brain:
A portion of a calvarium
A portion of an occiput
A portion of a temporal bone
A portion of an occipital bone
A portion of a parietal bone
A portion of a frontal bone
A portion of a facial bone
A portion or an entire bony structure inside the skull
Portions or all of select gyri
Portions or all of select sulci
A portion of a sinus
A portion of a venous sinus
A portion of a vessel
Organs:
A portion of an organ, e.g. a superior pole or inferior pole of a kidney
An edge or a margin of a liver, a spleen, a lung
A portion of a hepatic lobe
A portion of a vessel
A portion of a hiatus, e.g. in the liver or spleen
A portion of a uterus
The patient specific marker or template can be designed or fitted to any of the previously mentioned tissues, if applicable for a particular anatomic region, e.g. cartilage, subchondral bone, cortical bone, osteophytes etc. The patient specific marker or template can be designed or fitted to normal tissue only. The patient specific marker or template can be designed or fitted to abnormal or diseased tissue only. The patient specific marker or template can be designed or fitted to combinations of normal and abnormal or diseased tissue. For example, the patient specific marker can be designed to normal cartilage, or to diseased cartilage, or to combinations of normal and diseased cartilage, e.g. on the same or opposing joint surfaces. Patient specific markers can be used to register one or more normal or pathologic tissues or structures in a common coordinate system, for example with one or more OHMDs and virtual data of the patient. Virtual and physical surgical instruments and implant components can also be registered in the common coordinate system.

The patient specific marker or template can be designed using virtual data of the patient, e.g. from a pre-operative imaging study such as a CT scan, MRI scan or ultrasound scan. The patient specific marker or template includes one or more surfaces that are designed and/or manufacture to achieve a close fit with a corresponding surface of the patient.

In some embodiments, a surgeon or an operator can apply the patient specific marker or template to the corresponding tissue of the patient. Once a satisfactory fit has been achieved and the two corresponding surfaces are substantially in contact, the patient specific marker or template can be used to register the virtual data of the patient and an optional virtual surgical plan with the live data of the patient. By applying the patient specific marker or template to its corresponding surface(s) on the patient, the surgeon is effectively identifying corresponding structures or surfaces in the virtual data and the live data of the patient.

The position, location and/or orientation of the patient specific marker or template can then be determined in relationship to the OHMD. Any of the embodiments described herein can be applied for determining the position, location and/or orientation of the patient specific marker or template in relationship to the OHMD. For example, the side of the patient specific marker or template that is opposite the patient specific surface can include certain standardized geometric features, e.g. rectangles, triangles, circles and the like, that can be readily recognized by an image and/or video capture system integrated into or attached to or coupled to the OHMD. In alternative embodiments, the patient specific marker or template can include one or more IMU's, including, for example, accelerometers, magnetometers, and gyroscopes, similar, for example, to the OHMD. In some embodiments, the patient specific marker or template can include one or more radiofrequency tags or markers or retroreflective markers and its position, location and/or orientation can be captured by a surgical navigation system. Radiofrequency tags can be active or passive. Optionally, the OHMD may also include one or more radiofrequency tags or markers or retroreflective markers and its position, location and/or orientation can also be captured by the surgical navigation system and cross-referenced to the patient specific marker or template. The patient specific marker or template can also include light sources, such as lasers or LED's. A laser can be projected, for example, on a wall or a ceiling and the OHMD can be referenced in relationship to that. An LED attached to or integrated into the patient specific marker or template can be recognized, for example, by an image and/or video capture system integrated into or attached to r coupled to the OHMD.

In an additional embodiment, one or more of the surgical instruments and/or one or more of the implantable devices used during the surgery can include can include certain standardized geometric features, e.g. rectangles, triangles, circles and the like, that can be readily recognized by an image and/or video capture system integrated into or attached to or coupled to the OHMD. In alternative embodiments, one or more of the surgical instruments and/or one or more of the implantable devices used during the surgery can include one or more IMU's, including, for example, accelerometers, magnetometers, and gyroscopes, similar, for example, to the OHMD. In some embodiments, one or more of the surgical instruments and/or one or more of the implantable devices used during the surgery can include one or more radiofrequency tags or markers or retroreflective markers and its position, location and/or orientation can be captured by a surgical navigation system. Optionally, the OHMD may also include one or more radiofrequency tags or markers or retroreflective markers and its position, location and/or orientation can also be captured by the surgical navigation system and cross-referenced to the patient specific marker or template and/or the one or more of the surgical instruments and/or one or more of the implantable devices used during the surgery. One or more of the surgical instruments and/or one or more of the implantable devices used during the surgery can also include light sources, such as lasers or LED's. A laser can be projected, for example, on a wall or a ceiling and the OHMD and the patient can be referenced in relationship to that. An LED attached to or integrated into the one or more of the surgical instruments and/or one or more of the implantable devices used during the surgery can be recognized, for example, by an image and/or video capture system integrated into or attached to or coupled to the OHMD. Optionally, multiple LED's can be used. Optionally, two or more of the multiple LED's emit light with different wavelength or color. The two or more LED's can be located in spatially defined locations and orientations, e.g. at a pre-defined or fixed distance and at one or more pre-defined or fixed angles. In this manner, the two or more LED's can be located by an image and/or video capture system integrated into, attached to or separate from the OHMD and their measured distance and/or angles as seen through the image and/or video capture system can, for example, be used to determine the distance and or orientation of the operator to the target anatomy, e.g. when the image and/or video capture system is close to the operator's eyes. By using LED's with different wavelength or color, the image and/or video capture system can differentiate between different LED's; when the LED's are arranged in a known spatial orientation, this information can be helpful for increasing the accuracy of the registration and/or for obtaining accurate distance, angle, direction and/or velocity measurements. The use of two or more LED's with different wavelength and color and measurements or registration as described above are applicable throughout the specification in all embodiments that incorporate the use of LED's or that are amenable to using LED's.

Optionally, the patient specific marker or template and, optionally, one or more of the surgical instruments and/or one or more of the implantable devices used during the surgery can also include color markings, optionally with different geometric shapes or located or oriented at different, known locations and different, known angles, that can be used, for example, by an image and/or video capture system integrated into or attached to or coupled to an OHMD to recognize such patterns and, for example, to estimate distances and angles, e.g. from the surgical site to the OHMD, or distances and angles between two markings, two surgical instruments or medical device components.

Optionally, the patient specific marker or template and, optionally, one or more of the surgical instruments and/or one or more of the implantable devices used during the surgery can also include scales, e.g. of metric distances, inches, or angles that can be used, for example, by an image and/or video capture system integrated into or attached to or coupled to an OHMD to recognize such scales or angles and, for example, to estimate distances and angles, e.g. from the surgical site to the OHMD, or distances and angles between two surgical instruments or medical device components.

In some embodiments, the patient specific marker or template can be attached to the corresponding surface of the patient or to an adjacent surface of the patient, for example using tissue glue such as fibrin glue or a pin or a staple.

In some embodiments, the patient specific marker or template can include openings or guides, for example for accepting a surgical instrument or tool such as a bur, a saw, a reamer, a pin, a screw and any other instrument or tool known in the art.

By cross-referencing virtual patient data and live patient data with use of a patient specific marker or template and, optionally, one or more of the surgical instruments and/or one or more of the implantable devices used during the surgery and an OHMD, any coordinate information, distance information, axis information, functional information contained in the virtual patient data can now be available and used during the surgery.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Intraoperative Imaging In some embodiments, intraoperative imaging, for example using x-ray imaging or CT imaging and/or ultrasound imaging, can be performed. Virtual patient data obtained intraoperatively using intraoperative imaging can be used to register virtual patient data obtained preoperatively, for example using preoperative x-ray, ultrasound, CT or MRI imaging. The registration of preoperative and intraoperative virtual data of the patient and live data of the patient in a common coordinate system with one or more OHMDs can be performed, for example, by identifying and, optionally, marking corresponding landmarks, surfaces, object shapes, e.g. of a surgical site or target tissue, in the preoperative virtual data of the patient, the intraoperative virtual data of the patient, e.g. on electronic 2D or 3D images of one or more of the foregoing, and the live data of the patient. Virtual preoperative, virtual intraoperative and live data can include an osteophyte or bone spur or other bony anatomy or deformity. Virtual and physical surgical instruments and implant components can also be registered in the common coordinate system.

This embodiment can be advantageous when the amount of information obtained with intraoperative imaging is, for example, anatomically or in other ways more limited than the amount of information available with preoperative imaging or vice versa.

For example, intraoperative imaging may be performed using x-ray imaging, which is commonly only two-dimensional in nature. X-ray imaging can be augmented through image acquisition in more than one plane, e.g. orthogonal planes or one or more planes separated by a defined angle. Intraoperative x-ray images can be used to identify certain landmarks or shapes that can then be registered to preoperative imaging and/or live data of the patient during surgery. Preoperative imaging can, optionally, include 3D image data, for example obtained with CT or MRI. Acquisition of intraoperative images in multiple planes can be helpful to more accurately define the location of certain landmarks, contours or shapes intended for use in a registration of preoperative virtual data, intraoperative virtual data and live data of the patient. For purposes of clarification, intraoperative virtual data of the patient can be intraoperative images of the patient in 2D or 3D.

For example, in a spinal procedure such as vertebroplasty, kyphoplasty, pedicle screw placement, or placement of anterior spinal device including artificial disks or cages, intraoperative x-ray imaging can be used to identify, for example, the spinal level targeted for the surgery, in an AP projection certain landmarks or contours, e.g. the tip of a spinous process, a facet joint, the superior or inferior tip of a facet joint, the cortical edge of a lamina, a superior or inferior endplate or an osteophyte or bone spur or other bony anatomy or deformity. Optionally, the distance of the x-ray tube from the patient resulting in x-ray magnification can be factored into any registration in order to improve the accuracy of the registration of virtual preoperative data of the patient and virtual intraoperative data of the patient or live data of the patient. The intraoperative x-ray images can then be registered and, optionally, superimposed onto the preoperative data of the patient or the live data of the patient in the projection by the OHMD. The intraoperative virtual data of the patient, e.g. the tip of a spinous process, a facet joint, the superior or inferior tip of a facet joint, the cortical edge of a lamina, a superior or inferior endplate, can be registered to the live data of the patient, for example by touching the corresponding anatomic landmarks with a pointing device or a needle or a pin inserted through the skin and by cross-referencing the location of the tip of the live data pointing device with the intraoperative virtual data of the patient. In this manner, any one of preoperative virtual data of the patient, intraoperative virtual data of the patient, and live data of the patient and combinations thereof can be co-registered. Two or three of these data sets, preoperative virtual data of the patient, intraoperative virtual data of the patient, and live data of the patient, can optionally be seen in the OHMD. However, in many embodiments, intraoperative imaging may only be used for enhancing the accuracy of the registration of preoperative virtual data of the patient and live data of the patient and, for example, preoperative virtual data of the patient and/or a medical device intended for placement in a surgical site will be displayed by the OHMD together with the view of the live data of the patient or the surgical site.

In some embodiments, the registration of virtual patient data and live patient data using the techniques described herein can be repeated after one or more surgical steps have been performed and, optionally, intraoperative imaging can be repeated. In this case, the surgically altered tissue or tissue surface or tissue contour or tissue perimeter or tissue volume or other tissue features in the live patient or in the intraoperative repeat imaging data of the patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Skin Markers or Soft-Tissue Markers In some embodiments, skin markers and soft-tissue markers, calibration or registration phantoms or devices can be used for registering preoperative virtual data, optionally intraoperative virtual data such as data obtained from intraoperative x-ray imaging, and live data seen through the OHMD in a common coordinate system with one or more OHMDs. Virtual and physical surgical instruments and implant components can also be registered in the common coordinate system. For example, an initial registration between preoperative virtual data and live data of the patient can happen at the beginning of the procedure. The initial registration can, for example, be performed using corresponding anatomic landmarks, surfaces or shapes, or using intraoperative imaging resulting in intraoperative virtual data or any of the other embodiments described in the present disclosure. The registration can be used, for example, to place the virtual data and the live data and the optical head mounted display into a common coordinate system. Skin markers, calibration or registration phantoms or devices can then be applied. Virtual and physical surgical instruments and implant components can also be registered in the common coordinate system. Alternatively, or in addition, soft-tissue markers, calibration or registration phantoms or devices can be applied. Typically, more than one, such as two, three, four or more skin markers and soft-tissue markers, calibration or registration phantoms or devices will be applied. For clarity, the terms implantable markers, attachable markers, skin markers, soft-tissue markers, calibration or registration phantoms or devices as used through the application can include optical markers, e.g. optical markers with different geometric shapes or patterns, with QR codes, with bar codes, with alphanumeric codes. Skin markers and soft-tissue markers, calibration or registration phantoms or devices can, for example, be applied to the skin or the soft-tissue using a form of tissue compatible adhesive, including fibrin glue and the like. In some embodiments, one, two, three, four or more skin markers and soft-tissue markers, calibration or registration phantoms or devices can be included in a surgical drape or dressing or a transparent film applied to the skin prior to the procedure. The skin markers and soft-tissue markers, calibration or registration phantoms or devices can then be registered in the live data and cross-referenced to virtual data. The skin markers and soft-tissue markers, calibration or registration phantoms or devices can subsequently be used, for example, when the surgical site is altered and the landmarks, surface or shape that was used for the initial registration of virtual and live data have been altered or removed and cannot be used or cannot be used reliably for maintaining registration between virtual data and live data. Virtual preoperative, virtual intraoperative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

Registration of Virtual Patient Data and Live Patient Data Using Calibration or Registration Phantoms with Defined Dimensions or Shapes In some embodiments, calibration or registration phantoms with defined dimensions or shapes can be used to perform the registration of virtual data of the patient and live data of the patient. The calibration or registration phantoms can be of primarily two-dimensional or three-dimensional nature. For example, a calibration or registration phantom can be arranged or located primarily in a single plane. Other calibration phantoms can be located in multiple planes, thereby creating the opportunity for registration using more than one planes. For clarity, the terms calibration or registration phantoms, implantable markers, attachable markers, skin markers, soft-tissue markers, or devices as used through the application can include optical markers, e.g. optical markers with different geometric shapes or patterns, with QR codes, with bar codes, with alphanumeric codes.

Such calibration or registration phantoms can be, for example, attached to the patient's skin. The calibration or registration phantom can be integrated or attached to a surgical drape. The calibration or registration phantom can be attached to the patient's tissue. The calibration or registration phantom can be part of or a component of a medical device. The part or component of the medical device will typically have known dimensions. By using calibration or registration phantoms, as well as other markers, the live data of a patient and the virtual data of the patient can be registered in a common coordinate system, for example with one or more OHMDs. Virtual and physical surgical instruments and implant components can also be registered in the common coordinate system.

In some embodiments, the calibration or registration phantom includes known dimensions, angles or geometric 2D or 3D shapes. For example, the calibration or registration phantom can include structures such as circles, ovoids, ellipses, squares, rectangles, complex 2D geometries, 2D geometries with one or more defined distances, 2D geometries with one or more defined angles spheres, egg shaped structures, cylinders, cubes, cuboids, complex 3D geometries or shapes, 3D geometries with one or more defined distances, 3D geometries with one or more defined angles, 3D geometries with one or more defined surfaces Optionally, the calibration or registration phantoms can be radiopaque if pre-operative or intra-operative imaging is performed using an imaging modality with ionizing radiation, e.g. x-ray imaging, fluoroscopy in 2D or 3D, CT, cone beam CT etc.

In some embodiments, the calibration or registration phantom can be MRI visible or nuclear scintigraphy or SPECT visible or PET visible, for example by including portions or containers in the phantom containing Gadolinium-DTPA doped or radionuclide doped or PET isotope emitting water. Any contrast agent or MRI or nuclear scintigraphy or SPECT or PET visible agent known in the art can be used in this fashion.

In some embodiments, the calibration or registration phantom includes retroreflective markers or features which facilitate detection by an image and/or video capture system. The calibration or registration phantom can also be highlighted against the patient's tissue(s) including blood as well as surgical drapes through a choice of select colors, e.g. a bright green, bright blue, bright yellow, bright pink etc. Color combinations are possible. Any color or color combination known in the art can be used.

The calibration or registration phantom can optionally include LED's, optionally battery powered. More than one LED can be used. The LED's can emit a light of a known color, hue and intensity, preferably selected to be readily identifiable by the image and/or video capture system and any segmentation techniques or algorithms used for detecting the location, position and/or orientation of the LED's.

The LED's can be arranged in a spatially defined way, with two or more LED's arranged at a defined distance or distances, at a defined angle or angles, in substantially the same plane or different planes. If LED's are arranged in different planes, the spatial orientation of the planes is for example known and defined.

When two or more LED's are used, the two or more LED's can emit light utilizing different wavelengths, colors, intensity and, optionally also, blinking frequency. In this manner, an image and/or video capture system integrated into, attached to or separate from the OHMD can recognize each different LED based on one or more of their different wavelength, color, intensity and/or blinking frequency. When the LED's are arrange in a spatially defined and known manner, e.g. using known distances or angles within the same plane or different planes, the identification of each individual LED and the change in distances and angles measured by the image and/or video capture system can be used to determine the position, location and/or orientation of the OHMD and/or the operator's head (e.g. if the image and/or video capture system is integrated into the OHMD or attached to the OHMD) or, in some applications, the movement of the patient or body part to which the calibration or registration phantom and LED's are attached.

LED's used throughout the specification can be re-useable. LED's used throughout the specification can also be disposable, optionally with integrated, disposable battery cells/batteries. LED's can be operated utilizing wires, e.g. connected to a power supply and/or connected to a wired user interface or control unit. LED's can be wireless, e.g. without attached power supply (e.g. battery operated) and/or connected to a wireless (e.g. WIFI, Bluetooth) control unit.

LED's can be connected and/or organized in LIF networks. One or more LIF networks can be used, for example, to transmit or receive data or information back and forth from the one or more OHMDs to a control unit or computer, optionally with a user interface. In this example, LED's participating or connected in the one or more LIF networks can be integrated into or attached to the OHMD. LED's participating or connected in the one or more LIF networks can be attached to or, when applicable, integrated into any location or site on the surgeon, the OR staff, the patient, the surgical site, one or more OHMDs, one or more navigation systems, one or more navigation markers, e.g. retroreflective markers, infrared markers, RF markers; one or more optical markers, calibration or registration phantoms.

An LIF network can also be used to transmit or receive data or information about the spatial position, orientation, direction of movement, speed of movement etc. of individual LED's. The same LED's whose relative position, orientation, direction of movement, speed of movement, e.g. in relationship to the surgeon or the patient or the surgical site, is being measured, e.g. using an image and/or video capture system, can be used to transmit or receive information in the LIF network, optionally using different wavelengths, color, frequency, blinking patterns depending on the type of data being transmitted. The information can be about the position, orientation, direction of movement, speed of movement of individual LED's. The information can also be data that are being transmitted or received by the OHMD. The information can be the information or data that are being displayed by the OHMD. The information can be information generated or received by navigation markers, RF markers. The information can be information captured by one or more image and/or video capture systems or cameras.

1, 2, 3, 4 or more LED's can be connected to or attached to the patient, the target anatomy, the surgical site, the surgical site after a first, second or more surgical alterations, for example executed using a virtual surgical plan, the OHMD, a second, third and/or additional OHMDs, for example worn by a second surgeon, a scrub nurse, other OR personnel, the hand, forearm, upper arm and or other body parts of the surgeon/operator.

The relative position, orientation, movement, direction of movement, velocity of movement of each LED can be determined, for example using one or more image and/or video capture systems, e.g. integrated into, attached to or separate from the one or more OHMDs, e.g. when the one or more LED's emit light utilizing different wavelengths, colors, intensity and, optionally also, blinking frequency.

The calibration or registration phantom can optionally include one or more lasers, optionally battery powered. More than one laser can be used. The laser can emit a light of a known color, hue and intensity, for example selected to be readily identifiable by the image and/or video capture system and any segmentation techniques or algorithms used for detecting the location, position and/or orientation of the laser.

The laser can be arranged in a spatially defined way, with two or more lasers arranged at a defined distance or distances, at a defined angle or angles, in substantially the same plane or different planes. If lasers are arranged in different planes, the spatial orientation of the planes can be known and defined.

The calibration or registration phantom can optionally include radiofrequency (RF) transmitters, optionally battery powered. More than one RF transmitter can be used. The RF transmitters can transmit a signal or signals selected to be readily identifiable by an RF receiver system used for detecting the location, position and/or orientation of the RF transmitters. One or more RF transmitters can transmit signals with different frequency and intensity, thereby permitting differentiation of the different RF transmitters by the RF receiver system.

The RF transmitters can be arranged in a spatially defined way, with two or more RF transmitters arranged at a defined distance or distances, at a defined angle or angles, in substantially the same plane or different planes. If RF transmitters are arranged in different planes, the spatial orientation of the planes is can be known and defined.

The calibration or registration phantom can optionally include ultrasound (US) transmitters, optionally battery powered. More than one US transmitter can be used. The US transmitters can transmit a signal or signals selected to be readily identifiable by an US receiver or transducer system used for detecting the location, position and/or orientation of the US transmitters. One or more US transmitters can transmit signal with different frequency and intensity, thereby permitting differentiation of the different US transmitters by the US receiver or transducer system.

The US transmitters can be arranged in a spatially defined way, with two or more US transmitters arranged at a defined distance or distances, at a defined angle or angles, in substantially the same plane or different planes. If US transmitters are arranged in different planes, the spatial orientation of the planes is can be known and defined.

Calibration phantoms or registration phantoms can be used for pre-operative imaging and/or for intraoperative imaging and/or image capture of live data, for example using an image and/or video capture system attached to or integrated into the OHMD or coupled to the OHMD or separate from the OHMD. Virtual preoperative, virtual intraoperative and live data can include an osteophyte or bone spur or other bony anatomy or deformity.

If the same calibration or registration phantom is used for pre-operative imaging and for intra-operative imaging, optionally, the imaging can be performed using the same imaging modality, e.g. x-ray imaging, and, for example, using the same orientation of the patient in relationship to the x-ray source and the detector system and, for example using the same distance of the patient in relationship to the x-ray source and the detector system. Using this approach, the anatomic structures visualized on the pre-operative imaging and intra-operative imaging can be superimposed and registered, optionally in the same coordinate system.

In the event, the calibration or registration phantom has been positioned differently on the patient for the pre-operative imaging and for the intraoperative imaging data acquisition, the difference in location or position or coordinates can be determined using the co-registration of the anatomic data visualized on the pre-operative imaging and intraoperative imaging. An adjustment for the difference in phantom location from the pre-operative to the intraoperative data can be performed; this adjustment can optionally be defined as a phantom offset between pre-operative and intra-operative data. Virtual preoperative, virtual intraoperative and live data can include an osteophyte or bone spur or other bony anatomy or deformity.

As an alternative to the anatomic registration from the anatomic structures visualized on the pre-operative imaging and intra-operative imaging, the registration between pre-operative imaging data and intra-operative live data visualized through the OHMD or an attached, integrated or separate image and/or video capture system can be performed alternatively now using the calibration or registration phantom as visualized or as identified optically during the surgery, for example using the phantom offset between pre-operative and intra-operative data.

In general, the initial registration of virtual data and live data is possible using any of the techniques described herein, e.g. using anatomic features, anatomic landmarks, intraoperative imaging etc. Then co-registration of the calibration or registration phantom, e.g. in the same coordinate system, can be performed. If initial registration fails during the surgical procedure, registration can be maintained using the calibration or registration phantom. For this purpose, the position, location, orientation and/or alignment of the calibration or registration phantom will be continuously or intermittently monitored using an image and/or video capture system, which can be integrated into or attached to the OHMD or coupled to the OHMD or separate from the OHMD.

In some embodiments, the preoperative imaging can entail a cross-sectional imaging modality, e.g. computed tomography, which can optionally generate 3D data of the patient, e.g. in the form of a spiral or a helical CT scan and, optionally, a 3D reconstruction. The 3D data of the patient, e.g. the spiral or helical CT scan or 3D reconstruction, can be re-projected into a 2D image, creating an x-ray like transmission image of the patient, e.g. of the bony structures of the patient including, but not limited to an osteophyte or bone spur or other bony anatomy or deformity. Optionally, this 2D re-projection of the 3D data, e.g. CT data, can be performed using the same plane or projection or view angle and, for example, the same or similar magnification as can be used subsequently during surgery with an intraoperative x-ray imaging test. The film-focus and, optionally, object distance of the x-ray system used for the intraoperative imaging part can be known at the time of the re-projection of the preoperative 3D data, so that the magnification of the patient or anatomic data resulting for a given intraoperative film-focus and optionally object distance will be matched or reflected in the re-projected pre-operative data. If the film-focus and, optionally, object distance of the x-ray system used for the intraoperative imaging part is not known at the time of the re-projection of the preoperative 3D data, the magnification of the re-projected data can be adjusted when they are visualized with and optionally superimposed onto the 2D intraoperative imaging data of the patient or anatomic data resulting for a given intraoperative film-focus and optionally object distance so that the magnification of both re-projected and intraoperative imaging data will be matched or substantially similar. Such matching in magnification can be achieved, for example, by aligning certain features or anatomic landmarks or pathologic tissues including an osteophyte or bone spur or other bony anatomy or deformity in the pre-operative re-projected data with the intraoperative data and adjusting the magnification until the feature or landmarks are substantially superimposed or substantially matching. With this approach, pre-operative imaging data can use the benefit of 3D data including, for example, more accurate three-dimensional placement of an implant component such as a spinal component or a component for joint replacement or fracture repair. Similarly, certain anatomic landmarks or features can be detected and utilized for surgical planning in the 3D data set. When the 3D data are then re-projected into a 2D re-projection or view, anatomic landmarks, features or data or pathologic data can be readily matched up or aligned with corresponding anatomic landmarks, features or data or pathologic data in the corresponding portions of the intraoperative 2D imaging study, e.g. intraoperative x-rays. Thus, while different 3D preoperative and 2D intraoperative imaging modalities can be used, 2D re-projection allows for cross-referencing and, optionally, co-registration of the 2D and 3D data sets. Any 2D and 3D imaging modality known in the art can be used in this manner.

In additional embodiments, the calibration/registration phantom can be used

1.) To estimate distance, position, orientation of OHMD from the patient, for primary or back-up registration, for example used in conjunction with an image and/or video capture system integrated into, attached to or coupled to or separate from the OHMD 2.) To estimate distance, position, orientation of target tissue or surgical site underneath the patient's skin, e.g. after cross-registration with pre-operative and/or intra-operative imaging data 3.) To estimate the path of a surgical instrument or to estimate the location of a desired implantation site for a medical device or implant or transplant 4.) To update a surgical plan The calibration or registration phantom can be used in physical time mode, using physical time registration, for example using an image and/or video capture system integrated into, attached to, coupled to, or separate from the OHMD, which can optionally operate in physical time mode. Physical time mode can, for example, mean that image capture is performed with more than 5 frames/second, 10 frames/second, 15 frames/second, 20 frames/second, 30 frames/second etc.

If images generated with the image and/or video capture system are segmented or, for example, image processing or pattern recognition is performed, this can optionally be performed on each frame generated with the image and/or video capture system. Alternatively, segmentation or image processing or pattern recognition can be performed on a subset of the image frames captured with the image and/or video capture system. Segmentation, image processing or pattern recognition data can be averaged between frames. The foregoing embodiments are applicable to all embodiments in this specification that utilize image capture.

Image processing can be performed to include data from one or more osteophytes or bone spurs or other bony anatomy or deformity. The one or more osteophytes or bone spurs or other bony anatomy or deformity can be used for purposes of registration of virtual and live data, including virtual preoperative and virtual intraoperative imaging or virtual functional data. Image processing can also be performed to exclude data from one or more osteophytes or bone spurs or other bony anatomy or deformity. The one or more osteophytes or bone spurs or other bony anatomy or deformity can be excluded or omitted from any data used for purposes of registration of virtual and live data, including virtual preoperative and virtual intraoperative imaging or virtual functional data. The inclusion or exclusion of one or more osteophytes or bone spurs or other bony anatomy or deformity can be selected based on the anatomic site, the surgical site, and/or the desired accuracy of the segmentation or the registration of virtual data and live data.

The calibration or registration phantom can be used in non-physical time mode, e.g. an intermittent mode, for example using an image and/or video capture system integrated into, attached to, coupled to, or separate from the OHMD, which can optionally operate in intermittent mode. Intermittent mode use of the calibration or registration phantom can be performed, for example, by using a timer or timing device, wherein image capture and registration is performed every 10 seconds, 8 seconds, 5 seconds, 3 seconds, 2 seconds, 1 second etc.

In some embodiments, real-time and intermittent registration using the calibration or registration phantom will be selected or designed so that the data generated will for example not exceed the temporal resolution of the image and/or video capture system and/or the temporal resolution of the segmentation or image processing or pattern recognition used for the registration.

In any of the foregoing embodiments, the accuracy of registration can optionally be improved by using multiple registration points, patterns, planes or surfaces. In general, the accuracy of registration will improve with an increasing number of registration points, patterns, planes or surfaces. These may, in some embodiments, not exceed the spatial resolution of the image and/or video capture system. In some embodiments, these may exceed the spatial resolution of the image and/or video capture system. In that situation, optionally, down-sampling of data can be performed, e.g. by reducing the effective spatial resolution in one, two or three planes or by reducing the spatial resolution in select areas of the field of view seen through the OHMD or visualized in the virtual data. Virtual preoperative, virtual intraoperative and live data can include an osteophyte or bone spur or other bony anatomy or deformity.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

To Estimate Distance, Position, Orientation of OHMD from the Patient

If registration of virtual patient data and live patient data has occurred using any of the techniques or techniques described in this specification and if the calibration or registration phantom is also registered in relationship to the live patient data, the calibration or registration phantom can be used to maintain registration, for example on an intermittent or a real-time basis, including while the surgeon or operator moves his or her head or body. The calibration or registration phantom can, for example, not be moved during the surgery. If the calibration or registration phantom needs to be moved, it may optionally be re-registered in relationship to any live patient data, virtual patient data, pre-operative data and intra-operative data.

In this and related embodiments, the calibration or registration phantom will be identified with regard to its location, position, orientation, alignment, surfaces or shape using an image and/or video capture system and, optionally, segmentation, image processing or pattern recognition and any other techniques known in the art for identifying an object in image data. The image and/or video capture system can be integrated into or attached to the OHMD. The image and/or video capture system can be coupled to or separate from the OHMD. The image and/or video capture system will be used to determine the location, position, orientation, alignment, surfaces or shape of the calibration or registration phantom in relationship to the patient, the operator and/or the OHMD.

Any other techniques known in the art, including as described in this specification, that can be used to determine the location, position, orientation, alignment, surfaces or shape of the calibration or registration phantom in relationship to the patient, the operator and/or the OHMD, can be used, including, but not limited to surgical navigation including optical or RF tracking, laser based distance measurements and the like.

The calibration or registration phantom can be used for primary or back-up registration. Optionally, synchronized registration can be used, wherein, for example, more than one technique of registration is used simultaneously to maintain registration between virtual patient data and live patient data, for example by simultaneously maintaining registration between virtual patient data and live patient data using one or more calibration or registration phantoms in conjunction with maintaining registration using corresponding anatomic landmarks or surfaces between virtual patient data and live patient data. If synchronized registration is used, optionally, rules can be applied to resolve potential conflicts between a first and a second registration technique for registering virtual and live patient data.

For example, with an image and/or video capture system integrated into or attached to the OHMD or coupled to the OHMD, any change in the position, location or orientation of the surgeon's or operator's head or body will result in a change in the perspective view and visualized size and/or shape of the calibration or registration phantom. The change in perspective view and visualized size and/or shape of the calibration or registration phantom can be measured and can be used to determine the change in position, location or orientation of the surgeon's or operator's head or body, which can then be used to maintain registration between the virtual patient data and the live patient data, by moving the virtual patient data into a position, location, orientation and/or alignment that ensures that even with the new position location or orientation of the surgeon's or operator's head or body the registration is maintained and the virtual and the live patient data are, for example, substantially superimposed or matched where desired. Similarly, when more than one OHMD is used, e.g. one for the primary surgeon, a second OHMD for an assistant, a third OHMD for a resident, a fourth OHMD for a scrub nurse and a fifth OHMD for a visitor, with an image and/or video capture system integrated into or attached to each of the different OHMDs or coupled to each of the different OHMDs, any change in the position, location or orientation of the user's or viewer's head or body will result in a change in the perspective view and visualized size and/or shape of the calibration or registration phantom. The change in perspective view and visualized size and/or shape of the calibration or registration phantom can be measured and can be used to determine the change in position, location or orientation of the user's or viewer's head or body, which can then be used to maintain registration between the virtual patient data and the live patient data, by moving the virtual patient data into a position, location, orientation and/or alignment that ensures that even with the new position location or orientation of the user's or viewer's head or body the registration is maintained and the virtual and the live patient data are, for example, substantially superimposed or aligned or matched where desired, with substantially identical view angle of the virtual data of the patient seen by the viewer's left eye through the display of the OHMD unit and the live data of the patient seen by the viewer's left eye through the OHMD unit and substantially identical view angle of the virtual data of the patient seen by the viewer's right eye through the display of the OHMD unit and the live data of the patient seen by the viewer's right eye through the OHMD unit for each of the OHMDs used.

In some embodiments, the calibration or registration phantom can be used to check the accuracy of an integrated or attached or coupled or separate image and/or video capture system.

In a further embodiment, the calibration or registration phantom can be used to calibrate an integrated or attached or coupled or separate image and/or video capture system.

In some embodiments, the calibration or registration phantom can be used to calibrate the IMU, e.g. for distance measurements, movement, distance to object, since calibration or registration phantom includes known geometries, e.g. known distances or angles.

Registration of Virtual Patient Data and Live Patient Data Accounting for Tissue Deformation In some embodiments, tissue deformation, a shape change or removal of tissue caused by the surgery or surgical instruments can be simulated in the virtual data. The resultant simulated virtual data can then be registered related to the live patient data, either before and/or after deformation, alteration of shape or removal of tissue of the live patient. The tissue deformation, shape change or removal of tissue caused by the surgery or surgical instruments can include the shape alteration or removal of one or more osteophytes or bone spurs or other bony anatomy or deformity. The virtual data of the patient and the live data of the patient can be registered in a common coordinate system, for example with one or more OHMDs. Virtual and physical surgical instruments and implant components can also be registered in the common coordinate system.

In some embodiments, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. Re-registration of live patient data and virtual patient data can be particularly helpful if the surgical alteration or surgical step has led to some tissue deformation. For example, the re-registration can be performed by matching, superimposing, and/or registering tissues that have not been performed by the surgical step or surgical alteration. Alternatively, the re-registration can be performed by matching, superimposing and/or registering deformed live patient data, e.g. from surgically deformed tissue, with virtual patient data that simulate the same tissue deformation after the virtual surgical step, e.g. an osteophyte or tissue removal.

Registration of Virtual Patient Data and Live Patient Data at Multiple Time Points, for Example at Different Stages of a Surgical Procedure In some embodiments, registration of virtual patient data and live patient data can occur at multiple time points, for example during different phases of tissue removal or implantation of a medical device. For select or each time point, e.g. for select or all stages of the surgical procedure, the live data of the patient and the virtual data of the patient can be registered in a common coordinate system, for example with one or more OHMDs. Virtual and physical surgical instruments can also be registered in the common coordinate system.

In knee replacement surgery or hip replacement surgery, for example, registration of virtual patient data and live patient data can be performed using, for example, the femoral or tibial or acetabular surface shape or using femoral or tibial or acetabular landmarks prior to the resection of any tissue. Optionally pins or other rigid fixation markers can be placed, for example in an area that will not be surgically resected during at least part of the surgical procedure. The registration of virtual and live patient data can be repeated using different registration sites, surfaces or landmarks after tissue has been removed, e.g. after a burring of the articular surface has occurred or after a bone cut has been performed or after reaming has been performed or after one or more osteophytes or bone spurs or other bony anatomy or deformity have been removed. The registration can now occur to a newly created landmark, created by the surgical procedure, or, for example, a newly created surface, e.g. created by the surgical procedure. Such a newly created surface can be, for example, a planar surface on the residual femur or tibia created by a bone cut. Optionally implanted pins or rigid fixation markers can be used to aid with the registration of the virtual data after surgical alteration and the live data of the patient altered by the surgery. Thus, the present disclosure allows for multiple time point registration of virtual patient data and live patient data, for example by registered virtual patient data to the live patient data prior to surgical alteration and after one or more surgical alterations. In this manner, it is possible to re-register multiple times as surgical field changes.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using CAD Files or Data or 3D Files or Data, e.g. of a Medical Device In some embodiments, a CAD file or CAD data of a medical device can be displayed by the OHMD and superimposed on live data of the patient. The CAD file or CAD data can be a medical device intended for use or implantation during the surgical procedure. Any type of CAD file or CAD data or any type of 3D file or 3D data of a medical device, a surgical instrument or an implantable device can be superimposed and registered in relationship to the live data of the patient including normal anatomy or pathologic tissue, e.g. one or more osteophytes or bone spurs or other bony anatomy or deformity or soft-tissue or neoplastic tissue or abnormality in a common coordinate system, for example with one or more OHMDs. Physical surgical instruments and implant components can also be registered in the common coordinate system.

Medical devices can include non-biologic as well as biologic devices, e.g. tissue scaffolds, cells, cell matrices etc. that can be implanted in a human body.

In some embodiments, multiple CAD files and/or 3D files of virtual data can be superimposed onto the live data of the patient. For example, CAD files can be CAD files of a medical device available in different sizes or shapes. Virtual 2D or 3D data of the patient, for example obtained from a preoperative imaging test, can be superimposed onto live data of the patient, e.g. a surgical site. The surgeon can then optionally introduce a 3D CAD file of a medical device into the display by the OHMD. The surgeon can check the size or shape of the medical device in relationship to the virtual 2D or 3D data of the patient and/or the live data of the patient. If the surgeon is not satisfied with the projected size or shape of the medical device in relationship to the virtual 2D or 3D data of the patient and/or the live data of the patient, the surgeon can select a different CAD file of a medical device with a different size and/or shape, project the CAD file optionally onto the virtual 2D or 3D data of the patient and the live data of the patient in the OHMD display and repeat the process as many times as needed until the surgeon is satisfied with the resultant size or shape of the selected medical device in relationship to the virtual 2D or 3D data of the patient and/or the live data of the patient.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. For example, CAD files simulating the virtual surgical step or surgical alteration in the virtual patient data can be matched, superimposed or registered with live patient data after the physical surgical step or surgical alteration in the live patient. In this manner, live and virtual data can be re-registered after the surgical step or surgical alteration.

Registration of Virtual Patient Data and Live Patient Data Using Non-Anatomic Data Registration of virtual data of the patient and live data of the patient can be performed using data other than anatomic or pathologic structures. Registration can be performed, for example, based on motion data, kinematic data (for example to determine the center of rotation of a joint in the live data which can then be registered to an estimate or simulated center of rotation in the virtual data of the patient). Registration can be performed using metabolic data, for example using an area of high 18 FDG-PET uptake in a PET scan or PET-MRI or PET CT, which can be, for example matched to an area of increased body temperature in a target surgical site. Registration can be performed using functional data, e.g. using functional MRI studies. Virtual data and live data of the patient can be registered in a common coordinate system, for example with one or more OHMDs. Virtual and physical surgical instruments and implant components can also be registered in the common coordinate system.

Optionally, different types of data, e.g. anatomic, motion, kinematic, metabolic, functional, temperature and/or vascular flow data can be used alone or in combination for registered virtual and live data of the patient.

The registration of virtual patient data and live patient data using the techniques described herein can be repeated after one or more surgical steps have been performed using non-anatomic data. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, optionally using non-anatomic data. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data after Performing One or More Surgical Alterations to the Tissue or the Surgical Site In some embodiments, the registration of virtual patient data and live patient data using the techniques described herein can be repeated after one or more surgical steps have been performed and virtual data and live data of the patient can be registered in a common coordinate system after select steps or each surgical step or tissue alteration, for example with one or more OHMDs. Virtual and physical surgical instruments and implant components can also be registered in the common coordinate system after select steps or each surgical step or tissue alteration. The surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The matching, superimposing and/or registering of the live data of the patient and the virtual data of the patient after the surgical tissue alteration can be manual, semi-automatic or automatic using information about the surgically altered tissue or tissue surface or tissue contour or tissue perimeter or tissue volume or other tissue features. Automated re-registration can, for example, be performed using an image and/or video capture system integrated into, attached to or separate from the OHMD which can capture information about the surgically altered tissue or tissue surface or tissue contour or tissue perimeter or tissue volume or other tissue features in the live patient data after the surgical alteration and compare the information to information in the virtual data of the patient, e.g. for the virtual data after performing the comparable step in a virtual surgical plan.

The surgical alteration or surgical steps can include, but are not limited to the procedures in Table 6:

TABLE 6

Exemplary surgical alterations or steps applied to various patient tissues, e.g. bone, cartilage, ligaments, tendons, joint capsule, skin, fat, organ tissue, e.g. liver, spleen, kidney, intestines, gallbladder, lung, heart, thyroid, brain etc.

Cutting, e.g. a bone cut
Sawing, e.g. sawing a bone with a saw
Milling, e.g. milling a bone with a mill
Reaming, e.g. reaming a bone with a reamer
Impacting, e.g. impacting a bone with an impactor
Drilling, e.g. drilling a bone with a drill
Pinning, e.g. pinning a bone with a pin
Radiofrequency ablation
Heat ablation
Cryoablation
Cauterization
Tissue resection
Tissue removal
Resection of a neoplasm
Fracture fixation
Trauma repair
Trauma reconstruction
Soft-tissue repair
Soft-tissue reconstruction
Tissue grafting
Placement of a registration marker or calibration phantom on the tissue surface or inside the tissue
Placement of a surgical instrument, e.g. a pin or a saw
Placement of a medical implant or a component thereof, e.g. a biopsy needle, pedicle needle, pedicle screw, a spinal rod, a component of a knee replacement system, a component of a hip replacement system, a component of a shoulder replacement system, a component of an ankle replacement system
Placement/injection of bone cement or other substances, hardening or non- hardening
Placement of a trial implant
Placement of a tissue graft
Placement of a tissue matrix
Placement of a transplant
Placement of a catheter, e.g. an indwelling catheter
Placement or injection of cells, e.g. stem cells
Injection of a drug Optionally, the registration procedures described herein can be repeated after performing a surgical step. Optionally, the registration procedures described herein can be repeated after multiple surgical steps. Optionally, the registration procedures described herein can be repeated after each surgical step. Optionally, the registration procedures described herein can be repeated after major surgical steps. Optionally, the registration procedures described herein can be repeated when the surgeon wants to achieve high surgical accuracy. Optionally, the registration procedures described herein can be performed or repeated when the surgeon is concerned that the initial registration performed prior to the surgical step or surgical alteration was not accurate or is not accurate any longer or is affected by the surgical step or surgical alteration.

In some embodiments, the change on the patient's tissue induced by the surgical alteration or the surgical step can be known or estimated, for example as part of the virtual surgical plan using the virtual data of the patient. Surgical alterations and/or surgical steps applied to patient tissues can include any of the surgical alterations and/or surgical steps listed in the examples in Table 6, although any alteration to a patient's tissue known in the art can be included. The alteration and/or the change induced on the patient's tissue by the surgical alteration or surgical step can be estimated, for example in the virtual surgical plan and/or the virtual data of the patient. Exemplary changes induced on the patient's tissue by the surgical alteration or surgical step are tabulated in Table 7, which is only exemplary in nature and in no way meant to be limiting:

TABLE 7

Exemplary changes induced on the patient's tissue by a surgical alteration or surgical step.
These changes can be induced in the live patient.
These changes can also be planned/intended or simulated, e.g. for projection by one or more OHMDs, e.g. in a virtual surgical plan.

Change in tissue surface area
Change in tissue volume
Change in tissue surface shape
Change in tissue surface topography
Change in tissue perimeter
(e.g. from uncut to cut surface,
or from cut surface 1 to cut surface 2)
Change in tissue surface roughness
Change in tissue surface texture
Change in tissue surface color
Change in tissue surface reflexivity
(e.g. reflected light or ultrasound)
Change in tissue surface area with different color
(e.g. color change induced by surgical alteration)
Change in tissue surface perimeter,
e.g. cut vs. uncut tissue surface
Change in tissue temperature
Change in tissue elasticity
Change in tissue composition, e.g. fat content
(e.g. marrow fat on a cut bone surface)

Any of the foregoing changes can include all of the tissue or only a portion of the tissue. The embodiments of the present disclosure can be directed towards all of the tissue or only partial tissue or portions of the tissue.

Following initial registration of the live data of the patient with the virtual data of the patient using any of the techniques described in the specification or known in the art, a first or any subsequent surgical alteration or surgical step can be performed inducing changes to the patient's tissue. The surgical alteration or surgical step can be performed with optional guidance through the OHMD display, e.g. by displaying one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

Once a surgical alteration or surgical step has been performed or induced on a patient's tissue in the live patient, the physical changes induced or the resultant tissue appearance and/or tissue properties/characteristics can be determined in the live data of the patient/the live patient. The physical changes induced or the resultant tissue appearance and/or tissue properties/characteristics can be determined in the live data of the patient/the live patient using any technique known in the art for assessing tissue appearance, tissue properties and/or characteristics including, for example, area, volume, shape, topography, roughness, texture, color, reflexivity, area with different color, perimeter, temperature, elasticity, and/or composition. For example, an image and/or video capture system integrated into, attached to or separate from an OHMD can be used to assess one or more of an area, shape, topography, roughness, texture, color, reflexivity, area with different color, perimeter, temperature, elasticity, and/or composition of a surgically altered tissue. Tissue probes, e.g. temperature probes, elasticity probes, can be used to assess characteristics and/or properties of the surgically altered tissue. Mechanical probes, e.g. with one or more attached optical markers, LED's, infrared markers, retroreflective markers, RF markers, navigation markers and/or IMU's can be used to touch the tissue surface or perimeter and, for example, to circle a perimeter or to follow and assess a tissue topography of a surgically altered tissue.

Figure 6:
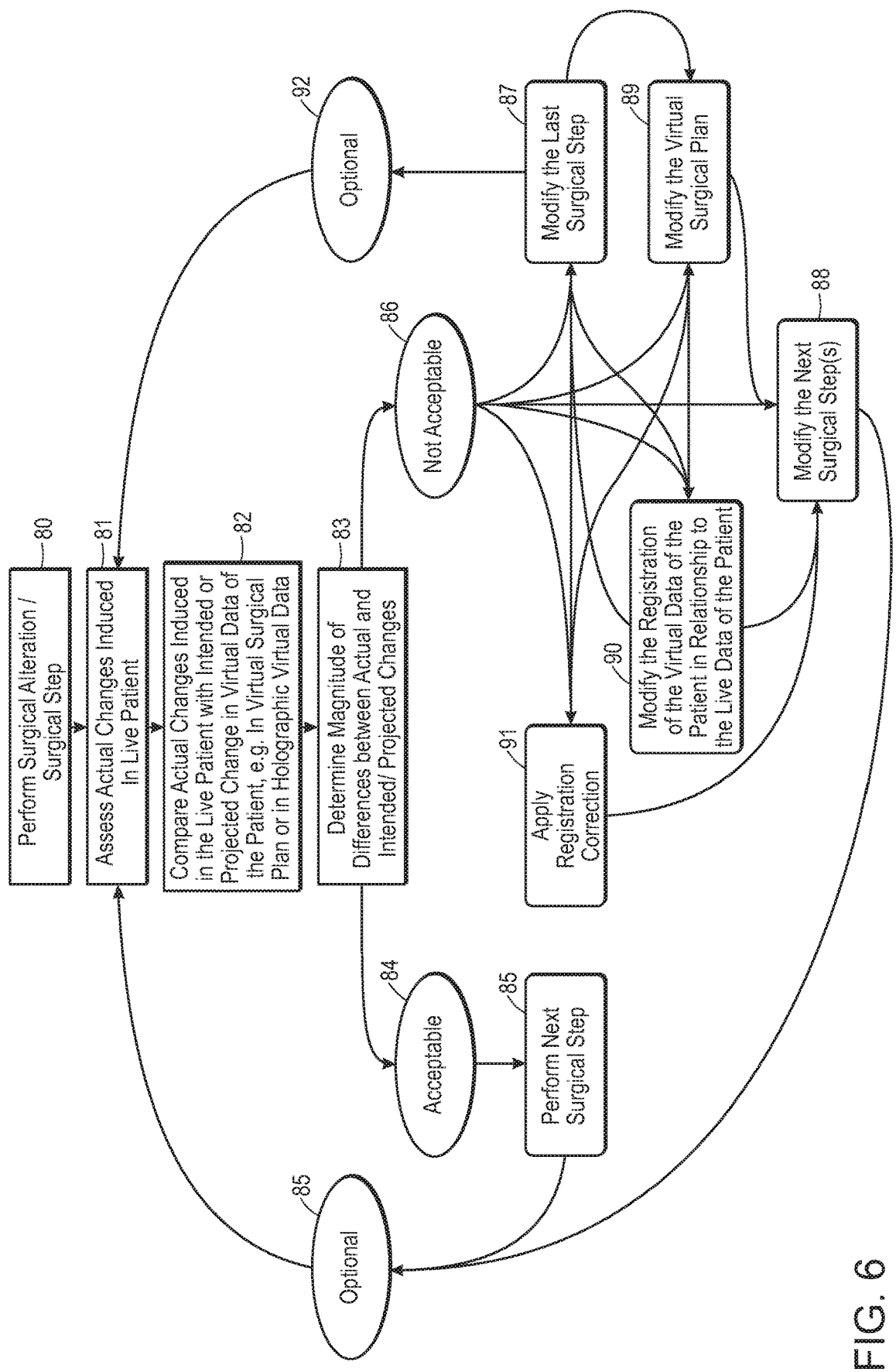
FIG. 6 is an illustrative flow chart that shows different methods of addressing inaccuracies between the changes induced by a surgical step and the intended, projected or predetermined changes in the virtual data of the patient according to some embodiments of the present disclosure.

The physical appearance, properties and/or characteristics of the surgically altered tissue can be assessed using any of the foregoing techniques or any of the techniques described in the specification or known in the art. The physical appearance, properties and/or characteristics of the surgically altered tissue can optionally be compared to the estimated or intended change or post-alteration appearance, e.g. surface area, volume, shape, topography, properties and/or characteristics of the tissue in the virtual data of the patient, for example the virtual surgical plan. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed: If the differences are deemed to be insignificant, for example, if they fall below an, optionally predefined, threshold in distance or angular deviation, the surgical procedure and subsequent surgical steps can continue as originally planned, e.g. in the virtual surgical plan. If the differences are deemed to be significant, for example, if they fall above an, optionally predefined, threshold in distance or angular deviation, the surgeon or the operator can have several options. The process and the options are also shown in illustrative form in FIG. 6: The surgeon can perform a surgical step 80. The surgeon can then assess the actual changes induced in the live patient 81. The surgeon can compare the actual changes induced in the live patient with the predetermined changes in the virtual data of the patient, e.g. in a virtual surgical plan or in a virtual 3D display 82. The magnitude of the difference(s) between the actual and the predetermined changes can be determined 83. If they are acceptable 84, the surgeon can perform the next surgical step 85. Optionally 85, the steps 81, 82, 83 can be repeated for the next surgical step. If the difference(s) between the actual and the predetermined changes are not acceptable 86, the surgeon has several means of addressing the difference(s), modify the last surgical step 87, modify the next surgical step 88, modify the virtual surgical plan 89, modify the registration of the virtual data of the patient in relationship to the live data of the patient 90, or apply registration correction 91. After the last surgical step has been modified b 87, optionally 92, the steps 81, 82, 83 can be repeated for the next surgical step.

A). Modify the Last Surgical Step so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification is more similar to and, optionally, more closely replicates the intended virtual appearance, virtual properties and/or virtual characteristics in the virtual data of the patient, e.g. a virtual surgical plan of the patient. This option can, for example, be chosen if the operator or surgeon is of the opinion that the last surgical step was subject to an inaccuracy, e.g. by a fluttering or deviating saw blade or a misaligned pin or a misaligned reamer or impactor or other problem, and should correct the inaccuracy. Once the modification has been completed, the surgeon or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or operator can optionally repeat option A, or revert to options B or C.

B). Modify the Next Surgical Step(s) so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification in the next surgical step(s) is more similar to and, optionally, more closely replicates the intended virtual appearance, virtual properties and/or virtual characteristics in the virtual data of the patient, e.g. a virtual surgical plan of the patient after the virtual modification in the next virtual surgical step(s). This option can, for example, be chosen if the operator or surgeon is of the opinion that the last surgical step was subject to an inaccuracy, e.g. by a fluttering or deviating saw blade or a misaligned pin or a misaligned reamer or impactor or other problem, and he or she should correct the inaccuracy in the next surgical step(s). Once the modification has been completed with the next surgical step(s), the surgeon or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or operator can optionally repeat option A and/or B and/or revert to options C and/or D and/or E.

C). Modify the Virtual Surgical Plan of the patient so that the virtual appearance, virtual properties and/or virtual characteristics (including, for example, shape, volume and dimensions, cut plane, perimeter or surface/surface area of a cut plane/tissue plane, drill depth, angle, rotation, implant site etc.) of the surgically altered tissue in the virtual data of the patient after the modification is/are more similar to and, optionally, more closely replicates the physical appearance, physical properties and/or physical characteristics in the physical live data of the patient after the physical surgical alteration. This option can, for example, be chosen if the operator or surgeon is of the opinion that the last surgical step was accurate or accounted for unexpected variations in tissue conditions that were not accounted for in the virtual surgical plan. Such unexpected variations in tissue conditions can, for example, be ligament laxity or tightness as can be observed, for example, in knee replacement surgery or hip replacement or other joint replacement surgeries. If the modified surgical plan is modified in this manner, all subsequent virtual surgical steps can then be referenced off the last or preceding physical surgical step, thereby maintaining continuity of the procedure. The OHMD can then be used for projecting all or some of the subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. The subsequent virtual surgical steps are thus modified to allow completion of the procedure and, optionally, placement of an implant or implant component or device or graft or transplant taking into account the one or more modified preceding physical surgical steps. Optionally, the modified subsequent virtual surgical steps can be further modified based on local tissue conditions/characteristics after the virtual or physical modification, for example, if subsequent surgical steps were to fall into a tissue void or would result in impairment of implant component placement.

D). Modify the Registration of the Virtual Data of the Patient in Relationship to the Live Data of the Patient. The operator or surgeon can optionally repeat the registration procedure using any of the techniques described in the specification or known in the art for registering the virtual data of the patient, including, for example the virtual surgical plan, in relationship to the live data of the patient after the physical surgical alteration. Once the virtual data of the patient and the live data of the patient after the surgical alteration have been re-registered, all subsequent virtual surgical steps displayed by the OHMD and any related virtual surgical plan can be referenced off the re-registration of the virtual and live data of the patient. For example, the OHMD can then be used after the re-registration for projecting all subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

E). Apply Registration Correction. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed and can be used to apply a coordinate correction, coordinate adjustment or coordinate transfer of registration of the virtual data of the patient, including, optionally, the virtual surgical plan, and the live data of the patient, e.g. for any subsequent surgical steps or surgical procedures. For example, the OHMD can then project/display all subsequent virtual surgical steps using the coordinate correction or adjustment or transfer, e.g. by projecting one or more of virtual surgical tool, virtual surgical instrument including virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the coordinate correction, adjustment and/or transfer.

Any combinations of the foregoing Options A, B, C, D and/or E are possible.

If an image and/or video capture system is used to measure/capture the physical changes, e.g. change in surface/surface area, perimeter, perimeter shape, and/or shape of the cut surface or otherwise modified or altered surface, the data/images captured by the image and/or video capture system can be corrected for any angular distortion or projection, for example if the camera(s) is/are positioned at an angle other than 90 degrees relative to the cut surface or otherwise modified or altered surface. Similarly, the physical changes measured by the image and/or video capture system, e.g. the size of the surface/surface area, perimeter, perimeter shape, and/or shape of the cut surface or otherwise modified or altered surface, can be corrected or adjusted for the distance between the camera or image and/or video capture system and the changed surface/surface area, perimeter, perimeter shape, and/or shape of the cut surface or otherwise modified or altered surface. The angle and/or the distance of the image and/or video capture system to the physical changes, e.g. surface/surface area, perimeter, perimeter shape, and/or shape of the cut surface or otherwise modified or altered surface, can be assessed, for example, using one or more RF markers, optical markers, navigation markers including, but not limited to, infrared markers, retroreflective markers, RF markers, LED's, and/or IMU's attached to the image and/or video capture system, and/or the OHMD, and/or the patient, and/or the cut, modified or altered surface.

For example, in a knee replacement, hip replacement or shoulder replacement procedure, a bone cut can be applied, optionally using virtual guidance of a bone saw by the OHMD, to a distal femur, proximal tibia, proximal femur or proximal humerus. The position, alignment and/or orientation of the bone cut, including, optionally, the surface/surface area, perimeter, perimeter shape, and/or shape of the cut surface can then be assessed in the live patient, for example using an image and/or video capture system integrated into, attached to or separate from the OHMD or using one or more probes, optionally with one or more attached optical markers, navigation markers including, but not limited to, infrared markers, retroreflective markers, RF markers, LED's, or IMU's.

If the physical position, alignment, orientation, surface, surface area, perimeter, perimeter shape, and/or shape of the cut surface differ from the virtually intended/projected position, alignment, orientation, surface, surface area, perimeter, perimeter shape, and/or shape of the cut surface, the software can, optionally, determine a virtually modified position, alignment, orientation, surface, surface area, perimeter, perimeter shape, and/or shape of the cut surface that would more closely resemble the physical position, alignment, orientation, surface, surface area, perimeter, perimeter shape, and/or shape of the cut surface. The difference in coordinates between the virtually modified position, alignment, orientation, surface, surface area, perimeter, perimeter shape, and/or shape of the cut surface and the physical position, alignment, orientation, surface, surface area, perimeter, perimeter shape, and/or shape of the cut surface can then be used to determine any coordinate correction, adjustment or transfer for subsequent virtual surgical steps. The coordinate correction, adjustment or transfer can then by applied to the OHMD displays, for example when the OHMD displays in any subsequent surgical steps one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the coordinate correction, adjustment and/or transfer.

The following is an exemplary description of a portion of a hip replacement procedure shown in the illustrative example in FIG. 7A-H, where the surgeon elects to make a correction to the proximal femoral cut prior to proceeding with the subsequent steps of the procedure. This example is in no way meant to be limiting, but only illustrative of certain aspects of the present disclosure.

Figure 7A:
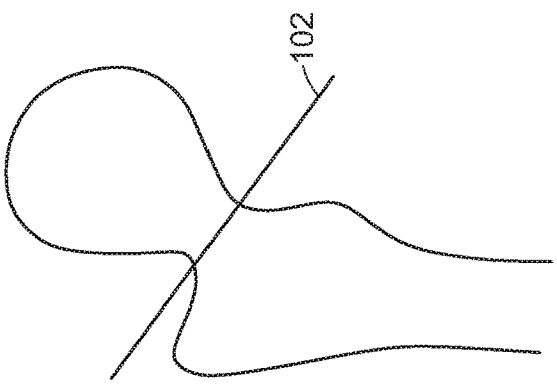
FIGS. 7A-H depict illustrative examples of a femoral neck cut and techniques to correct a femoral neck cut according to some embodiments of the present disclosure.

FIG. 7A shows a view of a predetermined femoral neck 95 cut or a virtual surgical plan, as optionally displayed by an OHMD in 2D or 3D, stereoscopic or non-stereoscopic, including using a digital holographic representation with a system such as a Microsoft Hololens (Microsoft, Redmond, Wash.). The OHMD can display a virtual predetermined path or plane (broken line) 96 for a saw blade selected to make the proximal femoral cut in this example. The OHMD can also display a digital hologram of the virtual femoral neck cut. The virtual projected path for a physical saw blade to make the proximal femoral neck cut and the virtual femoral neck cut can be the same; they can also be different, for example accounting for the thickness of the saw blade. For example, if a saw blade thickness is 2.0 mm, the predetermined path can be moved, e.g. in a proximal femur for hip replacement proximally, 1.00 mm or more to account for bone lost from the sawing so that the virtual femoral bone cut accounts for the bone lost by the sawing.

The display of the predetermined path can be in 2D or in 3D, stereoscopic or non-stereoscopic. The surgeon can align the physical saw blade with the predetermined path and the surgeon can then advance the saw blade while keeping the saw blade substantially aligned with the predetermined path as shown by the OHMD. Rather than display the predetermined path, the OHMD can also display a virtual bone saw aligned to make the virtual bone cut (optionally accounting for bone lost from the cutting or sawing) and the surgeon can align the physical bone saw with the virtual bone saw and make the cut.

Figure 7B:
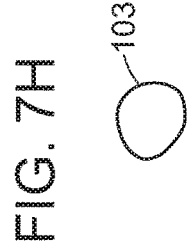

FIG. 7B shows a cross-section or top view of the intended virtual femoral neck cut (broken outline) 97, for example as developed in the virtual surgical plan. The perimeter and/or cross-section and/or surface area and/or shape of the virtually cut femur, for example simulated using data from a pre-operative imaging study of the patient, e.g. CT or MRI, is relatively round in this example with slightly greater diameter in medial-lateral direction.

Figure 7C:
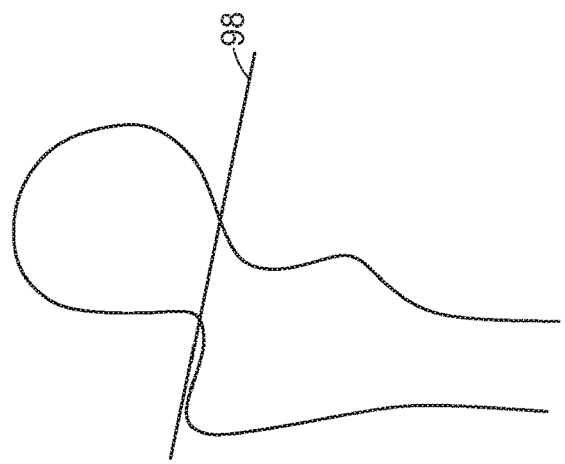

FIG. 7C shows the physical femoral neck cut 98 made in the live patient (straight solid line). The physical femoral neck cut is not aligned with the virtually projected or intended path for the saw blade and it is not aligned with the virtual femoral neck cut, for example in the virtual surgical plan, in this example. This can happen for various reasons in live surgery, for example unexpectedly sclerotic areas of bone that cause saw blade deviation. The difference in alignment between the virtually intended bone cut and the physical femoral bone cut can be difficult to detect for the surgeon intraoperatively, for example if the surgical field is small and deep seated, obscured or hidden or has limited lighting or if only a small portion of the cut bone is exposed.

Figure 7D:
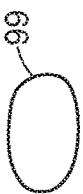

FIG. 7D shows the top view or cross-section of the physical femoral neck cut (solid outline) 99. The perimeter and/or cross-section and/or surface area and/or shape of the physical femoral neck cut is different than the perimeter and/or cross-section and/or surface area and/or shape of the virtually planned cut femur. It is more elliptical or oblong in medial-lateral direction. The perimeter and/or cross-section and/or surface area and/or shape of the physical cut proximal femur can be detected, for example using an image and/or video capture system and/or a 3D scanner integrated into, attached to or separate from the OHMD or using a mechanical or optical probe or pointer, e.g. with one or more attached optical markers, LED's, IMU's and/or navigation markers. It can then be compared to the perimeter and/or cross-section and/or surface area and/or shape of the virtual cut surface.

Figure 7E:

In FIG. 7E, once the perimeter and/or cross-section and/or surface area and/or shape of the physical cut proximal femur has been detected, for example using an image and/or video capture system and/or 3D scanner integrated into, attached to or separate from the OHMD or using a mechanical or optical probe or pointer, e.g. with one or more integrated or attached optical markers, LED's, IMU's and/or navigation markers, a corresponding perimeter and/or cross-section and/or surface area and/or shape of the physical cut proximal femur can be identified in the virtual data of the patient (broken outline) 100, for example using image processing algorithms known in the art.

Figure 7F:
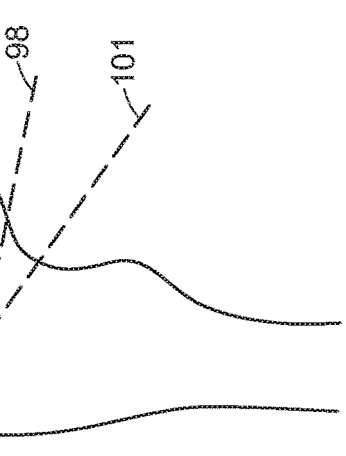

In FIG. 7F, once the corresponding perimeter and/or cross-section and/or surface area and/or shape has been identified in the virtual data of the patient (FIG. 7E), a new, substitute virtual femur cut 101 which approximates the intended femoral cut can be identified in the virtual data of the patient. The difference in position, location, orientation, coronal, sagittal, axial angle/angulation between the originally planned or predetermined virtual femoral bone cut and the substitute, new virtual femoral bone cut can be determined. Depending on the severity and/or clinical significance of the difference between the originally planned or predetermined virtual femoral bone cut 96 and the substitute, new virtual femoral bone cut 101, corresponding to the physical femoral bone cut 98 executed in the patient, the surgeon can then decide or chose between or combine any of the preceding Options A-E, e.g. modify the last surgical step, modify the next surgical step(s), modify the virtual surgical plan of the patient, modify the registration of the virtual data of the patient in relationship to the live data of the patient, and/or apply registration correction or combinations thereof.

Figure 7G:
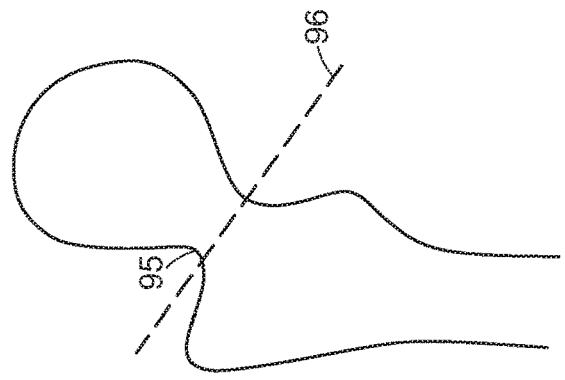

In FIG. 7G, the surgeon can elect to modify the last surgical step and correct the proximal femoral cut by applying a correction in the alignment and direction of the saw blade. The resultant corrected physical proximal femoral bone cut 102 can then closely approximate the originally intended, virtually planned, projected proximal femoral bone cut 97.

Figure 7H:

FIG. 7H shows that the perimeter and/or cross-section and/or surface area and/or shape of the corrected physical proximal femoral bone cut 103 approximates the perimeter and/or cross-section and/or surface area and/or shape of the original virtually planned proximal femoral bone cut.

In the example of a knee replacement, it is not uncommon that the distal femoral cut is not falling onto its intended location. For example, dense sclerotic bone underneath the arthritic area can cause a saw blade to deflect, thereby changing the angulation of the distal femoral cut. Once the distal femoral cut has been completed, the perimeter and/or cross-section and/or surface area and/or shape of the physical cut distal femoral bone can be assessed, for example using an image and/or video capture system integrated into, attached to or separate from the OHMD and/or using a 3D scanner and/or using one or more probes or pointers, which can, for example, touch and/or follow the cut femoral bone optionally with one or more attached optical markers, LED's, navigation markers including, but not limited to, infrared markers, retroreflective markers, RF markers, and/or IMU's. The perimeter and/or cross-section and/or surface area and/or shape of the of the physical cut distal femoral bone in the live patient can then be compared to the perimeter and/or cross-section and/or surface area and/or shape of the of the virtual cut distal femoral bone, for example in the virtual surgical plan of the patient. The perimeter and/or cross-section and/or surface area and/or shape of the physical cut distal femoral bone can be used to identify a corresponding perimeter and/or cross-section and/or surface area and/or shape of the virtual distal femoral bone or a corresponding virtual cut plane in the virtual data of the patient that can yield a similar perimeter and/or cross-section and/or surface area and/or shape of the virtual distal femoral bone.

If the difference between the physical cut distal femoral bone and the virtual cut distal femoral bone is below a certain threshold, e.g. 1, 2, 3 or more millimeters in cut depth from the distal femoral surface, and/or 1 degree, 2 degrees, 3 degrees or more in angulation, the surgery can proceed as originally planned. If the difference between the physical cut distal femoral bone and the virtual cut distal femoral bone is above a certain threshold, e.g. 1, 2, 3 or more millimeter in cut depth from the distal femoral surface, and/or 1 degree, 2 degrees, 3 degrees or more in angulation, the surgeon or operator can then decide or chose between the preceding Options A-E, e.g. modify the last surgical step, e.g. recut the distal femoral bone, optionally with use of thicker tibial inserts to compensate for the greater bone loss or a reduced tibial cut depth, modify one of the next surgical steps, e.g. cut the tibia to account for greater or lesser femoral bone loss and/or different femoral component angulation (e.g. in the sagittal plane or in the coronal plane (e.g. with different femoral mechanical axis alignment optionally corrected on the tibial side with different tibial mechanical axis alignment), modify the virtual surgical plan of the patient, modify the registration of the virtual data of the patient in relationship to the live data of the patient, and/or apply registration correction or combinations thereof.

Figure 8C:
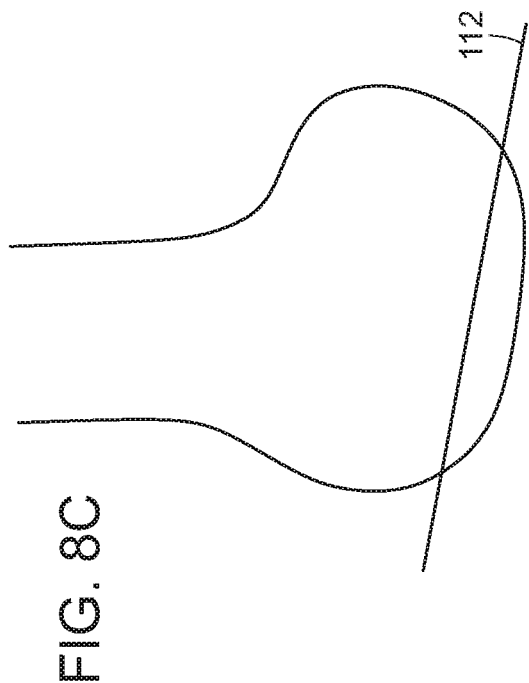
Figure 8D:
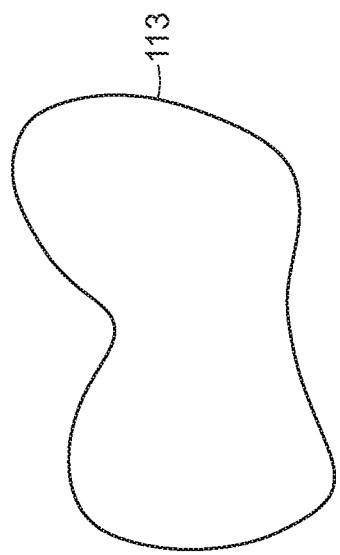
Figure 8A:
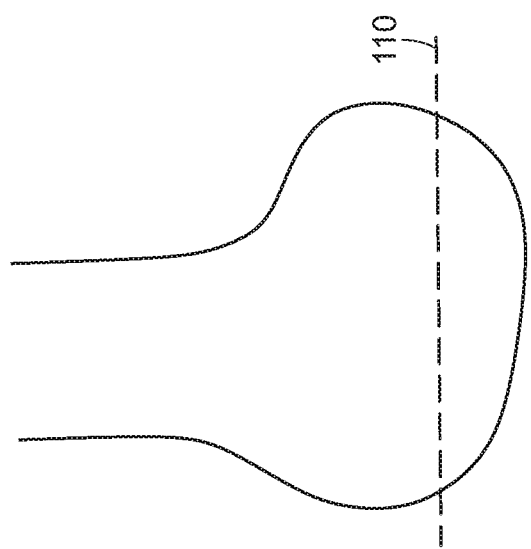

FIG. 8A shows a predetermined distal femoral cut, for example as part of a view of virtual surgical plan, as optionally displayed by OHMD in 2D or 3D, non-stereoscopic or stereoscopic. The OHMD can display a virtual intended path or plane 110 for a physical saw blade selected to make the distal femoral cut in this example. The virtual/ projected path or plane for the physical saw blade to make the distal femoral cut and the virtual distal femoral cut can coincide; they can also be different, for example accounting for the thickness of the saw blade. For example, if a saw blade thickness is 2.0 mm, the predetermined path can be moved, e.g. in a distal femur for knee replacement proximally, 1.00 mm or more to account for bone lost from the sawing so that the virtual femoral bone cut accounts for the bone lost by the sawing. The display of the predetermined path can be in 2D or in 3D, stereoscopic or non-stereoscopic. The surgeon can align the physical saw blade with the predetermined path and the surgeon can then advance the saw blade while keeping the saw blade substantially aligned with the predetermined path or plane as shown by the OHMD. Rather than display the predetermined path or plane, the OHMD can also display a virtual bone saw aligned to make the virtual bone cut (optionally accounting for bone lost from the cutting or sawing) and the surgeon can align the physical bone saw with the virtual bone saw and make the cut.

Figure 8B:
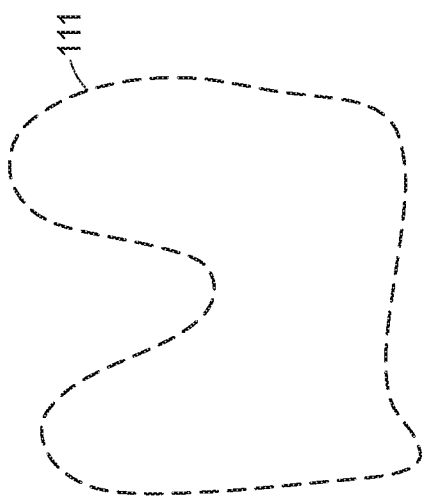

FIG. 8B shows a cross-section or view of the intended virtual distal femoral cut 111, for example as developed in the virtual surgical plan. The perimeter and/or cross-section and/or surface area and/or shape of the virtually cut femur, for example simulated using data from a pre-operative imaging study of the patient, e.g. CT or MRI or ultrasound or x-rays, is shown.

FIG. 8C shows the physical distal femoral cut made in the live patient 112. The physical distal femoral cut is not aligned with the virtually predetermined path for the saw blade and it is not aligned with the virtual distal femoral cut in the virtual surgical plan in this example. This can happen for various reasons in live surgery, for example unexpectedly sclerotic areas of bone that cause saw blade deviation. The difference in alignment between the virtually intended bone cut and the physical femoral bone cut can be difficult to detect for the surgeon intraoperatively.

FIG. 8D shows the view or cross-section of the physical distal femoral cut 113. The perimeter and/or cross-section and/or surface area and/or shape of the physical distal femoral cut is different than the perimeter and/or cross-section and/or surface area and/or shape of the virtually planned cut femur. The perimeter and/or cross-section and/or surface area and/or shape of the physical cut distal femoral cut can be detected, optionally using an image and/or video capture system and/or 3D scanner integrated into, attached to or separate from the OHMD or using a mechanical or optical probe, for example using RF, optical, navigation and/or other markers and/or IMU's. It can then be compared to the perimeter and/or cross-section and/or surface area and/or shape of the virtual cut surface.

FIG. 8E. Once the perimeter and/or cross-section and/or surface area and/or shape of the physical cut distal femur has been detected, for example using an image and/or video capture system and/or 3D scanner integrated into, attached to or separate from the OHMD or using a 3D scanner or using a mechanical or optical probe, optionally using RF, optical, navigation and/or other markers and/or IMU's, a corresponding perimeter and/or cross-section and/or surface area and/or shape of the physical cut distal femur can be identified in the virtual data of the patient 114, for example using image processing algorithms known in the art.

FIG. 8F. Once the corresponding perimeter and/or cross-section and/or surface area and/or shape has been identified in the virtual data of the patient (FIG. 8E), a new, substitute virtual femur cut which approximates the physical femoral cut can be identified 115 in the virtual data of the patient. The difference in position, location, orientation, coronal, sagittal, axial angle/angulation between the originally planned/predetermined virtual femoral bone cut and the substitute, new virtual femoral bone cut can be determined. Depending on the severity and/or clinical significance of the difference between the originally planned or predetermined virtual femoral bone cut and the physical femoral bone cut executed in the patient, the surgeon can then decide or chose between or combine any of the preceding options A-E, e.g. modify the last surgical step, modify the next surgical step(s), modify the virtual surgical plan of the patient, modify the registration of the virtual data of the patient in relationship to the live data of the patient, and/or apply registration correction or combinations thereof.

FIG. 8G The surgeon can elect to modify the last surgical step and correct the distal femoral cut by applying a correction in the alignment and direction of the saw blade, which can be, for example, in the sagittal plane (as shown in this example) or in the coronal plane if the physical cut was misaligned in the coronal plane. The resultant corrected physical distal femoral bone cut 116 can then closely approximate the originally intended, virtually planned, projected distal femoral bone cut.

FIG. 8H shows that the perimeter and/or cross-section and/or surface area and/or shape of the corrected physical distal femoral bone cut 117 approximates the perimeter and/or cross-section and/or surface area and/or shape of the original virtually planned distal femoral bone cut.

For example, if the comparison of the perimeter and/or cross-section and/or surface area and/or shape of the physical cut distal femoral bone with the perimeter and/or cross-section and/or surface area and/or shape of the virtually planned cut distal femoral bone and, for example, the optional identification of a new virtual cut plane that corresponds in the virtual data to the physical distal femoral cut show that the difference in location, position, orientation and/or angulation between the virtual planned distal femoral cut and the physical femoral cut exceeds a threshold value, e.g. 3 degrees more angulation in flexion direction and/or 2 mm greater cut depth (i.e. more bone removal), then the surgeon can modify the registration of the live data of the patient (e.g. the perimeter and/or cross-section and/or surface area and/or shape of the physical distal cut distal femoral bone) with the virtual data of the patient by registering the corresponding virtual cut plane with the physical cut plane and the surgeon or the software can modify the virtual surgical plan. The modifications to the virtual surgical plan can, in this example, include that the angulation of the anterior femoral cut, posterior femoral cuts and the chamfer cuts will be changed to align with the distal femoral cut consistent with the dimensions and angulation of the planar surfaces of the femoral implant component in order to avoid a gap between the implant and the bone or an area where the remaining physical cut bone is too wide, which may result in the bone being too wide in select areas, wider than the implant dimensions thereby not accepting the implant. If a femur first technique is used, the modifications of the virtual surgical plan can also include that the cut height or depth of the proximal tibial cut and the cut angulation of the proximal tibial cut be adjusted, for example by cutting less tibia and by changing the slope of the cut to account for a more flexed femoral component and to maintain better soft-tissue/ligament balance accounting for the different physical distal femoral cut. These adjustments to the virtual surgical plan can optionally be displayed by the OHMD, e.g. by displaying one or more virtual corrected or adjusted anterior, posterior, chamfer cuts, and/ or by displaying one or more corrected or adjusted proximal tibial cut(s) with a corrected or adjusted cut height/depth and/or corrected or adjusted tibial slope and/or corrected or adjusted tibial varus or valgus angle. The OHMD can display the virtually corrected or adjusted intended/projected path of the saw blade or surgical instrument, the virtually corrected or adjusted intended/projected cut planes, or the virtually corrected or adjusted intended/projected axes of the saw blade and/or power tools.

The following is another example, where the surgeon inadvertently mis-directs the femoral cut, with the assistance of the OHMD and an integrated or attached or separate image and/or video capture system and/or 3D scanner detects the femoral miscut and then decides to perform the necessary correction(s) in a subsequent surgical step on the tibial side.

Figure 9C:
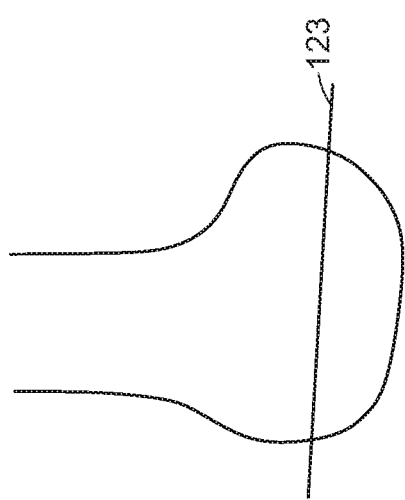
Figure 9D:
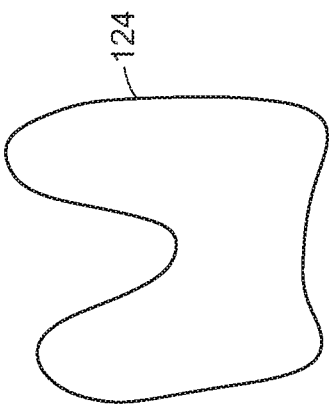
Figure 9A:
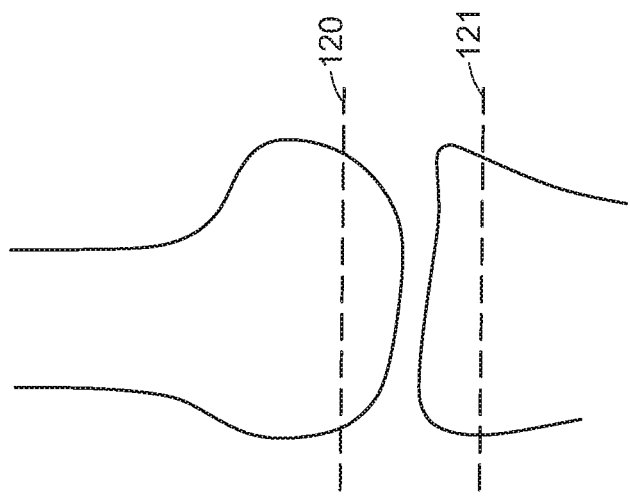

FIG. 9A shows a predetermined distal femoral cut and proximal tibial cut, for example as part of a view of a virtual surgical plan, as optionally displayed by OHMD in 2D or 3D, non-stereoscopic or stereoscopic. The OHMD can display a virtual predetermined path for a physical saw blade selected to make the distal femoral cut 120 and the proximal tibial cut 121 in this example. The OHMD can also display the virtual distal femoral and/or proximal tibial cut. The cut location can be adjusted for the thickness of the saw blade.

The display of the predetermined path can be in 2D or in 3D, non-stereoscopic or stereoscopic. The surgeon can align the physical saw blade with the predetermined path and the surgeon can then advance the saw blade while keeping the saw blade substantially aligned with the predetermined path as shown by the OHMD. Rather than display the predetermined path, the OHMD can also display a virtual bone saw aligned to make the virtual bone cut (optionally accounting for bone lost from the cutting or sawing) and the surgeon can align the physical bone saw with the virtual bone saw and make the cut.

Figure 9B:
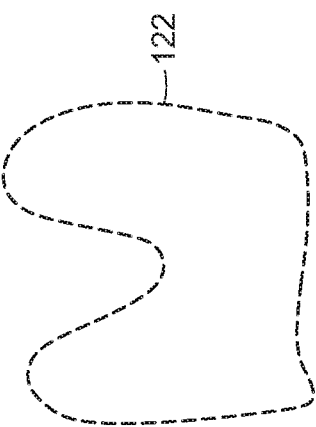

FIG. 9B shows a cross-section or view of the intended virtual distal femoral cut 122, for example as developed in the virtual surgical plan. The perimeter and/or cross-section and/or surface area and/or shape of the virtually cut femur, for example simulated using data from a pre-operative imaging study of the patient, e.g. CT or MRI or ultrasound is visible.

FIG. 9C shows the physical distal femoral cut 123 made in the live patient. The physical distal femoral cut 123 is not aligned with the virtually predetermined path for the saw blade and it is not aligned with the virtual distal femoral cut 120 in the virtual surgical plan in this example. This can happen for various reasons in live surgery, for example unexpectedly sclerotic areas of bone that cause saw blade deviation. The difference in alignment between the virtually intended bone cut and the physical femoral bone cut can be difficult to detect for the surgeon intraoperatively. Broken line indicates predetermined tibial cut based on virtual surgical plan.

FIG. 9D shows the view or cross-section of the physical distal femoral cut 124. The perimeter and/or cross-section and/or surface area and/or shape of the physical distal femoral cut is different than the perimeter and/or cross-section and/or surface area and/or shape of the virtually planned cut femur 122. The perimeter and/or cross-section and/or surface area and/or shape of the physical cut distal femur can be detected, for example using an image and/or video capture system and/or 3D scanner integrated into, attached to or separate from the OHMD or using a mechanical or optical probe, optionally using RF, optical, navigation and other markers and/or IMU's. It can then be compared to the perimeter and/or cross-section and/or surface area and/or shape of the virtual cut surface.

In FIG. 9E, once the perimeter and/or cross-section and/or surface area and/or shape of the physical cut distal femur has been detected, optionally using an image and/or video capture system and/or 3D scanner integrated into, attached to or separate from the OHMD or using a 3D scanner or using a mechanical or optical probe, optionally using RF, optical, navigation and/or other markers and/or IMU's, a corresponding perimeter and/or cross-section and/or surface area and/or shape of the physical cut distal femur can be identified in the virtual data of the patient 125, for example using image processing algorithms known in the art.

In FIG. 9F, once the corresponding perimeter and/or cross-section and/or surface area and/or shape has been identified in the virtual data of the patient (FIG. 9E), a new, substitute virtual femur cut can optionally be identified 126 in the virtual data of the patient. The difference in position, location, orientation, coronal, sagittal, axial angle/angulation between the originally planned or predetermined virtual femoral bone cut 120 and the new, substitute femoral bone cut 126 can be determined. Depending on the severity and/or clinical significance of the difference between the originally planned or predetermined virtual femoral bone cut and the physical femoral bone cut, the surgeon can decide or chose between or combine any of the preceding Options A-E, e.g. modify the last surgical step, modify the next surgical step(s), modify the virtual surgical plan of the patient, modify the registration of the virtual data of the patient in relationship to the live data of the patient, and/or apply registration correction or combinations thereof. In this example, the surgeon is electing to modify the next surgical step(s) by changing the angulation of the virtual tibial cut(s) from its original orientation 121 to a new orientation 127 that can optionally, at least partially, correct the overall alignment for the femoral mis-cut.

In FIG. 9G, the surgeon can elect to modify the next surgical step(s) and, in this example, change the proximal tibial cut by applying a correction in the alignment and direction of the saw blade to execute on the new, virtually modified tibial cut. The modified virtual and the resultant physical proximal tibial bone cut 128 can be placed to at least partially correct for the femoral mis-cut.

if the comparison of the perimeter and/or cross-section and/or surface area and/or shape of the physical cut distal femoral bone with the perimeter and/or cross-section and/or surface area and/or shape of the virtually planned cut distal femoral bone and, for example, the optional identification of a new virtual cut plane that corresponds in the virtual data to the physical distal femoral cut shows that the physical distal femoral cut surface is more angled, e.g. 3 degrees or more, in coronal direction than intended in the virtual surgical plan and/or the virtually cut distal femoral surface as displayed by the OHMD, then the surgeon can modify the last surgical step by re-cutting the distal femoral bone to correct the error in coronal plane angulation and to avoid any varus/valgus misalignment. The virtual predetermined cut plane or the virtual predetermined path for the saw blade or the virtual predetermined axis of the saw blade and/or power instrument and/or the virtual saw blade and/or power instrument aligned/oriented for the correction of the last surgical step can optionally be displayed by the OHMD. Alternatively, the surgeon can elect to correct one or more of the next surgical step(s), e.g. in this example by changing the intended cut for the tibial plateau to correct for the femoral cut coronal plane misangulation. The surgeon can align in either example the physical saw blade or surgical instrument with one or more of the virtual predetermined cut plane or the virtual predetermined path for the saw blade or the virtual predetermined axis of the saw blade and/or power instrument and/or the virtual saw blade and/or power instrument.

Figure 10C:
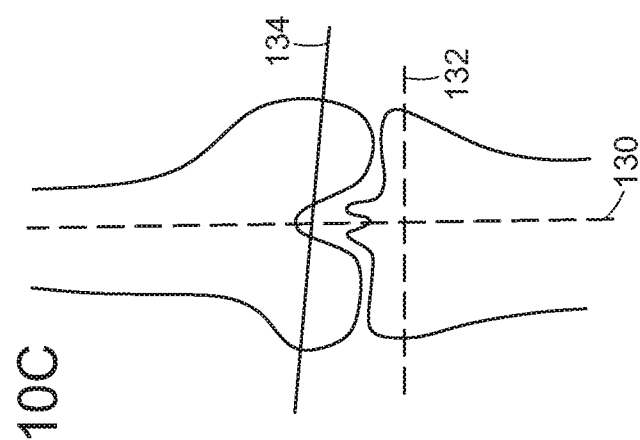
FIGS. 10A-G depict illustrative examples of a distal femoral cut and proximal tibial cut and techniques to correct the cuts according to some embodiments of the present disclosure.
Figure 10D:
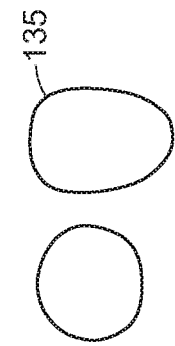
Figure 10A:
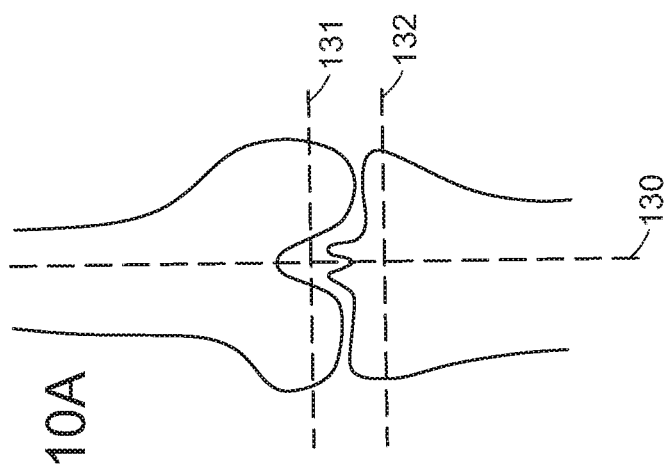

FIG. 10A shows a predetermined distal femoral cut and proximal tibial cut, for example as part of a view of a virtual surgical plan, as optionally displayed by OHMD in 2D or 3D, non-stereoscopic or stereoscopic. The OHMD can display a mechanical 130 or anatomic axis/axes of the knee, e.g. a femoral axis or a tibial axis, as well as various other kinematic or biomechanical axes, including a rotation axis of the knee. The virtual surgical plan can include the planning of femoral 131 and/or tibial 132 bone cuts that can be selected to correct any underlying mechanical axis deformity, e.g. varus or valgus deformity. For example, one or more of these bone cuts can be selected to be perpendicular to the patient's femoral or tibial mechanical axis. Alternatively, other alignments can be chosen and can be incorporated into the virtual surgical plan. For example, the medial femoral condyle surface, lateral femoral condyle surface and the medial tibial surface and lateral tibial surface can be optionally aligned with the patient's cartilage and/or subchondral bone or subchondral bone with an offset added to account for lost cartilage. The OHMD can display one or more virtual predetermined path (broken horizontal lines) for a physical saw blade selected to make the femoral cut and/or the tibial cut in this example. The OHMD can also display the virtual femoral and/or tibial cut. The virtual/projected path for a physical saw blade to make the femoral and/or tibial cut and the virtual femoral and/or tibial cut can be the same; they can also be different, for example accounting for the thickness of the saw blade. Rather than provide a virtual display of the predetermined path or plane, the OHMD can also display a virtual representation of a virtual bone saw or a 2D or 3D outline thereof aligned to make the virtual bone cuts (optionally accounting for bone lost from the cutting or sawing) and the surgeon can align the physical bone saw with the virtual bone saw or its 2D or 3D outline and make the cut.

Figure 10B:
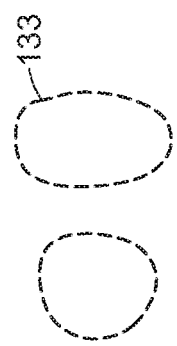

FIG. 10B shows a cross-section or view of the intended virtual femoral cut 133, for example as developed in the virtual surgical plan. The perimeter and/or cross-section and/or surface area and/or shape of the virtually cut femur, for example simulated using data from a pre-operative imaging study of the patient, e.g. CT or MRI or ultrasound, is relatively round in this example for the lateral condyle (left) and the medial condyle (right).

FIG. 10C shows the physical distal femoral cut made in the live patient 134. The physical femoral cut is not aligned with the virtually predetermined path for the saw blade and it is not aligned with the virtual femoral cut in the virtual surgical plan in this example. This can happen for various reasons in live surgery, for example unexpectedly sclerotic areas of bone or soft bone or osteoporotic bone that cause saw blade deviation.

FIG. 10D shows the view or cross-section of the physical femoral cut 135. The perimeter and/or cross-section and/or surface area and/or shape of the physical femoral cut is different than the perimeter and/or cross-section and/or surface area and/or shape of the virtually planned femoral cut. The perimeter and/or cross-section and/or surface area and/or shape of the physical cut distal femur can be detected, for example using an image and/or video capture system and/or 3D scanner integrated into, attached to or separate from the OHMD or using a laser scanner and/or 3D scanner or using a mechanical or optical probe, optionally using RF, optical, navigation and/or other markers and/or IMU's. It can then be compared to the perimeter and/or cross-section and/or surface area and/or shape of the virtual cut surface.

Figure 10G:
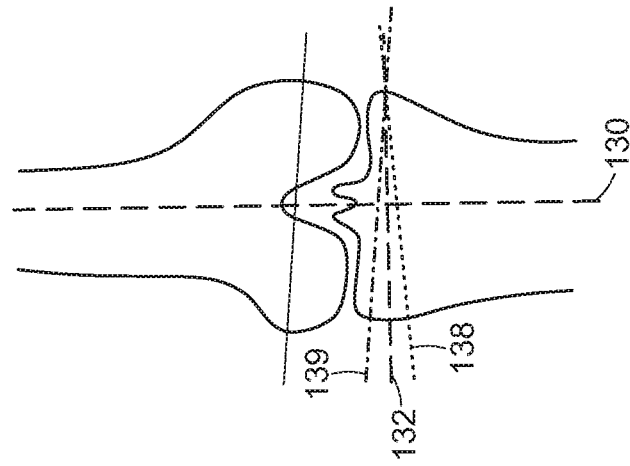
Figure 10E:
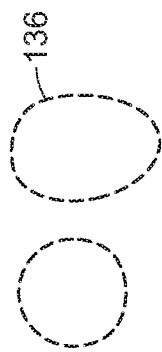

In FIG. 10E, once the perimeter and/or cross-section and/or surface area and/or shape of the physical cut distal femur has been detected, for example using an image and/or video capture system and/or 3D scanner integrated into, attached to or separate from the OHMD and/or using a mechanical or optical probe, optionally using RF, optical, navigation and other markers and/or IMU's, a corresponding perimeter and/or cross-section and/or surface area and/or shape of the physical cut distal femur can be identified in the virtual data of the patient 136, for example using image processing algorithms known in the art.

Figure 10F:
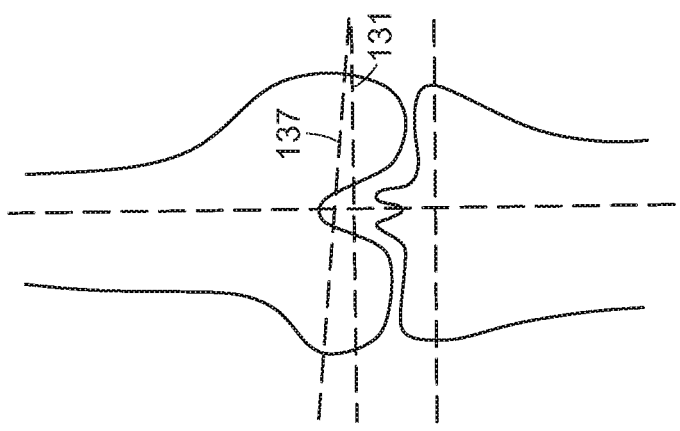

In FIG. 10F, once the corresponding perimeter and/or cross-section and/or surface area and/or shape has been identified in the virtual data of the patient (FIG. 10E), a virtual femur cut 137 which approximates the physical femoral cut can be identified in the virtual data of the patient. The difference in position, location, orientation, coronal, sagittal, axial angle/angulation between the originally planned or predetermined virtual femoral bone cut 131 and the new virtual femoral bone cut and the physical bone cut can be determined. Depending on the severity and/or clinical significance of the difference between them, the surgeon can then decide or chose between or combine any of the preceding Options A-E, e.g. modify the last surgical step (e.g. recut the femur), modify the next surgical step(s) (e.g. cut the tibia at a different coronal angulation than originally planned to account for the femoral mis-cut and, optionally, to achieve a composite alignment that is, for example, still within normal (180 degrees) mechanical axis alignment), modify the virtual surgical plan of the patient, modify the registration of the virtual data of the patient in relationship to the live data of the patient, and/or apply registration correction or combinations thereof.

In FIG. 10G, the surgeon can elect to modify the next surgical step and, in this example, modify the proximal tibial cut as shown in the two examples, one with a straight broken dotted line 139 and the other with a straight dotted line 138. In some embodiments, the surgeon can cut the tibia at a different coronal angulation than originally planned to account for the femoral mis-cut and, optionally, to achieve a composite alignment that is, for example, still within normal (180 degrees) mechanical axis alignment.

In another example, an OHMD can be used for guiding the placement of femoral pins or drills, which can be utilized for setting femoral component rotation, as is commonly done in total knee replacement procedures. Such femoral pins or drills can, for example, be placed through openings in a femoral cut block or a pin or drill block. In this example, the OHMD can guide the placement of the physical femoral cut block or pin or drill block by projecting a virtual femoral cut block or pin or drill block with which the surgeon can align the physical femoral cut block or drill or pin block, followed by the placement of the physical pins or drills. Alternatively, the OHMD can guide the placement of the physical pins or drills by projecting the virtual pins or drills or by projecting virtual pin or drill paths, followed by the placement of the physical pins or drills.

An image and/or video capture system and/or 3D scanner integrated into, attached to or separate from the OHMD, or an optical or mechanical probe, optionally with attached optical markers, LED's, navigation markers including, but not limited to, infrared markers, retroreflective markers, RF markers, and/or IMU's, optical markers, LED's, navigation markers including, but not limited to, infrared markers, retroreflective markers, RF markers, and/or IMU's attached to the drills or pins can be used for assessing the position and/or orientation and/or alignment of the one or more physical pins or drills or resultant physical pin or drill holes and to compare them to the position and/or orientation and/or alignment of the one or more virtual pins or drills or virtual pin or drill holes, e.g. in the patient's virtual surgical plan using, for example, the existing registration or a new registration of the live and virtual data using the surgically altered or modified surface. If a difference in position and/or orientation and/or alignment between the physical and the virtual pins or drills or pin holes or drill holes is detected and found to be clinically significant, the surgeon can then decide or chose between or combine any of the preceding options A-E, e.g. modify the last surgical step (e.g. repeat/ revise one or more pin placements), modify the next surgical step(s) (e.g. change femoral rotation to be different than indicated by the one or more pins or drills or pin holes or drill holes), modify the virtual surgical plan of the patient, modify the registration of the virtual data of the patient in relationship to the live data of the patient, and/or apply registration correction or combinations thereof.

In another example, an OHMD can be used for guiding the placement of tibial pins or drills, which can be utilized for setting tibial component rotation, as is commonly done in total knee replacement procedures. Such tibial pins or drills can, for example, be placed through openings in a tibial cut block or a pin or drill block. In this example, the OHMD can guide the placement of the physical tibial cut block or pin or drill block by projecting a virtual tibial cut block or pin or drill block with which the surgeon can align the physical tibial cut block or drill or pin block, followed by the placement of the physical pins or drills. Alternatively, the OHMD can guide the placement of the physical pins or drills by projecting the virtual pins or drills or by projecting virtual pin or drill paths, followed by the placement of the physical pins or drills. An image and/or video capture system and/or 3D scanner integrated into, attached to or separate from the OHMD, or an optical or mechanical probe, optionally with attached RF markers, optical markers, LED's, navigation markers including, but not limited to, infrared markers, retroreflective markers, RF markers, and/ or IMU's, or optical markers, LED's navigation markers including, but not limited to, infrared markers, retroreflective markers, RF markers, and/or IMU's attached to the drills or pins can be used for assessing the position and/or orientation and/or alignment of the one or more physical pins or drills or resultant physical pin or drill holes and to compare them to the position and/or orientation and/or alignment of the one or more virtual pins or drills or virtual pin or drill holes, e.g. in the patient's virtual surgical plan using, for example, the existing registration or a new registration of the live and virtual data using the surgically altered or modified surface. If a difference in position and/or orientation and/or alignment between the physical and the virtual pins or drills or pin holes or drill holes is detected and found to be clinically significant, the surgeon can then decide or chose between or combine any of the preceding options A-E, e.g. modify the last surgical step (e.g. repeat/ revise one or more pin placements), modify the next surgical step(s) (e.g. change tibial rotation to be different than indicated by the one or more pins or drills or pin holes or drill holes), modify the virtual surgical plan of the patient, modify the registration of the virtual data of the patient in relationship to the live data of the patient, and/or apply registration correction or combinations thereof.

Similarly, if the surgeon mis-cut, e.g. overcut the tibia, the OHMD can project optional modifications to the femoral cut, e.g. moving the virtual femoral cut and resultant physical femoral cut more distal to account for a tibial over-resection.

The preceding examples are in no way meant to be limiting, but are only exemplary. Someone skilled in the art can readily recognize how they can be applied to other types of surgery, e.g. ankle replacement, shoulder replacement, elbow replacement, ligament repair and/or reconstruction or replacement, spinal procedures, e.g. vertebroplasty, kyphoplasty, spinal fusion and/or pedicle screw and rod placement.

Pin Based Registration, Registration after Bone Cuts, Reaming, Milling, Etc.

If the tissue is being drilled or a pin or drill is placed in the tissue, for example for placement of a pedicle screw with pin placement or drilling through portions or all of the pedicle or for placement of a cut block in partial or total knee replacement or for planning a femoral cut or acetabular reaming for hip arthroplasty or for shoulder arthroplasty or for various types of surgery, e.g. cranial/brain surgery, the registration procedure can be repeated after the pin or drill has been placed or after the drilling has occurred. For example, an initial registration can be performed using an intraoperative x-ray, e.g. of a spine, or a knee, or a hip, e.g. with the patient in a prone position or supine position. The intraoperative x-ray can include one or more of an AP projection, PA projection, lateral projection, e.g. from left and/or from right side, oblique views, CT view using rotational x-ray acquisition, e.g. on rotating C-arm system. One or more of the intra-operative x-ray projections can be matched with pre-operative imaging data of the patient or virtual data of the patient including, optionally, a virtual surgical plan, using, for example, pattern recognition algorithms, image processing algorithms, or manual/visual matching by the surgeon or operator, optionally with magnification adjustment for a given film/detector focus distance, with magnification or de-magnification of either the intraoperative x-ray data, the pre-operative data, the virtual data of the patient, including, optionally, the virtual surgical plan, with the aim that all data used have similar or the same magnification.

In the example of spinal surgery, once the initial registration has been performed, a pin or drill can be placed in a first pedicle, e.g. in a cervical, thoracic or lumbar spine. Then a second pin or drill and/or additional pins or drills can be placed in a second pedicle, optionally at the same or different spinal levels, optionally on the same side of the spine (e.g. left or right) or alternatingly left and right from spinal level to spinal level. Similarly, pins or drills can be placed and registered for various aspects of knee replacement surgery, hip replacement surgery, shoulder replacement surgery, ACL repair or reconstruction and/or various sports related surgeries and/or cranial/brain surgery.

The position of the one or more pins or drills can be registered, for example using an image and/or video capture system integrated into, attached to or separate from the OHMD or using a 3D scanner that detects the one or more pins or drills. The position of the one or more pins or drills can be registered using attached or integrated optical markers or navigation markers including, but not limited to infrared markers, retroreflective markers, RF markers, e.g. with an optionally used navigation system, or IMU's. The position of the drill(s) or pin(s) can be detected using a touch probe or pointer, wherein the touch probe can be tracked directly using an image or video capture system and/or 3D scanner integrated into, attached to, or separate from the OHMD, and/or optionally including attached or integrated IMU's, optical markers, navigation markers including, but not limited to, infrared markers, retroreflective markers, RF markers and the like, for example for use with an image and/or video capture system and/or 3D scanner or a navigation system. If more than one marker is placed along the trajectory of the pin or drill or if image capture is used, the two or more markers or the trajectory of the visualized portions of the pin(s) or drill(s) using image capture can be used to estimate the trajectory of the pin(s) or drill(s) and to estimate a projected path as the pin(s) or drill(s) are advanced. If the length and the thickness of the pins are known, not only the endpoint outside the patient's tissue can be determined, but also the location of the tip can be estimated even though it can be seated deep inside the patient's tissue in spinal surgery, knee replacement, hip replacement, shoulder replacement, brain surgery and various types of other surgery.

The position of the pins or drills can be registered in relationship to the patient and/or the OHMD using any of the techniques described in the specification. The one or more optical markers can be retroreflective or can include LED's. Combinations of optical and RF markers can be used.

In some embodiments, a first drill or pin is registered, optionally followed by registration of a second or more pin and drills. The position and/or orientation of the one or more pins or drills can be used to maintain registration during the surgery, e.g. placement of pedicle screws and related devices, e.g. rods, or knee replacement with placement of one or more pins or drills in the femur and/or the tibia or hip replacement with placement of one or more pins or drills in the acetabulum or proximal femur. Since the one or more pins or drills are fixed to the bone, accurate registration can be maintained even if there is patient movement after the initial registration, if the pin or drill(s) are used for registration after the initial registration. Optionally, both the initial registration and the subsequent registration to the altered surgical surface/site after the placement of the pin or drill with registration to the pin or drill(s) can be used together. In this case, statistical techniques can be applied to reconcile small differences between the initial registration and the registration to the altered surgical surface or site including the one or more pins or drills. For example, the mean or the median of the different registrations can be used for any subsequent surgical steps.

In some embodiments, an initial registration can be performed between virtual data of the patient, e.g. pre-operative imaging, including optionally a virtual surgical plan for the patient, and live data of the patient during surgery. The initial registration can, for example, be performed using intra-operative imaging, which can be referenced to and registered with the live data of the patient. Any other technique of registration described in the specification or known in the art can be used for the initial registration. A first pin or drill or a first set of pins or drills can be placed using the initial registration of virtual data of the patient and live data of the patient.

Following the placement of a first pin or drill or a first set of pins or drills, intra-operative imaging can be repeated. In some embodiments, intra-operative imaging is used for the initial registration and the same intraoperative imaging modality and technique or similar intra-operative imaging modality or technique is used after placing the first pin or drill or the first set of pins or drills. Alternatively, a different intra-operative imaging modality is used after placing the first pin or drill or the first set of pins or drills. Intra-operative imaging modalities can include, for example, x-rays, e.g. AP, PA, lateral and oblique views, C-arm acquisition, optionally with CT capability, CT scan or ultrasound scan or MRI scan or any other imaging technique known in the art.

In some embodiments, after a first pin or drill or a first set of pins or drills is placed, the accuracy of the placement can be assessed. The accuracy of the placement can be assessed using, for example, any of the following:
Intraoperative imaging, e.g. also if the initial registration was performed without use of intraoperative imaging
Intraoperative imaging using the same or a different imaging modality used for an initial registration (if applicable)
Image capture of the visible portions of the pin(s) or drill(s), with optional projection/estimation of the location and/or orientation of any non-visualized portions inside the patient's tissue
Optical markers, navigation markers including, but not limited to, infrared markers, retroreflective markers, RF markers, IMU's, and any other electronic or optical or magnetic marker known in the art, with optional projection/estimation of the location and/or orientation of any non-visualized portions inside the patient's tissue Any deviations in the physical placement including the physical position and/or the physical orientation of the pin(s) or drill(s) compared to the intended position and/or intended orientation of the pin(s) or drill(s) in the virtual surgical plan can be measured in this manner. If one or more of the pins show a deviation in physical vs. intended virtual position and/or orientation, the difference in coordinates can be determined and a coordinate transfer or coordinate correction can be applied for any subsequent registration that uses one or more of the pins or drills placed inside the patient's tissue. A coordinate transfer or coordinate correction can be applied globally, e.g. to all pins or drills placed using the same values. Alternatively, a coordinate transfer or coordinate correction can be applied individually to each pin or drill accounting for their specific deviation from physical vs. intended virtual placement/position/and/or orientation. The former approach can be more time efficient. The latter approach can be more accurate for any subsequent registrations. A coordinate transfer or coordinate correction applied to each pin or drill individually using data on the amount of deviation/difference in coordinates between physical placement/position/and/or orientation compared to intended virtual placement/position/and/or orientation based on the virtual surgical plan can be particularly helpful in spinal surgery, when one or more spinal segment can move in relationship to each other during the surgery, e.g. if the surgeon has to adjust the position of the patient on the table. In this case, one or more pins or drills can optionally be placed at more than one spinal level, for example all spinal levels involved in the surgery, after the initial registration and the accuracy of the placement can be assessed using the foregoing techniques. A coordinate transfer or coordinate correction can then optionally be applied for more than one spinal level, e.g. all spinal levels involved in the surgery, wherein the difference in physical vs. intended virtual placement/position/and/or orientation of the pins or drills can be used to improve the accuracy of any subsequent registration using the one or more pins or drills for subsequent surgical steps for each spinal level for which the coordinate transfer or coordinate correction has been applied.

In the example of spinal surgery, one or more pedicle screws can be placed, at the same spinal level or different spinal levels. Optionally, the accuracy of the physical placement/position and/or orientation of each pedicle screw can be assessed compared to the intended virtual placement/ position/and/or orientation in the virtual surgical plan using any of the foregoing techniques. Optionally a coordinate transfer or coordinate correction can be determined based on any deviations between physical and intended virtual placement of the pedicle screw and the pedicle screw can be used for registration of the patient, the spine, and/or the OHMD during any subsequent surgical steps, e.g. placement of additional pedicle screws, e.g. at the same or other spinal levels, or placement of one or more connectors or rods and the like.

During the placement of the pedicle screw, registration can be maintained by referencing one or more of the pins or drills or pedicle screws placed in the pedicles at the same or adjacent spinal levels.

Similarly, in other surgical procedures, e.g. knee replacement, hip replacement, shoulder replacement, ACL repair and reconstruction, cranial, maxillofacial and brain surgery, the physical position of any drill, pin, instrument, implant, device or device component can be determined using any of the techniques described in the specification and any deviations or differences between the physical and the intended virtual placement/position/and/or orientation can be determined. The differences measured can be used to determine a coordinate transfer or coordinate correction for any subsequent registrations for subsequent surgical steps using now the one or more drill, pin, instrument, implant, device or device component as the registration reference or marker.

By referencing a pin or drill that is fixed inside the bone or a hard tissue (following the first surgical alteration), it is possible to maintain accurate registration, e.g. during pedicle screw placement, knee replacement, hip replacement, ACL repair and/or reconstruction, maxillofacial surgery, cranial and/or brain surgery.

In this case, the pinned or drilled tissue of the live patient or portions thereof can be matched to or superimposed and/or registered with the corresponding pinned or drilled tissue in the virtual surgical plan. Once an adequate match of the live and virtual cut pinned or drilled area has been obtained, registration can optionally be repeated. In some embodiments, the bone void or hole created by any pinning or drilling can be used for any subsequent registrations.

Optionally, a pin or drill can be temporarily placed back into the bone void or hole for any subsequent registration and subsequent surgical steps. If other surgical instruments are used, e.g. other than a drill or pin, such as a burr or a blade, other resultant bone voids can optionally also be used for any subsequent registrations.

Optionally, the position, location, and/or orientation and/or size and/or shape of any bone void or hole created by any surgical instrument can be assessed, e.g. using intraoperative imaging such as x-rays or ultrasound, and the difference between the physical and the intended virtual position, location, and/or orientation and/or size and/or shape of any bone void or hole can be assessed. The difference or deviation between the physical and the intended virtual position, location, and/or orientation and/or size and/or shape of the bone void or hole can be used to determine a coordinate difference or coordinate transfer or coordinate correction so that the bone void or hole can be used for any subsequent registration and subsequent surgical steps. Any subsequent registration can be performed by optionally introducing a partial or complete bone void filler (e.g. a pin or a drill) and registering the bone void filler. Any subsequent registration can also be performed by registering the bone void or hole directly, e.g. with intraoperative imaging. Any subsequent registration can also be performed by placing one or more IMU's, optical markers, and/or navigation markers including, but not limited to, infrared markers, retroreflective markers, RF markers inside or adjacent to the bone void and registered one or more of the IMU's, optical markers, LED's and/or navigation markers including, but not limited to, infrared markers, retroreflective markers, RF markers using any of the techniques described in the specification. Moreover, any subsequent registration can also be performed by marking portions or all of the bone void or hole with a color, e.g. toluidine blue, and by registering the marked and/or stained portions of the bone void or hole, e.g. using an image and/or video capture system and/or 3D scanner integrated into, attached to, or separate from the OHMD.

If a tissue cut is performed, for example with a scalpel or a saw, the registration procedure can be repeated after the tissue cut has been placed. In this case, the cut tissue surface of the live patient or portions thereof or the perimeter of the cut tissue surface of the live patient or portions thereof or the surface area of the cut tissue surface of the live patient or portions thereof or the volume of the removed tissue of the live patient or portions thereof can be matched to or superimposed and/or registered with the corresponding cut tissue surface of the virtual data or portions thereof or the perimeter of the cut tissue surface of the virtual data or portions thereof or the surface area of the cut tissue surface of the virtual data or portions thereof or the volume of the removed tissue of the virtual data or portions thereof in the virtual surgical plan. Once an adequate match of the live and virtual cut surfaces has been obtained, registration can optionally be repeated.

If a tissue cut is performed, the registration procedure can be repeated after the tissue cut has been completed. In this case, the cut tissue surface of the live patient or portions thereof or the perimeter of the cut tissue surface of the live patient or portions thereof can be matched to or superimposed onto and/or registered with the corresponding cut tissue surface or portions thereof in the virtual surgical plan or the perimeter of the cut tissue surface in the virtual surgical plan or portions thereof. Once an adequate match of the live and virtual cut surfaces has been obtained, registration can optionally be repeated.

If a bone cut is performed, for example with a saw, the registration procedure can be repeated after the bone cut has been placed. In this case, the cut bone surface of the live patient or portions thereof or the perimeter of the cut bone surface of the live patient or portions thereof or the surface area of the cut bone surface of the live patient or portions thereof or the volume of the removed bone of the live patient or portions thereof can be matched to or superimposed onto and/or registered with the corresponding cut bone surface of the virtual data or portions thereof or the perimeter of the cut bone surface of the virtual data or portions thereof or the surface area of the cut bone surface of the virtual data or portions thereof or the volume of the removed bone of the virtual data or portions thereof in the virtual surgical plan. Once an adequate match of the live and virtual cut surfaces has been obtained, registration can optionally be repeated.

If a milling, reaming or impacting procedure is performed, for example with a reamer, a mill or an impactor, the registration procedure can be repeated after the milling, reaming or impacting has been performed. In this case, the milled, reamed or impacted bone surface of the live patient or portions thereof or the perimeter of the milled, reamed or impacted bone surface of the live patient or portions thereof or the surface area of the milled, reamed or impacted bone surface of the live patient or portions thereof or the volume of the removed bone of the live patient or portions thereof can be matched to or superimposed onto and/or registered with the corresponding milled, reamed or impacted bone surface of the virtual data or portions thereof or the perimeter of the milled, reamed or impacted bone surface of the virtual data or portions thereof or the surface area of the milled, reamed or impacted bone surface of the virtual data or portions thereof or the volume of the removed bone of the virtual data or portions thereof in the virtual surgical plan. Once an adequate match of the live and virtual cut surfaces has been obtained, registration can optionally be repeated.

If a drilling procedure is performed, for example with a drill or a pin or a K-wire, the registration procedure can be repeated after the drill or pin or K-wire has been placed. In this case, the drilled surface of the live patient or portions thereof or the perimeter of the drilled surface of the live patient or portions thereof or the surface area of the drilled surface of the live patient or portions thereof or the volume of the removed bone of the live patient or portions thereof or the location of the drill hole or the orientation of the drill hole or the size of the drill hole or a marker such as a drill, a pin or a K-wire or an ink inserted into the drill hole can be matched to or superimposed onto and/or registered with the corresponding drilled surface in the virtual data or portions thereof or the perimeter of the drilled surface in the virtual data or portions thereof or the surface area of the drilled surface in the virtual data or portions thereof or the volume of the removed bone in the virtual data or portions thereof or the location of the drill hole in the virtual data or the orientation of the drill hole in the virtual data or the size of the drill hole in the virtual data or a marker such as a drill, a pin or a K-wire or an ink inserted into the drill hole in the virtual data, optionally in the virtual surgical plan. Once an adequate match of the live and virtual cut surfaces has been obtained, registration can optionally be repeated.

If a drilling procedure is performed, the drill holes can optionally be marked with india ink or another color in the live patient. The color marking can be recognized with use of an image and/or video capture system and/or 3D scanner integrated into, attached to or separate from the OHMD. The color markings in the live patient can then optionally be used to re-register the live data of the patient with the virtual data after one or more surgical alterations of the tissue has/have been performed. The color markings can be used with an image and/or video capture system and/or 3D scanner to detect them in the live patient data and to register them with the virtual patient data. Alternatively, the color markings can be used by the surgeon to identify the previously placed drill holes visually, for example after one or more surgical alterations or surgical steps have been performed. A drill, a pin, a K-wire, a screw, or another surgical instrument can then optionally be placed inside the drill hole and the registration of the live data and the virtual data can be performed by matching, superimposing and/or registering the live drill, pin, K-wire, screw, or other surgical instrument with a corresponding virtual drill, pin, K-wire, screw, or other surgical instrument or a corresponding drill hole in the virtual surgical plan.

For example, in a knee replacement procedure, a drill guide can be applied to the distal femur and/or the distal femoral condyles before the distal femoral cut and bone removal is performed. The drill guide can be integrated into the distal femoral cut block. Typically, two or more drill holes can be placed, for example with one or more drill holes located in the medial femoral condyle or in the medial femur and one or more drill holes located in the lateral femoral condyle or in the lateral femur. The location of the medial and lateral drill holes and the intersect between the two drill holes can be used to define the rotation axis of the femoral component.

The OHMD can display the desired location of the distal femoral cut block for achieving the desired mechanical axis correction and the desired location of the drill holes for setting the desired rotation axis of the femoral implant component. The drill holes can be drilled prior to performing the cut and can be optionally marked with ink prior to performing the distal femoral cut. The distal femoral cut can then be performed. The ink in the drill holes can then be identified on the cut surface. The ink seen in the live patient data can be registered using an image and/or video capture system and/or 3D scanner integrated into, attached to or separate from the OHMD and can be registered in relationship to the virtual drill holes as defined in the virtual surgical plan. Alternatively, the surgeon can elect to insert a drill, pin, K-wire, screw, or other surgical instrument into the drill holes in the live patient data and the location of the drill, pin, K-wire, screw, or other surgical instrument can be registered using an image and/or video capture system and/or 3D scanner integrated into, attached to or separate from the OHMD and can be registered in relationship to a virtual drill, pin, K-wire, screw or other surgical instrument optionally introduced into the virtual surgical plan.

In this manner, live patient data and virtual patient data can be re-registered after the distal femoral bone cut has been performed. The surgeon can also use the re-registration to check the accuracy of the initial registration and perform adjustments to the physical surgical plan or the virtual surgical plan depending on any discrepancies detected.

The foregoing embodiment can be applied to any type of joint replacement or joint sparing procedure including arthroscopy.

The term ink as used throughout the specification can include fluorescent ink. In embodiments, light of a discrete wavelength and/or intensity or including a range of discrete wavelengths and/or intensities can be shone on the surgical site and/or exposed tissues. Those tissues that have absorbed the fluorescent ink or that include fluorescent ink, e.g. by injection or by surface application, can display the fluorescence effect, which can be detected using or seen through the OHMD.

If a radiofrequency ablation, heat ablation, cryoablation, or cauterization is performed, the registration procedure can be repeated after the radiofrequency ablation, heat ablation, cryoablation, or cauterization has been performed. In this case, the ablated or cauterized tissue surface of the live patient or portions thereof or the perimeter of the ablated or cauterized tissue surface of the live patient or portions thereof or the surface area of the ablated or cauterized tissue surface of the live patient or portions thereof or the volume of the removed tissue of the live patient or portions thereof can be matched to or superimposed and/or registered with the corresponding ablated or cauterized tissue surface of the virtual data or portions thereof or the perimeter of the ablated or cauterized tissue surface of the virtual data or portions thereof or the surface area of the ablated or cauterized tissue surface of the virtual data or portions thereof or the volume of the removed tissue of the virtual data or portions thereof in the virtual surgical plan. Once an adequate match of the live and virtual ablated or cauterized surfaces has been obtained, registration can optionally be repeated.

If a placement of a medical implant component, a trial implant, a tissue graft, a tissue matrix, a transplant, a catheter, a surgical instrument or an injection of cells or a drug is performed, the registration procedure can be repeated after the surgical step or surgical alteration has been performed. In this case, the altered tissue of the live patient or portions thereof, the altered tissue surface of the live patient or portions thereof, or the perimeter of the altered tissue surface of the live patient or portions thereof, or the surface area of the altered tissue surface of the live patient or portions thereof, or the volume of the removed tissue of the live patient or portions thereof can be matched to or superimposed and/or registered with the corresponding altered tissue of the virtual data or portions thereof, altered tissue surface of the virtual data or portions thereof, or the perimeter of the altered tissue surface of the virtual data or portions thereof, or the surface area of the altered tissue surface of the virtual data or portions thereof, or the volume of the removed tissue of the virtual data or portions thereof in the virtual surgical plan. Once an adequate match of the live and virtual altered tissue has been obtained, registration can optionally be repeated.

Libraries of Surgical Instruments

In some aspects of the present disclosure, the system includes libraries of surgical instruments for different surgical procedures. The concept of a virtual library of surgical instruments used in a virtual surgical plan and optionally displayed by an OHMD during the live surgery, e.g. superimposed onto the physical surgical instruments to provide positional, orientation or directional guidance of the physical surgical instrument according to the virtual and/or intended surgical plan, is applicable to any surgical procedure, e.g. cardiovascular procedures, thoracic or pulmonary procedures, neurological procedures, urological procedures, gynecological procedures, hepatic or other inner organ procedures, intestinal procedures and/or musculoskeletal procedures. Virtual and physical surgical instruments and implant components can be registered in a common coordinate system, for example with one or more OHMDs and live data of the patient; the OHMD can project or display a virtual representation of the virtual surgical instrument.

In some embodiments, a virtual library of surgical instruments can correspond to a physical library of surgical instruments during surgery. Optionally, only a few, select surgical instruments can be included in the virtual library of surgical instruments. These few select surgical instruments can, for example, be the ones used for the principal, key surgical steps, or select sub-steps. Alternatively, all surgical instruments used during the live surgery can be included in a virtual library of virtual surgical instruments.

The virtual library of virtual surgical instruments can include these instruments in various file formats. In some embodiments, CAD file formats can be used. In general, any type of surface representation, 2D or 3D shape representation 3D volume representation, 3D display and different file formats can be used in a virtual surgical plan, followed by optional display by the OHMD during surgery.

Examples of libraries of surgical instruments that can be used in pedicle screw placement or spinal rod placement, artificial disk replacement, hip replacement and knee replacement are provided below. Any other surgical instruments used in any other surgical procedure can be utilized in a virtual surgical plan and/or can be displayed by the OHMD.

Pedicle Screw & Spinal Rod Placement

A virtual and/or physical library of surgical instruments for pedicle screw instrumentation and/or spinal rod placement can for example include:

For pedicle preparation: Awl, e.g. round awl; Single ended feeler probe; Dual ended feeler probe; Sounding/feeler probe; Thoracic ball handle probe; Lumbar ball handle probe; Straight probe, e.g. lumbar, thoracic, cervical; Curved probe, e.g. lumbar, thoracic, cervical; Ratcheting handle; Taps of different diameter/dimensions For screw insertion: Screw driver, e.g. Multi-axial screw driver, Self-retaining screw driver; Rod template; Rod inserter; Rod gripper; Bender, e.g. French bender; Single ended plug starter; Dual ended plug starter; Provisional driver For rod reduction: Compressor, e.g. parallel compressor; Distractor, e.g. parallel distractor.

For tightening: Break-off driver, e.g. self-retaining; Obturator; Counter torque Other instruments: Plug starter, e.g. non-break-off; Quick connector; Torque limiting driver;

Tissue retractors; Frame to hold tissue retractors; Clamps.

Plate instruments: Implant positioners; Screw driver, e.g. torque limiting or non-torque limiting; Measuring caliper; Measuring credit card; Counter torque; Plate holder, e.g. in line; Plate bender(s); Forceps plate holder; Removal driver, e.g. hex head shaft style.

The foregoing list of surgical instruments for pedicle screw instrumentation and/or spinal rod placement is only an example. It is by no means meant to be limiting. Any current and future surgical instrument for pedicle screw instrumentation and/or spinal rod placement can be used in a virtual surgical plan and live surgical plan for pedicle screw instrumentation and/or spinal rod placement.

All the surgical instruments can be provided in different sizes and/or diameters and/or widths and/or lengths and/or shapes and/or dimensions, for example based on the size or dimensions of the physical implant, implant component and/or medical device used.

Libraries of Medical Devices, Implants, Implant Components

Pedicle Screw & Spinal Rod Placement

A library of virtual and physical implants, implant components and/or medical devices for pedicle screw instrumentation and/or spinal rod placement can, for example, include screws including, but not limited to, screw heads, screw thread portion, multi-axial screws, single-axial screws, set screws, all of the foregoing in different sizes and/or diameters (optionally color coded during the display in the OHMD); plates including, but not limited to, fixed plates, cross-link plates, multi-span plates, all of the foregoing in different sizes and/or diameters (optionally color coded during the display in the OHMD); rods including, but not limited to, straight rods, contoured rods, all of the foregoing in different sizes and/or diameters (optionally color coded during the display in the OHMD). All of the foregoing device, device components, implants and implant components can be provided in different diameters, widths, lengths, dimensions, shapes, or sizes.

Knee Replacement

A library of virtual and physical implants, implant components and/or medical devices for partial and total knee replacement can, for example, include left and right femoral components of different sizes, e.g. size 1, 2, 3, 4, . . . , 17, 18, 19, 20, and shapes, e.g. without or with distal medial-lateral femoral offset, e.g. 1, 2, 3, 4, 5, 6, 7, 8 or more mm, without or with posterior medial-lateral femoral condyle offset, e.g. 1, 2, 3, 4, 5, 6, 7, 8 or more mm; left and right tibial components of different sizes, metal-backed or all polyethylene, e.g. size 1, 2, 3, 4, . . . , 17, 18, 19, 20, and shapes, e.g. symmetric, asymmetric, optionally with different degrees of asymmetry; left and right tibial inserts of different sizes, e.g. size 1, 2, 3, 4, . . . , 17, 18, 19, 20, and shapes, e.g. symmetric, asymmetric, optionally with different degrees of asymmetry; left and right patellar components of different of different sizes, e.g. size 1, 2, 3, 4, . . . , 17, 18, 19, 20, and shapes, e.g. symmetric, asymmetric.

Hip Replacement

A library of virtual and physical implants, implant components and/or medical devices for hip replacement can, for example, include left and right standard offset, high offset, coxa vara offset femoral components, with collar or collarless, cemented or non-cemented, with different porous ingrowth options, with different sizes, stem lengths, offsets, neck lengths, neck shaft angles; ceramic or metal femoral heads of different sizes, plus and minus heads; acetabular cups of different sizes, cemented or non-cemented with different porous ingrowth options; different acetabular liners including lipped and asymmetric liners, of different sizes. The foregoing lists are only of illustrative and exemplary nature and should not be construed as limiting. Any implant component known in the art can be included in one or more libraries of virtual and physical implants.

Virtual Placement, Virtual Fitting/Selection of Good or Best Fitting Device, Determination of Preferred Virtual Orientation, Determination of Preferred Virtual Alignment, Determination and/or Selection of Preferred Virtual Anchor/Attachment/Fixation Member in the Live, Physical Surgical Site of the Patient An optical head mounted display can display or project virtual representations, stereoscopic or non-stereoscopic of one or more virtual implants, virtual implant components and/or virtual medical devices and virtual instruments with or without the use of pre-operative or intra-operative imaging. The surgical field can be seen by the surgeon using a see-through OHMD or, when using a virtual reality type OHMD, by imaging it with one or more cameras or video systems, optionally integrated into, attached to or separate from the OHMD, and by projecting the video stream or select or intermittent images with the OHMD. By displaying a virtual implant, virtual implant component and/or virtual medical device and/or virtual instrument projected over the surgical field, the virtual implant, virtual implant component and/or virtual medical device and/or virtual instrument can be placed into a desired position, for example, in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site. The virtual placing or placement of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

Systems, methods, techniques and devices for placing or placement, sizing, fitting, alignment, and/or selection of virtual implants or virtual implant components are described in International Patent Application No. PCT/US17/21859 and U.S. Pat. No. 9,861,446, which are incorporated herein by reference in their entireties.

Throughout the specification, the placing or placement, sizing, fitting, alignment, selection, including the selection based on shape and/or function and the selection of the preferred anchor or attachment, of a virtual implant, virtual implant component and/or virtual medical device can be based on a single or a multiple parameters, i.e. can be single or multi-parametric, e.g. by evaluating, assessing, considering, using any one or more of the exemplary anatomic landmarks, anatomic dimensions, anatomic shapes, desired shape corrections, dimensions or shapes of tissue alterations or surgical alterations of tissue, e.g. by cutting, reaming, milling, drilling or tissue removal, pathology, pathologic areas, anatomic axis, biomechanical axis, surrounding tissue(s) and/or structure(s), tissue(s) and/or structure(s) adjacent to the implantation or surgical site, tissue(s) and/or structure(s) opposite the implantation or surgical site, tissue(s) and/or structure(s) interacting with the implantation or surgical site and/or one or more physical implants, physical implant components, and/or physical medical devices already placed, attached or implanted near the intended implantation or surgical site, and/or one or more virtual implants, virtual implant components, and/or virtual medical devices also intended for implantation near the intended implantation or surgical site, and/or one or more functional, e.g. kinematic, measurements and/or virtual surgical plan information and or virtual data including pre- or intra-operative imaging data mentioned in the specification or known in the art. For example, one or more anatomic parameters, e.g. the position, location, orientation, coordinates of a margin or edge or surface of an anatomic structure, e.g. a tooth or bone or cartilage, or dimensions or geometry or shapes of an anatomic structure can be used with one or more axis parameters, e.g. an anatomic axis or a biomechanical axis or a drilling axis, e.g. from a virtual surgical plan or a pre- or intra-operative imaging study, or an instrument axis, e.g. for preparing a site for a tissue anchor, or combinations thereof. One or more anatomic parameters from a first tissue, e.g. a cortical bone, can be used with one or more parameters from a second tissue, e.g. a cartilage or subchondral bone. One or more anatomic parameters from a first tissue, e.g. an enamel of a tooth, can be used with one or more parameters from a second tissue, e.g. a root or a mandibular or maxillary bone. One or more parameters from a first articular surface of a joint, e.g. an anatomic axis or a biomechanical axis, e.g. a rotation axis, can be used with parameters from a second articular surface of the joint, e.g. an anatomic axis or a biomechanical axis, e.g. a rotation axis. One or more anatomic parameters from a first articular surface can be used with one or more axis parameters, e.g. anatomic or biomechanical, including kinematic, from a second articular surface of the joint. One or more anatomic parameters from a tooth, e.g. a tooth intended for extraction or a tooth adjacent to a tooth intended for extraction or a tooth void, for example edge(s), ridge(s), coordinates of the tooth, or a gingiva can be used in conjunction with one or more anatomic parameters from a mandible or maxilla, e.g. the location of a root inside the mandible or maxilla, or a drilling axis or predetermined implant axis for a titanium or other stem or anchor of a dental prosthesis inside the mandible or maxilla, e.g. as determined in virtual surgical plan, e.g. based on a pre- or intra-operative imaging study. Any combination of any of the foregoing parameters or any combination of any other anatomic, biomechanical, functional, kinematic or other parameters mentioned in the specification can be used for the placing or placement, sizing, fitting, alignment, selection, including the selection based on shape and/or function and the selection of the preferred anchor or attachment, of a virtual implant, virtual implant component and/or virtual medical device using parameters from or within the same tissue or organ and/or from and between different tissues or organs. Any combination of any of the foregoing parameters or any combination of any other anatomic, biomechanical, functional, kinematic or other parameters mentioned in the specification can be used for the placing or placement, sizing, fitting, alignment, selection, including the selection based on shape and/or function and the selection of the preferred anchor or attachment, of a virtual implant, virtual implant component and/or virtual medical device using parameters from or within the same articular surface and/or from and between different articular surfaces. Any combination of any of the foregoing parameters or any combination of any other anatomic, biomechanical, functional, kinematic or other parameters mentioned in the specification can be used for the placing or placement, sizing, fitting, alignment, selection, including the selection based on shape and/or function and the selection of the preferred anchor or attachment, of a virtual implant, virtual implant component and/or virtual medical device using parameters from or within the same joint and/or from and between different joints, e.g. a hip joint, a knee joint and/or an ankle joint.

Any of the moving, placing or placement, sizing, fitting, alignment, selection, including the selection based on shape and/or function and the selection of the preferred anchor or attachment, of a virtual implant, virtual implant component and/or virtual medical device can be sequential. Any of the moving, placing or placement, sizing, fitting, alignment, selection, including the selection based on shape and/or function and the selection of the preferred anchor or attachment, of a virtual implant, virtual implant component and/or virtual medical device can be simultaneous. Any of the moving, placing or placement, sizing, fitting, alignment, selection, including the selection based on shape and/or function and the selection of the preferred anchor or attachment, of a virtual implant, virtual implant component and/or virtual medical device can be sequential and/or simultaneous. Any combination is possible. For example, the placing or placement and alignment, can be simultaneous, while the fitting and sizing can occur together, but sequential to the placing or placement, and can be followed by more aligning, which can be followed by an additional fitting and sizing, which can be simultaneous with or can be followed by a selection. The placing or placement, alignment and fitting can be simultaneous, which can be followed by the sizing and selection, which can be followed by the alignment. Any combination of simultaneous and/or sequential moving, placing or placement, sizing, fitting, alignment, selection, including the selection based on shape and/or function and the selection of the preferred anchor or attachment, of a virtual implant, virtual implant component and/or virtual medical device is possible. Repeat moving, placing or placement, sizing, fitting, alignment, selection, including the selection based on shape and/or function and the selection of the preferred anchor or attachment, of a virtual implant, virtual implant component and/or virtual medical device is possible, for example to evaluate the fit to an articular margin, edge, dimension, geometry, shape, surface for different implants selected.

In some embodiments, a first computer processor can be used to facilitate the placing of a virtual surgical guide, a virtual tool, a virtual instrument and/or a virtual implant or implant component, e.g. a knee, hip, ankle, shoulder, spinal, dental implant component or other implant component. A second computer processor can be used to facilitate the moving of a virtual surgical guide, a virtual tool, a virtual instrument and/or a virtual implant or implant component, e.g. a knee, hip, ankle, shoulder, spinal, dental implant component or other implant component. A third computer processor can be used to facilitate the orienting of a virtual surgical guide, a virtual tool, a virtual instrument and/or a virtual implant or implant component, e.g. a knee, hip, ankle, shoulder, spinal, dental implant component or other implant component. A fourth computer processor can be used to facilitate the aligning of a virtual surgical guide, a virtual tool, a virtual instrument and/or a virtual implant or implant component, e.g. a knee, hip, ankle, shoulder, spinal, dental implant component or other implant component. A fifth computer processor can be used to facilitate the fitting of a virtual implant or implant component, e.g. a knee, hip, ankle, shoulder, spinal, dental implant component or other implant component. A sixth computer processor can be used to facilitate the sizing of a virtual implant or implant component, e.g. a knee, hip, ankle, shoulder, spinal, dental implant component or other implant component. A seventh computer processor can be used to facilitate the selection of a virtual implant or implant component, e.g. a knee, hip, ankle, shoulder, spinal, dental implant component or other implant component.

The first processor can be the same or different than the second, third, fourth, fifth, sixth or seventh processor; the second processor can be the same or different than the first, third, fourth, fifth, sixth or seventh processor; the third processor can be the same or different than the first, second, fourth, fifth, sixth and seventh processor; the fourth processor can be the same or different than the first, second, third, fifth, sixth or seventh processor; the fifth processor can be the same or different than the first, second, third, fourth, sixth or seventh processor; the sixth processor can be the same or different than the first, second, third, fourth, fifth or seventh processor; the sixth processor can be the same or different than the first, second, third, fourth, fifth or sixth processor.

In some embodiments, a processor can be configured to facilitate simultaneous or sequential display of two or more virtual implant components with different sizes or shapes and the processor can be configured to receive input from a user interface to facilitate assessment of the fit and/or alignment of the two or more virtual implants to the surgical site of the patient. In some embodiments, a first user interface can be used to facilitate the placing of a virtual surgical guide, a virtual tool, a virtual instrument and/or a virtual implant or implant component, e.g. a knee, hip, ankle, shoulder, spinal, dental implant component or other implant component. A second user interface can be used to facilitate the moving of a virtual surgical guide, a virtual tool, a virtual instrument and/or a virtual implant or implant component, e.g. a knee, hip, ankle, shoulder, spinal, dental implant component or other implant component. A third user interface can be used to facilitate the orienting of a virtual surgical guide, a virtual tool, a virtual instrument and/or a virtual implant or implant component, e.g. a knee, hip, ankle, shoulder, spinal, dental implant component or other implant component. A fourth user interface can be used to facilitate the aligning of a virtual surgical guide, a virtual tool, a virtual instrument and/or a virtual implant or implant component, e.g. a knee, hip, ankle, shoulder, spinal, dental implant component or other implant component. A fifth user interface can be used to facilitate the fitting of a virtual implant or implant component, e.g. a knee, hip, ankle, shoulder, spinal, dental implant component or other implant component. A sixth user interface can be used to facilitate the sizing of a virtual implant or implant component, e.g. a knee, hip, ankle, shoulder, spinal, dental implant component or other implant component. A seventh user interface can be used to facilitate the selection of a virtual implant or implant component, e.g. a knee, hip, ankle, shoulder, spinal, dental implant component or other implant component.

The first user interface can be the same or different than the second, third, fourth, fifth, sixth or seventh user interface; the second user interface can be the same or different than the first, third, fourth, fifth, sixth or seventh user interface; the third user interface can the same or different than the first, second, fourth, fifth, sixth and seventh user interface; the fourth user interface can be the same or different than the first, second, third, fifth, sixth or seventh user interface; the fifth user interface can be the same or different than the first, second, third, fourth, sixth or seventh user interface; the sixth user interface can be the same or different than the first, second, third, fourth, fifth or seventh user interface; the sixth user interface can be the same or different than the first, second, third, fourth, fifth or sixth user interface.

The surgeon can evaluate the fit of the virtual implant, virtual implant component and/or virtual medical device and/or virtual instrument and can visually select a good or best fitting virtual implant, virtual implant component and/or virtual medical device in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site. The virtual fitting and/or selecting a good or best fitting virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon can evaluate the shape of a virtual implant, virtual implant component and/or virtual medical device and/or virtual instrument and can visually select the virtual implant, virtual implant component and/or virtual medical device with regard to its shape in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site. The virtual evaluation of the shape of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon can also determine the preferred position and/or orientation and/or alignment of the virtual implant, virtual implant component and/or virtual medical device and/or virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, using OHMD guidance. The virtual determining of a preferred position and/or orientation and/or alignment of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon can determine the preferred alignment of a virtual implant, virtual implant component and/or virtual medical device and virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, using OHMD guidance. The virtual aligning and/or virtual evaluation of the alignment of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site.

The surgeon can determine the preferred function of a virtual implant, virtual implant component and/or virtual medical device and virtual instrument in the live, physical surgical site in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site, and/or one or more physical implants, physical implant components, and/or physical medical devices already implanted near the intended implantation site, and/or one or more virtual implants, virtual implant components, and/or virtual medical devices also intended for implantation near the intended implantation site, and/or one or more functional tests, which can include any of these parameters and the virtual implant, virtual implant component and/or virtual medical device and virtual instrument. The virtual determining of the preferred function of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site, and/or one or more functional tests, which can include any of these parameters and the virtual implant, virtual implant component and/or virtual medical device and virtual instrument.

The surgeon can determine and/or select a preferred virtual anchor, attachment or fixation member for the virtual implant, virtual implant component and/or virtual medical device and virtual instrument, in relationship to or based on one or more anatomic landmarks, anatomic dimensions, anatomic shapes, desired shape corrections, pathology, pathologic areas, anatomic axes, biomechanical axes, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already implanted near the intended implantation site, and/or one or more virtual implants, virtual implant components, and/or virtual medical devices also intended for implantation near the intended implantation site, using OHMD guidance, for example when simultaneously projecting a registered and superimposed imaging study of the patient, e.g. an x-ray, an ultrasound, a CT, an MRI or a PET scan, e.g. for demonstrating underlying tissue such as bone and bone stock. The virtual determination and/or virtual selection of a preferred virtual anchor, attachment or fixation member of a virtual implant, virtual implant component and/or virtual medical device can be based on a single or a multiple parameters, i.e. can be single or multi-parametric, e.g. by evaluating, assessing, considering, using any one or more of the foregoing exemplary anatomic landmarks, anatomic dimensions, anatomic shapes, desired shape corrections, bone stock, pathology, pathologic areas, anatomic axis, biomechanical axis, surrounding tissue(s) and/or structure(s), tissue(s) and/or structure(s) adjacent to the implantation site, tissue(s) and/or structure(s) opposite the implantation site, tissue(s) and/or structure(s) interacting with the implantation site and/or one or more physical implants, physical implant components, and/or physical medical devices already placed, attached or implanted near the intended implantation site, and/or one or more virtual implants, virtual implant components, and/or virtual medical devices also intended for implantation near the intended implantation site. Table 15 shows non-limiting examples of select medical devices amenable to one or more of virtual placement, virtual fitting/selection of good or best fitting device, determination of preferred virtual orientation, determination of preferred virtual alignment, determination and/or selection of preferred virtual anchor/attachment/fixation member.

TABLE 15

Non-Limiting Examples of Select Medical Devices Amenable to One or More of Virtual Placement, Virtual Fitting/Selection of Good or Best Fitting Device, Evaluation of Virtual Shape with Selection of Device with Preferred Shape, Evaluation of Virtual Function with Selection of Device with Preferred Function, Determination of Preferred Virtual Orientation, Determination of Preferred Virtual Alignment, Determination and/or Selection of Preferred Virtual Anchor/Attachment/Fixation Member

| | 1 Virtual placement of virtual device | 2 Evaluation virtual fit, select best fitting device | 3 Evaluate virtual shape, select device with preferred | 4 Evaluate virtual function, select device with preferred | 5 Determine preferred virtual position | 6 Determine preferred virtual orientation | 7 Determine preferred virtual alignment | 8 Determine/select preferred virtual anchor/attachment |
|---|---|---|---|---|---|---|---|---|
| Biliary stent | ✓ | ✓ | ✓ | ✓ | ✓ | ✓ | ✓ | ✓ |
| Hepatic stent | ✓ | ✓ | ✓ | ✓ | ✓ | ✓ | ✓ | ✓ |
| Uretheral stent | ✓ | ✓ | ✓ | ✓ | ✓ | ✓ | ✓ | ✓ |
| Urethral stent | ✓ | ✓ | ✓ | ✓ | ✓ | ✓ | ✓ | ✓ |
| Other stents | ✓ | ✓ | ✓ | ✓ | ✓ | ✓ | ✓ | ✓ |
| Intravascular filter, e.g. vena cava filter | ✓ | ✓ | ✓ | ✓ | ✓ | ✓ | ✓ | ✓ |
| Cardiopulmonary bypass, including various components, e.g. connectors, clamps, other components | ✓ | ✓ | ✓ | ✓ | ✓ | ✓ | ✓ | ✓ |
| Wire | ✓ | | | | ✓ | ✓ | ✓ | ✓ |
| Screw | ✓ | ✓ | ✓ | ✓ | ✓ | ✓ | ✓ | ✓ |
| Implant endoosseous | ✓ | ✓ | ✓ | ✓ | ✓ | ✓ | ✓ | ✓ |
| Implant intraosseous | ✓ | ✓ | ✓ | ✓ | ✓ | ✓ | ✓ | ✓ |
| Implant transosseous | ✓ | ✓ | ✓ | ✓ | ✓ | ✓ | ✓ | ✓ |
| Joint prosthesis, e.g. knee, hip, ankle, foot, shoulder, elbow, hand, wrist, finger, TMJ, other, facet; for individual components or all components including from opposing articular surfaces, inserts, liners etc. | ✓ | ✓ | ✓ | ✓ | ✓ | ✓ | ✓ | ✓ |
| Plate | ✓ | ✓ | ✓ | ✓ | ✓ | ✓ | ✓ | ✓ |
| Fracture plate | ✓ | ✓ | ✓ | ✓ | ✓ | ✓ | ✓ | ✓ |
| Rod | ✓ | ✓ | ✓ | ✓ | ✓ | ✓ | ✓ | ✓ |
| Esophageal prosthesis | ✓ | ✓ | ✓ | ✓ | ✓ | ✓ | ✓ | ✓ |
| Otoplasty prosthesis | ✓ | ✓ | ✓ | ✓ | ✓ | ✓ | ✓ | ✓ |
| Shunt/tube, e.g. vascular, lymphatic, biliary, hepatic, central nervous system, cerebrospinal fluid, other | ✓ | ✓ | ✓ | ✓ | ✓ | ✓ | ✓ | ✓ |
| Ossicular prosthesis/implant | ✓ | ✓ | ✓ | ✓ | ✓ | ✓ | ✓ | ✓ |
| Stapes prosthesis/implant | ✓ | ✓ | ✓ | ✓ | ✓ | ✓ | ✓ | ✓ |
| Tympanic membrane magnet | ✓ | ✓ | ✓ | ✓ | ✓ | ✓ | ✓ | ✓ |
| Middle ear mold | ✓ | ✓ | ✓ | ✓ | ✓ | ✓ | ✓ | |
| Tympanostomy tube | ✓ | ✓ | ✓ | ✓ | ✓ | ✓ | ✓ | |
| Bone conduction hearing implant | ✓ | ✓ | ✓ | ✓ | ✓ | ✓ | ✓ | ✓ |
| Lacrimal stent | ✓ | ✓ | ✓ | ✓ | ✓ | ✓ | ✓ | ✓ |
| Surgical mesh, e.g. for hernia repair, vaginal/uterine prolapse, urinary incontinence | ✓ | ✓ | ✓ | ✓ | ✓ | ✓ | ✓ | ✓ |
| Seeds, e.g. metal, radiation, isotope seeds | ✓ | ✓ | ✓ | ✓ | ✓ | ✓ | ✓ | ✓ |
| Ligature | ✓ | | | | ✓ | ✓ | ✓ | |
| Dental bracket | ✓ | ✓ | ✓ | ✓ | ✓ | ✓ | ✓ | ✓ |
| Dental hook | ✓ | ✓ | ✓ | ✓ | ✓ | ✓ | ✓ | ✓ |
| Dental band | ✓ | ✓ | ✓ | ✓ | ✓ | ✓ | ✓ | ✓ |
| Dental wire | ✓ | ✓ | ✓ | ✓ | ✓ | ✓ | ✓ | ✓ |
| Dental tie wire | ✓ | ✓ | ✓ | ✓ | ✓ | ✓ | ✓ | ✓ |
| Dental arch wire | ✓ | ✓ | ✓ | ✓ | ✓ | ✓ | ✓ | ✓ |
| Dental O-ring | ✓ | ✓ | ✓ | ✓ | ✓ | ✓ | ✓ | ✓ |
| Buccal tube | ✓ | ✓ | ✓ | ✓ | ✓ | ✓ | ✓ | ✓ |
| Dental e-chain | ✓ | ✓ | ✓ | ✓ | ✓ | ✓ | ✓ | ✓ |
| Dental steel tie | ✓ | ✓ | ✓ | ✓ | ✓ | ✓ | ✓ | ✓ |
| Dental Koby tie | ✓ | ✓ | ✓ | ✓ | ✓ | ✓ | ✓ | ✓ |
| Dental coligation | ✓ | ✓ | ✓ | ✓ | ✓ | ✓ | ✓ | ✓ |
| Dental coil spring | ✓ | ✓ | ✓ | ✓ | ✓ | ✓ | ✓ | ✓ |
| Dental power thread | ✓ | ✓ | ✓ | ✓ | ✓ | ✓ | ✓ | ✓ |
| Dental implant | ✓ | ✓ | ✓ | ✓ | ✓ | ✓ | ✓ | ✓ |
| Dental implant components | ✓ | ✓ | ✓ | ✓ | ✓ | ✓ | ✓ | ✓ |
| Dental implant crown | ✓ | ✓ | ✓ | ✓ | ✓ | ✓ | ✓ | ✓ |
| Dental implant abutment | ✓ | ✓ | ✓ | ✓ | ✓ | ✓ | ✓ | ✓ |
| Dental implant fixture | ✓ | ✓ | ✓ | ✓ | ✓ | ✓ | ✓ | ✓ |
| Transmandibular implant | ✓ | ✓ | ✓ | ✓ | ✓ | ✓ | ✓ | ✓ |
| Penile prosthesis | ✓ | ✓ | ✓ | ✓ | ✓ | ✓ | ✓ | |
| Biliary catheter | ✓ | | ✓ | ✓ | ✓ | ✓ | ✓ | |
| Vascular catheter | ✓ | | ✓ | ✓ | ✓ | ✓ | ✓ | |
| Chin prosthesis | ✓ | ✓ | ✓ | ✓ | ✓ | ✓ | ✓ | ✓ |

TABLE 15-continued

Non-Limiting Examples of Select Medical Devices Amenable to One or More of Virtual Placement, Virtual Fitting/Selection of Good or Best Fitting Device, Evaluation of Virtual Shape with Selection of Device with Preferred Shape, Evaluation of Virtual Function with Selection of Device with Preferred Function, Determination of Preferred Virtual Orientation, Determination of Preferred Virtual Alignment, Determination and/or Selection of Preferred Virtual Anchor/Attachment/Fixation Member

| | 1 Virtual placement of virtual device | 2 Evaluation virtual fit, select best fitting device | 3 Evaluate virtual shape, select device with preferred | 4 Evaluate virtual function, select device with preferred | 5 Determine preferred virtual position | 6 Determine preferred virtual orientation | 7 Determine preferred virtual alignment | 8 Determine/ select preferred virtual anchor/ attachment |
|---|---|---|---|---|---|---|---|---|
| Ear prosthesis | ✓ | ✓ | ✓ | ✓ | ✓ | ✓ | ✓ | ✓ |
| Nose prosthesis | ✓ | ✓ | ✓ | ✓ | ✓ | ✓ | ✓ | ✓ |
| Clip | ✓ | ✓ | ✓ | ✓ | ✓ | ✓ | ✓ | ✓ |
| Staple | ✓ | ✓ | ✓ | ✓ | ✓ | ✓ | ✓ | ✓ |
| Cranial plate | ✓ | ✓ | ✓ | ✓ | ✓ | ✓ | ✓ | ✓ |
| Spinal cord stimulator | ✓ | ✓ | ✓ | ✓ | ✓ | ✓ | ✓ | ✓ |
| Peripheral nerve stimulator | ✓ | ✓ | ✓ | ✓ | ✓ | ✓ | ✓ | ✓ |
| Fallopian tube prosthesis | ✓ | ✓ | ✓ | ✓ | ✓ | ✓ | ✓ | |
| Eye sphere implant | ✓ | ✓ | ✓ | ✓ | ✓ | ✓ | ✓ | ✓ |
| Eye implant | ✓ | ✓ | ✓ | ✓ | ✓ | ✓ | ✓ | ✓ |
| Eye valve implant | ✓ | ✓ | ✓ | ✓ | ✓ | ✓ | ✓ | ✓ |
| Eye lid spacer/graft | ✓ | ✓ | ✓ | ✓ | ✓ | ✓ | ✓ | ✓ |
| Keratoprosthesis | ✓ | ✓ | ✓ | ✓ | ✓ | ✓ | ✓ | ✓ |
| Retinal prosthesis | ✓ | ✓ | ✓ | ✓ | ✓ | ✓ | ✓ | ✓ |
| Extraocular orbital implant | ✓ | ✓ | ✓ | ✓ | ✓ | ✓ | ✓ | ✓ |
| Hip replacement, e.g. partial, total, components/implant | ✓ | ✓ | ✓ | ✓ | ✓ | ✓ | ✓ | ✓ |
| Knee replacement, e.g. partial, total, components/implant | ✓ | ✓ | ✓ | ✓ | ✓ | ✓ | ✓ | ✓ |
| Ankle replacement, e.g. partial, total, components/implant | ✓ | ✓ | ✓ | ✓ | ✓ | ✓ | ✓ | ✓ |
| Foot implant components/implant | ✓ | ✓ | ✓ | ✓ | ✓ | ✓ | ✓ | ✓ |
| Toe implant components/implant | ✓ | ✓ | ✓ | ✓ | ✓ | ✓ | ✓ | ✓ |
| Shoulder replacement, e.g. partial, total, components/implant | ✓ | ✓ | ✓ | ✓ | ✓ | ✓ | ✓ | ✓ |
| Elbow replacement, e.g. partial, total, components/implant | ✓ | ✓ | ✓ | ✓ | ✓ | ✓ | ✓ | ✓ |
| Wrist replacement, e.g. partial, total, components/implant | ✓ | ✓ | ✓ | ✓ | ✓ | ✓ | ✓ | ✓ |
| Finger joint replacement, e.g. partial, total, components/implant | ✓ | ✓ | ✓ | ✓ | ✓ | ✓ | ✓ | ✓ |
| Spinal implant components/implant | ✓ | ✓ | ✓ | ✓ | ✓ | ✓ | ✓ | ✓ |
| Spinal cage, e.g. cervical, thoracic, lumbar | ✓ | ✓ | ✓ | ✓ | ✓ | ✓ | ✓ | ✓ |
| Spinal rod | ✓ | ✓ | ✓ | ✓ | ✓ | ✓ | ✓ | ✓ |
| Pedicle screw, e.g. cervical, thoracic, lumbar, sacral | ✓ | ✓ | ✓ | ✓ | ✓ | ✓ | ✓ | ✓ |
| Spinal plate for laminoplasty | ✓ | ✓ | ✓ | ✓ | ✓ | ✓ | ✓ | ✓ |
| Sacroiliac joint fixation devices | ✓ | ✓ | ✓ | ✓ | ✓ | ✓ | ✓ | ✓ |
| Sacroiliac joint fusion devices | ✓ | ✓ | ✓ | ✓ | ✓ | ✓ | ✓ | ✓ |
| Preformed bone cement for vertebroplasty | ✓ | ✓ | ✓ | ✓ | ✓ | ✓ | ✓ | ✓ |
| Disc replacement implant | ✓ | ✓ | ✓ | ✓ | ✓ | ✓ | ✓ | ✓ |
| Washer, bolt, nut | ✓ | ✓ | ✓ | ✓ | ✓ | ✓ | ✓ | ✓ |
| Rotator cuff repair device/anchor | ✓ | ✓ | ✓ | ✓ | ✓ | ✓ | ✓ | ✓ |
| Shoulder labrum repair/fixation device/anchor | ✓ | ✓ | ✓ | ✓ | ✓ | ✓ | ✓ | ✓ |
| Hip labrum repair/fixation device/anchor | ✓ | ✓ | ✓ | ✓ | ✓ | ✓ | ✓ | ✓ |
| Meniscal graft | ✓ | ✓ | ✓ | ✓ | ✓ | ✓ | ✓ | ✓ |
| Meniscal repair/fixation device/anchor | ✓ | ✓ | ✓ | ✓ | ✓ | ✓ | ✓ | ✓ |
| Ligament graft | ✓ | ✓ | ✓ | ✓ | ✓ | ✓ | ✓ | ✓ |
| Ligament repair device | ✓ | ✓ | ✓ | ✓ | ✓ | ✓ | ✓ | ✓ |
| Ligament fixation device | ✓ | ✓ | ✓ | ✓ | ✓ | ✓ | ✓ | ✓ |
| Ligament anchor | ✓ | ✓ | ✓ | ✓ | ✓ | ✓ | ✓ | ✓ |
| ACL repair device | ✓ | ✓ | ✓ | ✓ | ✓ | ✓ | ✓ | ✓ |
| ACL graft fixation device | ✓ | ✓ | ✓ | ✓ | ✓ | ✓ | ✓ | ✓ |
| ACL graft anchor | ✓ | ✓ | ✓ | ✓ | ✓ | ✓ | ✓ | ✓ |
| ACL graft | ✓ | ✓ | ✓ | ✓ | ✓ | ✓ | ✓ | ✓ |
| Intramedullary rod | ✓ | ✓ | ✓ | ✓ | ✓ | ✓ | ✓ | ✓ |
| Rod | ✓ | ✓ | ✓ | ✓ | ✓ | ✓ | ✓ | ✓ |
| Fracture fixation plate, bone plate | ✓ | ✓ | ✓ | ✓ | ✓ | ✓ | ✓ | ✓ |
| Osteosynthesis plate | ✓ | ✓ | ✓ | ✓ | ✓ | ✓ | ✓ | ✓ |
| Osteosynthesis screw | ✓ | ✓ | ✓ | ✓ | ✓ | ✓ | ✓ | ✓ |

TABLE 15-continued

Non-Limiting Examples of Select Medical Devices Amenable to One or More of Virtual Placement, Virtual Fitting/Selection of Good or Best Fitting Device, Evaluation of Virtual Shape with Selection of Device with Preferred Shape, Evaluation of Virtual Function with Selection of Device with Preferred Function, Determination of Preferred Virtual Orientation, Determination of Preferred Virtual Alignment, Determination and/or Selection of Preferred Virtual Anchor/Attachment/Fixation Member

| | 1 Virtual placement of virtual device | 2 Evaluation virtual fit, select best fitting device | 3 Evaluate virtual shape, select device with preferred | 4 Evaluate virtual function, select device with preferred | 5 Determine preferred virtual position | 6 Determine preferred virtual orientation | 7 Determine preferred virtual alignment | 8 Determine/ select preferred virtual anchor/ attachment |
|---|---|---|---|---|---|---|---|---|
| Pin | ✓ | ✓ | ✓ | ✓ | ✓ | ✓ | ✓ | ✓ |
| K-wire | ✓ | ✓ | ✓ | ✓ | ✓ | ✓ | ✓ | ✓ |
| Nail | ✓ | ✓ | ✓ | ✓ | ✓ | ✓ | ✓ | ✓ |
| Cerclage | ✓ | ✓ | ✓ | ✓ | ✓ | ✓ | ✓ | ✓ |
| Bone grafting material | ✓ | ✓ | ✓ | ✓ | ✓ | ✓ | ✓ | ✓ |
| Spinal cord stimulator | ✓ | | ✓ | ✓ | ✓ | ✓ | ✓ | |
| Facial prosthesis/implant | ✓ | ✓ | ✓ | ✓ | ✓ | ✓ | ✓ | ✓ |
| Mandibular prosthesis/implant | ✓ | ✓ | ✓ | ✓ | ✓ | ✓ | ✓ | ✓ |
| Maxillar prosthesis/implant | ✓ | ✓ | ✓ | ✓ | ✓ | ✓ | ✓ | ✓ |
| Tracheal prosthesis/implant | ✓ | ✓ | ✓ | ✓ | ✓ | ✓ | ✓ | ✓ |
| Esophagus prosthesis/implant | ✓ | ✓ | ✓ | ✓ | ✓ | ✓ | ✓ | ✓ |
| Tracheostomy tube | ✓ | ✓ | ✓ | ✓ | ✓ | ✓ | ✓ | ✓ |
| Arteriovenous shunt device | ✓ | ✓ | ✓ | ✓ | ✓ | ✓ | ✓ | ✓ |
| Arteriovenous fistula device | ✓ | ✓ | ✓ | ✓ | ✓ | ✓ | ✓ | ✓ |
| Vascular port | ✓ | ✓ | ✓ | ✓ | ✓ | ✓ | ✓ | |
| Intraventricular port | ✓ | ✓ | ✓ | ✓ | ✓ | ✓ | ✓ | |
| Muscle implant, e.g. pectoralis muscle | ✓ | ✓ | ✓ | ✓ | ✓ | ✓ | ✓ | ✓ |
| Subtalar prosthesis | ✓ | ✓ | ✓ | ✓ | ✓ | ✓ | ✓ | ✓ |
| Prosthetic disk, disk replacement device | ✓ | ✓ | ✓ | ✓ | ✓ | ✓ | ✓ | ✓ |
| Vertebral body replacement device | ✓ | ✓ | ✓ | ✓ | ✓ | ✓ | ✓ | ✓ |
| Spinal facet screw | ✓ | ✓ | ✓ | ✓ | ✓ | ✓ | ✓ | ✓ |
| Vagus nerve stimulator | ✓ | | ✓ | ✓ | ✓ | ✓ | ✓ | ✓ |
| Magnetic/thermal rods for prostate | ✓ | | ✓ | ✓ | ✓ | ✓ | ✓ | ✓ |
| Odontoid screw | ✓ | ✓ | ✓ | ✓ | ✓ | ✓ | ✓ | ✓ |
| Nail fixation | ✓ | ✓ | ✓ | ✓ | ✓ | ✓ | ✓ | ✓ |
| External fixator | ✓ | ✓ | ✓ | ✓ | ✓ | ✓ | ✓ | ✓ |
| Fascial anchor | ✓ | | ✓ | ✓ | ✓ | ✓ | ✓ | ✓ |
| Implantable radiographic marker | ✓ | | ✓ | ✓ | ✓ | ✓ | ✓ | ✓ |
| Tissue expander | ✓ | ✓ | ✓ | ✓ | ✓ | ✓ | ✓ | ✓ |
| Tissue anchor | ✓ | ✓ | ✓ | ✓ | ✓ | ✓ | ✓ | ✓ |
| Implantable radiofrequency transponder system | ✓ | | ✓ | ✓ | ✓ | ✓ | ✓ | ✓ |
| Endoscopic suture plication system | ✓ | | ✓ | ✓ | ✓ | ✓ | ✓ | ✓ |
| Hypertension electrical nerve stimulation system | ✓ | | ✓ | ✓ | ✓ | ✓ | ✓ | ✓ |
| Resorbable plate, e.g. for spine | ✓ | ✓ | ✓ | ✓ | ✓ | ✓ | ✓ | ✓ |
| Resorbable mesh, e.g. for spine | ✓ | ✓ | ✓ | ✓ | ✓ | ✓ | ✓ | ✓ |
| Tissue scaffold | ✓ | ✓ | ✓ | ✓ | ✓ | ✓ | ✓ | ✓ |
| Mesh for tendon repair | ✓ | ✓ | ✓ | ✓ | ✓ | ✓ | ✓ | ✓ |
| Mesh for chest wall repair | ✓ | ✓ | ✓ | ✓ | ✓ | ✓ | ✓ | ✓ |
| Mesh for plastic/reconstructive surgery | ✓ | ✓ | ✓ | ✓ | ✓ | ✓ | ✓ | ✓ |
| Mesh for abdominal wall defects | ✓ | ✓ | ✓ | ✓ | ✓ | ✓ | ✓ | ✓ |
| Mesh for organ support | ✓ | ✓ | ✓ | ✓ | ✓ | ✓ | ✓ | ✓ |
| Pacemaker | ✓ | | ✓ | ✓ | ✓ | ✓ | ✓ | |
| Pacemaker lead, including tip | ✓ | | ✓ | ✓ | ✓ | ✓ | | ✓ |
| Vascular graft | ✓ | ✓ | ✓ | ✓ | ✓ | ✓ | ✓ | ✓ |
| Vascular stent | ✓ | ✓ | ✓ | ✓ | ✓ | ✓ | ✓ | ✓ |
| Prosthetic heart valve, e.g. mitral, tricuspid, aortic, pulmonary valve | ✓ | ✓ | ✓ | ✓ | ✓ | ✓ | ✓ | ✓ |
| Allograft or autograft heart valve, e.g. mitral, tricuspid, aortic, pulmonary valve | ✓ | ✓ | ✓ | ✓ | ✓ | ✓ | ✓ | ✓ |
| Cardiac valve repair devices, e.g. mitral valve repair devices | ✓ | ✓ | ✓ | ✓ | ✓ | ✓ | ✓ | ✓ |
| Intra-ventricular catheter | ✓ | | ✓ | ✓ | ✓ | ✓ | ✓ | ✓ |
| Intra-ventricular electrode | ✓ | | ✓ | ✓ | ✓ | ✓ | ✓ | ✓ |
| Coronary guide wire | ✓ | ✓ | ✓ | ✓ | ✓ | ✓ | ✓ | ✓ |
| Coronary catheter | ✓ | ✓ | ✓ | ✓ | ✓ | ✓ | ✓ | ✓ |
| Atrial appendage closure system | ✓ | | ✓ | ✓ | ✓ | ✓ | ✓ | ✓ |
| Epicardial pacing electrode | ✓ | | ✓ | ✓ | ✓ | ✓ | ✓ | ✓ |
| Implantable aneurysm pressure sensor | ✓ | | ✓ | ✓ | ✓ | ✓ | ✓ | ✓ |
| Long-term implanted intra-vascular catheter | ✓ | ✓ | ✓ | ✓ | ✓ | ✓ | ✓ | ✓ |

TABLE 15-continued

Non-Limiting Examples of Select Medical Devices Amenable to One or More of Virtual Placement, Virtual Fitting/Selection of Good or Best Fitting Device, Evaluation of Virtual Shape with Selection of Device with Preferred Shape, Evaluation of Virtual Function with Selection of Device with Preferred Function, Determination of Preferred Virtual Orientation, Determination of Preferred Virtual Alignment, Determination and/or Selection of Preferred Virtual Anchor/Attachment/Fixation Member

| | 1 Virtual placement of virtual device | 2 Evaluation virtual fit, select best fitting device | 3 Evaluate virtual shape, select device with preferred | 4 Evaluate virtual function, select device with preferred | 5 Determine preferred virtual position | 6 Determine preferred virtual orientation | 7 Determine preferred virtual alignment | 8 Determine/ select preferred virtual anchor/ attachment |
|---|---|---|---|---|---|---|---|---|
| Pericardial patch | ✓ | ✓ | ✓ | ✓ | ✓ | ✓ | ✓ | ✓ |
| Neurovascular guide wire | ✓ | ✓ | ✓ | ✓ | ✓ | ✓ | ✓ | |
| Neurovascular catheter | ✓ | ✓ | ✓ | ✓ | ✓ | ✓ | ✓ | |
| Neurovascular coil | ✓ | ✓ | ✓ | ✓ | ✓ | ✓ | ✓ | ✓ |
| Guide wire | ✓ | ✓ | ✓ | ✓ | ✓ | ✓ | ✓ | |
| Catheter | ✓ | ✓ | ✓ | ✓ | ✓ | ✓ | ✓ | |
| Coil | ✓ | ✓ | ✓ | ✓ | ✓ | ✓ | ✓ | ✓ |
| Aneurysm clip | ✓ | ✓ | ✓ | ✓ | ✓ | ✓ | ✓ | ✓ |
| Hemodialysis catheter | ✓ | | ✓ | ✓ | ✓ | ✓ | ✓ | |
| Drug eluting stent | ✓ | ✓ | ✓ | ✓ | ✓ | ✓ | ✓ | ✓ |
| Vessel guard or cover | ✓ | ✓ | ✓ | ✓ | ✓ | ✓ | ✓ | |
| Endovascular suturing system | ✓ | | ✓ | ✓ | ✓ | ✓ | ✓ | ✓ |

1 Virtual placement of virtual device includes, for example, virtual placement of one or more virtual devices using, for example, a computer (e.g. PC) based interface, acoustic interface, and/or virtual interface (e.g. gesture recognition), other interface; e.g. with 1, 2, 3, 4, 5, 6 degrees of freedom, optionally alternating, e.g. in one direction followed by another direction or rotation; for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

2 Evaluate virtual fit, select good or best fitting device, e.g. from library of virtual devices, pre-existing CAD files, STL files etc., e.g. with different size, dimensions, geometry, shape, function, anchor/attachment mechanisms, anchor/attachment size, dimensions, geometry, shape; optionally each of the foregoing and/or following for different components, component combinations; select good or best fitting device for example by superimposing/projecting virtual device/device components on live data (visible through see-through OHMD or imaged with camera/scanner and displayed by OHMD) using, for example, target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

3 Evaluate virtual shape, select device with preferred shape, e.g. from library of virtual devices, pre-existing CAD files, STL files etc., e.g. with different size, dimensions, geometry, shape, function, anchor/attachment mechanisms, anchor/attachment size, dimensions, geometry, shape; optionally each of the foregoing and/or following for different components, component combinations; select device with preferred shape for example by superimposing/projecting virtual device/device components on live data (visible through see-through OHMD or imaged with camera/scanner and displayed by OHMD) using, for example, target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

4 Evaluate virtual function select device with preferred function e.g. from library of virtual devices, pre-existing CAD files, STL files etc., e.g. with different size, dimensions, geometry, shape, function, anchor/attachment mechanisms, anchor/attachment size, dimensions, geometry, shape, function; optionally each of the foregoing and/or following for different components, component combinations; select device with preferred function for example by superimposing/projecting virtual device/device components on live data (visible through see-through OHMD or imaged with camera/scanner and displayed by OHMD) using, for example, target anatomic/pathologic structure(s) for placement/alignment/attachment (using, for example, internal and/or external: margin, periphery, edge, AP, SI, ML and/or oblique dimensions, radius, radii, curvature, geometry, shape, function articular/tissue/organ/vascular surface/dimension/radius, radii/curvature/geometry/shape/volume, anatomical and/or biomechanical axis/axes, function; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, function, other portion of articular/tissue/organ/vascular surface/dimension/radius, radii/curvature/geometry/shape/volume/function or opposing articular/tissue/organ/vascular surface/dimension/radius, radii/curvature/geometry/shape/volume, anatomical and/or biomechanical axis/axes, function; including same or different tissues) and/or adjacent or subjacent or opposing or articulating or connected medical devices (including, for example, their dimensions, radius, radii, curvature, geometry, shape, placement position, orientation and/or alignment, function, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

5 Determine preferred virtual position, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

6 Determine preferred virtual orientation, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

7 Determine preferred virtual alignment, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

8 Determine and/or select preferred virtual anchor/attachment/fixation member (length, width, diameter, size, dimensions, radius, radii, geometry, shape, location, position, orientation, alignment, function) (monoblock or modular, e.g. attachable) and/or placement, for example, using live data (visible through see-through OHMD or imaged with camera/scanner and displayed by OHMD), e.g. target anatomic/pathologic structure(s) for placement/alignment/attachment (using, for example, internal and/or external: margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; including same or different tissues) and/or surrounding/adjacent/subjacent anatomic/pathologic structure(s) (using, for example, internal and/or external: margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues) and/or adjacent or subjacent or opposing or articulating or connected medical devices (including, for example, their dimensions, radius, radii, curvature, geometry, shape, placement position, orientation and/or alignment, e.g. relative to landmarks and/or anatomic or biomechanical axis/axes), and/or virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data Note: Numeric references above are used for purposes of cross-referencing text associated with headings. Numeric references are not meant to imply a particular sequence. The different aspects of the invention can be practiced in variable order or sequence, simultaneously or sequentially. In some embodiments for some devices, all of virtual placement, evaluating virtual fit, selecting good or best fitting implant, evaluating virtual shape, selecting implant with preferred shape, evaluating virtual function, selecting implant with preferred function, determining virtual position, virtual orientation, virtual alignment and determination and/or selection of preferred anchor/attachment/fixation member can be applied. In some embodiments for some devices, only one or more, but not all of virtual placement, evaluating virtual fit, selecting good or best fitting implant, evaluating virtual shape, selecting implant with preferred shape, evaluating virtual function, selecting implant with preferred function, determining virtual position, virtual orientation, virtual alignment and determination and/or selection of preferred anchor/attachment/fixation member can be applied.

Symbol "✓" denotes can be used or applied. Table 15 is only exemplary and not meant to be limiting.

Virtual placement of a virtual device and/or implant component and/or instrument can include, for example, virtual placement of one or more virtual devices and/or implant components and/or instruments using, for example, a computer (e.g. PC) based interface, acoustic interface, and/or virtual interface, e.g. using gesture recognition, and/or other interface; e.g. with 1, 2, 3, 4, 5, 6 degrees of freedom, optionally alternating, e.g. in one direction followed by another direction or rotation; for example, using live data, e.g. directly visible through a see-through OHMD or imaged with a camera or scanner, e.g. a 3D laser scanner, or a confocal imaging system, and displayed by the OHMD, and optionally virtually moving, aligning and/or superimposing a virtual device and/or implant component and/or instrument in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues. These can be the same or different tissues.

Virtual placement can include virtually moving, aligning, superimposing and/or attaching a virtual device and/or implant component and/or instrument in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues.

Virtual placement can include virtually moving, aligning, superimposing and/or attaching a virtual device and/or implant component and/or instrument in relationship to one or more external features of an adjacent or subjacent or opposing or articulating or connected medical devices and/or implant components and/or instruments including, for example, one or more of their dimensions, radius, radii, curvature, geometry, shape, placement position, orientation and/or alignment, e.g. relative to landmarks and/or anatomic or biomechanical axis/axes.

Virtual placement of virtual device and/or implant component and/or instrument can include, for example, virtually moving, aligning, superimposing and/or attaching a virtual device and/or implant component and/or instrument in relationship to one or more target anatomic and/or pathologic structure(s) for placement and/or alignment and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues. These can be the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for moving and/or placing virtual data, e.g. a virtual device and/or implant component and/or instrument, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the virtual placement can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Virtual placement can include virtually moving, aligning, superimposing and/or attaching a virtual device and/or implant component and/or instrument in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, anatomical and/or biomechanical axis/axes; including same or different tissues.

Virtual placement can include virtually moving, aligning and/or superimposing a virtual device and/or implant component and/or instrument in relationship to one or more internal, optionally hidden or not directly accessible features of an adjacent or subjacent or opposing or articulating or connected medical devices and/or implant components and/or instruments including, for example, one or more of their dimensions, radius, radii, curvature, geometry, shape, placement position, orientation and/or alignment, e.g. relative to landmarks and/or anatomic or biomechanical axis/axes.

Virtual placement can include virtually moving, aligning and/or superimposing a virtual device and/or implant component and/or instrument in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for virtual placement can be combined.

Evaluating the virtual fit and/or selecting a good fitting or the best fitting device and/or implant component and/or instrument can include selecting the device and/or implant component and/or instrument from library of virtual devices and/or implant components and/or instruments, including, for example, using pre-existing CAD files and/or STL files and/or other files of the device and/or implant component and/or instrument, e.g. with different size and/or dimensions and/or geometry and/or shape and/or function and/or anchor/attachment mechanisms and/or anchor/attachment size, dimensions, geometry, and/or shape. The foregoing and/or following embodiments can be applied to different components and/or component combinations.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to live data, e.g. directly visible through a see-through OHMD, e.g. visible with the bare eye without an OHMD, and/or imaged with camera and/or scanner and displayed by the OHMD.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for evaluating and/or selecting a good fitting or the best fitting device and/or implant component and/or instrument, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the evaluating and/or selecting a good fitting or the best fitting device and/or implant component and/or instrument can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a good fitting or the best fitting device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for evaluating and/or selecting a good fitting or the best fitting device and/or implant component and/or instrument can be combined.

Evaluating the virtual shape and/or selecting a device and/or implant component and/or instrument with a preferred shape can include selecting the device and/or implant component and/or instrument from library of virtual devices and/or implant components and/or instruments, including, for example, using pre-existing CAD files and/or STL files and/or other files of the device and/or implant component and/or instrument, e.g. with different size and/or dimensions and/or geometry and/or shape and/or function and/or anchor/attachment mechanisms and/or anchor/attachment size, dimensions, geometry, and/or shape. The foregoing and/or following embodiments can be applied to different components and/or component combinations.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for evaluating and/or selecting a device and/or implant component and/or instrument with a preferred shape, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the evaluating and/or selecting a device and/or implant component and/or instrument with a preferred shape can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Evaluating and/or selecting a device and/or implant component and/or instrument with a preferred shape can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for evaluating and/or selecting a device and/or implant component and/or instrument with a preferred shape can be combined.

Evaluating the virtual function and/or selecting a device and/or implant component and/or instrument with a preferred function can include selecting the device and/or implant component and/or instrument from library of virtual devices and/or implant components and/or instruments, including, for example, using pre-existing CAD files and/or STL files and/or other files of the device and/or implant component and/or instrument, e.g. with different size and/or dimensions and/or geometry and/or shape and/or function and/or anchor/attachment mechanisms and/or anchor/attachment size, dimensions, geometry, shape and/or function. The foregoing and/or following embodiments can be applied to different components and/or component combinations.

Evaluating and/or selecting a device and/or implant component and/or instrument with a preferred function can, for example, include moving, aligning, superimposing and/or projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/ geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/curvature/geometry/shape, function/volume, anatomical and/or biomechanical axis/axes, and/or function; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for evaluating and/or selecting a device and/or implant component and/or instrument with a preferred function, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/ geometry/shape/volume, anatomical and/or biomechanical axis/axes of one or more tissues. In some embodiments, the evaluating and/or selecting a device and/or implant component and/or instrument with a preferred function can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/ shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Evaluating and/or selecting a device and/or implant component and/or instrument with a preferred function can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for evaluating and/or selecting a device and/or implant component and/or instrument with a preferred function can be combined.

Determining the preferred position of a device and/or implant component and/or instrument can, for example, include moving, aligning, superimposing, projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Determining the preferred position of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Determining the preferred position of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/curvature/geometry/shape, function/volume, anatomical and/or biomechanical axis/axes, and/or function; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for determining the preferred position of a device and/or implant component and/or instrument, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the determining the preferred position of a device and/or implant component and/or instrument can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Determining the preferred position of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues.

Determining the preferred position of a device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Determining the preferred position of a device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining the preferred position of a device and/or implant component and/or instrument can be combined.

Determining the preferred orientation of a device and/or implant component and/or instrument can, for example, include moving, aligning, superimposing, projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Determining the preferred orientation of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Determining the preferred orientation of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/ tissue/organ/vascular surface/dimension/radius, radii/curvature/geometry/shape, function/volume, anatomical and/or biomechanical axis/axes, and/or function; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for determining the preferred orientation of a device and/or implant component and/or instrument, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the determining the preferred orientation of a device and/or implant component and/or instrument can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Determining the preferred orientation of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume, or opposing articular/tissue/organ/vascular surface/dimension/radius, radii/curvature/geometry/shape/function/volume, and/or anatomical and/or biomechanical axis/axes, and/or function; this can include the same or different tissues.

Determining the preferred orientation of a device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Determining the preferred orientation of a device and/or implant component and/or instrument can, for example, include moving, aligning, superimposing and/or projecting and/or attaching the virtual device and/or device components and/or implant components and/or instruments in relationship to one or more virtual data, e.g. pre- or intraoperative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining the preferred orientation of a device and/or implant component and/or instrument can be combined.

Determining the preferred alignment of a device and/or implant component and/or instrument can, for example, include moving, aligning, superimposing, projecting and/or attaching the virtual device and/or device components and/or implant components and/or instruments in relationship to live data, e.g. visible through a see-through OHMD, e.g. visible with the bare eye without an OHMD, and/or imaged with camera and/or scanner and displayed by the OHMD.

Determining the preferred alignment of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, function, articular/tissue/organ/vascular surface/dimension/radius, radii/curvature/geometry/shape/function/volume, anatomical and/or biomechanical axis/axes and/or function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume/function, and/or anatomical and/or biomechanical axis/axes, function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more external features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, function.

Determining the preferred alignment of a device and/or implant component and/or instrument can, for example, include moving, aligning, superimposing and/or projecting and/or attaching the virtual device and/or device components and/or implant components and/or instruments in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, function, articular/tissue/organ/vascular surface/dimension/radius, radii/curvature/geometry/shape, function/volume, anatomical and/or biomechanical axis/axes, and/or function; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for determining the preferred alignment of a device and/or implant component and/or instrument, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the determining the preferred alignment of a device and/or implant component and/or instrument can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Determining the preferred alignment of a device and/or implant component and/or instrument can, for example, include moving, aligning, superimposing and/or projecting and/or attaching the virtual device and/or device components and/or implant components and/or instruments in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, function, other portion of articular/tissue/organ/vascular surface/dimension/radius, radii/curvature/geometry/shape/function/volume or opposing articular/tissue/organ/vascular surface/dimension/radius, radii/curvature/geometry/shape/function/volume, and/or anatomical and/or biomechanical axis/axes, and/or function; this can include the same or different tissues.

Determining the preferred alignment of a device and/or implant component and/or instrument can, for example, include moving, aligning, superimposing and/or projecting and/or attaching the virtual device and/or device components and/or implant components and/or instruments in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, function, placement position, orientation and/or alignment, e.g. relative to landmarks and/or anatomic or biomechanical axis/axes, and/or function.

Determining the preferred alignment of a device and/or implant component and/or instrument can, for example, include moving, aligning, superimposing and/or projecting and/or attaching the virtual device and/or device components and/or implant components and/or instruments in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining the preferred alignment of a device and/or implant component and/or instrument can be combined.

Determining and/or selecting a preferred virtual anchor and/or attachment and/or fixation member, e.g. with regard to one or more of length, width, diameter, size, dimensions, radius, radii, geometry, shape, surface properties, location, position, orientation, alignment, and/or function, for example in a monoblock or modular, e.g. attachable, configuration can include selecting the virtual anchor and/or attachment and/or fixation member from a library of virtual devices and/or implant components and/or virtual anchors and/or attachments and/or fixation members, including, for example, using pre-existing CAD files and/or STL files and/or other files of the device and/or implant component and/or virtual anchors and/or attachments and/or fixation members, e.g. with different size and/or dimensions and/or geometry and/or shape and/or function and/or anchor/attachment mechanisms and/or anchor/attachment size, dimensions, geometry, and/or shape. The foregoing and/or following embodiments can be applied to different components and/or component and/or anchor and/or attachment and/or fixation member combinations.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to live data, e.g. visible through a see-through OHMD, e.g. visible with the bare eye without an OHMD, and/or imaged with camera and/or scanner and displayed by the OHMD.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more target anatomic and/or pathologic structure(s) for placement and/or alignment and/or superimposition and/or attachment using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more surrounding and/or adjacent and/or subjacent anatomic and/or pathologic structure(s) using, for example, an external margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more external features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more target anatomic and/or pathologic structure(s) for placement and/or alignment and/or superimposition and/or attachment using, for example, an internal, optionally hidden or not directly accessible margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes; this can include the same or different tissues. The internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues can optionally be determined using an imaging test, derived from an imaging test, or visualized using an imaging test, e.g. displayed by one or more OHMDs. The one or more OHMDs can optionally display the hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues using a computer processor configured for display of virtual data and/or for determining and/or selecting a preferred virtual anchor and/or attachment and/or fixation member, using the image information of the internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues. In some embodiments, the determining and/or selecting a preferred virtual anchor and/or attachment and/or fixation member can be performed using, for example, an external margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes of one or more tissues, e.g. on an exposed (including surgically exposed) external surface, directly visible through a see-through OHMD or directly imageable by a video camera integrated into, attached to, or separate from the OHMD, and image information of an internal, optionally hidden or not directly accessible margin, periphery, edge, AP, SI, ML and/or oblique dimensions, radius, radii, curvature, geometry, shape, articular and/or tissue and/or organ and/or vascular surface/dimension/radius, radii/curvature/geometry/shape/volume, anatomical and/or biomechanical axis/axes of one or more tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more surrounding and/or adjacent and/or subjacent anatomic and/or pathologic structure(s) using, for example, an internal, optionally hidden or not directly accessible margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes; this can include the same or different tissues.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more internal, optionally hidden or not directly accessible features of an adjacent and/or subjacent and/or opposing and/or articulating and/or connected medical device and/or implant component and/or instrument including, for example, their dimensions, radius, radii, curvature, geometry, shape, placement position, orientation and/or alignment, e.g. relative to landmarks and/or anatomic or biomechanical axis/axes.

Determining and/or selecting a preferred virtual anchor and/or attachment and/or fixation member can, for example, include moving, aligning, superimposing and/or projecting and/or attaching the virtual device and/or device components and/or implant components and/or virtual anchor and/or attachment and/or fixation member in relationship to one or more virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data. Any of the foregoing embodiments for determining and/or selecting a preferred virtual anchor and/or attachment and/or fixation member can be combined.

Virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can, for example, include moving, aligning, superimposing and/or projecting and/or attaching the virtual device and/or device components and/or implant components and/or instruments in relationship to live data, e.g. external data (e.g. surgically exposed tissue and/or tissue surface), e.g. visible through a see-through OHMD, e.g. visible with the bare eye without an OHMD, and/or imaged or imageable with camera and/or scanner and displayed by the OHMD, and/or live data, e.g. internal data, e.g. not visible through a see-through OHMD, e.g. not visible with the bare eye without an OHMD, e.g. hidden inside the tissue or inside a joint (for example detected and/or visualized using an imaging test such as an ultrasound, CT or MRI), and/or can, for example, include moving, aligning, superimposing and/or projecting and/or attaching the virtual device and/or device components and/or implant components and/or instruments in relationship to one or more external and/or internal target anatomic and/or pathologic structure(s) for placement and/or alignment and/or superimposition and/or attachment using, for example, an external and/or internal margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes, and/or can, for example, include moving, aligning, superimposing and/or projecting and/or attaching the virtual device and/or device components and/or implant components and/or instruments in relationship to one or more surrounding and/or adjacent and/or subjacent and/or opposing external and/or internal anatomic and/or pathologic structure(s) using, for example, an external and/or internal margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes, and/or can, for example, include moving, aligning, superimposing and/or projecting and/or attaching the virtual device and/or device components and/or implant components and/or instruments in relationship to one or more external and/or internal features of an adjacent and/or subjacent and/or opposing and/or articulating and/or connected external and/or internal medical device and/or implant component and/or instrument including, for example, their dimensions, radius, radii, curvature, geometry, shape, placement position, orientation and/or alignment, e.g. relative to landmarks and/or anatomic or biomechanical axis/axes, and/or can, for example, include moving, aligning, superimposing and/or projecting and/or attaching the virtual device and/or device components and/or implant components and/or instruments in relationship to one or more externally projected and/or internally projected virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data, and/or or any combinations of the foregoing, and can be based on a single or a multiple parameters, i.e. can be single or multi-parametric, e.g. by determining, evaluating, assessing, considering, using, for example, any one or more of the foregoing, e.g. by determining, evaluating, assessing, considering, using, for example, any one or more of external and/or internal target anatomic and/or pathologic structure(s), for example, an external and/or internal margin, periphery, edge, AP, SI, ML and/or oblique dimensions, radius, radii, curvature, geometry, shape, articular/tissue/organ/vascular surface/dimension/radius, radii/curvature/geometry/shape/volume, anatomical and/or biomechanical axis/axes, and/or surrounding and/or adjacent and/or subjacent and/or opposing external and/or internal anatomic and/or pathologic structure(s), for example, an external and/or internal margin, periphery, edge, AP, SI, ML and/or oblique dimensions, radius, radii, curvature, geometry, shape, other portion of articular/tissue/organ/vascular surface/dimension/radius, radii/curvature/geometry/shape/volume or opposing articular/tissue/organ/vascular surface/dimension/radius, radii/curvature/geometry/shape/volume, and/or anatomical and/or biomechanical axis/axes, and/or external and/or internal features of an adjacent and/or subjacent and/or opposing and/or articulating and/or connected external and/or internal medical device and/or implant component and/or instrument including, for example, their dimensions, radius, radii, curvature, geometry, shape, placement position, orientation and/or alignment, e.g. relative to landmarks and/or anatomic or biomechanical axis/axes, and/or externally projected and/or internally projected virtual data, e.g. pre- or intra-operative imaging studies, 2D, 3D images, graphical representations, CAD files, optionally registered, optionally superimposed, and/or other pre- or intra-operative data, optionally registered, optionally superimposed, e.g. pressure measurements, flow measurements, time of flight studies, metabolic data, functional data.

In a knee replacement, a hip replacement, a shoulder replacement, an ankle replacement, and any surgery in the knee, hip, shoulder, ankle, any other joints and the spine that involves implantation of a medical device, e.g. a pedicle screw, a disk replacement, an anchor and/or a graft, two or more parameters can be used using OHMD display and/or guidance for the virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member.

In a knee replacement or knee surgery, e.g. an ACL reconstruction, the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can use, for example, an AP dimension, an ML dimension, an SI dimension, e.g. of the distal femur and/or tibia, a surface, peripheral margin, dimension, shape, radius or radii, convexity, concavity of the posterior portion of medial femoral condyle, a surface, peripheral margin, dimension, shape, radius or radii, convexity, concavity of the posterior portion of lateral femoral condyle, a surface, peripheral margin, dimension, shape, radius or radii, convexity, concavity of the central portion of medial femoral condyle, a surface, peripheral margin, dimension, shape, radius or radii, convexity, concavity of the central portion of lateral femoral condyle, a surface, peripheral margin, dimension, shape, radius or radii, convexity, concavity of the anterior portion of medial femoral condyle, a surface, peripheral margin, dimension, shape, radius or radii, convexity, concavity of the anterior portion of lateral femoral condyle, a trochlear height, a trochlear angle, a trochlear sulcus line, a trochlear sulcus depth, a condylar offset, a tibial offset, a tibial height, e.g. medial or lateral, a medial joint line, a lateral joint line, a sagittal curvature, e.g. on the femur and/or the tibia and/or the patella, a patellar width and/or height and/or thickness, a shape of a medial patellar facet, a shape of a lateral patellar facet, a cartilage surface, a subchondral bone surface, one or more osteophytes, a cortical bone surface and/or shape, a subchondral bone surface and/or shape, a cartilage surface and/or shape, e.g. normal, damaged and/or diseased, e.g. of the distal femur and/or tibia and/or patella, any of the anatomic sites, landmarks, distances, dimensions, surfaces, edges, angles, axes, curvatures, shapes, lengths, widths, depths, features listed in Tables 11, 12 and 16 related to the knee joint and/or adjacent joints, e.g. the hip or ankle joint, one or more anatomic and/or biomechanical axes, one or more kinematic measurements, one or more pre-operative imaging studies, of the patient. The foregoing is only illustrative in nature and not meant to be limiting. Someone skilled in the art can recognize other landmarks, sites, shapes, pathology etc. that can be used in this manner. The AP dimension, ML dimension, SI dimension, e.g. of the distal femur and/or tibia, surface, peripheral margin, dimension, shape, radius or radii, convexity, concavity of the posterior portion of medial femoral condyle, surface, peripheral margin, dimension, shape, radius or radii, convexity, concavity of the posterior portion of lateral femoral condyle, surface, peripheral margin, dimension, shape, radius or radii, convexity, concavity of the central portion of medial femoral condyle, surface, peripheral margin, dimension, shape, radius or radii, convexity, concavity of the central portion of lateral femoral condyle, surface, peripheral margin, dimension, shape, radius or radii, convexity, concavity of the anterior portion of medial femoral condyle, surface, peripheral margin, dimension, shape, radius or radii, convexity, concavity of the anterior portion of lateral femoral condyle, trochlear height, trochlear angle, trochlear sulcus line, trochlear sulcus depth, condylar offset, tibial offset, tibial height, e.g. medial or lateral, medial joint line, lateral joint line, sagittal curvature, e.g. on the femur and/or the tibia and/or the patella, patellar width and/or height and/or thickness, one or more osteophytes, cortical bone surface and/or shape, subchondral bone surface and/or shape, cartilage surface and/or shape, e.g. normal, damaged and/or diseased, e.g. of the distal femur and/or tibia and/or patella, any of the anatomic sites, landmarks, distances, dimensions, surfaces, edges, angles, axes, curvatures, shapes, lengths, widths, depths, features listed in Tables 11, 12 and 16 related to the knee joint and/or adjacent joints, e.g. the hip or ankle joint, one or more anatomic and/or biomechanical axes can be directly visible through one or more see-through OHMDs, for example through or using a surgical incision and/or exposure, or directly imaged or imageable with an image capture system or video system integrated into, attached to or separate from the one or more OHMDs, for example through or using a surgical incision and/or exposure, and/or (for example, if hidden, not exposed or in subsurface location) can be visualized using imaging data, e.g. from a pre- and/or intra-operative imaging test, e.g. an ultrasound, CT or MRI. Both directly visible through one or more see-through OHMDs or directly imaged or imageable with an image capture system or video system integrated into, attached to or separate from the one or more OHMDs and hidden, not exposed, or subsurface location tissues, surfaces, landmarks and/or structures, e.g. displayed by the one or more OHMDs using imaging data, for example data from AP and lateral knee x-rays morphed into a patient specific 3D bone model or data from a CT scan or MRI of the knee, can be used alone or in combination for the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member in a knee replacement, knee arthroscopy, ACL reconstruction, or other knee surgery. For example, a femoral component in a knee replacement can be virtually placed, virtually fitted, virtually sized, virtually selected, and/or virtually aligned using information, shapes, geometries, surfaces, edges, margins and/or dimensions that are directly visible through a see-through OHMD. In addition, the femoral component can be virtually placed, virtually fitted, virtually sized, virtually selected, and/or virtually aligned using information, shapes, geometries, surfaces, edges, margins and/or dimensions that are not exposed through the incision and that are not directly visible, but that can be displayed using one or more OHMDs using, for example, imaging data or models derived therefrom and superimposed onto or aligned with the corresponding physical anatomy; the information, shapes, geometries, surfaces, edges, margins and/or dimensions that are not exposed through the incision and that are not directly visible can, for example, include a surface, peripheral margin, dimension, shape, radius or radii, curvature, convexity, concavity of the posterior portion of lateral femoral condyle, and, for example, optionally, a surface, peripheral margin, dimension, shape, radius or radii, convexity, concavity of the posterior portion of medial femoral condyle. Thus, the virtual placing, fitting, sizing, selecting and/or aligning of the femoral component can use one or both of information, shapes, geometries, surfaces, edges, margins and/or dimensions that are directly visible through a see-through OHMD and information, shapes, geometries, surfaces, edges, margins and/or dimensions that are not directly visible, but that can be virtually displayed, e.g. using imaging data, using one or more OHMDs. In another example, a tibial component in a knee replacement can be virtually placed, virtually fitted, virtually sized, virtually selected, and/or virtually aligned using information, shapes, geometries, surfaces, edges, margins and/or dimensions that are directly visible through a see-through OHMD. In addition, the tibial component can be virtually placed, virtually fitted, virtually sized, virtually selected, and/or virtually aligned using information, curvatures, shapes, geometries, surfaces, edges, margins and/or dimensions that are not exposed through the incision and that are not directly visible, but that can be displayed using one or more OHMDs using, for example, imaging data or models derived therefrom and superimposed onto or aligned with the corresponding physical anatomy; the information, curvatures, shapes, geometries, surfaces, edges, margins and/or dimensions that are not exposed through the incision and that are not directly visible can, for example, include a surface, peripheral margin, dimension, curvature, shape, radius or radii, convexity, concavity of the posterior portion of lateral tibial plateau, and, for example, optionally, a surface, peripheral margin, dimension, shape, radius or radii, convexity, concavity of the posterior portion of medial tibial plateau. Thus, the virtual placing, fitting, sizing, selecting and/or aligning of the tibial component can use one or both of information, curvatures, shapes, geometries, surfaces, edges, margins and/or dimensions that are directly visible through a see-through OHMD and information, curvatures, shapes, geometries, surfaces, edges, margins and/or dimensions that are not directly visible, but that can be virtually displayed using one or more OHMDs. In a hip replacement or other hip surgery, e.g. hip arthroscopy, the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can use, for example, a portion of or an entire acetabulum, a portion of or an entire edge of an acetabulum, multiple portions of an edge of an acetabulum, a portion or the entire acetabular wall, an acetabular radius, an acetabular curvature, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a portion of or an entire femoral shaft, a portion of or an entire femoral neck, a portion of or an entire femoral head, a femoral head radius, a femoral head curvature, a fovea capitis, a transverse acetabular ligament, a pulvinar, a labrum, one or more osteophytes, a cortical bone surface and/or shape, a subchondral bone surface and/or shape, a cartilage surface and/or shape, e.g. normal, damaged and/or diseased, an AP dimension, an ML dimension, an SI dimension, an acetabular anteversion, a femoral anteversion, a femoral neck angle, a femoral neck offset, a femoral neck length, a femoral shaft length, an acetabular bone width or bone stock, an iliac bone stock of the patient, any of the anatomic sites, landmarks, distances, dimensions, surfaces, edges, angles, axes, curvatures, shapes, lengths, widths, depths, features listed in Table 16 related to the hip joint and/or adjacent joints, e.g. the knee joint, one or more anatomic and/or biomechanical axes, one or more kinematic measurements, one or more pre-operative imaging studies, of the patient. The portion of or an entire acetabulum, portion of or an entire edge of an acetabulum, multiple portions of an edge of an acetabulum, portion or the entire acetabular wall, acetabular radius, acetabular curvature, portion of an iliac wall, portion of a pubic bone, portion of an ischial bone, an anterior superior iliac spine, an anterior inferior iliac spine, a symphysis pubis, portion of or an entire greater trochanter, portion of or an entire lesser trochanter, portion of or an entire femoral shaft, portion of or an entire femoral neck, portion of or an entire femoral head, femoral head radius, femoral head curvature, fovea capitis, transverse acetabular ligament, pulvinar, labrum, one or more osteophytes, cortical bone surface and/or shape, subchondral bone surface and/or shape, cartilage surface and/or shape, e.g. normal, damaged and/or diseased, AP dimension, ML dimension, SI dimension, acetabular anteversion, femoral anteversion, femoral neck angle, femoral neck offset, femoral neck length, femoral shaft length, acetabular bone width or bone stock, iliac bone stock of the patient, any of the anatomic sites, landmarks, distances, dimensions, surfaces, edges, angles, axes, curvatures, shapes, lengths, widths, depths, features listed in Table 16 related to the hip joint and/or adjacent joints, e.g. the knee joint, one or more anatomic and/or biomechanical axes can be directly visible through one or more see-through OHMDs, for example through or using a surgical incision and/or exposure, or directly imaged or imageable with an image capture system or video system integrated into, attached to or separate from the one or more OHMDs, for example through or using a surgical incision and/or exposure, and/or (for example, if hidden, not exposed or in subsurface location) can be visualized using imaging data, e.g. from a pre- and/or intra-operative imaging test, e.g. an ultrasound, CT or MRI. Both directly visible through one or more see-through OHMDs or directly imaged or imageable with an image capture system or video system integrated into, attached to or separate from the one or more OHMDs and hidden, not exposed, or subsurface location tissues, surfaces, landmarks and/or structures can be used alone or in combination for the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member in a hip replacement or other hip surgery. For example, a virtual femoral head component can be virtually fitted and/or sized and/or aligned by placing it virtually inside the patient's native femoral head, e.g. inside the cartilage and/or the subchondral bone envelope, either in situ, unresected inside the patient, or ex vivo, resected, e.g. on the OR table. A virtual femoral component, e.g. a femoral neck component, a femoral shaft component, a mono-block femoral neck and shaft component, can be fitted, sized, and/or aligned by virtually placing it inside the unresected femoral neck and/or shaft of the patient; the fitting, sizing and/or aligning can be performed in relationship to directly visible, e.g. exposed portions of the femoral neck and/or shaft and/or can be performed in relationship to non-visible, hidden, and/or subsurface portions of the femoral neck and/or shaft displayed by one or more OHMDs using imaging data superimposed and/or aligned with the corresponding portions of the physical femoral neck and/or shaft. A virtual acetabular component can be fitted, sized, and/or aligned by virtually placing it inside the patient's native acetabulum, e.g. inside the cartilage and/or the subchondral bone envelope, e.g. before or after reaming; the fitting, sizing and/or aligning and/or virtually determining and/or selecting a preferred virtual anchor and/or attachment and/or fixation member of the acetabular component can be performed in relationship to directly visible, e.g. exposed portions of the acetabulum and/or can be performed in relationship to non-visible, hidden, and/or subsurface portions of the acetabulum displayed by one or more OHMDs using imaging data superimposed and/or aligned with the corresponding portions of the physical acetabulum. The OHMD display of the non-visible, hidden, and/or subsurface portions of the acetabulum can, for example, show an underlying bone stock, acetabular wall thickness, and/or tear drop which can be used for virtually determining and/or selecting a preferred virtual anchor and/or attachment and/or fixation member, for example using a computer processor configured for displaying a virtual anchor and/or attachment and/or fixation member using one or more OHMDs, and/or for guiding and/or determining a reaming depth for placing the physical acetabular component, using, for example, a computer processor configured for displaying a virtual reamer or a predetermined reaming depth or depth stop using one or more OHMDs. The foregoing is only illustrative in nature and not meant to be limiting. Someone skilled in the art can recognize other landmarks, sites, shapes, pathology etc. that can be used in this manner.

In a shoulder replacement or other shoulder surgery, the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can use, for example, a portion of or an entire glenoid, a portion of or an entire edge of an glenoid, multiple portions of an edge of a glenoid, a glenoid radius, a glenoid bone stock, a glenoid bone width, a glenoid bone depth including bone stock depth, a portion of a coracoid and/or an acromion, a portion of or an entire greater tuberosity, a portion of or an entire lesser tuberosity, a portion of or an entire humeral shaft, a portion of or an entire humeral neck, a portion of or an entire humeral head, a labrum, one or more osteophytes, an AP dimension, an ML dimension, an SI dimension, a glenoid anteversion, a humeral anteversion, a humeral neck angle, a humeral neck offset, a humeral neck length, a humeral shaft length, a glenoid bone stock, one or more osteophytes, a cortical bone surface and/or shape, a subchondral bone surface and/or shape, a cartilage surface and/or shape, e.g. normal, damaged and/or diseased, e.g. of the glenoid, the scapula and/or the humerus, any of the anatomic sites, landmarks, distances, dimensions, surfaces, edges, angles, axes, curvatures, shapes, lengths, widths, depths, features listed in Table 16 related to the shoulder joint and/or adjacent joints, e.g. the elbow joint, one or more anatomic and/or biomechanical axes, one or more kinematic measurements, one or more pre-operative imaging studies, of the patient. The portion of or an entire glenoid, portion of or an entire edge of an glenoid, multiple portions of an edge of a glenoid, glenoid radius, glenoid bone stock, glenoid bone width, glenoid bone depth including bone stock depth, portion of a coracoid and/or an acromion, portion of or an entire greater tuberosity, portion of or an entire lesser tuberosity, portion of or an entire humeral shaft, portion of or an entire humeral neck, portion of or an entire humeral head, labrum, one or more osteophytes, AP dimension, ML dimension, SI dimension, glenoid anteversion, humeral anteversion, humeral neck angle, humeral neck offset, humeral neck length, humeral shaft length, glenoid bone stock, one or more osteophytes, cortical bone surface and/or shape, subchondral bone surface and/or shape, cartilage surface and/or shape, e.g. normal, damaged and/or diseased, e.g. of the glenoid, the scapula and/or the humerus, any of the anatomic sites, landmarks, distances, dimensions, surfaces, edges, angles, axes, curvatures, shapes, lengths, widths, depths, features listed in Table 16 related to the shoulder joint and/or adjacent joints, e.g. the elbow joint, one or more anatomic and/or biomechanical axes can be directly visible through one or more see-through OHMDs, for example through or using a surgical incision and/or exposure, or directly imaged or imageable with an image capture system or video system integrated into, attached to or separate from the one or more OHMDs, for example through or using a surgical incision and/or exposure, and/or (for example, if hidden, not exposed or in subsurface location) can be visualized using imaging data, e.g. from a pre- and/or intra-operative imaging test, e.g. an ultrasound, CT or MRI. Both directly visible through one or more see-through OHMDs or directly imaged or imageable with an image capture system or video system integrated into, attached to or separate from the one or more OHMDs and hidden, not exposed, or subsurface location tissues, surfaces, landmarks and/or structures can be used alone or in combination for the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member in a shoulder joint replacement or other shoulder surgery. For example, a virtual humeral head component can be virtually fitted and/or sized and/or by placing it virtually inside the patient's native humeral head, e.g. inside the cartilage and/or the subchondral bone envelope, either in situ, unresected inside the patient, or ex vivo, resected, e.g. on the OR table. A virtual humeral component, e.g. a humeral neck component, a humeral shaft component, a mono-block humeral neck and shaft component, can be fitted, sized, and/or aligned by virtually placing it inside the unresected humeral neck and/or shaft of the patient; the fitting, sizing and/or aligning can be performed in relationship to directly visible, e.g. exposed portions of the humeral neck and/or shaft and/or can be performed in relationship to non-visible, hidden, and/or subsurface portions of the humeral neck and/or shaft displayed by one or more OHMDs using imaging data superimposed and/or aligned with the corresponding portions of the physical humeral neck and/or shaft. A virtual glenoid component can be fitted, sized, and/or aligned by virtually placing it inside the patient's native glenoid, e.g. before or after reaming; the fitting, sizing and/or aligning and/or virtually determining and/or selecting a preferred virtual anchor and/or attachment and/or fixation member of the glenoid component can be performed in relationship to directly visible, e.g. exposed portions of the glenoid and/or can be performed in relationship to non-visible, hidden, and/or subsurface portions of the glenoid displayed by one or more OHMDs using imaging data superimposed and/or aligned with the corresponding portions of the physical glenoid. The OHMD display of the non-visible, hidden, and/or subsurface portions of the glenoid can, for example, show an underlying bone stock, glenoid bone thickness, and/or glenoid bone depth and/or underlying glenoid bone and bone stock dimensions which can be used for virtually determining and/or selecting a preferred virtual anchor and/or attachment and/or fixation member, for example using a computer processor configured for displaying a virtual anchor and/or attachment and/or fixation member using one or more OHMDs, and/or for guiding and/or determining a reaming depth for placing the physical glenoid component, using, for example, a computer processor configured for displaying a virtual reamer or reaming axis or a predetermined reaming depth or depth stop using one or more OHMDs. The foregoing is only illustrative in nature and not meant to be limiting. Someone skilled in the art can recognize other landmarks, sites, shapes, pathology etc. that can be used in this manner.

In an ankle replacement or other ankle surgery, the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can use, for example, a portion of or an entire talus, a portion of or an entire calcaneus, a portion of a distal tibia, one or more osteophytes, an AP dimension, an ML dimension, an SI dimension, a curvature, a bone stock of any of the bones of the patient. The foregoing is only illustrative in nature and not meant to be limiting. Someone skilled in the art can recognize other landmarks, sites, shapes, pathology etc. that can be used in this manner.

In a spinal fusion or other spinal surgery, the single or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can use, for example, an iliac spine, an iliac crest, a symphysis pubis, a portion of the sacrum, one or more osteophytes, a cortical bone surface and/or shape, a subchondral bone surface and/or shape, a cartilage surface and/or shape, e.g. normal, damaged and/or diseased, an intervertebral disk shape, an AP dimension, an ML dimension, an SI dimension, a pedicle width, a pedicle length, a pedicle height, a pedicle dimension, a pedicle shape, a pedicle angle, a vertebral body width, a vertebral body length, a vertebral body height, a vertebral body dimension, a vertebral body shape, a vertebral body angle, an intervertebral disk width, an intervertebral disk length, an intervertebral disk height, an intervertebral disk dimension, an intervertebral disk shape, an intervertebral disk angle, an endplate width, an endplate length, an endplate height, an endplate dimension, an endplate shape, an endplate angle, any of the anatomic sites, landmarks, distances, dimensions, surfaces, edges, angles, axes, curvatures, shapes, lengths, widths, depths, features listed in Table 16 related to the spine, one or more anatomic and/or biomechanical axes, one or more kinematic measurements, one or more pre-operative imaging studies, of the patient. For example, a virtual pedicle screw can be fitted, sized, and/or aligned by virtually placing it inside the pedicle of the patient; the pedicle anatomy can be projected by the OHMD simultaneously, e.g. using a pre-operative or intra-operative CT scan or O-arm scan that is registered in a common coordinate system with the patient's spine and one/or more OHMDs. For example, virtual spinal cage can be fitted, sized, and/or aligned by virtually placing it between two vertebral endplates of the patient; the vertebral anatomy can be projected by the OHMD simultaneously, e.g. using a pre-operative or intra-operative CT scan or O-arm scan that is registered in a common coordinate system with the patient's spine and one/or more OHMDs. The foregoing is only illustrative in nature and not meant to be limiting. Someone skilled in the art can recognize other landmarks, sites, shapes, pathology etc. that can be used in this manner.

With dental implants, dental implant components and all other dental devices and related procedures, single-parametric or multi-parametric virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can use, for example, one or more dental or oral structures including a crown, e.g. directly visible, enamel, e.g. directly visible, dentin, e.g. directly visible pulp, e.g. hidden inside a tooth, cementum, cementoenamel junction, periodontal ligaments, gingival tissue, alveolar bone, a root, e.g. hidden inside the alveolar bone, a root canal, apical foramina, a cingulum, marginal ridge(s), longitudinal ridge(s), oblique ridge(s), cusp ridge(s), secondary groove(s), auxiliary groove(s), dissectional groove(s), cusp, cusp tip, cusp of Carabelli, pit(s), fossa(s), occlusal table, gingival bulge, imbrication area, a clinical crown, an anatomical crown, central incisor(s), lateral incisor(s), cuspid(s), $1^{st}$ premolar(s), $2^{nd}$ premolar(s), $1^{st}$ molar(s), $2^{nd}$ molar(s), $3^{rd}$ molar(s), an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth, features and/or structures of an existing tooth, e.g. a tooth that the dentist intends to replace or repair or augment, or one or more teeth adjacent or opposite, e.g. in the opposing mandible or maxilla, to a tooth that the dentist intends to replace or repair or augment, e.g. dimensions, curves, curvatures, edges, plateaus, margins, ridges, cusps, grooves, and/or shape and/or color of one or more existing teeth, including a tooth selected for repair, resurfacing or replacement, one or more adjacent teeth and/or one or more opposing teeth on the opposing mandible or maxilla and combinations thereof, a bone shape or bone stock, e.g. a bone shape including anterior, posterior, inferior and/or superior shape and/or curvature(s) of a mandible or a maxilla and/or a bone stock of a mandible or maxilla, a bone density or bone quality, e.g. a bone density and/or a bone quality at or near an intended implantation site in the mandible or maxilla, a void created by a tooth that has been previously lost or extracted or in relationship to tissues remaining in the void, e.g. gingival tissue, alveolar bone, a residual root or root cavity etc., an existing dental implant, dental implant component and/or any other dental device including one or more of an abutment, e.g. a standard abutment or a custom made abutment, a crown, a fixture or implant and any combination thereof, dimensions, curvatures, curves, edges, plateaus, margins, ridges, cusps, grooves, and/or shape of one or more existing implants, implant components, abutments, crowns, fixtures or implants and combinations thereof, virtual data of the patient, e.g. from a scan, and/or optionally combined with live data of the patient, e.g. the surgical site or the intended implantation site. The surgical site or the intended implantation site can be seen through a see-through optical head mounted display or a non-see through optical head mounted display, e.g. a virtual reality display, for example using one or more cameras directed at the tooth or teeth for imaging the live data of the patient, which can be optionally superimposed or aligned with virtual data of the patient. The terms surgical site and implantation site or intended implantation site can be used interchangeably throughout the specification.

For example, a virtual dental implant can be fitted, sized, and/or aligned by virtually placing it tangent with, e.g. at least partially, or inside the tooth of the patient, e.g. a tooth intended for extraction. A virtual dental implant can be fitted, sized, and/or aligned by virtually placing it tangent with at least a portion of the anterior surface of the tooth of the patient, e.g. a tooth intended for extraction, the ridge of the tooth, the medial or lateral edge of the tooth, the posterior surface of the tooth or other structural aspects of the tooth. A virtual dental implant can be fitted, sized, and/or aligned by virtually placing into a tooth void of the patient and/or between two adjacent teeth, e.g. to the left and/or the right of the void. The foregoing is only illustrative in nature and not meant to be limiting. Someone skilled in the art can recognize other landmarks, sites, shapes, pathology etc. that can be used in this manner.

In any of the foregoing and following embodiments, a target anatomic or target pathologic tissue can include a surgical site and/or an intended implantation site, e.g. before or after surgical alteration, e.g. a resected bone, a cut bone, a resected cartilage, a cut cartilage, an unresected bone, an unresected cartilage, an unresected tissue, a partially resected tissue, a resected tissue, a distal femur or a proximal tibia before or after an ACL repair or reconstruction. For example, in knee replacement, a target tissue can be a cut or resected distal femoral or proximal tibial bone. In dental surgery, a target tissue can be a tooth, e.g. before or after removal, a cavity, a void from a previously pulled or lost tooth, etc.

In some embodiments, the OHMD can display an arbitrary virtual implant, virtual implant component and/or virtual medical device and virtual instrument over the surgical field. The projection can be a 2D outline similar to radiographic templates, optionally derived from radiographic templates, or a 3D image, e.g. a 3D CAD file of the virtual implant, virtual implant component and/or virtual medical device and virtual instrument. The arbitrary virtual implant, virtual implant component and/or virtual medical device and virtual instrument can, for example, be a virtual implant, virtual implant component and/or virtual medical device and virtual instrument selected from the middle of a size range or a shape range or function range. The arbitrary virtual implant, virtual implant component and/or virtual medical device and virtual instrument can be selected based on surgeon preferences. The arbitrary virtual implant, virtual implant component and/or virtual medical device and virtual instrument can be the most common size used in a particular patient population. The arbitrary virtual implant, virtual implant component and/or virtual medical device and virtual instrument can be moveable using, for example, a computer (e.g. PC based), virtual, acoustic, or other interface. For example, the virtual representation of the arbitrary virtual implant, virtual implant component and/or virtual medical device and virtual instrument can include a "touch area", wherein gesture recognition software, for example the one provided by Microsoft with the Microsoft Hololens including, for example, the integrated virtual "drag function" for holograms can be used to move the arbitrary virtual implant, virtual implant component and/or virtual medical device and virtual instrument. For example, one or more cameras integrated or attached to the OHMD can capture the movement of the surgeon's finger(s) in relationship to the touch area; using gesture tracking software, the arbitrary virtual implant, virtual implant component and/or virtual medical device and virtual instrument can then be moved by advancing the finger towards the touch area in a desired direction. A surgeon can, for example, also "hold" the arbitrary virtual implant, virtual implant component and/or virtual medical device and virtual instrument by closing two fingers, e.g. thumb and index finger, over the touch area and then moving the fingers in the desired direction, thereby moving the arbitrary virtual implant, virtual implant component and/or virtual medical device and virtual instrument into the desired position and/or orientation on the patient's joint. Movement can be possible with 6 degrees of freedom. For example, a virtual joint replacement implant, e.g. a knee or hip replacement implant can include a touch area on a medial edge and a lateral edge or a superior margin or an inferior margin or a left area and a right area—any combination of the foregoing and/or following is possible—and the surgeon can approach with the thumb and index finger the respective touch areas. When the thumb and index finger reach the virtual touch area and close over the touch area, the location of the thumb and index finger in the touch area can be recognized by the gesture recognition system, triggering a command that the surgeon can move the virtual implant by moving the thumb and index finger with 1, 2, 3, 4, 5 or 6 degrees of freedom. When the surgeon opens the thumb and index finger, e.g. widens the distance between the thumb and index finger so that one or both fingers are not aligned with their respective touch areas anymore, the gesture recognition system can optionally recognize this opening of thumb and index finger triggering a command, for example, to fixate the virtual implant in its last position and/or orientation with the coordinates of the last position and/or orientation. The last position and/or orientation can be, for example, a position and/or orientation where the implant component is tangent with at least a portion of an external margin or periphery or rim of a joint and/or where the implant component is tangent with at least a portion of the articular surface. Any combination of finger and hand gestures is possible and different finger and hand gestures can be used to execute different commands.

In embodiments, one or more virtual medical devices, virtual implants, virtual implant components, virtual implant portions, virtual anchors, attachment or fixation members, and/or virtual instruments and/or virtual surgical tools can be moved, aligned, superimposed, projected or attached using one or more assistive tools. Such assistive tools can, for example, include handheld devices. The one or more assistive tools can be tracked using any of the tracking means described in the specification, including combinations thereof, including, but not limited to, optical markers, e.g. with one or more geometric patterns, and/or LED's, for example tracked using an image and/or video capture system or camera system integrated into, attached to or separate from an OHMD, navigation markers, e.g. infrared or RF marker's, e.g. tracked with a navigation system, IMU's, calibration phantoms, and/or reference phantoms. The one or more assistive tools can also be tracked using intrinsic tracking methods. The one or more assistive tools can also be directly recognized by one or more image capture systems or video systems and/or 3D scanners integrated into, attached to or separate from an OHMD, wherein the direct recognition and tracking allows to track the one or more assistive tools in one or more coordinate systems, e.g. a common coordinate system. In embodiments, a handheld device can have a wand, baton, stick, dowel like shape, which can be tracked directly, e.g. using one or more image capture or video capture systems and/or 3D scanners, or optionally with one or more optical markers, LED's, navigation markers, IMU's, phantom's and the like attached to a first and, optionally, a second end. The surgeon can hold the wand, baton, stick or dowel like handheld device, for example, between a thumb and an index or other finger. The surgeon can execute commands, e.g. a virtual command or a voice command, to activate direct tracking or tracking of the wand, baton, stick or dowel like handheld device or to stop tracking of the wand, baton, stick or dowel like handheld device. One or more assistive tools can also be attached to the surgeon, e.g. the surgeon's wrist or arm. As the surgeon moves the wrist or arm, the position, orientation, alignment, direction of movement and/or speed of movement can be tracked. As the system tracks the position and/or orientation, and/or alignment and/or direction of movement and/or speed of movement, e.g. in a common coordinate system or any coordinate system, the position and/or orientation, and/or alignment and/or direction of movement and/or speed of movement can be translated into a corresponding position and/or orientation, and/or alignment and/or direction of movement and/or speed of movement or corresponding change in position and/or orientation, and/or alignment and/or direction of movement and/or speed of movement of the one or more projected virtual medical device, virtual implant or implant component, virtual anchor, attachment or fixation member, and/or virtual instrument and/or virtual tool. Thus, in this example, by moving the handheld device or assistive tool the surgeon can effect a movement of the virtual medical device, virtual implant or implant component, virtual anchor, attachment or fixation member, and/or virtual instrument and/or virtual tool displayed by the OHMD and the surgeon can virtually position, orient, align, superimpose or project the virtual medical device, virtual implant or implant component, virtual anchor, attachment or fixation member, and/or virtual instrument onto the physical anatomy or pathology of the patient, the physical surgical site, a resected tissue, a resected bone or cartilage, a hidden tissue, an area deep inside the tissue, e.g. inside a bone, a physical medical device present in the tissues of the patient and/or any surrounding, adjacent or subjacent tissues. As the surgeon moves the one or more assistive tools and the position, orientation, alignment, direction and/or speed of movement is tracked, the corresponding change in position, orientation, alignment, direction and/or speed of movement and/or coordinates of the virtual medical device, virtual implant, virtual implant component, virtual anchor, attachment or fixation member, and/or virtual instrument can be the same or can be less or more. For example, changes in position, orientation, alignment, direction and/or speed of movement and/or coordinates of the assistive tool can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1.5:1, 2:1, 3:1, 4:1, 5:1 or any other ratio. In this example, the movement of the virtual device, virtual implant, virtual implant component, virtual anchor, attachment or fixation member, virtual instrument and/or virtual surgical tool is smaller than the movement of the assistive tool, which can help the surgeon placing the virtual device, virtual implant, virtual implant component, virtual instrument and/or virtual surgical tool with high accuracy over an intended area, e.g. an implantation site. In another example, changes in position, orientation, alignment, direction and/or speed of movement and/or coordinates of the assistive tool can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1:1.5, 1:2, 1:3, 1:4, 1:5 or any other ratio. In this example, the movement of the virtual device, virtual implant, virtual implant component, virtual anchor, attachment or fixation member, virtual instrument and/or virtual surgical tool is larger than the movement of the assistive tool, which can help the surgeon placing the virtual device, virtual implant, virtual implant component, virtual instrument and/or virtual surgical tool with high speed over an intended area, e.g. an implantation site. The surgeon or an operator can optionally change these ratios. Non-linear ratios can be applied. For example, at the beginning of a virtual placement or alignment or fitting or selection, the movement of the virtual device, virtual implant, virtual implant component, virtual anchor, attachment or fixation member, virtual instrument or virtual surgical tool can intentionally be larger than the movement of the assistive tool in order to facilitate quick and time efficient placement, alignment and/or evaluation or any of the foregoing steps, including the ones tabulated in Table 15. As the procedure progresses, the movement of the virtual device, virtual implant, virtual implant component, virtual anchor, attachment or fixation member, virtual instrument or virtual surgical tool can intentionally be smaller than the movement of the assistive tool in order to facilitate accurate and reproducible placement, alignment and/or evaluation or any of the foregoing steps, including the ones tabulated in Table 15.

Alternatively, when the assistive tool and/or the virtual device, virtual implant, virtual implant component, virtual anchor, attachment or fixation member, virtual instrument or virtual surgical tool is in the periphery of the surgical field or the visual field of the surgeon, the movement of the virtual device, virtual implant, virtual implant component, virtual anchor, attachment or fixation member, virtual instrument or virtual surgical tool can be larger than the movement of the assistive tool in order to facilitate quick and time efficient placement or movement of the virtual device, virtual implant, virtual implant component, virtual anchor, attachment or fixation member, virtual instrument or virtual surgical tool towards or in the center of the surgical field or visual field of the surgeon. As the assistive tool and/or the virtual device, virtual implant, virtual implant component, virtual anchor, attachment or fixation member, virtual instrument or virtual surgical tool approaches the center of the surgical field or the visual field of the surgeon, the movement of the virtual device, virtual implant, virtual implant component, virtual anchor, attachment or fixation member, virtual instrument or virtual surgical tool can be smaller than the movement of the assistive tool in order to facilitate accurate and reproducible placement or movement of the virtual device, virtual implant, virtual implant component, virtual anchor, attachment or fixation member, virtual instrument or virtual surgical tool. The ratio, magnitude and speed of change in coordinates can change in a stepwise fashion or a continuous fashion, e.g. based on the location of the assistive tool or the virtual device, virtual implant, virtual implant component, virtual anchor, attachment or fixation member, virtual instrument or virtual surgical tool, e.g. from the periphery to the center of the surgical field and/or the visual field of the surgeon. The change can be automatic, e.g. based on coordinates of the assistive tool or the virtual device, virtual implant, virtual implant component, virtual anchor, attachment or fixation member, virtual instrument or virtual surgical tool in relationship to the surgical field and/or the OHMD, semi-automatic with user interaction, or manual with user interaction only. User interaction can be performed using any of the interfaces described in the specification, e.g. PC based, mouse based, voice based, gesture recognition based etc.

In embodiments using direct tracking, e.g. using one or more image capture or video capture systems and/or 3D scanners integrated into, attached to or separate from the OHMD, the surgeon can effect a movement of the virtual medical device, virtual implant or implant component, virtual anchor, attachment or fixation member, and/or virtual instrument displayed by the OHMD using finger, hand or arm movements which are tracked directly with the one or more image capture or video capture systems and/or 3D scanners, and the surgeon can virtually position, orient, align, superimpose or project the virtual medical device, virtual implant or implant component, virtual anchor, attachment or fixation member, and/or virtual instrument onto the physical anatomy or pathology of the patient, the physical surgical site, a resected tissue, a resected bone or cartilage, a hidden tissue, an area deep inside the tissue, e.g. inside a bone, a physical medical device present in the tissues of the patient and/or any surrounding, adjacent or subjacent tissues. Any of the foregoing embodiments described for assistive tools can also be applied to direct tracking. Changes in position, orientation, alignment, direction and/or speed of movement and/or coordinates of the surgeon's fingers, hands' or arms' can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1.5:1, 2:1, 3:1, 4:1, 5:1 or any other ratio. In this example, the movement of the virtual device, virtual implant, virtual implant component, virtual anchor, attachment or fixation member, virtual instrument and/or virtual surgical tool is smaller than the movement of the surgeon's finger(s), hand(s) or arm(s), which can help the surgeon placing the virtual device, virtual implant, virtual implant component, virtual instrument and/or virtual surgical tool with high accuracy over an intended area, e.g. an implantation site. In another example, changes in position, orientation, alignment, direction and/or speed of movement and/or coordinates of the surgeon's finger(s), hand(s) or arm(s) can optionally be translated into corresponding changes in the position, orientation, alignment, direction and/or speed of movement and/or coordinates of the virtual device, virtual implant, virtual implant component, virtual anchor, attachment or fixation member, virtual instrument or virtual surgical tool with a 1:1.5, 1:2, 1:3, 1:4, 1:5 or any other ratio. In this example, the movement of the virtual device, virtual implant, virtual implant component, virtual anchor, attachment or fixation member, virtual instrument and/or virtual surgical tool is larger than the movement of the surgeon's finger(s), hand(s) or arm(s), which can help the surgeon placing the virtual device, virtual implant, virtual implant component, virtual instrument and/or virtual surgical tool with high speed over an intended area, e.g. an implantation site. The surgeon or an operator can optionally change these ratios. Non-linear ratios can be applied. For example, at the beginning of a virtual placement or alignment or fitting or selection, the movement of the virtual device, virtual implant, virtual implant component, virtual anchor, attachment or fixation member, virtual instrument or virtual surgical tool can intentionally be larger than the movement of the surgeon's finger(s), hand(s) or arm(s) in order to facilitate quick and time efficient placement, alignment and/or evaluation or any of the foregoing steps, including the ones tabulated in Table 15. As the procedure progresses, the movement of the virtual device, virtual implant, virtual implant component, virtual anchor, attachment or fixation member, virtual instrument or virtual surgical tool can intentionally be smaller than the movement of the surgeon's finger(s), hand(s) or arm(s) in order to facilitate accurate and reproducible placement, alignment and/or evaluation or any of the foregoing steps, including the ones tabulated in Table 15.

Alternatively, when the surgeon's finger(s), hand(s) or arm(s) and/or the virtual device, virtual implant, virtual implant component, virtual anchor, attachment or fixation member, virtual instrument or virtual surgical tool is in the periphery of the surgical field or the visual field of the surgeon, the movement of the virtual device, virtual implant, virtual implant component, virtual anchor, attachment or fixation member, virtual instrument or virtual surgical tool can be larger than the movement of the surgeon's finger(s), hand(s) or arm(s) in order to facilitate quick and time efficient placement or movement of the virtual device, virtual implant, virtual implant component, virtual anchor, attachment or fixation member, virtual instrument or virtual surgical tool towards or in the center of the surgical field or visual field of the surgeon. As the surgeon's finger(s), hand(s) or arm(s) and/or the virtual device, virtual implant, virtual implant component, virtual anchor, attachment or fixation member, virtual instrument or virtual surgical tool approaches the center of the surgical field or the visual field of the surgeon, the movement of the virtual device, virtual implant, virtual implant component, virtual anchor, attachment or fixation member, virtual instrument or virtual surgical tool can be smaller than the movement of the assistive tool in order to facilitate accurate and reproducible placement or movement of the virtual device, virtual implant, virtual implant component, virtual anchor, attachment or fixation member, virtual instrument or virtual surgical tool. The ratio, magnitude and speed of change in coordinates can change in a stepwise fashion or a continuous fashion, e.g. based on the location of the surgeon's finger(s), hand(s) or arm(s) and/or the virtual device, virtual implant, virtual implant component, virtual anchor, attachment or fixation member, virtual instrument or virtual surgical tool, e.g. from the periphery to the center of the surgical field and/or the visual field of the surgeon. The change can be automatic, e.g. based on coordinates of the surgeon's finger(s), hand(s) or arm(s) and/or the virtual device, virtual implant, virtual implant component, virtual anchor, attachment or fixation member, virtual instrument or virtual surgical tool in relationship to the surgical field and/or the OHMD, semi-automatic with user interaction, or manual with user interaction only. User interaction can be performed using any of the interfaces described in the specification, e.g. PC based, mouse based, voice based, gesture recognition based etc.

Exemplary, Non-Limiting Dental Applications

With dental implants, dental implant components and all other dental devices, as tabulated for example in Table 15, the virtual placement, virtual fitting and/or selection of a good or best fitting dental implant, dental implant component and/or any other dental device, evaluation of virtual shape with selection of dental implant, dental implant component and all other dental devices with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be performed in relationship to one or more of a crown, e.g. directly visible, enamel, e.g. directly visible, dentin, e.g. directly visible pulp, e.g. hidden inside a tooth, cementum, cementoenamel junction, periodontal ligaments, gingival tissue, alveolar bone, a root, e.g. hidden inside the alveolar bone, a root canal, apical foramina, a cingulum, marginal ridge(s), longitudinal ridge(s), oblique ridge(s), cusp ridge(s), secondary groove(s), auxiliary groove(s), dissectional groove(s), cusp, cusp tip, cusp of Carabelli, pit(s), fossa(s), occlusal table, gingival bulge, imbrication area, a clinical crown, an anatomical crown, central incisor(s), lateral incisor(s), cuspid(s), $1^{st}$ premolar(s), $2^{nd}$ premolar(s), $1^{st}$ molar(s), $2^{nd}$ molar(s), $3^{rd}$ molar(s), an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth, features and/or structures of an existing tooth, e.g. a tooth that the dentist intends to replace or repair or augment, or one or more teeth adjacent or opposite, e.g. in the opposing mandible or maxilla, to a tooth that the dentist intends to replace or repair or augment, e.g. dimensions, curves, curvatures, edges, plateaus, margins, ridges, cusps, grooves, and/or shape and/or color of one or more existing teeth, including a tooth selected for repair, resurfacing or replacement, one or more adjacent teeth and/or one or more opposing teeth on the opposing mandible or maxilla and combinations thereof, a bone shape or bone stock, e.g. a bone shape including anterior, posterior, inferior and/or superior shape and/or curvature(s) of a mandible or a maxilla and/or a bone stock of a mandible or maxilla, a bone density or bone quality, e.g. a bone density and/or a bone quality at or near an intended implantation site in the mandible or maxilla, a void created by a tooth that has been previously lost or extracted or in relationship to tissues remaining in the void, e.g. gingival tissue, alveolar bone, a residual root or root cavity etc., an existing dental implant, dental implant component and/or any other dental device including one or more of an abutment, e.g. a standard abutment or a custom made abutment, a crown, a fixture or implant and any combination thereof, dimensions, curvatures, curves, edges, plateaus, margins, ridges, cusps, grooves, and/or shape of one or more existing implants, implant components, abutments, crowns, fixtures or implants and combinations thereof, virtual data of the patient and/or optionally combined with live data of the patient, e.g. the surgical site or the intended implantation site as seen through a see-through optical head mounted display or a non-see through optical head mounted display, e.g. a virtual reality display, for example using one or more cameras directed at the tooth or teeth for imaging the live data of the patient.

The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to an existing tooth, e.g. a tooth that the dentist intends to replace or repair or augment, or one or more teeth adjacent or opposite, e.g. in the opposing mandible or maxilla, to a tooth that the dentist intends to replace or repair or augment. The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to any of the dimensions, curves, curvatures, edges, plateaus, margins, ridges, cusps, grooves, and/or shape of one or more existing teeth, including a tooth selected for repair, resurfacing or replacement, one or more adjacent teeth and/or one or more opposing teeth on the opposing mandible or maxilla and combinations thereof. The placing and/or aligning can be with regard to any of the anatomic structure(s) or features mentioned in the specification, e.g. a gingival tissue, a gingival bulge, an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth.

The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to a bone shape or bone stock, e.g. a bone shape including anterior, posterior, inferior and/or superior shape and/or curvature(s) of a mandible or a maxilla and/or a bone stock of a mandible or maxilla. The bone shape can be displayed using one or more OHMDs while the dentist or dental surgeon is inspecting the oral cavity and/or the intended implantation site. Similarly, the bone stock can be displayed using one or more OHMDs. The display of the bone stock using one or more OHMDs can assist the surgeon in selecting an appropriate anchor with the dimensions and/or shape and/or fixation mechanism to select to best fit the individual shape of the patient. The OHMD can display the bone shape or geometry or bone stock using, for example, one or more pre- or intra-operative scans, e.g. a CT scan or cone beam CT scan. The one or more pre- or intra-operative scans can be registered with the live data of the patient, for example using any of the registration techniques described in the specification. For example, a patient specific marker can be generated based on a pre-operative scan, e.g. a CT scan or cone beam CT scan, and can be applied to one or more teeth. The coordinates of the patient specific marker applied to the one or more teeth can be determined, for example using an image capture system, if the patient specific marker includes one or more optical markers or LED's or other markers, or, for example, using a navigation system if the patient specific marker includes one or more navigation markers, e.g. IR or RF markers. With the coordinates of the patient specific marker known in the live data of the patient and in the pre-operative scan data of the patient based on which the surfaces and shape of the patient specific marker were derived and the patient specific marker was generated, the live data of the patient and the pre-operative scan data, e.g. of the teeth, mandible, or maxilla or other oral structures can be registered in a common coordinate system. One or more OHMDs can then display the pre-operative scan data or intra-operative scan data superimposed onto and/or aligned with one or more dental structures, e.g. teeth, roots, the mandible or maxilla. The pre- or intra-operative scan data registered to the dental structures or dental anatomy in this manner can include any imaging modality used in dental applications, e.g. x-rays, Panorex, ultrasound, cone beam CT, CT, MRI, 3D scanning, laser scanning etc.

The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to a bone density or bone quality, e.g. a bone density and/or a bone quality at or near an intended implantation site in the mandible or maxilla of the patient. The bone density or bone quality can be displayed by the OHMD, for example using regions of interest highlighted in an optionally co-displayed scan, e.g. a CT scan or x-ray or Panorex. The bone density or bone quality can be displayed by the OHMD using numeric means. The bone density or bone quality can be display using color coding, e.g. with a particular color assigned to normal bone density or bone quality, a different color assigned to bone density or bone quality with a T-score and/or z-score of −1 relative to a reference population, and again other colors assigned to bone density or bone quality with a T-score or z-score of −2, −2.5, −3.0, −3.5 etc. relative to a reference population. The color coding can be superimposed onto a gray-scale image of the patient, e.g. from a CT scan or Panorex. Someone skilled in the art will readily recognize other display means or display combinations for bone density or bone quality. The OHMD display of bone density or bone quality can be useful to the dental surgeon with the placement, selection, fitting, aligning, orienting, of one or more fixtures or implants in relationship to the underlying bone. The information can be combined with information about bone shape and bone stock.

The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to a void created by a tooth that has been previously lost or extracted or in relationship to tissues remaining in the void, e.g. gingival tissue, alveolar bone, a residual root or root cavity etc.

The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to an existing dental implant, dental implant component and/or any other dental device. For example, the dentist can virtually place, fit, and/or select a dental implant to align with an adjacent normal tooth and, optionally, an adjacent, on the other side, existing dental implant. The placing and/or aligning can be with regard to any of the anatomic structure(s) or features mentioned in the specification, e.g. a gingival tissue, a gingival bulge, an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth.

The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to an existing dental implant, dental implant component and/or any other dental device including one or more of an abutment, e.g. a standard abutment or a custom made abutment, a crown, a fixture or implant and any combination thereof. The virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to any of the dimensions, curvatures, curves, edges, plateaus, margins, ridges, cusps, grooves, and/or shape of one or more existing implants, implant components, abutments, crowns, fixtures or implants and combinations thereof; it can also be in combination with existing teeth and soft-tissue and bone including their dimensions, edges, plateaus, margins, ridges, cusps, grooves, and/or shape.

The virtual placement, virtual fitting and/or selection of a good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be in relationship to virtual data of the patient and/or optionally combined with live data of the patient, e.g. the surgical site or the intended implantation site as seen through a see-through optical head mounted display. Such virtual data of the patient can be pre- or intra-operative optical scans, confocal imaging scans, combinations thereof, dental x-rays, Panorex views, cone beam CT scans, CT scans, ultrasound scans and any other scan known in the art and any combination of scans. The virtual data can optionally be registered using any of the methods described in the specification or known in the art.

If the virtual data are of two-dimensional nature, e.g. dental x-rays or Panorex, i.e. panoramic dental x-ray, views, the 2D images can be registered with select anatomic landmarks and, for example, be oriented and projected relative to these landmarks at defined coordinates and/or a defined position and/or orientation and/or angle, e.g. 90 degrees or any other angle and/or tangent and/or intersecting or combinations thereof. For example, if the virtual data include dental x-rays, the one or more dental x-rays can optionally be corrected for magnification and can be aligned with the edge, a surface or any other landmark of a physical tooth, e.g. a tooth identified for potential repair or extraction or an adjacent tooth. The dental x-ray can then be registered with the anatomic landmark, e.g. the edge or surface of the physical tooth and/or a tooth void or combinations thereof, and it can be aligned and/or superimposed in the display to extend through or "touch" the tooth or adjacent teeth, e.g. in a tangent or near tangent or intersecting fashion, e.g. intersecting through the center of the tooth or the superior or inferior, e.g. biting, edge of the tooth, and/or, for example, parallel to a tooth in a plane in front of the tooth, e.g. parallel to a frontal surface of the tooth; in a plane intersecting the center of the tooth, e.g. parallel to the frontal or posterior surface of the tooth or an average of the anterior and posterior surface of the tooth; or in a plane posterior to the tooth, e.g. parallel to the tooth in a plane posterior to the posterior surface of the tooth.

The virtual display of the dental x-rays through the see through optical head mounted display can be aligned with or extend through other anatomic structures, including, for example, the alveolar ridge of the mandible, the body of the mandible or maxilla, a center line or plane, e.g. a curved line or plane, extending through the body of the mandible or maxilla, a line or plane connecting or extending through the base of multiple teeth of the mandible or maxilla, e.g. also curved or multiple flat planes, e.g. one through each tooth or one through every other tooth, a line or plane connecting or extending through the roots of multiple teeth of the mandible or maxilla, a line or plane connecting multiple teeth of the mandible or maxilla, the alveolar process of the maxilla, and any other anatomic structure or combination of structures someone skilled in the art can recognize.

If the virtual data include panorex x-rays, the one or more panorex x-rays can optionally be corrected for magnification and can be aligned with the edge of one or more physical teeth, e.g. teeth identified for potential repair or extraction and/or an adjacent tooth or any of the surface or planes of teeth or related to teeth mentioned in the embodiments, e.g. one or more planes parallel to one or more teeth and, for example, anterior to, posterior to, or intersecting one or more teeth, e.g. in a multi-planar or curved fashion. The panorex x-rays can be aligned with or extend through other anatomic structures, including, for example, the alveolar ridge of the mandible, the body of the mandible or maxilla, a center line or plane, e.g. curved or multi-planar, extending through the body of the mandible or maxilla, a line or plane connecting or extending through the base of multiple teeth of the mandible or maxilla, e.g. curved or multi-planar, a line or plane connecting or extending through the roots of multiple teeth of the mandible or maxilla, e.g. curved or multi-planar, a line or plane connecting multiple teeth of the mandible or maxilla, e.g. curved or multi-planar, the alveolar process of the maxilla, and any other anatomic structure or combination of structures someone skilled in the art can recognize. The panorex x-ray can then be registered with the anatomic landmark(s), e.g. the edge of the physical tooth or teeth or a tooth void or combinations thereof, and it can be aligned in the display to be superimposed onto or to extend through the tooth or adjacent teeth, e.g. in a tangent or near tangent or intersecting fashion, e.g. intersecting through the center of the tooth or the superior or inferior, biting, edge of the tooth, and/or, for example, parallel to a tooth in front of the tooth, in the same plane as the tooth or posterior to the tooth. The panorex x-ray can be aligned at a defined angle, e.g. 90 degrees or any other angle or tangent or intersecting or combinations thereof, aligned with or extending through one or more of the alveolar ridge of the mandible, the body of the mandible or maxilla, a center line or plane, e.g. curved or multi-planar, extending through the body of the mandible or maxilla, a line or plane connecting or extending through the base of multiple teeth of the mandible or maxilla, e.g. curved or multi-planar, a line or plane connecting or extending through the roots of multiple teeth of the mandible or maxilla, e.g. curved or multi-planar, a line or plane connecting multiple teeth of the mandible or maxilla, e.g. curved or multi-planar, the alveolar process of the maxilla, and any other anatomic structure or combination of structures someone skilled in the art can recognize. In this manner, 2D images can be aligned, superimposed and displayed with the physical, live anatomy of the patient. A dentist or dental surgeon can use the information to place, orient or align one or more of a dental implant, dental implant component and/or any other dental device in relationship to the virtual images and/or data and the live, physical anatomy of the patient, e.g. one or more teeth, tooth voids, bone etc.

For example, an optical scan and/or a confocal imaging scan or a combination thereof or a cone beam CT scan or CT scan can be used to generate one or more surfaces, e.g. from one or more teeth and/or a gingiva or gum, and to generate one, two or more patient specific markers that can be placed on one or more teeth, gingiva, dental implants, and/or other landmarks for registering the virtual data with the intra-operative live surgical field of the patient. One or more OHMDs can be registered in the same coordinate system with the live surgical field and the virtual data of the patient.

One or more optical markers, for example with one or more geometric patterns, can be attached to one or more teeth and/or a mandible and/or a maxilla. The optical markers can optionally be attached to known landmarks, e.g. at or along dimensions, curvatures, curves, edges, plateaus, margins, ridges, cusps, grooves, and/or shape of one or more existing teeth and/or dental implants. Alternatively, following the attachment of the one or more optical markers, the location and/or orientation and/or coordinates of one or more landmarks, e.g. dimensions, curvatures, curves, edges, plateaus, margins, ridges, cusps, grooves, and/or shape of one or more existing teeth and/or dental implants, can be defined relative to the optical markers and the landmarks, optical markers and one or more OHMDs can be registered in a common coordinate system.

Optionally, optical markers can be included in a scan with an imaging probe, e.g. like the iTero system offered by Align Technologies, Inc., San Jose, Calif., thereby allowing referencing of one or more anatomic landmarks with the one or more optical markers and registering the one or more optical markers in relationship to the anatomic landmark(s). One or more OHMDs can then be registered relative to the one or more optical markers, e.g. for display of a virtual surgical plan, e.g. defined intra-operatively or pre-operatively. The imaging probe can be an optical imaging system, it can be a confocal imaging system or combinations thereof. In addition to registering one or more OHMDs relative to the optical markers, one or more pre- or intra-operative scans, optionally paired with virtual surgical plan information, data or displays, can also be registered in the same coordinate system, e.g. for display by one or more OHMDs.

Optionally, optical markers with geometric patterns can include one or more radiopaque elements and/or can be referenced to one or more radiopaque markers or elements at the same location/coordinates or at a different location/coordinates. The optical markers and the one or more radiopaque elements can optionally be included in a pre- or intra-operative scan, e.g. dental x-rays, a Panorex scan, a CT scan or a cone beam CT scan. Since the spatial coordinates of the one or more optical markers are known in relationship to the one or more radiopaque elements and in relationship to the teeth or underlying bone based on the scan or imaging data, by including the optical markers and the radiopaque elements in the pre- or intra-operative scan, pre- and intra-operative data including live data, e.g. the intended implantation site, can be referenced and registered in the same coordinate system. This registration can include any virtual surgical plan aspects and/or data including the display of one or more virtual surgical plan data by one or more OHMDs. Someone skilled in the art will recognize that other markers can be used, e.g. navigation markers, i.e. RF or IR markers, LED's, optionally with integrated or attached radiopaque elements so that the markers can be detected on imaging studies that include ionizing radiation.

Optionally, optical markers and/or other markers, e.g. navigation markers, can be attached to the dental chair or headrest in which the patient is sitting and/or resting and the dental chair and/or headrest can be registered in the same coordinate system. Movement of one or more OHMDs can be measured in relationship to the dental chair and/or headrest and the coordinate system and the display by the OHMD can be adjusted so that it remains stationary relative to a surgical site and/or an intended implantation site, e.g. aligned with and/or superimposed onto an intended implantation site, even while the dentist or dental surgeon is moving his or her head and the OHMD.

Any of the registration techniques described in the specification can be used, including, but not limited to the use of navigation markers, e.g. RF or infrared markers, attached to dental or oral anatomy, using a navigation system, LED markers, e.g. used in conjunction with an imaging system integrated into, attached to or separate from an OHMD, spatial mapping by one or more imaging systems integrated into, attached to or separate from one or more OHMDs, laser scanning, confocal imaging, and/or IMU's. With any of the registration techniques, one or more OHMDs can also be registered in a coordinate system with the intended surgical site or implantation site.

In embodiments, a pre-operative and/or an intra-operative scan, e.g. an optical scan and/or confocal imaging scan of the patient's teeth and gums and surrounding tissue and/or a CT scan and/or cone beam CT scan and/or Panorex and/or dental x-rays and/or combinations thereof can be used to determine a virtual surgical plan. The virtual surgical plan can use or can be based on any of the dental or oral structures listed in the specification. The virtual surgical plan can include determining and/or defining one or more virtual axes, e.g. a drilling axis, and/or one or more predetermined virtual orientation and/or virtual alignment of a dental implant, dental implant component and/or any other dental device, e.g. in relationship to one or more of an existing tooth selected for repair or replacement, a void or cavity in the area of a previously lost or extracted tooth, adjacent teeth, opposing teeth, gingiva and other soft-tissues in the area of a tooth selected for repair or replacement, gingiva and other soft-tissues in the area of a void or cavity in the area of a previously lost or extracted tooth, gingiva and other soft-tissues in the area of adjacent or opposing teeth, underlying bone, e.g. in the area of a tooth selected for repair or replacement or in the area of a previously lost or extracted tooth and/or in the area of adjacent teeth or opposing teeth. Underlying bone can, for example, be located in the mandible or the maxilla. The virtual surgical plan can include planning and placement of a virtual bone graft and related attachment followed by placement and/or alignment of dental implant, dental implant component and/or any other dental device in relationship to the virtual bone graft and underlying bone.

The virtual surgical plan can include determining and/or defining the depth of placement of a dental implant, dental implant component and/or any other dental device, e.g. in relationship to one or more of an existing tooth selected for repair or replacement, a void or cavity in the area of a previously lost or extracted tooth, adjacent teeth, opposing teeth, gingiva and other soft-tissues in the area of a tooth selected for repair or replacement, gingiva and other soft-tissues in the area of a void or cavity in the area of a previously lost or extracted tooth, gingiva and other soft-tissues in the area of adjacent or opposing teeth, underlying bone, e.g. in the area of a tooth selected for repair or replacement or in the area of a previously lost or extracted tooth and/or in the area of adjacent teeth or opposing teeth. The depth of placement can be planned based on any of the foregoing information, including, for example, underlying bone, including width, depth, dimensions, thickness; bone stock; bone density and/or bone quality. The desired depth of placement and any of the other, foregoing and following information in the specification can be used to select an anchor or fixation system or implant from a library of anchors, fixation systems or implants. The desired depth of placement, optionally paired with some of the other information, e.g. dimensions, curvatures, curves, edges, plateaus, margins, ridges, cusps, grooves, and/or shape of one or more existing teeth and/or implants, can be used to select a combination of a crown, an abutment, a fixture or implant.

The virtual surgical plan can include determining and/or selecting a size and/or shape of a dental implant, dental implant component and/or any other dental device, e.g. in relationship to one or more of an existing tooth selected for repair or replacement, a void or cavity in the area of a previously lost or extracted tooth, adjacent teeth, opposing teeth, gingiva and other soft-tissues in the area of a tooth selected for repair or replacement, gingiva and other soft-tissues in the area of a void or cavity in the area of a previously lost or extracted tooth, gingiva and other soft-tissues in the area of adjacent or opposing teeth, underlying bone, e.g. in the area of a tooth selected for repair or replacement or in the area of a previously lost or extracted tooth and/or in the area of adjacent teeth or opposing teeth. The determining and/or selecting a size and/or shape of a dental implant, dental implant component and/or any other dental device can be planned based on any of the foregoing and/or following information, including, for example, underlying bone including bone shape and geometry, bone stock, bone density and/or bone quality, e.g. derived from scan data or imaging data.

The determining and/or selecting a size and/or shape of a dental implant, dental implant component and/or any other dental device can utilize any information related to dimensions, curvatures, curves, edges, plateaus, margins, ridges, cusps, grooves, and/or shape of one or more existing teeth, e.g. intended for repair or extraction, adjacent teeth or opposing teeth, e.g. derived from one or more scan data or imaging data.

The determining and/or selecting a size and/or shape of a dental implant, dental implant component and/or any other dental device can utilize any information related to dimensions, curvatures, curves, edges, plateaus, margins, ridges, cusps, grooves, and/or shape of one or more existing implants, implant components, abutments, crowns, fixtures or implants and combinations thereof, e.g. derived from scan data or imaging data.

The determining and/or selecting a size and/or shape of a dental implant, dental implant component and/or any other dental device can utilize information, including dimensions, shape, geometry and any other information from any dental or oral structures mentioned in the specification. The determining and/or selecting a size and/or shape of a dental implant, dental implant component and/or any other dental device can utilize any combination of information related to shape, dimensions, curvatures, curves, edges, plateaus, margins, ridges, cusps, grooves, of one or more existing implants, implant components, abutments, crowns, fixtures or implants and combinations thereof, and/or information related to underlying or opposing bone and/or information related to existing teeth and/or voids and/or soft-tissues including gingiva in the area of a tooth intended for repair or extraction, in the area of a tooth void or gap, and/or in the area of adjacent or opposing teeth, e.g. derived from scan data or imaging data.

The determining and/or selecting a size and/or shape of a dental implant, dental implant component and/or any other dental device can include selecting an anchor or fixation system or implant from a library of anchors, fixation systems or implants. The determining and/or selecting a size and/or shape of a dental implant, dental implant component and/or any other dental device can include selecting a crown, an abutment, a fixation system or implant from a library of crowns, abutments, fixation systems or implants. The determining and/or selecting a size and/or shape of a dental implant, dental implant component and/or any other dental device, optionally paired with some of the other information, e.g. dimensions, curvatures, curves, edges, plateaus, margins, ridges, cusps, grooves, and/or shape of one or more existing teeth and/or implants, can include selecting a combination of a crown, an abutment, a fixture or implant based on some of the information.

In some embodiments, virtual data can have the same magnification as the live data of the patient, e.g. a surgical site or intended implantation site. In some embodiments, virtual data can have a lower magnification, e.g. be smaller than, or higher magnification, e.g. be larger than, live data of the patient, e.g. a surgical site or an intended implantation site. Virtual data can, for example, be a predetermined axis, e.g. an intended or predetermined implant axis or drilling axis. Virtual data, can, for example, be a predetermined depth indicator, e.g. indicating where a drill should stop for a given patient, patient anatomy, bone dimension or shape, bone stock and/or implant size. Virtual data can include a virtually placed or aligned implant. When virtual data are magnified, optionally, pre- or intra-operative imaging data of the patient can also be magnified. Such imaging data can include an optical scan, a confocal imaging scan, x-rays, Panorex, CT and/or cone beam CT, ultrasound and/or other data. Optionally, live data of the patient can also be imaged using, for example, an image capture or video capture system or a 3D scanner or laser scanner. The magnification of different types of virtual data and/or imaging data can be the same. The magnification of different types of virtual data and/or imaging data can be different. When magnification is used, magnification can be linear or non-linear and can occur around select center of magnification points and/or select center of magnification axes, which can, for example, be an intended drilling axis or a predetermined implant axis, e.g. in spinal surgery a predetermined axis for placement of a pedicle screw. Optionally, when magnification of virtual data is used, e.g. a virtual drilling or implant axis and/or virtual imaging studies, optionally, live data seen though the see-through OHMD can be blended out, e.g. via electronic or other filters. When live data are blended out, they can optionally be replaced with images of the live patient, e.g. the surgical field or intended implantation site, acquired with one or more camera, image capture or video systems, an optical scanner, a confocal scanner, a 3D laser scanner and other imaging means; such image data of the live patient, e.g. the surgical field or intended implantation site, can optionally be displayed with the same magnification as the virtual data, e.g. a virtual predetermined implant axis or a virtual predetermined drilling axis. Any embodiment in the specification regarding magnification, minification, magnified and/or minified displays can be applied to the display of dental data including of a dental implant, dental implant component and/or any other dental device.

In embodiments, a dentist, dental surgeon or dental assistant can pre-operatively or intra-operatively place, align, orient, fit, select one or more virtual dental implant, virtual dental implant component and/or any other virtual dental device in the oral cavity of the patient at the intended implantation site. The moving, placing, orienting, aligning, fitting and/or selecting can be performed using a PC based interface and any other interface described in the specification or known in the art, including, for example, voice recognition and/or voice commands, virtual interfaces, e.g. using gesture recognition, and/or assistive tools. For example, in a pre-operative session or an intra-operative session with the patient, the dentist, dental surgeon or dental assistant can virtually move, place, align, orient, fit and/or select one or more virtual dental implant, virtual dental implant component and/or any other virtual dental device, e.g. by moving it and/or aligning it with a void created by a previously lost or extracted tooth; the dentist, dental surgeon or dental assistant can virtually move, place, align, orient, fit and/or select one or more virtual dental implant, virtual dental implant component and/or any other virtual dental device, e.g. by moving it and/or aligning it with a tooth intended for repair or replacement; the dentist, dental surgeon or dental assistant can virtually move, place, align, orient, fit and/or select one or more virtual dental implant, virtual dental implant component and/or any other virtual dental device, e.g. by moving it and/or aligning it with one or more teeth adjacent to an intended implantation or surgical site or opposing an intended implantation or surgical site. Optionally, the dentist, dental surgeon and/or dental assistant can move, place, orient, align, fit and/or select the one or more virtual dental implant, virtual dental implant component and/or any other virtual dental device to make it tangent with or orthogonal with or at a defined angle with or intersecting with any of the dental or oral structures mentioned in the specification. Optionally, the dentist, dental surgeon and/or dental assistant can move, place, orient, align, fit and/or select the one or more virtual dental implant, virtual dental implant component and/or any other virtual dental device to make it tangent with or orthogonal with or at a defined angle with or intersecting with one or more dimensions, curvatures, curves, edges, plateaus, margins, ridges, cusps, grooves, and/or shape of one or more existing teeth, e.g. a tooth intended for repair or replacement, or teeth adjacent to or opposing an intended implantation site, and/or existing implants, implant components, abutments, crowns, fixtures or implants, and/or soft-tissue features or shape, e.g. gingival shape, and combinations thereof. Optionally, virtual data, e.g. a pre-operative scan or intra-operative scan, can be co-displayed during the placement, orientation, alignment, fitting and/or selection of the one or more virtual dental implants, virtual dental implant components and/or other virtual dental devices. The virtual movement, placement, fitting, sizing, alignment, of the one or more virtual dental implant, virtual dental implant component and/or any other virtual dental device can be performed on a PC or server, e.g. with one or more built in processors, memory, one or more monitors, or using one or more optical head mounted displays, optionally connected to a PC or server, which can also include one or more processors. The virtual movement, placement, fitting, sizing, alignment can be performed using one or more user interfaces, e.g. a first, second, third and fourth or more interface, for different functions. Some interfaces can optionally address multiple functions, e.g. fitting and sizing, or moving and aligning etc.

Once the dentist, dental surgeon or dental assistant is satisfied with the placement, orientation, alignment, fit and/or selection, the coordinates of the one or more virtual dental implant, virtual dental implant component and/or any other virtual dental device can be saved and can be entered into a virtual surgical plan and/or can be used to derive or modify a virtual surgical plan. The virtual surgical plan, its components, aspects and steps can then be displayed during the surgical or dental procedure by one or more OHMDs, e.g. registered with the surgical field and/or intended implantation site and/or the bone and/or other teeth, aligned with, superimposed onto the surgical field and/or intended implantation site, and the surgeon can align the physical instruments and/or implant components with the aspects of the virtual surgical plan. For example, the surgeon can align a physical drill with an intended, predetermined virtual drilling axis or virtual implant axis displayed by the OHMD over the intended implantation site with the predetermined coordinates, e.g. with or without magnification. The virtual surgical plan can, for example, include virtual surgical guides, which can be 3D representations of physical surgical guides or placement indicators of physical surgical guides or combinations thereof. A virtual surgical guide can be a virtual cut plane. A virtual surgical guide can be a virtual axis, e.g. a drilling axis. The virtual surgical plan can also include virtual tools or virtual instruments, e.g. corresponding in at least some aspects, features dimensions or shape to physical tools or physical instruments. The virtual surgical plan can also include virtual implants and implant components, e.g. corresponding in at least some aspects, features, dimensions or shape to physical implants and implant components. The physical implants and implant components, e.g. crowns, screws, abutments and fixtures, can be available in a defined range of sizes and shapes, e.g. in a library of physical implants and implant components. A library of virtual implants and implant components corresponding to the physical implants and implant components can be available for display by the OHMD. The virtual surgical guides, virtual tools, virtual instruments and/or virtual implants or implant components can be displayed by one or more OHMDs during the dental or oral surgery procedure, for example superimposed onto the surgical site and, optionally, registered with the surgical site in a common coordinate system. By registering the virtual surgical plan and/or the virtual surgical guides, virtual tools, virtual instruments and/or virtual implants or implant components with the surgical site, which, in this example, can include any of the dental or oral structures mentioned in the specification, it is possible to maintain the display of the virtual surgical guide(s), virtual tool(s), virtual instrument(s) and/or virtual implant(s) or implant component(s) superimposed onto the surgical site, including any of the dental or oral structures mentioned in the specification, with the teeth occluded and/or, optionally, with the mouth open and the teeth not occluded.

The OHMD can be a see through OHMD or a non-see through OHMD, optionally with one or more video cameras integrated or attached to the OHMD for imaging the live data of the patient or optionally with one or more 3D scanners integrated or attached to the OHMD for imaging the live data of the patient.

In some embodiments, the dentist, dental surgeon, and/or dental assistant can perform the placing, aligning, orienting, fitting, selecting one or more virtual dental implant, virtual dental implant component and/or any other virtual dental device in the oral cavity of the patient at the intended implantation site with the mouth open and the teeth not occluded. Using registration techniques described in the specification, for example with registration of the site, e.g. mandible or maxilla, of the intended dental or oral or surgical intervention, or, for example, using registration of both mandible and maxilla, placing, aligning, orienting, fitting, selecting one or more virtual dental implant, virtual dental implant component and/or any other virtual dental device in the oral cavity of the patient at the intended implantation site can be evaluated visually using the display of one or more OHMDs with the teeth not occluded and/or occluded, thereby allowing the placing, aligning, orienting, fitting, selecting one or more virtual dental implant, virtual dental implant component and/or any other virtual dental device in the oral cavity of the patient at the intended implantation site both in open and in occluded position of the teeth. This type of functional assessment can be helpful to optimize the placing, aligning, orienting, fitting, selecting one or more virtual dental implant, virtual dental implant component and/or any other virtual dental device in the oral cavity of the patient at the intended implantation site for the patient's bite and can help to optimize the resultant open tooth position and occlusion, e.g. with the final physical dental implant, physical dental implant component or physical dental device placed using the virtual surgical plan and/or data developed, derived or modified using the placing, aligning, orienting, fitting, selecting of the one or more virtual dental implant, virtual dental implant component and/or any other virtual dental device in the oral cavity of the patient at the intended implantation site in open and occluded position.

The virtual surgical plan, virtual placement, virtual fitting and/or selection of good or best fitting dental implant, dental implant component and/or any other dental device, evaluation of virtual shape with selection of dental implant, dental implant component and/or any other dental device with preferred shape, evaluation of virtual function with selection of dental implant, dental implant component and/or any other dental device with preferred function, determination of preferred virtual orientation, determination of preferred virtual alignment, determination and/or selection of preferred virtual anchor and/or attachment and/or fixation member can be performed using any of the embodiments in the specification and any combination of embodiments, e.g. OHMD display techniques, magnification techniques, registration techniques, inside-out tracking, spatial mapping, optical markers with geometric patterns, etc.

All embodiments related to teeth, dental tissue, dental structures and/or related imaging and use of one or more optical head mounted displays for displaying virtual data of the patient or virtual tools, virtual instruments, virtual implants, virtual surgical plans, e.g. predetermined paths, predetermined drill paths, predetermined start or end points, are applicable to a range of dental procedures which include, but are not limited to, dental implant procedures and treatment of root canals.

For example, with root canals, a standard drill can be used access the inside of the tooth. An imaging study can be obtained prior to the procedure, which can, for example, be an x-ray, a Panorex, a CT scan, a cone beam CT scan, or an MRI. Using one or more markers, e.g. optical markers, navigation markers, for example RF or IR markers, or other markers, or using a 3D scanner or image capture system, the tooth and/or dental or oral structures can be registered in a coordinate system and the pre-operative imaging study, an optional virtual surgical plan and any optional graphical representations or 3D representations of one or more virtual tools, virtual instruments, virtual implants, virtual surgical plans [which can include predetermined paths, predetermined drill paths, predetermined start or end points, predetermined depth stops] and one or more OHMDs can be registered in the same coordinate system using any of the registration techniques described in the specification or known in the art. The virtual data of the patient, e.g. data from the pre-operative or an intra-operative imaging study, an optional virtual surgical plan and any optional graphical representations or 3D representations of one or more virtual tools, virtual instruments, virtual implants, virtual surgical plans, e.g. predetermined paths, predetermined drill paths, predetermined start or end points can then be aligned with and superimposed onto the corresponding anatomy of the patient, e.g. in the intended surgical site for a dental implant or the intended tooth or location for a root canal. The optional virtual surgical plan and any optional graphical representations or 3D representations of one or more virtual tools, virtual instruments, virtual implants, virtual surgical plans, e.g. predetermined paths, predetermined drill paths, predetermined start or end points can be superimposed onto and aligned with the surface of the tooth or dental tissue, e.g. gingiva, enamel, cementum. The imaging study can be displayed superimposed onto and aligned with the corresponding anatomic structures, for example underneath the gingiva or gums and/or for example inside the mandible or maxilla of the patient. The imaging study can, for example, show one or more roots. Buy displaying the one or more roots, including roots affected by decay, and any decay, image guidance can be used to minimize the amount of healthy tooth or dental tissue removed, e.g. enamel, dentin, pulp, cementum, healthy root or root portions. For example, the dentist can direct a drill using the superimposed image guidance using the OHMD to the damaged or diseased portions of the tooth or root, while avoiding health portions. Optionally, the display of normal or healthy and abnormal or pathologic tissue with the superimposed and/or aligned imaging study in the OHMD display can be paired with the display of portions of a virtual surgical plan, e.g. including one or more virtual tools, virtual instruments, virtual implants, virtual surgical plans, e.g. predetermined paths, predetermined drill paths, and/or predetermined start or end points, optionally projected onto the surface of the tooth and the dental tissue, e.g. gingiva, and/or optionally also projected underneath the surface of the tooth and dental tissue, e.g. gingiva, e.g. projected together with or separate from subsurface imaging data. Optionally, physical tools, instruments, implants and other devices can be tracked using any of the techniques described in the specification and known in the art and tracking data can be displayed by the one or more OHMDs. For example, if a tracked physical tool, e.g. a drill, instrument, implant or other device is aligned with the virtual tool, instrument, implant or device, the OHMD can give an indication to that effect, e.g. a display of the virtual tool, instrument, implant or device with a predetermined color, e.g. green, or an acoustic or other signal or indication. If the tracked physical tool, e.g. a drill, instrument, implant or device deviates from the predetermined position, location, orientation, alignment or direction of movement of the virtual tool, instrument, implant or device or virtual surgical plan, the OHMD can provide a warning, e.g. a display of the virtual tool, instrument, implant or device with a predetermined color, e.g. red, or a change in color. The OHMD can also provide acoustic warning signals. The OHMD can also indicate the percentage time that the tracked physical tool, e.g. a drill, instrument, implant or other device is aligned with the corresponding virtual tool, virtual instrument, virtual implant or virtual other device and it can provide an indication of the error or deviation in mm and/or the error or deviation in degrees, for example in form of a numerical value or a scale.

With treatment of one or more root canals, the dentist or oral surgeon can use a round drill, e.g. operating at lower speed, to remove decay and to expose root canal(s). One or more OHMDs can optionally display a predetermined path for the round drill and any other drills. The predetermined path can be projected onto the surface of the tooth and dental tissue, e.g. gingiva. The predetermined path can also be projected underneath the surface of the tooth or dental tissue, e.g. gingiva, i.e. in hidden areas or subsurface areas of the oral cavity. The predetermined path can be co-displayed with an imaging study. Alternatively, the surgeon can use only a display of the pre- or intra-operative imaging study superimposed onto and aligned with corresponding anatomic structures hidden below the surface, e.g. the surface of the tooth or dental tissue, e.g. gingiva. The imaging study can, for example, show the root of the tooth, any decay, damaged or diseased tissue, any areas of bone resorption, and/or mandibular or maxillary bone. Optionally, if the physical tool, e.g. a drill, physical instrument, physical implant or physical device is tracked using any of the techniques described in the specification or known in the art, and the geometry of the physical tool, e.g. a drill, physical instrument, physical implant or physical device is known, the portions of the physical tool, e.g. a drill, physical instrument, physical implant or physical device hidden inside the tissue, e.g. hidden inside the tooth, can also be displayed by the one or more OHMDs, for example with a co-display of the virtual surgical plan, virtual drill path, predetermined path, predetermined drill path, virtual tool, virtual instrument, virtual implant and/or virtual device, showing, for example, any potential deviations from a predetermined location, position, orientation, angulation or direction of movement. The portions of the physical tool, e.g. a drill, physical instrument, physical implant or physical device hidden inside the tissue, e.g. hidden inside the tooth, can also be displayed by the one or more OHMDs, for example with a co-display of a pre-operative imaging study, for example showing areas of health and/or diseased tissue, e.g. decay. The portions of the physical tool, e.g. a drill, physical instrument, physical implant or physical device hidden inside the tissue, e.g. hidden inside the tooth, can also be displayed by the one or more OHMDs, for example with a co-display of the virtual surgical plan, virtual drill path, predetermined path, predetermined drill path, virtual tool, virtual instrument, virtual implant and/or virtual device, showing, for example, any potential deviations from a predetermined location, position, orientation, angulation or direction of movement and it can be optionally simultaneously be co-displayed with the pre-operative imaging study, for example showing areas of health and/or diseased tissue, e.g. decay.

OHMD guidance can also be used for direction and/or aligning and/or superimposing one or more files for removing the contents of a root canal, e.g. by displaying virtual data showing, for example, a predetermined path or a predetermined stop, e.g. a depth stop, and/or imaging data, e.g. showing a root and/or other and/or surrounding dental tissue including damaged tissue or decay. The predetermined path can be projected onto the surface of the tooth and dental structures, e.g. gingiva. The predetermined path can be projected inside the tooth, root, and or mandibular or maxillary bone.

The OHMD display can provide virtual guidance by display virtual data for superimposing and/or aligning one or more different files, e.g. with different file sizes used for cleaning and shaping the root canal(s). For example, the physical files can be aligned with a virtual axis for the predetermined position and/or orientation and/or direction of travel of the file; or, alternatively, the OHMD can display a pre- or intra-operative image showing the tooth and/or root canal for aligning one or more files with the tooth and/or root canal. The virtual display can include graphical representations, e.g. predetermined start points, predetermined end points, a predetermined axis, a predetermined stop etc. Any of the foregoing and following embodiments can also be applied for cleaning and shaping the tooth's canal or root canal to enlarge and/or flare the canal using one or more tools using OHMD guidance, e.g. by superimposing a preor intra-operative imaging study showing the root canal and, optionally, an intended or predetermined size or dimension or margin after flaring and/or other virtual data, e.g. virtual tools or virtual flares. Virtual data for guiding the placement of one or more physical tools or physical flares can also include a predetermined path or a predetermined stop, e.g. a depth stop, superimposed onto and/or aligned with the physical root and/or the root as seen on an imaging study superimposed onto and/or aligned with the corresponding physical anatomy, e.g. a root or mandibular or maxillary bone.

Any of the foregoing and following embodiments can also be applied for placing one or more cones using OHMD guidance and for evaluating cone size and root filling, e.g. by superimposing a pre- or intra-operative imaging study and/or other virtual data, e.g. virtual cones with the size and/or shape corresponding to the size and/or shape of the physical cones used. Virtual data for guiding the placement of one or more cones can also include a predetermined path or a predetermined stop, e.g. a depth stop, superimposed onto and/or aligned with the physical root and/or the root as seen on an imaging study superimposed onto and/or aligned with the corresponding physical anatomy, e.g. a root or mandibular or maxillary bone.

OHMD guidance, e.g. using a superimposed imaging study and/or virtual data such as a display of a virtual tool, instrument, implant or device, which can include virtual cone(s), can be used to guide the use of a heating or heated instrument for removing excess cone portions and for optionally compacting cones and/or the filling of the root canal(s).

OHMD guidance, e.g. using a superimposed imaging study and/or virtual data such as a display of a virtual tool, instrument, implant or device, which can include one or more virtual post(s) [e.g. in a predetermined position inside the tooth] or a predetermined path or a predetermined stop, e.g. a depth stop, can be used for directing the placement, position and/or orientation of a physical post inside the tooth, extending, for example, partially into the root canal(s) to strengthen the tooth and to retain the filling.

OHMD guidance, e.g. using a superimposed imaging study and/or superimposed virtual data such as a display of a virtual tool, e.g. a burr or a mill, a virtual instrument, virtual implant or virtual device, or a predetermined path or a predetermined stop, e.g. a depth stop, or a predetermined tissue [e.g. enamel or dentin] removal or a predetermined tissue removal depth can be used for optional shaving and/or milling of a tooth, for example to prepare for placement of a crown or cap. The virtual data can be displayed by the OHMD superimposed onto the surface of the tooth or dental tissue, e.g. enamel or gingiva, and/or it can be displayed inside the tooth, e.g. indicating the amount of enamel or dentin to be removed. The virtual data can be a predetermined path or a predetermined stop or a predetermined end surface for a shaver, a burr or a mill or other dental instrument; the predetermined path can be aligned with and superimposed onto the surface of the tooth, e.g. the enamel; the predetermined stop or predetermined end surface can be projected inside the tooth, e.g. the enamel or dentin.

In some embodiments, the OHMD can display a target or a target like display, for example using two or more concentric rings, optionally, with a central dot or point, projected onto and/or aligned with the surface of the tooth, for example to guide a drill to a predetermined start point, wherein the predetermined start point is represented by the center of the target or target like display. In some embodiments, the OHMD can display a target or a target like display, for example using two or more concentric rings, optionally, with a central dot or point, aligned with a subsurface portion of a tooth, e.g. a root [for example the deepest ending of a root] for example to guide a drill to a predetermined end point or for aligning a drill while advancing it through a tooth, wherein the predetermined end point is represented by the center of the target or target like display.

Such a display can be advantageous when the dentist is looking at the tooth from the top; the OHMD display can show the dentist if the physical drill or instrument is aligned with the center of the virtual target or off center, not aligned with the virtual target. Optionally, the OHMD display can simultaneously show a sagittal view and/or coronal view with an imaging study and/or the tracked drill simultaneously displayed, e.g. in another part of the view area of the OHMD display, not directly superimposed onto directly visible physical tooth and target like image. The sagittal and/or coronal view and/or the superimposed tracked portions of the physical drill or instruments can optionally be magnified. The target or target like display can optionally also be magnified, which can assist the dentist in aiming the physical drill or instrument towards the center of the target.

Optionally, when the dentist is looking from the front of a tooth, the OHMD display can show a superimposed imaging study with the tooth and/or root canal(s) visible on the imaging study and superimposed onto the surface of the directly visible portions of the tooth and the subsurface portions of the tooth [e.g. a physical root or cementum]. The imaging study can be projected, for example, in a plane substantially parallel to the frontal or external facing plane of the tooth, e.g. a coronal plane for incisors or a sagittal plane for molars. The OHMD display can optionally simultaneously show a sagittal view and/or a coronal and/or an axial or top down view, with optional target or target like appearance, with an imaging study and/or the tracked portions of the drill, hidden inside the tooth, simultaneously displayed, e.g. in another part of the OHMD, not directly superimposed onto directly visible physical tooth and, in this example, target like image. For example, if two or more imaging planes are shown by the OHMD display, a first plane most closely resembling the view perspective of the surgeon, e.g. a plane substantially parallel to the frontal plane of the face of the surgeon, can be displayed in the imaging data of the patient superimposed onto and/or aligned with the visible portions of the tooth and/or dental tissue, e.g. enamel or gingiva, and/or superimposed and/or aligned with subsurface portions of the tooth, root, mandible or maxilla; optionally the virtual data [e.g. a target or endpoint or drill path] including any portions of one or more tracked tools [e.g. drills] or instruments hidden inside the tissue can be displayed using magnification. A second and third imaging plane, e.g. a plane orthogonal or at any other angle to the first plane, can be shown not superimposed onto the visible portions of the tooth and/or dental tissue, e.g. enamel or gingiva, and/or not superimposed onto subsurface portions of the tooth, root, mandible or maxilla, e.g. in other areas of the field of view of the OHMD display. Optionally, the virtual data [e.g. a target or endpoint or drill path] including any portions of one or more tracked tools [e.g. drills] or instruments hidden inside the tissue can be displayed in such additional display fields using magnification. In any of these and the following embodiments, superimposition of an imaging study, e.g. cone beam CT, can help identify all root canals that might otherwise be overlooked by the naked eye.

If tooth is in a difficult to access or visualize area and the dentist uses a mirror to visualize portions of a tooth, e.g. an area for a predetermined start point or entry for a drill, the tooth, any adjacent teeth or dental tissue or structures and/or the mirror can optionally include one or more optical markers, navigation markers, e.g. RF and/or IR markers. The position, location, orientation and/or alignment (e.g. x, y, z coordinates) of the tooth and/or the mirror can be registered in a common coordinate system along with one or more OHMDs and, optionally, tracked surgical instruments, e.g. drills (which can also include one or more markers, navigation markers, e.g. RF and/or IR markers). Using this approach, the position, location, orientation and/or alignment and/or coordinates of the mirror in relationship to the tooth and/or dental or oral structures (e.g. gingiva or enamel) and one or more OHMDs can be determined. Alternatively, the registration of the tooth and/or dental or oral structures and/or mirror can be determined and/or tracked using a 3D scanner or an image or video capture system.

One or more computer processors can then be used to display the OHMD information, e.g. an imaging study and/or other virtual data [e.g. portions of a virtual surgical plan, a virtual drill path, a predetermined path, a predetermined drill path, a predetermined start point, a predetermined end point, a predetermined depth stop, a virtual tool, a virtual instrument, a virtual implant and/or a virtual device] superimposed with and/or aligned with the reflected image or mirror image of the physical tooth and/or dental or oral structures visible in the mirror. Since left and right or superior and inferior relationships can be reversed in the mirror image of the physical tooth and/or dental structure depending how the dentist holds the mirror relative to the tooth or dental structure, the computer processor can reverse sides or superior and inferior relationships and "flip" [e.g. left to right or superior to inferior or 180 degrees] or "mirror image" the virtual data including any pre- or intra-operative imaging studies and/or a virtual surgical plan, a virtual tool, e.g. a drill, a burr or a mill, a virtual instrument, virtual implant or virtual device, or a predetermined path or a predetermined stop, e.g. a depth stop, or a predetermined tissue [e.g. enamel or dentin] removal or a predetermined tissue removal depth to match the virtual data and align and superimpose the virtual data with the mirror image of the patient's tooth and/or dental structures. If the mirror provides for magnification of the reflected image of the physical tooth and/or dental structures, the OHMD display can optionally also magnify the displayed virtual data and/or imaging study, e.g. using the same or a different magnification including lower magnification or higher magnification. If the dentists remove the mirror from the field of view, the OHMD display can optionally then display the virtual data and/or information directly superimposed with and/or aligned with the visible portions of the physical tooth and/or any subsurface portions of the physical tooth [e.g. using normal, non-reversed orientation]. A computer processor configured to analyze imaging data, e.g. from a video feed from an image capture system and/or video system integrated into, attached to or separate from the OHMD, can be used to detect if the mirror is present or has been removed, e.g. by detecting the presence or absence of one or more markers attached to the mirror, e.g. an optical marker, a navigation marker, an LED, and/or one or more IMU's. Optionally, if the physical tooth is directly visible and the dentist is also using a mirror for visualization of the tooth and/or dental structures, the OHMD display can display the virtual data superimposed with and aligned with the physical tooth and physical dental structures and/or any subsurface portions of the physical tooth, e.g. in non-flipped or reversed fashion, and, in a different part of the visual field, it can display the virtual data superimposed with and aligned with the image of the physical tooth and/or dental or oral structures visible in the mirror, e.g. in flipped or reversed fashion.

In some embodiments, an imaging study, e.g. obtained prior to or shortly before or at the time of the dental procedure, for example a dental x-ray, a Panorex, a cone beam CT scan, and/or a CT scan, can be displayed by the one or more OHMDs, for example superimposed onto and/or aligned with a physical tooth, physical root, physical mandible or maxilla. Optionally, the imaging study can be displayed by the one or more OHMDs superimposed, for example, with a central plane of the mandible or maxilla or a central plane extending through one or more teeth; this can be useful, for example, when the one or more OHMDs project a 2D x-ray or a Panorex film. Optionally, a computer processor configured to display the imaging study in the one or more OHMDs can apply an offset, projecting the imaging study, for example 0.5 cm, 1 cm, 1.5 cm or any other distance anterior or posterior, medial or lateral, superior or inferior to the gum, tooth, mandible or maxilla or any other anatomic structure.

In some embodiments, a virtual surgical guide can be projected by the one or more OHMDs, for example on the surface of a tooth, directly and, simultaneously, the virtual surgical can be projected onto a mirror image projected by a mirror held by the dentist or dental assistant in the oral cavity; thus, two virtual surgical guides can be projected, one being the virtual surgical guide with, for example, one or more dimensions or axes substantially matching a physical surgical guide or instrument, the other being a mirror image of the virtual surgical guide. The virtual surgical guide can be a virtual axis, e.g. for directing a drill. Thus, a virtual axis can be projected by the one or more OHMDs, for example on the surface of a tooth, directly and, simultaneously, the virtual axis can be projected onto a mirror image projected by a mirror held by the dentist or dental assistant in the oral cavity; thus, two virtual axes can be projected, one being the virtual axis to which the physical drill or instrument needs to be aligned, the other being a mirror image of the virtual axis to which the mirror image of the virtual drill needs to be aligned.

Optionally, the virtual information, e.g. an imaging study and/or other virtual data [e.g. portions of a virtual surgical plan, a virtual drill path, a predetermined path, a predetermined drill path, a predetermined start point, a predetermined end point, a predetermined depth stop, a virtual tool, a virtual instrument, a virtual implant and/or a virtual device] can be registered with an image of the physical tooth and/or dental or oral structures seen through a surgical microscope. For this purpose, for example, one or more optical markers, navigation markers, e.g. RF or IR, LED's, or other markers can be included, for example in the microscope view or outside the microscope view, to allow cross-referencing and registration of the virtual data displayed by the OHMD and/or the OHMD unit with the microscope view. Alternatively, a 3D scanner or an image or video capture system can be used for registration and/or tracking, e.g. of tools or instruments, as described in the specification. Any other registration and tracking technique described in the specification or known in the art can be used. The OHMD display can align and superimpose the virtual data with the image of the reflected light from the physical tooth and/or dental or oral structures seen through the microscope and it can optionally display the virtual data with the same magnification that the microscope is using or a different magnification. Someone skilled in the art can recognize that the foregoing embodiments are applicable to other embodiments throughout the specification, e.g. in spinal surgery, spinal fusion [e.g. with cages or pedicle screws], discectomies, joint replacement [e.g. in the knee, hip, shoulder, ankle] and ligament reconstruction or repair [e.g. ACL or rotator cuff].

Figure 41A:
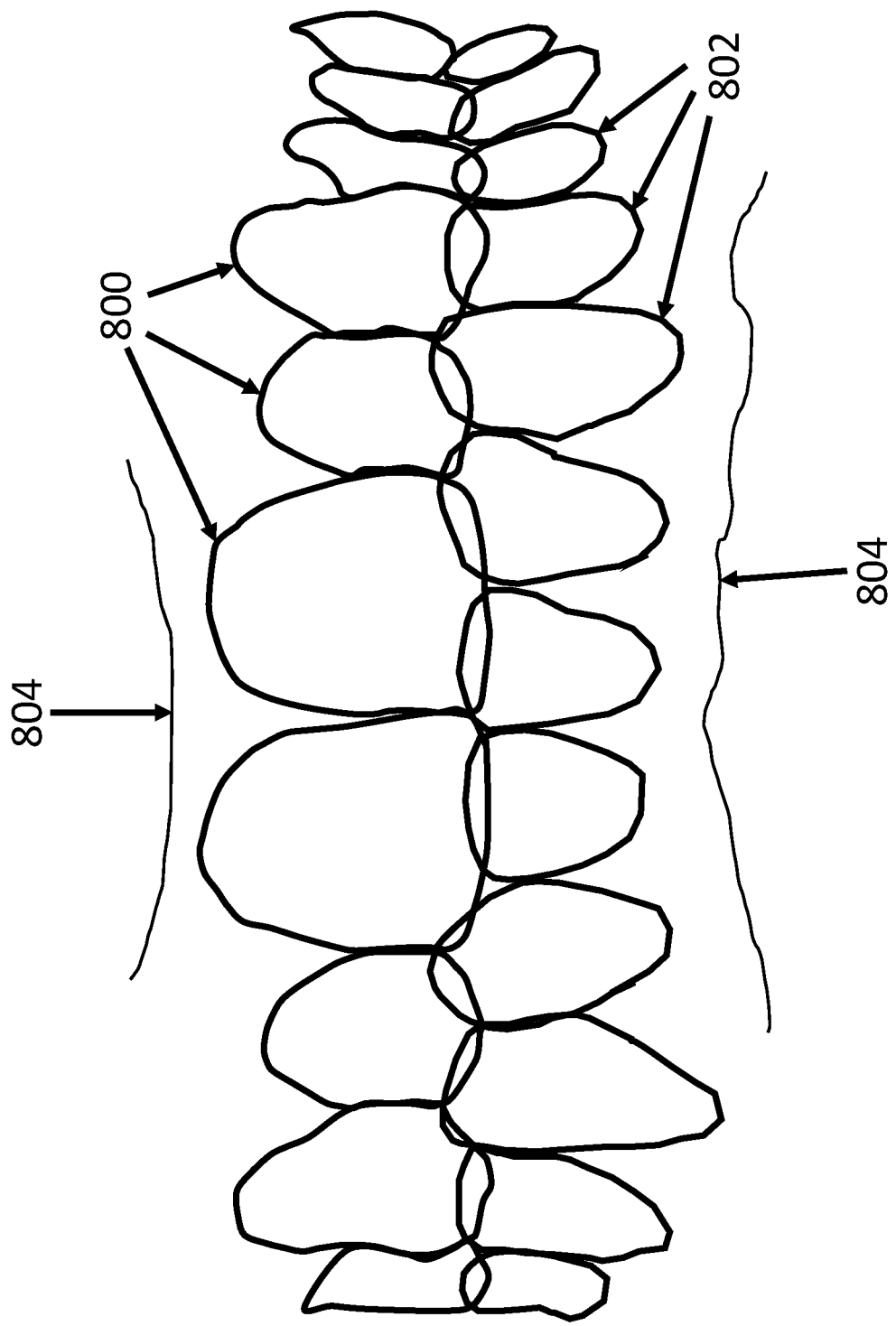
FIGS. 41A-M provide illustrative, non-limiting examples of one or more augmented reality OHMD displays for dental surgery or placement of dental implants, including display of virtual surgical guides, e.g. virtual axes, for aligning physical dental tools and instruments, e.g. drills, and/or physical dental implants.
Figure 41B:
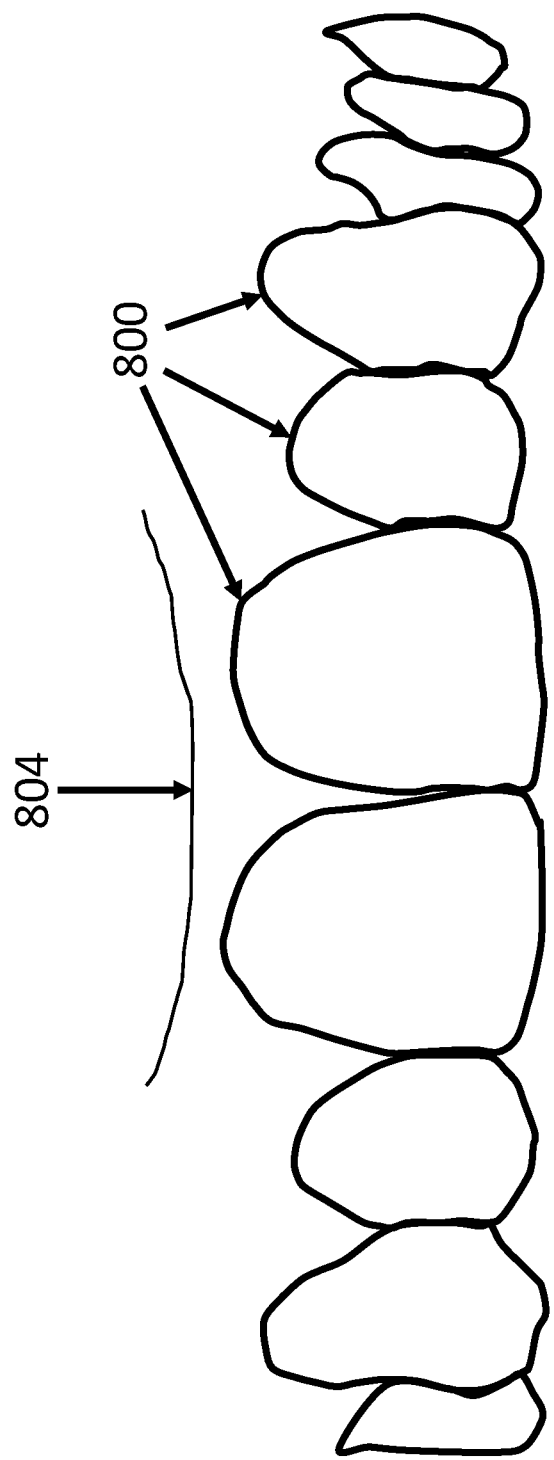
Figure 41C:
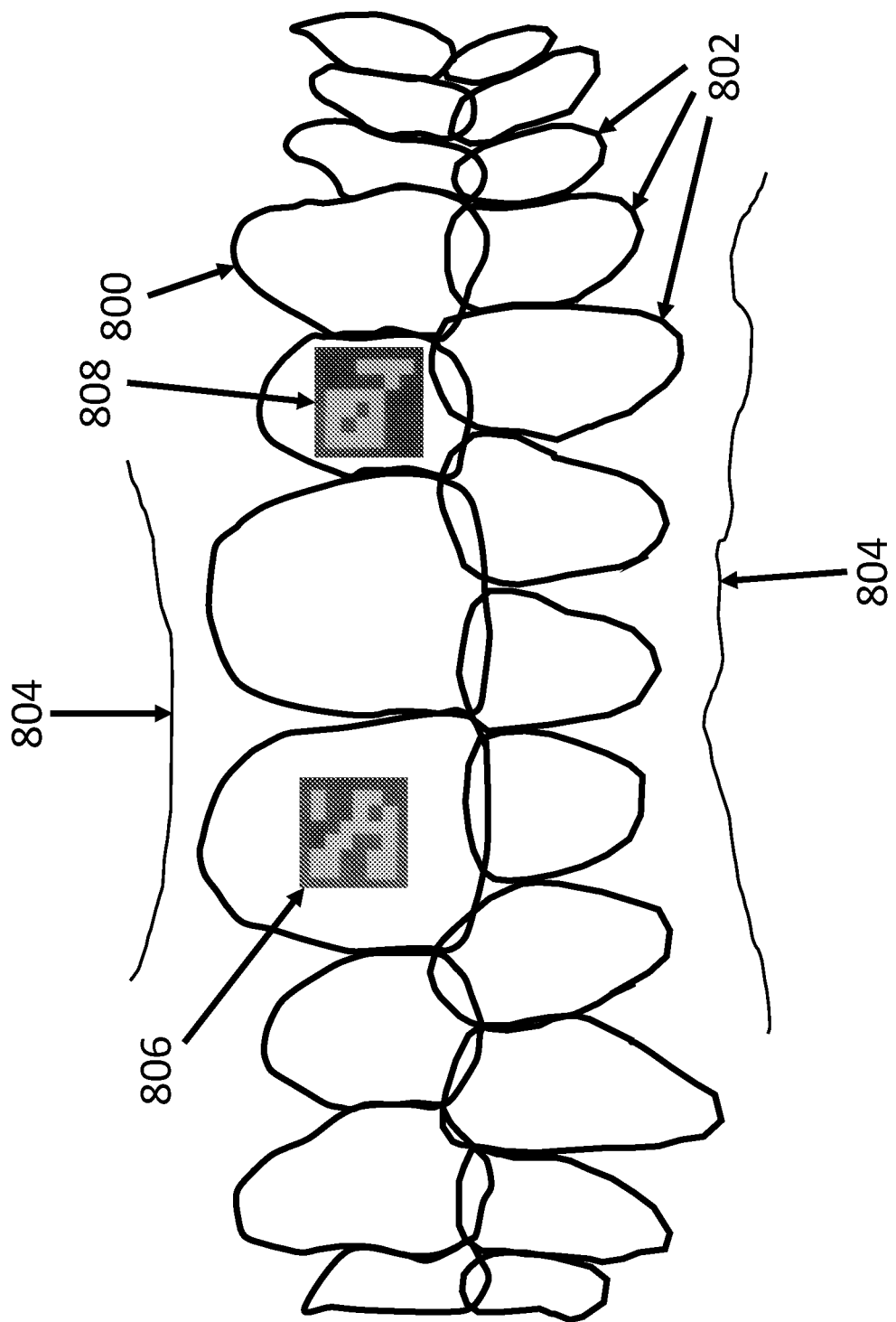

FIGS. 41A-M provide illustrative, non-limiting examples of one or more augmented reality OHMD displays for dental surgery or placement of dental implants, including display of virtual surgical guides, e.g. virtual axes, for aligning physical dental tools and instruments, e.g. drills, and/or physical dental implants. FIG. 41A shows mandibular teeth 800 and maxillary teeth 802 in occluded position. A fold is seen at the base of the gingival tissue 804. FIG. 41B shows maxillary teeth 800 with the jaw in open, non-occluded position. FIG. 41C shows two optical markers 806 and 808 applied to two teeth. The optical markers 806 and 808 have different geometric patterns. Instead of optical markers, other markers, e.g. navigation markers or LED's, can be used. The optical markers and/or navigation markers, LED's or other markers can optionally include radiopaque elements for identification using one or more scans with ionizing radiation, e.g. x-rays, Panorex, CT scan, cone beam CT, and can be applied during a pre- or intra-operative scan and/or during the dental or oral surgical procedure to the teeth or other dental or oral structures, thereby allowing registration of the pre- or intra-operative scan to the live data of the patient, e.g. the dental or oral structures visible through a see through optical head mounted display or the dental or oral structures imaged live using one or more video cameras, e.g. integrated into, attached to or separate from one or more OHMDs, for live display by a non-see through optical head mounted display. By registering the one or more optical markers and/or navigation markers, LED's or other markers in the live data of the patient, e.g. using an image capture or video capture system and/or a navigation system, and by registering one or more OHMDs as well as pre- or intra-operative scan data in a common coordinate system, the pre- or intra-operative scan data, including the one or more markers, can be superimposed into and/or aligned with corresponding marker or marker elements and/or anatomic structures; moreover, subsurface structures, e.g. roots, mandibular bone or maxillary bone, can also be visualized superimposed onto or within the live data of the patient, e.g. displayed in their respective anatomic location underneath the gingiva or underneath the tooth. Thus, information from different tissues, e.g. enamel and gingiva, cementum, roots, mandible or maxilla, can be seen simultaneously, e.g. through a see through or non see through optical head mounted display. For example, the enamel and gingiva, a tooth void in the area of an extracted or lost tooth and/or adjacent teeth can be directly visible through a see through optical head mounted display, while mandibular bone or maxillary bone and any graphical representations related thereto, e.g. a drilling axis, can be displayed virtually by the one or more optical head mounted displays, superimposed onto and/or aligned with the corresponding physical teeth, enamel, gingiva or dental or oral structures.

Figure 41D:
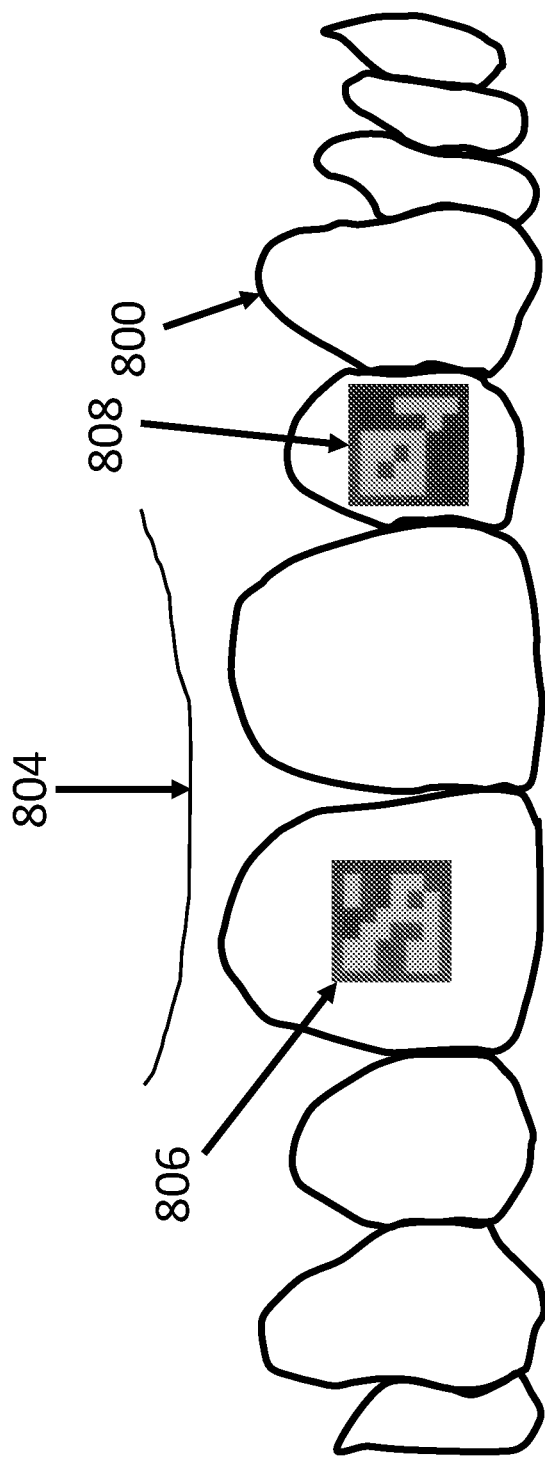

FIG. 41D shows the maxillary teeth 800 with the jaw open, in an unoccluded position. The optical markers 806 and 808 are also seen. By registering the teeth, gingiva, gums, dental or oral structures in a common coordinate system with the pre- or intra-operative scan data and/or one or more OHMDs, the display of any virtual data, e.g. virtual surgical guides, virtual tools, virtual instruments and/or virtual implants and implant components can be maintained over their corresponding physical structures with the teeth in occluded or non-occluded position. Thus, the virtual data, e.g. virtual surgical guides, virtual tools, virtual instruments and/or virtual dental implants and dental implant components can be projected onto the surface of the teeth, gingiva and/or other dental or oral structures and can be maintained in their position with the teeth in occluded or non-occluded position.

The virtual data, e.g. virtual surgical guides, virtual tools, virtual instruments and/or virtual dental implants and dental implant components can be projected onto and/or superimposed onto and/or aligned with and/or oriented with so that at least portions of them are tangent with, intersecting with, orthogonal to, at a defined angle to, and/or offset with, e.g. at a predetermined distance or angle, or a predetermined orientation or predetermined alignment with the surface of the teeth, e.g. adjacent teeth, a gingiva, a marginal gum, an attached gum, an interdental gum, and/or other dental or oral structures and can be maintained in their position and/or orientation and/or alignment and/or coordinates with the teeth in occluded or non-occluded position.

In addition, the virtual data, e.g. virtual surgical guides, virtual tools, virtual instruments and/or virtual implants and implant components can be projected onto the surface of the teeth, and/or the gingiva, e.g. a marginal gum, an attached gum, and/or interdental gum, and/or other dental or oral structures by the one or more computer processors and the one or more OHMD displays of the virtual data and can be maintained in their position when the physical guides, physical tools, physical instruments, physical implants or implant components are moved, for example into the field of view of the user. In addition, the one or more computer processors and the one or more OHMD displays can display the virtual surgical guides, virtual tools, virtual instruments and/or virtual implants and implant components optionally together with any virtual scan data, e.g. from a pre- or intraoperative imaging study registered in the common coordinate system with the virtual surgical guides, virtual tools, virtual instruments and/or virtual implants and implant components and the one or more OHMDs.

Figure 41E:
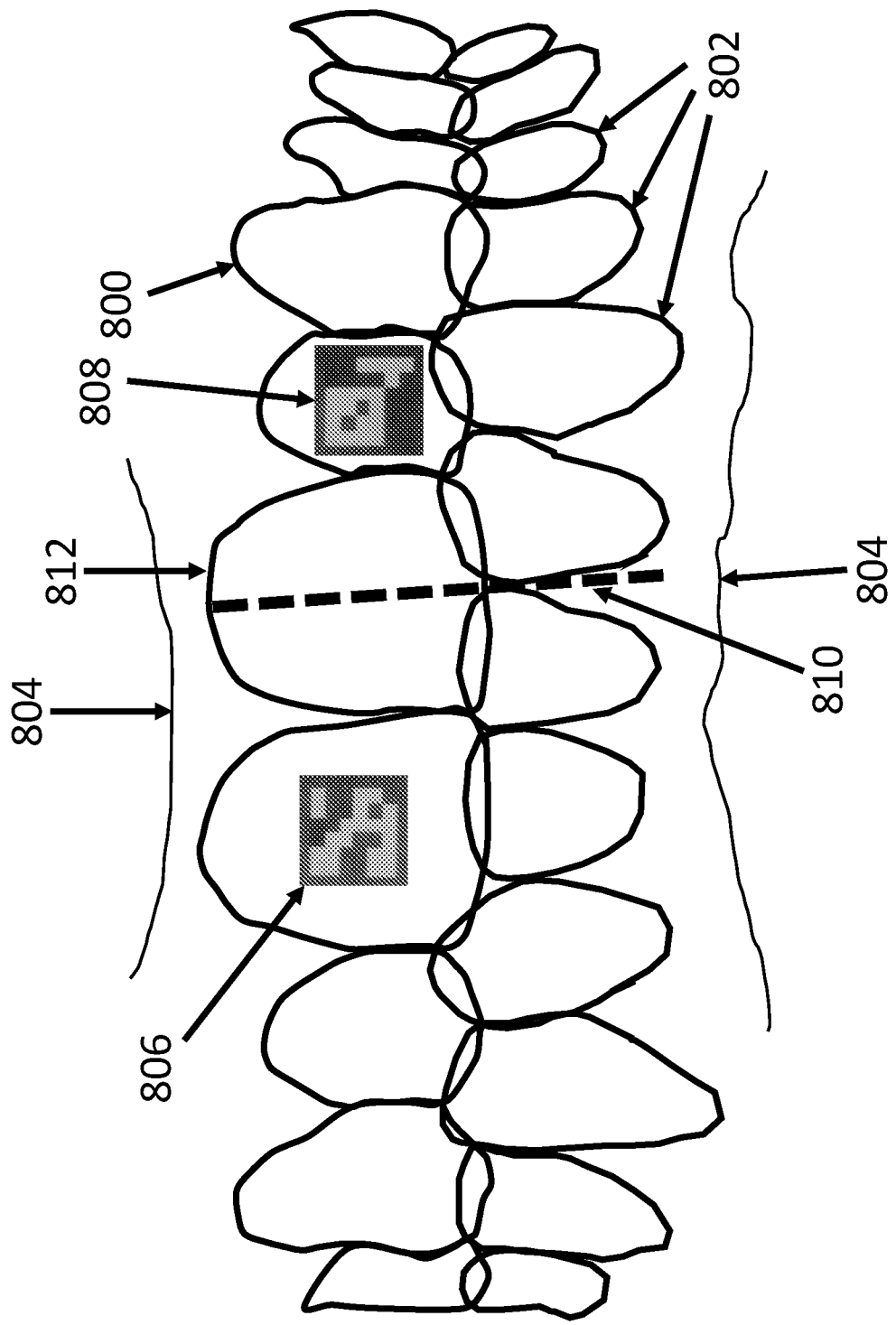

FIG. 41E shows the maxillary 800 and mandibular 802 teeth in occluded position. The optical markers 806 and 808 are also shown. Instead of optical markers, other markers, e.g. navigation markers, LED's etc., can be used. A virtual surgical guide 810, in this example a virtual axis 810 for aligning one or more physical dental tools, physical drills, physical instruments, or one or more dental implant components is also shown projected onto and superimposed onto and aligned with the tooth intended for extraction. The position, location, orientation, coordinates, depth, and/or length of the virtual axis 810 can be determined using, for example, information in the live data of the patient, for example by orienting the virtual axis 810 relative to the left and/or right edge of the tooth, for example centered relative to the edges or at a defined distance to one or more edges, or relative to the long axis and/or the frontal and or posterior surface of the tooth intended for extraction 812. The position, location, orientation, coordinates, depth, and/or length of the virtual axis 810 can be determined using, for example, some of the dental or oral structures in the live data of the patient, e.g. a crown, enamel, dentin, cementum, e.g. if visible, cementoenamel junction, e.g. if visible, gingival tissue, a marginal gum, an attached gum, an interdental gum, a cingulum, marginal ridge(s), longitudinal ridge(s), oblique ridge(s), cusp ridge(s), secondary groove(s), auxiliary groove(s), dissectional groove(s), cusp, cusp tip, cusp of Carabelli, pit(s), fossa(s), occlusal table, gingival bulge, imbrication area, a clinical crown, an anatomical crown, central incisor(s), lateral incisor(s), cuspid(s), $1^{st}$ premolar(s), $2^{nd}$ premolar(s), $1^{st}$ molar(s), $2^{nd}$ molar(s), $3^{rd}$ molar(s), an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth, features and/or structures of an existing tooth, e.g. a tooth that the dentist intends to replace or repair or augment, or one or more teeth adjacent or opposite, e.g. in the opposing mandible or maxilla, to a tooth that the dentist intends to replace or repair or augment, e.g. dimensions, curves, curvatures, edges, plateaus, margins, ridges, cusps, grooves, and/or shape and/or color of one or more existing teeth, including a tooth selected for repair, resurfacing or replacement, one or more adjacent teeth and/or one or more opposing teeth on the opposing mandible or maxilla and combinations thereof. The virtual surgical guide 810, e.g. the virtual axis, can also be placed, positioned, oriented, aligned using information about one or more of a void created by a tooth that has been previously lost or extracted or in relationship to tissues remaining in the void, e.g. gingival tissue, for example, a marginal gum, an attached gum, an interdental gum, visible bone, a visible residual root or root cavity etc., an existing dental implant, dental implant component and/or any other dental device including one or more of an abutment, e.g. a standard abutment or a custom made abutment, a crown, a fixture or implant and any combination thereof, dimensions, curvatures, curves, edges, plateaus, margins, ridges, cusps, grooves, and/or shape of one or more existing implants, implant components, abutments, crowns, fixtures or implants and combinations thereof. The position, location, orientation, coordinates, depth, and/or length of the virtual surgical guide, e.g. the virtual axis, can be determined using some of these data using a PC or server, for example with a graphical user interface and a display, for example displaying a video image of the live data of the patient. Optionally, the live data of the patient displayed using the display can be magnified using the user interface and the user or a computer processor can determine the position, location, orientation, coordinates, depth, and/or length of the virtual surgical guide, e.g. the virtual axis. Someone skilled in the art will recognize that the foregoing embodiments and examples of a virtual surgical guide 810, e.g. a virtual axis, can be applied to guiding a physical drill or other tools or instruments, e.g. a physical file or a physical flare or a physical cone or a physical post, for treating one or more root canals or for preparing a tooth [e.g. including tissue removal, burring, milling] for placement of a cap or crown.

In some embodiments, the position, location, orientation, coordinates, depth, and/or length of the virtual surgical guide, e.g. the virtual axis, can be determined in the live data of the patient, e.g. as seen through a see through optical head mounted display. Using a user interface, e.g. gesture recognition, voice recognition, a graphical user interface, an acoustic interface, a virtual interface, e.g. a virtual keyboard, the user can place, orient, and/or align the virtual surgical guide, e.g. the virtual axis, superimposed onto the live data of the patient, using, for example, some of the dental or oral structures mentioned in the specification for the live data, e.g. a crown, enamel, dentin, cementum, e.g. if visible, cementoenamel junction, e.g. if visible, gingival tissue including a marginal gum, an attached gum, an interdental gum, a cingulum, marginal ridge(s), longitudinal ridge(s), oblique ridge(s), cusp ridge(s), secondary groove(s), auxiliary groove(s), dissectional groove(s), cusp, cusp tip, cusp of Carabelli, pit(s), fossa(s), occlusal table, gingival bulge, imbrication area, a clinical crown, an anatomical crown, central incisor(s), lateral incisor(s), cuspid(s), $1^{st}$ premolar(s), $2^{nd}$ premolar(s), $1^{st}$ molar(s), $2^{nd}$ molar(s), $3^{rd}$ molar(s), an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth, features and/or structures of an existing tooth, e.g. a tooth that the dentist intends to replace or repair or augment, or one or more teeth adjacent or opposite, e.g. in the opposing mandible or maxilla, to a tooth that the dentist intends to replace or repair or augment, e.g. dimensions, curves, curvatures, edges, plateaus, margins, ridges, cusps, grooves, and/or shape and/or color of one or more existing teeth, including a tooth selected for repair, resurfacing or replacement, one or more adjacent teeth and/or one or more opposing teeth on the opposing mandible or maxilla and combinations thereof. The virtual surgical guide 810, e.g. the virtual axis, can also be placed, positioned, oriented, aligned using one or more of a void created by a tooth that has been previously lost or extracted or in relationship to tissues remaining in the void, e.g. gingival tissue including a marginal gum, an attached gum, an interdental gum, visible alveolar bone, a visible residual root or root cavity etc., an existing dental implant, dental implant component and/or any other dental device including one or more of an abutment, e.g. a standard abutment or a custom made abutment, a crown, a fixture or implant and any combination thereof, dimensions, curvatures, curves, edges, plateaus, margins, ridges, cusps, grooves, and/or shape of one or more existing implants, implant components, abutments, crowns, fixtures or implants and combinations thereof using a computer processor that facilitates placing, moving, orienting, aligning the virtual surgical guide superimposed onto the live data of the patient with one or more OHMDs, e.g. using an acoustic or a gesture recognition or other interface.

In some embodiments, the position, location, orientation, coordinates, depth, and/or length of the virtual surgical guide, e.g. the virtual axis, and/or a virtual implant can be determined in pre-operative or intra-operative scan data of the patient, for example x-rays, Panorex images, ultrasound images, a cone beam CT, CT scan data, MRI data. The user or a computer processor can determine the position, location, orientation, coordinates, depth, and/or length of the virtual surgical guide, e.g. the virtual axis, and/or a virtual implant using the image data and using, for example, some of the dental or oral structures mentioned in the specification, e.g. a crown, enamel, dentin, pulp, cementum, cementoenamel junction, periodontal ligaments, gingival tissue, e.g. a marginal gum, an attached gum, an interdental gum, alveolar bone, bone, a root, a root canal, apical foramina, a cingulum, marginal ridge(s), longitudinal ridge(s), oblique ridge(s), cusp ridge(s), secondary groove(s), auxiliary groove(s), dissectional groove(s), cusp, cusp tip, cusp of Carabelli, pit(s), fossa(s), occlusal table, gingival bulge, imbrication area, a clinical crown, an anatomical crown, central incisor(s), lateral incisor(s), cuspid(s), $1^{st}$ premolar(s), $2^{nd}$ premolar(s), $1^{st}$ molar(s), $2^{nd}$ molar(s), $3^{rd}$ molar(s), an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth, features and/or structures of an existing tooth, e.g. a tooth that the dentist intends to replace or repair or augment, or one or more teeth adjacent or opposite, e.g. in the opposing mandible or maxilla, to a tooth that the dentist intends to replace or repair or augment, e.g. dimensions, curves, curvatures, edges, plateaus, margins, ridges, cusps, grooves, and/or shape and/or color of one or more existing teeth, including a tooth selected for repair, resurfacing or replacement, one or more adjacent teeth and/or one or more opposing teeth on the opposing mandible or maxilla and combinations thereof, a bone shape or bone stock, e.g. a bone shape including anterior, posterior, inferior and/or superior shape and/or curvature(s) of a mandible or a maxilla and/or a bone stock of a mandible or maxilla, a bone density or bone quality, e.g. a bone density and/or a bone quality at or near an intended implantation site in the mandible or maxilla, a void created by a tooth that has been previously lost or extracted or in relationship to tissues remaining in the void, e.g. gingival tissue, alveolar bone, a residual root or root cavity etc., an existing dental implant, dental implant component and/or any other dental device including one or more of an abutment, e.g. a standard abutment or a custom made abutment, a crown, a fixture or implant and any combination thereof, dimensions, curvatures, curves, edges, plateaus, margins, ridges, cusps, grooves, and/or shape of one or more existing implants, implant components, abutments, crowns, fixtures or implants and combinations thereof. By registering the scan data with the live data of the patient, e.g. in a common coordinate system which can also include one or more OHMDs, the virtual data of the patient, e.g. the scan data, and/or the virtual surgical guide, e.g. a virtual axis, can be superimposed and aligned with the live data of the patient using the OHMD display. If a see through optical head mounted display is used, the live data can be seen directly through the OHMD display by the user, while the virtual data including, for example, the scan data and/or the virtual surgical guide, e.g. virtual axis, are displayed using the computer processor and the OHMD display. The virtual data, e.g. a virtual surgical guide (e.g. a virtual axis), a virtual tool, a virtual instrument, a virtual dental implant or implant component, can be superimposed onto and/or aligned with one or more of a crown, enamel, dentin, pulp, cementum, cementoenamel junction, periodontal ligaments, gingival tissue, e.g. a marginal gum, an attached gum, an interdental gum, alveolar bone, bone, a root, a root canal, apical foramina, a cingulum, marginal ridge(s), longitudinal ridge(s), oblique ridge(s), cusp ridge(s), secondary groove(s), auxiliary groove(s), dissectional groove(s), cusp, cusp tip, cusp of Carabelli, pit(s), fossa(s), occlusal table, gingival bulge, imbrication area, a clinical crown, an anatomical crown, central incisor(s), lateral incisor(s), cuspid(s), $1^{st}$ premolar(s), $2^{nd}$ premolar(s), $1^{st}$ molar(s), $2^{nd}$ molar(s), $3^{rd}$ molar(s), an anterior surface of a tooth, a posterior surface of a tooth, a medial surface of a tooth, a lateral surface of a tooth, a medial margin or edge of a tooth, a lateral margin or edge of a tooth, a bite surface of a tooth, a ridge or crest of a tooth, features and/or structures of an existing tooth, e.g. a tooth that the dentist intends to replace or repair or augment, or one or more teeth adjacent or opposite, e.g. in the opposing mandible or maxilla, to a tooth that the dentist intends to replace or repair or augment, e.g. dimensions, curves, curvatures, edges, plateaus, margins, ridges, cusps, grooves, and/or shape and/or color of one or more existing teeth, including a tooth selected for repair, resurfacing or replacement, one or more adjacent teeth and/or one or more opposing teeth on the opposing mandible or maxilla and combinations thereof, a bone shape or bone stock, e.g. a bone shape including anterior, posterior, inferior and/or superior shape and/or curvature(s) of a mandible or a maxilla and/or a bone stock of a mandible or maxilla, a bone density or bone quality, e.g. a bone density and/or a bone quality at or near an intended implantation site in the mandible or maxilla, a void created by a tooth that has been previously lost or extracted or in relationship to tissues remaining in the void, e.g. gingival tissue, alveolar bone, a residual root or root cavity etc., an existing dental implant, dental implant component and/or any other dental device including one or more of an abutment, e.g. a standard abutment or a custom made abutment, a crown, a fixture or implant and any combination thereof, dimensions, curvatures, curves, edges, plateaus, margins, ridges, cusps, grooves, and/or shape of one or more existing implants, implant components, abutments, crowns, fixtures or implants and combinations thereof.

In some embodiments, a combination of techniques can be used for determining the position, location, orientation, coordinates, depth, and/or length and/or dimensions and/or geometry and/or shape of the virtual data, e.g. a virtual surgical guide (e.g. a virtual axis), a virtual tool, a virtual instrument, a virtual dental implant or implant component. For example, the virtual surgical guide, e.g. the virtual axis, can be determined in pre- or intra-operative scan data and can be determined using a video image of the live data of the patient and an optional graphical user interface, hosted, for example on a PC or server. The virtual surgical guide, e.g. the virtual axis, can be determined in pre- or intra-operative scan data and can be determined using a virtual interface, for example displayed by a see through OHMD, wherein a computer processor, e.g. integrated in the OHMD or residing on a separate server, facilitates placing, moving, orienting, and aligning the virtual surgical guide, e.g. a virtual axis, relative to and superimposed onto the live data of the patient, e.g. some of the dental or oral structures mentioned in the specification. The same or a second, different computer processor can also be used to facilitate placing, moving, orienting, aligning, sizing and/or fitting of one or more dental implants or dental implant components superimposed into the live data of the patient, e.g. one or more of the dental or oral structures mentioned in the specification, e.g. as seen directly through a see through optical head mounted display.

In some embodiments, the position, orientation, alignment and/or coordinates of the virtual surgical guide, e.g. the virtual axis, can be determined using pre- or intra-operative scan data and can be displayed using a computer processor by one or more OHMDs registered with the corresponding anatomic structures of the patient and superimposed onto the live data of the patient, e.g. projected onto and/or superimposed onto and/or aligned with a surface of one or more tooth, a gingiva, an enamel; the position, orientation, alignment and/or coordinates of the virtual surgical guide, e.g. the virtual axis, can then optionally be adjusted using a virtual interface, for example displayed by a see through OHMD, wherein a computer processor, e.g. integrated in the OHMD or residing on a separate server, facilitates placing, moving, orienting, aligning adjusting the virtual surgical guide, e.g. a virtual axis, relative to and superimposed onto the live data of the patient.

In some embodiments, the position, orientation, alignment and/or coordinates of the virtual implant component, e.g. a dental implant component, can be determined using pre- or intra-operative scan data and can be displayed, e.g. as a virtual implant component or 2D or 3D placement indicator or combinations thereof, using a computer processor by one or more OHMDs registered with the corresponding anatomic structures of the patient and superimposed onto the live data of the patient, e.g. projected onto and/or superimposed onto and/or aligned with an anatomic surface, e.g. of one or more teeth, a gingiva, an enamel; the position, orientation, alignment and/or coordinates of the virtual implant component, e.g. a dental implant component, can then optionally be adjusted using a virtual interface, for example displayed by a see through OHMD, wherein a computer processor, e.g. integrated in the OHMD or residing on a separate server, facilitates placing, moving, orienting, aligning adjusting the virtual implant component, e.g. a dental implant component, relative to and superimposed onto the live data of the patient. In some embodiments, a first computer processor can be used to facilitate the placing of a virtual surgical guide, a virtual tool, a virtual instrument and/or a virtual implant or implant component, e.g. a dental implant component or other implant component. A second computer processor can be used to facilitate the moving of a virtual surgical guide, a virtual tool, a virtual instrument and/or a virtual implant or implant component, e.g. a dental implant component or other implant component. A third computer processor can be used to facilitate the orienting of a virtual surgical guide, a virtual tool, a virtual instrument and/or a virtual implant or implant component, e.g. a dental implant component or other implant component. A fourth computer processor can be used to facilitate the aligning of a virtual surgical guide, a virtual tool, a virtual instrument and/or a virtual implant or implant component, e.g. a dental implant component or other implant component. A fifth computer processor can be used to facilitate the fitting of a virtual implant or implant component, e.g. a dental implant component or other implant component. A sixth computer processor can be used to facilitate the sizing of a virtual implant or implant component, e.g. a dental implant component or other implant component. A seventh computer processor can be used to facilitate the selection of a virtual implant or implant component, e.g. a dental implant component or other implant component. The first processor can be the same or different than the second, third, fourth, fifth, sixth or seventh processor; the second processor can be the same or different than the first, third, fourth, fifth, sixth or seventh processor; the third processor can the same or different than the first, second, fourth, fifth, sixth and seventh processor; the fourth processor can be the same or different than the first, second, third, fifth, sixth or seventh processor; the fifth processor can be the same or different than the first, second, third, fourth, sixth or seventh processor; the sixth processor can be the same or different than the first, second, third, fourth, fifth or seventh processor; the sixth processor can be the same or different than the first, second, third, fourth, fifth or sixth processor.

In some embodiments, a first user interface can be used to facilitate the placing of a virtual surgical guide, a virtual tool, a virtual instrument and/or a virtual implant or implant component, e.g. a dental implant component or other implant component. A second user interface can be used to facilitate the moving of a virtual surgical guide, a virtual tool, a virtual instrument and/or a virtual implant or implant component, e.g. a dental implant component or other implant component. A third user interface can be used to facilitate the orienting of a virtual surgical guide, a virtual tool, a virtual instrument and/or a virtual implant or implant component, e.g. a dental implant component or other implant component. A fourth user interface can be used to facilitate the aligning of a virtual surgical guide, a virtual tool, a virtual instrument and/or a virtual implant or implant component, e.g. a dental implant component or other implant component. A fifth user interface can be used to facilitate the fitting of a virtual implant or implant component, e.g. a dental implant component or other implant component. A sixth user interface can be used to facilitate the sizing of a virtual implant or implant component, e.g. a dental implant component or other implant component. A seventh user interface can be used to facilitate the selection of a virtual implant or implant component, e.g. a dental implant component or other implant component. The first user interface can be the same or different than the second, third, fourth, fifth, sixth or seventh user interface; the second user interface can be the same or different than the first, third, fourth, fifth, sixth or seventh user interface; the third user interface can the same or different than the first, second, fourth, fifth, sixth and seventh user interface; the fourth user interface can be the same or different than the first, second, third, fifth, sixth or seventh user interface; the fifth user interface can be the same or different than the first, second, third, fourth, sixth or seventh user interface; the sixth user interface can be the same or different than the first, second, third, fourth, fifth or seventh user interface; the sixth user interface can be the same or different than the first, second, third, fourth, fifth or sixth user interface.

Similarly, in other embodiments, the position, orientation, alignment and/or coordinates of virtual tools or virtual instruments can be determined in pre- or intra-operative scan data and can be displayed using a computer processor by one or more OHMDs registered with the corresponding anatomic structures of the patient and superimposed onto the live data of the patient; the position, orientation, alignment and/or coordinates of the virtual tools or virtual instruments can then optionally be adjusted using a virtual interface, for example displayed by a see through OHMD, or any other interface, wherein a computer processor, e.g. integrated in the OHMD or residing on a separate server, facilitates placing, moving, orienting, aligning, and adjusting the virtual tools or virtual instruments relative to and superimposed onto the live data of the patient.

In some embodiments, the position, orientation, alignment and/or coordinates and/or size and/or fit and/or selection of virtual implants and/or virtual implant components can be determined in pre- or intra-operative scan data and can be displayed using a computer processor by one or more OHMDs registered with the corresponding anatomic structures of the patient and superimposed onto the live data of the patient; the position, orientation, alignment and/or coordinates and/or size and/or fit and/or selection of the virtual implants and/or virtual implant components can then optionally be adjusted using a virtual interface, for example displayed by a see through OHMD, or any other interface, wherein a computer processor, e.g. integrated in the OHMD or residing on a separate server, facilitates placing, moving, orienting, aligning, sizing, fitting, selecting and adjusting the virtual implants and/or virtual implant components relative to and superimposed onto the live data of the patient.

The virtual surgical guides, virtual tools, virtual instruments and/or virtual implants and implant components can be projected onto the surface of the teeth, gingiva (e.g. a marginal gum, an attached gum, an interdental gum) and/or other dental or oral structures by one or more computer processors and one or more OHMDs displays and can be maintained in their position when the physical guides, physical tools, physical instruments, physical implants or implant components are moved, for example into the field of view of the user.

Figure 41F:
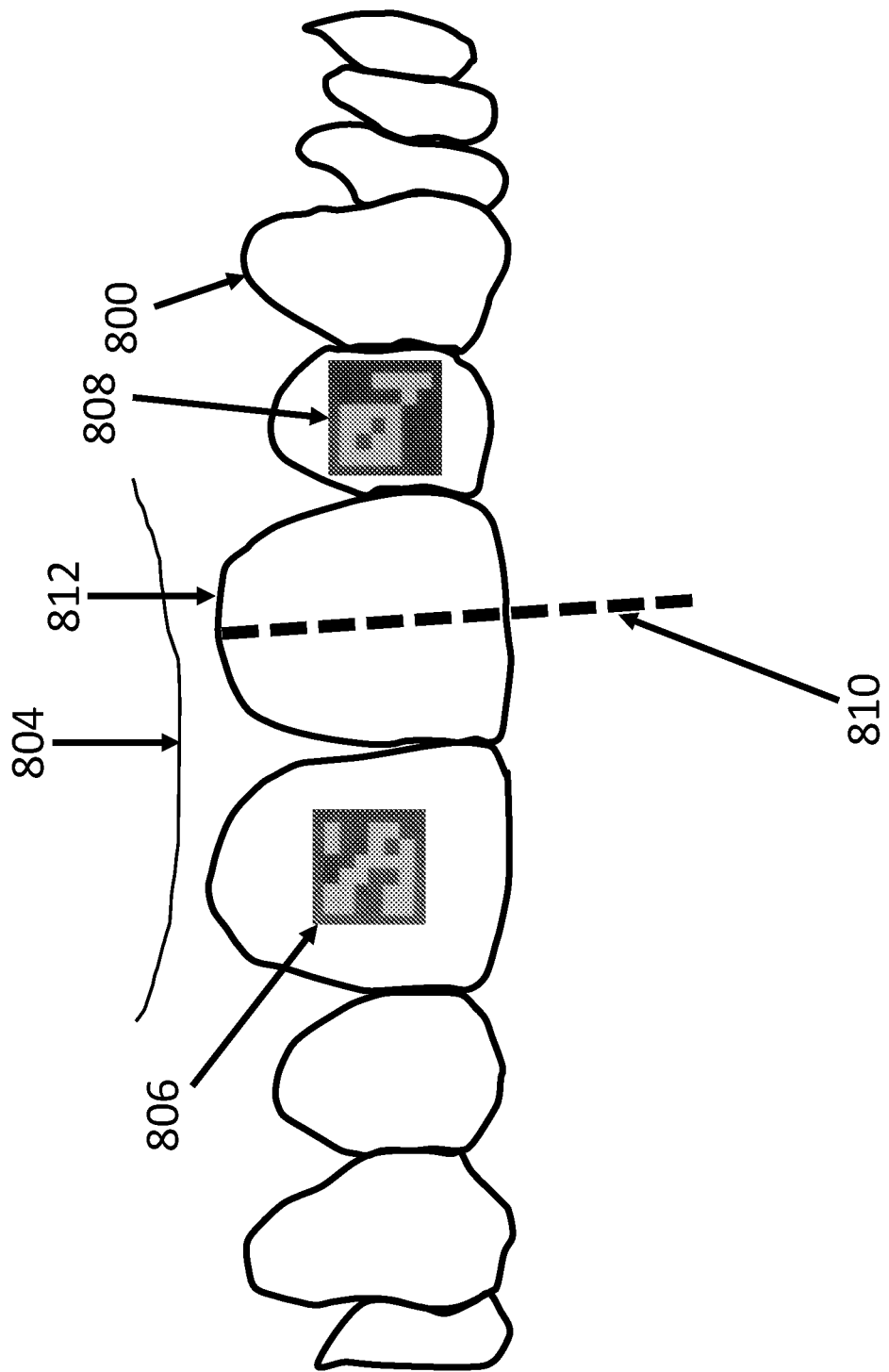

FIG. 41F shows the maxillary teeth 800 with the jaw open, in an unoccluded position. The optical markers 806 and 808 are also seen. The virtual surgical guide 810, in this example a virtual axis 810 for aligning one or more physical dental tools, physical drills, physical instruments, or one or more dental implant components is also shown. The virtual surgical guide 810 is maintained in its position, orientation and/or alignment superimposed onto the live data of the patient, e.g. the tooth earmarked for extraction 812, with the teeth in occluded and open, un-occluded position.

Figure 41G:
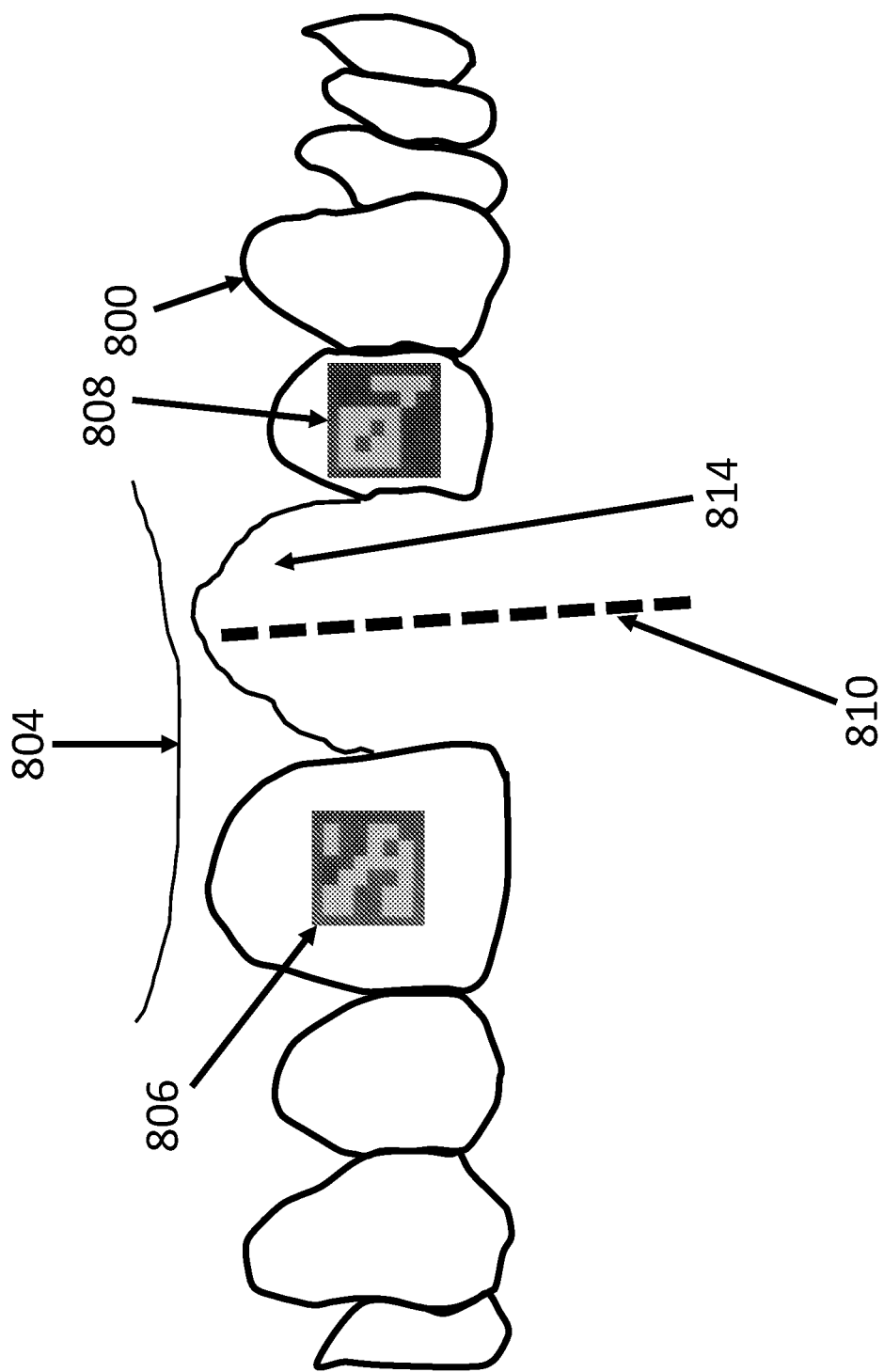

FIG. 41G shows the maxillary teeth 800 with the jaw open, in an unoccluded position after the tooth extraction. The optical markers 806 and 808 are also seen. The virtual surgical guide 810, in this example a virtual axis 810 for aligning one or more physical dental tools, physical drills, physical instruments, or one or more dental implant components is also shown. The virtual surgical guide 810 is maintained in its position, orientation and/or alignment superimposed onto the live data of the patient, e.g. the void 814 created by the extraction of the tooth. The virtual surgical guide 810 can be maintained in its position, orientation and/or alignment due to the registration of the virtual data and the live data using the one or more optical markers 806 and 808 or other markers or, for example, a video scan or 3D scan of the teeth and live data of the patient.

Figure 41H:
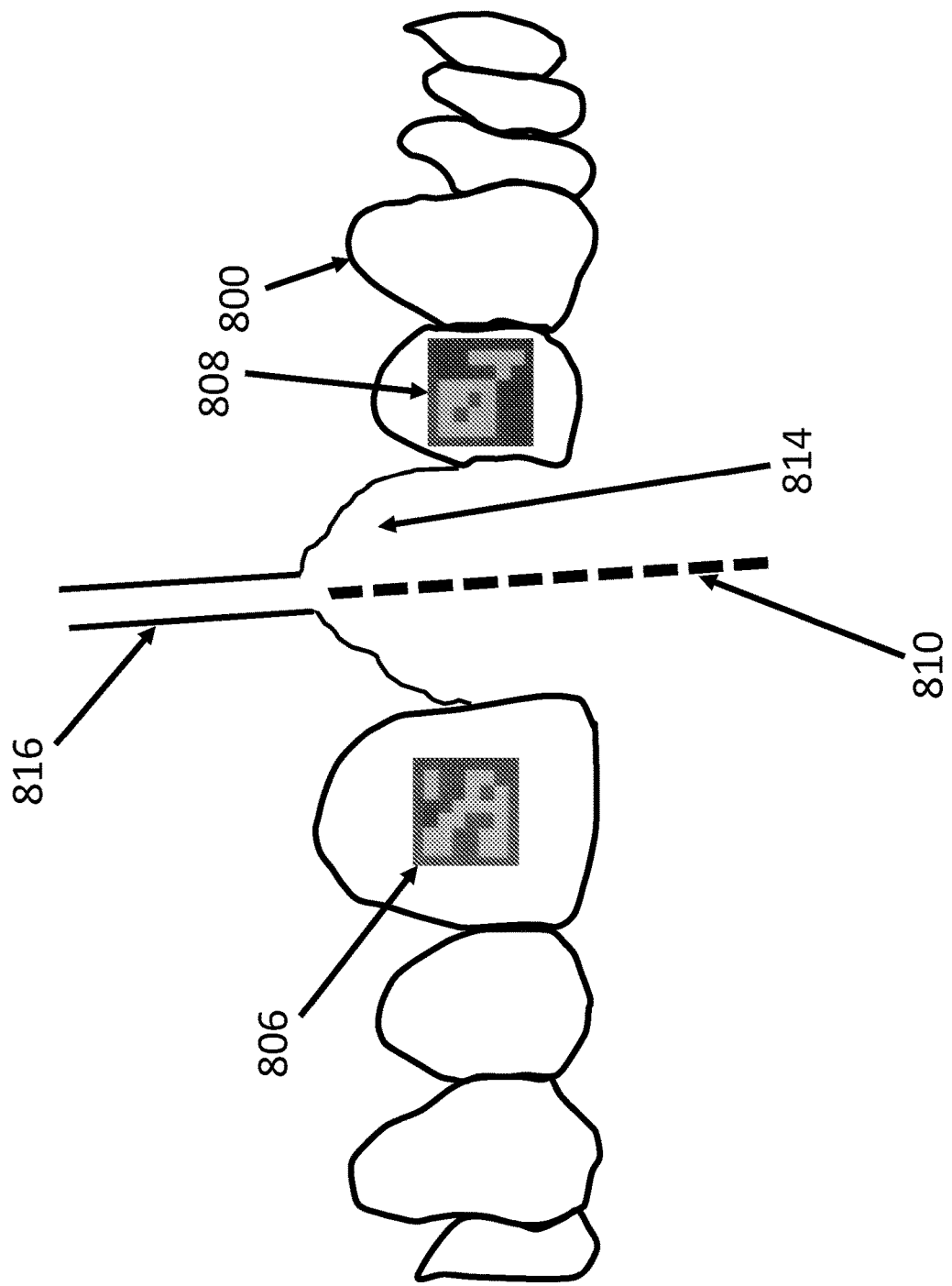

FIG. 41H shows a drill canal 816 for facilitating the placement of a dental implant component in the maxilla. The drill canal can be created by aligning and superimposing a physical drill (not shown) with the virtual axis 810 and by advancing the physical drill while maintaining the alignment and superimposition with the virtual axis 810. Optionally, after the drill canal 816 has been created, the drill bit can remain in the drill canal and one or more markers, e.g. optical markers, can be attached to the drill bit and the long axis of the drill bit and, with it, the long axis of the drill canal 816 can be determined, for example using an image capture or video capture system and one or more computer processors, and, optionally, it can be stored, e.g. in the virtual data.

Figure 41I:
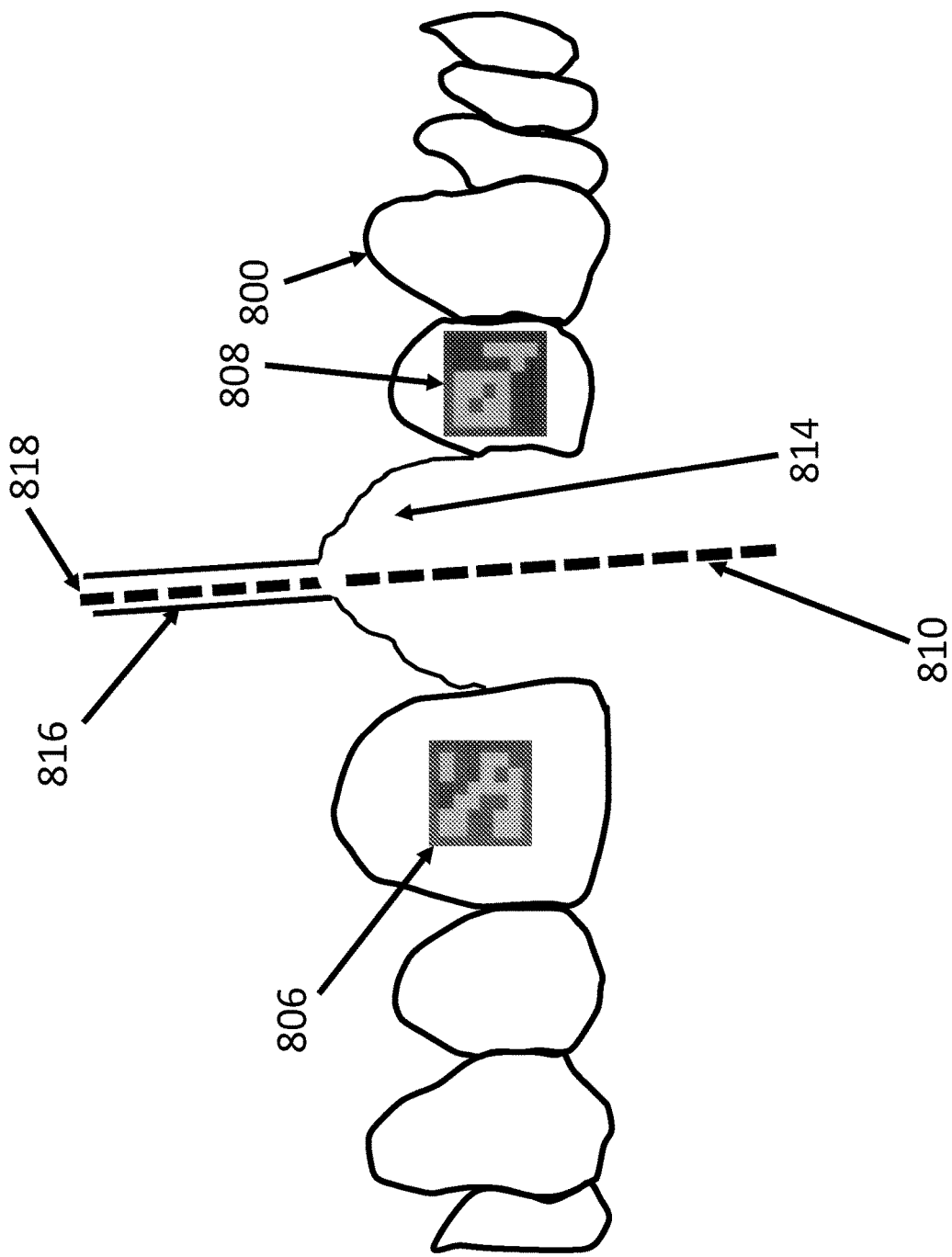

FIG. 41I shows the long axis 818 of the drill canal 816. The long axis 818 of the drill canal 816 can be determined as, for example, explained above in the written description of FIG. 41H. The long axis 818 of the drill canal 816 can also be determined using, for example, a pre-operative or intra-operative scan; it can be part of a virtual surgical plan developed using, for example, a pre- or intra-operative scan. The long axis 818 of the drill canal 816 can be a virtual guide for placing one or more physical implant components, e.g. by superimposing and/or aligning the physical implant component(s) with the virtual long axis 818 of the drill canal 816.

Figure 41J:
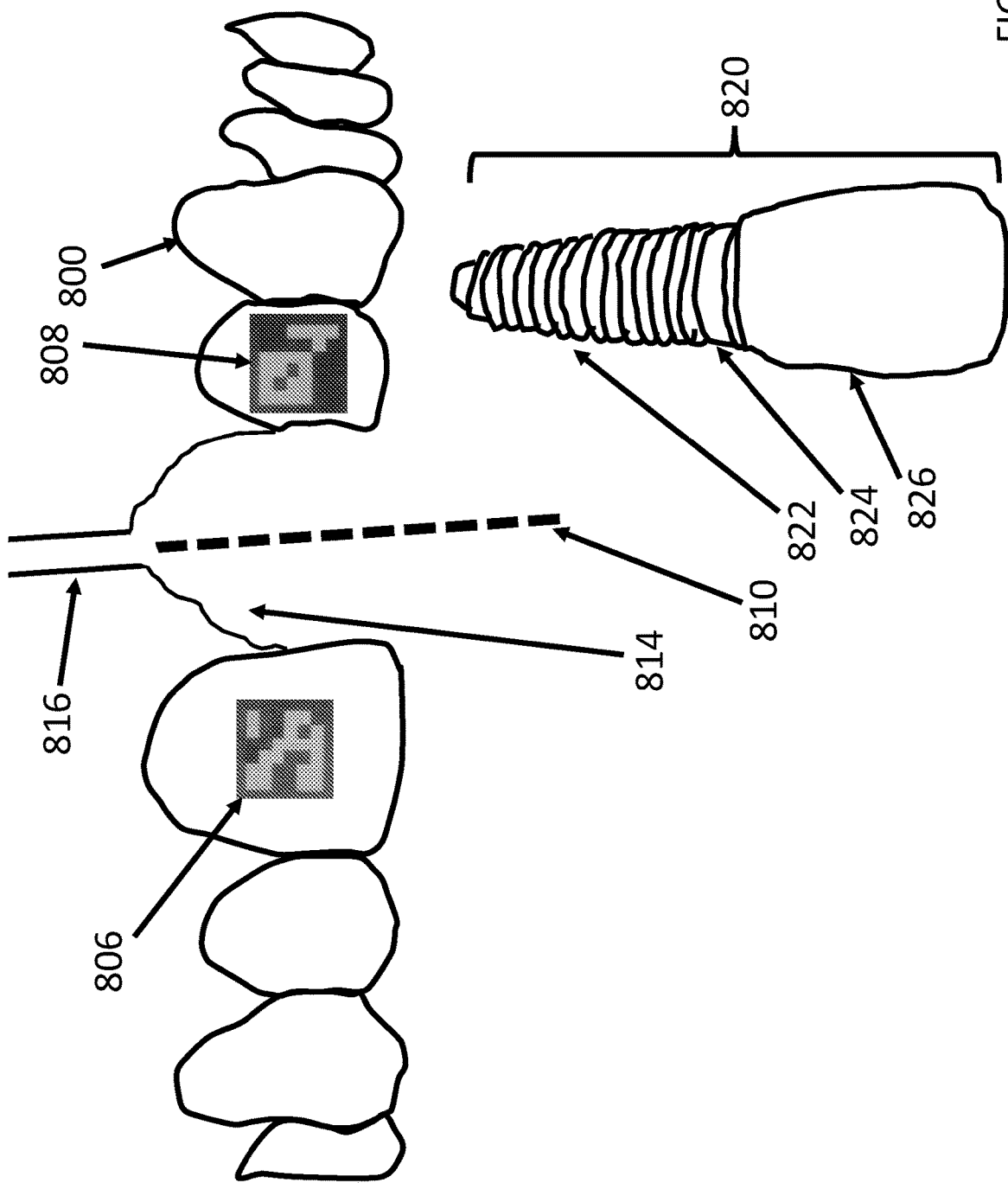

FIG. 41J shows the maxillary teeth 800 with the jaw open, in an unoccluded position after the tooth extraction. The optical markers 806 and 808 are also seen. The virtual surgical guide 810, in this example a virtual axis 810 for aligning one or more physical dental tools, physical drills, physical instruments, or one or more dental implant components is also shown. The virtual surgical guide 810 is maintained in its position, orientation and/or alignment superimposed onto the live data of the patient, including the void 814 created by the extraction of the tooth. A physical dental implant 820 is shown for placement in the void 814. The dental implant, in this example, has three components, a post 822, e.g. a titanium post, with a thread, an abutment 824, and a crown 826. The post 822 is intended to be advanced into the drill canal 816. Optionally, if the live data of the patient, e.g. the dental or oral structures, e.g. the void and the adjacent teeth, are imaged or captured with an image or video capture system, an electronic image of the live data of the dental or oral structures can be displayed by one or more OHMDs, optionally see through or non-see through, with the virtual data, e.g. the virtual axis 810 superimposed. Optionally, the electronic images or video feed of the live data of the patient, in this example the dental or oral structures, can be displayed with magnification, e.g. 1.5×, 2.0×, 2.5×, 3.0×. Any other magnification including negative magnification is possible. The virtual data, for example a virtual surgical guide, e.g. a virtual axis, a virtual tool, a virtual instrument, a virtual implant component and/or a virtual implant, can be superimposed onto the electronic images of the live data and can also be magnified, optionally with the same or different magnification as the electronic images of the live data. Someone skilled in the art will recognize that this embodiment can be applied to other parts of the body, e.g. a knee, e.g. for knee replacement or ACL reconstruction or arthroscopic procedures, a hip, e.g. for hip replacement or arthroscopic procedures, a shoulder, e.g. for shoulder replacement or arthroscopic procedures, e.g. rotator cuff repair or labral tear repair, an ankle, e.g. for ankle joint replacement, a spine, e.g. for spinal fusion, e.g. using pedicle screw instrumentation and/or cages.

Figure 41K:
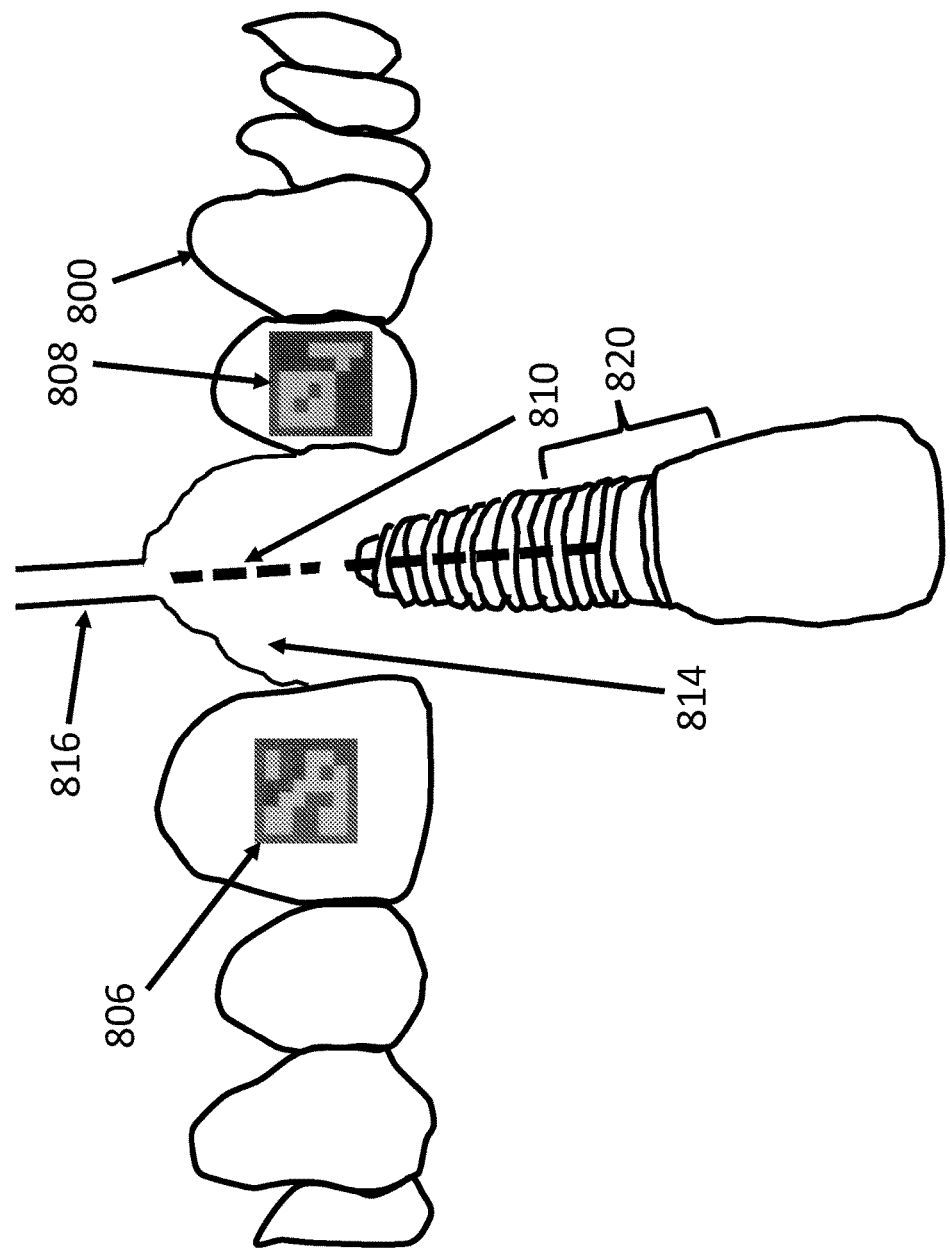

FIG. 41K shows how the physical dental implant 820 is advanced into the void 814. The physical dental implant 820 can be oriented to be aligned with the virtual surgical guide 810, e.g. a virtual axis 810, displayed and/or superimposed by the one or more OHMDs onto the surface of the dental or oral structures, e.g. a tooth or a gingiva (not shown). The virtual surgical guide 810, e.g. a virtual axis 810 or a virtual plane, can be displayed by the one or more OHMDs in a void 814 not filled by an anatomic structure, e.g. a dental or oral structure, or it can be projected onto the surface of a gingiva (e.g. a marginal gum, an attached gum, an interdental gum). The physical dental implant 820 or a physical tool or a physical instrument can be aligned with and superimposed onto the virtual surgical guide 810, in this example a virtual axis 810. If a see through optical head mounted display is used, the physical dental implant 820 or the physical tool or the physical instrument can be visible directly through the see through optical head mounted display while the physical dental implant 820 or the physical tool or the physical instrument can be aligned with and/or superimposed onto the virtual surgical guide 810, e.g. a virtual axis 810. The virtual surgical guide 810, e.g. the virtual axis 810, can be displayed in the void 814 and can be maintained in its position, orientation and/or alignment within the void 814, e.g. with the teeth in occluded and non-occluded position or with the jaw opening or closing. The virtual surgical guide 810, e.g. the virtual axis 810, can be projected onto and/or superimposed onto the surface of the gingiva and can be maintained in its position, orientation and/or alignment over the surface of the gingiva, e.g. with the teeth in occluded and non-occluded position or with the jaw opening or closing. In some embodiments, e.g. in a joint, e.g. a knee joint or a hip joint, a virtual surgical guide, virtual tool, virtual instrument, virtual implant or implant component can be displayed within a void and can be maintained in its position, orientation and/or alignment within a void during movement, e.g. movement of an adjacent anatomic structure, e.g. movement of the joint, e.g. flexion, extension, rotation, abduction, adduction etc., or movement of a physical tool, physical instrument and/or physical implant or implant component. The void 814 can be, for example, the result of a traumatic injury, e.g. in dental applications a previous loss of a tooth, or a tooth extraction. The void can be an area or volume of a previously lost or missing or extracted tooth. The void can be a space within a surgical site or implantation site not filled by an anatomic structure, e.g. a dental or oral structure. The void can be a defect, e.g. a defect in a tissue or an organ, e.g. a defect in an articular surface, or a defect in a tissue surface, or a defect in an organ surface. The void can be an area or a volume of lost or removed tissue, e.g. by a tissue resection, e.g. in an organ or a joint or a spine. The void can be the result of a bone or cartilage removal. The void can also be a space within a surgical site or implantation site, e.g. created by a tissue resection, e.g. a bone removal. The void can be a space between two implants or implant components. The void can be a body cavity. The void can be a recess, e.g. between two tissue folds or two tissue layers.

The virtual surgical guide 810, e.g. the virtual axis 810, can be displayed in the void 814 or superimposed onto or projected onto the surface of the gingiva and can be maintained in its position, orientation and/or alignment within the void 814 or maintained in its position, orientation and/or alignment over the surface of the gingiva while one or more physical tools, physical instruments, physical implant components or physical implants 820 are moved in the field of view of the user, e.g. are moved into the void while the user is looking at the void. The virtual surgical guide 810, e.g. the virtual axis 810, can be displayed in the void 814 or superimposed onto or projected onto the surface of the gingiva and can be maintained in its position, orientation and/or alignment within the void 814 or maintained in its position, orientation and/or alignment over the surface of the gingiva while one or more physical tools, physical instruments, physical implant components or physical implants 820 are being superimposed and/or aligned with the virtual surgical guide 810, e.g. a virtual axis 810.

In some embodiments, a virtual tool, virtual instrument, virtual implant component or virtual implant can be displayed by the one or more OHMDs in a void not filled by an anatomic structure, e.g. a dental or oral structure. A physical tool, physical instrument, physical implant component or physical implant can be aligned with and superimposed onto the virtual tool, virtual instrument, virtual implant component or virtual implant. If a see through optical head mounted display is used, the physical tool, physical instrument, physical implant component or physical implant can be visible directly through the see through optical head mounted display while the physical tool, physical instrument, physical implant component or physical implant can be aligned with and/or superimposed onto the virtual tool, virtual instrument, virtual implant component or virtual implant. The virtual tool, virtual instrument, virtual implant component or virtual implant can be displayed in a void and can be maintained in its position, orientation and/or alignment within the void, e.g. with the teeth in occluded and non-occluded position or with the jaw opening or closing. In some embodiments, e.g. in a joint, e.g. a knee joint or a hip joint, a virtual surgical guide, virtual tool, virtual instrument, virtual implant or implant component can be displayed within a void and can be maintained in its position, orientation and/or alignment within a void during movement, e.g. movement of an adjacent anatomic structure, e.g. movement of the joint, e.g. flexion, extension, rotation, abduction, adduction etc., or movement of a physical tool, physical instrument and/or physical implant or implant component. The void can be, for example, the result of a traumatic injury, e.g. in dental applications a previous loss of a tooth, or a tooth extraction. The void can also be a space within a surgical site or implantation site not filled by an anatomic structure, e.g. a dental or oral structure, or a defect in an articular surface, or a defect in a tissue surface, or a defect in an organ surface, or a void created by a tissue resection, e.g. in an organ or a joint or a spine. The void can be the result of a bone or cartilage removal. The void can also be a space within a surgical site or implantation site, e.g. created by a tissue resection, e.g. a bone removal. The void can be a space between two implants or implant components. The void can be a body cavity. The void can be a recess, e.g. between two tissue folds or two tissue layers. The virtual tool, virtual instrument, virtual implant component or virtual implant can be displayed in the void and can be maintained in its position, orientation and/or alignment within the void while one or more physical tools, physical instruments, physical implant components or physical implants are moved in the field of view of the user, e.g. are moved into the void while the user is looking at the void. The virtual tool, virtual instrument, virtual implant component or virtual implant can be displayed in the void and can be maintained in its position, orientation and/or alignment within the void while one or more physical tools, physical instruments, physical implant components or physical implants are being superimposed and/or aligned with the virtual tool, virtual instrument, virtual implant component or virtual implant.

In some embodiments, the virtual surgical guide 810, e.g. a virtual axis 810, can be displayed by the one or more OHMDs on the surface of an anatomic structure, e.g. a dental or oral structure, e.g. a tooth or a gingiva, and can be superimposed onto the surface of the anatomic structure, e.g. a dental or oral structure, e.g. a tooth or a gingiva, for example onto corresponding portions of an anatomic structure.

In some embodiments, the virtual surgical guide 810, e.g. the virtual axis 810, can be displayed and/or superimposed by the one or more OHMDs onto the surface of an anatomic structure, e.g. a dental or oral structure, e.g. a tooth or a gingiva, and can be maintained in its position, orientation and/or alignment on the surface of the anatomic structure, e.g. a dental or oral structure, e.g. a tooth or a gingiva, e.g. with the teeth in occluded and non-occluded position or with the jaw opening or closing.

In some embodiments, the virtual surgical guide 810, e.g. the virtual axis 810, can be displayed and/or superimposed by the one or more OHMDs onto the surface of the anatomic structure, e.g. a dental or oral structure, e.g. a tooth or a gingiva, and can be maintained in its position, orientation and/or alignment on the surface of the anatomic structure, e.g. a dental or oral structure, while one or more physical tools, physical instruments, physical implant components or physical implants 820 are moved in the field of view of the user, e.g. are moved for placing an implant, while the user is looking at the surface of the anatomic structure.

In some embodiments, the virtual surgical guide 810, e.g. the virtual axis 810, can be displayed and/or superimposed by the one or more OHMDs onto the surface of the anatomic structure, e.g. a dental or oral structure, e.g. a tooth or a gingiva, and can be maintained in its position, orientation and/or alignment on the surface of the anatomic structure, e.g. a dental or oral structure, while one or more physical tools, physical instruments, physical implant components or physical implants 820 are being superimposed and/or aligned with the virtual surgical guide 810, e.g. a virtual axis 810.

In some embodiments, a virtual tool, virtual instrument, virtual implant component or virtual implant can be displayed by the one or more OHMDs on the surface of an anatomic structure, e.g. a dental or oral structure, e.g. a tooth or a gingiva, and can be superimposed onto the surface of the anatomic structure, e.g. a dental or oral structure, e.g. a tooth or a gingiva, for example onto corresponding portions of the anatomic structure.

In some embodiments, a virtual tool, virtual instrument, virtual implant component or virtual implant can be displayed and/or superimposed by the one or more OHMDs onto the surface of an anatomic structure, e.g. a dental or oral structure, e.g. a tooth or a gingiva, and can be maintained in its position, orientation and/or alignment on the surface of the anatomic structure, e.g. a dental or oral structure, e.g. a tooth or a gingiva, e.g. with the teeth in occluded and non-occluded position or with the jaw opening or closing.

In some embodiments, a virtual tool, virtual instrument, virtual implant component or virtual implant can be displayed and/or superimposed by the one or more OHMDs onto the surface of the anatomic structure, e.g. a dental or oral structure, e.g. a tooth or a gingiva, and can be maintained in its position, orientation and/or alignment on the surface of the anatomic structure, e.g. a dental or oral structure, while one or more physical tools, physical instruments, physical implant components or physical implants are moved in the field of view of the user, e.g. are moved for placing an implant, while the user is looking at the surface of the anatomic structure.

In some embodiments, a virtual tool, virtual instrument, virtual implant component or virtual implant can be displayed and/or superimposed by the one or more OHMDs onto the surface of the anatomic structure, e.g. a dental or oral structure, e.g. a tooth or a gingiva, and can be maintained in its position, orientation and/or alignment on the surface of the anatomic structure, e.g. a dental or oral structure, while one or more physical tools, physical instruments, physical implant components or physical implants are being superimposed and/or aligned with the virtual tool, virtual instrument, virtual implant component or virtual implant.

Figure 41L:
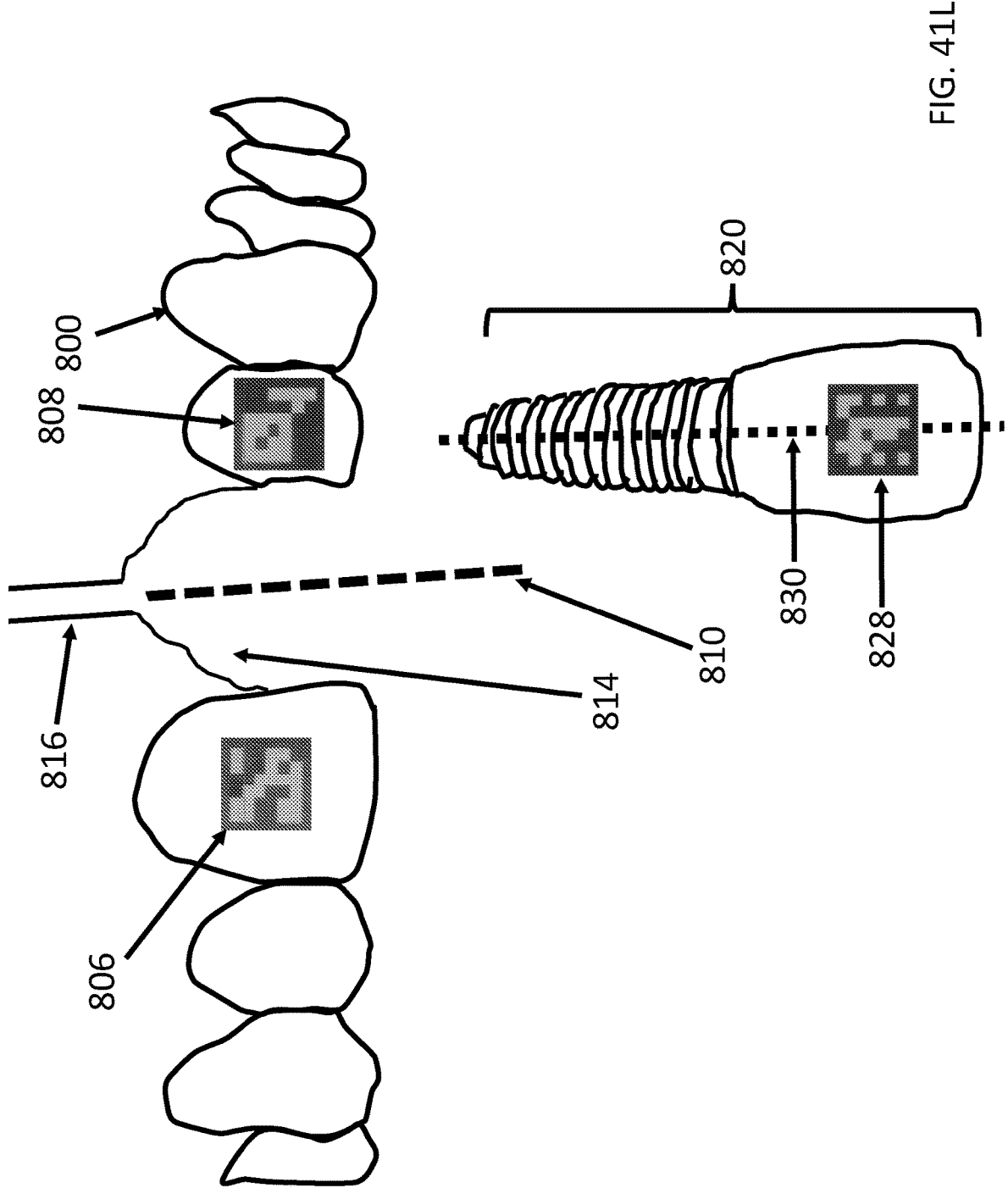

FIG. 41L shows a physical dental implant 820 which can include a marker 828 for tracking the position, orientation and/or alignment and/or coordinates of the physical dental implant, for example during movement. The marker can be an optical marker, a navigation marker, an LED or any other marker described in the specification or known in the art. The marker can be an IMU. The marker can be attachable and/or detachable. Rather than using a marker for tracking, direct tracking of the physical dental implant 820 can be performed using, for example, an image capture and/or video capture system and/or a 3D scanner. With the geometry of the implant and the location of the marker on the physical implant known, a central axis 830 of the physical implant can be determined by a computer processor. The central axis 830 or a virtual 2D or 3D outline of the physical implant can be displayed by the one or more OHMDs during movement and tracking of the physical dental implant 820 for superimposing and/or aligning it with the virtual surgical guide 810, e.g. a virtual axis 810.

Figure 41M:
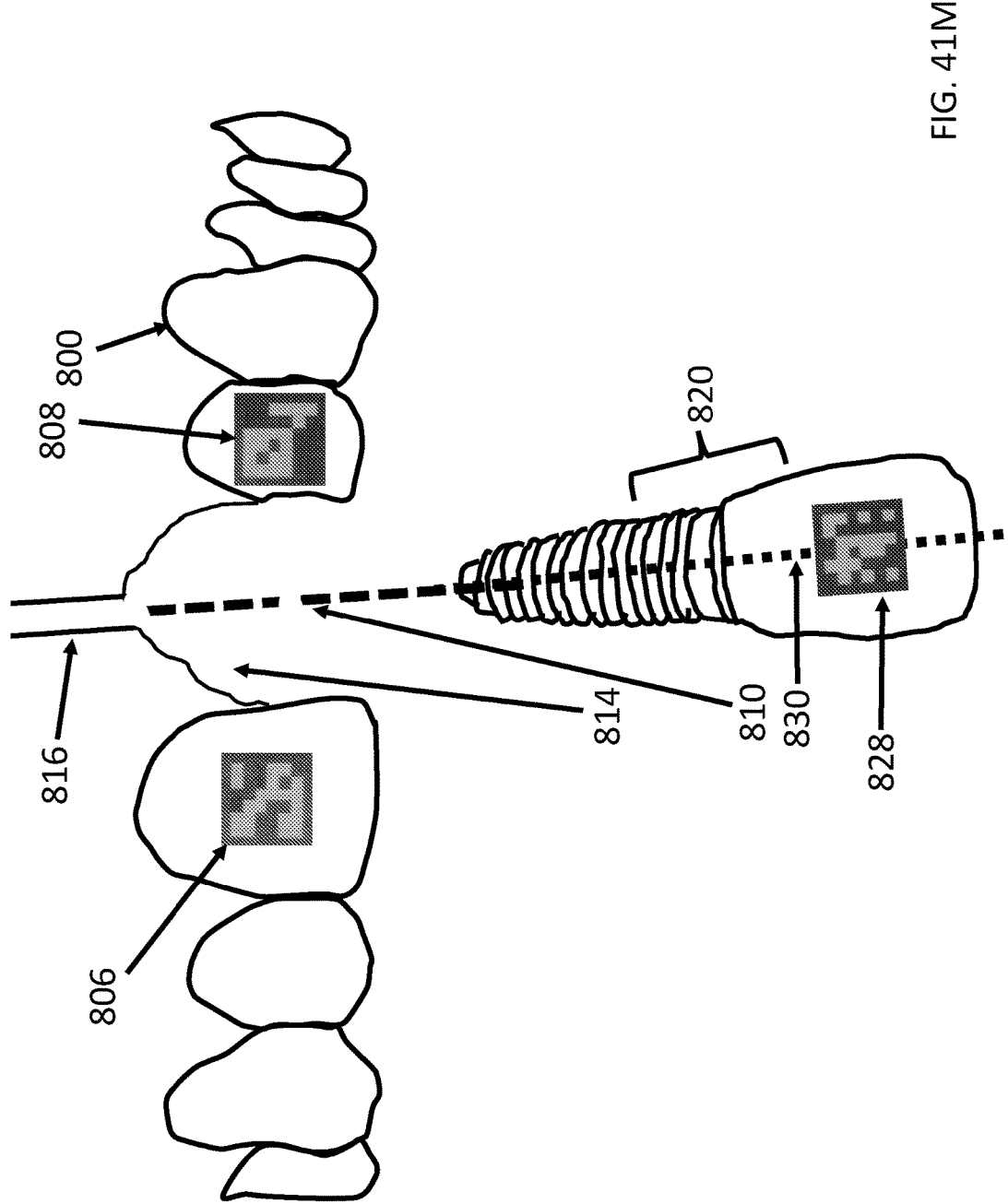

FIG. 41M shows the physical dental implant 820 which can include a marker 828 for tracking the position, orientation and/or alignment and/or coordinates of the physical dental implant, for example during movement. The physical dental implant 820 has been moved and aligned so that its central axis 830 is aligned with the virtual surgical guide 810, e.g. a virtual axis 810 in this example. By aligning the physical dental implant 820 including its central axis 830 with the virtual surgical guide 810, e.g. the virtual axis 810, the physical dental implant 820 can be placed in an accurate manner in the predetermined position, orientation, alignment and/or coordinates, for example developed in a virtual surgical plan and/or determined with use of pre- or intraoperative imaging.

Optionally, the live data of the patient, e.g. one or more anatomic structures, e.g. dental or oral structures, for example captured with a camera or video system and displayed in an electronic image or video stream by the OHMD, and/or the virtual data, e.g. a virtual surgical guide 810, e.g. a virtual axis, or a virtual tool, a virtual instrument, a virtual implant component or a virtual implant, and virtual tracking data, as seen for example in central axis 830, and a virtual display of the tracked physical tool, physical instrument, physical implant or physical implant component, or any combinations thereof can be magnified by the OHMD display during the moving, aligning, orienting and placing of the physical tool, physical instrument, physical implant component or physical implant, in this example the physical dental implant 820.

Optionally, only the virtual data, e.g. a virtual surgical guide 810, e.g. a virtual axis, or a virtual tool, a virtual instrument, a virtual implant component or a virtual implant, and virtual tracking data, as seen for example in central axis 830, and a virtual display of the tracked physical tool, physical instrument, physical implant or physical implant component can be magnified by the OHMD display during the moving, aligning, orienting and placing of the physical tool, physical instrument, physical implant component or physical implant, in this example the physical dental implant 820.

In some embodiments, the foregoing systems, methods, and devices can be combined with pre- or intra-operative imaging of one or more dental or oral structures using, for example, x-rays, Panorex views, ultrasound, cone beam CT, CT scan or MRI scan or any other imaging modality applicable to dental or oral imaging. The pre- or intraoperative images can be registered with the live data of the patient, e.g. anatomic, e.g. dental or oral, structures. For example, anatomic, e.g. dental or oral structures, including dimensions, edges, margins, curvatures and/or shapes of the structures in the live data of the patient can be registered with corresponding anatomic, e.g. dental or oral structures, including dimensions, edges, margins, curvatures and/or shapes of the structures in the pre- or intra-operative imaging data of the patient. Any registration technique described in the specification or known in the art can be used.

Figure 42A:
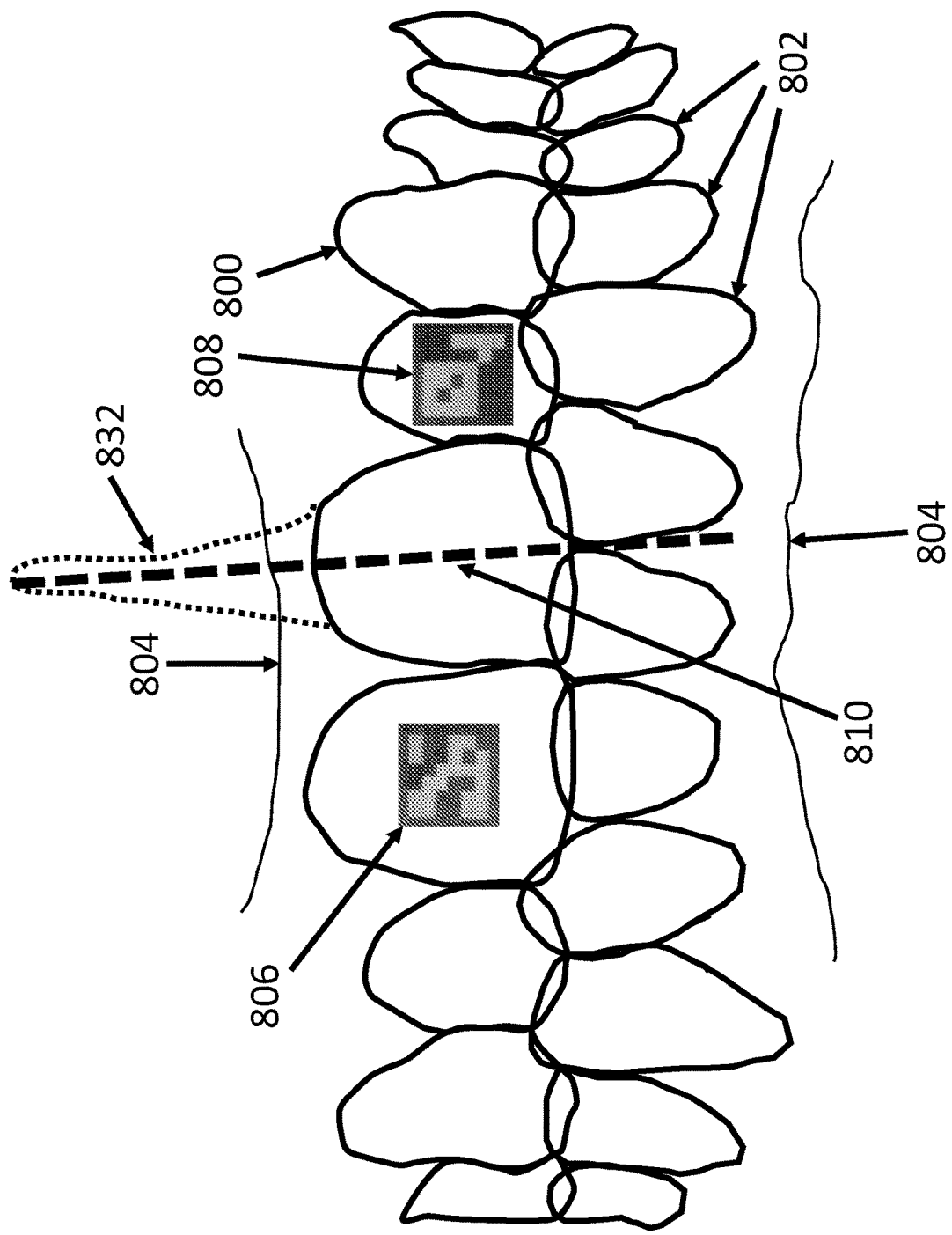
FIGS. 42A-J provide other illustrative, non-limiting examples of one or more augmented reality OHMD displays for dental surgery or placement of dental implants, including display of virtual surgical guides, e.g. virtual axes, for aligning physical dental tools and instruments, e.g. drills, and/or physical dental implants.

FIG. 42A shows an illustrative non-limiting example of registering live data of the patient, e.g. one or more teeth 800, a tissue fold 804, or any other data directly visible through a see through optical head mounted display with one or more structures hidden below the visible surface, e.g. visible only an imaging study, e.g. a root 832 (dotted line) of a tooth. The display of structures visible on an imaging study, e.g. a root 832, by one or more OHMDs can facilitate the moving, placing, aligning, fitting, sizing and/or selection of one or more virtual or physical tools, virtual or physical instruments, virtual or physical implants and/or virtual or physical implant components relative to a surgical site or implantation site, which can include tissue hidden below the surface directly visible through an optical head mounted display. Thus, one or more virtual or physical tools, virtual or physical instruments, virtual or physical implants and/or virtual or physical implant components can be oriented in relationship to and aligned with one or more anatomic structures (e.g. enamel, teeth, gingiva) and/or one or more voids visible directly through a see through optical head mounted display. One or more virtual or physical tools, virtual or physical instruments, virtual or physical implants and/or virtual or physical implant components can be oriented in relationship to and aligned with one or more anatomic structures visible on an imaging study only and superimposed by an optical head mounted display onto the live data, e.g. anatomic structures of the patient. One or more virtual or physical tools, virtual or physical instruments, virtual or physical implants and/or virtual or physical implant components can be oriented in relationship to and aligned with one or more anatomic structures (e.g. enamel, teeth, gingiva) and/or one or more voids visible directly through a see through optical head mounted display and can be oriented in relationship to and aligned with one or more anatomic structures visible on an imaging study only and superimposed by an optical head mounted display onto the live data, e.g. anatomic structures of the patient. The registration can be performed using one or more markers, e.g. optical markers 806 and 808, or navigation markers or other markers which can optionally include radiopaque elements for detection on imaging studies using ionizing radiation. Direct tracking can also be performed for registration using, for example, a video camera or 3D scanner, e.g. for tracking live data of the patient and/or physical tools, physical instruments, physical implant components and/or physical implants or devices. The video camera or 3D scanner can optionally be attached to an imaging apparatus, e.g. an x-ray machine, a Panorex machine, an ultrasound machine, a cone beam CT, or a CT scan, optionally with a known geometric arrangement between the video camera or 3D scanner and the imaging apparatus. In this manner, live data of the patient and live data of physical tools, physical instruments, physical implant components and/or physical implants or devices can be obtained simultaneous or near simultaneous or sequential to the data from the imaging apparatus, e.g. an x-ray machine, a Panorex machine, an ultrasound machine, a cone beam CT, or a CT scan and can be registered using the known geometric arrangement between the video camera or 3D scanner and the imaging apparatus.

FIG. 42A shows the teeth in occluded position, with the jaw closed. In some embodiments, a virtual surgical guide 810, e.g. a virtual axis 810, can be oriented in relationship to and aligned with one or more anatomic structures, e.g. a tooth, an enamel or a gingiva, and/or one or more voids visible directly through a see through optical head mounted display. In some embodiments, a virtual surgical guide 810, e.g. a virtual axis 810, can be oriented in relationship to and aligned with one or more anatomic structures visible on an imaging study only and superimposed by an optical head mounted display onto the live data, e.g. anatomic structures of the patient. In some embodiments, a virtual surgical guide 810, e.g. a virtual axis 810, can be oriented in relationship to and aligned with one or more anatomic structures and/or one or more voids visible directly through a see through optical head mounted display and/or can be oriented in relationship to and aligned with one or more anatomic structures visible on an imaging study only and superimposed by an optical head mounted display onto the live data, e.g. anatomic structures of the patient.

In some embodiments, a virtual axis can be determined pre-operatively, e.g. before the dental procedure, e.g. a root canal or dental implant placement. In some embodiments, a virtual axis can be determined intra-operatively, e.g. during the procedure, for example by aligning a virtual axis with one or more structures on the surface of a tooth, e.g. a cusp, a ridge, or a pit. The aligning can be performed using any user interface described in the specification, e.g. using gesture recognition and/or voice recognition. The virtual axis can adjusted based on directly visible information, e.g. anatomic landmarks, structures on the surface of a tooth, e.g. earmarked for extraction or a root canal, structures on adjacent opposing teeth, and/or subsurface data (for example visible on an imaging study or data derived from an imaging study co-projected by one or more OHMDs and optionally superimposed onto the tooth, and/or mandible and/or maxilla, and/or root), e.g. root location, root canal, and/or implant data/information, e.g. dimensions, CAD files, desired distance(s) or placement relative to adjacent teeth (for implant placement).

In any of the embodiments, a computer processor configured to display a virtual surgical guide by the one or more OHMDs can maintain the location and/or orientation of the virtual surgical guide superimposed onto and/or aligned with the surface of a tooth with movement of a mandible or maxilla, for example by tracking the x-, y- and/or z-coordinates of the tooth including during movement of the mandible or maxilla. Similarly, a computer processor configured to display a virtual surgical guide by the one or more OHMDs can maintain the location and/or orientation of the virtual surgical guide superimposed onto and/or aligned with the surface of a tooth with movement of a surgical or dental instrument. The movement of the surgical or dental instrument can include superimposition and/or alignment of the physical surgical instrument or dental instrument with the virtual surgical guide, e.g. a virtual axis. The registration can be performed using one or more markers, e.g. optical markers 806 and 808, or navigation markers or other markers which can optionally include radiopaque elements for detection on imaging studies using ionizing radiation. Direct tracking can also be performed for registration using, for example, a video camera or 3D scanner, optionally attached to an imaging apparatus, e.g. an x-ray machine, a Panorex machine, an ultrasound machine, a cone beam CT, or a CT scan, optionally with a known geometric arrangement between the video camera or 3D scanner and the imaging apparatus. FIG. 42A shows the teeth in occluded position, with the jaw closed.

Someone skilled in the art will recognize that the foregoing embodiments and examples of a virtual surgical guide 810, e.g. a virtual axis, can be applied to guiding a physical drill or other tools or instruments, e.g. a physical file or a physical flare or a physical cone or a physical post, for treating one or more root canals or for preparing a tooth [e.g. including tissue removal, burring, milling] for placement of a cap or crown. Structures hidden below the visible surface, e.g. visible only an imaging study, e.g. a root 832 (dotted line) of a tooth can be displayed and the dentist can use the display to align a physical tool [e.g. a physical drill, burr or mill], physical instrument, a physical file, a physical flare, a physical cone or a physical post with the displayed root 832 and/or the virtual surgical guide 810, which can be projected, superimposed onto and/or aligned with the surface of the tooth and/or the dental or oral structures, e.g. gingiva, and which can be co-displayed with subsurface structures hidden below the surface, e.g. the root 832 visible on the imaging study.

Figure 42B:
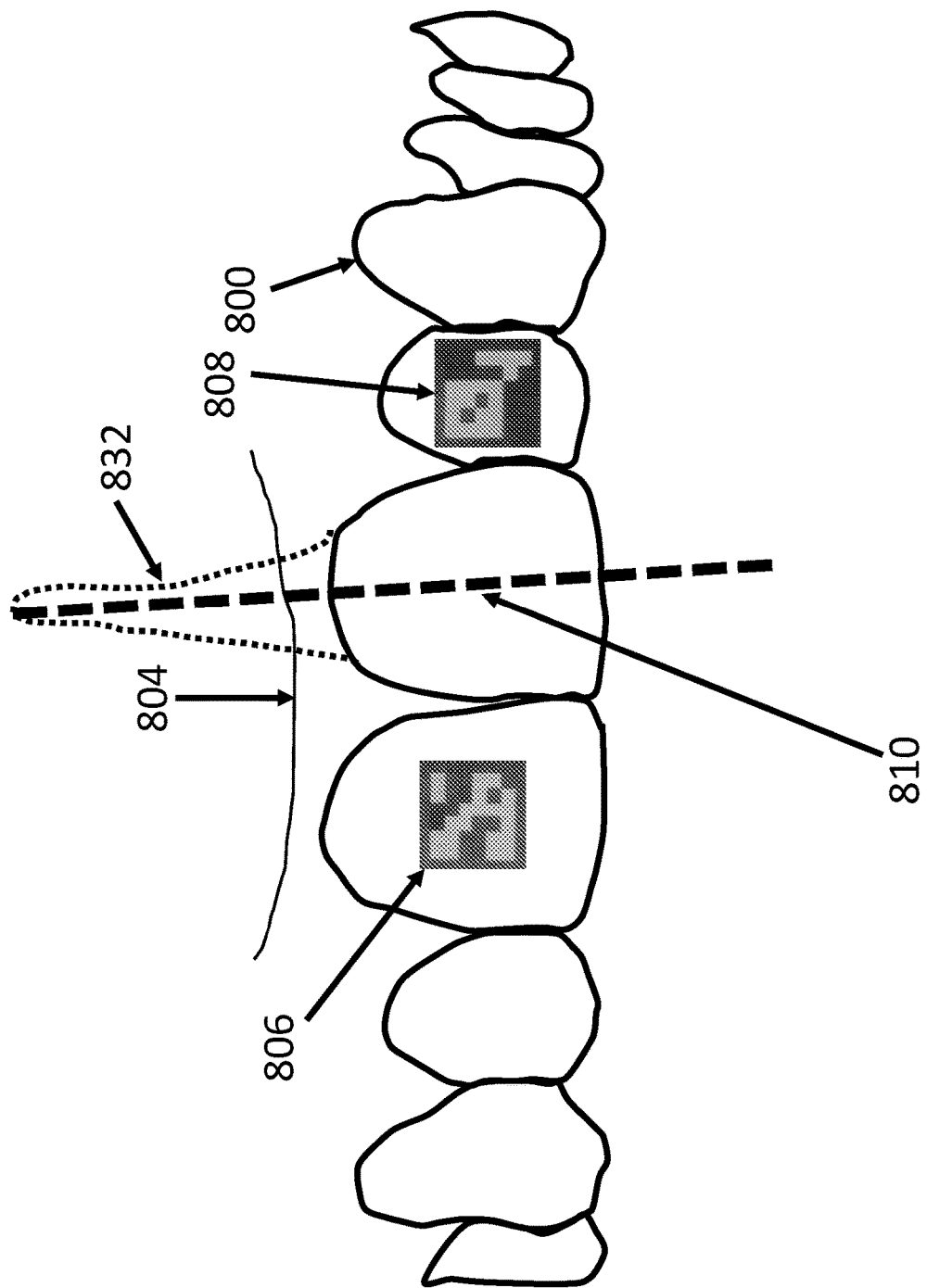

FIG. 42B is an illustrative non-limiting example with the teeth in non-occluded, open position. The display of the imaging study or one or more structures or graphical representations extracted from the imaging study, e.g. a root 832, can be maintained superimposed onto the corresponding location and/or coordinates in the bone, e.g. a maxilla or a mandible, by a computer processor and the one or more OHMDs irrespective of movement of the teeth or jaw or maxilla. Similarly, the display of a virtual surgical guide 810, e.g. a virtual axis 810, or a virtual tool, virtual instrument, virtual implant component and/or virtual implant can be maintained superimposed onto the surface of a corresponding anatomic structure, e.g. a dental or oral structure, or the bone, e.g. the mandible or maxilla, by a computer processor and the one or more OHMDs irrespective of movement of the teeth or jaw or maxilla. This can be possible, for example, by attaching the one or more markers, e.g. optical markers 806 and 808, or navigation markers to the oral side, e.g. maxilla side or mandible side, selected for surgery and/or for placement of a dental implant or other dental device. By placing the one or more markers, e.g. optical markers 806 and 808, or navigation markers or one or more patient specific markers or other markers on the side, e.g. maxilla or mandible, selected for surgery and/or for placement of a dental implant or other dental device, the registration of the imaging study and of the virtual data can be maintained to the live data of the patient, e.g. one or more anatomic structures, e.g. a dental or oral structure, irrespective of movement of the mandible or maxilla; thus, the display of the imaging study and/or the virtual data can be maintained in relationship to the anatomic structure, e.g. a dental or oral structure (e.g. a tooth or gingiva) and/or the surgical site or implantation site, irrespective of movement of the mandible or maxilla. Someone skilled in the art will recognize that the foregoing embodiments and examples of a virtual surgical guide 810, e.g. a virtual axis, can be applied to guiding a physical drill or other tools or instruments, e.g. a physical file or a physical flare or a physical cone or a physical post, for treating one or more root canals or for preparing a tooth [e.g. including tissue removal, burring, milling] for placement of a cap or crown. Structures hidden below the visible surface, e.g. visible only an imaging study, e.g. a root 832 (dotted line) of a tooth can be displayed and the dentist can use the display to align a physical tool [e.g. a physical drill, burr or mill], physical instrument, a physical file, a physical flare, a physical cone or a physical post with the displayed root 832 and/or the virtual surgical guide 810, which can be projected, superimposed onto and/or aligned with the surface of the tooth and/or the dental or oral structures, e.g. gingiva, and which can be co-displayed with subsurface structures hidden below the surface, e.g. the root 832 visible on the imaging study.

Figure 42C:
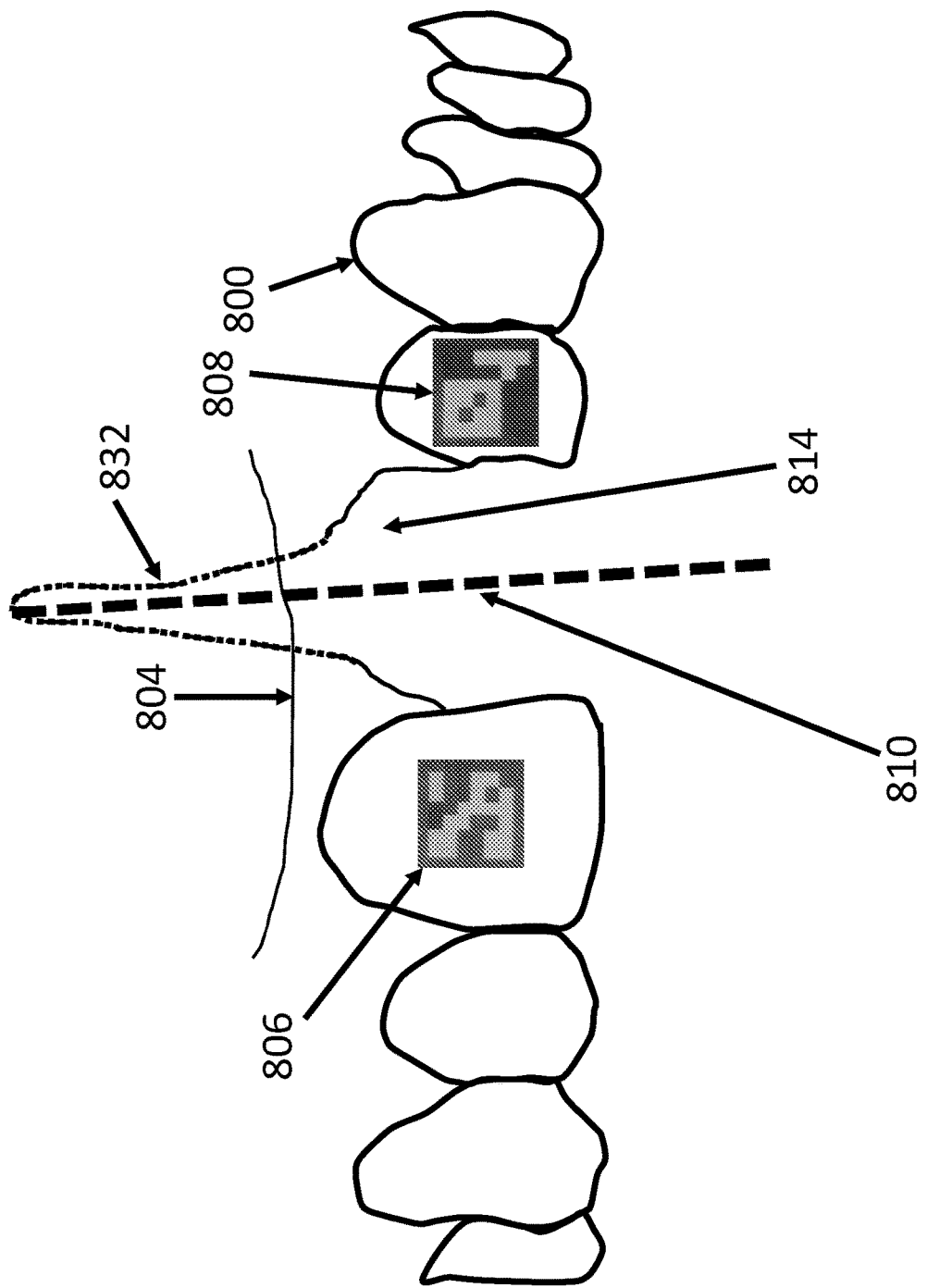

FIG. 42C is an example showing a surgical site after extraction of a tooth. The virtual surgical guide 810, e.g. a virtual axis 810, can be displayed by the one or more OHMDs in the void 814, and/or superimposed onto or aligned with a gingiva; the virtual axis 810 can extend or can be included in the virtual imaging data, e.g. the pre- or intra-operative imaging data, e.g. a root 832, displayed by one or more OHMDs. The position, location, orientation, alignment, and/or coordinates of the virtual surgical guide 810, e.g. the virtual axis 810, can be determined using one or more of the tooth selected for extraction, neighboring teeth or tissues, opposing teeth or tissues, the void, the imaging study, e.g. the visualization of an underlying root and/or other structures, or any combination thereof.

Figure 42D:
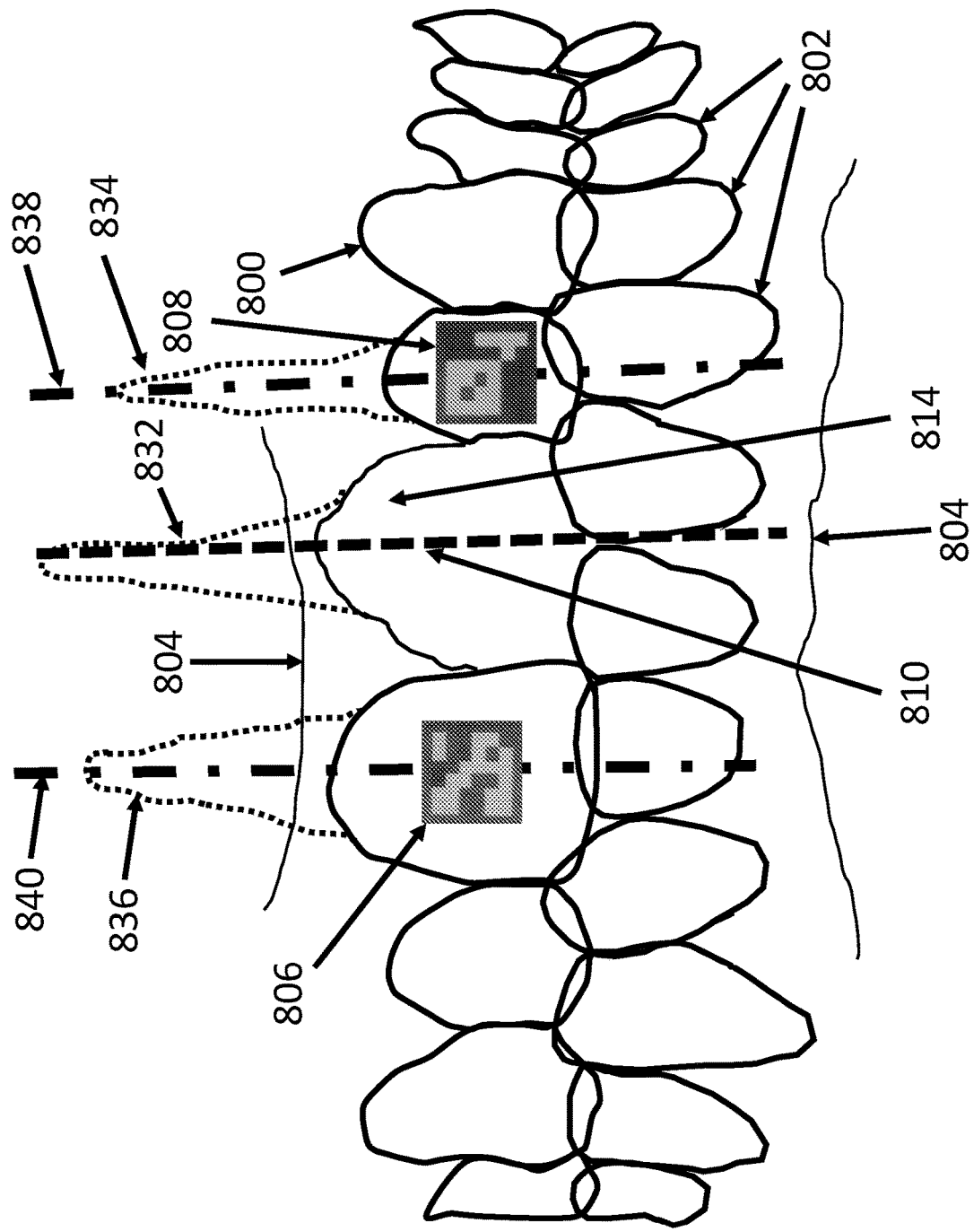

FIG. 42D shows an illustrative, non-limiting example with a missing tooth and a void 814. The teeth are in occluded position with the jaw closed. An imaging study can be co-registered and displayed by one or more OHMDs superimposed onto the corresponding anatomic structures. For example, the root(s) of teeth adjacent to the missing tooth area can be displayed, e.g. on the patient's left 834 and on the patient's right 836. The root of the missing tooth 832 or a void where the root used to be located can also be visible on the imaging study and can be displayed projected onto the corresponding coordinates of the physical bone, e.g. a maxilla or mandible, of the patient. The virtual surgical guide 810, e.g. a virtual axis 810, can be derived, for example, based on information from the visible portions of the adjacent teeth or portions of the adjacent teeth only visible on an imaging study or combinations thereof. Such a portion can be the central axis 838 and 840 of the adjacent teeth.

Figure 42E:
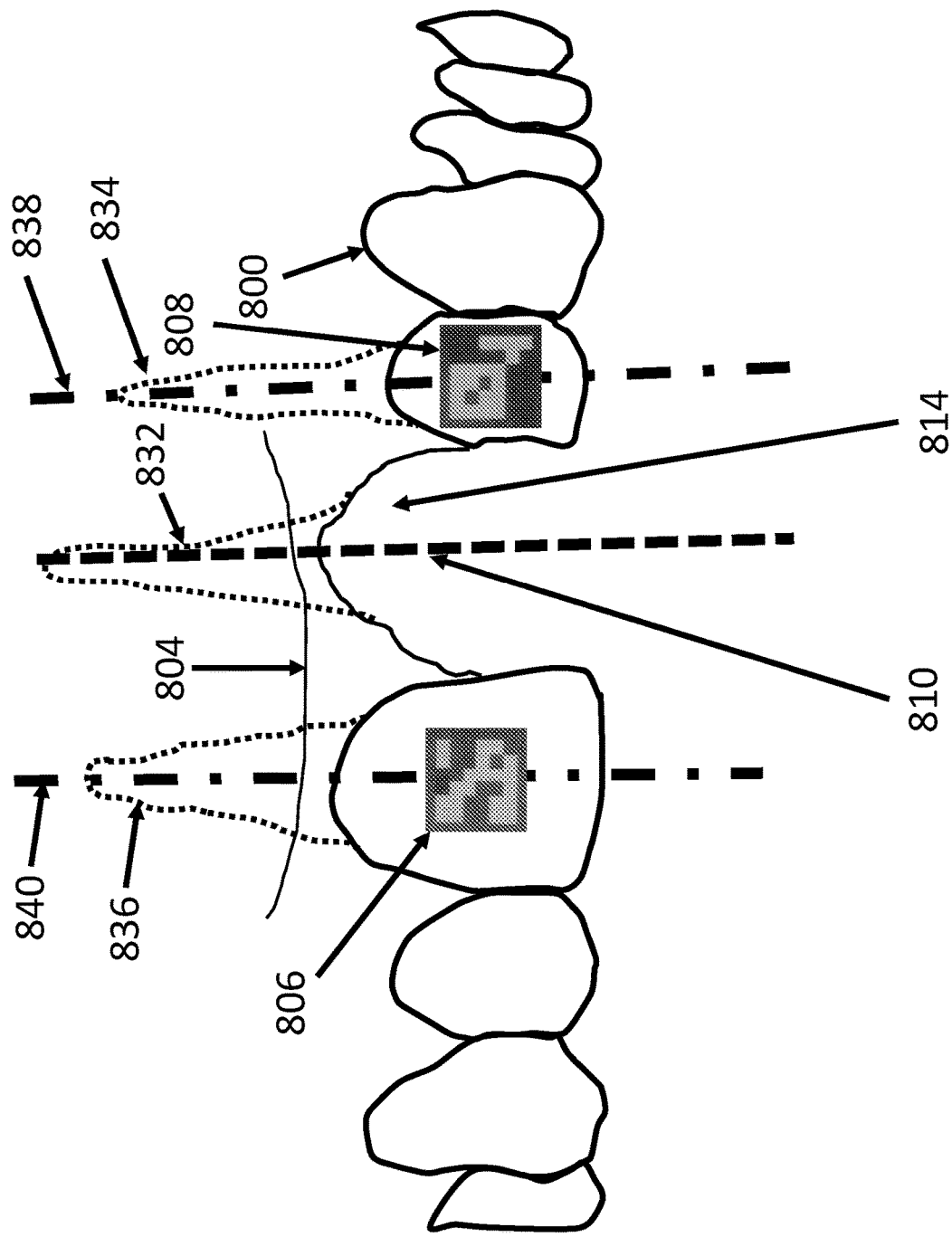

FIG. 42E is a similar, non-limiting example with the teeth in non-occluded position, e.g. the jaw open. The virtual surgical guide 810, e.g. a virtual axis 810, the imaging data, e.g. one or more roots 832, 834, 836 visible on an imaging study, and any other virtual data, e.g. one or more central axes of one or more teeth 838, 840, and one or more virtual tools, virtual instruments, virtual implant components and/or virtual implants can be maintained in their position relative to the surface of the anatomic structure, e.g. a dental or oral structures (e.g. a tooth, an enamel or a gingiva), and/or the underlying bone and structures, e.g. visible only on an imaging study, irrespective of jaw movement, occlusion or non-occlusion, and/or movement of the mandible or maxilla. FIG. 42E is an example how the virtual surgical guide 810, e.g. a virtual axis 810, can be derived based on information from the void 814, e.g. by extending through the deepest point or area of the void, and based on information from adjacent teeth, e.g. by being parallel to the central axis 838 of one or more adjacent teeth.

Figure 42F:
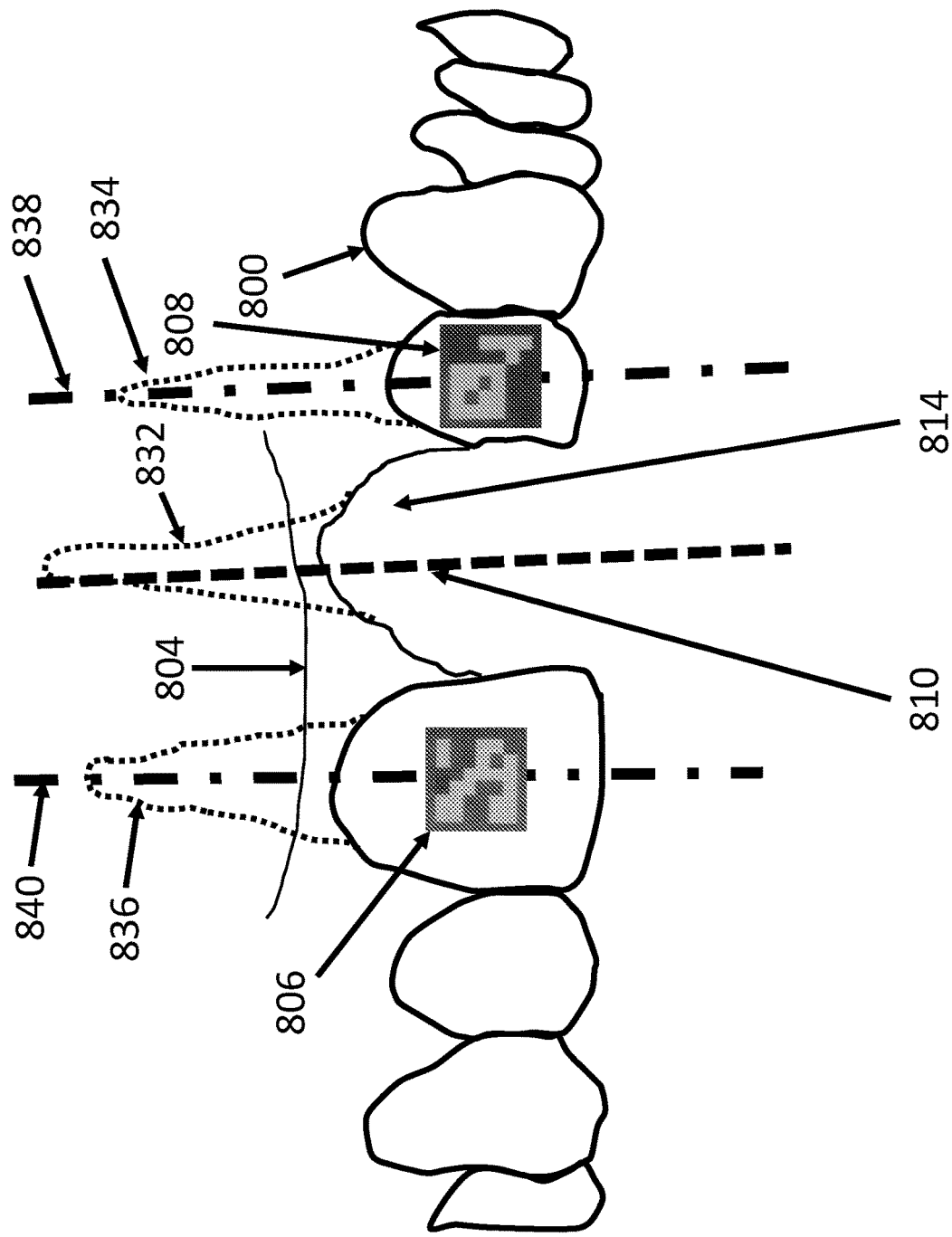

FIG. 42F is an example how the virtual surgical guide 810, e.g. a virtual axis 810, can be derived based on information from adjacent teeth, e.g. by being approximately centered or located between the central axes 838 and 840 of two adjacent teeth.

Figure 42G:
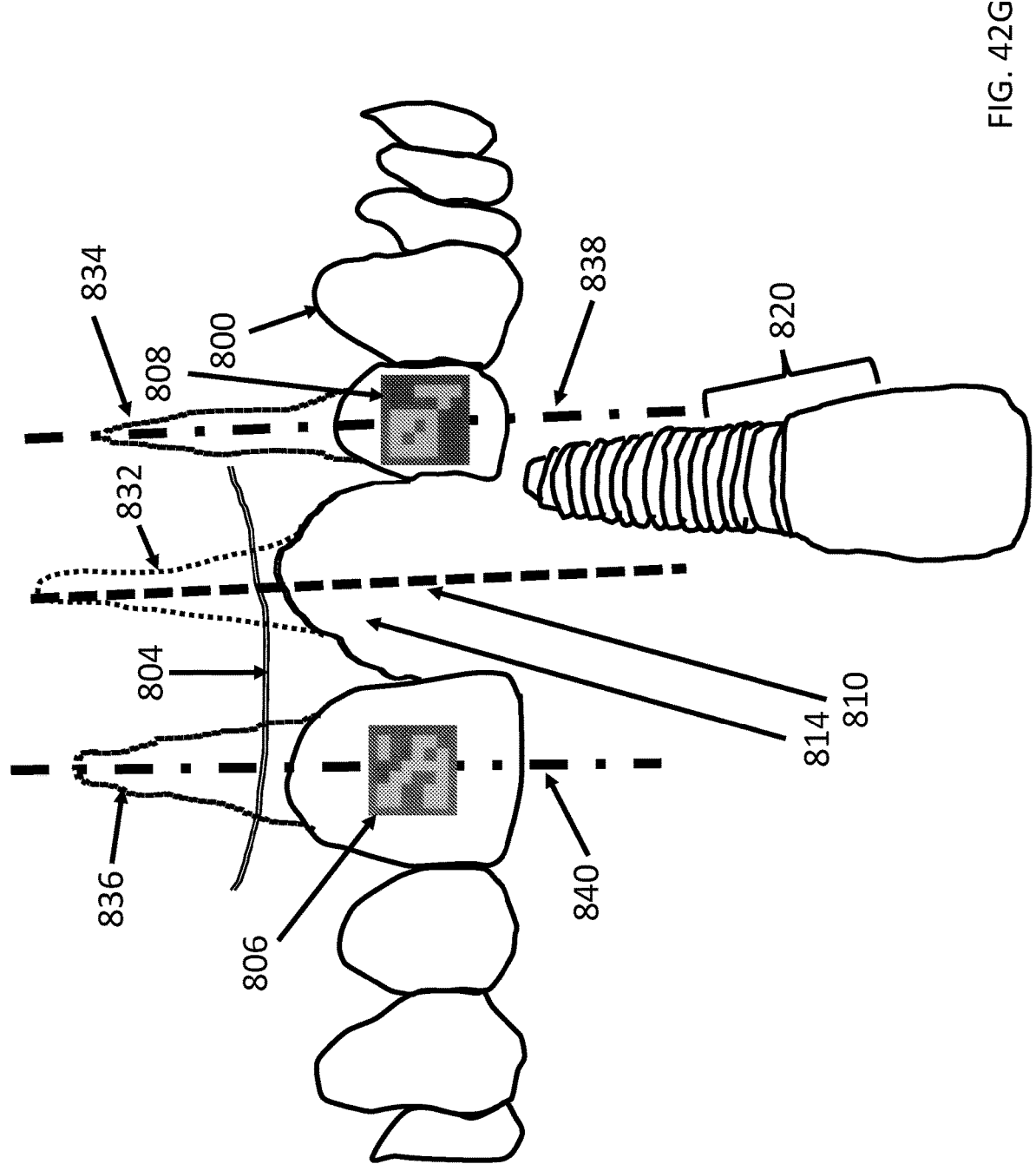

FIG. 42G is an example of a physical dental implant 820 selected for implantation in the void 814. The dental implant 820 can be placed, oriented, aligned and or advanced using information visible on the surface of the dental or oral structures, for example by aligning the physical dental implant 820 with a virtual axis 810 projected onto the surface of a dental or oral structure (e.g. a tooth, an enamel or a gingiva) or projected or displayed in a void 814, and/or information from a void 814, and/or using information from imaging data, e.g. displayed by one or more OHMDs aligned with and/or superimposed onto corresponding anatomic structures, e.g. one or more roots 832, 834, 836 or the mandibular or maxillary bone or portions thereof.

Figure 42H:
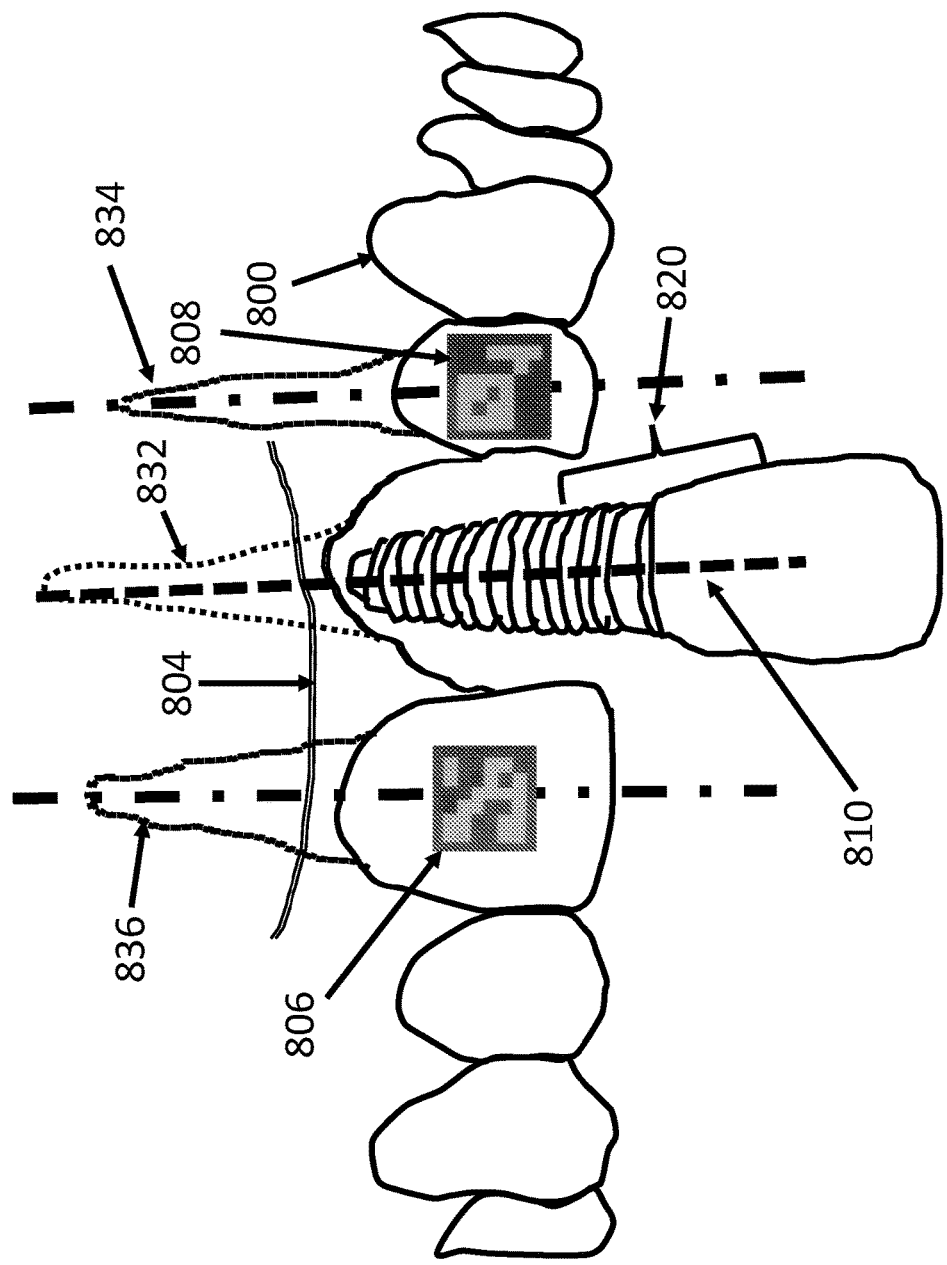

FIG. 42H is an example of a physical dental implant 820 as it is being moved and/or advanced towards the intended or predetermined implantation site. The physical dental implant 820 can be oriented to be aligned with and superimposed onto the virtual surgical guide 810, e.g. a virtual axis 810, which can be displayed and/or superimposed by the one or more OHMDs onto the surface of the dental or oral structures (e.g. a tooth, an enamel, a gingiva) and/or which can be superimposed by the one or more OHMDs on the root 832 or maxilla, superimposed by the OHMD from an imaging study or by superimposing an imaging study with the OHMD.

Figure 42I:
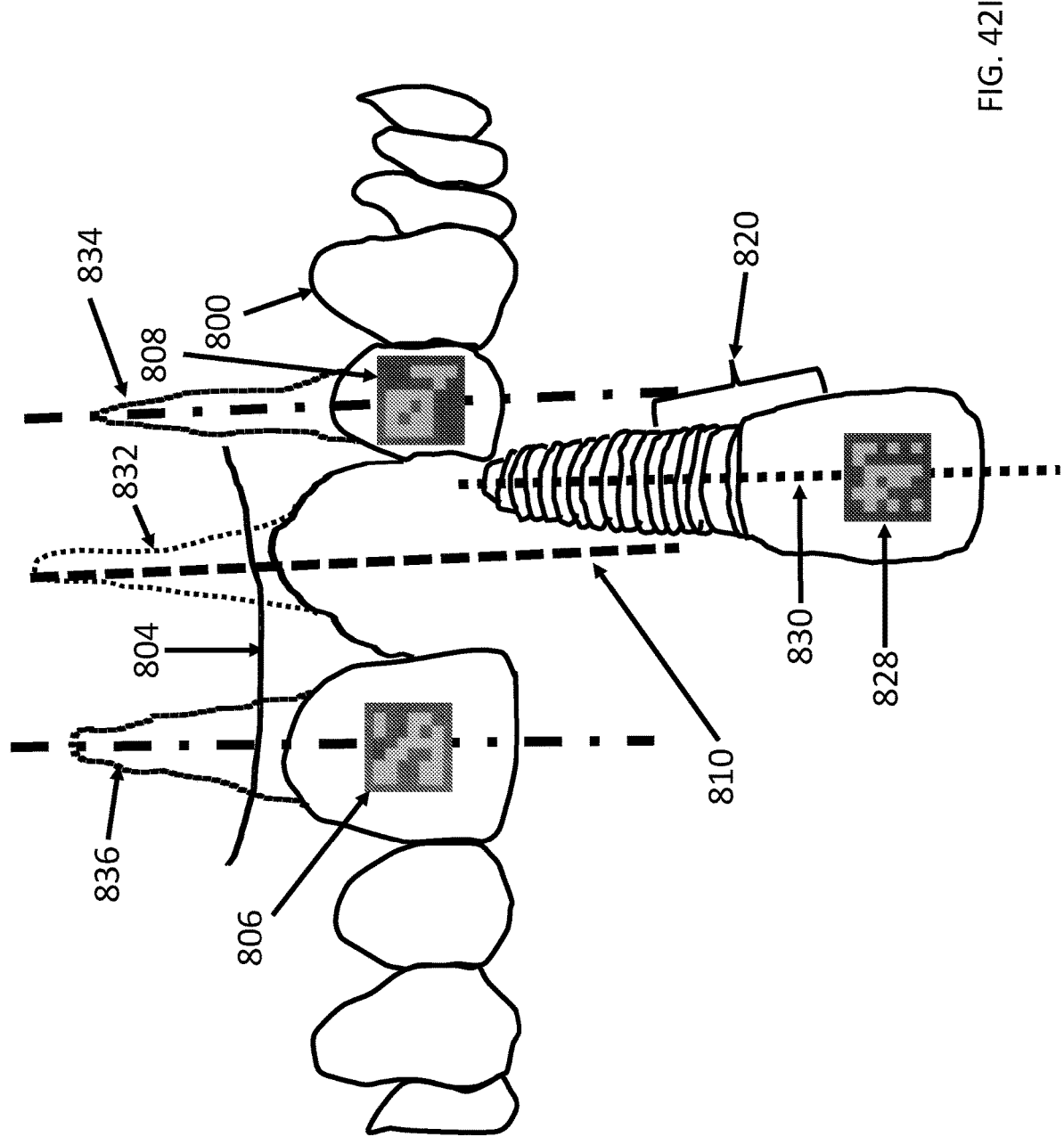

FIG. 42I shows a physical dental implant 820 which can include a marker 828 for tracking the position, orientation and/or alignment and/or coordinates of the physical dental implant, for example during movement. The marker can be an optical marker, a navigation marker, an LED or any other marker described in the specification or known in the art. The marker can be an IMU. The marker can be attachable and/or detachable. Rather than using a marker for tracking, direct tracking of the physical dental implant 820 can be performed using, for example, an image capture and/or video capture system and/or a 3D scanner. With the geometry of the implant and the location of the marker on the physical implant known, a central axis 830 of the physical implant can be determined by a computer processor. The central axis 830 or a virtual 2D or 3D outline of the physical implant can be displayed by the one or more OHMDs during movement and tracking of the physical dental implant 820 for superimposing and/or aligning it with the virtual surgical guide 810, e.g. a virtual axis 810.

In some embodiments, a dental implant placement can be performed in two or more stages. For example, after a drill or instrument has been advanced into the bone for placement of the implant and/or the implantation site for the implant has been prepared, a drill, a pin or a dummy implant can be placed in the implantation site, e.g. a drill hole. The drill, pin or dummy implant can include a marker, e.g. an optical marker, a navigation marker, an LED or any other marker known in the art or described in the specification. The coordinates of the marker can be determined, e.g. using an image capture or video capture system, for example integrated into or attached to an OHMD, or using a navigation system. If the drill, pin, dummy implant is in the expected location, e.g. have an expected/intended/predetermined central axis, the subsequent stages of the procedures can be initiated. If the drill, pin, dummy implant deviate in their alignment from the expected/intended/predetermined location and/or coordinates, e.g. have different central axis or central axis coordinates than the predetermined central axis, e.g. displayed in the form of a virtual axis, by the one or more OHMDs, one or more adjustments can be performed, e.g. by modifying the implantation site, e.g. until the physical central axis and/or coordinates of the drill, pin, or dummy implant are substantially similar or the same relative to the expected/intended/predetermined central axis and/or coordinates of the drill, pin or dummy implant.

Figure 42J:
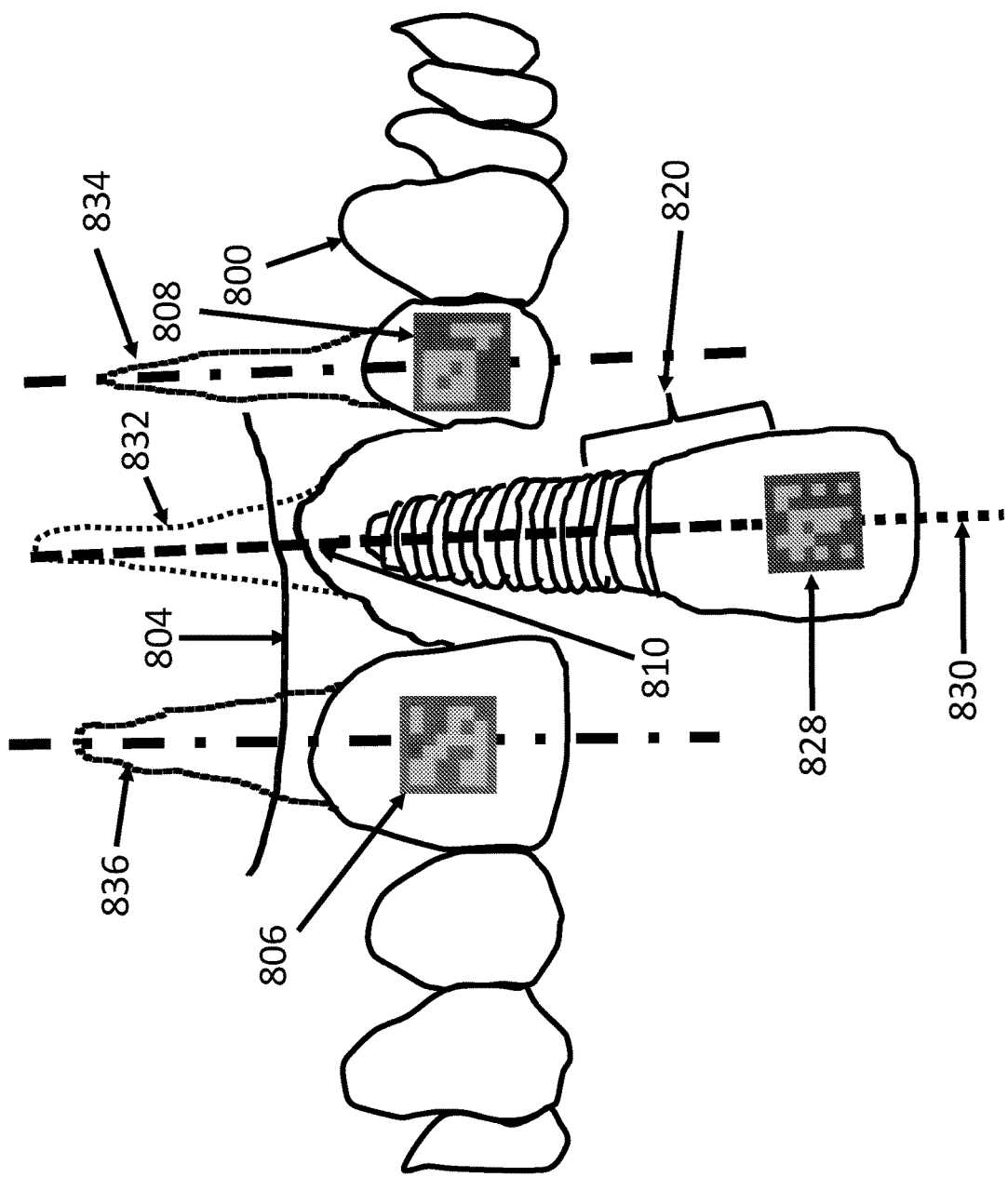

An abutment can be placed after preparation of the implantation site. One or more markers can optionally be attached to the abutment, including, for example, an optical marker, a navigation marker, an LED or any other marker known in the art or described in the specification. The coordinates of the marker can be determined, e.g. using an image capture or video capture system, for example integrated into or attached to an OHMD, or using a navigation system. If the coordinates of the marker are at the expected/intended/predetermined location and/or orientation, the crown can be placed. If the coordinates of the markers deviate from the expected/intended/predetermined location and/or orientation one or more adjustments can be made to the abutment position and/or orientation or to the crown position and/or orientation; an adjustable thread or exchangeable threads can optionally be used for the crown placement to allow for adjustments. Exchangeable threads can, for example, include an eccentric central void or female portion to fit in with the male portion of the abutment. The eccentric central void or female portion can be at angle equal to 180 degrees or different from 180 degrees relative to the central axis of the abutment and/or the crown. FIG. 42J shows the physical dental implant 820 which can include a marker 828 for tracking the position, orientation and/or alignment and/or coordinates of the physical dental implant, for example during movement. The physical dental implant 820 has been moved and aligned so that its central axis 830 is aligned with the virtual surgical guide 810, e.g. a virtual axis 810 in this example. By aligning the physical dental implant 820 including its central axis 830 with the virtual surgical guide 810, e.g. the virtual axis 810, the physical dental implant 820 can be placed in an accurate manner in the predetermined position, orientation, alignment and/or coordinates, for example developed in a virtual surgical plan and/or determined with use of pre- or intra-operative imaging.

In some of the embodiments, dental and/or or oro-maxillofacial surgery implants and/or instruments, e.g. a drill or a probe, can be tracked using any of the techniques described in the specification and/or known in the art. For example, markers, e.g. optical markers and/or navigation markers, and/or IMU's can be attached to the implants and/or instruments, e.g. a drill or a probe. With the implants and/or instruments being tracked, a central axis 830 of the one or more implants and/or instruments can, for example, be displayed by the one or more OHMDs. Alternatively, a 2D or 3D outline of the tracked implant and/or instrument can be displayed by the one or more OHMDs. The non-visible portions of the implant and/or instrument, e.g. of a probe or drill such as a probe tip or drill tip hidden inside the tissue, e.g. a pulp, a bone, a mandible and/or a maxilla, can be displayed by the one or more OHMDs using the tracking. The hidden portions of the implant and/or instrument, e.g. a probe or drill, can be projected by the one or more OHMDs; the projection can include one or more 3D images projected onto coordinates located subjacent to the gums and/or surface of the gums, internal to a tooth, internal to a maxilla and/or mandible. The OHMD display can include a central axis 830 of the tracked implant and/or instrument, including portions of the central axis that are hidden inside the tissue, e.g. with coordinates located subjacent to the gums and/or surface of the gums, internal to a tooth, internal to a maxilla and/or mandible.

In some embodiments, when the implant and/or instruments are tracked, e.g. using IMU's, navigation markers, other markers, optical markers, a central axis 830 can be projected through the implant and/or instrument, wherein the projection of the central axis is maintained extending through the physical long axis of the physical implant and/or instrument when the implant and/or instrument is moved. The projected central axis 830 of the tracked implant and/or instrument (e.g. a drill or probe) can then be aligned with the virtual axis 810 projected by the OHMD for the intended placement of a dental implant or root canal.

The accuracy of superimposition and alignment can be improved with increasing length of the projected virtual axis 810 for placement and/or superimposition and/or alignment of the physical implant and/or instrument or drilling of a root canal. In addition, the accuracy of superimposition and alignment can be improved with increasing length of the projected central axis 830 of the implant and/or the instrument for performing the root canal, e.g. a drill. The longer the virtual axis 810 and/or the projected central axis 830 of the tracked implant and/or instrument, the more apparent can any alignment errors between the projected central axis 830 of the tracked implant and/or instrument and the virtual axis 810 become. For this reason, in some embodiments, the projected central axis 830 of the implant and/or instrument displayed by the one or more OHMDs can be configured to extend beyond the confines or physical border(s) or edge(s) of the physical implant and/or instrument, as shown, for example, in FIG. 42I. For example, the projected central axis 830 of the implant and/or instrument displayed by the one or more OHMDs can be configured to extend beyond the confines or physical border(s) or edge(s) of the physical implant and/or instrument by more than 10 mm, 20 mm, 30 mm, 40 mm, 50 mm, 75 mm, 100 mm or any other length in one or more directions.

This embodiment is applicable to any tracked and non-tracked implant and/or instrument and/or tool. Thus, in any embodiments throughout the specification, e.g. in knee replacement, hip replacement, ankle replacement, shoulder replacement, ACL repair and/or reconstruction, spinal surgery, spinal fusion, ligament repair, vascular procedures, cardiac procedures, head and neck procedures etc., the borders and/or dimensions and/or any dimensional specifications, including any features, coordinates or axes, of a virtual surgical implant and/or virtual device can extend beyond the borders and/or dimensions and/or any dimensional specifications, including any features, coordinates or axes, of the corresponding physical surgical implant and/or physical device, e.g. in order to facilitate, for example, superimposition and/or alignment between the virtual surgical implant or virtual surgical device and the physical surgical implant or physical surgical device and/or between a first virtual surgical implant and or virtual surgical device, e.g. projected onto the surface of an intended implantation site by one or more OHMDs, and a second virtual surgical implant or virtual surgical device representing at least portions of a tracked physical surgical implant or physical surgical device; the borders and/or dimensions and/or any dimensional specifications, including any features, coordinates or axes, of a virtual surgical instrument and/or virtual surgical tool can extend beyond the borders and/or dimensions and/or any dimensional specifications, including any features, coordinates or axes, of the corresponding physical surgical instrument and/or physical surgical tool, e.g. in order to facilitate, for example, superimposition and/or alignment between the virtual surgical instrument or virtual surgical tool and the physical surgical instrument or physical surgical tool and/or between a first virtual surgical instrument and or virtual surgical tool, e.g. projected onto the surface of an intended implantation site by one or more OHMDs, and a second virtual surgical instrument or virtual surgical tool representing at least portions of a tracked physical surgical instrument or physical surgical tool; the borders and/or dimensions and/or any dimensional specifications, including any features, coordinates or axes, of a virtual surgical guide can extend beyond the borders and/or dimensions and/or any dimensional specifications, including any features, coordinates or axes, of the corresponding physical surgical guide, e.g. in order to facilitate, for example, superimposition and/or alignment between the virtual surgical guide and the physical surgical guide and/or between a first virtual surgical guide, e.g. projected onto the surface of an intended implantation site by one or more OHMDs, and a second virtual surgical guide representing at least portions of a tracked physical surgical guide. The virtual surgical guide (e.g. 304, 336, 614) can be a placement indicator of the physical surgical guide or of portions of the physical surgical guide, e.g. a 2D or 3D outline of portions of the physical surgical guide. The virtual surgical guide can be a virtual axis (e.g. 283, 650). The virtual surgical guide can be a virtual plane (e.g. 70, 74, 342). The virtual axis, virtual plane, and/or placement indicator can optionally extend beyond the borders and/or dimensions and/or any dimensional specifications, including any features, coordinates axes or planes, of the physical surgical guide. The OHMD can display the virtual implant component in any location initially, e.g. projected onto or outside the surgical field, e.g. a hip joint, knee joint, shoulder joint, ankle joint, or a spine. The OHMD can optionally display the virtual implant component at a defined angle, e.g. orthogonal or parallel, relative to a fixed structure in the operating room, which can, for example, be recognized using one or more cameras, image capture or video capture systems and/or 3D scanner integrated into the OHMD and spatial recognition software such as the one provided by Microsoft with the Microsoft Hololens or which can be recognized using one or more attached optical markers or navigation markers including, but not limited to, infrared or RF markers. For example, one or more optical markers can be attached to an extension of the operating table. The OHMD can detect these one or more optical markers and determine their coordinates and, with that, the horizontal plane of the operating room table. The virtual implant component can then be displayed perpendicular or at another, e.g. predetermined, angle relative to the operating room table. The virtual implant component can be displayed at a defined, e.g. predetermined, angle to one or more anatomic or biomechanical axes, e.g. a mechanical and/or anatomic and/or rotational axis when a knee replacement or a hip replacement is contemplated, for example when it was previously determined. The virtual implant component can be displayed or projected tangent with one or more anatomic landmarks or an articular surface of a joint, including an opposing articular surface. The virtual implant component can be displayed intersecting one or more anatomic landmarks or an articular surface of a joint, including an opposing articular surface.

The surgeon can move the virtual implant component to align it in the desired location and/or orientation over the implantation site. The surgeon can then evaluate the size of the virtual implant component and the fit of the virtual implant component by evaluating the size and fit of the virtual representation of the implant component superimposed onto the intended implantation site. The surgeon can move and align the virtual implant component so that, for example, its external surface co-locates, e.g. has similar or substantially the same coordinates, as the external surface of the intended implantation site, including, for example, the articular surface or an opposing articular surface. The surgeon can evaluate implant overhang or undersizing in different regions of the size, e.g. a trochlea, a medial and lateral condyle in the central or distal weight-bearing regions, in other weight-bearing regions, in high flexion regions and the surgeon can move, e.g. translate, flex or rotate the implant component to optimize coverage and minimize potential overhang. The OHMD can display the other portions of the virtual implant component which project underneath the external surface of the implantation site including any bone cuts or other implant features for bone fixation, such as a surface facing a burred bone surface, e.g. for manual burring or burring with a robot, or a peg or strut or a keel for fixation. If the virtual implant component is too large for an implantation site, for example resulting in implant overhang over the patient's bone, the surgeon can cancel the virtual display of the particular size of virtual implant component displayed and the surgeon can select a smaller virtual implant component from the library of virtual and physical implant components. If the virtual implant component is too small for an implantation site, for example resulting in poor coverage of the patient's bone, the surgeon can cancel the virtual display of the particular size of virtual implant component displayed and the surgeon can select a larger virtual implant component from the library of virtual and physical implant components. If the implant has a shape that resembles the patient's shape poorly, e.g. in the area of the articular surface(s), the surgeon can cancel the virtual display of the virtual implant component displayed and the surgeon can select a virtual implant component with a different shape from the library of virtual and physical implant components. Such different shape can, for example, be different distal and/or posterior condylar offsets, different medial and lateral condylar widths, different medial and lateral tibial shapes, e.g. on the articulating surfaces and/or on the tibial component perimeter, different medial and lateral polyethylene thicknesses, different trochlear flange shapes and/or heights, different patellar shapes and/or sizes. In this manner, the surgeon can optimize the implant size and fit in three-dimensions in the actual surgical site, rather than reverting to pre-operative sizing and fitting using, for example, 2D x-rays or 3D imaging studies, e.g. CT and MRI. If an implantation site is characterized by one or more asymmetries, e.g. in a knee joint or a tumor or an internal organ, the surgeon can optionally size and fit one or more asymmetric implant components, optionally with different asymmetries and geometries, for the implantation site. For example, in a knee replacement, the surgeon can observe the offset between the medial and lateral femoral condyles through the OHMD and virtually fit one or more implant components with an offset similar to the patient's native condylar offset, e.g. using the offset observed between a medial condyle cartilage, e.g. normal damaged or diseased, and/or subchondral bone surface and a lateral condyle cartilage, e.g. normal damaged or diseased, and/or subchondral bone surface.

The surgeon can move the virtual implant component to place it and/or align and/it or orient in a desired position, location, and/or orientation over the implantation site for a given patient. Since the moving and aligning is performed over the live implantation site of the patient, the surgeon can optimize the implant position, location, and/or orientation. The surgeon can further modify and/or optimize the position, location, and/or orientation of the virtual implant component and, with that, the physical implant component for a desired function in an implantation site, e.g. a desired flexion angle, rotation angle, range of motion, ligamentous laxity, desired movement. The surgeon can align at least a portion of the external surface of the virtual implant component with at least a portion of the external surface of the implantation site, including one or more of normal cartilage, damaged or diseased cartilage, subchondral bone, cortical bone, a portion of the articular surface, the entire articular surface, a portion of an opposing articular surface, the entire opposing articular surface. After the surgeon has placed, aligned and/or oriented the virtual implant component superimposed in the desired position and/or orientation over or aligned with the live implantation site, the coordinates of the virtual implant component can be saved, e.g. in a common coordinate system in which the OHMD and the implantation site can also be registered. The saved coordinates of the virtual implant component can, optionally be incorporated in a virtual surgical plan, which can optionally also be registered in the common coordinate system. The OHMD can subsequently display one or more digital holograms of one or more virtual surgical instruments and/or virtual implant components wherein the position, location, and/or orientation of the one or more digital holograms of the one or more virtual surgical instruments and/or virtual implant components are derived from or take into consideration the saved coordinates of the virtual implant component.

For example, in a hip replacement, a virtual acetabular cup can be displayed near the surgical site including the exposed acetabulum of a patient. The surgeon can move the virtual acetabular cup using a virtual or other, e.g. voice, interface and superimpose it onto the patient's exposed acetabulum. The surgeon can evaluate the size and fit of the virtual acetabular cup, e.g. relative to the physical acetabular rim and/or the physical acetabular center and/or a display of acetabular bone stock and/or the tear drop area registered with, superimposed onto and/or aligned with the corresponding physical structures by one or more computer processors configured to generate the OHMD display. The surgeon can upsize or downsize the virtual acetabular cup by selecting smaller or larger virtual acetabular cups until the surgeon is satisfied with the fit of the virtual representation of the acetabular cup and the patient's exposed acetabulum, e.g. the exposed acetabular rim. The surgeon can optionally center the virtual acetabular cup over the center of the patient's exposed acetabulum, matching the outer rim of the virtual acetabular cup to coincide with or be equidistant superiorly, inferiorly, medially and laterally to the acetabular rim of the patient's exposed acetabulum. The coordinates of the virtual acetabular cup can then be saved, e.g. in the same coordinate system in which the surgical site, e.g. the acetabulum and/or the proximal femur, and the OHMD are registered. The coordinates of the virtual acetabular cup identified in this manner can be used to set a desired acetabular anteversion, e.g. during a reaming or impacting of the acetabular cup and, for example, to generate a display of a virtual reaming axis for superimposing and/or aligning a physical acetabular reamer using one or more OHMDs. The virtual axis can also be displayed by one or more computer processors connected to the OHMD to guide an impacting of the physical acetabular cup. Optionally, the virtual representation of the virtual acetabular cup fitted and placed by the surgeon can be displayed by the OHMD prior to impacting the physical acetabular cup. The surgeon can then align the physical acetabular cup with the virtual projection of the acetabular cup; once the desired alignment has been achieved, the surgeon can start impact the physical acetabular cup, while optionally intermittently comparing its position and/or orientation including offset and anteversion with the virtual display of the virtual acetabular cup.

In some embodiments, in a hip replacement, a virtual femoral component, optionally including a head component, can be displayed near the surgical site including the exposed proximal femur of a patient. The surgeon can move the virtual femoral component, optionally including a head component, using a virtual or other interface and superimpose it onto the patient's exposed proximal femur, optionally before and/or after the femoral neck cut. The surgeon can evaluate the size and fit of the virtual femoral component, optionally including a head component; optionally, the OHMD can display one or more pre-operative or intra-operative x-ray images or other imaging study, e.g. CT or MRI, of the patient registered in a common coordinate system with the surgical site, for example registered with corresponding anatomic landmarks at or near the surgical site; the imaging study can be superimposed onto the corresponding portions of the proximal femur, e.g. greater trochanter of live patient with greater trochanter on x-ray or imaging study, lesser trochanter of live patient with lesser trochanter on x-ray or image study etc. The surgeon can upsize or downsize the virtual femoral component by selecting smaller or larger virtual femoral components until the surgeon is satisfied with the fit of the virtual representation of the femoral component and the patient's exposed proximal femur and/or with the fit of the virtual representation of the femoral component and/or femoral head and the patient's projected or displayed x-ray or imaging study, including marrow cavity, bone stock, and/or endosteal interface. The surgeon can optionally center the virtual femoral component over the exposed proximal femur, optionally before and/or after the femoral neck cut, centering also over the cut femoral neck surface, aligning the virtual femoral component and/or head with the corresponding anatomy and/or imaging data of the patient. The surgeon can optionally fit or select the virtual component so that the center of rotation of the femoral head of the virtual femoral component is similar to or coincides with the center of rotation of the patient's native femoral head. The coordinates of the virtual femoral component and/or head can then be saved, e.g. in the same coordinate system in which the surgical site, e.g. the acetabulum and/or the proximal femur, and the OHMD are registered. The coordinates of the virtual femoral component and/or head identified in this manner can be used to set a predetermined neck cut and/or a desired, predetermined femoral anteversion and/or offset, e.g. during a reaming or broaching of the femoral component. Optionally, the virtual representation of the virtual femoral component and/or head fitted and placed by the surgeon can be displayed by the OHMD prior to impacting the physical femoral component. The surgeon can then align the physical virtual femoral component and/or head with the virtual projection of the femoral component and/or head; once the desired alignment has been achieved, the surgeon can start impact the physical femoral component, while optionally intermittently comparing its position and/or orientation including offset and anteversion with the virtual display of the virtual femoral component. In a femur first technique, the surgeon can compare the final femoral component position including anteversion with the intended femoral component position including anteversion, for example by displaying the virtual femoral component superimposed onto the implanted physical femoral component. If the display indicates a difference in position and/or orientation including anteversion of the implanted physical femoral component relative to the virtual femoral component, the difference can be measured and can be used to modify the acetabular cup placement. For example, if the display of the virtual femoral component shows a difference in anteversion between the virtually displayed femoral component and the physical femoral component, the difference in anteversion can be used to modify the anteversion of the acetabular cup so that the combined anteversion is similar or the same as the patient's native combined anteversion prior to the surgery. In an acetabulum first technique, if the display of the virtual acetabular component shows a difference in anteversion between the virtually displayed acetabular component and the physical acetabular component, the difference in anteversion can be used to modify the anteversion of the femoral component so that the combined anteversion is similar or the same as the patient's native combined anteversion prior to the surgery.

In some embodiments, in a knee replacement, a virtual femoral component can be displayed near the surgical site including the exposed distal femur of a patient. A computer processor can move the virtual femoral component, using a virtual or other interface, e.g. a "touch zone" on the virtual representation of the virtual femoral component with image or video capture and/or 3D scan of the surgeon's hand and/or fingers and/or gesture tracking, and superimpose it onto the patient's exposed distal femur, optionally before and/or after any bone cuts. The computer processor can be configured to evaluate the size and fit of the virtual femoral component. The computer processor can be configured to evaluate the fit in three dimensions, anteriorly, posteriorly, at the medial aspect of the medial condyle, at the lateral aspect of the medial condyle, at the medial aspect of the lateral condyle, at the lateral aspect of the lateral condyle, in the intercondylar notch, in the medial and lateral trochlear region, with respect to one or more cartilage surfaces and/or shapes, e.g. normal, damaged or diseased, and/or one or more subchondral bone surfaces and/or shapes and/or one or more cortical bone surfaces and/or shapes, and/or one or more articular surfaces and/or shapes. The computer processor can be configured to evaluate the size, fit and shape or geometry of the virtual femoral component for different degrees of femoral component flexion and/or extension and different degrees of femoral component rotation, e.g. external rotation, relative to the physical distal femur of the patient including the articular surface, e.g. cartilage, normal, damaged or diseased, and subchondral bone. The computer processor can be configured to upsize or downsize the virtual femoral component by selecting smaller or larger virtual femoral components or different shapes from the virtual library until the surgeon is satisfied with the fit and/or shape or until the computer processor indicates a satisfactory fit and/or shape of the virtual representation of the femoral component relative to and superimposed onto the patient's exposed distal femur, e.g. relative to the medial and/or lateral rim or edge of the medial and/or the lateral condyle, relative to the trochlea, and/or any of the landmarks, features, dimensions, shapes, measurements, geometries listed in Table 16, for example, pertaining to the knee joint. If the virtual femoral implant component is too large for an implantation site, the computer processor can be configured to cancel or discard the virtual display of the particular size of virtual femoral component displayed and the computer processor can be configured to select a smaller virtual femoral component from the library of virtual and physical femoral components. If the femoral implant component is too small for an implantation site, the computer processor can be configured to cancel or discard the virtual display of the particular size of virtual femoral component displayed and the computer processor can be configured to select a larger virtual femoral component from the library of virtual and physical femoral components. If the implant has a shape that resembles the patient's shape poorly, e.g. in the area of the articular surface(s), the computer processor can be configured to cancel the virtual display of the virtual implant component displayed and computer processor can be configured to select a virtual implant component with a different shape from the library of virtual and physical implant components. The computer processor can be also configured to evaluate the position and/or orientation of the virtual femoral component for possible notching relative to the physical anterior cortex of the distal femur of the patient, e.g. by demonstrating or visualizing an intersect between the anterior planar surface of the femoral component and the anterior cortex of the distal femur (e.g. with the anterior cortex, for example, determined from an imaging test registered in the coordinate system or a point cloud or surface generated from a point cloud using a pointer with one or more attached markers), and virtually selecting a virtual femoral component that avoids notching, or moving the virtual femoral component in anterior direction to avoid notching, or flexion the virtual femoral component to avoid notching. The computer processor can be configured to virtually place the virtual femoral component in a manner so that its anterior flange can stay clear of the anterior cortex of the distal femur; the resultant position and/or orientation and/or alignment and/or coordinates of the virtual femoral component can be saved, stored and/or integrated into a virtual surgical plan. The position and/or orientation and/or alignment and/or coordinates of the virtual femoral component can be used to develop, adjust or modify a virtual surgical plan.

The computer processor can be configured to evaluate the shape of the virtual femoral component and compare it with the shape of the patient's distal femur, e.g. one or more cartilage surfaces and/or shapes, e.g. normal, damaged or diseased, and/or one or more subchondral bone surfaces and/or shapes, e.g. on a medial femoral condyle and/or a lateral femoral condyle and/or a trochlear region. The computer processor can be configured to optionally align at least portions of the external surface of the virtual femoral component with at least portions of the patient's articular surface, e.g. one or more cartilage surfaces and/or shapes, e.g. normal, damaged or diseased, and/or one or more subchondral bone surfaces and/or shapes, e.g. on the medial femoral condyle, the lateral femoral condyle and/or the trochlear articular surface. The computer processor can be configured to select different shapes of virtual femoral components from the virtual library of implants, e.g. femoral components with one or more offsets between the medial distal femoral condyle and the lateral distal femoral condyle and/or one or more offsets, the same or different, between the medial posterior femoral condyle and the lateral posterior femoral condyle. The offset can be a reflection of different radii of the medial distal and/or posterior and the lateral distal and/or posterior femoral condyle, e.g. one or more cartilage surfaces and/or shapes, e.g. normal, damaged or diseased, and/or one or more subchondral bone surfaces and/or shapes of the condyle(s). For example, the computer processor can be configured to align at least portions of the external surface or projection of the medial condyle of the virtual femoral component with at least portions of the external surface of the physical medial condyle of the patient; the computer processor can be configured to align at least portions of the external surface or projection of the lateral condyle of the virtual femoral component with at least portions of the external surface of the physical lateral condyle of the patient. If the external surface or projection of the medial condyle of the virtual femoral component is proud relative to the external surface of the physical medial condyle of the patient, i.e. extends beyond the external surface of the physical medial condyle of the patient, the surgeon can discard the digital hologram of the virtual femoral component and select a different virtual femoral component from the virtual library. If the external surface or projection of the lateral condyle of the virtual femoral component is proud relative to the external surface of the physical lateral condyle of the patient, i.e. extends beyond the external surface of the physical lateral condyle of the patient, the surgeon can discard the digital hologram of the virtual femoral component and select a different virtual femoral component from the virtual library. For example, the surgeon can select a virtual femoral component with a smaller lateral condyle radius than medial condyle radius and/or with a distal and/or posterior offset of the lateral condyle compared to the medial condyle.

Figure 43A:
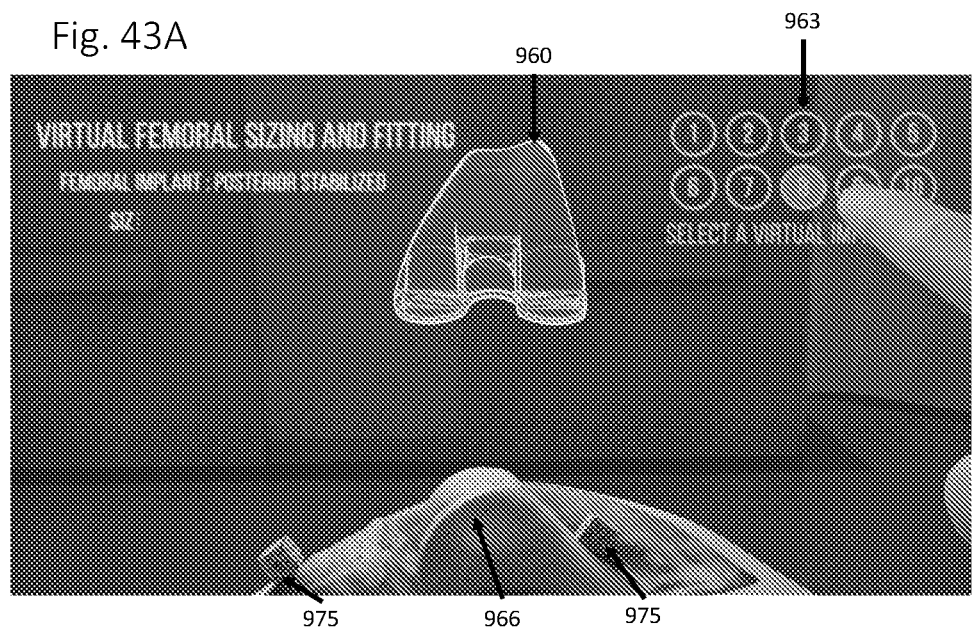
FIGS. 43A-B provide illustrative, non-limiting examples of one or more augmented reality OHMD displays for virtual placing, sizing, fitting, selecting and aligning of implant components.
Figure 43B:
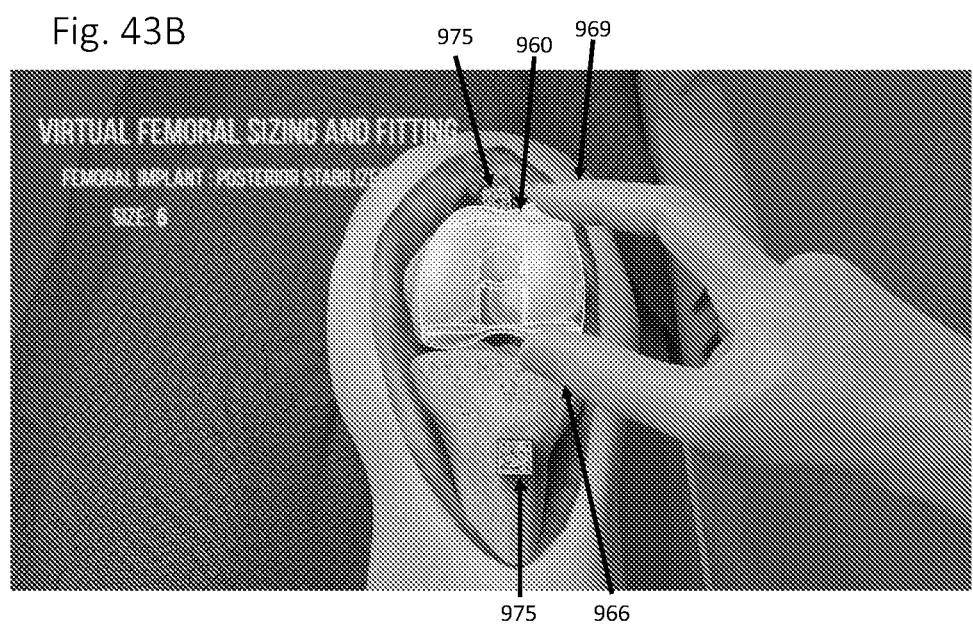

FIGS. 43A-B provide illustrative, non-limiting examples of one or more augmented reality OHMD displays for virtual placing, sizing, fitting, selecting and aligning of implant components. A virtual femoral component 960 can be displayed by one or more OHMD displays. A virtual user interface 963 can be configured for selecting different sizes of virtual femoral components. A computer processor can be configured to allowing placing and moving of the virtual femoral component onto the physical distal femur 966 of the patient. The computer processor can be configured for selecting different sizes of implants, using, for example, voice commands, e.g. a size 6, and for aligning the virtual implant 960 with the physical distal femur of the live patient using gesture recognition configured to recognize an index finger 969 and thumb 972, in the example in FIG. 43B. The virtual implant can be registered and/or displayed in relationship to a common coordinate system. One or more optical markers 975, e.g. with QR codes, can be registered in the same coordinate system.

If a femoral condyle is significantly deformed from osteoarthritis or rheumatoid arthritis or of a femoral condyle is hypoplastic, the surgeon can select a femoral component with one or more radii different than those of the deformed or hypoplastic femoral condyle. The virtual femoral component can be selected so that the selected virtual femoral component creates a more normal shape, e.g. similar to a normal healthy condyle of the patient. For example, a virtual femoral component can be selected so that its articular surface is proud relative to a portion or all of a flattened, deformed or hypoplastic articular surface of a deformed or hypoplastic femoral condyle in osteoarthritis. For example, a virtual tibial component can be selected so that its articular surface is proud relative to a portion or all of a flattened, deformed articular surface of a deformed tibial plateau in osteoarthritis.

In embodiments, a virtual femoral, tibial and/or patellar component can be virtually sized and/or selected and/or placed and/or aligned so that one or more portions of its articular surfaces extends beyond the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella.

In embodiments, a virtual femoral, tibial and/or patellar component can be virtually sized and/or selected and/or placed and/or aligned so that one or more portions of its articular surfaces remains internal of the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella.

In embodiments, a virtual femoral, tibial and/or patellar component can be virtually sized and/or selected and/or placed and/or aligned so that one or more portions of its articular surfaces is aligned with and/or superimposed with the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella.

In embodiments, a virtual femoral, tibial and/or patellar component can be virtually sized and/or selected and/or placed and/or aligned so that one or more portions of its articular surfaces can be aligned with and/or superimposed with and/or can extend beyond and/or can remain inside, internal to the outer surface of at least a portion of one or more articular surfaces of the patient's physical femur, tibia or patella, e.g. one or more cartilage surfaces and/or shapes, e.g. normal, damaged or diseased, and/or one or more subchondral bone surfaces and/or shapes of one or both condyle(s), a medial tibial plateau, a lateral tibial plateau and/or the trochlea and/or the patella. The surgeon can virtually place the virtual component(s) according to one or more of the foregoing embodiments; the resultant position and/or orientation and/or alignment and/or coordinates of the virtual component(s) can be saved, stored and/or integrated into a virtual surgical plan. For example, they can be used to develop, adjust or modify a virtual surgical plan.

The foregoing virtual sizing, selecting, placing, and/or aligning of one or more virtual implant components relative to one or more portions of an articular surface or an entire articular surface of the patient, e.g. relative to one or more physical cartilage surfaces and/or shapes, e.g. normal, damaged or diseased, and/or one or more physical subchondral bone surfaces and/or shapes, with portions or all of the articular surface of the virtual implant component extending beyond, remaining inside and/or being aligned with and/or superimposed with at least portions of the patient's articular surface can be applied to all joints, e.g. for a femoral or acetabular component in hip replacement, a humeral or a glenoid component in shoulder replacement, using, for example, also articular surface features and or shapes and/or geometries as listed in Table 16 for hip and shoulder, for a tibial component or a talar component in ankle replacement, etc.

The surgeon can project, move, align, e.g. with the external surface of the medial and/or the lateral femoral condyle, multiple different virtual femoral component shapes, e.g. with multiple different offsets, until the surgeon has identified a virtual femoral component that yields the desired shape, for example, similar to that of the patient's distal femur and, in case of a tibial component, the patient's proximal tibia, e.g. a medial tibial plateau, a lateral tibial plateau and/or both, e.g. using one or more physical cartilage surfaces and/or shapes, e.g. normal, damaged or diseased, and/or one or more physical subchondral bone surfaces and/or shapes, and/or one or more physical articular surfaces and/or shapes. If a virtual femoral component is chosen with an offset between the medial and the lateral femoral component, a matching offset can optionally be selected for the tibial polyethylene, wherein the lateral portion of the tibial insert can be 1, 2, 3, 4, 5, 6, 7, 8 or more mm or a range of 0.1 to 10 mm thicker than the medial portion of the tibial insert, corresponding to the smaller radius of the lateral femoral condyle of the virtual femoral component. The coordinates of the final position of the virtual femoral component can be saved and can, optionally, be incorporated into a virtual surgical plan and/or can be used for determining the position and/or orientation and/or coordinates of a virtual surgical guide, e.g. a virtual cut block or placement indicator thereof, a virtual axis, and/or a virtual plane. If the virtual surgical plan indicates a variation in position, orientation, alignment, rotation, implant flexion of the virtual femoral component relative to the virtual surgical plan, the surgeon can adjust the position of the virtual femoral component to come closer to the intended position, orientation, alignment, rotation, implant flexion of the virtual surgical plan or to replicate it. Alternatively, the virtual surgical plan can be modified based on the position, orientation, alignment, rotation, implant flexion of the virtual femoral component.

In some embodiments, in a knee replacement, a virtual tibial component can be displayed near the surgical site including the exposed proximal tibia of a patient. A computer processor can be configured to move the virtual tibial component, using a virtual or other, e.g. voice, interface, e.g. a "touch zone" on the virtual representation of the virtual tibial component with image or video capture of the surgeon's hand and/or fingers and/or gesture tracking, and superimpose it onto the patient's exposed proximal tibia, optionally before and/or after any bone cuts. The computer processor can be configured to evaluate the size and fit of the virtual tibial component, e.g. relative to one or more physical articular surfaces and/or shapes, physical cartilage surfaces and/or shapes, e.g. normal, damaged or diseased, and/or one or more physical subchondral bone surfaces and/or shapes on the medial and/or lateral tibial plateau. The computer processor can be configured to evaluate the fit in three dimensions, anteriorly, posteriorly, at the medial aspect of the medial tibial plateau, at the lateral aspect of the lateral tibial plateau. The computer processor can be configured to evaluate the size and fit of the virtual tibial component for different levels of tibial resection and different tibial slopes and different degrees of tibial component rotation, e.g. external rotation. For example, the computer processor can be configured to evaluate the size and fit and the amount of tibial bone coverage for different resection levels and/or different tibial slopes. This can be important for implant selection since the perimeter and/or surface area of the tibia changes, e.g. decreases, with progressive tibial resection owing to the tapering shape of a normal tibia from proximal to distal. In addition, the perimeter and/or surface area of the tibia can change as the slope of the resection is being increased or decreased; for example, with increasing slope, the perimeter and shape of the resected tibial bone surface can elongate. Thus, the computer processor can be configured to virtually place and/or align a virtual tibial component, including, for example, a virtual metal backed component and/or a virtual polyethylene simulating, for example, a virtual resection level, e.g. for a desired and/or predetermined resection level and/or for a given medial and/or lateral and/or medial and lateral tibial component thickness, including, for example, a composite thickness of metal and polyethylene and/or other components, and/or for a desired articular surface pressure, e.g. medial and/or lateral, and/or a desired ligament tension. The computer processor can be configured to virtually place and/or align a virtual tibial component, including, for example, a virtual metal backed component and/or a virtual polyethylene for a desired, e.g. predetermined, tibial slope, e.g. zero, 1, 2, 3, 4, 5, or more degrees, or selected from a range from 0 to 10 degrees, e.g. using a fixed slope, or the patient's native medial and/or lateral slope. The computer processor can be configured to evaluate the fit and/or the anterior, posterior, medial and/or lateral bone coverage for the desired and/or predetermined tibial resection level and/or tibial slope and the computer processor can be configured to select a tibial implant component that optimizes the anterior, posterior, medial and/or lateral bone coverage; in addition, the computer processor can be configured to select a tibial component that minimizes implant overhang and potential soft-tissue impingement for a desired and/or predetermined tibial resection level and/or tibial slope. The computer processor can be configured to select a tibial implant component that optimizes the anterior, posterior, medial and/or lateral bone coverage and that minimizes implant overhang and potential soft-tissue impingement for a desired and/or predetermined tibial resection level and/or tibial slope, using, for example single or multi-parametric optimization and/or selection and/or fitting and/or alignment. Optionally, the OHMD can display numeric values and/or measurements, e.g. of a tibial slope for various tibial resection levels and/or tibial slopes, indicating, for example, the distance from the unresected articular surface and/or the tibial slope for a given virtual tibial implant component position and/or alignment.

Optionally, the computer processor can be configured to virtually place and/or align the virtual implant component based on one or more of a predetermined component thickness, an intra-articular pressure or force measurement, e.g. using a Tekscan (Tekscan, Inc., South Boston, Mass.) like device with electronic pressure sensors or a femoral or tibial trial component with electronic pressure sensors, and/or a desired and/or predetermined tibial resection level and/or a desired and/or predetermined tibial slope; any of these parameters can be optimized in relationship to each other and a virtual placement and/or alignment of a virtual tibial component and a related virtual surgical plan can be developed and/or modified and/or updated accordingly. Such pressure or force measurements, e.g. in the medial and/or the lateral compartment, can also be used for optimizing the virtual placement, alignment, fitting and/or sizing of a virtual femoral component with related optional development, modification, adjustment of a virtual surgical plan.

The computer processor can be configured to rotate the virtual tibial component relative to the patient's live or physical tibia, including a cut tibia, and/or any kinematic measurements, e.g. using tracking of optical markers moving during flexion and extension of the knee, using a virtual or other interface. The computer processor can be configured to upsize or downsize the virtual tibial component by selecting smaller or larger virtual tibial components from the virtual library until the surgeon is satisfied with the fit or until the computer processor indicates a satisfactory fit of the virtual representation of the tibial component and the patient's exposed proximal tibia, including a cut tibia, e.g. by assessing the amount and/or percentage of tibial bone coverage, e.g. <60%, <70%, <80%, <90%, <95% or a range from 60 to 99%. Optionally, an OHMD can indicate a numeric value of estimated coverage of a virtually resected tibial surface for a given or predetermined virtual tibial implant component placement and/or alignment and a given or predetermined virtual tibial implant component size and/or shape, e.g. selected from a library, and a given or predetermined tibial resection level and/or slope. The percentage can be, for example, estimated based on a 3D model of the tibial bone, optionally superimposed onto the physical tibia of the patient by the OHMD, and by simulating the tibial resection in the 3D model.

Similarly, the computer processor can be configured to assess the amount of implant overhang over the resected bone, which can cause potential soft-tissue impingement, e.g. by assessing the amount and/or percentage of tibial implant overhang relative to the estimated resected bone surface, e.g. 1, 2, 3, 4, 5 or more mm or a range from 0 to 15 mm for one or more regions. Optionally, an OHMD can indicate a numeric value of estimated overhang of a virtually resected tibial surface for a given or predetermined virtual tibial implant component placement and/or alignment and a given or predetermined virtual tibial implant component size and/or shape, e.g. selected from a library, and a given or predetermined tibial resection level and/or slope. The amount of overhang can be, for example, estimated based on a 3D model of the tibial bone, optionally superimposed onto the physical tibia of the patient by the OHMD, and by simulating the tibial resection in the 3D model and, optionally, by superimposing and/or aligning a virtual tibial component relative to the post-resection bone surface.

The bone coverage and/or implant component overhang analysis can also be performed for the femoral component. The computer processor can be configured to upsize or downsize the virtual femoral component by selecting smaller or larger virtual tibial components from the virtual library until the surgeon is satisfied with the fit of the virtual representation of the femoral component and the patient's exposed distal femur, including a cut femur, e.g. by assessing the amount and/or percentage of femoral bone coverage, e.g. <60%, <70%, <80%, <90%, <95% or a range from 60 to 99%. Optionally, an OHMD can indicate a numeric value of estimated coverage of a virtually resected femoral surface for a given or predetermined virtual femoral implant component placement and/or alignment and a given or predetermined virtual femoral implant component size and/or shape, e.g. selected from a library, and a given or predetermined femoral component flexion and/or rotation. The percentage can be, for example, estimated based on a 3D model of the femoral bone, optionally superimposed onto the physical distal femur of the patient by the OHMD, and by simulating the femoral resection in the 3D model and, optionally, by superimposing and/or aligning a virtual femoral component relative to the post-resection bone surfaces.

Similarly, the computer processor can be configured to can assess the amount of implant overhang over the resected femoral bone, which can cause potential soft-tissue impingement, e.g. by assessing the amount and/or percentage of femoral implant overhang relative to the estimated resected bone surface, e.g. 1, 2, 3, 4, 5 or more mm or a range from 0-15 mm, for one or more medial and/or lateral and/or anterior and/or posterior regions. Optionally, an OHMD can indicate a numeric value of estimated overhang of a virtually resected femoral surface for a given or predetermined virtual femoral implant component placement and/or alignment and a given or predetermined virtual femoral implant component size and/or shape, e.g. selected from a library, and a given or predetermined femoral component flexion and/or rotation. The amount of overhang can be, for example, estimated based on a 3D model of the femoral bone, optionally superimposed onto the physical distal femur of the patient by the OHMD, and by simulating the femoral resection in the 3D model and, optionally, by superimposing and/or aligning a virtual femoral component relative to the post-resection bone surfaces.

If the virtual tibial implant component is too large for an implantation site, the computer processor can be configured to cancel the virtual display of the particular size of virtual tibial component displayed and the computer processor can be configured to select a smaller virtual tibial component from the library of virtual and physical tibial components. If the tibial implant component is too small for an implantation site, the computer processor can be configured to cancel the virtual display of the particular size of virtual tibial component displayed and the computer processor can be configured to select a larger virtual tibial component from the library of virtual and physical tibial components. The computer processor can also be configured to evaluate the position and/or orientation of the virtual tibial component for possible PCL impingement with cruciate retaining implants or patellar tendon impingement with bicruciate retaining, cruciate retaining, posterior cruciate substituting and bi-cruciate substituting implants. One or more OHMDs can optionally display the virtual tibial component superimposed onto and/or aligned with the corresponding portions of the tibial plateau, including a predetermined resection height and slope, and can display impingement of the virtual tibial component onto the PCL and/or ACL (in case of an ACL retaining tibial component/implant).

The computer processor can be configured to evaluate the shape of the virtual tibial component and compare it with the shape of the patient's proximal tibia. The surgeon can optionally select asymmetric virtual tibial components from an optional variety of different asymmetric tibial shapes from a virtual library of tibial components. The surgeon can optionally select virtual tibial components from an optional variety of different medial and lateral tibial heights and polyethylene thicknesses from a virtual library of tibial components. The computer processor can be configured to optionally align at least portions of the external surface of the virtual tibial component, e.g. the superior surface of one or more polyethylene inserts with at least portions of the patient's tibial articular surface, e.g. on the medial tibial plateau, the lateral tibial plateau, e.g. one or more cartilage surfaces and/or shapes, e.g. normal, damaged or diseased, and/or one or more subchondral bone surfaces, and/or one or more articular surfaces. By aligning at least portions of the external surface of the virtual tibial component, e.g. the superior surface of one or more polyethylene inserts with at least portions of the patient's tibial articular surface, e.g. on the medial tibial plateau, the lateral tibial plateau, e.g. one or more cartilage surfaces and/or shapes, e.g. normal, damaged or diseased, and/or one or more subchondral bone surfaces, the computer processor can be configured to determine the desired slope of the tibial resection, for example if the surgeon intends to cut the tibia and install the tibial component with a slope similar to the patient's native slope. By aligning at least portions of the external surface of the virtual tibial component, e.g. the superior surface of one or more polyethylene inserts with at least portions of the patient's tibial articular surface, e.g. on the medial tibial plateau, the lateral tibial plateau, e.g. one or more cartilage surfaces and/or shapes, e.g. normal, damaged or diseased, and/or one or more subchondral bone surfaces the computer processor can be configured to determine any desired medial to lateral offsets for the tibial polyethylene.

For example, the computer processor can be configured to align at least portions of the external, superior surface or projection of the medial portion of the virtual tibial component including the medial polyethylene with at least portions of the external surface of the physical medial tibial plateau of the patient, e.g. one or more articular and/or cartilage surfaces and/or shapes, e.g. normal, damaged or diseased, and/or one or more subchondral bone surfaces; if the external surface or projection of the external, superior surface of the lateral portion of the tibial polyethylene of the virtual tibial component is subjacent, inferior relative to the external surface of the physical lateral tibial plateau of the patient, i.e. remains below the external surface of the physical lateral tibial plateau of the patient, e.g. one or more articular and/or cartilage surfaces and/or shapes, e.g. normal, damaged or diseased, and/or one or more subchondral bone surfaces, the computer processor can be configured to discard the digital 3D display of the virtual tibial component and select a different virtual tibial component from the virtual library; for example, the computer processor can be configured to select a virtual tibial component including a polyethylene with a thicker lateral insert portion than medial insert portion. The computer processor can be configured to repeat this process until a desired medial and/or lateral joint line position and/or height, alignment, match or fit is achieved. The aligning of the external contour, shape or surface of the digital 3D display or representation of the virtual tibial component medially and/or laterally with the tibial plateau of the patient, e.g. one or more articular surface and/or shapes, one or more cartilage surfaces and/or shapes, e.g. normal, damaged or diseased, and/or one or more subchondral bone surfaces, can take any desired varus or valgus correction and/or slope and/or tibial resection and/or tibial composite implant thickness, and/or medial and/or lateral compartment pressures and/or forces, as measured, for example, with electronic sensors, into account, for example by adjusting a selected medial or lateral polyethylene thickness or shape based on the desired varus or valgus correction and/or slope or any of the other parameters. The coordinates of the final position of the virtual tibial component can be saved and can, optionally, be incorporated into a virtual surgical plan and/or can be used for determining the position and/or orientation and/or coordinates of a virtual surgical guide, e.g. a virtual cut block or placement indicator thereof, a virtual axis, and/or a virtual plane. If the virtual surgical plan indicates a variation in position, orientation, alignment, or slope of the virtual tibial component relative to the virtual surgical plan, the computer processor can be configured adjust the position of the virtual tibial component to come closer to the intended position, orientation, alignment, and/or slope of the virtual surgical plan or to replicate it. Alternatively, the virtual surgical plan can be modified based on the position, orientation, alignment, rotation and/or slope of the virtual tibial component and, similarly based on the position, orientation, alignment, flexion and/or rotation of a femoral component and/or a patellar component.

In embodiments, an OHMD can project a 3D anatomic model of a joint, e.g. a distal femur, a proximal tibia, and/or a patella, onto the patient's joint, i.e. the corresponding bone such as the distal femur, the proximal tibia and/or the patella of the patient. The 3D anatomic model can, for example, be a "standard joint", for example with a shape averaged from a population sample, or obtained, for example from data such as from the Visible Human Project. The surgeon can project, move, align and/or superimpose the 3D model onto the patient's joint, e.g. relative to the external surface of the distal femur including the medial and/or the lateral femoral condyle, or the external surface of the proximal tibial plateau including the medial and/or lateral tibial plateau, or the external surface of the patella. The projecting, moving, and/or aligning can be performed in relationship to the patient's cartilage, e.g. normal, diseased or damaged cartilage, subchondral bone and/or cortical bone. A computer processor can be configured to deform the 3D model using any of the interfaces described in the specification including, for example, a virtual interface, e.g. with gesture recognition. The deforming of the 3D model can be performed to improve the fit and/or alignment with regard to one or more of an ML, AP, SI dimension, a joint curvature, a joint geometry, a joint offset, a joint shape, a cartilage curvature or shape, e.g. normal, diseased, or damaged, a subchondral bone or shape, a cortical bone curvature or shape, an articular surface curvature and/or shape, and to improve the fit or alignment with regard to any of the exemplary parameters, landmarks, geometries, shapes and/or features listed, for example, in Tables 11, 12, 16. Once the surgeon has completed the deforming of the 3D model to achieve an improved fit and/or alignment of the 3D model to the 3D shape of the patient's joint, the software can select a virtual 3D model of an implant and/or implant component that most closely approximates the shape of the deformed 3D model for any of the foregoing parameters and/or any of the exemplary parameters, landmarks, geometries, shapes and/or features listed, for example, in Tables 11, 12, 16. The concept of deforming a 3D model of a knee joint to improve the fit and/or alignment to the patient's joint can be used in this manner for fitting, aligning, sizing and/or selecting of implants, for example, in knee replacement, hip replacement, shoulder replacement, ankle replacement, elbow replacement, and small joint replacement. It can also be applied to spinal devices, e.g. spinal cages and motion preservation implants.

In another embodiment, one or more OHMDs can project a 3D model with a shape, e.g. a sphere or a cylinder, onto a joint. The surgeon can move and/or align the 3D model with a portion of the joint. For example, an OHMD can project a cylinder onto a distal femur and the surgeon can move the cylinder using the virtual projection and an interface, e.g. a virtual interface, to superimpose it and/or align it with a medial and/or a lateral condyle. An OHMD can project a sphere or an ellipsoid volume/surface onto a proximal tibia and the surgeon can move the sphere or ellipsoid using the virtual projection and an interface, e.g. a virtual interface, to superimpose it and/or align it with a medial and/or a lateral tibial plateau. The surgeon can then evaluate the fit of the 3D model, e.g. in relationship to one or more articular surface radii, curvatures and/or shape, e.g. relative to normal, damaged or diseased cartilage or subchondral bone, or in relationship to a rotation or translation axis, and the surgeon can select a 3D model, e.g. a sphere, a cylinder, an ellipsoid, that most closely approximates the one or more articular surface radii, curvatures and/or shape, e.g. relative to normal, damaged or diseased cartilage or subchondral bone, or the one or more axes of the patient. Alternatively, the surgeon can deform the 3D model, e.g. a sphere, a cylinder, an ellipsoid, so that it approximates the one or more articular surface radii, curvatures and/or shape, e.g. relative to normal, damaged or diseased cartilage or subchondral bone, or that it aligns with the one or more axes. Once the surgeon has selected a 3D model, e.g. a sphere, a cylinder or an ellipsoid, or has completed the deforming of the 3D model, e.g. a sphere, a cylinder, an ellipsoid, to achieve an improved fit and/or alignment of the 3D model to the 3D shape of the patient's joint, the software can select a virtual 3D model of an implant and/or implant component that most closely approximates the shape of the deformed 3D model for any of the foregoing parameters and/or any of the exemplary parameters, landmarks, geometries, shapes and/or features listed, for example, in Tables 11, 12, 16. For example, the selected or deformed cylinder that the surgeon fitted and/or aligned to a medial and/or a lateral femoral condyle can be used to select a femoral component with a desired condylar radius or radii from a library. For example, the selected or deformed sphere or ellipsoid that the surgeon fitted and/or aligned to a medial and/or a lateral tibial plateau can be used to select a tibial component with a desired tibial articular surface bearing geometry, e.g. radius, radii or curvature, from a library. The concept of deforming a 3D model of a pre-existing shape, e.g. a cylinder, a sphere or an ellipsoid, can be used in this manner for fitting, aligning, sizing and/or selecting of implants, for example, in knee replacement, hip replacement, shoulder replacement, ankle replacement, elbow replacement, and small joint replacement. It can also be applied to spinal devices, e.g. spinal cages and motion preservation implants.

In embodiments, an OHMD can project a 3D model of an implant component, e.g. a distal femoral component, a proximal tibial component, and/or a patellar component, onto a patient's joint, i.e. onto the corresponding bone such as the distal femur, the proximal tibia and/or the patella of the patient. The 3D implant component model can, for example, be a "standard implant component model", for example with a shape averaged from a range of implant sizes and/or shapes. The surgeon can project, move, align, superimpose the 3D model onto the patient's joint, e.g. relative to the external surface of the distal femur including the medial and/or the lateral femoral condyle, or the external surface of the proximal tibial plateau including the medial and/or lateral tibial plateau, or the external surface of the patella. The projecting, moving, and/or aligning can be performed in relationship to the patient's cartilage, e.g. normal, diseased or damaged cartilage, subchondral bone and/or cortical bone. The surgeon can then deform the 3D model using any of the interfaces described in the specification including, for example, a virtual interface, e.g. with gesture recognition. The deforming of the 3D model can be performed to improve the fit and/or alignment with regard to one or more of an ML, AP, SI dimension, a joint curvature, a joint geometry, a joint offset, a joint shape, a cartilage curvature or shape, e.g. normal, diseased, or damaged, a subchondral bone or shape, a cortical bone curvature or shape, an articular surface curvature and/or shape, and to improve the fit or alignment of the 3D implant model with regard to any of the exemplary parameters, landmarks, geometries, shapes and/or features listed, for example, in Tables 11, 12, 16. Once the surgeon has completed the deforming of the 3D implant component model to achieve an improved fit and/or alignment of the 3D implant component model to the 3D shape of the patient's joint, the software can select a virtual 3D model of an implant and/or implant component that most closely approximates the shape of the deformed 3D implant component model for any of the foregoing parameters and/or any of the exemplary parameters, landmarks, geometries, shapes and/or features listed, for example, in Tables 11, 12, 16. The concept of deforming a 3D model of an implant component to improve the fit and/or alignment to the patient's joint can be used in this manner for fitting, aligning, sizing and/or selecting of implants, for example, in knee replacement, hip replacement, shoulder replacement, ankle replacement, elbow replacement, and small joint replacement. It can also be applied to spinal devices, e.g. spinal cages and motion preservation implants.

Alignment criteria can be displayed by the OHMD while the surgeon is moving, orienting or aligning a virtual femoral component, a virtual tibial component and/or a virtual patellar component. The resultant varus/valgus correction or alignment, external/internal rotation, of a femoral and/or tibial component, flexion of a femoral component and/or slope of a tibial component, Q-angle and axes can be numerically or graphically displayed and, optionally, compared, for example, with the desired varus/valgus correction or alignment, external/internal rotation of a femoral and/or tibial component, flexion of a femoral component and/or slope of a tibial component, Q-angle and axes based on a virtual surgical plan. The surgeon can elect to apply different alignment criteria, for example anatomic alignment wherein the surgeon can, for example, more closely match or approximate one or more virtual and physical implant surfaces with one or more articular surfaces of the patient, e.g. one or more cartilage surfaces and/or shapes, e.g. normal, damaged or diseased, and/or one or more subchondral bone surfaces, e.g. on one or two femoral condyles, on a medial and/or lateral tibial plateau, on a trochlea and/or a patella.

Figure 35A:
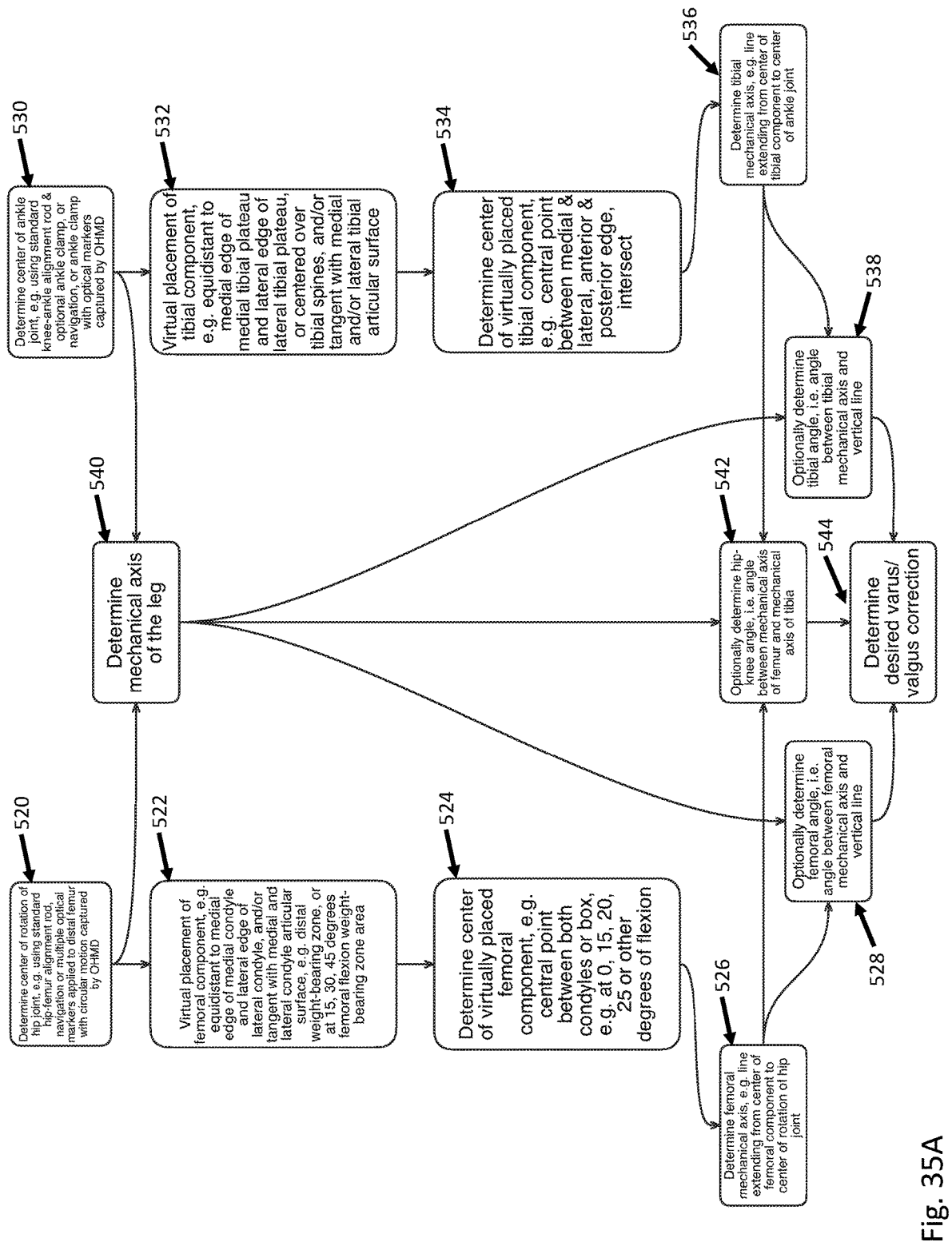
FIGS. 35A-B is an illustrative non-limiting flow chart describing approaches for virtually aligning femoral and/or tibial components in knee replacement and determining a desired alignment correction and related bone cuts or bone removal using standard bone removal tools, optionally with OHMD guidance or surgical navigation, or using a robot.
Figure 35B:
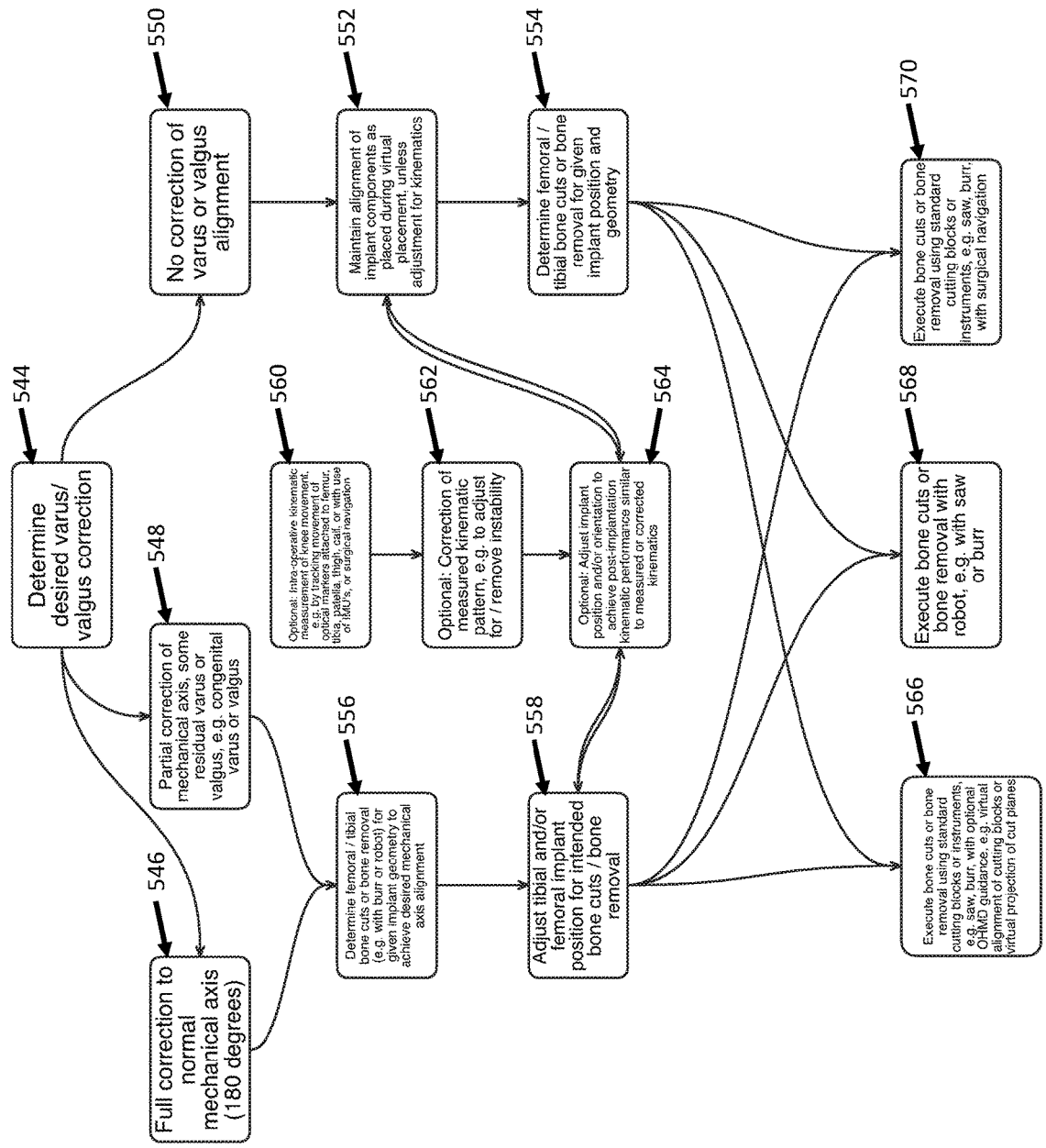

FIG. 35 is an illustrative, non-limiting example how the concept of virtually aligning implant components with the patient's live, physical joint including, for example, the articular surface, can be used in knee replacement. The center of rotation of the hip joint can be determined 520. This can be accomplished, for example, with use of a standard alignment rod extending from the knee to the center of the hip 520. It can also be accomplished with use of surgical navigation techniques known in the art, for example by performing a circular motion of the distal femur while tracking the movement of navigation markers with derivation of the center of rotation 520. Alternatively, optical markers can be applied to the distal femur, e.g. the patient's bone or skin or other tissue, and the distal femur can be moved in a circular fashion, wherein the movement of the optical markers can be tracked using a camera system integrated into, attached to or separate from the OHMD 520 and the center of rotation can be, for example, determined using a pivoting technique, as described in the Examples. One or more virtual femoral components can be placed by the surgeon using a virtual or standard interface 522. The surgeon can initially evaluate the fit and shape of the virtual femoral component relative to the patient's live, physical femur and, optionally, select different virtual femoral components until a virtual femoral component with an optimal size, fit and shape for a patient's distal femoral geometry has been identified. The surgeon can then place, e.g. move, rotate, translate, flex, the virtual femoral component projected by the OHMD using a virtual or other interface so that it is centered over the patient's physical distal femur, e.g. so that the medial edge of the component and the lateral edge of the component are equidistant to the medial edge and the lateral edge of the patient's native distal femur and/or so that, for example, the trochlear flange and the posterior condyles of the component are equidistant to the patient's native, physical trochlea and posterior condyles and/or so that the central area between the condyles or the box with PS designs is centered over the patient's native unoperated trochlea and/or so that the medial and/or lateral articular surface of the femoral implant component is tangent with the medial and/or lateral articular surface of the patient, e.g. cartilage and/or subchondral bone, in extension and/or at 10, 15, 20, 25, 30, 35, 40, 45, etc. degrees of flexion 522. Once the surgeon determines that the virtual femoral component has been centered over the distal femur of the patient, the center or central point of the femoral component can be determined 524, which can be the center between the medial and lateral condyles, e.g. at the 0 degree flexion, 15 degree flexion, 20 degree flexion or 25 degree flexion position of the condyles, or which can be the center of a PS box 524, and/or which can be the center between the anterior flange and the posterior bone cuts and/or which can be the center between the trochlear articular surface and the posterior condyle articular surface(s), and/or which can be the intersect of a line with the shortest distance between the anterior flange and the posterior cut surface(s) or a line with the shortest distance between the trochlear articular surface and posterior condylar articular surface(s) and a coronal plane through the center of the notch region and/or the condyles, e.g. at zero degree flexion, of the component. Someone skilled in the art can recognize other means of determining a center or central point of a femoral component. The center or central point of the virtually placed femoral component can be an approximation or estimate of the center or central point of the patient's native, unoperated physical distal femur. Once the center of the virtually placed femoral component is determined 524, the femoral mechanical axis can be determined, for example as the line extending from the center of the femoral component (or the center of the patient's distal native distal femur) to the center of rotation of the hip joint 526. Optionally, the femoral angle, i.e. the angle between the femoral mechanical axis and a vertical line, can be determined 528.

The center of the ankle joint can be determined 530. This can be accomplished, for example, with use of a standard alignment rod extending from the knee to the ankle 530. It can also be accomplished with use of surgical navigation techniques known in the art. Optical markers can be applied to the ankle, e.g. the medial and lateral malleolus, e.g. the patient's bone or skin or other tissue, or to an ankle clamp optionally touching the medial and lateral malleolus. The position of the optical markers can be determined using a camera system integrated into, attached to or separate from the OHMD 520 and, for example, with the dimensions of the ankle clamp known, the center of the ankle joint can be determined. One or more virtual tibial components can be placed by the surgeon using a virtual or standard interface 532. The surgeon can initially evaluate the fit and shape of the virtual tibial component relative to the patient's live, physical tibia and, optionally, select different virtual tibial components until a virtual tibial component with an optimal size, fit and shape for a patient's proximal tibial geometry has been identified. The surgeon can then place, e.g. move, rotate, translate, flex, the virtual tibial component projected by the OHMD using a virtual or other interface so that it is centered over the patient's physical proximal tibia 532, e.g. so that the medial edge of the component and the lateral edge of the component are equidistant to the medial edge and the lateral edge of the patient's proximal tibia and/or so that the anterior and posterior portions of the component are equidistant to the patient's physical proximal tibia (unless accounting for rotational adjustments) and/or so that the central area of the tibial component is centered over the patient's native unoperated tibial spines and/or so that the medial and/or lateral articular surface of the tibial implant component is tangent with the medial and/or lateral articular surface of the patient, e.g. cartilage (normal, damaged and/or diseased) and/or subchondral bone 532. The placement of the virtual tibial component tangent with the medial and/or lateral articular surface can also be used to determine the patient's native tibial slope, e.g. by comparing it with a coronal and/or sagittal plane which can be estimated based on the OR table, e.g. the main plane of the OR table on which the patient is positioned. Once the surgeon determines that the virtual tibial component has been centered over the proximal tibia of the patient, the center or central point of the tibial component can be determined 534, which can be the center between the medial and lateral and anterior and posterior edge of the implant 534. The center or central point of the virtually placed tibial component can be an approximation or estimate of the center or central point of the patient's native, unoperated physical proximal tibia. Once the center of the virtually placed tibial component is determined 534, the tibial mechanical axis can be determined, for example as the line extending from the center of the tibial component (or the center of the patient's native proximal tibia) to the center of the ankle joint 536. Optionally, the tibial angle, i.e. the angle between the tibial mechanical axis and a vertical line, can be determined 538.

With the center of rotation of the hip joint known 520 and the center of the ankle joint known 530, the mechanical axis of the leg can be determined 540. With the femoral mechanical axis known 526 and the tibial mechanical axis known 536, the hip-knee angle, i.e. the angle between the mechanical axis of the femur and the mechanical axis of the tibia can optionally be determined 542. Based on the angles in 528, 538, and 542 and/or axes in 526 and 536, the underlying varus/valgus deformity and the desired varus/valgus correction can be determined 544.

The surgeon can then decide if a full correction of the underlying varus or valgus deformity with neutral, i.e. 180-degree, mechanical axis alignment 546 or a partial correction of the underlying deformity with some residual varus or valgus, e.g. corresponding to a congenital varus or valgus of the patient's knee, 548 is preferable. The surgeon can also elect to perform no correction of underlying and varus valgus deformity 550 thereby maintaining the alignment of the implant components as placed during the virtual placement 552, e.g. tangent with the femoral and/or tibial articular surfaces, e.g. one or more cartilage surfaces and/or shapes, e.g. normal, damaged or diseased, and/or one or more subchondral bone surfaces, e.g. for one or more flexion angles. The femoral and or tibial bone cuts or bone removal can then be determined for the virtually determined implant position and the geometry of the femoral and tibial implant components 554.

With full correction of varus or valgus deformity to normal mechanical axis 546 and partial correction of the of varus or valgus deformity 548, the femoral and/or tibial bone cuts, e.g. their angles, orientation and/or position, or bone removal can be determined for a given implant and/or implant component geometry to achieve the desired mechanical axis correction 556. With full 546 and partial 548 correction of varus or valgus deformity and mechanical axis, the position of the femoral and/or tibial implant component can then be adjusted for the bone cuts or bone removal required to achieve the axis correction 558 accounting for the geometry of the selected implant and/or implant components.

Optionally, intra-operative kinematic measurements of the knee joint can be obtained to determine the patient's tibiofemoral and patellofemoral movement patterns and/or motion including range of motion, flexion, extension, rotation, translation, instability 560. Such intra-operative kinematic measurements can be performed, for example, by tracking the movement of navigation markers attached to femur, tibia and/or patella using a surgical navigation system, by measuring signals from one or more IMU's attached to the femur, tibia and/or patella, by motion analysis using motion capture with a camera system and/or 3D scanner integrated into, attached to, or separate from an OHMD, or by monitoring the movement of optical markers attached to the femur, tibia and/or patella using an image and/or video capture system and/or 3D scanner integrated into, attached to or separate from an OHMD 560. Optionally, the measured kinematic pattern or movement can be corrected, for example to remove an underlying instability 562 or to add more rollback or less rollback or to add more rotation or less rotation or to add more flexion or less flexion or to add more extension or less extension. Using the kinematic measurement 560 and/or any correction of the kinematic and motion patterns 562, the implant position and/or orientation can be modified to achieve a post-implantation performance similar to the measured or corrected kinematics or motion patterns of the patient 564. Such modification of the implant position and/or orientation can, for example, be effected in steps 558 or 552 and 554.

The coordinates for the bone cuts or bone removal can be entered into a virtual surgical plan for the femur, the tibia and/or the patella, which can be used for aligning virtual surgical tools, virtual instruments, virtual implants, and/or virtual cut planes or virtual bone removal with an OHMD or which can be used to guide a robot for executing bone cuts or bone removal or which can be used for a surgical navigation system to guide placement of cut blocks or instruments. The bone cuts or bone removal can then be effected, for example using standard including disposable cutting blocks or instruments, e.g. a bone saw or burr, with optional OHMD guidance, e.g. with alignment of physical cutting blocks or cutting tools with virtually displayed cutting blocks or cutting tools or virtual projection of cut planes for aligning the physical saw blade 566. The bone cuts or bone removal can also be executed with use of a robot, which can, for example, guide a bone saw or a burr, e.g. for use with resurfacing implants 568. The bone cuts or bone removal can also be executed using surgical navigation, for example with use of cut blocks, a bone saw or one or more burrs 570.

In another embodiment, the method or technique includes the steps of FIG. 35, Parts 1 and 2 in which the step 522 "Virtual placement of femoral component, e.g. equidistant to medial edge of medial condyle and lateral edge of lateral condyle, and/or tangent with medial and lateral condylar surface, e.g. distal weight-bearing zone, or at 15, 30, 45 degrees femoral flexion weight-bearing zone" is replaced with "Determine the geometry and/or shape of the distal femur, e.g. medial and/or lateral condyles, e.g. cartilage, subchondral bone, medial, lateral condylar edges/walls, trochlear shape, e.g. using a pointer or pointing device, e.g. tracked using a navigation system, navigation markers (e.g. infrared, RF), optical markers, e.g. with geometric patterns, LED's, e.g. tracked using an image or video capture system, IMU's, e.g. with optional "painting" of the femoral geometry and/or shape (as described in other parts of the specification) and/or using an optical imaging system and/or 3D scanner (as described in other parts of the specification)". Thus, in this embodiment, the femoral geometry and/or shape or portions thereof can be determined using a pointer or pointing device, which can be tracked using a navigation system and navigation markers (e.g. infrared, RF), or which can be tracked using optical markers, e.g. with geometric patterns, or LED's, e.g. tracked using an image or video capture system, or which can be tracked using IMU's, or combinations thereof. The points and point clouds generated can, for example, be used to "paint" the femoral geometry and/or shape and to generate a 3D model of the distal femur or portions thereof, e.g. as described in other parts of the specification. Alternatively, an optical imaging system and/or 3D scanner can be used to image the distal femur and generate a 3D model of the patient's distal femur or portions thereof as described in other parts of the specification.

In another embodiment, the method or technique includes the steps of FIG. 35, Parts 1 and 2 in which the step 524 "Determine center of virtually placed femoral component, e.g. central point between both condyles, e.g. at 0, 15, 20, 25 or other degrees of flexion" is replaced with "Determine center or center point of 3D model of distal femur". Thus, in this embodiment, the center or center point of the patient's distal femur is determined using the 3D model generated using any of the techniques described for "Determine the geometry and/or shape of the distal femur, e.g. medial and/or lateral condyles, e.g. cartilage, subchondral bone, medial, lateral condylar edges/walls, trochlear shape, e.g. using a pointer or pointing device, e.g. tracked using a navigation system, navigation markers (e.g. infrared, RF), optical markers, e.g. with geometric patterns, LED's, e.g. tracked using an image or video capture system, IMU's, e.g. with optional "painting" of the femoral geometry and/or shape (as described in other parts of the specification) and/or using an optical imaging system and/or 3D scanner (as described in other parts of the specification)", i.e. the substituted step 522. Optionally, the center of the distal femur can be determined from the 3D model using various geometric approaches, e.g. by defining intersects of sagittal and/or coronal and/or axial planes and/or lines, e.g. a sagittal plane placed parallel to one or two walls of the medial and lateral condyle and placed equidistant between the medial and lateral condyle, an axial plane placed at a defined distance from the distal articular surface, and a coronal plane placed equidistant between the anterior and the posterior cortex of the distal femoral shaft or placed equidistant between a most anterior point of a trochlea and a most posterior point of a posterior condyle. Someone skilled in the art will recognize other techniques for defining the center of the distal femur, which can also be applied at different flexion angles, e.g. 0, 15, 20, 25 or other degrees of flexion.

In another embodiment, the method or technique includes the steps of FIG. 35, Parts 1 and 2 in which the step 532 "Virtual placement of tibial component, e.g. equidistant to medial edge of medial tibial plateau and lateral edge of lateral tibial plateau, or centered over tibial spines, and/or tangent with medial and/or lateral tibial articular surface" is replaced with "Determine the geometry and/or shape of the proximal tibia, e.g. medial and/or lateral tibial plateau, e.g. cartilage, subchondral bone, medial, lateral, anterior, posterior tibial plateau edges/walls, cortical bone, e.g. using a pointer or pointing device, e.g. tracked using a navigation system, navigation markers (e.g. infrared, RF), optical markers, e.g. with geometric patterns, LED's, e.g. tracked using an image or video capture system, IMU's, e.g. with optional "painting" of the proximal tibial geometry and/or shape (as described in other parts of the specification) and/or using an optical imaging system and/or 3D scanner (as described in other parts of the specification)". Thus, in this embodiment, the proximal tibial geometry and/or shape or portions thereof can be determined using a pointer or pointing device, which can be tracked using a navigation system and navigation markers (e.g. infrared, RF), or which can be tracked using optical markers, e.g. with geometric patterns, or LED's, e.g. tracked using an image or video capture system, or which can be tracked using IMU's, or combinations thereof. The points and point clouds generated can, for example, be used to "paint" the proximal tibial geometry and/or shape and to generate a 3D model of the proximal tibia or portions thereof, e.g. as described in other parts of the specification. Alternatively, an optical imaging system and/or 3D scanner can be used to image the proximal tibia and generate a 3D model of the patient's proximal tibia or portions thereof as described in other parts of the specification.

In another embodiment, the method or technique includes the steps of FIG. 35, Parts 1 and 2 in which the step 534 "Determine center of virtually placed tibial component, e.g. central point between medial & lateral, anterior & posterior edge, intersect" is replaced with "Determine center or center point of 3D model of proximal tibia". Thus, in this embodiment, the center or center point of the patient's proximal tibia is determined using the 3D model generated using any of the techniques described for "Determine the geometry and/or shape of the proximal tibia, e.g. medial and/or lateral tibial plateau, e.g. cartilage, subchondral bone, medial, lateral, anterior, posterior tibial plateau edges/walls, cortical bone, e.g. using a pointer or pointing device, e.g. tracked using a navigation system, navigation markers (e.g. infrared, RF), optical markers, e.g. with geometric patterns, LED's, e.g. tracked using an image or video capture system, IMU's, e.g. with optional "painting" of the proximal tibial geometry and/or shape (as described in other parts of the specification) and/or using an optical imaging system and/or 3D scanner (as described in other parts of the specification)", i.e. the substituted step 532. Optionally, the center of the proximal tibia can be determined from the 3D model using various geometric approaches, e.g. by defining intersects of sagittal and/or coronal and/or axial planes and/or lines, e.g. the intersect of a first line connecting the most anterior point on the anterior tibial edge with the most posterior point on the posterior tibial edge and a second line connecting the most medial point on the medial tibial edge and the most lateral point on the lateral tibial edge, and/or a by finding the mid-point between the medial and the lateral tibial spine. Someone skilled in the art will recognize other techniques for defining the center of the proximal tibia.

Thus, the use of pointers and/or pointing devices and/or optical imaging systems and/or 3D scanners can be employed to generate a 3D model of the distal femur, the proximal tibia and/or the patella. The resultant geometric information and, for example, the center of the distal femur and center of the proximal tibia can be used for all subsequent steps in FIG. 35, Parts 1 and 2. In an embodiment, the step 552 "Maintain alignment of implant component as placed during virtual placement, unless adjustment for kinematics" can optionally be deleted. In an embodiment, the step 552 "Maintain alignment of implant component as placed during virtual placement, unless adjustment for kinematics" can be replaced with "Maintain alignment of implant component as determined using 3D model, unless adjustment for kinematics". In this embodiment, the 3D model generated using the pointer and/or pointing device and associated point clouds and surfaces and/or the 3D model generated using the optical imaging system and/or 3D scanner can be used to align and/or orient a virtual implant component, e.g. on a computer monitor, so that, for example, a portion of its medial femoral articular bearing surface is aligned with a portion of the patient's medial femoral condyle articular surface, and/or a portion of its lateral femoral articular bearing surface is aligned with a portion of the patient's lateral femoral condyle articular surface, and/or a portion of its medial tibial articular bearing surface is aligned with a portion of the patient's medial tibial articular surface, and/or a portion of its lateral tibial articular bearing surface is aligned with a portion of the patient's lateral tibial articular surface, e.g. any of the foregoing at one or more flexion angles, e.g. −5 (hyperextension), 0, 5, 10, 15, 20 or other degrees of flexion. For example, using one or more of these steps, a full correction to normal mechanical axis 546, a partial correction of mechanical axis alignment 548 and/or no correction of varus or valgus alignment 550 can be implemented. For example, partial correction of mechanical axis alignment 548 and/or no correction of varus or valgus alignment 550 can be performed by aligning, at least partially, one or more implant component articular surfaces, e.g. of the medial and/or lateral femoral condyle and/or the medial and/or the lateral tibial plateau of the implant, with one or more femoral and/or tibial articular surfaces, e.g. the medial femoral condyle articular surface, the lateral femoral condyle articular surface, the medial tibial plateau articular surface, the lateral tibial plateau articular surface of the patient, e.g. normal, damaged or diseased cartilage and/or subchondral bone, e.g. at 0, 5, 10, 15, 20, 25 or other degrees of knee flexion, e.g. in the 3D knee model(s), e.g. the distal femoral 3D model and/or the proximal tibial 3D model, and deriving the associated bone cuts and/or bone removal 556 or 554, and executing the bone cuts or bone removal using standard cutting blocks or instruments, e.g. with saws, burrs and optional OHMD guidance 566, executing the bone cuts or bone removal with a robot, e.g. utilizing a saw or burr 568, or executing the bone cuts or bone removal using standard cutting blocks or instruments, e.g. saw, burr, with surgical navigation 570. Any of the foregoing steps can be implemented using any of the registration techniques described in the specification and/or known in the art, e.g. for registering one or more 3D models to the patient's distal femur and/or the patient's proximal tibia, and/or for tracking one or more instruments and/or robotic tools and devices.

Someone skilled in the art can recognize that the foregoing embodiments can be modified and applied to patellar replacement, patellar resurfacing, hip replacement, shoulder replacement, and/or ankle replacement.

The display of virtual data, e.g. of aspects of a virtual surgical plan, of virtual planes, of virtual placement indicators, of projected paths, virtually displaying a device and/or implant component and/or instrument, including, for example, a virtual surgical guide, virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member can be performed in any of the embodiments in relationship to and/or with a predetermined location, orientation, and/or alignment to a normal, damaged and/or diseased cartilage, cartilage surface, and/or cartilage shape, and/or a subchondral bone, subchondral bone surface and/or subchondral bone shape and/or cortical bone, cortical bone surface and/or cortical bone shape. The predetermined location, orientation, and/or alignment can be external and/or internal to a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. The predetermined location, orientation, and/or alignment can be tangent with and/or intersecting with a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape. The intersecting can be at one or more predetermined angles. The predetermined location, orientation, and/or alignment can be at an offset to a normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape, e.g. an offset of 0.5, 1.0, 1.5, 2.0, 3.0, 4.0, 5.0, 7.0, 10.0, 15.0, 20.0 mm in x, y and/or z-direction relative to the normal, damaged and/or diseased cartilage, cartilage surface, and/or cartilage shape, and/or a subchondral bone, subchondral bone surface and/or subchondral bone shape, and/or cortical bone, cortical bone surface and/or cortical bone shape.

In some embodiments, an intra-operative 2D or 3D imaging study can be performed, e.g. one or more x-rays or a CT scan, for example using an O-arm system in spinal surgery. The intra-operative imaging study can be registered in a common coordinate system with the surgical site, e.g. a spine, and one or more OHMDs, for example worn by a first surgeon, a surgical resident and a physician assistant or a nurse. The OHMD can display one or more digital holograms of subsurface anatomy of the patient, hidden or obscured by overlying skin, soft-tissue and/or bone. The OHMD can display an arbitrary virtual pedicle screw over the surgical field. The arbitrary virtual pedicle screw can, for example, be pedicle screw selected from the middle of a size range or a shape range. The arbitrary virtual pedicle screw can be selected based on surgeon preferences. The arbitrary virtual pedicle screw can be the most common size used in a particular patient population. The arbitrary virtual pedicle screw can be moveable using a virtual or other interface. For example, the virtual representation of the arbitrary virtual pedicle screw can include a "touch area", wherein gesture recognition software, for example the one provided by Microsoft with the Microsoft Hololens including, for example, the integrated virtual "drag function" for holograms can be used to move the arbitrary virtual pedicle screw. For example, one or more cameras integrated or attached to the OHMD can capture the movement of the surgeon's finger(s) in relationship to the touch area; using gesture tracking software, the arbitrary virtual pedicle screw can then be moved by advancing the finger towards the touch area in a desired direction. A surgeon can, for example, also "hold" the arbitrary virtual pedicle screw by closing two fingers, e.g. thumb and index finger, over the touch area and then moving the fingers in the desired direction, thereby moving the arbitrary virtual pedicle screw into the desired position and/or orientation in the patient's spine, e.g. centered in the target pedicle, towards the medial pedicle wall, towards the lateral pedicle wall, towards the superior pedicle wall and/or towards the inferior pedicle wall, forward and, optionally, backward. As an alternative to virtually moving or aligning a virtual pedicle screw, a virtual predetermined path for a pedicle screw or for a vertebroplasty or kyphoplasty needle can also be virtually moved or aligned, e.g. using a virtual interface or other interface.

The OHMD can display the virtual pedicle screw in any location initially, e.g. projected onto or outside the surgical field, e.g. a lumbar, thoracic or cervical spine. The OHMD can optionally display the virtual pedicle screw at a defined angle, e.g. orthogonal or parallel, relative to a fixed structure in the operating room, which can, for example, be recognized using one or more cameras, image capture or video capture systems and/or 3D scanner integrated into the OHMD and spatial recognition software such as the one provided by Microsoft with the Microsoft Hololens or which can be recognized using one or more attached optical markers or navigation markers including infrared or RF markers. The virtual pedicle screw can then be displayed perpendicular or at another angle relative to the operating room table. The virtual pedicle screw can be displayed at a defined angle to one or more anatomic or biomechanical axes.

The surgeon can move the virtual pedicle screw to align it in the desired location and/or orientation in the pedicle and/or vertebral body. The surgeon can then evaluate the size of the virtual pedicle screw and the fit of the virtual pedicle screw by evaluating the size and fit of the virtual representation of the virtual pedicle screw superimposed onto the intended implantation site in the pedicle and vertebral body. The surgeon can move and align the virtual pedicle screw. If the virtual pedicle screw is too large for the patient's pedicle, the surgeon can cancel the virtual display of the particular size of virtual pedicle screw displayed and the surgeon can select a smaller virtual pedicle screw from the library of virtual and physical pedicle screws. If the virtual pedicle screw is too small for a patient's pedicle, the surgeon can cancel the virtual display of the particular size of virtual pedicle screw displayed and the surgeon can select a larger virtual pedicle screw from the library of virtual and physical pedicle screws. In this manner, the surgeon can optimize the pedicle screw size and fit in three-dimensions in the actual surgical site, level by level.

Virtual Surgical Plans

Virtual and physical surgical instruments and implant components can be registered in a common coordinate system, for example with one or more OHMDs and live data of the patient. When pre-operative imaging studies, intra-operative imaging studies or intra-operative measurements are registered in a common coordinate system with one or more OHMDs using, for example, anatomic features, anatomic landmarks, implantable and attachable markers, calibration and registration phantoms including optical markers, LED's with image capture, navigation markers, infrared markers, RF markers, IMU's, or spatial anchors and spatial recognition, one or more of an instrument or implant position, orientation, alignment can be predetermined using the information from the pre- and intra-operative imaging studies and/or the intra-operative measurements.

In some embodiments, a surgeon or an operator can develop a virtual surgical plan. The virtual surgical plan can include the virtual removal of select tissues, e.g. bone or cartilage or soft-tissue, e.g. for installing or implanting a medical device. The virtual surgical plan can include removal of a tumor or other tissues. The virtual surgical plan can include placing a graft or a transplant. Any surgical procedure known in the art can be simulated in a virtual surgical plan, for example spinal fusion including anterior and posterior, spinal disk replacement using motion preservation approaches, hip replacement, knee replacement, ankle replacement, shoulder replacement, ACL repair or reconstruction, ligament reconstruction.

A virtual surgical plan can be developed using intraoperative data or measurements, including measurements obtained using one or more optical markers which can, for example, be detected using one or more cameras, an image capture system, a video capture system and/or 3D scanner integrated into, attached to or separate from an OHMD. The one or more cameras, an image capture system, a video capture system and/or 3D scanner integrated into, attached to or separate from an OHMD can, for example, detect the coordinates of one or more optical markers attached to the surgical site, e.g. a bone or cartilage, an altered surgical site, e.g. a bone cut, the operating room table, an extension of the operating room table, and/or fixture structures in the operating room, e.g. walls. The one or more cameras, an image capture system, a video capture system and/or 3D scanner integrated into, attached to or separate from an OHMD can detect the one or more optical markers in static positions and/or dynamic, moving positions. The coordinates (x, y, z) of the optical markers can be measured in static and dynamic conditions.

Any other sensor described in the specification, e.g. IMU's, navigation markers, e.g. infrared markers and/or RF markers, LED's, can be used for obtaining intraoperative measurements and can be combined, for example with optical marker measurements, for deriving intra-operative measurements and for generating and/or developing a virtual surgical plan.

Intra-operative measurements using one or more cameras, an image capture system, a video capture system and/or 3D scanner integrated into or attached to an OHMD can be beneficial when measurements are desired to be obtained from the view angle of the surgeon or, when multiple OHMDs are used, from the view angle of a surgical assistant or second surgeon. Intra-operative measurements using one or more cameras, an image capture system, a video capture and/or 3D scanner separate from an OHMD can be advantageous when measurements are desired to be obtained from a view angle other than the surgeon or, when multiple OHMDs are used, from a view angle other than of a surgical assistant or second surgeon.

Pre-operative data, e.g. pre-operative imaging studies or kinematic studies of a patient, e.g. with the joint or the spine measured or imaged in motion, can also be incorporated into a virtual surgical plan. Pre-operative data alone can be used to develop a virtual surgical plan. The virtual surgical plan can be developed with use of a computer or computer workstation as well as a local or remote computer or computer network. The computer or computer workstation can include one or more displays, keyboard, mouse, trackball, mousepad, joystick, human input devices, processor, graphics processors, memory chips, storage media, disks, and software, for example for 3D reconstruction, surface displays, volume displays or CAD design and display, as well as optional CAM output. The software can include one or more interfaces for CAD design, for displaying the patient's anatomy, for displaying virtual surgical instruments and for displaying virtual implants, implant components, medical devices and/or medical device components.

The different anatomic and pathologic structures as well as the different virtual instruments, e.g. virtual surgical guides including drill guides or cut blocks, virtual implants, implant components, medical devices and/or medical device components can optionally be displayed simultaneously on the same screen or screen section or non-simultaneously, e.g. on different screens, on the same screen at different times, or no different screen sections. The different anatomic and pathologic structures including hidden and/or obscured or partially hidden and/or obscured anatomic and pathologic structures as well as the different virtual instruments, e.g. virtual surgical guides including drill guides or cut blocks, virtual implants, implant components, medical devices and/or medical device components can optionally be displayed using different colors or different shading. Some of the different anatomic and pathologic structures as well as the different virtual instruments, e.g. virtual surgical guides including drill guides or cut blocks, virtual implants, implant components, medical devices and/or medical device components can optionally be displayed in a form of outline mode or pattern mode, where only the outline or select features or patterns of the anatomic and pathologic structures as well as the virtual instruments, e.g. virtual surgical guides including drill guides or cut blocks, different virtual implants, implant components, medical devices and/or medical device components are being displayed, for example with solid, dotted or stippled lines or geometric patterns.

Figure 11:
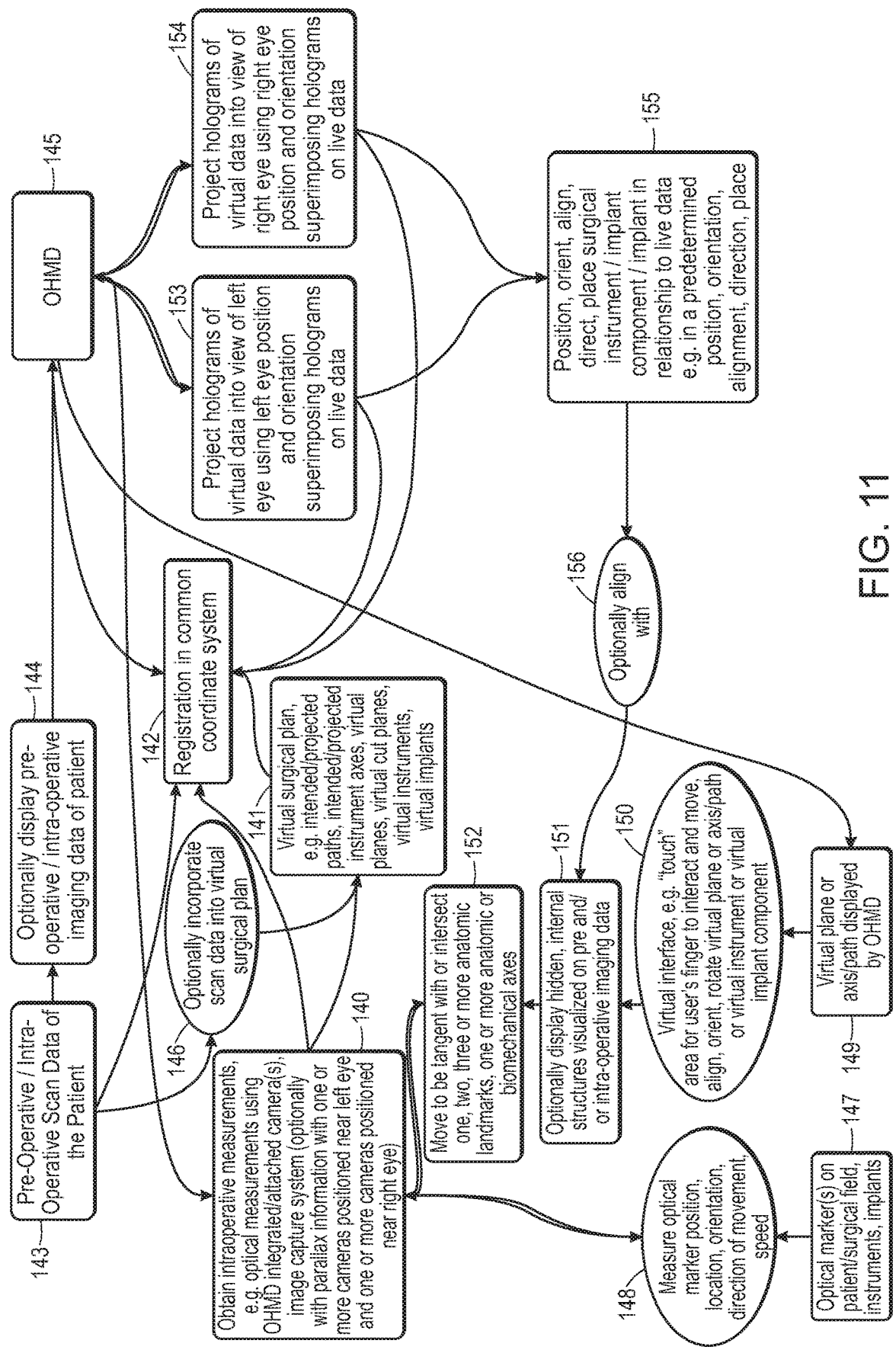
FIG. 11 is an illustrative example how a virtual surgical plan can be generated using intraoperative data, e.g. intraoperative measurements, for example measurements obtained with one or more cameras, an image capture system or a video capture system and/or a 3D scanner integrated into, attached to or separate from an optical head mount display according to some embodiments of the present disclosure.

FIG. 11 shows how a virtual surgical plan 141 can be generated using intraoperative data, e.g. intra-operative measurements 140, for example measurements obtained with one or more cameras, an image capture system or a video capture system and/or 3D scanner integrated into, attached to or separate from an optical head mount display. Intraoperative measurements 140 can be utilized to generate a virtual surgical plan 141 which can be registered in a common coordinate system 142. The intraoperative measurements 140 can also be directly registered in the common coordinate system 142. Preoperative and/or intraoperative scan data 143 can be generated and can be optionally displayed 144 in two or three dimensions in an OHMD 145. Preoperative and/or intraoperative scan data 143 can optionally be incorporated 146 in the virtual surgical plan 141. Optical markers 147 can be present on the patient, the surgical field, surgical instruments or implants and can be measured with regard to their position, location, orientation, direction of movement and/or speed 148. A virtual plane or path or axis 149 can be displayed by the OHMD 145 and, using a virtual interface 150, the plane or path or axis, as well as optionally virtual implants or instruments, can be moved by the surgeon. Optionally, the OHMD 145 can display hidden or internal structures 151, e.g. visualized on preoperative or intraoperative imaging studies or combinations of both, and the surgeon or the software can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The OHMD can project stereoscopic views for the left eye and right eye by displaying electronic holograms with virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

Figure 12:
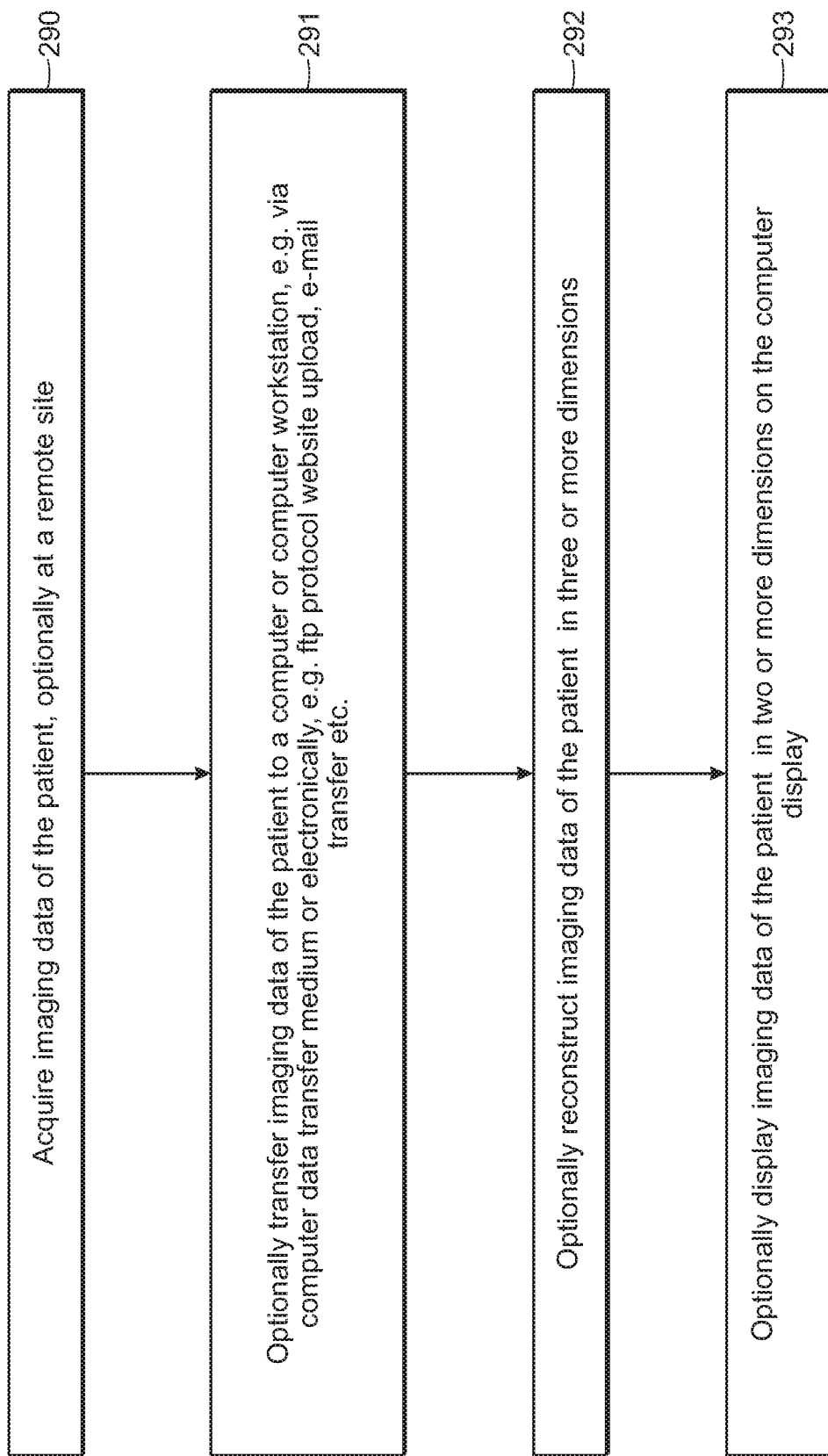
FIG. 12 is an exemplary workflow for generating a virtual surgical plan according to some embodiments of the present disclosure.

FIG. 12 is another exemplary workflow for generating a virtual surgical plan. Imaging data of a patient are acquired, e.g. at a site remote from the operating room 290. The imaging data can be transferred to a computer or workstation, e.g. via electronic data transfer routines such as ftp or internet 291. The imaging data of the patient can be reconstructed in three dimensions 292. The imaging data can be displayed in two or three dimensions on a computer display 293 or OHMD.

Figure 13:
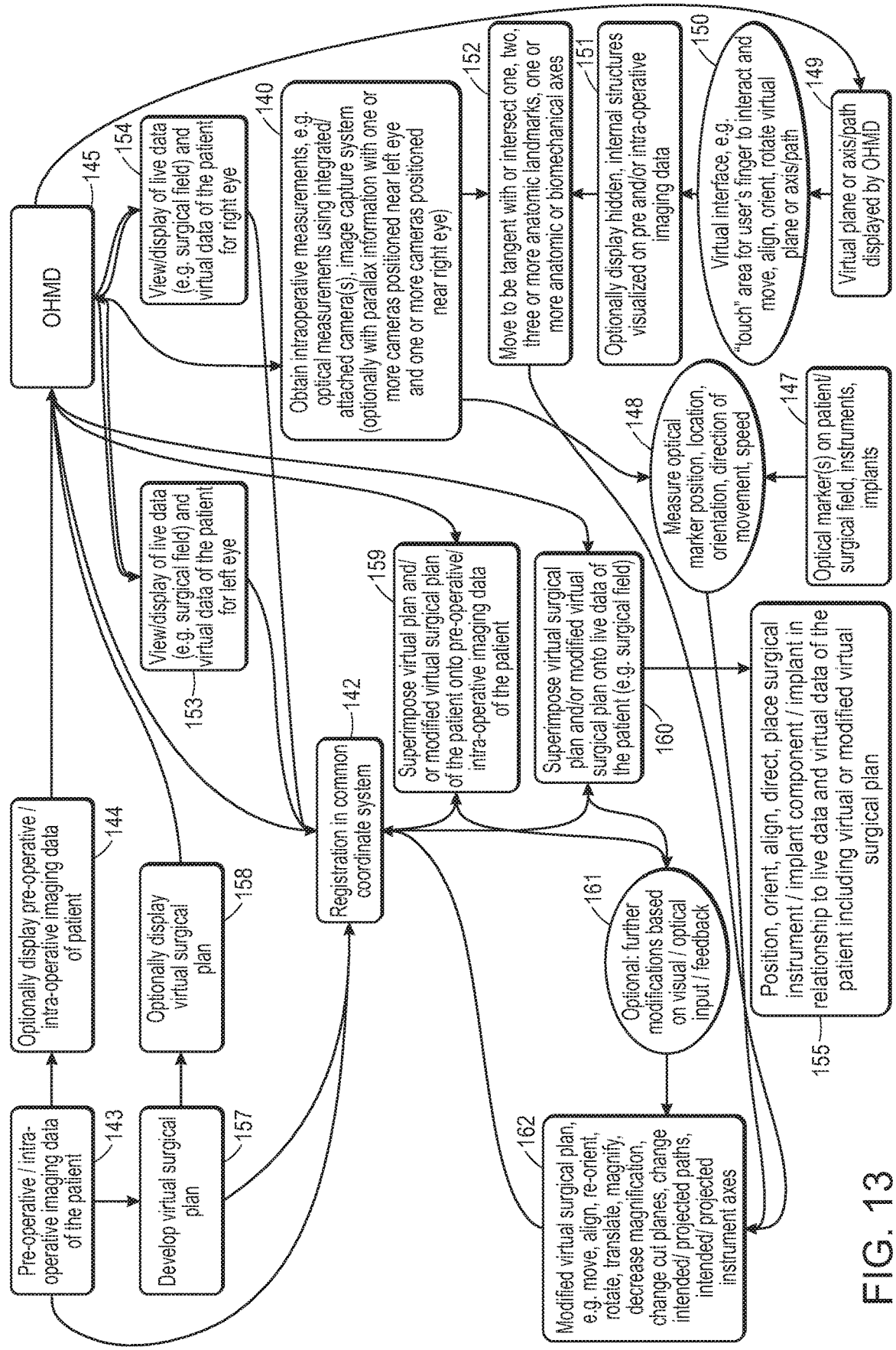
FIG. 13 shows an example how a virtual surgical plan can be modified using intraoperative data, e.g. intraoperative measurements according to some embodiments of the present disclosure.

FIG. 13 shows an example how a virtual surgical plan 157 can be modified using intraoperative data, e.g. intraoperative measurements 140. The virtual surgical plan 157 can be developed using pre-operative and intra-operative imaging data of the patient 143. The virtual surgical plan 157 can be registered in a common coordinate system 142. Preoperative and/or intraoperative scan data 143 can be generated and can be optionally displayed 144 in two or three dimensions in an OHMD 145. Preoperative and/or intraoperative scan data 143 can be used to develop the virtual surgical plan 157 which can be optionally displayed 158 by the OHMD 145. Optical markers 147 can be present on the patient, the surgical field, surgical instruments or implants and can be measured with regard to their position, location, orientation, direction of movement and/or speed 148. A virtual plane or path or axis 149 can be displayed by the OHMD 145 and, using a virtual interface 150, the plane or path or axis, as well as optionally virtual implants or instruments, can be moved by the surgeon. Optionally, the OHMD 145 can display hidden or internal structures 151, e.g. visualized on preoperative or intraoperative imaging studies or combinations of both, and the surgeon can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The OHMD can project stereoscopic views for the left eye and right eye by displaying virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Intraoperative measurements 140 can be utilized to generate or modify a virtual surgical plan 157. The virtual surgical plan 157 and/or a modified virtual surgical plan 162 can optionally be superimposed on pre-operative and intraoperative imaging data of the patient 159. The virtual surgical plan 157 and/or a modified virtual surgical plan 162 can optionally be superimposed on pre-operative and intraoperative imaging data of the patient 159. The modified virtual surgical plan 162 can be further modified based on visual or optical feedback or input 161 and it can be used to position, orient, align, direct, place one or more virtual or physical instruments, implant components and/or implants in a predetermined position 155. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

In some embodiments, one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be moved, re-oriented and/or re-aligned by the surgeon using a virtual or other interface. For example, the virtual representation of the one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can include a "touch area", wherein an image or video capture system and/or 3D scanner and gesture recognition software, for example the one provided by Microsoft with the Microsoft Hololens including, for example, the integrated virtual "drag function" for holograms can be used to move the virtual data. For example, one or more cameras integrated or attached to the OHMD can capture the movement of the surgeon's finger(s) in relationship to the touch area; using gesture tracking software, the hologram(s) can then be moved by advancing the finger towards the touch area in a desired direction. A surgeon can, for example, also "hold" the hologram(s) by closing two fingers, e.g. thumb and index finger, over the touch area and then moving the fingers in the desired direction.

Placement Rules, Selection Rules, Design Rules

A virtual surgical plan can optionally include placement rules for surgical instruments and/or medical devices, implants or implant components. These placement rules can be based on standard rules of surgery or on standard surgical techniques, e.g. placement rules of knee arthroplasty, hip arthroplasty or for pedicle screws. Placement rules or selection rules or design rules for a virtual surgical plan can be based on the patient's anatomy, desired implant, component or medical device position, location, orientation, rotation or alignment, one or more anatomical axes, one or more biomechanical axes, a mechanical axis of the knee or lower extremity, one or more rotational axes, a desired function of an implant, implant component or medical device. Placement rules or selection rules or design rules for a surgical plan can be used, for example, to select an implant. Placement rules or selection rules or design rules can include implant, implant component, or medical device dimensions or shape. Placement rules or selection rules or design rules can include avoidance of certain soft-tissues, vessels or neural structures as well as other sensitive tissues or structures, e.g. ligaments intended to be preserved. For example, in unicompartmental arthroplasty, a placement rule can include that a vertical tibial cut spare the medial tibial spine. In cruciate retaining total knee arthroplasty, a placement rule can include to spare the posterior cruciate ligament during the tibial resection, for example by designing a bone cut in a manner to avoid the posterior cruciate ligament. Placement rules, selection rules or design rules of a virtual surgical plan can include demographic information of the patient, e.g. weight, height, age, gender, other information such as bone mineral density or structure, clinical history, history of prior fractures, or functional information, e.g. on motion of a joint, or metabolic information, e.g. for certain organs or pathologic tissues. Automatic placement of a virtual medical device, device component or implant is possible, for example based on anatomic criteria, pathologic criteria, or functional criteria using placement rules, selection rules or design rules for virtual surgical plans. Placement of a virtual medical device using placement rules, selection rules or design rules can be manual, semi-automatic or automatic. Manual, semi-automatic or automatic placement rules will typically require a software and a user interface.

For example, in spinal surgery the placement of a pedicle screw in the virtual surgical plan can be based on
  Distance between pedicle screw or related bone void to accept the pedicle screw to the medial, lateral, superior, and/or inferior endosteal surface or cortical surface in portions or all of the pedicle.
  Area or volume between pedicle screw or related bone void to accept the pedicle screw to the medial, lateral, superior, and/or inferior endosteal surface or cortical surface in portions or all of the pedicle.
The foregoing information on distance or area can also be used for selecting a size, width, diameter or length of a pedicle screw.

In spinal surgery the placement of a pedicle screw in the virtual surgical plan can also be based on:
  Location of the pedicle screw including its tip in the vertebral body.
  Location of the pedicle screw including its tip in relationship to a spinal/vertebral body fracture.
  Location of the pedicle screw including its tip in relationship to a superior endplate.
  Location of the pedicle screw including its tip in relationship to an inferior endplate.
  Location of the pedicle screw including its tip in relationship to the anterior vertebral cortex.
  Location of the pedicle screw including its tip in relationship to a vessel.
  Location of the pedicle screw including its tip in relationship to the aorta.
  Location of the pedicle screw including its tip in relationship to the inferior vena cava.
  Location of the pedicle screw including its tip in relationship to neural structures, the thecal sac, nerve roots and/or the spinal cord.
  Distance, area or volume between the pedicle screw including its tip to a spinal/vertebral body fracture.
  Distance, area or volume between the pedicle screw including its tip to a superior endplate.
  Distance, area or volume between of the pedicle screw including its tip to an inferior endplate.
  Distance, area or volume between the pedicle screw including its tip to an anterior vertebral cortex.
  Distance, area or volume between the pedicle screw including its tip to a vessel.
  Distance, area or volume between the pedicle screw including its tip to the aorta.
  Distance, area or volume between the pedicle screw including its tip to the inferior vena cava.
  Distance, area or volume between the pedicle screw including its tip to neural structures, the thecal sac, nerve roots and/or the spinal cord.
The foregoing information on location or distance or area or volume can also be used for selecting a size, width, diameter or length of a pedicle screw.

The placement and the selection of a pedicle screw in spinal surgery can be based on any of the foregoing including any combinations thereof.

The surgeon can receive 2D or 3D or multi-dimensional information of the patient. The information can be displayed, for example using a display screen, e.g. a computer screen separate from the OHMD or the OHMD. The surgeon can mark anatomic structures or pathologic structures on the computer screen using the 2D or 3D or multi-dimensional information of the patient. The information can optionally be segmented or can be modified, for example using image processing techniques known in the art. The marking can be performed using the display of the OHMD unit, e.g. using a virtual user interface.

The surgeon can also mark sensitive tissue, e.g. nerves, brain structure, vessels etc., that the surgeon wants to preserve or protect during the surgery. Such sensitive structure(s) can be highlighted, for example using different colors, when the virtual surgical plan and the related anatomic data or pathologic tissue information is being transmitted to or displayed by the OHMD. The surgical plan can be designed, adapted or modified so that sensitive structures are avoided or only minimally perturbed. For example, if a virtual surgical plan would result in an interference between a surgical instrument, e.g. a scalpel, a saw, a drill or a bur and a sensitive structure such as a vessel or a nerve, the virtual surgical plan can be adapted or modified by moving the position, location, orientation and/or direction of the virtual surgical instrument in order to avoid any interference or contact of the sensitive structure(s) with the surgical instrument. The marking can be performed using the display of the OHMD unit, e.g. using a virtual user interface. For example, the surgeon can optionally point at or circle with his or her finger sensitive structure on the live surgical site including by optionally touching the sensitive tissue. One or more cameras, an image or video capture system and/or 3D scanner integrated into, attached to or separate from the OHMD can detect the finger movement and can highlight the sensitive areas pointed out or circled by the surgeon's finger. In some embodiments, if an interference or contact between the surgical instrument and one or more sensitive structures cannot be avoided (in the virtual data and/or the live or physical surgery), the virtual surgical plan can be adapted or modified to move, typically at least partially, the sensitive structure(s), for example using tissue retractors, in order to minimize or reduce any interference or contact of the surgical instrument with the sensitive structure(s).

In some embodiments, if an interference or contact between the surgical instrument and one or more sensitive structures cannot be avoided (in the virtual data and/or the live or physical surgery), the virtual surgical plan can be adapted or modified to protect, at least partially, the sensitive structure(s), for example using a virtual and in the live patient physical metal or plastic shield which can optionally be interposed between the sensitive structure(s) and the surgical instrument in order to minimize or reduce any interference or contact of the surgical instrument with the sensitive structure(s).

The surgeon can mark the desired location, position, orientation, and or alignment of a graft, transplant or an implant or components thereof. Implant materials can include organic and inorganic matter. Implant materials can include biologic and non-biologic matter.

In a hip replacement procedure, for example, the surgeon can indicate the desired location, position, orientation, alignment, anteversion or offset of an acetabular component or a femoral component. With the femoral component, the surgeon can also indicate the desired femoral neck resection level and the desired position of the component in the femoral canal including the desired entry point into the cut femoral neck, e.g. medially, laterally, anteriorly or posteriorly as well as the desired entry angle. With the acetabular component, the surgeon can also indicate the desired reaming depth and any desired medialization or lateralization.

With the implantation of any medical device, the surgeon can indicate the desired location, position, orientation, alignment of the medical device. Thus, the virtual surgical plan can show the desired location, position, orientation, or alignment of a medical device. The virtual surgical plan can also show the desired location, position, orientation, or alignment of a medical device relative to neighboring tissue. Neighboring tissue can be the tissue of the same organ or joint. Neighboring tissue can also be the tissue of adjacent sensitive structures, e.g. vessel, nerves, other organs and the like.

The surgeon can optionally simulate different locations, positions, orientations or alignments of a medical device. The simulation of different locations, positions, orientations or alignments of a medical device can be particularly helpful when the medical device entails more than one component as can be the case, for example, with Pedicle screws, connectors and spinal rods Artificial intervertebral disks, e.g. metallic endplates and ultra-high molecular weight polyethylene mobile sliding core Knee replacement components, including tibial tray, polyethylene inserts, femoral components, mobile bearings Hip replacement components, including acetabular cup, acetabular liner, femoral head, optionally modular femoral neck, femoral stem or mono-block femoral neck and stem With these multicomponent devices, the surgeon can plan the placement of individual components in the virtual surgical plan and the surgeon can optionally evaluate their location, position, orientation or alignment relative to each other. The surgeon can then make adjustments to the placement, e.g. the position, location, orientation, rotation or alignment of one or more of the components in the virtual plan and, optionally later, in the live surgery. Optionally, the surgeon can also test the function of these components in relationship to each other. For example, in a surgical plan for an artificial intervertebral disk, the software can allow the surgeon to virtually simulate spinal flexion or extension or lateral bending to the left and right with one or more of the medical device components included in the virtual surgical plan or the motion simulation. The surgeon can repeat the virtual surgical plan or the simulation with different degrees of flexion or extension or lateral bending to the left and the right and/or with differently sized or shaped medical devices or medical device components. If there is interchangeability of parts or components between different sizes and shapes or a medical device, the surgeon can optionally repeat the virtual surgical plan or the simulation using such different size components, e.g. a large size polyethylene insert or spacer with a medium size metal backing component or vice versa.

The surgeon can optionally superimpose medical device components with different size and/or shapes on the information and select the device component(s) that best fit the patient or that best match the patient.

In some embodiments, when, for example, a virtual surgical plan is developed using pre-operative data, e.g. pre-operative imaging data, the information is sent from the surgeon's or operator's office, e.g. a radiology office, to a central site, e.g. for image processing or for generating an initial draft surgical plan resulting in processed data or information. The processed information can be transmitted back to the surgeon or the operator. The surgeon or the operator can review the draft surgical plan. The surgeon or the operator can accept the draft surgical plan. The surgeon or the operator can optionally modify the draft surgical plan.

The accepted or modified draft surgical plan can optionally be transmitted back to the central site. The central site can, for example, generate instructions to ship certain medical device components that the surgeon has accepted or selected with the accepted or modified surgical plan.

When intra-operative data are used for developing the virtual surgical plan, the surgeon can develop portions or the entire virtual surgical plan on his or her own, for example using a computer, standard hardware components, display and software in his or her office, a computer, standard hardware components, display and software in the operating room, or the optical head mount display, e.g. using a virtual interface, or combinations thereof. Different computers including the OHMD can be connected via a network, e.g. a WIFI or LiFi network.

The surgeon can optionally incorporate pre-operative data into the virtual surgical plan. For example, in knee replacement, the surgeon can perform intra-operative measurements using, for example, optical markers to determine the mechanical axis of the leg and to define femoral and/or tibial and/or patellar landmarks and register them in the common coordinate system and can be used for the virtual surgical plan which can also be registered in the common coordinate system. The surgeon can then incorporate or import data from one or more pre-operative and/or intra-operative knee x-rays, for example femoral, tibial or patellar component size and/or desired varus or valgus correction and/or desired femoral and/or tibial component rotation and/or desired femoral component flexion and/or desired tibial slope, and/or desired femoral, tibial and/or patellar component position and/or orientation and/or alignment into the virtual surgical plan. Standard data, e.g. a fixed tibial slope, e.g. 0 degrees, 3 degrees or 5 degrees can also be incorporated into the virtual surgical plan. Any of the foregoing can be registered in the common coordinate system and optionally virtually displayed by the OHMD.

In hip replacement, the surgeon can perform intra-operative measurements using, for example, optical markers to determine the location of the center of rotation of the hip joint, to define femoral and acetabular landmarks, e.g. the top of the greater trochanter, the sulcus point, e.g. the lowest point between the greater trochanter and the femoral neck, and the lesser trochanter, the acetabular rim and/or the center of the acetabulum, e.g. by pointing at them using a pointer with one or more attached optical markers; these and other intra-operative measurements can be registered in the common coordinate system and can be used for the virtual surgical plan which can also be registered in the common coordinate system. The surgeon can then incorporate or import data from one or more pre-operative and/or intra-operative hip x-rays and/or pelvic x-rays, for example femoral and acetabular component size, desired liner including lipped and offset liners, desired femoral head size including plus and minus head sizes, and/or desired leg length, and/or desired center of rotation, and/or desired femoral neck length, and/or desired femoral neck angle, and/or desired femoral and/or acetabular component anteversion and/or offset, including combined anteversion. Standard data, e.g. a fixed femoral, acetabular or combined anteversion, a fixed femoral neck angle, a range of angles for an acetabular safe zone can also be incorporated into the virtual surgical plan. Any of the foregoing can be registered in the common coordinate system and optionally virtually displayed by the OHMD.

In some embodiments, aspects of the surgical plan, e.g. the intended location of a medical device that the surgeon is planning to implant can be displayed by the OHMD superimposed onto the live data. The intended location can be indicated, for example, by a virtual medical device component that is a representation of the medical device component selected for implantation. The virtual medical device component displayed by the OHMD in superimposition with the live data can be displayed, for example, in its final desired position.

The surgeon can then intraoperatively place or insert the medical device component aligning the physical device with the virtual device component.

In some embodiments, the intended location of a graft, transplant, medical device or other implantable can be indicated using virtual markers or targets displayed by the OHMD simultaneous with the live data of the patient. The surgeon can then align the graft, transplant, medical device or other implantable with the virtual markers or targets or the surgeon can direct the graft, transplant, medical device or other implantable towards the virtual markers or targets.

A visual or acoustic or other warning signal can be emitted or provided if the surgeon/operator deviates from the surgical plan. The visual warning signal can be provided by the OHMD, e.g. a red background flashing in the display of the virtual data or a color change, e.g. to red, of the virtual data.

In some embodiments, the virtual surgical plan can start by selecting or designing a desired implant or implant component or medical device size and/or dimension and/or shape based on the patient's anatomy, surgical site, pathologic conditions, deformity and other information including but not limited to a desired location, position, orientation, rotation or alignment in relationship to one or more anatomic or rotational or biomechanical axes. The selection or design of the desired size and/or dimension and/or shape can be followed by the placement of the implant, implant component or medical device in the desired location, position, orientation, rotation or alignment in relationship to one or more anatomic or biomechanical axes, the patient's anatomy surgical site, pathologic conditions or deformity. The process can be iterative. For example, the implant or implant component or medical device selection or design can be followed by a desired placement, which can be followed by changes in the selection or design of the implant or implant component or medical device selection, which can be followed by adjustments in placement and so forth. The iterative process can be automatic or semiautomatic.

Once the final implant selection or design and placement have been determined in the virtual surgical plan, the preceding surgical steps can be designed or selected in the virtual surgical plan in relationship to the patient's anatomy, the surgical site, the pathologic condition, one or more anatomic or biomechanical axes, functional information, information on sensitive tissues and other tissues. The preceding surgical steps can be designed or selected in reverse order starting with the final implant or implant component or medical device placement, in consecutive order or in random order or any combinations thereof. Surgical steps can be optionally repeated to optimize any tissue alterations and/or implant placement and/or implant selection and/or implant design. If a virtual surgical plan indicates the potential for complications during the surgery, e.g. placement too close to a vessel or neural structure or other sensitive structure, the surgical plan, portions of the surgical plan, the sequence of the surgical plan and the implant, implant component or medical device selection or design can be modified in order to avoid such potential complications. Thus, the entire process between selection and placement of the implant and surgical steps including display of surgical instruments can be iterative in the virtual surgical plan.

In some embodiments, the virtual surgical plan can start by placing a virtual implant or implant component or medical device in a desired location, position, orientation, rotation or alignment in relationship to one or more anatomic or biomechanical axes, the patient's anatomy surgical site, pathologic conditions or deformity. The implant used for this initial or final placement can be an implant selected from an average, a minimum or a maximum size, dimension or shape or combinations thereof. The placing of the implant or implant component or medical device can then be followed by the selection or design of a desired implant or implant component or medical device size and/or dimension and/or shape. The process can be iterative. For example, placement of the implant or implant component or medical device can be followed by a selection or design of the desired the implant or implant component or medical device size, dimension or shape, which can be followed by changes in the placement of the implant or implant component or medical device, which can be followed by changes in the selection or design of size, dimension or shape and so forth. The iterative process can be automatic or semiautomatic.

Once the final implant placement and selection or design have been determined in the virtual surgical plan, the preceding surgical steps can be designed or selected in the virtual surgical plan in relationship to the patient's anatomy, the surgical site, the pathologic condition, one or more anatomic or biomechanical axes, functional information, information on sensitive tissues and other tissues. The preceding surgical steps can be designed or selected in reverse order starting with the final implant or implant component or medical device placement, in consecutive order or in random order or any combinations thereof. Surgical steps can be optionally repeated to optimize any tissue alterations and/or implant placement and/or implant selection and/or implant design. If a virtual surgical plan indicates the potential for complications during the surgery, e.g. placement too close to a vessel or neural structure or other sensitive structure, the surgical plan, portions of the surgical plan, the sequence of the surgical plan and the implant, implant component or medical device selection or design can be modified in order to avoid such potential complications. Thus, the entire process between selection and placement of the implant and surgical steps including display of surgical instruments can be iterative in the virtual surgical plan.

In some embodiments, the virtual surgical plan can start out with the initial surgical step as defined, for example, in the surgical technique. This can be followed optionally by each or some of the subsequent surgical steps, for example only the major steps. The virtual surgical plan can then continue up to the selection and/or design and placement of the implant in the virtual data of the patient. If the resultant selection and/or design and/or placement of the implant, implant component or medical device differs from the desired result, for example as defined in the surgical plan or as desired by the surgeon, any of the foregoing surgical steps, the placement and/or the selection or the design of the implant, implant component or medical device can be modified. This process can be iterative, manual, semi-automatic or automatic until the desired virtual surgical plan, implant, implant component or medical device selection and/or design or placement are achieved.

Figure 14:
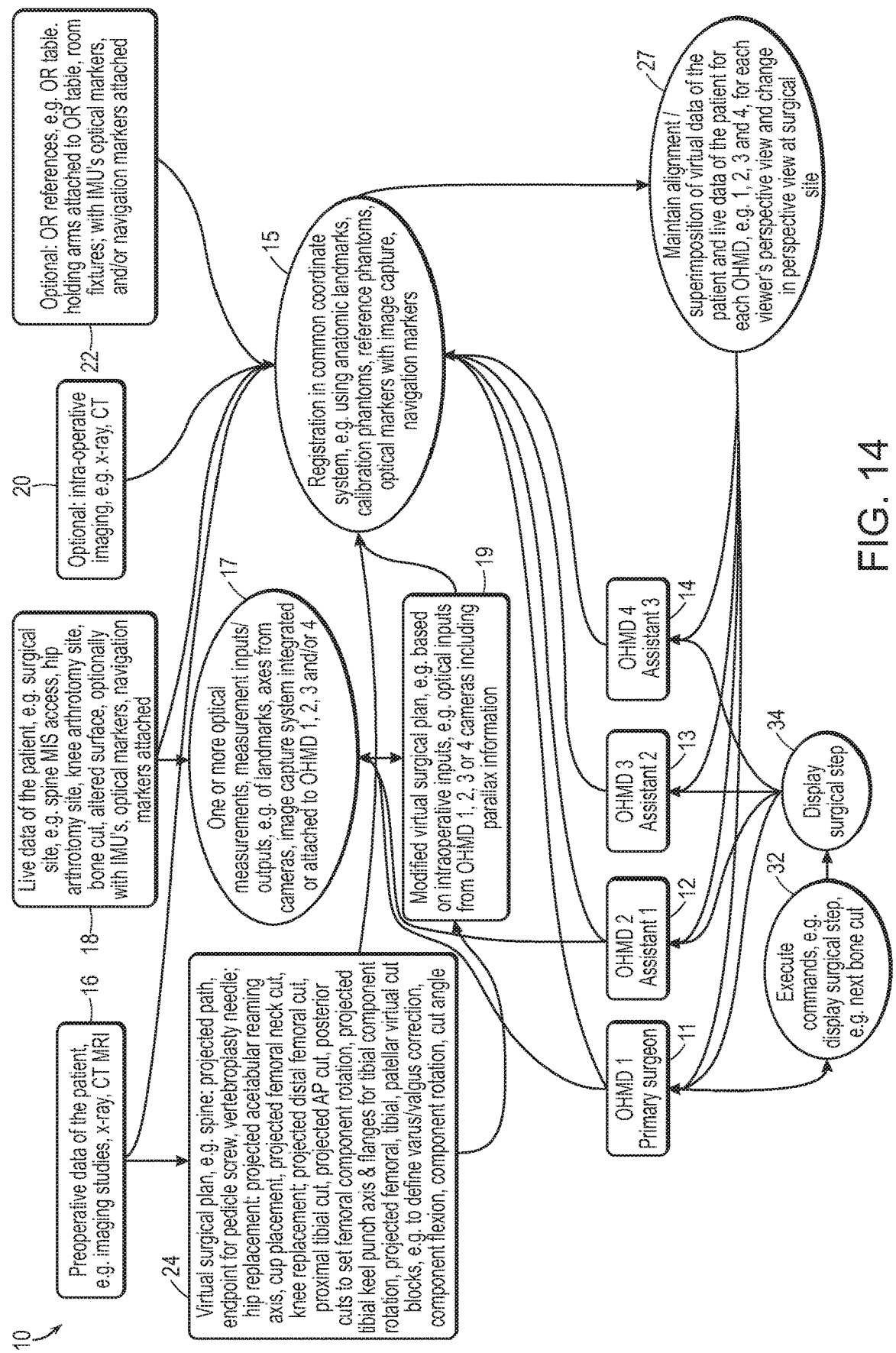
FIG. 14 shows an illustrative example how multiple OHMDs can be used during a surgery, for example by a first surgeon, a second surgeon, a surgical assistant and/or one or more nurses and how a surgical plan can be modified and displayed during the procedure by multiple OHMDs while preserving the correct perspective view of virtual data and corresponding live data for each individual operator according to some embodiments of the present disclosure.

FIG. 14 shows an illustrative example how multiple OHMDs can be used during a surgery, for example by a first surgeon, a second surgeon, a surgical assistant and/or one or more nurses and how a surgical plan can be modified and displayed during the procedure by multiple OHMDs while preserving the correct perspective view of virtual data and corresponding live data for each individual operator. A system 10 for using multiple OHMDs 11, 12, 13, 14 for multiple viewer's, e.g. a primary surgeon, second surgeon, surgical assistant(s) and/or nurses(s) is shown. The multiple OHMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMU's, optical markers, navigation markers, image or video capture systems and/or 3D scanner and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMU's, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The OHMDs 11, 12, 13, 14 can maintain alignment and superimposition of virtual data of the patient and live data of the patient for each OHMD 11, 12, 13, 14 for each viewer's perspective view and position and head position and orientation 27. Using a virtual or other interface, the surgeon wearing OHMD 1 11 can execute commands 32, e.g. to display the next predetermined bone cut, e.g. from a virtual surgical plan or an imaging study or intra-operative measurements, which can trigger the OHMDs 11, 12, 13, 14 to project virtual data of the next surgical step 34 superimposed onto and aligned with the surgical site in a predetermined position and/or orientation. Any of the OHMDs 11, 12, 13, 14 can acquire one or more optical measurements or measurement inputs, e.g. of anatomic landmarks, axes from cameras, anatomic axes, biomechanical axes, a mechanical axis of a leg 17, using for example an integrated or attached camera, image capture or video system. By using multiple OHMDs 11, 12, 13, 14 from different view angles with multiple cameras, image capture or video systems, the accuracy of the measurements can optionally be improved. Optionally, parallax measurements can be performed using the multiple OHMDs 11, 12, 13, 14 from different view angles with multiple cameras, image capture or video systems. The one or more optical measurements can be used to modify the virtual surgical plan 19, optionally using the information from multiple OHMDs 11, 12, 13, 14. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

Tissue Morphing Including Bone Morphing, Cartilage Morphing

In some embodiments, the shape of one or more of the patient's tissues, such as a bone, a cartilage, a joint or an organ, can be estimated or morphed in three dimensions intra-operatively, e.g. during the surgery. The estimating or morphing of the patient's tissue shape, e.g. bone shape, cartilage shape, joint shape or organ shape, can help reduce or obviate the need for pre-operative imaging and, in select embodiments, intra-operative imaging.

In some embodiments, 2D preoperative data can be used and the shape of one or more of the patient's tissues, such as a bone, a cartilage, a joint or an organ, can be estimated or morphed in three dimensions pre-operatively, e.g. prior to surgery.

Bone Morphing and/or Cartilage and/or Tissue Morphing Using Pre-Operative Imaging or Intra-Operative Imaging In some embodiments, one or more two-dimensional images of the patient can be obtained. These images can, for example, include one or more x-rays of the patient. X-rays can be obtained using digital acquisition techniques. X-rays can also be obtained using conventional film based technique, in which case the x-rays can be subsequently digitized using a scanner. Exemplary x-ray images can include:

- Spine: AP, PA, lateral, oblique views, and/or angled views, flexion, extension views, lateral bending views; upright, supine or prone
- Hip: AP, PA, lateral, oblique views, angled views, and/or frogleg view; standing or lying, weight-bearing or non-weight-bearing
- Knee: AP, PA, lateral, oblique views, angled views, tunnel view, and/or Merchant view, sunrise view and the like, any other patellar, femoral or tibial views known in the art; standing or lying, weight-bearing or non-weight-bearing
- Full leg x-rays films; standing or lying, weight-bearing or non-weight-bearing
- Full femur x-rays; standing or lying, weight-bearing or non-weight-bearing
- Full tibia x-rays; standing or lying, weight-bearing or non-weight-bearing
- Selective leg x-rays films, e.g. hip, knee, ankle; standing or lying, weight-bearing or non-weight-bearing X-rays can be obtained with the patient in upright, supine and/or prone position. X-rays can be obtained with the patient in weight-bearing and in non-weight-bearing position. In some embodiments, x-rays are obtained intra-operatively, for example with the patient already positioned and placed for the intended surgical procedure.

The x-ray data of the patient can be transferred into a computer. Optionally, image processing can be applied to segment select patient tissues, such as a bone or vertebra or vertebral structure, subchondral bone, cortical bone, osteophytes. Image processing can, for example, also be applied to determine the edge of select patient tissues, such as a bone or vertebra or vertebral structure, subchondral bone, cortical bone, osteophytes. When subchondral bone has been identified and/or derived from the images, including a subchondral bone curvature and/or geometry and/or shape, a cartilage shape, curvature or geometry can be superimposed or added to the subchondral bone shape. The cartilage shape, curvature or geometry can assume a standard cartilage thickness for a given joint and/or a given patient, e.g. 1.0 mm, 1.5 mm, 2.0 mm, 2.5 mm, 3.0 mm, 3.5 mm. The cartilage geometry can also assume a variable cartilage thickness, e.g. depending on the location of the cartilage in the joint and/or on the articular surface and/or based on the patient's age, gender, race, body weight, and/or BMI, as well as underlying deformity, e.g. varus or valgus deformity.

In some embodiments, the 2D x-rays images can be used to derive information about the dimensions and shape of the anatomic structure(s) included in the x-ray. Some of this information can be, for example:

- Anatomic landmark(s)
- Distances and/or dimensions between two or more known landmarks/structures
- Angles between landmarks
- Anatomic axes
- Biomechanical axes
- Curvature information
- Curvature information of a bone surface
- Curvature information of a subchondral bone surface
- Curvature information of an articular surface
- Change in curvature from convex to concave
- Change in curvature from concave to convex
- Surface information
- Edge information
- Shape information, e.g. when information from multiple x-rays images obtained with different projection or beam angles is combined or aggregated
- Length information, e.g. in AP, ML, SI direction, AP, ML, SI plane, oblique planes
- Width information, e.g. in AP, ML, SI direction, AP, ML, SI plane, oblique planes
- Depth information, e.g. in AP, ML, SI direction, AP, ML, SI plane, oblique planes Any of the foregoing information can be external on the surgical field, e.g. directly visible through a see-through OHMD or the eye of a surgeon without an OHMD and/or on an accessible surface. Any of the information can be internal to the surgical field, e.g. not directly visible through a see-through OHMD display or the eye of a surgeon without an OHMD and/or not on an accessible surface and/or hidden by other tissue, e.g. bone, cortical bone and/or soft-tissue.

Examples of landmarks, distances, dimensions, surfaces, edges, angles, axes, curvatures, shapes, lengths, widths, depths and/or other features for the spine, the hip, the knee and the shoulder joint that can be used for bone morphing and 3D model selection, development, derivations, and deformations in any surgeries of these or to these areas are provided below in Table 16. These examples are in no way meant to be limiting, but are only exemplary in nature. Someone skilled in the art will readily recognize other landmarks, distances, dimensions, surfaces, edges, angles, axes, curvatures, shapes, lengths, widths, depths and/or other features for these joints as well as any other joint in the human body. f For any of the embodiments, landmarks, distances, dimensions, surfaces, edges, angles, axes, curvatures, shapes, lengths, widths, depths and/or other features can be external on the surgical field, e.g. directly visible through a see-through OHMD or the eye of a surgeon without an OHMD and/or on an accessible surface; landmarks, distances, dimensions, surfaces, edges, angles, axes, curvatures, shapes, lengths, widths, depths and/or other features can be internal to the surgical field, e.g. not directly visible through a see-through OHMD display or the eye of a surgeon without an OHMD and/or not on an accessible surface and/or hidden by other tissue, e.g. bone, cortical bone and/or soft-tissue.

TABLE 16

Examples of landmarks, distances, dimensions, surfaces, edges, angles, axes, curvatures, shapes, lengths, widths, depths and/or other features for the spine, the hip, the knee and the shoulder joint that can be used for bone morphing and/or 3D model selection, development, derivations, and deformations in any surgeries of these or to these areas.

Spine:

Cortical bone of a pedicle; Endosteal bone of a pedicle; Posterior cortical bone of a vertebral body; Anterior cortical bone of a vertebral body; Lateral cortical bone of a vertebral body; Superior endplate; Inferior endplate; Intervertebral disk; Vertebral body; Trabecular bone of the vertebral body; Superior facet; Inferior facet; Spinous process; Any fracture components or fragments, e.g. involving a pedicle, a facet joint or a vertebral body; Endplate shape, e.g. sagittal plane; Endplate shape, e.g. coronal plane; Schmorl's node(s); Interpedicular distance; Intervertebral height or disk height; AP length of vertebral body, e.g. at level of inferior endplate, superior endplate, mid-portion; ML width of vertebral body, e.g. at level of inferior endplate, superior endplate, mid-portion; Oblique width vertebral body, e.g. at level of inferior endplate, superior endplate, mid-portion; Vertebral body height, e.g. anterior, mid-portion, posterior; Pedicle length; Pedicle width; Pedicle height; Pedicle angle; Spinous process SI thickness, e.g. anterior, mid-portion, tip; Spinous process width, e.g. anterior, mid-portion, tip; Spinous process inferior angle from origin; Facet dimensions, AP, ML, SI; Facet angle, e.g. angle of joint formed between inferior facet of superior vertebra and superior facet of inferior vertebra; Lamina SI height; Lamina AP width; Lamina ML radius, diameter; Spinal canal AP diameter, ML diameter; Lordosis; Kyphosis; Scoliosis; Side bending, e.g. left lateral, right lateral; Cobb angle; Lumbosacral angle Hip:

Lateral acetabular point or edge; Medial acetabular point or edge; Superior acetabular point or edge; Anterior acetabular point or edge; Posterior acetabular point or edge; Triradiate cartilage and region; Acetabular labrum, medial, lateral, anterior, posterior (e.g. when x-ray contrast has been injected into the joint); Fovea capitis; Femoral head subchondral bone, contour, outline; Femoral head-neck/junction, curvature, convex, concave; Greater trochanter, e.g. lateral cortex, superior cortex, anterior cortex, posterior cortex; Sulcus point (lowest point between greater trochanter and femoral neck), e.g. as seen on a frontal or AP x-ray; Sulcus curvature; Greater trochanter/sulcus transition, curvature, convex, concave; Lesser trochanter; Lesser trochanter/femoral neck transition, curvature; Lesser trochanter/femoral shaft transition; Femoral shaft, anterior cortex, posterior cortex, medial cortex, lateral cortex; Anterior cortex, posterior cortex, medial cortex, lateral cortex for any of the foregoing structures as applicable; Endosteal bone, anterior, posterior, medial, lateral for any of the foregoing structures as applicable; Femoral neck angle; Femoral shaft angle; Acetabular angle; Acetabular anteversion; Femoral anteversion; Femoral shaft angle; Pelvic tilt; Femoral offset; Shenton's line; Hilgenreiner line; Perkin line; Acetabular index Knee:

Medial wall of the femoral notch; Lateral wall of the femoral notch; Roof of the femoral notch; Femoral notch geometry; Femoral notch shape; Distance/line/plane from roof of femoral notch to lowest point or other point or surface on medial femoral condyle; Distance/line/plane from roof of femoral notch to lowest point or other point or surface on lateral femoral condyle; Medial wall of the medial condyle; Lateral wall of medial condyle; Medial wall of lateral condyle; Lateral wall of the lateral condyle; Medial edge of the medial condyle; Lateral edge of medial condyle; Medial edge of lateral condyle; Lateral edge of the lateral condyle; Medial edge of the medial condyle after one or more bone resections or bone removals; Lateral edge of medial condyle after one or more bone resections or bone removals; Medial edge of lateral condyle after one or more bone resections or bone removals; Lateral edge of the lateral condyle after one or more bone resections or bone removals; Medial epicondylar eminence; Lateral epicondylar eminence; Medial femoral condyle shape, e.g. radii, convexities, concavities, curvatures, e.g. sagittal J-curve; Lateral femoral condyle shape, e.g. radii, convexities, concavities curvatures, e.g. sagittal J-curve; Intercondylar notch shape; Intercondylar notch surface features; Medial tibial spine; Lateral tibial spine; Anteromedial tibial rim; Anterolateral tibial rim; Medial tibial rim; Lateral tibial rim; Posterior tibial rim; Anteromedial tibial edge; Anterolateral tibial edge; Medial tibial edge; Lateral tibial edge; Posterior tibial edge; Anteromedial tibial edge after one or more bone resections or bone removals; Anterolateral tibial edge after one or more bone resections or bone removals; Medial tibial edge after one or more bone resections or bone removals; Lateral tibial edge after one or more bone resections or bone removals; Posterior tibial edge after one or more bone resections or bone removals; Lowest point of the medial plateau; Lowest point of the lateral plateau; Highest point of the medial plateau; Highest point of the lateral plateau; Medial tibial plateau shape; Lateral tibial plateau shape; Medial tibial plateau sagittal curvature; Lateral tibial plateau sagittal curvature; Medial tibial plateau corona! curvature; Lateral tibial plateau corona! curvature; Medial tibial plateau surface features, e.g. radii, convexities, concavities; Lateral tibial plateau surface features, e.g. radii, convexities, concavities; Femoral osteophytes; Tibial osteophytes; Patellar osteophytes; Femoral subchondral cysts; Tibial subchondral cysts; Patellar osteophytes; Patellar subchondral cysts; Trochlea osteophytes; Trochlea subchondral cysts; Patellar sagittal curvature; Patellar coronal curvature; Patellar axial curvature; Patellar surface features, e.g. radii, convexities, concavities; Patellar surface features, e.g. radii, convexities, concavities; Patellar

TABLE 16-continued

Examples of landmarks, distances, dimensions, surfaces, edges, angles, axes, curvatures, shapes, lengths, widths, depths and/or other features for the spine, the hip, the knee and the shoulder joint that can be used for bone morphing and/or 3D model selection, development, derivations, and deformations in any surgeries of these or to these areas.

circumference shape; Patellar rise; Patellar thickness; Trochlear depth; Trochlear sagittal curvature; Trochlear axial curvature; Trochlear coronal curvature; Trochlea sagittal shape; Trochlea axial shape; Trochlea coronal shape; Trochlear angle; Trochlear sulcus depth; Epicondylar axis; Posterior femoral axis; Trochlear rotation axis; Mechanical axis; Q-angle
Shoulder:

Clavicle; AC joint; Acromion; Glenoid; Scapula; Coracoid; Humeral head; Humeral neck; Humeral shaft; Glenoid osteophytes; Humeral osteophytes; AC joint osteophytes; Glenoid subchondral cysts; Humeral subchondral cysts; AC joint subchondral cysts; Acromio-humeral distance; Acromio-humeral space; Deepest point of glenoid; Most anterior point or edge of glenoid; Most posterior point or edge of glenoid; Most superior point or edge of glenoid; Most inferior point or edge of glenoid; Glenoid shape; Humeral head shape; Glenoid sagittal curvature, e.g. radii, convexities, concavities; Glenoid axial curvature, e.g. radii, convexities, concavities; Glenoid coronal curvature, e.g. radii, convexities, concavities; Humeral head sagittal curvature, e.g. radii, convexities, concavities; Humeral head axial curvature, e.g. radii, convexities, concavities; Humeral head coronal curvature, e.g. radii, convexities, concavities; Mechanical axis; Anatomical axis; Angle of inclination; Axis of head and neck; Axis through epicondyles; Angle of retroversion.

These landmarks, distances, dimensions, surfaces, edges, angles, axes, curvatures, shapes, lengths, widths, depths and/or other features for the spine, the hip, the knee and the shoulder joint can also be used for the virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member. These landmarks, distances, dimensions, surfaces, edges, angles, axes, curvatures, shapes, lengths, widths, depths and/or other features for the spine, the hip, the knee and the shoulder joint can also be used for other applications throughout the application that utilize anatomic information, e.g. measurements, developments of virtual surgical plans, OHMD projection of virtual data onto such landmarks, distances, dimensions, surfaces, edges, angles, axes, curvatures, shapes, lengths, widths, depths and/or other features etc.

By measuring any of the foregoing landmarks, distances, dimensions, surfaces, edges, angles, axes, curvatures, shapes, lengths, widths, depths and/or other features, including external on the surgical field, e.g. directly visible through a see-through OHMD or the eye of a surgeon without an OHMD and/or on an accessible surface and/or internal to the surgical field, e.g. not directly visible through a see-through OHMD display or the eye of a surgeon without an OHMD and/or not on an accessible surface and/or hidden by other tissue, e.g. bone, cortical bone and/or soft-tissue, it is possible to estimate a 3D shape, volume or surface(s) of a bone, e.g. a proximal femur, a distal femur, a proximal tibia, an acetabulum, a vertebral body and spinal elements and a glenoid and/or a proximal humerus. The more landmarks, distances, dimensions, surfaces, edges, angles, axes, curvatures, shapes, lengths, widths, depths and/or other features are being measured, the more accurate can the estimation of the 3D shape, volume or surface(s) of the bone be. In addition, the more 2D images are being taken or acquired from different view angles, projection angles, beam angles, optionally with the same magnification or different magnifications, optionally with or without magnification correction applied, the more accurate can the estimation of the 3D shape, volume or surface(s) of the bone be.

The 3D shape, volume or surface or curvature of the bone can, for example, be estimated by filling in the information, e.g. intermediate or connecting landmarks, distances, dimensions, surfaces, edges, angles, axes, curvatures, shapes, lengths, widths, depths and/or other features between known landmarks, distances, dimensions, surfaces, edges, angles, axes, curvatures, shapes, lengths, widths, depths and/or other features derived from the one, two, three or more x-ray images. The 3D shape, volume or surface or curvature of the bone can, for example, be estimated by interpolating surfaces between multiple points or by fitting splines.

In some embodiments, a standard model of the bone can be used and can be deformed using one or more of the known landmarks, distances, dimensions, surfaces, edges, angles, axes, curvatures, shapes, lengths, widths, depths and/or other features derived from the x-ray images, including using landmarks, distances, dimensions, surfaces, edges, angles, axes, curvatures, shapes, lengths, widths, depths and/or other features external on the surgical field, e.g. directly visible through a see-through OHMD or the eye of a surgeon without an OHMD and/or on an accessible surface and/or landmarks, distances, dimensions, surfaces, edges, angles, axes, curvatures, shapes, lengths, widths, depths and/or other features internal to the surgical field, e.g. not directly visible through a see-through OHMD display or the eye of a surgeon without an OHMD and/or not on an accessible surface and/or hidden by other tissue, e.g. bone, cortical bone and/or soft-tissue. Such deformations can be performed using various statistical models known in the art.

In some embodiments, a database or library of bone models and tissue models can be used. The one or more of these anatomic landmarks, distances, dimensions, surfaces, edges, angles, axes, curvatures, shapes, lengths, widths, depths and/or other features, e.g. external and/or internal, can be used to identify a standard bone shape and/or a standard cartilage shape by comparing the one or more landmarks, distances, dimensions, surfaces, edges, angles, axes, curvatures, shapes, lengths, widths, depths and/or other external and/or internal features with data in a reference database of reference patients and/or reference bone and/or cartilage shapes and by selecting a 3D model that most closely matches the selected landmarks, distances, dimensions, surfaces, edges, angles, axes, curvatures, shapes, lengths, widths, depths and/or other features. In this manner, the 3D shape of the patient's bones and/or cartilage, e.g. the distal femur and/or the proximal tibia and/or the acetabulum and/or the proximal femur, and/or the vertebral body and/or the spinal elements and/or the glenoid and/or the proximal humerus, can be estimated without the need acquire 3D data or without the need of segmentation of the 3D data or limiting the amount of segmentation needed from available 3D data, e.g. a CT scan or an MRI scan of the patient. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement. Such scan data can be used to generate a database of 3D shapes of patients with different age, gender, ethnic background, race, weight, height and/or BMI.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment throughout the specification including for all other clinical applications, e.g. hip replacement, knee replacement, shoulder replacement spinal surgery, spinal fusion, vertebroplasty, kyphoplasty, ACL repair, ACL reconstruction, fracture fixation, brain surgery, liver surgery, cancer surgery etc.

In some embodiments, a standard model, optionally already deformed using the patient's landmarks, distances, dimensions, surfaces, edges, angles, axes, curvatures, shapes, lengths, widths, depths and/or other features, can be combined or fused with a model selected from a database using the patient's landmarks, distances, dimensions, surfaces, edges, angles, axes, curvatures, shapes, lengths, widths, depths and/or other features. In some embodiments, the model selected from the database can be deformed and/or adapted using the patient's landmarks, distances, dimensions, surfaces, edges, angles, axes, curvatures, shapes, lengths, widths, depths and/or other features. Such deformations can be performed using various statistical models known in the art.

If one or more x-rays are used, they can, for example, be obtained in an AP projection of the knee (or PA), and a lateral projection of the knee. Other views are possible, as known in the art, e.g. a tunnel view, Merchant view, patellar view, oblique views, standing views, supine views, prone views. Optionally, the medial and lateral femoral condyles can be identified on the AP/PA and/or lateral and/or oblique views; optionally, the medial and lateral tibial plateau can be identified on the AP/PA and/or lateral and/or oblique views. Other landmarks, distances, dimensions, surfaces, edges, angles, axes, curvatures, shapes, lengths, widths, depths and/or other features, e.g. external and/or internal, can be identified.

A lateral knee x-ray can, for example, be used to derive curvature information about the medial and the lateral condyle. Two distinct curves can be seen on a lateral knee radiograph, one representing the medial condyle and the other representing the lateral condyle. In most instances, the lateral condyle has a smaller radius than the medial condyle, for example in the central weight-bearing zone. Software can identify and/or segment each curve using, for example, some of the software packages described in Data Segmentation. This can be followed by a curvature analysis assessing the radii of each curve. In some embodiments, the curve with the smaller radii, e.g. in the central weight bearing area, can be assigned as the lateral condyle. Other combinations are possible. If the position of the leg is known relative to the x-ray source and detector panel, e.g. medial side or lateral side of the knee closer to the detector panel, e.g. with lower magnification, the dimensions or magnification of a first condyle can be compared to the dimensions or magnification of the second condyle and the difference in measured dimensions, and, optionally, estimated magnification, can be used to identify the condyle closer to the detector panel on the x-ray, e.g. less magnified, and the condyle further away from the detector panel, e.g. more magnified. The identification of the medial and/or lateral condyle can be manual, e.g. by the operator or surgeon, semi-automatic or automatic.

The foregoing description of techniques to estimate or morph the three-dimensional shape of a patient's bone is only exemplary in nature and is in no way meant to be limiting. Someone skilled in the art will readily recognize other means to estimate the shape of the patient's bone in three dimensions. Any technique known in the art for determining or estimating the three-dimensional shape of a bone from two-dimensional data can be used. Any technique known in the art for modeling and displaying the three-dimensional shape of a bone from two-dimensional data can be used. The resultant 3D model of the patient's bone using any of these techniques can then be displayed by one or more OHMDs, e.g. superimposed onto the patient's live, physical anatomy or surgical site.

Bone and/or Tissue Morphing Using Mechanical Probes and/or Opto-Electronic and/or RF Probes In some embodiments, a mechanical probe can be used to determine the three-dimensional shape of a patient's tissue, e.g. cartilage or bone or organ tissue, intra-operatively. The tissue probe can be attached to a stand or holder. The tissue probe can also be handheld.

The tissue probe can be configured similar to a mechanical detection device known in the art and used, for example, for industrial shape inspection purposes, e.g. coordinate measuring machines (CMM) known in the art, such as, for example, the Faro arm system.

In some embodiments, a mechanical probe can be used that has at least one of an optical marker, e.g. with one or more geometric patterns, e.g. one or more barcodes or QR codes, navigation marker, including infrared markers, retroreflective markers, RF markers, LED and/or IMU attached. The position and/or orientation and/or alignment and/or direction of movement of the probe can be determined then, for example, using a navigation system and/or an image and/or video capture system and/or 3D scanner integrated into, attached to or separate from the OHMD. In embodiments, the mechanical probe is tracked directly, for example using an image or video capture system or 3D scanner integrated into, attached to or separate from the OHMD.

By moving the mechanical probe along the bone, cartilage, tissue and/or organ surface, the position of the tip of the probe can, for example, be registered and, for example, a point cloud can be generated which can be used to generate a 3D surface. Standard techniques known in the art, e.g.

tessellation, can be used for this purpose. The point cloud generated by tracking the movement of the mechanical probe, e.g. with one or more attached optical markers with geometric patterns, can be used to generate a 3D model of one or more surface of the patient, e.g. the surgical site. The point cloud can optionally be used to select a 3D model of the patient, e.g. from a pre-existing library of models. The point cloud can optionally be used to deform a 3D model.

Bone and/or Tissue Morphing Using Optical Probes and/or 3D Scanners and/or Image and/or Video Capture Systems In some embodiments, an image and/or video capture system and/or 3D scanner integrated into, attached to or separate from the OHMD can be used to image the patient's bone and/or cartilage and/or tissue and/or ligaments and/or menisci and/or organ surface. With the position, orientation, alignment and/or direction of movement of the image and/or video capture system(s) and/or 3D scanner(s) optionally known, e.g. in a common coordinate system, for example using optical markers, navigation markers including infrared markers, retroreflective markers, RF markers, LEDs and/or IMUs, spatial mapping, and/or depth mapping, images of the patient's bone and/or cartilage and/or tissue and/or ligaments and/or menisci and/or organ surface can be acquired from multiple viewpoints or continuously and, using software and image processing as described in Data Segmentation or spatial mapping techniques as described in Spatial Mapping, images can be used to derive one or more 3D volumes, 3D surfaces and/or 3D shapes of the patient's bone and/or cartilage and/or tissue and/or ligaments and/or menisci and/or organ. The accuracy of such image acquisitions and reconstruction of 3D volumes, 3D surfaces and/or 3D shapes can optionally be enhanced with image and/or video capture systems and/or 3D scanners that use two or more cameras and/or scanners, which can be used to generated parallax information and/or stereoscopic information of the same structures, wherein, for example, the parallax and/or stereoscopic information can be used to enhance the accuracy of the reconstructions. Alternatively, the information from two or more cameras can be merged by averaging the 3D coordinates or detected surface points or other geometric structures such as planes or curved surfaces.

In some embodiments, 3D laser scanners or depth sensors known in the art, such as, for example, the Structure laser scanner provided by Occipital Inc., can be used to image the surface of the patient's bone and/or cartilage and/or tissue and/or ligaments and/or menisci and/or organ. Other 3D scanners known in the art can be used. Any laser scanning, optical or light scanning technique known in the art for determining, estimating or deriving the 3D volume, 3D surface or 3D shape of a structure known in the art can be used.

In some embodiments, the 3D scanner or image and/or video capture system and/or 3D scanner can be attached to an arm or tripod. Images of the patient's bone and/or cartilage and/or tissue and/or ligaments and/or menisci and/or organ can be acquired at a constant distance. Images of the patient's bone and/or cartilage and/or tissue and/or ligaments and/or menisci and/or organ can be acquired at a variable distance. The laser or optical scanner can optionally be used to measure the distance to the patient's bone and/or cartilage and/or tissue and/or ligaments and/or menisci and/or organ during the image acquisition. Using the laser's starting position or the starting position of the image and/or video capture system and/or 3D scanner and/or at least one of an optical marker, navigation marker including infrared markers, retroreflective markers, RF markers, LED and/or IMU, the position, orientation, alignment and/or direction of movement of the image and/or video capture system and/or 3D scanner can be known throughout the acquisition allowing for magnification correction and optional view angle adjustments and/or projection and/or surface generation calculation and/or adjustments and/or corrections.

Combining Pre-Operative and Intra-Operative Data

In some embodiments, 2D or 3D data obtained intra-operatively with a mechanical probe, opto-electronic probe, RF probe, optical probe, image and/or video capture system, laser scanner and/or 3D scanner can be combined with pre-operative data, e.g. pre-operative imaging data and/or a virtual surgical plan.

The 2D or 3D information obtained pre-operatively can, for example, include mechanical axis information, e.g. of the knee and/or lower extremity (e.g. obtained using a standing x-ray), rotation axis information, e.g. of a hip or a knee, e.g. using epicondylar axis information, posterior condylar axis information, tibial tubercle information, one or more AP dimensions of a joint, one or more ML dimensions of a joint, one or more SI dimensions of a joint, a medial condyle curvature and/or a lateral condyle curvature, e.g. as seen on a lateral and/or an AP radiograph, a medial tibial curvature and/or a lateral tibial curvature, e.g. as seen on a lateral and/or an AP radiograph, joint line information, e.g. the location of a medial and/or a lateral joint line in a knee, offset information, e.g. an offset in a hip or an offset between a medial and/or a lateral condyle.

The 2D or 3D data obtained intra-operatively can, for example, include dimensional information, geometric information, curvature information, volume information, shape information, and/or surface information of the tissue, organ, e.g. cartilage and/or bone. The 2D or 3D data obtained intra-operatively can, for example, include information about joint line location, e.g. medial and/or lateral, femoral offsets and/or tibial offsets, measured based on cartilage and/or subchondral bone.

Optionally, adjustments or corrections can be applied to data obtained pre-operatively and/or intra-operatively. For example, osteophytes and/or subchondral cysts can be virtually removed from the pre-operative and/or intra-operative 2D or 3D data. Flattening of a joint surface seen on any of the data can be optionally corrected, e.g. by applying a corrected shape, e.g. using spline surfaces or smoothing functions or averaging functions.

In some embodiments, 2D or 3D pre-operative data can be combined with 2D or 3D intra-operative data. For example, mechanical axis information obtained from a pre-operative standing x-ray can be combined with an intra-operative 3D scan of a joint, e.g. a knee joint or a hip joint. A virtual surgical plan can be developed or derived based on the combined data, for example with resections that are planned to maintain or restore normal mechanical axis alignment or any other alignment desired by the surgeon, e.g. 5% or less of varus or valgus alignment of a joint. If a virtual surgical plan has already been developed pre-operatively, the virtual surgical plan can be modified intra-operatively using intra-operative 3D scan information of one or more joints, for example using more accurate intra-operative surface information of the joint or organ.

In some embodiments, 3D surfaces morphed from 2D pre-operative data, e.g. using one or more pre-operative x-rays, can be combined with 3D surfaces derived intra-operatively, e.g. derived using an intra-operative mechanical and/or opto-electronic and/or laser and/or 3D scanner. For example, the pre-operative morphed surfaces of a femoral head can be matched, aligned, superimposed or merged in this manner with the intra-operative surfaces. Or the preoperative morphed surfaces of one or both femoral condyles and/or tibial plateaus can be matched, aligned superimposed or merged in this manner with their corresponding intra-operative surfaces. By matching, aligning, superimposing or merging surfaces derived from pre-operative and intra-operative data, axis information obtained on pre-operative data, e.g. standing x-rays can be readily superimposed or merged with intra-operative data. The resultant model can be used to develop, derive and/or modify a virtual surgical plan, for example with subsequent display of one or more cut planes or tissue resections or axes by an OHMD.

2D data obtained pre-operatively and/or intra-operatively using 2D to 3D tissue morphing, e.g. bone morphing, for example as described in the specification, and morphed into a 3D model can be displayed stereoscopically and/or non-stereoscopically using one or more OHMD displays. In addition, any of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be displayed by the OHMD concurrent with the 2D to 3D morphed 3D model, e.g. bone model, stereoscopically or non-stereoscopically. The one or more of a virtual surgical tool, virtual surgical instrument including a virtual surgical guide or cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be planned using the 2D to 3D morphed 3D model, for example using a virtual surgical plan.

Figure 15:
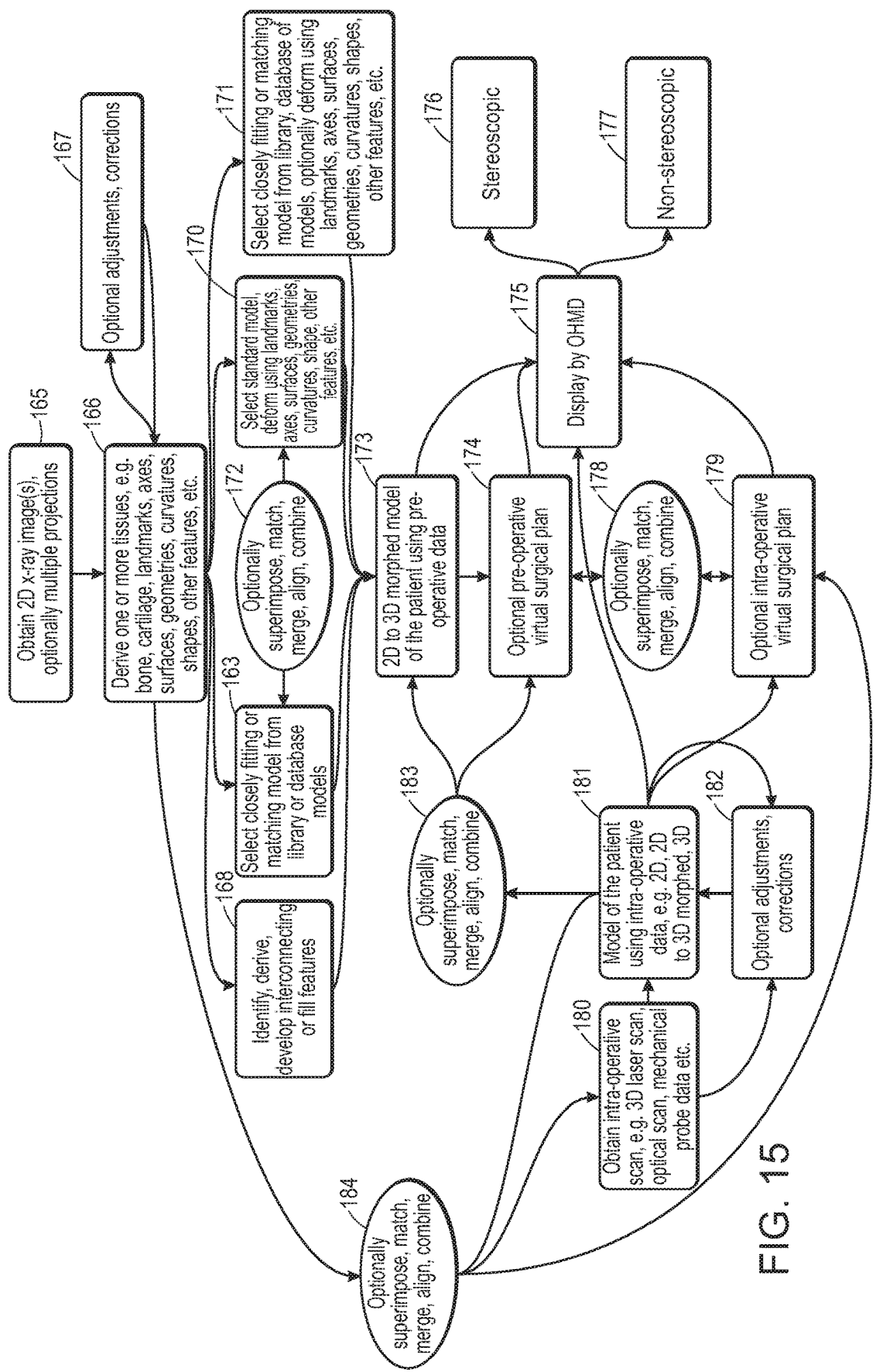
FIG. 15 is an example how 2D to 3D morphed data can be used or applied.

In some embodiments, at least one or more of the same landmarks, distances, dimensions, surfaces, edges, angles, axes, curvatures, shapes, lengths, widths, depths and/or other features used for 2D to 3D tissue morphing, e.g. bone morphing, can be used for intra-operative registration of live data and virtual data, e.g. pre-operative data, of the patient by identifying the at least one or more of the corresponding landmarks, distances, dimensions, surfaces, edges, angles, axes, curvatures, shapes, lengths, widths, depths and/or other features in the live data, using, for example, some of the techniques described in the specification. In this manner, the accuracy of registration can, for example, by improved by using real, physical data used for 2D to 3D tissue morphing, as compared to morphed data, for registration of the physical patient anatomy, e.g. a surgical site, with the virtual data. FIG. 15 is an example how 2D to 3D morphed data can be used or applied. The example is in no way meant to be limiting. In this example, 2D x-ray images can be obtained, optionally with multiple projections 165. One or more tissues, e.g. bone, cartilage, their landmarks, shapes and or geometries or other features can be derived 166 and can be optionally adjusted 167. Interconnecting or fill features can be determined 168, a closely fitting or matching model can be selected from a library or database of models 169, a standard model can be selected and optionally be deformed 170 using the shapes, geometries or features 166, a closely fitting or matching model can be selected from a library or database of models 171 and deformed using the information in 166. Steps and processes in 168, 169, 170, and 171 can optionally be combined 172. Steps and processes 168, 169, 170, 171, and 172 can be used to generate a 2D to 3D morphed model 173, which can be used to generate pre-operative virtual surgical plan 174. The morphed model 173 and the pre-operative virtual surgical plan 174 can be displayed by one or more OHMDs 175, optionally stereoscopic 176 or non-stereoscopic 177. An intra-operative virtual surgical plan 179 can optionally be superimposed, merged, matched or aligned with the pre-operative virtual surgical plan 174. An intra-operative scan or probe data 180 can be used to generate a model of the patient using intra-operative data, e.g. 2D, 2D to 3D morphed, 3D 181, which can optionally be superimposed, matched, merged or aligned 173 with the morphed model of the patient using pre-operative data 173 or the pre-operative virtual surgical plan 174. Optional adjustments to the model of the patient using intra-operative data 181 can be made 182.

Virtual Data and Live Data Seen Through One or More OHMDs

A virtual surgical plan using, for example, virtual data of the patient, can be used to develop or determine any of the following for placing or directing a surgical tool, a surgical instrument, a trial implant component, a trial implant, an implant component, an implant, a device including any type of biological treatment or implant or matrix known in the art:
  Predetermined start point
  Predetermined start position
  Predetermined start orientation/alignment
  Predetermined intermediate point(s)
  Predetermined intermediate position(s)
  Predetermined intermediate orientation/alignment
  Predetermined end point
  Predetermined end position
  Predetermined intermediate orientation/alignment
  Predetermined path
  Predetermined plane (e.g. for placing or orienting a surgical instrument or an implant component)
  Predetermined cut plane (e.g. for directing a saw or other surgical instruments (e.g. drills, pins, cutters, reamers, rasps, impactors, osteotomes) and/or for placing or orienting an implant component or a trial implant component)

Projected contour/outline/cross-section/surface features/shape/projection

Predetermined depth marker or depth gauge, predetermined stop, optionally corresponding to a physical depth marker or depth gauge on the physical surgical tool, surgical instrument, trial implant, implant component, implant or device Predetermined angle/orientation/rotation marker, optionally corresponding to a physical angle/orientation/rotation marker on the physical surgical tool, surgical instrument, trial implant, implant component, implant or device Predetermined axis, e.g. rotation axis, flexion axis, extension axis Predetermined axis of the physical surgical tool, surgical instrument, trial implant, implant component, implant or device, e.g. a long axis, a horizontal axis, an orthogonal axis, a drilling axis, a pinning axis, a cutting axis Estimated/projected non-visualized portions of device/implant/implant component/surgical instrument/surgical tool, e.g. using image capture or markers attached to device/implant/implant component/surgical instrument/surgical tool with known geometry Predetermined virtual tissue change/alteration.

Any of the foregoing, e.g. a cut plane or an outline, e.g. an outline of an implant or a surgical instrument, can be displayed in 2D and/or in 3D, optionally alternatingly. For example, a 2D visualization, e.g. a line, of a cut plane can be used when a surgeon looks substantially on end on a bone, e.g. a distal femur, for orienting and/or directing a cutting instrument, e.g. a saw or a saw blade. When the surgeon looks from the side, e.g. at an angle, the visualization can optionally switch to a 3D display to show the desired angular orientation of the cut and/or the blade in relationship to the bone. The display can also remain in 2D mode. The switching between 2D and 3D display can be manual, e.g. through a voice command or a command on a virtually projected keyboard or a virtually projected user interface, or automatic, e.g. based on the position and/or orientation of the operator's head and/or the OHMD in relationship to the surgical site (e.g. operator head/OHMD in frontal orientation relative to surgical site, or close to including 90 degree side (near orthogonal) orientation, or angular, non-90 degree side orientation, e.g. 30, 40, 50, 60, 70 degree angles). A 2D or 3D display of a cut plane can help determine/display the desired angular orientation of the intended cut. The angular orientation can, for example, be a reflection of a planned/intended mechanical axis correction in a knee replacement, a planned/intended femoral component flexion or extension in a knee replacement, a planned/intended tibial slope in a knee replacement or a planned/intended femoral neck resection for a planned/intended leg length in a hip replacement.

A 2D or 3D display can also include multiple cut planes, e.g. two or more femoral neck cuts in a hip replacement procedure, as can be used in hip replacement procedures involving, for example, an anterior approach and using a "napkin ring" like dual cut through the femoral neck. In this example, the 3D cut plane can include the distal cut plane at its inferior pointing surface and the proximal cut plane at its superior surface. These "napkin ring" inferior, distal facing, and superior, proximal facing cuts can be parallel or non-parallel, e.g. for easier extraction of the femoral head. Any cut planes visualized in 2D or 3D using the OHMD display can be parallel or non-parallel, using stereoscopic or non-stereoscopic display.

If the surgeon elects to change or adjust any of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration used in the one or more virtual surgical plans using, for example, a virtual interface displayed by the OHMD display, e.g. a finger slider or finger tab to move and/or rotate a virtual cut plane by virtually touching it, or any other interface, including, for example, a finger command or a voice command, the virtual representation of the virtual data can move accordingly and the virtual data displayed in the OHMD can be updated accordingly in the surgeon's display. The change in position and/or orientation of the virtual representation of the virtual data can also be seen in other OHMDs, e.g. worn by a second surgeon, a resident, a scrub nurse or a PA, and the projection of the virtual data can also be updated accordingly in a second, third or any additional OHMD units used, for example, by a second surgeon, a resident, a scrub nurse or a PA during the surgery. Optionally, the virtual interface or any other interface to change or adjust one or more of the virtual data can only be available for the surgeon's OHMD unit, i.e. the lead OHMD unit, while the other OHMD units can operate as slave units that simply follow the display of the lead OHMD unit. In this manner, potential intraoperative errors, for example with a non-surgeon modifying virtual data or aspects of the virtual surgical plan, can be avoided. Optionally, the lead can be passed over to any of the other units, in which case the surgeon's OHMD unit can operate as a slave unit. This can be beneficial when complex changes are required to the virtual surgical plan and/or the virtual data of the patient, which may require a separate person to implement such changes, while the surgeon is managing the physical operation in the live patient.

In some embodiments, the OHMD unit of the surgeon can capture the live data of the patient using one or more image and/or video capture systems and/or 3D scanners integrated into or attached to the OHMD. The captured live data of the patient can then be transmitted in electronic, digital form as live stream to slave OHMD units, optionally together with the virtual data of the patient, e.g. superimposed onto or co-displayed with the virtual data of the patient. Alternatively, the slave units in this example can be non-see through virtual reality (VR) systems such as the Google Daydream system or the Zeiss VR One system and others known in the art.

Any intended cut plane displayed by the OHMD can optionally include or account for the thickness of the saw blade to reflect bone last during the sawing step. Any intended path for a drill or pin or other surgical instrument can include or account for the thickness of the surgical instrument to reflect bone lost during the surgical step. In addition, any bone lost due to movement of a surgical instrument, e.g. movement not in the primary direction of the surgical step such as saw blade flutter or saw vibration or a slightly eccentric drill or drill vibration can be included in the virtual surgical plan, for example through estimations of saw blade flutter or saw vibrations in addition to a known saw blade thickness, and can be accounted for in the virtual resection planning and in the resultant display of one or more 2D or 3D cut planes by the OHMD.

Someone skilled in the art can readily recognize that accounting for the thickness of a saw blade or dimensions of other bone removing instruments as well as related instrument or device movement or vibration induced bone loss can be accounted for in one, two, three or more bone removing steps, if a surgical procedure involves multiple bone removing steps, such as the femoral preparation of a partial or total knee replacement, which can include two, three or more bone cuts.

When the OHMD is used to display the estimated/projected non-visualized portions of a device, an implant, an implant component, a surgical instrument and/or a surgical tool, the display of the non-visualized portion of the device, implant, implant component, surgical instrument and/or surgical tool can also account for any bone loss that may have been or will be induced by the device, implant, implant component, surgical instrument and/or surgical tool. By accounting for the bone loss induced by the device, implant, implant component, surgical instrument and/or surgical tool, the virtual surgical plan and the display of any surgical steps including subsequent surgical steps by the OHMD can be more accurate.

A virtual surgical plan can be used to define a predetermined start point for a surgical tool, a surgical instrument, a trial implant component, a trial implant, an implant component, an implant, a device. A start point can be, for example, the entry at the patient's skin. If pre-operative imaging, e.g. ultrasound, CT and/or MRI, is used for developing the surgical plan, the skin can be located in the imaging data and the start point can be defined at an area typically near the intended surgical site. A start point can also be defined at a select soft-tissue depth, e.g. 5, 8 or 10 cm into the soft-tissue, e.g. subcutaneous tissue or muscle or other tissues or organ tissue. A start point can be defined at the surface of an organ, e.g. a liver or a spleen or a kidney or a bladder or a brain. A start point can be defined at an anatomic landmark or in relationship to an anatomic landmark of an organ, e.g. a rim of a liver, a liver portal, an entry of an inferior vena cava into the liver, an entry of a portal vein into the liver, a superior or inferior pole of a kidney, a renal hilum. A start point can be defined at a bone surface or bony landmark The one or more of a virtual surgical tool, virtual surgical instrument including a virtual surgical guide or cut block, virtual trial implant, virtual implant component, virtual implant or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration used in the one or more virtual surgical plans can be highlighted in the one or more OHMD displays using various techniques known in the art, including but not limited to: Colored display; Grey scale display; Shaded display; Patterned display, e.g. squares, lines, bars; Line display, e.g. solid, stippled, dotted; Arrow display; Target like display; Intermittent display, e.g. blinking or flashing; Appearing or disappearing display; Magnified display; Minified display.

For example, a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration is displayed by the OHMD multiple colors can be chosen.

For example, a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be highlighted using an arrow display. The arrows can be aligned with the direction of the one or more surgical tools, surgical instruments, implant components, implants or devices. The arrows can also not be aligned with the direction of the one or more surgical tools, surgical instruments, implant components, implants or devices. The arrows can be orthogonal to the direction of the one or more surgical tools, surgical instruments, implant components, implants or devices. The arrows can be aligned with the one or more surgical tools, surgical instruments, implant components, implants or devices. The arrows cannot be orthogonal with the one or more surgical tools, surgical instruments, implant components, implants or devices.

One or more arrows can directly point at the one or more of a virtual surgical tool, virtual surgical instrument including a virtual surgical guide or cut block, virtual trial implant, virtual implant component, virtual implant or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. The one or more arrows can optionally be magnified or minified. The one or more arrows can optionally be displayed intermittently, e.g. blinking or flashing. The one or more arrows can optionally be appearing or disappearing. For example, the one or more arrows can disappear when the predetermined end point is reached by the physical surgical tool, surgical instrument, implant component, implant or device.

The one or more of a virtual surgical tool, virtual surgical instrument including a virtual surgical guide or cut block, virtual trial implant, virtual implant component, virtual implant or virtual device, one or more predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be highlighted using a target like display. More than one target-like display can be used.

The target-like display can, for example, be positioned over a starting point, one or more intermediate points, an end point, a starting position, one or more intermediate positions, an end position, an intended path, predetermined plane, predetermined cut plane, a predetermined axis of the physical surgical tool, surgical instrument, trial implant, implant component, implant or device. A line or an axis oriented in orthogonal fashion through the target and passing through the center of one or more targets can optionally be aligned with a predetermined path, predetermined plane, predetermined cut plane, or predetermined axis of the physical surgical tool, surgical instrument, trial implant, implant component, implant or device, and/or one or more of a predetermined tissue change/alteration.

An intermittent, e.g. blinking or flashing display can be used to show one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are not aligned with one or more of the virtual surgical tool, virtual surgical instrument including a virtual surgical guide or cut block, virtual trial implant, virtual implant component, virtual implant or virtual device, one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are aligned with one or more of the one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

An intermittent display can optionally change colors or have intermittent, varying color schemes. For example, a blinking or flashing red color can turn into solid, not intermittent green color when one or more of the physical surgical tool, surgical instrument, trial implant, implant component, implant and/or devices are aligned with one or more of a virtual surgical tool, virtual surgical instrument including a virtual surgical guide or cut block, virtual trial implant, virtual implant component, virtual implant or virtual device, or one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

An intermittent display can, for example, highlight if and when one or more of the surgical tool, surgical instrument, trial implant, implant component, implant or device are not aligned with one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration in the OHMD can turn from a solid color, e.g. green or blue, to a blinking or flashing red color. Different colors can be chosen for intermediate versus final, end positions, e.g. blue for intermediate and green for final/end.

An appearing or disappearing display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device inside the OHMD. An appearing or disappearing display can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In this example, the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can appear in the OHMD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can disappear in the OHMD display when alignment is achieved again. The reverse can be possible, e.g. with the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device disappearing when alignment is not achieved and appearing when alignment is achieved.

A magnified or minified display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The OHMD can also, optionally, provide or superimpose a magnified or minified display of the virtual anatomy or virtual data of the patient, for example after registration with the live anatomy/live data of the patient. The unmagnified, magnified or minified virtual anatomy or virtual data of the patient can be displayed by the OHMD simultaneously, e.g. with use of different colors, grey scale or patterns, or alternatingly with the unmagnified, magnified or minified display by the OHMD of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In some embodiments, the magnification (including no magnification) or minification of the display of the virtual anatomy or virtual data of the patient can be the same as the magnification (including no magnification) or minification of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. Virtual anatomy or virtual data of the patient as used in the foregoing includes all virtual data of the patient, including, for example, data from vascular flow studies, metabolic imaging, kinematic data and the like. A magnified or minified display by the OHMD can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In this example, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be magnified or minified in the OHMD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be set to zero magnification or minification or can go from magnified to minified or from minified to magnified in the OHMD display when alignment is achieved again.

If more than one a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device are displayed by the OHMD, any combination of display styles or techniques, e.g. multi-colored, grey scale, shaded, patterned, line, arrow, target, intermittent, appearing, disappearing, magnified, minified is possible. In some embodiments, different display styles or techniques can be chosen for different predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

Two-Dimensional and Three-Dimensional Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in two dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in two dimensions and/or three dimensions, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in three dimensions can be possible.

Stereoscopic and Non-Stereoscopic Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in a non-stereoscopic manner in three dimensions, with similar view angle of the virtual data of the patient seen by the surgeon's eyes through the display of the OHMD unit and the live data of the patient seen by the surgeon's eyes through the OHMD unit.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in a stereoscopic manner in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in a stereoscopic and/or a non-stereoscopic display, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in a non-stereoscopic manner with display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in a stereoscopic manner can be possible.

In some embodiments, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be located in a spine, more specifically a vertebral body, a pedicle, a vertebral fracture, a posterior element, a facet joint depending on the virtual surgical plan and the anatomy and clinical condition of the patient. The predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be located in the posterior elements of a spine, a pedicle and a vertebral body, for example, if spinal fusion with pedicle screws or vertebroplasty of kyphoplasty are contemplated.

If spinal fusion with pedicle screws is planned, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can coincide with, be parallel with, or be aligned and/or superimposed with the long axis of the pedicle screw in its intended virtual placement position from the virtual surgical plan, optionally using placement criteria, e.g. distance from cortex, as used in the virtual surgical plan.

If vertebroplasty or kyphoplasty or spinal biopsy is planned, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can coincide with, be parallel with, or be aligned and/or superimposed with the long axis of the vertebroplasty, kyphoplasty or biopsy needle or needle set in its intended virtual placement position from the virtual surgical plan, optionally using placement criteria, e.g. distance from cortex, as used in the virtual surgical plan.

When stereoscopic projection is used by the OHMD, the display for the left eye and the right eye can be adjusted for the surgeon's or operator's inter-ocular distance, including, for example, the inter-pupillary distance. For example, the distance between the left pupil and the right pupil can be measured prior to operating the OHMD. Such measurements can be performed using an image and/or video capture system and/or 3D scanner integrated into, attached to or separate from the OHMD. Such measurements can also be performed using any other technique known in the art, including, for example, mechanical rulers, optical measurement tools and standard tools used by optometrists.

Adjusting the OHMD Unit Including the Display

In some embodiments, once the inter-ocular, e.g. the inter-pupillary distance, of the surgeon or operator is known, it can be entered into the display system interface and/or software and the 3D projection of the left and the right eye can be adjusted for the user. For example, with a narrow inter-ocular or inter-pupillary distance, the projection for the left eye and the right eye can be moved closer to the nose so that the center of the left and the right projections will be aligned with the center of the left eye/pupil and the right eye/pupil. With a wide inter-ocular or inter-pupillary distance, the projection for the left eye and the right eye can be moved further away from the nose so that the center of the left and the right projections will be aligned with the center of the left eye/pupil and the right eye/pupil. Different user settings can be stored in the system, e.g. by user name. In this manner, when a different user is placing the OHMD on his or her head, the user or the system can call up their preferred user settings, including their respective inter-ocular or inter-pupillary distance. User settings can be called up, for example, using a visual or optical keyboard interface, projected by the OHMD, where the operator can select virtual buttons. User settings can also be called up using voice commands, keyboards and any other known technique or technique for executing user commands.

Refresh Rates, Addressing Image Flicker

In many embodiments of the present disclosure, a fast refresh rate can be desirable, e.g. 15 Hz, 20 Hz, 25 Hz, or 30 Hz, 50 Hz, 70 Hz, 80 Hz, 100 Hz, 120 Hz, 150 Hz, 175 Hz, 200 Hz or greater. When higher refresh rates are used, the spatial resolution of the display of the virtual data can optionally be reduced if bandwidth and transmission speed and/or display speed reach their limits. Alternatively, there can be an alternating of a high-resolution display, e.g. 1920×1080 pixel resolution, and lower resolution, e.g. 1024×768 pixel resolution. The ratio of high to lower resolution images can be 1:1, 2:1, 3:1, 1:2, 1:3, with any other combination possible.

Some users physicalize no flicker with refresh rates of 30 Hz, sometimes less. Other users can feel or experience flicker with refresh rates of 70 Hz or faster. If a user is experiencing flicker effects or a flicker feeling with the display of virtual data, the user can have the option of increasing the refresh rate and, optionally, decreasing the display resolution if necessary, for example for reasons of bandwidth or transmission speed. The user can also select alternating resolutions, e.g. 1920×1080 pixel resolution intermixed with 1024×768 pixel resolution; any other pixel resolution and combination of pixel resolutions is possible. In this manner, the user can select the setting that will yield a pleasant, substantially flicker free display while at the same time maintaining sufficient spatial and/or temporal resolution to enable an accurate physical/virtual work environment.

In some embodiments, the display will automatically turn of and, optionally, turn on depending where the user and/or operator and/or surgeon directs the view.

Automated Turning Off and/or Turning On

In select circumstances, the user and/or operator and/or surgeon may elect to turn off the OHMD display or to turn it back on. The turning off and/or on can be executed via voice commands. It can also be executed via gesture commands, eye commands, digital/finger commands on a physical or virtual keypad or keyboard, e.g. projected by the OHMD.

In some embodiments, the OHMD display can turn off and/or on automatically. The turning off and/or on can be triggered by any number of initiating events or movements, which can optionally be defined by the user. Events or movements triggering an automatic turning off and/or turning on can be different between different users and can be stored as user preferences.

Automatic turning off and/or turning on can, for example, also help reduce the times the OHMD display is on or active, which can be desirable when users experience a flicker like feeling or encounter a flicker experience with the OHMD display or other feelings of discomfort. In this way, the periods of potential flicker exposure or other feelings of discomfort can be reduced to the key parts or portions or sections when the user requires the OHMD to execute an activity, e.g. a physical surgical step optionally defined in a virtual surgical plan with display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In some embodiments, the OHMD display can optionally automatically turn on when the user looks at the target area of activity, e.g. a surgical field or an organ or a tissue located within the coordinates of a live surgical field or area and/or a virtual surgical field or area. In some embodiments, the OHMD display can optionally automatically turn off when the user looks away from the target area of activity, e.g. a surgical field or area or an organ or a tissue located within the coordinates of a live and/or virtual surgical field or area.

In some embodiments, the OHMD display can optionally automatically turn on when the user looks at the target area of activity, e.g. a surgical field or an organ or a tissue located within the coordinates of a live surgical field or area and/or a virtual surgical field or area, and one or more optical markers are detected in the surgical field or an organ or a tissue located within the coordinates of the live surgical field or area and/or a virtual surgical field or area by a camera, image or video capture system integrated into, attached to or separate from the OHMD. In some embodiments, the OHMD display can optionally automatically turn off when the user looks away from the target area of activity, e.g. a surgical field or area or an organ or a tissue located within the coordinates of a live and/or virtual surgical field or area, and one or more optical markers are absent from the surgeon's view and/or the view of a camera, an image or video capture system and/or 3D scanner integrated into, attached to or separate from the OHMD.

The target area of activity, e.g. a surgical field and/or a target tissue can be defined and/or identified using different means, e.g. image capture, optical markers, navigation markers including infrared markers, retroreflective markers, RF markers, surgical navigation, LED's, reference phantoms, calibration phantoms, marks drawn on the target area, e.g. on the skin or a surgical drape. If surgery is contemplated, any of the foregoing active and/or passive markers can be placed on the patient, e.g. underneath a surgical drape, or within the visible sterile, exposed area of the patient on which the surgery will be performed. Alternatively, any active or passive markers can also be placed on top of the sterile drape or on the patient's skin, e.g. surrounding the surgical area or surgical field. A target area can also be identified with use of one or more anatomic landmarks, e.g. in a hip a most inferior point, e.g. sulcus point, between the greater trochanter and the femoral neck, a most superior point on the greater trochanter, a most superior point on a lesser trochanter, an acetabular rim, an acetabular center or in a knee a most medial point on a medial condyle, a most lateral point on a lateral condyle, a center of a trochlear notch, a tibial spine, a most anterior point of a tibia, a central point of a patella. One or more of the same landmarks that have been/are being used for registration of virtual data and live data of the patient can be used for defining or identifying a target area of activity. The landmarks can be identified using, for example, an image and/or video capture system and/or 3D scanner integrated into, attached to or separate from an OHMD. The landmarks can be identified by attaching optionally one or more optical markers, navigation markers including infrared markers, retroreflective markers, RF markers, surgical navigation, LED's, reference phantoms, calibration phantoms, or marks. A target area can be enclosed by landmarks, e.g. by three or more landmarks. A target area can extend beyond one or more landmarks, e.g. by 2, 4, 5, 6, 8, 10 cm or more or any other distance or radius, e.g. selected by the surgeon or operator.

If image capture is used to define an area of intended activity, e.g. a surgical field, the user and/or the surgeon can optionally look at the area of intended activity, e.g. the intended field. Optionally, identify the center area of the area of activity and/or the surgical field can be defined by the user, e.g. by pointing at it with a finger or a pointing device or an RF marker, an optical marker, a navigation marker including infrared markers, retroreflective markers, RF markers, an LED and/or a calibration phantom or a reference phantom. Once the user's and/or the surgeon's view is focused on the intended area of activity and/or the intended surgical field, the user and/or surgeon can execute a command, e.g. a voice command or a finger command, to identify the intended area of activity and/or the surgical field and to store it in the image and/or video capture system and/or 3D scanner. The identified intended area of activity and/or the surgical field is in this manner memorized in the image and/or video capture system and/or 3D scanner. Using standard image processing techniques, the image and/or video capture system and/or 3D scanner can subsequently identify if 20%, 30%, 40%, 50%, 60%, 70%, 80%, 90% or 100% of the intended area of activity and/or the surgical field are included in the field of view of the user and/or the operator and/or the surgeon. Once a certain percentage, e.g. 50% or 60% or 70% or 80% or 90% of the area of intended activity and/or the surgical field is included in the field of view of the surgeon, the OHMD can automatically turn on the OHMD display. Optionally, as the user, operator and/or surgeon turns away his or her view, the OHMD display can automatically turn off, e.g. when less than 90%, 80%, 70%, 60% or 50% of the intended area of activity and/or surgical field area included in the field of view.

The area or percentage used for turning on the OHMD and for turning off the OHMD can be different. The percentage can be selected and, optionally, stored as a user preference.

The field of view can be defined in various different ways, optionally as a user preference. For example, the field of view can be the area covered by the OHMD display when the user is looking through the OHMD. The field of view can be the entire visual field available to the user and/or operator and/or surgeon. The field of view can be a subsection of the visual field of the user, operator and/or surgeon.

Rather than using a percentage of area of the intended area of activity and/or surgical field included, other triggers can be used using, for example, anatomic landmarks, image capture or optical markers, a navigation marker including infrared markers, retroreflective markers, RF markers, an LED and/or a calibration phantom or a reference phantom. For example, the OHMD display can automatically turn on when the user, operator and/or surgeon starts looking at the intended area of activity and/or the surgical field when an anatomic landmark, an optical marker, a navigation marker including infrared markers, retroreflective markers, RF markers, an LED or a calibration phantom or reference phantom (e.g. as seen through an image and/or video capture system and/or 3D scanner integrated into, attached to or separate from the OHMD) is located in the outer one third, central one third or inner one third or the inner half or other landmark or demarcation/separation of the field of view.

Alternatively, the OHMD display can also automatically turn on when the field of view reaches within a certain centimeter range of one or more of an anatomic landmark, an optical marker, a navigation marker including infrared markers, retroreflective markers, RF markers, an LED or a calibration phantom or reference phantom or IMU, e.g. within 15 cm, 10 cm, 5 cm etc. The OHMD display can also automatically turn on when the field of view reaches within a certain centimeter range of one or more of a marker of an area of intended activity and/or a surgical field, e.g. a pin or a screw, e.g. within 15 cm, 10 cm, 5 cm etc.

The OHMD display can optionally also automatically turn off when the intended area of activity or the surgical field or area decreases below a certain threshold percentage (optionally set by the user) of the field of view, e.g. 90%, 80%, 70%, 60%, 50%, 40%, 30%, 20%, 10%, etc. In some embodiments, the OHMD display can automatically turn off when the user, operator and/or surgeon starts looking away from the intended area of activity and/or the surgical field when an anatomic landmark, an optical marker, a navigation marker including infrared markers, retroreflective markers, RF markers, an LED or a calibration phantom or reference phantom (e.g. as seen through an image and/or video capture system and/or 3D scanner integrated into, attached to or separate from the OHMD) is located outside the outer one third, central one third or inner one third or the inner half or other landmark or demarcation/separation of the field of view.

Alternatively, the OHMD display can also automatically turn off when the field of view reaches outside a certain centimeter range of one or more of an anatomic landmark, an optical marker, a navigation marker including infrared markers, retroreflective markers, RF markers, an LED or a calibration phantom or reference phantom or IMU, e.g. outside 5 cm, 10 cm, 15 cm or more. The OHMD display can also automatically turn off when the field of view reaches outside a certain centimeter range of one or more of a marker of an area of intended activity and/or a surgical field, e.g. a pin or a screw, e.g. within 5 cm, 10 cm, 15 cm or more.

In some embodiments, the OHMD display can automatically turn on when a select surgical instrument, e.g. an awl or a pin driver or a reamer or a saw, or a select medical device component, or multiple thereof (either simultaneously or sequentially) appear in the field of view. Optionally, the OHMD display can automatically turn off when a select surgical instrument, e.g. an awl or a pin driver or a reamer or a saw, or a select medical device component, or multiple thereof (either simultaneously or sequentially) disappear from the field of view. The appearing or disappearing of the one or more surgical instruments or medical device components can be caused by the user/surgeon moving the head away from the intended area of activity and/or the surgical field; it can also be caused by the user/surgeon moving the surgical instrument and/or medical device component outside the field of view or away from the area of intended activity and/or surgical field while continuing to look at the area of intended activity and/or the surgical field.

In some embodiments, the OHMD display can automatically turn off when the user/operator/surgeon looks at a display monitor other than the OHMD. Such a display monitor can be a video screen or a TV screen or a computer monitor, or a PACS monitor or other display monitor, e.g. located in an operating room or in a factory. In some embodiments, the monitor can be recognized, e.g. based on its square or rectangular outline/shape using image capture combined with standard image processing techniques. In some embodiments, a video screen or a TV screen or a computer monitor, or a PACS monitor or other display monitor can be identified for example with optical markers, navigation markers including infrared markers, retroreflective markers, RF markers, LED's and other markers placed on, surrounding or nearby the monitor.

Optionally, the OHMD can automatically turn back on when the user/operator/surgeon looks away from the monitor. The turning on and turning off of the OHMD display can be triggered, for example, when the monitor occupies 25%, 50% or 75% or more of the field of view. The turning on and turning off of the OHMD display can be triggered, for example, when the field of view, e.g. through the OHMD display, reaches the central area of the point of the monitor, or within 5 cm, 10 cm, 15 cm or more of the central area or point of the monitor, or within a certain distance or area from an optical marker, navigation marker including infrared markers, retroreflective markers, RF markers, LED and/or other markers placed on, surrounding or nearby the monitor.

In select embodiments, it can be preferable that the OHMD display turns on when the user looks at the monitor and it turns off when the user looks away from the monitor. It can then optionally turn back on when the user looks at the intended area of activity, e.g. a surgical field or area.

In some embodiments, when flicker or the feeling of experiencing flicker with the OHMD display is a concern for a user, the OHMD can turn on an off on an intermittent basis, e.g. it can display the virtual data for 1, 2, 3, 4 or more seconds and then turn off for a break, e.g. 1, 2, 3, 4 or more seconds. The periods of display on and display off can be defined by the user based on user preferences. The periods of display on and off can be combined with various triggers of automatic turning on and off of the OHMD display, as outlined, for example in the foregoing.

The foregoing embodiments and examples describing non-automated and automated or automatic techniques for turning on an OHMD display and turning off an OHMD display are only exemplary in nature and are in no way meant to be limiting. Someone skilled in the art can recognize many different triggers for turning on and off an OHMD display automatically. The automatic turning on and off of an OHMD display can also be a useful feature for preserving battery life, e.g. disposable or rechargeable.

Managing Display, Hardware, Software or Bandwidth Limitations

In some embodiments, the display of the OHMD unit can display a subset of the data and/or images representing a smaller portion of the field of view visible through the OHMD or displayable by the display of the OHMD unit, using, for example, only a portion of the available display. If data from a pre-operative or intra-operative imaging study, e.g. x-rays, a CT scan, an MRI scan, are displayed, the data or images displayed by the OHMD can also be targeted to a volume smaller than the original scan volume or area covered by the imaging study in order to decrease the amount of data displayed. In addition, the data or images displayed by the OHMD can also be targeted to a volume or area smaller than the volume or area to be operated or smaller than the volume or area of the surgical site. This embodiment can, for example, be useful, when the software environment limits the amount of surface points or nodes displayed or limits the size or amount of the data displayed by the OHMD. This embodiment can also be useful when a WIFI or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD.

This smaller portion of the field of view visible through the OHMD or displayable by the display of the OHMD unit, smaller, targeted volume from an imaging study, or the volume or area smaller that the volume or area of the surgical site can be targeted to portions of the surgical site or to anatomic landmarks. For example, in a knee replacement, this smaller portion of the field of view can be targeted to the distal femur or portions of the distal femur while the surgeon is contemplating surgical steps on the femur, e.g. a distal femoral cut or an anterior or posterior cut or chamfer cuts; it can be targeted to the proximal tibia or portions thereof while the surgeon is contemplating surgical steps on the tibia, e.g. a proximal tibial cut or a tibial keel preparation and punch; it can be targeted to the patella, while the surgeon is contemplating surgical steps on the patella, e.g. a milling or cutting of the patella. In a hip replacement, the smaller portion of the field of view can be targeted to the proximal femur or portions thereof, while the surgeon is contemplating steps on the proximal femur, e.g. a femoral neck cut; it can be targeted to the acetabulum, while the surgeon is contemplating surgical steps on the acetabulum, e.g. an acetabular reaming or an impaction of an acetabular cup; it can be re-focused or re-targeted on the proximal femur when the surgeon contemplates femoral broaching or reaming, optionally followed by femoral component impaction. In a pedicle screw placement or a vertebroplasty or kyphoplasty, the smaller portion of the field of view can be targeted to the level and/or the side where the surgeon contemplates the next surgical step, e.g. an insertion of an awl, a pedicle screw, a needle, a vertebra- or kyphoplasty needle.

A targeted area or smaller portion of the field of view visible through the OHMD or displayable by the display of the OHMD, a smaller, targeted volume from an imaging study, or a volume or area smaller that the volume or area of the surgical site can also be defined with use of one or more anatomic landmarks, e.g. in a hip a most inferior point, e.g. sulcus point, between the greater trochanter and the femoral neck, a most superior point on the greater trochanter, a most superior point on a lesser trochanter, an acetabular rim or portions thereof, an acetabular center, or in a knee, a most medial point on a medial condyle, a most lateral point on a lateral condyle, a center of a trochlear notch, a tibial spine, a most anterior point of a tibia, a central point of a patella. One or more of the same landmarks that have been/are being used for registration of virtual data and live data of the patient can be used for defining or identifying a target area or a smaller portion of the field of view visible through the OHMD or displayable by the display of the OHMD. The landmarks can be identified using, for example, an image and/or video capture system and/or 3D scanner integrated into, attached to or separate from an OHMD. The landmarks can be identified by attaching optionally one or more optical markers, navigation markers including infrared markers, retroreflective markers, RF markers, surgical navigation, LED's, reference phantoms, calibration phantoms, or marks. A target area can be enclosed by landmarks, e.g. by three or more landmarks. A target area can extend beyond one or more landmarks, e.g. by 2, 4, 5, 6, 8, 10 cm or more or any other distance or radius, e.g. selected by the surgeon or operator.

By limiting the display to such a smaller portion of the field of view visible through the OHMD or displayable by the display of the OHMD or target area, a smaller, targeted volume from an imaging study, or a volume or area smaller that the volume or area of the surgical site the amount of data displayed can be reduced. In addition, the amount of data transmitted, e.g. using a WIFI, Bluetooth or LiF network can also be reduced.

Viewing 2D Computer Monitors Through an OHMD Unit

In some embodiments, the OHMD system can detect, e.g. automatically, if the surgeon or operator is looking at a computer or display monitor separate from the OHMD, for example, with use of an image and/or video capture system and/or 3D scanner integrated into, attached to or separate from the OHMD. The standalone or separate computer or display monitor can be used, for example, to display image data, e.g. of a patient, or to concurrently display virtual data displayed by the OHMD. The image and/or video capture system and/or 3D scanner can, for example, capture the outline of the computer or display monitor, e.g. round, square or rectangular, and the software can, optionally, automatically match, superimpose or align the items or structures displayed by the OHMD with the items or structures displayed by the standalone or separate computer or display monitor. Alternatively, the user, operator and/or surgeon can execute a command, e.g. a voice command or a command using a virtual finger/keyboard interface, indicating that he or she is looking at the standalone or separate computer or display monitor and the software can then match, superimpose or align the items or structures displayed by the OHMD with the items or structures displayed by the standalone or separate computer or display monitor. The OHMD system can match, superimpose, or align all of the structures displayed by the standalone or separate computer monitor. The OHMD system can match, superimpose or align a portion of the structures displayed by the standalone or separate computer monitor.

The OHMD can display the structures displayed by the standalone or separate computer monitor using the same color. The OHMD can display the structures displayed by the standalone or separate computer monitor using different colors. The OHMD can display structures not displayed by the standalone or separate computer monitor using a different color or greyscale or contrast than that used by the standalone or separate computer monitor.

The OHMD can display the structures displayed by the standalone or separate computer monitor using the same greyscale and/or contrast used by the standalone or separate computer monitor. The OHMD can display the structures displayed by the standalone or separate computer monitor using a different greyscale and/or contrast used by the standalone or separate computer monitor.

The OHMD can display the structures displayed by the standalone or separate computer monitor using the same image intensity used by the standalone or separate computer monitor. The OHMD can display the structures displayed by the standalone or separate computer monitor using a different image intensity used by the standalone or separate computer monitor, e.g. brighter or less bright.

In some embodiments, a standalone or separate computer or display monitor located in a user area, e.g. an operating room or a surgical suite, can be used as a calibration or reference or registration phantom for the OHMD unit including the frame and display position, orientation and/or alignment and/or direction of movement. The monitor can have a round, rectangular or square shape of known dimensions. An image and/or video capture system and/or 3D scanner integrated into, attached to or separate from the OHMD can be used to capture one or more images of the monitor. Since the dimensions of the monitor are known, the size, shape or dimensions, for example along its edges, or the area of the monitor on the captured image(s) can be used to determine the distance of the OHMD to the monitor; the shape of the circle, oval, rectangle or square can be used to determine the angle of the OHMD relative to the monitor. If the image and/or video capture system and/or 3D scanner integrated into or attached to the OHMD uses two or more cameras, the difference in shape of the circle, oval, rectangle or square detected between a first, second and any additional cameras can be used to increase the accuracy of any estimates of the angular orientation of the OHMD to the display monitor, e.g. by calibrating the measurement of a first camera against a second camera against a third camera and so forth. If two or more cameras are used integrated into or attached to different portions of the OHMD frame, e.g. the left side of the frame and the right side of the frame, the difference in projection of the monitor circle, oval, rectangle or square between the two cameras can also be used to estimate the user's head position and/or orientation and/or alignment and/or the position and/or orientation and/or alignment of the OHMD frame in relationship to the user's head and/or face.

In some embodiments, the user and/or surgeon can optionally look at the display monitor through the OHMD while maintaining his or her head in a neutral position, e.g. with no neck abduction, adduction, flexion, extension or rotation. This head position can be used to calibrate the position of the OHMD display in relationship to the target area and/or the patient and/or the surgical site, e.g. during an initial registration or a subsequent registration. This head position can also be used to calibrate the position of the OHMD unit/frame in relationship to the user's and/or the surgeon's head and face. Optionally, the user and/or surgeon can place his or her head on a chin stand or head holder for purposes of this calibration or registration. This process of using an external computer or display monitor as a reference for calibration and/or registration purposes can be performed at the beginning of an activity and/or a surgical procedure, e.g. as part of an initial registration process. This process of using an external display monitor as a reference for calibration and/or registration purposes can also be performed during an activity or after an activity and/or surgical procedure, for example when there is concern that the OHMD unit may have moved relative to the user's and/or surgeon's face.

In some embodiments, the position, location, orientation, and/or alignment of the outline of the standalone or separate computer or display monitor can be monitored, for example using an image and/or video capture system and/or 3D scanner integrated into, attached to or separate from the OHMD. Optionally, the position, location, orientation and/or alignment of the outline of the standalone or separate computer or display monitor can be monitored using attached optical markers, navigation markers including infrared markers, retroreflective markers, RF markers, LED's and/or IMU's as well as any other techniques described in the specification or known in the art for determining and/or tracking the position, location, orientation and/or alignment of an object. With the position, location, orientation and/or alignment of the standalone or external computer or display monitor known, the position, location, orientation, alignment and/or direction of movement of the OHMD unit can be tracked in relationship to it, e.g. via an image and/or video capture system and/or 3D scanner integrated into or attached to the OHMD or optical markers, navigation markers including infrared markers, retroreflective markers, RF markers, LED's and/or IMU's integrated into it or attached to it. As the position, location, orientation, alignment and/or direction of movement of the OHMD unit can be tracked, the display of the OHMD unit can at all times or, if preferred, intermittently, display the same structures, or at least a portion or subset thereof, displayed by the standalone or separate computer or display monitor, spatially matched. If the standalone or separate computer or display monitor occupies only a portion of the visual field covered by the OHMD display, the OHMD display can match the displayed structures with the structures displayed by the standalone or separate computer or display monitor only for the portion of the visual field occupied by the standalone or separate computer or display monitor. Optionally, the OHMD display can display structures extending beyond the portion of the visual field occupied by the standalone or separate computer or display monitor. The structures extending beyond the portion of the visual field occupied by the standalone or separate computer or display monitor can be continuous with the structures displayed by the standalone or separate computer or display monitor. The structures outside the portion of the visual field occupied by the standalone or separate computer or display monitor can be separate and/or from the structures displayed by the standalone or separate computer or display monitor. For example, in addition to displaying one or more structures matching or corresponding to what is displayed by the standalone or separate computer or display monitor, the OHMD display can display items such as vital signs or patient demographics, or pre-operative imaging studies in those portions of the visual field that do not include the standalone or separate computer or display monitor. This can be useful when the user, operator and/or surgeon is not looking at the patient.

In some embodiments, the OHMD can display surgical field related information, e.g. details or aspects of a virtual surgical plan, e.g. intended/projected cut planes, or anatomic information of the patient, e.g. from a pre-operative imaging study, when the user or surgeon is looking at the surgical field; the OHMD can display portions of information or all of the information displayed by a standalone or separate computer or display monitor, for example in 3D while the standalone or separate computer or display monitor display can be in 2D, when the user or surgeon is looking at the standalone or separate computer or display monitor; the OHMD can display non-surgical field related information and non-standalone or separate computer or display monitor related or displayed information when the user or surgeon is neither looking at the surgical field nor at the standalone or separate computer or display monitor or when the surgical field and/or the standalone or separate computer or display monitor occupy only a portion of the visual field covered by the OHMD display. The switching or toggling between surgical field related information, standalone or separate computer or display monitor information and other information by the OHMD display can be automatic, for example via image capture and related image processing and recognition which area the user or surgeon is currently looking at, e.g. optionally demarcated by optical markers, navigation markers including infrared markers, retroreflective markers, RF markers, and/or LED's, or it can be via commands executed by the user or surgeon, e.g. voice commands or finger/keyboard commands, for example using a virtual keyboard displayed by the OHMD display.

The OHMD can display information related to the information displayed on the standalone or separate computer display or monitor in two dimensions or three dimensions, the latter stereoscopically or non-stereoscopically. Any number of combinations of displays can be applied between the display by the OHMD display and the display by the standalone or separate computer or monitor display. For example, when the computer or monitor displays shows a pre-operative or intra-operative imaging study of the patient, these can be displayed in 2D (e.g. cross-sectional) or 3D using pseudo-3D display techniques, for example with surface reconstruction and shading. Overlaying or superimposing, for example, a true 3D, e.g. stereoscopic 3D, view of the anatomy from the pre- or intra-operative imaging study and/or virtual surgical plan of the patient using the OHMD display onto the same anatomic structures and/or virtual surgical plan displayed in 2D or pseudo 3D by the standalone or separate computer or display monitor can be beneficial for the surgeon as he or she executes surgical plans or plans next surgical plans during a procedure.

In some embodiments, the display of the OHMD unit or the standalone or separate computer or display monitor can display functional and/or time studies of the patient, e.g. the surgeon moving a leg or an arm of the patient using real-time fluoroscopic imaging, while the other of the two display modalities can simultaneously display and/or superimpose static images. For example, the standalone or separate computer or display monitor can display 2D or 3D function and/or time studies, e.g. of knee motion captured using real-time 2D single or biplane fluoroscopy or captured using 3D CT fluoroscopy, while the display of the OHMD unit can superimpose 2D or 3D non-stereoscopic or 3D stereoscopic images of the corresponding anatomy.

The following is an exemplary list of select possible combinations of 2D, 3D non-stereoscopic and stereoscopic displays by the OHMD and 2D and pseudo 3D displays of the standalone or separate computer or display monitor. The list in Table 8 is in no way meant to be limiting.

TABLE 8

Examples of possible combinations of display modes or types by the display of the OHMD unit and the display of the standalone or separate compute or display monitor.

| OHMD Display 2D | OHMD 3D Non-stereoscopic | OHMD 3D Stereoscopic | 3D Non-Stereoscopic with Function/Time | 3D Stereoscopic with Function/Time | Standalone or Separate Computer or Display Monitor 2D | Standalone or Separate Computer or Display Monitor Pseudo 3D | Standalone or Separate Computer or Display Monitor 2D with Function/Time | Pseudo 3D with Function/Time |
|---|---|---|---|---|---|---|---|---|
| X | | | | | X | | | |
| X | | | | | | X | | |
| X | | | | | | | X | |
| X | | | | | | | | X |
| | X | | | | X | | | |
| | X | | | | | X | | |
| | X | | | | | | X | |
| | X | | | | | | | X |
| | | X | | | X | | | |
| | | X | | | | X | | |
| | | X | | | | | X | |
| | | X | | | | | | X |
| | | | X | | X | | | |
| | | | X | | | X | | |
| | | | X | | | | X | |
| | | | X | | | | | X |

X denotes type of display mode used

The OHMD display can optionally display some virtual data, e.g. pre-operative images and/or image reconstructions, of the patient in 2D, while it can display other virtual data, e.g. aspects or components of the virtual plan, e.g. intended cut planes, in 3D. Similarly, the OHMD display can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

The standalone or separate computer or display monitor can optionally display some virtual data, e.g. pre-operative images and/or image reconstructions, of the patient in 2D, while it can display other virtual data, e.g. aspects or components of the virtual plan, e.g. intended cut planes, in pseudo 3D, e.g. with perspective views and shading. Similarly, the standalone or separate computer or display monitor can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

Aspects or components of the virtual surgical plan can, for example, include one or more of the following: a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

In an additional embodiment, the OHMD display can optionally display some of the aspects or components of the virtual surgical plan in 2D and other aspects and components in 3D, stereoscopic or non-stereoscopic. For example, the OHMD display can display an intended cut plane in 3D stereoscopic or non-stereoscopic, while it can display a virtual cut block as an outline in 2D, for example projected with a stereoscopic 3D view of the underlying tissue to be cut, e.g. a femoral neck for a hip replacement. The OHMD display can display a virtual surgical instrument, e.g. a reamer in 3D, e.g. stereoscopic or non-stereoscopic, and it can project the intended reaming axis in 2D or in 3D.

The standalone or separate computer or display monitor can optionally co-display some of the aspects or components of the virtual surgical plan in 2D and other aspects and components in pseudo 3D, optionally with different colors. For example, the standalone or separate computer or display monitor can display an intended cut plane in pseudo 3D, while it can display a virtual cut block as an outline in 2D, for example projected on a pseudo 3D view of the underlying tissue to be cut, e.g. a distal femur for a knee replacement. The standalone or separate computer or display monitor can display a virtual implant or trial implant in pseudo 3D, and it can project its intended central axis, e.g. a femoral shaft axis for a femoral component of a hip replacement, in 2D.

The different 2D and 3D displays by the OHMD display and the standalone or separate computer or display monitor can be displayed and viewed simultaneously, in many embodiments substantially or partially superimposed. Since the user or surgeon can view the standalone or separate computer or display monitor through the OHMD display, the user or surgeon can experience a combination of 2D and 3D display information, e.g. of virtual anatomy of the patient and/or aspects of the virtual surgical plan, not previously achievable.

TABLE 9

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| OHMD Display | Standalone or Separate Computer or Display Monitor ||||||||||||||||||||
|---|---|---|---|---|---|---|---|---|---|---|---|---|---|---|---|---|---|---|---|---|
| | Virtual Anatomic Data of the Patient |||| Components of Virtual Surgical Plan of the Patients |||| Virtual Surgical Instruments |||| Virtual Implant or Trial Implant Components |||| Intra-Operative Imaging of the Patient ||||
| | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time |
| Virtual Anatomic Data of the Patient | | | | | | | | | | | | | | | | | | | | |
| 2D | | | | | X | X | X | X | X | X | X | X | X | X | X | X | X | X | X | X |
| 3D Non-Stereoscopic | | | | | X | X | X | X | X | X | X | X | X | X | X | X | X | X | X | X |
| 3D Stereoscopic | | | | | X | X | X | X | X | X | X | X | X | X | X | X | X | X | X | X |
| 3D Non-Stereoscopic with Function/Time | | | | | X | X | X | X | X | X | X | X | X | X | X | X | X | X | X | X |
| 3D Stereoscopic with Function/Time | | | | | X | | | | X | | | | X | | | | X | | | |
| Components of Virtual Surgical Plan of the Patient | | | | | | | | | | | | | | | | | | | | |
| 2D | X | X | X | X | | | | | X | X | X | X | X | X | X | X | X | X | X | X |
| 3D Non-Stereoscopic | X | X | X | X | | | | | X | X | X | X | X | X | X | X | X | X | X | X |
| 3D Stereoscopic | X | X | X | X | | | | | X | X | X | X | X | X | X | X | X | X | X | X |
| 3D Non-Stereoscopic with Function/Time | X | X | X | X | | | | | X | X | X | X | X | X | X | X | X | X | X | X |
| 3D Stereoscopic with Function/Time | X | | | | | | | | X | | | | X | | | | X | | | |
| Virtual Surgical Instruments | | | | | | | | | | | | | | | | | | | | |
| 2D | X | X | X | X | X | X | X | X | | | | | X | X | X | X | X | X | X | X |
| 3D Non-Stereoscopic | X | X | X | X | X | X | X | X | | | | | X | X | X | X | X | X | X | X |
| 3D Stereoscopic | X | X | X | X | X | X | X | X | | | | | X | X | X | X | X | X | X | X |
| 3D Non-Stereoscopic with Function/Time | X | X | X | X | X | X | X | X | | | | | X | X | X | X | X | X | X | X |
| 3D Stereoscopic with Function/Time | X | | | | X | | | | | | | | X | | | | X | | | |

TABLE 9-continued

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| | Standalone or Separate Computer or Display Monitor | | | | | | | | | | | | | | | | | | | |
|---|---|---|---|---|---|---|---|---|---|---|---|---|---|---|---|---|---|---|---|---|
| | Virtual Anatomic Data of the Patient | | | | Components of Virtual Surgical Plan of the Patients | | | | Virtual Surgical Instruments | | | | Virtual Implant or Trial Implant Components | | | | Intra-Operative Imaging of the Patient | | | |
| OHMD Display | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time | 2D | Pseudo 3D | 2D with Function/Time | Pseudo 3D with Function/Time |
| Virtual Implant or Tried Implant Components | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | | X | | X | | X | | X | | X | | X | | X | | X | | X | |
| Intra-Operative Imaging of the Patient | | | | | | | | | | | | | | | | | | | | |
| 2D | X | X | X | X | X | X | X | X | X | X | X | X | X | X | X | X | X | X | X | X |
| 3D Non-Stereoscopic | X | X | X | X | X | X | X | X | X | X | X | X | X | X | X | X | X | X | X | X |
| 3D Stereoscopic | X | X | X | X | X | X | X | X | X | X | X | X | X | X | X | X | X | X | X | X |
| 3D Non-Stereoscopic with Function/Time | X | X | X | X | X | X | X | X | X | X | X | X | X | X | X | X | X | X | X | X |
| 3D Stereoscopic with Function/Time | X | | X | | X | | X | | X | | X | | X | | X | | X | | X | |

X denotes type of display mode combinations used or possible

Virtual data of the patient including anatomy, e.g. pre-operative imaging, and/or aspects and/or components of a virtual surgical plan, and/or virtual surgical instruments and/or virtual implants or implant components and/or intra-operative imaging of the patient can be displayed using different colors, greyscale values and image intensities by the display of the OHMD unit and the display of the standalone or separate computer or display monitor.

Intra-operative imaging of the patient can include, for example, x-ray imaging, laser scanning, 3D scanning or mechanical probe scanning of a joint, e.g. hip joint, knee joint, shoulder joint, or a spine. Intra-operative X-ray images, laser scans, 3D scans, mechanical probe scans, pre-operative imaging data of the patient including 2D and 3D reconstructions, aspects or components of a virtual surgical plan, virtual surgical instruments, and/or virtual implants and implant components can be displayed simultaneously and, optionally, superimposed by the display of the OHMD unit and the display of the standalone or separate computer or display monitor. If two or more imaging modalities or pre-operative and intra-operative imaging studies are co-displayed, they can optionally be anatomically matched and they can optionally be displayed using the same projection plane or, optionally, different projection planes.

If 2D views are co-displayed with 3D views or pseudo 3D views by the OHMD display alone, by the standalone or separate computer or display monitor alone, or the two together and partially or completely superimposed, the 2D views can optionally be displayed using certain standard projections, e.g. AP, lateral, oblique; the standard projection, e.g. AP, lateral and oblique, can optionally be referenced to the live data of the patient, e.g. the corresponding planes with the patient positioned on the OR table, or to the data of the patient displayed on the standalone or separate computer or display monitor. Standard projections or standard views can also include view angles from the patient's side, front, top, bottom, or oblique views.

Dynamic views or functional views, for example with two or three spatial dimensions and a time dimension can be displayed by the display of the OHMD unit and/or the display of the standalone or separate computer or display monitor, optionally superimposed onto or co-displayed with static images, e.g. 2D or 3D, by the second display unit, e.g. the display of the OHMD unit or the display of the standalone or separate computer or display monitor. Such dynamic views or functional views can include kinematic studies of a joint, e.g. obtained with an intraoperative laser or 3D scanner, which can be used by a surgeon to obtain scans of the knee, hip, shoulder an any other joint at different flexion angles, extensions angles, rotation angles, abduction angles, adduction angles, e.g. 0, 10, 15, 20, 30, 40, 45, 50, 60, 70, 80, 90, 100, 110, 120, 130, 140, 150 degrees etc. Any other type of dynamic scan, which can include a time element or time dimension or a functional element or functional dimension can be displayed by the display of the OHMD unit and/or the display of the standalone or separate computer or display monitor.

In some embodiments, the display of the OHMD unit can be used for displaying lower resolution data and/or images, while the display of the display of the standalone or separate computer or display monitor can be used for displaying corresponding or matching or overlapping higher resolution data and/or images. This embodiment can be particularly useful when, for example, the maximum available display resolution of the OHMD is lower than desirable for a particular application or surgical procedure. This embodiment can also be useful, when the software environment limits, for example, the amount of surface points or nodes displayed or limits the available resolution. This embodiment can also be useful when a WIFI or Bluetooth or other wireless connection is used with the OHMD with limitations in bandwidth and/or data transmission, thereby limiting the amount of data being transmitted to the OHMD and, ultimately, displayed, in particular when this limitation implies a limitation in available spatial resolution for the display of the data and/or images by the OHMD. By viewing the lower resolution data and/or images through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the higher resolution data and/or images on the display of the standalone or separate computer or display monitor the viewer can have the concurrent benefit of viewing the data and/or images in high resolution.

In some embodiments, the display of the OHMD unit can be used for displaying static data and/or images, while the display of the standalone or separate computer or display monitor can be used for displaying corresponding or matching or overlapping dynamic data and/or images, e.g. images demonstrating a function, e.g. kinematic movement of a joint, and/or a time element or dimension including a change in condition or function monitored over a time period. This embodiment can be particularly useful when, for example, the refresh rate of the OHMD display is lower than desirable for a particular application or surgical procedure. This embodiment can also be useful, when the software environment limits, for example, the amount of data and/or images displayed. This embodiment can also be useful when a WIFI or Bluetooth or other wireless connection is used for connecting the OHMD with limitations in bandwidth and/or data transmission, thereby limiting the amount of data being transmitted to the OHMD and, ultimately, displayed, in particular when this limitation implies a limitation in available temporal and/or spatial resolution for the display of the data and/or images by the OHMD. By viewing the static data and/or images through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the dynamic data and/or images on the display of the standalone or separate computer or display monitor the viewer can have the concurrent benefit of viewing the dynamic data and/or images, optionally in high resolution.

In some embodiments, the display of the OHMD unit can be used for displaying a subset of the data and/or images representing a smaller portion of the field of view displayed by the standalone or separate computer or display monitor, while the display of the display of the standalone or separate computer or display monitor can be used for displaying corresponding or matching or overlapping higher data and/or images using the full intended field of view of patient data. This embodiment can, for example, be useful, when the software environment limits the amount of surface points or nodes displayed or limits the size of the data displayed by the OHMD. This embodiment can also be useful when a WIFI or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD. By viewing data and/or images with a smaller, more narrow field of view through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the data and/or images with the full field of view on the display of the standalone or separate computer or display monitor the viewer can have the concurrent benefit of viewing the data and/or images using the full intended field of view of patient data. When 3D views are superimposed onto or co-displayed with 2D views by the display of the OHMD unit and the display of the standalone or separate computer or display monitor or when multiple 2D views are superimposed or co-displayed by the display of the OHMD unit and the display of the standalone or separate computer or display monitor, they can be anatomically matched, for example using corresponding landmarks and/or using common coordinates. They can also have different view angles, e.g. a view angle as the patient is positioned on the OR table, a view angle from the side, front, top, bottom, or oblique views. Thus, the OHMD display can, for example, show a stereoscopic 3D view of the patient's virtual anatomy, e.g. from a pre-operative imaging study, while the standalone or separate computer or display monitor can show a matching AP or lateral intra-operative radiographic view or a matching pseudo 3D laser view of the patient.

The matching of data displayed by the display of the OHMD unit and the display of the standalone or separate computer or display monitor can be achieved in different ways, e.g. using matching of data and/or image using coordinates; matching of data and/or image using content or combinations of matching of data and/or image coordinates and data and/or image content.

In some embodiments, data and/or images displayed by the OHMD and data and/or images displayed by the standalone or separate computer or display monitor can be matched using known image coordinates and can then optionally be partially or completely superimposed, e.g. as the user and/or surgeon moves his or her head and/or body while looking at the standalone or separate computer or display monitor. For example, if the OHMD is registered in space, e.g. with regard to the patient and/or the surgical site and/or the standalone computer or display monitor and/or the image data displayed on the standalone computer or display monitor, data and/or images displayed by the OHMD and/or displayed by the standalone computer or display monitor can be in the same or a common coordinate system, which can allow the matching or superimposition of the display by the OHMD with the display by the standalone or separate computer or display monitor, when portions or all of the separate computer or display monitor are included in the field of view of the user or surgeon through the OHMD.

In some embodiments, when both the display of the OHMD and the display of the separate computer or display monitor are registered in the same coordinate system, which can include that the image data displayed by the one or more OHMDs and the image data displayed by the separate computer or display monitor are registered in the same coordinate system, the OHMD can display then a set of data and/or images at least partially matching the coordinates and/or anatomic features, e.g. in 2D or 3D, of the data and/or images of the separate computer or display monitor. For example, the OHMD can display stereoscopic 3D views that share common coordinates and/or anatomic features, e.g. in 2D or 3D, with a pseudo 3D visualization displayed by the standalone or separate computer or display monitor. Such common coordinates can, for example, be corner points or edges or select geometric features and/or locations which can be superimposed then in the resultant composite OHMD/standalone monitor view that the user or surgeon sees. The OHMD can also, for example, display a stereoscopic 3D view of live data of the patient or virtual data of the patient or both, while the standalone or separate computer or display monitor displays a 2D view, e.g. a pre-operative imaging study, of the patient. The 2D plane or view display by the standalone or separate computer or display monitor can have the same or common coordinates and/or anatomic features, e.g. in 2D or 3D, with the corresponding 2D plane embedded in or contained in the 3D data and/or images displayed by the OHMD which can be matched or superimposed then in the resultant composite OHMD/standalone monitor view that the user or surgeon sees. Alternatively, in a similar example, if the OHMD provides only a surface display, for example, the periphery or outline or select peripheral points of the 2D plane displayed by the standalone or separate computer or display monitor can have the same or common coordinates and/or anatomic features, e.g. in 2D or 3D, with corresponding surface points and/or anatomic features, e.g. in 2D or 3D, in the location corresponding to the 2D plane in the 3D data and/or images displayed by the OHMD.

The data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching. In some embodiments, the surgical table can be moved. The movement of the surgical table can translate into a comparable movement of the patient and/or the surgical site in x, y, and/or z direction. When the magnitude and direction of the table movement is known, it can be used to move the common coordinate system by a corresponding amount or direction for matching or superimposing the data and/or images displayed by the OHMD and the data and/or images displayed by the standalone or separate display monitor. For example, if the OHMD displays live data of the patient, e.g. captured through an image and/or video capture system and/or 3D scanner integrated into, attached to or separate from the OHMD, and/or virtual data of the patient and/or virtual data of the patient superimposed onto live data of the patient and the standalone or separate computer or display monitor displays a pre-operative imaging study of the patient, the surgical table and the patient can be moved and the display of the live or virtual data by the OHMD can be moved by a corresponding amount, thereby maintaining registration including registration to the data displayed on the standalone or separate computer or display monitor.

In some embodiments, the data and/or images displayed by the OHMD and the data and/or images displayed by the standalone or separate computer or display monitor can be cross-registered and, for example, moved into a shared or common coordinate system with use of an image and/or video capture system and/or 3D scanner integrated into, attached to, or separate from the OHMD, capturing the data displayed by the standalone or separate computer or display monitor. For example, the standalone or separate computer or display monitor can display data from a real-time intra-operative imaging study of the patient, including, for example, imaging during movement of the patient or surgical table or both. Standard image processing techniques can, for example, recognize anatomic landmarks or features on the data or images displayed on the standalone or separate computer or display monitor and match these with the corresponding anatomic landmarks or features in the data and/or images available for display by the OHMD. The OHMD can then display the corresponding data and/or images, optionally superimposing the data based on landmark matching. The landmark matching can, for example, occur by moving and/or translating the data or images available for display by the OHMD by an amount that will superimpose or match in a common coordinate system corresponding anatomic landmarks and/or features.

In embodiments, the process can be applied with use of an image capture or video capture system or a 3D scanner capturing the information from the standalone or separate computer monitor or display, by comparing, registering, matching, moving, aligning and/or superimposing images acquired with the intra-operative imaging system, e.g. displayed by the standalone or separate computer monitor or display, with data and/or images obtained in a pre-operative imaging study, e.g. displayed by the OHMD. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images acquired with the intra-operative imaging system, e.g. displayed by the standalone or separate computer monitor or display, with data and/or images obtained in a pre-operative imaging study, e.g. displayed by the OHMD.

In embodiments, the process can be applied with use of an image capture or video capture system or a 3D scanner capturing the information from the standalone or separate computer monitor or display, by comparing, registering, matching, moving, aligning and/or superimposing images obtained in a pre-operative imaging study, e.g. displayed by the OHMD, with data and/or images acquired with an intra-operative imaging system, e.g. displayed by the standalone or separate computer monitor or display. In embodiments, the process can be applied directly, i.e. without use of an image capture or video capture system or a 3D scanner, using, for example, a computer workstation, optionally connected to the standalone or separate computer monitor or display, by comparing, registering, matching, moving, aligning and/or superimposing images obtained in a pre-operative imaging study, e.g. displayed by the OHMD, with data and/or images acquired with an intra-operative imaging system, e.g. displayed by the standalone or separate computer monitor or display.

Image processing techniques can, for example, recognize anatomic landmarks or features on the data or images acquired by the real-time imaging system and match these with the corresponding anatomic landmarks or features in the data and/or images available for display by the OHMD. The OHMD can then display the corresponding data and/or images, optionally superimposing the data based on landmark matching. The landmark matching can, for example, occur by moving and/or translating the data or images available for display by the OHMD by an amount that will superimpose or match in a common coordinate system corresponding anatomic landmarks and/or features.

In the foregoing embodiments, the data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching.

Matching of images displayed by the OHMD and a standalone or separate computer or display monitor can also be performed by combining coordinate based matching, e.g. using the same coordinate system for both displays, and landmark based matching using any of the foregoing techniques. Someone skilled in the art will readily recognize other means of coordinate matching and landmark matching.

In some embodiments, the magnification of the items displayed by the OHMD can be adjusted so that it is reflective of, corresponds to, is smaller or larger than the magnification used by the standalone or separate computer or display monitor. Alternatively, the standalone or separate computer or display monitor can have one or more markers, e.g. one or more LED's, that an image and/or video capture system and/or 3D scanner, e.g. integrated into, attached to or separate from the OHMD, can detect which, in turn, can then trigger the adjustment of the magnification of the items displayed by the OHMD, e.g. based on the distance of the OHMD to the monitor. In some embodiments, an image and/or video capture system and/or 3D scanner integrated into, attached to or separate from the OHMD can visualize the size and shape (round, oval, ellipsoid, rectangular, square) of the standalone or separate computer or display monitor; using standard image processing techniques and geometry, the size and shape can then be used to derive the distance and angle of the OHMD relative to the standalone or separate computer or display monitor. If more than one camera is used, additional parallax information (difference in size and/or shape of the standalone or separate computer or display monitor) can be used to further estimate or improve the estimation of the distance or angle of the OHMD to the standalone or separate computer or display monitor. The resultant estimation of the distance and/or angle of the OHMD display to the standalone or separate computer or display monitor can then optionally be used to match the magnification of the data displayed by the standalone or separate computer or display monitor or to display at a higher or lower magnification than the data display by the standalone or separate computer or display monitor.

Similarly, the OHMD can detect, e.g. automatically, if the surgeon or operator is not looking at the standalone or separate computer or display monitor, for example, with use of an image and/or video capture system and/or 3D scanner integrated into, attached to or separate from the OHMD. The image and/or video capture system and/or 3D scanner can, for example, detect that the outline of the standalone or separate computer or display monitor (e.g. round, square, rectangular) is not present in the captured image data and the software can the automatically adjust the magnification of the items displayed by the OHMD so that it is reflective of or corresponds to the distance of the OHMD or the surgeon's eyes to the patient's surgical site, or is smaller or larger than that. Alternatively, a standalone or separate computer or display monitor can have one or more markers, e.g. one or more LED's or optical markers, that the image and/or video capture system and/or 3D scanner can detect; in this case, when the image captures system notices that the one or more LED's or optical markers are not included in the image capture data, the software can then automatically adjust the magnification of the items displayed by the OHMD so that it is reflective of or corresponds to the distance of the OHMD or the surgeon's eyes to the patient's surgical site, or is smaller or larger than that. Similarly, markers or LED's placed on the patient's surgical site can be detected by the OHMD including an image and/or video capture system and/or 3D scanner integrated into, attached to or separate from the OHMD thereby triggering an adjustment in magnification so that it is reflective of, corresponds to the distance of the OHMD or the surgeon's eyes to the patient's surgical site, or is smaller or larger than that when the surgeon or operator is looking at the patient's surgical site.

In some embodiments, the OHMD can be used to display data and/or images instead of a standalone or separate computer or display monitor. Optionally, the OHMD can replace the standalone or separate computer or display monitor. In some embodiments, the OHMD can display the live data from the patient's surgical site and project them for the surgeon and superimpose them with virtual data. The OHMD can also display one or more aspects or components of the virtual surgical plan, e.g. projected paths for one or more surgical instruments, or it can display one or more virtual implants or implant components. In this embodiment, the OHMD can optionally match the magnification of the one or more projected paths, and/or one or more surgical instruments and/or one or more virtual implants or implant components relative to the magnification of the live data from the patient. The OHMD can also apply a larger or smaller magnification and/or size than the magnification of the live data from the patient for the one or more projected paths and/or virtual surgical instruments, and/or one or more virtual implants or implant components. The live data of the patient can be seen through the transparent display of the OHMD. Alternatively, the display can be partially or completely opaque and the live data can be capture through an image and/or video capture system and/or 3D scanner integrated into, attached to or separate from the OHMD and then subsequently be displayed by the OHMD display.

In some embodiments, for example when the OHMD is the primary display unit, the OHMD can be non-transparent to light or minimally transparent to light reflected from the patient's surgical field and can display, for example, live (electronic) images collected by the image and/or video capture system and/or 3D scanner and, optionally, it can display, in addition, aspects or components of the virtual surgical plan, e.g. one or more projected paths for one or more physical surgical instruments, probes, pointers, and/or one or more virtual instruments and/or one or more virtual implants or implant components (optionally with various chosen matching or non-matching magnifications). In this setting, the OHMD can also display electronic images of the physical surgical instruments and or devices and their respective movements, for example captured with an image and/or video capture system and/or 3D scanner integrated into, attached to, or separate from the OHMD (with various chosen matching or non-matching magnifications).

The OHMD can be permanently non-transparent to light or minimally transparent to light reflected from the patient's surgical field. Alternatively, the degree of transparency can be variable, for example with use of one or more optical filters, e.g. polarizing light filters, in front of or integrated into the OHMD or electronic, e.g. LCD, or optical filters in front or integrated into the OHMD, or via intensity adjustments. The OR theater can optionally use light sources, e.g. polarized or filtered light that will support modulation or aid with adjustments of the transparency of the OHMD to light reflected from the patient's surgical field.

Magnified Displays

Magnified displays of the following structures and/or devices can be shown with an OHMD for example for one or more of the following, simultaneously or non-simultaneously:

Physical anatomy (e.g. using intra-operative imaging with optional magnification or demagnification)

Static

Dynamic, e.g. with functional or time element or dimension

Virtual anatomy, e.g. from pre-operative or intra-operative imaging study [optionally displayed as a 3D reconstruction [optionally with stereoscopic display by the OHMD] and/or as 2D cross-section or image slices [optionally with stereoscopic display by the OHMD]]

Aspects or components of a virtual surgical plan, e.g. a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide [e.g. a virtual axis, virtual plane or virtual cut block], virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide [e.g. a virtual axis, virtual plane or virtual cut block], virtual trial implant, virtual implant component, implant or device Virtual surgical instrument(s)

Virtual implant(s) or implant component(s)

In some embodiments, the OHMD display can display live data of the patient captured through an image and/or video capture system and/or 3D scanner integrated into, attached to or separate from the OHMD with higher magnification than the live data seen through transparent portions of an OHMD by the user's or surgeon's eye. Thus, the live data of the patient captured through an image and/or video capture system and/or 3D scanner integrated into, attached to or separate from the OHMD can be displayed in a magnified manner for a given distance of the OHMD display to the surgical field. This has the benefit that select structures can be seen with greater detail, for example offering a low power microscopic, magnified view of portions or all of the surgical field. The distance of the OHMD to the surgical field can be determined using techniques described in the specification, e.g. optical markers, navigation markers including infrared markers, retroreflective markers, RF markers, IMU's, LED's and any other technique known in the art. The distance of the OHMD to a separate or standalone computer monitor or display can be considered in addition to the magnification of any images displayed using the standalone computer monitor or display in order to match the structures and the magnification of the structures displayed by the separate or standalone computer monitor with the OHMD display.

The magnified display of live data can be performed while partially or completely blending out live data seen through the OHMD, e.g. with the OHMD turned partially or completely opaque to light emitted from the surgical field and primarily or only data displayed captured through the image and/or video capture system and/or 3D scanner. The magnified display of live data captured through the image and/or video capture system and/or 3D scanner can be superimposed on live data seen through one or more partially or completely transparent portions of the OHMD. In this example, the magnified display of the live data can be a portion of the surgical field seen through the OHMD.

Optionally, a declining gradient of magnification can be applied to the live data so that the magnified live data can blend in seamlessly or near seamlessly with the non-magnified live data, e.g. the live data seen through one or more partially or completely transparent portions of the OHMD.

The magnification of a portion or all of the live data captured through an image and/or video capture system and/or 3D scanner can be at preset levels, e.g. 1.5×, 2.0×, 3.0×, 4.0×, or 5.0× or any other magnification level, e.g. a range from 0-1×, 0-5×, 0-10×, 0-20×. The magnification can be continuous, e.g. on a sliding scale. The magnification can be selected by the user and/or surgeon, for example using voice commands, eye commands or using a virtual keyboard interface displayed by the OHMD.

Virtual data [including, for example, any 2D or 3D imaging studies obtained pre- or intra-operatively] can optionally be displayed with the same magnification as the live data. Optionally, virtual data can be displayed with no magnification or lesser or greater magnification than live data.

In some embodiments, the OHMD display can display virtual data of the patient and, principally any virtual data, e.g. portions of a virtual surgical plan, a predetermined start point, a predetermined start position, a predetermined start orientation or alignment, a predetermined intermediate point(s), a predetermined intermediate position(s), a predetermined intermediate orientation or alignment, a predetermined end point, a predetermined end position, a predetermined end orientation or alignment, a predetermined path, a predetermined plane, a predetermined cut plane, a predetermined contour or outline or cross-section or surface features or shape or projection, a predetermined depth marker or depth gauge, a predetermined stop, a predetermined angle or orientation or rotation marker, a predetermined axis, e.g. rotation axis, flexion axis, extension axis, a predetermined axis of a virtual surgical tool, a virtual surgical instrument, a virtual surgical guide [e.g. a virtual axis, virtual plane or virtual cut block], a virtual trial implant, a virtual implant component, implant or device, non-visualized portions for one or more devices or implants or implant components or surgical instruments or surgical tools, and/or one or more of a predetermined tissue change or alteration, and/or one or more of a predetermined position and/or orientation of a virtual surgical tool, virtual surgical instrument, virtual surgical guide [e.g. a virtual axis, virtual plane or virtual cut block], a virtual trial implant, a virtual implant component, implant or device, with higher magnification than the live data seen through transparent portions of the OHMD by the user's or surgeon's eye. Thus, the virtual data of the patient can be displayed in a magnified manner for a given distance of the OHMD display to the surgical field. This has the benefit that select structures or aspects of components of a virtual surgical plan or virtual data can be seen with greater detail, for example offering a low power microscopic, magnified view of portions or all of the virtual data. The distance of the OHMD to the surgical field can be determined using techniques described in the specification, e.g. optical markers, navigation markers including infrared markers, retroreflective markers, RF markers, IMU's, LED's and any other technique known in the art.

The magnified display of virtual data can be performed while partially or completely blending out live data seen through the OHMD, e.g. with the OHMD turned partially or completely opaque to light emitted from the surgical field and primarily or only virtual data displayed. The magnified display of virtual data captured through the image and/or video capture system and/or 3D scanner can be superimposed on live data seen through one or more partially or completely transparent portions of the OHMD. In this example, the magnified display of the virtual data can be a portion of the surgical field seen through the OHMD.

Optionally, a declining gradient of magnification can be applied to the virtual data so that the magnified virtual data can blend in seamlessly or near seamlessly with the non-magnified live data, e.g. the live data seen through one or more partially or completely transparent portions of the OHMD. The magnification of a portion or all of the virtual data can be at preset levels, e.g. 1.5×, 2.0×, 3.0×, 4.0×, or 5.0× or any other magnification level, e.g. a range from 0-1×, 0-2×, 0-3×, 0-5×, 0-10×, 10-20×. The magnification can be continuous, e.g. on a sliding scale. The magnification can be selected by the user and/or surgeon, for example using voice commands, eye commands or using a virtual keyboard interface displayed by the OHMD.

Both portions or all of live data and virtual data can be displayed using magnification or no magnification. Non-limiting examples of possible magnification combinations between live data and virtual data are provided below.

TABLE 10

Exemplary, non-limiting combinations of magnifications of live data and/or virtual data.

| | Live data, e.g. as captured by image capture system and displayed by OHMD | | | | |
| --- | --- | --- | --- | --- | --- |
| | Original size | Portions magnified | All magnified | Portions minified | All minified |
| Virtual data | | | | | |
| Original size | X | X | X | X | X |
| Portions magnified | X | X | X | X | X |
| All magnified | X | X | X | X | X |

TABLE 10-continued

Exemplary, non-limiting combinations of magnifications of live data and/or virtual data.

Live data, e.g. as captured by image capture system and displayed by OHMD

| | Original size | Portions magnified | All magnified | Portions minified | All minified |
|---|---|---|---|---|---|
| Portions minified | X | X | X | X | X |
| All minified | X | X | X | X | X |

X denotes type of magnification mode combinations used or possible

The magnification of live data and virtual data can be the same. The magnification of live data and virtual data can be different. Virtual data can be partially, e.g. affecting only part of the displayed virtual data, or all magnified. Live data can be partially, e.g. affecting only part of the displayed live data, or all magnified. Virtual data can be magnified while live data are not magnified. Live data can be magnified while virtual data are not magnified. Any combination is possible.

The term magnification includes also displays wherein the live data or the virtual data are displayed in a format or with a magnification that is smaller than live data seen through transparent portions of the OHMD for a given distance or seen through one or more image or video capture systems with display by a virtual reality OHMD (e.g. non-see-through).

The magnification of live data (e.g. video images) and/or virtual data [e.g. virtual data of the patient and, principally any virtual data, e.g. portions of a virtual surgical plan, a predetermined start point, a predetermined start position, a predetermined start orientation or alignment, a predetermined intermediate point(s), a predetermined intermediate position(s), a predetermined intermediate orientation or alignment, a predetermined end point, a predetermined end position, a predetermined end orientation or alignment, a predetermined path, a predetermined plane, a predetermined cut plane, a predetermined contour or outline or cross-section or surface features or shape or projection, a predetermined depth marker or depth gauge, a predetermined stop, a predetermined angle or orientation or rotation marker, a predetermined axis, e.g. rotation axis, flexion axis, extension axis, a predetermined axis of a virtual surgical tool, a virtual surgical instrument, a virtual surgical guide [e.g. a virtual axis, virtual plane or virtual cut block], a virtual trial implant, a virtual implant component, implant or device, non-visualized portions for one or more devices or implants or implant components or surgical instruments or surgical tools, and/or one or more of a predetermined tissue change or alteration, and/or one or more of a predetermined position and/or orientation of a virtual surgical tool, virtual surgical instrument, virtual surgical guide [e.g. a virtual axis, virtual plane or virtual cut block], a virtual trial implant, a virtual implant component, implant or device] can be applied around a central point, e.g. an anchor point, an anatomic landmark, a pin entry into a bone, a screw head, or central axis of the field of view of the OHMD, a pin axis or a screw axis or any other axis, e.g. an anatomic axis (e.g. through a portion or the center of a pedicle) or a biomechanical axis or around an anchor point or a central point or an axis, e.g. a long axis, of a virtual and/or physical tool, instrument, implant and/or device. A central axis or axis around which the live and/or virtual data can be magnified can be an anatomic axis (e.g. through a portion or the center of a pedicle) or a biomechanical axis or an axis, e.g. a long axis, of a virtual and/or physical tool, instrument, implant and/or device, or a virtual axis, e.g. derived in a virtual surgical plan. When a central point is used, the coordinates of the central point in the live data of the patient as seen by the surgeon's right eye through the OHMD unit will be the same as the view coordinates of the central point in the virtual data of the patient seen by the surgeon's right eye projected by the display of the OHMD unit; the coordinates of the central point in the live data of the patient as seen by the surgeon's left eye through the OHMD unit will be the same as the view coordinates of the central point in the virtual data of the patient seen by the surgeon's left eye projected by the display of the OHMD unit. When a central axis or any other axis is used, the coordinates of the central axis or other axis in the live data of the patient as seen by the surgeon's right eye through the OHMD unit will be the same as the view coordinates of the central or other axis in the virtual data of the patient seen by the surgeon's right eye projected by the display of the OHMD unit; the coordinates of the central axis or other axis in the live data of the patient as seen by the surgeon's left eye through the OHMD unit will be the same as the view coordinates of the central axis or other axis in the virtual data of the patient seen by the surgeon's left eye projected by the display of the OHMD unit. When stereoscopic projection is used with the left and right displays of the OHMD unit, the view coordinates for the left display and the right display of the OHMD unit will be different for the left eye and the right eye; the difference in view coordinates is a reflection of the parallax. For example, when the user or surgeon elects to turn on magnification of live and/or virtual data, the magnification can be applied around a central point or axis, e.g. an anatomic or other axis, of the last unmagnified field of view. The system including its software can optionally apply the magnification automatically around the central point or axis, e.g. an anatomic or other axis, of the last field of view. Alternatively, the user and/or surgeon can use a different central point or central axis or other axis as the center around which the live and/or virtual data are being magnified. The central point or central axis can, for example, coincide with the center of a pedicle, when spinal surgery is contemplated. The central axis can coincide with an acetabular or femoral axis, e.g. an anteversion axis, or a predetermined reaming axis, e.g. in hip or shoulder joint replacement. The central axis can, for example, be a predetermined path. The central point, can, for example, be an endpoint. The central point or central axis can, for example, be the center of an acetabulum when hip replacement or other hip surgery is contemplated. The central point or central axis can, for example, be the center of a glenoid when shoulder surgery is contemplated. The central point or central axis or other axis for magnification can be pre-selected for various anatomic sites or surgical fields or surgeries contemplated, e.g. hip replacement, knee replacement surgery, knee arthroscopy or spinal fusion. Using, for example, one or more image and/or video capture systems and/or 3D scanner integrated into, attached to or separate from the OHMD, or using intra-operative imaging, one or more anatomic structures can optionally be identified using standard image processing techniques (e.g. the acetabulum and its center) and the central point or central axis for any magnified views can optionally be set or defined automatically.

View Patient/View Computer Monitor/Screen

In some embodiments, the magnification of the OHMD display can be matched with the magnification of a computer monitor, e.g. in the OR, so that corresponding tissues shown by the OHMD and/or the computer monitor are displayed using the same magnification and can, for example, be substantially aligned or superimposed between the OHMD and the computer monitor display.

Displaying Surgical Instruments and/or Medical Devices/Implantables

In some embodiments, surgical instruments or medical devices or implantables can be displayed virtually with the live data of the patient. The virtual data surgical instrument or virtual implantable can be shown by the OHMD superimposed onto the live data of the patient including the live data surgical instrument.

The OHMD can show the virtual surgical instrument or the virtual implantable indicating the desired orientation or direction or placement of the virtual surgical instrument or the virtual implantable, for example using a virtual surgical plan. Optionally, the OHMD can display directional markers such as an intended path derived from a surgical plan to help guide the surgeon direct the physical surgical instrument or the physical implantable.

The physical surgical instrument or physical implantable can be scanned preoperatively to derive its shape and/or dimensions for subsequent display of a derived shape or dimension of a virtual representation of the surgical instrument or the implantable by the OHMD. Alternatively, a CAD file or 3D file of the surgical instrument or the implantable can be used. Preoperative scanning of the surgical instrument or the implantable can be performed using any technique known in the art. Scanning of the surgical instrument or the implantable can be performed by the OHMD, for example using a built-in image capture device. Scanning of the surgical instrument or the implantable can be performed by a separate image capture device.

In some embodiments, scanning of the surgical instrument or the implantable can occur in two or more dimensions. The more dimensions are used typically the more accurate the resultant virtual representation of the surgical instrument or the implantable.

If an image capture device is used, e.g. one attached to or integrated into the OHMD or coupled to or separate from the OHMD, the surgical instrument or the implantable can be scanned in one, two or more projections, positions or orientation, e.g. by moving the OHMD or the surgical instrument or implantable into different positions or orientations. In some embodiments, the surgical instrument or the implantable can be placed on a tray or fixture for this purpose, which allows to move the surgical instrument or the implantable into different positions and, optionally, to rotate the surgical instrument or the implantable. In some embodiments, the distance between the surgical instrument or the implantable and the image capture device, including an image capture device attached to or integrated into the OHMD or coupled to or separate from the OHMD, is fixed, while the surgical instrument or the implantable are being scanned.

Scans of the physical surgical instrument or implantable can then be used to derive a virtual 2D or 3D representation of the surgical instrument or the implantable.

By scanning the surgical instrument or the implantable intraoperatively, the surgeon has great flexibility in using different surgical instruments or implantables which he can change and modify and, optionally, integrate into his physical or virtual surgical plan.

The surgeon can optionally store each surgical instrument or implantable that has been scanned in this manner in a virtual library of surgical instruments or implantables. The virtual surgical instruments or implantables stored in this manner can be named and stored for future use in subsequent surgical procedures in other patients. By storing the virtual surgical instruments or implantables the need for repeat scans of the same surgical instrument or same type or shape of implantable is obviated.

In some embodiments, the surgeon can use the virtual data of the surgical instrument or implantables that were previously generated in a new surgical plan for another, new patient. The surgeon can select a desired virtual surgical instrument or implantable from the virtual library and use the virtual surgical instrument or the virtual implantable in his or her virtual surgical plan.

When the surgeon performs the physical surgery and the OHMD displays optionally the virtual surgical instrument or implantable, optionally superimposed onto or displayed near the physical surgical instrument or implantable, the software can optionally compare the size and shape of the physical surgical instrument or implantable with that of the previously selected virtual surgical instrument or implantable. Alternatively, the surgeon can visually compare the size and/or shape of the virtual and the physical surgical instrument or implantable.

If a size and/or shape mismatch is detected, the software can send an alert or alarm to the surgeon, e.g. visual or audible, that indicates a mismatch. A mismatch can indicate to the surgeon that the accuracy of registration of virtual data and live data has been compromised and that re-registration may be required. A mismatch can also indicate to the surgeon that the wrong physical surgical instrument or implantable has been selected in comparison to the previously identified virtual surgical instrument or implantable. In this case, the surgeon can check the virtual surgical plan or the physical surgical plan and modify either or both, for example by selecting a different size or shape virtual or live surgical instrument or implantable.

Stereoscopic and Non-Stereoscopic 3D Display of Virtual Data of the Patient with Superimposition on Live Data of the Patient In some embodiments, the OHMD can display a virtual 2D or 3D image of the patient's normal or diseased tissue or an organ or a surgical site or target tissue with a view angle or a perspective or projection that is different for the display for the left eye compared to the display for the right eye resulting in a stereoscopic projection of the anatomy or the pathologic tissue. The virtual data of the patient is thus superimposed on the live data of the patient, e.g. the surgical site, for the left and right eye of the surgeon, respectively, using both the left and the right view angle for the surgeon. This means that two separate views are rendered from the virtual 2D or 3D data sets, one for the left eye and one for the right eye. Multidimensional views exceeding three dimensions generated for the left eye and the right eye are possible. For example, in addition to the virtual anatomy of the patient vascular flow or joint motion can be displayed separately for the left eye and the right eye. The difference in perspective between the left eye and the right eye projection of virtual data or parallax can be selected or programmed so that it will change, for example, with the distance of the OHMD, the surgeon's head or the surgeon's eye in relationship to the target site, surgical site or target tissue. The distance between the surgeon's or operator's eyes can also be taken into account. In some embodiments, the difference in perspective or parallax will be selected or programmed so that a 3D effect is generated in a stereoscopic 3D manner or effect. The difference in perspective or parallax can change depending on any changes in the distance of the OHMD, the surgeon's or operator's head or the surgeon's or operator's eye in relationship to the target site, surgical site or target tissue. For example, as the surgeon or operator moves away from the target site, surgical site or target tissue, the difference in perspective or parallax can decrease. As the surgeon or operator moves towards the target site, surgical site or target tissue, the difference in perspective or parallax can increase. The decrease or increase can be linear, non-linear, exponential or algorithmic. Any other mathematical function is possible. In some embodiments, the difference in perspective or parallax will change similar to the change experienced by the human eye as the surgeon or operator moves towards or away from a target.

The distance of the OHMD, the surgeon's or operator's head or the surgeon's or operator's eye in relationship to the target site, surgical site or target tissue can be measured via image capture, anatomic landmark embodiments, image capture used in conjunction with calibration or registration phantoms, surgical navigation or any of the other embodiments described in this specification and or spatial mapping. The distance and any changes in distance of the OHMD, the surgeon's or operator's head or the surgeon's or operator's eye in relationship to the target site, surgical site or target tissue can be used to change the difference in perspective views or parallax in views for the left eye and the right eye.

FIGS. 16A-B are flow charts summarizing model generation, registration and view projection for one or more OHMDs, e.g. by a primary surgeon, second surgeon, surgical assistant nurse, or others. Pre-operative, intra-operative or post-operative images of the patient can be acquired 240. The image data can optionally be segmented 241. 3D reconstructions of the patient's anatomy or pathology including multiple different tissues, e.g. using different colors or shading, can be generated 242. Virtual 3D models of surgical instruments and devices components can be generated which can include their predetermined position, location, rotation, orientation, alignment and/or direction 243. The virtual 3D models can be registered, for example in relationship to the OHMD and the patient 244. The virtual 3D models can be registered relative to the live patient data 245. Optionally, adjustments can be made for different view perspectives, parallax, skin, skin movement and other tissue specific issues 246. Different perspective views can be generated for the user's left eye and right eye to facilitate a stereoscopic viewing experience, e.g. like an electronic hologram, of the virtual models of subsurface or hidden anatomic or pathologic tissues 247 and the virtual 3D models of tools, instruments, implants and devices 248. Virtual patient data 249 and virtual 3D models of tools, instruments, implants and devices 250 can be displayed in the OHMD, optionally with different view perspectives adjusted for the left and the right eye of the user 251 and 252. Left eye and right eye offsets or parallax can optionally be adjusted based on the distance from the OHMD, surgeon head or surgeon eyes to the surgical site using, for example, depth sensors or spatial mapping or other registration techniques and also based on interocular distance 253. Polarization or color techniques for stereoscopic views 254 can be combined with electronic holograms such as those provided by the Microsoft Hololens.

In an alternative description in FIG. 16B, multiple 3D models 260, 261, 262 can be generated, e.g. one for subsurface anatomic or pathologic structures of the patient, one for virtual surgical tools or instruments and one for virtual surgical implant components. These can be registered, e.g. in a common coordinate system or multiple coordinate systems using coordinate transfers, also with the OHMD 263. Using shared coordinates for the different virtual 3D models 260, 261, 262 multiple viewers using multiple OHMDs can share a 3D World 264 with projection or display of one or more of the models onto the live data of the patient 265. The display can be generated separately for the left eye of each user using the user's left eye coordinates 266 and the right eye of each user using the user's right eye coordinates 267. Stereoscopic views or different perspective views or views with a parallax for the left eye and the right eye can be generated for multiple virtual data sets or data volumes of the patient. Any of the dimensions listed in Table 4 or virtual structures, tissues or data mentioned in the application can be displayed separately for the left eye and the right eye using stereoscopic views or different perspective views or views with a parallax, simultaneously, non-simultaneously, or sequentially. In addition, any of the virtual data in Table 11 can be displayed using stereoscopic views or different perspective views or views with a parallax for the left eye and the right eye. Multiple of the data listed in Table 11 can be displayed simultaneously, non-simultaneously or sequentially, for example also with the live data or images of the patient seen through the OHMD, stereoscopically or non-stereoscopically:

TABLE 11

Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

TABLE 11A: Exemplary virtual data of the patient that can be displayed stereoscopically or non-stereoscopically Native anatomy, e.g.
  Gyri of the brain
  Venous sinus of the brain
  Arterial structures of the brain
  Brain lesion
  Brain tumor
  Features of the face
  Features of an ear
  Liver margin
  Liver lobes
  Spleen margin TABLE 11-continued Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

Kidney, renal outline
One or more osteophytes
Bone spurs
Bony anatomy
Bony deformity
Acetabular rim of a hip
Tri-radiate cartilage region
Fovea capitis
Anterior superior iliac spine
Anterior inferior iliac spine
Symphysis pubis
Femoral head of a hip
Femoral neck
Greater trochanter
Lesser trochanter
Condyles of a knee
Trochlea of a knee
Patella of a knee
Tibial plateau of a knee
Medial tibial plateau of a knee
Lateral tibial plateau of a knee
Anterior cruciate ligament of a knee
Posterior cruciate ligament of a knee
Distal tibia of an ankle joint
Distal fibula of an ankle joint
Talus of an ankle joint
Any ligament or ligamentous structure of a patient
Glenoid rim of a shoulder
Glenoid of a shoulder
Humeral head or neck of a shoulder
Facet joint of a spine
Spinous process
Pedicle of a spine
Vertebral endplate
Intervertebral disk
Herniated disk
Any tumor affecting the human body
Any of the foregoing tissues on an exposed surface, e.g. surgically exposed
Any of the foregoing tissues in a hidden location or a subsurface location
Any of the foregoing tissues visualized using an imaging test TABLE 11B: Exemplary virtual surgical sites and alterations to a surgical site that can be displayed stereoscopically or non-stereoscopically Alterations planned to surgical site, e.g.
  Tissue removal
  Removal of normal tissue
  Removal of diseased tissue
  Removal of neoplastic tissue
  Bone cuts
  Reaming (e.g. in proximal femur)
  Broaching (e.g. in proximal femur)
  Impacting (e.g. in a femur or a tibia)
  Milling
  Drilling
  Tissue transplants
  Organ transplants
  Partial or complete resections, e.g. of organs
  Placement of a medical device
  Placement of a stent TABLE 11C: Exemplary virtual surgical instruments and surgical steps or procedures that can be displayed stereoscopically or non-stereoscopically Tissue cutters, e.g. scalpels, blades, drills, saws, burrs, reamers, broaches
Tissue ablation devices, e.g. heat or cryotherapy
Robotic arms
Instruments attached to robotic arms
Endoscopy devices
Endoscopic cameras
Endoscopic cutting devices
Endoscopic ablation devices TABLE 11-continued Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

A predetermined surgical path or predetermined placement or position, location, rotation, orientation, alignment, or direction of one surgical instrument
A predetermined surgical path or predetermined placement or position, location, rotation, orientation, alignment, or direction of more than one surgical instrument
A predetermined surgical path or predetermined placement or position, location, rotation, orientation, alignment, or direction of more than one surgical instrument used simultaneously
A predetermined surgical path or predetermined placement or position, location, rotation, orientation, alignment, or direction of more than one surgical instrument used non-simultaneously
A predetermined surgical path or predetermined placement or position, location, rotation, orientation, alignment, or direction of more than one surgical instrument used in succession
A predetermined surgical path or predetermined placement or position, location, rotation, orientation, alignment, or direction of more than one surgical instrument not used in succession
A predetermined surgical path or predetermined placement or position, location, rotation, orientation, alignment, or direction of more than one surgical instrument used on the same side of a joint
A predetermined surgical path or predetermined placement or position, location, rotation, orientation, alignment, or direction of more than one surgical instrument used on one or more opposing sides of a joint
A predetermined surgical path or predetermined placement or position, location, rotation, orientation, alignment, or direction of more than one surgical instrument used on the same vertebral levels
A predetermined surgical path or predetermined placement or position, location, rotation, orientation, alignment, or direction of more than one surgical instrument used on adjacent vertebral levels
A predetermined surgical path or predetermined placement or position, location, rotation, orientation, alignment, or direction of more than one surgical instrument used on non-adjacent vertebral levels
A predetermined surgical path or predetermined placement or position, location, rotation, orientation, alignment, or direction of one surgical instrument used on a vertebral endplate
A predetermined surgical path or predetermined placement or position, location, rotation, orientation, alignment, or direction of more than one surgical instrument used on a superior vertebral endplate and on an adjacent, inferior vertebral endplate
A predetermined surgical path or predetermined placement or position, location, rotation, orientation, alignment, or direction of an instrument used for disk removal TABLE 11D: Exemplary virtual medical devices and implants that can be displayed stereoscopically or non-stereoscopically Hip replacement components
  Acetabular cup including predetermined placement or position, location, rotation, orientation, alignment, anteversion, retroversion, inclination, offset, location in relationship to the safe zone
  Acetabular liner including predetermined placement or position, location, rotation, orientation, alignment, anteversion, retroversion, inclination, offset, location in relationship to the safe zone
  Femoral head including predetermined placement or position, location, rotation, orientation, alignment, anteversion, retroversion, inclination, offset, location in relationship to the safe zone
  Femoral neck including predetermined placement or position, location, rotation, orientation, alignment, anteversion, retroversion, inclination, offset, location in relationship to the safe zone (optionally with modular necks)
  Femoral stem including predetermined placement or position, location, rotation, orientation, alignment, anteversion, retroversion, inclination, offset, location in relationship to the femoral neck cut, the calcar, the greater or the lesser trochanter, the acetabulum
Knee replacement components
  Femoral component including predetermined placement or position, location, internal or external rotation, orientation, alignment, flexion, extension, position in relationship to anterior cortex, or mechanical axis or other axis alignment, all optionally through the range of motion
  Tibial component including predetermined placement or position, location, internal or external rotation, orientation, alignment, flexion, extension, slope, position in relationship to cortical rim, or mechanical axis or other axis alignment, all optionally through the range of motion
  Polyethylene or other inserts including predetermined placement or position, location, internal or external rotation, orientation, alignment, flexion, extension, slope, position in relationship to cortical rim, or mechanical axis or TABLE 11-continued Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

other axis alignment, all optionally through the range of motion
Patellar component including predetermined placement or position, location, internal or external rotation, orientation, alignment, position in relationship to patellar cortical rim, position in relationship to trochlea, optionally in flexion and/or extension and/or through the range of motion, position in relationship to mechanical axis, trochlear axis, trochlear groove, epicondylar axis or other axis alignment
Trial femoral component including predetermined placement or position, location, internal or external rotation, orientation, alignment, flexion, extension, position in relationship to anterior cortex, or mechanical axis or other axis alignment, all optionally through the range of motion
Trial tibial component including predetermined placement or position, location, internal or external rotation, orientation, alignment, flexion, extension, slope, position in relationship to cortical rim, or mechanical axis or other axis alignment, all optionally through the range of motion
Trial inserts including predetermined placement or position, location, internal or external rotation, orientation, alignment, flexion, extension, slope, position in relationship to cortical rim, or mechanical axis or other axis alignment, all optionally through the range of motion
Trial patellar component including predetermined placement or position, location, internal or external rotation, orientation, alignment, position in relationship to patellar cortical rim, position in relationship to trochlea, optionally in flexion and/or extension and/or through the range of motion, position in relationship to mechanical axis, trochlear axis, trochlear groove, epicondylar axis or other axis alignment
Spinal screws including predetermined placement or position, location, rotation, orientation, alignment, location in relationship to the pedicle, the cortical bone of the pedicle, the endosteal bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, the trabecular bone of the vertebral body, any fracture components or fragments, e.g. involving a pedicle, a facet joint or a vertebral body
Pedicle screws including predetermined placement or position, location, rotation, orientation, alignment, location in relationship to the pedicle, the cortical bone of the pedicle, the endosteal bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, the trabecular bone of the vertebral body, any fracture components or fragments, e.g. involving a pedicle, a facet joint or a vertebral body
Spinal rods including predetermined placement or position, location, rotation, orientation, alignment, location in relationship to one or more pedicles, the cortical bone of the pedicle?+0 the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a scoliotic deformity, and predetermined correction for a scoliotic deformity
Artificial spinal disks including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a scoliotic deformity, and predetermined correction for a scoliotic deformity
Metal screws, pins, plates, rods for trauma including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a long bone, a joint, an articular surface, and any predetermined correction for a fracture or fracture deformity
Intramedullary nails including predetermined placement or position, location, rotation, orientation, alignment, location in relationship to one or more fracture components or fragments, e.g. a long bone, a joint, an articular surface, and any predetermined correction for a fracture or fracture deformity
Vascular stents
   Coronary stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, TABLE 11-continued Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

adjacent nerves
Carotid stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
Aortic stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
Femoral stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
Cochlear implants including predetermined placement or position, location, rotation, orientation, alignment, for example in relationship to osseous structures, neural structures, auditory structures, the labyrinth
Retinal implants including predetermined placement or position, location, rotation, orientation, alignment, for example in relationship to osseous structures, neural structures, vascular structures
Neural implants including predetermined placement or position, location, rotation, orientation, alignment, for example in relationship to neural structures, vascular structures, osseous structures
Neuroprosthetics including predetermined placement or position, location, rotation, orientation, alignment, for example in relationship to neural structures, vascular structures, osseous structures
Implants for deep brain stimulation, e.g. for treatment of Parkinson's disease including predetermined placement or position, location, rotation, orientation, alignment, for example in relationship to neural structures, vascular structures, osseous structures The list in Table 11 is only exemplary and is not meant to be limiting. Any of the exemplary virtual data of the patient listed in Table 11A, exemplary virtual surgical sites and alterations to a surgical site listed in Table 11B, exemplary virtual surgical instruments and surgical steps or procedures listed in Table 11C, and exemplary virtual medical devices and implants listed in Table 11D can be displayed by the OHMD in two, three or more dimensions (e.g. as described also in Table 4), using stereoscopic as well as non-stereoscopic projections or view. Thus, the present disclosure is not limited to stereoscopic displays and/or 2D displays and/or 3D displays. Any combination of virtual displays is possible, e.g. 3D stereoscopic patient anatomy or surgical site with 2D surgical instrument displays and/or 2D medical device displays, or 3D patient anatomy, with 3D non-stereoscopic surgical instrument display and/or 3D stereoscopic medical device display.

Aligning or Superimposing Physical Surgical Instruments with Virtual Surgical Instruments With virtual displays of the surgical instruments in the OHMD, the surgical instruments displayed in the virtual data can be representative of the physical surgical instruments used in the live patient and can have the same projected dimensions and shape as the physical surgical instruments. As indicated in Table 11, the virtual view of the virtual surgical instrument or instruments can, for example, indicate the predetermined position, location, rotation, orientation, alignment, direction of a surgical instrument. When the physical surgical instrument is aligned with and/or superimposed onto the virtual representation of the virtual surgical instrument, the surgical step can optionally be executed or the surgeon can elect to make adjustments to the position, location, rotation, orientation, alignment, direction of a physical surgical instrument relative to the virtual surgical instrument, for example on the basis of a ligament tension or ligament balance, e.g. in flexion or extension. The resultant alteration of the live surgical site induced by the surgical step in the live patient is typically consistent with the virtual surgical plan, when the virtual and physical surgical instruments are superimposed in their respective position, location, rotation, orientation, alignment, or direction.

More than one surgical step can be executed in this manner, e.g. by aligning the physical surgical instruments with the corresponding virtual surgical instruments using stereoscopic or non-stereoscopic displays of virtual surgical instruments. The aligning can be performed in two dimensions, three dimensions, and more than three dimensions. The aligning can be performed with stereoscopic and non-stereoscopic displays. More than one virtual surgical step can be planned utilizing the virtual surgical plan. Two or more virtual surgical steps can be planned. The virtual surgical steps can include the major surgical steps of the intended procedure, they can include optionally sub-steps, or, optionally, the entire procedure. When the physical surgical steps are executed after aligning one or more physical instruments with the virtual instruments in the corresponding surgical steps, each surgical step using the physical instruments is effectively image guided using, optionally, the virtual surgical plan with the operator or the surgeon using the image guidance information, for example from a preoperative scan or imaging study obtained at a time different from the surgical procedure, typically preceding the surgical procedure, and typically with the surgical site in a different object coordinate system at the time of the preoperative imaging when compared to the time of the surgical procedure. The display of the virtual surgical instruments can be stereoscopic or non-stereoscopic.

Thus, by aligning physical surgical instruments seen through the OHMD or displayed by the OHMD with virtual surgical instruments using stereoscopic or non-stereoscopic displays of virtual surgical instruments in the OHMD, it is possible to execute accurately on a surgical plan in the live patient using pre-existing image information and image guidance information, as defined, for example, in a virtual surgical plan. In addition, by aligning physical surgical instruments seen through the OHMD or displayed by the OHMD with virtual surgical instruments using stereoscopic or non-stereoscopic displays of virtual surgical instruments in the OHMD, it is possible to achieve a predetermined position, location, rotation, orientation, alignment, direction of a medical implant including, but not limited to, for example the implants listed in Table 11D.

The OHMD can show the one or more virtual surgical instruments with a continuous surface view, for example, using one color or multiple colors for different features of the instrument. The continuous surface display can include shading based on light sources used in the operating room and/or over the surgical field. The directional orientation of the OR light sources can, for example, be measured using image capture, optionally integrated into, attached to or separate from the OHMD.

The OHMD can show the one or more virtual surgical instruments with an outline view which can be in 2D or in 3D. The outline view can include an outline of the entire virtual surgical instrument, for example in a particular plane or cross-sectional plane. The outline view can optionally only highlight select features of the virtual surgical instrument, e.g. a bone cutting surface or feature or a grip feature or combinations thereof. The OHMD can show two or more outline views, for example extending through or along the surface or the periphery of the virtual surgical instrument along different planes. These planes can be chosen to be different than at a 0 or 180 degree angles to each other. In some embodiments, the outline views can be orthogonal to each other. In this manner, even though the two or more outline views can be two-dimensional, the OHMD can still provide information to the surgeon or the operator on the intended orientation, position and/or direction of the surgical instrument in three-dimensions by providing two or more outline views with different angular orientations and by providing information on the x, y and z-axis alignment or position or orientation or direction of the surgical instrument. Outline views can help limiting the amount of information displayed by the OHMD, which can help the surgeon maintaining his or her focus on the surgical site, with full visibility of the surgical site. Outline view can help decrease the risk of obscuring important live information from the patient, e.g. a bleeding vessel, by inadvertently superimposing virtual data, e.g. 3D surface data, and obscuring portions of the live anatomy.

By aligning physical surgical instruments seen through the OHMD or displayed by the OHMD with virtual surgical instruments using stereoscopic or non-stereoscopic displays of virtual surgical instruments in the OHMD, it is possible to achieve certain alterations of a surgical site or certain implant placement or implant component placement in live patients that can, for example, determine at least one of a Surgical instrument position; Surgical instrument location; Surgical instrument orientation; Surgical instrument rotation; Surgical instrument alignment; Surgical instrument direction; Depth of advancement of a surgical instrument, e.g. for acetabular or glenoid reaming; Implant position; Implant location; Implant orientation; Implant rotation; Implant alignment; Implant position of two or more implant components in relationship to each other and/or in relationship to the patient; Implant location of two or more implant components in relationship to each other and/or in relationship to the patient; Implant orientation of two or more implant components in relationship to each other and/or in relationship to the patient; Implant rotation of two or more implant components in relationship to each other and/or in relationship to the patient; Implant alignment of two or more implant components in relationship to each other and/or in relationship to the patient. Anatomic or pathologic structures and/or tissue including but not limited to one or more osteophytes or bone spurs or other bony anatomy or deformity or soft-tissue or neoplastic tissue or abnormality can be used for referencing the patient both in the virtual and in the live data and for determining or cross-referencing to the other anatomy the desired instrument or implant component position, location, orientation, rotation or alignment.

Aligning or Superimposing Physical Surgical Instruments or Physical Medical Devices with Virtual Alterations to a Surgical Site The OHMD can display virtual alterations to a surgical site superimposed onto the live surgical site prior to the physical alteration of the live surgical site. The virtual alterations to a surgical can be simulated using a virtual surgical plan. The virtual surgical alterations and/or the virtual surgical plan can be executed or displayed in two, three or more dimensions, optionally with a stereoscopic or non-stereoscopic display.

In some embodiments, the OHMD can display a virtual alteration to a surgical site. The operator or the surgeon can then align the physical surgical instrument selected to perform the intended alteration to the physical surgical site and align the physical surgical instrument with the virtual alteration of the surgical site. The virtual alteration can, for example, be the removal or shape modification of one or more osteophytes or bone spurs or other bony anatomy or deformity or soft-tissue or neoplastic tissue or abnormality. The operator or surgeon can then advance or move the physical surgical instrument into the direction of or into the physical surgical site, optionally while maintaining alignment of the physical instrument with the virtual alteration of the surgical site. In this manner, the operator or the surgeon can effect the desired change or alteration to the surgical site in the live patient, and the change or alteration achieved in the surgical site of the live patient is typically similar to or aligned with or consistent with the intended virtual change or alteration to the surgical site and, if applicable, the virtual surgical plan.

For example, a surgeon can plan to make a bone cut to a distal femur of a patient. The OHMD can display the virtual bone cut superimposed onto the uncut bone of the live patient. The virtual bone cut and the intended physical bone cut can, for example, remove or correct one or more osteophytes or bone spurs or other bony anatomy or deformity or soft-tissue. The surgeon can then align the saw blade of the physical bone saw with the planar surface of the intended bone cut in the virtual alteration of the bone surface displayed by the OHMD. By advancing the saw blade in the direction of the cut while maintaining alignment between the physical saw blade, e.g. the flat surface of the physical saw blade, and the planar surface of the virtual bone cut, the surgeon can achieve an accurate physical bone cut in the live patient. Alternatively, the surgeon can align a cutting tool or cut block or cut guide to guide a bone saw with the planar surface of the intended bone cut in the virtual alteration of the bone surface displayed by the OHMD; the cutting tool or cut block or cut guide can then optionally be affixed to the tissue and/or bone, for example using one or more pins or screws and the cut can be performed using the cutting tool, cut block or cut guide.

In another example, a surgeon can plan to make a bone cut to a proximal femur of a patient, e.g. for partial or total hip arthroplasty, or to a distal femur or proximal tibia, e.g. for partial or total knee replacement, or to a proximal humerus, e.g. for partial or total shoulder arthroplasty. The OHMD can display the virtual bone cut superimposed onto the uncut bone of the live patient. The surgeon can then align the saw blade of the physical bone saw with the planar surface of the intended bone cut in the virtual alteration of the bone displayed by the OHMD. By advancing the saw blade in the direction of the cut while maintaining alignment between the physical saw blade and the planar surface of the virtual bone cut, the surgeon can achieve an accurate physical bone cut in the live patient. The bone cut can be oriented to achieve a desired component rotation and/or component flexion or extension. The bone cut can be oriented to achieve a desired slope. The same result can be achieved by aligning a cutting tool, cut block, or cut guide with the planar surface of the virtual bone cut, optionally affixing it to the tissue and/or bone, and performing the cut with the bone saw.

In another example, a surgeon can plan to ream or broach a bone, e.g. a proximal femur or a proximal humerus. The OHMD can display the bone after the virtual reaming or broaching procedure showing the intended virtual alteration of the inner bone surface after the reaming or broaching procedure; the display can optionally be superimposed onto the live image of the unaltered physical bone. The surgeon can then align the physical reamer or broach onto the intended virtual alteration and shape change of the bone after the reaming or broaching procedure displayed by the OHMD. By advancing the reamer or broach in the direction of the virtually reamed or broached bone surface while maintaining alignment between the physical reamer or broach and the virtually reamed or broached bone surface, the surgeon can achieve an accurate physical reaming or broaching of the bone in the live patient.

In another example, a surgeon can plan to place a pedicle screw in a pedicle of a patient, e.g. for spinal fusion. The OHMD can display the virtual bone void or space created by a virtual pedicle screw, optionally superimposed onto the unaltered pedicle of the live patient. The surgeon can then align a physical drill or a physical pedicle screw with the virtual bone void or space for the pedicle screw in the virtual alteration of the pedicle displayed by the OHMD. By advancing the physical drill or pedicle screw in the direction of the virtual bone void or space in the pedicle while maintaining alignment between the physical drill or pedicle screw and the virtual bone void or space in the pedicle, the surgeon can achieve accurate placement of the physical drill or pedicle screw in the live patient. The bone void in the pedicle or the position of the pedicle screw can be chosen in the virtual surgical plan so that there is one or more desired minimum distance or a minimum area or volume of bone between the bone void or the pedicle screw and the endosteal bone surface or cortical bone surface of the pedicle, medially, laterally, superiorly, and/or inferiorly.

In another example, a surgeon can plan to place an intervertebral disk replacement in an intervertebral disk space of a patient, e.g. for motion preserving disk replacement. The OHMD can display the virtual alteration required for the placement of the disk replacement, for example with virtual alterations to the superior and/or inferior endplates of the two adjacent vertebral bodies, optionally superimposed onto the endplates of the live patient. The virtual and intended physical alterations can include, for example, the removal of one or more osteophytes or bone spurs or other bony anatomy or deformity or the resection of portions of or all of the endplate(s). The surgeon can then align physical instruments used for altering the vertebral endplates to accept the intervertebral disk replacement with the virtual alteration of the endplates displayed by the OHMD. By advancing the physical surgical instruments in the direction of the virtual alteration of the endplates while optionally maintaining alignment between the physical surgical instrument and the virtual alteration of the endplates, the surgeon can achieve accurate placement of the physical surgical instruments and the physical disk replacement in the live patient.

Thus, by aligning with or directing physical surgical instruments or medical devices towards a display of virtual alterations to a surgical site in the OHMD it is possible to achieve certain alterations of a surgical site or certain implant placement or implant component placement in live patient that can, for example, determine at least one of a Surgical instrument position; Surgical instrument location; Surgical instrument orientation; Surgical instrument rotation; Surgical instrument alignment; Surgical instrument direction; Depth of advancement of a surgical instrument, e.g. for acetabular reaming; Implant position; Implant location; Implant orientation, e.g. anteversion, retroversion, offset (e.g. in a hip replacement acetabular cup or femoral component), abduction, adduction, internal rotation, external rotation, flexion, extension (e.g. in a knee replacement femoral component or tibial component); Implant rotation; Implant alignment; Implant position of two or more implant components in relationship to each other and/or in relationship to the patient; Implant location of two or more implant components in relationship to each other and/or in relationship to the patient; Implant orientation of two or more implant components in relationship to each other and/or in relationship to the patient; Implant rotation of two or more implant components in relationship to each other and/or in relationship to the patient; Implant alignment of two or more implant components in relationship to each other and/or in relationship to the patient. Optionally, the surgeon can toggle the display of the virtual data between a display of the surgical site prior to the alteration and/or after the alteration. Optionally, the surgeon can advance the display of the virtual data several surgical steps so that, for example, not the next but one or more subsequent virtual alterations to the surgical site be displayed.

Optionally, the surgeon can use displays with different colors for simultaneously or non-simultaneously viewing the physical, live surgical site and the virtual surgical site before and after one or more consecutive or non-consecutive virtual alterations intended or planned for the surgical site, optionally superimposed onto the live or virtual surgical site before the one or more alterations are made.

Optionally, the virtual display of the planned alteration can be superimposed onto the physical surgical site after the surgical alteration has been made to check for the accuracy of the physical alteration in the live patient. If the surgeon notices a discrepancy between the planned virtual alteration and the physical alteration, the surgeon can modify the physical alteration. For example, if the surgeon has executed a bone cut, for example in a proximal femur for a hip replacement or in a distal femur or proximal tibia for a knee replacement, the surgeon can use the OHMD to superimpose the planned, intended virtual bone cut onto the physical bone cut after the bone cut was made. If the surgeon notices that the physical bone cut took less bone than intended when compared to the planned, intended virtual bone cut, the surgeon can recut the bone to more closely match the physical bone cut with the intended virtual bone cut and, optionally the virtual surgical plan.

If the surgeon notices a discrepancy between the planned virtual alteration and the physical alteration, the surgeon can optionally also modify the virtual alteration to match the physical alteration induced by the patient. The virtual surgical plan can then be modified, for example for one or more of the subsequent surgical steps or procedures so that the virtual surgical plan will continue to work with the physical surgical alterations achieved with or induced in the live patient. The modification of the virtual surgical plan can be performed manually by the operator or surgeon, semi automatically or automatically using the input from the physical surgical alteration induced in the patient.

For example, if the surgeon has executed a bone cut, e.g. in a proximal femur for a hip replacement or in a distal femur or proximal tibia for a knee replacement, the surgeon can use the OHMD to superimpose the planned, intended virtual bone cut onto the physical bone cut after the bone cut was made. If the surgeon notices that the physical bone cut took more bone than intended when compared to the planned, intended virtual bone cut, the surgeon can modify the virtual surgical plan. The modified surgical plan can then, for example, included that a subsequent bone cut or reaming step on the opposite articular surface will take less bone, typically the same amount less bone on the opposite articular surface than was removed too much during the prior physical bone cut in the live patient. Alternatively, the modified surgical plan can include that one or more components of the medical device be thicker to compensate for the larger bone cut. In a knee replacement, for example, a thicker tibial insert can optionally be used. In a hip replacement, for example, a thicker acetabular liner or an offset liner can optionally be used.

Aligning Physical Medical Devices and Implants with Virtual Medical Devices and Implants By aligning with or directing physical medical devices or medical device components towards a display of virtually implanted medical devices or medical device components, for example in their intended final virtual position, location, orientation, rotation or alignment, in the OHMD, it is possible to achieve predetermined implant placement or implant component placement in the live patient that can, for example, determine at least one of a physical, final Implant position
Implant location
Implant orientation, e.g. anteversion, retroversion, offset (e.g. in a hip replacement acetabular cup or femoral component), internal rotation, external rotation, flexion, extension (e.g. in a knee replacement femoral component or tibial component)
Implant rotation
Implant alignment
Implant position of two or more implant components in relationship to each other and/or in relationship to the patient
Implant location of two or more implant components in relationship to each other and/or in relationship to the patient
Implant orientation of two or more implant components in relationship to each other and/or in relationship to the patient
Implant rotation of two or more implant components in relationship to each other and/or in relationship to the patient
Implant alignment of two or more implant components in relationship to each other and/or in relationship to the patient The OHMD can show the one or more virtual and, optionally, virtually implanted medical devices or medical device components with a continuous surface view, for example, using one color or with multiple colors for different features of the device or for different device components. The continuous surface display can include shading based on light sources used in the operating room and/or over the surgical field. The directional orientation of the OR light sources can, for example, be measured using image capture, optionally integrated into, attached to or separate from the OHMD.

The OHMD can show the one or more virtual and, optionally, virtually implanted medical devices or medical device components with an outline view which can be in 2D or in 3D. The outline view can include an outline of the entire virtual medical device or virtual medical device component, for example in a particular plane or cross-sectional plane. The outline view can optionally only highlight select features of the virtual medical device or virtual medical device component, e.g. a bone facing surface or a surface between two or more components facing each other, or a linking portion of the device or component or combinations thereof. The OHMD can show two or more outline views, for example extending through or along the surface or the periphery of the virtual medical device or virtual medical device component along different planes. These planes can be chosen to be different than at a 0 or 180 degree angle to each other. In some embodiments, the outline views can be orthogonal to each other. In this manner, even though the two or more outline views can be two-dimensional, the OHMD can still provide information to the surgeon or the operator on the intended orientation, position and/or direction of the device or device component in three-dimensions by providing two or more outline views with different angular orientations and by providing information on the x, y and z-axis alignment or position or orientation of the device or device component. Outline views can help limiting the amount of information displayed by the OHMD, which can help the surgeon maintaining his or her focus on the surgical site, with full visibility of the surgical site. Outline view can help decrease the risk of obscuring important live information from the patient, e.g. an exposed nerve root, by superimposing virtual data in a reduced format.

Optionally, the surgeon can toggle the display of the virtual data between a display of one or more of the virtual medical device components and, optionally, the live medical device components.

Optionally, the surgeon can use displays with different colors for simultaneously or non-simultaneously viewing the two or more virtual medical device components, optionally superimposed onto or displayed with the physical medical device.

Optionally, the virtual display of the medical device or medical device component after virtual implantation can be superimposed onto the physical medical device or medical device component after the physical implantation or placement to check for the accuracy of the physical implantation or placement in the live patient. If the surgeon notices a discrepancy between the planned virtual position, location, orientation, rotation, alignment of the medical device or medical device components and the physical position, location, orientation, rotation, alignment of the physical medical device or medical device components, the surgeon can modify the physical device placement or the surgeon can utilize different device components, e.g. in a knee replacement use a thicker or a thinner or a differently shaped tibial polyethylene insert or in a hip replacement use a different polyethylene liner, e.g. thicker, thinner or with offsets.

Visors

In some embodiments, a visor or splash shield can be integrated into the OHMD to protect the surgeon including his or her eyes from bodily fluids, e.g. blood. In some embodiments, a visor or splash shield can be attached to the OHMD to protect the surgeon including his or her eyes from bodily fluids, e.g. blood. In some embodiments, a visor or splash shield can be placed in front of the OHMD to protect the surgeon including his or her eyes from bodily fluids, e.g. blood.

Color Coding

Optionally, the different surgical instruments, devices or device components can be color coded during the display in the OHMD. For example, the color coding in the OHMD display will correspond to the color coding of the physical surgical instruments, devices or device components, if applicable. An exemplary color coding chart is provided below:

Physical device: 4.0 mm screw—grey; 4.5 mm screw—pink; 5.0 mm screw—brown; 5.5 mm screw—blue; 6.0 mm screw—orange; 6.5 mm screw—yellow; 7.0 mm screw—no color; 7.5 mm screw—green; 8.5 mm screw—black;

Virtual device display: 4.0 mm screw—grey; 4.5 mm screw—pink; 5.0 mm screw—brown; 5.5 mm screw—blue; 6.0 mm screw—orange; 6.5 mm screw—yellow; 7.0 mm screw—no color; 7.5 mm screw—green; 8.5 mm screw—black Such screws can, for example, be used with pedicle screws or glenoid components or acetabular components. The foregoing color coding is only exemplary. Any colors, combination of colors, stripes, patterns can be used for identifying different sizes, dimensions, shapes, diameters, widths or lengths. Any instrument or implant can be color coded.

Color coding is applicable to any surgical instrument, medical device or medical device component, e.g. also with vascular stents, cardiac implants, cardiac defibrillators, hip replacement components, knee replacement components etc.

Optionally, in addition to the color coding or as an alternative to color coding, the OHMD can display one or more numerical values next to the virtual surgical instrument or medical device, e.g. a thickness or diameter or a size from a sizing chart.

In some embodiments, the OHMD can recognize if there is a discrepancy in diameter, width, length, dimension, shape, or size of a physical surgical instrument or device and a virtual device chosen in a surgical plan. For example, an image and/or video capture system and/or 3D scanner integrated into, attached to or connected to the OHMD or separate from the OHMD can be used to image a surgical instrument, medical device or medical device component, optionally correct its diameter, width, length, dimension, shape, or size based on the distance of the surgical instrument or device from the image and/or video capture system and/or 3D scanner (e.g. using parallax based measurements or registration or calibration phantoms) and then determine if the physical medical device or medical device component chosen by the operator or surgeon matches that selected in the virtual surgical plan. If the physical surgical instrument or medical device or medical device component is mismatched, for example with regard to diameter, width, length, dimension, shape, or size relative to the virtual instrument or component, the system can provide a warning signal, such as an acoustic alert or a visual warning sign (e.g. a red exclamation mark displayed by the OHMD).

Partially Visible or Partially Obscured Instruments, Tools, Devices, Implants, Implant Components In certain situations during surgery or in certain surgical sites, one or more physical surgical instruments or tools or one or more physical devices, implants, implant components and systems for implantation may only be partially visible during aspects or a period of the surgery. This is particular the case with surgeries involving deep seated organs, e.g. a liver or a kidney, a brain, or deep seated, obscured or hidden body structures, e.g. a hip joint or aspects of a spine, where important parts of one or more physical surgical instruments or tools or one or more physical devices, implants, implant components and systems for implantation may be at least partially obscured from view. This may be aggravated if the portion that is obscured from view is a portion that is inducing one or more alteration to a tissue surface, for example by electro-cautery, ablation, cutting or reaming or impacting. This reduction or limitation in visualization of the one or more physical surgical instruments or tools or one or more physical devices, implants, implant components and systems for implantation can result in a decreased accuracy of the surgical technique and, for example, placement errors of a device, implant, implant component or system for implantation or potential complications.

In an embodiment, one or more of the physical surgical instruments or tools and/or one or more of the physical devices, implants, implant components and systems for implantation can include certain standardized geometric features, e.g. rectangles, triangles, circles and the like, that can be readily recognized by an image and/or video capture system and/or 3D scanner integrated into or attached to or coupled to or separate from the OHMD. Alternatively, the image and/or video capture system and/or 3D scanner may simply recognize the visible geometric shapes, surfaces, features or portions of the one or more of the physical surgical instruments or tools and/or one or more of the physical devices, implants, implant components and systems for implantation. The information can then be used to compute the shape, geometry, outline, surface or other features of the non-visualized, non-visible portions of the one or more of the physical surgical instruments or tools and/or one or more of the physical devices, implants, implant components and systems for implantation. With any of the foregoing techniques, the position, location, orientation, alignment, motional direction, and/or trajectory of the one or more of the surgical instruments or tools and/or one or more of the devices, implants, implant components and systems for implantation can be determined even though the one or more of the surgical instruments or tools and/or one or more of the devices, implants, implant components and systems for implantation is only partially or incompletely visualized or visible in the surgical site.

The non-visualized or non-visible portions of the one or more of the physical surgical instruments or tools and/or one or more of the physical devices, implants, implant components and systems for implantation can then optionally be displayed by the OHMD and projected onto the view of the surgical site. Optionally, the non-visualized or non-visible portions of the one or more of the physical surgical instruments or tools and/or one or more of the physical devices, implants, implant components and systems for implantation can be displayed by the OHMD simultaneous with the one or more of the corresponding virtual surgical instruments or tools and/or one or more of the corresponding virtual devices, implants, implant components and systems for implantation. Different colors or display patterns can optionally be used to display and differentiate the virtual from the physical of the one or more of the surgical instruments or tools and/or one or more of the devices, implants, implant components and systems for implantation in the OHMD display.

In alternative embodiments, one or more of the physical surgical instruments or tools and/or one or more of the physical devices, implants, implant components and systems for implantation can include one or more IMU's, including, for example, with accelerometers, magnetometers, and gyroscopes, similar, for example, to the OHMD. In some embodiments, one or more of the physical surgical instruments or tools and/or one or more of the physical devices, implants, implant components and systems for implantation can include one or more radiofrequency tags or markers or retroreflective markers and the like and its/their position, location and/or orientation can be captured by a surgical navigation system. Optionally, the OHMD may also include one or more radiofrequency tags or markers or retroreflective markers and the like and its position, location and/or orientation can also be captured by the surgical navigation system and cross-referenced to the one or more of the physical surgical instruments or tools and/or one or more of the physical devices, implants, implant components and systems for implantation. One or more of the physical surgical instruments or tools and/or one or more of the physical devices, implants, implant components and systems for implantation can also include light sources, such as lasers or LED's. A laser can be projected, for example, on a wall or a ceiling and the OHMD and the patient can be referenced in relationship to that. An LED attached to or integrated into the one or more of the physical surgical instruments or tools and/or one or more of the physical devices, implants, implant components and systems for implantation can be recognized, for example, by an image and/or video capture system and/or 3D scanner integrated into or attached to or coupled to or separate from the OHMD.

With any of the foregoing techniques, the position, location, orientation, alignment, motional direction, and/or trajectory of the one or more of the physical surgical instruments or tools and/or one or more of the physical devices, implants, implant components and systems for implantation can be determined even though the one or more of the physical surgical instruments or tools and/or one or more of the physical devices, implants, implant components and systems for implantation is only partially or incompletely visualized or visible in the surgical site. A computer program or software can then optionally compute the shape, geometry, outline, surface of other features of the non-visualized, non-visible portions of the one or more of the physical surgical instruments or tools and/or one or more of the physical devices, implants, implant components and systems for implantation. The non-visualized or non-visible portions of the one or more of the physical surgical instruments or tools and/or one or more of the physical devices, implants, implant components and systems for implantation can then optionally be displayed by the OHMD and projected onto the view of the surgical site. Optionally, the non-visualized or non-visible portions of the one or more of the physical surgical instruments or tools and/or one or more of the physical devices, implants, implant components and systems for implantation can be displayed by the OHMD simultaneous with the one or more of the corresponding virtual surgical instruments or tools and/or one or more of the corresponding virtual devices, implants, implant components and systems for implantation. Different colors or display patterns can optionally be used to display and differentiate the virtual from the physical of the one or more of the surgical instruments or tools and/or one or more of the devices, implants, implant components and systems for implantation in the OHMD display.

Difficult Lighting and Tissue Contrast Conditions

In certain situations during surgery or in certain surgical sites, the lighting conditions and tissue contrast may be such that any virtual anatomic data or structures, virtual surgical plans, virtual tool or instrument or device paths, virtual surgical instruments or tools and/or any virtual devices, implants, implant components and systems for implantation may be difficult to see in the OHMD display by the human operator. In any of these circumstances, the system can optionally allow the operator or the surgeon to change the display mode or it can actively change the display mode of one or more the virtual anatomic data or structures, virtual surgical plans, virtual tool or instrument or device paths, virtual surgical instruments or tools and/or the virtual devices, implants, implant components and systems for implantation, for example by changing the color, brightness, intensity, and/or contrast of one or more of the virtual anatomic data or structures, virtual surgical plans, virtual tool or instrument or device paths, virtual surgical instruments or tools and/or the virtual devices, implants, implant components and systems for implantation. Different changes in color, brightness, intensity, and/or contrast can be applied to different virtual data, e.g. virtual anatomic data or structures, virtual surgical plans, virtual tool or instrument or device paths, virtual surgical instruments or tools and/or the virtual devices, implants, implant components and systems for implantation.

The surgeon or operator or the software or the system may change the color of one or more of the virtual anatomic data or structures, virtual surgical plans, virtual tool or instrument or device paths, virtual surgical instruments or tools and/or the virtual devices, implants, implant components and systems for implantation. The surgeon or operator or the software or the system may change the brightness of one or more of the virtual anatomic data or structures, virtual surgical plans, virtual tool or instrument or device paths, virtual surgical instruments or tools and/or the virtual devices, implants, implant components and systems for implantation. The surgeon or operator or the software or the system may change the intensity of one or more of the virtual anatomic data or structures, virtual surgical plans, virtual tool or instrument or device paths, virtual surgical instruments or tools and/or the virtual devices, implants, implant components and systems for implantation. The surgeon or operator or the software or the system may change the contrast of one or more of the virtual anatomic data or structures, virtual surgical plans, virtual tool or instrument or device paths, virtual surgical instruments or tools and/or the virtual devices, implants, implant components and systems for implantation. The surgeon or the operator or the software or the system may change the display pattern of the one or more of the virtual anatomic data or structures, virtual surgical plans, virtual tool or instrument or device paths, virtual surgical instruments or tools and/or the virtual devices, implants, implant components and systems for implantation. For example, one or more of the virtual anatomic data or structures, virtual surgical plans, virtual tool or instrument or device paths, virtual surgical instruments or tools and/or the virtual devices, implants, implant components and systems for implantation may be displayed with a raster pattern or a line pattern or a point pattern or any other display pattern known in the art. Alternatively, one or more of the virtual anatomic data or structures, virtual surgical plans, virtual tool or instrument or device paths, virtual surgical instruments or tools and/or the virtual devices, implants, implant components and systems for implantation may be displayed with a temporally changing display pattern, including, but not limited to a blinking pattern or a flashing pattern, e.g. with only intermittent display of the virtual information. Alternatively, one or more of the virtual anatomic data or structures, virtual surgical plans, virtual tool or instrument or device paths, virtual surgical instruments or tools and/or the virtual devices, implants, implant components and systems for implantation may be displayed with a "skeletonization pattern", wherein, for example, only key features or key outlines of one or more of the virtual anatomic data or structures, virtual surgical plans, virtual tool or instrument or device paths, virtual surgical instruments or tools and/or the virtual devices, implants, implant components and systems for implantation can be displayed. Alternatively, one or more of the virtual anatomic data or structures, virtual surgical plans, virtual tool or instrument or device paths, virtual surgical instruments or tools and/or the virtual devices, implants, implant components and systems for implantation may be displayed with a "highlighting pattern" or mode, wherein, for example, key features or key outlines of one or more of the virtual anatomic data or structures, virtual surgical plans, virtual tool or instrument or device paths, virtual surgical instruments or tools and/or the virtual devices, implants, implant components and systems for implantation may be displayed using an enlargement of the feature or outline or a color or brightness or contrast or other display enhancement of the feature or outline. Optionally, less important features or outline components or portions may be reduced in display intensity or removed from the display. The foregoing display adjustments can be performed via operator controlled commands, e.g. manual or voice or other commands. Alternatively, these adjustments can be semi-automatic with operator input or automatic using, for example, information about brightness, contrast and/or color of the virtual and/or the live data of the patient as well as ambient light conditions, e.g. OR light intensity, light reflections, etc. For semi-automatic or automated adjustment of the display of select, one or more virtual data, e.g. virtual anatomic data or structures, virtual surgical plans, virtual tool or instrument or device paths, virtual surgical instruments or tools and/or the virtual devices, implants, implant components and systems for implantation, light intensity and contrast sensors can be employed which can optionally be integrated into, attached to or separate from one or more OHMDs. Alternatively, the information about color, brightness, intensity, contrast of the live data seen through the OHMD and/or ambient lighting conditions can be obtained through one or more image and/or video capture systems and/or 3D scanner integrated into, attached to or separate from the OHMD.

Any of the foregoing changes to the display of virtual anatomic data or structures, virtual surgical plans, virtual tool or instrument or device paths, surgical instruments or tools and/or the devices, implants, implant components and systems for implantation can also be applied to any partially obscured or non-visible portions of the physical surgical instruments or tools and/or the physical devices, implants, implant components and systems for implantation.

Any of the virtual anatomic data or structures, virtual surgical plans, virtual tool or instrument or device paths, surgical instruments or tools and/or the devices, implants, implant components and systems for implantation described anywhere in the present disclosure can be modified in the display using one or more of these techniques or any other technique of display modification known in the art.

In certain situations during surgery or in certain surgical sites, the lighting conditions and tissue contrast may be such that any obscured portions of the anatomy or obscured pathology or obscured target tissue(s) or deep seated, obscured or hidden portions of the anatomy or target tissue(s) or intended alterations to deep seated tissue(s) may be difficult to see in the OHMD display by the human operator. This includes also normal tissue and normal anatomic structures, hidden or obscured or deep seated. In any of these circumstances, the system can optionally allow the operator or the surgeon to change the display mode or the system can actively change the display mode of the anatomy or deep-seated portions of the anatomy or target tissue(s) or intended alterations to deep seated, obscured or hidden tissue(s). For example, the surgeon or operator may change the color of the anatomy or deep seated, obscured or hidden portions of the anatomy or target tissue(s) or intended alterations to deep seated, obscured or hidden tissue(s). Alternatively, the surgeon or the operator may change the display pattern of the anatomy or deep seated, obscured or hidden portions of the anatomy or target tissue(s) or intended alterations to deep seated, obscured or hidden tissue(s). For example, the anatomy or deep seated, obscured or hidden portions of the anatomy or target tissue(s) or intended alterations to deep seated, obscured or hidden tissue(s) may be displayed with a raster pattern or a line pattern or a point pattern or any other display pattern known in the art. Alternatively, the anatomy or deep seated, obscured or hidden portions of the anatomy or target tissue(s) or intended alterations to deep seated, obscured or hidden tissue(s) may be displayed with a temporally changing display pattern, including, but not limited to a blinking pattern or a flashing pattern, e.g. with only intermittent display of the information. Alternatively, the anatomy or deep seated, obscured or hidden portions of the anatomy or target tissue(s) or intended alterations to deep seated, obscured or hidden tissue(s) may be displayed with a "skeletonization pattern", wherein, for example, only key features or key outlines of the anatomy or deep seated, obscured or hidden portions of the anatomy or target tissue(s) or intended alterations to deep seated, obscured or hidden tissue(s) may be displayed. Alternatively, the anatomy or deep seated, obscured or hidden portions of the anatomy or target tissue(s) or intended alterations to deep seated, obscured or hidden tissue(s) may be displayed with a "highlighting pattern" or mode, wherein, for example, key features or key outlines of the anatomy or deep seated, obscured or hidden portions of the anatomy or target tissue(s) or intended alterations to deep seated, obscured or hidden tissue(s) may be displayed using an enlargement of the feature or outline or a color or brightness or contrast or other display enhancement of the feature or outline. Optionally, less important features or outline components or portions may be reduced in display intensity or removed from the display. Any of the tissues described anywhere in the present disclosure, such as by way of example, a cerebral cortex, gyri, a pedicle, vertebral endplates, an anterior vertebral wall, a posterior vertebral wall, an acetabulum, vessels, nerves, tumors, can be modified in the display using one or more of these techniques or any other method of display modification known in the art.

Any of the foregoing adjustments in color, brightness, intensity, and/or contrast can be applied to 2D or 3D, stereoscopic and non-stereoscopic displays of one or more of the virtual anatomic data or structures, virtual surgical plans, virtual tool or instrument or device paths, virtual surgical instruments or tools and/or the virtual devices, implants, implant components and systems for implantation. If live data of the patient are not directly seen through the OHMD, but are captured through an image and/or video capture system and/or 3D scanner integrated into, attached to or separate from the OHMD and then displayed by the OHMD, optionally in combination with virtual anatomic data or structures, virtual surgical plans, virtual tool or instrument or device paths, virtual surgical instruments or tools and/or the virtual devices, implants, implant components and systems for implantation, the same or similar adjustments can be applied to one or more of the live data of the patient, e.g. select anatomic structures, or all of the live data of the patient.

In some aspects, the present disclosure provides a method for preparing a joint for a prosthesis in a patient. In some embodiments, the method comprises registering the patient's joint and one or more optical head mounted displays worn by a surgeon or surgical assistant in a coordinate system, obtaining one or more intra-operative measurements, registering the one or more intra-operative measurements in the coordinate system, developing a virtual surgical plan based on the one or more intra-operative measurements, and displaying or projecting aspects of the virtual surgical plan superimposed onto the corresponding portions of the patient's joint with the optical head mounted display. In some embodiments, the one or more optical head mounted displays are registered in the same coordinate system. In some embodiments, the one or more intra-operative measurements are morphological measurements, optical measurements or combinations thereof. In some embodiments, the one or more intra-operative measurements are not pressure measurements.

In some aspects, the present disclosure provides a method for preparing an orthopedic procedure in a patient. In some embodiments, the method comprises registering the patient's surgical site and one or more optical head mounted display worn by a surgeon or surgical assistant in a common coordinate system, obtaining one or more intra-operative optical measurements using one or more optical markers, registering the one or more intra-operative optical measurements using one or more optical markers in the common coordinate system, developing a virtual surgical plan based on the one or more intra-operative optical measurements, and displaying or projecting aspects of the virtual surgical plan superimposed onto the corresponding portions of the patient's physical joint with the optical head mounted display. The virtual surgical plan can be displayed or projected onto the patient's physical joint based at least in part on coordinates of the predetermined position of the virtual surgical plan.

In some embodiments, the virtual surgical plan incorporates data from a pre-operative scan. In some embodiments, the virtual surgical plan incorporates data from an intra-operative scan. In some embodiments, the virtual surgical plan incorporates data from a pre-operative scan and an intra-operative scan. The scan includes one or more x-rays, a CT scan, an MRI scan, an ultrasound or combinations thereof.

In some embodiments, the scan data are registered in the common coordinate system. In some embodiments, the registered scan data are displayed superimposed onto the surgical site by the optical head mounted display. In some embodiments, the scan data include a three-dimensional display of the surgical site.

In some embodiments, the registering step includes identifying one or more landmarks in the live surgical site. In some embodiments, one or more corresponding anatomic landmarks are identified in the patient's scan data.

In some embodiments, the registering step includes identifying one or more anatomic axes or biomechanical axes in the live surgical site. In some embodiments, the one or more corresponding anatomic axes or biomechanical axes are identified in the patient's scan data.

In some embodiments, the live surgical site includes one or more of a bone, a cartilage, a joint, a joint surface, an opposing joint surface, a ligament, a meniscus, a labrum, an intra-articular structure, a spinous process, a pedicle, a facet joint, a superior or inferior process or a vertebral body.

In some embodiments, the registering step includes detecting one or more optical markers attached to one or more structures in the live surgical site. In some embodiments, the registering step includes detecting one or more optical markers attached to the OR table. In some embodiments, the detecting of the one or more optical markers includes determining one or more of a position, orientation, alignment, direction of movement or speed of movement of the one or more optical markers.

The optical marker can include a geometric pattern, a QR code, a barcode or combinations thereof. The QR code or barcode can be included in or integrated into or attached to the geometric pattern.

In some embodiments, the optical head mounted display includes one or more cameras or image capture or video capture systems and/or 3D scanner. The one or more cameras or image capture or video capture system and/or 3D scanner s can detect the one or more optical markers including their coordinates (x, y, z).

In some embodiments, the optical marker includes information about implant inventory management. For example, the QR code can include information about implant inventory management.

In some embodiments, the one or more cameras or image capture or video capture systems and/or 3D scanner included in the optical head mounted display reads the inventory management in the QR and transmits it to another computer.

In some embodiments, the intraoperative measurement includes identifying coordinates (x, y, z) of a live anatomic landmark in the patient's joint using one or more optical markers. In some embodiments, the intraoperative measurement includes identifying coordinates (x, y, z) of an anatomic landmark in the intra-operative scan data.

In some embodiments, the one or more optical markers are radiopaque and their coordinates (x, y, z) can be detected in the intra-operative scan data.

In some embodiments, the optical markers are detected using the one or more cameras or image capture or video capture systems and/or 3D scanner included in the optical head mounted display and detected in the intra-operative scan data are registered in the common coordinate system.

In some embodiments, the intraoperative measurement includes identifying an anatomic axis or a biomechanical axis of the patient. The biomechanical axis can be a mechanical axis of the leg. In some embodiments, the intraoperative measurement includes obtaining information from a surgically altered surface.

In some embodiments, the intraoperative measurement includes identifying a center of rotation of a joint of the patient. The joint can be the joint being operated on, or the joint can be a joint different than the joint being operated on.

In some embodiments, the intraoperative measurement includes identifying an anatomic plane. The anatomic plane can be tangent with one or more anatomic landmarks. The anatomic plane can intersect one or more anatomic landmarks. In some embodiments, the anatomic plane can be found by placing a virtual plane to be tangent with or intersect with one or more anatomic landmarks. The virtual plane can be placed using a virtual interface.

In some embodiments, the virtual surgical plan includes predetermined path for a surgical instrument. In some embodiments, the virtual surgical plan includes a projected or intended cut plane. In some embodiments, the virtual surgical plan includes a virtual cut block projected in a desired or intended position, orientation and/or alignment. In some embodiments, the virtual surgical plan includes a projected or intended reaming, milling or impacting axis. In some embodiments, the virtual surgical plan includes a virtual surgical instrument displayed or projected in a desired or predetermined position, orientation, alignment and/or direction of movement. In some embodiments, the virtual surgical plan includes a virtual surgical implant component displayed or projected in a desired or predetermined position, orientation and/or alignment.

In some aspects, the method of preparing a joint for a prosthesis in a patient comprises obtaining scan data associated with the joint of the patient; preparing a virtual surgical plan for the patient's joint based on the scan data; registering the patient's physical joint, the virtual surgical plan, and one or more optical head mounted displays worn by a surgeon or surgical assistant in a common coordinate system, obtaining one or more intra-operative measurements, adjusting or modifying the virtual surgical plan based on the one or more intra-operative measurements, and displaying or projecting aspects of the adjusted or modified surgical plan superimposed onto corresponding portions of the patient's physical joint with the optical head mounted display. In some embodiments, the one or more intra-operative measurements are morphological measurements, optical measurements or combinations thereof.

In some embodiments, the method of preparing an orthopedic procedure in a patient comprises obtaining scan data associated with the surgical site of the patient; preparing a virtual surgical plan for the patient based on the scan data; registering the patient's live surgical site, the virtual surgical plan, and one or more optical head mounted displays worn by a surgeon or surgical assistant in a common coordinate system, obtaining one or more intra-operative measurements; adjusting or modifying the virtual surgical plan based on the one or more intra-operative measurements, and displaying or projecting aspects of the adjusted or modified surgical plan superimposed onto corresponding portions of the patient's live surgical site with the optical head mounted display.

In some embodiments, the one or more intra-operative measurements include one or more optical markers.

In some embodiments, the scan data is obtained pre-operatively and/or intra-operatively. In some embodiments, the scan data include pre-operative and intra-operative scan data. In some embodiments, the scan data include one or more x-rays, a CT scan, an MRI scan, an ultrasound or combinations of the foregoing.

In some embodiments, the scan data are registered in the common coordinate system. In some embodiments, the registered scan data are displayed superimposed onto the surgical site by the optical head mounted display.

In some embodiments, the scan data include a three-dimensional display of the surgical site.

In some embodiments, the registering includes identifying one or more anatomic landmarks in the patient's scan data. In some embodiments, the registering includes identifying one or more corresponding landmarks in the live surgical site. In some embodiments, the registering includes identifying one or more anatomic axes or biomechanical axes in the patient's scan data. In some embodiments, the registering includes identifying one or more corresponding anatomic axes or biomechanical axes in the live surgical site.

In some embodiments, the live surgical site includes one or more of a bone, a cartilage, a joint, a joint surface, an opposing joint surface, a ligament, a meniscus, a labrum, an intra-articular structure, a spinous process, a pedicle, a facet joint, a superior or inferior process or a vertebral body.

In some embodiments, the registering includes detecting one or more optical markers attached to one or more structures in the live surgical site. In some embodiments, the registering includes detecting one or more optical markers attached to the OR table. In some embodiments, the detecting of the one or more optical markers includes determining one or more of a position, orientation, alignment, direction of movement or speed of movement of the one or more optical markers.

The optical marker can include a geometric pattern, a QR code, a barcode or combinations thereof. The QR code or barcode can be included in or integrated into or attached to the geometric pattern.

In some embodiments, the optical head mounted display includes one or more cameras or image capture or video capture systems and/or 3D scanner. The one or more cameras or image capture or video capture systems and/or 3D scanner can detect the one or more optical markers including their coordinates (x, y, z).

In some embodiments, the optical marker includes information about implant inventory management. For example, the QR code can include information about implant inventory management.

In some embodiments, the QR code includes information about implant inventory management. In some embodiments, the one or more cameras or image capture or video capture systems and/or 3D scanner included in the optical head mounted display reads the inventory management in the QR and transmits it to another computer.

In some embodiments, the intraoperative measurement includes identifying coordinates (x, y, z) of a live anatomic landmark in the patient's joint using one or more optical markers. In some embodiments, the intraoperative measurement includes identifying coordinates (x, y, z) of an anatomic landmark in the intra-operative scan data.

In some embodiments, the one or more optical markers are radiopaque and their coordinates (x, y, z) can be detected in the intra-operative scan data.

In some embodiments, the optical markers are detected using the one or more cameras or image capture or video capture systems and/or 3D scanner included in the optical head mounted display and detected in the intra-operative scan data are registered in the common coordinate system.

In some embodiments, the intraoperative measurement includes identifying an anatomic axis or a biomechanical axis of the patient. For example, the biomechanical axis can be a mechanical axis of the leg.

In some embodiments, the intraoperative measurement includes identifying a center of rotation of a joint of the patient. The joint can be the joint being operated on or a joint different than the joint being operated on.

In some embodiments, the intraoperative measurement includes identifying an anatomic plane. The anatomic plane can be tangent with one or more anatomic landmarks. The anatomic plane can intersect one or more anatomic landmarks. In some embodiments, the anatomic plane is found by placing a virtual plane to be tangent with or intersect with one or more anatomic landmarks. The virtual plane can be placed using a virtual interface.

In some embodiments, the intraoperative measurement includes obtaining information from a surgically altered surface.

In some embodiments, the adjusting or modifying the virtual surgical plan includes placing or moving a predetermined path for a surgical instrument. In some embodiments, the adjusting or modifying the virtual surgical plan includes the placing or moving of a virtual cut plane. In some embodiments, the adjusting or modifying the virtual surgical plan includes the placing or moving of a virtual cut block. In some embodiments, the adjusting or modifying the virtual surgical plan includes the placing or moving of a virtual reaming, milling or impacting axis. In some embodiments, the adjusting or modifying the virtual surgical plan includes the placing or moving of a virtual surgical instrument. In some embodiments, the adjusting or modifying the virtual surgical plan includes the placing or moving of a virtual surgical implant component.

According to some embodiments, the method of preparing a joint for a prosthesis in a patient comprises registering the patient's live surgical site and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative measurements, the virtual surgical plan including at least one virtual cut plane, and displaying or projecting the one or more virtual cut planes superimposed onto the corresponding portions of the patient's live surgical site with the optical head mounted display.

According to some embodiments, the method of preparing a joint for a prosthesis in a patient comprises registering the patient's live surgical site and an optical head mounted display worn by a surgeon or surgical assistant in a common coordinate system, developing a virtual surgical plan, registering the virtual surgical plan in the common coordinate system, the virtual surgical plan including at least one virtual cut plane, and displaying or projecting the at least one virtual cut planes superimposed onto the corresponding portions of the patient's live surgical site with the optical head mounted display. In some embodiments, the method further comprises obtaining one or more intra-operative measurements. In some embodiments, the method further comprises registering the one or more intra-operative measurements in the common coordinate system. In some embodiments, the one or more intra-operative measurements comprise intra-operative morphological and optical measurements.

In some embodiments, the prosthesis is a knee replacement and the virtual cut plane defines a tibial slope after implantation of the tibial implant component(s). In some embodiments, the prosthesis is a knee replacement and the virtual cut plane defines an angle of varus or valgus correction in relationship to the patient's mechanical axis of the leg for a tibial component and related bone cuts. In some embodiments, the prosthesis is a knee replacement and the virtual cut plane defines an angle of varus or valgus correction in relationship to the patient's mechanical axis of the leg for a femoral component and related bone cuts. In some embodiments, the prosthesis is a knee replacement and the virtual cut planes define an angle of varus or valgus correction in relationship to the patient's mechanical axis of the leg for a femoral component and a tibial component and related bone cuts including a combined correction. In some embodiments, the prosthesis is a knee replacement and the virtual cut plane corresponds to a distal femoral cut and defines a femoral component flexion. In some embodiments, the prosthesis is a knee replacement and the virtual cut plane corresponds to an anterior femoral cut and defines a femoral component rotation. In some embodiments, the prosthesis is a knee replacement and the virtual cut plane corresponds to a posterior femoral cut and defines a femoral component rotation. In some embodiments, the prosthesis is a knee replacement and the virtual cut plane corresponds to chamfer cut and defines a femoral component rotation. In some embodiments, the prosthesis is a hip replacement and wherein the virtual cut plane defines a leg length after implantation.

According to some embodiments, the method for preparing a joint for a prosthesis in a patient comprises registering the patient's live surgical site and one or more optical head mounted displays worn by a surgeon or surgical assistant in a common coordinate system, developing a virtual surgical plan, registering the virtual surgical plan in the common coordinate system, the virtual surgical plan including at least two or more projected or intended pin or drill paths, and displaying or projecting the two or more projected or intended pin or drill paths superimposed onto the corresponding portions of the patient's bone or cartilage in the live surgical site with the optical head mounted display.

In some embodiments, a first physical pin or drill is aligned with the first virtual pin or drill path and the pinning or drilling is executed while maintaining the alignment. In some embodiments, a second physical pin or drill is aligned with the second virtual pin or drill path and the pinning or drilling is executed while maintaining the alignment. In some embodiments, the first and second pins or drills are used to fixate or reference a surgical guide or cut block. In some embodiments, the drill holes created by the physical first and second pins or drills are used to fixate or reference a surgical guide or cut block.

In some embodiments, the surgical guide or cut block is used to execute a bone cut. The bone cut can define a leg length based on the virtual surgical plan. The bone cut can define a varus or valgus correction based on the virtual surgical plan. The bone cut can define a femoral component flexion based on the virtual surgical plan. The bone cut can define a femoral component rotation based on the virtual surgical plan. The bone cut can determine a tibial slope based on the virtual surgical plan. In some embodiments, the bone cut is a keel punch and determines a tibial component rotation based on the virtual surgical plan.

According to some aspects, the method for preparing a joint for a prosthesis in a patient comprises registering the patient's joint and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative [morphological or optical] measurements, the virtual surgical plan including a virtual surgical drill guide, and displaying or projecting the virtual drill guide superimposed onto the corresponding portions of the patient's live surgical site intended for the drilling with the optical head mounted display. In some embodiments, the one or more intra-operative measurements are morphological and/or optical measurements. In some embodiments, the physical drill corresponding to the virtual drill guide includes at least two openings to accommodate two or more drills. In some embodiments the virtual drill guide corresponds to a physical drill guide and has at least one or more dimensions similar to the physical drill guide. According to some aspects, the method for preparing a joint for a prosthesis in a patient comprises registering the patient's joint and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative measurements, the virtual surgical plan including at least one virtual axis for a reamer, a mill or an impactor, and displaying or projecting the at least one virtual axis for a reamer, a mill or an impactor superimposed onto the corresponding portions of the patient's live surgical site with the optical head mounted display.

According to some aspects, the method for preparing a joint for a prosthesis in a patient comprises registering the patient's joint and an optical head mounted display worn by a surgeon or surgical assistant in a common coordinate system, developing a virtual surgical plan, registering the virtual surgical plan in the common coordinate system, the virtual surgical plan including at least one virtual axis for a reamer, a mill or an impactor, and displaying or projecting the at least one virtual axis for a reamer, a mill or an impactor superimposed onto the corresponding portions of the patient's live surgical site with the optical head mounted display. In some embodiments, the method further comprises obtaining one or more intra-operative measurements. In some embodiments, the method further comprises registering the one or more intra-operative measurements in the common coordinate system.

In some embodiments, the prosthesis is a hip replacement and the virtual axis defines an acetabular anteversion after implantation of the acetabular component(s) based on the virtual surgical plan. In some embodiments, the prosthesis is a hip replacement and the virtual axis defines an acetabular offset after implantation of the acetabular component(s) based on the virtual surgical plan. In some embodiments, the prosthesis is a hip replacement and the virtual axis defines a combined acetabular and femoral component anteversion. A physical reamer, mill or impactor can be aligned with the virtual axis for the reamer, mill or impactor and the reaming, milling or impacting can be executed while maintaining the alignment.

According to some aspects, the method for preparing a joint for a prosthesis in a patient comprises registering the patient's live surgical site and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative measurements, the virtual surgical plan including a virtual tibial template, and displaying or projecting the virtual tibial template superimposed onto the cut tibia with the optical head mounted display.

In some embodiments, the physical tibial template is aligned with the virtual cut tibial template, a tibial keel punch is inserted, and the proximal tibia is punched to accommodate the tibial keel and fins.

In some embodiments, the virtual and the physical tibial template determine the alignment and rotation of the tibial implant component.

According to some aspects, the method for preparing an orthopedic procedure in a patient comprises registering the patient's surgical site and one or more optical head mounted displays worn by a surgeon or surgical assistant in a common coordinate system, wherein the registration of the patient's surgical site in the common coordinate system is performed using one or more optical markers attached to the patient in or around the surgical site, wherein the optical marker includes one or more geometric patterns, wherein the optical markers are detected with a camera, an image capture or video system integrated into, attached to or separate from the optical head mounted display. In some embodiments, the optical marker includes at least one portion that is radiopaque. In some embodiments, internal structures of the patient or the surgical site are visualized using an imaging test with ionizing radiation. For example, the imaging test can be one or more x-rays and/or a CT scan.

In some embodiments, the radiopaque portions of the optical marker are detected on the imaging test using image processing software. In some embodiments, the radiopaque portions of the optical marker detected on the imaging test are cross-referenced with the visible portions of the optical marker detected with the camera, image capture or video system and wherein the information is used to register the internal structures of the patient or the surgical site in the common coordinate system.

In some embodiments, the optical head mounted display displays the internal structures of the patient or the surgical site superimposed onto the corresponding external surfaces of the patient or the surgical site. In some embodiments, the optical head mounted display superimposes a virtual surgical plan onto the corresponding external and internal structures. The virtual surgical plan can be a predetermined path for a surgical device.

Examples

The following examples show representative applications of various embodiments of the present disclosure. The examples are not meant to be limiting. Someone skilled in the art will recognize other applications or modifications of the methods, techniques, devices and systems described. Any embodiment described for one joint or anatomic region, e.g. a spine or pedicle, can be applied to other joints or other regions, e.g. a hip, hip replacement, knee, knee replacement, vascular imaging study, angiography etc.

In some embodiments, when a physical guide, tool, instrument or implant is aligned with or superimposed onto a virtual surgical guide, tool, instrument or implant displayed or projected by the OHMD, the aligning or superimposing can be performed with a location accuracy of about 10 mm, about 9 mm, about 8 mm, about 7 mm, about 6 mm, about 5 mm, about 4 mm, about 3 mm, about 2 mm, about 1 mm, about 0.5 mm, about 0.25 mm, or less, 0.25 mm to 0.5 mm, 0.25 mm to 1 mm, 0.25 mm to 2 mm, 0.25 mm to 3 mm, 0.25 mm to 4 mm, 0.25 mm to 5 mm, 0.25 mm to 6 mm, 0.25 mm to 7 mm, 1 mm to 2 mm, 1 mm to 3 mm, 1 mm to 4 mm, 1 mm to 5 mm, 1 mm to 6 mm, 1 mm to 7 mm, 2 mm to 3 mm, 2 mm to 4 mm, 2 mm to 5 mm, 2 mm to 6 mm, 2 mm to 7 mm, 3 mm to 4 mm, 3 mm to 5 mm, 3 mm to 6 mm, 3 mm to 7 mm, 4 mm to 5 mm, 4 mm to 6 mm, 4 mm to 7 mm, 5 mm to 6 mm, 5 mm to 7 mm, 6 mm to 7 mm or as needed depending on the clinical application, in one, two or three directions, x, y, z. When the physical guide, tool, instrument or implant is aligned with or superimposed onto the virtual surgical guide, tool, instrument or implant displayed or projected by the OHMD, the aligning or superimposing can be performed with an orientation or angle accuracy of about 10°, about 9°, about 8°, about 7°, about 6°, about 5°, about 4°, about 3°, about 2°, about 1°, about 0.5°, about 0.25° or less, 0.25-10°, 0.25 to 9°, 0.25-8°, 0.25-7°, 0.25-6°, 0.25-5°, 0.25-4°, 0.25-3°, 0.25-2°, 0.25-1°, 0.25-0.5°, 0.5 to 9°, 0.5-8°, 0.5-7°, 0.5-6°, 0.5-5°, 0.5-4°, 0.5-3°, 0.5-2°, 0.5-1°, 1 to 9°, 1-8°, 1-7°, 1-6°, 1-5°, 1-4°, 1-3°, 1-2°, 2-9°, 2-8°, 2-7°, 2-6°, 2-5°, 2-4°, 2-3°, 3-9°, 3-8°, 3-7°, 3-6°, 3-5°, 3-4°, 4-9°, 4-8°, 4-7°, 4-6°, 4-5°, 5-9°, 5-8°, 5-7°, 5-6°, 6-9°, 6-8°, 6-7°, 7-9°, 7-8°, 8-9° or as needed depending on the clinical application, in one, two or three directions, x, y, z.

The mechanical axis of the lower extremity is determined by drawing a line from the center of the femoral head to the center of the ankle joint, which corresponds typically to an approximately 3° slope compared with that of the vertical axis. This can be subdivided into the femoral mechanical axis, which runs from the head of the femur to the intercondylar notch of the distal femur, and the tibial mechanical axis, which extends from the center of the proximal tibia to the center of the ankle. The medial angle formed between the mechanical axis of the femur and the mechanical axis of the tibia is called the hip-knee-ankle angle, which represented the overall alignment of the lower extremity and is usually about or slightly less than 180° in normal knees, also called normal mechanical axis alignment. The position of the mechanical axis causes it to usually pass just medial to the tibial spine, but this can vary widely based on the patient height and pelvic width.

Pedicle Screw, Spinal Rod Placement for Example for Correction of Spinal Deformities, Scoliosis and/or Fracture Treatment Pedicle screw and rod placement is one of the most common spinal procedures. It can be performed for a number of different conditions, including, for example, spinal instability, correction of spinal deformities, e.g. scoliosis, kyphosis and combinations thereof, as well as congenital spinal defects. Pedicle screw and rod placement can be combined with bone graft, e.g. allograft or autograft. Sometimes, infusible or injectable bone morphogenic protein can be used during the procedure to facilitate healing and stabilization of bone graft.

Preoperatively, patients will commonly undergo x-ray imaging, for example in anteroposterior, lateral and oblique views. Special views of select regions, e.g. the sacrum or the occipito-atlantic junction can be obtained. X-rays can be obtained in standing and lying position. X-rays can also be obtained in prone or supine position. X-rays may be obtained with the patient erect, spinal flexion and spinal extension. X-rays may also be obtained with the patient bending to the left side or to the right side.

Patients may optionally undergo CT scanning or MRI scanning. CT scanning and MRI scanning have the added advantage of providing a 3D dataset of the patient's anatomy. Moreover, the thecal sac and the nerve roots can be visualized. With MRI, the spinal cord can also be visualized.

Virtual Surgical Plan

The surgeon can develop a virtual surgical plan for the pedicle screw and rod placement which can optionally incorporate any desired deformity correction. Typical criteria for placement of pedicle screws can include the following:

The entry point of the pedicle screw and any awl, probe, tap, k-wire, y-wire, other wires, and other surgical instruments can be chosen, for example, to be at the lateral border of the superior articular process with the intersect to a horizontal line bisecting the transverse processes on the left and right side.

In the lumbar spine, the trajectory of the pedicles will typically converge 5-10 degrees in the upper lumbar spine, 10-15 degrees in the lower lumbar spine. Typically, no cephalad or caudad tilt of the trajectory is needed in the lumbar spine.

In the thoracic spine, the entry point can be just below the rim of the upper facet joint, and approximately 3 mm lateral to the center of the joint near the base of the transverse process. In the thoracic spine, the pedicles and with that the screws can converge to the midline at approximately 7-10 degrees; in the sagittal plane, they can be oriented 10-20 degrees caudally. In accessing T12, the virtual surgical plan can include removal of transverse process to open the marrow space. The angulation can be medial and caudal angulation.

Surgeon can generally use between a lateral intersection method for pedicle screw placement, with the lateral border of the superior articular processes forming an intersect to a horizontal line bisecting the transverse processes on the left and right side. A more medial entry point can be chosen, in which case a rangeur may be required to remove the base of the articular process. This can be included in the virtual surgical plan.

For S1, the entry point can be chosen at the intersect of a vertical line tangential to the S1 articular process and a horizontal line tangential to its inferior border. Typically, at S1, pedicle screws converge, but an overhanging pelvis may limit this in vivo. The screws will typically aim at the superior border of sacral promontory. The instrument placement and the pedicle screw placement in the virtual surgical plan will be selected or defined in a manner where the pedicle screw and/or the instruments will avoid the S1 foramen and any nerve roots. If bicortical screws are used, the screw position will be selected or oriented in order to avoid any injury to the L5 nerve roots; any imaging test such as a CT scan or an MRI scan can be used to identify the L5 nerve root and to place the pedicle screw(s) in the virtual surgical plan, with optional display of the CT or MRI scan and the nerve root, so that its tip and body have a safety margin relative to the nerve root.

The virtual surgical plan can comprise a 2D or 3D display of the spinal structures. The 2D display can be a multiplanar display, for example showing the spine in axial, oblique axial, sagittal, oblique or curved sagittal, coronal, oblique or curved coronal projections. A 3D display can show the spine, for example, from a posterior projection, an anterior projection, a lateral projection, a projection from the top or the bottom, or a projection along a nerve root or the thecal sac or the cord. Representative bony structures that can be displayed in this manner include, for example, the spinous processes, the lamina, the facet joints, the pedicles and the vertebral bodies including the endplates, anterior, posterior, medial and lateral cortex. In some embodiments, the view perspective will be the perspective that the surgeon's head and the OHMD have relative to the surgical field and the patient. The perspective can be different for the left eye display and the right eye display, in particular when stereoscopic display technique is used, with substantially identical view angles of the virtual data of the patient seen by the surgeon's left eye through the display of the OHMD unit and the live data of the patient seen by the surgeon's left eye through the OHMD unit and substantially identical view angles of the virtual data of the patient seen by the surgeon's right eye through the display of the OHMD unit and the live data of the patient seen by the surgeon's right eye through the OHMD unit.

In some embodiments, the thecal sac, neural structures and nerve roots, e.g. L4, L5, and S1 are highlighted in the surgical plan in addition to the bony structures. The nerve roots can be highlighted using segmentation techniques known in the art, e.g. automatic or semi-automatic or manual segmentation. Alternatively, an operator or a surgeon can click on the nerve root in the vicinity of a pedicle or intended pedicle screw placement. The location of the click can be stored in the image data volume and can be highlighted with a different color. The area or volume that includes the click can be registered as a safety zone which the pedicle screw and any instruments used for the placement should not enter. A safety margin, e.g. of 2, 3, 4, 5, 7 or 10 mm can be added to the safety zone. The surgical plan and the placement or position or orientation of any pedicle screw and related instrumentation will be modified or adapted during the virtual planning to ensure that no nerve damage or impingement will be caused by the surgical procedure.

In some embodiments, vascular structures can be highlighted using automated, semi-automated, or manual segmentation techniques or simple clicks or image markings performed by a surgeon or operator. Such vascular structures can, for example, include the aorta, the inferior vena cava, any branches of the aorta or the inferior vena cava, intercostal arteries, the innominate artery. A safe zone and/or a safety margin of 2, 3, 4, 5, 7 or 10 mm or more mm can be defined around these vascular structures. The surgical plan and the placement or position or orientation of any pedicle screw and related instrumentation will be modified or adapted during the virtual planning to ensure that no vascular damage will be caused in the surgical procedure.

The virtual surgical plan can include
Identifying the desired pedicle screw position and/or location and/or orientation
Identifying the desired position and/or location and/or orientation and/or trajectory of any surgical instrument used for placing the pedicle screw, e.g. an awl, a probe, a wire, a tab, a screw driver and the like, including the pedicle screw itself.
Identifying the desired rod position and/or location and/or orientation
Identifying the desired spinal deformity correction if applicable, e.g. correction of kyphosis, lordosis, scoliosis, sagittal deformity, coronal deformity, rotational deformity, facture deformity
Identifying sensitive structures, e.g. neural structures, nerve roots, vascular structures
Defining safe zone, e.g. for cortical penetration, e.g. in a pedicle, neural structures, nerve roots and/or vascular structures The virtual surgical plan can include, optionally predefined, criteria to automated or semi-automated virtual placement of a pedicle screw in the patient's data. Such criteria can include the distance between the pedicle screw or related bone void to accept the pedicle screw to the medial, lateral, superior, and/or inferior endosteal surface or cortical surface in portions or all of the pedicle or the area or volume between pedicle screw or related bone void to accept the pedicle screw to the medial, lateral, superior, and/or inferior endosteal surface or cortical surface in portions or all of the pedicle. If the surgeon manually, visually places the virtual pedicle screw on the 2D or 3D display, the same or similar criteria can be applied by the software to highlight potential areas that may result in clinical problems, e.g. a cortical breach or a nerve root injury. For example, if a virtual pedicle screw comes within 1, 2, or 3 mm of the medial cortex of a pedicle, the software, using image processing and segmentation of the bone, endosteal bone or cortical bone, can highlight such proximity and potential risk. The highlighting can occur, for example, by color coding areas of proximity to a cortex or to a neural or vascular structure or by other visual cues and acoustic warning signals. Such highlighted areas can optionally also be displayed by the OHMD during the surgical procedure, stereoscopically or non-stereoscopically. Optionally, highlighted areas can be displayed in outline format.

The selection of a size, width, diameter or length of a pedicle screw can also be performed in a manual, semi-automatic or automatic matter using criteria such as the distance between the pedicle screw or related bone void to accept the pedicle screw to the medial, lateral, superior, and/or inferior endosteal surface or cortical surface in portions or all of the pedicle or the area or volume between pedicle screw or related bone void to accept the pedicle screw to the medial, lateral, superior, and/or inferior endosteal surface or cortical surface in portions or all of the pedicle.

The surgeon can place the digital hologram of the virtual pedicle screw manually, for example using a virtual interface, on the virtual display of the patient's hidden subsurface anatomy using criteria such as location of the pedicle screw including its tip in the vertebral body, location of the pedicle screw including its tip in relationship to a spinal/vertebral body fracture, location of the pedicle screw including its tip in relationship to a superior endplate, location of the pedicle screw including its tip in relationship to an inferior endplate, location of the pedicle screw including its tip in relationship to an anterior vertebral cortex and/or a posterior vertebral cortex, location of the pedicle screw including its tip in relationship to a vessel, location of the pedicle screw including its tip in relationship to the aorta, location of the pedicle screw including its tip in relationship to the inferior vena cava, location of the pedicle screw including its tip in relationship to neural structures, the thecal sac, nerve roots and/or the spinal cord, distance, area or volume between the pedicle screw including its tip to a spinal/vertebral body fracture, distance, area or volume between the pedicle screw including its tip to a superior endplate, distance, area or volume between of the pedicle screw including its tip to an inferior endplate, distance, area or volume between the pedicle screw including its tip to the an anterior and/or posterior vertebral cortex, distance, area or volume between the pedicle screw including its tip to a vessel, distance, area or volume between the pedicle screw including its tip to the aorta, distance, area or volume between the pedicle screw including its tip to the inferior vena cava, distance, area or volume between the pedicle screw including its tip to neural structures, the thecal sac, nerve roots and/or the spinal cord. The surgeon can use this information on location or distance or area or volume also to select the size, width, diameter or length of the pedicle screw in the virtual surgical plan or using the virtual representations of the pedicle screw(s) and the patient's anatomy. Safe zone criteria can be defined for the foregoing criteria, for example 1, 2 or 3 or 5 or more mm from a cortex or a neural structure. If the surgeon places the pedicle screw or any related surgical instruments for the placement of the pedicle screw too close to the safe zone or within the safe zone, the area can be highlighted or another visual or acoustic alert can be triggered by the software.

Alternatively, the software can place the pedicle screw automatically or semi-automatically on the virtual display of the patient using criteria such as location of the pedicle screw including its tip in the vertebral body, location of the pedicle screw including its tip in relationship to a spinal/vertebral body fracture, location of the pedicle screw including its tip in relationship to a superior endplate, location of the pedicle screw including its tip in relationship to an inferior endplate, location of the pedicle screw including its tip in relationship to the an anterior and/or posterior vertebral cortex, location of the pedicle screw including its tip in relationship to a vessel, location of the pedicle screw including its tip in relationship to the aorta, location of the pedicle screw including its tip in relationship to the inferior vena cava, location of the pedicle screw including its tip in relationship to neural structures, the thecal sac, nerve roots and/or the spinal cord, distance, area or volume between the pedicle screw including its tip to a spinal/vertebral body fracture, distance, area or volume between the pedicle screw including its tip to a superior endplate, distance, area or volume between of the pedicle screw including its tip to an inferior endplate, distance, area or volume between the pedicle screw including its tip to the an anterior and/or posterior vertebral cortex, distance, area or volume between the pedicle screw including its tip to a vessel, distance, area or volume between the pedicle screw including its tip to the aorta, distance, area or volume between the pedicle screw including its tip to the inferior vena cava, distance, area or volume between the pedicle screw including its tip to neural structures, the thecal sac, nerve roots and/or the spinal cord. The software can use the information on location or distance or area or volume can also to select the size, width, diameter or length of the pedicle screw in the virtual surgical plan. Safe zone criteria can be defined for the foregoing criteria, for example 1, 2 or 3 or more mm from a cortex or a neural structure. If the software cannot place the pedicle screw or any related surgical instruments for the placement of the pedicle screw without violating one of the safe zones or places it too close to the safe zone, the area can be highlighted or another visual or acoustic alert can be triggered by the software. The surgeon can then manually adjust the virtual position of the pedicle screw or any related surgical instruments for the placement of the pedicle screw such as an awl, a probe, a needle, a wire, a tap and the like.

The virtual surgical plan can only simulate the final desired placement of the pedicle screw(s) and any related rods. The desired trajectory of any surgical instruments used for placing the pedicle screw such as an awl, a probe, a needle, a wire, a tap and the like can then be projected during the surgery based on the virtual surgical plan and the final desired placement position of the pedicle screw(s) and any related rods.

In some embodiments, each instrument or, for example, the principal instruments used for the placement of the pedicle screw(s) and/or the rods can be displayed during the surgery in the virtual display. The physical instruments seen through the OHMD can be aligned with the corresponding virtual instruments displayed by the OHMD, optionally in 3D, stereoscopic or non-stereoscopic, thereby achieving the desired surgical alterations, for example according to the virtual surgical plan.

Figure 17A:
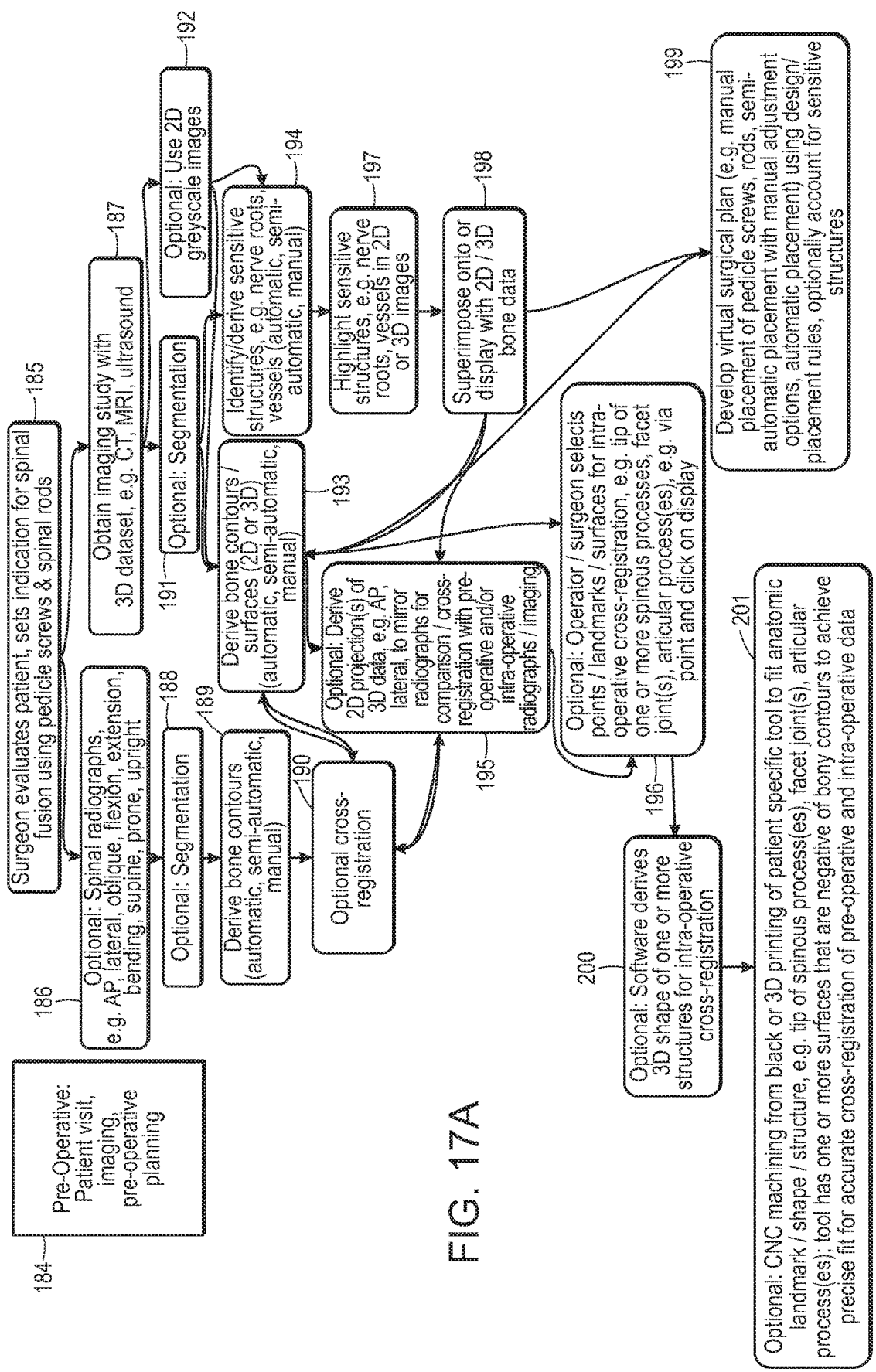
FIGS. 17A-D are illustrative flow charts of select options and approaches for performing spine surgery in a mixed reality environment according to some embodiments of the present disclosure.

FIGS. 17A-D are illustrative flow charts of select options and approaches for performing spine surgery in a mixed reality environment. In FIG. 17A, pre-operative patient visit, imaging, pre-operative planning 184, a surgeon evaluates a patient and sets the indication for spinal fusion using pedicle screws and spinal rods 185. Optionally spinal radiographs 186 and/or 3D imaging, e.g. CT or MRI 187, can be obtained. Optionally the data can be segmented 188 and 191. Optionally 2D data can be used 192. Bone contours can be derived automatically, semi-automatically or manually 189 from the radiographs 189 or CT or MRI 193. Optionally, sensitive structures such as nerve roots and vessels can be determined 194 and superimposed on the display of the 2D or 3D bone data 198. Bone contours from radiographs and other imaging studies such as CT or MRI can optionally be cross-registered, e.g. using coordinate transfer or using registration in a common coordinate system 190. Optionally, 2D projections of 3D data can be generated, for example to generate matching projections that can align with and/or be superimposed with intra-operative radiographs 195. Optionally, a surgeon or operator can select points or landmarks or surfaces for intra-operative registration 196. Bone contours 189 and/or 193 and other data, e.g. 198, 197, 196 can be used to develop a virtual surgical plan for placement of the pedicle screw(s) and rod(s) 199. Optionally, the shape of one or more structures used for intra-operative registration can be derived 200 using software as described for example in Data Segmentation. Optionally, a patient specific template can be generated for the spine 201, as described, for example in WO9325157A1.

Figure 17B:
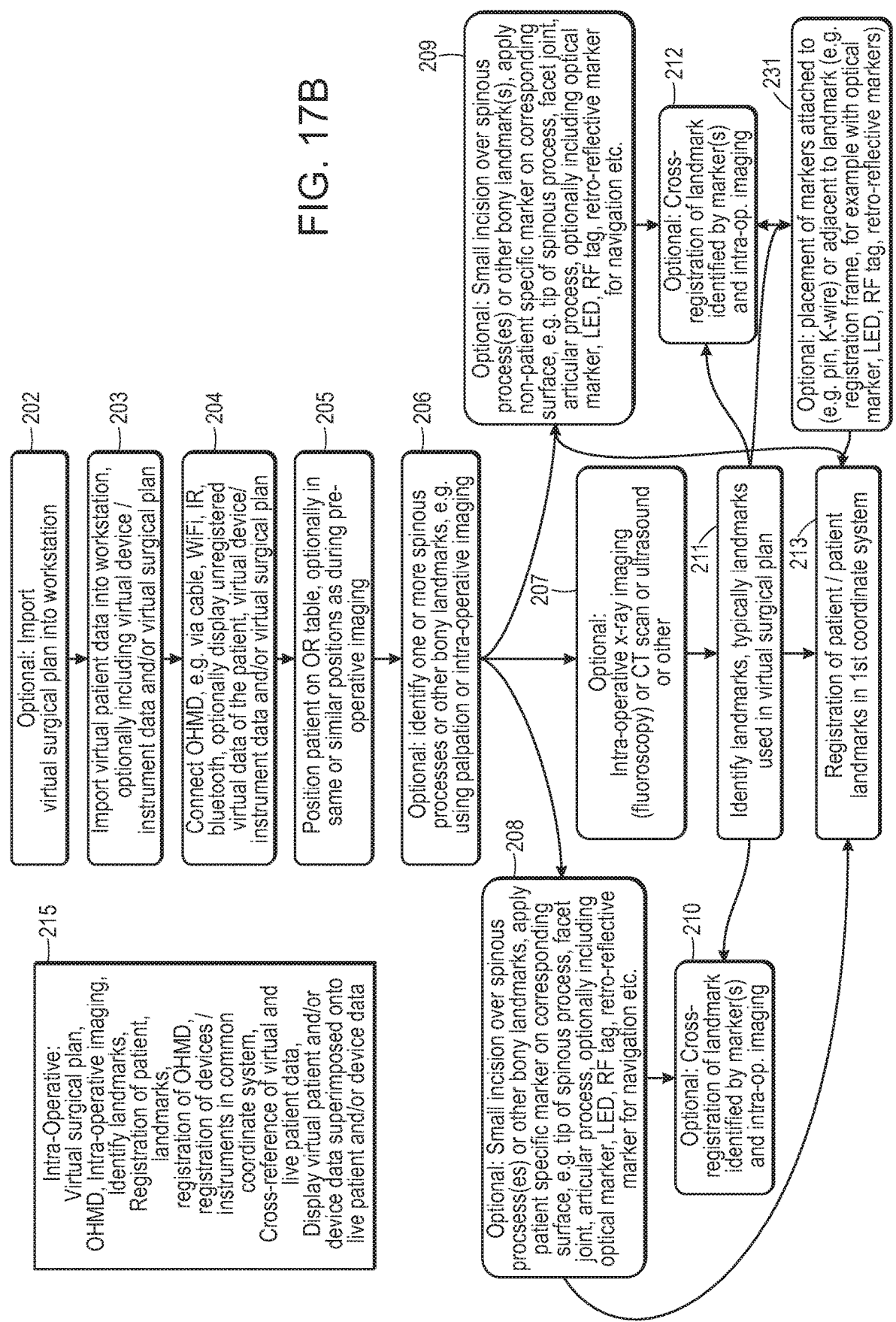

In FIG. 17B, intra-operative virtual surgical plan, imaging, landmarks, registration, cross-reference of virtual and live patient data 215, the data from FIG. 17A, e.g. 189, 193, 194, 195, 199, 200, can be imported into a workstation 202. The virtual data of the patient can also be imported, optionally including virtual instrument data, virtual device data and/or the virtual surgical plan 203. The OHMD can be connected to the workstation 204 and can, optionally, display unregistered virtual data 204. The patient can be positioned on the OR table, optionally in the same position as that used for pre-operative imaging 205. Step 205 can optionally be performed before 202, 203 and 204. Optionally, one or more spinous processes or other bone landmarks or skin references can be identified 206. Optionally, intra-operative imaging can be performed 207 using, for example, x-rays or CT/O-arm imaging 207. Optionally, an incision can be performed over a spinous process and a patient specific marker or template, an optical marker or other markers can be applied for registration 208 and 209. Landmarks, e.g. ones used in the virtual surgical plan 199, can be identified 211, and can optionally be cross-referenced or registered with landmarks identified by intra-operative imaging or patient specific markers or optical markers or other markers 210 and 212, for example in a common coordinate system, e.g. with the OHMD, or in different coordinate systems using coordinate transfers. The patient can then be registered in a common, e.g. first, coordinate system 213. Optionally, markers can be attached to rigid structures fixed to the spine and/or landmarks 231.

Figure 17C:
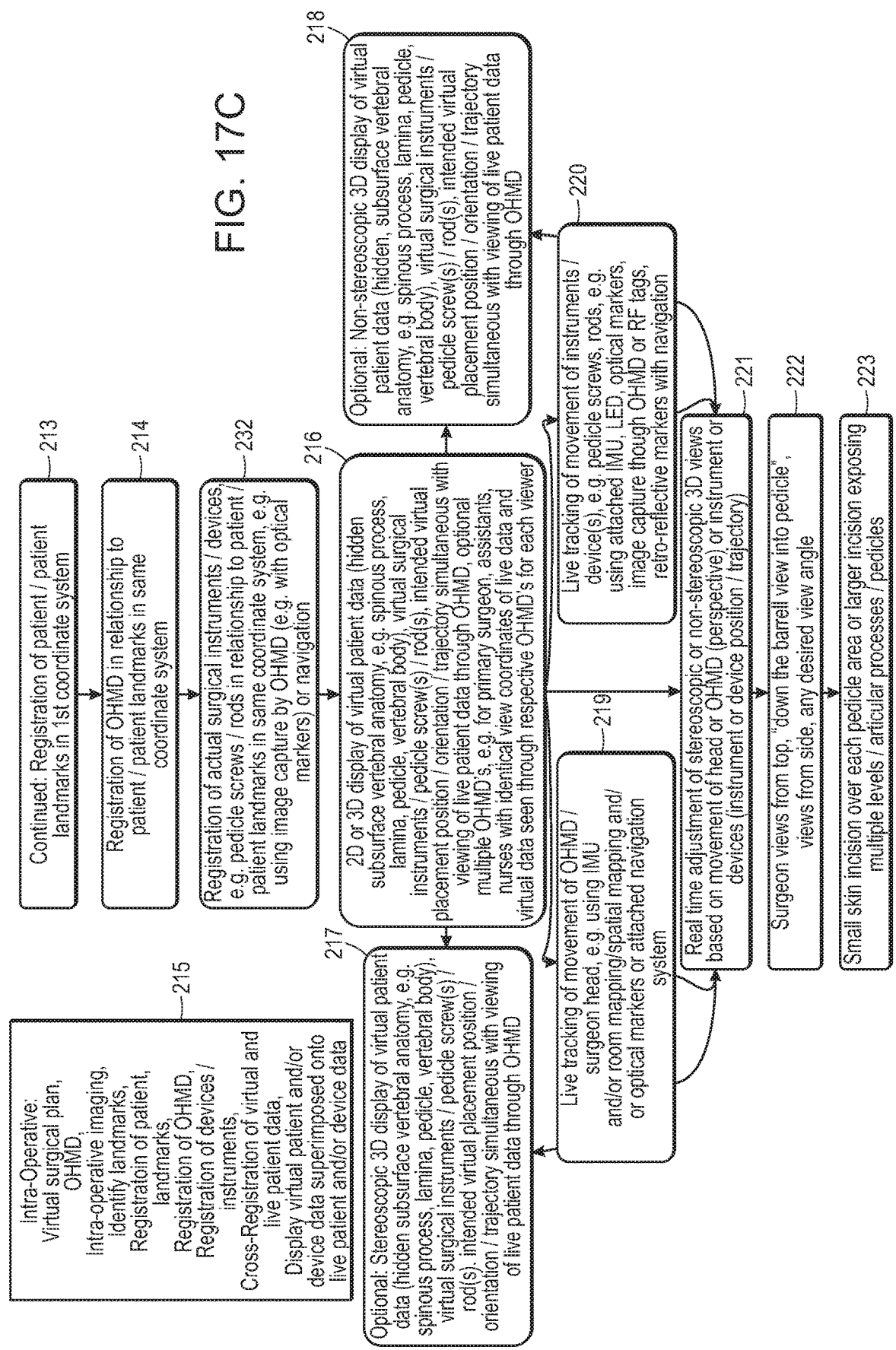

In FIG. 17C, continuation of intra-operative virtual surgical plan, imaging, landmarks, registration, cross-reference of virtual and live patient data 215, after the registration of patient landmarks 213 one or more OHMD/s can be registered in relationship to the patient or patient landmarks 214, e.g. using spatial mapping or optical markers or navigation markers or combinations thereof or any other registration technique described in the application. Actual surgical instruments such as awls and pins and implants such as pedicle screws and rods can also be registered 232. A 2D or 3D display can be generated, which can include hidden subsurface anatomy, e.g. of a vertebral body, pedicle, facet joints, virtual surgical instruments and virtual implants 216. These can be superimposed with and aligned with the corresponding live data of the patient, e.g. the center of a pedicle in which an awl or a screw can be placed in a predetermined position 216. Stereoscopic 217 and non-stereoscopic 218 displays can be generated. Multiple viewers can see the virtual data and the live data superimposed using multiple OHMDs each displaying the virtual data with the view perspective matching the view perspective of the live data for the individual viewer 216, 217, 218. The viewer(s) can move their head freely and the OHMD worn by each viewer can remain registered with the live data using, for example, one or more of IMU's attached to the OHMD, room mapping, spatial mapping, e.g. of the surgical site or the patient or both, optical markers or navigation markers 219. Instruments or implants, e.g. pedicle screws or rods, can also be tracked using, for example, IMU's, LED's, optical markers, or navigation markers 220. The display of the OHMD can be adjusted in real time, e.g. 30 frames per second or more, based on head movement or instrument or device movement or combinations thereof 221. The surgeon can obtain a down the barrel view of a pedicle for placing tools, such as pins, or screws, for example in real time 222. A skin incision can be performed over select pedicle or multiple spine levels 223.

Figure 17D:
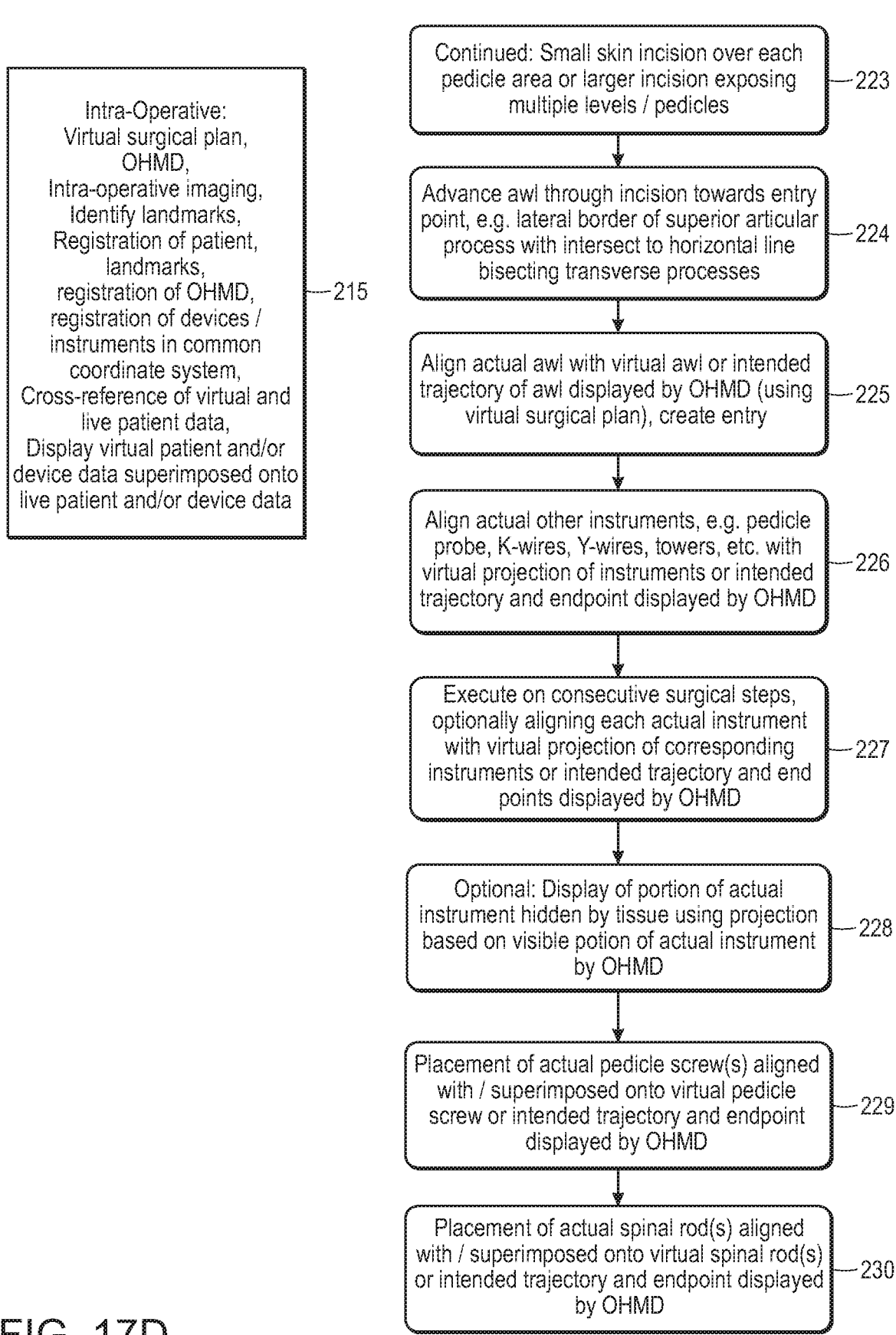

In FIG. 17D, continuation of intra-operative virtual surgical plan, imaging, landmarks, registration, cross-reference of virtual and live patient data 215, the surgeon can, for example, advance an awl towards the entry point for a pedicle screw 224. The actual or physical awl can be aligned with a virtual awl 225. Other physical instruments can be aligned with their corresponding virtual instrument or, for example, an intended path or endpoint 226. Consecutive surgical steps can be executed aligning physical with virtual tools, instruments or implants 227. Optionally, portions of the physical instrument that are hidden inside or by the tissue can be displayed in the virtual display in the augmented reality system using, for example, the alignment information from the visible portions of the instrument 228. For this purpose, optical markers or navigation markers can, for example, be attached to the instrument to register it and compute its hidden portions. The physical or actual pedicle screw can be placed aligned with or superimposed with the hidden subsurface anatomy, e.g. the pedicle, or a virtual pedicle screw, or an intended path or endpoint or combinations thereof 229. The physical spinal rod can be placed aligned with or superimposed onto a virtual spinal rod 230; optionally, the spinal rod can be placed aiming at virtual representations of the rod receptacle or receiving or holding or attachment mechanisms of the pedicle screw(s). The rod receptacle or receiving or holding or attachment mechanisms can be magnified by the OHMD for this purpose, for example around a central axis or central point, to facilitate aiming of the physical rod. The hidden portions of the physical rod can be virtually displayed by the OHMD, optionally also magnified, and aimed at the rod receptacle or receiving or holding or attachment mechanisms.

FIGS. 45A-E provide illustrative, non-limiting examples of one or more augmented reality OHMD displays including a virtual user interface 990 for virtual placing, sizing, fitting, selecting and aligning of virtual pedicle screws and including OHMD displays for guidance of spinal instruments and implants. A virtual user interface 990 can be configured for selecting different sizes of virtual pedicle screws, e.g. in mm of diameter. A computer processor can be configured to allowing placing and moving of the virtual pedicle screws onto the virtually displayed spine 993 of the patient, e.g. using a 3D model generated based on a pre-operative CT scan or an intra-operative O-arm scan. The computer processor can be configured for selecting different sizes of implants (e.g. in mm), using, for example, voice commands or gesture commands, e.g. a size 6.0 mm. A virtual path 996 can be displayed for guiding the placement of the one or more physical pedicle screws. A computer processor can be configured to move, place, size, and align virtual pedicle screws 1000 using, for example, gesture recognition or voice commands, and, optionally to display magnified views 1003, e.g. from a CT scan, demonstrating the pedicle 1006 including the medial wall of the pedicle 1009. A target placement location 1012 for the virtual pedicle screw 1000 can also be shown. The virtual screw can be adjusted to be placed in the center of the pedicle. The physical screw and/or awl or screw driver can be tracked, e.g. using a navigation system or video system (for example with navigation markers or optical markers or direct optical tracking). When the screw path, awl path or screw driver path extends beyond the medial wall of the pedicle, a computer processor can generate an alarm, e.g. via color coding or acoustic signals. Physical instruments, e.g. a physical awl 1015 (see FIG. 45C), can be aligned with and superimposed onto the virtual path 996 projected by an OHMD.

A computer processor can track the physical awl 1015, for example using direct video detection or one or more markers, e.g. navigation markers or optical markers (not shown), e.g. with a navigation system and/or image capture system, and can track the percentage superimposition 1018 of the physical awl 1015 with the virtual path 996. The superimposition can be indicated as a percent volume superimposition between the physical awl and the virtual path, percent surface superimposition, percent area superimposition, percent superimposition in a first, second, and/or third direction, e.g. x-, y- and z-, e.g. in mm, percent superimposition with regard to angular alignment, e.g. in x-, y-, and z-direction, e.g. in degrees, percent coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical awl 1015 is completely superimposed onto the virtual path 996 (e.g. 100% match or >95% match or >90% match, or any other amount), the physical awl can be advanced, for example to a predetermined endpoint (not shown).

Figure 45A:
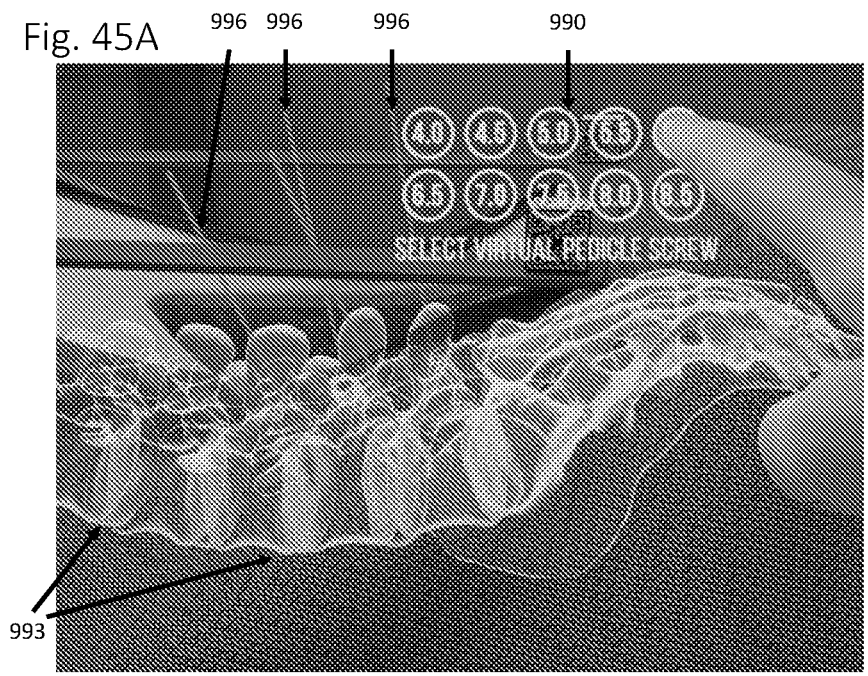
FIGS. 45A-E provide illustrative, non-limiting examples of one or more augmented reality OHMD displays including a virtual user interface for virtual placing, sizing, fitting, selecting and aligning of virtual pedicle screws and including OHMD displays for guidance of spinal instruments and implants.
Figure 45B:
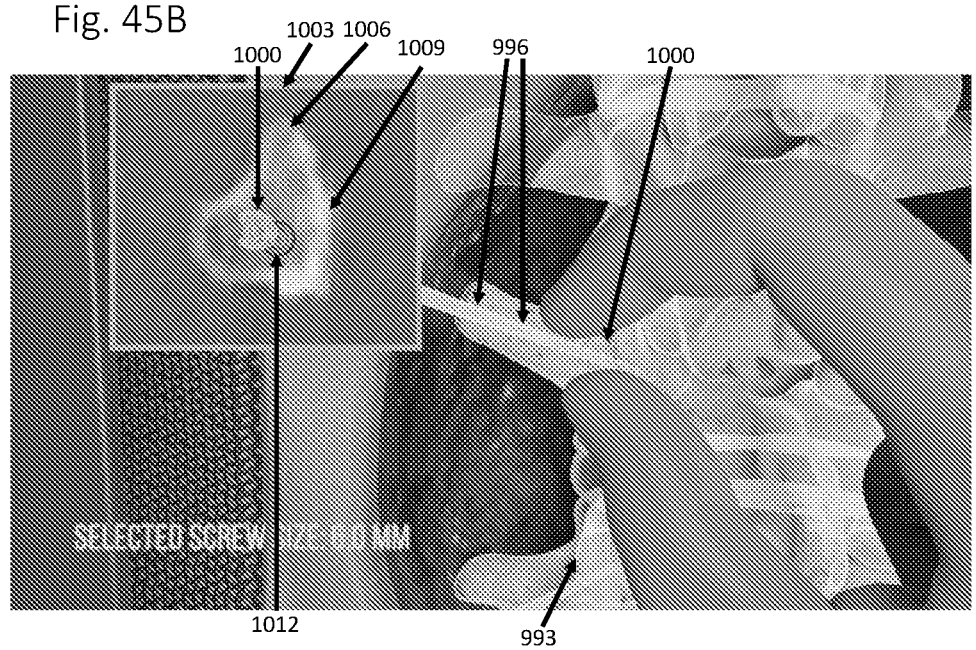
Figure 45C:
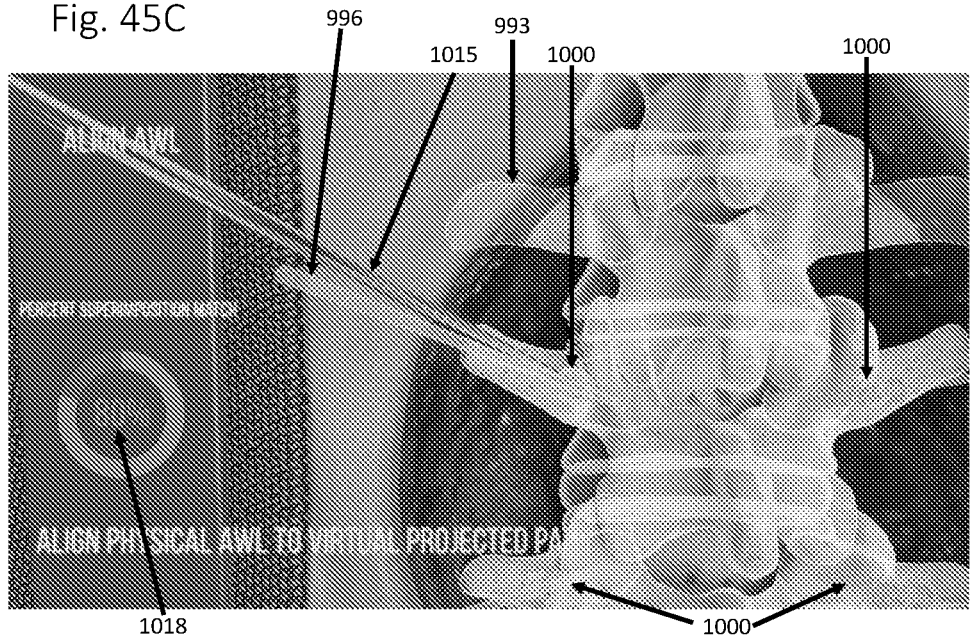
Figure 45D:
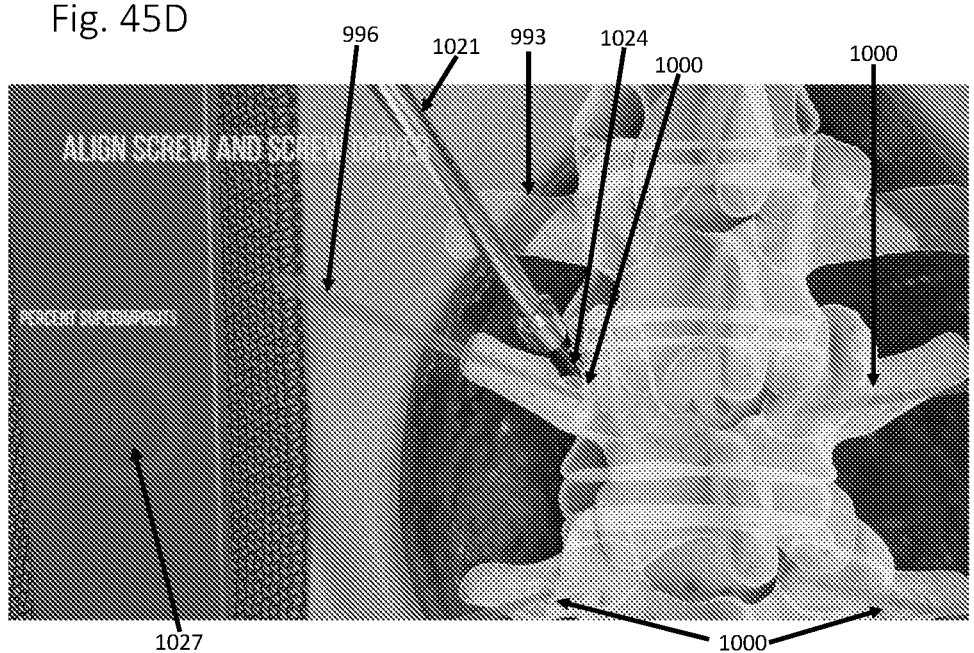
Figure 45E:
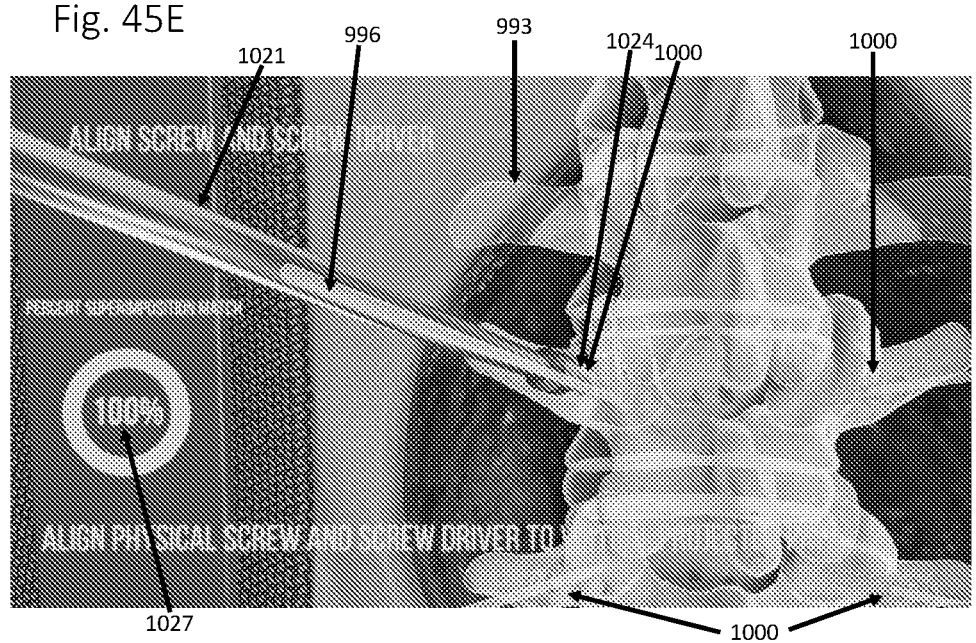

In the example of FIG. 45D, a computer processor can track the physical screw driver 1021 and, optionally, the physical screw 1024, for example using direct video detection or one or more markers, e.g. navigation markers or optical markers (not shown), e.g. with an image capture and/or a navigation system, and can track the percentage superimposition 1027 of the physical screw driver 1021 (and/or, optionally, the physical screw 1024) with the virtual path 996. The superimposition can be indicated as a percent volume superimposition between the physical screw driver (or screw) and the virtual path, percent surface superimposition, percent area superimposition, percent superimposition in a first, second, and/or third direction, e.g. x-, y- and z-, e.g. in mm, percent superimposition with regard to angular alignment, e.g. in x-, y-, and z-direction, e.g. in degrees, percent coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical screw driver 1021 (and/or, optionally, the physical screw 1024) is completely superimposed onto the virtual path 996 (e.g. 100% match or >90% match or >95% match, or any other amount), the physical screw driver and screw can be advanced, for example to a predetermined endpoint (not shown). Once the superimposition is completed (e.g. 100% match or >95% match or >90% match, or any other amount), the OHMD can provide an optical signal, e.g. a color change from red to green. Physical instruments and pedicle, in this example a screwdriver and a pedicle screw, can be aligned with and superimposed onto the virtual path projected by the OHMD. If the superimposition is incomplete (e.g. <100%, <97%, <94% or any other amount or value), the OHMD can provide an optical warning signal, e.g. a red color of the indicator. The foregoing embodiments on tracking and/or displaying and/or determining and/or measuring superimposition can be applied to many different embodiments throughout the application, e.g. for knee replacement, hip replacement, shoulder replacement, ankle replacement, ACL reconstruction or repair, dental surgery, root canals, dental implant placement, etc.

Any of the registration techniques and/or techniques described in the embodiments including implantable and attachable markers, calibration and registration phantoms including optical markers, navigation markers, infrared markers, RF markers, LED's with image capture and IMU's can be applied for spinal surgery and procedures. For example, in a spinal surgery or procedure, one or more patient specific markers or templates can be applied to one or more spinous processes or articular processes or transverse processes or other spinal structures, for example through a small incision. By applying the patient specific markers or templates to the corresponding structure(s) on the patient, reliable identification of spinal levels is possible, optionally without intraoperative imaging. Moreover, pedicle screws and related instruments or vertebroplasty or kyphoplasty needles and trocars and related instruments can be placed reliably following a trajectory or desired position of the pedicle screws and related instruments or vertebroplasty or kyphoplasty needles and trocars projected by the OHMD using an optional virtual surgical plan. Of note, reliable identification of spinal levels and reliable placement of pedicle screws, rods, and related instruments and or vertebroplasty or kyphoplasty needles and trocars is also possible using the OHMD with the other registration and cross-referencing techniques described in the present disclosure or known in the art. The same steps and OHMD guided spinal procedures are also possible using the OHMD with the other registration and cross-referencing techniques described in the present disclosure or known in the art, such as, for example, registration using anatomic landmarks or registration or calibration phantoms including optical markers or image capture, optionally using optical markers, or surgical navigation.

In some embodiments, the registration of virtual patient data and live patient data using the techniques described herein can be repeated after one or more surgical steps have been performed in an OHMD guided spinal procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the digital holograms of the patient's tissue and/or surgical site including hidden and/or obscured parts after the surgical tissue alteration can be performed using the same techniques described in the foregoing or any of the other registration techniques described in the specification or any other registration technique known in the art.

Hip Replacement

Any of the registration techniques and/or techniques described in the embodiments can be applied for hip replacement surgery, including resurfacing, partial and total hip replacement including implantable and attachable markers, calibration and registration phantoms including optical markers, navigation markers, infrared markers, RF markers, patient specific markers, LED's with image capture and IMU's. Optical markers and/or LED's and/or calibration and/or reference phantoms and/or other markers can, for example, be detected and/or tracked using an optical imaging system and/or a 3D scanner, for example integrated into, attached to or separate from an OHMD. For example, one or more markers, e.g. optical markers, navigation markers, patient specific markers or templates, can be applied to the edge of the acetabulum, the inside of the acetabulum or a pelvic wall. Similarly, one or more markers, e.g. optical markers, navigation markers, e.g. infrared or radiofrequency markers, patient specific markers or templates, can be applied to a greater trochanter, a lesser trochanter, a femoral shaft or a femoral neck. By applying the one or more patient specific markers or templates and/or optical markers, for example, to the corresponding structures on the patient, virtual data and live data can be effectively cross-referenced and/or registered in a common coordinate system, for example with one or more OHMDs. By registering the patient specific marker or template and/or optical marker in relationship to the OHMD also or by using any of the other registration techniques or techniques described herein or known in the art, the OHMD can display or superimpose the desired position, location, orientation, alignment and/or trajectory of any surgical instrument used during hip replacement. For example, an acetabular reamer can be applied at a predetermined angle, with the long axis of the reamer typically matching the desired acetabular cup angle, offset, medial or lateral position and/or anteversion and/or inclination, e.g. from a virtual surgical plan for the patient. Registration can be performed using anatomic structures such as the anterior superior iliac spine, the symphysis pubis, the greater trochanter, the lesser trochanter, the anterior, posterior, medial or lateral surface of the femoral neck, the anterior, posterior, medial or lateral surface of the femoral head, the anterior, posterior, medial or lateral surface of the femoral shaft, the anterior, posterior, superior or inferior acetabular margin or the center of the acetabulum or the center of rotation of the hip joint, the ilioischial line, the iliopectineal line, the anterior, posterior, medial or lateral surface of the sacrum or coccyx, the superior surface or endplate of the sacrum, and any other anatomic structure within the hip and pelvic region. One or more patient specific markers or templates and/or optical markers and/or navigation markers can be applied to one or more of these anatomic structures and can be registered within a common coordinate system, for example along with one or more OHMDs, the patient and, optionally, the OR table. Optionally, a pin or screw can be attached to or introduced into the bony anatomic structure and one or more optical markers and/or navigation markers and/or IMU's can be attached to the pin or screw.

In the hip joint, one or more OHMDs, one or more virtual data sets or virtual data can be registered in a common coordinate system. In a hip joint, two opposing articular surfaces, e.g. with opposing cartilage surfaces and underlying subchondral bone, can be registered separately and/or optionally jointly in a coordinate system, e.g. a common coordinate system. A first articular surface can be located on the pelvic side, i.e. on the acetabulum, a second articular surface can be located on the proximal femur. Registering the first articular surface and/or or associated bones and/or structures and the second articular surface and/or or associated bones and/or structures separately in a common coordinate system can have the benefit of allowing movement, e.g. flexion and/or extension and/or rotation and/or abduction, and/or adduction, and/or elevation and/or other movements, e.g. translation, of the first articular surface and/or or associated bones and/or structures, e.g. on the acetabular side, in relationship to the second articular surface and/or or associated bones and/or structures, e.g. on the proximal femoral side, while maintaining registration of the first articular surface and/or associated bones and/or structures, e.g. on the acetabular side, and/or the second articular surface and/or or associated bones and/or structures, e.g. on the proximal femoral side, e.g. in a common coordinate system or a subcoordinate system, for example optionally along with one or more OHMDs and/or fixed structures in the operating room, e.g. the OR table, and/or other structures or anatomic landmarks of the patient, e.g. irrespective movement of the individual portions of the joint; the foregoing applies to any joint in the human body, e.g. a shoulder, elbow, wrist, finger, knee, ankle, foot or toe joint or a temporomandibular joint. In this manner, the hip joint or any other joint can be placed in different positions, e.g. flexion, extension, rotation, abduction, adduction, e.g. a degree of hip abduction, e.g. 20, 30, 40 or other degrees, e.g. during placement of a femoral component, and a degree of hip abduction, e.g. 30, 40, or 50 or other degrees, during placement of the acetabular component, or any other degrees for either component placement depending on surgical technique and surgeon preference, while the registration of the acetabular and/or the registration of the proximal femoral side and the display of any virtual data, e.g. a virtual surgical guide, a virtual cut plane, a virtual implant component on the acetabular side and/or the proximal femoral side can be maintained and superimposed onto the corresponding anatomic area, e.g. the area intended for implant component placement, irrespective of the movement of individual portions of the joint, thereby allowing the one or more OHMDs to maintain anatomically registered displays of virtual data superimposed onto the corresponding portions of the physical joint anatomy, e.g. an articular surface, including a normal, damaged and/or diseased cartilage and/or subchondral bone and/or cortical bone, e.g. in a tangent, intersecting and/or offset manner, e.g. external and/or internal to the normal, damaged and/or diseased cartilage and/or subchondral bone and/or cortical bone.

Figure 18A:
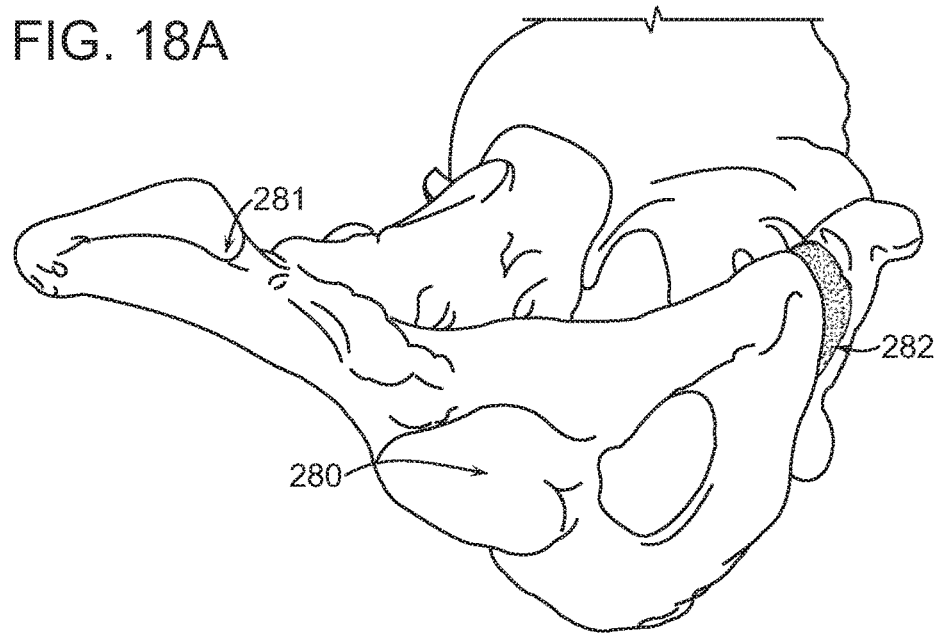
FIGS. 18A-F are illustrative examples of displaying a virtual acetabular reaming axis using one or more OHMDs and aligning a physical acetabular reamer with the virtual reaming axis for placing an acetabular cup with a predetermined cup angle, offset, medial or lateral position and/or anteversion according to some embodiments of the present disclosure.
Figure 18B:
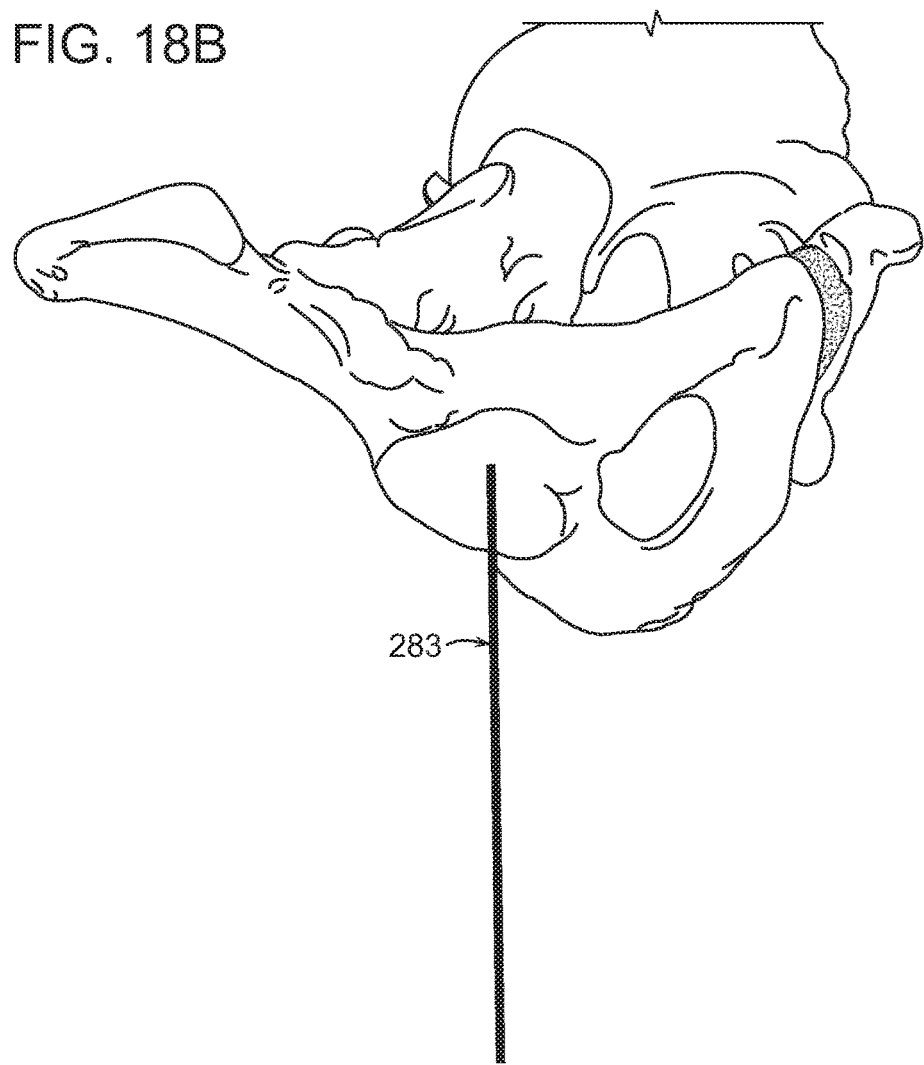
Figure 18C:
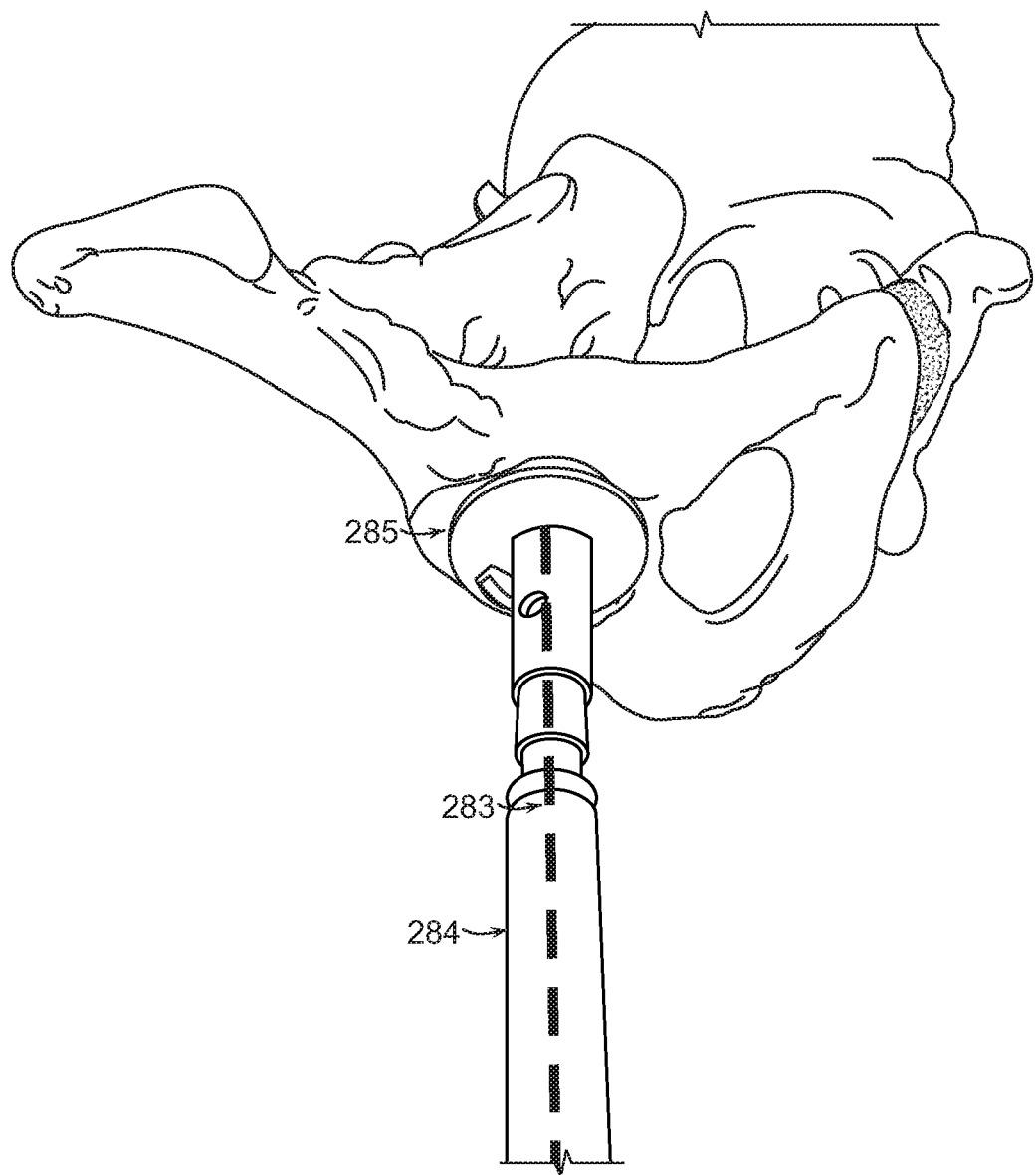

FIGS. 18A-F are illustrative examples of displaying a virtual acetabular reaming axis using one or more OHMDs and aligning a physical acetabular reamer with the virtual reaming axis for placing an acetabular cup with a predetermined cup angle, offset, medial or lateral position and/or anteversion and/or inclination. FIG. 18A shows a first surgeon's view, e.g. through an OHMD, onto the patient's exposed acetabulum 280. Note also the anterior superior iliac spine 281 and the symphysis pubis 282, which can optionally be used for registration purposes, for example using attached optical markers or navigation markers. In FIG. 18B, the first surgeon can see a virtual acetabular reaming axis 283 through the OHMD, which can be oriented in a predetermined manner to achieve a predetermined acetabular cup angle, offset, medial or lateral position and/or anteversion and/or inclination, e.g. from a virtual surgical plan for the patient. In FIG. 18C, the first surgeon aligns the physical acetabular reamer shaft 284 so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Figure 18D:
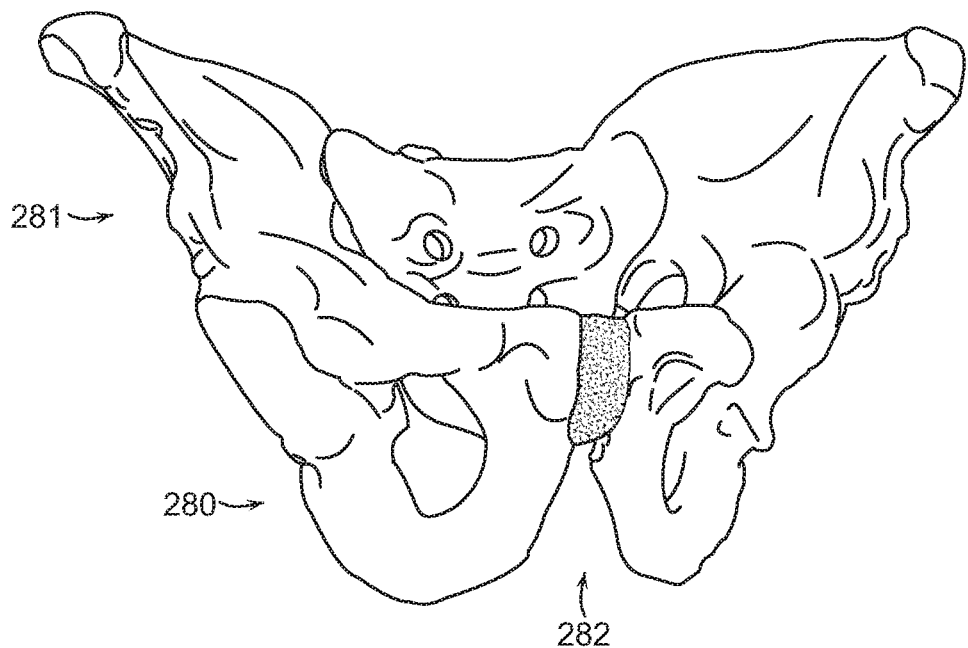
Figure 18E:
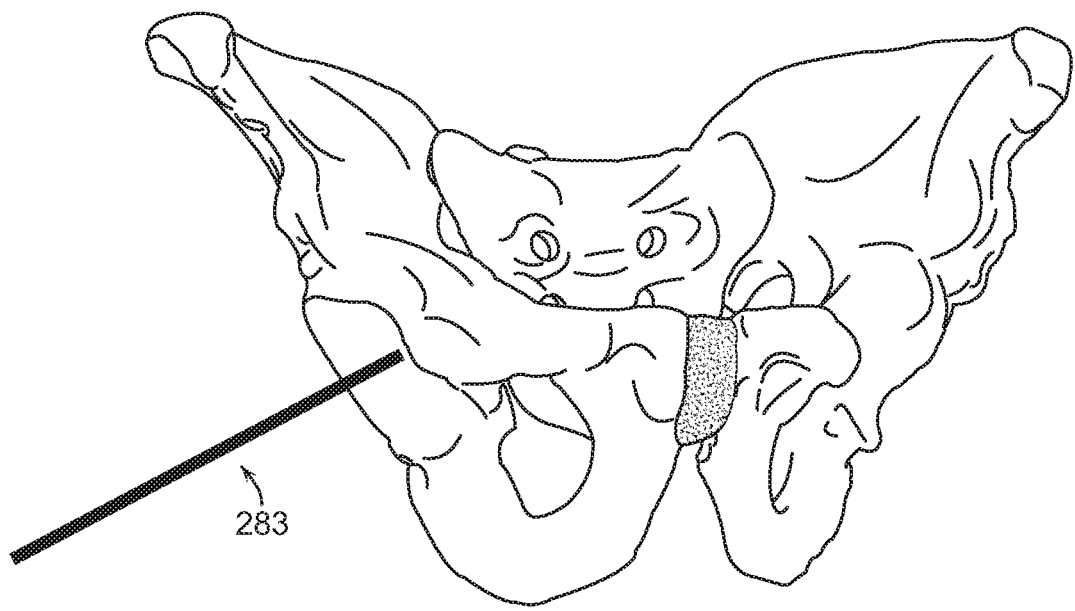
Figure 18F:
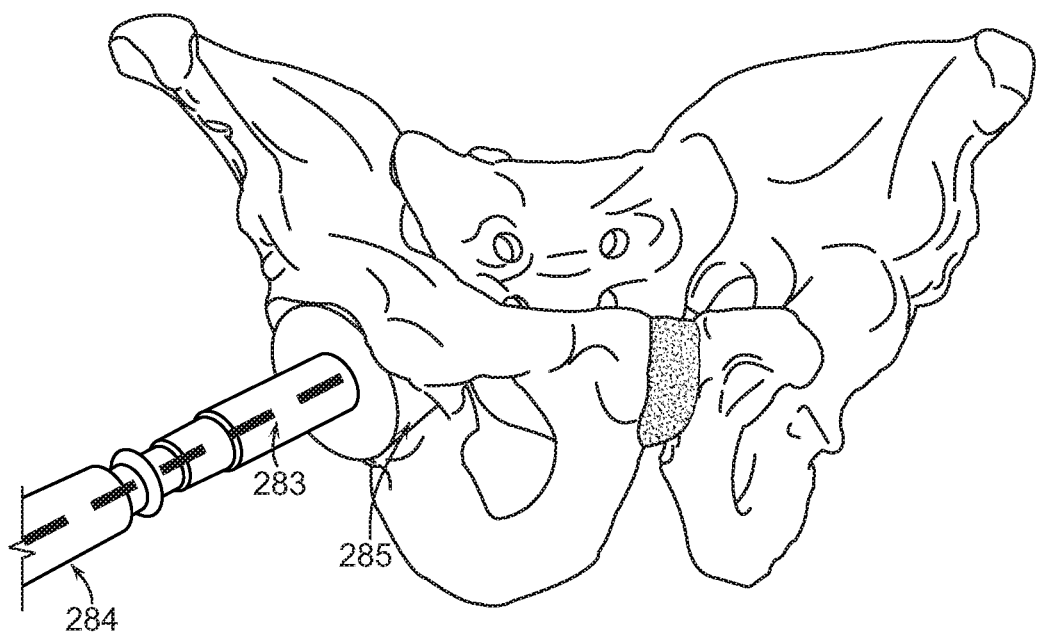

FIG. 18D shows a second surgeon's view with his or her respective view perspective of live data and virtual data through the OHMD onto the patient's exposed acetabulum 280. Note also the anterior superior iliac spine 281 and the symphysis pubis 282, which can optionally be used for registration purposes, for example using attached optical markers or navigation markers. In FIG. 18E, the second surgeon can see the virtual acetabular reaming axis 283 through the OHMD, which can be oriented in a predetermined manner to achieve a predetermined acetabular cup angle, offset, medial or lateral position and/or anteversion and/or inclination, e.g. from a virtual surgical plan for the patient. The virtual acetabular reaming axis is projected with a view angle or view perspective matching the view angle or view perspective of the live data of the patient seen by the second surgeon. In FIG. 18F, the second surgeon can see how the physical acetabular reamer shaft 284 is aligned by the first surgeon so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Thus, the surgeon can hold the physical acetabular reamer seeing the live data through the OHMD; at the same time, the OHMD can display or project a digital hologram of the corresponding virtual acetabular reamer with the virtual acetabular reamer aligned and oriented to achieve a desired acetabular cup position, e.g. anteversion, inclination, as optionally defined in a virtual surgical plan. Alternatively, the OHMD can display a partial (e.g. broken or dotted) or complete 2D or 3D outline of the virtual acetabular reamer or one or more placement indicators, e.g. lines indicating the predetermined placement position and orientation of the acetabular reamer, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position and/or or virtual predetermined rim position and/or a virtual predetermined central axis orientation or position and/or a virtual predetermined anteversion.

The surgeon can now align the physical acetabular reamer with the virtual acetabular reamer or its 2D or 3D outline or placement indicator or predetermined or virtual reaming axis displayed by the OHMD so that the physical acetabular reamer is substantially superimposed or aligned with or oriented along the virtual acetabular reamer or its 2D or 3D outline or placement indicator or virtual reaming axis. The OHMD can also indicate the desired or predetermined reaming depth as optionally defined in a virtual surgical plan, for example derived from one or more intra-operative measurement and/or a pre- or intra-operative scan, e.g. a CT or MRI scan [optionally displayed by the OHMD as one or more 2D slices or a 3D reconstruction of the anatomy]. The desired or predetermined reaming depth can be displayed by the OHMD, e.g. as a virtual red border to which the physical reamer can be advanced. If the reaming surface of the physical reamer is not visible since it is hidden by tissue, e.g. soft-tissue or bone, it can be estimated based on the visible portions of the physical reamer and it can be optionally displayed by the OHMD, e.g. using a different color than the display of the virtual reamer or the virtual "red border" for the reaming depth. The physical reaming depth of the physical reamer can also be measured, for example via image capture or mechanical data capture of a numeric scale on the physical reamer which indicates reaming depth, or by attaching IMU's or one or more optical markers, RF tags or retro-reflective markers for navigation to the reamer and by comparing physical measured reaming depth to the virtual surgical plan. The OHMD can indicate when the desired or predetermined reaming depth has been achieved, for example with a visual or acoustic signal. One or more optical markers can also be attached to the shaft of the acetabular reamer. By measuring the position of the one or more optical markers, e.g. two optical markers in two different locations along the shaft of the reamer, the long axis of the physical acetabular reamer can be determined using image or video capture and can be compared to the predetermined virtual reaming axis to achieve a desired or predetermined cup placement, including a desired or predetermined offset and/or cup angle and/or anteversion.

By attaching or integrating one or more optical markers, navigation markers, infrared markers, RF markers, patient specific markers, LED's with image capture and IMU's to a reamer or a broach or an impactor in hip replacement or any other instrument or tool in other joint replacement procedures or arthroscopic procedures in the hip, knee, shoulder, ankle, elbow, wrist or any other joint, e.g. a cut block, drill, pin, mill, reamer, broach, impactor, drill tower, template, or patient specific instrument, the instruments or tools can be tracked in regards to their position, location, orientation, direction of movement, speed of movement and/or coordinates in the coordinate system. Similarly, a video system or a 3D scanner can be used for tracking the instruments and their position, location, orientation, direction of movement, speed of movement and/or coordinates in the coordinate system. The position, location, orientation, direction of movement, speed of movement and/or coordinates in the coordinate system of the tracked instruments or tools can be compared to the predetermined or intended position, location, orientation, direction of movement, speed of movement and/or coordinates in the coordinate system of the instruments or tools in a virtual surgical plan. If an instrument or tool deviates from the predetermined or intended position, location, orientation, direction of movement, speed of movement and/or coordinates in the coordinate system this can be indicated or displayed in the OHMD. For example, if the instrument or tool deviates from the predetermined or intended position, location, orientation, direction of movement, speed of movement and/or coordinates in the coordinate system the OHMD can display an optical warning, optionally color coded, e.g. red, or optionally blinking or flashing. The OHMD can also emit an acoustic or any other signal, e.g. a vibration. The tracked instrument or tool can optionally be displayed with a color highlighting the deviation from the predetermined or intended position, location, orientation, direction of movement, speed of movement in the coordinate system, e.g. a red color. The optical, acoustic, or other warning signals can stop when the instrument or tool is in or returns to the predetermined or intended position, location, orientation, direction of movement, speed of movement and/or coordinates in the coordinate system, or is within a certain range of the predetermined or intended position, location, orientation, direction of movement, speed of movement and/or coordinates in the coordinate system, e.g. 1%, 2%, 3%, 5%, 10%, 15%, 20%, 30% etc., or 1 degree, 2 degrees, 3 degrees, 5 degrees, 10 degrees, 15 degrees, 20 degrees etc., or 0.5 mm, 1.0 mm, 2.0 mm, 3.0 mm, 5.0 mm, 10.0 mm, 15.0 mm, 20.0 mm etc. Any value can be used. Optionally, the system can measure the percentage time the instrument or tool was outside the predetermined or intended position, location, orientation, direction of movement, speed of movement and/or coordinates in the coordinate system. Optionally, the system can measure the average deviation from the predetermined or intended position, location, orientation, direction of movement, speed of movement and/or coordinates in the coordinate system, e.g. in %, degrees or mm. Optionally, the system can generate a warning or a report if the instrument or tool deviated from the predetermined or intended position, location, orientation, direction of movement, speed of movement and/or coordinates in the coordinate system for more than a defined percentage of time or average or median or other statistical value, e.g. in %, degrees or mm. Optionally, when the instrument or tool is in or returns to the predetermined or intended position, location, orientation, direction of movement, speed of movement and/or coordinates in the coordinate system, the display including the color of the instrument or tool can change in the OHMD, e.g. from red to green, or from blinking or flashing to steady or disappearing.

In another embodiment, the percentage overlap or alignment of a virtual implant, instrument or tool with a physical implant, instrument or tool can be shown in the form of a numeric display, e.g. 10%, 20%, 30%, 40%, 50%, 60%, 70%, 80%, 90%, 95%, 98%, 99%, 100%. The percentage overlap or alignment can be computed by comparing the tracked physical implant, instrument, or tool against the virtual implant, instrument or tool, e.g. in the virtual surgical plan. The percentage overlap or alignment can be based on coordinates, an outline of the implant, instrument or tool, a placement indicator, an area or a volume of overlap, e.g. between the virtual implant, virtual instrument or virtual tool and the physical implant, physical instrument or physical tool.

In certain circumstances, the percentage overlap or alignment of a virtual implant, instrument or tool with a tracked physical implant, instrument or tool can be greater than 90%, greater than 95%, greater than 98%, greater than 99% or can be 100%, but the physical implant, instrument or tool seen through a see through optical head mounted display may not appear to be aligned with the virtual implant, instrument or tool, contrary to the indication based on the tracking data. This can happen, for example, if the OHMD moves on the surgeon's head, for example after an initial calibration or registration in the coordinate system. Thus, it can be possible that the virtual display can be offset relative to the surgeon's eyes or pupils, for example similar to the amount of movement of the optical head mounted display on the surgeon's head or face. If a discrepancy between the percentage overlap or alignment of a virtual implant, instrument or tool with a tracked physical implant, instrument or tool between the tracking data and the visible superimposition of the two is apparent, the registration and/or calibration can optionally be repeated for the one or more optical head mounted displays to ensure accurate registration of the OHMD in the coordinate system.

Figure 25:
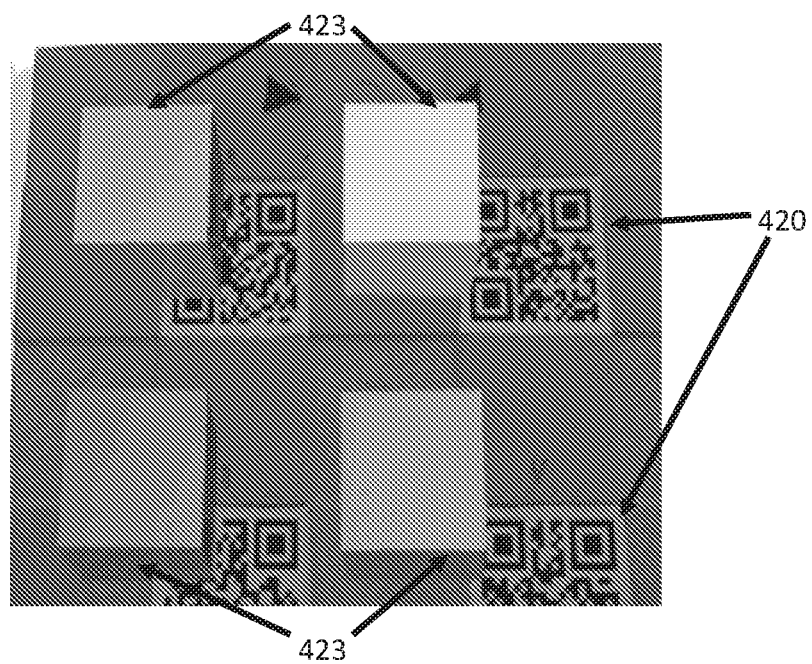
FIG. 25 shows an illustrative, non-limiting example of registration of four cubes in relationship to four optical markers using the image capture system of an OHMD.

In some embodiments, a calibration structure, a reference phantom, an optical marker, a navigation marker [e.g. an RF or IR marker], or an LED can be applied to a portion of the surgical site and/or a fixed structure in the operating room. A computer processor can then display a virtual reference body superimposed onto the one or more calibration structure, reference phantom, optical marker, navigation marker [e.g. an RF or IR marker], or LED; the superimposition can be at or near 100%. If the virtual reference body is not superimposed onto or aligned with the one or more calibration structure, reference phantom, optical marker, navigation marker [e.g. an RF or IR marker], or LED, it can be an indication that the OHMD can have moved on the surgeon's face or head. FIG. 25 can be an example of a virtual reference body, e.g. a virtual cube 423, superimposed onto a calibration structure, reference phantom, optical marker, navigation marker [e.g. an RF or IR marker], or LED, in this example an optical marker 420. When the virtual reference body is not aligned with the marker, it can be an indication that the registration is not accurate or has been lost, which can, for example, be an indication of a technical problem or an indication that the OHMD can have moved on the surgeon's face at some point after the initial registration. Thus, the use of a calibration structure or reference phantom, for example applied to portions of the surgical site or a fixed structure in the OR, e.g. the OR table, with virtual projection and superimposition of a corresponding virtual calibration structure or virtual reference phantom can be useful for detecting potential registration and/or tracking issues, including problems related to the registration of one or more OHMDs in the coordinate system. This can, in turn, be used to initiate or trigger a re-registration. In some embodiments, the surgeon can visually observe the virtual calibration structure or virtual and reference phantom in relationship to the physical calibration structure or physical reference phantom; the surgeon can decide if there is a registration issue. In other embodiments, one or more cameras can be positioned near one or both eyes of the surgeon, and the cameras can obtain an image or video projection of the physical calibration structure or reference phantom. A computer processor can then compare the position and/or location and/or alignment and/or alignment of the physical calibration phantom or reference structure with the position and/or location and/or alignment and/or coordinates of the virtual calibration phantom or reference structure. Optionally the images or video obtained from the one or more cameras positioned near one or both eyes of the surgeon can be corrected for parallax relative to the surgeon's eye. For this purpose, two, three, four or more cameras can be used, for example at defined positions and/or orientations relative to the eye or the pupil of the surgeon. If the computer processor detects a significant discrepancy, e.g. in mm, degrees, or percentage superimposition (e.g. area or volume) between the position and/or location and/or alignment and/or coordinates of the physical calibration phantom or reference structure with the position and/or location and/or alignment and/or coordinates of the virtual calibration phantom or reference structure, the system can trigger an alarm, initiating, for example, a re-calibration or re-registration, e.g. of the OHMD, one or more tracked instruments, tools or implants, the surgical site and/or the one or more physical calibration structures or reference phantoms in the coordinate system.

In another embodiment, one or more cameras directed at the eye(s) of the surgeon can image both the position and/or location and/or alignment and/or coordinates of the physical calibration phantom or reference structure and the position and/or location and/or alignment and/or coordinates of the virtual calibration phantom or reference structure visible on and/or reflected from the lens or cornea or other structures of the eye of the surgeon or user. If the two reflections are not aligned and/or superimposed, it can be an indication that the registration is not accurate. The system can then determine the discrepancy, e.g. in mm, degrees, or percentage superimposition, between the position and/or location and/or alignment and/or coordinates of the physical calibration phantom or reference structure with the position and/or location and/or alignment and/or coordinates of the virtual calibration phantom or reference structure, and the system can trigger an alarm, initiating, for example, a re-calibration or re-registration, e.g. of the OHMD, one or more tracked instruments, tools or implants, the surgical site and/or the one or more physical calibration structures or reference phantoms in the coordinate system.

The physical acetabular cup can be placed by obtaining substantial or near substantial superimposition with the virtual acetabular cup or its 2D or 3D outline or placement indicator(s) projected by the OHMD using, for example, the virtual surgical plan for the patient, whereby the virtual acetabular cup or its 2D or 3D outline or placement indicator(s) show the desired anteversion and inclination. Depending on the surgical approach, e.g. anterior, posterior or posterolateral, only those portions of the virtual acetabular cup can be displayed that correspond to the portions of the physical acetabular cup which would be visible for the surgical approach or surgical site. Optionally, the physical values, e.g. numerical values in degrees, of anteversion and inclination can be numerically displayed, e.g. by the OHMD, showing, for example, the desired values for the patient from the virtual surgical plan and the physical values based on the physical cup or trial cup position, location, orientation, and/or alignment. If there is a visual discrepancy, i.e. incomplete superimposition between virtual cup displayed by the OHMD and the physical or trial cup, or a numeric discrepancy, e.g. in virtual cup anteversion and/or inclination from the virtual surgical plan versus physical cup anteversion and/or inclination, the surgeon can correct the position, location, orientation, and/or alignment of the physical cup prior to impaction. The surgeon can also monitor the visual alignment and the numeric alignment or discrepancy between the virtual and the physical acetabular cup, e.g. during impaction, or the surgeon can also monitor the numeric concordance or discrepancy between the virtual and the physical acetabular impactor.

Figure 33:
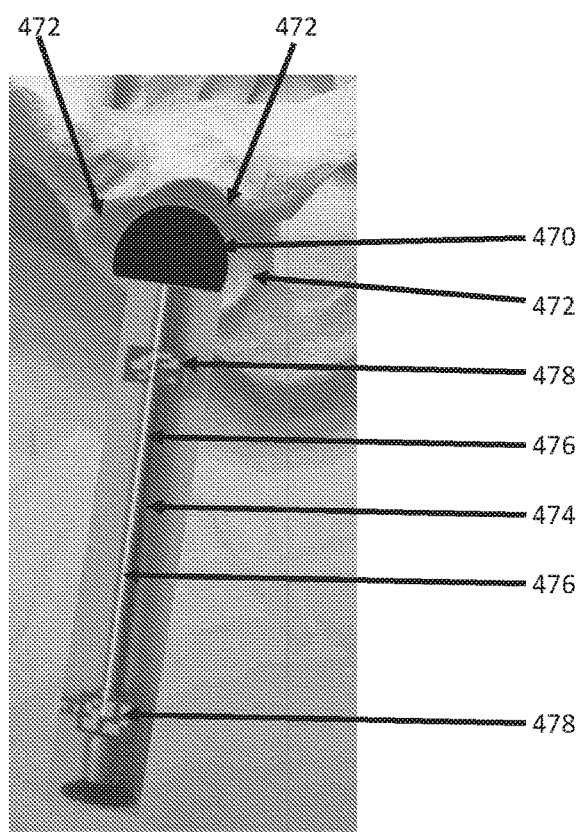
FIG. 33 shows an illustrative, non-limiting example of an acetabular placement instrument or tool with attached optical markers.

In another example, an acetabular placement instrument 470 can be placed by the surgeon in the exposed acetabular fossa as shown in an illustrative example in FIG. 33. The acetabular placement instrument can have the same shape and/or dimensions and/or radius and/or radii on the acetabular fossa facing surface as the acetabular cup or trial cup selected for implantation. The acetabular placement instrument can have a shape and/or dimension and/or radius and/or radii on the acetabular fossa facing surface matching the shape and/or dimensions and/or radius of the patient's acetabular fossa. The acetabular placement tool 470 can also have a similar or a smaller shape and/or dimensions and/or radius and/or radii than the acetabular cup or trial cup or than the patient's acetabular fossa as seen in FIG. 33.

By placing the acetabular placement instrument under visual control equidistant from the anterior, posterior, superior and inferior acetabular margin 472 of the patient, the surgeon can determine the patient's acetabular inclination and anteversion. The surgeon can choose the use the same cup inclination and anteversion during the surgery for the implantation of the prosthetic acetabular cup. Alternatively, the surgeon can choose a different position, e.g. by medializing the position of the acetabular placement instrument or by changing the anteversion of the acetabular placement instrument.

The acetabular placement instrument can have a handle 474 with a central axis 476 (yellow line in FIG. 33). Two or more optical markers 478 can be integrated into or attached to the handle 474. The position of the optical markers 478 can be detected with a video camera integrated into, attached to or separate from the OHMD. With the optical markers located, for example, at defined positions on the acetabular placement instrument and with the geometry of the instrument known, the position and orientation of the instrument can be calculated, including the location of the acetabulum facing portion of the instrument. More markers 478 can be used, e.g. in different geometric locations on the instrument with overlapping or separate, distinct x, y, and z coordinates. Alternatively, navigation markers, e.g. infrared or RF, can be used in conjunction with a surgical navigation system. The 3D coordinates of the optical markers or, alternatively any other markers, e.g. LED's, are recognized by the image and/or video capture system and/or 3D scanner integrated into or attached to the OHMD or separate from the OHMD using the methods described in the specification including the examples. Using the coordinates of a first and second marker, a central axis and vector 476, yellow line in FIG. 33, is calculated. The acetabular placement instrument can then be removed from the acetabular fossa. The surgeon can optionally make adjustments to the acetabular inclination and anteversion or the reaming axis determined in this manner, for example on a standalone or separate computer in the operating room which can host a virtual surgical plan, e.g. determined pre-operatively or intra-operatively, e.g. based on x-rays and x-ray templates, or based on intra-operative measurements including measurements using the acetabular placement instrument. The surgeon can also use a virtual interface to change the orientation of the vector and with that the acetabular inclination and anteversion and the intended reaming axis. The OHMD can subsequently display the intended acetabular reaming axis, which can be the axis or vector measured with the acetabular placement tool or which can be an axis modified or derived based on the axis or vector measured with the acetabular placement tool or which can be any other axis, e.g. a predetermined axis or an axis with a fixed angle, e.g. relative to the OR table.

By utilizing the 3D anatomic information of the patient from the pre-operative data or by using intra-operative measurements, for example optical markers for determining a center of rotation of a hip joint or for determining a desired anteversion, the surgeon can work more accurately in this manner, thereby reducing, for example, the need for offset or asymmetric liners.

In another embodiment, the dimensions and/or shape of the resected bone can be measured and the information can be combined with information obtained using optical markers, IMU's, navigation markers and/or calibration phantoms. For example, in a hip replacement, the surgeon can determine the center of a resected femoral head and the anteversion of the resected femoral head and neck as well as the neck length, combined head-neck length and neck resection angle. Measurements on resected bone specimens can be performed using mechanical devices, including but not limited to rulers, calipers and angle measurement tools as well as more sophisticated instruments such as CMM machines, e.g. a Faro arm (Faro, Warwickshire, UK). Alternatively, optical scanners and laser scanners can be used to measure the resected bone specimens. A representative scanner is, for example, the Structure 3D scanner by Occipital, Inc., San Francisco, Calif. Bone lost from cutting, e.g. by the thickness of the saw blade can be accounted for in any of the measurements. If more than one bone cut was performed, e.g. in case of "napkin ring" resection of the femoral neck in an anterior hip replacement, the bone lost by the two bone cuts can also be accounted for. The napkin ring dimensions and thickness can also be measured. By measuring the resected bone in this manner, any deviations of the actual surgery including the actual, physical bone cuts from the virtual surgical plan can be detected and can be accounted for in subsequent surgical steps or with use of different implant components, e.g. in a hip replacement by using plus or minus size heads or various liner thicknesses or stem components with different neck angles.

Of note, the same steps and OHMD guided acetabular procedures are also possible using the OHMD with any of the registration and cross-referencing techniques described in the present disclosure and known in the art, such as, for example, registration using anatomic landmarks or registration or calibration phantoms including optical markers or image capture, optionally using optical markers, or surgical navigation or patient specific markers or intra-operative imaging.

Any of the registration techniques or techniques described herein including implantable and attachable markers, calibration and registration phantoms including optical markers, navigation markers, infrared markers, RF markers, patient specific markers, LED's with image capture and IMU's can be applied for registering the patient's proximal femur in relationship to, for example, one or more OHMDs worn by the surgeon and/or is assistants, and/or in relationship to one or more surgical instruments, pins, drills, saws, reamers, impactors, broaches and the like and/or in relationship to one or more femoral or acetabular implants, including metal and/or polyethylene components. For example, by applying one or more optical markers and/or patient specific markers or templates to a greater trochanter, a lesser trochanter, a femoral shaft or a femoral neck, or femoral osteophytes, virtual and physical live patient data can be cross-referenced on the femoral side. Optionally, a pin or a screw can be inserted into the proximal femur, e.g. in a greater trochanter, which can be used as a reference for registration, for example if an optical marker or patient specific marker moves. Optical markers can be optionally attached to the pin or screw. Multiple pins or screws can be used in this manner. The virtual surgical plan can include a desired neck cut location for a particular femoral component. The neck cut can be designed or selected to avoid any offset issues and to maintain the patient's leg length in the virtual surgical plan. By registering the optical marker and/or patient specific marker or template in relationship to the OHMD also, e.g. in a common coordinate system with the OHMD, the surgical site, the proximal femur, the OHMD can display or superimpose and/or project digital holograms with different view coordinates for the left eye and the right eye of the user wearing the OHMD showing the desired or predetermined position, location, orientation, alignment and/or trajectory or predetermined plane of any surgical instrument including a saw for performing the femoral neck cut. After successful registration of virtual and live data of the patient using any of the techniques or techniques described herein, the OHMD can show the desired 3D trajectory including the desired location, entry point and angles in x, y and z direction for the femoral neck cut or the OHMD can display one or more digital holograms of a virtual cut plane and/or a virtual saw or saw blade in the position, location, angular orientation, and trajectory (e.g. as a dotted line or arrow) defined in the surgical plan which the surgeon can then match with the physical saw, i.e. the surgeon can orient and align the physical saw so that it will be aligned with or substantially superimposed onto the virtual saw (see also FIGS. 4A-C).

Alternatively, the OHMD can show a digital hologram of a partial (e.g. broken or dotted) or complete 2D or 3D outline of the virtual saw or placement indicators, e.g. lines indicating the predetermined placement position and orientation of the saw, e.g. a virtual predetermined medial placement or position, a virtual predetermined lateral placement or position, a virtual predetermined anterior placement or position, a virtual predetermined posterior placement or position, a virtual predetermined superior placement or position and/or a virtual predetermined inferior placement or position. Alternatively, the OHMD can show a digital hologram of a virtual femoral neck cut plane.

Optionally, for example once the entry point on the femoral neck has been defined or the desired location, orientation and/or direction of the saw has been determined with assistance from the OHMD, the surgeon can apply a standard saw guide to the femoral neck to facilitate the neck cut. Alternatively, the OHMD can display a digital hologram of a virtual femoral neck saw guide or its corresponding 2D or 3D outline or placement indicators in its desired position or location on the femoral neck. The physical saw guide can then be aligned with the corresponding virtual saw guide or its corresponding 2D or 3D outline or placement indicators placed in the desired position, orientation and angulation based on the virtual surgical plan of the patient. The virtual saw guide can have the same or similar shape and/or one or more dimensions or planes as the physical saw guide. Once the physical saw guide is substantially superimposed in position with the virtual saw guide or its corresponding 2D or 3D outline or placement indicators displayed by the OHMD, the surgeon can optionally pin the physical saw guide in place and perform the neck cut. By executing the neck cut using one of these approaches which utilize accurate 3D anatomic information of the patient from the pre-operative scan and/or intra-operative measurements including registration, e.g. using optical markers, leg length and offset can be more accurately preserved or addressed.

Similarly, the OHMD can project the desired position, location, orientation and trajectory of any virtual femoral reamers and impactors. Alternatively, the OHMD can only show a partial (e.g. broken or dotted) or complete 2D or 3D outline of the virtual femoral reamers or impactors or placement indicators, e.g. lines indicating the predetermined placement position and orientation of the reamers or impactors, e.g. a virtual predetermined medial placement or position, a virtual predetermined lateral placement or position, a virtual predetermined anterior placement or position, a virtual predetermined posterior placement or position, a virtual predetermined superior placement or position or a virtual predetermined inferior placement or position or a virtual reaming axis, e.g. a central axis through the reamer shaft. The OHMD can also display a digital hologram of a predetermined virtual reaming and/or broaching axis, which can provide a desired femoral component position including one or more of an offset and/or anteversion including, for example, composite anteversion for both femoral and acetabular components. The virtual femoral reamers and impactors can have the same or similar shape and dimensions as the physical femoral reamers and impactors. The surgeon can then match the position, location, orientation and trajectory (e.g. indicated by a dotted line or an arrow in the virtual data) of the physical femoral reamers and impactors with the virtual reamers and impactors or their corresponding 2D or 3D outlines or placement indicators or a virtual reaming or broaching axis, thereby reducing the possibility of mal-seating of the femoral stem and possibly incorrect femoral anteversion, incorrect femoral offset or femoral component angulation or leg length discrepancy. In some embodiments, the surgeon can align the OHMD so that the view angle is perpendicular to the femoral shaft axis or, alternatively, the femoral neck axis. The OHMD can then display a bulls-eye or target like structure whereby the surgeon will aim the femoral reamers, impactors, femoral trials and the physical femoral component to be located in the center of the bulls-eye or target. The OHMD can display the desired entry point, e.g. with regard to medial or lateral, anterior or posterior location on the cut femoral neck, and/or entry angle based on the virtual surgical plan including, for example, the virtual femoral component placement. The OHMD can also display the desired femoral version, for example via a solid or dotted line or arrows on the cut femoral neck surface or in relationship to the cut femoral neck surface. The desired femoral version can also be displayed by the OHMD by displaying one or more digital holograms of the femoral reamers, impactors, femoral trials and the final femoral component or their respective 2D or 3D outlines or placement indicators in the desired virtual location and orientation including femoral version based on the virtual surgical plan. In this manner, the surgeon can align the physical femoral reamers, physical impactors, physical femoral trials and the physical final femoral component to be substantially aligned or superimposed with the digital holograms of the one or more virtual femoral reamers, virtual impactors, virtual femoral trials and virtual final femoral component thereby achieving a result near the desired femoral version and, optionally, leg length based on the virtual surgical plan.

All of the foregoing steps and OHMD guided femoral procedures are also possible using the OHMD with any of the other registration and cross-referencing techniques described in the present disclosure or known in the art, such as, for example, registration using anatomic landmarks or implantable and attachable markers, calibration and registration phantoms including optical markers, navigation markers, infrared markers, RF markers, patient specific markers, LED's with image capture and IMU's.

In some embodiments, an ultrasound scan can be used to derive the shape information used for designing and producing the patient specific template, e.g. for use on the acetabular side or the femoral side. Optionally, the ultrasound scan can be obtained in supine and/or upright position. By obtaining the ultrasound scan in upright position, information about femoro-acetabular alignment and orientation can be obtained under weight-bearing positions including, for example, femoral or acetabular anteversion, femoral/acetabular/hip flexion, extension, abduction, adduction and/or rotation. By obtaining the ultrasound scan in supine position, information about femoro-acetabular alignment and orientation can be obtained under non-weight-bearing positions including, for example, femoral or acetabular anteversion, femoral/acetabular/hip flexion, extension, abduction, adduction and/or rotation. By comparing data from one or more upright and one or more supine ultrasound scans, e.g. by comparing the relative movement of corresponding anatomic landmarks, information can be obtained about pelvic tilt. The information from the upright and/or supine scan can be used for selecting the desired femoral and acetabular components including, for example, the shape and length of the femoral neck, the offsets, the femoral head component, as well as the shape of the acetabular component, including, for example, offset, mesialized, lateralized, or rimmed acetabular components. The information from the upright and/or supine scan can be used for developing or adjusting the virtual surgical plan, for example by changing the predetermined cup position based on the upright scan information or based on information on pelvic tilt. Similar information can be obtained using supine and upright x-rays studies.

Optionally, the information from the upright and/or supine imaging data can be used to assess information on pelvic tilt, which in turn can be introduced into the surgical plan and component selection in order to avoid or minimize the risk of postoperative complications such as component dislocation.

Thus, by performing hip replacement using the different embodiments of the present disclosure, it is possible for the surgeon to conduct the surgery with high accuracy thereby reducing the possibility of common complications in hip replacement such as offset error or wrong acetabular or femoral anteversion leading to hip dislocation or leg length discrepancy. Optionally, the OHMD can also display sensitive vascular or neural structures, thereby reducing the possibility of vascular injury or, for example, sciatic nerve injury.

In some embodiments, the registration of virtual patient data and live patient data using the techniques described herein can be repeated after one or more surgical steps have been performed in an OHMD guided hip replacement procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. For example, the re-registration can be performed using a cut bone surface, e.g. a cut femoral neck using the surface shape, surface area or perimeter or other feature, optionally measured with image capture or mechanical or physical probes, to match, superimpose and/or register the live patient data and the virtual patient data prior to performing subsequent surgical steps, e.g. a reaming, milling or impacting of the femoral canal for placement of a femoral component. For example, the re-registration can be performed using a milled bone surface, e.g. a milled acetabulum using the surface shape, surface area or perimeter or other feature, optionally measured with image capture or mechanical or physical probes, to match, superimpose and/or register the live patient data and the virtual patient data prior to performing subsequent surgical steps, e.g. a placement of an acetabular component including trial components.

Figure 39F:
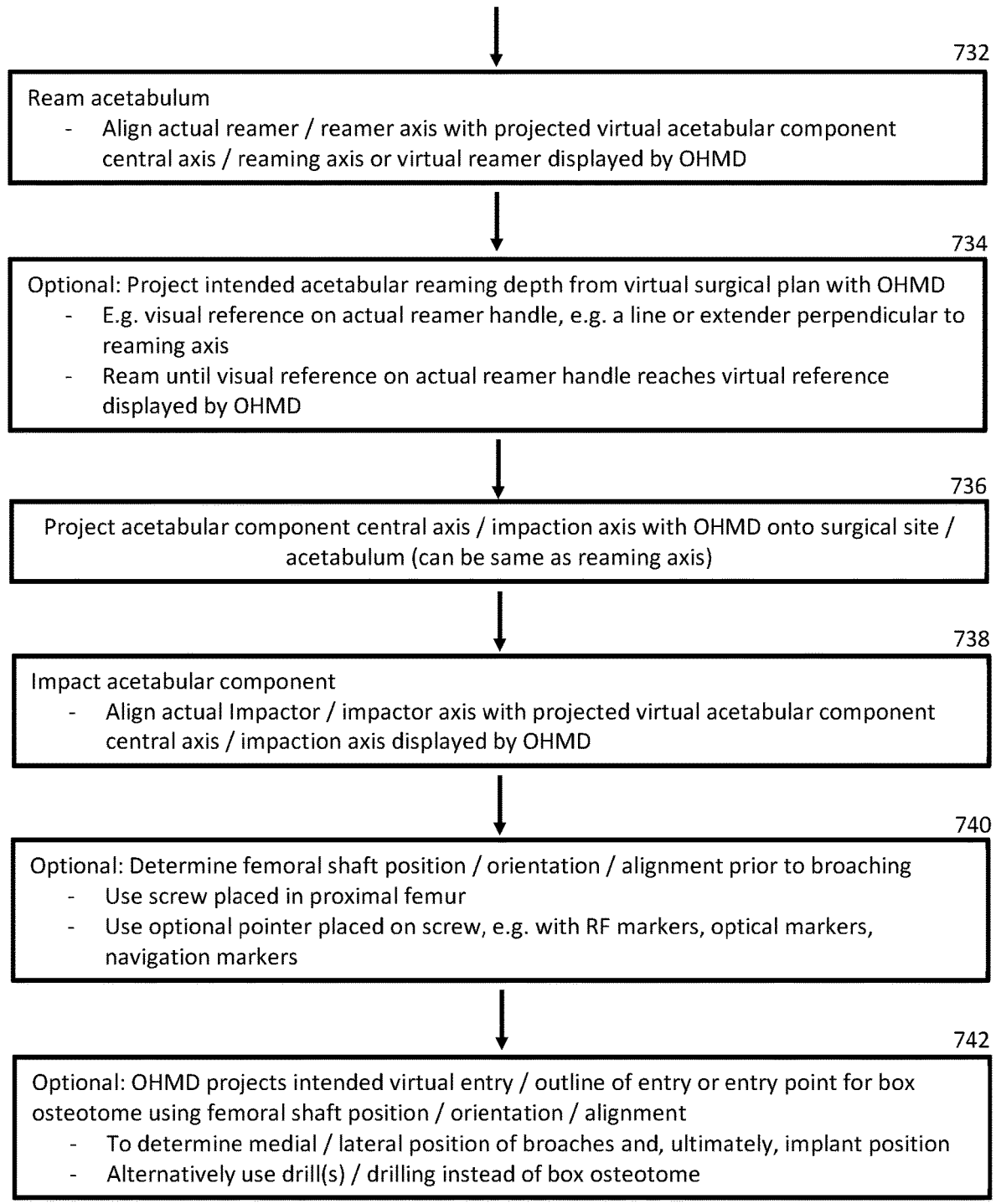
Figure 39G:
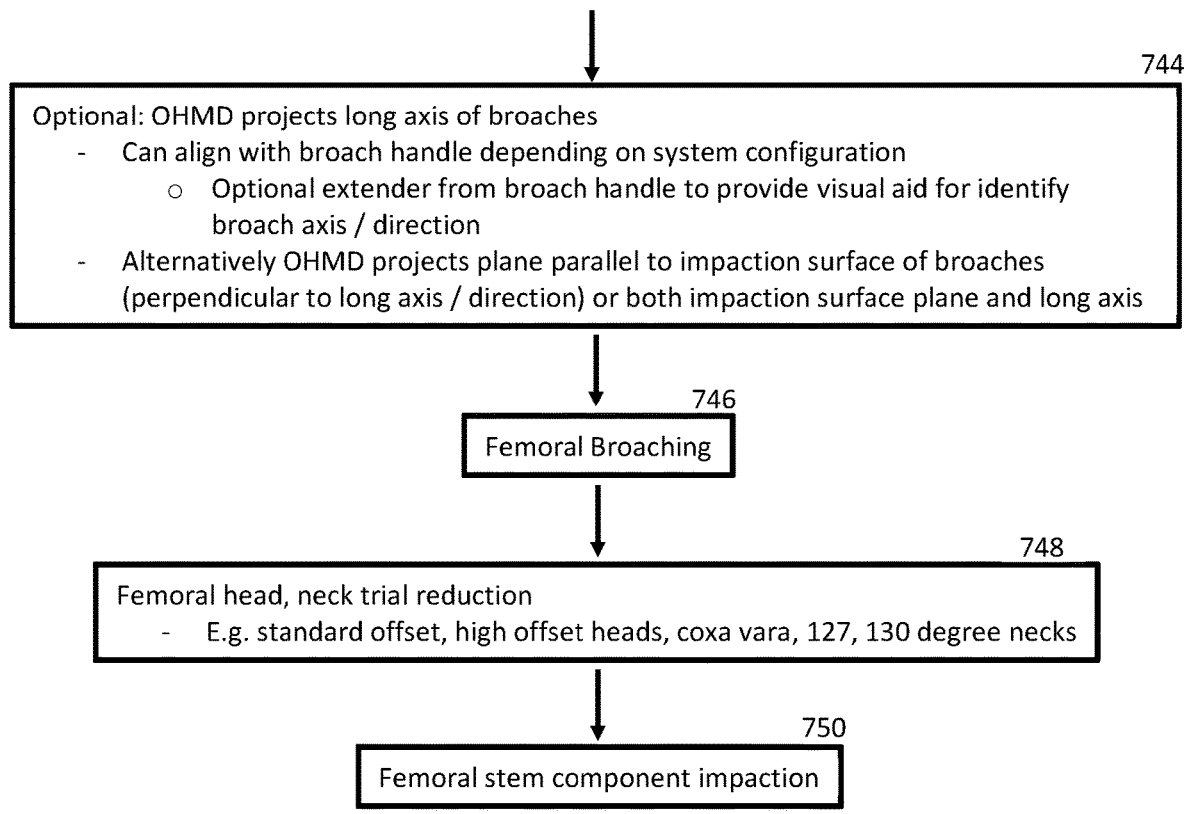

FIG. 39 is an illustrative, non-limiting exemplary flow chart demonstrating some of the foregoing examples and embodiments as well as additional examples and embodiments. In step 700, one or more pelvic x-rays are displayed, for example on an OHMD or a standalone computer monitor for templating and/or sizing of a femoral and/or acetabular component. Optionally, the x-rays can be obtained with the patient in supine and/or upright position. In step 702, the patient is positioned on the OR table, for example in neutral position or any other position. Optionally, the leg can be positioned in the same position in which it was when the x-rays were obtained, e.g. for templating and sizing. This can, for example, be helpful for planning and execution of the femoral neck cut. In step 704, the femoral and/or acetabular sizing and alignment data, e.g. from x-rays and templating, can be imported into an OHMD system. Optionally, the templating and/or sizing can be performed on a cross-sectional imaging study, e.g. a CT scan or MRI scan or can be obtained using upright imaging with an EOS or similar system (EOS, Paris, France). The system can comprise the OHMD display unit, one or more processors or computer chips, software, memory, e.g. RAM memory, sensors, e.g. depth sensors or acoustic sensors, and/or one or more cameras. Optionally, the data can also reside or be imported into a standalone computer, e.g. a PC, or server, in the OR or outside the OR and, optionally, computationally intensive steps, e.g. virtually moving, fitting, sizing, aligning implant components on the physical joint of the patient via a user interface, e.g. a graphical user interface, acoustic interface, optical interface, virtual interface, gesture recognition interface or any other interface known in the art, can occur on the standalone computer or server; alternatively, they can occur on the OHMD or a network of OHMD sharing computational and processor power and capacity. In step 706, the surgeon can perform the incision, exposure, capsulotomy, and expose the femoral neck and proximal femur. In step 708, the surgeon can optionally identify the sulcus point, e.g. the lowest point between the greater trochanter and the femoral neck. The sulcus or any other point or anatomic landmark can optionally be marked, e.g. with an optical marker, a navigation marker, e.g. an IR or RF marker, a pointer, e.g. with one or more optical markers and/or one or more navigation markers, a screw, and LED marker and/or India ink or any other marker known in the art. In step 710, the surgeon can identify additional points on the proximal femur, e.g. the highest point or multiple points on the greater trochanter, the highest or lowest point or multiple points on the lesser trochanter, one or more points on the femoral neck, one or more points on the femoral shaft, one or more points on the femoral head, one or more points on osteophytes. These points can be used for registration of virtual data and physical data. These points can be used for generating point clouds, e.g. for surface matching of virtual data, e.g. a preoperative ultrasound, CT or MRI scan, and physical surfaces on the proximal femur and, similarly, the acetabulum, acetabular edge and ilium or pubis. In step 712, one or more of the foregoing points, e.g. the sulcus point or any other points, or one or more of the point clouds or surfaces can be used for computing the femoral neck cut. For example, corresponding points can be identified intraoperatively on the live surgical site, e.g. the exposed femoral neck, greater trochanter or lesser trochanter, and in pre-operative or intra-operative imaging studies, e.g. x-rays, CT, MRI or ultrasound scans. For example, the highest point on the greater trochanter and the lesser trochanter can be identified intra-operatively on the physical joint or bone of the patient and on a pre- or intra-operative imaging study. If the imaging study is two-dimensional, e.g. x-rays, a first plane can be defined intersecting these two points and being, for example, orthogonal or at a defined angle relative to the OR table. Since the femoral neck cut plane can be visualized as part of the templating software and display, the angle and distance of the first plane to the femoral neck cut plane can be determined. Accounting for x-ray magnification, the angle and distance between the first plane and the femoral neck cut plane identified on the imaging study can be applied to the first plane, the plane intersecting the greater and lesser trochanter in this example, and a virtual femoral neck cut plane can be computed for projecting onto the physical proximal femur of the patient. One or more OHMDs can then project the femoral neck cut plane onto the surgical site, e.g. the uncut proximal femur in this example. The femoral neck cut plane can be oriented to be orthogonal to the coronal plane or the OR table; the femoral neck cut plane can be at any other angle relative to the coronal plane or the OR table, e.g. depending on the surgical approach, e.g. anterior vs. posterior vs. posterolateral, or surgeon preference. If a napkin ring cut approach is used, e.g. in anterior hip replacement, with two femoral neck cuts, the OHMD can optionally project the two femoral neck cuts. Optionally, an outline of a femoral neck cut tool or a virtual femoral neck cut tool can be displayed by the OHMD. In step 714, the surgeon can perform the one or more femoral neck cuts and expose the acetabulum, by removing the femoral head with optional resection of the acetabular labrum, pulvinar, fat, osteophytes. In step 716, the center of the acetabulum can be defined. A partial or full radius acetabular placement took can be used, e.g. with radius ½ or ⅔ or 1/1 of acetabular radius of the patient, e.g. on x-ray, and/or of the implant and optional central stem/extender indicating the center of the acetabulum and/or anteversion if the placement tool is placed substantially centered in the acetabulum of the patient. The central stem or extender can include one or more optical markers or navigation markers or LED's or other markers. Alternatively, or additionally, direct image capture and image analysis by a computer processor can be performed for identifying the center of the acetabulum. For this purpose, the image capture apparatus or system, e.g. video camera(s), can be registered in a common coordinate system, e.g. with the patient and/or one or more OHMDs. In some embodiments, a laser scan or 3D scan of the acetabulum can also be obtained, for example with the laser or 3D scanner also registered in the common coordinate system. Mechanical probes, e.g. a pointer probe with attached RF markers, IR markers for navigation, optical markers, LED's and/or IMU's can be used to determine one or more points on the acetabulum and, for example, to generate a point cloud. The points can be used for identifying the geometric center of the acetabulum. Optionally, the center of the acetabulum can be medialized or lateralized, e.g. by moving the partial acetabular placement tool medially or laterally or by moving the center of the acetabulum for reaming and/or impacting medially or laterally on the point cloud with subsequent medialized or lateralized guidance of the reamer and/or impactor in the one or more OHMDs' displays. Alternatively, the acetabular cup and with it the center of the acetabulum can be moved medially or laterally on a graphical user interface, e.g. using a computer display or an OHMD, and the virtual surgical plan can utilize the new, adjusted medialized or lateralized center. In step 718, the surgeon can select the acetabular component, e.g. with use of x-rays and/or intra-operative physical trials and/or intra-operative virtual trial components projected by one or more OHMDs onto the acetabulum. In step 720, the center of rotation of the hip joint can be determined, for example, using the patient's center of the acetabulum, measured, for example, using the partial or full radius acetabular placement tool, measured by estimating or determining the rim location, or derived either based on the selected acetabular component or derived from the femoral head radius/center of femoral head measured on an AP and/or frogleg radiograph, or measured on the excised femoral head of the patient. In step 722, the resected femoral head and neck portion can be measured to determine, for example, femoral anteversion and/or offset. The measurements can be used to adjust the reaming or broaching or selection of implant components, e.g. the femoral component or the head component including head offsets and to adjust the reaming or broaching and/or implant components for under-resection or over-resection. Optionally, saw blade thickness can be considered in the calculation and adjustments. Optionally, pre-existing leg length discrepancy and optional correction thereof can be considered in the calculation and adjustment(s). In step 724, the surgeon, the software and/or the system can check if the center of rotation is maintained for a combination of acetabular component and acetabular liner; optionally, different liner(s) can be selected or the virtual surgical plan and/or physical surgical plan can be modified or changed. In step 726, the surgeon, the software and/or the system can check if the center of rotation is maintained for select medialization or lateralization of the cup, which can, for example, be performed during reaming or impacting; optionally, different liner(s) can be selected or the virtual surgical plan and/or physical surgical plan can be modified or changed. In step 728, optionally a desired or predetermined reaming depth can be determined in the virtual surgical plan, e.g. based on pre-operative x-rays or imaging studies, e.g. a pre- or intra-operative CT scan or MRI scan, which can optionally be co-displayed by the one or more OHMDs or based on intra-operative findings. In step 730, an acetabular component central axis and/or an acetabular component reaming axis can be projected onto the surface of the acetabulum and onto the surface of the surgical site. The acetabular component central axis and/or acetabular component reaming axis can account for a pre-determined anteversion, e.g. from a pre- or intra-operative imaging study, e.g. a CT scan or one or more x-rays. The acetabular component central axis and/or acetabular component reaming axis can account for a desired medialization or lateralization and/or offset. Optionally, the OHMD can display a pre- or intra-operative imaging study projected onto the surface of the acetabulum as well as subjacent to the surface of the acetabulum. The imaging study can be an x-ray, e.g. projected through an anterior portion, central portion, posterior portion, medial portion or lateral portion of the acetabulum, optionally registered with corresponding anatomic structures, e.g. the acetabular rim or edge or the anterior inferior iliac spine. The x-ray(s) can be parallel in projection to the OR table or parallel to the coronal plane of the patient or any other plane of the patient, or it/they can be perpendicular or at any other defined angle to the OR table or the coronal plane of the patient or any other plane of the patient. Alternatively, volumetric data can be displayed, e.g. from a CT scan or an MRI scan. The volumetric data can be registered to corresponding landmarks and/or surfaces in the physical patient, e.g. an acetabular edge or rim, an acetabular articular surface, an iliac wing surface, a symphysis pubis etc. By display the imaging study, optionally multiple 2D or 3D imaging studies, superimposed onto the live, physical anatomy of the patient, the OHMD can facilitate display of the underlying bone stock as well as display of hidden structures, e.g. nerves, nerve roots or vascular structures. Thus, the OHMD display of the imaging data can be used to guide the direction, speed and depth of any steps involving bone removal, e.g. reaming or broaching. In this manner, the OHMD display can facilitate the surgical procedure ensuring that no over-reaming of an acetabular fossa can occur since the underlying bone stock can be displayed. The imaging studies, e.g. one or more x-rays, a CT scan or MRI scan [optionally displayed by the OHMD as one or more 2D slices or a 3D reconstruction of the anatomy], and/or the underlying bone stock, and/or the acetabular component central axis and/or acetabular component reaming axis can be displayed concurrently thereby facilitating guidance of the reamer or other surgical instrument and determination of the reaming depth. For example, a computer processor can display one or more x-rays, a CT scan or MRI scan [optionally displayed by the OHMD as one or more 2D slices or a 3D reconstruction of the anatomy] using the OHMD superimposed onto and/or aligned with the corresponding anatomic structures of the patient, e.g. an acetabular rim or acetabular fossa [or, in a shoulder joint, a glenoid rim or glenoid fossa]. The display by the OHMD can include a display of the underlying bone stock, e.g. in the patient's pubic, iliac or ischial bone or an area of a tear drop, which can be used to determine a desired or predetermined reaming depth or which can be used to determine a desired or predetermined residual bone thickness, area of volume following the reaming or other forms of bone removal. Optionally the acetabular component central axis and/or acetabular component reaming axis can be displayed onto the surface of the acetabulum and underneath the surface of the acetabulum, e.g. extending into the one or more imaging studies, e.g. one or more x-rays, a CT scan or MRI scan [optionally displayed by the OHMD as one or more 2D slices or a 3D reconstruction of the anatomy], displayed by the OHMD. Optionally, one or more pre- or intra-operative imaging studies, e.g. one or more x-rays, a CT scan or MRI scan [optionally displayed by the OHMD as one or more 2D slices or a 3D reconstruction of the anatomy], can be used to determine a predetermined reaming depth, e.g. using a graphical user interface or virtual or other interface, which can optionally be displayed, e.g. in the form of a virtual stop for the physical reamer. The virtual stop can be a virtual indicator which shows how far the surgeon can advance a corresponding physical portion of the reamer in order to achieve the predetermined reaming depth. In some embodiments a reaming depth, e.g. for reaming an acetabulum, a proximal femur, a glenoid, or a proximal humerus, a patella or any other bone, or a depth for a bone removal can be determined using a pre- or intra-operative imaging test, e.g. one or more x-rays, a CT scan or MRI scan [optionally displayed by the OHMD as one or more 2D slices or a 3D reconstruction of the anatomy], which can show the bone in and underneath or subjacent to the area of intended reaming or bone removal [e.g. milling, drilling, burring, impacting] and which can also be used to determine the thickness, area or volume of the bone in and underneath or subjacent to the area of intended reaming or bone removal. The amount of bone removal can also be a predetermined fixed value, e.g. with a predetermined fixed depth [e.g. 0.5, 1.0, 2.0, 3.0, 4.0 mm etc.] or with a predetermined fixed area [e.g. 0.5, 1.0, 2.0, 3.0, 4.0 mm$^2$ etc.] or volume [e.g. 0.5, 1.0, 2.0, 3.0, 4.0 mm$^3$ etc.]. The surface, e.g. an articular or bone surface, of the area of intended reaming or bone removal [e.g. milling, drilling, burring, impacting] can then be detected using any of the techniques described in the specification or known in the art, e.g. using an intra-operative scan, e.g. an ultrasound scan, optionally with a tracked ultrasound probe, a mechanical probe or pointer applied to multiple points of the surface while tracking the probe in a coordinate system and generating a point cloud [e.g. for generating a surface from the point cloud] or an image or video capture system or a 3D scanner, e.g. a laser scanner. A computer processor can then display the predetermined reaming depth or depth of bone removal (e.g. for drilling, burring, milling, reaming, impacting) with use of the OHMD, e.g. superimposed onto and/or aligned with the surface of the area of intended reaming or bone removal and/or subjacent to or underneath the surface of the area of intended reaming or bone removal. For example, the depth can be displayed subjacent to the area of intended reaming or bone removal, e.g. subjacent to a glenoid articular surface [e.g. inside the glenoid or glenoid vault] or subjacent to an acetabular articular surface, e.g. inside the acetabular bone or bone structures of the patient; the depth can optionally be displayed as a 2D or 3D depth indicator. The depth can be displayed in the OHMD as a virtual 2D or 3D outline of the outer surface of the physical instrument or physical tool used for the bone removal, e.g. the outer surface of a drill, a burr, a reamer, a mill, an impactor, e.g. in their final desired or predetermined position and/or orientation and/or alignment and/or coordinates. The depth can be displayed in the OHMD as a graphical, virtual representation of the physical instrument or physical tool used for the bone removal, e.g. the outer surface of a drill, a burr, a reamer, a mill, an impactor, e.g. in their final desired or predetermined position and/or orientation and/or alignment and/or coordinates. A surgeon can advance the tool or instrument for bone removal, e.g. a drill, a burr, a reamer, a mill, an impactor, which can be optionally tracked using any of the techniques described in the specification or known in the art, and a computer processor can display virtually the portions of the tool or instrument for bone removal hidden inside the tissue using the registration and tracking data in the OHMD display superimposed onto the corresponding anatomic structures, e.g. the bone underneath an acetabular or glenoid surface, of the patient and it can also display the predetermined depth. The physical tool or physical instrument for bone removal, e.g. a drill, a burr, a reamer, a mill, an impactor, can then be advanced until the OHMD display indicates superimposition of the hidden portions of the physical tool or instrument hidden inside the tissue and the predetermined depth, e.g. a virtual 2D or 3D outline of the outer surface of the physical instrument or physical tool used for the bone removal or a graphical, virtual representation of the physical instrument or physical tool used for the bone removal, e.g. the outer surface of a drill, a burr, a reamer, a mill, an impactor, e.g. in their final desired or predetermined position and/or orientation and/or alignment and/or coordinates.

In step 732, the surgeon can ream the acetabulum, for example by aligning the physical reamer with the projected virtual reaming axis or a projected virtual reamer. In step 734, an intended or predetermined virtual acetabular reaming depth can be displayed and the physical reamer can be advanced until the virtual reaming depth reference is reached by a corresponding physical part of the physical reamer. Alternatively or additionally, the OHMD can also display an imaging study, e.g. registered with the patient, [e.g. one or more x-rays, a CT scan or MRI scan [optionally displayed by the OHMD as one or more 2D slices or a 3D reconstruction of the anatomy] to show the underlying bone stock so that the surgeon can monitor the remaining bone stock while advancing the reamer. The reamer can be tracked, e.g. using optical markers, navigation markers, a video system or a 3D scanner, and the position, e.g. x, y, z coordinates, and known geometry of the reamer can be used to determine how far the reamer has advanced into the bone. This information, in turn, can be used to compute or display the residual bone stock, e.g. in the acetabular wall [or, in a shoulder replacement, a glenoid fossa or the underlying bone, e.g. in the glenoid vault], by subtracting the reamer advancement, e.g. the distance travelled from the articular surface into the bone, from the overall acetabular bone stock, e.g. in mm or mm$^3$. In step 736, optionally an acetabular impaction axis can be projected by the OHMD. The acetabular impaction axis, acetabular component central axis and/or acetabular component reaming axis can be the same. In step 738, the acetabular component can be impacted, for example by aligning the impactor with the acetabular component impaction or reaming axis. In step 740, optionally, the position of the physical position and/or orientation of the femoral shaft of the patient can be determined, e.g. prior to reaming or broaching. For this purpose, for example, a screw placed in the proximal femur, e.g. with an attached optical marker or navigation marker, can be used for determining the position, orientation and/or coordinates of the proximal femur, e.g. at the level of the neck resection. In step 742, the OHMD can project a predetermined virtual entry or a virtual placement indicator, e.g. an outline, of an entry, e.g. an entry box, for a box osteotome for a given femoral shaft position and/or orientation and a desired femoral stem placement. The virtual entry or placement indicator can facilitate in guiding to a medial or lateral position, e.g. of reamer or broaches. Alternatively, a drill can be used instead of using a box osteotome. In step 744, the OHMD can optionally project the long axis of one or more broaches. The physical broach(es) can then be aligned with the virtual broach axis projected by the OHMD. Optionally, the physical broach can include extenders, e.g. from the broach handle; optionally the OHMD can display one or more virtual extenders to which the physical extenders can be aligned to. In step 746, femoral broaching can be performed. In step 748, optional trial reduction can be performed, e.g. for standard or different offsets, or different femoral stem or neck configurations. In step 750, femoral stem component impaction can be performed. The foregoing sequence or order can be modified based on surgeon preference. The sequence or order can be modified based on anterior vs. posterior approach. Select steps can be added or omitted based on surgeon preference. Select steps can be added or omitted based on anterior vs. posterior approach. Pelvic tilt, pelvic incidence and sacral slope can be introduced into the virtual surgical plan. In addition to supine pelvic x-rays, upright, standing pelvic x-rays can also be used. In a preferred embodiment, additional x-ray views, e.g. lateral view or sacral view can also be used to provide additional information. Pelvic tilt, pelvic incidence and/or sacral slope can be measured on supine and upright x-rays. The difference in pelvic tilt between supine and upright x-rays can, for example, be used to modify the virtual surgical plan, e.g. by changing the acetabular and/or femoral anteversion and/or the offset. When frontal, e.g. AP, x-rays of the pelvis are used in supine and upright position, the change in pelvic position, e.g. outline of acetabulum, width of ellipse, obliquity, change in shape and size of the obturator foramen can be applied to a standard model of a pelvis, which can optionally be deformed using statistical models and patient landmarks obtained from one or more x-rays, in order to estimate the difference in pelvic tilt between the supine and upright position.

Knee Replacement, Partial or Total

With knee replacement general alignment and orientation recommendations exist, some of which have been summarized in a review (Gromov et al. Acta Orthop 2014, 85, 5, 480-487): Neutral overall coronal alignment is currently the gold standard, and a neutral mechanical axis of the leg or 2-7° valgus anatomical tibial femoral axis can be targeted. The femoral component can be placed in 2-8° coronal valgus with respect to the femoral anatomic axis (e.g., 2°, 3°, 4°, 5°, 6°, 7°, 8°, 2-3°, 2-4°, 2-5°, 2-6°, 2-7°, 2-8°, 3-4°, 3-5°, 3-6°, 3-7°, 3-8°, 4- 5°, 5-6°, 5-7°, 5-8°, 6-7°, 6-8°, 7-8°) and >3 mm of implant component overhang over the bone should be avoided. The tibial component can be placed in neutral coronal alignment)(90° with maximum bone coverage and minimal, if any, implant component overhang. In the sagittal plane, the femoral component can be placed with 0-3° of flexion (e.g. 0°, 1°, 2°, 3°, 0-1°, 0-2°, 0-3°, 1-2°, 1-3°, 2-3°), and the tibial slope can be 0-7° (e.g. 0°, 1°, 2°, 3°, 4°, 5°, 6°, 7°, 0-1°, 0-2°, 0-3°, 0-4°, 0-5°, 0-6°, 0-7°, 1-2°, 1-3°, 1-4°, 1-5°, 1-6°, 1-7°, 2-3°, 2-4°, 2-5°, 2-6°, 2-7°, 3-4°, 3-5°, 3-6°, 3-7°, 4-5°, 4-6°, 4-7°, 5-6°, 5-7°, 6-7°). Internal rotation of the femoral component should be avoided, as the femoral component should be placed in 2-5° of external rotation in relation to surgical transepicondylar axis (e.g. 2°, 3°, 4°, 5°, 2-3°, 2-4°, 2-5°, 3-4°, 3-5°, 4-5°). Excessive tibial rotation with respect to neutral transverse axis of the tibia, tibial tubercle axis and also combined internal tibiofemoral rotation should also be avoided.

Any of the registration techniques and/or techniques described in the embodiments can be applied for knee replacement, e.g. resurfacing, partial and total knee replacement procedures, including implantable and attachable markers, calibration and registration phantoms including optical markers, navigation markers, infrared markers, RF markers, patient specific markers, LED's with image capture, e.g. using an optical imaging system and/or a 3D scanner, e.g. integrated into, attached to or separate from an OHMD, and IMU's. For example, one or more optical marker and/or patient specific markers or templates or other markers and/or LED's and/or IMU's or combinations thereof can be applied to the distal femur, for example the distal anterior cortex and/or the superior trochlea, optionally along with any osteophytes when present. Similarly, one or more optical markers and/or patient specific markers or templates or other markers and/or LED's and/or IMU's or combinations thereof can be applied to the proximal tibia, e.g. the anterior tibial cortex, for example in the tibial plateau area, optionally along with any osteophytes when present, or a tibial spine. One or more optical markers and/or patient specific markers or templates or other markers and/or LED's and/or IMU's or combinations thereof can be applied to the proximal tibia, e.g. the anterior tibial cortex By applying the one or more optical markers and/or patient specific markers or templates or any of the other registration techniques including implantable and attachable markers, calibration and registration phantoms, navigation markers, infrared markers, RF markers, LED's with image capture and IMU's to the corresponding structures on the patient, virtual data, e.g. derived from pre-operative imaging, and live data can be effectively cross-referenced for knee replacement surgery and can be, for example registered in a common coordinate system, e.g. with one or more OHMDs worn by the surgeon and his or her surgical assistants and nurses. By registering optical marker and/or the patient specific marker or template in relationship to the OHMD also, the OHMD can display or superimpose the desired position, location, orientation, alignment and/or axes and/or trajectory of any surgical instrument used during knee replacement.

The patient's joint, one or more OHMDs, one or more virtual data sets or virtual data can be registered in a common coordinate system. In a knee joint, two or more opposing articular surfaces, e.g. with opposing cartilage surfaces and underlying subchondral bone, can be registered separately and/or optionally jointly in a coordinate system, e.g. a common coordinate system. A first articular surface can be located on the distal femur, a second articular surface can be located on the proximal tibia, a third articular surface can be located on the patella. Registering the first articular surface and/or or associated bones and/or structures and the second articular surface and/or or associated bones and/or structures separately can have the benefit of allowing movement, e.g. flexion and/or extension and/or rotation and/or abduction, and/or adduction, and/or elevation and/or other movements, e.g. translation, of the first articular surface and/or or associated bones and/or structures, e.g. the distal femur, in relationship to the second articular surface and/or or associated bones and/or structures, e.g. the proximal tibia, while maintaining registration of the first articular surface and/or associated bones and/or structures, e.g. on the distal femur, and/or the second articular surface and/or or associated bones and/or structures, e.g. on the proximal tibia, e.g. in a common coordinate system or a subcoordinate system, optionally along with one or more OHMDs and/or fixed structures in the operating room, e.g. the OR table, and/or other structures or anatomic landmarks of the patient, e.g. irrespective movement of the individual portions of the joint. In this manner, the knee joint can be placed in different positions, e.g. flexion, extension, rotation, abduction, adduction, e.g. a degree of knee flexion, e.g. 90, 100, 110, 120 degrees, e.g. during placement of a femoral component, and a degree of knee flexion, e.g. 60, 70, 80 or other degrees, during placement of the tibial component, while the registration of the distal femur and/or the registration of the proximal tibia and the display of any virtual data, e.g. a virtual surgical guide, a virtual cut plane, a virtual implant component on the distal femur and/or the proximal tibia can be maintained and superimposed onto the corresponding anatomic area, e.g. the area intended for implant component placement, irrespective of the movement of individual portions of the joint, thereby allowing the one or more OHMDs to maintain anatomically registered displays of virtual data superimposed onto the corresponding portions of the physical joint anatomy, e.g. an articular surface, including a normal, damaged and/or diseased cartilage and/or subchondral bone and/or cortical bone, e.g. in a tangent, intersecting and/or offset manner, e.g. external and/or internal to the normal, damaged and/or diseased cartilage and/or subchondral bone and/or cortical bone.

In some embodiments, an ultrasound scan can be used to obtain the shape information of the distal femur and/or the proximal tibia and/or the patella, for example for designing, selecting or manufacturing a patient specific marker or template. For example, a handheld ultrasound or an ultrasound probe attached to a holding device, stand, tripod or the like can be used to image the distal anterior cortex and the superior trochlea of the femur, optionally along with any osteophytes when present. The ultrasound device can then be used to optionally image the proximal tibia, e.g. the anterior tibial cortex, for example in the tibial plateau area, optionally along with any osteophytes when present. The ultrasound device can then be used to optionally image the patella, e.g. the patellar surface, the whole patella or portions of the patella, for example the superior pole or inferior pole, medial or lateral edge, optionally along with any osteophytes when present. The ultrasound data can optionally be segmented. For example, bone shape and/or cartilage shape as well as, optionally, meniscal shape, when present, can be derived. Moreover, information about ligament location and/or morphometry, including, but not limited to, the origin, insertion, location, length, movement with flexion, extension, rotation of the knee, of the medial collateral ligament, lateral collateral ligament, anterior cruciate ligament, posterior cruciate ligament, patellofemoral ligament or tendon and quadriceps insertion can optionally also be captured with ultrasound.

In some embodiments, the shape information derived from the ultrasound data can optionally be used to design, select and/or manufacture a patient specific marker or template, for example one that fits on the distal anterior cortex and the superior trochlea of the femur of the patient, optionally along with any osteophytes when present; or one that fits on the proximal tibia of the patient, e.g. the anterior tibial cortex, for example in the tibial plateau area, optionally along with any osteophytes when present; or one or more that fits on the patella of the patient, e.g. the patellar surface, the whole patella or portions of the patella, for example the superior pole or inferior pole, medial or lateral edge, optionally along with any osteophytes when present.

Optionally, the ultrasound probe can also be used to image portions of the patient's hip joint, for example, to identify the center of the hip joint. Optionally, the ultrasound probe can also be used to image portions of the patient's ankle joint, for example to identify the ankle mortise or the center of the ankle joint or the ⅓ or ⅔ equidistant distance of the ankle joint in the coronal plane or select radii or distance from the medial or lateral ankle mortise. Optionally, the ultrasound scan(s) of the knee, optionally the hip and optionally the ankle can be obtained in supine or in upright position. By obtaining the ultrasound scan or scans in upright position, optionally more accurate information on mechanical axis alignment, in particular during weight-bearing, can be obtained. For example, varus or valgus deformity of the knee can be more pronounced under weight-bearing conditions. Correction of varus or valgus deformity using mechanical axis information under weight-bearing conditions can be more accurate than correction of varus or valgus deformity based on non-weight-bearing information. This information can be beneficial when planning any desired mechanical axis corrections.

Optionally, the location of the ultrasound probe can be captured while performing the hip scan and/or the ankle scan and, optionally, the knee scan, for example using optical markers with image capture or video capture, retro-reflective markers, infrared markers or RF markers or other tracking means used in conjunction with a surgical navigation system or, for example, using image capture, e.g. integrated into, attached to, coupled to or separate from an OHMD, or using one or more IMU's. By imaging the hip joint and the ankle joint, and, optionally, the knee joint in this manner and by capturing information of the ultrasound probe location and orientation, e.g. by tracking the coordinates of the ultrasound probe including its location, position, orientation, alignment and/or direction of movement and/or speed of movement, using one or more attached markers or any of the registration and/or tracking techniques described in the specification or known in the art, including 3D scanning or image or video capture, during the ultrasound scan, it is possible to derive information on the mechanical axis and/or the anatomic axis of the patient's leg and knee joint.

Of note, an ultrasound probe or ultrasound transducer used in any of the embodiments throughout the specification can be registered and/or tracked in a coordinate system, e.g. a common coordinate system in which, for example, the surgical site, and/or physical tissue of the patient, and/or one or more OHMDs and/or one or more virtual tools, virtual instruments, virtual implants, virtual devices, a virtual surgical plan or portions thereof, and/or physical tools, physical instruments, physical implants, physical devices can also be registered and, optionally, be tracked. By tracking the ultrasound probe, the images generated by the probe or transducer and ultrasound system, e.g. 2D slices or cross-sections or 3D images, can be registered also, optionally in real time, in the coordinate system and can be simultaneously displayed by the OHMD superimposed onto and/or aligned with the corresponding physical tissue or tissue slice or tissue volume of the patient, with the proper position, orientation, alignment of the ultrasound image displayed by the OHMD for a given viewer's perspective through the OHMD and for a given transducer position, orientation, alignment. Thus, when an operator moves the tracked transducer, e.g. with the left hand, and, with that, the ultrasound imaging plane or direction or orientation inside the patient, the computer processor can move the imaging plane or data or volume superimposed onto or aligned with the corresponding physical tissue of the patient in real time in the OHMD display. In some embodiments, the geometry of a tracked physical biopsy needle, surgical tool, instrument, implant or device, can be known and can be stored, for example, in a CAD file, and/or accessed by a computer processor associated with the OHMD display. As portions of the tracked physical biopsy needle, surgical tool, instrument, implant or device, disappear below the surface or inside the patient's tissue, a computer processor can display using the OHMD the hidden portions of the tracked physical biopsy needle, surgical tool, instrument, implant or device, e.g. hidden inside the tissue or underneath an organ surface.

In some embodiments, when an operator moves a tracked transducer, e.g. with the left hand, and, with that, the ultrasound imaging plane or direction or orientation inside the patient or the patient's tissue, and moves simultaneously, e.g. with the right hand, a physical biopsy needle, surgical tool, instrument, implant or device, the computer processor associated with the OHMD display can display both the ultrasound image and the tracked hidden portions of the physical biopsy needle, surgical tool, instrument, implant or device hidden inside the tissue [e.g. displayed using known geometries, e.g. using a CAD file of the physical biopsy needle, surgical tool, instrument, implant or device] in the OHMD display. If the tracked hidden portions of the physical biopsy needle, surgical tool, instrument, implant or device hidden inside the tissue are not within the imaging range or field of view of the ultrasound probe, the computer processor can display in the OHMD display the tracked hidden portions of the physical biopsy needle, surgical tool, instrument, implant or device using the tracking data while the OHMD display simultaneously can show the ultrasound image. Using the OHMD display and the tracking, the physical biopsy needle, surgical tool, instrument, implant or device can then be moved inside the tissue until it approaches the ultrasound beam and associated field of view and appears in the ultrasound image, displayed by the computer processor in the OHMD. This embodiment can, for example, be advantageous if it is desirable to maintain the ultrasound probe and image(s) over a lesion, e.g. a tumor, while advancing the physical biopsy needle, surgical tool, instrument, implant or device towards the ultrasound imaging field or volume and, ultimately, using ultrasound visualization into the lesion.

In some embodiments, information from an ultrasound, e.g. of the distal femur, proximal tibia, and/or patella, can be combined or fused with information from another imaging modality, e.g. an MRI, CT or x-ray. X-rays can include x-rays in prone, supine, non-weight-bearing position or in standing, weight-bearing position. X-rays can be limited to the knee only. X-rays can be obtained in different poses of the knee, e.g. in extension and at different flexion angles, weight-bearing or non-weight-bearing. Flexion/extension x-rays can, for example, be used to derive information about the rotational axes of the knee, e.g. an epicondylar or trochlear axis. X-rays can also include other portions of the lower extremity or the entire lower extremity, such as a standing full-length x-ray of the leg in weight-bearing position. A standing full-length x-ray of the leg in weight-bearing position can be used to identify the center of the hip joint as well as the ankle mortise, for example to estimate or derive a mechanical axis and/or an anatomic axis of the knee. In some embodiments, mechanical axis and/or anatomic axis and/or rotational axis information of the knee obtained from x-rays can be included in a patient specific marker or template derived from ultrasound. For example, a patient specific, ultrasound derived surface of the patient-specific marker can fit to a select anatomic region of the patient, e.g. a distal femur including portions of the superior trochlea or an anterior tibial cortex, for example in the tibial plateau area. One or more external facing surfaces of the patient specific marker or template can have a standard shape and can, optionally, include markers or indicators to show an anatomic axis of the knee of the patient, a mechanical axis of the knee of the patient, a desired new mechanical axis of the knee of the patient after the surgery is performed, e.g. as defined in an optional virtual surgical plan, and/or a rotational axis of the knee of the patient and/or a desired new rotational axis of the knee of the patient after the surgery is performed, e.g. as defined in an optional virtual surgical plan. These external markers or indicators including optical markers can then optionally be used during the surgery to confirm, for example, a desired mechanical axis correction or rotational axis correction or combinations thereof. An image and/or video capture system and/or 3D scanner attached to, integrated with, coupled to or separate from an OHMD can optionally be used to identify such corrections using, for example, one or more of the optical markers or indicators on the patient specific marker or template and, optionally to compare them to a virtual surgical plan. Any deviations or differences from the virtual surgical plan can be identified and the surgeon or operator can optionally perform modifications to the surgical technique, e.g. using additional ligament releases, bone cuts or different implant components including, for example, different medial, lateral or combined insert heights, insert shapes, spacers, and augments.

In some embodiments, the accuracy of the placement of an optical marker or a patient specific marker can be checked during the surgery. For example, in a knee replacement, the optical marker or patient specific marker can be placed on a distal femur or a proximal tibial or combinations thereof. A visual or an optical marker, e.g. an LED or a laser light, can indicate a mechanical axis of the patient, e.g. by projecting an arrow or a beam towards the center of the hip and/or the ankle. Alternatively, a mechanical marker, e.g. a femoral alignment rod pointing towards the hip or a tibial alignment rod pointing towards the ankle, can be used to indicate the mechanical axis of the patient as determined using the optical marker or patient specific marker. The femoral and/or tibial alignment rod can be integral, attachable or physically or visually linkable to the optical marker or patient specific marker. One or more optical markers can be integrated into or attached to a femoral and/or tibial alignment rod.

An intraoperative x-ray or an intra-operative ultrasound or an intra-operative CT can then be used to determine the physical center of the hip and/or the physical center of the ankle in the live patient on the OR table and, optionally, the patient's physical mechanical axis prior to any corrections. If the projected mechanical axis from optical marker or the patient specific marker coincides with the physical center of the hip and/or the physical center of the ankle, the placement or the information from the optical marker or patient specific marker is accurate. If the projected mechanical axis from the optical marker and/or patient specific marker does not coincide with the physical center of the hip and/or the physical center of the ankle, the placement of the optical marker and/or patient specific marker is not accurately placed and can be repositioned. The degree or amount of difference between the physical and the projected center of the hip and/or the ankle can be used to determine the amount of correction of placement needed. Alternatively, the optical marker and/or patient specific marker can remain in place; however, a correction can be applied to any subsequent registration, wherein the correction is based on the degree or amount of difference between the physical (from the intra-operative imaging study) and the projected center of the hip and/or the ankle (from the optical marker(s) and/or patient specific marker(s)). Someone skilled in the art can recognize that these types of corrections in placement or corrections can be applied to other measurements, e.g. rotational axes, and other joints.

Once any correction of placement inaccuracies of the optical markers and/or patient specific markers has been performed, if applicable, the intended axis correction, e.g. a correction of the patient's abnormal mechanical or rotational axis or both, can be executed on.

Femur

In some embodiments, once the femur is registered using any of the techniques described in the present disclosure and/or any of the other registration techniques described in the present disclosure or known in the art, including implantable and attachable markers, calibration and registration phantoms including optical markers, navigation markers, infrared markers, RF markers, patient specific markers, LED's with image capture and IMU's, the OHMD can display a virtual distal femoral cut block for performing the distal femoral cut.

Figure 19B:
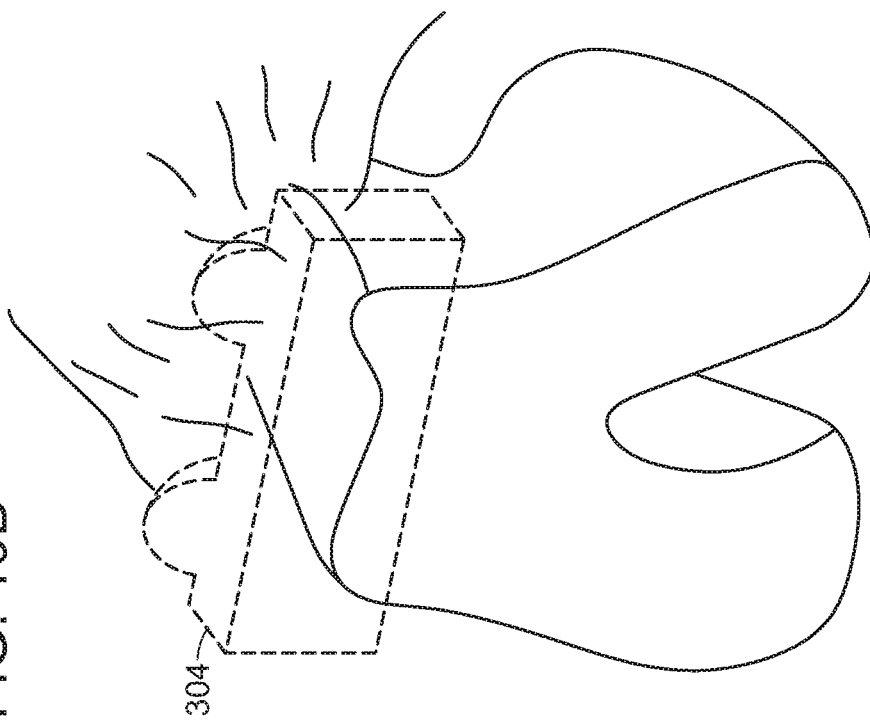
Figure 19A:
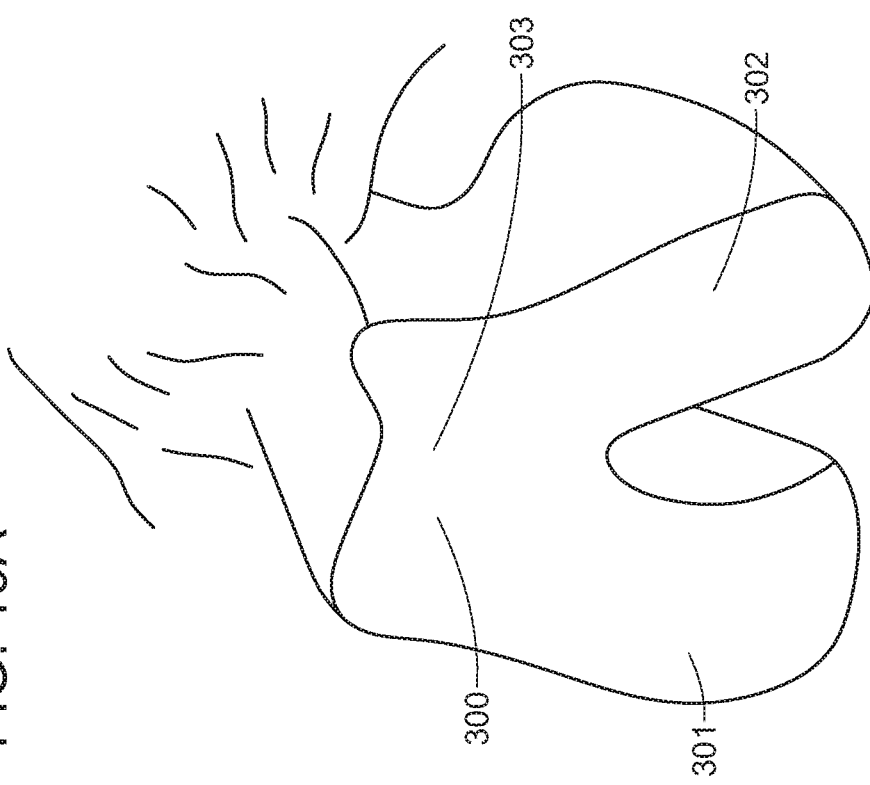

FIGS. 19A-D provide an illustrative, non-limiting example of the use of virtual surgical guides such as a distal femoral cut block displayed by an OHMD and physical surgical guides such as physical distal femoral cut blocks. FIG. 19A shows live data of a patient with a distal femur 300 exposed during knee replacement surgery, a medial condyle 301, a lateral condyle 302 and a trochlea 303. In FIG. 19B, one or more OHMDs can display a virtual distal femoral cut block, e.g. in a stereoscopic manner for the left eye and the right eye of the surgeon(s) creating a form of electronic hologram of the virtual surgical guide, i.e. the virtual distal cut block. The virtual distal femoral cut block 304 in this example is an outline of the physical distal femoral cut block with substantially similar dimensions as those of the physical distal femoral cut block. The virtual distal femoral cut block 304 is aligned based at least in part on coordinates of a predetermined position for guiding the distal femoral cut, for example for achieving a predetermined varus or valgus correction and/or a predetermined femoral component flexion relative to the distal femur and, for example, its anatomic or biomechanical axes. In FIG. 19C, the physical surgical guide 305, i.e. the physical distal femoral cut block 305 (solid line) in this example, can be moved and aligned to be substantially superimposed with or aligned with the virtual surgical guide 304, i.e. the virtual distal femoral cut block 304 (broken line) in this example. The hidden areas of the knee joint 306, obscured or hidden by the physical distal femoral cut block 305, can optionally also be displayed by the OHMD. In FIG. 19 D, the physical distal femoral cut block 305 can be attached to the distal femoral bone using two pins 307. These pins 307 can be used for subsequent surgical steps, for example for referencing a flexion gap or an extension gap or for ligament balancing. The OHMD can stop display the virtual surgical guide, i.e. the virtual distal femoral cut block in this example, but can optionally continue display the hidden anatomy 306.

Figure 44A:
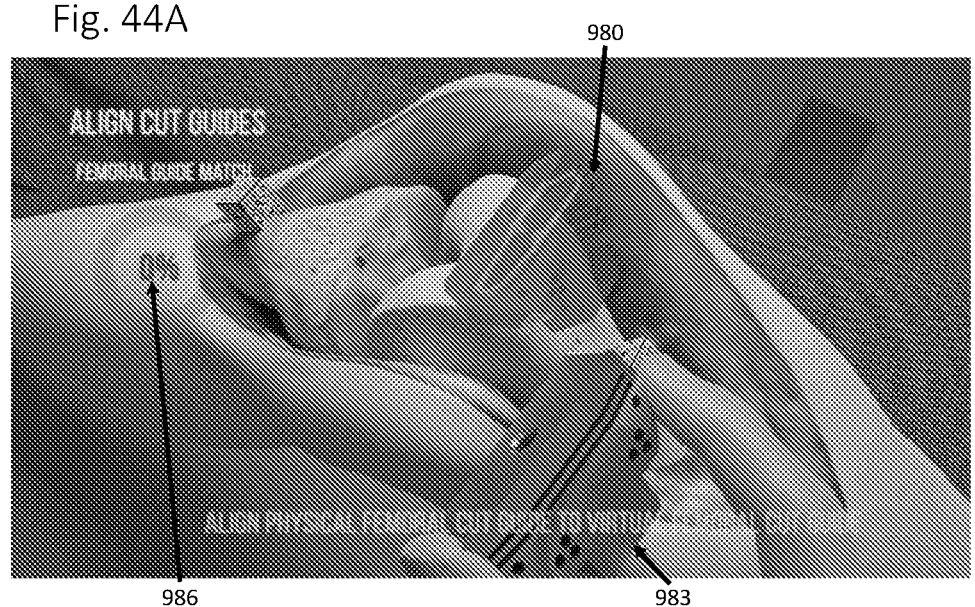
FIGS. 44A-B provide an illustrative, non-limiting example of the use of virtual surgical guides such as a distal femoral cut block displayed by an OHMD and physical surgical guides such as physical distal femoral cut blocks for knee replacement according to some embodiments of the present disclosure.
Figure 44B:
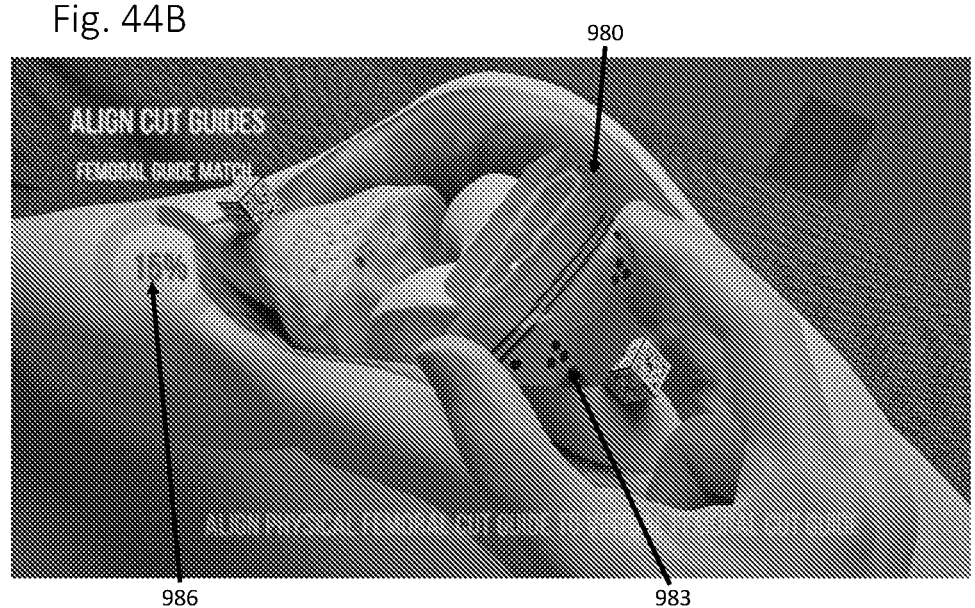

FIG. 44A shows an example of an optical head mounted display projecting a virtual surgical guide 980 onto the surface of the joint. A physical surgical guide 983 can then be superimposed onto and aligned with the virtual surgical guide. A computer processor can track the physical surgical guide 983, for example using direct video detection or one or more markers, e.g. navigation markers or optical markers (not shown), e.g. with a navigation system and/or image capture system, and can track the percentage superimposition 986 of the physical surgical guide 983 with the virtual surgical guide 980. The superimposition can be indicated as a percent volume superimposition between the physical and the virtual surgical guide, percent surface superimposition, percent area superimposition, percent superimposition in a first, second, and/or third direction, e.g. x-, y- and z-, e.g. in mm, percent superimposition with regard to angular alignment, e.g. in x-, y-, and z-direction, e.g. in degrees (e.g. for slope or flexion), percent coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical surgical guide is completely superimposed onto the virtual surgical guide (e.g. 100% match or >90% match or >95% match, or any other amount), the physical surgical guide can be pinned to the bone (not shown). The foregoing embodiments on tracking and/or displaying and/or determining and/or measuring superimposition can be applied to many different embodiments throughout the application, e.g. for spinal surgery, spinal fusion, hip replacement, shoulder replacement, ankle replacement, ACL reconstruction or repair, dental surgery, root canals, dental implant placement, etc.

The virtual distal femoral cut block can have the same or similar shape and one or more dimensions and one or more planes as the physical distal femoral cut block. Alternatively, the OHMD can only show a partial (e.g. broken or dotted) or complete 2D or 3D outline of the virtual distal femoral cut block or placement indicators, e.g. lines or planes indicating the predetermined placement position and orientation of the distal femoral cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. In the virtual surgical plan, the distal femoral cut will typically be perpendicular to the mechanical axis of the femur in order to restore mechanical axis alignment, unless the surgeon desires to preserve a mild varus deformity, for example, as can be the case with partial or some total knee replacements, or unless the surgeon uses a different alignment approach, e.g. kinematic alignment, or unless the surgeon desires to maintain a certain amount of pre-existing varus or valgus alignment in a patient. The surgeon can then take the physical distal femoral cut block and substantially align or superimpose the physical distal femoral cut block with the virtual distal femoral cut block or its 2D or 3D outline or its placement indicators displayed by the OHMD. Once adequate alignment or superimposition of the physical distal femoral cut block with the virtual distal femoral cut block or its 2D or 3D outline or its placement indicators displayed by the OHMD based on the patient's virtual surgical plan is achieved, the surgeon can pin or attach the physical distal femoral cut block to the bone and perform the cut. By utilizing preoperative 3D data information or intra-operative measurements of combinations of both for the alignment of the physical distal femoral cut block with the assistance of the OHMD, the surgeon can perform the distal femoral cut in an accurate manner, without the need for intramedullary rods or patient specific instrumentation for performing the cut. Alternatively, the OHMD can display a digital hologram of a virtual cut plane corresponding to the distal femoral cut and the surgeon can align the saw blade with the digital hologram of the virtual distal femoral cut plane.

The display of a virtual surgical guide, which can be a virtual plane or a predetermined path for guiding a bone cut or a tissue cut, using an OHMD is applicable to any surgical procedure that includes placing one or more bone cuts or tissue cuts. In some embodiments, the display of a virtual plane or a predetermined path for guiding a bone cut, e.g. with a bone saw, using an OHMD display can be used to evaluate the accuracy of a cut that is being executed using another guidance or cutting technique, for example with surgical navigation and/or a robot. The OHMD can display the predetermined virtual plane or the predetermined path for the cut, for example imported into a computer processor associated with the OHMD from a virtual surgical plan used by a surgical navigation system and/or a robot. If the surgical navigation system and/or the robot fail to execute the physical bone cut according to its predetermined location, position, orientation, and/or alignment, the difference between the actual, physical bone cut and the predetermined virtual plane or the predetermined path for the bone cut can be visible through the see-through optical head mounted display and/or also an optical head mounted VR display, e.g. non see-through, using one or more cameras for imaging the live data of the patient and/or the physical saw blade. If the surgical navigation system and/or the robot fail to direct or move the bone saw according to its predetermined location, position, orientation, and/or alignment and/or direction, the difference between the actual, physical location, position, orientation, and/or alignment of the physical bone saw and the predetermined virtual plane or the predetermined path can be visible through the see-through optical head mounted display and/or also an optical head mounted VR display, e.g. non see-through, using one or more cameras for imaging the live data of the patient and/or the physical saw blade. For example, bone saws can bend or skive when they hit or enter hard bone, e.g. cortical bone or sclerotic bone as can be present in an arthritic joint. As the bone saw bends or skives, the deviation of the bone saw from the virtual surgical plane and/or its predetermined path can be visualized in the see-through optical head mounted display and/or also an optical head mounted VR display, e.g. non-see-through, using one or more cameras for imaging the live data of the patient and/or the physical saw blade. Similarly, as the bone cut deviates from the virtual surgical plane and/or its predetermined path as a result of the bending or skiving of the saw blade, the deviation or difference of the physical bone cut from the virtual surgical plane can be visualized in the see-through optical head mounted display and/or also an optical head mounted VR display, e.g. non-see-through, using one or more cameras for imaging the live data of the patient and/or the physical saw blade.

Similarly, when physical gut guides or cut blocks are used, for example in conjunction with a virtual surgical plan developed for OHMD guided surgery, as the bone saw bends or skives, the deviation of the bone saw from the virtual surgical plane and/or its predetermined path can be visualized in the see-through optical head mounted display and/or also an optical head mounted VR display, e.g. non see-through, using one or more cameras for imaging the live data of the patient and/or the physical saw blade. Similarly, as the bone cut deviates from the virtual surgical plane and/or its predetermined path as a result of the bending or skiving of the saw blade, the deviation or difference of the physical bone cut from the virtual surgical plane can be visualized in the see-through optical head mounted display and/or also an optical head mounted VR display, e.g. non-see-through, using one or more cameras for imaging the live data of the patient and/or the physical saw blade. This can be particularly apparent when there is a gap between the exit portion of a slot of the physical surgical guide, e.g. a physical cut block, and the joint, e.g. the articular surface of the joint, which can be frequently present for physical femoral and/or tibial cut guides, for example due to the variable shape and curvature of the joints of different patients.

Optionally, the OHMD can display a digital hologram of a virtual femoral alignment rod or a placement indicator thereof, e.g. indicating a central axis for an alignment rod, which can extend from the distal femur to the hip joint. The surgeon can compare the alignment of the virtual femoral alignment rod or placement indicator with the physical femoral alignment rod in the live patient and assess if both align with the center of the hip joint of the live patient. If the virtual (including a placement indicator) and the physical femoral alignment rod are not aligned with each other and/or the center of the hip joint, the surgeon can check the accuracy of alignment of the physical alignment rod in the live patient, the accuracy of registration of live data of the patient and virtual data of the patient and/or the accuracy of the virtual surgical plan. The surgeon can then optionally make adjustments to the alignment of the physical alignment rod in the live patient, the registration or the virtual surgical plan.

The surgeon can then, for example, select to display or project a digital hologram of the virtual femoral AP cut block in the OHMD. The virtual femoral AP cut block can have the same or similar shape and dimensions as the physical femoral AP cut block. The OHMD can display the virtual femoral AP cut block or a partial (e.g. broken or dotted) or complete 2D or 3D outline of the virtual distal femoral cut block or placement indicators, e.g. planes or lines indicating the predetermined placement position and orientation of the AP femoral cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual surgical plan can include the predetermined position and rotation for the virtual femoral AP cut block. The rotation of the femoral AP cut block can determine the rotation of the resultant anterior and posterior femoral cuts in relationship to, for example, a femoral rotation axis or other axis or anatomic landmark, and, with that, can determine the femoral component implant rotation. The OHMD can display the virtual femoral AP cut block or its 2D or 3D outline or one or more placement indicators.

Figure 20A:
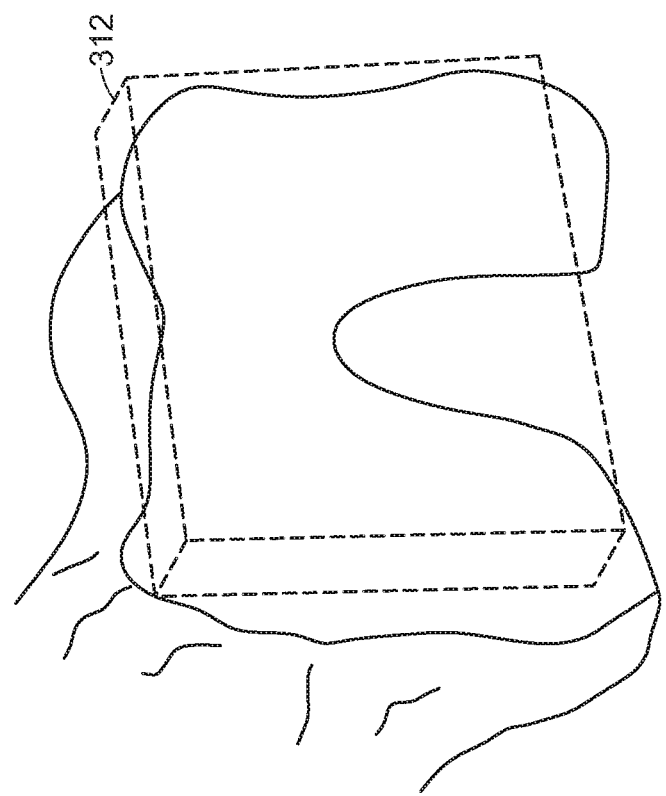
FIGS. 20A-C provide an illustrative, non-limiting example of the use of virtual surgical guides such as an AP femoral cut block displayed by an OHMD and physical surgical guides such as physical AP cut blocks for knee replacement according to some embodiments of the present disclosure.
Figure 20B:
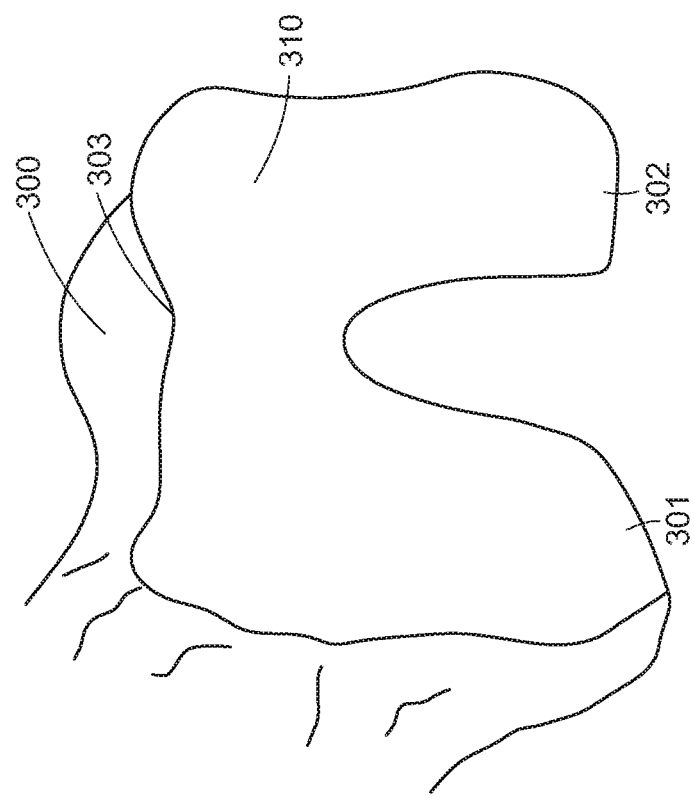
Figure 20C:
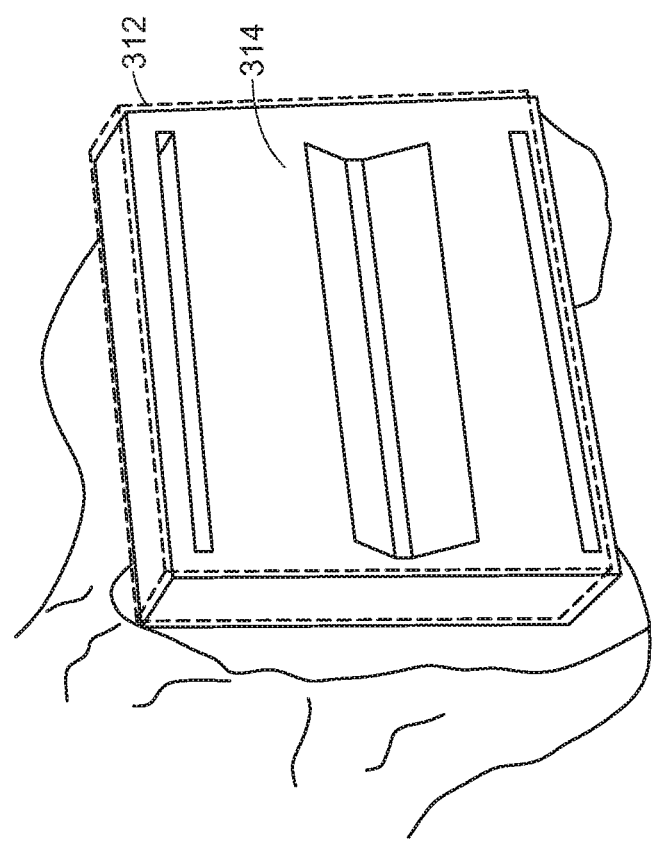

FIGS. 20A-C provide an illustrative, non-limiting example of the use of virtual surgical guides such as an AP femoral cut block displayed by an OHMD and physical surgical guides such as physical AP cut blocks for knee replacement. FIG. 20A shows live data of a patient with a distal femur 300 exposed during knee replacement surgery after a distal femoral cut creating a planar distal surface 310, a medial condyle 301, a lateral condyle 302 and a trochlea 303. In FIG. 20B, one or more OHMDs can display a virtual femoral AP cut block 312, e.g. in a stereoscopic manner for the left eye and the right eye of the surgeon(s) creating a form of electronic or digital hologram of the virtual surgical guide, i.e. the virtual femoral AP cut block 312. The virtual femoral AP cut block 312 in this example is an outline of the physical femoral AP cut block with similar dimensions, edges, or planes as those of the physical femoral AP cut block. The virtual femoral AP cut block 312 is aligned based at least in part on coordinates of a predetermined position for guiding the different bone cuts, e.g. an anterior cut, posterior cut and/or chamfer cuts depending on the configuration of the physical femoral AP cut block, for example for achieving a predetermined femoral component rotation. In FIG. 20C, the physical surgical guide 314, i.e. the physical femoral AP cut block 314 (solid line) in this example, can be moved and aligned to be substantially superimposed with or aligned with the virtual surgical guide 312, i.e. the virtual femoral AP cut block 312 (broken line) in this example. The physical femoral AP cut block can be attached to the distal femoral bone using pins (not shown) and the cuts can be performed. Subsequent surgical steps can optionally be referenced based on one or more of the cuts executed using the physical femoral AP cut block. The surgeon can align or substantially superimpose the physical femoral AP cut block with the digital hologram of the virtual femoral AP cut block or its 2D or 3D outline or one or more placement indicators projected by the OHMD. Once adequate alignment or superimposition of the physical AP cut block with the virtual AP cut block or its 2D or 3D outline or one or more placement indicators displayed by the OHMD has been achieved, the surgeon can pin the physical AP cut block and perform the cuts. By utilizing preoperative 3D data information or intra-operative information, e.g. from optical marker and image or video capture measurements, for the position, alignment and rotation of the physical femoral AP cut block with the assistance of the OHMD, the surgeon can perform the anterior and posterior femoral cuts in a highly accurate manner, thereby achieving accurate rotational alignment of the femoral component. The same approaches and display options, e.g. virtual cut blocks, 2D or 3D outline or one or more placement indicators, can be applied to all subsequent femoral preparation steps including chamfer cuts and chamfer cut blocks.

Of note, similar steps and OHMD guided femoral procedures are also possible using the OHMD with any of the other registration and cross-referencing techniques described in the present disclosure or known in the art, for example intraoperative image guidance.

Tibia

In some embodiments, once the tibia is registered using any of the techniques described in the present disclosure or known in the art, including, for example, implantable and attachable markers, calibration and registration phantoms including optical markers, navigation markers, infrared markers, RF markers, patient specific markers, LED's with image capture and IMU's, the OHMD can display a virtual proximal tibial cut block for performing the proximal tibial cut. Alternatively, the OHMD can only show a partial (e.g. broken or dotted) or complete 2D or 3D outline of the virtual proximal tibial cut block or placement indicators, e.g. planes or lines indicating the predetermined placement position and orientation of the proximal tibial cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual proximal tibial cut block can have the same or similar shape and dimensions as the physical proximal tibial cut block or it can have at least one or more dimensions or planes that are identical to the physical proximal tibial cut block or guide.

Figure 21A:
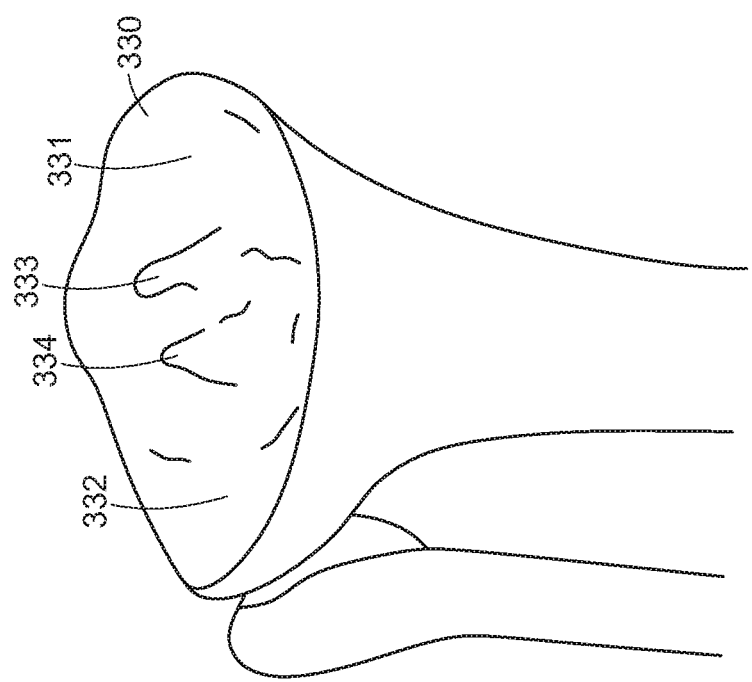
FIGS. 21A-F provide an illustrative, non-limiting example of the use of virtual surgical guides such as a virtual proximal tibial cut guide displayed by an OHMD and physical surgical guides such as physical proximal tibial cut guide according to some embodiments of the present disclosure.
Figure 21C:
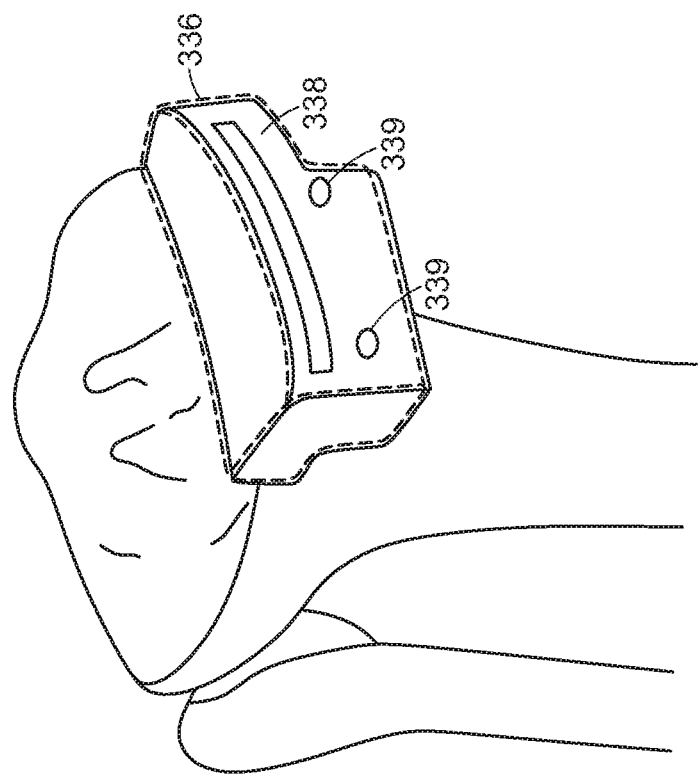
Figure 21B:
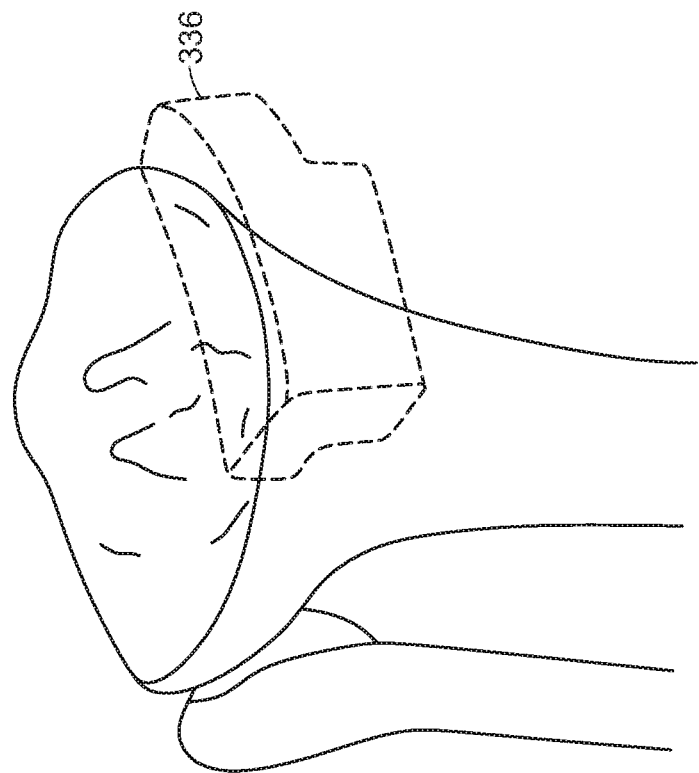
Figure 21E:
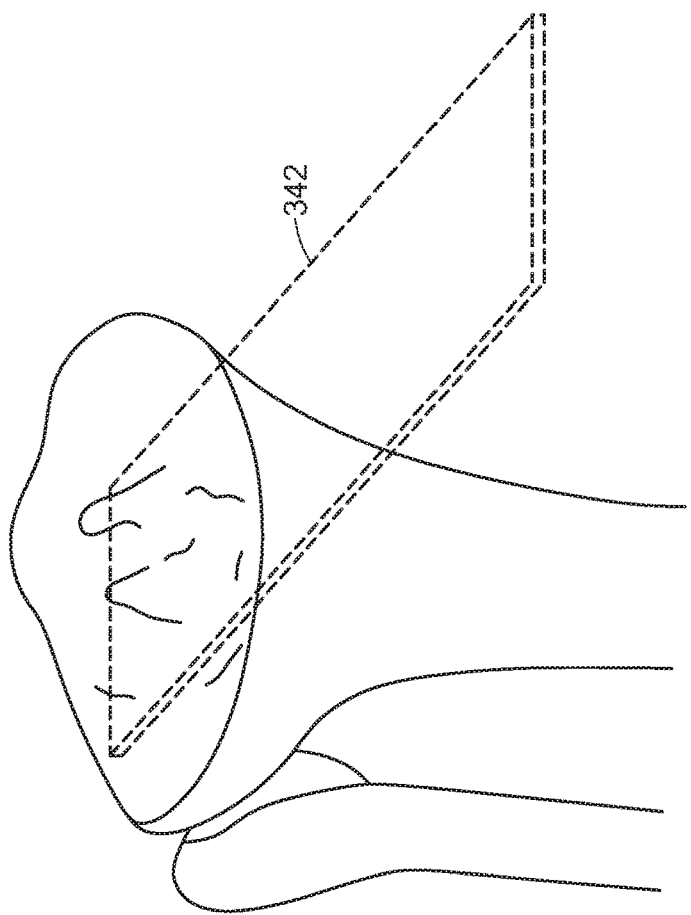
Figure 21D:
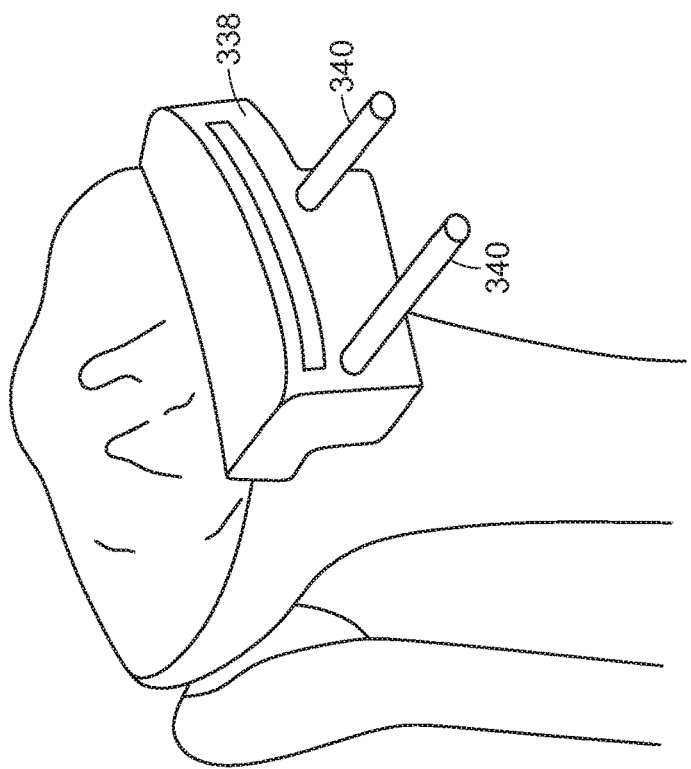
Figure 21F:
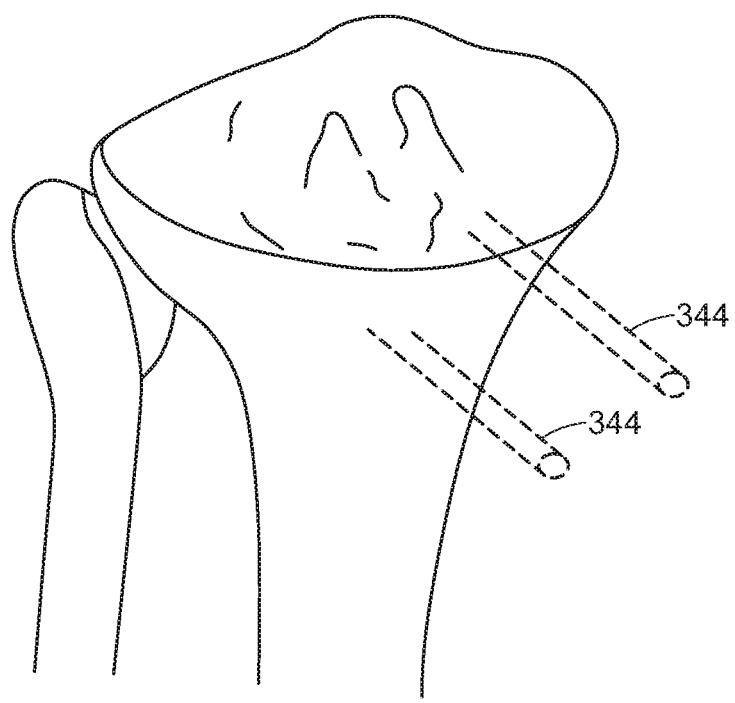

FIGS. 21A-F provide an illustrative, non-limiting example of the use of virtual surgical guides such as a virtual proximal tibial cut guide displayed by an OHMD and physical surgical guides such as physical proximal tibial cut guide. FIG. 21A shows live data of a patient with a proximal tibia 330 exposed during knee replacement surgery, a medial tibial plateau 331, a lateral tibial plateau 332 and a medial tibial spine 333 and a lateral tibial spine 334. In FIG. 21B, one or more OHMDs can display a virtual proximal tibial cut guide, e.g. in a stereoscopic manner for the left eye and the right eye of the surgeon(s), creating a form of electronic hologram of the virtual surgical guide, i.e. the virtual proximal tibial cut guide. The virtual proximal tibial cut guide 336 in this example can be an outline of the physical proximal tibial cut guide with substantially similar dimensions as those of the physical proximal tibial cut guide. The virtual proximal tibial cut guide 336 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. In FIG. 21C, the physical surgical guide 338, i.e. the physical proximal tibial cut guide 338 (solid line) in this example, can be moved and aligned to be substantially superimposed with or aligned with the virtual surgical guide 336, i.e. the virtual proximal tibial cut guide 336 (broken line) in this example. Note two pin holes 339 in the physical proximal tibial cut guide 338. In FIG. 21D, the physical proximal tibial cut guide 338 can be attached to the proximal tibia bone using two pins 340. These pins 307 can be used for subsequent surgical steps, for example for referencing a flexion gap or an extension gap or for ligament balancing. In FIG. 21E, an alternative embodiment is shown to FIG. 21B. One or more OHMDs can display a virtual proximal tibial cut plane 342, e.g. in a stereoscopic manner for the left eye and the right eye of the surgeon(s), creating a form of electronic hologram of the virtual tibial cut plane. The virtual proximal tibial cut plane 342 in this example is parallel with and substantially aligned and superimposed with the predetermined cut plane for the physical proximal tibial cut guide. The virtual proximal tibial cut plane 342 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. A physical saw blade or a slot for aligning the physical saw blade in a physical proximal tibial cut guide or an open guide area for accommodating the saw blade in a physical proximal tibial cut guide can then be aligned and at least partially superimposed with the virtual proximal tibial cut plane 342. In FIG. 21F, an alternative embodiment is shown to FIG. 21B. One or more OHMDs can display two or more virtual drills or pins 344 for placement in the proximal tibia, e.g. in a stereoscopic manner for the left eye and the right eye of the surgeon(s), creating a form of electronic hologram of the virtual tibial pins or drills. The virtual drills or pins 344 in this example can be an outline or a projected path of the physical pins or drills that can be used to fixate a physical proximal tibial cut guide to the proximal tibia. The virtual drills or pins 344 are aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. The physical drills or pins (not shown) can then be aligned and superimposed with the virtual drills or pins 344 and placed in the proximal tibia. A physical proximal tibial cut guide can then be attached to the physical pins and the proximal tibial cut can be executed.

In some embodiments, a physical and a corresponding virtual proximal tibial guide or a physical and a corresponding virtual distal femoral guide can also be pin guides, wherein the physical guide can be used to place two or more pins in the bone for attaching physical cut guides for subsequent surgical steps. The embodiments for aligning physical with virtual guides, as shown for example in FIGS. 19B and 19C, 20B and 20C, and 21B and 21C, can also be applied to pin guides.

Someone skilled in the art can recognize that the use of virtual and physical surgical guides, including cut guides and pin guides, can be applied to any joint of the human body and the spine.

In the virtual surgical plan, the proximal tibial cut can be perpendicular to the mechanical axis of the tibia in order to restore neutral mechanical axis alignment, unless the surgeon desires to preserve a mild varus deformity, for example, as can be the case with partial or some total knee replacements, or unless the surgeon uses a different alignment approach, e.g. kinematic alignment, or unless the surgeon desires to maintain a certain amount of pre-existing varus or valgus alignment in a patient. The surgeon can then take the physical proximal tibial cut block and substantially align or superimpose the physical proximal tibial cut block with the virtual proximal tibial cut block or its 2D or 3D outline or its placement indicators displayed by the OHMD. The virtual surgical plan and/or the intraoperative measurements can optionally determine not only the alignment of the proximal tibial cut in relationship to the mechanical axis of the leg, but can also determine the anterior-posterior slope with which the proximal tibia is cut in sagittal direction. In some embodiments, the surgeon, the operator or semi-automatic or automatic software may elect to cut the proximal tibia with a fixed sagittal slope, e.g. 5 degrees or 7 degrees or 3 degrees, for example with a Cruciate Retaining (CR) knee replacement system. Or the surgeon, the operator or semi-automatic or automatic software may elect to cut the proximal tibia with a fixed sagittal slope, e.g. 0 degrees or 2 degrees or 3 degrees, for example with a Posterior Substituting (PS) knee replacement system. Or the surgeon, the operator or semi-automatic or automatic software may elect to cut the proximal tibia with a patient specific slopes, which can be identical to or derived from the medial slope of the native, un-operated medial tibial plateau, the lateral slope of the native, un-operated lateral tibial plateau, or combinations or averages thereof. Once adequate alignment or superimposition of the physical proximal tibial cut block with the virtual representation of the virtual proximal tibial cut block or its 2D or 3D outline or its placement indicators displayed by the OHMD based on the patient's virtual surgical plan and/or intra-operative measurements is achieved, the surgeon can pin the physical proximal tibial cut block and perform the cut, which can then reflect an alignment with the desired mechanical axis correction and the desired tibial slope. By utilizing preoperative 3D data information and/or intraoperative measurements and/or information for the alignment of the physical proximal tibial cut block with the assistance of the OHMD, the surgeon can perform the proximal tibial cut in an accurate manner, without the need for intramedullary rods or patient specific instrumentation for performing the cut. At the same time, the surgeon retains the ability to perform intraoperative adjustments, which can be as simple as manually moving the distal or other femoral cut blocks or moving the proximal tibial cut block or other tibial cut blocks, for example also with use of a stylus like device, e.g. for checking and measuring slope. Any such adjustment can be checked against the virtual surgical plan and/or the intraoperative measurements, by displaying in the OHMD, for example, the final desired implant position or the predetermined position of the corresponding virtual surgical instruments for which the adjustment is contemplated in the physical surgical instrument. Any difference in alignment between any virtual surgical instrument and any physical surgical instrument can be indicated in numeric values by the OHMD, e.g. distance in millimeters or angles in degrees, e.g. difference in external rotation of the femoral component. Any subsequent steps in the virtual surgical plan can be modified in the event the surgeon or operator elected to perform an adjustment, e.g. of tibial slope or femoral or tibial resection levels.

Of note, the same steps and OHMD guided tibial procedures are also possible using the OHMD with any of the other registration and cross-referencing techniques described in the present disclosure or known in the art, for example using intraoperative image guidance and implantable and attachable markers, calibration and registration phantoms including optical markers, navigation markers, infrared markers, RF markers, patient specific markers, LED's with image capture and IMU's.

A tibial template or tibial base trial can be used to prepare the proximal tibia for accepting the tibial implant component. A drill can be used to remove the bone in the center of the proximal tibia to accept the central bore of the keel of the tibial component. A keel punch can be used to punch out the space to accept the keel wings of the tibial component. The final seating and orientation of the tibial keel and keel wings can determine tibial implant rotation. Accurate tibial rotation, for example aligned with the rotation axis of the native knee, is an important objective for avoiding postoperative pain.

In some embodiments, the OHMD can display a digital hologram of a virtual tibial template or virtual tibial base trial as well as virtual tibial drill towers and virtual keel punches. Other virtual tibial preparation instruments can be displayed depending on the configuration and surgical technique of the knee replacement system used. Alternatively, the OHMD can only show a partial (e.g. broken or dotted) or complete 2D or 3D outline of the virtual tibial template or virtual tibial base trial as well as virtual tibial drill towers and virtual keel punches or other virtual tibial preparation instruments or placement indicators, e.g. planes or lines indicating the predetermined placement position and orientation of the tibial template or tibial base trial as well as tibial drill towers and keel punches or other tibial preparation instruments, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual tibial template or tibial base trial as well as virtual tibial drill towers and virtual keel punches and other virtual tibial preparation instruments can have the same or similar shape and dimensions as the physical tibial template or physical tibial base trial as well as physical tibial drill towers and physical keel punches and physical tibial preparation instruments. In the virtual surgical plan, the virtual tibial template or tibial base trial as well as virtual tibial drill towers and virtual keel punches and virtual tibial preparation instruments can be aligned in a manner to achieve close to zero tibial rotation error of the final, physical tibial tray implanted in relationship to the native rotation axis of the tibia of the un-operated knee, if intended. The surgeon or operator has the option to deviate from zero rotation and can add optionally 1, 2, 3 or more degrees of internal or external tibial component rotation to the virtual surgical plan and/or the intra-operative measurements.

For each step of the tibial preparation, the OHMD can display digital holograms of the virtual tibial instrument(s) used or its (their) 2D or 3D outline or its (their) placement indicators along with its (their) desired alignment and rotation based on the virtual surgical plan. The surgeon can then align or superimpose the corresponding physical tibial instrument with the virtual tibial instrument(s) or its (their) 2D or 3D outline or its (their) placement indicators thereby achieving the desired alignment and/or rotation of the physical tibial instrument in relationship to the virtual surgical plan and/or the intraoperative measurements. All virtual tibial preparation tools and instruments including virtual tibial templates or virtual tibial base trials as well as virtual tibial drills, drill towers or saws and keel punches can be displayed using digital holograms by the OHMD if desired. Alternatively, the OHMD can display digital holograms of a 3D contour or placement indicators of the virtual tibial instruments. Optionally, the OHMD can only display the key instruments used for setting tibial component alignment and rotation. By utilizing preoperative 3D data information and/or intra-operative measurements and/or information for the position, alignment and rotation of the virtual tibial preparation instruments, the tibial trials and final tibial components or their respective 2D or 3D outlines or placement indicators displayed with the assistance of the OHMD, the surgeon can perform the physical tibial preparation in an accurate manner by matching physical instruments and components with the alignment and rotation of the virtual instruments and components or their respective 2D or 3D outlines or placement indicators, thereby achieving accurate rotational alignment of the tibial component.

Optionally, the OHMD can display a digital hologram of a virtual tibial alignment rod, which can extend from the proximal tibia to the ankle joint. The surgeon can compare the alignment of the virtual tibial alignment rod with the physical tibial alignment rod in the live patient and assess if both align with the desired location in the ankle joint of the live patient. If the virtual and the physical tibial alignment rod are not aligned with each other and/or the desired location in the ankle joint, the surgeon can check the accuracy of alignment of the physical alignment rod in the live patient, the accuracy of registration of live data of the patient and virtual data of the patient and/or the accuracy of the virtual surgical plan and/or the intra-operative measurements. The surgeon can then optionally make adjustments to the alignment of the physical alignment rod in the live patient, the registration or the virtual surgical plan.

Of note, the same steps and OHMD guided tibial procedures are also possible using the OHMD with the other registration and cross-referencing techniques described in the present disclosure or known in the art including implantable and attachable markers, calibration and registration phantoms including optical markers, navigation markers, infrared markers, RF markers, patient specific markers, LED's with image capture and IMU's.

Patella

In some embodiments, one or more optical markers and/or patient specific markers or templates or combinations thereof can be applied to the patella or patellar surface or portions of the patella, for example the superior pole or inferior pole, medial or lateral edge, optionally along with any osteophytes when present. By applying the one or more optical markers and/or patient specific markers or templates to the corresponding structures on the patient or using any of the other techniques and techniques for registration described in the present disclosure or known in the art, e.g. implantable and attachable markers, calibration and registration phantoms, navigation markers, infrared markers, RF markers, LED's with image capture and IMU's, virtual data and live data can be effectively cross-referenced for patellar replacement or partial or complete resurfacing. By registering the optical marker and/or patient specific marker or template in relationship to the OHMD, e.g. in a common coordinate system with the OHMD and the femur, tibia and patella, or by registering the OHMD in relationship to the live data and virtual data of the patient using any of the registration techniques described in the present disclosure, the OHMD can display or superimpose digital holograms indicating the desired position, location, orientation, alignment and/or trajectory of any surgical instrument used during patellar replacement or partial or complete resurfacing, including with a virtual display of the patellar preparation instrument, a 2D or 3D outline of the patellar preparation instrument or a virtual display of predetermined placement indicators.

In some embodiments, once the patella is registered using any of the techniques described in the present disclosure, including, for example, implantable and attachable markers, calibration and registration phantoms including optical markers, navigation markers, infrared markers, RF markers, patient specific markers, LED's with image capture and IMU's, the OHMD can display or project a digital hologram of a virtual patellar clamp, patellar tool, patellar cutting device, patellar milling device, predetermined milling axis and/or patellar cut block or other patellar preparation instrument for performing the patellar cut or patellar preparation.

Alternatively, the OHMD can only show a partial (e.g. broken or dotted) or complete 2D or 3D outline of the virtual patellar clamp, patellar tool, patellar cutting device, patellar milling device, and/or patellar cut block or other patellar preparation instrument or placement indicators, e.g. lines indicating the predetermined placement position and orientation of the virtual patellar clamp, patellar tool, patellar cutting device, patellar milling device, and/or patellar cut block or other patellar preparation instrument, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The digital holograms of the virtual patellar clamp, patellar tool, patellar cutting device, patellar milling device, and/or patellar cut and/or other patellar preparation instrument block can have the same or similar shape and at least one or more dimensions or planes that are identical to those of the corresponding physical patellar clamp, patellar tool, patellar cutting device, patellar milling device, and/or patellar cut block and/or other patellar preparation instrument. In the virtual surgical plan, the patellar cut or milling can be planned, for example at a desired resection depth or angle selected for a particular patellar implant or replacement and/or a particular patient anatomy, and/or based on patellar shape, patellar tracking, patellofemoral kinematics or knee rotation axes. The surgeon can then take the physical patellar clamp, patellar tool, patellar cutting device, patellar milling device, and/or patellar cut block and/or other patellar preparation instrument and substantially align or superimpose the physical patellar clamp, patellar tool, patellar cutting device, patellar milling device, and/or patellar cut block and/or other patellar preparation instrument with the corresponding virtual patellar clamp, patellar tool, patellar cutting device, patellar milling device, and/or patellar cut block and/or other patellar preparation instrument or its respective virtual contour or placement indicators displayed by the OHMD. Once adequate alignment or superimposition of the physical patellar clamp, patellar tool, patellar cutting device, patellar milling device, and/or patellar cut block and/or other patellar preparation instrument with the digital holograms of the virtual patellar clamp, patellar tool, patellar cutting device, patellar milling device, and/or patellar cut block and/or other patellar preparation instrument or its respective contour or placement indicators displayed by the OHMD based on the patient's virtual surgical plan and/or intra-operative measurements is achieved, the surgeon can optionally pin or fixate the physical virtual patellar clamp, patellar tool, patellar cutting device, patellar milling device, and/or patellar cut block and/or other patellar preparation instrument and perform the cut or milling. By utilizing preoperative 3D data information or intraoperative data and/or measurements or combinations thereof for the alignment of the physical virtual patellar clamp, patellar tool, patellar cutting device, patellar milling device, and/or patellar cut block and/or other patellar preparation instrument with the assistance of the OHMD, the surgeon can perform the patellar cut or milling in a highly accurate manner.

The patellar procedures described in the present disclosure can also be implemented using any of the other registration techniques described in the present disclosure or known in the art including implantable and attachable markers, calibration and registration phantoms including optical markers, navigation markers, infrared markers, RF markers, patient specific markers, LED's with image capture and IMU's. For example, using an image and/or video capture system and/or 3D scanner integrated into, attached to, coupled to or separate from the OHMD, it is possible to image the patellar shape or surface or contour. The information can be compared to pre-operative imaging information about patellar shape or surface or contour and a match can optionally be performed for purposes of registration. Any of the other registration techniques described in the present disclosure or known in the art including, but not limited to, surgical navigation can be used. Optionally, an IMU including, for example, pyrometers, magnetometers and accelerometers can be applied to the patella during the surgery or pre-operatively.

Assessment of Tibial Slope: In some embodiments, a tibial slope can be determined. The tibial slope can be a medial tibial slope. The tibial slope can be a lateral tibial slope. The medial tibial slope can be measured, for example, by connecting the highest point on the anterior medial tibia with the highest point on the posterior medial tibia as seen, for example, on a lateral radiograph or a 2D or 3D scan, e.g. an ultrasound, a CT or MRI scan. The lateral tibial slope can be measured, for example, by connecting the highest point on the anterior lateral tibia with the highest point on the posterior lateral tibia as seen, for example, on a lateral radiograph or a 2D or 3D scan, e.g. an ultrasound, a CT or MRI scan.

A tibial slope can be measured for the anterior tibia and the posterior tibia. For example, an anterior medial tibial slope can be measured by connecting the highest point on the anterior medial tibia with the lowest point in the medial tibial plateau. A posterior medial tibial slope can be measured by connecting the lowest point in the medial tibial plateau with the highest point on the posterior medial tibia. An anterior lateral tibial slope can be measured by connecting the highest point on the anterior lateral tibia with the lowest point in the lateral tibial plateau. A posterior lateral tibial slope can be measured by connecting the lowest point in the lateral tibial plateau with the highest point on the posterior lateral tibia. The tibial slope can be determined, for example, by measuring the angle between any of the resultant lines and the perpendicular line to the ground or, for example, by measuring the angle between any of the resultant lines and one or more tibial axes, e.g. the long axis of the tibia. Optionally, the distance from the anterior medial cortex or the posterior medial cortex to lowest point on the medial tibial plateau can be determined. Optionally, the distance from the anterior lateral cortex or the posterior lateral cortex to lowest point on the lateral tibial plateau can be determined.

The one or more measurement(s) of one or more tibial slopes can optionally be introduced into a virtual surgical plan, for example as displayed by the OHMD during the surgery. The virtual surgical plan can entail that the same one or more tibial slopes, e.g. a medial slope and/or a lateral slope, or an average of the two or other combinations of the two be preserved after placement of the one or more virtual implant components in the virtual surgical plan, e.g. as displayed by the OHMD, and, ultimately, after placement of the actual one or more implant components during the live surgery. Alternatively, a medial slope, a lateral slope, an average of the two or other combinations of the two can be corrected. For example, they can be set to a fixed medial slope, a fixed lateral slope, a fixed average of the two or a fixed other combination of the two. For example, a 5-degree fixed slope medially and laterally can be chosen in the virtual surgical plan. Or a 3-degree fixed slope medially or laterally can be chosen in the virtual surgical plan. Or a 2-degree fixed slope medially or laterally can be chosen in the virtual surgical plan. Or a 0-degree fixed slope medially or laterally can be chosen in the virtual surgical plan.

With some posterior stabilized implants, a 0-degree fixed slope can be chosen, although other fixed slopes such as 2, 3, and 5 degrees or any other value are possible. With some posterior cruciate retaining implants, a 5-degree fixed slope can be chosen, although other slopes such 0 degrees, 2 degrees or 4 degrees or any other value are possible.

In some embodiments, at least one slope that is similar to or identical to the native slope of the unoperated patient will be preferred. For example, in some embodiments, the patient's medial slope and/or the patient's lateral slope will be preserved. In some embodiments, the patient's native medial slope will be preserved in the virtual surgical plan, while the lateral slope may not be preserved. For example, the lateral slope may be fixed or may be set equal to the patient's medial slope or at a value or ratio between the two. In some embodiments, the patient's native lateral slope will be preserved in the virtual surgical plan, while the medial slope may not be preserved. For example, the medial slope may be fixed or may be set equal to the patient's lateral slope or at a value or ratio between the two.

Replicating the patient's native medial tibial slope and lateral tibial slope can be achieved in the virtual surgical plan, for example as displayed by the OHMD, and during the actual surgery by choosing separate medial and lateral tibial plateau components which can then be placed with different slopes relative to each other by placing the virtual tibial cuts and, in the live patient, the actual tibial cuts at an angle close to or substantially similar to the patient's native medial and lateral slopes.

In some embodiments, the OHMD can display the patient's medial and/or lateral slope, for example through a colored or dotted line. The OHMD can also display the intended medial and/or lateral slope, for example as defined in a virtual surgical plan. The intended medial and/or lateral slope can be displayed with a colored or dotted line or plane, optionally different from the patient's native slope(s) if they are also being displayed. The surgeon can then direct a bone saw or burr or other surgical instrument so that the bone saw, burr or other surgical instrument will substantially execute a removal of portions of the proximal tibial plateau to achieve placement of the implant with the one or more of the intended medial and/or lateral slopes.

In some embodiments, measurements of one or more tibial slopes can be obtained with the patient in supine position. Alternatively, measurements of the patient's tibial slope can be obtained with the patient in prone position. Alternatively, measurements of the patient's tibial slope can be obtained in upright position. In another embodiment, the imaging data, e.g. x-ray, ultrasound, CT scan or MRI, can be obtained with use of a positioning device or a leg holder. Typically, the positioning device or leg holder can be used to control the degree of knee flexion or extension (see, for example, the Synaflex knee positioning device by Synarc, Inc.). The positioning device or leg holder can be used to control the degree of knee rotation or leg rotation. In an embodiment, x-ray, ultrasound, CT and/or MRI scans are obtained with the leg in zero rotation or, alternatively, a defined degree of internal or external rotation, e.g. 5 degrees of internal or external rotation. In another embodiment, the same or a similar positioning device or leg holder can be used during the surgery, preferably utilizing the same degrees of flexion or extension and/or rotation as was used during any of the pre-operative imaging studies.

Display of Tibial Joint Line(s): In another embodiment, the medial and/or the lateral joint line can be determined. The joint line can be measured on an x-ray, an ultrasound scan, CT scan or MRI scan. Joint line measurements can be based on 2D and/or 3D data and can be displayed by one or more OHMDs.

In some embodiments, measurements of one or more tibial joint lines can be obtained with the patient in supine position. Alternatively, measurements of the patient's tibial joint line(s) can be obtained with the patient in prone position. Alternatively, measurements of the patient's tibial joint line(s) can be obtained in upright position.

In some embodiments, the medial and/or the lateral joint line can be measured in relationship to the ground, e.g. by measuring the distance of the medial and/or lateral joint line in relationship to the ground. In another embodiment, the medial and/or the lateral joint line can be measured in relationship to the undersurface of the calcaneus, e.g. by measuring the distance of the medial and/or lateral joint line in relationship to the undersurface of the calcaneus. In an embodiment, the medial and/or lateral joint line can be measured in relationship to each other and the difference in height of the medial and the lateral joint line for a given position or a given radiographic view or ultrasound scan or CT scan or MRI scan, can be measured, for example in mm. The difference in height of the medial and the lateral joint line for a given position or a given radiographic view or ultrasound scan or CT scan or MRI scan can be 0 mm, 0.5 mm, 1 mm, 2 mm, 3 mm, 4 mm, 5 mm, 6 mm, 7 mm, or 8 mm, or more. The medial joint line can be more distal than the lateral joint line. The lateral joint line can be more distal than the medial joint line. Measurements can be performed for the joint line(s) along the anterior medial and lateral tibial plateau. Measurements can be performed for the joint line(s) along the posterior medial and lateral tibial plateau. Measurements can be performed for the joint line(s) where they extend through the lowest point in the medial and lateral tibial plateau. Measurements can be performed for the joint lines using a composite projection of the medial and lateral tibial plateau in AP orientation. The medial and/or the lateral joint line or a composite thereof can be projected by one or more OHMDs, e.g. prior to resection femoral or tibial bone and/or after one or more femoral or tibial bone resections.

In another embodiment, the imaging data, e.g. x-ray, ultrasound, CT scan or MRI, can be obtained with use of a positioning device or a leg holder. Typically, the positioning device or leg holder can be used to control the degree of knee flexion or extension (see, for example, the Synaflex knee positioning device by Synarc, Inc.). The positioning device or leg holder can be used to control the degree of knee rotation or leg rotation. In an embodiment, x-ray, ultrasound, CT and/or MRI scans are obtained with the leg in zero rotation or, alternatively, a defined degree of internal or external rotation, e.g. 5 degrees of internal or external rotation. In another embodiment, the imaging data can be obtained with the knee in extension. In another embodiment, the imaging data can be obtained with the knee in flexion, e.g. 5, 10, 15, 20 or more degrees of flexion. In another embodiment, if x-rays are used, the x-ray tube and film or detector system will be preferably positioned so that the x-ray beam is substantially perpendicular to the joint space.

Display of femoral offset(s) and related information: In another embodiment, one or more offsets between the medial and the lateral femoral condyle can be measured. An offset between the medial and the lateral femoral condyle can be determined distally, for example with the knee in extension. An offset between the medial and the lateral femoral condyle can be determined posteriorly, for example with the knee in 90 degrees or more of flexion. An offset between the medial and the lateral femoral condyle can be determined for any other flexion angle or extension angle. Offsets can be measured with the knee in extension on the imaging study; a line perpendicular to the ground or a line corresponding to the y-axis of the scan can be determined through the lowest point of the medial femoral condyle and the lowest point of the lateral femoral condyle; where the lines intersects the medial distal femoral condyle articular surface and the respective lateral femoral condyle articular surface, the distal offset can be measured. Additional lines or planes can be placed at other angles, e.g. 15 degrees relative to the perpendicular or y-axis or 30 degrees relative to the perpendicular or y-axis, corresponding to 15 degrees of knee flexion or 30 degrees of knee flexion and so forth. Any possible flexion angle or extension angle can be simulated in this manner and the respective lines or planes can be displayed by one or more OHMDs.

An offset between the medial femoral condyle and the lateral femoral condyle can be measured on an x-ray, an ultrasound scan, CT scan or MRI scan. Femoral offset measurements can be based on 2D and/or 3D data. In some embodiments, measurements of one or more femoral offsets can be obtained with the patient in supine position. Alternatively, measurements of one or more femoral offsets can be obtained with the patient in prone position. Alternatively, measurements of one or more femoral offsets can be obtained in upright position.

In some embodiments, one or more femoral offsets can be measured in relationship to the ground, e.g. by measuring the distance of the medial and lateral femoral condyle in relationship to the ground, e.g. for different flexion and extension angles, and by determining the difference between the medial and the lateral distance measurement(s). In another embodiment, one or more femoral offsets can be measured in relationship to the undersurface of the calcaneus, e.g. by measuring the distance of the medial and lateral femoral condyle in relationship to the undersurface of the calcaneus, e.g. for different flexion and extension angles in relationship to the undersurface of the calcaneus, and by determining the difference between the medial and the lateral distance measurement(s). One or more distal or posterior offsets or offsets at different extension and flexion angles can be 0 mm, 0.5 mm, 1 mm, 2 mm, 3 mm, 4 mm, 5 mm, 6 mm, 7 mm, or 8 mm, or more. The medial femoral condyle can be more distal than the lateral femoral condyle. The lateral femoral condyle can be more distal than the medial femoral condyle. The one or more femoral offsets can be similar to the difference in medial and lateral joint lines.

In other embodiments, the imaging data, e.g. x-ray, ultrasound, CT scan or MRI, can be obtained with use of a positioning device or a leg holder. Typically, the positioning device or leg holder can be used to control the degree of knee flexion or extension (see, for example, the Synaflex knee positioning device by Synarc, Inc.). The positioning device or leg holder can be used to control the degree of knee rotation or leg rotation. In an embodiment, x-ray, ultrasound, CT and/or MRI scans are obtained with the leg in zero rotation or, alternatively, a defined degree of internal or external rotation, e.g. 5 degrees of internal or external rotation. Control of rotation of the leg and beam angulation, e.g. for x-ray and ultrasound, can be important to avoid over- or under-estimation of femoral offsets, e.g. on lateral radiographs, e.g. for one or more extension or flexion angles. In an embodiment, offsets are measured with any x-ray beam directed perpendicular at the joint space in an AP view and directed perpendicular to the knee in a lateral view. In an embodiment, magnification correction can be applied to the medial and/or the lateral femoral condyle depending on the tube film or detector and/or condyle/film or detector distance. The magnification correction can be different for the medial and the lateral condyle to account for difference in distance to the detector and resultant differences in magnification. In another embodiment, femoral offset(s) are corrected for any radiographic magnification. For example, if the radiographic magnification is 1.2, then the femoral offset can optionally be divided by 1.2. In another embodiment, the imaging data can be obtained with the knee in extension. In another embodiment, the imaging data can be obtained with the knee in flexion, e.g. 5, 10, 15, 20 or more degrees of flexion. In another embodiment, if x-rays are used, the x-ray tube and film or detector system will be preferably positioned so that the x-ray beam is substantially perpendicular to the joint space.

Once one or more offsets between a medial and a lateral femoral condyle have been determined, e.g. a distal offset corresponding to the knee in extension, a flexion offset corresponding to the knee in 15 degrees flexion, a flexion offset corresponding to the knee in 30 degrees flexion, a flexion offset corresponding to the knee in 60 degrees flexion and/or a posterior offset corresponding to the knee in 90 degrees flexion, the measurements can be used to determine desired femoral offsets on the femoral implant component.

In some embodiments, a femoral component is selected that has similar offsets as the native knee of the patient, e.g. in extension and 90 degrees of flexion, in extension, in 15 degrees of flexion, 30 degrees of flexion, and 90 degrees of flexion or any other values. For example, in a patient with no or little distal femoral offset, a femoral component with no or little offset such as the Zimmer Nexgen CR or PS femoral component can be used. For example, in a patient with more significant distal femoral offset, e.g. between 3 and 4 mm, a femoral component with a more significant femoral offset can be used, e.g. a Smith & Nephew Journey femoral component. For example, in a patient with a posterior femoral offset, a femoral component with a posterior femoral offset can be used, e.g. a Smith & Nephew Profix femoral component. A virtual surgical plan displayed by one or more OHMDs can be used to display the intended bone resection or virtual surgical instruments, e.g. virtual cut blocks, needed for executing the bone resections for these different types of implants and guide the resections. The virtual cut depth in the virtual surgical plan as displayed by the OHMD during the surgery can be chosen in the virtual surgical plan so that with the virtual implant placed, accounting for its composite thickness, the articulating surface of the medial and the lateral insert can be close to the patient's native joint line on the medial side or the lateral side, while at the same time replicating the medial-lateral femoral offset.

The OHMD can display the different bone resections needed for various off-the-shelf implants; the bone resections can be determined, for example, based on the radiographic template information available for each implant type and the different implant sizes available for each implant type. Alternatively, implants and implant components can be scanned using a 3D scanner. Alternatively, CAD files, e.g. STL files, can be obtained from the different manufacturers for each implant type and size. The OHMD can then display the individual bone resections for the different cuts for different implant types and sizes, e.g. for a distal femoral, anterior, posterior and chamfer bone cuts of the femur and a proximal tibial cut as well as the bone removal for the tibial template to accommodate the tibial keel. The cuts can be executed using standard metal cut guides and instruments or disposable cut guides and instruments. Disposable instruments and/or cut guides can, for example, be made using different plastic types, e.g. various polycarbonates, and using different manufacturing techniques, e.g. injection molding and/or 3D printing. In order to account for the variability in off-the-shelf implant designs from different manufacturers, the variability in size, the variability in shape, and the variability in bone resections, ratchet like mechanisms and/or insert like mechanisms can be used to make disposable instrumentation and cut blocks applicable to a wide range of off-the-shelf implants. The distal femoral and proximal tibial cut guides can be configured not require implant specific dimensions. The distal femoral and proximal tibial cut guides can be configured with a single plastic component to be applicable to a wide range of implant types and their respective size range. A femoral multi-cut guide, which can be used to place the anterior, posterior, and chamfer cuts, can be designed in two or three pieces which can include a ratchet like mechanism with resultant bone cut dimensions adjustable, for example, in 0.5 mm or 1° increments; a mm or ° scale can be included in the plastic mold adjacent to the ratchet. The ratchet can be moved so that the mm and degree setting matches the corresponding mm and degrees in the radiographic templates and/or CAD file or STL file of an implant component. The OHMD can visually display the numeric values, e.g. in mm and/or degrees, needed for a particular cut for a given implant and the surgeon can match these values on the mm and/or degree scale of the ratchet-like mechanism. An image capture and/or video capture system integrated into, attached to or separate from the OHMD can capture the mm and/or degree setting on the physical ratchet like mechanism; an alarm can be triggered if the mm and/or degree setting on the physical ratchet like mechanism differs from the mm and/or degree setting determined based on the radiographic template and/or the CAD or STL file of the implant. The anterior, posterior and chamfer cuts can be adjusted in position and angle for a given implant geometry based on the information obtained, for example, from the radiographic implant templates and/or the CAD or STL files of the implant, which can be reflected in the OHMD display. The OHMD can optionally add the thickness of the saw blade, e.g. 0.5 mm, 0.75 mm, 1.0 mm, 1.25 mm, 1.5 mm to the planned resection; thus if a resection plane has been planned based on a virtual surgical plan and for a given implant geometry, measured or determined, for example, from a radiographic template and/or a CAD or STL file of the implant, the resection plane can be adjusted, e.g. anteriorly, posteriorly, superiorly, inferiorly, medially, laterally, and/or also in oblique planes, to account for the saw blade thickness and to move the virtual cut plane in the OHMD display by a corresponding distance. The OHMD can optionally add an additional offset to account for saw blade flutter, e.g. 0.5 mm, 0.75 mm, 1.0 mm, 1.25 mm, 1.5 mm to the planned resection. The saw blade flutter can be smaller with increasing saw blade thickness.

It can be measured in a separate experiment, for example by cutting a bone with the saw mounted on a fixed frame that allows only movement along the intended direction of the saw blade; the increase in bone resection in the physical bone beyond the thickness of the saw blade can be measured for different saw blade thicknesses to account for saw blade flutter. Thus, if a resection plane has been planned based on a virtual surgical plan and for a given implant geometry, measured or determined, for example, from a radiographic template and/or a CAD or STL file of the implant, and for a given saw blade thickness, the resection plane can be adjusted, e.g. anteriorly, posteriorly, superiorly, inferiorly, medially, laterally, and/or also in oblique planes, to account for not only the saw blade thickness, but also the saw blade flutter and to move the virtual cut plane in the OHMD display by a corresponding distance. A ratchet like mechanism in a disposable instrument and/or cut block can also allow the surgeons to make additional adjustments, for example by increasing or decreasing the cut depth by an additional 0.5 or 1.0 mm or 0.5 or 1.0 degrees in order to account for the saw blade thickness and/or saw blade flutter, e.g. as displayed or accounted for by the OHMD. As an alternative or in addition, adjustable inserts can be used with different dimensions and thicknesses, e.g. 1, 2, 3, 4, 5, 6, 7 or more mm and/or 1, 2, 3, 4, 5, 6, 7, 8, 9, 10 or more degrees. The inserts can, for example, be inserted in a standard injection molded piece of a cut guide, e.g. between the gut guide and the articular surface or a cut bone surface. By inserting the insert between the gut guide and the articular surface or a cut bone surface, the next cut executed with the cut guide can be moved, e.g. by the thickness and/or angle added by the insert. Alternatively, the chamfer cuts can be disaggregated from the plastic multi-cut block and separate chamfer cut blocks, also optionally injection molded can be used, which can also include ratchet like mechanisms and/or inserts for adjusting the depth, position, and/or angle of each cut. The OHMD can display a virtual ratchet, e.g. as part of a virtual instrument and/or cut block, including a virtual ratchet setting, e.g. in mm or degrees, and/or a virtual insert including a virtual insert thickness or angle, corresponding to the angle and/or mm setting chosen for a given implant geometry. The surgeon can compare the virtual display with the physical ratchet and or insert including their respective settings and/or thickness and/or angle. Optionally, the physical instrument and/or cut block including its ratchet and/or inserts can be registered in common coordinate system with the patient's joint, e.g. a knee, and one or more OHMDs. The OHMD can display the virtual instrument and/or cut block including optionally its ratchet and/or inserts in a predetermined position, location and/or orientation and/or coordinates over the patient's joint, e.g. external to a distal femur after a distal femoral cut has been executed or external to a proximal tibia after a proximal tibial cut has been executed. The surgeon can align the physical instrument and/or cut block, e.g. without registration and without tracking it, including optionally its ratchet and/or insert(s) with the virtual cut block including optionally the virtual ratchet and/or insert(s) displayed by the OHMD. The OHMD can display numeric values, e.g. in mm or degrees, e.g. for a desired position and/or location and/or angle of a chamfer cut. The surgeon can ensure that the settings of the physical instrument and/or cut block including its ratchet and/or inserts, e.g. settings in mm or degrees, match the virtually displayed instrument and/or cut block including its ratchet and/or inserts. These embodiments related to virtual and physical ratchets, inserts and adjustment mechanisms and their corresponding virtual displays including in numeric values can be applied to any joint, e.g. for hip replacement, shoulder replacement, ankle replacement and/or elbow replacement surgery.

Figure 40C:
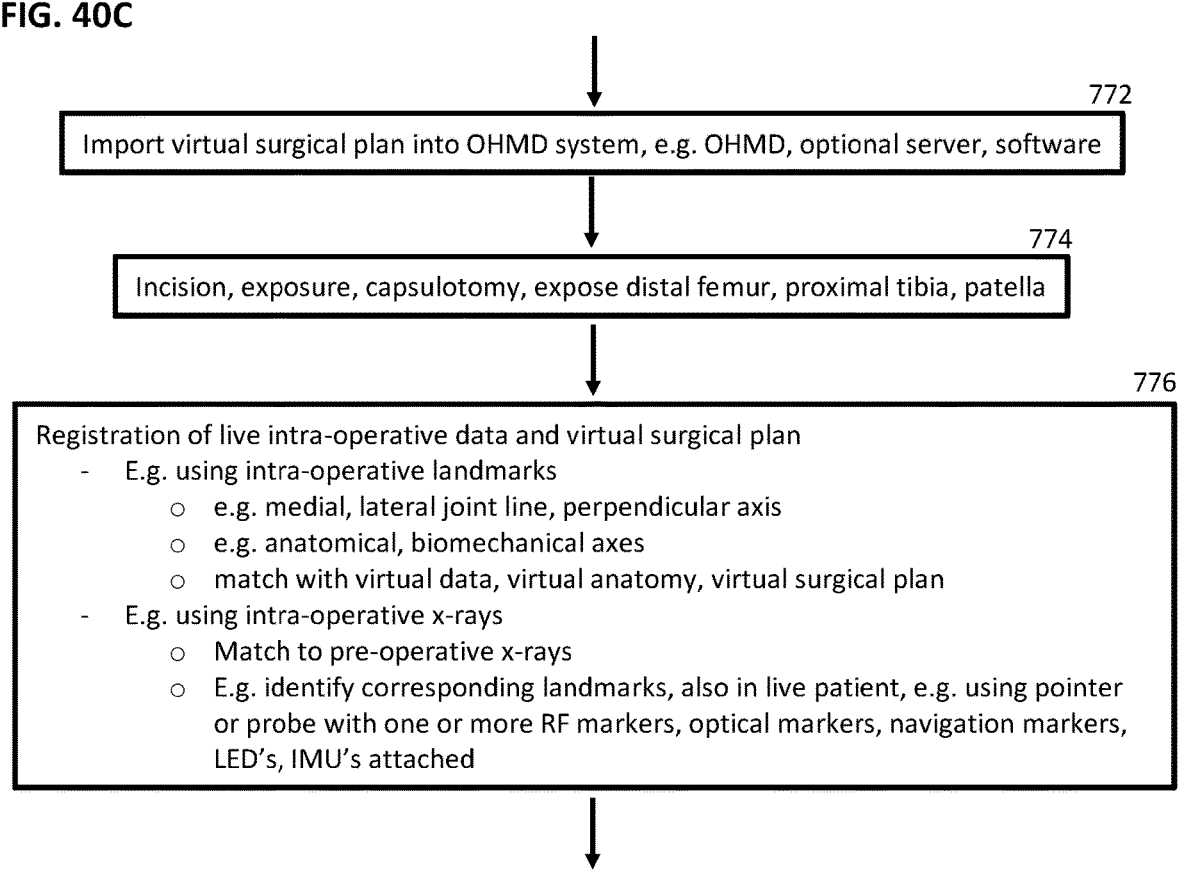

FIG. 40 is an illustrative, non-limiting example of a process flow for OHMD guided surgery for knee replacement, for example with femur first or tibia first technique, measured resection or ligament balancing. In step 760, x-rays of the leg can be obtained. These can be standing lower extremity x-rays, e.g. including the hip, knee and ankle. The standing, load bearing x-rays can be used to determine the mechanical axis of the leg and to determine the degree of varus or valgus deformity and any desired direction, e.g. back to normal mechanical axis alignment (180 degrees) or some residual deformity, e.g. a constitutional varus deformity, e.g. of 1 degree, 2 degrees, 3 degrees, 4 degrees, etc. In some embodiments, lateral view standing, weight-bearing x-rays can be obtained. These can be used to determine, for example, an underlying sagittal deformity and to plan any desired or predetermined correction. In some embodiments, non-weight-bearing x-rays of the leg can be obtained; optionally, these can be obtained, for example, while exerting varus or valgus stress. Imaging under varus or valgus stress can be useful, for example, for determining ligamentous instability and can be used to determine any predetermined corrections, e.g. by adjusting one or more femoral or tibial resection to correct a ligamentous instability. In some embodiments, the mechanical axis can be determined with use of one or more optical markers, e.g. placed on the distal femur and/or the proximal tibia. The leg can be moved on a circular pathway, which can be used to compute the center of rotation of the hip joint by monitoring or measuring the path of the marker movement, e.g. using one or more video cameras. An ankle clamp can be placed on the medial and lateral malleolus. The ankle clamp can include one or more optical markers at defined geometric locations relative to the ankle clamp and the medial and lateral malleolus; by measuring the coordinates of the optical marker, e.g. using one or more video cameras, the center of the ankle joint can be determined. The center of rotation of the hip joint and the center of the ankle joint can be used to determine the mechanical axis of the leg. In some embodiments, the mechanical axis can be determined with use of one or more navigation markers, e.g. placed on the distal femur and/or the proximal tibia. The leg can be moved on a circular pathway, which can be used to compute the center of rotation of the hip joint by monitoring or measuring the path of the movement of the navigation markers, e.g. IR or RF, using a navigation system. An ankle clamp can be placed on the medial and lateral malleolus. The ankle clamp can include one or more navigation markers at defined geometric locations relative to the ankle clamp and the medial and lateral malleolus; by measuring the coordinates of the navigation markers, the center of the ankle joint can be determined using a navigation system. The center of rotation of the hip joint and the center of the ankle joint can be used to determine the mechanical axis of the leg. In step 762, knee x-rays, e.g. AP, lateral, oblique, patellar views, e.g. sunrise patellar or Merchant view, can be obtained to determine one or more dimensions or curvatures or shapes of the knee joint, e.g. an ML width, a condylar width, an AP length, a condylar length, a trochlear angle, a PF joint width, patellar dimensions, a trochlear flange height, femoral offsets, a tibial slope, femoral curvature(s), tibial curvature(s), an axis, e.g. an epicondylar axis, Q-angle etc. In step 764, bone morphing can be performed, e.g. from 2D to 3D, using, for example, 2D x-ray images and landmarks, dimensions, axes, curvatures, offsets to derive a 3D shape of the patient's knee, e.g. for the distal femur, the proximal tibia and/or the patella. Optionally, an intra-operative scan, e.g. a laser scan, optical scan, e.g. using image or video capture, a scan using a mechanical probe with one or more optical markers or navigation markers, e.g. RF or IR, LED's or IMU's attached can be obtained. If a mechanical probe with any of the foregoing markers or tracking devices is used, points or a point cloud of the bones can be generated, e.g. a distal femur or proximal tibia, or any other articular surface in any other joint, e.g. in a hip, shoulder or ankle joint. The point cloud can be registered in a common coordinate system, e.g. together with one or more OHMDs, or an OR table, or fixed structures in the OR, or other body parts of the patient. The point cloud or point(s) within the measured surface can be used for determining the distance of one or more points to the OHMD worn by the user or one or more users; the distance can be used to display, for example, a virtual tool, a virtual instrument, or a virtual implant component with the proper size in the OHMD display for a given distance to the virtual tool, virtual instrument or virtual implant component. For example, when a virtual implant is displayed, placed, sized, fitted or aligned on a physical articular surface or a physical joint of the patient, one or more points on the articular surface or the physical joint of the patient can be registered in the coordinate system along with one or more OHMDs. Similarly, when a virtual axis, virtual plane, virtual tool or virtual instrument is displayed at a predetermined position, e.g. relative to a bone, a cartilage, or a physical joint or a physical spine of the patient, one or more points on the physical bone, physical cartilage, or physical joint or physical spine of the patient or physical tissue of the patient can be registered in the coordinate system along with one or more OHMDs.

As the distance of the OHMD to the points on the physical articular surface or the physical joint of the patient changes, the size of the display of the virtual implant will change, e.g. it will become smaller with an increase in distance of the OHMD from the point(s) or point cloud and it will become larger with a decrease in distance of the OHMD from the point(s) or point cloud, corresponding to the physical joint becoming larger as seen through a see through OHMD or a video camera and a VR system as the see through OHMD or video camera move closer to the physical joint and it will become smaller with an increase in distance of the OHMD from the point(s) or point cloud, corresponding to the physical joint becoming smaller as seen through a see through OHMD or a video camera and a VR system as the see through OHMD or video camera move further away from the physical joint.

As the distance of the OHMD to the points on the physical bone, physical cartilage, or physical joint or physical spine of the patient or physical tissue of the patient changes, the size of the display of the virtual axis, virtual plane, virtual tool or virtual instrument will change, e.g. it will become smaller with an increase in distance of the OHMD from the point(s) or point cloud and it will become larger with a decrease in distance of the OHMD from the point(s) or point cloud, corresponding to the physical bone, physical cartilage, or physical joint or physical spine of the patient or physical tissue of the patient becoming larger as seen through a see through OHMD or a video camera and a VR system as the see through OHMD or video camera move closer to the physical bone, physical cartilage, or physical joint or physical spine of the patient or physical tissue of the patient and it will become smaller with an increase in distance of the OHMD from the point(s) or point cloud, corresponding to the physical bone, physical cartilage, or physical joint or physical spine of the patient or physical tissue of the patient becoming smaller as seen through a see through OHMD or a video camera and a VR system as the see through OHMD or video camera move further away from the physical joint.

In some embodiments, one or more markers, e.g. optical markers, attached to a joint, a bone, a cartilage or any other anatomic landmark of the patient, e.g. a tissue surface, can be used for determining the display size of a virtual tool, virtual instrument or virtual implant component in the OHMD display by registering the one or more markers in a common coordinate system and by registering the one or more OHMD displays in the common coordinate system and by adjusting the display size of the virtual tool, instrument or implant relative to the distance between the optical marker and the one or more OHMDs, for example, as described in the foregoing paragraphs. In some embodiments, one or more markers, e.g. navigation markers or LED's, attached to a joint, a bone, a cartilage or any other anatomic landmark of the patient, e.g. a tissue surface, can be used for determining the display size of a virtual tool, virtual instrument or virtual implant component in the OHMD display by registering the one or more markers in a common coordinate system and by registering the one or more OHMD displays in the common coordinate system and by adjusting the display size of the virtual tool, instrument or implant relative to the distance between the optical marker and the one or more OHMDs, for example, as described in the foregoing paragraphs.

In step 766, the size of one or more femoral, tibial and/or patellar components can be selected, for example using templates or outlines of the implant and using x-rays or other imaging studies, e.g. CT or MRI, and/or bone models and/or joint models morphed in 3D, e.g. from 2D x-rays or ultrasound.

In step 768, a virtual surgical plan can be generated, e.g. using 2D or 3D sizing and/or accounting for a predetermined axis correction, e.g. to neutral mechanical axis alignment or alignment to a constitutional varus or valgus, optionally accounting for a desired or predetermined sagittal deformity correction, a desired or predetermined correction for a flexion or extension deficit, optionally accounting for a predetermined tibial slope or the patient's anatomic slope, e.g. on a medial or lateral tibial plateau or both, optionally accounting for planned or predetermined bone removal, e.g. using bone cuts or burring or milling or drilling or reaming or broaching, optionally accounting for a desired or predetermined femoral component rotation, optionally accounting for a desired or predetermined tibial component rotation, optionally accounting for the patient's measured knee kinematics and/or a desired or predetermined kinematic correction, optionally accounting for femoral and/or tibial offsets, and optionally accounting for implant selection, e.g. one or more implant components with one or more femoral or tibial offsets. In step 770, the patient can be positioned on the OR table, e.g. with the leg positioned similar to the position the leg had when 2D x-rays were obtained or when other pre- or intra-operative imaging studies were obtained.

In step 772, a virtual surgical plan can be imported into an OHMD system, e.g. the optical head mounted display(s), processors, software, any servers hosting some of the system components etc. Virtual surgical plans can be generated pre-operatively and can, optionally, be modified intra-operatively. Virtual surgical plans can be generated intra-operatively and can, optionally, be modified intra-operatively. In step 774, an incision, exposure, capsulotomy and other surgical steps can be performed, exposing, for example, the distal femur, the proximal tibia, and the patella. Optionally, the patella can be everted. In step 776, registration of live intra-operative data and a virtual surgical plan can be performed, e.g. using intra-operative landmarks corresponding, for example, to landmarks on a pre-operative imaging study or on a 3D model of the bone, the patient's joint including, for example, one or more articular surfaces, optionally generated via bone morphing. These landmarks can include or can define a medial or lateral joint line, an anatomical or biomechanical axis. The registration can allow the matching of virtual data and physical data from the live joint of the patient. The registration can optionally also be performed using intra-operative imaging, e.g. using x-rays, ultrasound or CT scanning. Optionally intra-operative imaging studies, e.g. x-rays, can be matched to pre-operative imaging studies, e.g. x-rays. Optionally, landmarks can be defined or identified using one or more probes, e.g. with one or more attached optical markers, navigation markers, e.g. IR or RF markers, LED's or IMU's, which can be moved over the surface of the one or more landmarks, e.g. an articular surface, for obtaining one or more points and, optionally, generating one or more point clouds of one or more landmarks. In step 778, one or more femoral and/or tibial and/or patellar virtual surgical guides can be projected. The femoral and/or tibial and/or patellar virtual surgical guides can be a 3D representation of a physical cut guide or cut block, or a placement indicator of a physical cut guide or cut block, or a combination thereof. The femoral and/or tibial and/or patellar virtual surgical guides can be a virtual plane, e.g. a virtual cut plane, or a virtual axis, e.g. for a drill, a burr, a reamer, a mill, a broach or an impactor. One, two or more virtual axes can be projected, e.g. on a distal femur or a proximal tibia, e.g. for placing one, two or more physical pins or drills. A physical tool, instrument or cut guide or cut block can then be attached to the two or more physical pins or drills. The one or more virtual surgical guides can be projected by the OHMD(s) to include, for example, a predetermined mechanical axis correction, a predetermined flexion contracture correction, a predetermined femoral component or tibial component rotation, a predetermined tibial slope. Virtual cuts can be projected using one or more OHMDs. The cut(s) can optionally be projected as a 2D line or 3D axis, e.g. on the surface of the bone. In some embodiments, the cuts can be projected as a 3D cut plane, e.g. for aligning a physical saw blade or a physical saw blade or dummy saw blade inserted into a physical guide or physical cut block with the virtual 3D cut plane.

The OHMD can project a virtual patellar cut. One or more measurements can be taken of the patella, e.g. intra-operatively from the physical patella or pre-operatively, e.g. from an imaging study of the patella. If a pre-operative imaging study is used, the imaging data, e.g. 2D or 3D data or surfaces or shape, e.g. from a CT or MRI scan or from a 3D model obtained using bone morphing, can be registered intra-operatively with physical landmarks, surface(s) or shape of the patella. Alternatively, a 3D model of the patella can be generated intra-operatively, for example by measuring multiple points on the surface of the patella, for example using a pointer with one or more optical markers, navigation markers, LED's, other markers and/or IMU's. A 3D model of the patella can also be obtained using an image capture or video capture system, for example obtaining images of the patella from multiple view angles and/or distances, or using a 3D scanner or laser scanner. A patellar implant component can then be selected, e.g. using the 3D model, for example for a desired resection depth and/or a desired articular surface geometry and/or location of the implant component, e.g. relative to the patient's native patellar articular surface and/or the patellar bone stock of the patient. The patellar implant component can also be selected based on the patient's patellar shape, e.g. dome shaped or sombrero shaped and/or symmetric or asymmetric. The patellar implant component can also be selected based on the patellar size, e.g. an ML or SI dimension, e.g. from the medial edge of the patella to the lateral edge of the patella or from the inferior pole of the patella to the superior pole of the patella, respectively. The patellar implant component can also be selected based on an AP dimension, e.g. a dimension in the thickest area of the patella in AP direction; for example, a patellar component thickness can be selected based on an AP dimension. Thus, the patellar implant component can be selected based on multiple parameters, e.g. predetermined bone resection level or depth, predetermined amount of bone preservation, patellar dimension(s), patellar shape, patellar thickness, patellar articular surface location of the native patella and/or an implant component, patellar symmetry or asymmetry, predetermined cut and/or implant position, orientation, angulation, coordinates, and/or predetermined amount of bone coverage of cut patella by the patellar implant component and/or predetermined patellar anchor, e.g. peg, length and/or size. Once a patellar component has been selected, the bone cut for the selected patellar component can be determined, e.g. using a graphical user interface on a PC or server in the OR, or, for example, using a virtual interface on an OHMD. In some embodiments, the patellar bone cut is determined as the undersurface of the patellar implant component, for example during the fitting, sizing, selection and aligning process of the patellar implant component. A virtual cut plane corresponding to the predetermined patellar bone cut, optionally accounting for saw blade thickness, can then be projected by the OHMD. The virtual cut plane can be projected onto the surface, e.g. the perimeter or the articular surface, of the patella. The virtual cut plane can, optionally, also be projected or displayed as it extends through the bone, e.g. connecting entry and exit points of the predetermined bone cut for a physical bone saw. If a physical patellar cut guide is used, a virtual cut guide, e.g. a 3D representation of the physical patellar cut guide, a placement indicator of the physical patellar cut guide, or a combination thereof can be projected by the OHMD onto the surface or the perimeter or the edge of the patella, where the physical cut guide can be placed. If the patellar bone is removed using a mill rather than a saw for placing the patellar component, the saw in the foregoing embodiments can be substituted by the mill and the virtual surgical guide can, for example, be a virtual axis and/or a virtual mill and/or a virtual stop, including 2D or 3D outlines or placement indicators thereof, or combinations thereof. The OHMD can, for example, project a central axis for the mill, which can, for example, correspond to the central axis of the patellar implant component or, which can, for example, correspond to a peg or anchor of the patellar implant component. In some embodiments, the OHMD can also project a virtual stop for the mill; the virtual stop can correspond to the desired milling depth or depth of bone removal. The virtual stop can optionally correspond to a physical component or extender of the mill or milling machine; once the physical component or extender of the mill or milling maching reaches the virtual stop and is, for example, aligned with and/or superimposed onto the virtual stop, the surgeon or, optionally, a robot can stop with the milling process.

In step 780, ligament balancing can be performed, for example using soft-tissue releases or additional bone removal, e.g. bone cuts or recuts. In some embodiments, the OHMD can display a virtual surgical guide indicating, for example, a +1 mm, +2 mm, +3 mm, +4 mm recut or additional bone cut, e.g. if a flexion or extension deficit is identified intra-operatively, or for optimizing a flexion gap or extension gap during the procedure.

Knee Kinematics and Morphology

In some embodiments, IMU's and/or navigation markers and/or image capture markers, e.g. optical markers with geometric patterns and/or LED's, including combinations thereof can be applied to the knee in desired, predetermined locations and/or other portions of the extremity, e.g. the ankle, the calf, the thigh and/or the hip and/or the pelvis, the patient can perform various types of exercise and the data and/or coordinates from the IMU's and/or navigation markers and/or image capture markers, e.g. optical markers with geometric patterns and/or LED's, including combinations thereof can be collected during these exercises and/or the location, speed, moments, forces and trajectory and changes in location, coordinates, speed, moments, forces and trajectory of the IMU's and/or navigation markers and/or image capture markers, e.g. optical markers with geometric patterns and/or LED's, including combinations thereof can be measured, e.g. using a navigation system and/or an image and/or video capture system and/or 3D scanner integrated into, attached to or separate from the OHMD. Systems and devices for measuring joint alignment and kinematics are described in U.S. provisional application No. 62/624,138, filed Jan. 31, 2018, which is incorporated herein by reference in its entirety.

Kinematic measurements can optionally be obtained at a first timepoint, e.g. T1, and/or optionally at a second timepoint T2 and/or, optionally a third time point T3, and/or optionally a fourth timepoint T4 and/or optionally a fifth timepoint T5. The first timepoint T1 can, for example, be prior to a surgery when, for example, kinematic measurements can be obtained in an outpatient or inpatient setting, prior to an incision of the skin, joint capsule, ligaments and/or other articular structures. The second timepoint T2 can, for example, be in the operating room during a knee, hip, shoulder or ankle replacement surgery, ligament reconstruction or ligament repair or labral repair surgery. The second timepoint T2 can, optionally, be prior to an incision of one or more of a skin, joint capsule, ligaments and/or other articular structures. The third timepoint T3 can, for example, be in the operating room during a knee, hip, shoulder or ankle replacement surgery, ligament reconstruction or ligament repair or labral repair surgery following incision of one or more of a skin, joint capsule, ligaments and/or other articular structures. The fourth timepoint T4 can, for example, be in the operating room during a knee, hip, shoulder or ankle replacement surgery, ligament reconstruction or ligament repair or labral repair surgery following incision of one or more of a skin, joint capsule, ligaments and/or other articular structures and following removal of one or more osteophytes and/or following removal of one or more adhesions. The fifth timepoint T5 can, for example, be in the operating room during a knee, hip, shoulder or ankle replacement surgery, ligament reconstruction or ligament repair or labral repair surgery following incision of one or more of a skin, joint capsule, ligaments and/or other articular structures and following removal of bone, e.g. with a bone cut or a burring, milling or reaming. Data from a single time point can be used for placing, fitting, sizing, selecting and/or aligning virtual implant components and/or for placing and/or aligning one or more virtual surgical guides, e.g. a virtual cut block, a virtual axis or a virtual plane. Data from multiple time points can be used for placing, fitting, sizing, selecting and/or aligning virtual implant components and/or for placing and/or aligning one or more virtual surgical guides, e.g. a virtual cut block, a virtual axis or a virtual plane.

If optical markers, e.g. with geometric patterns and/or LED's, are used and are applied, for example, an extremity, e.g. around the hip joint and/or knee joint and/or ankle joint and/or to the thigh and/or to the calf region, the movement of the optical markers can be captured using, for example, a camera system integrated into or attached to a smart phone, a tablet and/or an OHMD. If IMU's are used and are applied, for example, an extremity, e.g. around the hip joint and/or knee joint and/or ankle joint and/or to the thigh and/or to the calf region, the movement of the IMU's including, for example, relative force(s), estimated coordinates, direction of movement, and/or speed of movement, and/or positional information can be captured using, for example, a computer processor integrated into or attached to a smart phone, a tablet and/or an OHMD. The computer processor can optionally connect to the one or more IMU's using an RF, WIFI, Bluetooth or LiFi signal. Both optical markers and IMU's can be used in conjunction with a smart phone, tablet and/or an OHMD. Other markers, including navigation, e.g. RF or IR, markers can be used.

Exercises that can be performed for obtaining kinematic measurements can, for example, include, but are not limited to: Normal gait, e.g. on a defined path; gait with an upward angle simulating walking uphill, e.g. on a belt oriented at an upward angle; gait with a downward angle simulating walking downhill, e.g. on a belt oriented at a downward angle; stair climbing; walking downstairs; getting up from chair; getting up from chair and walking; getting up from chair and walking upstairs and/or downstairs; kneeling; squatting; standing; dual legged stance; single legged stance Optionally, exercises can be performed on one or more force plates to measure, for example, contact forces, contact time, time to heel strike, speed and any other known measurement of activity known in the art.

In some embodiments, the information obtained from the joint on its location, orientation, alignment, speed, direction of movement, trajectory, moments, forces, kinematics, e.g. tibiofemoral or patellofemoral movement, and changes thereof using the IMU's and/or navigation markers and/or image capture markers, e.g. optical markers with geometric patterns and/or LED's, including combinations thereof, can be generated during resting position(s), e.g. standing and/or lying down, and/or can be generated during exercises; the data from the exercise can be analyzed to derive information on the patient's knee kinematics and/or the shape and morphology of the patient's knee.

The location, orientation, alignment, speed, trajectory, coordinates and changes thereof of the IMU's and/or navigation markers and/or image capture markers, e.g. optical markers with geometric patterns and/or LED's, including combinations thereof can yield information on knee kinematics and/or shape and morphology of the joint, e.g. a knee joint, shoulder joint, ankle joint, hip joint.

The location, orientation, alignment, speed, trajectory, coordinates and changes thereof of the IMU's and/or navigation markers and/or image capture markers, e.g. optical markers with geometric patterns and/or LED's, including combinations thereof can also yield information on the mechanical axis alignment of the patient. For example, if the IMU's and/or navigation markers and/or image capture markers, e.g. optical markers with geometric patterns and/or LED's, including combinations thereof are positioned in select locations around the hip, knee and/or the ankle, the data can be used to determine, for example, the center of rotation or flexion and extension or abduction and adduction of the hip for certain exercises or activities or the center of rotation or flexion and extension or abduction and adduction of the ankle for certain exercises or activities or the center of rotation or flexion and extension or abduction and adduction of the knee for certain exercises or activities, e.g. tibiofemoral rotation, tibiofemoral rotation axes, or patellofemoral rotation, patellofemoral rotation axes. This information can then be used to determine, for example, a mechanical axis, which can, for example, be used to determine the degree of varus or valgus deformity, and which can be used in a virtual surgical plan, for example with select partial or complete deformity correction, e.g. towards partial varus or valgus deformity correction or towards restoration of a neutral mechanical axis. This information can also be used to determine one or more rotation axes, e.g. tibiofemoral rotation axes, patellofemoral rotation axes, for example around the knee, hip or ankle, which can optionally be used to determine any rotational deformity if applicable and any desired rotational correction, if applicable, and which can be used in a virtual surgical plan, for example with select partial or complete rotational deformity correction. In another embodiment, the determination of the one or more rotation axes, e.g. around the knee, e.g. a tibiofemoral rotation axis or a patellofemoral rotation axis can be used in a virtual surgical plan with the aim, for example, to place one or more implant components so that the one or more articulating surfaces substantially or partially restore the rotation axes of the patient for a given implant system, e.g. a femoral component and a tibial component or a femoral component and a patella femoral component, e.g. also by aligning one or more articular surfaces of an implant component with one or more articular surface(s) of the patient, for example using OHMD guidance by projecting and/or superimposing the virtual implant component onto the physical joint of the patient and aligning the one or more articular surfaces of the implant component with the physical articular surface(s) of the patient.

The following exemplary information can be captured about the operator and the patient and respective body parts including a moving joint: Speed, velocity, acceleration, position in space, positional change, angular orientation, change in angular orientation, coordinates, alignment, orientation, and/or direction of movement and or speed of movement (e.g. through sequential measurements), moments and/or forces, vectors. Operator and/or patient body parts about which such information can be transmitted by the one or more IMUS or can be measured using one or more optical markers and/or navigation markers include, but are not limited to: Head, chest, trunk, shoulder, elbow, wrist, hand, fingers, arm, hip, knee, ankle, foot, toes, leg, inner organs, e.g. brain, heart, lungs, liver, spleen, bowel, bladder, etc.

The relative movement and change in coordinates or any of the foregoing data generated by IMU's and/or navigation markers and/or image capture markers, e.g. optical markers with geometric patterns and/or LED's, including combinations thereof, applied to a first articular side can be compared to the relative movement and change in coordinates or any of the foregoing data generated by IMU's and/or navigation markers and/or image capture markers, e.g. optical markers with geometric patterns and/or LED's, including combinations thereof, applied to a second articular side.

For example, the relative movement and change in coordinates or any of the foregoing data generated by IMU's and/or navigation markers and/or image capture markers, e.g. optical markers [e.g. with geometric patterns and/or LED's], including combinations thereof, applied to a femoral articular side, e.g. a distal femur and/or surrounding soft-tissues including ligaments, muscle or skin, can be compared to the relative movement and change in coordinates or any of the foregoing data generated by IMU's and/or navigation markers and/or image capture markers, e.g. optical markers with geometric patterns and/or LED's, including combinations thereof, applied to a tibial articular side, e.g. a proximal tibia and/or surrounding soft-tissues including ligaments, muscle or skin. For example, the relative movement and change in coordinates or any of the foregoing data generated by IMU's and/or navigation markers and/or image capture markers, e.g. optical markers with geometric patterns and/or LED's, including combinations thereof, applied to a femoral articular side, e.g. a distal femur and/or surrounding soft-tissues including ligaments, muscle or skin, can be compared to the relative movement and change in coordinates or any of the foregoing data generated by IMU's and/or navigation markers and/or image capture markers, e.g. optical markers with geometric patterns and/or LED's, including combinations thereof, applied to a patellar articular side, e.g. a patella and/or surrounding soft-tissues including ligaments, muscle or skin. For example, the relative movement and change in coordinates or any of the foregoing data generated by IMU's and/or navigation markers and/or image capture markers, e.g. optical markers with geometric patterns and/or LED's, including combinations thereof, applied to a tibial articular side, e.g. a proximal tibia and/or surrounding soft-tissues including ligaments, muscle or skin, can be compared to the relative movement and change in coordinates or any of the foregoing data generated by IMU's and/or navigation markers and/or image capture markers, e.g. optical markers with geometric patterns and/or LED's, including combinations thereof, applied to a patellar articular side, e.g. a patella and/or surrounding soft-tissues including ligaments, muscle or skin. In any of the embodiments, optical markers and/or LED's can be detected and their coordinates can be determined using an optical imaging system and/or a 3D scanner, for example integrated into, attached to or separate from an OHMD and/or in a stationary, e.g. fixed position in the OR, e.g. attached to the OR table.

By comparing the data from a first and second and, optionally, third articular side including their relative motion compared to each other, estimates of contact surface shape, contact forces, moments, vectors, articular shape and/or articular geometry along with kinematic parameters can be derived, as further detailed below. Various software algorithms known in the art, e.g. nearest neighbor algorithms, can be used for this purpose. Parameters or data that can be measured or obtained or derived or estimated in this manner using IMU's and/or navigation markers and/or image capture markers, e.g. optical markers with geometric patterns and/or LED's, including combinations thereof applied to and around the joint(s) include, but are not limited to: Location of medial joint line in coronal plane and/or sagittal plane, location of lateral joint line in coronal plane and/or sagittal plane, location of lowest point of medial tibial plateau, location of lowest point of lateral tibial plateau, location of highest anterior point of medial tibial plateau, location of highest anterior point of lateral tibial plateau, location of highest posterior point of medial tibial plateau, location of highest posterior point of lateral tibial plateau, medial distal femoral offset, lateral distal femoral offset, medial posterior femoral offset, lateral posterior femoral offset, medial femoral offset at different flexion angles, e.g. at 15 degrees of flexion or 20 degrees flexion or 30 degrees flexion or any other flexion angle, lateral femoral offset at different flexion angles, e.g. at 15 degrees of flexion or 20 degrees flexion or 30 degrees flexion or any other flexion angle, medial femoral offset in hyperextension, e.g. in 5 degrees or 10 degrees of hyperextension or any other hyperextension angle, lateral femoral offset in hyperextension, e.g. in 5 degrees or 10 degrees of hyperextension or any other hyperextension angle, medial tibial plateau height, optionally center, anterior, posterior, medial, lateral; lateral tibial plateau height, optionally center, anterior, posterior, medial, lateral; lowest point on the medial tibial plateau, highest point on the medial tibial plateau, lowest point on the lateral tibial plateau, highest point on the lateral tibial plateau; contact area, change in contact area, movement of contact area, e.g. for medial tibiofemoral articulation, lateral tibiofemoral articulation, patellofemoral articulation; contact force, change in contact force, e.g. estimated using IMU's, e.g. for medial tibiofemoral articulation, lateral tibiofemoral articulation, patellofemoral articulation; femoral rollback, roll forward, e.g. for medial tibiofemoral articulation, lateral tibiofemoral articulation; femoral rotation, medial femoral condyle; femoral rotation, lateral femoral condyle; femoral rotation, entire distal femur; tibial rotation, medial tibial plateau; tibial rotation, lateral tibial plateau; tibial rotation, entire tibia, tibial plateau; tibial adduction; tibial abduction; estimated medial femoral shape, e.g. in the sagittal plane; estimated lateral femoral shape, e.g. in the sagittal plane; estimated medial tibial shape, e.g. in the sagittal plane; estimated lateral tibial shape, e.g. in the sagittal plane; femoral abduction, femoral adduction; tibial slope, e.g. medial, lateral, average medial lateral or other combinations of medial and lateral; tibiofemoral stability, e.g. in AP direction or ML direction; tibiofemoral instability, e.g. in AP direction or ML direction; osteophyte location; osteophyte volume; muscle forces, e.g. hamstring, quadriceps, e.g. rectus femoris, vastus medialis, vastus lateralis, calf muscles, e.g. gastrocnemius, soleus. These measurements can be obtained at a single timepoint T1, T2, T3, T4 or T5 or at multiple timepoints, e.g. T1 and T3, T1 and T4, T2 and T3, T2 and T4, T2, T3 and T4, T2 and T5, T1 and T5 or any other combination. These measurements and/or parameters from one or more timepoints can optionally be introduced into a knee motion simulation. The knee motion simulation can include a generic knee model. The knee motion simulation can include a patient specific knee model of the patient, e.g. generated using 2D x-rays with 3D bone morphing (e.g. using 2D x-ray data of the patient to deform a generic bone model into a patient specific bone model of the patient) as described in the specification, or using a CT scan or MRI scan, from which a computer processor configured for image processing and segmentation can generate a 3D model. The knee motion simulation using any of the measurements or parameters measured at one or more of the timepoints T1, T2, T3, T4, T5 can include a virtually placed virtual implant, for example, a virtually placed virtual femoral component, virtual tibial component, virtual patellar component, virtual acetabular component, virtual proximal femoral component, virtual distal tibial component, virtual talar component, virtual humeral component and/or a virtual glenoid component. The virtual placing can be performed using any of the embodiments described in the specification. The virtual placing and include or can be supplemented with a virtual fitting, virtual sizing, and/or virtual aligning using any of the embodiments described in the specification. The coordinates and geometry of the virtually placed implant components can be used to simulate the articular motion after placement of one or more implant components, e.g. a distal femoral component and a proximal tibial component in a knee replacement, a distal femoral component and a patellar component in a knee replacement, a distal femoral, a proximal tibial and a patellar component in a knee replacement, an acetabular component and a proximal femoral component in a hip replacement, a glenoid component and a humeral component in a shoulder replacement, using the information, measurements and/or parameters from one or more of the timepoints T1, T2, T3, T4 and/or T5. A computer processor configured to generate the motion simulation using the information, measurements and/or measured parameters from one or more of the timepoints T1, T2, T3, T4 and/or T5 and configured to include the coordinates and/or geometry including articular surface geometry of one or more virtually placed virtual implant components in the simulation, e.g. a femoral component, a tibial component and/or a patellar component in a knee replacement, can be used to identify any potential motion conflicts for given knee kinematics measured during one or more of the timepoints T1, T2, T3, T4 and/or T5 and the virtually placed implant components. For example, a motion conflict can be a virtual femoral component extending or "diving" into or overlapping a virtual tibial component in the simulation, e.g. a tibial articular surface, by 1 or 2 or 3 or 4 or more mm or any other amount of mm, for example on the medial articular surface and/or the lateral articular surface, during part of the simulation, e.g. between 20 and 35 degrees of flexion or between 0 and 5 degrees of extension or any other value, or all of the simulation. A motion conflict can be a virtual patellar component extending or "diving" into a virtual femoral component in the simulation, e.g. a trochlea articular surface of the virtual femoral component, by 1 or 2 or 3 or 4 or more mm or any other amount of mm, for example on the articular surface of the medial trochlea and/or the articular surface of the lateral trochlea. A motion conflict can be a virtual tibial component extending or "diving" into a virtual femoral component in the simulation, e.g. a femoral articular surface, by 1 or 2 or 3 or 4 or more mm or any other amount of mm, for example on the medial articular surface and/or the lateral articular surface, during part of the simulation, e.g. between 20 and 35 degrees of flexion or between 0 and 5 degrees of extension or any other value, or all of the simulation. A motion conflict can be a virtual humeral component extending or "diving" into a virtual glenoid component in the simulation, e.g. a glenoid articular surface, by 1 or 2 or 3 or 4 or more mm or any other amount of mm, during part or all of the simulation, for example during abduction, adduction, elevation, rotation, flexion and/or extension, e.g. between 20 and 35 degrees of abduction or between 40 and 55 degrees of flexion or any other value. A motion conflict can be a virtual femoral component extending or "diving" into a virtual acetabular component in the simulation, e.g. an acetabular articular surface, by 1 or 2 or 3 or 4 or more mm or any other amount of mm during part of the simulation, e.g. between 25 and 40 degrees of hip flexion or between 10 and 20 degrees of abduction or any other value, or all of the simulation. A motion conflict can be indicative of a need for a recut or a ligament release during the placement of the physical implant or implant components. The computer processor can optionally be configured to perform operations to reduce or remove the motion conflict, for example by adjusting the position and/or orientation of one or more virtual implant components in the simulation. The computer processor can optionally be configured to perform operations to achieve a desired distance between a first and a second implant component, e.g. a virtual femoral component and a virtual tibial component or a virtual femoral component and a virtual patellar component, for example by adjusting the position and/or orientation of one or more virtual implant components in the simulation. The one or more coordinates of the adjusted position and/or orientation of the virtual implant component can be used, for example, to modify and/or determine a virtual surgical plan and/or to determine and/or adjust the position and/or orientation and/or coordinates of a virtual surgical guide projected by one or more OHMDs, e.g. onto the surface of the joint, e.g. a virtual cut block or placement indicator thereof, a virtual axis and/or a virtual plane for superimposing and/or aligning a physical surgical guide and/or a physical surgical instrument and/or a physical surgical tool as described in the specification. For example, in a knee replacement a virtual femoral or a virtual tibial surgical guide can be moved superiorly or inferiorly and can be changed in orientation and/or angulation (e.g. for tibial slope or femoral flexion) in order to modify the cuts and the resultant planar bone surfaces determining the position and/or orientation of the physical femoral and/or tibial component. The modified cuts and resultant planar bone surfaces and position and/or orientation of the physical femoral and/or tibial components and/or of the physical femoral and/or patellar component can be optimized to reduce or resolve any potential motion conflicts between the femoral and the tibial, the femoral and the patellar components.

In some embodiments, a computer processor configured to generate the motion simulation using the information, measurements and/or measured parameters from one or more of the timepoints T1, T2, T3, T4 and/or T5 and configured to include the coordinates and/or geometry including articular surface geometry of one or more virtually placed virtual implant components in the simulation, e.g. a femoral component, a tibial component and/or a patellar component in a knee replacement, can be used to determine the distance between a first articular surface, e.g. a femoral articular surface, a second articular surface, e.g. a tibial articular surface, and/or a third articular surface, e.g. a patellar articular surface, for the different respective virtual implant components, e.g. a virtual femoral, virtual tibial and/or virtual patellar implant component, for given knee kinematics measured during one or more of the timepoints T1, T2, T3, T4 and/or T5 and for a portion of or the entire range of motion or for select or all exercises for which kinematic measurements were obtained; the distance determination can, for example, be performed using a nearest neighbor algorithm. The computer processor can, optionally, be configured to allow for modification of the position and/or orientation and/or coordinates of one or more virtual implant components, e.g. a virtual femoral component, a virtual tibial component, and/or a virtual patellar component or a virtual humeral component and/or a virtual glenoid component and/or a virtual acetabular component and/or a virtual femoral component, to modify the distance between a first articular surface, e.g. a bearing surface of a virtual femoral component, and/or a second articular surface, e.g. a bearing surface of a virtual tibial component, and/or a third articular surface, e.g. a bearing surface of a virtual patellar component, e.g. for certain angles of flexion and/or extension, rotation, abduction, adduction, elevation, etc., e.g. at 0 and 90 degrees of flexion in a knee replacement. The computer processor can optionally be configured to allow for selection of a predetermined distance between a first articular surface, e.g. a bearing surface of a virtual femoral component, and/or a second articular surface, e.g. a bearing surface of a virtual tibial component, and/or a third articular surface, e.g. a bearing surface of a virtual patellar component, e.g. for certain angles of flexion and/or extension, rotation, abduction, adduction, elevation, etc., e.g. at 0, 30, 45 and/or 90 degrees of flexion in a knee replacement or any other value. For example, in a knee replacement, the computer processor can be configured to generate a graphical user interface which can allow selection of a predetermined flexion and/or extension gap, e.g. 1.0 mm, 1.5 mm or 2.0 mm medial and/or 2.0 mm, 2.5 mm, 3.0 mm, 3.5 mm lateral gap, or any other value between virtual femoral and virtual tibial components. The selection of a predetermined flexion and/or extension gap can be automated. The computer processor can optionally be configured to allow for selection of a predetermined distance between a first articular surface, e.g. a bearing surface of a virtual acetabular component, and/or a second articular surface, e.g. a bearing surface of a virtual femoral head component, e.g. for certain angles of flexion and/or extension, rotation, abduction, adduction, etc., e.g. at 0, 30, 45 and/or 90 degrees of flexion in a hip replacement or any other value. The computer processor can optionally be configured to allow for selection of a predetermined distance between a first articular surface, e.g. a bearing surface of a virtual glenoid component, and/or a second articular surface, e.g. a bearing surface of a virtual humeral head component, e.g. for certain angles of flexion and/or extension, rotation, abduction, adduction, etc., e.g. at 0, 30, 45 and/or 90 degrees of extension and/or abduction in a shoulder replacement or any other value.

The one or more coordinates of the position and/or orientation of the virtual implant component(s) adjusted in position and/or orientation to achieve the predetermined distance between a first virtual articular surface, and/or a second virtual articular surface and/or a third virtual articular surface for given angles and/or ranges of angles of flexion, extension, rotation, internal rotation, external rotation, abduction, adduction, elevation etc. and/or for given physical activities can be used, for example, to determine and/or modify a virtual surgical plan and/or to determine and/or adjust the position and/or orientation and/or coordinates of a virtual surgical guide projected by one or more OHMDs, e.g. onto the surface of the joint, e.g. a virtual cut block or placement indicator thereof, a virtual axis and/or a virtual plane for superimposing and/or aligning a physical surgical guide and/or a physical surgical instrument and/or a physical surgical tool as described in the specification. For example, in a knee replacement a virtual femoral or a virtual tibial surgical guide can be moved superiorly or inferiorly and can be changed in orientation and/or angulation (e.g. for tibial slope or femoral flexion) in order to determine and/or modify the cuts and the resultant planar bone surfaces determining the position and/or orientation of the physical femoral and/or tibial component. The determined and/or modified cuts and resultant planar bone surfaces and position and/or orientation of the physical femoral and/or tibial component or of the physical femoral and/or patellar component can be placed to achieve a desired and/or predetermined distance between the femoral and the tibial, the femoral and the patellar components, e.g. for the entire range of motion or for select angles, e.g. 0 degrees and/or 90 degrees of knee flexion and/or any other values. The predetermined distance can be selected separately for a medial and/or a lateral compartment and/or a patellofemoral compartment. Biomechanical and kinematic modeling software known in the art such as the AnyBody Modeling System or Joint Track Software (https://sourceforge.net/projects/joint-track/files/?source=navbar) can optionally be used to derive estimates of these and any kinematic or biomechanical or morphological or shape parameter known in the art based on the data obtained from the IMU's and/or navigation markers and/or image capture markers, e.g. optical markers with geometric patterns and/or LED's, including combinations thereof and one or more image and/or video capture systems and/or 3D scanner.

Various algorithms such as shortest path algorithm's, Dijkstra's algorithm, alternating projection method algorithms, Dykstra's projection algorithm, nearest neighbor algorithms and any algorithm known in the art can be applied for obtaining and/or deriving and/or estimating any of the above parameters and any other parameter desired for the particular application, e.g. joint replacement, including a predetermined distance between a first and/or a second and/or a third bearing surface of virtual and/or physical implant component(s), e.g. a predetermined medial flexion gap, lateral flexion gap, medial extension gap, lateral extension gap between a virtual femoral and/or a virtual tibial and/or a virtual patellar component. The location, orientation, alignment, speed, moment, vector(s), force(s) trajectory and changes thereof of the IMU's and/or navigation markers and/or image capture markers, e.g. optical markers with geometric patterns and/or LED's, including combinations thereof can be used to derive more accurate estimates of the location and orientation of the medial and lateral joint space or joint line or the patellofemoral joint space or joint line, the medial and lateral tibial slope, the medial-lateral femoral offsets for different angles of extension and flexion, and patellar movement during various knee exercises, including, for example, flexion and extension and/or internal or external rotation. Various types of algorithms can be applied to determine the location and/or orientation of the medial and lateral joint space or joint line, the medial and lateral tibial slope, the medial-lateral femoral offsets for different angles of extension and flexion, and/or the patellofemoral articulation. For example, one of the known constraints of tibiofemoral motions during gait is that a portion of the femur will be in contact with a portion of the tibial plateau. If more than one IMU and/or navigation marker and/or image capture marker, e.g. one or more optical markers with geometric patterns or LED's, has been applied to the distal femur and, similarly, to the proximal tibia and, for example, the patella, the location of the closest femoral and tibial IMU's or navigation markers or image capture markers can provide an estimate of the tibiofemoral contact point or contact area for a given flexion or extension angle, which in turn can be used to determine or estimate the medial and lateral joint space or joint line, the medial and lateral tibial slope, the medial-lateral femoral offsets for different angles of extension and flexion. Moreover, grids or arrays of IMU's, navigation markers or image capture markers can be applied to a joint, e.g. the knee joint, e.g. for measurements at one or more timepoints T1, T2, T3, T4 and/or T5. In the example of the knee joint, such grids or arrays can be applied, for example, over the medial aspect of the knee in the area of the medial joint space, over the lateral aspects of the knee in the area of the lateral joint space, over the medial, lateral, inferior, or superior aspect of the patella and/or patellofemoral joint space, or over the entire knee or only the anterior aspect, medial aspect, lateral aspect or posterior aspect. In an alternative embodiment, an initial registration of the location of the IMU's, navigation markers or image capture markers in the grid or array can be performed in a first static position, e.g. upright standing with the knee extended, or upright position with the knee flexed, e.g. at 90 degrees or any other value, or supine position with the knee extended or supine position with the knee flexed, e.g. at 90 degrees or any other value. Additional registrations can be performed in a second, third, fourth and more static positions, e.g. at different flexion angles, upright or supine, or during dynamic joint motion, e.g. knee bending or flexing including rotation. For example, the areas of greatest and/or least IMU or marker movement, e.g. in opposite or different directions, e.g. different rotation, e.g. in an axial plane, as seen in the IMU data, or the navigation or image capture data or combinations thereof can be indicative of or can be used to derive the location of the joint space or joint line, e.g. medially, laterally or patellofemoral, or the medial and lateral tibial slope, the medial-lateral femoral offsets for different angles of extension and flexion. Moreover, such measurements can be used to derive estimates of femoral offsets and tibial slope, in addition to medial or lateral joint line location. The use of a grid pattern or array of IMU's and/or navigation markers and/or image capture markers, e.g. optical markers [e.g. with geometric patterns and/or LED's], including combinations thereof is only exemplary in nature. Any spatial arrangement known in the art can be used, e.g. two, three, four or more lines or layers of femoral IMU's and/or navigation markers and/or image capture markers, e.g. optical markers [e.g. with geometric patterns and/or LED's], including combinations thereof or two, three, four or more lines or layers of tibial IMU's and/or navigation markers and/or image capture markers, e.g. optical markers with geometric patterns and/or LED's, including combinations thereof. Multiple arrays can be used and can, for example, be integrated into a soft brace surrounding all or portions of the knee joint. If navigation is used, the different arrays can, for example, emit RF signals at different frequencies. If image capture is used, the different arrays can, for example, emit light at different wavelengths or use optical markers with different geometric patterns, for example also identifying select anatomic or biomechanical sites, e.g. medial distal femur, lateral distal femur, medial proximal tibia, lateral proximal tibia, anterior tibia, superior patellar pole, inferior patellar pole, medial patellar edge, lateral patellar edge. Optionally, software algorithms and methods known in the art to account for soft-tissue deformation during knee motion can be applied to the data generated by the IMU's and/or navigation markers and/or image capture markers.

The accuracy of some of the measurements can optionally be improved by using a finer grid or an array with more IMU's and/or navigation markers and/or image capture markers, e.g. optical markers with geometric patterns and/or LED's, including combinations thereof. For example, in some embodiments, the finer the grid or the more measurement devices are used in the grid or array, the greater the spatial resolution of the resultant data can be.

Optionally, the medial or lateral joint space or the patellofemoral joint can initially be identified using manual palpation and, optionally, be marked, e.g. using visual marks (e.g. pen marks and the like), IMU's and/or navigation markers and/or image capture markers. For example, an operator, e.g. a physical therapist, can palpate the medial joint space, for example by gently moving the knee through a range of motion. The operator can then optionally mark the joint space, e.g. with a pen. The operator can then optionally place IMU's and/or navigation markers and/or image capture markers, e.g. optical markers with geometric patterns and/or LED's, including combinations thereof proximal to the joint space, e.g. proximal to a visual mark made on the patient's skin, on the femoral side. The operator can then optionally place IMU's and/or navigation markers and/or image capture markers, e.g. optical markers with geometric patterns and/or LED's, including combinations thereof distal to the joint space, e.g. proximal to a visual mark made on the patient's skin, on the tibial side. The operator can perform the same maneuvers for the patellofemoral joint space, e.g. medial or laterally, with the placement of IMU's and/or navigation markers and/or image capture markers, e.g. optical markers with geometric patterns and/or LED's, including combinations thereof, optionally with or without visual marks placed on the patient's skin.

The shape information on the patient's knee can optionally be augmented with an imaging test, e.g. an ultrasound, CT or MRI scan. Shape information can optionally include bone or cartilage information or combinations thereof. Alternatively, the shape information can be derived initially using an imaging test, e.g. a CT or MRI, for example with generation of a 3D model of the joint. The shape information can then optionally be augmented with some of the data obtained using the kinematic measurements. Similarly, the medial, lateral and/or patellofemoral joint space can be identified with an imaging test, e.g. an ultrasound, CT and MRI. An operator can then optionally mark the joint space on the patient's skin, e.g. with a pen, and place IMU's and/or navigation markers and/or image capture markers on both sides of the joint space for subsequent measurements as described in the specification. Optionally, for example if an ultrasound transducer is used for any measurements of medial, lateral or patellofemoral joint space location and/or orientation, tibial slope, and femoral or tibial shape, the ultrasound transducer can also include or have attached one or more IMU's and/or navigation markers and/or image capture markers, e.g. optical markers with geometric patterns and/or LED's, including combinations thereof so that the location of the ultrasound transducer can be readily cross-referenced or registered in the patient's coordinate system. This can be particularly useful when the imaging test or device, e.g. the ultrasound transducer, is also used to generate, for example, an image and resultant shape of the distal femur, e.g. the distal anterior cortex and superior trochlea, optionally with any osteophytes when present, or the proximal anterior tibia and tibial plateau, optionally with any osteophytes when present, which is then used to generate a patient specific marker or template for intraoperative referencing and navigation. In this manner, any preoperative morphological models of the patient (e.g. before and after implant component placement), preoperative kinematic models of the patient (e.g. before and after implant component placement), virtual surgical plans, for example as displayed by an OHMD during surgery, and actual surgical instruments and actual implant components and live surgical sites including alterations to a live surgical site can be cross-referenced. Other methods of registration and cross-referencing including registration and cross-referencing surgical sites and one or more OHMDs such as the ones described in PCT International Application Serial No. PCT/US2017/021859 and PCT/US2018/13774 can be used. These applications are hereby incorporated by reference in their entirety.

In another embodiment, the location of the medial and/or lateral joint space and/or patellofemoral joint space, a tibial slope, a distal femoral offset, a posterior femoral offset, a mechanical axis and/or a rotation axis, and any other anatomic landmark or anatomical or biomechanical axis known in the art can be measured and/or estimated on an imaging test, e.g. a supine or upright x-ray, a full leg length standing x-ray and any other imaging technique known in the art, e.g. an ultrasound, and can optionally be entered into a biomechanical or kinematic model of the patient together with, before or after the data generated with use of the IMU's and/or navigation markers and/or image capture markers, e.g. optical markers with geometric patterns and/or LED's, including combinations thereof and/or the image capture markers and system, navigation system etc., acquired for any of the timepoints T1, T2, T3, T4 and/or T5.

In another embodiment, a motion simulation generated by the computer processor using the information, measurements and/or measured parameters from one or more of the timepoints T1, T2, T3, T4 and/or T5 and configured to include the coordinates and/or geometry including articular surface geometry of one or more virtually placed virtual implant components in the simulation, e.g. a femoral component, a tibial component and/or a patellar component in a knee replacement, can be used to identify any potential motion conflicts for given knee kinematics measured during one or more of the timepoints T1, T2, T3, T4 and/or T5 and the virtually placed implant components and can optionally be modified using data obtained from one or more imaging tests, e.g. the location of the medial and/or lateral joint space and/or patellofemoral joint space, a tibial slope, a distal femoral offset, a posterior femoral offset, a mechanical axis and/or a rotation axis, and any other anatomic landmark or anatomical or biomechanical axis known in the art. In some embodiments, the motion simulation generated using the information, measurements and/or measured parameters from one or more of the timepoints T1, T2, T3, T4 and/or T5 and configured to include the coordinates and/or geometry including articular surface geometry of one or more virtually placed virtual implant components in the simulation, e.g. a femoral component, a tibial component and/or a patellar component in a knee replacement, can be used to determine the distance between a first articular surface, e.g. a femoral articular surface, a second articular surface, e.g. a tibial articular surface, and/or a third articular surface, e.g. a patellar articular surface, for the different respective virtual implant components, e.g. a virtual femoral, virtual tibial and/or virtual patellar implant component, for given knee kinematics measured during one or more of the timepoints T1, T2, T3, T4 and/or T5 and for a portion of or the entire range of motion or for select or all exercises for which kinematic measurements were obtained; the motion simulation can optionally consider or be modified to include data obtained from one or more imaging tests, e.g. the location of the medial and/or lateral joint space and/or patellofemoral joint space, a tibial slope, a distal femoral offset, a posterior femoral offset, a mechanical axis and/or a rotation axis, and any other anatomic landmark or anatomical or biomechanical axis known in the art. The motion simulation using the combined kinematic, virtual implant component and imaging information can then be modified to achieve a desired or predetermined distance between two or more virtual implant components for select angles, select ranges of motion and/or select exercises or physical activities, e.g. in a knee replacement, hip replacement, shoulder replacement, ankle replacement, ligament repair or ligament reconstruction. Optionally, any of the measurements described in the specification can be performed on a joint, e.g. the knee, hip and/or ankle joint, or shoulder, elbow and/or wrist joint prior to performing surgery, e.g. by placing one or more IMU's, navigation markers, e.g. RF or retroreflective markers, image capture markers, e.g. optical markers with geometric patterns or LED's, on the patient's skin, for example near the joint or the joint space. Optionally, any of the measurements described in the specification can be performed on a joint, e.g. the knee, hip and/or ankle joint, or shoulder, elbow and/or wrist joint during surgery, e.g. by placing one or more IMU's, navigation markers, e.g. RF or retroreflective markers, image capture markers, e.g. optical markers with geometric patterns or LED's, on the patient's bone or cartilage exposed during the surgery, for example near the joint or the joint space, for example before or after an osteophyte removal.

In some embodiments, the registration of virtual patient data and live patient data using the techniques described herein can be repeated after one or more surgical steps have been performed in an OHMD guided joint replacement procedure, e.g. a knee replacement. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art including implantable and attachable markers, calibration and registration phantoms including optical markers, navigation markers, infrared markers, RF markers, patient specific markers, LED's with image capture and IMU's. For example, the re-registration can be performed using a cut bone surface, e.g. a cut distal femur using the surface shape, surface area or perimeter or other feature to match, superimpose and/or register the live patient data and the virtual patient data prior to performing subsequent surgical steps.

Someone skilled in the art that the same concepts and embodiments described for spinal surgery, knee replacement and hip replacement can be applied to other surgeries of the human body, e.g. repair or reconstruction of the anterior cruciate ligament, posterior cruciate ligament, other ligaments, shoulder replacement, ankle replacement, and/or wrist replacement. For example, an OHMD can display or project digital holograms of one or more surgical instruments, trial implants or implant components or one or more outlines or axes of the surgical instruments, trial implants, or implant components or digital holograms of predetermined start point, predetermined start position, predetermined start orientation/alignment, predetermined intermediate point(s), predetermined intermediate position(s), predetermined intermediate orientation/alignment, predetermined end point, predetermined end position, predetermined end orientation/alignment, predetermined path, predetermined plane, predetermined cut plane, projected contour/outline/cross-section/surface features/shape/projection, predetermined depth marker or depth gauge, predetermined stop, predetermined angle/orientation/rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated/projected non-visualized portions for one or more devices/implants/implant components/surgical instruments/surgical tools, and/or one or more of a predetermined tissue change/alteration for a shoulder replacement, wherein the one or more digital holograms can be used to determine a humeral resection, arm length, glenoid component version, orientation and/or position, humeral component version, orientation and/or position.

An OHMD can display or project digital holograms of one or more surgical instruments, trial implants or implant components or one or more outlines or axes of the surgical instruments, trial implants, or implant components or digital holograms of a predetermined start point, predetermined start position, predetermined start orientation/alignment, predetermined intermediate point(s), predetermined intermediate position(s), predetermined intermediate orientation/ alignment, predetermined end point, predetermined end position, predetermined end orientation/alignment, predetermined path, predetermined plane, predetermined cut plane, projected contour/outline/cross-section/surface features/ shape/projection, predetermined depth marker or depth gauge, predetermined stop, predetermined angle/orientation/ rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated/projected non-visualized portions for one or more devices/implants/ implant components/surgical instruments/surgical tools, and/or one or more of a predetermined tissue change/ alteration for an ankle replacement, wherein the one or more digital holograms can be used to display or project an predetermined tibial resection and/or talar resection with desired coordinates, angles, orientation and/or alignment to achieve a desired ankle alignment including at least one of a coronal plane implant component alignment, sagittal plane implant component alignment including flexion and axial plane component alignment or rotation The foregoing embodiments can be used to measure and/or determine the motion and/or kinematics of various joints in the human body, e.g. a knee joint, hip joint, ankle joint, foot joint, toe joint, shoulder joint, elbow joint, wrist joint. Kinematic parameters that can be measured in this fashion include, but are not limited to, loading patterns, load lines, contact lines, contact forces, articular surface forces, moments, load conditions of various implant components, e.g. for different movements [e.g. flexion, extension, rotation, rollback], constraints, medial femoral rollback during flexion, lateral femoral rollback during flexion, patellar position, medial, superior, inferior for different flexion and/ or extension angles, patellar tracking, internal/external rotation of one or both femoral condyles, internal/external rotation of a tibia, tibial abduction, tibial adduction, flexion and extension angles of one or more articular surfaces, anterior/posterior slide of one or both femoral condyles during flexion or extension, medial and/or lateral laxity of a joint, e.g. during motion or stress testing, anterior and/or posterior laxity of a joint, e.g. during motion or stress testing [e.g. varus stress or valgus stress], contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles. Any combination of parameters can be measured for various activities for any joint of the human body, e.g. a hip, knee, ankle, foot, shoulder, elbow, wrist, hand, spinal joint. Any one or more parameters can be used for kinematic simulations involving one or more virtual implant components, e.g. virtually placed on a bone, e.g. a cut or burred or milled or reamed bone or an unaltered bone, as described in the specification, e.g. for virtual gap balancing using virtually placed implant components.

In some embodiments, the kinematics of one or more joints or an extremity or a limb of a patient can be measured using the foregoing embodiments for different physical activities. The kinematics of the joint can be determined during a surgical procedure. The kinematics of the joint can be determined during the surgical procedure, for example, before the skin has been cut, after the skin has been cut, before a joint capsule has been opened, after a joint capsule has been opened, before a ligament has been pie crusted or partially or completely released, after a ligament has been pie crusted or partially or completely released, before one or more osteophytes are removed, after one or more osteophytes are removed, before a cartilage or bone has been removed or after a cartilage or bone has been removed, before a ligament is repaired or reconstructed or after a ligament has been repaired or reconstructed [e.g. an ACL or a rotator cuff], before a labrum or a meniscus is repaired or resected, or after a labrum or a meniscus is repaired or resected. Any combination is possible. Kinematic measurements can also be obtained before and/or after certain stress maneuvers, e.g. varus stress, valgus stress, Lachman testing, instability testing, abduction stress, adduction stress, hyperflexion stress and/or hyperextension stress or any other stress testing known in the art. Repeat measurements after performing various of the foregoing steps or any additional surgical steps or procedures, including, for example, the placement of trial implants, can be performed.

In some embodiments, one or more virtual implant components can be virtually placed, sized, fitted, selected and/or aligned as described in other parts of the specification. Such virtual implant components can, for example, be a virtual femoral, virtual tibial or virtual patellar component in a knee replacement, a virtual femoral or a virtual acetabular component in a hip replacement, a virtual glenoid or a virtual humeral component in a shoulder replacement, a virtual talar or a virtual tibial component in an ankle replacement, a virtual pedicle screw or a virtual cage in a spinal fusion, or a virtual motion preservation intervertebral device in a motion preservation spinal procedure [e.g. a Charite disk or a ProDisk]. The position and/or orientation and/or alignment and/or coordinates of the virtual implant component(s), e.g. on a first, second or third articular surface or combinations thereof, can be stored in a coordinate system after the virtual placing, virtual sizing, virtual fitting, virtual selecting, and/ or virtual aligning.

A computer processor can optionally introduce the position and/or orientation and/or alignment and/or coordinates of the virtually placed, sized, fitted, selected and/or aligned virtual implant component(s) into a kinematic model, which can, for example, use the same coordinate system or which can, for example, introduce different parts of the joint, e.g. a distal femur or a proximal tibia or a proximal femur and an acetabulum in an object specific coordinate system, optionally referenced to or including the coordinate system used for the virtual placing, sizing, fitting, selecting and/or aligning of the one or more virtual implant component(s). The kinematic model can include data from one or more kinematic measurements obtained from the patient, e.g. prior to surgery, e.g. using a smartphone, tablet or OHMD, or during surgery. Kinematic measurements from the patient can include intra-operative measurements obtained during the surgery, e.g. before the skin has been cut, after the skin has been cut, before a joint capsule has been opened, after a joint capsule has been opened, before a ligament has been pie crusted or partially or completely released, after a ligament has been pie crusted or partially or completely released, before one or more osteophytes has been removed and/or after one or more osteophytes has been removed, before a cartilage or bone has been removed or after a cartilage or bone has been removed, before a ligament is repaired or reconstructed or after a ligament has been repaired or reconstructed [e.g. an ACL or a rotator cuff], before a labrum or a meniscus is repaired or resected, or after a labrum or a meniscus is repaired or resected, before and/or after certain stress maneuvers, e.g. varus stress, valgus stress, Lachman testing, instability testing, abduction stress, adduction stress, hyperflexion stress and/or hyperextension stress, or any other stress test known in the art, or any combination thereof. In some embodiments, the computer processor can introduce the position and/or orientation and/or alignment and/or coordinates of the virtually placed, sized, fitted, selected and/or aligned virtual implant component(s) into multiple kinematic models, e.g. before the skin has been cut, after the skin has been cut, before a joint capsule has been opened, after a joint capsule has been opened, before a ligament has been pie crusted or partially or completely released, after a ligament has been pie crusted or partially or completely released, before one or more osteophytes has been removed and/or after one or more osteophytes has been removed, before a cartilage or bone has been removed or after a cartilage or bone has been removed, before a ligament is repaired or reconstructed or after a ligament has been repaired or reconstructed [e.g. an ACL or a rotator cuff], before a labrum or a meniscus is repaired or resected, or after a labrum or a meniscus is repaired or resected, before and/or after certain stress maneuvers, e.g. varus stress, valgus stress, Lachman testing, instability testing, abduction stress, adduction stress, hyperflexion stress and/or hyperextension stress or any other stress test known in the art. The one or more kinematic models can then be evaluated for any instability or pathologic motion patterns, for any kinematic conflicts [e.g. a first virtual component overlapping, interfering or "diving into" a second virtual implant component during motion, e.g. flexion] with the virtually placed, sized, fitted, selected and/or aligned virtual implant component(s) in the model(s). For example, a kinematic model can be used to evaluate the movement of a virtual femoral component in relationship to a virtual tibial and/or a virtual patellar component. The model can simulate movement of the virtually placed femoral, virtual placed tibial and/or virtually placed patellar component, e.g. by superimposing and/or aligning the virtual implant component(s) with the physical joint, e.g. the physical articular surface, using one or more computer processors configured to display the virtual implant by one or more OHMDs in superimposition and/or alignment with the surface of the physical joint, e.g. wherein at least a portion of the virtual implant is superimposed and/or aligned with at least one anatomic structure of the physical joint, and/or to maintain the display of the virtual implant by the one or more OHMDs in superimposition and/or alignment with the surface of the physical joint, e.g. wherein the display of the virtual implant or virtual implant component (including a plurality thereof) is maintained superimposed and/or aligned with at least one anatomic structure of the joint, for example also when the physical joint moves, through a range of motion, or for select pose angles of the joint. If any signs of abnormal motion, pathologic motion, instability or motion conflict between the virtual femoral, virtual tibial or virtual patellar component are detected, e.g. visually or by the at least one computer processor, e.g. a femoral component interfering with or "diving" or 1, or 2, or 3, or 4, or 5 or more mm into a tibial component or a patellar component, the display of the virtual implant components by the optical head mounted display, e.g. the position, location, orientation, alignment and/or coordinates of one or more of the virtual implant components, e.g. a virtual femoral, virtual tibial or virtual patellar component, displayed onto the joint, e.g. the surface of the joint or subsurface portions of the joint displayed by the optical head mounted display, can be adjusted or moved by until the abnormal motion, pathologic motion, instability or motion conflict between the virtual components is resolved. In some embodiments, one or more virtual components can be exchanged in the model and/or the simulation, e.g. for a smaller or larger virtual component or a virtual component with a different shape and the model can, optionally, be re-run, e.g. in an iterative fashion until a predetermined or desired result is achieved. The modified position, location, orientation, alignment and/or coordinates of the one or more of virtual implant components, e.g. a virtual femoral, virtual tibial and/or virtual patellar component, can then be used to determine and/or modify a virtual surgical plan and/or to determine and/or modify the position and/or orientation and/or coordinates of a virtual surgical guide (e.g. a virtual cut block, a virtual axis, a virtual plane), and/or one or more bone resections [e.g. bone cuts] for placing the physical implant component(s).

A kinematic model can be used to evaluate the movement of a virtual femoral component in relationship to a virtual acetabular component in hip replacement. The model can simulate movement of a virtually placed femoral and/or virtually placed acetabular component (e.g. by superimposing and/or aligning the virtual implant component(s) with the physical joint, e.g. the physical articular surface, using one or more computer processors configured to display the virtual implant by one or more OHMDs in superimposition and/or alignment with the surface of the physical joint and/or to maintain the display of the virtual implant by the one or more OHMDs in superimposition and/or alignment with the surface of the physical joint, e.g. also when the physical joint moves) through a range of motion and can be used to detect abnormal motion, pathologic motion, instability or motion conflict between the virtual femoral and the virtual acetabular component or any impingement of one or more components, for example on the acetabular rim, the femoral neck or head, and/or surrounding soft-tissues. If any signs of abnormal motion, pathologic motion, instability or motion conflict, e.g. impingement, between the virtual femoral and virtual acetabular component [e.g. an acetabular liner] are detected, e.g. a femoral component "diving" 1, or 2, or 3, or 4, or 5 or more mm into an acetabular component or impingement of one or more virtual components onto surrounding tissue, e.g. an acetabular rim or soft-tissue, the position, location, orientation, alignment and/or coordinates of one or more of the virtual implant components, e.g. the virtual femoral or virtual acetabular component, can be adjusted until the abnormal motion, pathologic motion, instability or motion conflict between the virtual components or impingement is resolved. Optionally, one or more virtual components can be exchanged in the simulation and/or model, e.g. for a smaller or larger virtual component or a virtual component with a different shape and the model can, optionally, be re-run, e.g. in an iterative fashion until a predetermined or desired result is achieved. The modified position, location, orientation, alignment and/or coordinates of the one or more of virtual implant components, e.g. a virtual femoral or virtual acetabular component, can then be used to modify a virtual surgical plan and/or to determine or adjust the position and/or orientation of a virtual surgical guide, e.g. a virtual axis for acetabular reaming, and/or one or more bone resections [e.g. a bone cut or a reaming] for placing the physical implant component(s).

A kinematic model can be used to evaluate the movement of a virtual humeral component in relationship to a virtual glenoid component in shoulder replacement. The model can simulate movement of the virtually placed humeral and/or virtually placed glenoid component (e.g. by superimposing and/or aligning the virtual implant component(s) with the physical joint, e.g. the physical articular surface, using one or more computer processors configured to display the virtual implant by one or more OHMDs in superimposition and/or alignment with the surface of the physical joint and/or to maintain the display of the virtual implant by the one or more OHMDs in superimposition and/or alignment with the surface of the physical joint, e.g. also when the physical joint moves) through a range of motion and can be used to detect abnormal motion, pathologic motion, instability or motion conflict between the virtual humeral and the glenoid component or any impingement of one or more components, for example on the glenoid rim, the humeral neck or head, and/or surrounding soft-tissues. If any signs of abnormal motion, pathologic motion, instability or motion conflict between the virtual humeral and virtual glenoid component are detected, e.g. a humeral component "diving" 1, or 2, or 3, or 4, or 5 or more mm into a glenoid component or impingement of one or more virtual components onto surrounding tissue, e.g. a glenoid rim or soft-tissue, the position, location, orientation, alignment and/or coordinates of one or more of the virtual implant components, e.g. the virtual humeral or virtual glenoid component, can be adjusted until the abnormal motion, pathologic motion, instability or motion conflict between the virtual components or impingement is resolved. Optionally, one or more virtual components can be exchanged in the kinematic simulation and/or model, e.g. for a smaller or larger virtual component or a virtual component with a different shape and the model can, optionally, be re-run, e.g. in an iterative fashion until a predetermined or desired result is achieved. The modified position, location, orientation, alignment and/or coordinates of the one or more of virtual implant components, e.g. a virtual humeral or virtual glenoid component, can then be used to determine and/or modify a virtual surgical plan and/or to determine and/or modify the position and/or orientation and/or coordinates of a virtual surgical guide, e.g. a virtual cut block, a virtual axis, a virtual plane, and/or one or more bone resections [e.g. a bone cut or a reaming] for placing the physical implant component(s). Someone skilled in the art can recognize that the foregoing embodiments can be applied to any joint of the human body, e.g. an ankle joint, an elbow joint, a wrist joint.

The one or more kinematic models and/or simulations can also be used for gap balancing with the virtually placed, sized, fitted, selected and/or aligned virtual implant component(s). For example, in a knee replacement, a virtually placed, sized, fitted, selected and/or aligned virtual femoral implant component and virtual tibial implant component can be used in one or more kinematic models of the patient as described in the foregoing embodiments. The position and/or orientation and/or alignment and/or coordinates of the virtually placed, sized, fitted, selected and/or aligned virtual femoral and/or tibial implant component can be determined, e.g. by moving the knee through a range of motion, e.g. for different angles of flexion, extension and/or rotation, abduction and/or adduction, or through a biomotion simulation and the distance between the articular surface(s) of the medial condyle of the virtual femoral component and the medial tibial plateau of the virtual tibial component and the articular surface(s) of the lateral condyle of the virtual femoral component and the lateral tibial plateau of the virtual tibial component can be determined through the range of motion, including and/or also for different angles of flexion, extension and/or rotation, abduction and/or adduction, or through the biomotion simulation, using, for example, the kinematic data of the patient measured as described in the foregoing embodiments. Using a computer processor configured to display one or more virtual implant components using one or more OHMDs and/or configured to run the kinematic models and/or measurements, the position and/or orientation and/or alignment and/or coordinates of the virtually placed, sized, fitted, selected and/or aligned virtual femoral and/or tibial implant component can then optionally be modified to achieve a predetermined or desired distance between the articular surface(s) of the medial condyle of the virtual femoral component and the medial tibial plateau of the virtual tibial component and/or the articular surface(s) of the lateral condyle of the virtual femoral component and the lateral tibial plateau of the virtual tibial component through the range of motion, for different angles of flexion, extension and/or rotation, or through the biomotion simulation.

For example, the position and/or orientation and/or alignment and/or coordinates of the virtually placed, sized, fitted, selected and/or aligned virtual femoral and/or tibial implant component can then optionally be modified to achieve a predetermined or desired distance between the articular surface(s) of the medial condyle of the virtual femoral component and the medial tibial plateau of the virtual tibial component of 1, 2, 3, 4 mm or any other distance selected by the computer processor or the surgeon, using, for example, the biomotion simulation, through the range of motion, for different angles of flexion, extension and/or rotation, or through the biomotion simulation. The position and/or orientation and/or alignment and/or coordinates of the virtually placed, sized, fitted, selected and/or aligned virtual femoral and/or tibial implant component can optionally be modified to achieve a predetermined or desired distance between the articular surface(s) of the lateral condyle of the virtual femoral component and the lateral tibial plateau of the virtual tibial component of 1, 2, 3, 4 mm or any other distance selected by the computer processor or the surgeon, using, for example, the biomotion simulation, through the range of motion, for different angles of flexion, extension and/or rotation, or through the biomotion simulation. The distance between the medial and the lateral articular surfaces of the virtual femoral and tibial implant components can be the same or can be different through the range of motion, for different angles of flexion, extension and/or rotation, or through the biomotion simulation.

The modified position, location, orientation, alignment and/or coordinates of the one or more virtual implant components, e.g. the virtual femoral or virtual tibial component, can then be used to determine and/or modify a virtual surgical plan and/or to determine and/or modify the position and/or orientation and/or coordinates of a virtual surgical guide (e.g. a virtual cut block, virtual axis, virtual plane) and/or to determine and/or modify the position and/or orientation and/or coordinates of a virtual surgical instrument or tool, and/or to determine and/or modify one or more bone resections [e.g. bone cuts] for placing the physical implant component(s). Someone skilled in the art can recognize that this form of virtual gap balancing can result in intra-operative time savings, for example, by reducing the number of trial implants and stress tests in the physical joint of the patient and by reducing the need for bone recuts or ligament releases.

In some embodiments, a system is provided comprising at least on computer. In some embodiments, the at least one computer can be the same or different computers. In some embodiments, the at least one computer can comprise one or more processors. In some embodiments, the at least one processor can be the same or different processors. In some embodiments, the displaying, placing, fitting, sizing, selecting, aligning, moving, modifying any of the foregoing of at least one virtual implant can be performed by at least one computer, at least one computer processor, at least one network for computers, at least one OHMD, optionally, with at least one computer or computer processor integrated into or attached to the OHMD.

In some embodiments, at least one computer can be configured to generate a virtual implant, wherein the virtual implant can be a three-dimensional digital representation corresponding to at least one portion of a physical implant, a placement indicator of the physical implant, or a combination thereof. The virtual implant can comprise a first virtual implant component, a second virtual implant component, a third virtual implant component, and a fourth virtual implant component. Any number of virtual implant components can be possible. In some embodiments, at least one computer can be configured to generate a virtual trial implant, wherein the virtual trial implant can be a three-dimensional digital representation corresponding to at least one portion of a physical implant, a placement indicator of the physical implant, a physical trial implant, a placement indicator of the physical trial implant, or a combination thereof. The virtual implant can comprise a first virtual trial implant component, a second virtual trial implant component, a third virtual trial implant component, and a fourth virtual trial implant component. Any number of virtual trial implant components can be possible.

The virtual implant, e.g. a first virtual implant component, a second virtual implant component or a combination thereof, can be configured to allow superimposition and alignment of the at least a portion of the virtual implant, e.g. the first virtual implant component, the second virtual implant component or a combination thereof, onto a surface of the physical joint, e.g. visible directly through a see through optical head mounted display. The virtual implant, e.g. a first virtual implant component, a second virtual implant component or a combination thereof, can be configured to allow superimposition and alignment of the at least a portion of the virtual implant, e.g. the first virtual implant component, the second virtual implant component or a combination thereof, over a surface of the physical joint, e.g. visible directly through a see through optical head mounted display. The virtual implant, e.g. a first virtual implant component, a second virtual implant component or a combination thereof, can be configured to allow superimposition and alignment of the at least a portion of the virtual implant, e.g. the first virtual implant component, the second virtual implant component or a combination thereof, tangent with a surface of the physical joint, e.g. visible directly through a see through optical head mounted display. The virtual implant, e.g. a first virtual implant component, a second virtual implant component or a combination thereof, can be configured to allow superimposition and alignment of the at least a portion of the virtual implant, e.g. the first virtual implant component, the second virtual implant component or a combination thereof, intersecting with a surface of the physical joint, e.g. visible directly through a see through optical head mounted display. The virtual implant, e.g. a first virtual implant component, a second virtual implant component or a combination thereof, can be configured to allow superimposition and alignment of the at least a portion of the virtual implant, e.g. the first virtual implant component, the second virtual implant component or a combination thereof, subjacent or under a surface of the physical joint, e.g. not visible directly through a see through optical head mounted display, but optically displayed by the optical head mounted display, e.g. using a computer generated 3D model of the joint.

The surface of the physical joint can be a cortical surface, e.g. of cortical bone adjacent to an articular surface, an articular surface, a cartilage surface, a normal cartilage surface, a diseased or damaged cartilage surface, a subchondral bone surface, a meniscal surface, a ligament surface, a labral surface, a drilled, pinned, milled, reamed, impacted or cut bone surface, or a combination thereof.

In some embodiments, at least one computer can be configured to allow superimposition and alignment of at least a portion of a virtual implant, e.g. a first virtual implant component, a second virtual implant component or a combination thereof, with at least one anatomic structure of the physical joint, e.g. visible directly through a see through optical head mounted display, or in subsurface location of the physical joint of the patient, or combinations thereof.

A virtual implant, e.g. a first virtual implant component, a second virtual implant component or a combination thereof, can be configured to allow superimposition and alignment of at least a portion of the virtual implant, e.g. the first virtual implant component, the second virtual implant component or a combination thereof, with at least one anatomic structure of the physical joint, e.g. visible directly through a see through optical head mounted display, or in subsurface location of the physical joint of the patient, or combinations thereof.

In some embodiments, at least one computer can be configured to allow superimposition and alignment of at least a portion of a virtual implant, e.g. a first virtual implant component, a second virtual implant component or a combination thereof, tangent with and/or intersecting with at least one anatomic structure of the physical joint, e.g. visible directly through a see through optical head mounted display, and/or in subsurface location of the physical joint of the patient, or combinations thereof.

A virtual implant, e.g. a first virtual implant component, a second virtual implant component or a combination thereof, can be configured to allow superimposition and alignment of at least a portion of the virtual implant, e.g. the first virtual implant component, the second virtual implant component or a combination thereof, tangent with and/or intersecting with at least one anatomic structure of the physical joint, e.g. visible directly through a see through optical head mounted display, and/or in subsurface location of the physical joint of the patient, or combinations thereof.

In some embodiments, at least one computer can be configured to allow superimposition and alignment of at least a portion of a virtual implant, e.g. a first virtual implant component, a second virtual implant component or a combination thereof, with at least one anatomic structure of the physical joint, e.g. visible directly through a see through optical head mounted display, or in subsurface location of the physical joint of the patient, or combinations thereof.

A virtual implant, e.g. a first virtual implant component, a second virtual implant component or a combination thereof, can be configured to allow superimposition and alignment of at least a portion of the virtual implant, e.g. the first virtual implant component, the second virtual implant component or a combination thereof, with at least one anatomic structure of the physical joint, e.g. visible directly through a see through optical head mounted display, or in subsurface location of the physical joint of the patient, or combinations thereof.

In some embodiments, at least one computer can be configured to allow superimposition and alignment of at least a portion of a first virtual implant component with a first anatomic structure of the physical joint of the patient visible directly through the see through optical head mounted display; at least one computer can be configured to allow superimposition and alignment of at least a portion of a second virtual implant component with a second anatomic structure of the physical joint of the patient visible directly through the see through optical head mounted display. The first anatomic structure and the second anatomic structure can be the same or different.

In some embodiments, at least one computer can be configured to allow superimposition and alignment of at least a portion of a first virtual implant component tangent with and/or intersecting a first anatomic structure of the physical joint of the patient visible directly through the see through optical head mounted display; at least one computer can be configured to allow superimposition and alignment of at least a portion of a second virtual implant component tangent with and/or intersecting a second anatomic structure of the physical joint of the patient visible directly through the see through optical head mounted display. The first anatomic structure and the second anatomic structure can be the same or different.

The at least one anatomic structure can comprise at least one of an anatomic landmark, an anatomic plane, an articular surface, a cartilage surface, a subchondral bone surface, a cortical bone surface, a cut bone surface, a reamed bone surface, a milled bone surface, an impacted bone surface, a tissue resection, a surface, one or more surface points, an anterior-posterior dimension of at a least portion of a joint, e.g. a medial condyle, a medio-lateral dimension of at least a portion of a joint, e.g. a lateral condyle or both condyles or between the medial and lateral epicondylar points, a superior-inferior dimension of at least a portion of a joint, a joint space, e.g. between a distal femur and a proximal tibia, e.g. in extension or at different flexion angles, an articular radius, an articular curvature, an articular shape, a flexion gap, e.g. between a virtual or a physical femoral and a virtual or a physical tibial implant component or combinations of virtual and physical components, an extension gap, e.g. between a virtual or a physical femoral and a virtual or a physical tibial implant component or combinations of virtual and physical components, an anatomic axis, a biomechanical axis, a mechanical axis, a structure not visible within the exposed portions of a joint, e.g. a posterior condyle, a posterior tibial plateau in a knee replacement, a tear drop in a hip replacement, or a combination thereof. The at least one anatomic structure can be registered in a coordinate system.

The first anatomic structure and/or the second anatomic structure can comprise at least one of an anatomic landmark, an anatomic plane, an articular surface, a cartilage surface, a subchondral bone surface, a cortical bone surface, a cut bone surface, a reamed bone surface, a milled bone surface, an impacted bone surface, a tissue resection, a surface, one or more surface points, an anterior-posterior dimension of at a least portion of a joint, e.g. a medial condyle, a medio-lateral dimension of at least a portion of a joint, e.g. a lateral condyle or both condyles or between the medial and lateral epicondylar points, a superior-inferior dimension of at least a portion of a joint, a joint space, e.g. between a distal femur and a proximal tibia, e.g. in extension or at different flexion angles, an articular radius, an articular curvature, an articular shape, a flexion gap, e.g. between a virtual or a physical femoral and a virtual or a physical tibial implant component or combinations of virtual and physical components, an extension gap, e.g. between a virtual or a physical femoral and a virtual or a physical tibial implant component or combinations of virtual and physical components, an anatomic axis, a biomechanical axis, a mechanical axis, a structure not visible within the exposed portions of a joint, e.g. a posterior condyle, a posterior tibial plateau in a knee replacement, a tear drop in a hip replacement, or a combination thereof. The first anatomic structure and/or the second anatomic structure can be registered in a coordinate system.

In some embodiments, at least one computer can be configured to superimpose at least a portion of a first virtual implant component onto at least a portion of a first articular surface of the physical joint of the patient visible directly through the see through optical head mounted display. In some embodiments, at least one computer can be configured to superimpose at least a portion of a second virtual implant component onto at least a portion of a second articular surface of the physical joint of the patient visible directly through the see through optical head mounted display. In some embodiments, at least one computer can be configured to superimpose at least a portion of a third virtual implant component onto at least a portion of a third articular surface of the physical joint of the patient visible directly through the see through optical head mounted display. In some embodiments, at least one computer can be configured to superimpose at least a portion of a first, second and/or third virtual implant component onto at least a portion of a first, second, and/or third articular surface of the physical joint of the patient visible directly through the see through optical head mounted display. In some embodiments, at least one computer can be configured to superimpose at least a portion of a first, second and/or third virtual implant component onto at least a portion of at least one articular surface. In some embodiments, at least one computer can be configured to superimpose at least a portion of a first, second and/or third virtual implant component onto at least a portion of two or more articular surfaces.

In some embodiments, at least one computer can be configured to superimpose at least a portion of a first virtual implant component tangent with and/or intersecting at least a portion of a first articular surface of the physical joint of the patient visible directly through the see through optical head mounted display. In some embodiments, at least one computer can be configured to superimpose at least a portion of a second virtual implant component tangent with and/or intersecting at least a portion of a second articular surface of the physical joint of the patient visible directly through the see through optical head mounted display. In some embodiments, at least one computer can be configured to superimpose at least a portion of a third virtual implant component tangent with and/or intersecting at least a portion of a third articular surface of the physical joint of the patient visible directly through the see through optical head mounted display. In some embodiments, at least one computer can be configured to superimpose at least a portion of a first, second and/or third virtual implant component tangent with and/or intersecting at least a portion of a first, second, and/or third articular surface of the physical joint of the patient visible directly through the see through optical head mounted display. In some embodiments, at least one computer can be configured to superimpose at least a portion of a first, second and/or third virtual implant component tangent with and/or intersecting at least a portion of at least one articular surface. In some embodiments, at least one computer can be configured to superimpose at least a portion of a first, second and/or third virtual implant component tangent with and/or intersecting at least a portion of two or more articular surfaces.

In some embodiments, at least one computer can be configured to superimpose at least a portion of a first virtual implant component onto at least a portion of a first surface of the physical joint of the patient of the physical joint of the patient visible directly through the see through optical head mounted display. In some embodiments, at least one computer can be configured to superimpose at least a portion of a second virtual implant component onto at least a portion of a second surface of the physical joint of the patient of the physical joint of the patient visible directly through the see through optical head mounted display. In some embodiments, at least one computer can be configured to superimpose at least a portion of a third virtual implant component onto at least a portion of a third surface of the physical joint of the patient of the physical joint of the patient visible directly through the see through optical head mounted display. In some embodiments, at least one computer can be configured to superimpose at least a portion of a first, second and/or third virtual implant component onto at least a portion of a first, second, and/or third surface of the physical joint of the patient of the physical joint of the patient visible directly through the see through optical head mounted display. In some embodiments, at least one computer can be configured to superimpose at least a portion of a first, second and/or third virtual implant component onto at least a portion of at least one surface of the physical joint of the patient. In some embodiments, at least one computer can be configured to superimpose at least a portion of a first, second and/or third virtual implant component onto at least a portion of two or more surface of the physical joint of the patients.

In some embodiments, at least one computer can be configured to superimpose at least a portion of a first virtual implant component tangent with and/or intersecting at least a portion of a first surface of the physical joint of the patient of the physical joint of the patient visible directly through the see through optical head mounted display. In some embodiments, at least one computer can be configured to superimpose at least a portion of a second virtual implant component tangent with and/or intersecting at least a portion of a second surface of the physical joint of the patient of the physical joint of the patient visible directly through the see through optical head mounted display. In some embodiments, at least one computer can be configured to superimpose at least a portion of a third virtual implant component tangent with and/or intersecting at least a portion of a third surface of the physical joint of the patient of the physical joint of the patient visible directly through the see through optical head mounted display. In some embodiments, at least one computer can be configured to superimpose at least a portion of a first, second and/or third virtual implant component tangent with and/or intersecting at least a portion of a first, second, and/or third surface of the physical joint of the patient of the physical joint of the patient visible directly through the see through optical head mounted display. In some embodiments, at least one computer can be configured to superimpose at least a portion of a first, second and/or third virtual implant component tangent with and/or intersecting at least a portion of at least one surface of the physical joint of the patient. In some embodiments, at least one computer can be configured to superimpose at least a portion of a first, second and/or third virtual implant component tangent with and/or intersecting at least a portion of two or more surface of the physical joint of the patients.

In some embodiments, at least one computer can be configured to superimpose at least a portion of a first virtual implant component onto at least a portion of a first anatomic structure of the physical joint of the patient visible directly through the see through optical head mounted display. In some embodiments, at least one computer can be configured to superimpose at least a portion of a second virtual implant component onto at least a portion of a second anatomic structure of the physical joint of the patient visible directly through the see through optical head mounted display. In some embodiments, at least one computer can be configured to superimpose at least a portion of a third virtual implant component onto at least a portion of a third anatomic structure of the physical joint of the patient visible directly through the see through optical head mounted display. In some embodiments, at least one computer can be configured to superimpose at least a portion of a first, second and/or third virtual implant component onto at least a portion of a first, second, and/or third anatomic structure of the physical joint of the patient visible directly through the see through optical head mounted display. In some embodiments, at least one computer can be configured to superimpose at least a portion of a first, second and/or third virtual implant component onto at least a portion of at least one anatomic structure. In some embodiments, at least one computer can be configured to superimpose at least a portion of a first, second and/or third virtual implant component onto at least a portion of two or more anatomic structures.

In some embodiments, at least one computer can be configured to superimpose at least a portion of a first virtual implant component tangent with and/or intersecting at least a portion of a first anatomic structure of the physical joint of the patient visible directly through the see through optical head mounted display. In some embodiments, at least one computer can be configured to superimpose at least a portion of a second virtual implant component tangent with and/or intersecting at least a portion of a second anatomic structure of the physical joint of the patient visible directly through the see through optical head mounted display. In some embodiments, at least one computer can be configured to superimpose at least a portion of a third virtual implant component tangent with and/or intersecting at least a portion of a third anatomic structure of the physical joint of the patient visible directly through the see through optical head mounted display. In some embodiments, at least one computer can be configured to superimpose at least a portion of a first, second and/or third virtual implant component tangent with and/or intersecting at least a portion of a first, second, and/or third anatomic structure of the physical joint of the patient visible directly through the see through optical head mounted display. In some embodiments, at least one computer can be configured to superimpose at least a portion of a first, second and/or third virtual implant component tangent with and/or intersecting at least a portion of at least one anatomic structure. In some embodiments, at least one computer can be configured to superimpose at least a portion of a first, second and/or third virtual implant component tangent with and/or intersecting at least a portion of two or more anatomic structures.

In some embodiments, at least one computer can be configured to maintain the display of at least a portion of a virtual implant, e.g. a first virtual implant component, a second virtual implant component or a combination thereof, onto at least one anatomic structure when the physical joint of the patient moves.

In some embodiments, at least one computer can be configured to maintain the display of at least a portion of a virtual implant, e.g. a first virtual implant component, a second virtual implant component or a combination thereof, over at least one anatomic structure when the physical joint of the patient moves.

In some embodiments, at least one computer can be configured to maintain the display of at least a portion of a virtual implant, e.g. a first virtual implant component, a second virtual implant component or a combination thereof, subjacent to at least one anatomic structure when the physical joint of the patient moves.

In some embodiments, at least one computer can be configured to maintain the display of at least a portion of a virtual implant, e.g. a first virtual implant component, a second virtual implant component or a combination thereof, tangent with and/or intersecting at least one anatomic structure when the physical joint of the patient moves.

In some embodiments, at least one computer can be configured to maintain the display of at least a portion of a virtual implant, e.g. a first virtual implant component, a second virtual implant component or a combination thereof, onto, over, subjacent, tangent with, intersecting or combinations thereof of at least one anatomic structure when the physical joint of the patient moves.

In some embodiments, at least one computer can be configured to maintain the display of at least a portion of a virtual implant, e.g. a first virtual implant component, a second virtual implant component or a combination thereof, onto, over, subjacent, tangent with, intersecting or combinations thereof of at least one anatomic structure when the physical joint of the patient moves.

In some embodiments, at least one computer can be configured to maintain the display of at least a portion of a virtual implant, e.g. a first virtual implant component, a second virtual implant component or a combination thereof, onto at least one articular surface when the physical joint of the patient moves.

In some embodiments, at least one computer can be configured to maintain the display of at least a portion of a virtual implant, e.g. a first virtual implant component, a second virtual implant component or a combination thereof, over at least one articular surface when the physical joint of the patient moves.

In some embodiments, at least one computer can be configured to maintain the display of at least a portion of a virtual implant, e.g. a first virtual implant component, a second virtual implant component or a combination thereof, subjacent to at least one articular surface when the physical joint of the patient moves.

In some embodiments, at least one computer can be configured to maintain the display of at least a portion of a virtual implant, e.g. a first virtual implant component, a second virtual implant component or a combination thereof, tangent with and/or intersecting at least one articular surface when the physical joint of the patient moves.

In some embodiments, at least one computer can be configured to maintain the display of at least a portion of a virtual implant, e.g. a first virtual implant component, a second virtual implant component or a combination thereof, onto, over, subjacent, tangent with, intersecting or combinations thereof of at least one articular surface when the physical joint of the patient moves.

In some embodiments, at least one computer can be configured to maintain the display of at least a portion of a virtual implant, e.g. a first virtual implant component, a second virtual implant component or a combination thereof, onto, over, subjacent, tangent with, intersecting or combinations thereof of at least one articular surface when the physical joint of the patient moves.

In some embodiments, at least one computer can be configured to maintain the display of at least a portion of a virtual implant, e.g. a first virtual implant component, a second virtual implant component or a combination thereof, onto at least one surface of the physical joint of the patient when the physical joint of the patient moves.

In some embodiments, at least one computer can be configured to maintain the display of at least a portion of a virtual implant, e.g. a first virtual implant component, a second virtual implant component or a combination thereof, over at least one surface of the physical joint of the patient when the physical joint of the patient moves.

In some embodiments, at least one computer can be configured to maintain the display of at least a portion of a virtual implant, e.g. a first virtual implant component, a second virtual implant component or a combination thereof, subjacent to at least one surface of the physical joint of the patient when the physical joint of the patient moves.

In some embodiments, at least one computer can be configured to maintain the display of at least a portion of a virtual implant, e.g. a first virtual implant component, a second virtual implant component or a combination thereof, tangent with and/or intersecting at least one surface of the physical joint of the patient when the physical joint of the patient moves.

In some embodiments, at least one computer can be configured to maintain the display of at least a portion of a virtual implant, e.g. a first virtual implant component, a second virtual implant component or a combination thereof, onto, over, subjacent, tangent with, intersecting or combinations thereof of at least one surface of the physical joint of the patient when the physical joint of the patient moves.

In some embodiments, at least one computer can be configured to maintain the display of at least a portion of a virtual implant, e.g. a first virtual implant component, a second virtual implant component or a combination thereof, onto, over, subjacent, tangent with, intersecting or combinations thereof of at least one surface of the physical joint of the patient when the physical joint of the patient moves.

In some embodiments, at least one computer can be configured to maintain the display of at least a portion of a first virtual implant component onto a first anatomic structure when the physical joint of the patient moves. At least one computer can be configured to maintain the display of at least a portion of a second virtual implant component onto a second anatomic structure when the physical joint of the patient moves.

In some embodiments, at least one computer can be configured to maintain the display of at least a portion of a first virtual implant component tangent with and/or intersecting a first anatomic structure when the physical joint of the patient moves. At least one computer can be configured to maintain the display of at least a portion of a second virtual implant component onto a second anatomic structure when the physical joint of the patient moves.

In some embodiments, at least one computer can be configured to maintain the display of at least a portion of a first virtual implant component over a first anatomic structure when the physical joint of the patient moves. At least one computer can be configured to maintain the display of at least a portion of a second virtual implant component over a second anatomic structure when the physical joint of the patient moves.

In some embodiments, at least one computer can be configured to maintain the display of at least a portion of a first virtual implant component subjacent to a first anatomic structure when the physical joint of the patient moves. At least one computer can be configured to maintain the display of at least a portion of a second virtual implant component subjacent to a second anatomic structure when the physical joint of the patient moves.

In some embodiments, at least one computer can be configured to maintain the display of at least a portion of a first virtual implant component and/or a second virtual implant component onto, over, subjacent, tangent with, intersecting, or combinations thereof of the first anatomic structure and/or the second anatomic structure when the physical joint of the patient moves.

In some embodiments, at least one computer can be configured to maintain the display of at least a portion of a first virtual implant component onto a first articular surface when the physical joint of the patient moves. At least one computer can be configured to maintain the display of at least a portion of a second virtual implant component onto a second articular surface when the physical joint of the patient moves.

In some embodiments, at least one computer can be configured to maintain the display of at least a portion of a first virtual implant component tangent with and/or intersecting a first articular surface when the physical joint of the patient moves. At least one computer can be configured to maintain the display of at least a portion of a second virtual implant component tangent with and/or intersecting a second articular surface when the physical joint of the patient moves.

In some embodiments, at least one computer can be configured to maintain the display of at least a portion of a first virtual implant component over a first articular surface when the physical joint of the patient moves. At least one computer can be configured to maintain the display of at least a portion of a second virtual implant component over a second articular surface when the physical joint of the patient moves.

In some embodiments, at least one computer can be configured to maintain the display of at least a portion of a first virtual implant component subjacent to a first articular surface when the physical joint of the patient moves. At least one computer can be configured to maintain the display of at least a portion of a second virtual implant component subjacent to a second articular surface when the physical joint of the patient moves.

In some embodiments, at least one computer can be configured to maintain the display of at least a portion of a first virtual implant component and/or a second virtual implant component onto, over, subjacent, tangent with, intersecting or combinations thereof of the first articular surface and/or the second articular surface when the physical joint of the patient moves.

In some embodiments, at least one computer can be configured to maintain the display of at least a portion of a first virtual implant component onto a first surface of the physical joint of the patient when the physical joint of the patient moves. At least one computer can be configured to maintain the display of at least a portion of a second virtual implant component onto a second surface of the physical joint of the patient when the physical joint of the patient moves.

In some embodiments, at least one computer can be configured to maintain the display of at least a portion of a first virtual implant component tangent with and/or intersecting a first surface of the physical joint of the patient when the physical joint of the patient moves. In some embodiments, at least one computer can be configured to maintain the display of at least a portion of a second virtual implant component tangent with and/or intersecting a second surface of the physical joint of the patient when the physical joint of the patient moves.

In some embodiments, at least one computer can be configured to maintain the display of at least a portion of a first virtual implant component over a first surface of the physical joint of the patient when the physical joint of the patient moves. In some embodiments, at least one computer can be configured to maintain the display of at least a portion of a second virtual implant component over a second surface of the physical joint of the patient when the physical joint of the patient moves.

In some embodiments, at least one computer can be configured to maintain the display of at least a portion of a first virtual implant component subjacent to a first surface of the physical joint of the patient when the physical joint of the patient moves. In some embodiments, at least one computer can be configured to maintain the display of at least a portion of a second virtual implant component subjacent to a second surface of the physical joint of the patient when the physical joint of the patient moves.

In some embodiments, at least one computer can be configured to maintain the display of at least a portion of a first virtual implant component and/or a second virtual implant component onto, over, subjacent, tangent with, intersecting or combinations thereof of the first surface of the physical joint of the patient and/or the second surface of the physical joint of the patient when the physical joint of the patient moves.

In some embodiments, at least one computer can be configured to maintain the display of at least a portion of a first virtual implant component in relationship to, e.g. over, tangent with, intersecting, and/or subjacent to, a first anatomic structure when the physical joint of the patient moves.

In some embodiments, at least one computer can be configured to maintain the display of the at least a portion of a second virtual implant component in relationship to, e.g. over, tangent with, intersecting, and/or subjacent to, a second anatomic structure when the physical joint of the patient moves.

In some embodiments, at least one computer can be configured to maintain the display of at least a portion of a first virtual implant component in relationship to, e.g. over, tangent with, intersecting, and/or subjacent to, a first surface of the physical joint of the patient when the physical joint of the patient moves.

In some embodiments, at least one computer can be configured to maintain the display of the at least a portion of a second virtual implant component in relationship to, e.g. over, tangent with, intersecting, and/or subjacent to, a second surface of the physical joint of the patient when the physical joint of the patient moves.

In some embodiments, at least one computer can be configured to maintain the display of at least a portion of a first virtual implant component in relationship to, e.g. over, tangent with, intersecting, and/or subjacent to, a first articular surface when the physical joint of the patient moves.

In some embodiments, at least one computer can be configured to maintain the display of the at least a portion of a second virtual implant component in relationship to, e.g. over, tangent with, intersecting, and/or subjacent to, a second first articular surface when the physical joint of the patient moves.

In some embodiments, at least one computer can be configured to maintain the display of at least a portion of a first virtual implant component onto at least a portion of a first articular surface when the physical joint of the patient moves.

In some embodiments, at least one computer can be configured to maintain the display of at least a portion of a second virtual implant component onto at least a portion of a second articular surface when the physical joint of the patient moves.

The virtual implant, e.g. the first virtual implant component, the second virtual implant component or a combination thereof, can be registered in the coordinate system.

In some embodiments, at least one computer can be configured to superimpose at least a portion of a first virtual implant component onto a first articular surface of the physical joint of the patient, e.g. a femoral surface in a knee replacement or an acetabular surface in a hip replacement.

In some embodiments, at least one computer can be configured to superimpose at least a portion of a second virtual implant component onto a second articular surface of the physical joint of the patient, e.g. a tibial surface in a knee replacement or a femoral, e.g. femoral head, surface in a hip replacement.

In some embodiments, at least one computer can be configured to superimpose at least a portion of a third virtual implant component onto a third articular surface of the physical joint of the patient, e.g. a patellar surface in a knee replacement. The term articular surface can be a portion of an articular surface or an entire articular surface.

In some embodiments, at least one computer can be configured to allow superimposition and alignment of at least a portion of a virtual implant, e.g. a first virtual implant component, a second virtual implant component or a combination thereof, with at least one anatomic structure of the physical joint, a surface of the physical joint, and/or an articular surface of the physical joint, e.g. visible directly through a see through optical head mounted display, or in subsurface location of the physical joint of the patient, or combinations thereof; the superimposition and alignment can be over, onto, tangent with, intersecting, subjacent to or combinations thereof with the at least one anatomic structure of the physical joint, the surface of the physical joint, and/or the articular surface of the physical joint. The superimposition and/or alignment can be at a distance of 0.01, 0.05, 0.1, 0.2, 0.3, 0.4, 0.5, 1.0, 1.5, 2.0, 2.5, 3.0, 3.5 mm or any other distance to the at least one anatomic structure of the physical joint, the surface of the physical joint, and/or the articular surface of the physical joint. The superimposition and/or alignment can be at an angle of 0.01, 0.05, 0.1, 0.2, 0.3, 0.4, 0.5, 1.0, 1.5, 2.0, 2.5, 3.0, 3.5 degrees or any other angle to the at least one anatomic structure of the physical joint, the surface of the physical joint, and/or the articular surface of the physical joint.

In some embodiments, at least one computer can be configured to display, by one or more optical head mounted displays, one or more of a normal motion, an abnormal motion, a pathologic motion, or an instability of a first virtual implant component, a second virtual implant component or a combination thereof or a motion conflict between a first virtual implant component and a second virtual implant component superimposed onto, over, subjacent, tangent with, intersecting or combinations thereof of the physical joint of the patient, e.g. at select pose angles of the knee, for example different angles of extension or flexion, or when the physical joint of the patient moves, e.g. during a range of motion, range of motion testing, and/or stress testing, e.g. varus stress, valgus stress, Lachman testing, instability testing, abduction stress, adduction stress, hyperflexion stress and/or hyperextension stress, or any other stress test known in the art, or any combination thereof.

In some embodiments, at least one computer can be configured to display, by one or more optical head mounted displays, one or more of a normal motion, an abnormal motion, a pathologic motion, or an instability of a first virtual implant component, a second virtual implant component or a combination thereof or a motion conflict between a first virtual implant component and a second virtual implant component, e.g. at select pose angles of the knee, for example different angles of extension or flexion, or when the physical joint of the patient moves, e.g. during a range of motion, range of motion testing, and/or stress testing, e.g. varus stress, valgus stress, Lachman testing, instability testing, abduction stress, adduction stress, hyperflexion stress and/or hyperextension stress, or any other stress test known in the art, or any combination thereof.

In some embodiments, the at least on computer can be the same or different computers. In some embodiments, the at least one computer can comprise one or more processors.

A motion conflict can be, for example, a first virtual component, e.g. a femoral virtual component, overlapping, interfering with or diving into a second virtual component, e.g. a tibial virtual component, e.g. by 0.5, 1.0, 1.5, 2.0, 2.5, 3.0, 3.5 or more mm at select angles of flexion or extension, e.g. −10, −5, 0, 5, 10, 15, 20, 25, 30, 35, 40, 50, 60, 70, 80, 90, 100, 110, 120, 130, 140, 150 degrees of flexion, e.g. in the medial compartment and/or the lateral compartment of the knee. A motion conflict can be, for example, a first virtual component, e.g. a patellar virtual component, overlapping, interfering with or diving into a second virtual component, e.g. a femoral virtual component, e.g. by 0.5, 1.0, 1.5, 2.0, 2.5, 3.0, 3.5 or more mm at select angles of flexion or extension, e.g. −10, −5, 0, 5, 10, 15, 20, 25, 30, 35, 40, 50, 60, 70, 80, 90, 100, 110, 120, 130, 140, 150 degrees of flexion. A motion conflict can be, for example, a first virtual component, e.g. a femoral virtual component, overlapping, interfering with or diving into a second virtual component, e.g. an acetabular virtual component, e.g. by 0.5, 1.0, 1.5, 2.0, 2.5, 3.0, 3.5 or more mm at select angles of flexion or extension, abduction or adduction, e.g. −10, −5, 0, 5, 10, 15, 20, 25, 30, 35, 40, 50, 60, 70, 80, 90, 100, 110, 120, 130, 140, 150 degrees. A motion conflict can be, for example, a first virtual component, e.g. a humeral virtual component, overlapping, interfering with or diving into a second virtual component, e.g. a glenoid virtual component, e.g. by 0.5, 1.0, 1.5, 2.0, 2.5, 3.0, 3.5 or more mm at select angles of flexion or extension, abduction or adduction, or elevation, e.g. −10, −5, 0, 5, 10, 15, 20, 25, 30, 35, 40, 50, 60, 70, 80, 90, 100, 110, 120, 130, 140, 150 degrees.

The motion conflict, e.g. overlapping or interfering can also be measured in volume of overlap between the first and the second virtual component for any of these angles, or as average volume of overlap through a range of motion, e.g. from 0-90 degrees, 0-100 degrees, 0-110 degrees, 0-120 degrees or any other value of flexion or extension. By detecting such a motion conflict between a first virtual implant component and a second virtual implant component, the position, orientation, varus/valgus correction, rotation, resection level, position relative to an anterior cortex (e.g. in a knee femoral component), position relative to a trochlear sulcus, position relative to a cortical rim (e.g. in a knee tibial component), anteversion, offset, inclination, medialization of lateralization, neck resection level (e.g. in an acetabular component or a femoral component in a hip replacement) of the first and/or second virtual implant component can be changed by the at least one computer in the display by the optical head mounted display to correct, at least partially or completely, reduce or resolve the motion conflict. The resultant change in coordinates of the first and/or second virtual implant component in the coordinate system can be used to determine the coordinates of a bone removal for the placement of a physical implant, e.g. the coordinates of a bone cut, a bone drilling, pinning, burring, milling, reaming, or impacting.

An abnormal motion or a pathologic motion can be, for example, a distance traveled or a distance moved, and/or an angular displacement or an angular movement, and/or a translation, and/or a rotation by a first virtual component, e.g. a femoral virtual component, a second virtual component, e.g. a tibial or patellar virtual component, or combinations thereof, or a distance traveled or a distance moved, and/or an angular displacement or an angular movement, and/or a translation, and/or a rotation between a first virtual component and a second virtual component exceeding a certain value, e.g. a threshold value, e.g. by 0.5, 1.0, 1.5, 2.0, 2.5, 3.0, 3.5 or more mm or any other value (e.g. for distance and/or translation) or by 0.5, 1.0, 1.5, 2.0, 2.5, 3.0, 3.5, 5.0, 7.5, 10.0 or more degrees or any other value (e.g. for angular displacement, angular movement and/or rotation), e.g. at select angles of flexion or extension, e.g. −10, −5, 0, 5, 10, 15, 20, 25, 30, 35, 40, 50, 60, 70, 80, 90, 100, 110, 120, 130, 140, 150 degrees of flexion or any other value, or select forces applied, e.g. 1 N, 2 N, 5 N, 10 N, 50 N, 100 N, 500 N, 1000 N or any other value.

By detecting an abnormal motion or a pathologic motion of a first virtual implant component, a second virtual implant component or combinations thereof or between a first and a second virtual implant component, the position, orientation, varus/valgus correction, rotation, resection level, position relative to an anterior cortex (e.g. in a knee femoral component), position relative to a trochlear sulcus, position relative to a cortical rim (e.g. in a knee tibial component), anteversion, offset, inclination, medialization of lateralization, neck resection level (e.g. in an acetabular component or a femoral component in a hip replacement) of the first and/or second virtual implant component can be changed by the at least one computer in the display by the optical head mounted display to correct, at least partially or completely, reduce or resolve the abnormal motion or pathologic motion. The resultant change in coordinates of the first and/or second virtual implant component in the coordinate system can be used to determine the coordinates of a bone removal for the placement of a physical implant, e.g. the coordinates of a bone cut, a bone drilling, pinning, burring, milling, reaming, or impacting.

An instability or a laxity can be, for example, a distance between a first virtual component, e.g. a femoral virtual component, and a second virtual component, e.g. a tibial virtual component exceeding a certain value, e.g. a threshold value, which can be, for example, 0.5, 1.0, 1.5, 2.0, 2.5, 3.0, 3.5 or more mm or any other value at select angles of flexion or extension, e.g. −10, −5, 0, 5, 10, 15, 20, 25, 30, 35, 40, 50, 60, 70, 80, 90, 100, 110, 120, 130, 140, 150 degrees of flexion or extension. An instability or laxity can be, for example, a distance traveled or a distance moved, and/or an angular displacement or an angular movement, and/or a translation, and/or a rotation by a first virtual component, e.g. a femoral virtual component, a second virtual component, e.g. a tibial or patellar virtual component, or combinations thereof, or a distance traveled or a distance moved, and/or an angular displacement or an angular movement, and/or a translation, and/or a rotation between a first virtual component and a second virtual component exceeding a certain value, e.g. a threshold value, e.g. by 0.5, 1.0, 1.5, 2.0, 2.5, 3.0, 3.5 or more mm or any other value (e.g. for distance and/or translation) or by 0.5, 1.0, 1.5, 2.0, 2.5, 3.0, 3.5, 5.0, 7.5, 10.0 or more degrees or any other value (e.g. for angular displacement, angular movement and/or rotation), e.g. at select angles of flexion or extension, e.g. −10, −5, 0, 5, 10, 15, 20, 25, 30, 35, 40, 50, 60, 70, 80, 90, 100, 110, 120, 130, 140, 150 degrees of flexion or any other value, or select forces applied, e.g. 1 N, 2 N, 5 N, 10 N, 50 N, 100 N, 500 N, 1000 N or any other value.

By detecting an instability or a laxity motion of a first virtual implant component, a second virtual implant component or combinations thereof or between a first and a second virtual implant component, the position, orientation, varus/valgus correction, rotation, resection level, position relative to an anterior cortex (e.g. in a knee femoral component), position relative to a trochlear sulcus, position relative to a cortical rim (e.g. in a knee tibial component), anteversion, offset, inclination, medialization of lateralization, neck resection level (e.g. in an acetabular component or a femoral component in a hip replacement) of the first and/or second virtual implant component can be changed by the at least one computer in the display by the optical head mounted display to correct, at least partially or completely, reduce or resolve the abnormal motion or pathologic motion. The resultant change in coordinates of the first and/or second virtual implant component in the coordinate system can be used to determine the coordinates of a bone removal for the placement of a physical implant, e.g. the coordinates of a bone cut, a bone drilling, pinning, burring, milling, reaming, or impacting.

The correcting, at least partially or completely, reducing or resolving of at least one of a motion conflict, an abnormal or pathologic motion, or an instability or laxity in any of the foregoing or following embodiments can be by 0.1, 0.2, 0.4, 0.4, 0.5, 1.0, 1.5, 2.0, 2.5, 3.0, 3.5 or more mm or any other value (e.g. for distance and/or translation) or by 0.5, 1.0, 1.5, 2.0, 2.5, 3.0, 3.5, 5.0, 7.5, 10.0 or more degrees or any other value (e.g. for angular displacement, angular movement and/or rotation), e.g. at select angles of flexion or extension, e.g. −10, −5, 0, 5, 10, 15, 20, 25, 30, 35, 40, 50, 60, 70, 80, 90, 100, 110, 120, 130, 140, 150 degrees of flexion or any other value, or select forces applied, e.g. 1 N, 2 N, 5 N, 10 N, 50 N, 100 N, 500 N, 1000 N or any other value.

An instability or a laxity can be, for example, a distance, a translation, an angular displacement, a rotation between a first virtual component, e.g. a femoral virtual component, and a second virtual component, e.g. a tibial or patellar virtual component, exceeding a certain value, e.g. a threshold value, e.g. by 0.5, 1.0, 1.5, 2.0, 2.5, 3.0, 3.5 or more mm or any other value or by 0.5, 1.0, 1.5, 2.0, 2.5, 3.0, 3.5, 5.0, 7.5, 10.0 or more degrees or any other value at select angles of flexion or extension, e.g. −10, −5, 0, 5, 10, 15, 20, 25, 30, 35, 40, 50, 60, 70, 80, 90, 100, 110, 120, 130, 140, 150 degrees or any other value of flexion, e.g. in the medial compartment and/or the lateral compartment of the knee. The threshold value can be different for different compartments, e.g. a medial compartment of the knee (e.g. 0.5, 1.0, 1.5 mm or any other value or 0.5, 1.0, 1.5 degrees or any other value) and a lateral compartment of the knee (e.g. 1.0, 1.5, 2.0, 2.5, 3.0 mm or any other value or 0.5, 1.0, 1.5 degrees or any other value).

An instability or a laxity can be, for example, a distance between a first virtual component, e.g. a femoral virtual component, and a second virtual component, e.g. a tibial virtual component exceeding a certain value, e.g. a threshold value, which can be, for example, 0.5, 1.0, 1.5, 2.0, 2.5, 3.0, 3.5 or more mm at select angles of flexion or extension, e.g. −10, −5, 0, 5, 10, 15, 20, 25, 30, 35, 40, 50, 60, 70, 80, 90, 100, 110, 120, 130, 140, 150 degrees of flexion or extension. An instability or a laxity can be, for example, a distance between a first virtual component, e.g. a femoral virtual component in a hip replacement, and a second virtual component, e.g. an acetabular virtual component, exceeding a certain value, e.g. a threshold value, which can be, for example, 0.1, 0.2, 0.3, 0.4, 0.5, 1.0, 1.5, or more mm at select angles of flexion or extension, abduction or adduction, e.g. −10, −5, 0, 5, 10, 15, 20, 25, 30, 35, 40, 50, 60, 70, 80, 90, 100, 110, 120, 130, 140, 150 degrees. An instability or a laxity can be, for example, a distance between a first virtual component, e.g. a humeral virtual component in a shoulder replacement, and a second virtual component, e.g. a glenoid virtual component, exceeding a certain value, e.g. a threshold value, which can be, for example, 0.2, 0.3, 0.4, 0.5, 1.0, 1.5, 2.0, 2.5, 3.0, or more mm at select angles of flexion or extension, abduction or adduction, or elevation, e.g. −10, −5, 0, 5, 10, 15, 20, 25, 30, 35, 40, 50, 60, 70, 80, 90, 100, 110, 120, 130, 140, 150 degrees.

The instability or laxity can also be measured in volume, e.g. interposed or located, between the first and the second virtual component for any of these angles. The instability or laxity can also be measured as an average volume, e.g. interposed or located, between the first and the second virtual component for a range of motion, e.g. from 0-90 degrees, from 0-100 degrees, from 0-120 degrees of flexion, or any other range of values. By detecting an instability or laxity between a first virtual implant component and a second virtual implant component, the position, orientation, varus/valgus correction, rotation, resection level, position relative to an anterior cortex (e.g. in a knee femoral component), position relative to a trochlear sulcus, position relative to a cortical rim (e.g. in a knee tibial component), anteversion, offset, inclination, medialization of lateralization, neck resection level (e.g. in an acetabular component or a femoral component in a hip replacement) of the first and/or second virtual implant component can be changed by the at least one computer in the display by the optical head mounted display to correct, at least partially or completely, reduce or resolve the instability or laxity. The resultant change in coordinates of the first and/or second virtual implant component in the coordinate system can be used to determine the coordinates of a bone removal for the placement of a physical implant, e.g. the coordinates of a bone cut, a bone drilling, pinning, burring, milling, reaming, or impacting (for example the depth of an acetabular or glenoid reaming or the neck resection level of a femur or humerus). In some embodiments, at least one computer can be configured to display, by the at least one optical head mounted display, at least a portion of a virtual implant onto the surface of the physical joint, e.g. onto a cartilage surface, a subchondral bone surface, an articular surface, a cortical bone surface. In some embodiments, at least one computer can be configured to display, by the at least one optical head mounted display, at least a portion of a virtual implant over the surface of the physical joint, e.g. over a cartilage surface, a subchondral bone surface, an articular surface, a cortical bone surface. At least one computer can be configured to display, by the at least one optical head mounted display, at least a portion of a virtual implant subjacent to the surface of the physical joint, e.g. subjacent to a cartilage surface, a subchondral bone surface, an articular surface, a cortical bone surface. At least one computer can be configured to display, by the at least one optical head mounted display, at least a portion of a virtual implant tangent with and/or intersecting the surface of the physical joint, e.g. tangent with and/or intersecting a cartilage surface, a subchondral bone surface, an articular surface, a cortical bone surface.

At least one computer can be configured to display, by the at least one optical head mounted display, at least a portion of a virtual implant component(s) over the surface, onto the surface, subjacent to the surface, tangent with and/or intersecting the surface or combinations thereof of the physical joint, e.g. onto a cartilage surface, a subchondral bone surface, an articular surface, a cortical bone surface.

In some embodiments, at least one computer can be configured to modify the position and/or orientation of the display of a first virtual implant component relative to a first articular surface, the position and/or orientation of the display of a second virtual implant component relative to a second articular surface, or a combination thereof to correct an abnormal motion, pathologic motion, or instability or motion conflict.

In some embodiments, at least one computer can be configured to change the alignment of the display of a first virtual implant component relative to a first articular surface, the alignment of the display of a second virtual implant component relative to a second articular surface, or a combination thereof to correct an abnormal motion, pathologic motion, or instability or the motion conflict, e.g. by changing, moving, or adjusting the coordinates of the first and/or second virtual implant component, e.g. by changing, moving or adjusting one or more coordinates superiorly, inferiorly, medially, laterally, anteriorly or posteriorly or in one or more oblique directions. Any bone removal contemplated for the placement of the first and/or second physical implant component can be corrected and/or adjusted correspondingly, e.g. by changing, moving, or adjusting the coordinates of the bone removal, e.g. a bone cut or a drilling, pinning, reaming, milling, or impacting of the bone.

The at least one computer can display the first virtual implant component and the second virtual implant component by the at least one optical head mounted display at select pose angles of the knee, for example different angles of extension or flexion, or when the physical joint of the patient moves, e.g. during a range of motion, range of motion testing, and/or stress testing, e.g. varus stress, valgus stress, Lachman testing, instability testing, abduction stress, adduction stress, hyperflexion stress and/or hyperextension stress, or any other stress test known in the art, or any combination thereof. The at least one computer can be configured so as to display the first virtual implant component and/or the second virtual implant component by the at least one optical head mounted display at select pose angles of the knee, for example different angles of extension or flexion, or when the physical joint of the patient moves, e.g. during a range of motion, range of motion testing, and/or stress testing, e.g. varus stress, valgus stress, Lachman testing, instability testing, abduction stress, adduction stress, hyperflexion stress and/or hyperextension stress, or any other stress test known in the art, or any combination thereof. In any of the embodiments, the one or more see through optical head mounted display can be registered in a coordinate system. In any of the embodiments, the first virtual implant component, the second virtual implant component or a combination thereof can be registered in the coordinate system.

In some of the embodiments, at least one computer can configured to display, by the optical head mounted display, a first virtual implant component onto a first articular surface, a second virtual implant component onto a second articular surface, or a combination thereof, at a predetermined position, predetermined orientation, predetermined rotation, predetermined alignment, predetermined varus correction, predetermined valgus correction, predetermined resection level, predetermined flexion, predetermined slope, predetermined version, predetermined anteversion, predetermined inclination, predetermined offset, predetermined leg length, predetermined sagittal plane alignment, predetermined coronal plane alignment, predetermined axial plane alignment or combination thereof. The predetermined position, predetermined orientation, predetermined rotation, predetermined alignment, predetermined varus correction, predetermined valgus correction, predetermined resection level, predetermined flexion, predetermined slope, predetermined version, predetermined anteversion, predetermined inclination, predetermined offset, predetermined leg length, predetermined sagittal plane alignment, predetermined coronal plane alignment, predetermined axial plane alignment or combination thereof can be from a virtual surgical plan, which can be generated pre-operatively, e.g. using one or more pre-operative imaging studies, or intra-operatively, e.g. by obtaining one or more measurements from the physical joint of the patient, e.g. coordinate measurements and/or a surface painting. The predetermined position, predetermined orientation, predetermined rotation, predetermined alignment of a virtual femoral component can include a position, orientation, rotation and/or alignment relative to a trochlear sulcus or a trochlear sulcus line of the physical joint of a patient. In some of the embodiments, the first virtual implant component, the second virtual implant component, or a combination thereof can have at least one of a predetermined rotation axis, a predetermined flexion axis, a predetermined extension axis, a predetermined adduction axis, a predetermined abduction axis, a predetermined direction of translation. In some of the embodiments, at least one computer can be configured to facilitate modification of the a predetermined position, predetermined orientation, predetermined rotation, predetermined alignment, predetermined varus correction, predetermined valgus correction, predetermined resection level, predetermined flexion, predetermined slope, predetermined version, predetermined anteversion, predetermined inclination, predetermined offset, predetermined leg length, predetermined sagittal plane alignment, predetermined coronal plane alignment, predetermined axial plane alignment or combination thereof of the first virtual implant component, the second virtual implant component or a combination thereof to account for ligamentous laxity or instability.

In some embodiments, the predetermined position, predetermined orientation, predetermined rotation, predetermined alignment, predetermined varus correction, predetermined valgus correction, predetermined resection level, predetermined flexion, predetermined slope, predetermined version, predetermined anteversion, predetermined inclination, predetermined offset, predetermined leg length, predetermined sagittal plane alignment, predetermined coronal plane alignment, predetermined axial plane alignment or combination thereof of the first virtual implant component, the second virtual implant component, or a combination thereof, can comprise a predetermined varus correction, a predetermined valgus correction, a predetermined femoral component flexion, a predetermined femoral component extension, a predetermined femoral component rotation, a predetermined femoral component position relative to an anterior cortex, a predetermined tibial component slope, a predetermined tibial component rotation, a predetermined tibial component position relative to a tibial cortical rim in a knee replacement.

In some embodiments, the predetermined position, predetermined orientation, predetermined rotation, predetermined alignment, predetermined varus correction, predetermined valgus correction, predetermined resection level, predetermined flexion, predetermined slope, predetermined version, predetermined anteversion, predetermined inclination, predetermined offset, predetermined leg length, predetermined sagittal plane alignment, predetermined coronal plane alignment, predetermined axial plane alignment or combination thereof of the first virtual implant component, the second virtual implant component, or a combination thereof, can comprise a predetermined femoral neck resection for a femoral component, a predetermined leg length, a predetermined femoral component anteversion, a predetermined acetabular component anteversion, a predetermined acetabular component inclination, a predetermined acetabular component offset in a hip replacement.

In some embodiments, at least one computer can be configured to select a first virtual implant component, a second virtual implant component, or a combination thereof, from a library of virtual implants.

In some embodiments, a library of virtual implant components can be composed of virtual implant components of different sizes and/or shapes, wherein each virtual implant component of the library can be a three-dimensional digital representation corresponding to at least one portion of a corresponding physical implant component, a placement indicator of a corresponding physical implant component, a physical trial implant component, a placement indicator of a corresponding physical trial implant component, or a combination thereof.

In some embodiments, different sizes and/or shapes of the virtual implant components can be color coded, e.g. red, green brown, blue, gold, etc.

In some embodiments, at least one computer system can be configured to adjust a transparency of the first virtual implant component, a second virtual implant component, or combination thereof, and wherein at least one portion of the physical joint can be visible through the first virtual implant component, second virtual implant component, or combination thereof.

In some embodiments, at least one computer can be configured to display a first and a second virtual implant component with a different color. In some embodiments, at least one computer can be configured to display a first and a second virtual implant component with a different degree of transparency.

In some embodiments, at least one computer can be configured to display a first virtual implant component, a second virtual implant component, or combination thereof, in a predetermined position, a predetermined orientation, a predetermined alignment or a combination thereof relative to at least one of an anatomic axis, a biomechanical axis, or a deformity, e.g. a varus or valgus deformity, a torsion deformity, a genu recurvatum, a genu antecurvatum or any other deformity.

In some embodiments, at least one computer can be configured to display a first virtual implant component, a second virtual implant component, or a combination thereof, with at least one of a predetermined resection level, a predetermined varus angle, a predetermined valgus angle, a predetermined rotation, a predetermined flexion, a predetermined slope, a predetermined alignment or a combination thereof.

In some embodiments, at least one computer can be configured to facilitate changing the position or orientation of the display of a first virtual implant component, a second virtual implant component, or combination thereof, relative to a predetermined position, predetermined orientation, predetermined rotation, predetermined alignment, predetermined varus correction, predetermined valgus correction, predetermined resection level, predetermined flexion, predetermined slope, predetermined version, predetermined anteversion, predetermined inclination, predetermined offset, predetermined leg length, predetermined sagittal plane alignment, predetermined coronal plane alignment, predetermined axial plane alignment or combination thereof.

In some embodiments, a user interface can be used and at least one computer can be configured to facilitate moving a first virtual implant component in relationship to a first articular surface, a second virtual implant component in relationship to a second articular surface or a combination thereof by the user interface.

In some embodiments, a user interface can be used and at least one computer can be configured to facilitate moving a first virtual implant component in relationship to a first surface of the physical joint, a second virtual implant component in relationship to a second surface of the physical joint or a combination thereof by the user interface.

In some embodiments, a user interface can be used and at least one computer can be configured to facilitate moving a first virtual implant component in relationship to a first anatomic structure, a second virtual implant component in relationship to a second anatomic structure or a combination thereof by the user interface.

In some embodiments, a user interface can comprise at least one of a graphical user interface, a voice recognition, a gesture recognition, a virtual interface displayed by the optical head mounted display, a virtual keyboard displayed by the optical head mounted display, a physical keyboard, a physical computer mouse, or a physical track pad.

In some embodiments, a first virtual implant component, a second virtual implant component, or combination thereof can be a virtual trial implant. In some embodiments, a virtual trial implant can be a three-dimensional representation of at least a portion of a physical trial implant, a placement indication of at least a portion of a physical trial implant, or a combination thereof. In some embodiments, a first virtual trial implant component, a second virtual trial implant component, or a combination thereof can comprise at least one of a virtual trial femoral component, a virtual trial tibial component, a virtual trial tibial insert, a virtual trial patellar component.

In some embodiments, at least one computer can be configured to display, by the optical head mounted display, the position, orientation, alignment, flexion gap, extension gap, or combinations thereof, of a first virtual component, a second virtual component, or a combination thereof, in flexion, extension or through a range of motion. The flexion gap and/or extension gap between a first virtual component, e.g. a virtual femoral component, and a second virtual component, e.g. a virtual tibial component, can be displayed, by the one or more optical head mounted displays, for different angles of extension and/or flexion, e.g. −15, −10, −5, 0, 5, 10, 15, 20, 25, 30, 35, 40, 45, 50, 70, 80, 90, 100, 110, 120, 130, 140, 150 degrees or any other value. The flexion gap and/or extension gap between a first virtual component, e.g. a virtual femoral component, and a second virtual component, e.g. a virtual tibial component, can be displayed, by the one or more optical head mounted displays, for a range of motion, e.g. 0-90, 0-100, 0-110, 0-120, 0-130, 0-140, 0-150 degrees or any other value. The flexion gap and/or extension gap between a first virtual component, e.g. a virtual femoral component, and a second virtual component, e.g. a virtual tibial component, can be displayed, by the one or more optical head mounted displays, visually, e.g. as the distance and/or space or volume between the first virtual component and the second virtual component, e.g. separately in a medial and/or a lateral compartment of a knee joint. The flexion gap and/or extension gap between a first virtual component, e.g. a virtual femoral component, and a second virtual component, e.g. a virtual tibial component, can be displayed, by the one or more optical head mounted displays, numerically, e.g. as distance and/or the space or volume between the first virtual component and the second virtual component, e.g. separately in a medial and/or a lateral compartment of a knee joint, e.g. in mm$^3$ or cc. The flexion gap and/or extension gap between a first virtual component, e.g. a virtual femoral component, and a second virtual component, e.g. a virtual tibial component, can be displayed, by the one or more optical head mounted displays, numerically, e.g. as minimum distance between the first virtual component and the second virtual component, e.g. separately in a medial and/or a lateral compartment of a knee joint, e.g. in mm. The flexion gap and/or extension gap between a first virtual component, e.g. a virtual femoral component, and a second virtual component, e.g. a virtual tibial component, can be determined for a medial flexion gap, a lateral flexion gap, a medial extension gap, a lateral extension gap, for example, by determining a minimum distance. The minimum distance between two non-intersecting surfaces $S_1$ and $S_2$ can be determined, for example, by using the following approach; determining multiple discrete sampling points on each surface; calculating distances between each discrete point on surface $S_1$ to each point on surface $S_2$ and determining a pair of closest sampling points $(p_1, p_2)$, e.g. using a nearest neighbor search. Such measurements can optionally be refined as follows: Using $p_1$ as a seed, determining a new closest $p_2$ point on $S_2$ as intersection between $S_2$ and a line extending perpendicular to $S_1$ in $p_1$, repeating for $p_2$ and $S_1$, iterating for fixed number of iterations or until convergence. The volume of the space between two or more surfaces can be determined, for example, as follows: by dividing the space into sub-volumes, e.g. cubes, of fixed known size and counting the number of sub-volumes inside the space and multiplying by the size of the sub-volume.

It is understood that any of the displays, e.g. visual, numeric distance, numeric volume, distance line, distance bar chart, volume line, volume bar chart or any other displays can be generated for any static joint pose and any dynamic joint motion, e.g. for different angles of extension and/or flexion, e.g. −15, −10, −5, 0, 5, 10, 15, 20, 25, 30, 35, 40, 45, 50, 70, 80, 90, 100, 110, 120, 130, 140, 150 degrees or any other value, and for any range of motion e.g. 0-90, 0-100, 0-110, 0-120, 0-130, 0-140, 0-150 degrees or any other value.

In some embodiments, at least one computer system can be configured to superimpose, by the optical head mounted display, a first virtual implant component onto a corresponding first physical implant component after implantation and/or a second virtual implant component onto a corresponding second physical implant component after implantation, wherein the display of the first virtual implant component can be configured to compare the position and/or orientation of the corresponding first physical implant component with the position and/or orientation of the display of the first virtual implant component and wherein the display of the second virtual implant component can be configured to compare the position and/or orientation of the corresponding second physical implant component with the position and/or orientation of the display of the second virtual implant component.

In some embodiments, at least one computer can be configured to adjust the position, location, orientation, alignment and/or coordinates of the display of a first virtual implant component, a second virtual implant component, or combination thereof, by the optical head mounted display, to correct one or more of an abnormal motion, a pathologic motion, an instability of a first and/or second virtual implant component or motion conflict between a first virtual implant component and a second virtual implant component.

In some embodiments, at least one computer can be configured to display during stress testing of the joint one or more of a normal motion, an abnormal motion, a pathologic motion, an instability of a first and/or second virtual implant component or a motion conflict between a first virtual implant component and a second virtual implant component.

In some embodiments, the stress testing can comprise a varus stress, a valgus stress, a Lachman test, an instability test, an abduction stress, an adduction stress, a hyperflexion stress test, a hyperextension stress test or combinations thereof.

In some embodiments, at least one computer can use a kinematic simulation. The kinematic simulation can comprise kinematic data obtained from the physical joint of the patient.

In some embodiments, at least one computer can be configured to obtain one or more intra-operative measurements from the physical joint of the patient to determine one or more coordinates of the physical joint.

At least one computer can be configured to display, by the at least one optical head mounted display, the position and/or orientation and/or alignment and/or coordinates of the virtually placed, sized, fitted, selected and/or aligned virtual implant component(s) onto the surface of the physical joint, e.g. onto a cartilage surface, a subchondral bone surface, an articular surface, a cortical bone surface.

The position and/or orientation and/or alignment and/or coordinates of a virtually placed, sized, fitted, selected and/or aligned first virtual component, e.g. a virtual femoral component, and/or a virtually placed, sized, fitted, selected and/or aligned second virtual component, e.g. a virtual tibial implant component, can be modified, by at least one computer, to achieve a predetermined or desired distance or volume between the articular surface(s), e.g. the articular surface of the medial condyle of the virtual femoral component and the physical medial tibial plateau or the medial surface of the virtual tibial component of 1, 2, 3, 4 mm or any other distance or 3, 4, 5, 6, 7, 8, 9, 10 cc or any other volume selected by the computer processor or the surgeon with a user interface, through the range of motion or for different angles of flexion, extension and/or rotation.

The position and/or orientation and/or alignment and/or coordinates of a virtually placed, sized, fitted, selected and/or aligned first virtual component, e.g. a virtual femoral component, and/or a virtually placed, sized, fitted, selected and/or aligned second virtual component, e.g. a virtual tibial implant component, can be modified, by at least one computer, to achieve a predetermined or desired distance or volume between the articular surface(s), e.g. the articular surface of the medial plateau of the virtual tibial component and the physical medial femoral condyle or the medial condyle of the virtual femoral component of 1, 2, 3, 4 mm or any other distance or 3, 4, 5, 6, 7, 8, 9, 10 cc or any other volume selected by the computer processor or the surgeon with a user interface, through the range of motion or for different angles of flexion, extension and/or rotation.

The position and/or orientation and/or alignment and/or coordinates of a virtually placed, sized, fitted, selected and/or aligned first virtual component, e.g. a virtual femoral component, and/or a virtually placed, sized, fitted, selected and/or aligned second virtual component, e.g. a virtual tibial implant component, can be modified, by at least one computer, to achieve a predetermined or desired distance or volume between the articular surface(s), e.g. the articular surface of the lateral condyle of the virtual femoral component and the physical lateral tibial plateau or the lateral surface of the virtual tibial component of 1, 2, 3, 4 mm or any other distance or 3, 4, 5, 6, 7, 8, 9, 10 cc or any other volume selected by the computer processor or the surgeon with a user interface, through the range of motion or for different angles of flexion, extension and/or rotation.

The position and/or orientation and/or alignment and/or coordinates of a virtually placed, sized, fitted, selected and/or aligned first virtual component, e.g. a virtual femoral component, and/or a virtually placed, sized, fitted, selected and/or aligned second virtual component, e.g. a virtual tibial implant component, can be modified, by at least one computer, to achieve a predetermined or desired distance or volume between the articular surface(s), e.g. the articular surface of the lateral plateau of the virtual tibial component and the physical lateral femoral condyle or the lateral condyle of the virtual femoral component of 1, 2, 3, 4 mm or any other distance or 3, 4, 5, 6, 7, 8, 9, 10 cc or any other volume selected by the computer processor or the surgeon with a user interface, through the range of motion or for different angles of flexion, extension and/or rotation.

The distance between the medial and the lateral articular surfaces of the virtual femoral and tibial implant components can be the same or can be different through the range of motion, for different angles of flexion, extension and/or rotation.

The modified position, location, orientation, alignment and/or coordinates of the one or more virtual implant components, e.g. the virtual femoral or virtual tibial component, can then be used to determine and/or modify a virtual surgical plan and/or to determine and/or modify the position and/or orientation and/or coordinates of a virtual surgical guide (e.g. a virtual cut block, virtual axis, virtual plane) and/or to determine and/or modify the position and/or orientation and/or coordinates of a virtual surgical instrument or tool, and/or to determine and/or modify one or more bone resections [e.g. a bone cut, a drilling, pinning, reaming, milling, broaching or impacting] for placing the physical implant component(s). Someone skilled in the art can recognize that this form of virtual gap balancing can result in intra-operative time savings, for example, by reducing the number of trial implants and stress tests in the physical joint of the patient and by reducing the need for bone recuts or ligament releases.

In some embodiments, one or more optical head mounted displays can display one or more of a virtual loading pattern, load line, contact line, contact force, articular surface force, moment, vector, load conditions of various implant components, e.g. for different movements [e.g. flexion, extension, rotation, rollback, adduction, abduction], constraints, medial femoral rollback during flexion, e.g. of hidden portions of the femoral condyle or of the virtual implant component, lateral femoral rollback during flexion, e.g. of hidden portions of the femoral condyle or of the virtual implant component, patellar position, medial, superior, inferior for different flexion and/or extension angles, patellar tracking, internal/external rotation of one or both femoral condyles, e.g. of hidden portions of the femoral condyle or of the virtual implant component internal/external rotation of a tibia, e.g. of hidden portions of the tibia, rotation axis of a femur, rotation axis of a tibia, rotation axis of a first articular side, rotation axis of a second, e.g. opposing, articular side, rotation axis of a bone, tibial and/or femoral abduction, tibial and/or femoral adduction, transepicondylar axis, Whiteside's line, posterior condylar axis, sulcus line, depth of sulcus line, flexion and extension angles of one or more articular surfaces, anterior/posterior slide of one or both femoral condyles during flexion or extension, e.g. of hidden portions of the femoral condyle or of the virtual implant component, medial and/or lateral laxity of a joint, e.g. during motion or stress testing, anterior and/or posterior laxity of a joint, e.g. during motion or stress testing [e.g. varus stress or valgus stress], e.g. in the form of a vector or distance indicator, contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles, e.g. in the form of a vector or distance indicator, superimposed onto and/or aligned with a joint, e.g. corresponding portions of a joint, for example an articular surface, e.g. a femoral articular surface and/or a tibial articular surface or superimposed onto and/or aligned with the space between the femoral articular surface and the tibial articular surface. The display of the virtual loading pattern, load line, contact line, contact force, articular surface force, moment, vector, load conditions of various implant components, e.g. for different movements [e.g. flexion, extension, rotation, rollback, adduction, abduction], constraints, medial femoral rollback during flexion, e.g. of hidden portions of the femoral condyle or of the virtual implant component, lateral femoral rollback during flexion, e.g. of hidden portions of the femoral condyle or of the virtual implant component, patellar position, medial, superior, inferior for different flexion and/or extension angles, patellar tracking, internal/external rotation of one or both femoral condyles, e.g. of hidden portions of the femoral condyle or of the virtual implant component internal/external rotation of a tibia, e.g. of hidden portions of the tibia, rotation axis of a femur, rotation axis of a tibia, rotation axis of a first articular side, rotation axis of a second, e.g. opposing, articular side, rotation axis of a bone, tibial and/or femoral abduction, tibial and/or femoral adduction, transepicondylar axis, Whiteside's line, posterior condylar axis, sulcus line, depth of sulcus line, flexion and extension angles of one or more articular surfaces, anterior/posterior slide of one or both femoral condyles during flexion or extension, e.g. of hidden portions of the femoral condyle or of the virtual implant component, medial and/or lateral laxity of a joint, e.g. during motion or stress testing, anterior and/or posterior laxity of a joint, e.g. during motion or stress testing [e.g. varus stress or valgus stress], e.g. in the form of a vector or distance indicator, contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles, e.g. in the form of a vector or distance indicator, superimposed onto and/or aligned with a joint, e.g. corresponding portions of a joint, for example an articular surface, e.g. a femoral articular surface and/or a tibial articular surface or superimposed onto and/or aligned with the space between the femoral articular surface and the tibial articular surface can be maintained superimposed and/or aligned with the joint, e.g. corresponding portions of the joint, for example with movement of the joint and/or with movement of a physical implant and/or instrument. The OHMD display of the virtual loading pattern, load line, contact line, contact force, articular surface force, moment, vector, load conditions of various implant components, e.g. for different movements [e.g. flexion, extension, rotation, rollback, adduction, abduction], constraints, medial femoral rollback during flexion, e.g. of hidden portions of the femoral condyle or of the virtual implant component, lateral femoral rollback during flexion, e.g. of hidden portions of the femoral condyle or of the virtual implant component, patellar position, medial, superior, inferior for different flexion and/or extension angles, patellar tracking, internal/external rotation of one or both femoral condyles, e.g. of hidden portions of the femoral condyle or of the virtual implant component internal/external rotation of a tibia, e.g. of hidden portions of the tibia, rotation axis of a femur, rotation axis of a tibia, rotation axis of a first articular side, rotation axis of a second, e.g. opposing, articular side, rotation axis of a bone, tibial and/or femoral abduction, tibial and/or femoral adduction, transepicondylar axis, Whiteside's line, posterior condylar axis, sulcus line, depth of sulcus line, flexion and extension angles of one or more articular surfaces, anterior/posterior slide of one or both femoral condyles during flexion or extension, e.g. of hidden portions of the femoral condyle or of the virtual implant component, medial and/or lateral laxity of a joint, e.g. during motion or stress testing, anterior and/or posterior laxity of a joint, e.g. during motion or stress testing [e.g. varus stress or valgus stress], e.g. in the form of a vector or distance indicator, contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles, e.g. in the form of a vector or distance indicator, superimposed onto and/or aligned with a joint, e.g. corresponding portions of a joint, for example an articular surface, e.g. a femoral articular surface and/or a tibial articular surface or superimposed onto and/or aligned with the space between the femoral articular surface and the tibial articular surface can be in the form of 2D or 3D graphical representation, 2D, 3D and/or 4D or higher simulations (e.g. a simulation of biomotion) and/or numerical values and/or color coding, e.g. for abnormal and/or pathologic values of any of the parameters and/or data.

In some of the embodiments, a virtual surgical guide, e.g. a virtual cut block, a virtual axis, a virtual plane, a virtual instrument, a virtual tool, a virtual implant component and/or a virtual implant, and/or a physical surgical guide, e.g. a physical cut block, a physical axis, a physical plane, a physical instrument, a physical tool, a physical implant component and/or a physical implant can be placed, oriented, fitted and/or aligned using the OHMD display of the virtual loading pattern, load line, contact line, contact force, articular surface force, moment, vector, load conditions of various implant components, e.g. for different movements [e.g. flexion, extension, rotation, rollback, adduction, abduction], constraints, medial femoral rollback during flexion, e.g. of hidden portions of the femoral condyle or of the virtual implant component, lateral femoral rollback during flexion, e.g. of hidden portions of the femoral condyle or of the virtual implant component, patellar position, medial, superior, inferior for different flexion and/or extension angles, patellar tracking, internal/external rotation of one or both femoral condyles, e.g. of hidden portions of the femoral condyle or of the virtual implant component internal/external rotation of a tibia, e.g. of hidden portions of the tibia, rotation axis of a femur, rotation axis of a tibia, rotation axis of a first articular side, rotation axis of a second, e.g. opposing, articular side, rotation axis of a bone, tibial and/or femoral abduction, tibial and/or femoral adduction, transepicondylar axis, Whiteside's line, posterior condylar axis, sulcus line, depth of sulcus line, flexion and extension angles of one or more articular surfaces, anterior/posterior slide of one or both femoral condyles during flexion or extension, e.g. of hidden portions of the femoral condyle or of the virtual implant component, medial and/or lateral laxity of a joint, e.g. during motion or stress testing, anterior and/or posterior laxity of a joint, e.g. during motion or stress testing [e.g. varus stress or valgus stress], e.g. in the form of a vector or distance indicator, contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles, e.g. in the form of a vector or distance indicator, superimposed onto and/or aligned with a joint, e.g. corresponding portions of a joint, for example an articular surface, e.g. a femoral articular surface and/or a tibial articular surface or superimposed onto and/or aligned with the space between the femoral articular surface and the tibial articular surface, for example by aligning and/or superimposing the virtual surgical guide, e.g. virtual cut block, virtual axis, virtual plane, virtual instrument, virtual tool, virtual implant component and/or virtual implant, and/or physical surgical guide, e.g. physical cut block, physical axis, physical plane, physical instrument, physical tool, physical implant component and/or physical implant with one or more of the OHMD displays of the virtual data and/or by superimposing and/or aligning one or more of the OHMD displays with the one or more of the virtual surgical guide, e.g. virtual cut block, virtual axis, virtual plane, virtual instrument, virtual tool, virtual implant component and/or virtual implant, and/or physical surgical guide, e.g. physical cut block, physical axis, physical plane, physical instrument, physical tool, physical implant component and/or physical implant. For example, one or more of a virtual surgical guide, e.g. virtual cut block, virtual axis, virtual plane, virtual instrument, virtual tool, virtual implant component and/or virtual implant, and/or physical surgical guide, e.g. physical cut block, physical axis, physical plane, physical instrument, physical tool, physical implant component and/or physical implant can be superimposed and/or aligned with an OHMD display of a virtual biomechanical axis. Thus, a physical femoral component can be aligned with a virtual femoral rotation axis projected by the one or more OHMDs superimposed and/or aligned with the surface of the joint. A physical femoral component can be aligned with a virtual transepicondylar axis projected by the one or more OHMDs superimposed and/or aligned with the surface of the joint. A physical femoral component can be aligned with a virtual Whiteside's line projected by the one or more OHMDs superimposed and/or aligned with the surface of the joint. The trochlear portion of a physical femoral component can be aligned with a virtual sulcus line of the trochlea projected by the one or more OHMDs superimposed and/or aligned with the surface of the joint. A virtual femoral component can also be placed, oriented, and/or aligned in relationship to a physical trochlea, a physical medial facet of a trochlea, a physical lateral facet of a trochlea, a physical trochlear sulcus, a physical trochlear sulcus line, e.g. at a predetermined distance, predetermined angle and/or predetermined orientation. A physical femoral component can be aligned with a virtual posterior condylar axis projected by the one or more OHMDs superimposed and/or aligned with the surface of the joint. A physical tibial component can be aligned with a virtual tibial rotation axis projected by the one or more OHMDs superimposed and/or aligned with the surface of the joint.

A virtual femoral component can be aligned with a virtual femoral rotation axis projected by the one or more OHMDs superimposed and/or aligned with the surface of the joint. A virtual femoral component can be aligned with a virtual transepicondylar axis projected by the one or more OHMDs superimposed and/or aligned with the surface of the joint. A virtual femoral component can be aligned with a virtual Whiteside's line projected by the one or more OHMDs superimposed and/or aligned with the surface of the joint. The trochlear portion of a virtual femoral component can be aligned with a virtual sulcus line of the trochlea projected by the one or more OHMDs superimposed and/or aligned with the surface of the joint. A virtual femoral component can be aligned with a virtual posterior condylar axis projected by the one or more OHMDs superimposed and/or aligned with the surface of the joint. A virtual tibial component can be aligned with a virtual tibial rotation axis projected by the one or more OHMDs superimposed and/or aligned with the surface of the joint.

In some embodiments, information about one or more of a loading pattern, load line, contact line, contact force, articular surface force, moment, vector, load conditions of various implant components, e.g. for different movements [e.g. flexion, extension, rotation, rollback, adduction, abduction], constraints, medial femoral rollback during flexion, lateral femoral rollback during flexion, patellar position, medial, superior, inferior for different flexion and/or extension angles, patellar tracking, internal/external rotation of one or both femoral condyles, internal/external rotation of a tibia, rotation axis of a femur, rotation axis of a tibia, rotation axis of a first articular side, rotation axis of a second, e.g. opposing, articular side, rotation axis of a bone, tibial and/or femoral abduction, tibial and/or femoral adduction, flexion and extension angles of one or more articular surfaces, anterior/posterior slide of one or both femoral condyles during flexion or extension, medial and/or lateral laxity of a joint, e.g. during motion or stress testing, anterior and/or posterior laxity of a joint, e.g. during motion or stress testing [e.g. varus stress or valgus stress], contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles, can be used to determine and/or modify the position and/or orientation and/or coordinates of a virtual surgical guide, virtual instrument and/or virtual tools and one or more OHMD displays can be used to superimpose and/or align the virtual surgical guide, e.g. virtual cut block, virtual axis, virtual plane, virtual tibial template, virtual keel punch, virtual instrument and/or virtual tools with the surface of a joint or with subsurface structures of a joint, e.g. for guiding the placement and/or aligning one or more physical surgical guides, e.g. physical cut block, physical axis, physical plane, physical instruments, physical tools, physical implant components and/or physical implants. In any of the embodiments one or more of the virtual loading pattern, load line, contact line, contact force, articular surface force, moment, vector, load conditions of various implant components, e.g. for different movements [e.g. flexion, extension, rotation, rollback, adduction, abduction], constraints, medial femoral rollback during flexion, e.g. of hidden portions of the femoral condyle or of the virtual implant component, lateral femoral rollback during flexion, e.g. of hidden portions of the femoral condyle or of the virtual implant component, patellar position, medial, superior, inferior for different flexion and/or extension angles, patellar tracking, internal/external rotation of one or both femoral condyles, e.g. of hidden portions of the femoral condyle or of the virtual implant component internal/external rotation of a tibia, e.g. of hidden portions of the tibia, rotation axis of a femur, rotation axis of a tibia, rotation axis of a first articular side, rotation axis of a second, e.g. opposing, articular side, rotation axis of a bone, tibial and/or femoral abduction, tibial and/or femoral adduction, transepicondylar axis, Whiteside's line, posterior condylar axis, sulcus line, depth of sulcus line, flexion and extension angles of one or more articular surfaces, anterior/posterior slide of one or both femoral condyles during flexion or extension, e.g. of hidden portions of the femoral condyle or of the virtual implant component, medial and/or lateral laxity of a joint, e.g. during motion or stress testing, anterior and/or posterior laxity of a joint, e.g. during motion or stress testing [e.g. varus stress or valgus stress], e.g. in the form of a vector or distance indicator, contact pressure or forces on one or more articular or implant surfaces, contact area of one or more articular or implant surfaces, forces at the implant component—bone or implant component—cement or cement—bone interface(s), one or more ligament locations, e.g. origin and/or insertion, e.g. ACL, PCL, MCL, LCL, ligament tension, strain, estimated failure forces, loads for different angles of flexion, extension, rotation, abduction, adduction, elevation, shear forces, impingement onto other articular structures, e.g. in a hip joint and/or a knee joint, flexion/extension angle(s) of one or more articular surface(s), joint laxity, varus gap, valgus gap, e.g. for different flexion and/or extension angles, e.g. in the form of a vector or distance indicator, can be determined using, for example, an imaging test, e.g. an x-ray, ultrasound, CT scan, or MRI and one or more kinematic tests, e.g. each at one or more time points, e.g. T1, T2, . . . T5 . . . .

The preceding and the following embodiments are applicable to knee replacement, hip replacement, shoulder replacement, ankle replacement and any other joint replacement. Knee replacement will be discussed in the following in exemplary form. It is to be understood that in any of the following embodiments involving a distal femur and a proximal tibia for a knee replacement, the following substitutions can be made for hip replacement: distal femur=proximal femur, virtual femoral component=virtual femoral component, proximal tibia=acetabulum, virtual tibial component=virtual acetabular component; the following substitutions can be made for shoulder replacement: distal femur=proximal humerus, virtual femoral component=virtual humeral component, proximal tibia=glenoid, virtual tibial component=virtual glenoid component.

In some embodiments, a computer system with one or more computer processors can support the surgeon in ligament balancing during knee replacement surgery. For example, in a first step, the knee joint can be moved through a range of motion. The moving through the range of motion can be through the entire range of motion or a portion of the range of motion of the joint. The moving through the range of motion can be a moving from a first position, e.g. in extension, to a second position, e.g. at 15 degrees of flexion, to a third position, e.g. at 30 degrees of flexion, to a fourth position, e.g. at 45 degrees of flexion, to a $5^{th}$ position, e.g. at 60 degrees of flexion, to a $6^{th}$ position, e.g. at 75 degrees or flexion, and to a $7^{th}$ position, e.g. at 90 degrees of flexion; any flexion angle and any number of stops are possible. Flexion angles above 90 degrees are possible, e.g. up to 120, 130, 140 or 150 degrees of flexion. Measurements can be obtained at any angle and using any range of motion. Measurements can be obtained without varus or valgus stress and/or can be repeated with varus stress and/or valgus stress. A computer system with one or more computer processors can continuously or intermittently record the tracked position and orientation of the femur and tibia (or femur and acetabulum in a hip joint or humerus and glenoid in a shoulder joint, or tibia and talus in an ankle joint) and store the tracking information and related x, y, and z coordinates in a coordinate system in memory. The tracking information and related x, y, and z coordinates of the joint, e.g. the distal femur and the distal tibial can be stored for measurements without varus or valgus stress and/or for measurements with varus and/or valgus stress. Measurements without varus or valgus stress and/or for measurements with varus and/or valgus stress can be used in any of the following embodiments and in any embodiments related to kinematic measurements and use and/or OHMD display of kinematic data, e.g. flexion or extension gap data and/or displays, throughout the specification. The steps can be performed and/or repeated at one or more of the timepoints T1-T5 described in the specification. In addition, any of the maneuvers performed while displaying one or more virtual implant components throughout the specification, e.g. moving a joint to select angles of extension and/or flexion or moving a joint through a range of motion, can be performed without varus or valgus stress and/or with varus stress and/or with valgus stress. In some of the embodiments, measurements to determine a flexion gap and/or an extension gap or the display of a virtual flexion gap or a virtual extension gap, e.g. using an OHMD display of a virtual vector, a virtual distance, a virtual frame, virtual bone cuts (see below) can be performed with a tensioner in place. The tensioner can be used, for example, to stress and/or to open up the medial and/or the lateral joint space. The tensioner can, optionally, include pressure sensors, for example to measure a pressure in a medial compartment and/or a lateral compartment.

In one embodiment, one or more virtual implant components can be virtually placed and, optionally, virtually fitted, sized, selected and/or aligned on the articular surface(s) of the physical joint of the patient. For example, a virtual femoral component can be virtually placed and, optionally, virtually fitted, sized, selected and/or aligned with the physical distal femur of the patient (including the femoral articular surface, e.g. cartilage and/or subchondral bone, and/or cortical bone). A virtual tibial component can be virtually placed and, optionally, virtually fitted, sized, selected and/or aligned with the physical proximal tibia of the patient (including the tibial articular surface, e.g. cartilage and/or subchondral bone, and/or cortical bone).

In another embodiment, one or more virtual implant components can be virtually placed and, optionally, virtually fitted, sized, selected and/or aligned on the articular surface(s) of the joint of the patient visualized in an imaging test, e.g. an ultrasound, CT or MRI scan. For example, a virtual femoral component can be virtually placed and, optionally, virtually fitted, sized, selected and/or aligned with the virtual distal femur of the patient (including the femoral articular surface, e.g. cartilage and/or subchondral bone, and/or cortical bone) as visualized on an imaging test, e.g. an ultrasound, CT or MRI scan. A virtual tibial component can be virtually placed and, optionally, virtually fitted, sized, selected and/or aligned with the virtual proximal tibia of the patient (including the tibial articular surface, e.g. cartilage and/or subchondral bone, and/or cortical bone) as visualized on an imaging test, e.g. an ultrasound, CT or MRI scan. For this purpose, the virtual femoral and/or tibial articular surface can be extracted from the imaging data, e.g. using image segmentation, and can be displayed as a virtual 3D model on a computer monitor using, for example, a graphical user interface powered by one or more computer processors. The virtual 3D model of the patient's femur and/or tibia derived from the imaging data and/or the virtual femoral and/or tibial components can then be registered with the physical joint of the patient and one or more OHMDs can display the virtual femoral and/or tibial components and, optionally, the virtual 3D model of the patient's femur and/or tibia derived from the imaging data superimposed onto and/or aligned with the physical joint of the patient.

In another embodiment, one or more virtual implant components can be virtually placed and, optionally, virtually fitted, sized, selected and/or aligned on the articular surface(s) of the joint of the patient visualized in a surface generated from a point cloud of the articular surface, e.g. using a pointer with one or more attached markers, e.g. optical markers (for a video system) or navigation markers (for a navigation system) for identifying points and generating the point cloud or for "painting" the articular surface. For example, a virtual femoral component can be virtually placed and, optionally, virtually fitted, sized, selected and/or aligned with the virtual distal femur of the patient (including the femoral articular surface, e.g. cartilage and/or subchondral bone, and/or cortical bone) as visualized in a surface generated from a point cloud of the articular surface. A virtual tibial component can be virtually placed and, optionally, virtually fitted, sized, selected and/or aligned with the virtual proximal tibia of the patient (including the tibial articular surface, e.g. cartilage and/or subchondral bone, and/or cortical bone) as visualized in a surface generated from a point cloud of the articular surface. For this purpose, the virtual femoral and/or tibial articular surface generated from a point cloud of the articular surface can be displayed as a virtual 3D model on a computer monitor using, for example, a graphical user interface powered by one or more computer processors. The virtual 3D model of the patient's femur and/or tibia derived from the point cloud of the articular surface and/or the virtual femoral and/or tibial components can then be registered with the physical joint of the patient and one or more OHMDs can display the virtual femoral and/or tibial components and, optionally, the virtual 3D model of the patient's femur and/or tibia derived from the point cloud superimposed onto and/or aligned with the physical joint of the patient.

Using these different technical approaches for projecting a virtual femoral component and/or a virtual tibial component (or other implant components in other joints, e.g. hip, shoulder, ankle) on the corresponding articular surface, the relative position and orientation of the virtual femoral component (and its x-, y- and z-coordinates) and the patient's physical distal femur (including the femoral articular surface, e.g. cartilage and/or subchondral bone, and/or cortical bone) (and its x-, y- and z-coordinates) can be known. The relative position and orientation of the virtual tibial component (and its x-, y- and z-coordinates) and the patient's physical tibia (including the tibial articular surface, e.g. cartilage and/or subchondral bone, and/or cortical bone) (and its x-, y- and z-coordinates) can also be known. Similarly, the relative position and orientation of the virtual femoral component (and its x-, y- and z-coordinates) and the patient's physical distal femur (including the femoral articular surface, e.g. cartilage and/or subchondral bone, and/or cortical bone) (and its x-, y- and z-coordinates) can be known. The relative position and orientation of a virtual patellar component (and its x-, y- and z-coordinates) and the patient's physical patella (including the patellar articular surface, e.g. cartilage and/or subchondral bone, and/or cortical bone) (and its x-, y- and z-coordinates) can also be known.

From the tracking information on femur and tibia, the computer system can then take the femoral position and orientation and tibial position and orientation or the patellar position and orientation and their x, y, z coordinates for a given flexion angle A1 during the range of motion. From the known relative position and orientation between the femur and the virtual femoral component, one or more computer processors can compute the 3D position and orientation of the virtual femoral implant in the tracking coordinate system at A1. From the known relative position and orientation between the tibia and the virtual tibial component, one or more computer processors can compute the 3D position and orientation of the virtual tibial component in the tracking coordinate system at A1. From the known relative position and orientation between the patella and the virtual patellar component, one or more computer processors can compute the 3D position and orientation of the virtual patellar component in the tracking coordinate system at A1.

After these steps the relative position and orientation between the virtual femoral component and the virtual tibial component at A1 is known. The computer system with one or more computer processors can then calculate any overlap or intersection between the virtual femoral component and virtual tibial component, e.g. using geometric Boolean operations, for example in a medial compartment or a lateral compartment and a medial compartment and lateral compartment. The boundary representation of the virtual femoral component and the virtual tibial component can be a parametric surface. The boundary representation of the virtual femoral component and the virtual tibial component can be a polygon surface. The boundary representation of the virtual femoral component and the virtual tibial component can be a mix of one or more parametric surfaces and one or more polygon surfaces.

Or, after these steps the relative position and orientation between the virtual femoral component and the virtual patellar component at A1 is known. The computer system with one or more computer processors can then calculate any overlap or intersection between the virtual femoral component and virtual patellar component, e.g. using geometric Boolean operations. The boundary representation of the virtual femoral component and the virtual patellar component can be a parametric surface. The boundary representation of the virtual femoral component and the virtual patellar component can be a polygon surface. The boundary representation of the virtual femoral component and the virtual patellar component can be a mix of one or more parametric surfaces and one or more polygon surfaces.

If an overlap or intersection between the virtual femoral component and the virtual tibial component or a virtual femoral component and a virtual patellar component exists, the system can display the overlapping volume in the OHMD. The overlapping volume can be highlighted, e.g. in red or any other color, to indicate to the surgeon that the joint may be overstuffed (e.g. in a patellofemoral joint) and/or to indicate that there is a potential motion conflict between the virtual femoral component and the virtual tibial component or the virtual femoral component and the virtual patellar component.

If no overlap or intersection between the virtual femoral component and the virtual tibial component or the virtual femoral component and the virtual patellar component exists, the minimum distance between the virtual femoral component and the virtual tibial component or the virtual femoral component and the virtual patellar component can be calculated.

The process of determining the overlap or intersection or minimum distance between the virtual femoral component and the virtual tibial component can be repeated for a second flexion angle A2. It can be repeated for as many flexion angles as desired. The results can all be displayed in the same image superimposed onto and/or aligned with the patient's joint using one or more computer processors for generating the OHMD display of the vector or distance and/or the virtual femoral component and/or the virtual tibial component. All minimum distance values displayed together form a collection of vectors. All overlap or intersection volumes can form a single large volume formed by the union of all overlap or intersection volumes for each flexion angle.

If an overlap or intersection between the virtual femoral component and the virtual tibial component or a virtual femoral component and a virtual patellar component exists, the system can display the overlapping volume in the OHMD.

One or more OHMDs can display the overlapping volume between the virtual femoral component and the virtual tibial component or the virtual femoral component and the virtual patellar component superimposed onto and/or aligned with the physical joint of the patient, optionally with the virtual femoral component and the virtual tibial component and/or the virtual patellar component also superimposed onto and/or aligned with the joint. The OHMD display of the overlapping volume between the virtual femoral component and the virtual tibial component or the virtual femoral component and the virtual patellar component and, optionally, the OHMD display of the virtual femoral component and the virtual tibial component and/or the virtual patellar component can be maintained on the surface or between the surfaces of the distal femur and/or the proximal tibia when the joint moves, e.g. through the range of motion or from a first to a second to a third flexion angle. Optionally, the overlapping volume can be displayed numerically or in graphic form, e.g. using a line, a bar or column(s). The overlapping volume can be color coded.

If no overlap or intersection between the virtual femoral component and the virtual tibial component exists, the minimum distance between the virtual femoral component and the virtual tibial component can be calculated. The minimum distance can be the distance between the two closest points on the virtual femoral component and the virtual tibial component. In the OHMD, the minimum distance can then, for example, be displayed as a vector extending from the closest point on the surface of the virtual femoral component and point in the direction of the closest point on the surface of the virtual tibial component, with a length proportional to the minimum distance, or vice versa. One or more OHMDs can display the vector from the virtual femoral component to the virtual tibial component (or vice versa) superimposed onto and/or aligned with the physical joint of the patient, e.g. with the virtual femoral component and the virtual tibial components also superimposed onto and/or aligned with the joint. The OHMD display of the vector from the virtual femoral component to the virtual tibial component (or vice versa) and, optionally, the OHMD display of the virtual femoral component and the virtual tibial component can be maintained on the surface of or between the surfaces of the distal femur and/or the proximal tibia when the joint moves, e.g. through the range of motion or from a first to a second to a third flexion angle. The OHMD can display the vector or distance and, with that, the medial and/or lateral gap and, with that, the distance between the virtual femoral and the virtual tibial component, superimposed onto and/or aligned with the physical joint of the patient for example through the range of motion. Optionally, the length can be displayed numerically or in graphic form, e.g. using a line, a bar or column(s). The vector can be color coded, for example to indicate whether the minimum distance measurement for A1 exceeds a certain threshold for the gap or distance between the virtual femoral component and the virtual tibial component. The vector can be displayed as a distance indicator, e.g. a bar.

If no overlap or intersection between the virtual femoral component and the virtual patellar component exists, the minimum distance between the virtual femoral component and the virtual patellar component can be calculated. The minimum distance can be the distance between the two closest points on the virtual femoral component and the virtual patellar component. In the OHMD, the minimum distance can then, for example, be displayed as a vector extending from the closest point on the surface of the virtual femoral component and point in the direction of the closest point on the surface of the virtual patellar component, with a length proportional to the minimum distance, or vice versa. One or more OHMDs can display the vector from the virtual femoral component to the virtual patellar component (or vice versa) superimposed onto and/or aligned with the physical joint of the patient, e.g. with the virtual femoral component and the virtual patellar components also superimposed onto and/or aligned with the joint. The OHMD display of the vector from the virtual femoral component to the virtual patellar component (or vice versa) and, optionally, the OHMD display of the virtual femoral component and the virtual patellar component can be maintained on the surface or between the surfaces of the distal femur and/or the patella when the joint moves, e.g. through the range of motion or from a first to a second to a third flexion angle. The OHMD can display the vector or distance and, with that, the medial and/or lateral gap and, with that, the distance between the virtual femoral and the virtual patellar component, superimposed onto and/or aligned with the physical joint of the patient for example through the range of motion. Optionally, the length can be displayed numerically or in graphic form, e.g. using a line, a bar or column(s). The vector can be color coded, for example to indicate whether the minimum distance measurement for A1 exceeds a certain threshold for the gap or distance between the virtual femoral component and the virtual tibial component. The vector can be displayed as a distance indicator, e.g. a bar.

Using one or more computer processors and, for example, a graphical user interface, the threshold for an acceptable or predetermined distance or gap can be set separately for a medial compartment, a lateral compartment and/or a patellofemoral compartment. The threshold for an acceptable or predetermined distance or gap can be different for different angles of flexion and/or extension and can be different for different portions of the range of motion. For example, the threshold for an acceptable or predetermined distance or gap can be greater with higher degrees of flexion and lesser with lower degrees of flexion. The threshold for an acceptable or predetermined distance or gap can be less medially than laterally, e.g. 1.0 mm, 1.5 mm or 2.0 mm for a medial distance or gap and 2.0, 2.5, 3.0 or any other amount for a lateral distance or gap.

With traditional knee replacement, with tight flexion and extension gaps of the physical femoral and physical tibial component the surgeon can recut the tibia. With a tight flexion gap and a balanced extension gap, the surgeon can, for example, increase the posterior slope of the tibial component and recut tibia. With augmented reality display, the OHMD can display one or more of the overlapping volume between the virtual femoral component and the virtual tibial component, the vector or distance from the virtual femoral component to the virtual tibial component (or vice versa), the virtual femoral component and/or the virtual tibial component superimposed onto or between the surface(s) of the physical distal femur and the physical proximal tibia for one or more flexion or extension angles or through the range of motion. The position and/or orientation and coordinates of the virtual femoral component and/or virtual tibial component can then be modified, for example, to avoid overlapping of the virtual femoral component and/or the virtual tibial component, to achieve a predetermined distance or gap between the virtual femoral component and/or the virtual tibial component for select angles of extension and or flexion (e.g. 0 and 90 degrees) or through the range of motion; the change in position and/or orientation and coordinates of the virtual femoral component and/or virtual tibial component can be performed in a manner to maintain a predetermined mechanical axis correction, to maintain a predetermined femoral component flexion, to maintain a predetermined tibial slope, to avoid femoral notching, to maintain a predetermined femoral or tibial component rotation, and/or to make adjustments to any of the foregoing within a clinically acceptable predetermined range, e.g. of varus/valgus correction, femoral component flexion, tibial slope, femoral or tibial component rotation. One or more adjustments to the position and/or orientation of the virtual femoral and/or tibial component can be made in this manner which can then be used to determine the position and/or location of any bone cuts (and the position and/or orientation of any surgical guides) which can help reduce the need for recuts or ligament releases.

In some embodiments, one or more of the overlapping distance or volume between the virtual femoral component and the virtual tibial component, the vector or distance from the virtual femoral component to the virtual tibial component (or vice versa) can be displayed by the OHMD in graphical format, for example in form of a graph or curve showing the overlapping distance or volume between the virtual femoral component and the virtual tibial component, the vector or distance from the virtual femoral component to the virtual tibial component (or vice versa) (the gap between the virtual femoral and the virtual tibial component) for different extension and flexion angles, e.g. through the range of motion. One or more computer processors can be configured to facilitate one or more of the placing, fitting, sizing, selecting and/or aligning of virtual implant components, e.g. a virtual femoral component or a virtual tibial component, on the physical joint of the patient; as the computer processor(s) place and/or move the virtual implant components, e.g. a virtual femoral component or a virtual tibial component, on the physical joint (e.g. articular surface(s)) of the patient, the OHMD or a computer monitor can be used to display changes in the one or more graphical representations of the overlapping distance or volume between the virtual femoral component and the virtual tibial component and/or the vector or distance from the virtual femoral component to the virtual tibial component (or vice versa).

In this manner, the position and/or orientation and coordinates of the virtual femoral component and/or virtual tibial component can be modified, for example, to avoid overlapping of the virtual femoral component and/or the virtual tibial component, to achieve a predetermined distance or gap between the virtual femoral component and/or the virtual tibial component for select angles of extension and or flexion (e.g. 0 and 90 degrees) or through the range of motion; the change in position and/or orientation and coordinates of the virtual femoral component and/or virtual tibial component can be performed in a manner to maintain a predetermined mechanical axis correction, to maintain a predetermined femoral component flexion, to maintain a predetermined tibial slope, to avoid femoral notching, to maintain a predetermined femoral or tibial component rotation, and/or to make adjustments to any of the foregoing within a clinically acceptable predetermined range, e.g. of varus/valgus correction, femoral component flexion, tibial slope, femoral or tibial component rotation. One or more adjustments to the position and/or orientation of the virtual femoral and/or tibial component can be made in this manner which can then be used to determine the position and/or location of any bone cuts (and the position and/or orientation of any virtual surgical guides) which can help reduce the need for recuts or ligament releases.

In some embodiments, one or more of a 2D or 3D graphical indicator of a desired, predetermined or target flexion gap or extension gap can be displayed by the OHMD in graphical format, e.g. for a medial compartment, a lateral compartment or both. The 2D or 3D graphical indicator can be a square, a rectangle, a square, a cube, a brick like shape, a rectangular prism, two rectangular prisms, a complex shape (e.g. with steps to indicate a different medial vs. lateral and/or a different central/extension vs. posterior/flexion gap). The 2D or 3D graphical indicator can be a frame-like display. One or more computer processors can be configured to facilitate one or more of the placing, fitting, sizing, selecting and/or aligning of virtual implant components, e.g. a virtual femoral component or a virtual tibial component, on the physical joint of the patient. One or more computer processors can be configured to display the 2D or 3D graphical indicator of the desired, predetermined or target flexion gap or extension gap superimposed onto and/or aligned with the physical joint of the patient, e.g. between the medial and/or lateral articular surface of the femoral condyle and the tibial plateau. Optionally, the OHMD can simultaneously display the virtual femoral component and/or virtual tibial component superimposed onto and/or aligned with the physical joint of the patient, e.g. the femoral articular surface and/or the tibial articular surface. In some embodiments, the computer processors can be configured so that the OHMD display can maintain the display of the 2D or 3D graphical indicator of the desired, predetermined or target flexion gap or extension gap superimposed onto and/or aligned with the physical joint of the patient, e.g. between the medial and/or lateral articular surface of the femoral condyle and the tibial plateau, and can maintain the optional display of the virtual femoral component and/or virtual tibial component superimposed onto and/or aligned with the physical joint of the patient, e.g. the femoral articular surface and/or the tibial articular surface, when the physical joint of the patient moves, e.g. between different extension and/or flexion positions, e.g. 0 degrees of extension, 45 degrees of flexion, 90 degrees of flexion.

In this manner, the position and/or orientation and coordinates of the virtual femoral component and/or virtual tibial component can be evaluated for different angles of flexion and/or extension, e.g. 0 degrees and 90 degrees, and can be modified so that the position of the virtual femoral component and/or the virtual tibial component, e.g. their bearing surface, approximate or are tangent with or are substantially tangent with the 2D or 3D graphical indicator of the desired, predetermined or target flexion gap or extension gap superimposed onto and/or aligned with the physical joint of the patient. The modification or change in position and/or orientation and coordinates of the virtual femoral component and/or virtual tibial component can be performed in a manner to maintain a predetermined mechanical axis correction, to maintain a predetermined femoral component flexion, to maintain a predetermined tibial slope, to avoid femoral notching, to maintain a predetermined femoral or tibial component rotation, and/or to make adjustments to any of the foregoing within a clinically acceptable predetermined range, e.g. of varus/valgus correction, femoral component flexion, tibial slope, femoral or tibial component rotation. One or more adjustments to the position and/or orientation of the virtual femoral and/or tibial component can be made in this manner which can then be used to determine the position and/or location of any bone cuts (and the position and/or orientation of any virtual surgical guides) which can help reduce the need for recuts or ligament releases.

In some embodiments, one or more computer processors can be configured to facilitate one or more of the placing, fitting, sizing, selecting and/or aligning of virtual implant components, e.g. a virtual femoral component or a virtual tibial component, on the physical joint of the patient. The position and/or orientation of the virtual femoral component displayed by the OHMD superimposed and/or aligned with the physical distal femur of the patient and the position and/or orientation of the virtual tibial component displayed by the OHMD superimposed and/or aligned with the physical proximal tibia of the patient can be used by one or more computer processors to compute the position and/or orientation of one or more bone cuts for the respective femoral component and the respective tibial component, for example taking into account the patient's femoral bone and tibial bone geometry and the implant geometry of the virtual femoral component and the virtual tibial component. One or more computer processors can be configured so that the OHMD can then display the virtual femoral and/or tibial bone cuts superimposed into and/or aligned with the physical joint of the patient, e.g. the distal femur and/or the proximal tibia. Optionally, the OHMD can simultaneously display the virtual femoral component and/or virtual tibial component superimposed onto and/or aligned with the physical joint of the patient, e.g. the femoral articular surface and/or the tibial articular surface. In some embodiments, the computer processors can be configured so that the OHMD display can maintain the display of the virtual femoral bone cuts and the virtual tibial bone cuts superimposed onto and/or aligned with the physical joint of the patient, e.g. the medial and/or lateral articular surface of the femoral condyles and the tibial plateau, and can maintain the optional display of the virtual femoral component and/or virtual tibial component superimposed onto and/or aligned with the physical joint of the patient, e.g. the femoral articular surface and/or the tibial articular surface, when the physical joint of the patient moves, e.g. between different extension and/or flexion positions, e.g. 0 degrees of extension, 45 degrees of flexion, 90 degrees of flexion, or through a range of motion. By displaying the virtual femoral and tibial bone cuts for different angles of extension, e.g. 0 degrees, and flexion, e.g. 90 degrees, or through the range of motion, the distance between the femoral and tibial bone cuts can be evaluated. Accounting, for example, for implant thickness, e.g. femoral component thickness and/or tibial component thickness, the distance between the virtual femoral bone cut and the virtual tibial bone cut can provide a measurement or an estimate of the extension gap and/or flexion gap of the virtual femoral component and the virtual tibial component. The virtual femoral component and the virtual tibial components can optionally be co-displayed with their respective bone cuts by the OHMD, which can be used to highlight any areas of overlap and the amount of overlap (e.g. distance in mm or volume in cc). Alternatively, the computer processors can be configured to display the virtual femoral bone cut and the virtual tibial cut for different angles of extension and/or flexion optionally together with a display of femoral and/or tibial implant thickness or optionally with a display of the amount of overlap (e.g. in mm or cc) or the extension gap or flexion gap between the virtual femoral component and the virtual tibial component (e.g. in mm).

In this manner, the gap of the virtual femoral component and/or virtual tibial component can be evaluated for different angles of flexion and/or extension, e.g. 0 degrees and 90 degrees, and can be modified so that the position and/or orientation of the virtual femoral component and/or the virtual tibial component is optimized to achieve a desired, intended or predetermined extension gap or flexion gap. The modification or change in position and/or orientation and coordinates of the virtual femoral and tibial bone cuts and/or of the virtual femoral component and/or virtual tibial component can be performed in a manner to maintain a predetermined mechanical axis correction, to maintain a predetermined femoral component flexion, to maintain a predetermined tibial slope, to avoid femoral notching, to maintain a predetermined femoral or tibial component rotation, and/or to make adjustments to any of the foregoing within a clinically acceptable predetermined range, e.g. of varus/valgus correction, femoral component flexion, tibial slope, femoral or tibial component rotation.

The foregoing embodiments can be applied to any joint of the human body, e.g. a shoulder joint, elbow joint, wrist joint, hip joint and/or ankle joint. For example, in any of the foregoing embodiments involving a distal femur and a proximal tibia for a knee replacement, the following substitutions can be made for hip replacement: distal femur=proximal femur, virtual femoral component=virtual femoral component, proximal tibia=acetabulum, virtual tibial component=virtual acetabular component; the following substitutions can be made for shoulder replacement: distal femur=proximal humerus, virtual femoral component=virtual humeral component, proximal tibia=glenoid, virtual tibial component=virtual glenoid component.

Shoulder Replacement, Partial or Total, Other Shoulder Surgeries

Any of the embodiments in the specification can also be applied to partial or total shoulder replacement as well as other types of shoulder surgery including, for example, rotator cuff repair, surgery to repair or remove labral tears and various arthroscopic and/or open shoulder procedures. For example, OHMD guidance can be used to guide shoulder arthrography, or injections, e.g. into the subacromial/subdeltoid bursa as well as intra-articular injections; for example, intra-procedural imaging, e.g. x-ray fluoroscopy can be performed which can include one or more optical markers with one or more radiopaque elements superimposed onto and/or attached to the patient, e.g. the patient's skin, for registration purposes. Once the patient, the optical markers and one or more OHMDs have been registered in the same coordinate system, the fluoroscopic images can be displayed by the one or more OHMDs, e.g. in a predetermined plane relative to the patient, e.g. an AP shoulder view in a projection parallel to the fluoroscopy unit table tube on which the patient is resting and/or parallel with the image intensifier and/or the x-ray tube and through the center of the humeral head or glenoid, while the surgeon is advancing a needle or trocar, without need for repeat fluoroscopy, thereby reducing radiation exposure to the patient and the operator, e.g. a radiologist or surgeon.

In the example of partial or total shoulder arthroplasty, Table 17 shows some of the embodiments for using optical head mounted displays for guidance of the procedure.

TABLE 17

Benefits of OHMD guidance for performing shoulder arthroplasty. Exemplary surgical steps are listed in an illustrative, non-limiting sequence along with corresponding embodiments for using one or more OHMDs to guide the procedure.

| Illustrative Surgical Steps | Optical Guidance with OHMD, e.g. using optical markers, LED's, navigation markers, spatial mapping, etc. | Embodiments |
|---|---|---|
| Surgical incision, exposure of humeral head | ✓ | Display of sensitive structures, e.g. axillary nerve, brachial artery & vein, e.g. using registration & superimposition of MRI and/or other imaging data with OHMD; optionally same extremity position intra-op as during pre-op scan and/or optionally motion tracking with re-positioning, re-orientation of virtual data, e.g. data to match intra-operative position/orientation/alignment of muscles, tendons, ligaments, labrum, glenoid, humerus, other bony and soft-tissue structures |
| Biceps tenotomy, subscapularis incision, exposure of proximal humerus | ✓ | Display of sensitive structures, e.g. axillary nerve, brachial artery & vein, e.g. using registration & superimposition of MRI and/or other imaging data with OHMD; optionally same extremity position intra-op as during pre-op scan and/or optionally motion tracking with re-positioning, re-orientation of virtual data, e.g. scan data to match intra-operative position/orientation/alignment of muscles, tendons, ligaments, labrum, glenoid, humerus, other bony and soft-tissue structures |
| Pin humeral cutting block, humeral head osteotomy | ✓ | OHMD can project virtual cut block or cut plane, surgeon aligns/superimposes physical cut block or saw, sets retroversion, cut height/level; virtual cut block can be displayed external to articular surface, optionally tangent with articular surface, e.g. not intersecting articular surface |
| Humeral canal reaming | ✓ | OHMD can project virtual reamer, e.g. with position/orientation/alignment based on combined glenoid-humeral version or only humeral version; surgeon can align and/or superimpose physical reamer with virtual reamer; surgeon can align physical reamer and/or stem, e.g. based on combined glenoid-humeral version or only humeral version, with |

TABLE 17-continued

Benefits of OHMD guidance for performing shoulder arthroplasty. Exemplary surgical steps are listed in an illustrative, non-limiting sequence along with corresponding embodiments for using one or more OHMDs to guide the procedure.

| Illustrative Surgical Steps | Optical Guidance with OHMD, e.g. using optical markers, LED's, navigation markers, spatial mapping, etc. | Embodiments |
|---|---|---|
| | | virtual reamer external to the patient's bone and/or soft-tissue and/or optionally also with virtual reamer hidden by or inside the patient's bone and/or soft-tissue; alternatively, OHMD can project humeral reaming axis, e.g. external to the bone, optionally also hidden portions inside the bone; surgeon can align physical reamer shaft or long axis of physical reamer so that physical reamer shaft and/or long axis of physical reamer is superimposed onto virtual reaming axis, optionally for portions external to the patient's bone and/or subchondral bone and/or cartilage including normal and/or damaged or diseased cartilage and/or portions hidden by or inside the patient's bone and/or soft-tissues |
| Broach humeral canal | ✓ | OHMD can project virtual broach, e.g. with position/orientation/alignment based on combined glenoid-humeral version or only humeral version; surgeon can align and/or superimpose physical broach and/or stem with virtual broach; surgeon can align physical broach and/or stem, e.g. based on combined glenoid-humeral version or only humeral version, with virtual broach external to the patient's bone and/or soft-tissue and/or optionally also with virtual broach hidden by or inside the patient's bone and/or soft-tissue; alternatively, OHMD can project humeral broaching axis, e.g. external to the bone, optionally also hidden portions inside the bone; surgeon can align physical broach shaft or long axis of physical broach so that physical broach shaft and/or long axis of physical broach is superimposed onto virtual broaching axis, optionally for portions external to the patient's bone and/or subchondral bone and/or cartilage including normal and/or damaged or diseased cartilage and/or portions hidden by or inside the patient's bone and/or soft-tissues |
| Virtual implant component placement, sizing & fitting on live 3D anatomy of the patient | ✓ | OHMD can project virtual implant, e.g. glenoid component superimposed onto physical glenoid. Using virtual or other interface, surgeon can move implant, evaluate size, fit, e.g. relative to external facing bony glenoid and/or glenoid rim and/or relative to internal, hidden bony glenoid bone stock, adjust for soft-tissue impingement; evaluate screw position and/or placement in glenoid bone vault on superimposed CT, e.g. for optimal bone fixation and/or maximal amount of bone stock surrounding screw and/or anchor |
| Identify center of glenoid, place central drill hole | ✓ | OHMD can project virtual glenoid template or virtual drill hole(s) registered with and superimposed onto physical glenoid, align & superimpose physical template or drill with virtual glenoid template or virtual glenoid drill hole(s) |
| Ream glenoid, glenoid reamer | ✓ | OHMD can project virtual reaming axis registered with and superimposed onto physical glenoid, surgeon can align physical reamer with virtual reaming axis; optionally, OHMD can project glenoid reaming axis external to glenoid bone for aligning and/or superimposing physical reamer, e.g. long axis, shaft; optionally, OHMD can also project glenoid reaming axis inside the glenoid bone, e.g. in order to show position relative to glenoid bone stock, e.g. for placement of a central screw or anchor aligned with the glenoid reaming axis; glenoid reaming axis and/or glenoid component position, |

TABLE 17-continued

Benefits of OHMD guidance for performing shoulder arthroplasty. Exemplary surgical steps are listed in an illustrative, non-limiting sequence along with corresponding embodiments for using one or more OHMDs to guide the procedure.

| Illustrative Surgical Steps | Optical Guidance with OHMD, e.g. using optical markers, LED's, navigation markers, spatial mapping, etc. | Embodiments |
|---|---|---|
|  |  | orientation, alignment, version, inclination can be optimized to achieve best possible compromise between glenoid bone coverage, e.g. relative to glenoid rim, glenoid component position, orientation, alignment, version, and/or inclination near the patient's native, unoperated glenoid position, orientation, alignment, version, inclination and/or joint space, and/or optimal bone fixation, e.g. with maximum amount of glenoid bone surrounding glenoid component screws and/or anchors. |
| Drill template, place drill holes | ✓ | OHMD can project virtual drill template registered with and superimposed onto physical glenoid; virtual drill template can be projected and/or superimposed onto external surface of physical glenoid, optionally in tangent, e.g. non-intersecting fashion to facilitate non-intersecting placement of physical glenoid template; surgeon can align physical drills and/or screws with virtual drill template; optionally virtual drill holes and/or paths can be projected by OHMD inside the patient's glenoid bone |
| Place trial glenoid component | ✓ | OHMD can project virtual implant component or virtual implant trial component registered with and superimposed onto physical glenoid, surgeon can check position/alignment of physical trial component relative to virtual implant component or virtual implant trial component |
| Place, impact humeral component | ✓ | OHMD can project virtual impactor axis registered with and superimposed onto glenoid, surgeon can align physical impactor with virtual impactor axis, e.g. projected by one or more OHMDs external to the humeral bone and/or optionally also projected onto the coordinates of the inside of the bone and/or soft-tissues |
| Sizing of humeral head with trial components, e.g. at beginning or later phases of the procedure | ✓ | Using, for example, optical markers and/or IMU's and/or navigation markers on humeral epicondyles and circular motion, determine center of rotation using optical or other detection & pivoting algorithm; surgeon can select humeral head size and glenoid component thickness to maintain center of rotation of shoulder joint; optionally combine with virtual implant component placement, sizing & fitting, e.g. surgeon can select glenoid component that approximate the patient's glenoid articular surface and a humeral head component with a diameter that approximates that of the native humeral head and/or a humeral head component with a bearing surface that approximates the location of the native articular surface of the patient's humeral head, e.g. for a given stem position and neck length, angle, inclination and offset |

One or more optical markers, e.g. with geometric patterns, LED's, navigation markers, e.g. RF or infrared markers, calibration or reference phantoms, 3D scanner, and other techniques described in the specification or known in the art can be used for registration of the intra-operative anatomy with, for example, the pre-operative anatomy, for example as visualized or detected in a scan, and one or more OHMDs. Registration can be performed using one or more coordinate systems, e.g. a common coordinate system and, optionally, sub-coordinate systems, e.g. coordinate systems referenced to the common coordinate system. One or more optical markers, e.g. optical markers with geometric patterns, LED's, navigation markers, e.g. RF or infrared markers, calibration or reference phantoms can be attached to the shoulder joint, e.g. the coracoid process, the acromion and the greater tuberosity of the proximal humerus, or other anatomic structures. The one or more optical markers and/or LED's can be detected using a camera, video or image capture system and/or 3D scanner integrated into, attached to or separate from one or more OHMDs using the techniques described in the specification. Navigation markers can be detected using a navigation system. Surgical instruments can be tracked using the techniques described in the specification, for example in the Example entitled "Tracking of Surgical Instruments" and their visible portion, e.g. an axis, can be aligned with a virtual surgical instrument or a virtual axis, e.g. a reaming axis, e.g. a glenoid reaming axis or a humeral broaching axis. The hidden portion of surgical instruments, e.g. hidden inside the soft-tissue, can be displayed if the geometry of the instrument is known and the instrument is tracked, for example using optical markers, LED's, IMU's, navigation markers, calibration or reference phantoms, 3D scanners, and/or spatial mapping. The hidden portion of physical surgical instruments can optionally be displayed with and, optionally, aligned with a virtual reaming or broaching or other axis or a predetermined virtual instrument position and/or orientation and/or alignment and/or direction of travel, which can be simultaneously displayed by the OHMD.

A pointer or pointing device, e.g. with one or more attached optical markers, e.g. with geometric patterns, and/or LED's, IMU's, navigation markers, calibration or reference phantoms, can be used to touch and point at anatomic structures in the shoulder joint, e.g. the glenoid, coracoid or greater tuberosity of the humerus or other structures, for example, while performing a rotating or circular or elliptical movement and a pivoting algorithm or other algorithms can be used for tracking the instrument movement and, with that, for determining the location of the tip of the pointer or pointing instrument and the coordinates of the anatomic landmark that the tip is touching or in contact with.

As an alternative to tracking the anatomy and/or instruments using one or more of optical markers, LED's, IMU's, navigation markers, calibration or reference phantoms, the patient anatomic landmarks, e.g. the coracoid, glenoid, or greater tuberosity of the humerus, and the surgical instruments, e.g. a reamer, a saw or a broach, can be captured, registered and tracked during the procedure with an optical imaging device, e.g. a 3D scanner. The patient anatomic landmarks, e.g. the coracoid, glenoid, or greater tuberosity of the humerus, and the surgical instruments, e.g. a reamer, a saw or a broach, can be captured, registered and tracked during the procedure using image capture and/or video capture, for example using an image capture or video system integrated into, attached to or separate from the OHMD. Images can be processed to detect anatomic landmarks and/or to detect instruments and track either or both of them during the procedure.

For example, the software can utilize the OpenCV code (e.g. OpenCV 2.4, Intel Inc., Santa Clara, Calif.), which can be used to define a local marker coordinate system and pose of each marker. The Microsoft Hololens spatial mapping library (Microsoft, Redmond, Wis.) can be used to produce a surface mesh using depth camera scans; planes can be identified using the MS Hololens object detection library. Spatial mapping information can be used to define marker coordinates relative to the OHMD. Marker coordinates can be further refined using depth information based on pre-existing information on the known shape and dimensions of the markers. Scaling factors can be applied to the virtual data using the pre-existing known shape and dimensional information of the markers. The spatial maps can be used to translate from local marker coordinate system, e.g. markers attached to the patient's shoulder or the OR table, to global OHMD coordinates.

In the patient's shoulder joint, one or more OHMDs, one or more virtual data sets or virtual data can be registered in a common coordinate system. In a shoulder joint, two opposing articular surfaces, e.g. with opposing cartilage surfaces and underlying subchondral bone, can be registered separately and/or optionally jointly in a coordinate system, e.g. a common coordinate system. A first articular surface can be located on the scapular side, i.e. on the glenoid, a second articular surface can be located on the proximal humerus. Registering the first articular surface and/or or associated bones and/or structures and the second articular surface and/or or associated bones and/or structures separately in a common coordinate system can have the benefit of allowing movement, e.g. flexion and/or extension and/or rotation and/or abduction, and/or adduction, and/or elevation and/or other movements, e.g. translation, of the first articular surface and/or or associated bones and/or structures, e.g. on the glenoid, in relationship to the second articular surface and/or or associated bones and/or structures, e.g. on the proximal humerus, while maintaining registration of the first articular surface and/or associated bones and/or structures, e.g. on the glenoid, and/or the second articular surface and/or or associated bones and/or structures, e.g. on the proximal humerus, e.g. in a common coordinate system or a subcoordinate system, optionally along with one or more OHMDs and/or fixed structures in the operating room, e.g. the OR table, and/or other structures or anatomic landmarks of the patient, e.g. irrespective movement of the individual portions of the joint. In this manner, the shoulder joint can be placed in different positions, e.g. flexion, extension, rotation, abduction, adduction, e.g. a degree of shoulder abduction, e.g. 70, 80, 90 or other degrees, e.g. during placement of a glenoid component, and a degree of shoulder abduction, e.g. 0, 20, 30 or other degrees, during placement of the humeral component, or any other degrees for either component placement depending on surgical technique and surgeon preference, while the registration of the glenoid and/or the registration of the proximal humerus and the display of any virtual data, e.g. a virtual surgical guide, a virtual cut plane, a virtual implant component on the glenoid and/or the proximal humerus can be maintained and superimposed onto the corresponding anatomic area, e.g. the area intended for implant component placement, irrespective of the movement of individual portions of the joint, thereby allowing the one or more OHMDs to maintain anatomically registered displays of virtual data superimposed onto the corresponding portions of the physical joint anatomy, e.g. an articular surface, including a normal, damaged and/or diseased cartilage and/or subchondral bone and/or cortical bone, e.g. in a tangent, intersecting and/or offset manner, e.g. external and/or internal to the normal, damaged and/or diseased cartilage and/or subchondral bone and/or cortical bone.

Surgical instruments, e.g. a humeral cut guide, a humeral reamer, a humeral broach, a glenoid reamer, a glenoid template, drills, pins, saws, etc., can be tracked in the surgeon's live view of the patient through one or more OHMDs and one or more OHMDs can project the invisible parts of an instrument hidden by the tissue and its direction relative to the OMHD. A predetermined reaming axis, broaching axis, drill axis, instrument path, position, orientation and/or alignment inside the patient's tissue, e.g. bone and/or soft-tissue, can be co-projected by the OHMD in addition to the hidden portion of the instrument. Optical markers can be attached to the instrument, e.g. a humeral cut guide, a humeral reamer, a humeral broach, a glenoid reamer, a glenoid template, drills, pins, saws, etc. The markers can be fixed at defined positions on the instrument. With the geometry of the instrument known, e.g. a humeral cut guide, a humeral reamer, a humeral broach, a glenoid reamer, a glenoid template, drills, pins, saws, etc., the position and orientation of the instrument can be calculated. For example, for an instrument like a pointer with a tip for which its rotary orientation is aligned with the pointing axis, only two markers can be used or one marker with sufficient geometric information, e.g. along the long axis of the instrument, for accurate coordinate determination, e.g. 2, 3, 4, 5, 6, 7, 8, 9 or 10 cm long and/or apart in length and, for example, 1, 2, 3, 4, 5, 6, or 7 or other cm wide and/or apart in width, depending also on the spatial resolution of the camera system. Generally, the greater the spatial resolution of the camera or video system, the smaller the possible marker size can be. The markers' 3D coordinates can be recognized by the one or more OMHD's using a camera or video system integrated into or attached to the OHMD. Using the coordinates of the first and second marker, or a single marker with sufficient size and/or length and/or width and/or depth to determine a long axis, e.g. 2, 3, 4, 5, 6, 7, 8, 9 or 10 cm long and/or 1, 2, 3, 4, 5, 6, or 7 or other cm wide and/or 1, 2, 3, 4, 5, 6, or 7 or other cm deep, a vector pointing in the direction of the tip can be calculated and displayed by the one or more OHMDs to indicate the direction of the hidden portions of the instrument superimposed onto the surgical site, enabling the surgeon to align the instrument with the predetermined path, e.g. a reaming axis of the glenoid, a reaming axis of the humerus or a broaching axis of the humerus, defined using the standard or virtual planning interface and also optionally projected by the one or more OHMDs, e.g. together with a projection of any portions of the instruments hidden inside the tissue. The second approach can use pivoting, a mathematical technique for determining the position of the tip. With pivoting, the instruments tip can be fixed in one position on the tissue while the whole instrument can be moved. The attached optical markers can move on a spherical surface. This leads to an accurate registration of an entry or touch point.

In another example, spatial maps can be used determine the coordinates of anatomical landmarks. Anatomical landmarks on the patient's physical anatomy can be digitized for registration with virtual models. For this purpose, the motion of a pointer instrument with optical markers, LED's or navigation markers or other markers attached can be tracked while its tip can be moved by the surgeon over the surface of the anatomical landmark, e.g. the coracoid process, glenoid rim or humeral head or other anatomical landmark. As the surgeon "paints" the landmark surface, the position of the instrument tip can be calculated from the optical markers, LED's or navigation markers or other markers using some of the methods described in the specification, for example in the section with heading "Tracking of Surgical Instruments", thereby generating a point cloud and/or surface of the anatomic landmark or the patient's anatomy, e.g. an articular surface.

Generating Virtual Models

In another embodiment, a PC or Mac based application that imports CT data in standard DICOM 3.0 format can be used for surgical planning of shoulder arthroplasty, e.g. prior to the actual procedure. An open-source DCMTK DICOM Toolkit (OFFIS, Oldenburg, Germany) can be used to implement DICOM related functionality. Surfaces of the shoulder bones can be extracted from the CT scan using an isosurface algorithm, e.g. similar to the one published by Lorensen (Lorensen WE, Cline HE. [ed.], in M. C. Stone. 1987. Marching cubes: A high resolution 3d surface construction algorithm. Proceedings of SIGGRAPH 87. pp. 163-169). A user interface can be used to manually separate surfaces for humerus and scapula. Furthermore, the user interface can be used to mark the surfaces of bony landmarks such as the humeral head and greater tubercle or the coracoid process and glenoid rim of the scapula, for example using a tracing tool or a seed point deployment tool. All virtual bone model surfaces can be saved as mesh data in OBJ file format. For communication between the OHMD and the PC, a client-server communication system can be used employing, for example, the Unity Transport Layer application programming interface. Data can be transferred via a WIFI connection between the OHMD and the PC and/or computer.

Surface Registration Methods to Register Virtual Models with the Live Surface Data For the alignment of a virtual model derived from a CT scan and a live view through the see-through OHMD, an algorithm for surface registration of the bony landmarks identified in the virtual model of the humerus and the scapula with, for example, landmarks digitized by the surgeon using a pointer "painting" or touching the bony surfaces and generating surface points as described in the preceding specification can be used. This algorithm can be based on the Iterative Closest Point technique as described, for example by Besl et al. (Besl P J, McKay N D. 2, 1992. A method for registration of 3-D shapes. IEEE Trans PAMI, Vol. 14, pp. 239-256), which can minimize the distance between pairs of corresponding points in the surfaces to be registered using a rigid transformation. The result of the registration of the bone models with the digitized landmarks can consist of two transformations $H_1$ and $S_1$ for the humerus and scapula describing the alignment. Any changes in position or orientation of the view through the OHMD can require an update of the registration. For this purpose, one can, for example, attach optical markers, LED's, navigation markers or other markers to the humerus and scapula, e.g. the coracoid process, at the beginning of the surgery. The baseline 3D coordinates of these markers can be measured and saved during the registration, which can include the initial OHMD position and orientation. The information from the markers can, for example, be used to update the registration information.

Software components to display virtual model(s) overlaid with the live view through the OHMD.

The optical markers attached to humerus and scapula can be continuously or intermittently tracked and, using, for example, the spatial relationship between the virtual model and the optical markers as described in the preceding sections, the position of the display of the virtual model, e.g. a 3D reconstruction of a CT or MRI scan or other virtual data, e.g. data display or highlighting sensitive anatomic structures, overlaid on the live, physical anatomy of the patient can be updated in real time. After transformation into the coordinate system of the OHMD live view using, for example, the transformation matrices $H_1$ and $S_1$, the meshes of the virtual humerus and scapula models or any related virtual surgical plan, e.g. a virtual humeral neck cut or a glenoid or humeral reaming or broaching axis, can be rendered as holograms using, for example, the Microsoft HoloToolkit programming interface (Microsoft, Redmond, Wis.). Afterwards, the registration can be updated continuously to compensate for changes in the OHMD view in real time. For this purpose, the optical markers attached to humerus and scapula and/or glenoid, including, for example, the coracoid process, can be continuously tracked. The registration can, for example, be continuously updated as follows: For the humerus and the scapula and/or glenoid, transformation matrices $H_2$ and $S_2$ can be calculated that map the initial marker coordinates, e.g. determined during the first registration, to the current marker coordinates in the OHMD coordinate system. The updated alignment of the virtual bone models with the live view of the OHMD can then result from the concatenation of $H_2$ with $H_1$ and $S_2$ with $S_1$, respectively.

Surgical planning system for total shoulder arthroplasty using, for example, a PC based and/or a novel virtual OHMD user interface and software to project a predetermined reaming path and virtual surgical instruments, including external to the tissue and/or internal to the tissue, e.g. hidden inside the tissue.

A PC based user interface for surgical planning can be implemented on a server in the OR. The interface can allow a dual or multiple display mode of axial, sagittal and coronal 2D views including, for example, oblique projections. The interface can also allow display of a 3D reconstruction of the bony anatomy, optionally with transparency views, e.g. with simultaneous display of 2D images and/or reconstructions or multiple 3D displays of various tissues. The interface can provide for importing and display of 3D CAD files of different implant components as well as screws or anchors for placement in the glenoid bone vault. The interface can allow for display of 2D and 3D CT slices and/or images through the glenoid, e.g. showing the glenoid bone stock, optionally with concurrent display of virtual implant component(s), and/or a predetermined instrument path and/or a predetermined anchor placement and/or a predetermined reaming, broaching and/or impaction axis, optionally external to the articular surface, e.g. for virtual guides or templates, e.g. in non-tangent or tangent position relative to the articular surface, e.g. non-intersecting, and, optionally, also interior to the articular surface inside the patient's bone, optionally with co-display of hidden portions of the physical instrument. The interface can provide for importing and display of 3D CAD files of different instruments and instrument component, e.g. saw guides, reamers, broachers etc. CAD files for all components can use the STL (Stereolithography) mesh file format. The CAD files can optionally be converted into Wavefront Object file format (*.obj) for display by the OHMD. Using a mouse or track ball, the interface can allow the surgeon to define entry points and vectors for instruments and glenoid screws or anchors, e.g. a central glenoid screw. The PC based interface can allow the surgeon to project glenoid and humeral components onto the glenoid and humerus. The PC based interface can allow to set the following exemplary, non-limiting parameters for the virtual surgical plan: 1. Glenoid component retroversion and/or inclination, 2. Glenoid component reaming and/or drill depth, 3. Glenoid component screw location and/or orientation, screw length, 4. Humeral component placement incl. proximal humerus cut location, 5. Humeral component neck angle for component selection, 6. Humeral component version, 7. Glenoid and/or humeral component version, e.g. for a combined glenoid-humeral version similar to or substantially the same as the patient's native, unoperated anatomy, optionally corrected for deformity, 8. Humeral offset. Planning data generated in this manner, for example using combined gleno-humeral version, can be used with surgical navigation, robotic guided surgery and OHMD guided surgery and can be used with or entered into their respective virtual surgical plan and surgical plan executions. The planning data can, for example, be displayed by one or more OHMDs in addition to the 2D or 3D CT or MRI or other images and can serve as input for real-time optical guidance during the intervention. 3D data can be displayed by the OHMD registered with and superimposed onto the patient's shoulder anatomy; if the surgeon selects to display 2D images, e.g. oblique coronal or axial, the software can display the selected slice(s) registered with and superimposed onto the corresponding coordinates in the patient. A virtual interface for implant placement superimposed onto the live anatomy of the patient for sizing and evaluating implant fit can also be implemented. The virtual, e.g. stereoscopic and/or electronic holographic interface can combine hand gestures and hologram menu buttons for user interaction. It can be based on the functionality offered by the HoloToolkit Application Programming Interface (API) (Microsoft, Redmond, Wis.) and can, for example, consist of 3 modes for manipulation of the implant components. Additionally, a cursor that is controlled by the view direction (gaze cursor) can be used for implant placement, movement, sizing and/or fitting. A virtual menu can be projected into the field of view, e.g. next to the surgical field. It can include a button for selection of the implant component (e.g. a glenoid or a humeral component, available, for example, in multiple sizes and shapes), a button for size selection, and multiple buttons, e.g. three, for mode selection. The three modes can be 1.) translation along the x-axis (horizontal) and y-axis (vertical), 2.) rotation around the x- and y-axis, and 3.) translation along and rotation around the z-axis.

The initial placement of an implant component can be controlled by a gaze cursor, e.g. integrated into the OHMD. The user can point the gaze cursor to the shoulder joint where the implant component can be placed by changing the view direction. The component can be locked in place using a finger tap gesture or a voice command. The initial z position (e.g. distance from the OHMD display) can be based on a surface mesh, e.g. created by a depth camera, e.g. integrated or attached to the OHMD or separate from the OHMD. After this initial placement, the user can adjust the position and orientation of the component using any of the 3 modes. A mode can be selected by pointing the gaze cursor to one of the respective menu buttons and by selecting the button, for example with a finger tap gesture or voice command. Once a mode has been selected, position or orientation of the component can, for example, also be adjusted with horizontal or vertical hand movements. For example, using gesture recognition, e.g. as integrated in the Microsoft HoloLens utilizing the HPU (Microsoft, Redmond, Wis., the surgeon's hands and/or fingers can be tracked. The software can project the implant component using the OHMD at a defined location relative to the coordinates of the surgeon's hand or select fingers, e.g. offset 1, 2, 3, 4, 5, 6, 7, 8, 9 or 10 cm in z-direction, x-direction, y-directions or combinations thereof relative to the coordinate(s) of the surgeon's hand or select fingers, e.g. the fingertip(s). As the surgeon moves the hand or select fingers towards or away from the joint, the OHMD projection of the implant component can follow accordingly, e.g. traveling the same distance or a lesser distance or a greater distance. For example, distances traveled by the virtual projection of the implant component(s) can be a ratio of the distance traveled of the hands or fingers, e.g. 3:1, 2:1, 1.5:1, 1.2:1, 1:1, 1:1.1, 1:1.3, 1:1.5, 1:2, 1:3, 1:4. Any ratio is possible. Any linear or non-linear relationship is also possible between movement of the hands or fingers and the virtual implant component(s). A low ratio of hand or finger movement to virtual implant component movement, e.g. 1:3, or 1:4, can be desirable when quick placement, e.g. during initial virtual implant placement, is desirable. A high ratio of hand or finger movement to virtual implant component movement, e.g. 3:1, or 2:1, can be desirable when careful accurate placement of a virtual implant component is desired, e.g. in small spaces or small joints. A low ratio of hand or finger movement to virtual implant component movement (small hand or finger movement results in large virtual implant component movement) can be desirable during implant sizing, i.e. evaluation of different implant sizes projected onto the physical implantation site of the patient. A high ratio of hand or finger movement to virtual implant component movement (large hand or finger movement results in small virtual implant component movement) can be desirable during the final implant fitting and/or alignment. Once the final implant position including alignment has been achieved, the surgeon can execute a voice, gesture or other command to "lock" the coordinates of the virtual implant coordinate in the common coordinate system. The coordinates can then be used to develop, adjust or modify one or more surgical steps for implant placement, e.g. a burring of bone, a drilling, reaming, broaching or cutting of bone.

As an alternative, a rod or wand with two or more attached optical markers, LED's or navigation markers or other markers can be used to place, move, align, orient, fit and size the one or more implant components. The coordinates of the optical markers, LED's or navigation markers or other markers can be tracked as described in the specification. The rod or wand can be shaped to be held between the thumb and index finger of the surgeon. The software can project the implant component using the OHMD at a defined location relative to the coordinates of the wand, e.g. offset 1, 2, 3, 4, 5, 6, 7, 8, 9 or 10 cm in z-direction, x-direction, y-directions or combinations thereof relative to the mid-point or other coordinate(s) of the rod or wand. As the surgeon moves the rod or wand towards or away from the joint, the OHMD projection of the implant component can follow accordingly, e.g. traveling the same distance or a lesser distance or a greater distance. For example, distances traveled by the virtual projection of the implant component(s) can be a ratio of the distance traveled of the physical rod or wand, e.g. 3:1, 2:1, 1.5:1, 1.2:1, 1:1, 1:1.1, 1:1.3, 1:1.5, 1:2, 1:3, 1:4. Any ratio is possible. Any linear or non-linear relationship is also possible between movement of the physical rod or wand and the virtual implant component(s). A low ratio of physical rod or wand movement to virtual implant component movement, e.g. 1:3, or 1:4, can be desirable when quick placement, e.g. during initial virtual implant placement, is desirable. A high ratio of physical rod or wand movement to virtual implant component movement, e.g. 3:1, or 2:1, can be desirable when careful accurate placement of a virtual implant component is desired, e.g. in small spaces or small joints. A low ratio of physical rod or wand movement to virtual implant component movement (small rod or wand movement results in large virtual implant component movement) can be desirable during implant sizing. A high ratio of physical rod or wand movement to virtual implant component movement (large rod or wand movement results in small virtual implant component movement) can be desirable during the final implant fitting and/or alignment.

Once the surgeon moves the 3D projection of the implant into the desired position and orientation relative to the joint, the position and orientation can be locked using a voice command or another command. In another example, the rod or wand can include a switch or button that can be activated by pressing it, e.g. with the thumb, when the rod or wand and, with that, the virtual implant component has reached the desired position over the joint.

Different implant components or sizes can be selected with the respective menu buttons. Triggering a button using gaze and finger tap or voice commands, a drop-down list for selection of the implant component and/or size and/or can be displayed.

Someone skilled in the art can recognize that the foregoing embodiments on virtual and other interfaces or methods, systems or devices for placing, moving, aligning, orienting, fitting, sizing etc. of one or more virtual implant components can be applied to any of the other applications in the specification, e.g. partial or total knee replacement, hip replacement, shoulder replacement, ankle replacement, spinal fusion, spinal surgery, disk replacement, ligament repair and/or reconstruction including ACL or other ligaments, dental surgery, dental implants and other dental devices, vascular or other devices etc.

Optionally, a CT scan of the patient can be superimposed by the OHMD, e.g. paired with a display of glenoid screws or anchors. In this manner, the surgeon can optimize the component position with the virtual or other interface relative to the glenoid surface and/or the glenoid rim and/or the underlying bone stock. The surgeon can also optimize the position and/or length and/or thickness of the glenoid screws thereby optimizing bone fixation for the patient. Thus, the glenoid component can be placed using one or more OHMDs by evaluating multiparametric information including, but not limited to, for example: External articular surface shape and size, dimensions, shape of the glenoid; External shape of the glenoid rim; Glenoid version, inclination; Underlying bone stock; Size, depth, width, length, dimensions of underlying bone; Size, depth, width, length, dimensions of bone anchor(s).

Accordingly, the OHMD can, for example, display one or more of the following during one or more of virtual implant or instrument moving, aligning, orienting, sizing, fitting and/or selecting:

Display of virtual data external to the articular surface of the glenoid of one or more of a virtual implant, virtual implant component, a virtual surgical guide, virtual surgical instrument, virtual reaming axis, virtual drilling axis, virtual drill, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration Display of virtual data subjacent to or internal to the articular surface, e.g. inside the bone, e.g. hidden portions of virtual implant, hidden portions of virtual implant component, hidden portions of virtual anchor, hidden portions of virtual instrument, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, size, length, width, depth, dimensions, e.g. length, width, depth, height, volume of area of bone stock, e.g. as seen on a co-displayed CT scan or CT scan information A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in tangent position and/or orientation relative to at least a portion of the articular surface external to the articular surface. A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in non-tangent position and/or orientation relative to at least a portion of the articular surface external to the articular surface. A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in intersecting position and/or orientation relative to at least a portion of the articular surface external to the articular surface. A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in non-intersecting position and/or orientation relative to at least a portion of the articular surface external to the articular surface.

A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in tangent position and/or orientation relative to at least a portion of the articular surface internal or subjacent to the articular surface. A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in non-tangent position and/or orientation relative to at least a portion of the articular surface internal or subjacent to the articular surface. A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in intersecting position and/or orientation relative to at least a portion of the articular surface internal or subjacent to the articular surface. A virtual implant, virtual implant component, a virtual surgical guide, virtual surgical instrument, virtual surgical guide or cut block, virtual surgical tool, virtual reaming axis, virtual drilling axis, virtual drill, and other virtual information or displays can be displayed in non-intersecting position and/or orientation relative to at least a portion of the articular surface internal or subjacent to the articular surface.

Thus, the surgeon can use information about the external anatomy of the patient, the internal anatomy of the patient including bone stock. If the final implant position defined using the virtual interface differs from that developed in a virtual surgical plan, the virtual surgical plan and all subsequent steps can optionally be adjusted accordingly.

Figure 36A:
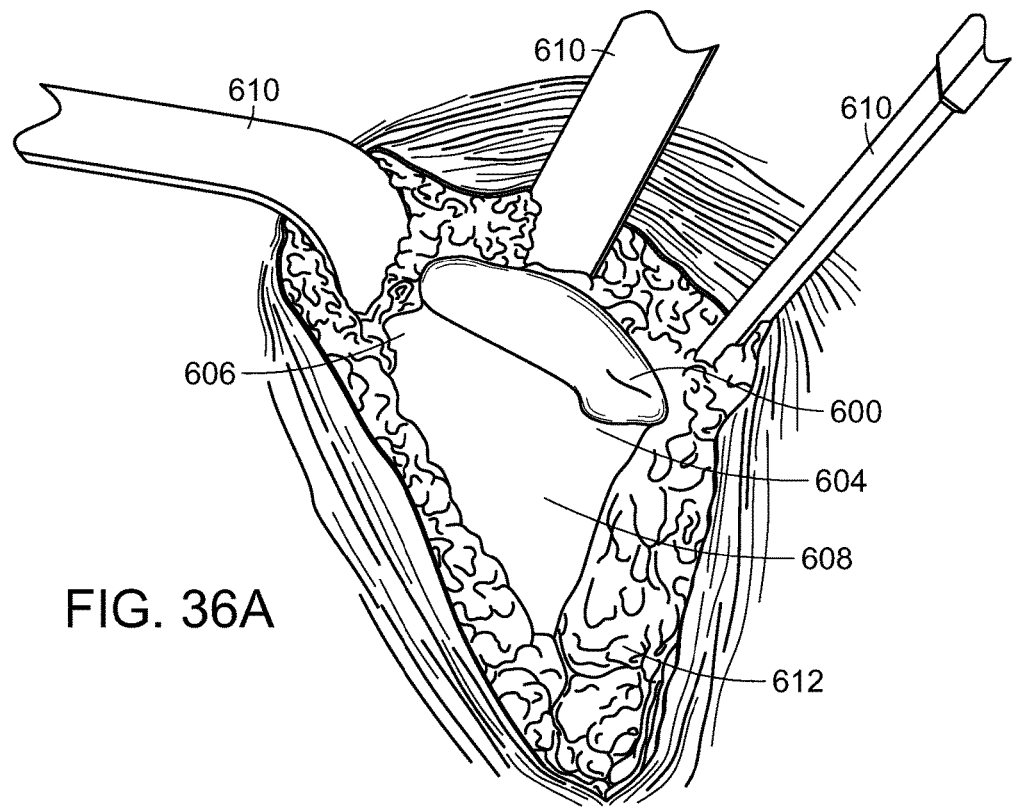
FIGS. 36A-D is an illustrative, non-limiting example of an augmented reality OHMD display of a virtual cut block registered with and superimposed onto the patient's live, physical humerus for aligning a physical cut block.
Figure 36B:
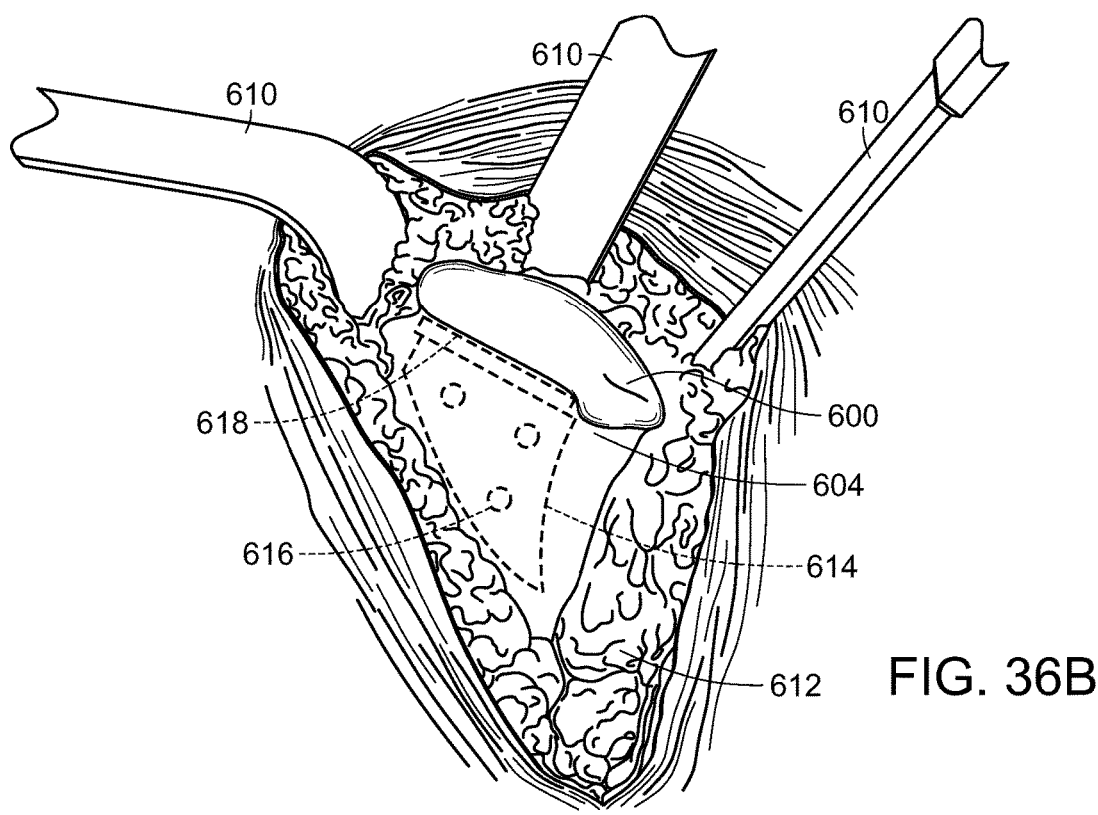
Figure 36C:
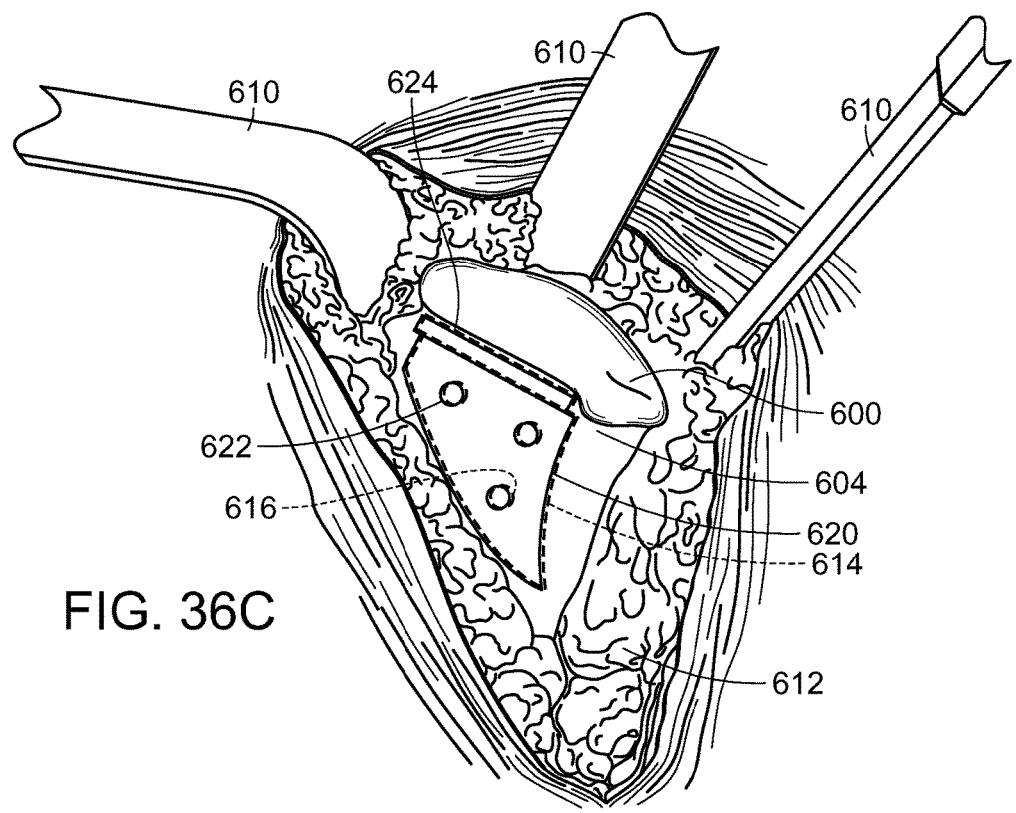
Figure 36D:
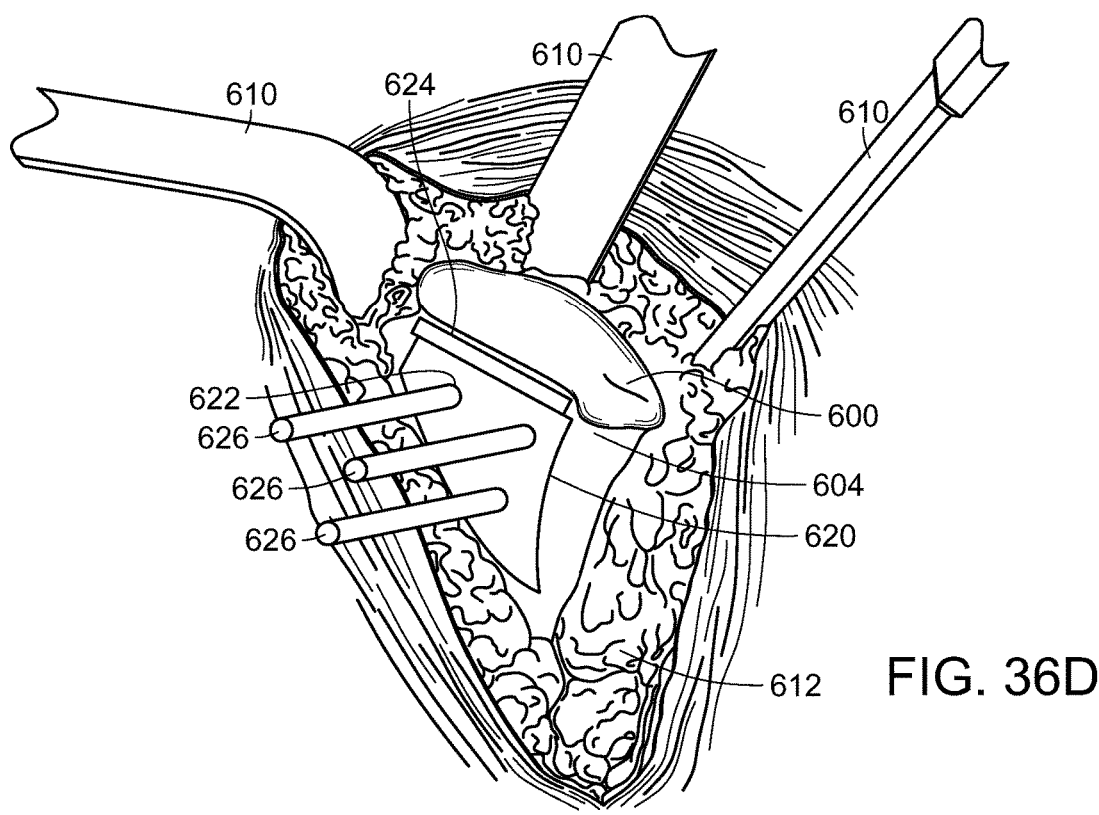
Figure 37A:
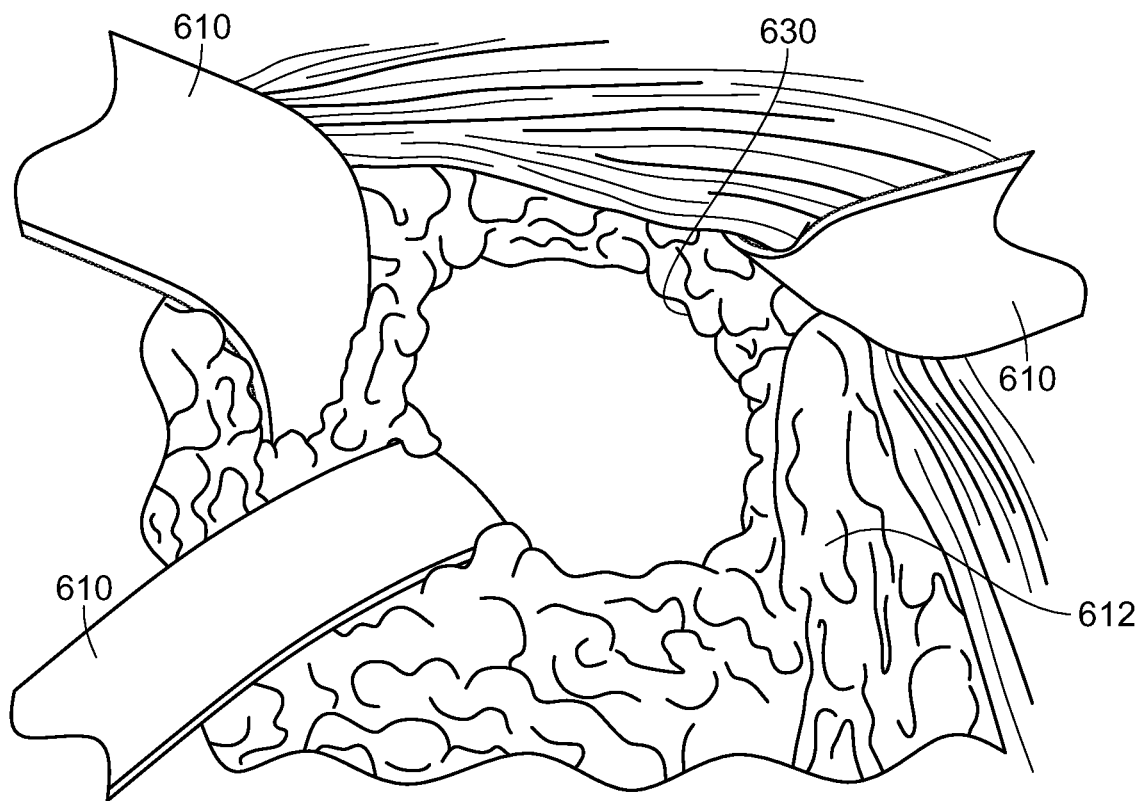
FIGS. 37A-D is an illustrative, non-limiting example of a virtual glenoid template registered with and superimposed onto the patient's live, physical glenoid by the OHMD for aligning a physical glenoid template.
Figure 37B:
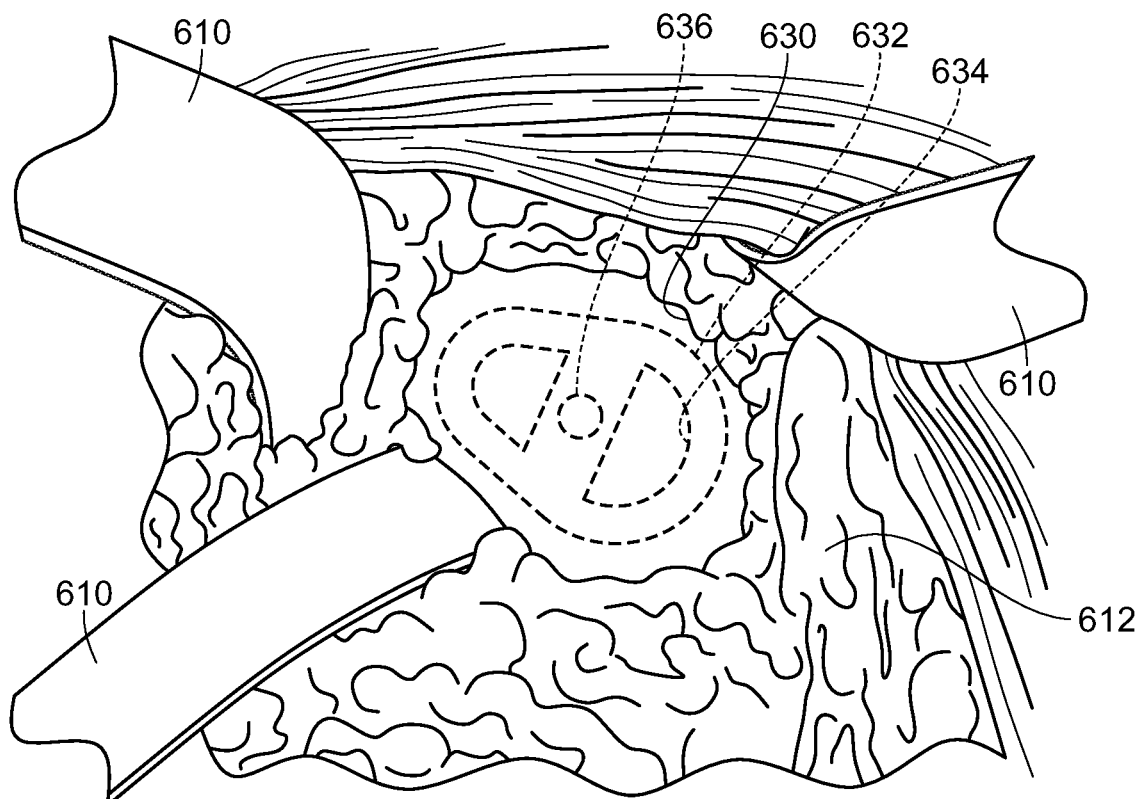
Figure 37C:
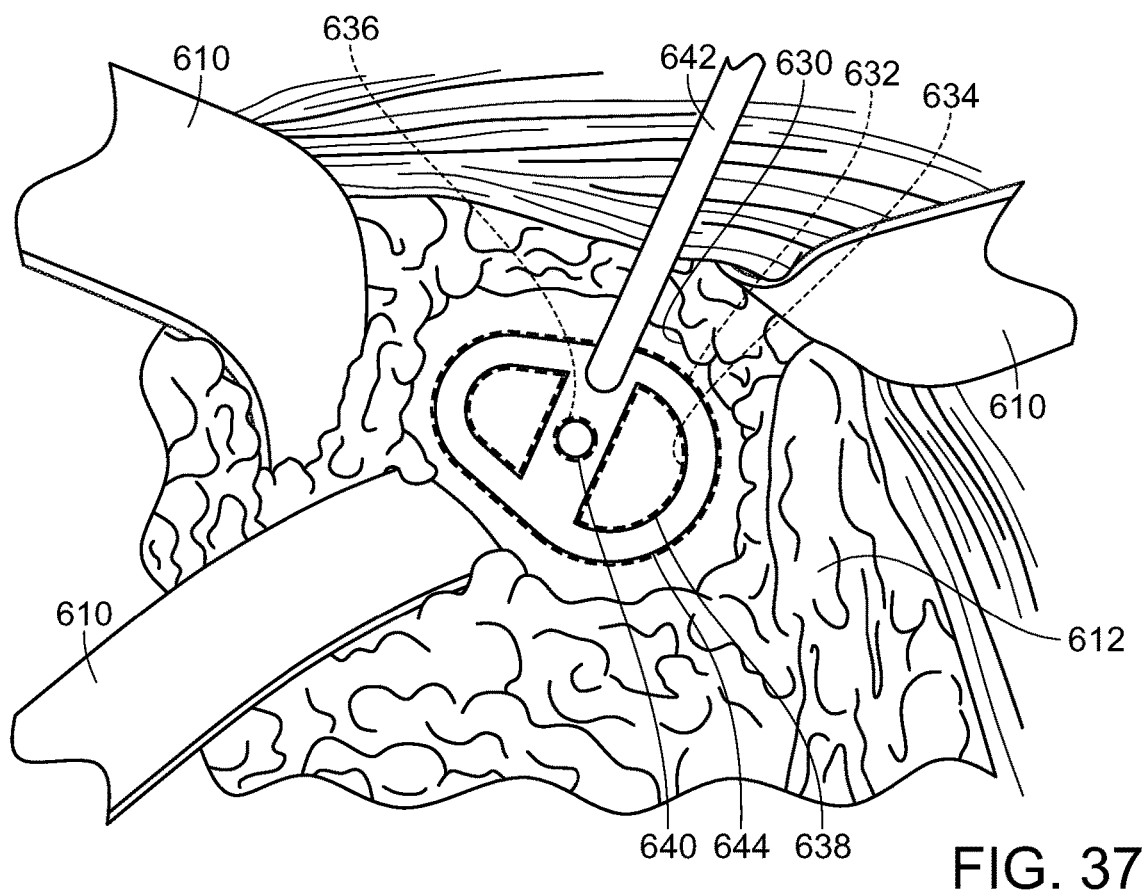
Figure 37D:
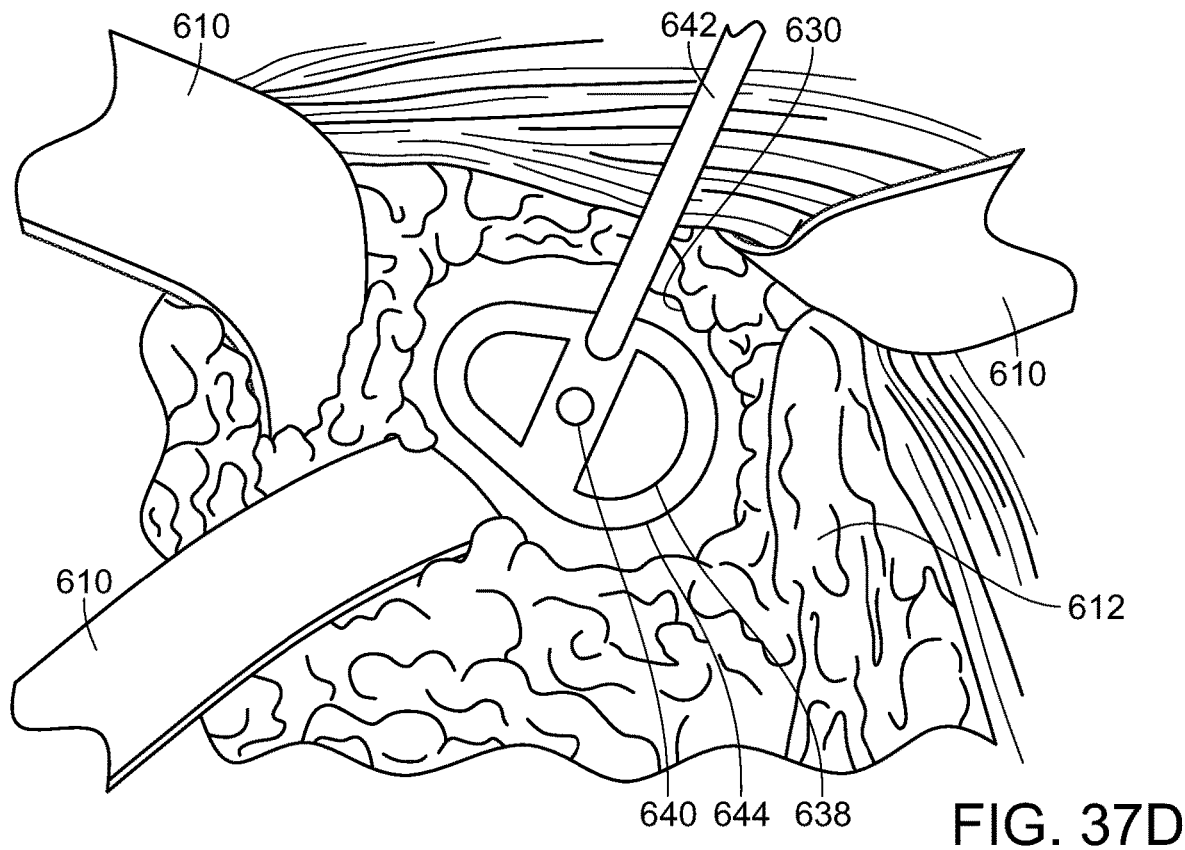

FIGS. 36A-D is an illustrative, non-limiting example of an augmented reality OHMD display of a virtual cut block registered with and superimposed onto the patient's live, physical humerus for aligning a physical cut block. In FIG. 36A, the external surface of the humeral head 600 and the external surface of the humeral neck 604 are exposed. An osteophyte is present 606 at the external surface of the humeral neck 604. The external surface of the humeral shaft 608 is also partially exposed. Various tissue retractors 610 are seen that retract, for example, subcutaneous tissue and/or fat 612. In FIG. 36B, a virtual humeral cut block 614 (stippled line) is projected by the OHMD onto the external surface of the humeral shaft 608 and the external surface of the humeral neck 604 in a predetermined location and orientation for a neck cut, e.g. based on a virtual surgical plan and, for example, a particular implant size and/or dimensions, e.g. a neck length, neck angle, humeral head size. The virtual humeral cut block 614 includes virtual drill holes 616 and a virtual surgical guide 618. The virtual drill holes 616 can facilitate alignment of the physical cut block by aligning the physical drill holes in the physical cut block with the virtual drill holes 616. The virtual drill holes 616 can also facilitate placement of the physical drill(s) by aiming the physical drill at the virtual drill holes. The virtual surgical guide 618 can be used for aligning the physical surgical guide in the physical cut block and for aligning the physical saw blade. In FIG. 36C, the surgeon aligned and superimposed the physical humeral cut block 620 (solid line) seen through the see-through OHMD with the virtual humeral cut block 614 (stippled line) projected by the see-through OHMD onto the external surface of the patient's humeral neck 604 and shaft 608. The physical drill holes 622 are aligned and superimposed onto the virtual drill holes 616. The physical surgical guide 624 is aligned with and superimposed onto the virtual surgical guide 618 seen in FIG. 36B. In FIG. 36D, the surgeon has pinned the physical cut block 620 to the patient's humeral shaft and neck using drills or pins 626 inserted through the physical drill holes 622.

FIG. 37 is an illustrative, non-limiting example of a virtual glenoid template registered with and superimposed onto the patient's live, physical glenoid by the OHMD for aligning a physical glenoid template. In FIG. 37A, various tissue retractors 610 are seen, retracting muscle and subcutaneous tissue and/or fat 612. The glenoid and glenoid rim 630 are exposed. In FIG. 37B, one or more OHMDs project a virtual glenoid template 632 (stippled line), for example in a position and/or orientation and/or alignment for a predetermined and/or intra-operatively determined virtual surgical plan, superimposed onto the external, exposed surface of the glenoid. A concurrent display of radiographic, CT or MRI or other images, for example showing the glenoid bone vault or bone stock or the coraco-acromial arch, by one or more OHMDs is possible, which can be useful for determining or adjusting the position and/or orientation and/or alignment of a virtual and/or physical glenoid template, for example for optimizing the external implant alignment and glenoid coverage, while at the same time optimizing the amount of bone available for fixating one or more glenoid screws or anchors. The virtual glenoid template 632 can include features that correspond to features in the physical glenoid template, e.g. one or more openings with their corresponding edge 634 and a central drill hole 636 for placement of a central screw or anchor in this example. In FIG. 37C, the physical glenoid template 644 (solid line) is aligned with the virtual glenoid template 632 (stippled line); the physical opening including its edge 638 in the physical glenoid template is aligned with the virtual opening 634 in the virtual glenoid template 632. The physical central drill hole 640 is aligned with the virtual central drill hole 636. A handle 642 is also present in the physical glenoid template 644. Once the physical glenoid template 644 is aligned with the virtual glenoid template 632 including one or more of its features, the surgeon can, for example, optionally turn off the OHMD display (FIG. 37D) and execute the surgical step, e.g. drilling for placement of a central screw or anchor or multiple screws or anchors, or pinning the glenoid template. The inclusion of multiple internal or external features, e.g. a central drill hole or multiple drill holes, or one or more openings or extensions or extenders, in the virtual display that correspond to features and have the same or similar dimensions of features in the physical surgical instrument can help improve the accuracy of alignment and superimposition of the physical instrument with the virtual instrument, for example when the virtual instrument is projected onto the external surface of a joint or a bone or a tooth or other anatomic region.

Figure 38A:
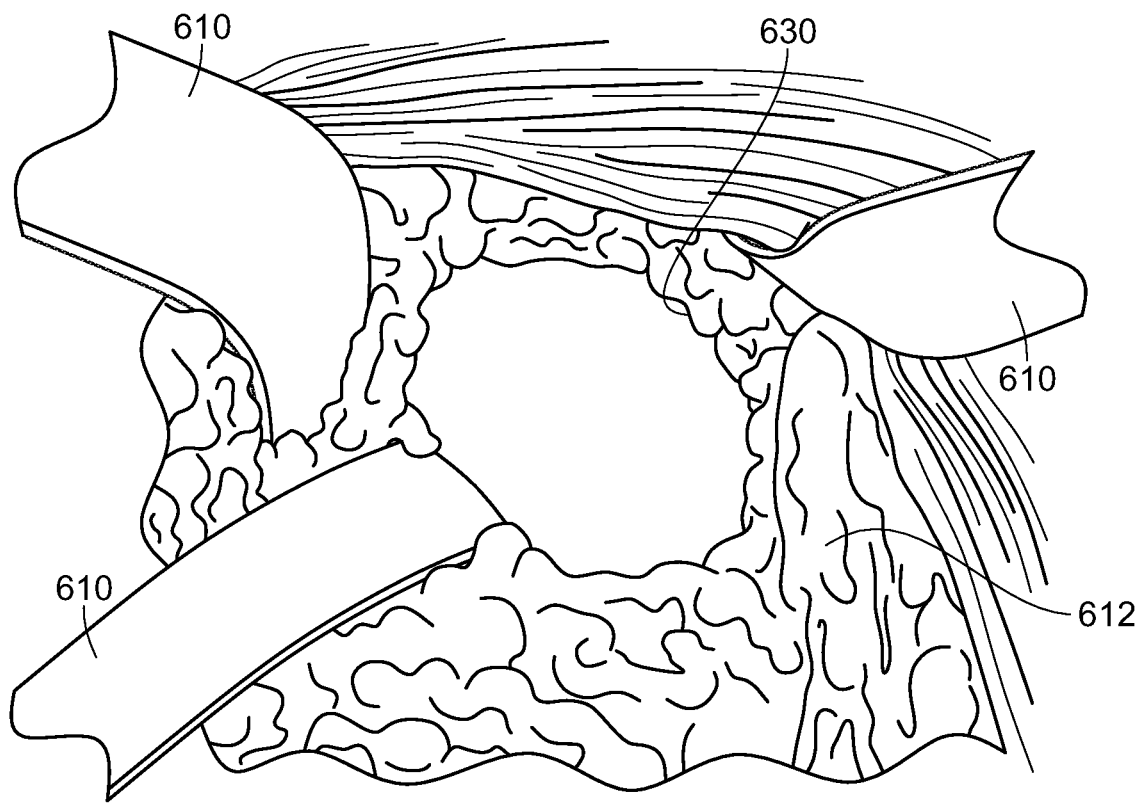
FIGS. 38A-C is an illustrative, non-limiting example of a projection of virtual reaming axis by one or more OHMDs.
Figure 38B:
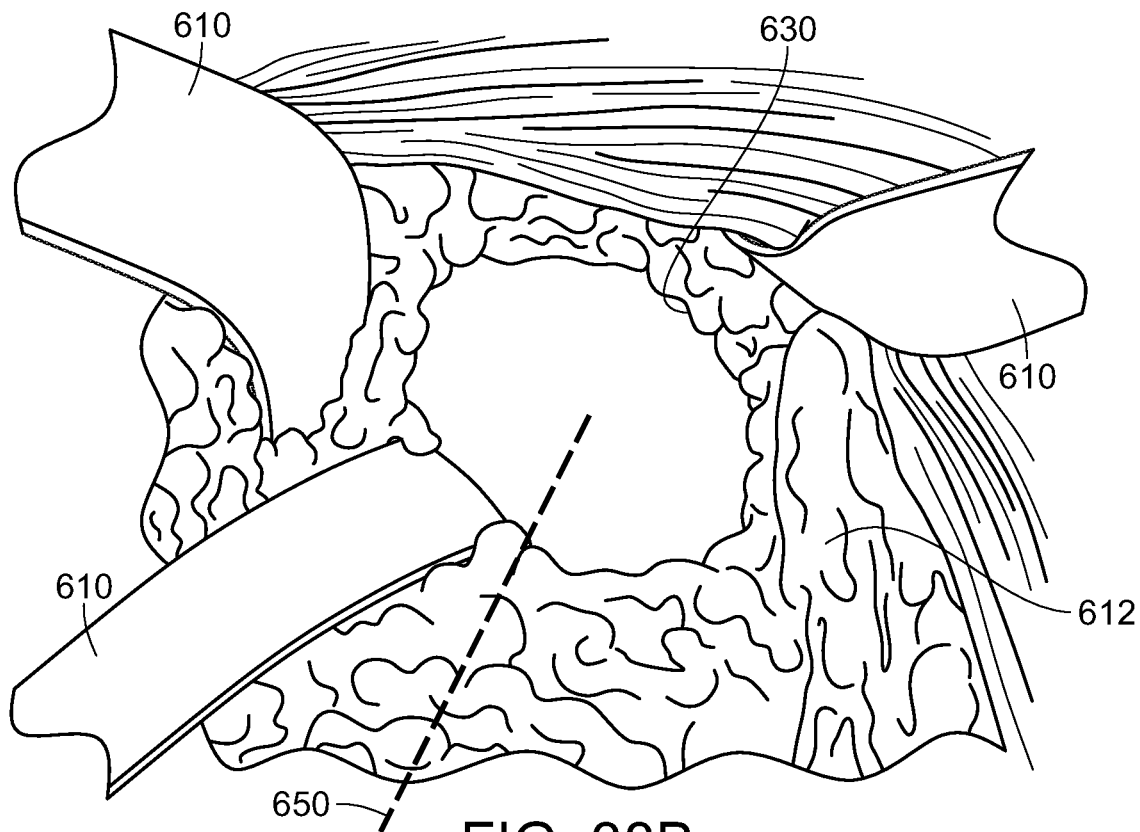
Figure 38C:
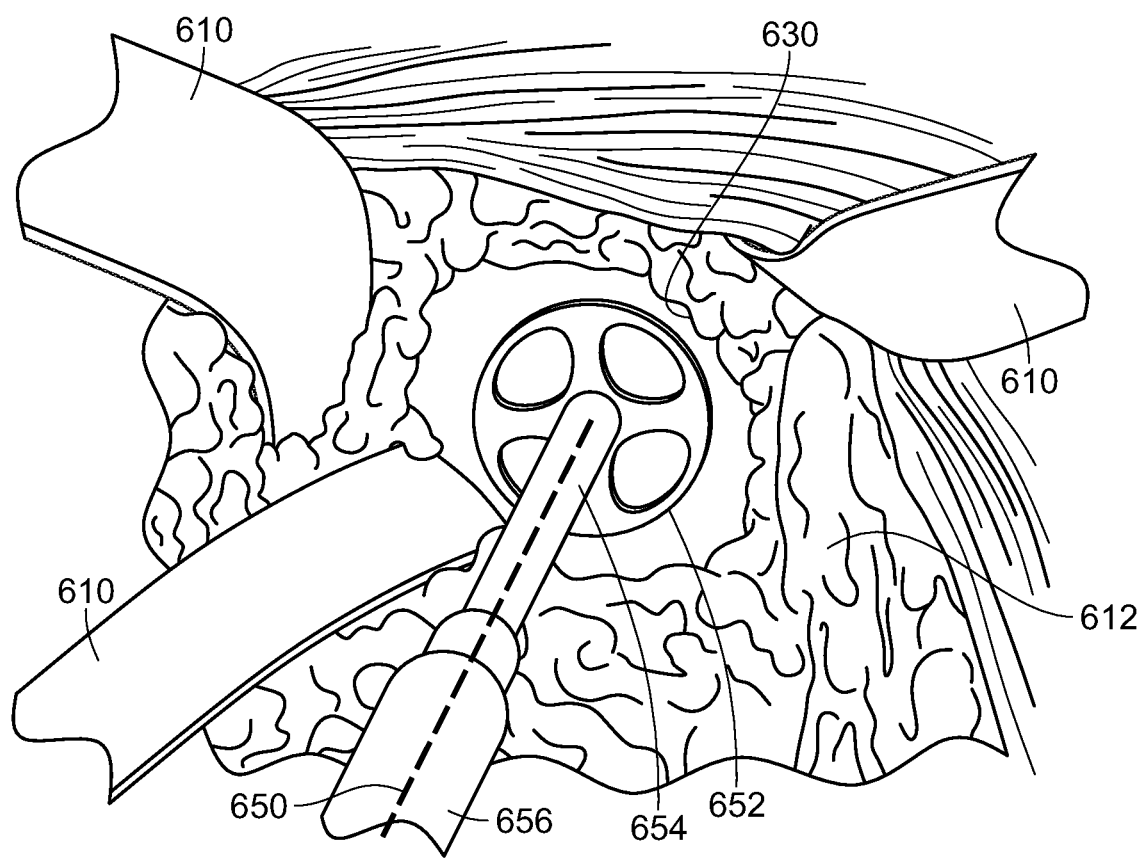

FIGS. 38A-C is an illustrative, non-limiting example of a projection of virtual reaming axis by one or more OHMDs. In FIG. 38A, various tissue retractors 610 are seen, retracting muscle and subcutaneous tissue and/or fat 612. The glenoid and glenoid rim 630 are exposed. In FIG. 38B, one or more OHMDs display a virtual reaming axis 650 (stippled line), e.g. based on virtual surgical plan. The virtual reaming axis 650 is selected, placed, oriented and/or designed to result in a predetermined glenoid component or implant position, orientation, alignment, inclination, and/or version, e.g. based on a combined gleno-humeral version. The virtual reaming axis 650 is projected onto the external articular surface of the joint, e.g. the glenoid. The shaft 654 of the physical glenoid reamer 656 is then aligned with the virtual reaming axis 650 so that, in this example, the virtual reaming axis 650 passes through the center of the shaft and/or the long axis of the reamer/surgical instrument. The physical reaming surface 652 is advanced against the physical glenoid 630 while the alignment and/or superimposition of the center of the shaft 654 of the physical reamer with the virtual reaming axis 650 is maintained and/or while the alignment and/or superimposition of the long axis or central axis of the reamer/surgical instrument with the virtual reaming axis 650 is maintained.

The software can also provide for display of virtual instruments based on a virtual surgical plan, e.g. display of a virtual glenoid template projected by the OHMD onto the glenoid for aligning a physical glenoid template for screw placement. CAD files of virtual instruments, e.g. a glenoid reamer or a glenoid template, can be generated with use of laser scanning or can be obtained directly from the manufacturer. CAD files can be in STL format. CAD files can be converted into Wavefront Object file format (*.obj) for display by one or more OHMDs. The one or more OHMDs can project the virtual surgical instruments with final coordinates based on implant positions determined in the virtual surgical plan.

The accuracy of an OHMD guided surgical technique can be assessed using surgical navigation in cadavers. A commercially available navigation system (Exactech, Gainesville, Fla.) for TSA can be used. Navigation markers can be placed on the coracoid process, glenoid rim and standard locations in addition to, for example, optical markers, LED's, IMU's, navigation markers and/or combinations thereof for OHMD guidance. Both the navigation system and the optical guidance system using OHMDs can be registered to the physical shoulder joint and a virtual model of the shoulder derived from a CT scan by identifying corresponding landmarks in the cadavers and cadaver CT scans, e.g. coracoid, glenoid rim, etc. using navigation and, separately, OHMD guidance pointers, e.g. for "painting" the surface(s) of the one or more anatomic landmarks. The procedure can be performed using OHMD guidance including surgical preparation (reaming, drilling) of the glenoid and implantation of the glenoid component. A navigation pointer can then be used to map the coordinates and version of the component implanted using OHMD guidance. The coordinates and version can be compared to the intended coordinates and version in the navigation based surgical plan and the OHMD virtual surgical plan.

Determining the Center or Rotation, Measuring Shoulder Kinematics

In another example, by attaching optical markers to the medial and/or lateral epicondyles and/or other sites on the humerus and by performing a circular motion, the video system of one or more OHMDs can track the motion of one or more optical markers, e.g. with geometric patterns, LED's, image capture markers and/or other markers and the center of rotation of the shoulder joint can be determined using, for example, a pivoting algorithm. This information, in turn, can be used to select a humeral head size and glenoid component thickness that will help maintain the center of rotation of the patient similar to the patient's native, unoperated shoulder for a given surgical plan. Moreover, the actual position of the implanted glenoid trial component or glenoid component can be determined, e.g. using a pointer with optical markers attached, and can be compared to the planned glenoid component position, e.g. version and inclination, in the virtual surgical plan. The difference between planned and actual version can be used, for example, to adjust the humeral component version which can be incorporated in the projection of a virtual reamer and broach by the OHMD with alignment of the physical reamer and broach with the projection thereby aiming, for example, to achieve a combined humeral-glenoid version that will approximate that of the patient. Conversely, if the humeral component is implant first, the actual position of the implanted humeral trial component or humeral component or, optionally, the humeral reamer or broach in situ, can be determined, e.g. using a pointer with optical markers or navigation markers attached, and can be compared to the planned humeral component position, e.g. version, offset, inclination, in the virtual surgical plan. The difference between planned and actual version can be used, for example, to adjust the glenoid component version which can be incorporated in the projection of a virtual reamer by the OHMD with alignment of the physical reamer with the projection thereby, for example, aiming to achieve a humeral version that results in a combined humeral-glenoid version that will approximate that of the patient.

In embodiments, the video system of one or more OHMDs can track the motion of one or more optical markers, e.g. with geometric patterns, LED's, image capture markers and/or other markers, optionally combined with IMU's, e.g. attached to a distal humerus and/or a glenoid and/or a coracoid, and the biomotion and/or kinematics of the shoulder joint can be determined. Alternatively, the video system can track the motion of the arm directly via motion capture. Alternatively, a navigation system can be used to track the motion of one or more navigation markers, e.g. RF or infrared markers, optionally combined with IMU's, e.g. attached to a distal humerus and/or a glenoid and/or a coracoid, and the biomotion and/or kinematics of the shoulder joint can be determined. For example, a shoulder rotation, abduction, adduction, elevation, flexion, extension, and/or pathologic instability can be measured prior to implantation. The implantation of one or more implant components can then be simulated and one or more implant components can be selected, for example to achieve post-implantation kinematics similar to the pre-implant kinematics or to achieve post-implantation kinematics corrected for, for example, pre-implant instability or other pathologic motion or motion conditions. The fitting, sizing, selection, orientation and/or alignment of one or more shoulder implant components can be performed or adjusted using kinematic information obtained in this manner.

The terms combined glenoid-humeral version and combined humeral-glenoid version can be used interchangeably. A combined glenoid-humeral or humeral-glenoid version of the glenoid and humeral implant components can be, for example, substantially similar or similar or substantially the same or the same as the combined version of the patient's unoperated glenoid and the patient's unoperated humerus. For example, if the patient's unoperated glenoid has a version of –8 degrees, i.e. is retroverted by 8 degrees, and the patient's unoperated humerus has a version of 6 degrees, i.e. is anteverted by 6 degrees, the combined glenohumeral version can be –2 degrees in the unoperated shoulder. If the surgeon inadvertently implants the glenoid component with a version of –2 degrees, the difference between the version of the glenoid implant component and the unoperated glenoid of the patient can be determined, in this example as 6 degrees; the virtual surgical plan can then optionally be adjusted to change the humeral version from 6 degrees in the patient's unoperated humerus to 0 degrees in the patient's operated shoulder with the humeral implant component in place in a modified orientation, yielding a combined glenoid-humeral version of –2 degrees.

This intended combined glenoid humeral version of the glenoid and humeral implant components can, for example, be described as:

$$\text{Version}_{Unoperated\ Glenoid} + \text{Version}_{Unoperated\ Humeral\ Head\&Neck} = \text{Version}_{Glenoid\ Implant\ Component} + \text{Version}_{Humeral\ Implant\ Component}$$

Alternatively, threshold values can be used for setting glenoid and humeral version, either combined or individually, e.g. for the glenoid separate from the humerus. For example, a target value of 5 degrees retroversion can be set for the glenoid. Or, for example, a target range of 2 to 7 degrees of retroversion can be set for the glenoid. A target value of 30 degrees of retroversion of the humeral head relative, for example, to the transepicondylar axis of the humerus can be set. Or a target range of 25 to 35 degrees of retroversion of the humeral head relative, for example, to the transepicondylar axis of the humerus can be set.

The center of rotation of the shoulder joint and/or the humeral head size, dimensions and/or shape and/or one or more of the humeral anteversion, offset, inclination, head-neck angle, neck-shaft angle, medullary canal size, dimensions and/or shape, cortical bone size, dimensions and/or shape and/or one or more of the glenoid size, dimensions, and/or shape, glenoid rim size, dimensions and/or shape, glenoid bone stock, glenoid bone vault size, dimensions, and/or shape, glenoid anteversion and/or inclination can also be assessed using a CT scan, MRI scan, radiographic imaging or any other applicable imaging technology and/or optical imaging and/or intra-operative scanning, e.g. with a 3D scanner or confocal imaging, and/or by "painting" some of their respective surfaces and by generating, for example, point clouds and/or surfaces, e.g. with a pointer using optical markers and/or navigation markers and/or LED's and/or IMU's and/or calibration phantoms or reference phantoms and/or other markers. The information can be used to select one or more glenoid and one or more humeral components, for example for a virtual surgical plan; the components, e.g. a humeral head size and a glenoid polyethylene thickness, can be selected to maintain one or more of a center of rotation, humeral anteversion, offset, inclination, head-neck angle, neck-shaft angle, arm length, glenoid anteversion, glenoid inclination, and/or a combined gleno-humeral anteversion and/or center of rotation. The resultant information, e.g. with a virtual surgical plan with humeral and glenoid implant components selected to maintain a center of rotation and/or a combined glenoid-humeral anteversion of the patient's shoulder, can be used to guide a surgical navigation system, a robot and/or one or more optical head mounted systems to execute one or more surgical steps for partial or total shoulder arthroplasty. For example, the humeral and glenoid implant components can be selected so that the glenoid component thickness or composite thickness if a metal backed glenoid component is used with a polyethylene insert paired with a certain humeral head component diameter will maintain the center of rotation of the patient, e.g. the coordinates of the center of rotation of the patient's shoulder after placement of the implant components are substantially similar to the coordinates of the center of rotation of the patient's shoulder prior to implantation, in the unoperated shoulder. Optionally, the surgeon can choose the glenoid component thickness to ensure maintenance of a joint space or joint line similar to the one that the patient had in the unoperated shoulder. Alternatively, the glenoid component and its articular surface can extend beyond the joint space or joint line of the unoperated shoulder, in which case the surgeon can choose a humeral head with a smaller diameter in order to maintain a center of rotation similar to that of the patient's unoperated shoulder; for example, the humeral head implant component diameter can be chosen to be the patient's native humeral head diameter minus the amount in mm that the glenoid component extends beyond the patient's native joint space. Alternatively, the glenoid component can be seated with its articular surface interior to or more medial than the joint space or joint line of the unoperated shoulder, in which case the surgeon can choose a humeral head with a larger diameter in order to maintain a center of rotation similar to that of the patient's unoperated shoulder; for example, the humeral head implant component diameter can be chosen to be the patient's native humeral head diameter plus the amount in mm that the glenoid component is interior to or medial to the patient's native joint space.

In embodiments, optionally combined with the foregoing and the following embodiments, the center of the humeral head can be centered over the center of the glenoid, e.g. as determined intra-operatively and/or in a virtual surgical plan. The center of the glenoid can be the geometric center point, e.g. at the intersect between a line connecting the most superior and inferior point of the glenoid and a line connecting the most anterior and posterior point of the glenoid or the glenoid component. The center of the glenoid can also be the deepest point within the concavity of the glenoid or the glenoid component. The virtual surgical plan can optionally account for some translation of the humeral head in relationship to the glenoid, e.g. during shoulder motion. In embodiments, the center of the humeral head can be centered over the anterior portion(s) of the glenoid, e.g. as determined intra-operatively and/or in a virtual surgical plan, e.g. the anterior one third of the glenoid. In embodiments, the center of the humeral head can be centered over the posterior portion(s) of the glenoid, e.g. as determined intra-operatively and/or in a virtual surgical plan, e.g. the posterior one third of the glenoid. The selection of a humeral and a glenoid component in any of the embodiments can take into account to maintain the alignment of the center of the humeral head in relationship to the center of the glenoid. Thus, both the selection of a humeral and/or a glenoid component and the virtual surgical plan can be designed, selected or executed to maintain or achieve the desired position, orientation, alignment of the center of the humeral head component in relationship to the glenoid and/or the glenoid component. In another embodiment, the surgeon can visually move, place, orient, align, size and/or fit one or more virtual humeral components, including virtual humeral shafts, necks, if applicable, and heads, and one or more virtual glenoid components, optionally with one or more virtual glenoid anchors using the display by one or more optical head mounted displays paired with, for example, a virtual, e.g. gesture recognition, or other interface, e.g. a rod or wand using one or more optical markers, LED's, IMU's, navigation markers, calibration or reference phantoms and/or other markers, and superimpose the display of one or more virtual components onto the patient's anatomy, e.g. a humeral head, neck, shaft and/or a glenoid rim, glenoid fossa and/or glenoid bone vault, as optionally seen using a co-projected CT scan. The moving, placing, orienting, aligning, sizing and/or fitting can include selecting a size and/or shape of a glenoid component, a size, thickness, length width of a glenoid anchor or screw, and/or a size and/or shape of a humeral component, e.g. a humeral shaft, a humeral neck if applicable, a humeral neck angle, a humeral head size and/or diameter. By projecting the one or more virtual implant components onto the live, physical 3D anatomy of the patient and, optionally, any co-registered pre-operative scan data, the surgeon can avoid the need for pre-operative templating and can select the implant components based on the live 3D anatomy of the patient, rather than using 2D radiographs with radiographic templates. Optionally, 2D radiographs with radiographic templates can be used to pre-select one or more implant components pre-operatively, e.g. based on a radiographic AP, ML, SI or oblique dimension(s) and/or a radiographic shape. The radiographic information can then be used to ship a limited size range to the hospital prior to the surgery, e.g. +1 or +2 and/or −1 or −2 sizes relative to the radiographically selected implant components; the final implant component selection can then happen intra-operatively in the live patient using the live 3D anatomy of the patient.

Using the virtual moving, placing, orienting, aligning, sizing and/or fitting and/or selecting of one or more virtual implant components, the surgeon can select one or more virtual implant components to maintain or achieve a similar or substantially similar center of rotation of the shoulder joint and/or humeral head size, dimensions and/or shape and/or one or more of humeral anteversion, offset, inclination, head-neck angle, neck-shaft angle, and/or one or more of a glenoid size, dimensions, and/or shape, glenoid rim size, dimensions and/or shape, glenoid bone stock, glenoid bone vault size, dimensions, and/or shape, glenoid anteversion and/or inclination, so that the post-operative, post-implantation anatomy with the implant components in place is similar or substantially similar to the pre-operative anatomy of the patient for those parameters that the surgeon uses for the virtual moving, placing, orienting, aligning, sizing and/or fitting and/or selecting of implant components.

Optionally, during the virtual moving, placing, orienting, aligning, sizing and/or fitting and/or selecting of implant components, the surgeon can choose a virtual glenoid component thickness to ensure maintenance of a joint space or joint line similar to the one that the patient has in the unoperated shoulder. Alternatively, the virtual glenoid component and its virtual articular surface can extend beyond the joint space or joint line of the unoperated shoulder, in which case the surgeon can choose a virtual humeral head with a smaller diameter in order to maintain a center of rotation similar to that of the patient's unoperated shoulder; for example, the virtual humeral head implant component diameter can be chosen to be the patient's native humeral head diameter minus the amount in mm that the virtual glenoid component extends beyond the patient's native joint space. Alternatively, the virtual glenoid component can be seated with its articular surface interior to or more medial than the joint space or joint line of the unoperated shoulder, in which case the surgeon can choose a virtual humeral head with a larger diameter in order to maintain a center of rotation similar to that of the patient's unoperated shoulder; for example, the virtual humeral head implant component diameter can be chosen to be the patient's native humeral head diameter plus the amount in mm that the virtual glenoid component is interior to or medial to the patient's native joint space.

Optionally, one or more OHMDs can display the coordinates or indicators or outlines of the center of rotation of the unoperated shoulder joint and/or unoperated humeral head size, dimensions and/or shape and/or one or more of an unoperated humeral anteversion, offset, inclination, an unoperated head-neck angle, neck-shaft angle, and/or one or more of an unoperated glenoid size, dimensions, and/or shape, an unoperated glenoid rim size, dimensions and/or shape, an unoperated glenoid bone stock, glenoid bone vault size, dimensions, and/or shape, an unoperated glenoid anteversion and/or inclination; optionally these can be projected on the patient's shoulder following implantation of one or more components and the differences between the operated, post-implantation result and the unoperated state of the patient's shoulder can be assessed. Optionally, any differences detected can be used to modify or adjust or correct subsequent surgical steps and/or to change the selection of one or more implant components, e.g. with regard to size, dimensions or shape.

Someone skilled in the art can recognize that the foregoing embodiments on partial and total shoulder replacement and other shoulder surgeries, e.g. repair of the rotator cuff or glenoid labrum, can be applied to any of the other applications in the specification, e.g. partial or total knee replacement, hip replacement, shoulder replacement, ankle replacement, spinal fusion, spinal surgery, disk replacement, ligament repair and/or reconstruction including ACL or other ligaments, dental surgery, dental implants and other dental devices, vascular or other devices etc. For example, the words "glenoid" and "humeral" in the foregoing embodiments are representative of two articulating surfaces in a joint and can be exchanged for the words "acetabular" and "femoral" in hip replacement or "tibial" and "femoral" in knee replacement and "tibial" and "talar" or "talar" and "calcaneal" in ankle replacement or fusion. For example, in embodiments pertaining to virtual moving, placing, orienting, aligning, sizing and/or fitting and/or selecting of implant components, the words "glenoid" and "humeral" in the foregoing embodiments are representative of two articulating surfaces in a joint and can be exchanged for the words "acetabular" and "femoral" in hip replacement or "tibial" and "femoral" in knee replacement and "tibial" and "talar" or "talar" and "calcaneal" in ankle replacement or fusion.

Arthroscopic and Various Joint Procedures Using OHMD Guidance

OHMD guidance can be used during various arthroscopic procedures including, but not limited to anterior cruciate ligament repair and/or reconstruction, meniscal repair, meniscectomy, cartilage debridement and/or repair, cartilage matrix placement, cartilage transplantation, placement of cartilage grafts, placement of osteochondral auto-, allo- and/or other grafts, treatment of bone marrow edema lesions, labral tears in the shoulder or hip joint or other joints, femoroacetabular impingement, e.g. CAM and pincer type impingement, rotator cuff tears, glenoid labrum tears, ligamentous injuries and repair or reconstruction, e.g. tears of the middle or inferior glenohumeral ligaments, tears and/or reconstruction of capsular structures, e.g. in the knee, hip, shoulder, ankle, wrist, elbow, tears and/or reconstruction of ligamentous structures, e.g. in the knee, hip, shoulder, ankle, wrist, elbow, tears and/or reconstruction of the triangular fibrocartilage. OHMD guidance can also be used in various other surgeries involving joints, e.g. replacement of a knee, hip, ankle, shoulder, elbow, wrist, foot, finger and/or toe joint. One or more OHMDs can, for example, be used to display virtual data, e.g. one or more virtual surgical plans or data from pre-operative imaging studies. Such pre-operative imaging studies can, for example, show select lesions, e.g. bone marrow edema like (BMEL) lesions, e.g. in a knee joint, that can be projected with one or more OHMDs superimposed onto and aligned with the corresponding anatomic regions or portions of the proximal tibia or distal femur. The OHMD display of a subsurface, hidden lesion, e.g. a BMEL, can be used to direct a treatment, e.g. a trocar for injecting bone cement, a drug, a cellular treatment, a growth factor etc.

Virtual Data

One or more OHMDs can be used to superimpose virtual data on the respective joint, e.g. a hip, knee, ankle, shoulder, elbow, wrist, finger or foot joint. Virtual data can include any of the virtual data mentioned in the specification including, but not limited to pre- and/or intra-operative imaging data, e.g. x-rays, x-ray data, CT, and/or MRI, ultrasound, one or more virtual surgical plans, any aspect, component or step of a virtual surgical plan and related display, a virtual implant, a virtual implant component, a virtual surgical guide, a virtual surgical instrument, a virtual reaming axis, a virtual drilling axis, a virtual drill, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined stop, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration, one or more virtual anchors, one or more virtual fixation devices, one or more virtual sutures, one or more virtual suture devices, one or more virtual tissue grafts, one or more virtual implants, one or more virtual implant components, one or more virtual trial implant components.

If virtual data include one or more pre- and/or intra-operative imaging data, e.g. x-rays, x-ray data, CT, and/or MRI, ultrasound, optical coherence tomography, PET, SPECT scans, and/or combinations thereof, the imaging studies can be used to highlight areas of pathology or sensitive areas, e.g. vessels, nerves etc. The highlighting can, for example, be performed by a radiologist or a surgeon using a user interface to circle or mark the areas of pathology or sensitive areas in a 2D, 3D or multi-dimensional display. By registering the virtual data with the live anatomy and/or surgical site of the patient, one or more OHMDs can display the x-rays, x-ray data, CT, and/or MRI, ultrasound, optical coherence tomography, PET, SPECT scans, and/or combinations thereof, including any highlighted areas. In this manner, the x-rays, x-ray data, CT, and/or MRI, ultrasound, optical coherence tomography, PET, SPECT scans, and/or combinations thereof, including any highlighted areas can be seen by the surgeon registered with, superimposed onto, aligned with the live patient anatomy including the surgical site and/or target tissue while performing the surgery. The x-rays, x-ray data, CT, and/or MRI, ultrasound, optical coherence tomography, PET, SPECT scans, and/or combinations thereof, including any highlighted areas can, for example, help the surgeon to identify hidden or subtle pathology more readily. For example, the OHMD display of the x-rays, x-ray data, CT, and/or MRI, ultrasound, optical coherence tomography, PET, SPECT scans, and/or combinations thereof, including any highlighted areas can show the surgeon a subtle meniscal tear, a glenoid or acetabular labrum tear, a ligamentous tear, a rotator cuff tear, an intra-articular body, a soft-tissue cyst, e.g. a Baker cyst, a ganglion, any type of intra-substance tear of a meniscus, labrum, ligament, cartilage, disc, tendon, rotator cuff, Achilles tendon that cannot be readily detected by inspecting the surface of the structure, as well as any deep seated neoplasm or other lesion.

Registration of Different Articular Surface

The patient's joint, one or more OHMDs, one or more virtual data sets or virtual data can be registered in a common coordinate system. In joints that have two or more opposing articular surfaces, e.g. with opposing cartilage surfaces and underlying subchondral bone, e.g. diarthrodial joints, a first articular surface and/or or associated bones and/or structures can be registered separately from a second articular surface and/or or associated bones and/or structures and/or optionally jointly. Registering the first articular surface and/or or associated bones and/or structures and the second articular surface and/or or associated bones and/or structures separately can have the benefit of allowing movement of the first articular surface and/or or associated bones and/or structures and the second articular surface and/or or associated bones and/or structures, e.g. flexion and/or extension and/or rotation and/or abduction, and/or adduction, and/or elevation and/or other movements, e.g. translation, while maintaining registration of the first articular surface and/or or associated bones and/or structures and/or the second articular surface and/or or associated bones and/or structures, e.g. in a common coordinate system or a subcoordinate system, optionally along with one or more OHMDs and/or fixed structures in the operating room, e.g. the OR table, and/or other structures or anatomic landmarks of the patient, e.g. irrespective movement of the individual portions of the joint. In this manner, the joint can be placed in different positions, e.g. flexion, extension, rotation, abduction, adduction, e.g. a degree of knee flexion, e.g. 100, 110, 120 degrees, or, for example, a range between 75 and 150 degrees of knee flexion, during placement of a femoral tunnel for ACL reconstruction and a degree of knee extension, e.g. 0, −5, −10, +5, degrees, or, for example, a range between −10 and 15 degrees of knee extension to early flexion, during placement of a tibial tunnel during ACL reconstruction, while the registration of the first articular surface and/or or associated bones and/or structures and/or the registration of the second articular surface and/or or associated bones and/or structures can be maintained irrespective of the movement of individual portions of the joint, thereby allowing the one or more OHMDs to maintain anatomically registered displays of virtual data superimposed onto the corresponding portions of the physical joint anatomy, e.g. an articular surface, an articular defect, a ligamentous defect and/or another defect targeted for repair, or a femoral tunnel superimposed onto a distal femur in a predetermined position and/or orientation and/or a tibial tunnel superimposed onto a proximal tibia in a predetermined position and/or orientation, irrespective of movement of the first articular surface and/or or associated bones and/or structures and/or movement of the second articular surface and/or or associated bones and/or structures. Someone skilled in the art can recognize that the same advantages of individual registration of the first articular surface and/or or associated bones and/or structures and the second articular surface and/or or associated bones and/or structures can be advantageous for other joint surgeries, e.g. joint replacement in the knee, hip, shoulder and/or ankle and/or other joints, by allowing movement of the first articular surface and/or or associated bones and/or structures and the second articular surface and/or or associated bones and/or structures without losing registration and/or superimposition of virtual data on the corresponding live data and/or anatomy and/or surgical site of the patient. Someone skilled in the art can recognize that individual registration of articular surface(s) and/or associated bones and/or structures can be expanded to joints that have three or more articular surfaces and or associated bone and/or structures.

Registration Techniques

Any of the registration techniques described in the specification or known in the art can be used for registering one or more articular surfaces and/or associated bone and/or associated structures, one or more OHMDs, other portions of the patient's anatomy and/or fixed structures in the operating room, e.g. the OR table, in a common coordinate system or subcoordinate systems, e.g. within the common coordinate system. For example, anatomic landmarks can be detected and/or identified using pointers, e.g. with one or more attached optical markers, e.g. with geometric patterns, one or more navigation markers, one or more IMU's, one or more reference or calibration phantoms etc. Pointers or pointing devices can also be imaged and/or detected using optical imaging systems and/or 3D scanners. When pointers and/or pointing devices are located inside a joint during an arthroscopic procedure, e.g. with the tip introduced through an arthroscopic portal, one or more optical imaging systems and/or 3D scanners, for example as described in the specification, can be introduced into the joint as well, e.g. through a portal or integrated into or attached to or as part of the arthroscope.

Pointers or pointing devices and any other instruments including arthroscopic instruments and arthroscopes can be tracked, e.g. using one or more optical markers, e.g. using geometric patterns, LED's, IMU's, navigation markers, e.g. RF or infrared markers, calibration and/or reference phantoms. The one or more optical markers, e.g. using geometric patterns, LED's, IMU's, navigation markers, e.g. RF or infrared markers, calibration and/or reference phantoms can be integrated into or attached to pointers or pointing devices and any other instruments including arthroscopic instruments and arthroscopes. The one or more one or more optical markers, e.g. using geometric patterns, IMU's, navigation markers, e.g. RF or infrared markers, calibration and/or reference phantoms can be located outside the joint, e.g. external to a portal, a surgical access or the patient's skin. The one or more optical markers, e.g. using geometric patterns, LED's IMU's, navigation markers, e.g. RF or infrared markers, calibration and/or reference phantoms can be located inside the joint. One or more optical markers, e.g. using geometric patterns, IMU's, navigation markers, e.g. RF or infrared markers, calibration and/or reference phantoms can be located both outside the joint, e.g. external to a portal, a surgical access or the patient's skin, and inside the joint, e.g. inside the cavity formed by the synovial lining of the joint. In embodiments, it can be advantageous to track the one or more optical markers, e.g. using geometric patterns, LED's IMU's, navigation markers, e.g. RF or infrared markers, calibration and/or reference phantoms only outside the joint, e.g. when no optical imaging system and/or 3D scanner is available inside the joint or when an optical imaging system and/or 3D scanner is active with other tasks. In embodiments, it can be advantageous to track the one or more optical markers, e.g. using geometric patterns, LED's IMU's, navigation markers, e.g. RF or infrared markers, calibration and/or reference phantoms only inside the joint. In embodiments, it can be advantageous to track the one or more optical markers, e.g. using geometric patterns, LED's IMU's, navigation markers, e.g. RF or infrared markers, calibration and/or reference phantoms inside and outside the joint.

A navigation system can track navigation markers attached to one or more pointers or pointing devices and any other instruments including arthroscopic instruments and arthroscopes and portions thereof outside the joint and/or inside the joint. With the geometry of the one or more pointers or pointing devices and any other instruments including arthroscopic instruments and arthroscopes known and the position, location and or orientation of the one or more navigation markers on the pointers or pointing devices and any other instruments including arthroscopic instruments and arthroscopes known, the location, position, orientation, direction and/or coordinates of the tip or of other portions and/or geometries of the one or more pointers or pointing devices and any other instruments including arthroscopic instruments and arthroscopes can be tracked outside and/or inside the joint, also in relationship to one or more target tissues and/or virtual surgical plans.

One or more optical imaging systems and/or 3D scanners can track one or more optical markers, e.g. with one or more geometric patterns, LED's, calibration and/or reference phantoms and/or reference marks (e.g. depth marks on the surface of an arthroscope or arthroscopic instrument, e.g. intra-articular, e.g. starting at tip, and/or outside the skin) attached to or integrated into one or more pointers or pointing devices and any other instruments including arthroscopic instruments and arthroscopes and/or portions thereof outside the joint and/or inside the joint. With the geometry of the one or more pointers or pointing devices and any other instruments including arthroscopic instruments and arthroscopes known and the position, location and or orientation of the one or more optical markers, e.g. with one or more geometric patterns, LED's, calibration and/or reference phantoms and/or reference marks on the pointers or pointing devices and any other instruments including arthroscopic instruments and arthroscopes known, the location, position, orientation, direction and/or coordinates of the tip or of other portions and/or geometries of the one or more pointers or pointing devices and any other instruments including arthroscopic instruments and arthroscopes can be tracked outside and/or inside the joint, also in relationship to one or more target tissues and/or virtual surgical plans.

In embodiments, it can be advantageous to track the one or more optical markers, e.g. using geometric patterns, LED's IMU's, navigation markers, e.g. RF or infrared markers, calibration and/or reference phantoms both outside and inside the joint. In this example, the tracking data obtained outside the joint can be compared with the tracking data obtained inside the joint. Any differences in measured coordinates of the one or more pointers or pointing devices and any other instruments including arthroscopic instruments and arthroscopes can be determined. If these differences exceed, for example, a threshold value, e.g. greater than 0.5, 1.0, 1.5, 2.0 mm or degrees in x, y and/or z-direction or angular orientation, it can trigger an alert. An alert can, for example, suggest repeating the registration outside the joint, inside the joint or both. Any differences in coordinates of the one or more pointers or pointing devices and any other instruments including arthroscopic instruments and arthroscopes measured inside the joint as compared to measured outside the joint can optionally also be reconciled using, for example, statistical methods, e.g. using means, weighted means, medians, standard deviations etc. of measured coordinates.

In embodiments, one or more optical markers, e.g. using geometric patterns, LED's IMU's, navigation markers, e.g. RF or infrared markers, calibration and/or reference phantoms can be attached to and/or affixed to an articular surface and/or a structure or tissue associated with an articular surface, e.g. a cartilage, a subchondral bone and/or an osteophyte. The one or more optical markers, e.g. using geometric patterns, LED's IMU's, navigation markers, e.g. RF or infrared markers, calibration and/or reference phantoms can be attached by inserting them through an arthroscopic portal and affixing them to a cartilage, bone or other tissue, e.g. using a tissue anchor, a pin, a screw, a staple or other fixation device. In embodiments, one or more optical markers, e.g. using geometric patterns, LED's IMU's, navigation markers, e.g. RF or infrared markers, calibration and/or reference phantoms can be attached to a first articular surface and/or associated structure and/or tissue. In embodiments, one or more optical markers, e.g. using geometric patterns, LED's IMU's, navigation markers, e.g. RF or infrared markers, calibration and/or reference phantoms can also be attached to a second articular surface and/or associated structure and/or tissue. By affixing the one or more optical markers, e.g. using geometric patterns, LED's IMU's, navigation markers, e.g. RF or infrared markers, calibration and/or reference phantoms to a first and/or a second and/or, optionally, a third articular surface and/or associated structure and/or tissue, each articular surface and/or associated structure and/or tissue can be tracked individually, for example as the joint is moved into different positions during a surgical procedure or as a joint is moved through a range of motion. A screw and/or a pin and/or a tissue anchor can also be used as a calibration or reference phantom in any of the embodiments.

One or more optical markers, e.g. using geometric patterns, LED's, navigation markers, e.g. RF, infrared markers, or IMU's, calibration and/or reference phantoms can also be attached to an optical imaging system and/or a 3D scanner for tracking the position, orientation, alignment, direction of travel and/or coordinates of the optical imaging system and/or 3D scanner. The one or more optical markers, e.g. using geometric patterns, LED's, navigation markers, e.g. RF, infrared markers, or IMU's, calibration and/or reference phantoms can be attached to the portions of the optical imaging system and/or 3D scanner that are located inside the joint. The one or more optical markers, e.g. using geometric patterns, LED's, navigation markers, e.g. RF, infrared markers, or IMU's, calibration and/or reference phantoms can be attached to the portions of the optical imaging system and/or 3D scanner that are located outside the joint, e.g. external to the target tissue, external to the surgical field, and/or external to the patient's skin. The one or more optical markers, e.g. using geometric patterns, LED's, navigation markers, e.g. RF, infrared markers, or IMU's, calibration and/or reference phantoms can be attached to the portions of the optical imaging system and/or 3D scanner that are located outside the joint and inside the joint. For example, when the optical imaging system and/or 3D scanner is moveable, e.g. inside the joint, outside the joint and/or both, the position of the optical imaging system and/or 3D scanner can also be tracked, e.g. using additional optical imaging systems and/or 3D scanners, which can also be inside the joint, outside the joint and/or both inside and outside the joint, and which can optionally be stationary. Similarly, when the optical imaging system and/or 3D scanner is moveable, e.g. inside the joint, outside the joint and/or both, the position of the optical imaging system and/or 3D scanner can also be tracked, e.g. using a navigation system, which can be stationary. By monitoring and/or tracking the position, orientation, alignment, direction of travel and/or coordinates of an optical imaging system and/or 3D scanner, the accuracy of any coordinate measurements and/or 3D surface measurements and/or any measurements of optical markers, LED's, IMU's, calibration and/or reference phantoms can be improved in embodiments. In embodiments, tracking the one or more optical imaging systems and/or 3D scanners outside and/or inside the joint (or any other structure of the human body, e.g. an abdominal cavity, a lumen etc.) can be useful for directing the optical imaging system and/or 3D scanner to a desired location, for example for real-time imaging of a lesion or pathologic area with optional surgical intervention. In embodiments, tracking the one or more optical imaging systems and/or 3D scanners outside and/or inside the joint (or any other structure of the human body, e.g. an abdominal cavity, a lumen etc.) can be useful for improving the accuracy of any registration and/or tracking of surgical instruments and/or virtual sizing, fitting, aligning, placement of virtual implant components.

Any of the optical markers, e.g. using geometric patterns, LED's IMU's, navigation markers, e.g. RF or infrared markers, calibration and/or reference phantoms attached to one or more of a first and/or a second and/or, optionally, a third articular surface and/or associated structure and/or tissue, and/or attached to one or more of pointers or pointing devices and any other instruments including arthroscopic instruments and arthroscopes, e.g. in locations inside the joint and/or outside the joint, e.g. external to the patient's skin, and/or the surgical field, and/or the target tissue, and/or fixed structures in the operating room, e.g. the OR table, and/or one or more OHMDs can be registered in a common coordinate system or subcoordinate systems and can be tracked during the procedure. The foregoing techniques, e.g. using optical markers, e.g. using geometric patterns, LED's IMU's, navigation markers, e.g. RF or infrared markers, calibration and/or reference phantoms, can be combined with any other registration techniques known in the art or described in the specification, e.g. spatial mapping, e.g. using one or more OHMDs, optical scanners, 3D scanners, direct registration using optical scanners and/or 3D scanners, etc. For example, with the size, dimensions, geometry and/or shape and/or spatial arrangement and/or orientation (e.g. when multiple of markers, LED's, IMU's, calibration and/or reference phantoms are used) of one or more of optical markers, e.g. using geometric patterns, LED's, IMU's, calibration and/or reference phantoms known, an optical imaging system and/or a 3D scanner can be used to detect and image them, e.g. outside a joint, e.g. in a location external to the patient's skin, and/or inside a joint, e.g. in a location internal to the synovial lining of the joint; the measured size, dimensions, geometry and/or shape and/or spatial arrangement and/or orientation of one or more of optical markers, e.g. using geometric patterns, LED's, IMU's, calibration and/or reference phantoms can be used to determine the distance, orientation, alignment and/or angular orientation of the optical imaging system and/or 3D scanner, e.g. integrated into, attached to, or separate from an arthroscope, inside and/or outside the patient's joint, and/or the one or more of optical markers, e.g. using geometric patterns, LED's, IMU's, calibration and/or reference phantoms, e.g. in the common coordinate system and/or any subcoordinate systems.

Intra-operative scans can also include scans obtained with an arthroscopic optical scanner or 3D scanner, e.g. introduced through the scope portal, a separate portal and/or integrated into or attached to the arthroscope. In embodiments, the images seen through the arthroscope can be captured and/or processed to derive one or more anatomic landmarks, surfaces, geometries, shapes and/or features. In embodiments, the arthroscope can be used as an optical imaging system. In embodiments, an optical imaging system and/or a 3D scanner can use the optics of the arthroscope. In embodiments, when the optics of the arthroscope are used for an optical imaging system and/or a 3D scanner, one or more beam splitters can be employed. Optionally, an intra-articular optical scanner, e.g. using the optics of the arthroscope, and/or 3D scanner, e.g. using the optics of the arthroscope, can be used to detect and/or monitor the position, location, orientation, and/or direction of movement of one or more markers attached to the distal femur and/or proximal tibia in intra-articular location, e.g. optical markers, e.g. with one or more geometric patterns, IMU's, LED's and other markers, e.g. pins and/or screws and/or tissue anchors attached or affixed to a first and/or a second articular side, e.g. a cartilage, a subchondral bone, a cortical bone, a ligament, a ligament attachment and/or any other structure. When pins, screws, and/or tissue anchors are used as markers, the known shape and/or geometry of the pins, screws and/or tissue anchors can be utilized to improve the accuracy of the registration and any coordinate measurements, for example using triangulation techniques.

Expandable Markers

In embodiments, a marker can be placed on one or more landmarks or can be registered on a first articular surface and/or associated structures and/or a second articular surface and/or associated structures, e.g. a femoral and/or a tibial surface, a femoral notch, an ACL origin, an ACL insertion etc. The marker can, for example, be an optical marker, e.g. with one or more geometric patterns. The marker can be a tissue anchor. The marker can be introduced through a portal and can optionally be attached to or fixated onto a first surface or landmark, e.g. a femoral surface, an acetabular surface, a glenoid surface, or a second surface or landmark, e.g. a tibial surface, a proximal femoral surface, a proximal humeral surface. The marker position and/or coordinates can be registered on the first surface or landmark and/or the second surface or landmark using the optical scanner and/or 3D laser scanner. The marker position and/or coordinates can be registered on a 3D model, e.g. generated using an optical imaging system and/or a 3D scanner. The marker can optionally be expandable. The marker can be inserted through one or more portals in collapsed state. Once inside the joint, the marker can be expanded. For example, one or more geometric patterns can become visible when the marker is expanded. The marker can have non-expandable portions, e.g. a screw or a pin portion entering the bone for affixing the marker. The expandable and the non-expandable portions of the marker can have known geometries, which can be advantageous for improving the accuracy of any coordinate measurements. The marker can have expandable portions, e.g. one or more geometric patterns integrated into or attached to the marker. The marker can be a screw or a pin, which can be affixed to the femoral or other bone.

Surface Generation, Surface Registration

In embodiments, a virtual 3D model of the patient's anatomy, e.g. a target site and/or target tissue, can be generated from an imaging study, e.g. an x-ray, a CT scan, an MRI scan, a PET scan, a SPECT scan, a PET/CT scan, a SPECT/CT scan, an ultrasound. In embodiments, one or more x-rays can be used to generate and/or select a virtual 3D model of the patient's bone, e.g. as described in the section on Tissue Morphing Including Bone Morphing, Cartilage Morphing and other sections throughout the specification.

In embodiments, an optical imaging system and/or a 3D scanner, e.g. introduced through an arthroscopic portal, can be used to generate an intra-articular 3D model of the patient's joint during the procedure. For example, if an optical imaging system and/or 3D scanner is part of an arthroscope, integrated into or attached to an arthroscope, the surgeon can perform an arthroscopic procedure starting, for example, with an initial survey of the patient's joint. As the surgeon inspect the joint through the arthroscope, the optical imaging system and/or 3D scanner can simultaneously acquire surface data. The surgeon can also acquire a full sweep of one or more intra-articular surfaces, e.g. a surface of a target tissue or target graft placement, using the optical imaging system and/or 3D scanner. Optionally, a marker, e.g. an optical marker, an IMU, an LED, a screw, a pin, a tissue anchor etc., can be placed on a first and/or a second or additional articular surfaces and/or any related structures. The marker can be included in the surface data and intra-articular 3D scan of the patient's joint. In embodiments, the surface data in a sweep with the optical imaging system and/or 3D scanner is acquired in one or more overlapping surface patches. Multiple overlapping surface patches can be merged into a single surface using a surface matching of the overlapping areas. The tracking information of the imaging system and/or 3D scanner that is acquired as described in the specification can also be used to determine the position of the multiple surface patches relative to each other. The tracking information can be used to increase the accuracy of the surface matching. Alternatively, the tracking information can be used instead of a surface matching to avoid the need for overlapping surface areas of the multiple surface patches. The surface patches can be transformed into a common coordinate system by determining a transformation matrix for each surface patch that is based on the tracking information for that patch.

For the alignment of a virtual 3D model of the patient's joint, e.g. from a pre-operative imaging test or generated through bone and/or cartilage morphing from x-rays, and an intra-articular 3D scan, e.g. obtained with an optical imaging system and/or a 3D scanner, e.g. using an optical imaging system and/or 3D scanner integrated into or attached to an arthroscope or inserted through an arthroscopy portal, an algorithm for surface registration of the virtual 3D model with the intra-articular 3D scan can be used. This algorithm can be based on the Iterative Closest Point technique as described, for example by Besl et al. (Besl P J, McKay N D. 2, 1992. A method for registration of 3-D shapes. IEEE Trans PAMI, Vol. 14, pp. 239-256), which can minimize the distance between pairs of corresponding points in the surfaces to be registered using a rigid transformation. The result of the registration of the virtual 3D models with the intra-articular 3D models can consist of two transformations $FA_1$ and $SA_1$ for a first articular side and a second articular side, respectively, describing the alignment. Any changes in position and/or orientation of the view through the optical imaging system and/or 3D scanner or in the position and/or orientation of the first articular side and/or second articular side can require an update of the registration. For this purpose, one can, for example, attach optical markers, LED's, navigation markers or other markers to the first articular side, e.g. a distal femur, a glenoid, and the second articular side, e.g. a proximal tibia, a proximal humerus, at the beginning of the surgery. The baseline 3D coordinates of these markers can be measured and saved during the registration, which can include the initial position and orientation of the optical imaging system and/or 3D scanner and the initial position and orientation of the first articular side and the second articular side. The information from the markers, e.g. change in marker position, orientation, angular projection, projected size, can, for example, be used to update the registration information, including for different joint poses, e.g. flexion, extension, rotation. Alternatively, any changes in the perspective view of the generated intra-articular 3D surface(s) of the patient's joint detected through the optical imaging system and/or 3D scanner can be used to update the registration.

Software Components to Display Virtual Model(s) Overlaid with the Live View of the Patient Using One or More OHMDs The markers attached to a first and/or a second articular surface and/or associated structures and/or the intra-articular 3D surfaces generated with the optical imaging system and/or 3D scanner can be continuously or intermittently tracked using, for example, an intra-articular optical imaging system and/or 3D scanner (which can also be tracked in a common coordinate system) and, using, for example, the spatial relationship between the virtual 3D model and the intra-articular markers and/or the intra-articular 3D surface as described in the preceding sections, the position and/or orientation of the display of the virtual 3D model, e.g. a 3D reconstruction of a CT or MRI scan or a 3D model generated based on x-rays, or other virtual data, e.g. a display of a virtual ACL tunnel or virtual ACL graft, or display of a virtual rotator cuff repair, or display of a virtual anchor, or a display of a virtual lesion, e.g. a bone marrow edema like lesion, can be overlaid onto and superimposed with the live anatomy of the patient and can be updated in real time. The overlaying and superimposition can be on the live physical anatomy of the patient, e.g. a joint being operated on using arthroscopic surgery, e.g. a knee joint, a hip joint, a shoulder joint of the patient, and/or on a computer monitor, e.g. a computer monitor that displays images obtained from inside the joint using the arthroscope, using, for example, the methods and techniques described in various parts of the specification including the section entitled "Viewing 2D Computer Monitors through an OHMD Unit". For example, when the surgeon looks at the patient's physical joint, e.g. a knee, hip or shoulder joint, the virtual data can be superimposed onto and aligned with the joint without magnification using the OHMD. When the surgeon looks at the arthroscopic images of the patient's joint on a 2D computer monitor, the virtual data can be superimposed onto and aligned with the intra-articular structures, e.g. a distal femur and/or a proximal tibia matching the monitor and/or display magnification of the arthroscopic images. This can be performed, for example, by tracking the position and orientation of the arthroscope, e.g. using an attached tracking marker, and by taking into account the optical properties of the arthroscope such as view angle and zoom factor/magnification.

After transformation into the coordinate system of the OHMD live view using, for example, the transformation matrices $FA_1$ and $SA_1$, the meshes of the virtual first articular surface and associated structures and the second articular surface and associated structures models or any related virtual surgical plan, e.g. a virtual femoral or tibial tunnel, a virtual femoral or tibial graft, a virtual anchor, a virtual drilling or coring, can be rendered as holograms using, for example, the Microsoft HoloToolkit programming interface (Microsoft, Redmond, Wis.). Afterwards, the registration can be updated continuously to compensate for changes in the OHMD view in real time. For this purpose, the optical markers or other markers attached to the first articular side and associated structures and the second articular side and associated structures can be continuously tracked. Alternatively, changes in the perspective of the intra-articular 3D surface measured with the optical imaging system and/or 3D scanner can be tracked. The registration can, for example, be continuously updated as follows: For the first articular surface and associated structures and the second articular surface and associated structures, transformation matrices $FA_2$ and $SA_2$ can be calculated that map the initial marker coordinates and/or 3D surface, e.g. determined during the first registration, to the current marker coordinates and/or 3D surface in the OHMD coordinate system. The updated alignment of the virtual models with the live view of the OHMD can then result from the concatenation of $FA_2$ with $FA_1$ and $SA_2$ with $SA_1$, respectively.

The foregoing techniques and the embodiments of the specification can be applied to any number of arthroscopic and non-arthroscopic procedures, e.g.

anterior cruciate ligament repair and/or reconstruction: e.g. OHMD display of one or more virtual tunnels and/or grafts in one or more predetermined positions and/or orientations meniscal repair: e.g. OHMD display of meniscal tears and/or areas to be repaired, e.g. displayed on co-registered prior imaging studies or highlighted and displayed on prior imaging studies, e.g. MRI meniscectomy: e.g. OHMD display of areas to be resected, e.g. from prior imaging studies cartilage debridement and/or repair, cartilage matrix placement, cartilage transplantation, placement of cartilage grafts, placement of osteochondral auto-, allo- and/or other grafts: e.g. OHMD display of areas to be resected or debrided, OHMD display of areas intended for placement of a cartilage matrix, transplant, graft, OHMD display of virtual grafts, e.g. in predetermined position and/or orientation and/or alignment treatment of bone marrow edema lesions (BMEL): e.g. OHMD display of BMEL's, e.g. in subsurface locations using co-registered MRI data, OHMD guidance of surgical instruments and guidance of injection/needles/trocars for injectables, cells for treating BMEL's labral tears in the shoulder or hip joint or other joints: OHMD display of the labral tear, e.g. using co-registered pre-operative images, OHMD guidance of debridement, resection or repair femoroacetabular impingement: OHMD display of areas of CAM and/or pincer type impingement, OHMD guidance for resection, e.g. indicating predetermined resection planes intersecting the bone hip arthroscopy, hip replacement: OHMD display of pre-operative imaging studies, e.g. x-rays, CT, MRI, ultrasound. For example, if x-rays are co-displayed, they can be displayed in a predetermined plane extending, for example, through select anatomic landmarks. For example, an AP radiograph of the hip and/or pelvis can be by the OHMD superimposed onto the patient, e.g. in a plane parallel to the OR table or parallel to the original acquisition plane and extending, for example, through the anterior iliac spine, or the most anterior aspect of the acetabular rim, or through the center of the acetabular fossa, or through the center of the femoral head, or through the center of rotation; the center of rotation can, for example, be determined using one or more optical markers applied to the extremity and tracking the marker motion when performing a circular movement, e.g. as described in other sections of the specification.

rotator cuff tears, glenoid labrum tears: OHMD display of RTC or glenoid labrum tears, e.g. via superimposition and alignment of co-registered pre-operative MRI scans or MRI arthrography images or CT arthrography images and/or 3D reconstructions of any of these scans; OHMD guidance for targeting areas of rotator cuff repair, e.g. intra-substance tears, bursal surface tears, and for guiding placement of sutures, anchors, grafts, repair materials.

ligamentous injuries and repair or reconstruction, e.g. tears of the middle or inferior glenohumeral ligaments, tears and/or reconstruction of capsular structures, e.g. in the knee, hip, shoulder, ankle, wrist, elbow, tears and/or reconstruction of ligamentous structures, e.g. in the knee, hip, shoulder, ankle, wrist, elbow, tears and/or reconstruction of the triangular fibrocartilage: OHMD display of the torn sections, e.g. using co-display of pre-operative imaging studies demonstrating a tear or injury; OHMD guidance of anchor, suture or repair placement, orientation, alignment, location.

implant fixation: OHMD display of bone stock underlying an intended implantation site, OHMD guided selection of best fitting anchor achieving, for example, best fixation, OHMD guidance of anchor placement, e.g. using predetermined trajectory and/or predetermined end point and/or predetermined position and/or orientation and/or alignment and/or depth.

In any of these examples, the OHMD display including any virtual data can be superimposed onto and aligned with the corresponding portions of the patient's anatomy so that a surgeon can, for example, align physical instruments and/or physical devices and/or implantables with the corresponding virtual data projected in a predetermined position, orientation, alignment, e.g. external to the surgical site or a cartilage or bone, e.g. offset to the surgical site or cartilage or bone by 1, 2, 3, 4, 5 or more 5 mm, or a range of 0-5 mm or 5-10 mm, or tangent with or intersecting the surgical site or cartilage or bone.

Repair and/or Reconstruction of the Anterior Cruciate Ligament

The following embodiments and description on performing an ACL repair are only meant to be exemplary and are not meant to be limiting. Any of the devices, systems, techniques and/or methods described in the specification can be applied or used. Any of the imaging techniques, patient positioning techniques, registration techniques, methods for developing surgical plans including at different flexion and extension or rotation angles, displaying virtual and live patient data can be applied to any of the other embodiments in the specification, including, for example, knee replacement, hip replacement, pedicle screw placement and spinal fusion, and vertebroplasty or kyphoplasty.

Tears of the anterior cruciate ligament (ACL) represent one of the most common injuries of the human knee. They can result in knee instability, for example with flexing or bending the knee. Surgical treatment of an ACL tear can include the placement of an autograft or an allograft or another graft material. ACL repair can be performed using the so-called single bundle technique or double bundle technique. The objective of ACL repair or reconstruction is the restoration of normal knee kinematics in patients with unstable or ACL deficient knees. Anatomical reconstruction of the ACL may help restore normal knee kinematics and reduce the possibility of developing osteoarthritis of the knee after ACL injury. Anatomically, two different portions or bundles of the ACL have been described, an antero-medial bundle and a postero-lateral bundle.

ACL reconstruction can be performed using a so-called single bundle technique or a double bundle technique. One of the objectives of the surgical ACL reconstruction includes placing the graft tissue in an isometric position to restore knee function and to reduce the possibility of postoperative graft complications and graft failure. Placement of the graft near or at the location of the native, torn ACL has the benefit that the ACL graft is placed in a location that ensure primarily isometric ligament function which can help the long-term survival of the graft.

The surgeon will typically try to place the ACL graft in the location and/or orientation of the native, torn ACL. A femoral and a tibial bone tunnel need to be placed to accommodate the graft. The femoral tunnel extends from the posterior femoral cortex into the area of the femoral notch, for example, where the origin of the native ACL was located. The tibial canal extends, for example, from the medial tibial spine, the attachment of the native, torn ACL, to the antero-medial tibial cortex. An anchor can, for example, be placed in the area where the graft enters the femoral bone and/or exits the tibial bone.

Tunnel positions can be chosen in a predetermined position and/or orientation to achieve such an isometric function. Tunnel positions can be placed in a predetermined position and/or orientation using OHMD guidance so that the femoral tunnel will exit the distal femur near the origin of the ACL. The tibial tunnel can be placed in a predetermined position and/or orientation using OHMD guidance so that it enters the proximal tibia near the insertion of the ACL on the medial tibial spine. The angle and/or orientation of the femoral and/or tibial tunnel can be placed in a predetermined position and/or orientation using OHMD guidance so that they result in a position and/or orientation of the ACL graft similar to the natural angle and/or orientation of the native ACL or, optionally, different from the natural orientation of the native ACL of the patient. If a single bundle technique is used, the angle and/or orientation of the femoral and/or tibial tunnel including their entry and exit areas can be directed in predetermined positions and/or orientations using OHMD guidance so that the location and/or orientation of the graft is a compromise between the location and/or orientation of the antero-medial bundle of the ACL and the postero-lateral bundle of the ACL. A trans-tibial technique can be used as a method for tunnel placement using OHMD guidance, wherein the femoral tunnel can be drilled in a predetermined position and/or orientation through the tibial tunnel. This can have the benefit that both tunnels can be linked using OHMD guidance. Alternatively, the tibial tunnel can be drilled first in a predetermined position and/or orientation using OHMD guidance, for example through a small incision in the skin of the anterior tibia, followed by drilling of the femoral tunnel using OHMD guidance, for example through a small incision and portal into the knee joint. Optionally, the tunnel location can be placed in a predetermined position and/or orientation with arthroscopic visualization, for example by evaluating the location of residual ACL fibers on the femur and/or on the tibia. Placement of the graft outside the intended location and/or orientation can be caused by incorrect placement of the femoral and/or tibial tunnel. Incorrect placement of one or both tunnels and incorrect placement of the graft can lead to limitations in knee function and early wear and tear of the graft.

Figure 22A:
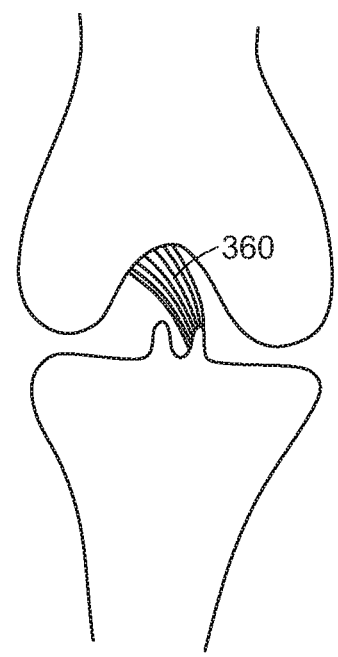
FIGS. 22A-B show AP and lateral views demonstrating exemplary normal ACL including antero-medial and postero-lateral fibers.
Figure 22B:
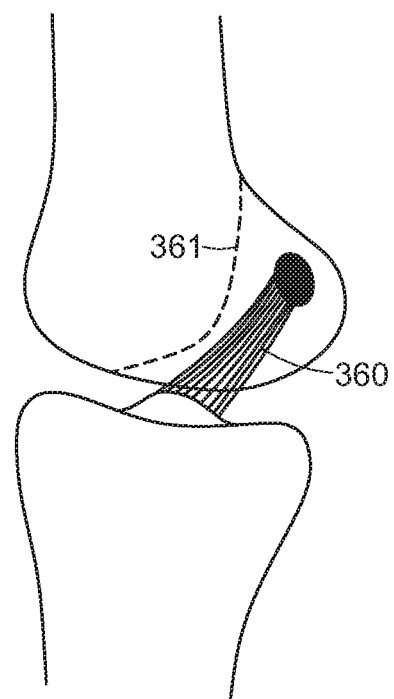

FIGS. 22A AP and 22B lateral views demonstrating exemplary normal ACL 360 including antero-medial and postero-lateral fibers. Curved broken line on femoral side indicates intercondylar notch area/roof 361.

Figure 22C:
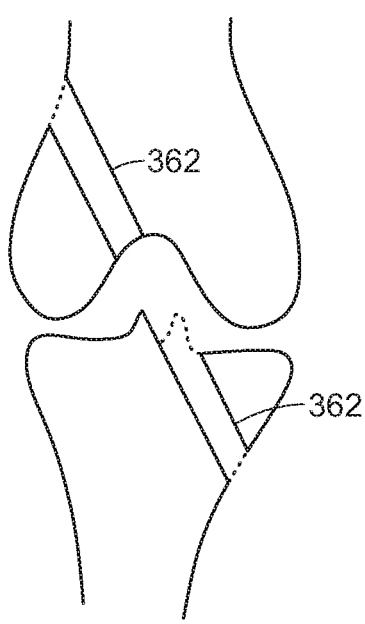
FIGS. 22C-D show AP and lateral views demonstrating exemplary ACL tunnels (solid straight lines) on femoral side and tibial side.
Figure 22D:
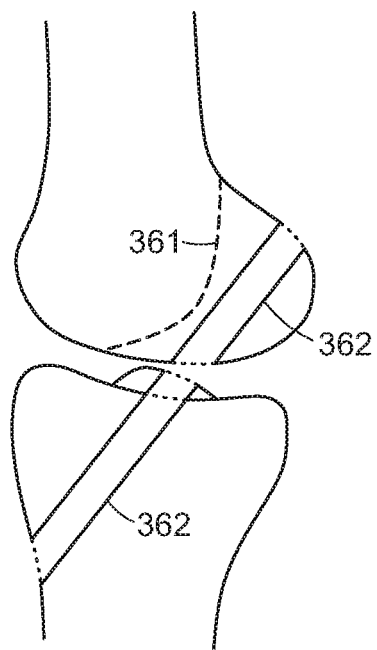

FIGS. 22C AP and 22D lateral views demonstrating exemplary ACL tunnels 362 (solid straight lines) on femoral side and tibial side. Curved broken line on femoral side indicates intercondylar notch area/roof 361.

Imaging

In some embodiments, the patient can undergo a pre-operative or intra-operative scan, e.g. a CT scan, an MRI scan or an ultrasound scan. Optionally, the femoral and tibial bones can be segmented and displayed in two or three dimensions. In some embodiments, the origin and the insertion of the native, torn ACL can be identified. Alternatively or in addition, one or more portions of the torn native ACL can be identified. The information can be used to develop a virtual surgical plan for placement of the femoral and/or the tibial tunnel or the graft using OHMD guidance, e.g. by displaying one or more virtual femoral or tibial tunnels or one or more virtual grafts.

For example, if an MRI scan is used, the MRI data can be imported into a software program to segment the femoral and/or tibial bones. For this purpose, a T1-weighted MRI sequence can be chosen without fat suppression. On the T1-weighted sequence without fat suppression, the marrow space can display intermediate to high signal intensity. The marrow space is bounded by low signal intensity cortical bone. The high intensity marrow space can be segmented, for example using a thresholding algorithm or a seed growing algorithm or an active contour or level set technique or any other algorithm or technique known in the art. A two or three millimeter or other thickness cortical bone and sub-chondral bone envelope can be added. The thickness envelope can be applied using a reference database, e.g. for bones of known size or dimensions. The cortical bone or subchondral bone envelope can vary in thickness depending on the location on the tibia or the femur. The thickness can be derived based on anatomic reference data. Alternatively, the cortical bone and subchondral bone can be segmented using any method and/or algorithm known in the art. Optionally, a 3D display of the data can be generated. Alternatively, the original 2D data can be displayed. The surgeon can use a pointer or marking tool to mark the origin of the torn ACL and the insertion of the torn ACL and/or to identify any other anatomic landmark, e.g. landmarks shown in the illustrative example in Table 12. The location of the origin and insertion of the antero-medial bundle and the postero-lateral can be marked separately. Any ACL remnants or portions thereof can be marked by the surgeon or operator.

If a CT scan is used, the CT data can be imported into a software program to segment the femoral and/or tibial bones using, for instance a thresholding or isosurface algorithm. Optionally, an algorithm can be applied that detects surface roughness and based on this information identifies the femoral original of the ACL. Alternatively, the femoral surface in the posterolateral femoral notch can be visually inspected on the 2D or 3D images to identify the origin of the ACL. The medial tibial spine can be identified to mark the insertion of the ACL.

If an ultrasound is used, the femoral and tibial bones can be visualized in 2D. The ultrasound data can optionally be imported into a software program to segment the femoral and/or tibial bones. The residual femoral fibers of the ACL can optionally be identified to determine the location of the native ACL origin. Or the femoral surface roughness in the location of the ACL origin can be used for this purpose. The medial tibial spine can be identified to mark the insertion of the ACL. Any other imaging test known in the art can be used.

Optionally, the medial and lateral femoral condyles can be identified on the ultrasound images or ultrasound data; optionally, the medial and lateral tibial plateau can be identified on the ultrasound images or ultrasound data. Other anatomic landmarks, surfaces, geometries, shapes and/or features (for example as provided in the Table 12 below entitled "Exemplary anatomic landmarks, surfaces, geometries, shapes and/or features in the knee for registration of virtual and live data including, optionally, pre-operative and intraoperative imaging data, for ACL Repair/Reconstruction and/or Knee Replacement and/or other Knee Related Surgeries; exemplary anatomic landmarks, surfaces, geometries, shapes and/or features for one or more of virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member for ACL Repair/Reconstruction and/or Knee Replacement and/or other Knee Related Surgeries" can be identified. Optionally, one or more of these anatomic landmarks, surfaces, geometries, shapes and/or features of the distal femur and/or the proximal tibial can be used to identify a standard femoral shape or a standard tibial shape by comparing the one or more anatomic landmarks, surfaces and features with data in a reference database of reference patients and/or reference femoral shapes and/or reference tibial shapes and by selecting a 3D model of the distal femur and/or proximal tibial that most closely matches the selected anatomic landmarks, surfaces, geometries, shapes and/or features. In this manner, the 3D shape of the patient's bones, e.g. the distal femur and/or the distal tibia, can be estimated without the need acquire 3D data or without the need of segmentation of the 3D data or limiting the amount of segmentation needed. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement. One or more anatomic landmarks, surfaces, geometries, shapes and/or features can also be used to deform a standard 3D model of a femur and/or tibia.

If one or more x-rays are used, they can, for example, be obtained in an AP projection of the knee (or PA), and a lateral projection of the knee. Other views are possible, as known in the art, e.g. a tunnel view, Merchant view, patellar view, oblique views, standing views, supine views, prone views. Optionally, the medial and lateral femoral condyles can be identified on the AP/PA and/or lateral and/or oblique views; optionally, the medial and lateral tibial plateau can be identified on the AP/PA and/or lateral and/or oblique views. Other anatomic landmarks, surfaces, geometries, shapes and/or features (for example as provided in Table 12 can be identified. Optionally, one or more of these anatomic landmarks, surfaces and features of the distal femur and/or the proximal tibial can be used to identify a standard femoral shape or a standard tibial shape by comparing the one or more anatomic landmarks, surfaces, geometries, shapes and/or features with data in a reference database of reference patients and/or reference femoral shapes and/or reference tibial shapes and by selecting a 3D model of the distal femur and/or proximal tibial that most closely matches the selected anatomic landmarks, surfaces, geometries, shapes and/or features. In this manner, the 3D shape of the patient's bones, e.g. the distal femur and/or the distal tibia, can be estimated without the need acquire 3D data or without the need of segmentation of the 3D data or limiting the amount of segmentation needed. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment of the present disclosure throughout the specification including for all other clinical applications, e.g. hip replacement, knee replacement, spinal surgery, spinal fusion, vertebroplasty, kyphoplasty, fracture fixation, brain surgery, liver surgery, cancer surgery etc.

Virtual Surgical Plans

With the location of the origin and the insertion or the remnants of the patient's native ACL identified using any of the foregoing methods or any other method known in the art, the surgeon or the software can develop and/or generate a virtual surgical plan using the 2D or 3D imaging data or, optionally, kinematic data, e.g. data simulating knee flexion and/or extension and/or rotation. For example, software can display the virtual data, e.g. imaging data or 3D model data, of the patient. The surgeon or the software can optionally select a desired size or diameter femoral tunnel and/or tibial tunnel for a given patient and/or a given graft size. The diameter and size of the tunnel can be chosen, for example, based on the size of the patient's bone, the size of the patient's tendon, e.g. if a tendon autograft is contemplated, the size of the patient's patellar tendon, e.g. if a patellar autograft is contemplated, the size of the patient's semitendinosus tendon, e.g. if a semitendinosus autograft is contemplated, or the expected size of an allograft or an artificial graft or the expected biomechanical loads or stresses applied to the graft; the same or similar or other parameters can also be used in choosing a femoral and/or a tibial anchor for the graft, which can include one or more interference screws or other types of anchors including button type anchors. The surgeon or the software can optionally select a predetermined femoral or tibial tunnel location and/or orientation, for example using the femoral origin of the native, torn ACL as an entry point in the femur and the medial tibial spine as an entry point into the tibia. Note, the term entry and exit point can be used interchangeably in the specification.

The surgeon or the software can optionally select a desired size and length graft, e.g. an allograft or an autograft, for a given patient. The diameter and size of the graft can be chosen, for example, based on the size of the patient's bone, the size of the patient's tendon, e.g. if a tendon autograft is contemplated, the size of the allograft tendon, e.g. if an allograft is contemplated, or the expected size of an artificial graft or the expected biomechanical loads or stresses applied to the graft; the same or other parameters can also be used in choosing a femoral and/or a tibial anchor for the graft, which can include one or more interference screws or other types of anchors including button type anchors. The surgeon or the software can optionally select a predetermined femoral or tibial tunnel location and/or orientation, for example using the femoral origin of the native, torn ACL as an entry point in the femur and the medial tibial spine as an entry point into the tibia. Note, the term entry and exit point can be used interchangeably in the specification.

The projected femoral and/or tibial tunnel location and/or entry points and/or orientation can be the extension of a line created by connecting the femoral origin and tibial insertion of the native ACL, optionally the antero-medial bundle or the postero-lateral bundle or intermediate positions between the two, for example in extension or 15 degrees flexion. In embodiments, the intra-osseous portions of the graft can have the same orientation as the intra-articular portions of the graft. In embodiments, the intra-osseous portions of the graft can have a different orientation than the intra-articular portions of the graft. The orientation of the intra-osseous/intra-tunnel portions of the graft and/or the orientation of the femoral and/or tibial tunnels can be chosen in relationship to the patient's bone, bone thickness, e.g. condylar thickness or distance from entry point near the tibial spine to the tibial cortical exit point, and in relationship to the desired position and/or orientation of the intra-articular portions of the graft, e.g. a position and/or orientation similar to the native ACL, e.g. a line connecting the femoral origin(s) and the tibial insertion(s). The projected femoral and/or tibial tunnel location and/or orientation and/or the projected intra-osseus and intra-articular graft position, location and/or orientation can be determined for different flexion and extension and/or rotation angles. In embodiments, the OHMD can display the tibial and/or the femoral tunnels and the intra-articular portions of the graft. In embodiments, the OHMD can display the intra-osseous portions of the graft, e.g. in the femur and/or the tibia, and the intra-articular portions of the graft. If the location and/or orientation of the projected femoral and/or tibial tunnel and/or the projected intra-osseous and/or intra-articular graft portions vary depending on the degree of flexion, extension and/or rotation, a statistical average can be chosen for select values or other statistical measures or methods can be applied to determine the location, position and/or orientation of the projected femoral and/or tibial tunnel and/or the projected graft portions.

A graphical user interface, for example implemented on a standard PC or Apple computer, can be utilized for displaying the 2D and/or 3D data of the patient and for identifying the ACL origin and/or insertion and/or the ACL remnants as well as any other bony landmarks, features, surfaces, and/or shapes that can be of interest for developing the surgical plan. The surgeon or the operator can optionally execute the virtual surgical plan on the graphical user interface. The surgeon or the operator can place virtual femoral and/or tibial tunnels and/or the intra-osseous and/or intra-articular portions of the virtual graft(s), e.g. for single and for double bundle technique, on the graphical user interface and the associated display of the data. The surgeon or the operator can place virtual grafts, e.g. for single and for double bundle technique, on the graphical user interface and the associated display of the data. The surgeon or the operator can place both virtual tunnels and virtual grafts on the graphical user interface and the associated display of the data. The software can optionally display the tunnels and/or the graft in one or more degrees of knee flexion and/or extension and/or rotation. The software and/or the operator can virtually assess the tunnel and/or graft position, location, and/or orientation for one or more flexion, extension, and/or rotation angles and can perform a virtual assessment of graft performance for these one or more different angles. The software and/or the operator/surgeon can optionally make adjustments to the tunnel and/or intra-articular and/or intra-osseous graft positions, locations, and/or orientations based on the information obtained in this manner from the one or more flexion, extension, and/or rotation angles.

Optionally, the graphical user interface can provide or display an assessment of the mechanical forces applied to the graft portions and/or the anchors as well as the surrounding bone. Software can be used for assessing the mechanical forces which can, for example, include finite element modeling. In addition, software can be used for assessing the kinematics of the knee for different tunnel and/or graft positions, locations and/or orientations. Such software can, for example, include Anybody or other kinematic modeling software.

Figure 22E:
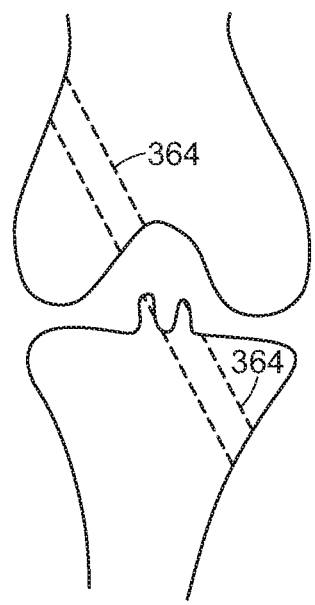
FIGS. 22E-F show AP and lateral views demonstrating exemplary virtual ACL tunnels on femoral side and tibial side (straight broken lines) according to some embodiments of the present disclosure.
Figure 22F:
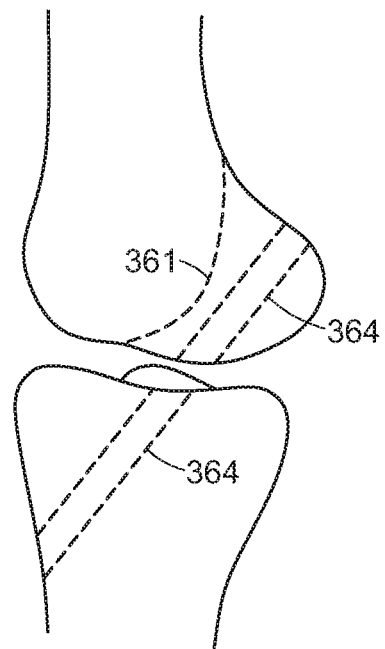

FIGS. 22E AP and F lateral views demonstrating exemplary virtual ACL tunnels 364 on femoral side and tibial side (straight broken lines). Curved broken line on femoral side indicates intercondylar notch area/roof.

Figure 22G:
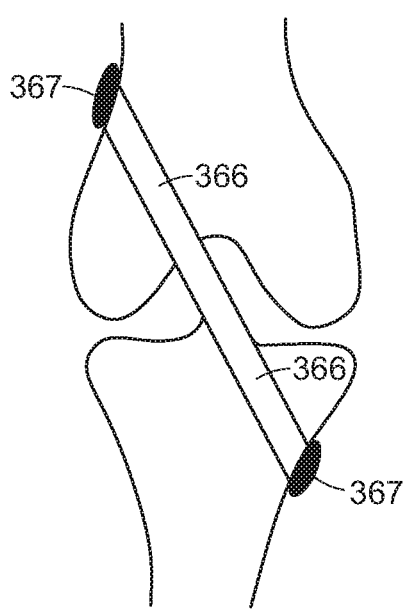
FIGS. 22G-H show AP and lateral views demonstrating exemplary virtual ACL graft on femoral side and tibial side extending through intra-articular space between femur and tibia (straight solid lines) according to some embodiments of the present disclosure.
Figure 22H:
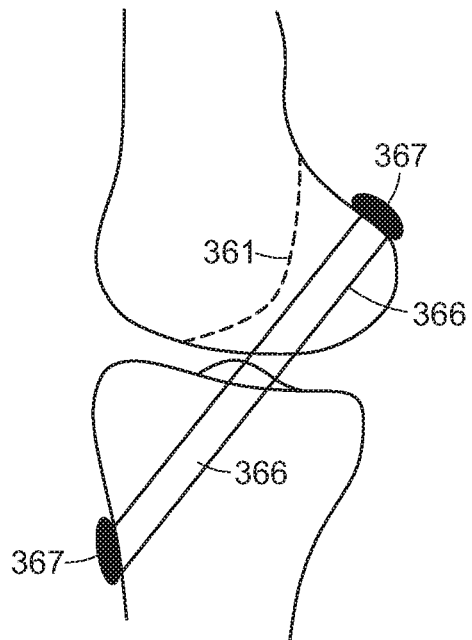

FIGS. 22G AP and 22H lateral views demonstrating exemplary virtual ACL graft 366 on femoral side and tibial side extending through intra-articular space between femur and tibia (straight solid lines). Virtual anchors are also shown on femoral and tibial side (solid black oval structures) 367. Note, instead of virtual anchors, virtual interference screws could be used on the femoral and/or the tibial side or any other means of fixation. Curved broken line on femoral side indicates intercondylar notch area/roof.

Figure 23:
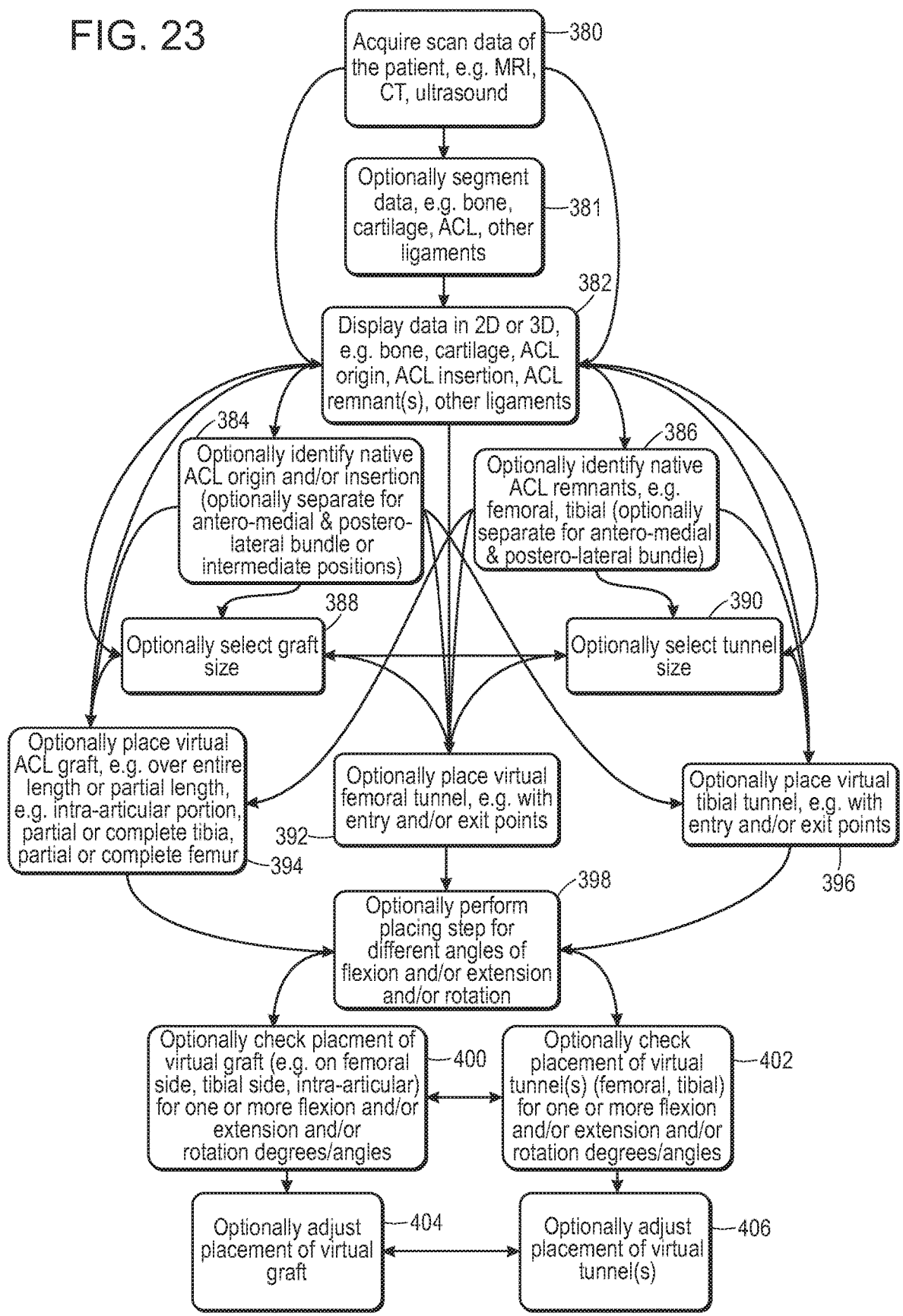
FIG. 23 is an illustrative non-limiting flow chart describing different approaches to planning the location, position, orientation, alignment and/or direction of one or more femoral or tibial tunnels (e.g. for single or double bundle technique) or for placing an ACL graft according to some embodiments of the present disclosure.

FIG. 23 is an illustrative non-limiting flow chart describing different approaches to planning the location, position, orientation, alignment and/or direction of one or more femoral or tibial tunnels (e.g. for single or double bundle technique) or for placing an ACL graft. Scan data can be acquired initially, e.g. ultrasound, CT, MRI 380. The scan data can optionally be segmented 381, e.g. for bone, cartilage, ACL tissue or structures. The segmented 381 or unsegmented 380 scan data can be displayed in 2D or 3D 382. Optionally, the native ACL origin and insertion, optionally separate for anteromedial and posterolateral bundle, can be identified 384. Optionally, the native ACL remnants can be identified, also for anteromedial and posterolateral bundle 386. Optionally, using the information from 384 and/or 386, a graft size 388 or tunnel size 390 or both can be selected. Optionally, the virtual femoral 392 and tibial 396 tunnels can be projected by the OHMD in their respective predetermined position and orientation; alternatively, their central axis can be projected by the OHMD in its predetermined position and orientation, all optionally with entry and exit points displayed. Optionally, a virtual ACL graft can be displayed by the OHMD 394 in its predetermined position, e.g. for the intra-articular portion and/or the femoral intra-osseous portion and/or the tibial intra-osseous portion. Optionally, steps 392, 394 and/or 396 can be performed or repeated for different degrees of knee flexion or extension and/or rotation including instability testing 398. Optionally, the predetermined position and orientation of the virtual femoral tunnel 392, virtual tibial tunnel 396 and/or virtual ACL graft can be checked in steps 400 and/or 402. Optionally, the predetermined position and orientation of the virtual femoral tunnel 392, virtual tibial tunnel 396 and/or virtual ACL graft can be adjusted or modified in steps 404 and/or 406.

Optionally, the software can simulate different degrees of femoral and tibial flexion and/or rotation during the range of motion or portions of the range of motion.

Registration of Virtual Data and Live Data of the Patient for ACL Repair or Reconstruction In some embodiments, the pre-operative imaging or scan data or virtual data of the patient, e.g. from an MRI scan, CT scan, ultrasound scan (2D or 3D), x-ray imaging, or x-ray imaging, ultrasound, CT or MRI with selection of a 3D femoral and/or tibial model of the patient from a reference database, or deformation of an existing model based on one or more anatomic landmarks, surfaces, geometries, shapes or features of the patient's knee, or morphing of a 3D model of the patient's knee using x-rays of the patient's knee, or any combination thereof, can be displayed on a computer screen and an operator, e.g. a surgeon or a radiologist, can manually or semi-automatically identify one or more of the following: lateral femoral notch wall, ACL origin, proximal ACL remnant(s) on the femoral side, including, for example, antero-medial or postero-lateral bundle portions or intermediate portions, medial tibial spine, distal ACL remnant(s) on the tibial side, including, for example, antero-medial or postero-lateral bundle portions or intermediate portions, ACL insertion or any other anatomic structure of the knee. The operator, surgeon or radiologist can, for example, click or circle on one more of these structures to identify them. Optionally, the operator, surgeon or radiologist can assign a label designating the name of the anatomic structure that has been identified with the click or circle, e.g. lateral femoral notch wall, ACL origin, proximal ACL remnant(s) on the femoral side, including, for example, antero-medial or postero-lateral bundle portions or intermediate portions, medial tibial spine, distal ACL remnant(s) on the tibial side, including, for example, antero-medial or postero-lateral bundle portions or intermediate portions, ACL insertion or any other anatomic structure of the knee.

Intra-operatively, the surgeon can then, for example, use a pointer or pointing device to touch the corresponding structures in the live data of the patient. The pointer or pointing device can be registered in relationship to an OHMD and/or a navigation system and/or the patient and/or the patient's knee and/or a common coordinate system, for example with use of one or more IMU's or one or more optical markers, e.g. with geometric patterns, or navigation markers including infrared markers, retroreflective markers, RF markers, or an image and/or video capture system and/or 3D scanner integrated into, attached to or separate from the OHMD, which can image and detect the pointer or pointing device, e.g. with a known geometry and/or tip location, so that the position of the pointer and the location, position, orientation and direction of the tip of the pointer is captured in a 3D object coordinate system. The surgeon can then optionally touch the structures corresponding to what was marked, clicked or circled in the pre-operative imaging/virtual data of the patient in the live data of the patient, i.e. the patient's live knee, as seen, for example, through the arthroscope or with an intraoperative ultrasound probe and scan with a pointer. Such structure can, for example, be one or more of a lateral femoral notch wall, ACL origin, proximal ACL remnant(s) on the femoral side, including, for example, antero-medial or postero-lateral bundle portions or intermediate portions, medial tibial spine, distal ACL remnant(s) on the tibial side, including, for example, antero-medial or postero-lateral bundle portions or intermediate portions, ACL insertion or any other anatomic structure of the knee. In this manner, virtual data and live data can be registered in space.

The foregoing anatomic landmarks, surfaces and features are only exemplary and are not meant to be limiting. Someone skilled in the art can readily identify other anatomic landmarks, surfaces or features that can be used for purposes of registration of virtual data and live data of the patient or other data of the patient and/or surgical instruments, for example some of the landmarks in Table 12.

Any of the registration techniques described in the specification can be used for registering virtual data of the patient and live data of the patient for ACL repair or reconstruction. For example, a pre-operative imaging test such as an ultrasound scan, CT scan or MRI scan or one or more x-ray images can be used to produce a patient specific marker. The patient specific marker can be designed to have at least one patient specific surface that can mate with the patient's anatomy, e.g. a femoral surface or a tibial surface. The patient specific marker can be applied to the patient's femur or tibia. Optionally, the patient specific marker can be designed so that it can be passed through a small incision or a small portal inside the knee joint in intra-articular location. For this purpose, the patient specific markers can consist of multiple parts, which can, optionally, be assembled inside the joint. The sub-parts or components of the patient specific marker can have engage-able connectors. Once the patient specific marker has been applied to the corresponding patient surface(s) and is properly seated in a mating position, it can optionally be affixed to the underlying bone or cartilage or ligament structure. The patient specific surface on the physical patient specific marker which mates with the live patient surface corresponds to the virtual patient surface in the virtual patient data. Once the patient specific marker is located in the predetermined position and orientation on the mating surface in the live patient, registration between the virtual data and the live data of the patient can be performed, e.g. using any of the means described in the specification. In embodiments, at least one patient specific marker can be placed on one or more portions of the distal femur and at least one patient specific marker can be placed on one or more portions of the proximal tibia. In this manner, the femur and the tibia can be registered separately and/or optionally jointly. Registering the femur and the tibia separately can have the benefit of allowing knee flexion and/or extension and/or other movements, e.g. rotation, while maintaining registration of the femoral side and/or tibial side in the common coordinate system along with one or more OHMDs. In this manner, the knee can be placed in different positions, e.g. flexion, extension, rotation, while the femoral and/or tibial registration is maintained thereby allowing the one or more OHMDs to maintain the anatomically registered displays of the virtual femoral tunnel, virtual tibial tunnel, virtual femoral intra-osseous position of the graft, virtual tibial intra-osseous position of the graft and/or the intra-articular portion of the graft.

The position of the patient specific marker can optionally be captured optically through the arthroscope, for example using an image and/or video capture system and/or 3D scanner integrated into or attached to the arthroscope system and associated display system. The arthroscope or any related instruments or pointers can be registered in relationship to an OHMD and/or a navigation system and/or the patient and/or the patient's knee, for example with use of one or more IMU's or one or more optical markers, e.g. with one or more geometric patterns, or navigation markers including infrared markers, retroreflective markers, RF markers, or an image and/or video and/or 3D scanner integrated into, attached to or separate from the OHMD, which can image and detect the arthroscope, e.g. facilitated by a known geometry and/or shape, so that the position of the arthroscope, instrument and/or pointer and the location, position, orientation and direction of the tip of the arthroscope, instrument and/or pointer is captured in a 3D object coordinate system, e.g. a common coordinate system, that can be cross-referenced and registered in relationship to the patient's knee, for example by registering it in relationship to the patient specific marker and/or in relationship to the OHMD or any other reference coordinate system used in the operating room.

The patient specific marker or any other marker applied to the distal femur or the proximal tibia, e.g. an optical marker with a geometric pattern, can have a known geometric shape, e.g. a square or a triangle or a cube or any other 3D shape. As the projected shape of the known geometric shape changes in the projection of the arthroscope, the information about the change in shape and size of the projected shape of the known geometric shape can be used, for example with an image and/or video capture system and/or an intra-articular 3D scanner, to compute or estimate the position of the arthroscope in relationship to the patient specific marker or other marker, e.g. optical marker with geometric pattern, and/or the live data, e.g. the live arthroscopic images obtained from inside the patient's joint, during the procedure. Instead of a known geometric shape, the patient specific marker and/or other marker can include other markers or marking devices, e.g. one, two, three or more LED's. The change in position and/or spatial orientation of the one, two, three or more LED's projected by the arthroscope from within the patient's joint can be used to compute or estimate the position of the arthroscope in relationship to the patient specific marker and/or other marker and/or the LED's and/or the live data, e.g. the live arthroscopic images obtained from inside the patient's joint, during the procedure. The patient specific marker and/or other marker and/or LED's can also include physical reference areas or points, e.g. a groove or a recess that can accommodate the tip of a pointer. In this manner, the tip of the pointer can be placed in the groove or recess. The pointer can have one or more IMU's or one or more optical or navigation markers including infrared markers, retroreflective markers, RF markers attached to it, e.g. inside the joint or outside the joint, e.g. external to the surgical site, the target tissue or the patient's skin, which can be detected by the OHMD or a navigation system. The position of the can also be detected with use of an image and/or video capture system and/or an intra-articular 3D scanner, e.g. introduced through one of the portals, for example integrated into, attached to or separate from the OHMD, e.g. for markers including optical markers and/or LED's located outside the joint, e.g. external to the surgical site, the target tissue and/or the patient's skin.

In some embodiments, the patient's knee can be imaged intra-operatively, for example using an x-ray or multiple x-ray images or a CT or an ultrasound scan. Intra-operative scans can also include scans obtained with an arthroscopic optical scanner or 3D scanner, e.g. introduced through the scope portal, a separate portal and/or integrated into or attached to the arthroscope. In embodiments, the images seen through the arthroscope can be captured and/or processed to derive one or more anatomic landmarks, surfaces, geometries, shapes and/or features. Optionally, an intra-articular optical scanner, e.g. using the optics of the arthroscope, and/or 3D scanner, e.g. using the optics of the arthroscope, can be used to detect and/or monitor the position, location, orientation, and/or direction of movement of one or more markers attached to the distal femur and/or proximal tibia in intra-articular location, e.g. optical markers, e.g. with one or more geometric patterns, IMU's, LED's and other markers. In embodiments, an intra-articular optical scanner, e.g. using the optics of the arthroscope, and/or 3D scanner, e.g. using the optics of the arthroscope, can be used to derive and track the 3D surface of the distal femur, e.g. in the notch area, e.g. for registering the femur and/or for maintaining registration of the distal femur, and/or to derive and track the 3D surface of the proximal tibia, e.g. in the area around the tibial spine, e.g. for registering the tibia and/or for maintaining registration of the tibia. Anatomic landmarks can be identified on the scan, which can, for example, include:

TABLE 12

Exemplary anatomic landmarks, surfaces, geometries, shapes and/or features in the knee for registration of virtual and live data including, optionally, pre-operative and intraoperative imaging data, for ACL Repair/Reconstruction and/or Knee Replacement and/or other Knee Related Surgeries; exemplary anatomic landmarks, surfaces, geometries, shapes and/or features for one or more of virtually placing a device and/or implant component and/or instrument, virtually evaluating and/or selecting a good fitting or the best fitting device and/or implant component and/or instrument, evaluating the virtual shape and/or selecting a virtual device and/or implant component and/or instrument with a preferred shape, evaluating the virtual function and/or selecting a device and/or implant component and/or instrument with a preferred virtual function, virtually determining the preferred position of a device and/or implant component and/or instrument, virtually determining the preferred orientation of a device and/or implant component and/or instrument, virtually determining the preferred alignment of a device and/or implant component and/or instrument, and/or virtually determining and/or selecting a preferred virtual anchor and/or attachment and/or fixation member for ACL Repair/Reconstruction and/or Knee Replacement and/or other Knee Related Surgeries Medial wall of the femoral notch
Lateral wall of the femoral notch
Roof of the femoral notch
Residual ACL origin
Residual ACL insertion
Medial wall of the medial condyle
Lateral wall of the lateral condyle
Medial epicondylar eminence
Lateral epicondylar eminence
Medial femoral condyle dimensions, shape, e.g. radii, convexities, concavities
Lateral femoral condyle dimensions, shape, e.g. radii, convexities, concavities
Posterior portion of medial femoral condyle including surface, peripheral margins, dimensions, shape, radii, convexities, concavities
Posterior portion of lateral femoral condyle including surface, peripheral margins, dimensions, shape, radii, convexities, concavities
Central portion of medial femoral condyle including surface, peripheral margins, dimensions, shape, radii, convexities, concavities
Central portion of lateral femoral condyle including surface, peripheral margins, dimensions, shape, radii, convexities, concavities
Anterior portion of medial femoral condyle including surface, peripheral margins, dimensions, shape, radii, convexities, concavities TABLE 12-continued Exemplary anatomic landmarks, surfaces, geometries, shapes and/or features in
the knee for registration of virtual and live data including, optionally, pre-operative and
intraoperative imaging data, for ACL Repair/Reconstruction and/or Knee Replacement
and/or other Knee Related Surgeries; exemplary anatomic landmarks, surfaces, geometries,
shapes and/or features for one or more of virtually placing a device and/or implant
component and/or instrument, virtually evaluating and/or selecting a good fitting or the best
fitting device and/or implant component and/or instrument, evaluating the virtual shape
and/or selecting a virtual device and/or implant component and/or instrument with a
preferred shape, evaluating the virtual function and/or selecting a device and/or implant
component and/or instrument with a preferred virtual function, virtually determining the
preferred position of a device and/or implant component and/or instrument, virtually
determining the preferred orientation of a device and/or implant component and/or
instrument, virtually determining the preferred alignment of a device and/or implant
component and/or instrument, and/or virtually determining and/or selecting a preferred
virtual anchor and/or attachment and/or fixation member for ACL Repair/Reconstruction
and/or Knee Replacement and/or other Knee Related Surgeries Anterior portion of lateral femoral condyle including surface, peripheral margins, dimensions, shape, radii, convexities, concavities
Intercondylar notch shape
Intercondylar notch surface features
Intercondylar notch ceiling
Intercondylar notch medial wall
Intercondylar notch lateral wall
Posterior portion of medial tibial plateau including surface, peripheral margins, dimensions, shape, radii, convexities, concavities
Posterior portion of lateral tibial plateau including surface, peripheral margins, dimensions, shape, radii, convexities, concavities
Central portion of medial tibial plateau including surface, peripheral margins, dimensions, shape, radii, convexities, concavities
Central portion of lateral tibial plateau including surface, peripheral margins, dimensions, shape, radii, convexities, concavities
Anterior portion of medial tibial plateau including surface, peripheral margins, dimensions, shape, radii, convexities, concavities
Anterior portion of lateral tibial plateau including surface, peripheral margins, dimensions, shape, radii, convexities, concavities
Medial tibial spine
Lateral tibial spine
Anteromedial tibial rim
Anterolateral tibial rim
Medial tibial rim
Lateral tibial rim
Lowest point of the medial plateau
Lowest point of the lateral plateau
Highest point of the medial plateau
Highest point of the lateral plateau
Medial tibial plateau surface, peripheral margins, dimensions, shape, radii, convexities, concavities
Lateral tibial plateau surface, peripheral margins, dimensions, shape, radii, convexities, concavities
Medial tibial plateau surface features, e.g. radii, convexities, concavities
Lateral tibial plateau surface features, e.g. radii, convexities, concavities Any of the foregoing tissues and/or structures on an exposed surface, e.g. surgically exposed Any of the foregoing tissues and/or structures in a hidden location (e.g. unexposed by an incision) or a subsurface location Any of the foregoing tissues and/or structures visualized using an imaging test, including, for example, x-rays with optionally 2D to 3D bone morphing to a 3D model The foregoing anatomic landmarks, surfaces and features are only exemplary and are not meant to be limiting. Someone skilled in the art can readily identify other anatomic landmarks, surfaces, geometries, shapes or features that can be used for purposes of registration of virtual data and live data of the patient or other data of the patient and/or surgical instruments.

The anatomic landmarks, surfaces, geometries, shapes or features can be used for registering one or more of the following: pre-operative data, e.g. pre-operative kinematic data, pre-operative imaging data; pre-operative biomechanical data, e.g. finite element data, e.g. to evaluate and/or show graft stresses, areas of increased stress, etc.; intra-operative data, e.g. intra-operative kinematic data, intra-operative imaging data; intra-operative biomechanical data, e.g. intra-operative pressure measurements, e.g. on the medial tibial plateau and/or the lateral tibial plateau, intra-operative force and/or tension measurements, e.g. involving portions of the ACL graft; virtual data of the patient, e.g. virtual kinematic data, virtual imaging data, virtual anatomic data, virtual instrument data, virtual device data, virtual surgical plan of the patient, live data of the patient including physical surgical instruments and arthroscope, for example as seen through the OHMD or as captured by an image and/or video capture system and/or 3D scanner integrated into, attached to or separate from the OHMD, e.g. an image and/or video capture system and/or 3D scanner integrated into, attached to or separate from the arthroscope, entered through the same or a different portal, in intra-articular location, or an image capture and image analysis system integrated into the arthroscope, e.g. using the optics of the arthroscope, or as seen through the arthroscope. The anatomic landmarks, surfaces and features can, for example, be marked, clicked on or circled or can be identified automatically on one or more of the virtual data of the patient, and/or on one or more of the intraoperative imaging data of the patient, e.g. intraoperatively obtained x-rays or ultrasound, optical scans, 3D laser scans, e.g. obtained from within the joint, e.g. by introducing the optical scanner and/or the 3D laser scanner through one or more arthroscopic portals or integrated into, attached to or separate from the arthroscope, and, in some embodiments, the corresponding anatomic landmarks, surfaces, geometries, shapes and/or features in the live patient/knee can, for example, be touched with a pointer or probe by the surgeon or registered using direct scanning of the patient's live anatomy and/or markers attached to the distal femur and/or proximal tibia using an optical scanner and/or a 3D laser scanner inside the patient's joint. In embodiments, a marker can be placed on one or more landmarks or can be registered on a femoral and/or a tibial surface. The marker can, for example, be an optical marker, e.g. with one or more geometric patterns. The marker can be introduced through a portal and can optionally be attached to or fixated onto a femoral surface or landmark or a tibial surface or landmark. The marker position and/or coordinates can be registered on the femoral surface and/or tibial surface using the optical scanner and/or 3D laser scanner. The marker position and/or coordinates can be registered on the femoral and/or tibial 3D model generated using the optical scanner and/or 3D scanner. The marker can optionally be expandable: The marker can be inserted through one or more portals in collapsed state. Once inside the joint, the marker can be expanded. For example, one or more geometric patterns can become visible when the marker is expanded. The marker can have non-expandable portions, e.g. a screw or a pin portion entering the bone for affixing the marker. The marker can have expandable portions, e.g. one or more geometric patterns integrated into or attached to the marker. The marker can be a screw or a pin, which can be affixed to the femoral or other bone.

In embodiments, a pointer or probe can be registered in relationship to an OHMD or a navigation system and/or the patient and/or the patient's knee, for example with use of one or more IMU's or one or more optical or navigation markers including infrared markers, retroreflective markers, RF markers or an image and/or video capture system and/or 3D scanner integrated into, attached to or separate from the OHMD so that the position of the pointer and the location, position, orientation and direction of the tip of the pointer is captured in a 3D object coordinate system which can be cross-referenced to the intra-operative data. The one or more IMU's or one or more optical or navigation markers including infrared markers, retroreflective markers, RF markers can be located inside the joint, e.g. inside the synovial lining of the joint, e.g. near the tip of the pointer or probe. The one or more IMU's or one or more optical or navigation markers including infrared markers, retroreflective markers, RF markers can be located outside the joint, e.g. external to the target tissue, the surgical site and/or the patient's skin. The one or more IMU's or one or more optical or navigation markers including infrared markers, retroreflective markers, RF markers can be internal to the joint and external to the target tissue, the surgical site and/or the patient's skin.

The intra-operative data, e.g. intra-operative imaging data, can be manually or semi-automatically or automatically (e.g. through image processing and/or pattern recognition techniques) cross-referenced and registered to the virtual data of the patient, virtual surgical plan and/or the live data of the patient. Virtual data, virtual surgical plan, intra-operative data, e.g. intra-operative imaging, and live data of the patient can be registered in the same coordinate system, optionally through various coordinate transfers. The surgeon can optionally touch the structures corresponding to what was clicked or circled in the pre-operative imaging/virtual data and/or the intra-operative data, e.g. intra-operative imaging data, of the patient in the live data of the patient, i.e. the patient's live knee, as seen, for example, through the arthroscope with a pointer which can include or carry one or more IMU's or one or more optical or navigation markers including infrared markers, retroreflective markers, RF markers or which can be registered with use of an image and/or video capture system and/or 3D scanner integrated into, attached to or separate from the OHMD. Optionally, an ultrasound probe can be introduced through one or more of the portals and the ultrasound probe can be used for intra-operative imaging, e.g. in addition to x-ray imaging. The ultrasound probe can be used to identify, for example, the ACL origin, ACL insertion and/or any proximal or distal ACL remnants. The ultrasound probe can include or carry one or more IMU's or one or more optical or navigation markers including infrared markers, retroreflective markers, RF markers which can be registered with use of an image and/or video capture system and/or 3D scanner integrated into, attached to or separate from the OHMD.

Alternatively, an optical pointer, e.g. a laser can be used to point at one or more of the anatomic landmarks, surfaces and features in the live patient, corresponding to the anatomic landmarks, surfaces and features that had been marked in the virtual data of the patient and/or the intra-operative data of the patient. The optical pointer can include or carry one or more IMU's or one or more optical or navigation markers including infrared markers, retroreflective markers, RF markers which can be registered with use of an image and/or video capture system and/or 3D scanner integrated into, attached to or separate from the OHMD or a navigation system; one or more IMU's or one or more optical or navigation markers including infrared markers, retroreflective markers, RF markers can be internal to the joint, external to the joint and/or internal and external to the joint. Whenever the optical pointer highlights one or more of the anatomic landmarks, surfaces and features in the live patient, the area can be captured through the imaging system of the arthroscope or through an image and/or video capture system and/or 3D scanner integrated into, attached to or separate from the OHMD. In this manner, corresponding anatomic landmarks, surfaces and features can be identified in the live data of the patient and can be cross-referenced to and registered with the virtual data of the patient and/or the intra-operative data of the patient. The arthroscope, surgical instruments, probes, pointers ACL grafts, femoral and/or tibial anchors and other devices can also be registered in relationship to any of the anatomic landmarks, surfaces or features of the distal femur and/or the proximal tibia, together or separately, used for registration of the virtual, intra-operative, live or other data of the patient. For this purpose, the physical and, optionally, the virtual arthroscope, surgical instruments, probes, pointers, ACL grafts, femoral and/or tibial anchors and other virtual devices and/or virtual femoral and/or tibial tunnels can be registered in relationship to an OHMD or a navigation system and/or the patient and/or the patient's knee, e.g. in a common coordinate system that includes, for example the OHMD, for example with use of one or more IMU's or one or more optical or navigation markers including infrared markers, retroreflective markers, RF markers or an image and/or video capture system and/or 3D scanner integrated into, attached to or separate from the OHMD so that the position of the arthroscope, surgical instruments, probes, pointers ACL grafts, femoral and/or tibial anchors and other devices and the location, position, orientation and direction of the arthroscope, surgical instruments, probes, pointers ACL grafts, femoral and/or tibial anchors and other devices is captured in a 3D object coordinate system.

Optionally, one or more anatomic landmarks identified on the intraoperative scan, e.g. using an optical imaging system and/or a 3D scanner, can be cross-referenced to the virtual data of the patient obtained prior to the surgical procedure, e.g. pre-operative x-rays, a CT scan, an MRI scan, or an ultrasound scan, for example used in developing the virtual surgical plan. The imaging modality used during the surgery, e.g. ultrasound, and/or an optical imaging scan and/or a 3D scan can be different from the imaging modality used to generate the virtual data of the patient and, optionally, the virtual surgical plan, e.g. an MRI.

Optionally, the arthroscope and/or one or more instruments introduced through any of the portals can carry one, two, three or more IMU's, optical, light or other markers, navigation markers including infrared markers, retroreflective markers, RF markers, image capture markers (e.g. LED's) and the like, e.g. on the inside of the joint, e.g. inside the synovial lining, and/or outside the joint, e.g. external to the patient's joint and/or external to the patient's skin. Only one or more instruments can be registered in relationship to the virtual data of the patient or the intra-operative data of the patient, while the scope cannot be registered. Only the scope can be registered in relationship to the virtual data of the patient or the intra-operative data of the patient, while the one or more instruments cannot be registered. Any marker described in the specification or known in the art can be used. The position and/or orientation of the scope and/or the one or more instruments can be registered, for example in relationship to one or more anatomic landmarks identified on the intra-operative imaging data, e.g. obtained using an ultrasound, an optical scanning system and/or a 3D scanner, or in relationship to the virtual data of the patient, e.g. a pre-operative x-ray, CT, MRI or ultrasound, or in relationship to the virtual surgical plan.

Other markers that can be used for any of the foregoing embodiments for ACL repair and/or ACL reconstruction include, but are not limited to, skin markers, intra-articular markers, RF markers, optical markers, arthroscopic anchors, arthroscopic tags, pins and/or screws.

In some embodiments, the surgeon can obtain an image of the origin and/or the insertion of the ACL or an image of a proximal and/or a distal remnant of the ACL or a combination of both through the arthroscope or through use of an intraoperative imaging technology such as an ultrasound, an optical imaging system, a 3D scanner, e.g. inserted through one of the portals. A comparable projection can then be obtained on a computer monitor or in the projection of the OHMD, wherein the view angle and the magnification of the virtual data and the live data of the patient can be substantially similar and can be superimposed, e.g. visually in the OHMD. Once substantial similarity for a view angle and magnification of the live data and the virtual data of the patient has been obtained, the data can be registered, e.g. in the same coordinate system or in separate coordinate systems with a known coordinate transfer. The arthroscope, surgical instruments, probes, pointers, ACL grafts, femoral and/or tibial anchors and other devices can include or can have attached one or more IMU's or one or more optical or navigation markers including infrared markers, retroreflective markers, RF markers, LED's, or an image and/or video capture system and/or 3D scanner can be used that can be integrated into, attached to or separate from the OHMD so that the arthroscope, surgical instruments, probes, pointers, ACL grafts, femoral and/or tibial anchors and other devices can remain registered as they are being moved, for example after the initial registration using the substantially similar projections of the physical and the virtual data of the patient.

In some embodiments, the landmarks of the distal femur can be registered, optionally in relationship to the tibia or, optionally separate from the tibia. The tibia can optionally be in a fixed and/or flexed position, e.g. with or without use of a leg holder in relationship to the femur, e.g. at 90, 100, 110, 120 or more degrees of flexion. Optionally, pins or screws can be placed, e.g. in the bone, e.g. at or near the predetermined position of the femoral tunnel. The position of the one or more pins can be registered, for example with use of an image and/or video capture system and/or 3D scanner or one or more attached IMU's or optical markers or navigation markers including infrared markers, retroreflective markers, RF markers. In this manner, by keeping the pin or screw and/or one or more IMU's, optical markers or navigation markers in place or by using an image and/or video capture system and/or 3D scanner integrated into, attached to or separate from the OHMD, the femoral and/or tibial registration can be maintained even as the knee is moved into different positions, e.g. different flexion, extension, rotation, abduction, adduction angles.

In some embodiments, the landmarks of the proximal tibia can be registered, optionally in relationship to the femur. The femur can optionally be in a fixed or extended position, e.g. with or without use of a leg holder, in relationship to the tibia, e.g. at 0 degrees of flexion, 5 degrees of hyperextension, 10 degrees of hyperextension, 5 degrees flexion, 10 degrees of flexion, 15 degrees of flexion etc. Optionally, pins or screw can be placed, e.g. in the bone, e.g. at or near the predetermined position of the tibial tunnel. The position of the one or more pins can be registered, for example with use of an image and/or video capture system and/or 3D scanner or one or more attached IMU's or optical markers or navigation markers. In this manner, by keeping the pin or screw and/or one or more IMU's or optical markers or navigation markers in place or by using an image and/or video capture system and/or 3D scanner integrated into, attached to or separate from the OHMD, the tibial and/or femoral registration can be maintained even as the knee is moved into different positions, e.g. different flexion, extension, rotation, abduction, adduction angles.

The following data can be registered in relationship to each other using one or more of the methods described herein:

Virtual data of the patient, e.g. pre-operative imaging data, pre-operative kinematic data Virtual surgical plan, e.g. virtual femoral and/or tibial tunnels, virtual grafts, e.g. intra-articular and/or intraosseous femoral and/or tibial portions Intraoperative imaging data, e.g. select landmarks, surfaces or features of the patient visualized using an intraoperative scan (see for example foregoing list), e.g. one or more x-rays, CT, MRI, ultrasound Intraoperative image capture data, e.g. data from an optical imaging system, e.g. inserted into the joint through a portal, e.g. select landmarks, surfaces or features of the patient's knee (see for example foregoing list) or the patient's joint One or more patient specific markers applied to the joint, e.g. applied to one or more articular surfaces or osteophytes, optionally visualized using an image and/or video capture system and/or 3D scanner integrated into, attached to or separate from the arthroscopy system or optionally visualized through the arthroscopy system Scope position, location, orientation, alignment and direction, for example measured via direct tracking using an image and/or video capture system and/or 3D scanner integrated into, attached to or separate from the OHMD external to the joint and/or direct tracking using an image and/or video capture system and/or 3D scanner integrated into, attached to or separate from the arthroscope, inserted through a portal, internal to the joint, and/or attached IMU's, optical markers, navigation markers including infrared markers, retroreflective markers, RF markers, or an image and/or video capture system and/or 3D scanner integrated into, attached to or separate from the OHMD external to the joint and/or internal to the joint Instrument, probe, graft, anchor or other device position, location, orientation, alignment and direction, for example measured via direct tracking using an image and/or video capture system and/or 3D scanner integrated into, attached to or separate from the OHMD and/or direct tracking using an image and/or video capture system and/or 3D scanner integrated into, attached to or separate from the arthroscope, inserted through a portal, internal to the joint, and/or attached IMU's, optical markers, navigation markers including infrared markers, retroreflective markers, RF markers, or an image and/or video capture system and/or 3D scanner integrated into, attached to or separate from the OHMD Projected Path of the Physical Instruments, Devices or Grafts and Virtual Path of Virtual Instruments, Devices, Grafts or Tunnels Registration can be effected or achieved using any of the techniques described in the specification. For example, the position, location, orientation, direction of any of the IMU's or optical markers, LED's, or navigation markers including infrared markers, retroreflective markers, RF markers, integrated into or attached to any of the arthroscope, surgical instruments, probes, pointers, ACL grafts, femoral and/or tibial anchors and other devices can be captured using an image capture system integrated into, attached to or separate from the OHMD, e.g. when external to the joint, or using an image capture system, e.g. optical scanning system, or a 3D scanner integrated into, attached to or separate from the arthroscopy, inserted through a portal inside the joint, or a navigation system or the position, location, orientation, direction of the arthroscope, surgical instruments, probes, pointers, ACL grafts, femoral and/or tibial anchors and other devices can be captured using an image and/or video capture system and/or 3D scanner, e.g. integrated into, attached to or separate from the OHMD or arthroscope, and, for example, a projected path for an physical surgical instrument, e.g. a probe or a drill, can be computed and/or displayed by the OHMD and/or the display monitor(s) of the arthroscopy system once registration has been completed. The projected path or virtual path or virtual axis of a physical surgical instrument or tool, e.g. a drill for preparing an ACL tunnel in the femur or tibia, can, for example, be parallel to, coinciding with, superimposed onto, or orthogonal to or at a defined angle to the predetermined position and/or orientation of one or more of the predetermined virtual femoral tunnel, virtual tibial tunnel, virtual ACL graft or virtual anchor(s) or virtual interference screws and/or aspects or portions of a virtual surgical plan and/or it can be projected onto and/or superimposed onto the external surface of the joint, e.g. the patient's skin or subcutaneous tissue [if exposed], or joint capsule [if exposed], and/or the arthroscopy portal [e.g. the external opening of the arthroscopy portal] and/or a separate skin incision [e.g. the external opening of the skin incision], for example used for introducing a physical tool or instrument into the joint for creating one or more femoral or tibial tunnels for the ACL graft.

The position, location, orientation, alignment and/or coordinates of the projected path or virtual path or virtual axis projected inside the joint, e.g. displayed on a separate or standalone computer monitor and superimposed onto the arthroscopic images or projected by and superimposed onto the articular structures by the OHMD [e.g. when the surgeon looks at the joint], can change as the position, location, orientation, direction of the physical arthroscope, surgical instruments, probes, pointers, ACL grafts, femoral and/or tibial anchors and other devices changes inside or outside the joint.

The position, location, orientation, alignment and/or coordinates of the projected path or virtual path or virtual axis projected inside the joint, e.g. displayed on a separate or standalone computer monitor and superimposed onto the arthroscopic images or projected by and superimposed onto the articular structures by the OHMD [e.g. when the surgeon looks at the joint], can be maintained, e.g. by a computer processor, as the position, location, orientation, direction of the physical arthroscope, surgical instruments, probes, pointers, ACL grafts, femoral and/or tibial anchors and other devices changes inside or outside the joint.

The position, location, orientation, alignment and/or coordinates of the projected path or virtual path or virtual axis projected onto and/or superimposed onto and/or aligned with the external surface of the joint by the OHMD display, e.g. the patient's skin or subcutaneous tissue [if exposed], or joint capsule [if exposed], and/or the arthroscopy portal [e.g. the external opening of the arthroscopy portal] and/or a separate skin incision [e.g. the external opening of the skin incision], can change as the position, location, orientation, direction of the physical arthroscope, surgical instruments, probes, pointers, ACL grafts, femoral and/or tibial anchors and other devices changes inside or outside the joint.

The position, location, orientation, alignment and/or coordinates of the projected path or virtual path or virtual axis projected onto and/or superimposed onto and/or aligned with the external surface of the joint by the OHMD display, e.g. the patient's skin or subcutaneous tissue [if exposed], or joint capsule [if exposed], and/or the arthroscopy portal [e.g. the external opening of the arthroscopy portal] and/or a separate skin incision [e.g. the external opening of the skin incision], can be maintained, e.g. by a computer processor, as the position, location, orientation, direction of the physical arthroscope, surgical instruments, probes, pointers, ACL grafts, femoral and/or tibial anchors and other devices changes inside or outside the joint.

The position, location, orientation, alignment and/or coordinates of the projected path or virtual path or virtual axis for directing one or more physical tools or instruments for creating a femoral tunnel [e.g. a drill] projected inside the joint, e.g. displayed on a separate or standalone computer monitor and superimposed onto the arthroscopic images or projected by and superimposed onto the articular structures by the OHMD [e.g. when the surgeon looks at the joint], can be maintained in relationship to the distal femur and/or the predetermined virtual femoral tunnel or virtual femoral graft and their respective coordinates, e.g. by a computer processor, as the position, location, orientation, or pose of the joint changes, e.g. by moving the joint or extremity during surgery or by flexing the joint during surgery. The computer processor can, for example, maintain the position, location, orientation, alignment and/or coordinates of the projected path or virtual path or virtual axis by maintaining the registration of the projected path or virtual path or virtual axis in relationship to a femoral coordinate system, which can also include coordinate information on the predetermined virtual femoral tunnel or virtual femoral graft. The femoral coordinate system can optionally be registered in a common or global coordinate system, which can, for example, include spatial information, coordinate data, registration data and/or tracking data of the surgical site, the femur, the tibia, the skin, the subcutaneous tissue, the arthroscopy portal, the external surface of a separate incision, the patient, one or more OHMDs, one or more virtual data, e.g. a projected path, virtual path or virtual axis, virtual tool, virtual instrument, and/or one or more physical tools, physical instruments and/or physical devices.

The position, location, orientation, alignment and/or coordinates of the projected path or virtual path or virtual axis for directing one or more physical tools or instruments for creating a femoral tunnel [e.g. a drill] projected onto and/or superimposed onto and/or aligned with the external surface of the joint by the OHMD display, e.g. the patient's skin or subcutaneous tissue [if exposed], or joint capsule [if exposed], and/or the arthroscopy portal [e.g. the external opening of the arthroscopy portal] and/or a separate skin incision [e.g. the external opening of the skin incision], can be maintained in relationship to the distal femur and/or the predetermined virtual femoral tunnel or virtual femoral graft and their respective coordinates, e.g. by a computer processor, as the position, location, orientation, or pose of the joint changes, e.g. by moving the joint or extremity during surgery or by flexing the joint during surgery. The computer processor can, for example, maintain the position, location, orientation, alignment and/or coordinates of the projected path or virtual path or virtual axis by maintaining the registration of the projected path or virtual path or virtual axis in relationship to a femoral coordinate system, which can also include coordinate information on the predetermined virtual femoral tunnel or virtual femoral graft. The femoral coordinate system can optionally be registered in a common or global coordinate system, which can, for example, include spatial information, coordinate data, registration data and/or tracking data of the surgical site, the femur, the tibia, the skin, the subcutaneous tissue, the arthroscopy portal, the external surface of a separate incision, the patient, one or more OHMDs, one or more virtual data, e.g. a projected path, virtual path or virtual axis, virtual tool, virtual instrument, and/or one or more physical tools, physical instruments and/or physical devices. The position, location, orientation, alignment and/or coordinates of the projected path or virtual path or virtual axis for directing one or more physical tools or instruments for creating a tibial tunnel [e.g. a drill] projected inside the joint, e.g. displayed on a separate or standalone computer monitor and superimposed onto the arthroscopic images or projected by and superimposed onto the articular structures by the OHMD [e.g. when the surgeon looks at the joint], can be maintained in relationship to the proximal tibia and/or the predetermined virtual tibial tunnel or virtual tibial graft and their respective coordinates, e.g. by a computer processor, as the position, location, orientation, or pose of the joint changes, e.g. by moving the joint or extremity during surgery or by flexing the joint during surgery. The computer processor can, for example, maintain the position, location, orientation, alignment and/or coordinates of the projected path or virtual path or virtual axis by maintaining the registration of the projected path or virtual path or virtual axis in relationship to a tibial coordinate system, which can also include coordinate information on the predetermined virtual tibial tunnel or virtual tibial graft. The tibial coordinate system can optionally be registered in a common or global coordinate system, which can, for example, include spatial information, coordinate data, registration data and/or tracking data of the surgical site, the femur, the tibia, the skin, the subcutaneous tissue, the arthroscopy portal, the external surface of a separate incision, the patient, one or more OHMDs, one or more virtual data, e.g. a projected path, virtual path or virtual axis, virtual tool, virtual instrument, and/or one or more physical tools, physical instruments and/or physical devices.

The position, location, orientation, alignment and/or coordinates of the projected path or virtual path or virtual axis for directing one or more physical tools or instruments for creating a tibial tunnel [e.g. a drill] projected onto and/or superimposed onto and/or aligned with the external surface of the joint by the OHMD display, e.g. the patient's skin or subcutaneous tissue [if exposed], or joint capsule [if exposed], and/or the arthroscopy portal [e.g. the external opening of the arthroscopy portal] and/or a separate skin incision [e.g. the external opening of the skin incision], can be maintained in relationship to the proximal tibia and/or the predetermined virtual tibial tunnel or virtual tibial graft and their respective coordinates, e.g. by a computer processor, as the position, location, orientation, or pose of the joint changes, e.g. by moving the joint or extremity during surgery or by flexing the joint during surgery. The computer processor can, for example, maintain the position, location, orientation, alignment and/or coordinates of the projected path or virtual path or virtual axis by maintaining the registration of the projected path or virtual path or virtual axis in relationship to a tibial coordinate system, which can also include coordinate information on the predetermined virtual tibial tunnel or virtual tibial graft. The tibial coordinate system can optionally be registered in a common or global coordinate system, which can, for example, include spatial information, coordinate data, registration data and/or tracking data of the surgical site, the femur, the tibia, the skin, the subcutaneous tissue, the arthroscopy portal, the external surface of a separate incision, the patient, one or more OHMDs, one or more virtual data, e.g. a projected path, virtual path or virtual axis, virtual tool, virtual instrument, and/or one or more physical tools, physical instruments and/or physical devices.

The projected path can be an extension of the long or other axis or the direction of travel of the one or more of the physical arthroscope, surgical instruments, probes, pointers, ACL grafts, femoral and/or tibial anchors and other devices. The projected path can be displayed by the OHMD, in 3D stereoscopic or 3D non-stereoscopic or 2D form, optionally with different colors or patterns. The projected path can be displayed by the display monitor of the arthroscopy system and/or both.

If the display is through the OHMD, the magnification can be adjusted if the operator looks at the patient or the patient's knee, which can require, for example, no magnification, or if the operator looks at the display of the arthroscopic images obtained through the scope and, optionally, displayed by the monitor system of the arthroscopy unit. Since images of the patient's knee and internal structures obtained through the arthroscope and optionally displayed by the arthroscopy system display monitor are typically magnified, the display of the projected path can be magnified as well, for example matching the magnification factor of the arthroscopy display or system. The display of the projected path and/or any virtual instruments or virtual displays of any non-visualized portions of physical instruments can be matched in magnification to the magnification of the arthroscopic images or the inherent magnification of the arthroscopy system or, optionally, it can be slightly less or more in magnification than the magnification of the arthroscope or the arthroscopy monitor display unit.

In some embodiments, a virtual path for one or more the arthroscope, surgical instruments, drills, ramers, impactors, probes, pointers, ACL grafts, femoral and/or tibial anchors and other devices can be displayed by the OHMD and/or the arthroscopy system display monitor(s). The virtual path can coincide or be substantially aligned with or parallel with or be identical with the predetermined path of the surgical instrument. The virtual path can, for example, be parallel to, coinciding with, superimposed onto, or orthogonal to or at a defined angle to the predetermined position and/or orientation of one or more of the predetermined femoral tunnel, tibial tunnel, ACL graft, e.g. intra-articular and/or intra-osseous femoral and/or tibial portion, or anchor(s) or interference screws. The virtual path can be projected through the OHMD, optionally in 3D stereoscopic or 3D non-stereoscopic or 2D form, optionally with different colors or patterns. The virtual path can be projected by the display monitor of the arthroscopy system. Virtual instruments and or devices such as virtual arthroscope, surgical instruments, probes, pointers, ACL grafts, femoral and/or tibial anchors and other virtual devices can also be displayed by the OHMD and/or the arthroscopy system display monitor(s). If the display is through the OHMD, the magnification can be adjusted if the operator looks at the patient or the patient's knee, which can require, for example, no magnification, or if the operator looks at the display of the arthroscopic images obtained through the scope and, optionally, displayed by the display monitor system of the arthroscopy unit. Since images of the patient's knee and internal structures obtained through the arthroscope and optionally displayed by the arthroscopy system display monitor are typically magnified, the display of the virtual path or any virtual instruments or devices such as the arthroscope, surgical instruments, probes, pointers, ACL grafts, femoral and/or tibial anchors and other virtual devices can be magnified as well, for example matching the magnification factor of the arthroscopy display or system. The display of the virtual path and/or any virtual instruments or devices can be matched in magnification to the magnification of the arthroscopic images or the inherent magnification of the arthroscopy system or, optionally, it can be slightly less or more in magnification than the magnification of the arthroscope or the arthroscopy monitor display unit. The display of the virtual path and/or any virtual instruments or devices can be using different colors or patterns, for example different than the live data of the patient, including the arthroscopic images of the internal structures of the knee.

In some embodiments, the extremity, in the case of shoulder surgery or elbow surgery the arm, in the case of knee or hip surgery, including ACL repair or reconstruction, is held or positioned in the same position, e.g. the same degrees of flexion, extension, abduction, adduction, internal or external rotation, for the acquisition of data that will be used for purposes of registration of pre-operative data, e.g. pre-operative imaging data and/or kinematic data, intra-operative data, e.g. intra-operative imaging data and/or kinematic data, and/or live data of the patient, e.g. data observed through the OHMD such as live patient data of the knee joint or data observed through the OHMD or the display monitor unit of the arthroscopy system, e.g. live patient data of the internal structures of the patient's knee. By acquiring these pre-operative, intra-operative and live patient data in the same position of the extremity or the target tissue or the joint, less variability in positioning can be encountered which can help facilitate registration using any of the methods described in the specification. For example, an upper arm holder or a leg holder can be used for obtaining pre-operative imaging data, e.g. x-ray images, ultrasound data, CT or MRI data of the extremity or target joint or target tissue; the upper arm or leg holder can fixate the extremity or target joint or target tissue in one or more positions. The same or a similar upper arm holder or a leg holder can be used for obtaining intra-operative imaging data, e.g. x-ray images, ultrasound data, CT or MRI data, optical scanning system data and/or 3D scanner data of the extremity or target joint or target tissue; the upper arm or leg holder can fixate the extremity or target joint or target tissue in one or more positions for the intra-operative data acquisition. The live patient data including arthroscopic data obtained from inside the patient's joint can be obtained with the extremity, the target joint or the target tissue in a similar position than that used when the pre-operative or intra-operative data were obtained. Registration of two or more of pre-operative data of the patient, intra-operative data of the patient, virtual data of the patient, virtual surgical plan of the patient or live data of the patient, including arthroscopic image or other data obtained from within the patient's joint can be facilitated in this manner. Replicating the same or similar position and/or orientation of the extremity, e.g. an arm for shoulder surgery or a leg for hip, knee or ankle surgery, can be particularly beneficial when one or more OHMDs are used to display soft-tissue lesions or areas of damage or injury and guide the placement of treatments. For example, in repair of tears of the rotator cuff, replicating the same or similar position and/or orientation of the arm during a pre-op MRI scan and during the actual surgery can facilitate superimposing a display of the torn portions of the rotator cuff using one or more OHMDs onto the live surgical site of the patient. Optionally, software can also simulate motion of the arm, e.g. abduction, with a related medial movement of the rotator cuff, e.g. by 1, 2, 3, 4, or 5 or more cm, corresponding, for example, to the angular degrees of abduction. Someone skilled in the art can recognize that the same concept can be expanded to other joints and to other types of soft-tissue surgery, e.g. labral tears and repair or debridement, etc.

Any of the foregoing embodiments, e.g. those related to virtual surgical plans, registration, and extremity or target joint or tissue positioning are applicable to other surgical procedures, e.g. knee replacement, hip replacement, spinal surgery, spinal fusion, vertebroplasty, kyphoplasty, brain surgery, other organ surgery, e.g. liver, renal, spleen, intestinal surgery as well as removal of any kind of neoplasms.

OHMD

The OHMD can optionally display the one or more virtual tunnels or the virtual graft or the virtual graft position and/or alignment. In any of the embodiments, the virtual graft position and/or alignment can be the intra-articular portion of the graft and/or the intra-osseous femoral portion of the graft and/or the intra-osseous tibial portion of the graft. The intra-osseous portion of the virtual femoral tunnel and/or virtual graft can be placed and/or oriented and/or aligned so that it cannot violate a femoral cartilage surface at its entry and exit areas into and from the distal femur. The OHMD can also display a projected path of one or more physical surgical instruments or devices, e.g. an arthroscope, surgical instruments, e.g. femoral and/or tibial drills, tamps, ACL footprint templates, pin guides, drill guides, femoral guides and/or tibial guides, probes, pointers, ACL grafts, femoral and/or tibial anchors and other devices. The OHMD can also display the virtual path of one or more physical surgical instruments or devices, e.g. an arthroscope, surgical instruments, e.g. femoral and/or tibial drills, tamps, ACL footprint templates, pin guides, drill guides, femoral guides and/or tibial guides, probes, pointers, ACL grafts, femoral and/or tibial anchors and other devices. The virtual path can be the predetermined path from the virtual surgical plan. The virtual data can include the display of a virtual depth indicator or a virtual depth stop for any of the instruments, which the surgeon can use, for example, to align a physical depth stop in the physical instrument with the virtually displayed depth stop, thereby controlling the depth of penetration or advance of the physical instrument.

Optionally, one or more physical surgical instrument(s), e.g. femoral and/or tibial drills, tamps, ACL footprint templates, pin guides, drill guides, femoral guides and/or tibial guides, or devices, e.g. an arthroscope, probes, pointers, ACL grafts, femoral and/or tibial anchors and other devices, and/or their projected path can be aligned with the display of the virtual tunnel(s), virtual graft or virtual graft position. The aligning can be at the same or different angle than the angle of the tunnel, e.g. in the coronal or sagittal plane. Alternatively, the OHMD can display the virtual position of the corresponding virtual surgical instrument(s), e.g. femoral and/or tibial drills, tamps, ACL footprint templates, pin guides, drill guides, femoral guides and/or tibial guides, or devices, e.g. an arthroscope, surgical instruments, probes, pointers, ACL grafts, femoral and/or tibial anchors and other devices, and the operator can optionally align the one or more physical surgical instruments, e.g. femoral and/or tibial drills, tamps, ACL footprint templates, pin guides, drill guides, femoral guides and/or tibial guides, or devices with the virtual surgical instruments or devices. Alternatively, the OHMD can display the position and/or orientation and/or alignment or direction of travel of the virtual surgical instruments, e.g. femoral and/or tibial drills, tamps, ACL footprint templates, pin guides, drill guides, femoral guides and/or tibial guides, or devices as well as one or more of the virtual tunnel(s), virtual graft or virtual graft position and the physical surgical instruments or devices, e.g. a probe or drill, and/or their projected path can be aligned with combinations of both of the virtual surgical instruments, e.g. femoral and/or tibial drills, tamps, ACL footprint templates, pin guides, drill guides, femoral guides and/or tibial guides, or devices and or the virtual tunnel(s), virtual graft or virtual graft.

The projected path, virtual path, predetermined path, virtual surgical instruments and/or devices, the arthroscope, surgical instruments, e.g. femoral and/or tibial drills, tamps, ACL footprint templates, pin guides, drill guides, femoral guides and/or tibial guides, probes, pointers, ACL grafts, femoral and/or tibial anchors and other virtual devices, virtual tunnel(s), and/or virtual graft can be displayed by the OHMD and/or the display unit of the arthroscopy system using different patterns and colors, e.g. solid lines, broken lines, dotted lines, different colors, e.g. green, red, blue, orange, different thickness, different opacity or transparency.

In some embodiments, one or more IMU's and/or optical markers, LED's, navigation markers including infrared markers, retroreflective markers, RF markers, calibration phantoms can be applied to the arthroscope, surgical instruments, e.g. femoral and/or tibial drills, tamps, ACL footprint templates, pin guides, drill guides, femoral guides and/or tibial guides, probes, pointers, ACL grafts, femoral and/or tibial anchors and other devices. The arthroscope, surgical instruments, probes, pointers, ACL grafts, femoral and/or tibial anchors and other devices can be registered, e.g. in relationship to the virtual data of the patient. The arthroscope or one or more arthroscope instruments, e.g. probes or pointers, can be applied to various landmarks inside the knee joint, visualized through the arthroscope, and registered with the patient's virtual data, e.g. pre-operative scan data, and/or intra-operative scan data and/or intra-operative data from an optical imaging system and/or 3D scanner, which can be located external to the joint, e.g. external to the patient's skin, and internal to the joint, e.g. inside the synovial lining of the joint.

Once virtual data and live data of the patient are registered, the physical drill or instrument, e.g. femoral and/or tibial drills, ACL footprint templates, pin guides, drill guides, femoral guides and/or tibial guides, used for preparing the tunnel can be aligned with the axis, position and/or orientation of the virtual drill or virtual tunnel displayed by the OHMD and/or the display unit of the arthroscopy system, both on the femoral and on the tibial side. Alternatively, a virtual path can be displayed by the OHMD and/or the display unit of the arthroscopy system, and the physical drill, e.g. the long axis of the physical drill, and the entry point of the physical drill can be aligned with the virtual path. This can be performed with single and double bundle technique. This can also be performed separately for the femoral and/or the tibial tunnel and the femoral and/or the tibial side of the graft. If a transtibial technique is used, the femoral and the tibial tunnels can be linked for a given angle of knee flexion (and/or rotation) in the virtual surgical plan and the virtual display by the OHMD or the display unit of the arthroscopy system so that the virtual surgical plan is consistent with the intended transtibial technique of the surgeon.

In embodiments, the scope can optionally have one or more IMU's or optical markers or navigation markers including infrared markers, retroreflective markers, RF markers attached and the scope can be registered in its location in relationship to the OHMD or in relationship to an optical imaging system and/or 3D scanner, which can be located external to the joint, e.g. external to the patient's skin, and internal to the joint, e.g. inside the synovial lining of the joint. The position and/or orientation of the scope can also be captured with an image and/or video capture system and/or 3D scanner integrated into, attached to or separate from the OHMD. The surgeon can move the arthroscope back and forth over a target area of the distal femur or the proximal tibia, e.g. the area(s) of the approximate tunnel placement or the area(s) of the ACL origin and/or insertion. By moving the scope back and forth over the target area, a visual perception of the surface topography and/or shape can be obtained. In addition, since the scope can be registered in a coordinate system with use of the one or more IMU's, optical markers, navigation markers including infrared markers, retroreflective markers, RF markers and/or the image and/or video capture system and/or 3D scanner, the surface topography and/or shape of the target area can also be captured and registered in relationship to the scope and/or the OHMD and their respective object coordinate systems, e.g. for example also using the image and/or video capture system and/or 3D scanner. As the scope is moved back and forth over the target area, multiple projections of the target area can be obtained by the scope at different angular orientations of the scope. Optionally, these multiple angular projections of the target area can be used to reconstruct a 3D surface of the target area or estimate a target area surface or topography or shape from the scope image data. The surface topography and/or the shape can be compared to the surface topography and/or shape of the target area in the virtual data of the patient or, optionally, the intra-operative data of the patient. Substantially similar surface topographies and/or shapes can be identified in the scope image data and the virtual data of the patient and registration of the scope image data and with that live data of the patient, virtual data of the patient, and/or OHMD can be performed. Any object coordinate transfers can now be known for purposes of the registration.

If the virtual surgical instruments, devices, grafts or tunnels and/or the virtual surgical plan are displayed by the OHMD and/or the display unit of the arthroscopy system, the surgeon can move the arthroscope back and forth or, for example, in a circular fashion to obtain a depth perspective or pseudo 3D effect of the intra-articular structures including, for example, the visual representation by the arthroscopy unit of the respective tunnel entry areas; while the surgeon is moving the arthroscope in this manner, the arthroscope motion including the change in angular orientation or direction can be monitored using one or more IMU's or optical markers and/or navigation markers including infrared markers, retroreflective markers, RF markers attached to the arthroscope or it can be monitored by an image and/or video capture system and/or 3D scanner integrated into, attached to or separate from the OHMD, e.g. located external to the patient's skin or located inside the joint or both. The software can maintain the registration of the arthroscopy system in relationship to the virtual data of the patient and the live data of the patient through the change in angular orientation and or direction and the display of the virtual surgical instruments, devices, grafts or tunnels and/or the virtual surgical plan can remain steady in the OHMD.

The following is an exemplary list of physical and virtual instruments that can be used during the ACL reconstruction. The OHMD can display one or more or all of these instruments in virtual form during the course of the surgical procedure following the virtual surgical plan. For example, each virtual instrument can be displayed with the predetermined position, location, orientation and/or direction to execute on the virtual surgical plan so that the surgeon can align the physical instruments used for the ACL reconstruction with the virtual instruments displayed by the OHMD or the virtual tunnels on the femoral or tibial side or a central tunnel axis on the femoral or the tibial side or a virtual ACL graft. The OHMD can also display a virtual path of the virtual surgical instruments, wherein the virtually path can be the predetermined path from the virtual surgical plan. The OHMD can also display the projected path of the physical surgical instruments used in the live data of the patient.

TABLE 13

Exemplary list of physical surgical instruments and virtual surgical instruments displayed by the OHMD for ACL reconstruction (multiple of each can be used, e.g. with different dimensions, lengths, shapes):

Arthroscope
Power instrument
Power tool
Arthroscopy portal
Arthroscopy sheath
Obturator
Grasper, e.g. alligator grasper, bulldog grasper
Duckster
Up biter TABLE 13-continued Exemplary list of physical surgical instruments and virtual surgical instruments displayed by the OHMD for ACL reconstruction (multiple of each can be used, e.g. with different dimensions, lengths, shapes):

Punch, e.g. wishbone punch
Burr
Shaver
Suture cutter
Scissors
Drill, various kinds, different diameters, solid, cannulated
Drill guide
Offset drill guide
Offset drill guide screw or pin
Drill sleeve(s), various kinds, e.g. stepped drill sleeve, straight drill sleeve
Chuck key
Hook probe
Parallel guide
Parallel guide sleeve
Tendon stripper, e.g. semitendinosus tendon stripper, hamstring tendon stripper
Rasp, e.g. notchplasty rasp
Reamer
Reamer handle
Pin puller
Tunnel plug
Tunnel notcher
Retractor, e.g. graft harvesting retractor
Hook, e.g. femoral or tibial ACL marking hook
ACL guide, e.g. femoral or tibial, left, right
Screwdriver, e.g. retro-screwdriver, interference screw driver
Screwdriver shaft, cannulated or non-cannulated
ACL guides, e.g. transportal ACL guide
ACL drill guide, e.g. transtibial ACL drill guide
Tibial or femoral tunnel guides, e.g. with single point elbow slide, single point forked slide, dual point forked slide
Femoral aimer
Tibial aimer
Osteotome
Handle
Cannula, e.g. tibial tunnel cannula, optionally with one or more obturators
Cut guides, e.g. for graft harvesting
Graft sizing tool
Graft knife
Graft knife holder/handle
Interference screw, resorbable, non-resorbable
Femoral and/or tibial tamps
ACL footprint templates
Pin guides
Femoral guides
Tibial guides.

The OHMD can display the complete femoral and/or tibial tunnel, it can display only a central line or axis, it can display an anterior, posterior, medial and/or lateral wall, it can display a 3D outline, or it can display a directional arrow for the tunnel(s). The OHMD can display the complete femoral and/or intra-articular and/or tibial graft portions, it can display only a central line or axis in the femoral, intra-articular or tibial area, or it can display a directional arrow for the graft(s) or a 3D outline.

Optionally, if the surgeon elects to change the physical surgical plan, the virtual surgical plan can be adapted accordingly, for example via a computer interface, and the sequence of steps and virtual instruments displayed in the OHMD can be changed by changing the virtual surgical plan. Changes to the virtual surgical plan can include a change in sequence of surgical steps, a change in surgical approach, e.g. femur first, tibia first, transtibial, omitting select surgical steps, adding surgical steps, re-orienting virtual surgical tunnel(s), re-orienting virtual surgical graft etc.

If the surgeon elects to adjust the position, location and/or orientation of the femoral or the tibial tunnel, the software can adjust the position of the tunnel on the opposing side in the virtual surgical plan. Such adjustments can be automatic, e.g. if a transtibial technique is used, the femoral tunnel can be an extension of an adjusted tibial tunnel. The adjustments in the virtual surgical plan of the opposing tunnel can also be manual, e.g. by the surgeon, for example after the surgeon has adjusted the first physical tunnel and altered its position in relationship to the virtual surgical plan. The software can optionally re-compute the location of the opposing tibial tunnel for different angles of extension, flexion and rotation after the position and/or orientation of the first tunnel has been changed, either in the virtual surgical plan or in the physical surgery.

Any surgical technique or approach known in the art for ACL reconstruction and also for ACL repair can be used. Accordingly, virtual surgical plans can be used for any surgical technique or approach known in the art for ACL reconstruction and also for ACL repair and can be displayed by the OHMD. Such surgical techniques or approaches can include, but are not limited to, open surgical ACL reconstruction or repair, arthroscopic surgical ACL reconstruction or repair, all inside ACL reconstruction or repair, trans-tibial ACL reconstruction, femur first techniques, tibia first techniques, use of interference screws or other types of anchors, single and double bundle techniques, patellar autograft techniques, semitendinosus tendon techniques, other types of tendon graft techniques, allograft techniques.

In embodiments, the OHMD can display a virtual 3D model of the patient's distal femur and/or the proximal tibia, for example generated from 2D x-ray images with 3D model generation, e.g. bone morphing, and/or derived from a CT or MRI scan, registered with and superimposed on the physical distal femur and/or the physical proximal tibia. The OHMD can also co-display one or more of a virtual tunnel and/or virtual graft, e.g. intra-osseous and/or intra-articular, and/or virtual anchors. The surgeon can virtually move, place, orient, align, fit and/or size and/or select virtual tunnels, virtual grafts, and/or virtual anchors using the techniques described in the specification, e.g. using a PC based interface and/or a virtual interface. The virtual moving, placing, orienting, aligning, fitting and/or sizing and/or selection of virtual tunnels, virtual grafts, and/or virtual anchors can happen de novo in the patient without predetermined virtual surgical plan and/or the virtual moving, placing, orienting, aligning, fitting and/or sizing and/or selection of virtual tunnels, virtual grafts, and/or virtual anchors can be used to modify a predetermined virtual surgical plan, e.g. originally developed using the virtual 3D model only, prior to superimposition of the data onto the physical distal femur and/or proximal tibia of the patient.

In some embodiments, the OHMD can optionally display any non-visualized portions of one or more of the physical arthroscope, surgical instruments, e.g. as tabulated in Table 13, probes, pointers, ACL grafts, femoral and/or tibial tunnels, femoral and/or tibial anchors and other devices. Since the geometries, shapes and dimensions of the physical arthroscope, surgical instruments, probes, pointers, ACL grafts, femoral and/or tibial anchors and other devices are known, optionally an image and/or video capture system and/or 3D scanner can be used to capture the visualized portions of the one or more arthroscope, surgical instruments, probes, pointers, ACL grafts, femoral and/or tibial anchors and other devices. Optional markers, e.g. cm or mm marks, can be used to identify which portions of the physical arthroscope, surgical instruments, probes, pointers, ACL grafts, femoral and/or tibial anchors and other devices are visualized and which ones are not visualized. The software can then identify which portions of the arthroscope, surgical instruments, probes, pointers, ACL grafts, femoral and/or tibial tunnels, femoral and/or tibial anchors and other devices are not included in the image capture data or are not visualized and the software can compute the position, location, orientation and size/magnification (if applicable) of the non-visualized portions of the arthroscope, surgical instruments, probes, pointers, ACL grafts, femoral and/or tibial tunnels, femoral and/or tibial anchors and other devices, which can then optionally be displayed by the OHMD, e.g. as an extension of the visualized portions of the physical arthroscope, surgical instruments, probes, pointers, ACL grafts, femoral and/or tibial tunnels, femoral and/or tibial anchors and other devices. Other means described in the specification for displaying the non-visualized portions of the physical arthroscope, surgical instruments, probes, pointers, ACL grafts, femoral and/or tibial tunnels, femoral and/or tibial anchors and other devices can be used. The non-visualized portions of the physical arthroscope, surgical instruments, probes, pointers, ACL grafts, femoral and/or tibial tunnels, femoral and/or tibial anchors and other devices can be displayed by the OHMD, the display unit of the arthroscopy system or both.

In some embodiments, the OHMD can display one or more projected paths for one or more physical arthroscope, surgical instruments, e.g. as tabulated in Table 13, probes, pointers, ACL grafts, femoral and/or tibial tunnels, femoral and/or tibial anchors and other devices and/or it can display one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices. In some embodiments, the display unit of the arthroscopy system, e.g. one or more electronic monitors used, can display one or more projected paths for one or more physical arthroscope, surgical instruments, probes, pointers, ACL grafts, femoral and/or tibial tunnels, femoral and/or tibial anchors and other devices and/or it can display one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices. In some embodiments, both the OHMD and the display unit of the arthroscopy system, e.g. one or more electronic monitors used, can display one or more projected paths for one or more physical arthroscope, surgical instruments, probes, pointers, ACL grafts, femoral and/or tibial tunnels, femoral and/or tibial anchors and other devices and/or it can display one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices.

The OHMD can display the one or more projected paths for one or more physical arthroscope, surgical instruments, probes, pointers, ACL grafts, femoral and/or tibial tunnels, femoral and/or tibial anchors and other devices and/or it can display the one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices using a magnification or size that is reflective of or corresponds to the distance of the OHMD or the surgeon's or operator's eyes to the patient's knee joint when the surgeon looks at the knee joint. The display unit, e.g. one or more electronic monitors, of the arthroscopy system can display the one or more projected paths for one or more physical arthroscope, surgical instruments, probes, pointers, ACL grafts, femoral and/or tibial tunnels, femoral and/or tibial anchors and other devices and/or it can display the one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices using a magnification or size that is reflective of or corresponds to the magnification of the display unit of the arthroscopy system for the display of the live data of the patient from inside the patient's knee joint so that the size and/or magnification of the one or more projected paths for one or more physical arthroscope, surgical instruments, probes, pointers, ACL grafts, femoral and/or tibial tunnels, femoral and/or tibial anchors and other devices and/or the one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices is matched to the live display of the intra-articular structures of the patient's knee joint visualized by the arthroscopy system. In this manner, the surgeon can work in a seamless manner between live intra-articular image data of the patient and projected data and virtual data of the patient since they can have matching size and/or magnification.

The magnification used by the OHMD for displaying the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can change as the surgeon moves closer to or further away from the patient's knee. The magnification of the display unit of the arthroscopy system can change; for example, it can be increased or decreased, and the magnification for displaying the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can be adjusted correspondingly.

The OHMD can optionally display the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices when the surgeon looks at the display unit of the arthroscopy system through the OHMD using a magnification or size that is reflective of or corresponds to or is larger or smaller than the magnification used by the display unit of the arthroscopy system for the display of the live data from inside the patient's knee joint. The display of the virtual data by the OHMD can be registered with the corresponding anatomic structures display by the computer display unit of the arthroscopy system using any of the registration techniques in the specification and any related techniques including, for example, registration and display techniques outlined in the section entitled "Viewing 2D computer monitors through an OHMD unit".

The magnification used by the OHMD for the display of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can switch back to be reflective of or correspond to the distance of the OHMD or the surgeon's eyes to the patient's knee or it can be smaller or larger when the surgeon looks at the patient's knee again, rather than the display unit of the arthroscopy system.

In embodiments, the display unit of the arthroscopy system can display the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices. The display unit of the arthroscopy system, e.g. one or two electronic monitors, can display the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices at a magnification that is reflective of or corresponds to the magnification of the live data of the structures projected from inside the patient's knee seen through the arthroscope and displayed by the display unit of the arthroscopy unit, or at a magnification that is smaller or larger than that.

When the surgeon looks through the OHMD at the display unit of the arthroscopy system, e.g. one or two electronic monitors, the OHMD can optionally turn of the display of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices. The turning off or turning on of the display of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can be performed via manual commands, voice commands, various commands from various input systems, or automatically. An automatic turning on or off can be achieved, for example, with use of an image and/or video capture system and/or 3D scanner integrated into, attached to or separate from the OHMD. The image and/or video capture system and/or 3D scanner can, for example, capture the outline of the display unit of the arthroscopy system and the software can the automatically turn off the OHMD display or aspects of the OHMD display. Alternatively, the display unit of the arthroscopy system can have one or more markers, e.g. one or more LED's, that the image and/or video capture system and/or 3D scanner can detect which, in turn, can then trigger the turning on or off of the OHMD display.

In some embodiments, the OHMD can detect, e.g. automatically, if the surgeon or operator is looking at the display unit of the arthroscopy system, for example, with use of an image and/or video capture system and/or 3D scanner integrated into, attached to or separate from the OHMD. The image and/or video capture system and/or 3D scanner can, for example, capture the outline of the display unit of the arthroscopy system and the software can the automatically adjust the magnification of the items displayed by the OHMD so that it is reflective of, corresponds to, is smaller or larger than the magnification used by the display unit of the arthroscopy system for the live data/images from inside the patient's knee. Alternatively, the display unit of the arthroscopy system can have one or more markers, e.g. one or more LED's, that the image and/or video capture system and/or 3D scanner can detect which, in turn, can then trigger the adjustment of the magnification of the items displayed by the OHMD.

Similarly, the OHMD can detect, e.g. automatically, if the surgeon or operator is not looking at the display unit of the arthroscopy system, for example, with use of an image and/or video capture system and/or 3D scanner integrated into, attached to or separate from the OHMD. The image and/or video capture system and/or 3D scanner can, for example, detect that the outline of the display unit of the arthroscopy system is not present in the captured image data and the software can the automatically adjust the magnification of the items displayed by the OHMD so that it is reflective of or corresponds to the distance of the OHMD or the surgeon's eyes to the patient's knee, or is smaller or larger than that. Alternatively, the display unit of the arthroscopy system can have one or more markers, e.g. one or more LED's, that the image and/or video capture system and/or 3D scanner can detect; in this case, when the image captures system notices that the one or more LED's are not included in the image capture data, the software can the automatically adjust the magnification of the items displayed by the OHMD so that it is reflective of or corresponds to the distance of the OHMD or the surgeon's eyes to the patient's knee, or is smaller or larger than that. Similarly, markers or LED's placed on the patient's knee can be detected by the OHMD including an image and/or video capture system and/or 3D scanner integrated into, attached to or separate from the OHMD thereby triggering an adjustment in magnification so that it is reflective of, corresponds to the distance of the OHMD or the surgeon's eyes to the patient's knee, or is smaller or larger than that when the surgeon or operator is looking at the patient's knee.

In some embodiments, the OHMD can be used to display the live data collected by the arthroscope from inside the patient's knee, for example instead of the display unit of the arthroscopy system or in addition to the display unit of the arthroscopy system. Optionally, the OHMD can replace the display unit of the arthroscopy system or it can be the display unit of the arthroscopy system. In this example, the OHMD can display the live data from inside the patient's knee collected by the arthroscope and project them for the surgeon. The OHMD can also display one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices in addition to the live images from inside the patient's knee. In this embodiment, the OHMD can optionally match the magnification of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices relative to the magnification of the live data from inside the patient's knee collected by the arthroscope. The OHMD can also can apply a larger or smaller magnification and or size than the magnification of the live data from inside the patient's knee collected by the arthroscope for the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices.

In some embodiments, for example when the OHMD is the primary display unit of the arthroscopy system, the OHMD can be non-transparent to light or minimally transparent to light reflected from the patient's knee or surgical theatre and can display, for example, live (electronic) images collected by the arthroscope from within the patient's knee and, optionally, it can display, in addition, one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices (with various chosen matching or non-matching magnifications). In this setting, the OHMD can also display electronic images of the physical arthroscope, surgical instruments, probes, pointers, ACL grafts, femoral and/or tibial tunnels, femoral and/or tibial anchors and other devices and their respective movements, for example captured with an image and/or video capture system and/or 3D scanner integrated into, attached to, or separate from the OHMD (with various chosen matching or non-matching magnifications).

The OHMD can be permanently non-transparent to light or minimally transparent to light reflected from the patient's knee or surgical theatre. Alternatively, the degree of transparency can be variable, for example with use of one or more optical filters, e.g. polarizing light filters, in front of or integrated into the OHMD or electronic, e.g. LCD, or optical filters in front or integrated into the OHMD. The OR theater can optionally use light sources, e.g. polarized or filtered light that will support modulation or aid with adjustments of the transparency of the OHMD to light reflected from the patient's knee or surgical theatre.

Someone skilled in the art will readily recognize that all examples and embodiments provided in the foregoing for ACL repair and ACL reconstruction are applicable to all other arthroscopic procedures such as arthroscopy of the shoulder, hip and ankle and can be applied to many endoscopic procedures as well as to other embodiments and hip replacement, knee replacement, spinal surgery, spinal fusion, pedicle screw fixation, vertebroplasty and/or kyphoplasty, any type of robotic surgery, any type of guided surgery using 2D computer display monitors, and many others.

Optical Markers

Data were obtained using an OHMD manufactured by Microsoft, the Microsoft Hololens (Microsoft, Redmond, Wis.). The Hololens can use, for example, Windows holographic APIs including Unity (Unity Technologies, San Francisco, Calif.) and Vuforia 6.2 (PTC, Inc., Needham, Mass.).

Registration of Optical Markers Using Microsoft Hololens and Vuforia 6.2

Figure 24:
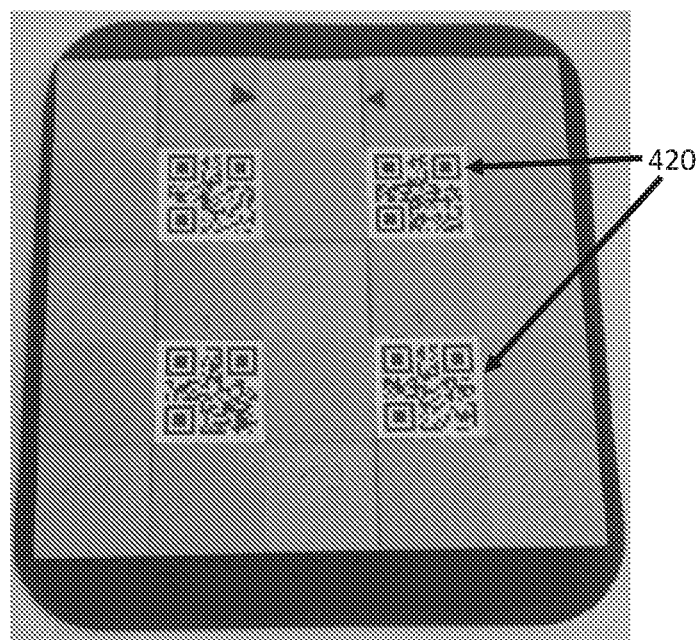
FIG. 24 shows a wooden board with 25 squares and four 4.0×4.0 cm optical markers.

FIG. 24 shows a wooden board with 25 squares which was prepared and four 4.0×4.0 cm optical markers 420 with four distinct QR codes were applied in equidistant locations, 4.0 cm apart. As seen in FIG. 25, a software routine was implemented to project four cubes 423 with dimensions of 4.0×4.0×4.0 cm superimposed onto the squares and to maintain registration over the squares irrespective of head movement. The results are shown in FIG. 25. The Microsoft Hololens was not able to maintain registration of the four cubes over the designated optical markers; the cubes were at times displaced by as much as 3-4 cm and were also tilted.

Registration of Optical Markers Using Hololens and OpenCV 2.4

Figure 26:
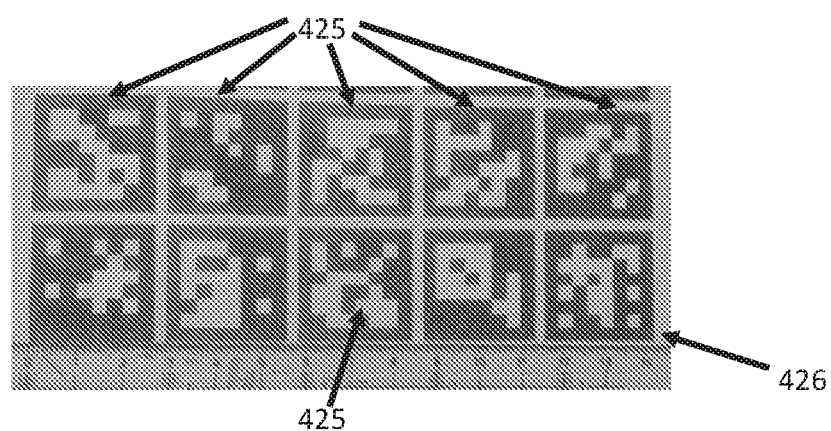
FIG. 26 shows an illustrative, non-limiting example of optical markers.
Figure 27:
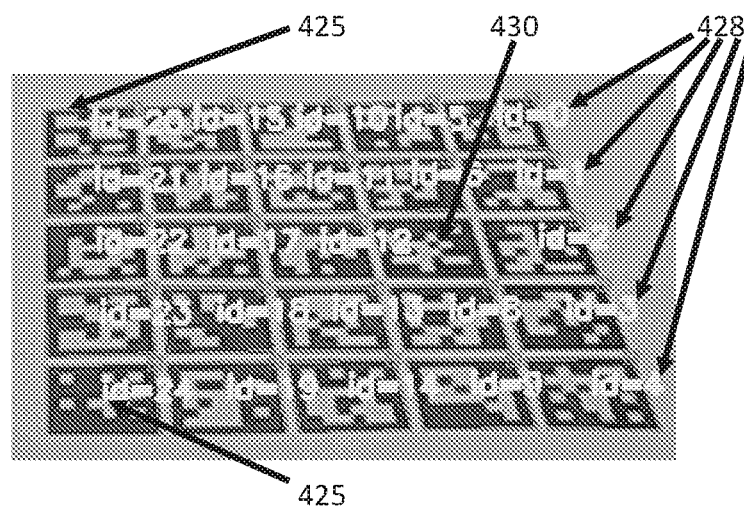
FIG. 27 shows an illustrative, non-limiting example of detection of optical markers using the image capture system of an OHMD.

OpenCV 2.4, an open source computer vision framework (Intel Inc., Santa Clara, Calif.), was implemented on the Hololens system using OpenCVForUnity. 25 As seen in FIG. 26, ArUco markers 425 available with OpenCV with a size of 2.8×2.8 cm were arranged at a distance of 3.0×3.0 cm. A cm scale 426 is shown at the bottom of FIG. 26. No further calibrations, e.g. camera calibration or calibration to reference frames, were performed. Using this approach shown with the results shown in FIG. 27, acquisition of the 25 markers 425 using the internal Hololens camera required 1 second, corresponding to approximately 40 ms per marker. Markers were consistently recognized as indicated by the displayed green marker ID number 428, with only few occasional drop outs with no green marker ID number displayed 430 as seen in FIG. 27.

Static Accuracy Measurements

Figure 28:
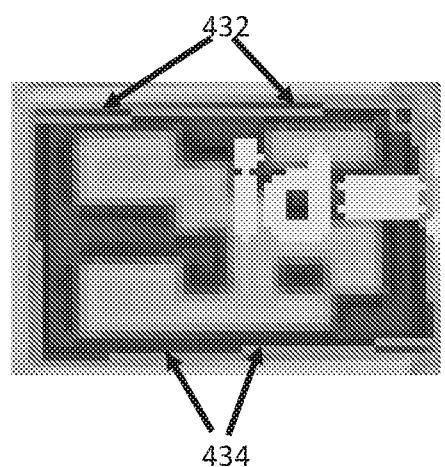
FIG. 28 shows an illustrative, non-limiting example of the accuracy of detecting an optical marker using a video camera integrated into an OHMD.

Markers were mounted on a wooden board with a size of 2.8×2.8 cm and arranged at a distance of 3.0×3.0 cm and static measurements of displacement of optically detected marker positions vs. actual marker positions were obtained at an angle of approximately 40 degrees between the Hololens and the board at a distance of approximately 32.5 cm to the center of the board. FIG. 28 shows an example comparing the actual marker dimensions (2.8×2.8 cm) and position in black 432 with the optically detected marker using the Hololens camera seen as red outline 434. The marker is not square in the image due to the angulation. The pixel size was approximately 0.5 mm in horizontal direction and 0.75 mm in vertical direction in this test. The data indicated sub-pixel accuracy which is why the following analysis of the data was implemented: Pixels at the superior, inferior, left and right border were considered incorrectly detected if more than half had a grey value lower than the average grey value (i.e. the grey value between black and the grey background). For example, the horizontal red line at the superior border in FIG. 28 would need to be exactly 1 pixel higher in order to be counted as correctly detected. Conversely, the inferior second and third horizontal red line from the left were counted as accurately detected. The percentage of each edge (superior, inferior, left, right) that was correctly detected was then determined, e.g. 100% for the superior edge and 50% for the inferior edge in FIG. 28. The analysis over the 25 markers showed that the maximum deviation between the optically detected marker position and the actual marker was 0.75 mm, i.e. one pixel size in vertical direction, with an average deviation between the optically detected marker position and the actual marker of 0.349 pixel=0.26 mm.

Dynamic Accuracy Measurements During Movement

Figure 29:
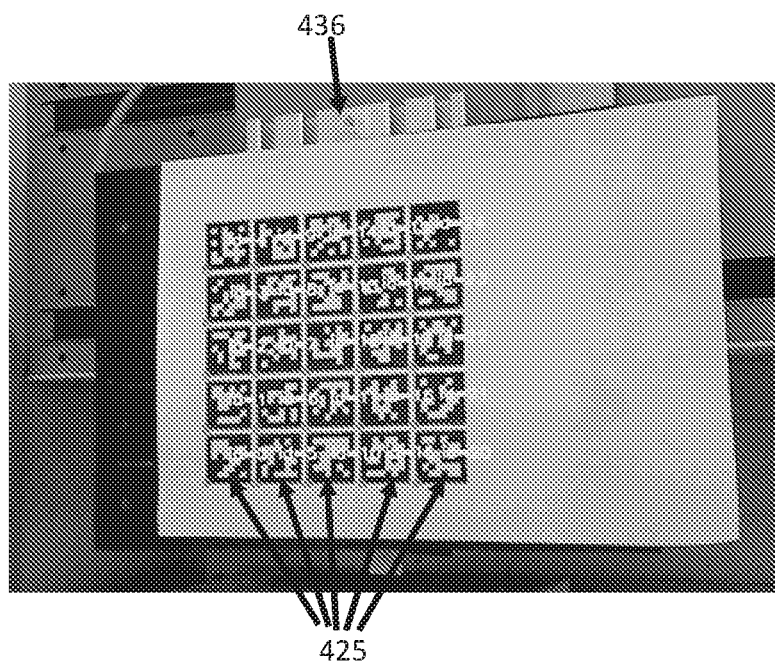
FIG. 29 shows an illustrative, non-limiting example of detection of optical markers during movement using an image capture or video camera system of an OHMD.

In FIG. 29, The wooden board with 25 ArUco 425 markers measuring 2.8×2.8 cm arranged at 3.0 cm interval as described in the foregoing section was mounted on a CNC machine 436 (isel CPM 4030, isel, Eichenzell, Germany). The CNC machine was programmed to move the board in x and z direction at a defined speed of 7.5 cm per second to simulate surgeon head movement. At this speed the 25 markers were detected consistently with only intermittent dropouts of 1 or 2 markers. The pixel size in this experiment was approximately 0.58 mm. The maximum deviation between the optically detected marker position using the Hololens image and/or video capture system and the actual optical marker position in this experiment was 2 pixels corresponding to approximately 1.16 mm.

In a separate experiment, the accuracy regarding a movement in the y-direction was measured. The y-axis was directed into the image plane and corresponded to a movement towards to or away from the patient. The markers were again mounted on a moving CNC machine with the same velocity used in the prior experiment (7.5 cm per second). Four different snapshots were taken at distances from 30 cm to 68 cm away from the OHMD. The evaluation for all markers and the four different depths resulted in an average deviation between the optically detected positions using the Hololens image and/or video capture system and the actual marker position of 0.71±0.32 mm (mean±std). The largest deviation observed in this experiment was 1.75 mm and occurred at the greatest distance of 68 cm, which is beyond the typical work space of the surgeon.

The accuracy of registration can be further enhanced by optimizing marker geometries and patterns, by using pre-existing knowledge about marker size and dimensions with size and dimensions known, e.g. in x and y direction or z direction or y and z direction or combinations of all three, and by using reference frames with optical markers attached to the patient and, optionally, the OR table. In addition, the implementation of a network of OHMDs using real-time spatial maps generated by each OHMD can further increase the accuracy of registration of the live image of the different OHMDs and the virtual data of the patient including a virtual surgical plan.

Developing Optical Markers for Biomedical Applications

Figure 30:
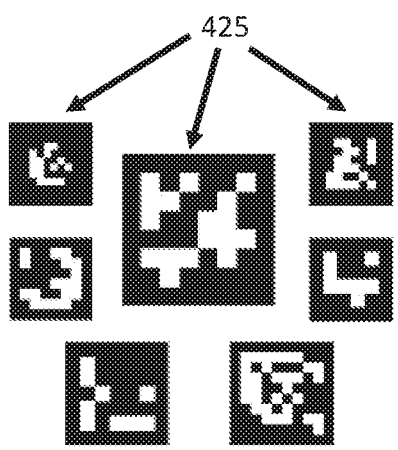
FIG. 30 shows an illustrative, non-limiting example of various optical markers with different dimensions and different geometric patterns.

In order to develop an optimal geometric pattern for detection and recognition using images from an OHMD's video camera for a particular biomedical application, candidate recognition can be tested for different parameters. FIG. 30 shows potential test candidates 425. The test candidates 425 can, for example, use ArUco patterns which utilize a square shape comprising a solid black border frame on the outside and a binary pattern inside as seen in FIG. 30. ArUco patterns can be developed based on OpenCV code. Any other optical marker and pattern can be used and optimized. In a first step in this example, an acceptable minimum size of a marker can be determined, for example for a desired registration accuracy, starting, for example, with a 4×4 binary pattern of 0.5 cm or 1.0 cm border length and increasing the size in 5 mm increments until the pattern is reliably detected with the video camera integrated in a Hololens or other OHMD. Any other marker patterns and dimensions can be used. Tests can be performed for different distances, angles, illuminance and light color parameters, for example like some of the exemplary parameters listed in Table 14. Tests can be performed using any possible parameter combinations, for example from Table 14 or any other set of parameters and parameter ranges. Tests can be conducted in static and moving conditions, e.g. at different speeds. A set-up with a CNC machine can be used for dynamic motion measurements, since speeds can be accurately programmed using this approach.

TABLE 14

Exemplary testing conditions and parameters. Any combination of parameters listed below as well as other parameters are possible.

| Distance (cm) | 35 | 50 | 75 |
|---|---|---|---|
| View angle (°) | 30 | 45 | 90 |
| Illuminance (lux) | 50 | 100 | 200 |
| Light color temperature (Kelvin) | 3000 | 4000 | 5000 |
| Static | ✓ | ✓ | ✓ |
| Dynamic, speed (cm/sec) | 3.25 | 7.5 | 15 |

ArUco optical markers can consist of multiple patterns and can be attached to a plastic, metal or other material holder. Two shapes of holders, e.g. triangular vs. square, can be tested for performance: the detectability of each shape in the spatial maps acquired by the OHMD can be compared between the two shapes. Other shapes can be tested, e.q. rectangles, pentagon, sexagons, septagons, octagons, round, ovoid, elliptical, cubic, ellipoid, irregular shapes. Performance criteria can be position error as well as runtime and behavior in case of partial occlusion of markers. A radiopaque element can be attached to the markers in order to intraoperatively reference anatomic landmarks with fluoroscopy for determining the intended path of the surgical instruments or the intended placement of implant components. The edges of the radiopaque element can be aligned with the edges of the ArUco markers. Other geometric or density features of the radiopaque element can be aligned with features of the ArUco markers. Radiopaque elements or reference or calibration phantoms can be integrated or attached to optical markers. Radiopaque elements or reference or calibration phantoms can also be separate from optical markers at defined distances or geometric arrangements. A registration frame with attached optical markers or separate optical markers at defined distances or geometric arrangements to the registration frame can also be partially or completely radiopaque.

The software can utilize the OpenCV code and can be used to define a local marker coordinate system and pose of each marker. The MS Hololens spatial mapping library can be used to produce a surface mesh using depth camera scans; planes can be identified using the MS Hololens object detection library. Spatial mapping information can be used to define marker coordinates relative to the OHMD. Marker coordinates can be further refined using depth information based on the known shape and dimensional information of the markers. Scaling factors can be applied to the virtual data using the known shape and dimensional information of the markers. The spatial maps can be used to translate from local marker coordinate system, e.g. on a reference frame attached to the patient's back or the OR table, to global OHMD coordinates. The marker coordinate system can be used to determine coordinates of radiopaque elements, which can then be translated into global coordinates for registration with fluoroscopy data.

Registering Intra-Operative Fluoroscopic Images with Live Data of the Patient

For merging fluoroscopy images with live images captured by an OHMD, a registration reference frame can be used. The frame can consist of rigid plastic rods made from a sterilizable plastic (e.g. PEEK) and arranged in a square or rectangular shape, e.g. with an edge length of 35 cm, 40 cm, 45 cm, 50 cm. Multiple frames can be used, e.g. one placed over the lumbar spine, a second placed over the thoracic spine and a third placed over the cervical spine. Optionally, frame can be connectable, e.g. by including connectable members or mechanisms. Other materials, e.g. metal, can be used for the construction of the frame. Optionally, the frame can be radiopaque. An optical marker with an ArUco pattern and a radiopaque element can be attached to each corner of the frame. The markers can be attached at different heights (offsets) from the plane of the frame in order to avoid that the markers are co-planar and to ensure that at least some of the markers are not co-planar.

The registration algorithm can be prototyped and tested in the MATLAB development environment (Mathworks, Waltham, Mass.) and then ported to C# and the Microsoft Hololens platform or another OHMD. For performing the registration between fluoroscopy images and live images, the radiopaque marker elements can, for example, be located in the fluoroscopy image using gray level thresholding and a template matching technique. The optical marker coordinates can be determined from the video image using the techniques described in the preceding sections. A single or multiple optical marker can be attached or integrated into the one or more frames. More than one optical marker can be used on a first side of the patient's anatomy, e.g. a left side or an anterior side. More than one optical marker can be used on a second side of the patient's anatomy, e.g. a right side or a posterior side.

The 3D model of the reference frame including its shape and dimension are known, so that a transformation matrix $T_1$ can be determined, which maps the positions of the markers, e.g. 4 markers $M_0$-$M_3$, in the model coordinate system to the coordinates of the optical markers, e.g. for the 4 optical markers $O_1$-$O_4$, as measured using the OHMD video image. This transformation matrix contains a rotation and a translation component.

Similarly, markers $M_0$-$M_3$ in the model coordinate system can be mapped to the markers $R_0$-$R_3$ identified in the fluoroscopy image using a transformation matrix $T_2$. $T_2$ can contain rotation, translation, projection and scaling components. The overall registration matrix $T_3$ between marker coordinates $R_0$-$R_3$ from the fluoroscopy image and coordinates $O_1$-$O_3$ derived from the video image results from the concatenation of the inverse of $T_1$ with $T_2$.

This transformation can be used to merge and superimpose fluoroscopy images onto the live view. It can be updated to account for changes in position of the OHMD and/or the patient. For this purpose, in order speed up the recalculation and allow for real time updating, only the optical marker coordinates can be updated. This will result in updates to $T_1$ and thus $T_3$ and assumes that the fluoroscopy image is not changing. If the fluoroscopy image is updated as well, a more time-consuming complete re-initialization of $T_1$, $T_2$ and $T_3$ as described can be triggered.

The accuracy of the registration can be tested. For example, the OHMD captures the location of the four optical markers on the edges of the registration frame placed on an OR table; a fluoroscopic image is obtained and the registration of live, optical data and fluoroscopic data using the reference markers is performed. Three square radiopaque lead phantoms measuring 1×1×1 cm are placed on the OR table within the bounds of the registration reference frame or adjacent to the registration frame. Using the registration transformations, the OHMD projects the fluoroscopy image into the live view, thus overlaying fluoroscopy and live views of the radiopaque lead phantoms. The difference between the projected, lead phantom in the fluoroscopy and the physical, visible phantom is captured similar to the technique shown in FIG. 25. The test is repeated for the distances and view angles listed in Table 14.

Using any of the foregoing techniques, fluoroscopic images of the patient can be registered with the live data of the patient including the live anatomy of the patient. If the surgical site is moving during the procedure, for example relative to the OR table or relative to the fluoroscopic images obtained prior to the movement, the fluoroscopic images displayed by the OHMD can be moved correspondingly reflecting any type of translation or rotation of the live surgical site to maintain registration between corresponding live anatomic landmarks and fluoroscopic landmarks using the techniques described above. Thus, fluoroscopy does not need to be repeated or can, optionally, be repeated intermittently which can help reduce radiation dose to the patient and the surgeon.

In certain situations the match between fluoroscopic images and also pre-operative or intra-operative x-ray images can be imperfect or partial, for example due to cone beam geometry of the x-ray beam or magnification affecting different parts of the patient's anatomy differently, e.g. depending on the angle of the x-ray tube. In order to mitigate this effect, registration can optionally be performed using radiopaque optical markers located on the side of the patient intended to be operated or radiopaque optical markers located near the intended surgical site. For example, in a spinal surgery, if the surgeon is planning to place a pedicle screw in the left L4 pedicle, radiopaque optical markers on the left side of a registration frame applied to the patient's back can optionally be used for the registration procedures, for example using the techniques described above. If the surgeon is planning to place a pedicle screw in the right L4 pedicle, radiopaque optical markers on the right side of a registration frame applied to the patient's back can optionally be used for the registration procedures, for example using the techniques described above. Optionally, markers present along the entire frame can be used.

Using any of the other registration techniques described in the specification, the registration can also be performed using corresponding anatomic landmarks in the live data of the patient and the radiographic or fluoroscopic data of the patient, e.g. the tip of a spinous process or several spinous processes which are readily accessible during surgery. If corresponding anatomic landmarks are used in the live data of the patient and the radiographic or fluoroscopic data of the patient, these can be chosen to be on the same side as the surgical site or near the surgical site to minimize the impact of distortions from cone beam geometry of the x-ray beam and to minimize any other distortions, e.g. from magnification affecting select parts of the anatomy further away from the x-ray tube. In this example, the x-ray tube and beam can be intentionally centered over the surgical site to decrease the effect of the cone beam geometry. Fluoroscopic images can be repeated with updated centering for the side to be operated on, for example, if the surgeon switches from a left T3 pedicle to a right T3 pedicle.

Co-Display of Intra-Operative Fluoroscopic Images with Live Data of the Patient

The display of fluoroscopic images registered with the corresponding live data and anatomic landmarks of the patient and superimposed onto the corresponding live data and/or anatomic landmarks of the patient by the OHMD can be advantageous for any type of surgery that utilizes intra-operative fluoroscopy, e.g. spinal surgery, spinal fusions, hip replacement surgery, hip arthroscopy, shoulder replacement surgery and others. Hand-eye coordination can be greatly improved by superimposing the fluoroscopic images directly onto the corresponding live data of the patient and/or anatomic structures using the OHMD. In addition, fluoroscopic images can be acquired less frequently or only intermittently, thereby reducing radiation dose. Such concurrent display of fluoroscopic images can, for example, be advantageous for spinal surgery, wherein the OHMD can display the fluoroscopic images superimposed onto the live anatomy of the patient, e.g. skin, muscle or exposed spinal elements, and, optionally, wherein the OHMD can also display an intended path and/or endpoint for a surgical instrument superimposed onto the corresponding live structures of the patient and the display of the fluoroscopic images. Concurrent display by the OHMD of the fluoroscopic images superimposed onto the corresponding live data of the patient, e.g. anatomic structures and/or landmarks, e.g. the center of a pedicle from a posterior view (live and/or virtual), and, optionally, the intended path and/or endpoint for a surgical instrument, an awl, or a pedicle screw can help the surgeon in aiming or directing an instrument or an implant, e.g. a pedicle screw. Optionally, the OHMD can also co-display a virtual image of any portions of the instrument or implant hidden inside the patient's tissue. For example, in spinal surgery the surgeon can align the instrument or awl or pedicle screw including any hidden portions, optionally virtually displayed, with the intended path displayed by the OHMD while at the same time monitoring the distance of the instrument or awl or pedicle screw including any hidden portions, optionally also virtually displayed by the OHMD, to the pedicle wall visible on the co-displayed fluoroscopic images, ensuring a safe distance from the pedicle wall and avoiding a pedicle wall penetration using concurrent display of the fluoroscopic image. Similarly, the surgeon can advance the instrument, awl or pedicle screw including any hidden portions virtually displayed by the OHMD towards the intended endpoint displayed by the OHMD while at the same time visually monitoring the distance of the instrument, awl or pedicle screw from the wall of the vertebral body seen on the fluoroscopic image co-displayed by the OHMD.

In hip replacement or during other surgical procedures involving the hip joint including arthroscopy or trauma surgery, e.g. fracture repair, one or more OHMDs can also display fluoroscopic images with the fluoroscopically visualized anatomic structures superimposed onto the patient's live data including, for example, the corresponding actual, live anatomic structures such as the pelvis, the pelvic wall, the acetabulum, the acetabular wall, the tear drop, the anterior superior iliac spine, the symphysis pubis, the ilioischial line, the iliopectineal line, the sacrum, the top of the sacrum, the coccyx, the anterior or posterior surface of the sacrum and/or coccyx, the lateral margin or edge of the sacrum or coccyx, portions or all of the femoral head, neck or shaft, the greater or lesser trochanter, including an anterior, posterior, medial, lateral, superior or inferior surface, where applicable. With concurrent display of fluoroscopic images by the OHMD, the fluoroscopic images can be superimposed onto the live hip, femoral or pelvic anatomy of the patient and, optionally, the OHMD can also display an intended path, e.g. for a saw to cut the femoral neck or for a reamer or broach to ream or broach the medullary cavity of the femur, or for an acetabular reamer to ream the acetabulum, and/or an endpoint for a surgical instrument superimposed onto the corresponding live structures of the patient, e.g. an intended stop for an acetabular reamer to avoid penetration of the acetabular wall. Display by the OHMD of the fluoroscopic images superimposed onto the corresponding live data of the patient, e.g. anatomic structures and/or landmarks, e.g. the medial acetabular wall or the tear drop, and, optionally, additional virtual display of the intended path and/or endpoint for a surgical instrument, e.g. a saw, a femoral broach or reamer, or an acetabular reamer, or virtual display of the intended position or orientation of a femoral or acetabular implant component including a trial implant component can help the surgeon in aiming or directing an instrument or an implant, e.g. an acetabular reamer or an acetabular cup or a femoral stem.

Optionally, the OHMD can also co-display a virtual image of any portions of the instrument or implant hidden inside the patient's tissue. For example, in hip replacement surgery, the surgeon can align the instrument such as an acetabular reamer or a femoral broach or reamer including any hidden portions, optionally virtually displayed, with the intended reaming axis or path while at the same time monitoring the distance of the instrument such as an acetabular reamer or a femoral broach or reamer including any hidden portions, optionally virtually displayed, to sensitive structures, e.g. a medial acetabular wall visible on the co-displayed fluoroscopic images, ensuring a safe distance from the acetabular wall and avoiding an acetabular wall penetration using the OHMD display of the fluoroscopic image. Similarly, the surgeon can advance the instrument such as an acetabular reamer or a femoral broach or reamer including any hidden portions virtually displayed by the OHMD towards the intended endpoint displayed by the OHMD while at the same time visually monitoring the distance of the instrument from the intended endpoint seen on the fluoroscopic image co-displayed by the OHMD. For example, the OHMD can display a fluoroscopic image of the patient's hip joint, e.g. in an AP projection, registered with the live data of the patient while the surgeon is performing acetabular reaming. The fluoroscopic image can be displayed by the OHMD in a plane parallel to the OR table or at a predetermined angle to the OR table or in a coronal plane, sagittal plane, axial plane or any other plane relative to the patient and extending through the center of the hip joint or through another landmark. The intended reaming axis can be displayed by the OHMD, for example based on a virtual surgical plan or an intra-operatively determined desired cup inclination and anteversion. The surgeon can align the physical acetabular reamer with the intended virtual reaming axis displayed by the OHMD and can ream the acetabular cavity. As the reamer advances, the OHMD can also visualize or display any hidden portions of the acetabular reamer, including the hidden portions of the reamer handle and the spherical portions of the reamer surface facing the acetabular cavity. As the reamer advances, the surgeon can visually compare the visible and the virtually displayed hidden portions of the acetabular reamer including the position of the acetabular cavity facing reamer surface projected by the OHMD against the co-displayed fluoroscopic image and the surgeon can determine the position and distance of the reamer surface in relationship to the acetabular wall, e.g. the medial acetabular wall, and the tear drop on the co-displayed fluoroscopic images. The virtual co-display of the hidden portions of the reamer including the acetabular cavity facing reamer surface and the fluoroscopic image data including the acetabular wall and tear drop can help the surgeon in determining the appropriate reaming depth and in avoiding a potential acetabular wall penetration. By co-displaying registered fluoroscopic image data with the OHMD, the need for repeat fluoroscopy to ascertain the reamer position can also be reduced thereby reducing radiation exposure to the surgeon and the patient.

In shoulder replacement or during other surgical procedures involving the shoulder joint including arthroscopy or trauma surgery, e.g. fracture repair, one or more OHMDs can also display fluoroscopic images with the fluoroscopically visualized anatomic structures superimposed onto the patient's live data including, for example, the corresponding actual, live anatomic structures such as the glenoid, the glenoid cavity, the glenoid rim, the coracoid process, the acromion, the scapula, the medial or lateral or superior scapular edge, the inferior scapular edge or angle, the proximal humerus, the humeral head, the greater tubercle, the lesser tubercle, the surgical neck, the anatomic neck and/or any osteophytes when present. The fluoroscopic image(s) can be displayed by the OHMD in a plane parallel to the OR table or at a predetermined angle to the OR table or in a coronal plane, sagittal plane, axial plane or any other plane relative to the patient and extending through the center of the shoulder joint [e.g. the glenoid or the humeral head] or through another landmark. With concurrent display of fluoroscopic images by the OHMD, the fluoroscopic images can be superimposed onto the live shoulder, humeral, scapular or glenoid anatomy of the patient and, optionally, the OHMD can also display an intended path, e.g. for a saw to cut the proximal humerus or for a reamer or broach to ream or broach the medullary cavity of the humerus, or for a glenoid reamer to ream the glenoid, and/or an endpoint for a surgical instrument superimposed onto the corresponding live structures of the patient, e.g. an intended stop for a glenoid reamer to avoid overreaming and loss of bone stock. Display by the OHMD of the fluoroscopic images superimposed onto the corresponding live data of the patient, e.g. anatomic structures and/or landmarks, e.g. the glenoid and glenoid bone stock, and, optionally, additional virtual display of the intended path and/or endpoint for a surgical instrument, e.g. a saw, a broach or reamer, or virtual display of the intended position or orientation of a humeral or glenoid implant component including a trial implant component can help the surgeon in aiming or directing an instrument or an implant, e.g. a glenoid reamer or a glenoid or humeral component.

In ankle replacement or during other surgical procedures involving the ankle joint including ankle fusion, arthroscopy or trauma surgery, e.g. fracture repair, one or more OHMDs can also display fluoroscopic images with the fluoroscopically visualized anatomic structures superimposed onto the patient's live data including, for example, the corresponding actual, live anatomic structures such as the medial malleolus, the lateral malleolus, the tibial plafond, the talus, the talar dome, the medial, lateral, anterior or posterior or inferior surface of the talus, and/or portions of or the entire calcaneus and/or any osteophytes when present. The fluoroscopic image(s) can be displayed by the OHMD in a plane parallel to the OR table or at a predetermined angle to the OR table or in a coronal plane, sagittal plane, axial plane or any other plane relative to the patient and extending through the center of the ankle joint [e.g. the distal tibia, the joint space or the talus or talar surface] or through another landmark, e.g. a malleolus. With concurrent display of fluoroscopic images by the OHMD, the fluoroscopic images can be superimposed onto the live ankle, tibial, talar or calcaneal anatomy of the patient and, optionally, the OHMD can also display an intended path, e.g. for a saw to cut the distal tibia or the talus or for a reamer or broach to ream or broach the medullary cavity of the tibia, and/or an endpoint for a surgical instrument superimposed onto the corresponding live structures of the patient, e.g. an intended stop for a tibial reamer to avoid overreaming and loss of bone stock. Display by the OHMD of the fluoroscopic images superimposed onto the corresponding live data of the patient, e.g. anatomic structures and/or landmarks, e.g. the talus, tibia or tibial bone stock, and, optionally, additional virtual display of the intended path and/or endpoint for a surgical instrument, e.g. a saw, a broach or reamer, or virtual display of the intended position or orientation of a tibial or talar implant component including a trial implant component can help the surgeon in aiming or directing an instrument or an implant, e.g. a tibial reamer or a tibial or talar component.

Since the fluoroscopic image is a 2D image and the patient's anatomy is three-dimensional, fluoroscopic images can be displayed centered over an anatomic structure, e.g. as an anchor point, and/or aligned with or parallel with a plane defined by anatomic structures or the OR table. For example, in spinal surgery, an AP fluoroscopic image of the spine can be projected by the OHMD so that the projection extends through the center of a left pedicle, the center of a right pedicle, the center of both pedicles, a left facet joint, a right facet joint, a left and a right facet joint, a lamina, a spinous process, a posterior vertebral wall or an anterior vertebral wall. Other locations are possible, e.g. an anterior third of a pedicle, a posterior third of a pedicle. Any other anatomic structure can be chosen to place the fluoroscopic image in tangent or intersecting fashion. Any of these structures can be selected for multiple spinal levels and the projection plane can be placed by the OHMD to intersect or be tangent with with three or more points chosen in this manner. Alternatively, the projection plane can be parallel to or at a predefined angle and, optionally, distance to the OR table, e.g. as determined using a video camera of an OHMD and one or more optical markers attached to the OR table, and can extend through an anatomic structure in intersecting or tangent fashion, e.g. one of the foregoing anatomic structures. A lateral fluoroscopic image of the spine can be projected by the OHMD so that the projection extends through the center of a left pedicle, the center of a right pedicle, a left facet joint, a right facet joint, a lamina, a spinous process, a left vertebral body wall or a right vertebral body wall. Other locations are possible, e.g. an outer third of a pedicle, an inner third of a pedicle. Any of these structures can be selected for multiple spinal levels and the projection plane can be placed by the OHMD to intersect or be tangent with three or more points chosen in this manner. Alternatively, the projection plane can be perpendicular to or at a predefined angle to the OR table, e.g. as determined using a video camera of an OHMD and one or more optical markers attached to the OR table, and can extend through one or more anatomic structures, e.g. one of the foregoing anatomic structures. Optionally, the projection plane can be parallel to the edge plane of the OR table or at a predefined angle to the edge of the OR table. The projection plane can be chosen to be near the area, tangent with or intersecting the area where the surgeon is operating. For example, if the surgeon is operating on a left pedicle, the OHMD can project a lateral x-ray extending, for example, through the left pedicle of the operated level and, for example, perpendicular to the OR table or parallel to the original projection/acquisition plane, when the surgeon is looking at the patient predominantly from the side. If the surgeon is operating on a right pedicle, the OHMD can project a lateral x-ray extending, for example, through the right pedicle of the operated level and, for example, perpendicular to the OR table or parallel to the original projection/acquisition plane, when the surgeon is looking at the patient predominantly from the side.

If the surgeon is operating on a left pedicle, the OHMD can project an AP x-ray extending, for example, through the central point of the left pedicle of the operated level and, for example, parallel to the OR table or parallel to the original projection/acquisition plane, when the surgeon is looking at the patient predominantly from the top. If the surgeon is operating on a right pedicle, the OHMD can project an AP x-ray extending, for example, through the central point of the right pedicle of the operated level and, for example, parallel to the OR table or parallel to the original projection/acquisition plane, when the surgeon is looking at the patient predominantly from the top.

Optionally, the display can change automatically from AP to lateral or from lateral to AP review, if the surgeon looks more from an AP view perspective (e.g. 90-46 degrees angle relative to OR table) or more from a lateral view perspective (e.g. 0-45 degree angle relative to OR table).

Optionally, both AP and lateral x-rays can be projected simultaneously, centered, in the foregoing examples, over the pedicle or, in other examples, the anatomic structure or one of its landmarks that the surgeon is operating on. Thus, the surgeon can see both x-rays, for example also when looking from a view point that is located between true lateral and true AP view perspective.

The x-rays can be scaled to account for magnification. Using manual or automated image processing techniques to highlight anatomic landmarks or structures, e.g. a pedicle or its cortex, or an acetabulum, the projections of the x-rays can optionally be aligned in the OHMD display so that they are directly superimposed with the corresponding live structure in the patient, which can be helpful, if the patient moved after the x-ray acquisition.

In surgery involving the hip joint, e.g. hip replacement surgery or hip arthroscopy, a fluoroscopic image can be projected by the OHMD so that the projection extends through the left anterior superior iliac spine or the right anterior superior iliac spine, or the symphysis pubis, or the left and right anterior superior iliac spine and the symphysis pubis, co-planar with the anterior pelvic plane; or a fluoroscopic image can be projected parallel to the OR table or at another angle to the OR table, optionally predefined, with the projection plane intersecting or tangent with one or more of the symphysis pubis or the greater trochanter or the lesser trochanter or the anterior surface of the femoral neck or the anterior surface of the femoral head or the anterior surface of the femoral shaft or the posterior surface of the femoral neck or the posterior surface of the femoral head or the posterior surface of the femoral shaft or the center of the femoral head or the anterior or posterior acetabular margin or the center of the acetabulum or the center of rotation of the hip joint, for example determined by tracking multiple optical markers attached to the distal femur during rotatory movement using an image and/or video capture system and/or 3D scanner integrated into, attached to or separate from the OHMD. Any other anatomic structure can be chosen to place the fluoroscopic image in tangent or intersecting fashion.

In surgery involving the shoulder, e.g. shoulder replacement or shoulder arthroscopy, a fluoroscopic image can be projected by the OHMD so that the projection extends through one or more of the glenoid, e.g. the most medial point of the glenoid cavity, the superior, inferior, anterior or posterior edge of the glenoid, the acromion, the coracoid process, the labrum, any of the tendinous structures or muscles, the humeral head, the most medial aspect or surface of the humeral head, the most lateral aspect or surface of the humeral head, the most anterior aspect or surface of the humeral head, the most posterior aspect or surface of the humeral head, the center of the humeral head or the center of rotation of the humeral head. Any other anatomic structure can be chosen to place the fluoroscopic image in tangent or intersecting fashion. The fluoroscopic image can be projected parallel or perpendicular to the OR table or at another angle to the OR table, optionally predefined, with the projection plane intersecting or tangent with one or more of the preceding structures or any other structure; the projection plane can be projected at a predefined distance and angle relative to the plane of the OR table on which the patient is resting. The fluoroscopic image can be projected parallel to the glenoid plane or perpendicular to the glenoid plane, for example depending on the original beam direction or angle of the x-ray system.

In surgery involving the ankle joint, e.g. ankle replacement or ankle arthroscopy, a fluoroscopic image can be projected by the OHMD so that the projection extends through one or more of the medial malleolus, the lateral malleolus, the talus, the anterior, posterior, medial or lateral aspect or surface of the talus, the talar dome, the tibial plafond, the anterior, posterior, medial or lateral aspect or surface of the distal tibia, the calcaneus, the anterior, posterior, medial or lateral aspect or surface of the calcaneus, any of the tendinous structures or muscles, or the flexion/extension axis of the ankle joint. Any other anatomic structure can be chosen to place the fluoroscopic image in tangent or intersecting fashion. The fluoroscopic image can be projected parallel or perpendicular to the OR table or at another angle to the OR table, optionally predefined, with the projection plane intersecting or tangent with one or more of the preceding structures or any other structure; the projection plane can be projected at a predefined distance and angle relative to the plane of the OR table on which the patient is resting. The fluoroscopic image can be projected using the original beam direction or angle of the x-ray system.

For any of the foregoing examples, the projection plane can be selected to mirror the original beam direction or angle of the x-rays system or to be a derivative of the original beam direction or angle of the x-ray system. Someone skilled in the art can identify other anatomic areas or structures or anchor points for placing a virtual projection of an x-ray image or a fluoroscopic image so that it intersects or is tangent with the anatomic areas or structures or anchor points.

Figure 34:
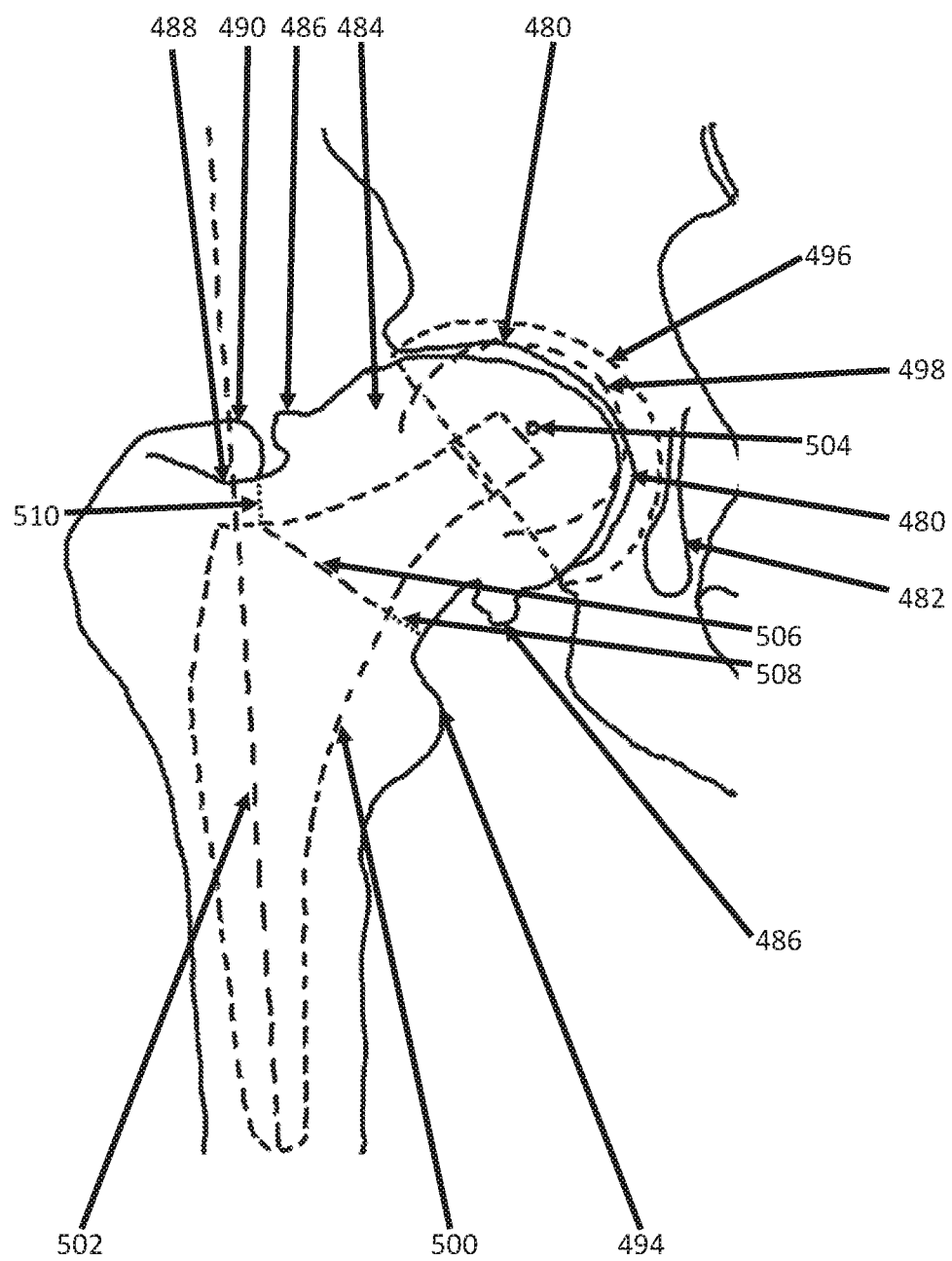
FIG. 34 shows an illustrative, non-limiting example of an AP radiograph of a hip in a patient with sizing and templating information for a hip replacement included, superimposed onto the live surgical site of the patient.

Co-Display of Pre-Operative or Intra-Operative X-Ray Images Including Implant Sizing and/or Templating Information with Live Data of the Patient In some embodiments, pre-operative x-ray images can be used to select an implant from a library. For example, one or more hip x-rays can be used to size or template an acetabular component, an acetabular liner, and a femoral stem including a femoral shaft. An illustrative example is seen in FIG. 34. An AP radiograph of a hip in a patient with arthritis shows radiographic landmarks of the patient such as the acetabulum 480, the tear drop 482, the femoral head 484, osteophytes 486, the sulcus point 488, the highest point of the greater trochanter 490, the most medial point of the lesser trochanter 494. Sizing and templating information is provided with broken lines for the acetabular cup 496, femoral head component 498, femoral stem component 500, femoral stem axis 502, center of rotation 504. The femoral neck cut 506 is also shown at the junction between the femoral shaft and stem. The medial extension of the femoral neck cut into the surrounding bone 508 (dotted line) is shown. The lateral extension in this example requires a second cut 510 (dotted line) since the main portion of the femoral neck cut 506 would interfere with the greater trochanter. The femoral neck cut 506 including its medial extension 508 (dotted line) and lateral extension 510 (dotted line) can be displayed by the OHMD along with the radiographic landmark information such as the acetabulum 480 including the acetabular wall, the tear drop 482, the femoral head 484, osteophytes 486, the sulcus point 488, the highest point of the greater trochanter 490, the most medial point of the lesser trochanter 494. A physical femoral reamer or femoral broach can optionally be aligned with the femoral stem axis 502 virtually displayed by the OHMD, for example along with the radiographic information or radiographic landmarks. For this purpose, radiographic femoral landmarks can be aligned with physical femoral landmarks in the surgical site, e.g. by aligning the radiographic contour of the greater trochanter with the physical shape of the greater trochanter. Someone skilled in the art will recognize how the same templating, virtual template display, virtual radiographic information display can be applied to other joints, e.g. knee, shoulder and ankle as well as spine.

Similar templating approaches using one or more x-rays, e.g. an AP, a lateral and/or oblique x-rays, are used for pedicle screws, e.g. for sizing and/or templating pedicle screws relative to a patient's pedicles and vertebral body dimensions and/or shape, partial and total knee replacements, e.g. for sizing and/or templating femoral, tibial and/or patellar implant components relative to ML and AP dimensions or other dimensions and/or shapes of the distal femur, proximal tibia and patella, partial and total shoulder replacements, e.g. for sizing and/or templating glenoid and humeral components relative to ML, AP and/or SI dimensions or other dimensions and/or shapes of the proximal humerus and glenoid, partial and total ankle replacements, e.g. for sizing and/or templating tibial and talar components relative to ML and AP dimensions or other dimensions and/or shapes of the distal tibial and talus.

Corresponding anatomic structures are identified in or near the physical surgical site of the patient and in the pre-operative x-ray of the patient and the x-ray can be registered to the patient using any of the registration techniques described in the specification including the examples or known in the art. The x-ray including the sizing and templating information can be displayed by the OHMD in a plane defined by anatomic landmarks of the patient and/or parallel to the OR table and/or at a predefined or predetermined distance and/or angle to the OR table and/or at a predefined or predetermined distance and/or angle to the patient, e.g. an anatomic landmark [e.g. in a sagittal, coronal or axial or oblique plane] and/or at an angle corresponding to the x-ray beam, extending through one or more structures or landmarks of the patient, e.g. in a hip replacement the center of the acetabulum or the center of rotation of the hip joint or the anterior edge of the acetabulum or the anterior surface of the patient's femoral neck or femoral shaft, or in a knee replacement the center of the femoral notch or the transepicondylar axis or the tibial tuberosity or the medial or lateral tibial spine or the patella, or in a shoulder replacement the center or anterior rim or posterior rim of the glenoid or the medial aspect of the humerus, or in an ankle replacement the center of the tibial plafond or the talar dome. Optionally, the x-ray is scaled to correct for any magnification. For this purpose, the surgeon can for example place two or more virtual points on anatomic landmarks of the patient, e.g. a most superior or most medial point of the lesser trochanter and a most superior and lateral point on the greater trochanter, and the distance between the two points can be measured in the surgical site of the patient and on the x-ray. Someone skilled in the art will recognize different landmarks in a hip joint, knee joint, shoulder joint, ankle joint, other joint and a spine that can be used in this manner. If the distance measured on the x-ray differs from the distance measured in the patient, a magnification correction can be applied to the x-ray and the included template information so that the radiographic distance will match the distance in the live surgical site of the patient. The OHMD displays the pre-operative x-ray, optionally scaled to match the patient, registered with anatomic landmarks of the patient and superimposed onto the live surgical site of the patient. Optionally the x-rays is registered to and superimposed onto the same anatomic landmarks of the patient, e.g. a sulcus point, i.e. the lowest point between the greater trochanter and the femoral neck, and/or the most superior point on the greater trochanter and/or the most superior point on the lesser trochanter. The display of the pre-operative x-ray includes also the sizing and templating information of one or more implant components and the location and/or orientation of a bone cut, e.g. a femoral neck cut, which can be located at the shaft/stem junction of the prosthesis. The display of the pre-operative x-ray includes also the sizing and templating information of one or more implant components and the location and/or orientation of one or more implant components in relationship to the bone or the surgical site as shown in FIG. 34.

By projecting the pre- or intra-operative x-ray, optionally with the sizing and/or templating information and the related information for any bone cuts, directly onto the patient with use of the OHMD, the surgeon can align a bone saw with the projected cut from the projected template and perform the cut, for example one or more femoral neck cuts 506, 508, 510. Optionally, the OHMD can project a virtual plane extending through the projected cut from the templating information, wherein the virtual plane can be perpendicular to the OR table or at a predetermined angle relative to the OR table. In this manner, the saw blade can be aligned relative to a 3D structure displayed by the OHMD rather than a 2D line. Optionally, the OHMD can also display a virtual cut block which is aligned with the projected cut line from the template and radiograph projected by the OHMD.

By projecting the pre-operative radiograph(s) with the included sizing and/or templating information and implant position directly onto the patient with use of the OHMD, the surgeon can also use the projected information to align a physical surgical instrument or a physical implant with the projected information. For example, in hip replacement, the projected information can include information on the position of an acetabular component relative to the acetabular wall and a tear drop and it can guide the surgeon on how far to advance an acetabular reamer, e.g. when the OHMD projects also virtually any hidden portions of the reamer including, for example, the acetabular fossa facing surface of the reamer. Using OHMD guidance, the surgeon can advance the reamer until the acetabular fossa facing surface of the projected hidden portions of the reamer reach the projected intended position of the implant component from the radiographic template of the implant projected by the OHMD; the surgeon can monitor this visually through the OHMD while also observing the advance of the hidden portions of the reamer relative to the radiographic landmarks projected by the OHMD, e.g. the acetabular wall and the tear drop. Similarly, the surgeon can place a physical implant including any hidden portions projected by the OHMD in relationship to the radiographic template projected by the OHMD as well as the projected radiographic landmarks. The projected information can include information on the position of a femoral stem component relative to the proximal femur and it can guide the surgeon on how far to advance a femoral reamer or broach, e.g. when the OHMD projects also virtually any hidden portions of the reamer or broach including, for example, the bone facing surface of the reamer or broach. Using OHMD guidance, the surgeon can advance the reamer or broach until the bone facing surface of the projected hidden portions of the reamer or broach reach the projected intended position of the femoral stem component from the radiographic template of the implant projected by the OHMD; the surgeon can monitor this visually through the OHMD while also observing the advance of the hidden portions of the reamer or broach relative to the radiographic landmarks projected by the OHMD.

In a shoulder replacement, the projected information can include information on the position of a glenoid component relative to the glenoid and any underlying bone stock and it can guide the surgeon on how far to advance a glenoid reamer. Using OHMD guidance, the surgeon can advance the reamer until the reamer reaches the projected intended position of the implant component from the radiographic template of the implant projected by the OHMD; the surgeon can monitor this visually through the OHMD while also observing the advance of the the glenoid reamer relative to the radiographic landmarks projected by the OHMD. Similarly, the surgeon can place a physical glenoid component including in relationship to the radiographic template projected by the OHMD as well as the projected radiographic landmarks.

The foregoing examples can also be used with cross-sectional imaging techniques such as CT or MRI, wherein the OHMD can co-display 2D cross-sectional images or a 3D model of the surgical site or the anatomy to be operated on, including at different simulated steps of the procedure with corresponding surgically induced changes to the anatomic site, with co-displayed sizing and/or templating information in 2D or 3D of implant components.

Co-Display of Pre-Operative Ultrasound, CT, MRI, SPECT and/or PET Scan Data with Live Data of the Patient In some embodiments, a surgeon can use one or more OHMDs to co-display a pre-operative CT scan or MRI scan of the patient with the patient's live intra-operative anatomy. The display of ultrasound, CT, MRI, SPECT and/or PET scan data, optionally displayed in 2D or 3D, registered with the corresponding live data and anatomic landmarks of the patient and superimposed onto the corresponding live data and/or anatomic landmarks of the patient by the OHMD can be advantageous for any type of surgery in which surgeons utilize pre-operative ultrasound, CT, MRI, SPECT and/or PET scan data, e.g. spinal surgery, spinal fusions, hip replacement surgery, shoulder replacement surgery and others. Hand-eye coordination can be greatly improved by superimposing the pre-operative ultrasound, CT, MRI, SPECT and/or PET scan data, optionally displayed in 2D or 3D, directly onto the corresponding live data of the patient and/or anatomic structures using the OHMD. Such concurrent display of pre-operative ultrasound, CT, MRI, SPECT and/or PET scan data, optionally displayed in 2D or 3D, can, for example, be advantageous for spinal surgery, wherein the OHMD can display the pre-operative ultrasound, CT, MRI, SPECT and/or PET scan data, optionally displayed in 2D or 3D, registered with and superimposed onto the live anatomy of the patient, e.g. skin, muscle or exposed spinal elements, and, optionally, wherein the OHMD can also display an intended path and/or endpoint for a surgical instrument superimposed onto the corresponding live structures of the patient and the display of the pre-operative ultrasound, CT, MRI, SPECT and/or PET scan data, optionally displayed in 2D or 3D. Concurrent display by the OHMD of the pre-operative ultrasound, CT, MRI, SPECT and/or PET scan data, optionally displayed in 2D or 3D, registered with and superimposed onto the corresponding live data of the patient, e.g. anatomic structures and/or landmarks, e.g. the center of a pedicle (live and/or virtual), and, optionally, the intended path and/or endpoint for a surgical instrument, an awl, or a pedicle screw can help the surgeon in aiming or directing an instrument or an implant, e.g. a pedicle screw. Optionally, the OHMD can also co-display a virtual image of any portions of the instrument or implant hidden inside the patient's tissue. For example, in spinal surgery the surgeon can align the instrument or awl or pedicle screw including any hidden portions, optionally virtually displayed, with the intended path displayed by the OHMD while at the same time monitoring the distance of the instrument or awl or pedicle screw including any hidden portions, optionally also virtually displayed by the OHMD, to the pedicle wall visible on the co-displayed pre-operative ultrasound, CT, MRI, SPECT and/or PET scan data, optionally displayed in 2D or 3D, ensuring a safe distance from the pedicle wall and avoiding a pedicle wall penetration using concurrent display of the pre-operative ultrasound, CT, MRI, SPECT and/or PET scan data, optionally displayed in 2D or 3D. Similarly, the surgeon can advance the instrument, awl or pedicle screw including any hidden portions virtually displayed by the OHMD towards the intended endpoint displayed by the OHMD while at the same time visually monitoring the distance of the instrument, awl or pedicle screw from the wall of the vertebral body seen on the pre-operative ultrasound, CT, MRI, SPECT and/or PET scan data, optionally displayed in 2D or 3D by the OHMD.

In hip replacement or during other surgical procedures involving the hip joint including arthroscopy or trauma surgery, e.g. fracture repair, one or more OHMDs can also display pre-operative ultrasound, CT, MRI, SPECT and/or PET scan data, optionally displayed in 2D or 3D, with the visualized anatomic structures, registered with and superimposed onto the patient's live data including, for example, the corresponding actual, live anatomic structures such as the pelvis, the pelvic wall, the acetabulum, the acetabular wall, the anterior superior iliac spine, the symphysis pubis, the ilioischial line, the iliopectineal line, the sacrum, the top of the sacrum, the coccyx, the anterior or posterior surface of the sacrum and/or coccyx, the lateral margin or edge of the sacrum or coccyx, portions or all of the femoral head, neck or shaft, the greater or lesser trochanter, including an anterior, posterior, medial, lateral, superior or inferior surface, where applicable. With concurrent display of pre-operative ultrasound, CT, MRI, SPECT and/or PET scan data, optionally displayed in 2D or 3D, by the OHMD, the CT data can be superimposed onto the live hip, femoral or pelvic anatomy of the patient, anatomically registered, and, optionally, the OHMD can also display an intended path, e.g. for a saw to cut the femoral neck or for a reamer or broach to ream or broach the medullary cavity of the femur, or for an acetabular reamer to ream the acetabulum, and/or an endpoint for a surgical instrument superimposed onto the corresponding live structures of the patient, e.g. an intended stop for an acetabular reamer to avoid penetration of the acetabular wall. Display by the OHMD of the pre-operative ultrasound, CT, MRI, SPECT and/or PET scan data, optionally displayed in 2D or 3D, registered with and superimposed onto the corresponding live data of the patient, e.g. anatomic structures and/or landmarks, e.g. the acetabular wall, and, optionally, additional virtual display of the intended path and/or endpoint for a surgical instrument, e.g. a saw, a femoral broach or reamer, or an acetabular reamer, or virtual display of the intended position or orientation of a femoral or acetabular implant component including a trial implant component can help the surgeon in aiming or directing an instrument or an implant, e.g. an acetabular reamer or an acetabular cup or a femoral stem.

Optionally, the OHMD can also co-display a virtual image of any portions of the instrument or implant hidden inside the patient's tissue. For example, in hip replacement surgery, the surgeon can align the instrument such as an acetabular reamer or a femoral broach or reamer including any hidden portions, optionally virtually displayed, with the intended reaming axis or path while at the same time monitoring the distance of the instrument such as an acetabular reamer or a femoral broach or reamer including any hidden portions, optionally virtually displayed, to sensitive structures, e.g. a medial acetabular wall visible on the co-displayed pre-operative ultrasound, CT, MRI, SPECT and/or PET scan data, optionally displayed in 2D or 3D, ensuring a safe distance from the acetabular wall and avoiding an acetabular wall penetration using the OHMD display of the pre-operative ultrasound, CT, MRI, SPECT and/or PET scan data. Similarly, the surgeon can advance the instrument such as an acetabular reamer or a femoral broach or reamer including any hidden portions virtually displayed by the OHMD towards the intended endpoint displayed by the OHMD while at the same time visually monitoring the distance of the instrument from the intended endpoint seen on the pre-operative ultrasound, CT, MRI, SPECT and/or PET scan data, optionally displayed in 2D or 3D by the OHMD. For example, the OHMD can display pre-operative ultrasound, CT, MRI, SPECT and/or PET scan data, optionally displayed in 2D or 3D, of the patient's hip joint, registered with the live data of the patient while the surgeon is performing acetabular reaming. If a 2D ultrasound, CT, MRI, SPECT and/or PET image is displayed, image can be displayed by the OHMD in a plane parallel to the OR table or at a predetermined angle to the OR table and extending through the center of the hip joint or through another landmark. The intended reaming axis can be displayed by the OHMD, for example based on a virtual surgical plan or an intra-operatively determined desired cup inclination and anteversion. The surgeon can align the physical acetabular reamer with the intended virtual reaming axis displayed by the OHMD and can ream the acetabular cavity. As the reamer advances, the OHMD can also visualize or display any hidden portions of the acetabular reamer, including the hidden portions of the reamer handle and the spherical portions of the reamer surface facing the acetabular cavity. As the reamer advances, the surgeon can visually compare the visible and the virtually displayed hidden portions of the acetabular reamer including the position of the acetabular cavity facing reamer surface projected by the OHMD against the co-displayed pre-operative ultrasound, CT, MRI, SPECT and/or PET scan data, optionally displayed in 2D or 3D, and the surgeon can determine the position and distance of the reamer surface in relationship to the acetabular wall, e.g. the medial acetabular wall, on the co-displayed ultrasound, CT, MRI, SPECT and/or PET images. The virtual co-display of the hidden portions of the reamer including the acetabular cavity facing reamer surface and the pre-operative ultrasound, CT, MRI, SPECT and/or PET scan data, optionally displayed in 2D or 3D, including the acetabular wall can help the surgeon in determining the appropriate reaming depth and in avoiding a potential acetabular wall penetration. By co-displaying registered ultrasound, CT, MRI, SPECT and/or PET scan data with the OHMD, the need for intra-operative fluoroscopy to ascertain the reamer position can also be reduced thereby reducing radiation exposure to the surgeon and the patient.

In shoulder replacement or during other surgical procedures involving the shoulder joint including arthroscopy or trauma surgery, e.g. fracture repair, one or more OHMDs can also display pre-operative ultrasound, CT, MRI, SPECT and/or PET scan data, optionally displayed in 2D or 3D, with the visualized anatomic structures registered with and superimposed onto the patient's live data including, for example, the corresponding actual, live anatomic structures such as the glenoid, the glenoid cavity, the glenoid rim, the coracoid process, the acromion, the scapula, the medial or lateral or superior scapular edge, the inferior scapular edge or angle, the proximal humerus, the humeral head, the greater tubercle, the lesser tubercle, the surgical neck, the anatomic neck and/or any osteophytes when present. With concurrent display of pre-operative ultrasound, CT, MRI, SPECT and/or PET scan data, optionally displayed in 2D or 3D, by the OHMD, the ultrasound, CT, MRI, SPECT and/or PET scan data can be superimposed onto the live shoulder, humeral, scapular or glenoid anatomy of the patient and, optionally, the OHMD can also display an intended path, e.g. for a saw to cut the proximal humerus or for a reamer or broach to ream or broach the medullary cavity of the humerus, or for a glenoid reamer to ream the glenoid, and/or an endpoint for a surgical instrument superimposed onto the corresponding live structures of the patient, e.g. an intended stop for a glenoid reamer to avoid overreaming and loss of bone stock. Display by the OHMD of the pre-operative ultrasound, CT, MRI, SPECT and/or PET scan data, optionally displayed in 2D or 3D, registered with and superimposed onto the corresponding live data of the patient, e.g. anatomic structures and/or landmarks, e.g. the glenoid and glenoid bone stock, and, optionally, additional virtual display of the intended path and/or endpoint for a surgical instrument, e.g. a saw, a broach or reamer, or virtual display of the intended position or orientation of a humeral or glenoid implant component including a trial implant component can help the surgeon in aiming or directing an instrument or an implant, e.g. a glenoid reamer or a glenoid or humeral component.

In ankle replacement or during other surgical procedures involving the ankle joint including ankle fusion, arthroscopy or trauma surgery, e.g. fracture repair, one or more OHMDs can also display pre-operative ultrasound, CT, MRI, SPECT and/or PET scan data, optionally displayed in 2D or 3D, with the visualized anatomic structures registered with and superimposed onto the patient's live data including, for example, the corresponding actual, live anatomic structures such as the medial malleolus, the lateral malleolus, the tibial plafond, the talus, the talar dome, the medial, lateral, anterior or posterior or inferior surface of the talus, and/or portions of or the entire calcaneus and/or any osteophytes when present. With concurrent display of pre-operative ultrasound, CT, MRI, SPECT and/or PET scan data, optionally displayed in 2D or 3D, by the OHMD, the ultrasound, CT, MRI, SPECT and/or PET scan data can be registered with and superimposed onto the live ankle, tibial, talar or calcaneal anatomy of the patient and, optionally, the OHMD can also display an intended path, e.g. for a saw to cut the distal tibia or the talus or for a reamer or broach to ream or broach the medullary cavity of the tibia, and/or an endpoint for a surgical instrument superimposed onto the corresponding live structures of the patient, e.g. an intended stop for a tibial reamer to avoid overreaming and loss of bone stock. Display by the OHMD of the pre-operative ultrasound, CT, MRI, SPECT and/or PET scan data, optionally displayed in 2D or 3D, registered with and superimposed onto the corresponding live data of the patient, e.g. anatomic structures and/or landmarks, e.g. the talus, tibia or tibial bone stock, and, optionally, additional virtual display of the intended path and/or endpoint for a surgical instrument, e.g. a saw, a broach or reamer, or virtual display of the intended position or orientation of a tibial or talar implant component including a trial implant component can help the surgeon in aiming or directing an instrument or an implant, e.g. a tibial reamer or a tibial or talar component.

Projecting 2D Cross-Sectional Image Data with an OHMD

In some embodiments, ultrasound, CT, MRI, SPECT and/or PET can be displayed by the OHMD as a 2-dimensional (2D) cross-sectional image or as a 3-dimensional (3D) reconstruction. Since the patient's anatomy is three-dimensional, when 2D cross-sectional images are used, 2D images can be displayed centered over an anatomic structure, e.g. as an anchor point, and/or aligned with or parallel with a plane defined by anatomic structures or the OR table. For example, in spinal surgery, a 2D cross-sectional image of the spine can be projected by the OHMD so that the projection extends through the center of a left pedicle, the center of a right pedicle, the center of both pedicles, a left facet joint, a right facet joint, a left and a right facet joint, a lamina, a spinous process, a posterior vertebral wall or an anterior vertebral wall. Other locations are possible, e.g. an anterior third of a pedicle, a posterior third of a pedicle. Any other anatomic structure can be chosen to place the 2D cross-sectional cross-sectional image in tangent or intersecting fashion. Any of these structures can be selected for multiple spinal levels and the projection plane can be placed by the OHMD to intersect or be tangent with three or more points chosen in this manner. Alternatively, the projection plane can be parallel to or at a predefined angle and, optionally, distance to the OR table, e.g. as determined using a video camera of an OHMD and one or more optical markers attached to the OR table, and can extend through an anatomic structure in intersecting or tangent fashion, e.g. one of the foregoing anatomic structures. Optionally, the projection plane can be parallel to the edge plane of the OR table or at a predefined angle to the edge of the OR table.

In surgery involving the hip joint, e.g. hip replacement surgery or hip arthroscopy, a 2D cross-sectional image can be projected by the OHMD so that the projection extends through the left anterior superior iliac spine or the right anterior superior iliac spine, or the symphysis pubis, or the left and right anterior superior iliac spine and the symphysis pubis, co-planar with the anterior pelvic plane; or a 2D cross-sectional image can be projected parallel to the OR table or at another angle to the OR table, optionally predefined, with the projection plane intersecting or tangent with one or more of the symphysis pubis or the greater trochanter or the lesser trochanter or the anterior surface of the femoral neck or the anterior surface of the femoral head or the anterior surface of the femoral shaft or the posterior surface of the femoral neck or the posterior surface of the femoral head or the posterior surface of the femoral shaft or the center of the femoral head or the anterior or posterior acetabular margin or the center of the acetabulum or the center of rotation of the hip joint, for example determined by tracking multiple optical markers attached to the distal femur during rotatory movement using an image and/or video capture system and/or 3D scanner integrated into, attached to or separate from the OHMD. Any other anatomic structure can be chosen to place the 2D cross-sectional cross-sectional image in tangent or intersecting fashion.

In surgery involving the shoulder, e.g. shoulder replacement or shoulder arthroscopy, a 2D cross-sectional image can be projected by the OHMD so that the projection extends through one or more of the glenoid, e.g. the most medial point of the glenoid cavity, the superior, inferior, anterior or posterior edge of the glenoid, the acromion, the coracoid process, the labrum, any of the tendinous structures or muscles, the humeral head, the most medial aspect or surface of the humeral head, the most lateral aspect or surface of the humeral head, the most anterior aspect or surface of the humeral head, the most posterior aspect or surface of the humeral head, the center of the humeral head or the center of rotation of the humeral head. Any other anatomic structure can be chosen to place the 2D cross-sectional cross-sectional image in tangent or intersecting fashion. The 2D cross-sectional image can be projected parallel or perpendicular to the OR table or at another angle to the OR table, optionally predefined, with the projection plane intersecting or tangent with one or more of the preceding structures or any other structure; the projection plane can be projected at a predefined distance and angle relative to the plane of the OR table on which the patient is resting. The 2D cross-sectional image can be projected parallel to the glenoid plane or perpendicular to the glenoid plane, for example depending on the original beam direction or angle of the x-ray system.

In surgery involving the ankle joint, e.g. ankle replacement or ankle arthroscopy, a 2D cross-sectional image can be projected by the OHMD so that the projection extends through one or more of the medial malleolus, the lateral malleolus, the talus, the anterior, posterior, medial or lateral aspect or surface of the talus, the talar dome, the tibial plafond, the anterior, posterior, medial or lateral aspect or surface of the distal tibia, the calcaneus, the anterior, posterior, medial or lateral aspect or surface of the calcaneus, any of the tendinous structures or muscles, or the flexion/extension axis of the ankle joint. Any other anatomic structure can be chosen to place the 2D cross-sectional cross-sectional image in tangent or intersecting fashion. The 2D cross-sectional image can be projected parallel or perpendicular to the OR table or at another angle to the OR table, optionally predefined, with the projection plane intersecting or tangent with one or more of the preceding structures or any other structure; the projection plane can be projected at a predefined distance and angle relative to the plane of the OR table on which the patient is resting.

In some embodiments, a virtual implant component can be registered in the coordinate system in which the physical structure, e.g. a joint, of the patient is registered. One or more computer processors can be configured to place the virtual implant component, e.g. a virtual femoral component or a virtual tibial component, on the physical joint of the patient, e.g. the distal femur and/or the proximal tibia, displayed by one or more OHMDs. One or more computer processors can be configured to do one or more of the following with the virtual implant component: virtual placing, virtual sizing, virtual fitting, virtual selecting and/or virtual aligning relative to the physical joint of the patient. One or more computer processors can be configured to provide an OHMD display of the virtual implant component superimposed onto the physical joint of the patient in 3D mode or 2D mode; in 2D mode, one or more computer processors can be configured to allow scrolling through the virtual implant component placed on the physical joint of the patient, e.g. a distal femur or a proximal tibia, for example to evaluate the fit or the size or the alignment. The scrolling can be a scrolling of consecutive 2D slides, e.g. in a sagittal, a coronal, an axial or an oblique plane. Optionally, a transparent 3D display of the virtual implant component can be co-displayed. Alternatively, a 3D display of the virtual implant component can be provided by one or more of the computer processors, wherein the computer processor allows for removal of consecutive 2D slices or sections from the 3D virtual implant component to provide one or more sliced type views of the virtual implant component, for example through different cross-sections (with different orientations) of the virtual 3D display of the virtual implant component.

Network of OHMD Devices

In some embodiments, several OHMD devices can be interconnected to create a network for a shared experience of the augmented views. The devices can be organized in a client-server network where multiple OHMD clients are centralized around a single server. Thus, OHMD devices can be relieved of computing power when outsourcing tasks which are computational intensive (e.g. image processing) to the server. Moreover, battery life of the OHMDs can be significantly prolonged which makes this strategy applicable even in case of a single OHMD client. The server can by accessible in the OR. The server can have a computer monitor and user interface separate from the OHMD.

In case of multiple clients, different data inputs from the various perspectives can be used by the server to increase the accuracy of the calculations (e.g. by averaging out errors). A technique to merge the spatial maps from multiple OHMD clients on the server can be implemented. Spatial maps consist of triangular meshes built from each OHMD's depth sensor information. Once spatial maps have been transferred from each OHMD to the server, the different meshes are combined into a combined, more accurate mesh using the following exemplary, non-limiting averaging algorithm: The data from a first OHMD is used as the baseline. From each face in the baseline mesh, a ray is cast along the surface normal of the face. Intersection points between the ray and all other meshes are calculated. A new vertex for the combined mesh is derived as the average of all intersection points along the ray. The new vertices from adjacent triangles in the baseline mesh are connected to form the faces in the combined mesh. The combined mesh is then transferred back to the individual OHMD for refinement of the registration with the fluoroscopy data.

Exemplary User Interfaces

A standard user interface for surgical planning is implemented on the server in the OR. The server is configured to include a DICOM server for transfer of the fluoroscopic images of the patient. The interface allows a dual or multiple display mode of AP and lateral views, as well as any oblique views obtained. Using a standard mouse or track ball, the interface allows the surgeon to define entry points and vectors of instruments and pedicle screws. 3D coordinates of points and vectors of the plan are determined using a minimum of 2 approximately perpendicular fluoroscopy views. Other angles between the fluoroscopy images or views are possible, known or defined or not known or defined. The planning data are displayed by the OHMD in addition to the fluoroscopic images and serve as input for to the real-time optical guidance during the intervention.

Figure 31A:
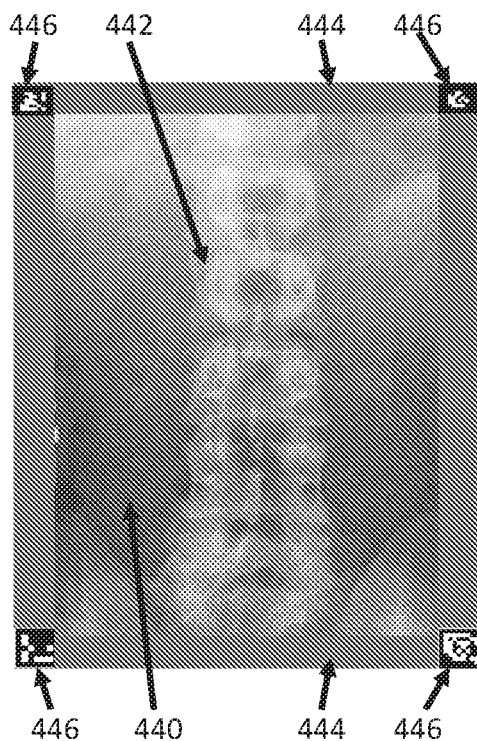
FIGS. 31A-E show an illustrative, non-limiting example for placing an intended path of a pedicle screw using a virtual interface.
Figure 31B:
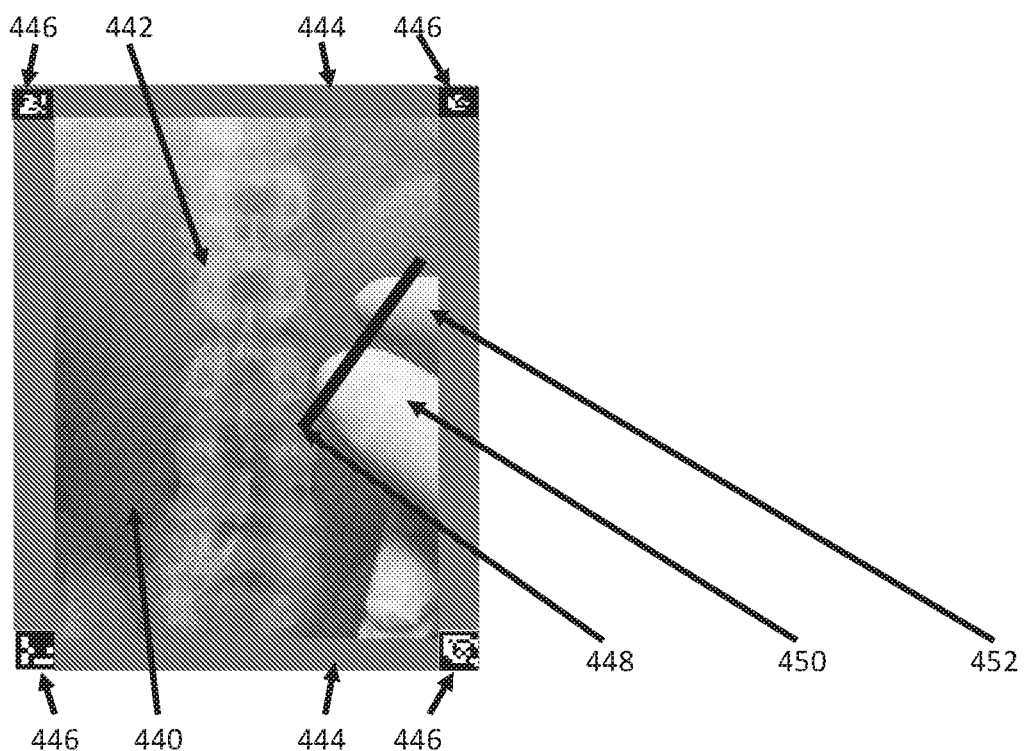
Figure 31C:
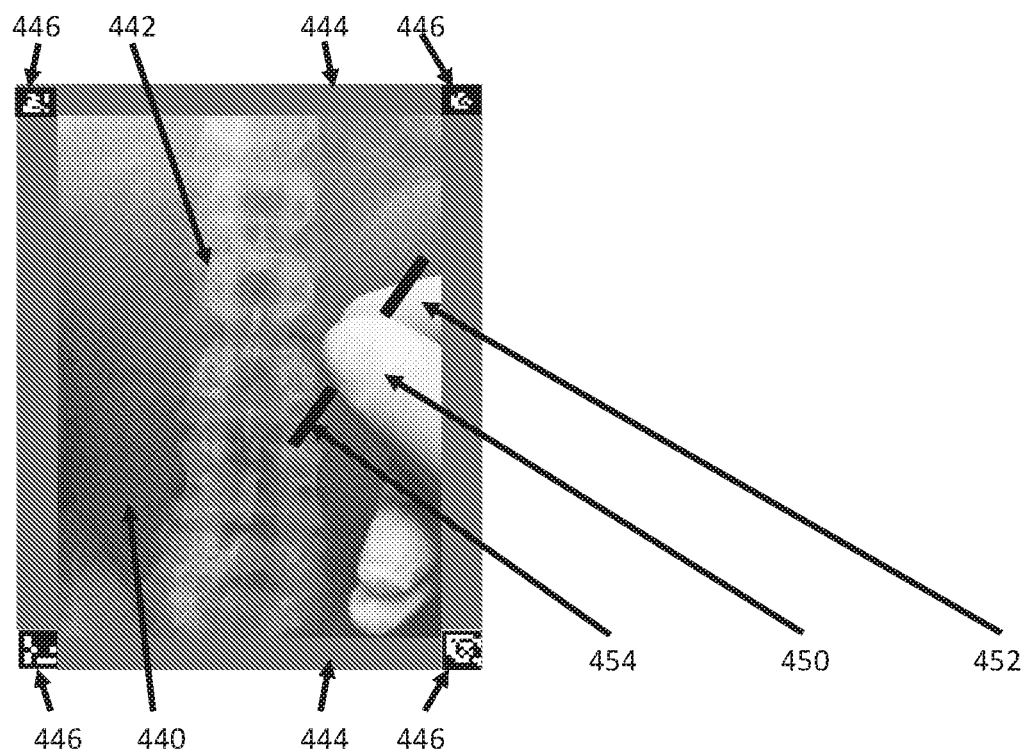
Figure 31D:
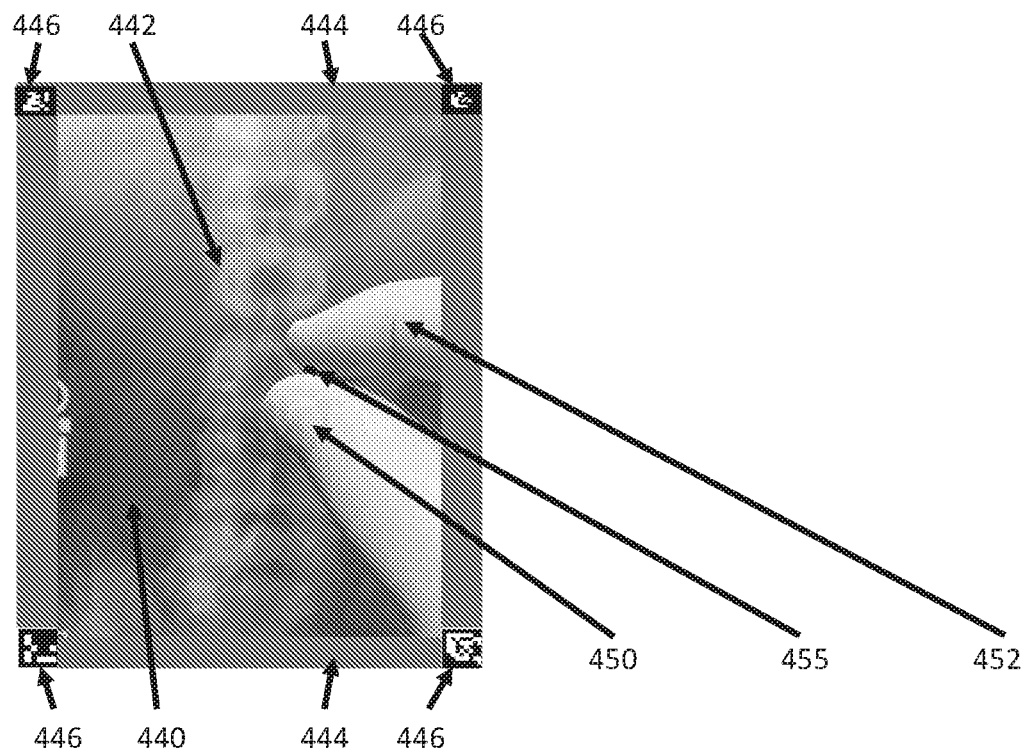
Figure 31E:
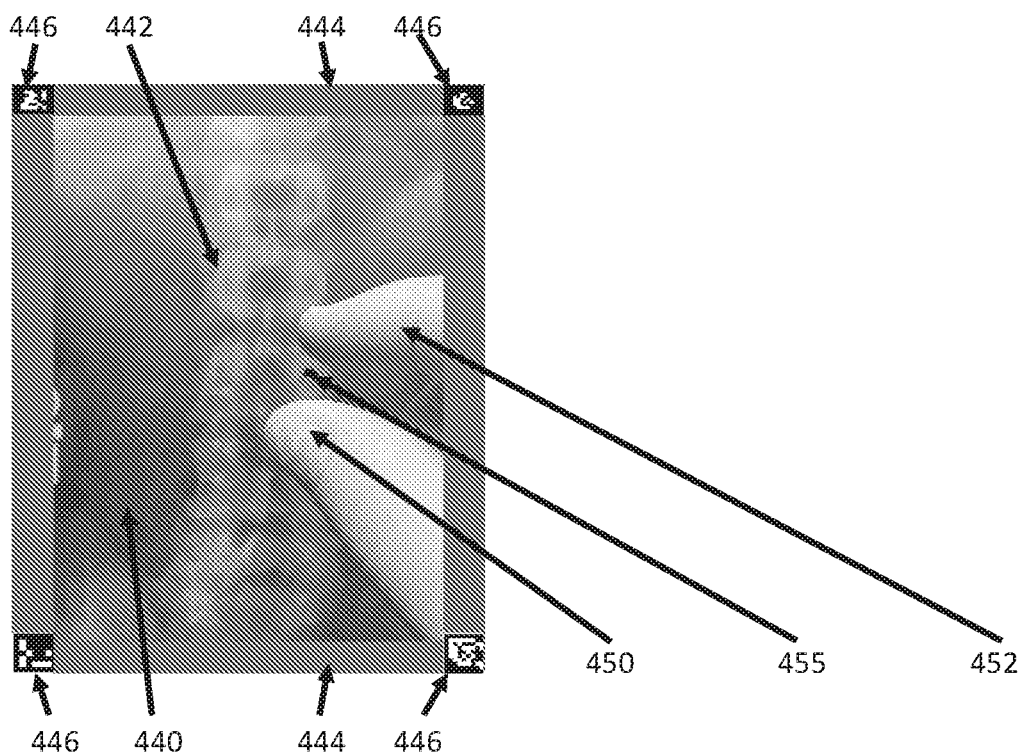

In addition, a prototype virtual interface for the path of a pedicle screw is used using, for example, the Unity for HoloLens engine (Unity Technologies, San Francisco, Calif.). Unity's GestureRecognizer interface allows for recognition of different hold, navigation and manipulation functions. Additionally, the Gaze functionality is available for implementation of a cursor controlled by the user's view direction. Thus, in select application, the user's gaze is controlling the cursor including cursor movement. Closure of the eye lid can, for example, also be used as a command to execute a function. With the virtual interface, the planning can be performed on the fluoroscopic images displayed by the OHMD using gesture commands which are mapped to entry points and vectors. A vector corresponding to the intended path of the surgical instrument(s), e.g. an awl or the pedicle screw, can be placed by the surgeon using gesture commands, e.g. a closed position of the thumb and index finger or an open position of a thumb and index finger as shown in FIGS. 31A-E. FIGS. 31A-E show an illustrative example for placing an intended path of a pedicle screw. In FIGS. 31A-E, a fluoroscopic image 440 of a lumbar spine 442 showing lumbar levels L1-L5 is displayed by the OHMD, registered with anatomic landmarks using reference frame 444 with optical markers 446 attached to patient's back. Each optical marker has its own unique QR or other code, thereby optionally identifying the patient's left and right side, superior and inferior. In FIG. 31B, the OHMD displays a preliminary path 448 in arbitrary location; thumb 450 and index finger 452 are also seen. The surgeon moves fingers towards the arbitrary path with fingers open. In FIG. 31C, the surgeon closes thumb 450 and index fingers 452 over the intended path 454, triggering a command via gesture recognition to move the intended path following the finger movement. In FIG. 31D, the surgeon moves the intended path 455 into desired orientation over the pedicle by moving the thumb 450 and index finger 452. In FIG. 31E, the surgeon opens the thumb 450 and index finger 452 triggering a command via gesture recognition to fixate the vector of the intended path 455 in the coordinate system. An open position indicates in this non-limiting example that the vector is anchored and the intended path is fixated relative to the global coordinate system and the anatomic landmarks. A closed position indicates in this non-limiting example that the vector can be moved with six degrees of freedom following the movement of the fingers. Any other finger symbols and movements can be used.

The accuracy of the virtual interface can tested in comparison to the standard interface developed for the PC implementation. For example, fluoroscopic images of saw bone lumbar spines are obtained and an intended path for a pedicle screw is placed in the L1-L5 pedicles using the standard PC interface. The intended path is placed at a different time by the same operator using the virtual interface. The results of the intended path placement including its entry points and vector using the virtual interface are captured and are compared to the results obtained using the standard PC based interface as the ground truth. Standard interfaces and virtual interfaces can optionally be combined or can be available simultaneously.

Tracking of Surgical Instruments, "Painting" of Patient Surfaces

Figure 32:
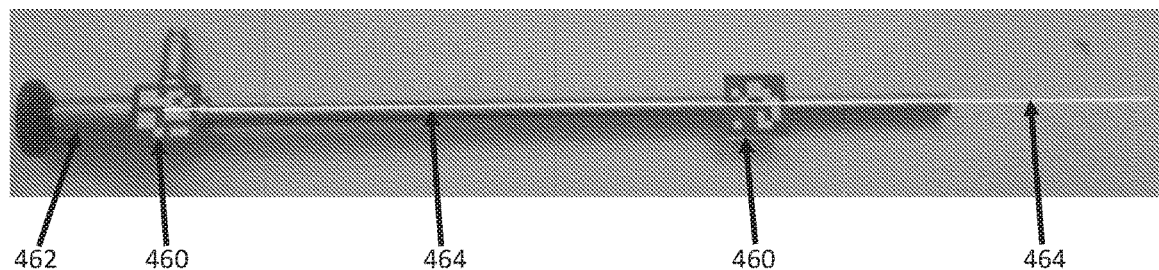
FIG. 32 shows an illustrative, non-limiting example of a surgical instrument with multiple optical markers attached for tracking the surgical instrument.

Multiple different technical approaches are possible to track the surgical instruments in the surgeon's live view of the patient through the OHMD and to project the invisible parts of an instrument hidden by the tissue and its direction with the OMHD. None of these approaches are meant to be limiting, but are only exemplary in nature. Someone skilled in the art can recognize other approaches for tracking surgical instruments using embodiments of the present disclosure. Multiple optical markers 460 can be attached to a surgical instrument 462 as shown in FIG. 32. For example, the markers can be fixed at defined positions on the instrument. With the geometry of the instrument known, the position and orientation of the instrument can be calculated, e.g. for an instrument like an awl with a tip for which its rotary orientation is aligned with the pointing axis only two markers 460 are needed as shown in FIG. 32. More markers can be used, e.g. in different geometric locations on the instrument with overlapping or separate, distinct x, y, and z coordinates. The markers' 3D coordinates are recognized by the OMHD using the methods described in the preceding sections. Using the coordinates of a first and second marker, a vector 464, yellow line in FIG. 32, pointing in the direction of the tip is calculated and displayed by the OHMD to indicate the direction of the hidden portions of the instrument superimposed onto the surgical site, enabling the surgeon to align the physical awl or pedicle screw including its hidden portions with the intended path defined using the standard or virtual planning interface and also projected by the OHMD. Rather than using two or more markers, a single marker can be used, for example with sufficient geometric information, e.g. along the long axis or other axis of the instrument, for accurate coordinate determination, e.g. 2, 3, 4, 5, 6, 7, 8, 9 or 10 cm long and, for example, 1, 2, 3, 4, 5, 6, or 7 or other cm wide, depending also on the spatial resolution of the camera system. In general, the greater the spatial resolution of the camera or video system, the smaller the marker size that can be used for accurate coordinate and/or vector determination. In addition, smaller marker sizes can be possible when markers are stationary, e.g. rigidly attached to a non-moving anatomic part of the patient or the OR table. Larger marker sizes can be used, for example, when markers are attached to a moveable anatomic landmark, e.g. a distal femoral condyle or a proximal tibial plateau, or a humerus, or a humeral tuberosity, or when they are attached to the OHMD and are thus, for example, subject to movement as the surgeon moves his or her head.

Another approach uses pivoting, a mathematical technique for determining the position of the tip. With pivoting, the instruments tip is fixed in one position on the tissue while the whole instrument is moved. The attached optical markers move on a spherical surface. This leads, for example, to an accurate registration of an entry point. The accuracy of tracking the instruments can be measured, for example, by mounting them on a CNC machine using the methods described in the preceding sections. The accuracy of tracking instrument position and orientation can be tested for different parameter combinations, e.g. for parameters and parameter ranges selected from Table 14, for moving conditions at different speeds. Optionally, different instrument tracking techniques, e.g. the two foregoing examples, as well as tracking using attached IMU's or navigation markers can be combined.

In another example, spatial maps can be used determine the coordinates of anatomical landmarks. Anatomical landmarks on the patient's physical anatomy can be digitized for registration with virtual models. For this purpose, the motion of a pointer instrument with optical markers, LED's or navigation markers or other markers attached can be tracked while its tip can be moved by the surgeon over the surface of the anatomical landmark, e.g. a femoral condyle, a tibial plateau, an articular surface or any other anatomical landmark. As the surgeon "paints" the landmark surface, the position of the instrument tip can be calculated from the optical markers, LED's or navigation markers or other. For example, the coordinates of multiple surface points can be determined as the pointer instrument is being moved along the surface, thereby generating a point cloud which can be used to define the surface. On an articular surface, the pointer can be moved to touch surface points on the cartilage surface, thereby creating a point cloud and/or surface mesh or surface that corresponds to cartilage. The pointer can be moved to touch surface points on the subchondral bone surface, thereby creating a point cloud and/or surface mesh or surface that corresponds to subchondral bone; when there is overlying cartilage, a sharp pointer can be used which can be advanced to the tidemark and/or subchondral bone. The touched or "painted" portions of the surface can optionally be displayed by a computer monitor for visual feedback to the surgeon by converting the recorded tip positions to a surface mesh. The touched or "painted" portions of the surface can optionally be displayed as a hologram or virtual 3D representation of the point cloud or resultant 3D surface by the OHMD for visual feedback to the surgeon by converting the recorded tip positions to a surface mesh. One or more computer processors can be configured to display the virtual 3D representation of the point cloud or resultant 3D surface by the OHMD superimposed onto and/or aligned with the physical surface from which the surface points are obtained using the pointer, e.g. a brain surface, an organ surface, a joint surface (e.g. an articular surface). One or more computer processors can be configured to maintain the display of the virtual 3D representation of the point cloud or resultant 3D surface by the OHMD superimposed onto and/or aligned with the physical surface from which the surface points are obtained when the pointer is moved and/or when the physical surface moves, e.g. with movement of a joint or an articular surface or a spine. The OHMD display can, for example, color code the virtual 3D representation of the point cloud or resultant 3D surface, e.g. with green, blue, red or any other color. The virtual 3D representation of the point cloud or resultant 3D surface displayed by the OHMD can be transparent, partially transparent or non-transparent. Areas that have not been touched by the pointer (and no surface points have been generated yet) can remain transparent or void, with no virtual 3D representation or 3D surface covering the physical surface. In this manner, areas that remain to be touched or "painted" can be readily highlighted as voids over the physical surface. In some embodiments a target point cloud or 3D surface can be co-displayed by the OHMD. One or more computer processors can compare the virtual 3D representation of the point cloud or resultant 3D surface obtained from the physical surface with the target point cloud or 3D surface, highlighting, for example with a different color, areas that remain to be touched and/or painted.

In any of the foregoing embodiments, the density of points can be variable; higher density maps can be desirable when high spatial resolution and/or high registration accuracy is required, as can, for example, be the case during brain surgery or resection of a tumor in the brain or other organs or as can be necessary for placement of a medical device, e.g. a knee implant or shoulder or hip implant. The point cloud(s) or surface mesh can be registered with a virtual model, e.g. of the patient's anatomy, e.g. based on pre- or intra-operative scan data thereby registering, for example, intra-operative physical surface(s) and/or landmarks of the patient with virtual data, e.g. a pre-operative or intra-operative scan, imaging data or other virtual data including one or more virtual surgical plans. If the density of points is too low, the surgeon can be warned to add more points to the surface section, e.g. via visual feedback in the virtual 3D representation of the point cloud or resultant 3D surface displayed by the OHMD or acoustic or other feedback. In addition to the dense mesh acquired via digitization of anatomic landmarks, a coarser, but more general spatial map can be generated by a depth camera. This spatial map can also consist of a 3-dimensional surface mesh, which can, for example, be read out using the OHMD's programming interface. This information can be used to supplement the digitized landmarks for registration.

Augmented Reality Guidance of Robots and Robotic Arms

Display of a Virtual Surgical Guide, e.g. a Virtual Plane, for Detecting Deviation of a Saw Blade, a Saw, and/or Robot or Robotic Arm from its Predetermined Path In some embodiments, an OHMD, optionally a see-through OHMD or a non-see-through OHMD using a video camera with live stream of video images of the surgical field into the OHMD display, can display a virtual surgical guide, e.g. a virtual plane, superimposed onto and/or aligned with a bone of a patient, e.g. a distal femur or a proximal tibia exposed during a knee replacement procedure. The virtual surgical guide, e.g. a virtual plane, can be at a predetermined position, predetermined orientation and/or predetermined position and/or orientation, e.g. for a predetermined or intended anteversion and/or offset and/or rotation and/or flexion and/or extension and/or slope, for an intended bone cut for an implant component, e.g. a femoral component in a knee replacement, a tibial component in a knee replacement, a femoral component in a hip replacement, a humeral component in a shoulder replacement, a tibial or talar component in an ankle replacement. The predetermined position, predetermined orientation and/or predetermined position and/or orientation can be selected to define or determine, for example, a leg length, e.g. in a hip replacement and a proximal femoral bone cut, an implant component varus or valgus position, an implant component rotation, an implant component flexion or extension position, an implant component slope, e.g. in a proximal tibial plateau in a knee replacement. The virtual surgical guide, e.g. a virtual plane, can be derived, for example, using data from an imaging test, e.g. an x-ray, an ultrasound, a CT scan, an MRI scan. The virtual surgical guide, e.g. a virtual plane, can be derived, for example, by touching select landmarks of a joint, e.g. portions of an articular surface or osteophytes, or by "painting" portions of the joint, e.g. portions of an articular surface, e.g. of a distal femur with a pointer, e.g. with one or more attached optical markers, navigation markers and/or IMU's and/or by generating a point cloud and surface of an articular surface. A bone cut can then be referenced in relationship to the articular surface, e.g. for a given implant component geometry, e.g. a planar surface on the implant. A bone cut can be referenced, e.g. in relationship to an articular surface, using a CAD file of an implant component. A bone cut can be referenced, e.g. in relationship to an articular surface, using a CAD file of a cut block. A bone cut can be referenced, e.g. in relationship to an articular surface, using any combination of the foregoing.

In some embodiments, a bone cut can be executed by a saw attached to or integrated into a robot. In any of the embodiments throughout the specification, a robot can be active, e.g. with an actively guided robotic arm and attached or integrated saw, actively cutting the bone, or semi-active, e.g. letting a surgeon perform the cut, but stopping a movement of the saw blade or covering the saw blade, if the saw blade is moved outside a predetermined or intended area of cutting or volume of cutting or coordinates for cutting, or passive, e.g. positioning a guide for the surgeon making the cut. A robot can be attached to an arm or to a base via an arm. A robot can be handheld. A robot can be attached to an arm and handheld. Any saw or saw mechanism known in the art can be used, e.g. reciprocating saws or oscillating saws.

A bone cut can be executed using a robot, for example using a predetermined virtual surgical plan. The predetermined virtual surgical plan can be generated using an imaging study, e.g. an ultrasound, CT or MRI scan of the patient. The predetermined virtual surgical plan can be generated by touching select landmarks of a joint, e.g. portions of an articular surface or osteophytes, or by "painting" portions of the joint, e.g. portions of an articular surface, e.g. of a proximal tibia, followed by optional point cloud generation. The predetermined virtual surgical plan can be generated using augmented reality techniques described in the specification, for example by virtually placing, fitting, sizing, selecting and/or aligning a virtual implant component on the live physical joint of the patient and/or by utilizing one or more coordinates of the virtually placed virtual implant component; and/or by deriving the plane and/or coordinates of the bone cut surface or plane using the virtually placed implant component, including its coordinates and geometry, including the geometry of a planar surface of the implant facing the bone cut. Information and/or data from pre- or intra-operative imaging study, touching of landmarks, surface painting and/or point cloud generation and/or augmented reality techniques can be combined.

When the robot executes the bone cut or, in case of a semi-active or passive robot, assists the surgeon in executing the bone cut, the saw blade attached to the saw and/or robotic system can deviate from the predetermined and/or intended cut, for example in the presence of sclerotic bone, which can cause the saw blade to deviate from its predetermined or intended path and/or which can cause the saw blade to bend and/or to deviate from its predetermined or intended path ("saw blade skiving"). Saw blade deviation (saw blade skiving) can be difficult to detect for a surgeon. Thus, it is possible that a surgeon trusts the surgical plan and bone cuts executed by the robot or with assistance by the robot, while in fact the actual cuts in the physical bone can deviate significantly from the predetermined and/or intended cut.

In some embodiments, one or more OHMDs can display and/or project a virtual surgical guide, e.g. a virtual plane, onto the surface of the joint, e.g. an articular surface, for example a cartilage and/or bone and/or subchondral bone and/or an osteophyte, with the predetermined position, predetermined location and/or predetermined orientation, e.g.

from the virtual surgical plan, e.g. the virtual plan developed for or by the robotic system, e.g. using imaging data and/or painting of one or more articular surfaces using a pointer or combinations thereof, and the OHMD can maintain the display of the virtual surgical guide, e.g. a virtual plane, relative to one or more anatomic structures of the joint, e.g. an articular surface and/or an osteophyte, while the robot executes the bone cut with the saw or assists in executing the bone cut with the saw. In any of the embodiments throughout the specification, the OHMD or multiple OHMDs can be registered in the same coordinate system as the robot or robotic arm, e.g. a common coordinate system. In the event of a deviation of the saw blade, the difference between the actual saw path and/or the actual saw blade position, location and/or orientation and the virtual surgical guide, e.g. a virtual plane, including its predetermined position, predetermined location and/or predetermined orientation can be detected.

In some embodiments, the OHMD display can be configured using a computer system and/or computer processor to display or project a virtual surgical guide, e.g. a virtual plane, in a predetermined position, predetermined location, predetermined orientation superimposed onto the surface of a joint, e.g. a cartilage, a bone, a subchondral bone, a cortical bone, and to allow for superimposition and/or alignment of a physical saw, saw blade, and/or robot, e.g. a robotic arm. The OHMD display of the virtual surgical guide, e.g. a virtual plane, can be configured so that a deviation of the physical saw, saw blade, and/or robot from the virtual surgical guide, e.g. a virtual plane, can be readily detected. For example, display colors and transparencies can be selected by the computer system that support visual distinction between the virtual surgical guide, e.g. a virtual plane, and the physical saw, saw blade, and/or robot. The virtual surgical guide, e.g. a virtual plane, can be maintained by the one or more OHMDs superimposed onto the joint, for example in fixed position and/or orientation relative to one or more anatomic landmarks of the joint, while the physical saw, saw blade, and/or robot is/are moving. The virtual surgical guide, e.g. a virtual plane, can be maintained by the one or more OHMDs superimposed onto the joint, for example in fixed position and/or orientation relative to one or more anatomic landmarks of the joint, while the physical joint moves or is being moved. The virtual surgical guide, e.g. a virtual plane, can be maintained by the one or more OHMDs superimposed onto the joint, for example in fixed position and/or orientation relative to one or more anatomic landmarks of the joint, while the physical saw, saw blade, and/or robot are moving and while the physical joint, e.g. one or more articular surfaces, moves or is being moved.

Optionally, a saw blade can be tracked using, for example, optical markers, e.g. with geometric patterns, navigation markers, e.g. using infrared or RF markers, or IMU's or any other marker or tracking mechanism known in the art or described in the specification. The saw blade can be tracked using a 3D scanner, a laser scanner and/or a video imaging system. The saw blade can be attached to a bone saw or other power instrument. The saw blade can be attached to or integrated into an active, semi-active or a passive robot. Any deviation of the physical saw blade from its predetermined position, location, and/or orientation and/or predetermined or intended path can be detected, e.g. automatically or semi-automatically and can, optionally, trigger an alert, e.g. an acoustic or visual alert, e.g. displayed by the OHMD, to the surgeon. Thus, physical saw blade deviation from its intended or predetermined path can be detected using the display of a virtual surgical guide, e.g. a virtual plane, by one or more OHMDs, for example, configured to visualize deviation of the physical saw blade from the virtual surgical guide, e.g. a virtual plane; physical saw blade deviation from its intended or predetermined path can also be detected using tracking and measurement of the coordinates of the saw blade, or any combination of both. Physical saw blade deviation from its intended or predetermined path can be detected using the display of a virtual surgical guide, e.g. a virtual plane, by one or more OHMDs and using tracking and measurement of the coordinates of the physical saw blade.

With the physical saw blade or cutting tool (e.g. a pin, a drill, a mill, a reamer), e.g. attached to a robotic arm, being tracked, the percent superimposition of the physical saw blade or cutting tool with the virtual surgical guide, e.g. a virtual plane or virtual axis, can be determined. The percent superimposition can be displayed on a computer monitor or via the OHMD display. The percent superimposition can be color coded, e.g. with the color changing from red to green when greater than 90, 95, 97, 98, 99 or any other percentage of superimposition is achieved. When the percent superimposition of the physical saw blade or cutting tool (e.g. a pin, a drill, a mill, a reamer), e.g. attached to a robotic arm, with the virtual surgical guide, e.g. a virtual plane or a virtual axis, falls below a predefined or predetermined threshold value, an alarm can be generated, which can be visual, acoustic, vibratory or haptic feedback. A computer processor tracking the coordinates of the physical saw blade or cutting tool, e.g. held by a robotic arm, and comparing the coordinates of the physical saw blade or cutting tool with the coordinates of the virtual surgical guide, e.g. a virtual plane or a virtual axis, can also determine the absolute time or percentage of time of the total "on-time" of the physical saw or cutting tool, e.g. a drill or a burr, when the physical saw or cutting tool is operating above a predefined or predetermined percentage superimposition, e.g. 90, 95, 97, 98, or 99% or any other percentage.

Display of a Virtual Axis for Detecting Deviation of a Pin, Drill, Mill, Reamer, and/or Robot or Robotic Arm from its Predetermined Path In some embodiments, an OHMD, optionally a see-through OHMD or a non-see-through OHMD using a video camera with live stream of video images of the surgical field into the OHMD display, can display a virtual axis superimposed onto and/or aligned with a bone of a patient, e.g. a distal femur or a proximal tibia exposed during a knee replacement procedure. The virtual axis can, for example, be used for placing a first and, optionally, a second pin or screw for attaching a cut block and performing a bone cut. The virtual axis can, for example, be used for burring or milling a first and, optionally, a second hole in a bone for attaching or inserting at least portions of a cut block (for example with a corresponding peg) and performing a bone cut. The virtual axis can be at a predetermined position, predetermined orientation and/or predetermined position and/or orientation, e.g. for a predetermined or intended anteversion and/or offset and/or rotation and/or flexion and/or extension and/or slope, for an intended bone cut for an implant component, e.g. a femoral component in a knee replacement, a tibial component in a knee replacement, a femoral component in a hip replacement, a humeral component in a shoulder replacement, a tibial or talar component in an ankle replacement. The predetermined position, predetermined orientation and/or predetermined position and/or orientation can be selected to define, for example, a leg length, e.g. in a hip replacement and a proximal femoral bone cut, an implant component varus or valgus position, an implant component rotation, an implant component flexion or extension position, an implant component slope, e.g. in a proximal tibial plateau in a knee replacement. The virtual axis can be derived, for example, using data from an imaging test, e.g. an x-ray, an ultrasound, a CT scan, an MRI scan. The virtual axis can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface.

A bone cut can then be referenced in relationship to the articular surface, e.g. for a given implant component geometry, e.g. a planar surface on the implant. A bone cut can be referenced, e.g. in relationship to an articular surface, using a CAD file of an implant component. A bone cut can be referenced, e.g. in relationship to an articular surface, using a CAD file of a physical cut block with, for example, holes for pin placement (and OHMD display of a corresponding virtual axis) or pegs (and OHMD display of a corresponding virtual axis for burring, milling or drilling one or more holes in the bone). Any combination of embodiments is possible.

In some embodiments, a hole or void can be created by a pin or a drill or a burr or a mill or a reamer attached to or integrated into a robot. The robot can be active, e.g. with an actively guided robotic arm and attached or integrated pin, or drill, or burr, or mill or reamer, actively pinning or drilling or burring or milling or reaming the bone, or semi-active, e.g. letting a surgeon perform the pinning or drilling or burring or milling or reaming, but stopping a movement of the pin or drill or burr or mill or reamer or covering the pin, or drill, or burr, or mill or reamer, if the pin, or drill, or burr, or mill or reamer is moved outside a predetermined or intended area of pinning or drilling or burring or milling or reaming or volume of pinning or drilling or burring or milling or reaming or coordinates for pinning or drilling or burring or milling or reaming, or passive, e.g. positioning a guide for the surgeon to perform a pinning or drilling or burring or milling or reaming. The robot can be attached to an arm or to a base via an arm. The robot can be handheld. The robot can be attached to an arm and handheld. Any pinning or drilling or burring or milling or reaming mechanism known in the art can be used.

The pinning or drilling or burring or milling or reaming can be executed using a robot, for example using a predetermined virtual surgical plan. The predetermined virtual surgical plan can be generated using an imaging study, e.g. an ultrasound, CT or MRI scan of the patient. The predetermined virtual surgical plan can be generated using touching of landmarks, surface painting of a joint followed by optional point cloud generation. The predetermined virtual surgical plan can be generated using augmented reality techniques described in the specification, for example by virtually placing, fitting, sizing, selecting and/or aligning a virtual implant component on the live physical joint of the patient and/or by using one or more coordinates of the virtually placed implant component. Information and/or data from pre- or intra-operative imaging study, touching of landmarks, surface painting and/or optional point cloud generation and/or augmented reality techniques, e.g. virtual placement of virtual implant components on the live physical joint of the patient, can be combined.

When the robot executes the pinning or drilling or burring or milling or reaming or, in case of a semi-active or passive robot, assists the surgeon in executing the pinning or drilling or burring or milling or reaming, the pin or drill or burr or mill or reamer can deviate from the predetermined and/or intended pinning or drilling or burring or milling or reaming, for example in the presence of sclerotic bone, which can cause the pin or drill or burr or mill or reamer to deviate from its predetermined or intended path and/or which can cause the pin or drill or burr or mill or reamer to bend and/or to deviate from its predetermined or intended path. Pin or drill or burr or mill or reamer deviation can be difficult to detect for a surgeon. Thus, it is possible that a surgeon trusts the surgical plan and pinning or drilling or burring or milling or reaming executed by the robot or with assistance by the robot, while in fact the actual pinning or drilling or burring or milling or reaming in the physical bone can deviate significantly from the predetermined and/or intended pinning or drilling or burring or milling or reaming and related holes in the bone or bone voids.

In some embodiments, one or more OHMDs can display and/or project a virtual surgical guide, e.g. a virtual axis, onto the surface of the joint, e.g. an articular surface, for example a cartilage and/or bone and/or subchondral bone and/or an osteophyte, with the predetermined position, predetermined location and/or predetermined orientation, e.g. from the virtual surgical plan, and the OHMD can maintain the display of the virtual axis relative to one or more anatomic structures of the joint, e.g. an articular surface and/or an osteophyte, while the robot executes the pinning or drilling or burring or milling or reaming or assists in executing the pinning or drilling or burring or milling or reaming. In the event of a deviation of the pin or drill or burr or mill or reamer from its predetermined or intended path and/or axis, the difference between the actual pin or drill or burr or mill or reamer path and/or the actual pin or drill or burr or mill or reamer position, location and/or orientation and the virtual surgical guide, e.g. the virtual axis or a 2D or 3D placement indicator of the pin or drill or burr or mill or reamer, including its predetermined position, predetermined location and/or predetermined orientation can be detected.

In some embodiments, the OHMD display can be configured using a computer system and/or computer processor to display a virtual surgical guide, e.g. a virtual axis, in a predetermined position, predetermined location, predetermined orientation superimposed onto the surface of a joint, e.g. a cartilage, a bone, a subchondral bone, a cortical bone, and to allow for superimposition and/or alignment of a physical pin, or drill, or mill or robot and/or robot. The OHMD display of the virtual surgical guide, e.g. a virtual axis, can be configured so that a deviation of the physical drill or pin or mill or reamer and/or robot from the virtual axis can be readily detected. For example, display colors and transparencies can be selected by the computer system that support visual distinction between the virtual surgical guide, e.g. a virtual axis, and the physical pin or drill or burr or mill or reamer and/or robot. The virtual surgical guide, e.g. a virtual axis, can be maintained by the one or more OHMDs superimposed onto the joint, for example in fixed position and/or orientation relative to one or more anatomic landmarks of the joint, while the physical pin, or drill, or mill, or reamer, and/or robot are moving. The virtual surgical guide, e.g. a virtual axis, can be maintained by the one or more OHMDs superimposed onto the joint, for example in fixed position and/or orientation relative to one or more anatomic landmarks of the joint, while the physical joint moves or is being moved. The virtual surgical guide, e.g. a virtual axis, can be maintained by the one or more OHMDs superimposed onto the joint, for example in fixed position and/or orientation relative to one or more anatomic landmarks of the joint, while the physical pin, or drill, or mill, or reamer, and/or robot are moving and while the physical joint moves or is being moved. Optionally, a pin or drill or burr or mill or reamer can be tracked using, for example, optical markers, e.g. with geometric patterns, navigation markers, e.g. using infrared or RF markers, or IMU's or any other marker or tracking mechanism known in the art or described in the specification. The pin or drill or burr or mill or reamer can be tracked using a 3D scanner, a laser scanner and/or a video imaging system. The pin or mill or drill or burr or reamer can be attached to a power instrument. The pin or mill or drill or burr or reamer and/or power instrument can be attached to or integrated into an active, semi-active or a passive robot. Any deviation of the physical saw pin or drill or burr or mill or reamer from its predetermined position, location, and/or orientation and/or predetermined or intended path can be detected, e.g. automatically or semi-automatically and can, optionally, trigger an alert, e.g. an acoustic or visual alert, e.g. displayed by the OHMD, to the surgeon. Thus, deviation of the pin or drill or burr or mill or reamer from its intended or predetermined path can be detected using the display of a virtual surgical guide, e.g. a virtual axis, by one or more OHMDs configured to visualize deviation of the physical pin or mill or drill or reamer and/or robot from the virtual surgical guide, e.g. a virtual axis; the deviation from its intended or predetermined path can also be detected using tracking and measurement of the coordinates of the physical pin or drill or burr or mill or reamer and/or robot, e.g. robot arm. Deviation of the physical pin or drill or burr or mill or reamer from its intended or predetermined path can be detected using the display of a virtual surgical guide, e.g. a virtual axis, by one or more OHMDs and using tracking and measurement of the coordinates of the physical pin or drill or burr or mill or reamer and/or robot, including robotic arm or portions thereof. With the physical saw blade or cutting tool (e.g. a pin, a drill, a mill, a reamer), e.g. attached to a robotic arm, being tracked, the percent superimposition of the physical saw blade or cutting tool with the virtual surgical guide, e.g. a virtual plane or virtual axis, can be determined. The percent superimposition can be displayed on a computer monitor or via the OHMD display. The percent superimposition can be color coded, e.g. with the color changing from red to green when greater than 90, 95, 97, 98, 99 or any other percentage of superimposition is achieved. When the percent superimposition of the physical saw blade or cutting tool (e.g. a pin, a drill, a mill, a reamer), e.g. attached to a robotic arm, with the virtual surgical guide, e.g. a virtual plane or a virtual axis, falls below a predefined or predetermined threshold value, an alarm can be generated, which can be visual, acoustic, vibratory or haptic feedback. A computer processor tracking the coordinates of the physical saw blade or cutting tool, e.g. held by a robotic arm, and comparing the coordinates of the physical saw blade or cutting tool with the coordinates of the virtual surgical guide, e.g. a virtual plane or a virtual axis, can also determine the absolute time or percentage of time of the total "on-time" of the physical saw or cutting tool, e.g. a drill or a burr, when the physical saw or cutting tool is operating above a predefined or predetermined percentage superimposition, e.g. 90, 95, 97, 98, or 99% or any other percentage.

OHMD Displays for Projecting One or More Virtual Portions of a Robot or Placement Indicators of a Robot, Augmented Reality Guidance of Robots or Robotic Arms In some embodiments, a physical surgical instrument or a physical surgical tool can include a robotic arm, e.g. for bone removal, e.g. with an attached drill, mill, burr, reamer, impactor, broach, and/or saw and/or saw blade. The robotic arm can, for example, move with 2, 4 or 6 degrees of freedom and can be attached to a stand. At least portions of the robot can be handheld. The robot can optionally provide haptic feedback, e.g. when a surgeon is holding a portion of a robot and the robot operates within or outside an intended or predetermined perimeter, area or volume of bone removal, slowing or stopping, for example the advancement of the robot or robotic arm if the robot operates outside the intended or predetermined perimeter, area or volume of bone removal. In some embodiments, a sharp tool for bone removal, e.g. a drill, a mill, a burr, a reamer, a broach, a saw, can be exposed by the robot when the user is advancing the robot within a predetermined surgical plan, e.g. within a perimeter or area or volume predetermined for bone removal; the sharp tool for bone removal can be covered by a protective sleeve when the robot or robotic arm is advanced outside a predetermined surgical plan, e.g. outside a perimeter or area or volume predetermined for bone removal.

One or more optical head mounted displays can display a virtual surgical instrument, e.g. a virtual representation or a virtual display of portions of a robot, e.g. a robotic arm, or virtual images or a virtual representation or a virtual display of a robotic arm, including, for example, any handheld portions, for example with an attached drill, mill, burr, reamer, impactor, broach, and/or saw and/or saw blade. The virtual display or virtual representation can be a 2D or a 3D display. The 2D or 3D display can be an outline of the robot or robotic arm or portions thereof. The 2D or 3D display can be a placement indicator of the virtual surgical instrument, e.g. a robot or robotic arm or portions thereof. The 2D or 3D display can be based on an STL file of the robot or robotic arm or portions thereof. The 2D or 3D display can be based on a CAD file of the robot or robotic arm or portions thereof. One or more portions of the robot or robotic arm and/or its virtual display can include one or more of a drill, mill, burr, reamer, impactor, broach, and/or saw and/or saw blade. One or more portions of the robot or robotic arm displayed by the OHMD, e.g. in form of a virtual surgical instrument, can include one or more of a handheld portion of a robot and/or at least a portion of a robotic arm.

The one or more optical head mounted displays can be registered in a coordinate system, e.g. a common coordinate system. The robot or robotic arm or at least portions of the robot can be registered in the same coordinate system. One or more anatomic sites, e.g. a knee exposed during knee replacement surgery, or an acetabulum or a proximal femur exposed during hip replacement surgery, or a spine, e.g. a spinous process, a facet joint, a pedicle, a vertebral body, or any other joint or portion of the body can be registered in the same coordinate system.

A physical surgical instrument and/or the physical surgical tool can be or can include a physical robotic arm or portions thereof, including, for example, with an attached physical drill, mill, burr, reamer, impactor, broach, and/or saw and/or saw blade, or a physical portion of a robot to which one or more of a drill, mill, burr, reamer, impactor, broach, and/or saw and/or saw blade are attached, or a physical handheld portion of a robot or a robotic arm or any other physical component of a robot, including, for example, one or more physical optical markers, e.g. using one or more geometric patterns, navigation markers, e.g. using RF or infrared markers, calibration phantoms, IMU's and/or any other marker known in the art or described, for example, in U.S. provisional application No. 62/700,096, filed Jul. 18, 2018, which is incorporated herein by reference in its entirety.

In some embodiments, the at least one optical head mounted display can be configured to display a virtual surgical instrument, a virtual surgical tool, a virtual display, or virtual representation, e.g. of a robot or portions thereof, superimposed onto a physical joint, e.g. the surface of the physical joint, for example a cartilage, subchondral bone or cortical bone, or spine based, for example, at least in part on coordinates of a predetermined position and/or orientation or combinations thereof of the virtual surgical instrument, virtual surgical tool, virtual display, or virtual representation, and the virtual surgical instrument, virtual surgical tool, virtual display, or virtual representation can configured to allow for superimposing and/or aligning the physical surgical instrument or physical surgical tool, e.g. portions of a physical robot, with the virtual surgical instrument, virtual surgical tool, virtual display, or virtual representation to guide a bone cut and/or bone and/or cartilage removal of the joint, e.g. using a pin, a drill, a mill, a burr, a reamer, a broach and/or an impactor, e.g. attached to or integrated into the robot.

The virtual surgical instrument, virtual surgical tool, virtual display, or virtual representation, e.g. of at least a portion of a robot or any components thereof, including, for example, an attached or integrated pin, drill, burr, mill, reamer, broach and/or impactor, can be at a predetermined position, predetermined orientation and/or predetermined position and/or orientation, e.g. for a predetermined or intended anteversion and/or offset and/or rotation and/or flexion and/or extension and/or slope and/or leg length and/or arm length, for an intended bone cut for an implant component, e.g. a femoral component in a knee replacement, a tibial component in a knee replacement, a femoral component in a hip replacement, an acetabular component in a hip replacement, a humeral component in a shoulder replacement, a tibial or talar component in an ankle replacement or a femoral and/or tibial tunnel or intended graft site for an ACL or other ligament reconstruction. The predetermined position, predetermined orientation and/or predetermined position and/or orientation can be selected to define, for example, a leg length, e.g. in a hip replacement and a proximal femoral bone cut, an implant component varus or valgus position, an implant component rotation, an implant component flexion or extension position, an implant component slope, e.g. in a proximal tibial plateau in a knee replacement. The predetermined position, predetermined orientation and/or predetermined position and/or orientation of the virtual surgical instrument, virtual surgical tool, virtual display, or virtual representation, e.g. of at least a portion of a robot or any components thereof, including, for example, an attached or integrated pin, drill, burr, mill, reamer, broach and/or impactor, can be derived, for example, using data from an imaging test, e.g. an x-ray, an ultrasound, a CT scan, an MRI scan. In any of the embodiments throughout the specification, the data from the imaging test can, for example, include data generated by placing and/or fitting and/or sizing and/or selecting and/or aligning a virtual implant component, e.g. an STL file or CAD file of an implant component, in imaging data or using imaging data of the patient. The virtual surgical instrument, virtual surgical tool, virtual display, or virtual representation, e.g. of at least a portion of a robot or any components thereof, including, for example, an attached or integrated pin, drill, burr, mill, reamer, broach and/or impactor, can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut or bone removal, e.g. using a pin, a drill, a burr, a mill, a reamer, a broach, and/or an impactor and/or a saw, can then be referenced in relationship to the articular surface, e.g. for a given implant component geometry, e.g. a planar surface on the implant. A bone cut can be referenced, e.g. in relationship to an articular surface, using a CAD file of an implant component. A bone cut or bone removal, e.g. using a pin, a drill, a burr, a mill, a reamer, a broach, and/or an impactor and/or a saw, can be referenced, e.g. in relationship to an articular surface, using a CAD file of a physical cut block with, for example, holes for pin placement (and optional OHMD display of a corresponding virtual surgical guide, virtual surgical instrument, virtual surgical tool, virtual display or virtual representation, e.g. a virtual axis) or pegs (and optional OHMD display of a corresponding virtual surgical guide, virtual surgical instrument, virtual surgical tool, virtual display or virtual representation, e.g. a virtual axis for burring, milling or drilling one or more holes in the bone). A bone cut or bone removal, e.g. using a pin, a drill, a burr, a mill, a reamer, a broach, and/or an impactor and/or a saw, can be referenced in relationship to coordinates of a virtually placed, fitted, sized, selected and/or aligned virtual implant component, placed, for example, on portions of a physical joint of the patient. Any combination of embodiments is possible.

In some embodiments, the at least one optical head mounted display can be configured to display the virtual surgical instrument, virtual surgical tool, virtual display or virtual representation, e.g. of a robot or a robotic arm or portions thereof, including, for example, an attached or integrated pin, drill, burr, mill, reamer, broach and/or impactor and/or saw or saw blade, superimposed onto and/or aligned with a physical joint, e.g. the surface of the physical joint including a surgically exposed surface, or onto a spine, e.g. an exposed surface of the spine, for example, a spinous process or a lamina, and to maintain the display of the virtual surgical instrument, virtual surgical tool, virtual display or virtual representation superimposed onto and/or aligned with one or more anatomic landmarks and/or the surface of the physical joint or spine when the one or more physical surgical instrument, e.g. portions of a physical robot or robotic arm, for example a handheld portion of the robot or a robotic arm, physical surgical tool, physical medical device, e.g. an implant, move, e.g. in the coordinate system.

In some embodiments, the at least one optical head mounted display can be configured to display the virtual surgical instrument, virtual surgical tool, virtual display or virtual representation, e.g. of a robot or a robotic arm or portions thereof, including, for example, an attached or integrated pin, drill, burr, mill, reamer, broach and/or impactor and/or saw or saw blade, superimposed onto and/or aligned with a physical joint, e.g. the surface including a surgically exposed surface, or spine, e.g. a surface and/or anatomic landmark, including surgically exposed surfaces or anatomic landmarks, and to maintain the display of the virtual surgical instrument, virtual surgical tool, virtual display or virtual representation superimposed onto and/or aligned with one or more anatomic landmarks and/or surfaces of the physical joint or spine when at least portions of the physical joint or spine move, e.g. in the coordinate system. The portions of the physical joint can, for example, be a first and/or a second articular surface, which can, for example move into different degrees of flexion and/or extension and/or rotation and/or abduction and/or adduction. The portions of the physical spine can, for example, be a first vertebral level, a second vertebral level, a portion of or all of posterior elements, e.g. at one or more spinal levels, a portion of a vertebral body or vertebral bodies, e.g. at one or more spinal levels, a portion of or all of a facet joint, e.g. at one or more spinal levels.

In some embodiments, the at least one optical head mounted display can be configured to display the virtual surgical instrument, virtual surgical tool, virtual display or virtual representation, e.g. of a robot or portions thereof, including, for example, an attached or integrated pin, drill, burr, mill, reamer, broach and/or impactor and/or saw or saw blade, superimposed onto and/or aligned with a physical joint or spine and to maintain the display of the virtual surgical instrument, virtual surgical tool, virtual display or virtual representation superimposed onto and/or aligned with one or more anatomic landmarks of the physical joint or spine when the one or more physical surgical tool or physical surgical instrument, e.g. portions of a physical robot, for example a handheld portion of the robot or a robotic arm, or a physical implant or device move, e.g. in the coordinate system, and when also at least portions of the physical joint or spine move, e.g. in the coordinate system.

OHMD Displays for Projecting One or More Virtual Active Boundaries or Planes and/or One or More Safety Boundaries and/or Safety Planes for a Robot or Robotic Arm In some embodiments, a physical surgical instrument or a physical surgical tool can include a robotic arm, e.g. for bone removal, e.g. with an attached drill, mill, burr, reamer, impactor, broach, and/or saw and/or saw blade. The robotic arm can, for example, move with 2, 4 or 6 degrees of freedom and can be attached to a stand. At least portions of the robot can be handheld. The robot can optionally provide haptic feedback, e.g. when a surgeon is holding a portion of a robot and the robot operates within or outside an intended or predetermined perimeter, area or volume of bone removal, slowing or stopping, for example the advancement of the robot or robotic arm if the robot operates outside the intended or predetermined perimeter, area or volume of bone removal. In some embodiments, a sharp tool for bone removal, e.g. a drill, a mill, a burr, a reamer, a broach, a saw, can be exposed by the robot when the user is advancing the robot within a predetermined surgical plan, e.g. within a perimeter or area or volume predetermined for bone removal; the sharp tool for bone removal can be covered by a protective sleeve when the robot or robotic arm is advanced outside a predetermined surgical plan, e.g. outside a perimeter or area or volume predetermined for bone removal.

In some embodiments, an active zone or boundary or plane can be defined or predetermined for a robot. The active zone or boundary or plane can, for example, be the zone or boundary or plane of a perimeter or area or volume within which the robot can be active, e.g. with an active sharp tool or cutting tool such as a saw, a drill, a mill, a reamer, or the zone or boundary or plane of a perimeter or area or volume within which a sharp tool for bone removal, e.g. a drill, a mill, a burr, a reamer, a broach, a saw, can be exposed by the robot when the user is advancing the robot or robotic arm.

In some embodiments, a safety zone or boundary or plane can be defined or predetermined for a robot. The safety zone or boundary or plane can, for example, be the zone or boundary or plane of a perimeter or area or volume within which the robot can be deactivated or slowed down, e.g. with a deactivated or slowed down sharp tool or cutting tool such as a saw, a drill, a mill, a reamer, or the zone or boundary or plane of a perimeter or area or volume within which a sharp tool for bone removal, e.g. a drill, a mill, a burr, a reamer, a broach, a saw, can be covered by the robot when the user is operating or moving the robot or robotic arm within the safety zone. Other zones, boundaries or planes can be defined based on the operating characteristics of the robot. One or more computer processors can be programmed for different robot functions so that the virtual robot operating zone, virtual robot operating boundary or virtual robot plane is a visual 3D indicator of operating within the boundaries of that robot function or outside boundaries of that function. One or more optical head mounted displays can display a virtual active zone, virtual active boundary or virtual active plane, a virtual safety zone, virtual safety boundary or virtual safety zone, or a virtual robot operating zone, virtual robot operating boundary or virtual robot plane, for example superimposed onto a joint (e.g. an articular surface), e.g. a knee joint, hip joint, shoulder joint or ankle joint. The virtual active zone, virtual active boundary or virtual active plane, a virtual safety zone, virtual safety boundary or virtual safety zone, or a virtual robot operating zone, virtual robot operating boundary or virtual robot plane can be a 2D or a 3D display.

In some embodiments, the virtual active zone, virtual active boundary or virtual active plane, the virtual safety zone, virtual safety boundary or virtual safety zone, or the virtual robot operating zone, virtual robot operating boundary or virtual robot plane can be defined or determined using one or more pre-operative scans of the patient, e.g. an ultrasound, CT or MRI scan. One or more computer processors can generate a graphical user interface providing for tools, e.g. segmentation tools, to determine the one or more virtual active zone, virtual active boundary or virtual active plane, a virtual safety zone, virtual safety boundary or virtual safety zone, or a virtual robot operating zone, virtual robot operating boundary or virtual robot plane.

The one or more optical head mounted displays can be registered in a coordinate system, e.g. a common coordinate system. The robot or robotic arm or at least portions of the robot can be registered in the same coordinate system. The virtual active zone, virtual active boundary or virtual active plane, a virtual safety zone, virtual safety boundary or virtual safety zone, or a virtual robot operating zone, virtual robot operating boundary or virtual robot plane can be registered in the same coordinate system. One or more anatomic sites, e.g. a knee exposed during knee replacement surgery, or an acetabulum or a proximal femur exposed during hip replacement surgery, or a spine, e.g. a spinous process, a facet joint, a pedicle, a vertebral body, or any other joint or portion of the body can be registered in the same coordinate system.

A physical surgical instrument and/or the physical surgical tool can be or can include a physical robotic arm or portions thereof, including, for example, with an attached physical drill, mill, burr, reamer, impactor, broach, and/or saw and/or saw blade, or a physical portion of a robot to which one or more of a drill, mill, burr, reamer, impactor, broach, and/or saw and/or saw blade are attached, or a physical handheld portion of a robot or a robotic arm or any other physical component of a robot, including, for example, one or more physical optical markers, e.g. using one or more geometric patterns, navigation markers, e.g. using RF or infrared markers, calibration phantoms, IMU's and/or any other marker known in the art or described, for example, in U.S. provisional application No. 62/700,096, filed Jul. 18, 2018, which is incorporated herein by reference in its entirety. The physical surgical instrument and/or the physical surgical tool can be registered in the coordinate system, for example using the markers.

In some embodiments, the at least one optical head mounted display can be configured to display a virtual active zone, virtual active boundary or virtual active plane, a virtual safety zone, virtual safety boundary or virtual safety zone, or a virtual robot operating zone, virtual robot operating boundary or virtual robot plane superimposed onto a physical joint, e.g. the surface of the physical joint, for example a cartilage, subchondral bone or cortical bone, or spine based, for example, at least in part on coordinates of a predetermined position and/or orientation or combinations thereof of the virtual surgical instrument, virtual surgical tool, virtual display, or virtual representation or of the virtual active zone, virtual active boundary or virtual active plane, a virtual safety zone, virtual safety boundary or virtual safety zone, or a virtual robot operating zone, virtual robot operating boundary or virtual robot plane, and the virtual active zone, virtual active boundary or virtual active plane, a virtual safety zone, virtual safety boundary or virtual safety zone, or a virtual robot operating zone, virtual robot operating boundary or virtual robot plane can be configured to allow for superimposing and/or aligning the physical surgical instrument or physical surgical tool, e.g. portions of a physical robot, within or outside one or more of the virtual active zone, virtual active boundary or virtual active plane, a virtual safety zone, virtual safety boundary or virtual safety zone, or a virtual robot operating zone, virtual robot operating boundary or virtual robot plane.

The virtual active zone, virtual active boundary or virtual active plane, a virtual safety zone, virtual safety boundary or virtual safety zone, or a virtual robot operating zone, virtual robot operating boundary or virtual robot plane can be at a predetermined position, predetermined orientation and/or predetermined position and/or orientation for an intended bone cut or bone removal for an implant component, e.g. a femoral component in a knee replacement, a tibial component in a knee replacement, a femoral component in a hip replacement, an acetabular component in a hip replacement, a humeral component in a shoulder replacement, a tibial or talar component in an ankle replacement or a femoral and/or tibial tunnel or intended graft site for an ACL or other ligament reconstruction.

The predetermined position, predetermined orientation and/or predetermined position and/or orientation of the virtual active zone, virtual active boundary or virtual active plane, a virtual safety zone, virtual safety boundary or virtual safety zone, or a virtual robot operating zone, virtual robot operating boundary or virtual robot plane can be derived, for example, using data from an imaging test, e.g. an x-ray, an ultrasound, a CT scan, an MRI scan. In any of the embodiments throughout the specification, the data from the imaging test can, for example, include data generated by placing and/or fitting and/or sizing and/or selecting and/or aligning a virtual implant component, e.g. an STL file or CAD file of an implant component, in imaging data or using imaging data of the patient. The predetermined position, predetermined orientation and/or predetermined position and/or orientation of the virtual active zone, virtual active boundary or virtual active plane, a virtual safety zone, virtual safety boundary or virtual safety zone, or a virtual robot operating zone, virtual robot operating boundary or virtual robot plane can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut or bone removal, e.g. using a pin, a drill, a burr, a mill, a reamer, a broach, and/or an impactor and/or a saw, can be referenced in relationship to the articular surface, e.g. for a given implant component geometry, e.g. a planar surface on the implant. A bone cut can be referenced, e.g. in relationship to an articular surface, using a CAD file of an implant component. A bone cut or bone removal, e.g. using a pin, a drill, a burr, a mill, a reamer, a broach, and/or an impactor and/or a saw, can be referenced, e.g. in relationship to an articular surface, using a CAD file of a physical cut block with, for example, holes for pin placement (and optional OHMD display of a corresponding virtual surgical guide, virtual surgical instrument, virtual surgical tool, virtual display or virtual representation, e.g. a virtual axis) or pegs (and optional OHMD display of a corresponding virtual surgical guide, virtual surgical instrument, virtual surgical tool, virtual display or virtual representation, e.g. a virtual axis for burring, milling or drilling one or more holes in the bone). A bone cut or bone removal, e.g. using a pin, a drill, a burr, a mill, a reamer, a broach, and/or an impactor and/or a saw, can be referenced in relationship to coordinates of a virtually placed, fitted, sized, selected and/or aligned virtual implant component, placed, for example, on portions of a physical joint of the patient. A predetermined position, predetermined orientation and/or predetermined position and/or orientation of the virtual active zone, virtual active boundary or virtual active plane, a virtual safety zone, virtual safety boundary or virtual safety zone, or a virtual robot operating zone, virtual robot operating boundary or virtual robot plane can be derived using any of the foregoing information including the coordinates of a bone cut or bone removal. Any combination of embodiments is possible.

In some embodiments, the at least one optical head mounted display can be configured to display the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with a physical joint, e.g. the surface of the physical joint including a surgically exposed surface, or onto a spine, e.g. an exposed surface of the spine, for example, a spinous process or a lamina, and to maintain the display of the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with one or more anatomic landmarks and/or the surface of the physical joint or spine when the one or more physical surgical instrument, e.g. portions of a physical robot or robotic arm, for example a handheld portion of the robot or a robotic arm, physical surgical tool, physical medical device, e.g. an implant, move, e.g. in the coordinate system.

In some embodiments, the at least one optical head mounted display can be configured to display the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with a physical joint, e.g. the surface including a surgically exposed surface, or spine, e.g. a surface and/or anatomic landmark, including surgically exposed surfaces or anatomic landmarks, and to maintain the display of the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with one or more anatomic landmarks and/or surfaces of the physical joint or spine when at least portions of the physical joint or spine move, e.g. in the coordinate system. The portions of the physical joint can, for example, be a first and/or a second articular surface, which can, for example move into different degrees of flexion and/or extension and/or rotation and/or abduction and/or adduction. The portions of the physical spine can, for example, be a first vertebral level, a second vertebral level, a portion of or all of posterior elements, e.g. at one or more spinal levels, a portion of a vertebral body or vertebral bodies, e.g. at one or more spinal levels, a portion of or all of a facet joint, e.g. at one or more spinal levels.

In some embodiments, the at least one optical head mounted display can be configured to display the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with a physical joint or spine and to maintain the display of the virtual active zone, virtual active boundary or virtual active plane, a virtual safety zone, virtual safety boundary or virtual safety zone, or a virtual robot operating zone, virtual robot operating boundary or virtual robot plane superimposed onto and/or aligned with one or more anatomic landmarks of the physical joint or spine when the one or more physical surgical tool or physical surgical instrument, e.g. portions of a physical robot, for example a handheld portion of the robot or a robotic arm, or a physical implant or device move, e.g. in the coordinate system, and when also at least portions of the physical joint or spine move, e.g. in the coordinate system.

Tracking Physical Robots, Measuring Percent Superimposition Between Physical Robots or Portions Thereof and Virtual Surgical Guides, e.g. Virtual Placement Indicators In some embodiments, portions of a robot or the entire robot, including, for example, an attached or integrated pin, drill, burr, mill, reamer, broach and/or impactor and/or saw or saw blade, can be tracked, e.g. by measuring one or more coordinates, for example using optical markers integrated or attached to the robot or portions thereof, e.g. with geometric patterns, detected by a video system, e.g. integrated into, attached to, or separate from an OHMD, navigation markers integrated or attached to the robot or portions thereof, e.g. RF or infrared markers, detected by a navigation system, calibration phantoms integrated or attached to the robot or portions thereof, IMU's integrated or attached to the robot or portions thereof. Portions of a robot or the entire robot, including, for example, an attached or integrated pin, drill, burr, mill, reamer, broach and/or impactor and/or saw or saw blade, can be tracked using direct imaging techniques, for example with optional feature or contour detection, or 3D scanners, e.g. laser scanners, as described, for example, in U.S. provisional application No. 62/700,096, filed Jul. 18, 2018, which is incorporated herein by reference in its entirety.

As the physical surgical guide, physical surgical instrument and/or physical surgical tool, e.g. at least a portion of a robot, for example including a pin, a drill, a burr, a mill, a reamer, a broach, an impactor, a saw blade and/or a saw, is moved, for example actively or passively, to align it and/or superimpose it with a virtual surgical guide, virtual surgical instrument, and/or virtual surgical tool, e.g. a virtual portion of the robot or a virtual placement indicator of the robot or portions thereof, including, for example, an attached or integrated pin, drill, burr, mill, reamer, broach and/or impactor and/or saw or saw blade, the superimposition can be indicated as a percent or graphical volume superimposition between the physical and the virtual surgical guide, or the physical and the virtual surgical instrument and/or the physical and the virtual surgical tool, or the physical and the virtual portion of the robot or portions thereof, a percent or graphical surface superimposition, a percent or graphical area superimposition, a percent or graphical superimposition in a first, second, and/or third direction, e.g. x-, y- and z-, e.g. in mm, a percent or graphical superimposition with regard to angular alignment, e.g. in x-, y-, and z-direction, e.g. in degrees (e.g. for slope or flexion), a percent or graphical coordinate superimposition, e.g. in mm (all optionally indicated in graphical, color coded and/or numerical form). The superimposition can be visualized using color coding, for example from red (e.g. "poor"), to orange (e.g. "medium") to green (e.g. "good"). When the physical surgical guide, physical surgical instrument, physical surgical tool or physical device is sufficiently well or completely superimposed onto the virtual surgical guide, virtual surgical instrument, virtual surgical tool or virtual device (e.g. 100% match or >90% match or >95% match, or any other amount), the physical robot can, for example, be activated and/or a cover can be removed from a pin, drill, burr, mill, reamer, broach, impactor and/or saw and/or saw blade, and a bone removal can be initiated or continued; the bone removal can be a pinning, drilling, burring, milling, reaming, broaching, impacting, and/or cutting. The foregoing embodiments on tracking and/or displaying and/or determining and/or measuring superimposition can be applied to many different embodiments throughout the application using robots including handheld robots, e.g. for spinal surgery, spinal fusion, hip replacement, shoulder replacement, ankle replacement, ACL reconstruction or repair, dental surgery, root canals, dental implant placement, etc.

In other embodiments, the at least one OHMD can be configured to display the surgical plan. The surgical plan can, for example, consist of virtual models of the patient's anatomy, such as the femoral or tibial bone, or spinal bone, which can be derived from the preoperative images, and/or implants and/or implant geometries, e.g. derived using STL or CAD files, to be inserted or placed into the patient. The surgical plan can also include virtual surgical guides, e.g. virtual cut guides, virtual axes, virtual cut planes. Areas or portions of bone to be resected, removed, cut or milled can be highlighted in the virtual model, for example in a different color.

The surgical plan and the virtual anatomical models can be registered and superimposed with the patient's anatomy, for example to enable the surgeon to compare the surgical plan derived from preoperative images with the real intraoperative anatomy of the patient, e.g. a physical joint or spine or vertebral level or portions thereof. The surgeon can then make updates to the surgical plan based on the intraoperative assessment and comparison between virtual anatomical model and live physical patient anatomy. For example, the surgeon can assess the tracking of the patella relative to the planned internal/external rotation of the femoral implant and adjust the planned rotation of the femoral implant. In another embodiment, the surgeon can adjust the tibial slope angle based on the intraoperative assessment. Any changes in the surgical plan can then be translated into updated control commands for the robot and updated display of virtual data by one or more OHMDs.

In another embodiment, the progress of a robotic milling procedure, for example with a semi-active robot, can be displayed in real time to the surgeon. For example, the section or volume of bone to be removed by drilling, pinning, burring, milling, reaming, broaching, impacting and/or sawing and/or cutting can be marked in a different color and/or transparency, for example, in a virtual anatomical model, which can be superimposed onto and/or aligned with the patient's intraoperative anatomy by the one or more OHMDs. The pathway of the bone removal, e.g. from a pin, drill, burr, mill, reamer, broach, impactor, and/or saw can be tracked continuously or intermittently, and the pinned, drilled, burred, milled, reamed, broached, impacted and/or cut bone can optionally be virtually removed from the virtual anatomical model displayed by the one or more OHMDs. In this manner, the surgeon can easily see which parts of the bone still need to be removed, and direct the robot, e.g. a tip or edge or bone removing portion of a robotic pin, drill, burr, mill, reamer, broach, impactor, and/or saw, accordingly. Thus, the one or more OHMDs can be configured using a computer processor so that the display facilitates visualization of areas of bone removed and areas of bone remaining to be removed and/or targeted for removal and/or highlighted for removal superimposed onto and/or aligned with corresponding anatomic structures of the physical patient, e.g. the physical joint, e.g. the physical articular surface. One or more OHMDs can also display any areas of over-resection, i.e. areas where too much bone has been removed, superimposed onto and/or aligned with the joint, e.g. the articular surface, subchondral bone, marrow bone and/or cortical bone. Thus, one or more OHMDs can display a virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte.

In some embodiments, the at least one optical head mounted display can be configured to display a virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte superimposed onto a physical joint, e.g. the surface of the physical joint, for example a cartilage, subchondral bone or cortical bone, or spine based, for example, at least in part on coordinates of a predetermined position and/or orientation or combinations thereof of a virtual surgical instrument, virtual surgical tool, virtual display, or virtual representation or of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte.

The virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be at a predetermined position, predetermined orientation and/or predetermined position and/or orientation for an intended bone cut or bone removal for an implant component, e.g. a femoral component in a knee replacement, a tibial component in a knee replacement, a femoral component in a hip replacement, an acetabular component in a hip replacement, a humeral component in a shoulder replacement, a tibial or talar component in an ankle replacement or a femoral and/or tibial tunnel or intended graft site for an ACL or other ligament reconstruction.

The predetermined position, predetermined orientation and/or predetermined position and/or orientation of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be derived, for example, using data from an imaging test, e.g. an x-ray, an ultrasound, a CT scan, an MRI scan. In any of the embodiments throughout the specification, the data from the imaging test can, for example, include data generated by placing and/or fitting and/or sizing and/or selecting and/or aligning a virtual implant component, e.g. an STL file or CAD file of an implant component, in imaging data or using imaging data of the patient. The predetermined position, predetermined orientation and/or predetermined position and/or orientation of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be derived, for example, by touching select landmarks of a joint, e.g. portions of an articular surface or osteophytes, or by "painting" portions of the joint, e.g. portions of an articular surface, e.g. of a distal femur, with a pointer, e.g. with one or more attached optical markers, navigation markers and/or IMU's and/or by generating a point cloud and surface of an articular surface. A bone cut or bone removal, e.g. using a pin, a drill, a burr, a mill, a reamer, a broach, and/or an impactor and/or a saw, can be referenced in relationship to the articular surface, e.g. for a given implant component geometry, e.g. a planar surface on the implant. A bone cut can be referenced, e.g. in relationship to an articular surface, using a CAD file of an implant component. A bone cut or bone removal, e.g. using a pin, a drill, a burr, a mill, a reamer, a broach, and/or an impactor and/or a saw, can be referenced, e.g. in relationship to an articular surface, using a CAD file of a physical cut block with, for example, holes for pin placement (and optional OHMD display of a corresponding virtual surgical guide, virtual surgical instrument, virtual surgical tool, virtual display or virtual representation, e.g. a virtual axis) or pegs (and optional OHMD display of a corresponding virtual surgical guide, virtual surgical instrument, virtual surgical tool, virtual display or virtual representation, e.g. a virtual axis for burring, milling or drilling one or more holes for pegs in the bone). A bone cut or bone removal, e.g. using a pin, a drill, a burr, a mill, a reamer, a broach, and/or an impactor and/or a saw, can be referenced in relationship to coordinates of a virtually placed, fitted, sized, selected and/or aligned virtual implant component, placed, for example, on portions of a physical joint of the patient. A predetermined position, predetermined orientation and/or predetermined position and/or orientation of the virtual display or virtual anatomic 3D model of the section or volume of bone and/or cartilage to be removed, the pathway of bone and/or cartilage removal, the bone and/or cartilage removed, the area of volume of over-resection, an osteophyte to be removed, an area of over-resection of an osteophyte can be derived using any of the foregoing information including the coordinates of a bone cut or bone removal. Any combination of embodiments is possible.

In some embodiments, the at least one optical head mounted display can be configured to display the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with a physical joint, e.g. the surface of the physical joint including a surgically exposed surface, or onto a spine, e.g. an exposed surface of the spine, for example, a spinous process or a lamina, and to maintain the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with one or more anatomic landmarks and/or the surface of the physical joint or spine when the one or more physical surgical instrument, e.g. portions of a physical robot or robotic arm, for example a handheld portion of the robot or a robotic arm, physical surgical tool, physical medical device, e.g. an implant, move, e.g. in the coordinate system.

In some embodiments, the at least one optical head mounted display can be configured to display the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with a physical joint, e.g. the surface including a surgically exposed surface, or spine, e.g. a surface and/or anatomic landmark, including surgically exposed surfaces or anatomic landmarks, and to maintain the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with one or more anatomic landmarks and/or surfaces of the physical joint or spine when at least portions of the physical joint or spine move, e.g. in the coordinate system. The portions of the physical joint can, for example, be a first and/or a second articular surface, which can, for example move into different degrees of flexion and/or extension and/or rotation and/or abduction and/or adduction. The portions of the physical spine can, for example, be a first vertebral level, a second vertebral level, a portion of or all of posterior elements, e.g. at one or more spinal levels, a portion of a vertebral body or vertebral bodies, e.g. at one or more spinal levels, a portion of or all of a facet joint, e.g. at one or more spinal levels.

In some embodiments, the at least one optical head mounted display can be configured to display the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with a physical joint or spine and to maintain the virtual display or virtual anatomic 3D model of the section or volume of bone and/or cartilage to be removed, the pathway of bone and/or cartilage removal, the bone and/or cartilage removed, the area of volume of over-resection, the osteophyte to be removed, the area of over-resection of an osteophyte superimposed onto and/or aligned with one or more anatomic landmarks of the physical joint or spine when the one or more physical surgical tool or physical surgical instrument, e.g. portions of a physical robot, for example a handheld portion of the robot or a robotic arm, or a physical implant or device move, e.g. in the coordinate system, and when also at least portions of the physical joint or spine move, e.g. in the coordinate system.

The techniques and examples and any modifications thereof for using and optimizing optical markers, for optimizing geometric patterns of optical markers, for optimizing the shape of optical markers, for aligning optical markers and/or geometric patterns with radiopaque elements, for registering fluoroscopic images with the patient's live anatomy, for utilizing pre-existing information on the known size, shape and/or dimensions of one or more optical markers, for networks of OHMDs and combining multiple spatial maps, for various interfaces including virtual interfaces and for tracking surgical instruments are applicable to any type of surgical procedure, surgical instruments and implants and implant components, including trial components, including, but not limited to partial and total knee replacement, partial and total hip replacement, partial and total shoulder replacement, partial and total ankle replacement, partial and total elbow replacement, partial and total wrist replacement, partial and total mid-foot and forefoot joint replacement, partial and total small joint replacement in hand and feet, arthroscopy of the knee, hip, shoulder, ankle, elbow, wrist and other joints, ligament repair including ACL and/or PCL repair, ligament repair in the knee, hip, shoulder, elbow, ankle or wrist joint, spinal fusion, anterior and/or posterior, spinal disk replacement, spinal motion preservation surgery, different types of spinal surgery approaches and procedures, e.g. PLIF, TLIF, ALIF and others known in the art.

Someone skilled in the art can recognize that the embodiments in the specification are applicable to many different types of medical device related surgery and, for example, implant placement, as tabulated, in a non-limiting manner, for example in Table 15, including, for example, partial and total shoulder replacement and other shoulder surgeries, e.g. repair of the rotator cuff or glenoid labrum, partial or total knee replacement, partial or total hip replacement, partial or total shoulder replacement, partial or total ankle replacement, spinal fusion, spinal surgery, disk replacement, ligament repair and/or reconstruction including ACL or other ligaments, dental surgery, dental implants and other dental devices, vascular or other devices etc. Anatomy or pathology related terms for a particular anatomic region, e.g. the knee, can be exchanged with anatomy or pathology related terms for another anatomic region, e.g. a hip or a shoulder joint. For example, the words "femoral" and "tibial" in the embodiments are representative of two articulating surfaces in a joint, e.g. a knee joint, e.g. during knee replacement surgery, and can be exchanged for the words "acetabular" and "femoral" in hip replacement or "glenoid" and "humeral" in shoulder replacement and "tibial" and "talar" or "talar" and "calcaneal" in ankle replacement or fusion. For example, in embodiments pertaining to virtual moving, placing, orienting, aligning, sizing and/or fitting and/or selecting of implant components, the words "femoral" and "tibial" in the embodiments are representative of two articulating surfaces in a joint and can be exchanged for the words "acetabular" and "femoral" in hip replacement or "glenoid" and "humeral" in shoulder replacement and "tibial" and "talar" or "talar" and "calcaneal" in ankle replacement or fusion. Throughout the specification, the meaning of "a,"

"an," and "the" include plural references. Various embodiments of the present disclosure may be readily combined, without departing from the scope or spirit of the present disclosure.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

The invention claimed is:

1. A system for preparing a patient for a dental procedure, the system comprising:
at least one processor,
at least one see through optical head mounted display,
at least one camera, and
at least one marker,
wherein the at least one marker comprises a radiopaque portion and is configured to be attached to a mandibular tissue, a maxillary tissue, a dental tissue or combination thereof of the patient,
wherein the at least one processor is configured to receive 2D x-ray image data of at least one anatomic structure of the mandible, at least one anatomic structure of the maxilla, at least one anatomic structure of a tooth or a combination thereof,
wherein the radiopaque portion of the at least one marker is included in the 2D x-ray image data,
wherein the at least one processor is configured to register the 2D x-ray image data with the at least one physical anatomic structure of the mandible, the at least one physical anatomic structure of the maxilla, the at least one physical anatomic structure of the tooth or a combination thereof using the radiopaque portion of the at least one marker included in the 2D x-ray image data,
wherein the at least one processor is configured to generate a display of the 2D x-ray image data by the at least one see through optical head mounted display, and is configured to superimpose or align the display of the 2D x-ray image data at a predetermined position, orientation or position and orientation with at least a portion of the at least one physical anatomic structure of the mandible, at least a portion of the at least one physical anatomic structure of the maxilla, at least a portion of the at least one physical anatomic structure of the tooth, or a combination thereof.

2. The system of claim 1, wherein the display of the 2D x-ray image data at the predetermined position, orientation or position and orientation is parallel, tangent, or intersecting in relationship to the at least one physical anatomic structure of the mandible, the at least one physical anatomic structure of the maxilla, the at least one physical anatomic structure of the tooth, or the combination thereof.

3. The system of claim 1, wherein the at least one processor is configured to perform a magnification correction of the 2D x-ray image data.

4. The system of claim 1, wherein the at least one processor is configured to track the at least one marker in a coordinate system during movement.

5. The system of claim 1, wherein the dental procedure comprises a root canal procedure or a dental implant procedure.

6. The system of claim 1, wherein the at least one physical anatomic structure of the mandible or the at least one physical anatomic structure of the maxilla comprises an area between two teeth, an area of a missing tooth, an area of an extracted tooth, a portion of a gum, a gingival tissue, an alveolar bone or a combination thereof.

7. The system of claim 1, wherein the at least one physical anatomic structure of the tooth comprises the entire tooth, a portion of the tooth, an enamel, a dentin, a pulp, a cementum, a cementoenamel junction, a periodontal ligament, a root, a root canal or a combination thereof.

8. The system of claim 1, wherein the at least one see through optical head mounted display is registered in a coordinate system.

9. The system of claim 1, wherein the display of the 2D x-ray image data by the at least one see through optical head mounted display comprises a virtual axis.

10. The system of claim 9, wherein the virtual axis is a digital representation indicating a predetermined position, predetermined orientation, or combination thereof in relationship to the at least one physical anatomic structure of the mandible, the at least one physical anatomic structure of the maxilla, the at least one physical anatomic structure of the tooth or a combination thereof for at least one physical dental tool, or wherein the virtual axis is a digital representation indicating a predetermined position, predetermined orientation, or combination thereof in relationship to the at least one anatomic structure of the mandible, the at least one anatomic structure of the maxilla, the at least one anatomic structure of the tooth or a combination thereof in the 2D x-ray image data for at least one physical dental tool.

11. The system of claim 10, wherein the at least one physical dental tool comprises a probe or a drill.

12. The system of claim 10, wherein the at least one physical dental tool is registered in a coordinate system.

13. The system of claim 10, wherein the at least one physical dental tool is tracked.

14. The system of claim 9, wherein the system is configured to allow at least partial superimposition or alignment between at least one physical dental tool and at least a portion of the virtual axis displayed by the at least one see through optical head mounted display, or wherein the system is configured to allow at least partial superimposition or alignment between at least one physical dental implant and at least a portion of the virtual axis displayed by the at least one see through optical head mounted display.

15. The system of claim 1, wherein the marker comprises an active marker, a passive marker, an infrared marker, a radiofrequency marker, a retroreflective marker, an LED, or a combination thereof.

16. The system of claim 1, wherein the system comprises a surgical navigation system, a video camera, an image capture system, a 3D scanner or a combination thereof.

17. The system of claim 1, wherein the system comprises a user interface.

18. The system of claim 17, wherein the at least one user interface comprises a graphical user interface, a voice recognition, a gesture recognition, a virtual interface displayed by the at least one see through optical head mounted display, a virtual keyboard displayed by the at least one see through optical head mounted display, a physical keyboard, a physical computer mouse, a physical track pad, or combinations thereof.

19. The system of claim 1, wherein the at least one camera is head mounted with the stereoscopic optical see-through head mounted display, or wherein the at least one camera is separate from the stereoscopic optical see-through head mounted display.

* * * * *